US012448369B2

(12) United States Patent
Hawryluk et al.

(10) Patent No.: US 12,448,369 B2
(45) Date of Patent: Oct. 21, 2025

(54) QUINOLINONE AMIDE COMPOUNDS AND USES THEREOF

(71) Applicant: Edgewise Therapeutics, Inc., Boulder, CO (US)

(72) Inventors: Natalie Anne Hawryluk, Nederland, CO (US); Stephen Thomas Schlachter, Boulder, CO (US); Kevin Koch, Niwot, CO (US); Michael Joseph Luzzio, Groton, CT (US); Alan James Russell, Boulder, CO (US); Marc Justin Evanchik, Boulder, CO (US); Carlos Luis Del Rio, San Mateo, CA (US); Kevin Hunt, Boulder, CO (US)

(73) Assignee: Edgewise Therapeutics, Inc., Boulder, CO (US)

( * ) Notice: Subject to any disclaimer, the term of this patent is extended or adjusted under 35 U.S.C. 154(b) by 0 days.

(21) Appl. No.: 18/882,644

(22) Filed: Sep. 11, 2024

(65) Prior Publication Data

US 2025/0026740 A1 Jan. 23, 2025

Related U.S. Application Data

(63) Continuation of application No. PCT/US2024/021528, filed on Mar. 26, 2024.

(60) Provisional application No. 63/492,441, filed on Mar. 27, 2023.

(51) Int. Cl.

| | |
|---|---|
| ***C07D 405/12*** | (2006.01) |
| ***A61K 31/4353*** | (2006.01) |
| ***A61K 31/506*** | (2006.01) |
| ***C07D 221/04*** | (2006.01) |
| ***C07D 401/12*** | (2006.01) |

(52) U.S. Cl.

CPC ........ *C07D 405/12* (2013.01); *A61K 31/4353* (2013.01); *A61K 31/506* (2013.01); *C07D 221/04* (2013.01); *C07D 401/12* (2013.01)

(58) Field of Classification Search

CPC .. C07D 405/12; C07D 221/04; C07D 401/12; A61K 31/4353; A61K 31/506

See application file for complete search history.

(56) References Cited

U.S. PATENT DOCUMENTS

| | | | |
|---|---|---|---|
| 5,846,514 | A | 12/1998 | Foster et al. |
| 6,334,997 | B1 | 1/2002 | Foster et al. |
| 7,429,604 | B2 | 9/2008 | Corte et al. |
| 7,875,636 | B2 | 1/2011 | Barrow et al. |
| 9,464,065 | B2 | 10/2016 | Schultz et al. |
| 9,522,140 | B2 | 12/2016 | Inoue et al. |
| 9,585,883 | B2 | 3/2017 | Oslob et al. |
| 11,052,092 | B2 | 7/2021 | Delhomel et al. |
| 11,306,098 | B2 | 4/2022 | Letourneau et al. |
| 11,931,358 | B2 | 3/2024 | Honarpour et al. |
| 11,945,803 | B2 | 4/2024 | Lennek et al. |
| 2007/0148185 | A1 * | 6/2007 | Rathore ............... C07K 14/445 514/217.09 |
| 2009/0023169 | A1 | 1/2009 | Hartman et al. |
| 2010/0113391 | A1 | 5/2010 | Koga et al. |
| 2012/0108597 | A1 | 5/2012 | Guo et al. |
| 2016/0176868 | A1 | 6/2016 | Oslob et al. |
| 2019/0077793 | A1 | 3/2019 | Ashcraft et al. |
| 2020/0369626 | A1 | 11/2020 | Tu et al. |
| 2021/0276991 | A1 | 9/2021 | Morgan et al. |
| 2022/0106265 | A1 | 4/2022 | Thiele et al. |
| 2023/0012449 | A1 | 1/2023 | Bondy et al. |
| 2023/0149394 | A1 | 5/2023 | Honarpour et al. |
| 2024/0164138 | A1 | 5/2024 | Ham et al. |
| 2024/0279206 | A1 | 8/2024 | Lennek et al. |

FOREIGN PATENT DOCUMENTS

| | | | |
|---|---|---|---|
| CN | 1521171 | A | 8/2004 |
| CN | 109836477 | A | 6/2019 |
| CN | 114149423 | A | 3/2022 |
| EP | 0561252 | A1 | 9/1993 |
| EP | 0585913 | A2 | 3/1994 |
| EP | 1724264 | A1 | 11/2006 |
| EP | 2010493 | A2 | 1/2009 |
| EP | 2729448 | B1 | 9/2015 |
| EP | 3573960 | B1 | 8/2023 |
| JP | S6463518 | A | 3/1989 |
| JP | H01125369 | A | 5/1989 |
| MA | 30462 | B1 | 6/2009 |
| WO | WO-0032587 | A1 | 6/2000 |
| WO | WO-0142216 | A2 | 6/2001 |
| WO | WO-0206264 | A1 | 1/2002 |
| WO | WO-02064578 | A1 | 8/2002 |

(Continued)

OTHER PUBLICATIONS

I. Ukrainets, et al. Chemistry of Heterocyclic Compounds 36, 1319-1325 (2000). doi.org/10.1023/A:1017527702970. (Year: 2000).*

Arranz, Esther et al. Synthesis And Pharmacological Evaluationof 2,3-dihydro-3-oxo-4h-thieno[3,4-e][1,2,4]Thiadiazine 1,1-Dioxidesas Voltage-Dependent Calcium Channel Blockers. European Journal of Medicinal Chemistry 35(7-8):751-759 (2000).

Awinda et al., Mavacamten decreases maximal force and $Ca^{2+}$ sensitivity in the N47K-myosin regulatory light chain mouse model of hypertrophic cardiomyopathy. Am J. Physio. Heart Cir. Physiol., 320(2): Feb. 1, 2021;H881-H890.

Chatterjee, Tanmay et al. Base-Promoted Synthesis of 2-Aryl Quinazolines from 2-Aminobenzylamines in Water. The Journal of Organic Chemistry 83(14):7423-7430 (2018).

(Continued)

*Primary Examiner* — James H Alstrum-Acevedo
*Assistant Examiner* — Manahil Mirghani Ali Abdalhameed
(74) *Attorney, Agent, or Firm* — WILSON SONSINI GOODRICH & ROSATI

(57) ABSTRACT

The present disclosure generally relates to substituted quinolinone amide compounds or salts of Formula (I), (II-A), (IV), or (III) and pharmaceutical compositions thereof. The substituted quinolinone amide compounds or salts of Formula (I), (II-A), (IV), or (III) disclosed herein may be used to treat or prevent cardiac disease in an individual in need thereof.

56 Claims, No Drawings

(56) References Cited

FOREIGN PATENT DOCUMENTS

| | | | |
|---|---|---|---|
| WO | WO-2005085210 | A1 | 9/2005 |
| WO | WO-2007078839 | A2 | 7/2007 |
| WO | WO-2007120729 | A2 | 10/2007 |
| WO | WO-2007124617 | A1 | 11/2007 |
| WO | WO-2008010964 | A1 | 1/2008 |
| WO | WO-2008016648 | A2 | 2/2008 |
| WO | WO-2008016669 | A2 | 2/2008 |
| WO | WO-2008076225 | A2 | 6/2008 |
| WO | WO-2008107436 | A1 | 9/2008 |
| WO | WO-2009023655 | A1 | 2/2009 |
| WO | WO-2009054983 | A1 | 4/2009 |
| WO | WO-2010002779 | A2 | 1/2010 |
| WO | WO-2010056549 | A1 | 5/2010 |
| WO | WO-2010137351 | A1 | 12/2010 |
| WO | WO-2013006738 | A1 | 1/2013 |
| WO | WO-2014205223 | A1 | 12/2014 |
| WO | WO-2016004417 | A1 | 1/2016 |
| WO | WO-2016162390 | A1 | 10/2016 |
| WO | WO-2017161119 | A1 | 9/2017 |
| WO | WO-2019028360 | A1 | 2/2019 |
| WO | WO-2020005888 | A1 | 1/2020 |
| WO | WO-2020033413 | A2 | 2/2020 |
| WO | WO-2020097265 | A1 | 5/2020 |
| WO | WO-2020123675 | A1 | 6/2020 |
| WO | WO-2020172565 | A1 | 8/2020 |
| WO | WO-2020210032 | A1 | 10/2020 |
| WO | WO-2020221376 | A1 | 11/2020 |
| WO | WO-2021092598 | A1 | 5/2021 |
| WO | WO-2021231546 | A1 | 11/2021 |
| WO | WO-2021231565 | A1 | 11/2021 |
| WO | WO-2022212902 | A1 | 10/2022 |
| WO | WO-2023277605 | A1 | 1/2023 |
| WO | WO-2023159234 | A2 | 8/2023 |
| WO | WO-2023208165 | A1 | 11/2023 |
| WO | WO-2023240134 | A1 | 12/2023 |
| WO | WO-2024050139 | A1 | 3/2024 |
| WO | WO-2024073426 | A1 | 4/2024 |
| WO | WO-2024138042 | A1 | 6/2024 |
| WO | WO-2024182469 | A1 | 9/2024 |
| WO | WO-2024206339 | A1 | 10/2024 |
| WO | WO-2024206345 | A1 | 10/2024 |
| WO | WO-2024206347 | A1 | 10/2024 |

OTHER PUBLICATIONS

Chem, Ji-Wang et al. Studies on 1, 2, 4-Benzothiadiazine 1, 1-Dioxide IX.1 Synthesis and Pharmacological Evaluation of 1, 2, 4-Benzothiadiazine 1, 1-Dioxide Biphenyl Tetrazoles as Angiotensin II Antagonists. Journal of the Chinese Chemical Society 45(6):805-810 (1998).

Davis, J. S. et al., The Overall pattern of Cardiac contraction depends on a spatial gradient of Myosin Regulatory Light Chain Phosphorylation. Cell, vol. 107, 631-641, Nov. 30, 2001.

Engler, Thomas A. et al. Substituted 3-imidazo[1,2-a]pyridin-3-yl-4-(1,2,3,4-tetrahydro-[1,4]diazepino-[6,7,1-hi]indol-7-yl)pyrrole-2,5-diones as highly selective and potent inhibitors of glycogen synthase kinase-3. Journal of Medicinal Chemistry 47(16):3934-3937 (2004).

Evans, Anthony E. Synthesis of Radiolabeled Compounds. Journal of Radioanalytical and Nuclear Chemistry 64(1-2):9-32 (1981).

Fedorak, Richard N. et al. A novel colon-specific steroid prodrug enhances sodium chloride absorption in rat colitis. American Journal of Physiology 269(2 Pt 1):G210-G218 (1995).

Fieser, Louis. F, and Mary Fieser. Reagents for Organic Synthesis. John Wiley and Sons:119-121 (1994).

Highlights of Prescribing Information These highlights do not include all the information needed to use CAMZYOS safely and effectively. Apr. 2022, 27 Pages.

Higuchi, T, and V. Stella. Pro-Drugs as Novel Delivery Systems, vol. 14 of the A.C.S. Symposium Series. American Chemical Society (1975).

Hochhaus, Gunther. et al. A Selective HPLC/RIA for Dexamethasone and its Prodrug Dexamethasone-21-sulphobenzoate Sodium in Biological Fluids. Biomedical Chromatography 6(6):283-286 (1992).

Kabalka, George W. et al. The Synthesis of Radiolabeled Compounds via Organometallic Intermediates. Tetrahedron 45(21):6601-6621 (1989).

Larsen, Jorn Drustrup, and Hans Bundgaard. Prodrug forms for the sulfonamide group. I. Evaluation of N-acyl derivatives, N-sulfonylamidines, N-sulfonylsulfilimines and sulfonylureas as possible prodrug derivatives. International Journal of pharmaceutics 37(1-2):87-95 (1987).

Larsen, Jorn Drustrup. et al. Prodrug forms for the Sulfonamide Group. II. Water-soluble Amino Acid Derivatives of N-methylsulfonamides as Possible Prodrugs. International Journal of Pharmaceutics 47:103-110 (1988).

Liu, Dazhi et al. Design, synthesis and evaluation of 1, 2-benzisothiazol-3-one derivatives as potent caspase-3 inhibitors. Bioorganic & medicinal chemistry 21(11):2960-2967 (2013).

Mcleod, Andrew D. et al. A glucocorticoid prodrug facilitates normal mucosal function in rat colitis without adrenal suppression. Gastroenterology 106(2):405-413 (1994).

PCT/US2023/075138 International Search Report and Written Opinion dated Nov. 28, 2023.

PCT/US2024/021528 International Search Report and Written Opinion dated Aug. 6, 2024.

PCT/US2024/021537 International Search Report and Written Opinion dated Jul. 18, 2024.

PCT/US2024/021539 International Search Report and Written Opinion dated Aug. 12, 2024.

Ro, R. et al., Vector Flow Mapping in Obstructive Hypertrophic Cardiomyopathy to Assess the Relationship of Early Systolic Left Ventricular Flow and the Mitral Valve. Journal of the American College of Cardiology, 2014, vol. 64. No. 19; 1984-95.

Sinkula, A A, and Samuel H. Yalkowsky. Rationale for design of biologically reversible drug derivatives: prodrugs. Journal of pharmaceutical sciences 64(2):181-210 (1975).

Smith, Joshua D. Isoform selectivities of novel 4-hydroxycoumarin imines as inhibitors of myosin II. European journal of medicinal chemistry 247:115008, 1-38 (2023).

Sun, Lin et al. Design, Synthesis, and Mechanism Study of Benzenesulfonamide-Containing Phenylalanine Derivatives as Novel HIV-1 Capsid Inhibitors with Improved Antiviral Activities. Journal of Medicinal Chemistry 63(9):4790-4810 (2020).

Wang, Min et al. [11C]GSK2126458 and [18F]GSK2126458, The First Radiosynthesis Of New Potential PET Agents For Imaging Of PI3K And mTOR In Cancers. Bioorganic & Medicinal Chemistry Letters 22(4):1569-1574 (2012).

Zhang, J. et al., Hypertrophic cardiomyopathy associated E22K mutation in myosin regulatory light chain decreases calcium-activated tension and stiffness and reduces myofilament Ca2+ sensitivity. FEBS J. Aug. 2021 ; 288(15): 4596-4613. doi:10.1111/febs. 15753.

DataBase CaPlus [Online] ChemicA1 Abstracts Service, Jan. 1, 1990 (Jan. 1, 1990). Chen Qingping Et A1: Proton NMR spectra of 7[beta]-(6-substituted-2-quinolone-3-aceta mido)- and 7[beta]-(6-substituted-4-hydroxyquinoline- 3-formamido)-cephA1osporins. XP093279164, Database accession No. 1991:631920.

Database Registry, ChemicA1 Abstracts Service; (Nov. 9, 2021), Database accession No. 2727956-55-8, XP093279204.

Database Registry, Chemical Abstracts Service (Aug. 2, 2012), Database accession No. 1385267-38-8, XP093279922.

Database Registry, Chemical Abstracts Service (Jun. 18, 2015), Database accession No. 1783105-24-7, XP093279920.

Database Registry, Chemical Abstracts Service; (Dec. 16, 2015), Database accession No. 1831179-14-6, XP093277426.

Database Registry, Chemical Abstracts Service; (Dec. 18, 2015), Database accession No. 1832193-03-9, XP093277424.

Database Registry, Chemical Abstracts Service; (Jul. 6, 2016), Database accession No. 1946404-58-5, XP093277421.

Database Registry, Chemical Abstracts Service; (Jul. 10, 2016), Database accession No. 1948573-95-2, XP093277416.

Database Registry, Chemical Abstracts Service (Jan. 25, 2017), Database accession No. 2058772-64-6, XP093279919.

(56) References Cited

OTHER PUBLICATIONS

Database Registry, Chemical Abstracts Service; (Jan. 27, 2017), Database accession No. 2060133-05-1, XP093277413.
Database Registry, Chemical Abstracts Service; (Jul. 26, 2017), Database accession No. 2103065-64-9, XP093277409.
Database Registry, Chemical Abstracts Service; (Aug. 4, 2017), Database accession No. 2173908-64-8, XP093277403.
Database Registry, Chemical Abstracts Service; (Feb. 15, 2018), Database accession No. 2173908-64-8, XP093277398.
Database Registry, Chemical Abstracts Service; (Mar. 12, 2018), Database accession No. 2189172-68-5, XP093277394.
Database Registry, Chemical Abstracts Service; (Jul. 28, 2019), Database accession No. 2361760-55-4, XP093277429.
Database Registry, Chemical Abstracts Service; (Jul. 28, 2019), Database accession No. 2361838-41-5, XP093277392.
Database Registry, Chemical Abstracts Service; (Jul. 28, 2019), Database accession No. 2361907-19-7, XP093277513.
Database Registry, Chemical Abstracts Service (Aug. 29, 2019), Database accession No. 2369930-64-1, XP093279918.
Database Registry, Chemical Abstracts Service (Jan. 1, 2020), Database accession No. 2398077-26-2, XP093279916.
Database Registry, Chemical Abstracts Service (Jan. 2, 2020), Database accession No. 2398164-43-5, XP093279914.
Database Registry, Chemical Abstracts Service (Jan. 8, 2020), Database accession No. 2402509-76-4, XP093279912.
Database Registry, Chemical Abstracts Service (Jan. 10, 2020), Database accession No. 2404419-52-7, XP093279910.
Database Registry, Chemical Abstracts Service (Jan. 13, 2020), Database accession No. 2405463-55-8, XP093279908.
Database Registry, Chemical Abstracts Service (Jun. 8, 2020), Database accession No. 2420362-92-9, XP093279906.
Database Registry, Chemical Abstracts Service (Jun. 9, 2020), Database accession No. 2421242-17-1, XP093279905.
Database Registry, Chemical Abstracts Service (Jun. 22, 2020), Database accession No. 2431889-47-1, XP093279901.
Database Registry, Chemical Abstracts Service (Jun. 23, 2020), Database accession No. 2432461-84-0, XP093279900.
Database Registry, Chemical Abstracts Service (Aug. 31, 2020), Database accession No. 2468117-82-8, XP093279897.
Database Registry, Chemical Abstracts Service; (Sep. 23, 2021), Database accession No. 2699886-11-6, XP093277387.
Database Registry, Chemical Abstracts Service; (Oct. 14, 2021), Database accession No. 2712289-98-8, XP093277386.
Database Registry, Chemical Abstracts Service; (Oct. 15, 2021), Database accession No. 2712788-51-5, XP093277508.
Database Registry, Chemical Abstracts Service; (Oct. 17, 2021), Database accession No. 2713664-04-9, XP093277384.
Database Registry, Chemical Abstracts Service (Jul. 26, 2022), Database accession No. 2797160-72-4, XP093279894.
Database Registry, Chemical Abstracts Service; (Sep. 1, 2022), Database accession No. 2816805-43-1, X P093277382.
Database Registry, Chemical Abstracts Service; (Jun. 23, 2023), Database accession No. 2935080-68-3, XP093277525.
Database Registry, Chemical Abstracts Service; (Aug. 29, 2023), Database accession No. 2966899-34-1, XP093277520.
Database Registry, Chemical Abstracts Service; (Aug. 31, 2023), Database accession No. 2968160-16-7, XP093277515.
Database Registry, Chemical Abstracts Service; (Oct. 18, 2023), Database accession No. 2990803-91-1, XP093277379.
Database Registry, Chemical Abstracts Service; (Dec. 1, 2023), Database accession No. 3009361-40-1, XP093277454.
Madhu, Desagoni et al. 3-Trifluoroacetyl-quinolin-2(1 H)-ones as Carbonyl and Acid Surrogates in the Passerini-/Ugi-Type Reaction. The Journal of Organic Chemistry 87(5):2301-2314 (2022).
Okuzumi, Tatsuya et al. Efficient solid-phase synthesis of quinazoline-2, 4-diones with various substituents on aromatic rings. Tetrahedron 59(29):5603-5608 (2003).
PCT/US2025/021324 International Search Report and Written Opinion dated Jun. 13, 2025.
PCT/US2025/021387 International Search Report and Written Opinion dated Jun. 13, 2025.
PCT/US2025/021402 International Search Report and Written Opinion dated Jun. 13, 2025.
PCT/US2025/021405 International Search Report and Written Opinion dated Jun. 16, 2025.
Sivakamasundari, S. et al. Pyrroloquinolines: Part IV—Synthesis of 1-Aryl-1H-pyrrolo [2,3- b]quinolines. Indian Journal of Chemistry XP002950352, 26B 744-747 (1987).
Ukrainets, I. et al. 4 Hydroxy-2-quinolones. 35. Synthesis and Study of Antithyroid Properties of 1H-2-OxO-3-(coumarin-3-yl)-4-hydroxyquinolines. Chemistry of Heterocyclic Compounds, Xp093278695 33(8):959-963 (1999).
Ukrainets I. V. et al. 4-Hydroxyquinolin-2-ones. 45. Synthesis, Structure, and Biological Activity of N-Substituted 1H-4-Hydroxy-2-oxoquinoline-3-acetic Acid Amides. Chemistry of Heterocyclic Compounds XP093278700, 36(11):1319-1325 (2000).

* cited by examiner

QUINOLINONE AMIDE COMPOUNDS AND USES THEREOF

CROSS-REFERENCE

This application is a continuation application of International Patent Application No. PCT/US 2024/021528, filed Mar. 26, 2024. which claims the benefit of U.S. Provisional Patent Application No. 63/492,441, filed Mar. 27, 2023, each of which is incorporated by reference herein in its entirety.

BACKGROUND OF THE INVENTION

Over 80 million people are affected by one or more forms of cardiac diseases and is a leading cause of death of the population, with nearly 18 million people dying each year. The onset of cardiac diseases can be due to either genetics or lifestyle. The cardiac muscle is an involuntary, striated muscle with electrical stimulation in the form of cardiac action potential. The cardiac action potential triggers release of calcium from the sarcoplasmic reticulum. Diseases of the cardiac muscle, include, but are not limited to cardiomyopathies, which can lead to symptoms including, but not limited to heart failure, irregular heart beating, shortness of breath, tiredness, and fainting, with those affected at an increased risk of sudden cardiac death.

Many medical therapies for cardiac diseases are limited to treatment of symptoms instead of addressing the underlying cause of the disease. Additionally, some treatments have decreased efficacy with increasing disease duration. Thus, there remains a need to develop new compounds for the improved treatment of cardiac diseases.

Hypertrophic cardiomyopathy HCM is a chronic, progressive disease of the cardiac sarcomere. The etiology of HCM is multifactorial; a significant portion of affected people have at least one mutation in the genes that encode cardiac sarcomere proteins. Regardless of the cause of HCM, in many cases, excess myosin-actin crossbridge formation in systole and diastole leads to hyperdynamic contraction and impaired relaxation. Over time this excess stress leads to tissue remodeling characterized histologically by myocyte hypertrophy, myofilament disarray, microvascular remodeling, and fibrosis. HCM may be genetic (e.g., heritable) or not genetic. HCM includes a group of highly penetrant, monogenic, autosomal dominant myocardial diseases. Such HCM may be caused by one or more of over 1,000 known point mutations in any one of the proteins contributing to the functional unit of myocardium, the sarcomere. About 1 in 500 individuals in the general population are found to have left ventricular hypertrophy unexplained by other known causes (e.g., hypertension or valvular disease), and many of these can be shown to have HCM, e.g., once other heritable (e.g., lysosomal storage diseases), metabolic, or infiltrative causes have been excluded.

Medical therapy for HCM is limited and many patients' symptoms are empirically managed with beta-blockers, non-dihydropyridine calcium channel blockers, and/or disopyramide. None of these agents carry labeled indications for treating HCM, and essentially no rigorous clinical trial evidence is available to guide their use. In approximately 60% of patients with HCM, the left ventricular outflow tract becomes obstructed, impeding the flow of blood and creating a pressure gradient between the LV cavity and the aorta. For patients with hemodynamically significant outflow tract obstruction (gradient>50 mmHg), surgical myectomy or alcohol septal ablation can be utilized to alleviate the hemodynamic obstruction albeit with significant clinical morbidity and mortality. Provided herein are new therapeutic-agents and methods that remedy the long-felt need for improved treatment of HCM and related cardiac disorders.

SUMMARY OF THE INVENTION

In an aspect, the present disclosure provides a pharmaceutical composition comprising a compound or salt disclosed herein and a pharmaceutically acceptable excipient. The disclosure provides compound and salts thereof for use in treating disease. In certain aspects, the disclosure provides a compounds of Formula (I), (II-A), (IV), and (III), pharmaceutical compositions thereof, as well as methods of use in the treatment of disease. In some aspects, methods of treating cardiac disease may comprise administering a compound or salt of any one of Formula (I), (II-A), (IV), or (III) in an individual in need thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

In certain aspects, the disclosure provides methods for treating a cardiac disease in an individual in need thereof, the method comprising administering a therapeutically effective amount of a compound of Formula (I), (II-A), (IV), or (III).

Diseases treated by the methods described herein include, but are not limited to, cardiac diseases. Cardiac diseases treated by the method described herein include, but are not limited to, heart muscle disease (cardiomyopathy), hypertrophic cardiomyopathy (HCM), abnormal heart rhythms, aorta disease, Marfan syndrome, coronary artery disease, heart attack, heart failure, rheumatic heart disease, peripheral vascular disease, stroke, deep vein thrombosis and pulmonary embolism.

Cardiomyopathy is a heart disease wherein the heart may be abnormally enlarged, thicked, and/or stiffened and may have few or no symptoms early on. As the disease gets worse, symptoms include, but are not limited to, shortness of breath, feeling tired, irregular heartbeat, fainting, and onset of heart failure. Types of cardiomyopathy include, but are not limited to arrhythmogenic right ventricular dysplasia, dilated cardiomyopathy, hypertrophic cardiomyopathy, restrictive cardiomyopathy, and Takotsubo cardiomyopathy.

Hypertrophic cardiomyopathy (HCM) may be genetic (e.g., heritable) or not genetic (e.g., not heritable). HCM may be obstructive or nonobstructive. Genetic hypertrophic cardiomyopathy (HCM) comprises a group of highly penetrant, monogenic, autosomal dominant myocardial diseases. HCM may be caused by one or more of over 1,000 known point mutations in any one of the proteins contributing to the functional unit of myocardium, the sarcomere.

In approximately two-thirds of HCM subjects, the path followed by blood exiting the heart, known as the left ventricular outflow tract (LVOT), becomes obstructed by the enlarged and diseased muscle, restricting the flow of blood from the heart to the rest of the body (obstructive HCM). In other subjects, the thickened heart muscle does not block the LVOT, and their disease is driven by diastolic impairment due to the enlarged and stiffened heart muscle (non-obstructive HCM). In either obstructive or non-obstructive HCM subjects, exertion can result in fatigue or shortness of breath, interfering with a subject's ability to participate in activities of daily living. HCM has also been associated with increased risks of atrial fibrillation, stroke, heart failure and sudden cardiac death.

Currently available therapies for HCM may be variably effective in alleviating symptoms but may show decreased efficacy with increasing disease duration. Patients may be thus empirically managed with beta-blockers, non-dihydropyridine calcium channel blockers, and/or disopyramide. Mavacamten may also be used. In approximately 60% of patients with HCM, the left ventricular outflow tract becomes obstructed, impeding the flow of blood and creating a pressure gradient between the LV cavity and the aorta. For patients with hemodynamically significant outflow tract obstruction (gradient>50 mmHg), surgical myectomy or alcohol septal ablation can be utilized to alleviate the hemodynamic obstruction albeit with significant clinical morbidity and mortality. Provided are new therapeutic agents and methods that remedy the long-felt need for improved treatment of HCM and related cardiac disorders.

The compounds of the invention or their pharmaceutically acceptable salts can alter the natural history of HCM and other diseases rather than merely palliating symptoms. The mechanisms conferring clinical benefit to HCM patients can extend to patients with other forms of heart disease sharing similar pathophysiology, with or without demonstrable genetic influence. For example, an effective treatment for HCM, by improving ventricular relaxation during diastole, can also be effective in a broader population characterized by diastolic dysfunction. The compounds of the invention or their pharmaceutically acceptable salts can specifically target the root causes of the conditions or act upon other downstream pathways. Accordingly, the compounds of the invention or their pharmaceutically acceptable salts can also confer benefit to patients suffering from diastolic heart failure with preserved ejection fraction, ischemic heart disease, angina pectoris, or restrictive cardiomyopathy. Compounds of the invention or their pharmaceutically acceptable salts can also promote salutary ventricular remodeling of left ventricular hypertrophy due to volume or pressure overload; e.g., chronic mitral regurgitation, chronic aortic stenosis, or chronic systemic hypertension; in conjunction with therapies aimed at correcting or alleviating the primary cause of volume or pressure overload (valve repair/replacement, effective antihypertensive therapy). By reducing left ventricular filling pressures the compounds could reduce the risk of pulmonary edema and respiratory failure. Reducing or eliminating functional mitral regurgitation and/or lowering left atrial pressures may reduce the risk of paroxysmal or permanent atrial fibrillation, and with it reduce the attendant risk of arterial thromboembolic complications including but not limited to cerebral arterial embolic stroke. Reducing or eliminating either dynamic and/or static left ventricular outflow obstruction may reduce the likelihood of requiring septal reduction therapy, either surgical or percutaneous, with their attendant risks of short- and long term complications. The compounds or their pharmaceutically acceptable salts may reduce the severity of the chronic ischemic state associated with HCM and may thereby reduce the risk of Sudden Cardiac Death (SCD) or its equivalent in patients with implantable cardioverter-defibrillators (frequent and/or repeated ICD discharges) and/or the need for potentially toxic antiarrhythmic medications. The compounds or their pharmaceutically acceptable salts could be valuable in reducing or eliminating the need for concomitant medications with their attendant potential toxicities, drug-drug interactions, and/or side effects. The compounds or their pharmaceutically acceptable salts may reduce interstitial myocardial fibrosis and/or slow the progression, arrest, or reverse left ventricular hypertrophy.

Definitions

Unless defined otherwise, all technical and scientific terms used herein have the same meaning as is commonly understood by one of skill in the art to which this invention belongs.

As used in the specification and claims, the singular form "a", "an" and "the" includes plural references unless the context clearly dictates otherwise.

The term "$C_{x-y}$" or "$C_x$-$C_y$" (e.g., when used in conjunction with a chemical moiety, such as alkyl, alkenyl, or alkynyl) is meant to include groups that comprise a number of carbon atoms greater than or equal to x carbon atoms and less than or equal to y carbon atoms in the chemical moiety, subject to the following. The term "$C_{x-y}$ " or "$C_x$-$C_y$" is not meant to limit the number of carbon atoms which may be attached to the chemical moiety when the chemical moiety is substituted with a second chemical moiety. For example, the term "$C_{1-6}$ alkyl" or "$C_1$ to $C_6$ alkyl" refers to saturated, substituted or unsubstituted, hydrocarbon groups, including straight-chain alkyl groups (e.g., linear alkyl groups) and branched alkyl groups that contain 1, 2, 3, 4, 5, or 6 carbon atoms, plus however many carbon atoms may be present in any substituents of the $C_{1-6}$ alkyl. For example, if a $C_{1-6}$ alkyl is optionally substituted with a second chemical moiety comprising two carbon atoms, then it will be understood that the $C_{1-6}$ alkyl can include between 1 and 8 carbon atoms.

The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively.

"Amino" refers to the —$NH_2$ moiety.

"Cyano" refers to the —CN moiety.

"Nitro" refers to the —$NO_2$ moiety.

"Oxa" refers to the —O— moiety.

"Oxo" refers to the =O moiety.

"Thioxo" refers to the =S moiety.

"Imino" refers to the =N—H moiety.

"Oximo" refers to the =N—OH moiety.

"Hydrazino" refers to the =N—$NH_2$ moiety.

"Alkyl" refers to a straight (e.g., linear) or branched (e.g., nonlinear) hydrocarbon moiety consisting solely of carbon and hydrogen atoms, fully saturated. In certain embodiments, "alkyl" comprises one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In certain embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl, e.g., methyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (2-propyl, iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond.

"Aminoalkyl" refers to a moiety boded through a nitrogen atom of the form —N(H)(alkyl) or N(alkyl)(alkyl), wherein when the moiety is N(alkyl)(alkyl), the two alkyl groups bonded to nitrogen can be the same alkyl groups or different alkyl groups.

"Alkoxy" refers to a moiety bonded through an oxygen atom of the formula —O-alkyl, where alkyl is an alkyl chain as defined above.

"Alkenyl" refers to a straight (e.g., linear) or branched (e.g., nonlinear) hydrocarbon moiety consisting solely of carbon and hydrogen atoms, the moiety comprising at least one carbon-carbon double bond. In certain embodiments, an alkenyl comprises two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (e.g., vinyl), prop-1-enyl (e.g., allyl), but-1-enyl, pent-1-enyl, penta-1,4-dienyl, and the like.

"Alkynyl" refers to a straight (e.g., linear) or branched (e.g., nonlinear) hydrocarbon moiety consisting solely of carbon and hydrogen atoms, the moiety comprising at least one carbon-carbon triple bond. In some embodiments, an alkynyl comprises from two to twelve carbon atoms. In some embodiments, an alkynyl optionally further comprises at least one carbon-carbon double bond. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like.

"Alkylene" or "alkylene chain" refers to a linear (e.g., straight), or branched (e.g., nonlinear), divalent, hydrocarbon moiety. An "alkylene" or "alkylene chain" can link a portion of the molecule to a second moiety. An "alkylene" or "alkylene chain" consists solely of carbon and hydrogen atoms (substitution of an alkylene with one or more substituents comprising atoms other than hydrogen, such as N, O, and S, may be specified). An "alkylene" or "alkylene chain" can contain no unsaturation (notwithstanding the points of attachment of an alkylene to the rest of the molecule). In certain embodiments, the "alkylene" or "alkylene chain" and comprises one to twelve carbon atoms, for example, methylene, ethylene, propylene, n-butylene, and the like. The alkylene chain can be attached to the portion of the molecule through a single bond and to the second moiety through a single bond. The points of attachment of an alkylene chain to the rest of the molecule and to the second moiety can be through one carbon atom in the alkylene chain or can be through any two carbon atoms within the alkylene. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene).

"Alkenylene" or "alkenylene chain" refers to a linear (e.g., straight), or branched, divalent, hydrocarbon moiety. An "alkenylene" or "alkenylene chain" can link a portion of the molecule to a second moiety. An "alkenylene" or "alkenylene chain" consists solely of carbon and hydrogen atoms (substitution of an alkenylene with one or more substituents comprising atoms other than hydrogen, such as N, O, and S, may be specified). An "alkenylene" or "alkenylene chain" comprises at least one carbon-carbon double bond. In certain embodiments, an "alkenylene" or "alkenylene chain" comprises from two to twelve carbon atoms. The alkenylene chain can be attached to the portion of the molecule through a single bond and to the second moiety through a single bond. The points of attachment of an alkenylene chain to the rest of the molecule and to the second moiety can be through one carbon atom in the alkenylene chain or through any two carbon atoms within the alkenylene chain. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises five to eight carbon atoms (e.g., $C_5$-$C_8$ alkenylene). In other embodiments, an alkenylene comprises two to five carbon atoms (e.g., $C_2$-$C_5$ alkenylene). In other embodiments, an alkenylene comprises three to five carbon atoms (e.g., $C_3$-$C_5$ alkenylene).

"Alkynylene" or "alkynylene chain" refers to a linear (e.g., straight), or branched, divalent, hydrocarbon moiety. An "alkynylene" or "alkynylene chain" can link a portion of the molecule to a second moiety. An "alkynylene" or "alkynylene chain" consists solely of carbon and hydrogen (substitution of an alkynylene with one or more substituents comprising atoms other than hydrogen, such as N, O, and S, may be specified). An "alkynylene" or "alkynylene chain" comprises at least one carbon-carbon triple bond. In certain embodiments, an "alkynylene" or "alkynylene chain" comprises from two to twelve carbon atoms. An alkynylene chain can be attached to the portion of the molecule through a single bond and to the second moiety through a single bond. The points of attachment of an alkynylene chain to the rest of the molecule and to the second moiety can be through one carbon atom in the alkynylene chain or through any two carbon atoms within the alkynylene chain. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene).

The term "carbocycle" as used herein refers to a saturated or unsaturated (e.g., aromatic or nonaromatic unsaturated) ring or ring system in which each atom of the ring is carbon. The term "carbocycle" comprises "aryls," "cycloalkenyls," and "cycloalkyls." For example, the term "carbocycle" includes 3- to 12-membered monocyclic rings (e.g., 3- to 10-membered monocyclic rings) and 4- to 20-membered polycyclic ring systems (e.g., 5- to 15-membered spiro polycyclic ring systems, 5- to 15-membered bridged polycyclic ring systems, or 4- to 15-membered fused polycyclic ring systems). For example, carbocycle includes 4- to 15-membered bicyclic rings (e.g., 5- to 15-membered spiro bicycles, 5- to 15-membered bridged bicyclic ring systems, or 4- to 15-membered fused bicyclic ring systems). For example, carbocycle includes tricyclic ring systems, which may be bridged, fused, spiro, or a combination thereof. For example, carbocycle includes tetracyclic ring systems, which may be bridged, fused, spiro, or a combination thereof. For example, carbocycle includes ring systems that are both fused and bridged; ring systems that are both fused and spiro; ring systems that are both bridged and spiro; and ring systems that are both fused and bridged and are also spiro. Each ring of a polycyclic carbocycle may be selected from saturated and unsaturated (e.g., aromatic or nonaromatic unsaturated) rings. In an exemplary embodiment, an aromatic ring (e.g., phenyl) of a polycyclic carbocycle may be fused to a saturated or unsaturated ring (e.g., cyclohexane, cyclopentane, cyclohexene, or phenyl). A polycyclic carbocycle includes any combination of saturated and unsaturated (e.g., aromatic or nonaromatic unsaturated) rings, as valence permits. For example, polycyclic carbocycles can be spiro bicyclic rings, such as spiropentane. For example, a polycyclic carbocycle includes any combination of ring sizes such as 2-2 spiro ring systems (e.g., spiro[2.2]pentane), 3-3 spiro ring systems, 4-4 spiro ring systems, 4-5 fused ring systems (e.g., bicyclo[4.5.0] fused ring systems), 5-5 fused ring systems, 5-6 fused ring systems, 6-6 fused ring systems (e.g., naphthalene), 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, naphthyl, trans-bicyclo[4.4.0]decane, cis-bicylo[4.4.0]decane, spiro[3.4]octane, fluoranthene, and bicyclo[1.1.1]pentanyl.

The term "aryl" refers to an aromatic monocyclic or aromatic polycyclic hydrocarbon ring system comprising at least one cyclic, delocalized (4n+2) π-electronic system, wherein n is an integer greater than or equal to 0, in accordance with Hückel theory. In some embodiments, the aromatic monocyclic or aromatic polycyclic hydrocarbon ring system comprises only hydrogen atoms and carbon atoms. In some embodiments, the aromatic monocyclic or polycyclic system contains from three to twenty carbon atoms. In some embodiments, at least one of the rings in the polycyclic aromatic ring system is aromatic. In some embodiments, the aromatic monocyclic or aromatic polycyclic hydrocarbon ring system comprises a cyclic, delocalized (4n+2) π-electronic system in accordance with Hückel theory. In some embodiments, the ring system from which aryl groups are derived include, but are not limited to, groups such as benzene, fluorene, indane, indene, anthracene, tetralin, and naphthalene. In some embodiments, the aryl substituent is not charged (e.g., neutral). In some embodiments, the aryl substituent bears no charges. In some embodiments, the aryl substituent bears no net charge. In some embodiments, the aryl substituent bears no net charge and is not zwitterionic. In some embodiments, none of the carbon atoms of the aryl substituent are charged. In some embodiments, none of the carbon atoms of the aryl substituent are charged.

The term "cycloalkyl" refers to a saturated ring in which each atom of the ring is carbon. Cycloalkyl may include monocyclic and polycyclic rings such as 3- to 10-membered monocyclic rings, 5- to 12-membered bicyclic rings, 5- to 12-membered spiro bicycles, and 5- to 12-membered bridged rings. In certain embodiments, a cycloalkyl comprises three to ten carbon atoms. In other embodiments, a cycloalkyl comprises three to seven carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Examples of polycyclic cycloalkyls include, but are not limited to, adamantyl, spiropentane, norbornyl (e.g., bicyclo[2.2.1]heptanyl), decalinyl, 7,7 dimethyl bicyclo[2.2.1]heptanyl, bicyclo[1.1.1]pentanyl, spiropentane, and the like.

The term "cycloalkenyl" refers to a saturated ring in which each atom of the ring is carbon and there is at least one double bond between two ring carbon atoms. Cycloalkenyl may include monocyclic and polycyclic rings, such as 3- to 10-membered monocyclic rings and 4- to 12-membered bicyclic rings (e.g., 5- to 12-membered bridged bicyclic rings, fused 4- to 12-membered bicyclic rings, and spiro 5- to 12-membered bicyclic rings). In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl.

The term "halo" or, alternatively, "halogen" or "halide," means fluoro, chloro, bromo or iodo. In some embodiments, a halo is fluoro, chloro, or bromo. In some embodiments, a halo is a fluoro or a chloro. In some embodiments, a halo is a fluoro. In some embodiments, a halo is a chloro.

The term "haloalkyl" refers to an alkyl, as defined above, that is substituted by one or more halogens, for example, trifluoromethyl, dichloromethyl, bromomethyl, 2,2,2-trifluoroethyl, 1-chloromethyl-2-fluoroethyl, and the like. In some embodiments, the alkyl part of the haloalkyl is optionally further substituted as described herein.

The term "heterocycle" as used herein refers to a saturated or unsaturated (e.g., aromatic or nonaromatic unsaturated) ring or ring system in which one or more heteroatom(s) is(are) member(s) of the ring or ring system. Exemplary heteroatoms include N, O, Si, P, B, and S atoms. For example, heterocycles include 3- to 12-membered monocyclic rings (e.g., 3- to 10-membered monocyclic rings) and 4- to 20-membered polycyclic ring systems (e.g., 4- to 15-membered fused poly ring systems, 5- to 15-membered spiro polycyclic ring systems, and 5- to 15-membered bridged polycyclic ring systems). For example, heterocycles include 4- to 20-membered bicyclic ring systems (e.g., 4- to 15-membered fused bicyclic ring systems, 5- to 15-membered spiro bicyclic ring systems, and 5- to 15-membered bridged bicyclic ring systems). For example, heterocycle includes tricyclic ring systems, which may be bridged, fused, spiro, or a combination thereof. For example, heterocycle includes tetracyclic ring systems, which may be bridged, fused, spiro, or a combination thereof. For example, heterocycle includes ring systems that are both fused and bridged; ring systems that are both fused and spiro; ring systems that are both bridged and spiro; and ring systems that are both fused and bridged and are also spiro. Each ring of a polycyclic heterocycle may be selected from saturated and unsaturated (e.g., aromatic or nonaromatic unsaturated) rings. A polycyclic heterocycle includes any combination of saturated, and unsaturated (e.g., aromatic or nonaromatic unsaturated) rings, as valence permits. In an exemplary embodiment, an aromatic ring, e.g., pyridyl or phenyl, may be fused to a saturated or unsaturated ring, e.g., cyclohexane, cyclopentane, morpholine, piperidine or cyclohexene, in a heterocycle, as long as at least one atom in the resulting fused ring system is a heteroatom. A polycyclic heterocycle includes any combination of ring sizes such as 3-3 spiro, 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. A bicyclic heterocycle further includes spiro bicyclic rings, e.g., 5 to 12-membered spiro bicycles, such as 2-oxa-6-azaspiro[3.3]heptane. In some embodiments, a heterocycle comprises multiple heteroatoms. In some embodiments, a heterocycle comprises an atom selected from nitrogen, oxygen, and sulfur. In some embodiments, a heterocycle comprises multiple atoms selected from nitrogen, oxygen, and sulfur. In some embodiments, a heterocycle comprises one or more atom(s) selected from nitrogen, oxygen, and sulfur. In some embodiments, a heterocycle comprises one or more atom(s) selected from nitrogen and oxygen. In some embodiments, a heterocycle comprises one or more atom(s) selected from nitrogen and sulfur. In some embodiments, a heterocycle comprises one or more atom(s) selected from oxygen and sulfur. In some embodiments, a heterocycle comprises one or more atom(s) selected from nitrogen. In some embodiments, a heterocycle comprises one or more atom(s) selected from oxygen. In some embodiments, a heterocycle comprises one or more atom(s) selected from sulfur. Nonlimiting examples of heterocycles include pyridine, pyrrole, indole, carbazole, piperidine, oxazole, morpholine, thiophene, benzothiophene, furan, tetrahydrofuran, and pyran. Nonlimiting examples of heterocycles include azepinyl, acridinyl, benzimidazolyl, benzindolyl, 1,3-benzodioxolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (e.g., thienyl).

In some embodiments, a heterocycle is attached to the molecule by a carbon atom. In some embodiments, the heterocycle is attached to the molecule by a nitrogen atom.

In some embodiments, a heterocycle comprises a moiety selected from a heteroaryl, a heterocycloalkyl, and a heterocycloalkenyl. In some embodiments, the heterocycle is a heteroaryl. In some embodiments, the heterocycle is a heterocycloalkyl. In some embodiments, the heterocycle is a heterocycloalkenyl.

In some embodiments, a heterocycle comprises an atom selected from nitrogen and oxygen. In some embodiments, a heterocycle comprises an atom selected from nitrogen and sulfur. In some embodiments, a heterocycle comprises an atom selected from oxygen and sulfur. In some embodiments, a heterocycle comprises an atom selected from nitrogen. In some embodiments, a heterocycle comprises an atom selected from oxygen. In some embodiments, a heterocycle comprises an atom selected from sulfur.

In some embodiments, a heterocycle comprises 1 to 8 heteroatoms. In some embodiments, the heterocycle comprises 1 to 5 heteroatoms. In some embodiments, the heterocycle comprises 1 to 3 heteroatoms. In some embodiments, the heterocycle comprises 1 to 2 heteroatoms. In some embodiments, the heterocycle comprises 1 heteroatom. In some embodiments, the heterocycle comprises 2 heteroatoms. In some embodiments, the heterocycle comprises 3 heteroatoms. In some embodiments, the heterocycle comprises 4 heteroatoms. In some embodiments, the heterocycle comprises 5 heteroatoms. In some embodiments, the heterocycle comprises 6 heteroatoms.

In some embodiments, a heterocycle comprises a 3-membered ring, 4-membered ring, 5-membered ring, 6-membered ring, 7-membered ring, 8-membered ring, 9-membered ring, 10-membered ring, 11-membered ring, 12-membered ring, 13-membered ring, 14-membered ring, or 15-20 membered ring. In some embodiments, a heterocycle is 3- to 10-membered. In some embodiments, a heterocycle is 3- to 6-membered. In some embodiments, a heterocycle is 5- to 6-membered. In some embodiments, a heterocycle is 9- to 10-membered. In some embodiments, a heterocycle is 9- to 11-membered. In some embodiments, a heterocycle is 9- to 15-membered.

In some embodiments, the heterocycle is monosubstituted, disubstituted, trisubstituted, tetrasubstituted, or pentasubstituted (e.g., with further substituents in addition to the point of attachment). In some embodiments, the total number of substituents (e.g., atoms other than hydrogen) on the heterocycle (e.g., bonded to the ring of the heterocycle) is 1, 2, 3, 4, 5, 6, 7, 8, 9, 10, or more.

In some embodiments, in the molecule or moiety (e.g., in a heterocycle), one or more nitrogen atoms, if present, can be optionally quaternized. In some embodiments, the heterocycle substituent is positively charged. some embodiments, the heterocycle moiety is neutral. In some embodiments, the heterocycle substituent is zwitterionic. Alternatively, or in addition, in some embodiments, the heterocycle substituent is not charged. In some embodiments, the heterocycle substituent bears no charges. In some embodiments, the heterocycle substituent bears no net charge. In some embodiments, no atoms within the heterocycle substituent bear any net charge. In some embodiments, the heterocycle substituent bears no net charge and is not zwitterionic. The term "heteroaryl" refers to a moiety derived from an aromatic monocyclic or aromatic polycyclic ring system, in which one or more heteroatom(s) is(are) member(s) of the ring system, and the ring system comprises at least one cyclic, delocalized (4n+2) π-electronic system, wherein n is an integer greater than or equal to 0, in accordance with Hückel theory. In some embodiments, one or more heteroatom(s) is(are) member(s) of the ring system comprising the cyclic, delocalized (4n+2) π-electronic system (e.g., the ring with aromaticity). Exemplary heteroatoms include N, O, Si, P, B, and S atoms. In some embodiments, a heteroaryl comprises an aromatic ring, in which one or more heteroatom(s) is(are) member(s) of the ring system, to which one or more nonaromatic rings, each of which may or may not comprise one or more heteroatom(s), may be fused. In some embodiments, a heteroaryl includes one or more heteroatoms selected from nitrogen, oxygen, and sulfur. In some embodiments, a heteroaryl includes multiple heteroatoms selected from nitrogen, oxygen, and sulfur. In certain embodiments, "heteroaryl" includes rings and ring systems comprising 3 to 20 atoms. In some embodiments, "heteroaryl" includes rings and ring systems that comprise two to seventeen carbon atoms and from one to six heteroatoms selected from nitrogen, oxygen and sulfur. As used herein, the heteroaryl moiety is a monocyclic or polycyclic (e.g., bicyclic, tricyclic or tetracyclic) ring system, wherein at least one of the rings in the ring system is aromatic, e.g., it contains a cyclic, delocalized (4n+2) π-electron system in accordance with the Hückel theory. Heteroaryl includes fused, bridged, and spiro ring systems. The heteroatom(s) in the heteroaryl moiety is(are) optionally oxidized. One or more nitrogen atom(s), if present, is(are) optionally quaternized. The heteroaryl is attached to the rest of the molecule through any atom of the ring(s). Examples of heteroaryls include, but are not limited to, acridinyl, benzimidazolyl, benzindolyl, 1,3-benzodioxolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, oxazolyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (e.g., thienyl). In some embodiments, further examples of "heteroaryl" include 5,6,7,8-tetrahydroquinoline; 1,2,3,4-tetrahydro-1,8-naphthyridine; 6,7-dihydro-5H-cyclopenta[b]pyridine; 2,3-dihydro-1H-pyrrolo[2,3-b]pyridine; 4,5,6,7-tetrahydrobenzofuran; 4,5,6,7-tetrahydrofuro[2,3-b]pyridine; 5,6-dihydro-4H-cyclopenta[b]furan; 4,5-dihydrothieno[2,3-b]furan. In some embodiments, the heteroaryl substituent is positively or negatively charged. In some embodiments, the heteroaryl substituent is neutral. In some embodiments, the heteroaryl substituent is zwitterionic; alternatively, or in addition, in some embodiments, the heteroaryl substituent is not charged. In some embodiments, the heteroaryl substituent bears no charges. In some embodiments, the heteroaryl substituent bears no net charge. In some embodiments, the heteroaryl substituent bears no net charge and is not zwitterionic.

The term "heterocycle" comprises "heteroaryls," "heterocycloalkenyls," and "heterocycloalkyls."

The term "heterocycloalkyl" refers to a moiety comprising a saturated ring (e.g., a ring with only single bonds connecting the members of the ring), wherein the saturated ring comprises carbon atom(s) and one or more heteroatom(s) as member(s) of the saturated ring, and wherein the saturated ring may be optionally fused, bridged with, or spiro to an additional ring, wherein the additional ring may comprise only carbon atoms as members of the additional ring or wherein the additional ring may comprise one or more heteroatom(s) as member(s) of the additional ring. In some embodiments, a heterocycloalkyl may be covalently bound to one or more carbocycle(s) or heterocycle(s). Exemplary heteroatoms include N, O, Si, P, B, and S atoms. Heterocycloalkyl may include monocyclic and polycyclic rings such as 3- to 10-membered monocyclic rings, 6- to 12-membered bicyclic rings, 5- to 12-membered spiro bicycles, or 5- to 12-membered bridged rings. The heteroatoms in the heterocycloalkyl radical are optionally oxidized. One or more nitrogen atoms, if present, are optionally quaternized. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 2-oxa-6-azaspiro[3.3]heptane, and 1,1-dioxo-thiomorpholinyl. In some embodiments, a heterocycloalkyl comprises one heteroatom. In some embodiments, a heterocycloalkyl comprises one heteroatom selected from N, O, and S. In some embodiments, a heterocycloalkyl comprises multiple heteroatoms. In some embodiments, a heterocycloalkyl comprises multiple heteroatoms selected from N, O, and S.

The term "heterocycloalkenyl" refers to a moiety comprising an unsaturated ring (e.g., a ring with either single bonds or double bonds connecting the members of the ring): wherein the unsaturated ring comprises carbon atoms and one or more heteroatom(s); wherein the unsaturated ring may be optionally fused, bridged with, or spiro to an additional ring, wherein the additional ring may comprise only carbon atoms as members of the additional ring or wherein the additional ring may comprise one or more heteroatom(s) as member(s) of the additional ring; and wherein there is at least one double bond between two ringcarbon atoms (e.g., carbon atoms that are members of the unsaturated ring). Heterocycloalkenyl does not include heteroaryl rings. Exemplary heteroatoms include N, O, Si, P, B, and S atoms. Heterocycloalkenyl may include monocyclic and polycyclic rings such as 3- to 10-membered monocyclic rings, 6- to 12-membered bicyclic rings, and 5- to 12-membered bridged rings. In other embodiments, a heterocycloalkenyl comprises five to seven ring atoms. The heterocycloalkenyl may be attached to the rest of the molecule by a single bond. Examples of monocyclic cycloalkenyls include, e.g., pyrroline (dihydropyrrole), pyrazoline (dihydropyrazole), imidazoline (dihydroimidazole), triazoline (dihydrotriazole), dihydrofuran, dihydrothiophene, oxazoline (dihydrooxazole), isoxazoline (dihydroisoxazole), thiazoline (dihydrothiazole), isothiazoline (dihydroisothiazole), oxadiazoline (dihydrooxadiazole), thiadiazoline (dihydrothiadiazole), dihydropyridine, tetrahydropyridine, dihydropyridazine, tetrahydropyridazine, dihydropyrimidine, tetrahydropyrimidine, dihydropyrazine, tetrahydropyrazine, pyran, dihydropyran, thiopyran, dihydrothiopyran, dioxine, dihydrodioxine, oxazine, dihydrooxazine, thiazine, and dihydrothiazine.

A "spirocyclic" moiety (e.g., a "spiro" moiety) (e.g., a spirocyclic heterocycle, a spirocyclic heterocycloalkenyl, a spirocyclic carbocycle, a spirocyclic heterocycloalkyl, a spirocyclic cycloalkenyl, or a spirocyclic cycloalkyl) is a polycyclic system (e.g., bicyclic, tricyclic, tetracyclic) system wherein two rings share exactly one atom. Examples of spirocyclic moieties include, but are not limited to:

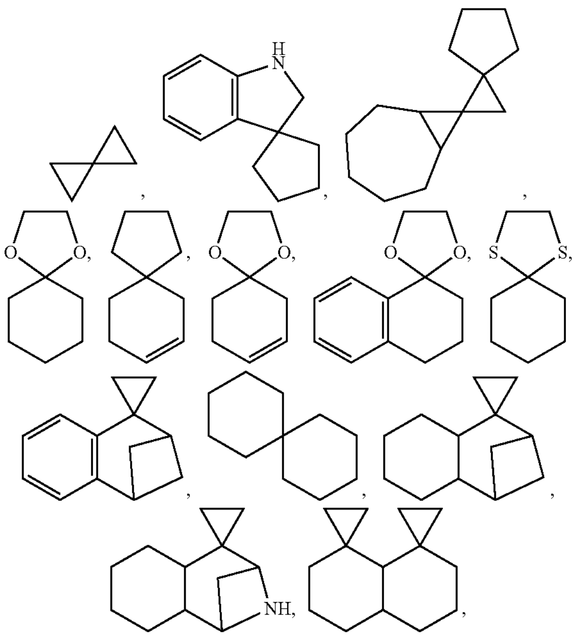

-continued

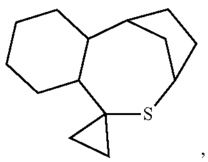

, and

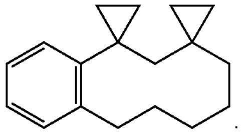

.

A spirocyclic heterocycle comprises a spirocyclic moiety that comprises at least one heteroatom in the ring system of the spirocyclic moiety. Examples of spirocyclic heterocycles include, but are not limited to:

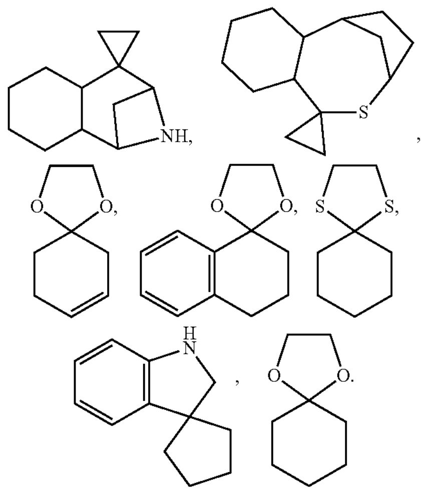

A spirocyclic carbocycle comprises a spirocyclic moiety that comprises only carbon atoms in the ring system of the spirocyclic moiety. Examples of spirocyclic carbocycles include, but are not limited to:

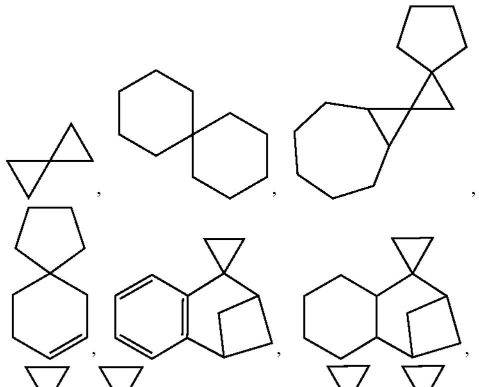

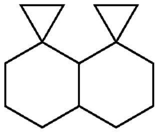

, and

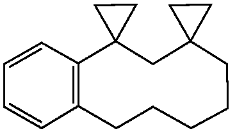

.

A "fused" moiety (e.g., a fused heterocycle, a fused carbocycle, a fused heterocycloalkyl, or a fused cycloalkyl) is a polycyclic system (e.g., bicyclic, tricyclic, tetracyclic) wherein two rings share exactly two atoms. Examples of fused moieties include, but are not limited to:

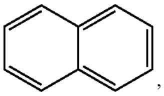, 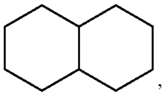, 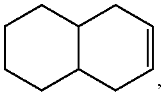, 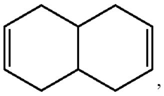, 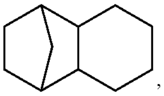, 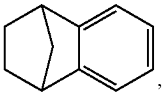, 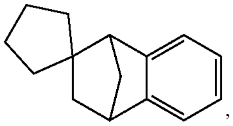, 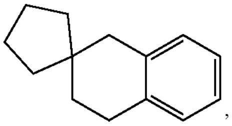, 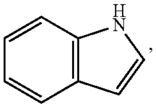, 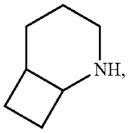 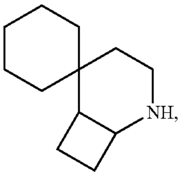 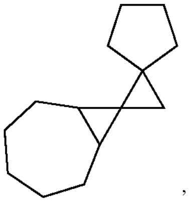, 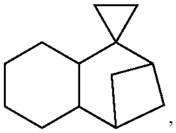, 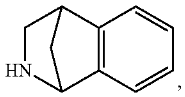, and 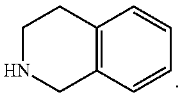.

A "fused" heterocycle comprises a fused moiety that comprises at least one heteroatom in the ring system of the fused moiety. Examples of fused heterocycles include, but are not limited to:

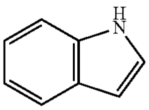, 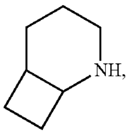 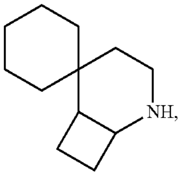 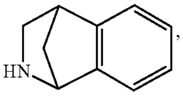, and 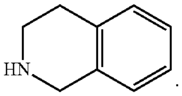.

A "fused" carbocycle comprises a fused moiety that comprises only carbon atoms in the ring system of the fused moiety. Examples of fused carbocycles include, but are not limited to:

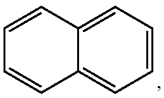, 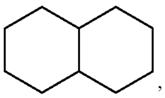, 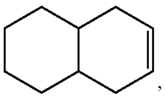,

-continued

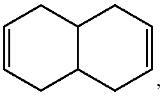, 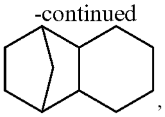, 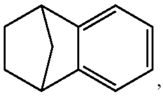, 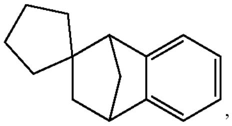, 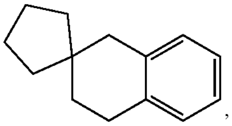, 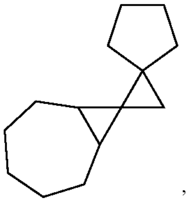, and 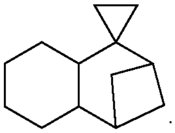.

A "bridged" moiety (e.g., a bridged heterocycle, a bridged carbocycle, a bridged heterocycloalkyl, a bridged heterocycloalkenyl, or a bridged cycloalkyl) is a polycyclic system (e.g., bicyclic, tricyclic, tetracyclic) which comprises two or more bridgeheads, wherein in at least one combination of two bridgeheads, each bridgehead in the combination of two bridgeheads is separated from the other bridgehead in the combination of two bridgeheads by three bridges, each bridge comprising at least one atom, wherein each of the three bridges does not contain any of the same atoms as either of the other two bridges.

In some embodiments, a "bridged" moiety (e.g., a bridged heterocycle, a bridged carbocycle, a bridged heterocycloalkyl, a bridged heterocycloalkenyl, or a bridged cycloalkyl) is a polycyclic system (e.g., bicyclic, tricyclic, tetracyclic) which comprises two or more bridgeheads, wherein in at least one pair of bridgeheads, each bridgehead in the pair is separated from the other bridgehead in the pair by three bridges, each bridge comprising at least one atom, wherein each of the three bridges does not contain any of the same atoms as either of the other two bridges.

In some embodiments, a bridgehead atom is a $sp^3$-hybridized carbon or nitrogen atom that forms a nexus between two or more rings. In some embodiments, a bridge comprises one or more atom(s) connecting two bridgehead atoms.

Examples of bridged moieties include, but are not limited to:

(bicyclo[1.1.1]pentane),

(bicyclo[2.1.1]hexane), norbornane (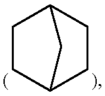), norbornene (  ), 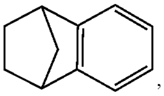, 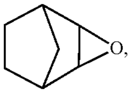,

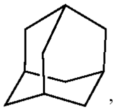, 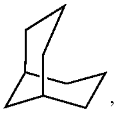, 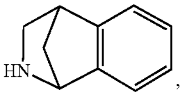,

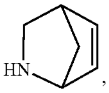, 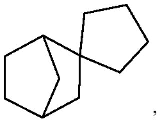, 2-oxa-5-azabicyclo[2.2.1]heptane ( 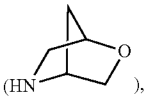 ), 7-oxabicyclo[2.2.1]heptane ( 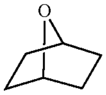 ), 7-azabicyclo[2.2.1]heptane ( 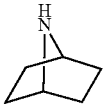 ), bicyclo[3.1.1]heptane

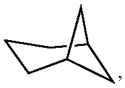, bicyclo[2.2.2]octane, twistane

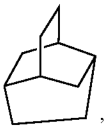, isotwistane

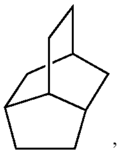,

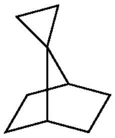

spiro[bicyclo[2.2.1]heptane-7,1'-cyclopropane],

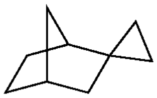

spiro[bicyclo[2.2.1]heptane-2,1'-cyclopropane],

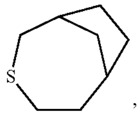, 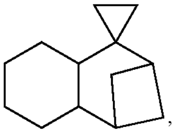, and 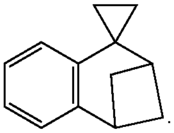.

A “bridged” carbocycle comprises a bridged moiety that comprises only carbon atoms in the ring system of the bridged moiety. Examples of bridged carbocycles include, but are not limited to:

(bicyclo[1.1.1]pentane),

(bicyclo[2.1.1]hexane), norbornane ( 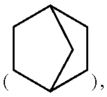 ), norbornene ( 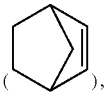 ),

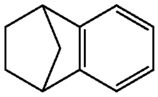, 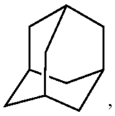, 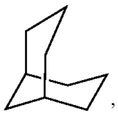,

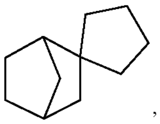, bicyclo[3.1.1]heptane

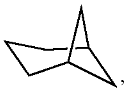, bicyclo[2.2.2]octane, twistane

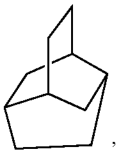, isotwistane

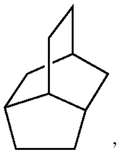, 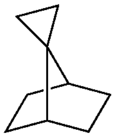

spiro[bicyclo[2.2.1]heptane-7,1'-cyclopropane], and

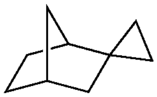

spiro[bicyclo[2.2.1]heptane-2,1'-cyclopropane].

A "bridged" heterocycle comprises a bridged moiety that comprises at least one heteroatom in the ring system of the bridged moiety. Examples of bridged heterocycles include, but are not limited to:

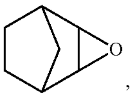, 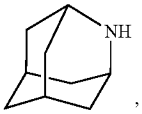, 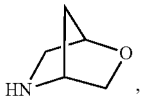,

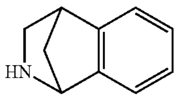, 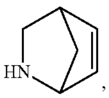, 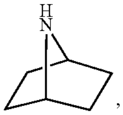, or

-continued

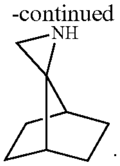.

The term "substituted" refers to moieties having substituents replacing a hydrogen on one or more carbon atom(s) or substitutable heteroatoms, e.g., an NH or $NH_2$ of a compound. It will be understood that "substitution" or "substituted with" includes the implicit proviso that such substitution is in accordance with permitted valence of the substituted atom and the substituent and further includes the proviso that the substitution results in a stable compound, e.g., a compound which does not rapidly undergo rearrangement, cyclization, elimination, etc. In certain embodiments, substituted refers to moieties having substituents replacing two hydrogen atoms on the same carbon atom, such as substituting the two hydrogen atoms on a single carbon atom with an oxo, imino, oxime, hydrazone, or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, the term "one or more substituents" may refer to one substituent, or two substituents, or three substituents, or four substituents, or five substituents, or six substituents, or more than six substituents. In some embodiments, the term "one or more substituents" may refer to one substituent. In some embodiments, the term "one or more substituents" may refer to two substituents. In some embodiments, the term "one or more substituents" may refer to three substituents. In some embodiments, the term "one or more substituents" may refer to four substituents. In some embodiments, the term "one or more substituents" may refer to five substituents. In some embodiments, the term "one or more substituents" may refer to more than five substituents. In some embodiments, the term "one or more substituents" may refer to 1 substituent to 10 substituents. In some embodiments, the term "one or more substituents" may refer to at least 1 substituent. In some embodiments, the term "one or more substituents" may refer to at most 10 substituents. In some embodiments, the term "one or more substituents" may refer to at most 5 substituents. In some embodiments, the term "one or more substituents" may refer to at most 2 substituents. In some embodiments, the term "one or more substituents" may refer to 1 substituent to 2 substituents. In some embodiments, the term "one or more substituents" may refer to 1 substituent to 1 substituent. 1 substituent to 3 substituents, 1 substituent to 4 substituents, 1 substituent to 5 substituents, 1 substituent to 6 substituents, 1 substituent to 7 substituents, 1 substituent to 10 substituents, 2 substituents to 3 substituents, 2 substituents to 4 substituents, 2 substituents to 5 substituents, 2 substituents to 6 substituents, 2 substituents to 7 substituents, 2 substituents to 10 substituents, 3 substituents to 4 substituents, 3 substituents to 5 substituents, 3 substituents to 6 substituents, 3 substituents to 7 substituents, 3 substituents to 10 substituents, 4 substituents to 5 substituents, 4 substituents to 6 substituents, 4 substituents to 7 substituents, 4 substituents to 10 substituents, 5 substituents to 6 substituents, 5 substituents to 7 substituents, 5 substituents to 10 substituents, 6 substituents to 7 substituents, 6 substituents to 10 substituents, or 7 substituents to 10 substituents. In some embodiments, the term "one or more substituents" may refer to 1 substituent, 2 substituents, 3 substituents, 4 substituents, 5 substituents, 6 substituents, 7 substituents, or 10 substituents.

In some embodiments, substituents may include any substituents described herein, for example: halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2), and —$R^b$—$S(O)_tN(R^a)_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2); wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain.

Double bonds to oxygen atoms, such as oxo groups, are represented herein as both "=O" and "(O)". Double bonds to nitrogen atoms are represented as both "=NR" and "(NR)". Double bonds to sulfur atoms are represented as both "=S" and "(S)".

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "salt" or "pharmaceutically acceptable salt" refers to salts derived from a variety of organic and inorganic counter ions well known in the art. Pharmaceutically acceptable acid addition salts can be formed with inorganic acids and/or organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and/or organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

As used herein, "treatment" or "treating" refers to an approach for obtaining beneficial or desired results with respect to a disease, disorder, or medical condition including but not limited to a therapeutic benefit and/or a prophylactic benefit. A therapeutic benefit can include, for example, the eradication or amelioration of the underlying disorder being treated. Also, a therapeutic benefit can include, for example, the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treatment via administration of a compound described herein does not require the involvement of a medical professional.

Chemical entities having carbon-carbon double bonds or carbon-nitrogen double bonds may exist in Z- or E- form (or cis- or trans- form). Furthermore, some chemical entities may exist in various tautomeric forms. Unless otherwise specified, all structures described herein are intended to disclose, implicitly or explicitly, all Z-, E-, and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibria include, but are not limited to:

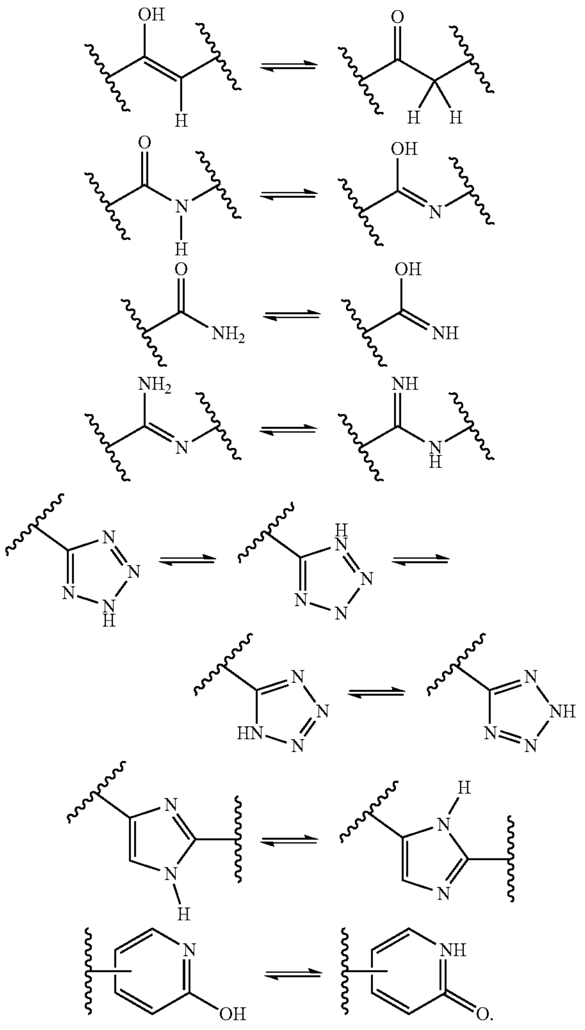

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy of drugs, thus increasing the duration of action of drugs.

Unless otherwise stated, compounds described herein are intended to include compounds which differ only in the presence of one or more isotopically enriched atoms. For example, compounds having the present structures except for the replacement of one or more proton(s) by one or more deuterium(deuteria) or tritium(tritia), or combinations thereof, or except for the replacement of one or more $^{12}C$ atom(s) in the structure by one or more $^{13}C$ atom(s), one or more $^{14}C$ atom(s), or combinations thereof, in the structure are within the scope of the present disclosure.

The compounds of the present disclosure optionally comprise unnatural proportions of atomic isotopes at one or more atom(s) that constitute such compounds. For example, the compounds may be labeled with one or more isotope(s), such as for example, deuterium ($^{2}H$), tritium ($^{3}H$), iodine-125 ($^{125}I$) or carbon-14 ($^{14}C$). Isotopic substitution with $^{2}H$, $^{3}H$, $^{11}C$, $^{13}C$, $^{14}C$, $^{15}C$, $^{12}N$, $^{13}N$, $^{15}N$, $^{16}N$, $^{17}O$, $^{18}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

Deuterium-substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)]2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as MilliporeSigma.

Included in the present disclosure are salts, particularly pharmaceutically acceptable salts, of the compounds described herein. The compounds of the present disclosure that comprise one or more sufficiently acidic functional group(s), one or more sufficiently basic functional group(s), or both one or more sufficiently acidic functional group(s) and one or more sufficiently basic functional group(s) to form a salt (particularly a pharmaceutically acceptable salt), can react with any of a number of inorganic organic bases or inorganic or organic acids, to form a salt.; combinations thereof); or combinations thereof. Alternatively, compounds that are inherently charged, such as those with a quaternary nitrogen, can form a salt with an appropriate counterion.

The compounds and salts described herein may in some cases exist as diastereomers, enantiomers, or other stereoisomeric forms. Unless otherwise specified (e.g., in tables of biological data), the structures disclosed herein are intended to include, explicitly or implicitly, disclosure of all diastereomeric (e.g., epimeric) and enantiomeric forms as well as mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In certain embodiments, the compounds or salts of the compounds may be prodrugs. For example, in some embodiments, a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) may be prodrugs of the present disclosure. In some embodiments, a prodrug for an amine might rely on enzymatic activation. In some embodiments, a prodrug for an amine might rely on physiological chemical conditions for release of the drugs. In some embodiments, a prodrug for an amine may be selected from an amide, a carbonate, an N-acyloxy alkyl derivative, an N-acyloxy carbonyl derivative, a beta-aminoketone, an (oxodioxolenyl)methyl derivative, an N-Mannich base, an imine (e.g., a Schiff base), an enamine, an enaminone, an azo compound, a system capable of undergoing lactonization, a tetrahydrothiadiazine-2-thione, a redox system, or a PEG.

Prodrug forms of the herein described compounds, wherein the prodrug is metabolized in vivo to produce a compound as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J. Physiol.,* 269:G210-218 (1995); McLoed et al., Gastroenterol, 106: 405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems*, Vol. 14 of the *A.C.S. Symposium Series*; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Compounds

The following is a discussion of compounds and salts thereof that may be used in the methods of the disclosure. In certain embodiments, the compounds and salts are described in Formulas (I), (II), and (III). In certain embodiments, the compounds and salts are described in Formulas (I), (II-A), (IV), and (III).

In one aspect, disclosed herein is a compound represented by Formula (I):

(I)

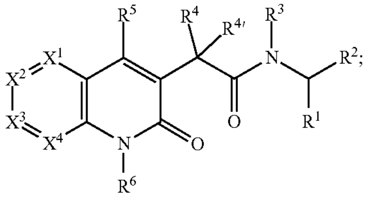

or a salt thereof, wherein:

$X^1$, $X^2$, and $X^3$ are independently selected from C(R), and N wherein at least one of $X^1$, $X^2$, and $X^3$ is N and no more than two of $X^1$, $X^2$, and $X^3$ are N;

$X^4$ is selected from C(R);

each R is independently selected from:

hydrogen, halogen, $-NO_2$, —CN, $-N_3$, $-OR^8$, $-SR^8$, $-N(R^8)_2$, $-C(O)R^8$, $-C(O)N(R^8)_2$, $-N(R^8)C(O)R^8$, $-N(R^8)C(O)N(R^8)_2$, $-OC(O)N(R^8)_2$, $-N(R^8)C(O)OR^8$, $-C(O)OR^8$, $-OC(O)R^8$, $-S(O)R^8$, and $-S(O)_2R^8$;

$C_{1-6}$ alkyl, $C_{2-6}$ alkenyl, and $C_{2-6}$ alkynyl, each of which is optionally substituted with one or more substituents independently selected from halogen, $-OR^8$, $-SR^8$, $-N(R^8)_2$, $-C(O)R^8$, $-C(O)N(R^8)_2$, $-N(R^8)C(O)R^8$, $-C(O)OR^8$, $-OC(O)R^8$, $-N(R^8)C(O)N(R^8)_2$, $-OC(O)N(R^8)_2$, $-N(R^8)C(O)OR^8$, $-S(O)R^8$, $-S(O)_2R^8$, $-NO_2$, =O, =S, $=N(R^8)$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^7$; and $C_{3-10}$ carbocycle and 3- to 10-membered heterocycle, each of which is optionally substituted with one or more substituents independently selected from halogen, $-OR^8$, $-SR^8$, $-N(R^8)_2$, $-C(O)R^8$, $-C(O)N(R^8)_2$, $-N(R^8)C(O)R^8$, $-N(R^8)C(O)N(R^8)_2$, $-OC(O)N(R^8)_2$, $-N(R^8)C(O)OR^8$, $-C(O)OR^8$, $-OC(O)R^8$, $-S(O)R^8$, $-S(O)_2R^8$, $-NO_2$, =O—, =S, $=N(R^8)$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^7$;

$R^1$ is selected from:

hydrogen;

$C_{1-6}$ alkyl, $C_{2-6}$ alkenyl, and $C_{2-6}$ alkynyl, each of which is optionally substituted with one or more substituents independently selected from halogen, —$OR^{8a}$, —$SR^{8a}$, —$N(R^{8a})_2$, —$C(O)R^{8a}$, —$C(O)N(R^{8a})_2$, —$N(R^{8a})C(O)R^{8a}$, —$C(O)OR^{8a}$, —$OC(O)R^{8a}$, —$N(R^{8a})C(O)N(R^{8a})_2$, —$OC(O)N(R^{8a})_2$, —$N(R^{8a})C(O)OR^{8a}$, —$S(O)R^{8a}$, —$S(O)_2R^{8a}$, —$NO_2$, =O, =S, =$N(R^{8a})$, —CN, $C_{3-10}$ carbocycle, and 3- to 10-membered heterocycle, wherein the $C_{3-10}$ carbocycle, and 3- to 10-membered heterocycle, are each optionally substituted with one or more substituents independently selected from $R^{7a}$; and $C_{3-10}$ carbocycle, and 3- to 10-membered heterocycle, each of which is optionally substituted with one or more substituents independently selected from halogen, —$OR^{8a}$, —$SR^{8a}$, —$N(R^{8a})_2$, —$C(O)R^{8a}$, —$C(O)N(R^{8a})_2$, —$N(R^{8a})C(O)R^{8a}$, —$N(R^{8a})C(O)N(R^{8a})_2$, —$OC(O)N(R^{8a})_2$, —$N(R^{8a})C(O)OR^{8a}$, —$C(O)OR^{8a}$, —$OC(O)R^{8a}$, —$S(O)R^{8a}$, —$S(O)_2R^{8a}$, —$NO_2$, =O—, =S, =$N(R^{8a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{7a}$; or $R^1$ together with $R^2$ form a $C_{3-10}$ carbocycle, or 3- to 10-membered heterocycle, each of which is optionally substituted with one or more substituents independently selected from halogen, —$OR^{8a}$, —$SR^{8a}$, —$N(R^{8a})_2$, —$C(O)R^{8a}$, —$C(O)N(R^{8a})_2$, —$N(R^{8a})C(O)R^{8a}$, —$N(R^{8a})C(O)N(R^{8a})_2$, —$OC(O)N(R^{8a})_2$, —$N(R^{8a})C(O)OR^{8a}$, —$C(O)OR^{8a}$, —$OC(O)R^{8a}$, —$S(O)R^{8a}$, —$S(O)_2R^{8a}$, —$NO_2$, =O—, =S, =$N(R^{8a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{7b}$;

$R^2$ is selected from:

hydrogen;

$C_{1-6}$ alkyl, $C_{2-6}$ alkenyl, and $C_{2-6}$ alkynyl, each of which is optionally substituted with one or more substituents independently selected from halogen, —$OR^{8b}$, —$SR^{8b}$, —$N(R^{8b})_2$, —$C(O)R^{8b}$, —$C(O)N(R^{8b})_2$, —$N(R^{8b})C(O)R^{8b}$, —$C(O)OR^{8b}$b, —$OC(O)R^{8b}$, —$N(R^{8b})C(O)N(R^{8b})_2$, —$OC(O)N(R^{8b})_2$, —$N(R^{8b})C(O)OR^{8b}$, —$S(O)R^{8b}$, —$S(O)_2R^{8b}$, —$NO_2$, =O, =S, =$N(R^{8b})$, —CN, $C_{3-10}$ carbocycle, and 3- to 10-membered heterocycle, wherein the $C_{3-10}$ carbocycle, and 3- to 10-membered heterocycle, are each optionally substituted with one or more substituents independently selected from $R^{7b}$; and $C_{3-10}$ carbocycle, and 3- to 10-membered heterocycle, each of which is optionally substituted with one or more substituents independently selected from halogen, —$OR^{8b}$, —$SR^{8b}$, —$N(R^{8b})_2$, —$C(O)R^{8b}$, —$C(O)N(R^{8b})_2$, —$N(R^{8b})C(O)R^{8b}$, —$N(R^{8b})C(O)N(R^{8b})_2$, —$OC(O)N(R^{8b})_2$, —$N(R^{8b})C(O)OR^{8b}$, —$C(O)OR^{8b}$, —$OC(O)R^{8b}$, —$S(O)R^{8b}$, —$S(O)_2R^{8b}$, —$NO_2$, =O—, =S, =$N(R^{8b})$, —CN, —$N_3$, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{7b}$; or $R^1$ together with $R^2$ form a $C_{3-10}$ carbocycle, or 3- to 10-membered heterocycle, each of which is optionally substituted with one or more substituents independently selected from halogen, —$OR^{8a}$, —$SR^{8a}$, —$N(R^{8a})_2$, —$C(O)R^{8a}$, —$C(O)N(R^{8a})_2$, —$N(R^{8a})C(O)R^{8a}$, —$N(R^{8a})C(O)N(R^{8a})_2$, —$OC(O)N(R^{8a})_2$, —$N(R^{8a})C(O)OR^{8a}$, —$C(O)OR^{8a}$, —$OC(O)R^{8a}$, —$S(O)R^{8a}$, —$S(O)_2R^{8a}$, —$NO_2$, =O—, =S, =$N(R^{8a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{7b}$;

$R^3$ is selected from:

hydrogen, halogen, —$OR^{8c}$, —$SR^{8c}$, —$N(R^{8c})_2$, —$NO_2$, and —CN; and $C_{1-6}$ alkyl optionally substituted with one or more one or more substituents independently selected from $R^{7c}$;

$R^4$ is selected from:

hydrogen, halogen, —$OR^{8d}$, —$SR^{8d}$, —$N(R^{8d})_2$, —$NO_2$, and —CN; and $C_{1-6}$ alkyl optionally substituted with one or more substituents independently selected from halogen, —$OR^{8d}$, —$SR^{8d}$, —$N(R^{8d})_2$, —$NO_2$, and —CN, $C_{3-10}$ carbocycle, and 3- to 10-membered heterocycle, wherein the $C_{3-10}$ carbocycle, and 3- to 10-membered heterocycle, are each optionally substituted with one or more substituents independently selected from $R^{7d}$;

$R^{4'}$ is selected from:

hydrogen, halogen, —$OR^{8d}$, —$SR^{8d}$, —$N(R^{8d})_2$, —$NO_2$, and —CN; and $C_{1-6}$ alkyl optionally substituted with one or more substituents independently selected from halogen, —$OR^{8d}$, —$SR^{8d}$, —$N(R^{8d})_2$, —$NO_2$, and —CN, $C_{3-10}$ carbocycle, and 3- to 10-membered heterocycle, wherein the $C_{3-10}$ carbocycle, and 3- to 10-membered heterocycle, are each optionally substituted with one or more substituents independently selected from $R^{7d}$;

or $R^4$ and $R^{4'}$ together form a $C_{3-10}$ carbocycle, or 3- to 10-membered heterocycle, wherein the $C_{3-10}$ carbocycle, or 3- to 10-membered heterocycle, is optionally substituted with one or more substituents independently selected from $R^{7d}$;

$R^5$ is selected from:

hydrogen, halogen, —$OR^{8e}$, —$SR^{8e}$, —$N(R^{8e})_2$, —$NO_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more substituents independently selected from $R^{7e}$;

$R^6$ is selected from:

hydrogen, halogen, —$OR^{8f}$, —$SR^{8e}$, —$N(R^{8f})_2$, —$NO_2$, and —CN; and $C_{1-6}$ alkyl optionally substituted with one or more substituents independently selected from $R^{7f}$;

each $R^7$, $R^{7a}$, $R^{7b}$, $R^{7c}$, $R^{7d}$, $R^{7e}$, and $R^{7f}$ is independently selected from:

halogen, —$OR^{8g}$, —$SR^{8g}$, —$N(R^{8g})_2$, —$C(O)R^{8g}$, —$C(O)N(R^{8g})_2$, —$N(R^{8g})C(O)R^{8g}$, —$N(R^{8g})C(O)N(R^{8g})_2$, —$OC(O)N(R^{8g})_2$, —$N(R^{8g})C(O)OR^{8g}$, —$C(O)OR^{8g}$, —$OC(O)R^{8g}$, —$S(O)R^{8g}$, —$S(O)_2R^{8g}$, —$NO_2$, =O, =S, =$N(R^{8g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{8g}$, —$SR^{8g}$, —$N(R^{8g})_2$, —$C(O)R^{8g}$, —$C(O)N(R^{8g})_2$, —$N(R^{8g})C(O)R^{8g}$, —$N(R^{8g})C(O)N(R^{8g})_2$, —$OC(O)N(R^{8g})_2$, —$N(R^{8g})C(O)OR^{8g}$, —$C(O)OR^{8g}$, —$OC(O)R^{8g}$, —$S(O)R^{8g}$, —$S(O)_2R^{8g}$, —$NO_2$, =O, =S, =$N(R^{8g})$, and —CN;

each $R^8$, $R^{8a}$, $R^{8b}$, $R^{8c}$, $R^{8d}$, $R^{8e}$, $R^{8f}$, and $R^{8g}$ is independently selected from:

hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In certain embodiments, for a compound or salt of Formula (I) or Formula (I'), $X^1$, $X^2$, and $X^3$ are independently selected from C(R) and N wherein at least one of $X^1$, $X^2$, and $X^3$ is N and no more than two of $X^1$, $X^2$, and $X^3$ are N. In some embodiments, $X^1$ is N. In some embodiments, $X^1$ is C(R). In some embodiments, $X^2$ is N. In some embodiments, $X^2$ is C(R). In some embodiments, $X^3$ is N. In some embodiments, $X^3$ is C(R). In some embodiments, $X^1$ is N, $X^2$ is C(R), and $X^3$ is C(R). In some embodiments, $X^1$ is C(R), $X^2$ is N, and $X^3$ is C(R). In some embodiments, $X^1$ is C(R), $X^2$ is C(R), and $X^3$ is N. In some embodiments, $X^1$ is N, $X^2$ is C(R), and $X^3$ is N.

In certain embodiments, for a compound or salt of Formula (I) or Formula (I'), R can be any suitable functional group known by one of skill in the art. In some embodiments, each R is independently selected from: hydrogen, halogen, —$NO_2$, —CN, —$N_3$, —$OR^8$, —$SR^8$, —$N(R^8)_2$, —C(O)R, —$C(O)N(R^8)_2$, —$N(R^8)C(O)R^8$, —$N(R^8)C(O)N(R^8)_2$, —$OC(O)N(R^8)_2$, —$N(R^8)C(O)OR^8$, —$C(O)OR^8$, —$OC(O)R^8$, —$S(O)R^8$, and —$S(O)_2R^8$; $C_{1-6}$ alkyl, $C_{2-6}$ alkenyl, and $C_{2-6}$ alkynyl, each of which is optionally substituted with one or more substituents independently selected from halogen, —$OR^8$, —$SR^8$, —$N(R^8)_2$, —$C(O)R^8$, —$C(O)N(R^8)_2$, —$N(R^8)C(O)R^8$, —$C(O)OR^8$, —$OC(O)R^8$, —$N(R^8)C(O)N(R^8)_2$, —$OC(O)N(R^8)_2$, —$N(R^8)C(O)OR^8$, —$S(O)R^8$, —$S(O)_2R^8$, —$NO_2$, =O, =S, =$N(R^8)$, —CN, $C_{3-10}$ carbocycle and 3- to 10-membered heterocycle, wherein the $C_{3-10}$ carbocycle and 3- to 10-membered heterocycle are each optionally substituted with one or more $R^7$; and $C_{3-10}$ carbocycle and 3- to 10-membered heterocycle, each of which is optionally substituted with one or more substituents independently selected from halogen, —$OR^8$, —$SR^8$, —$N(R^8)_2$, —$C(O)R^8$, —$C(O)N(R^8)_2$, —$N(R^8)C(O)R^8$, —$N(R^8)C(O)N(R^8)_2$, —$OC(O)N(R^8)_2$, —$N(R^8)C(O)OR^8$, —$C(O)OR^8$, —$OC(O)R^8$, —$S(O)R^8$, —$S(O)_2R^8$, —$NO_2$, =O—, =S, =$N(R^8)$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^7$.

In certain embodiments, for a compound or salt of Formula (I) or Formula (I'), each R is independently selected from: hydrogen, halogen, —$NO_2$, —CN, —$N_3$, —$OR^8$, —$SR^8$, —$N(R^8)_2$, —$C(O)R^8$, —$C(O)N(R^8)_2$, —$N(R^8)C(O)R^8$, and —$N(R^8)C(O)N(R^8)_2$; $C_{1-6}$ alkyl, $C_{2-6}$ alkenyl, and $C_{2-6}$ alkynyl, each of which is optionally substituted with one or more substituents independently selected from halogen, —$OR^8$, —$SR^8$, —$N(R^8)_2$, —$NO_2$, =O, =S, =$N(R^8)$; and $C_{3-10}$ carbocycle and 3- to 10-membered heterocycle. In some embodiments, each R is independently selected from hydrogen, halogen, —CN, —$N_3$, —$OR^8$, —$SR^8$, —$N(R^8)_2$, —$C(O)R^8$, —$C(O)N(R^8)_2$, and —$N(R^8)C(O)R^8$; $C_{1-6}$ alkyl, $C_{2-6}$ alkenyl, and $C_{2-6}$ alkynyl, each of which is optionally substituted with one or more substituents independently selected from halogen, —$OR^8$; and $C_{3-10}$ carbocycle and 3- to 10-membered heterocycle. In some embodiments, each R is independently selected from: hydrogen, halogen, —CN, —$N_3$, —$OR^8$, —$SR^8$, —$N(R^8)_2$; $C_{1-6}$ alkyl and $C_{2-6}$ alkynyl, each of which is optionally substituted with one or more substituents independently selected from halogen; and $C_{3-10}$ carbocycle and 3- to 10-membered heterocycle. In some embodiments, each R is independently selected from: —F, —Cl, —Br, —I, —CN, —$N_3$, —$OR^8$, —$SR^8$, —$N(R^8)_2$, —$CF_3$, methyl, ethyl, cyclopropyl, —CCMe, phenyl, morpholinyl, and pyrrolidinyl. In some embodiments, each R is independently selected from: —F, —Cl, —Br, —I, —CN, —$N_3$, —$OR^8$, —$SR^8$, —$N(R^8)_2$, —$CF_3$, methyl, ethyl, cyclopropyl, —CCMe, phenyl, morpholinyl, and pyrrolidinyl, wherein each $R^8$ is independently selected from the group consisting of hydrogen, methyl, ethyl, propyl, isopropyl, cyclopropyl, isobutyl, —$CF_3$, —$CH_2CF_3$, —$CH_2CHF_2$, —$CH_2CF(Me)_2$, —$CH_2CHMe_2$, —$CH_2$-phenyl. In some embodiments, each R is independently selected from: —H, —F, Cl, —Br, —I, —CN, —$N_3$, —OH, —OMe, —OEt, —O-propyl, —O-isopropyl, —O-butyl, —O-isobutyl, —$OCF_3$, —$OCH_2CFMe_2$, —$OCH_2CHF_2$, —$OCH_2CF_3$, —$OCH_2CF(CH_3)_2$, —O-cyclopropyl, —SMe, —SEt, —$NH_2$, —NHMe, —NHEt, —NH-propyl, —NH— cyclopropyl, —NH-butyl, —NH-isobutyl, —NH-cyclobutyl, —$NMe_2$, —$NEt_2$, —NH-phenyl, -Me, -Et, -cyclopropyl, -n-propyl, isopropyl, —$CF_3$, —CCMe, -morpholinyl, and pyrrolidinyl. In some embodiments, each R is independently selected from: —H, —F, Cl, —Br, —I, —OH, -Me, -Et, —$OCH_2CF_3$, —$OCH_2CHF_2$, —OMe, -cyclopropyl, —CN, —OEt, —$CF_3$, —O—$CF_3$, —O-cyclopropyl, -n-propyl, isopropyl, —$OCH_2CF(CH_3)_2$, —O-propyl, —O-isopropyl, —$OCH_2CFMe_2$, —SMe, —NHMe, —$NH_2$, —NHEt, —CCMe, —$NMe_2$, —$NEt_2$, —$N_3$, —NH-cyclopropyl, —NH-isobutyl, —NH-phenyl, -morpholinyl, pyrrolidinyl In some embodiments, each R is independently selected from: —H, —F, Cl, —Br, —I, —CN, —$N_3$, —OH, —OMe, —OEt, —O-propyl, —O-isopropyl, —$OCF_3$, —$OCH_2CFMe_2$, —$OCH_2CHF_2$, —$OCH_2CF_3$, —$OCH_2CF(CH_3)_2$, —O— cyclopropyl, —SMe, —$NH_2$, —NHMe, —NHEt, —NH-cyclopropyl, —NH-isobutyl, —$NMe_2$, —$NEt_2$, —NH— phenyl, -Me, -Et, -cyclopropyl, -n-propyl, isopropyl, —$CF_3$, —CCMe, -morpholinyl, and pyrrolidinyl. In some embodiments, each R is independently selected from: —H, —F, Cl, —Br, —I, —CN, —$N_3$, —OH, —OMe, —OEt, —O-propyl, —O-isopropyl, —$OCF_3$, —$OCH_2CFMe_2$, —$OCH_2CHF_2$, —$OCH_2CF_3$, —$OCH_2CF(CH_3)_2$, —O-cyclopropyl, —SMe, —$NH_2$, —NHMe, —NHEt, —$NEt_2$, -Me, -Et, -cyclopropyl, -n-propyl, isopropyl, —$CF_3$, and —CCMe.

In certain embodiments, for a compound or salt of Formula (I) or Formula (I'), $R^1$ can be any suitable functional group known by one of skill in the art. In some embodiments, $R^1$ is selected from: hydrogen; $C_{1-6}$ alkyl, $C_{2-6}$ alkenyl, and $C_{2-6}$ alkynyl, each of which is optionally substituted with one or more substituents independently selected from halogen, —$OR^{8a}$, —$SR^{8a}$, —$N(R^{8a})_2$, —C(O)$R^{8a}$, —C(O)$N(R^{8a})_2$, —$N(R^{8a})C(O)R^{8a}$, —C(O)$OR^{8a}$, —OC(O)$R^{8a}$, —$N(R^{8a})C(O)N(R^{8a})_2$, —OC(O)$N(R^{8a})_2$, —$N(R^{8a})C(O)OR^{8a}$, —S(O)$R^{8a}$, —$S(O)_2R^{8a}$, —$NO_2$, =O, =S, =$N(R^{8a})$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{7a}$; and $C_{3-10}$ carbocycle, and 3- to 10-membered heterocycle, each of which is optionally substituted with one or more substituents independently selected from halogen, —$OR^{8a}$, —$SR^{8a}$, —$N(R^{8a})_2$, —C(O)$R^{8a}$, —C(O)$N(R^{8a})_2$, —$N(R^{8a})C(O)R^{8a}$, —$N(R^{8a})C(O)N(R^{8a})_2$, —OC(O)$N(R^{8a})_2$, —$N(R^{8a})C(O)OR^{8a}$, —C(O)$OR^{8a}$, —OC(O)$R^{8a}$, —S(O)$R^{8a}$, —$S(O)_2R^{8a}$, —$NO_2$, =O—, =S, =$N(R^{8a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7a}$; or $R^1$ together with $R^2$ form a $C_{3-10}$ carbocycle, or 3- to 10-membered heterocycle, each of which is optionally substituted with one or more substituents independently selected from halogen, —$OR^{8a}$, —$SR^{8a}$, —$N(R^{8a})_2$, —C(O)$R^{8a}$, —C(O)$N(R^{8a})_2$, —$N(R^{8a})C(O)R^{8a}$, —$N(R^{8a})C(O)N(R^{8a})_2$, —OC(O)$N(R^{8a})_2$, —$N(R^{8a})C(O)OR^{8a}$, —C(O)$OR^{8a}$, —OC(O)$R^{8a}$, —S(O)$R^{8a}$, —$S(O)_2R^{8a}$, —$NO_2$, =O—, =S, =$N(R^{8a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$. In some embodiments, $R^1$ is selected from: hydrogen; $C_{1-6}$ alkyl, $C_{2-6}$ alkenyl, and $C_{2-6}$ alkynyl, each of which is optionally substituted with one or more substituents independently selected from halogen, —$OR^{8a}$, —$SR^{8a}$, —$N(R^{8a})_2$, —C(O)$R^{8a}$, —S(O)$R^{8a}$, —$S(O)_2R^{8a}$, —$NO_2$, and —CN; and $C_{3-10}$ carbocycle, and 3- to 10-membered heterocycle, each of which is optionally substituted with one or more substituents independently selected from halogen, —$OR^{8a}$, —$SR^{8a}$, —$N(R^{8a})_2$, —C(O)$R^{8a}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7a}$, or $R^1$ together with $R^2$ form a $C_{3-10}$ carbocycle, or 3- to 10-membered heterocycle, each of which is optionally substituted with one or more substituents independently selected from halogen, —$OR^{8a}$, —$SR^{8a}$, —$N(R^{8a})_2$, —C(O)$R^{8a}$, —S(O)$R^{8a}$, —$S(O)_2R^{8a}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$. In some embodiments, $R^1$ is selected from hydrogen; $C_{1-6}$ alkyl, $C_{2-6}$ alkenyl, and $C_{2-6}$ alkynyl, each of which is optionally substituted with one or more substituents independently selected from halogen, —$OR^{8a}$, —$SR^{8a}$, —$N(R^{8a})_2$, —C(O)$R^{8a}$, —S(O)$R^{8a}$, —$S(O)_2R^{8a}$, —$NO_2$, and —CN; and $C_{3-10}$ carbocycle, and 3- to 10-membered heterocycle, each of which is optionally substituted with one or more substituents independently selected from halogen, —C(O)$R^{8a}$, —CN, $C_{1-6}$ alkyl, or $R^1$ together with $R^2$ form a $C_{3-10}$ carbocycle, or 3- to 10-membered heterocycle, each of which is optionally substituted with one or more substituents independently selected from halogen, —$OR^{8a}$, —$SR^{8a}$, —$N(R^{8a})_2$, —C(O)$R^{8a}$, —$NO_2$, —CN, and $C_{1-6}$alkyl, wherein $C_{1-6}$alkyl is optionally substituted with one or more $R^{7b}$. In some embodiments, $R^1$ is hydrogen, methyl, —$CH_2OH$, —$CH_2CH_2OH$, $C(Me)_2OH$, —$CH_2OMe$, or $R^1$ together with $R^2$ form a $C_{3-10}$ carbocycle, or 3- to 10-membered heterocycle, each of which is optionally substituted with one or more substituents independently selected from —F, —COMe, —CN, and methyl. In some embodiments, $R^1$ is hydrogen, methyl, —$CH_2OH$, —$CH_2CH_2OH$, $C(Me)_2OH$, —$CH_2OMe$, or $R^1$ together with $R^2$ form:

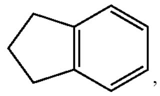,
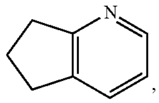,
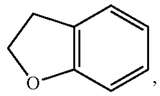,
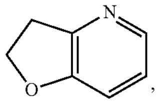,
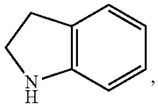, or
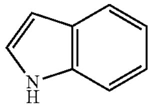

each of which are optionally substituted with one or more fluoro, —C(O)Me, —CN, and methyl.

In certain embodiments, for a compound or salt of Formula (I) or Formula (I'), $R^2$ can be any suitable functional group known by one of skill in the art. In some embodiments, $R^2$ is selected from: hydrogen; $C_{1-6}$ alkyl, $C_{2-6}$ alkenyl, and $C_{2-6}$ alkynyl, each of which is optionally substituted with one or more substituents independently selected from halogen, —$OR^{8b}$, —$SR^{8b}$, —$N(R^{8b})_2$, —C(O)$R^{8b}$, —C(O)$N(R^{8b})_2$, —$N(R^{8b})C(O)R^{8b}$, —C(O)$OR^{8b}$, —OC(O)$R^{8b}$, —$N(R^{8b})C(O)N(R^{8b})_2$, —OC(O)$N(R^{8b})_2$, —$N(R^{8b})C(O)OR^{8b}$, —S(O)$R^{8b}$, —$S(O)_2R^{8b}$, —$NO_2$, =O, =S, =$N(R^{8b})$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{7b}$; and $C_{3-10}$ carbocycle, and 3- to 10-membered heterocycle, each of which is optionally substituted with one or more substituents independently selected from halogen, —$OR^{8b}$, —$SR^{8b}$, —$N(R^{8b})_2$, —C(O)$R^{8b}$, —C(O)$N(R^{8b})_2$, —$N(R^{8b})C(O)R^{8b}$, —$N(R^{8b})C(O)N(R^{8b})_2$, —OC(O)$N(R^{8b})_2$, —$N(R^{8b})C(O)OR^{8b}$, —C(O)$OR^{8b}$, —OC(O)$R^{8b}$, —S(O)$R^{8b}$, —$S(O)_2R^{8b}$, —$NO_2$, =O—, =S, =$N(R^{8b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$; or $R^1$ together with $R^2$ form a $C_{3-10}$ carbocycle, or 3- to 10-membered heterocycle, each of which is optionally substituted with one or more substituents independently selected from halogen, —$OR^{8a}$, —$SR^{8a}$, —$N(R^{8a})_2$, —C(O)$R^{8a}$, —C(O)$N(R^{8a})_2$, —$N(R^{8a})C(O)R^{8a}$, —$N(R^{8a})C(O)N(R^{8a})_2$, —OC(O)$N(R^{8a})_2$, —$N(R^{8a})C(O)OR^{8a}$, —C(O)$OR^{8a}$, —OC(O)$R^{8a}$, —S(O)$R^{8a}$, —$S(O)_2R^{8a}$, —$NO_2$, =O—, =S, =$N(R^{8a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$.

In certain embodiments, for a compound or salt of Formula (I) or Formula (I'), $R^2$ is selected from: hydrogen, $C_{1-6}$ alkyl, and $C_{2-6}$ alkenyl, each of which is optionally substituted with one or more substituents independently selected from halogen, —$OR^{8b}$, —SRS, —$N(R^{8b})_2$, —C(O)$R^{8b}$, —S(O)$R^{8b}$, —$S(O)_2R^{8b}$, —$NO_2$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{7b}$; and $C_{3-10}$ carbocycle, and 3- to 10-membered heterocycle, each of which is optionally substituted with one or more substituents independently selected from halogen, —$OR^{8b}$, —$SR^{8b}$, —$N(R^{8b})_2$, —C(O)$R^{8b}$, —S(O)$R^{8b}$, —$S(O)_2R^{8b}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$; or $R^1$ together with $R^2$ form a $C_{3-10}$ carbocycle, or 3- to 10-membered heterocycle, each of which is optionally substituted with one or more substituents independently selected from halogen, —$OR^{8a}$, —$SR^{8a}$, —$N(R^{8a})_2$, —$C(O)R^{8a}$, —$S(O)R^{8a}$, —$S(O)_2R^{8a}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$. In some embodiments, $R^2$ is selected from: hydrogen, $C_{1-6}$ alkyl, and $C_{2-6}$ alkenyl, each of which is optionally substituted with one or more substituents independently selected from halogen, —$OR^{8b}$, —$SR^{8b}$, —$N(R^{8b})_2$, —$C(O)R^{8b}$, —$S(O)R^{8b}$, —$S(O)_2R^{8b}$, —$NO_2$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{7b}$; and $C_{3-10}$ carbocycle, and 3- to 10-membered heterocycle, each of which is optionally substituted with one or more substituents independently selected from halogen, —$OR^{8b}$, —$C(O)R^{8b}$, —$S(O)_2R^{8b}$, —CN, and $C_{1-6}$ alkyl, wherein $C_{1-6}$ alkyl is optionally substituted with one or more $R^{7b}$; or $R^1$ together with $R^2$ form a $C_{3-10}$ carbocycle, or 3- to 10-membered heterocycle, each of which is optionally substituted with one or more substituents independently selected from halogen, —$C(O)R^{8a}$, —CN, and $C_{1-6}$ alkyl, wherein $C_{1-6}$ alkyl is optionally substituted with one or more $R^{7b}$. In some embodiments, $R^2$ is selected from hydrogen, $C_{1-6}$ alkyl, and $C_{2-6}$ alkenyl, each of which is optionally substituted with one or more substituents independently selected from halogen, —$OR^{8b}$, $C_{3-10}$ carbocycle, and 3- to 10-membered heterocycle; and $C_{3-10}$ carbocycle, and 3- to 10-membered heterocycle, each of which is optionally substituted with one or more substituents independently selected from halogen, —$OR^{8b}$, —$C(O)R^{8b}$, —$S(O)_2R^{8b}$, —CN, and $C_{1-6}$ alkyl; or $R^1$ together with $R^2$ form a $C_{3-10}$ carbocycle, or 3- to 10-membered heterocycle, each of which is optionally substituted with one or more substituents independently selected from halogen, —$C(O)R^{8a}$, —CN, and $C_{1-6}$ alkyl, wherein $C_{1-6}$ alkyl is optionally substituted with one or more $R^{7b}$. In some embodiments, $R^2$ is hydrogen, $C_{1-2}$ alkyl, phenyl, or pyridinyl, wherein the $C_{1-2}$ alkyl is optionally substituted with one or more substituents independently selected from —OH and phenyl, and wherein the phenyl or pyridinyl is optionally substituted with one or more substituents independently selected from —F, —OH, —OMe, —COMe, —$SO_2Me$, —CN, and methyl. In some embodiments, $R^2$ is phenyl, or pyridinyl, wherein the phenyl or pyridinyl is optionally substituted with one or more substituents independently selected from —F, —OH, —OMe, —COMe, —$SO_2Me$, —CN, and methyl. In some embodiments, $R^2$ together with $R^1$ form:

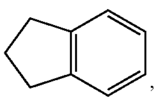, 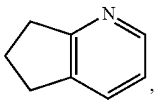, 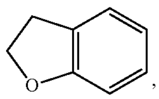,
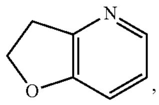, 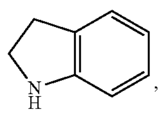, or 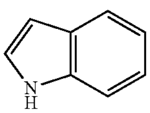

each of which are optionally substituted with one or more fluoro, —C(O)Me, —CN, and methyl.

In certain embodiments, for a compound or salt of Formula (I) or Formula (I'), $R^3$ can be any suitable functional group known by one of skill in the art. In some embodiments, $R^3$ is selected from: hydrogen, halogen, —$OR^{8c}$, —$SR^{8c}$, —$N(R^{8c})_2$, —$NO_2$, and —CN; and $C_{1-6}$ alkyl optionally substituted with one or more one or more $R^{7c}$. In some embodiments, $R^3$ is selected from: hydrogen, halogen, —$OR^{8c}$, —CN, and $C_{1-6}$ alkyl. In some embodiments, $R^3$ is selected from hydrogen and $C_{1-6}$ alkyl. In some embodiments, $R^3$ is selected from hydrogen and $C_{1-3}$ alkyl. In some embodiments, $R^3$ is hydrogen.

In some embodiments,

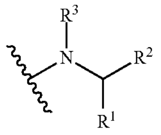

is selected from:

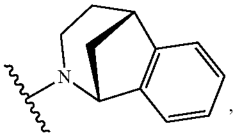, 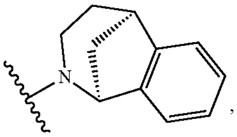,
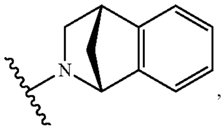, and 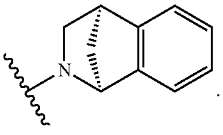.

In some embodiments,

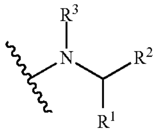

is selected from:

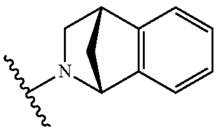 and 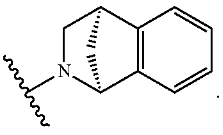.

In some embodiments,

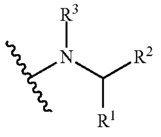

selected from:

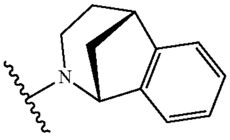 and 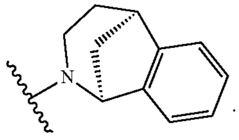.

In certain embodiments, for a compound or salt of Formula (I) or Formula (I'), $R^4$ can be any suitable functional group known by one of skill in the art. In some embodiments, each $R^4$ is independently selected from hydrogen, halogen, —$OR^{8d}$, —$SR^{8d}$, —$N(R^{8d})_2$, —$NO_2$, and —CN; and $C_{1-6}$ alkyl optionally substituted with one or more substituents independently selected from halogen, —$OR^{8d}$, —$SR^{8d}$, —$N(R^{8d})_2$, —$NO_2$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{7d}$. In some embodiments each $R^4$ is independently selected from hydrogen, halogen, —$OR^{8d}$, and —CN; and $C_{1-6}$ alkyl optionally substituted with one or more substituents independently selected from halogen, —$OR^{8d}$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{7d}$. In some embodiments, each $R^4$ is independently selected from hydrogen, halogen, —$OR^{8d}$, —$SR^{8d}$, —$N(R^{8d})_2$, —$NO_2$, and —CN; and $C_{1-6}$ alkyl optionally substituted with one or more substituents independently selected from $C_{3-10}$ carbocycle. In some embodiments, each $R^4$ is independently selected from hydrogen, halogen; and $C_{1-6}$ alkyl optionally substituted with one or more substituents independently selected from $C_{3-10}$ carbocycle. In some embodiments, each $R^4$ is independently selected from hydrogen, —F, and $C_1$ alkyl optionally substituted with phenyl. In some embodiments, each $R^4$ is independently hydrogen or methyl. In some embodiments, each $R^4$ is hydrogen. In some embodiments, each $R^4$ is methyl.

In certain embodiments, for a compound or salt of Formula (I) or Formula (I'), $R^{4'}$ can be any suitable functional group known by one of skill in the art. In some embodiments, each $R^{4'}$ is independently selected from hydrogen, halogen, —$OR^{8d}$, —$SR^{8d}$, —$N(R^{8d})_2$, —$NO_2$, and —CN; and $C_{1-6}$ alkyl optionally substituted with one or more substituents independently selected from halogen, —$OR^{8d}$, —$SR^{8d}$, —$N(R^{8d})_2$, —$NO_2$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{7d}$. In some embodiments each $R^{4'}$ is independently selected from hydrogen, halogen, —$OR^{8d}$, and —CN; and $C_{1-6}$ alkyl optionally substituted with one or more substituents independently selected from halogen, —$OR^{8d}$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{7d}$. In some embodiments, each $R^{4'}$ is independently selected from hydrogen, halogen, —$OR^{8d}$, —$SR^{8d}$, —$N(R^{8d})_2$, —$NO_2$, and —CN; and $C_{1-6}$ alkyl optionally substituted with one or more substituents independently selected from $C_{3-10}$ carbocycle. In some embodiments, each $R^{4'}$ is independently selected from hydrogen, halogen; and $C_{1-6}$ alkyl optionally substituted with one or more substituents independently selected from $C_{3-10}$ carbocycle. In some embodiments, each $R^{4'}$ is independently selected from hydrogen, —F, and $C_1$ alkyl optionally substituted with phenyl. In some embodiments, each $R^{4'}$ is independently hydrogen or methyl. In some embodiments, each $R^{4'}$ is hydrogen. In some embodiments, each $R^{4'}$ is methyl. $R^5$ can be any suitable functional group known by one of skill in the art. In some embodiments, $R^5$ is selected from hydrogen, halogen, —$OR^{8e}$, —$SR^{8e}$, —$N(R^{8e})_2$, —$NO_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more $R^{7e}$.

In certain embodiments, for a compound or salt of Formula (I) or Formula (I'), $R^5$ is selected from: hydrogen, halogen, —$OR^{8e}$, —$N(R^{8e})_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more $R^{7e}$. In some embodiments, $R^5$ is selected from: hydrogen, halogen, —$OR^{8e}$, —$N(R^{8e})_2$, —CN, $C_{1-6}$ alkyl, and $C_{3-10}$ carbocycle, wherein the $C_{1-6}$ alkyl, and $C_{3-10}$ carbocycle, are each optionally substituted with one or more $R^{7e}$. In some embodiments, $R^5$ is selected from: hydrogen, halogen, —$OR^{8e}$, —$N(R^{8e})_2$, —CN, $C_{1-3}$ alkyl, and $C_{3-6}$ carbocycle, wherein the $C_{1-6}$ alkyl, and $C_{3-10}$ carbocycle, are each optionally substituted with one or more $R^{7e}$. In some embodiments, $R^5$ is selected from: hydrogen, —Cl, —OH, —OMe, —NHMe, —CN, $C_{1-2}$ alkyl, and cyclopropyl, wherein the $C_{1-2}$ alkyl and cyclopropyl are each optionally substituted with one or more —F. In some embodiments, $R^5$ is selected from hydrogen, —Cl, —OH, —OMe, —NHMe, —CN, methyl, ethyl, —$CF_3$, —$CHF_2$, and cyclopropyl.

In certain embodiments, for a compound or salt of Formula (I) or Formula (I'), $R^6$ can be any suitable functional group known by one of skill in the art. In some embodiments, $R^6$ is selected from: hydrogen, halogen, —$OR^{8f}$, —$SR^{8f}$, —$N(R^{8f})_2$, —$NO_2$, and —CN; and $C_{1-6}$ alkyl optionally substituted with one or more $R^{7f}$. In some embodiments, $R^6$ is selected from: hydrogen, halogen, —$OR^{8f}$; and $C_{1-6}$ alkyl optionally substituted with one or more $R^{7f}$. In some embodiments, $R^6$ is selected from: hydrogen, halogen, —$OR^{8f}$, and $C_{1-6}$ alkyl. In some embodiments, $R^6$ is selected from hydrogen and $C_{1-6}$ alkyl. In some embodiments, $R^6$ is selected from hydrogen and $C_{1-3}$ alkyl. In some embodiments, $R^6$ is hydrogen.

In certain embodiments, for a compound or salt of Formula (I) or Formula (I'), Each of $R^7$, $R^{7a}$, $R^{7b}$, $R^{7c}$, $R^{7d}$, $R^{7e}$, and $R^{7f}$ can be any suitable functional group known by one of skill in the art. In some embodiments, each of $R^7$, $R^{7a}$, $R^{7b}$, $R^{7c}$, $R^{7d}$, $R^{7e}$, and $R^{7f}$ are independently selected from halogen, —$OR^{8g}$, —$SR^{8g}$, —$N(R^{8g})_2$, —$C(O)R^{8g}$, —$C(O)N(R^{8g})_2$, —$N(R^{8g})C(O)R^{8g}$, —$N(R^{8g})C(O)N(R^{8g})_2$, —$OC(O)N(R^{8g})_2$, —$N(R^{8g})C(O)OR^{8g}$, —$C(O)OR^{8g}$, —$OC(O)R^{8g}$, —$S(O)R^{8g}$, —$S(O)_2R^{8g}$, —$NO_2$, =O, =S, =$N(R^{8g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{8g}$, —$SR^{8g}$, —$N(R^{8g})_2$, —$C(O)R^{8g}$, —$C(O)N(R^{8g})_2$, —$N(R^{8g})C(O)R^{8g}$, —$N(R^{8g})C(O)N(R^{8g})_2$, —$OC(O)N(R^{8g})_2$, —$N(R^{8g})C(O)OR^{8g}$, —$C(O)OR^{8g}$, —$OC(O)R^{8g}$, —$S(O)R^{8g}$, —$S(O)_2R^{8g}$, —$NO_2$, =O, =S, =$N(R^{8g})$, and —CN.

In certain embodiments, for a compound or salt of Formula (I) or Formula (I'), each $R^7$ is independently selected from: halogen, —$OR^{8g}$, —$N(R^{8g})_2$, —$C(O)R^{8g}$, and $C_{1-3}$ alkyl. In some embodiments, each $R^7$ is independently selected from: halogen, —$OR^{8g}$, and $C_{1-3}$ alkyl. In some embodiments, each $R^7$ is independently selected from: halogen, —OH, and —OMe.

In some embodiments, each $R^{7a}$ is independently selected from: halogen, —$OR^{8g}$, —$N(R^{8g})_2$, —$C(O)R^{8g}$, and $C_{1-3}$ alkyl. In some embodiments, each $R^{7a}$ is independently selected from: halogen, —$OR^{8g}$, and $C_{1-3}$ alkyl. In some embodiments, each $R^{7a}$ is independently selected from: halogen, —OH, and —OMe.

In some embodiments, each $R^{7b}$ is independently selected from: halogen, —$OR^{8g}$, —$N(R^{8g})_2$, —$C(O)R^{8g}$, and $C_{1-3}$ alkyl. In some embodiments, each $R^{7b}$ is independently selected from: halogen, —$OR^{8g}$, and $C_{1-3}$ alkyl. In some embodiments, each $R^{7b}$ is independently selected from: halogen, —OH, and —OMe.

In some embodiments, each $R^{7c}$ is independently selected from: halogen, —$OR^{8g}$, —$N(R^{8g})_2$, —$C(O)R^{8g}$, and $C_{1-3}$ alkyl. In some embodiments, each $R^{7c}$ is independently selected from: halogen, —$OR^{8g}$, and $C_{1-3}$ alkyl. In some embodiments, each $R^{7c}$ is independently selected from: halogen, —OH, and —OMe.

In some embodiments, each $R^{7d}$ is independently selected from: halogen, —$OR^{8g}$, —$N(R^{8g})_2$, —$C(O)R^{8g}$, and $C_{1-3}$ alkyl. In some embodiments, each $R^{7d}$ is independently selected from: halogen, —$OR^{8g}$, and $C_{1-3}$ alkyl. In some embodiments, each $R^{7d}$ is independently selected from: halogen, —OH, and —OMe.

In some embodiments, each $R^{7e}$ is independently selected from: halogen, —$OR^{8g}$, —$N(R^{8g})_2$, —$C(O)R^{8g}$, and $C_{1-3}$ alkyl. In some embodiments, each $R^{7e}$ is independently selected from: halogen, —$OR^{8g}$, and $C_{1-3}$ alkyl. In some embodiments, each $R^{7e}$ is independently selected from: halogen, —OH, and —OMe. In some embodiments, each $R^{7e}$ is fluoro.

In some embodiments, each $R^{7f}$ is independently selected from: halogen, —$OR^{8g}$, —$N(R^{8g})_2$, —$C(O)R^{8g}$, and $C_{1-3}$ alkyl. In some embodiments, each $R^{7f}$ is independently selected from: halogen, —$OR^{8g}$, and $C_{1-3}$ alkyl. In some embodiments, each $R^{7f}$ is independently selected from: halogen, —OH, and —OMe.

In certain embodiments, for a compound or salt of Formula (I) or Formula (I'), each of $R^8$, $R^{8a}$, $R^{8b}$, $R^{8c}$, $R^{8d}$, $R^{8e}$, $R^{8f}$, and $R^{8g}$ can be any suitable functional group known by one of skill in the art. In some embodiments, each of $R^8$, $R^{8a}$, $R^{8b}$, $R^{8c}$, $R^{8d}$, $R^{8e}$, $R^{8f}$, and $R^{8g}$ are independently selected from hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —$SO_2$—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In certain embodiments, for a compound or salt of Formula (I) or Formula (I'), each $R^8$ is independently selected from: hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —SH, —$NO_2$, —$NH_2$, $C_{3-10}$ carbocycle, 3- to 10-membered heterocycle; and $C_{3-10}$ carbocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —$SO_2$—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^8$ is independently selected from: hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —$NH_2$, $C_{3-10}$ carbocycle, and $C_{3-10}$ carbocycle, each of which is optionally substituted with one or more substituents independently selected from halogen, —CN, —OH, —O—$C_{1-6}$ alkyl, —S—$C_{1-6}$ alkyl, —$SO_2$—$C_{1-6}$ alkyl, —$N(C_{1-6}$ alkyl$)_2$, —$NH(C_{1-6}$ alkyl), $C_{1-6}$ alkyl, $C_{2-6}$ alkenyl, and $C_{2-6}$ alkynyl. In some embodiments, each $R^8$ is independently selected from hydrogen; and $C_{1-6}$ alkyl, and $C_{3-10}$ carbocycle, each of which is optionally substituted with one or more substituents independently selected from halogen, $C_{3-10}$ carbocycle; and $C_{3-10}$ carbocycle, each of which is optionally substituted with —OH. In some embodiments, each $R^8$ is hydrogen, methyl, ethyl, propyl, isopropyl, cyclopropyl, isobutyl, —$CF_3$, —$CH_2CF_3$, —$CH_2CHF_2$, —$CH_2CF(Me)_2$, —$CH_2CHMe_2$, or —$CH_2$-phenyl.

In some embodiments, each $R^{8a}$ is independently selected from: hydrogen, halogen, $C_{1-6}$ alkyl, $C_{2-6}$ alkenyl, and $C_{2-6}$ alkynyl. In some embodiments, each $R^{8a}$ is independently selected from: hydrogen and $C_{1-6}$ alkyl. In some embodiments, each $R^{8a}$ is independently selected from: hydrogen and methyl.

In some embodiments, each $R^{8b}$ is independently selected from: hydrogen, halogen, $C_{1-6}$ alkyl, $C_{2-6}$ alkenyl, and $C_{2-6}$ alkynyl. In some embodiments, each $R^{8b}$ is independently selected from: hydrogen and $C_{1-6}$ alkyl. In some embodiments, each $R^{8b}$ is independently selected from: hydrogen and methyl.

In some embodiments, each $R^{8c}$ is independently selected from: hydrogen, halogen, $C_{1-6}$ alkyl, $C_{2-6}$ alkenyl, and $C_{2-6}$ alkynyl. In some embodiments, each $R^{8c}$ is independently selected from: hydrogen and $C_{1-6}$ alkyl. In some embodiments, each $R^{8c}$ is independently selected from: hydrogen and methyl.

In some embodiments, each $R^{8d}$ is independently selected from: hydrogen, halogen, $C_{1-6}$ alkyl, $C_{2-6}$ alkenyl, and $C_{2-6}$ alkynyl. In some embodiments, each $R^{8d}$ is independently selected from: hydrogen and $C_{1-6}$ alkyl. In some embodiments, each $R^{8d}$ is independently selected from: hydrogen and methyl.

In some embodiments, each $R^{8e}$ is independently selected from: hydrogen, halogen, $C_{1-6}$ alkyl, $C_{2-6}$ alkenyl, and $C_{2-6}$ alkynyl. In some embodiments, each $R^{8e}$ is independently selected from: hydrogen and $C_{1-6}$ alkyl. In some embodiments, each $R^{8e}$ is independently selected from: hydrogen and methyl. In some embodiments, each $R^{8e}$ is independently hydrogen.

In some embodiments, each $R^{8f}$ is independently selected from: hydrogen, halogen, $C_{1-6}$ alkyl, $C_{2-6}$ alkenyl, and $C_{2-6}$ alkynyl. In some embodiments, each $R^{8f}$ is independently selected from: hydrogen and $C_{1-6}$ alkyl. In some embodiments, each $R^{8f}$ is independently selected from: hydrogen and methyl.

In some embodiments, each $R^{8g}$ is independently selected from: hydrogen, halogen, $C_{1-6}$ alkyl, $C_{2-6}$ alkenyl, and $C_{2-6}$ alkynyl. In some embodiments, each $R^{8g}$ is independently selected from: hydrogen and $C_{1-6}$ alkyl. In some embodiments, each $R^{8g}$ is independently selected from: hydrogen and methyl.

In certain embodiments, for a compound or salt of Formula (I) or Formula (I'), $X^2$ is N, $X^1$ is C(R), and $X^3$ is C(R). In some embodiments, $X^2$ is N, $X^1$ is C(R), and $X^3$ is C(H). In some embodiments, $R^1$ is $CH_3$, and $R^2$ is

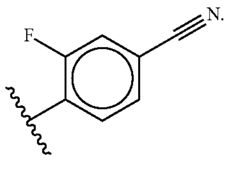

In some embodiments $R^1$ is $CH_3$, and $R^2$ is

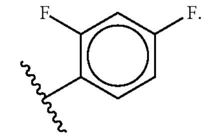

In some embodiments, $R^1$ is $CH_2OH$, and $R^2$ is

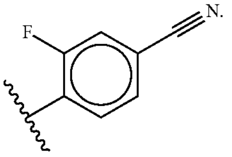

In some embodiments, $R^1$ is $CH_2OH$, and $R^2$ is

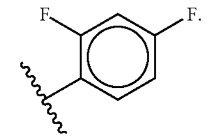

In certain embodiments, for a compound or salt of Formula (I) or Formula (I'), $X^2$ is N, $X^1$ is $C(CH_3)$, and $X^3$ is C(R). In some embodiments, $X^2$ is N, $X^1$ is $C(CH_3)$, and $X^3$ is C(H). In some embodiments, $X^2$ is N, $X^1$ is $C(CH_3)$, $X^3$ is C(H), and $R^5$ is $CH_3$. In some embodiments, $X^2$ is N, $X^1$ is $C(CH_3)$, $X^3$ is C(H), and $R^6$ is H. In some embodiments, $X^2$ is N, $X^1$ is $C(CH_3)$, $X^3$ is C(H), $R^4$ is H, and $R^{4'}$ is H. In some embodiments, $X^2$ is N, $X^1$ is $C(CH_3)$, $X^3$ is C(H), and $R^3$ is H. In some embodiments, $X^2$ is N, $X^1$ is $C(CH_3)$, $X^3$ is C(H), and $R^1$ is $CH_3$. In some embodiments, $X^2$ is N, $X^1$ is $C(CH_3)$, $X^3$ is C(H), and $R^1$ is $CH_2OH$. In some embodiments, $X^2$ is N, $X^1$ is $C(CH_3)$, $X^3$ is C(H), and $R^2$ is

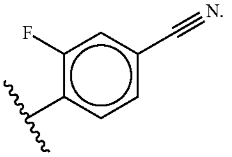

In some embodiments, $X^2$ is N, $X^1$ is $C(CH_3)$, $X^3$ is C(H), and $R^2$ is

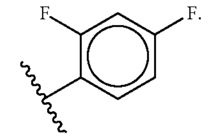

In some embodiments, $X^2$ is N, $X^1$ is $C(CH_3)$, $X^3$ is C(H), $R^1$ is $CH_3$, and $R^2$ is

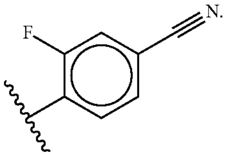

In some embodiments, $X^2$ is N, $X^1$ is $C(CH_3)$, $X^3$ is C(H), $R^1$ is $CH_3$, and $R^2$ is

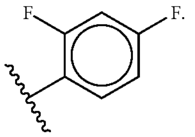

In some embodiments, $X^2$ is N, $X^1$ is $C(CH_3)$, $X^3$ is C(H), $R^1$ is $CH_2OH$, and $R^2$ is

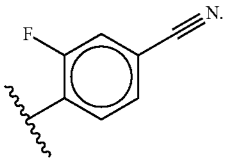

In some embodiments, $X^2$ is N, $X^1$ is $C(CH_3)$, $X^3$ is C(H), $R^1$ is $CH_2OH$, and $R^2$ is

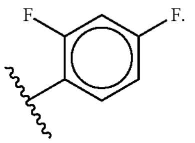

In some embodiments, $X^2$ is N, $X^1$ is $C(CH_3)$, $X^3$ is C(H), $R^5$ is $CH_3$, and $R^2$ is

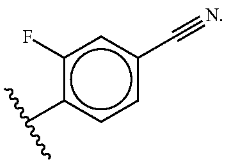

In some embodiments, $X^2$ is N, $X^1$ is $C(CH_3)$, $X^3$ is C(H), $R^5$ is $CH_3$, and $R^2$ is

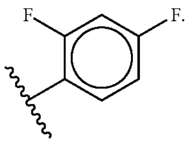

In some embodiments, $X^2$ is N, $X^1$ is $C(CH_3)$, $X^3$ is C(H), $R^1$ is $CH_3$, $R^5$ is $CH_3$, and $R^2$ is

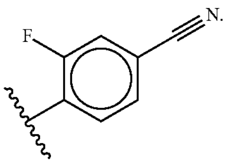

In some embodiments, $X^2$ is N, $X^1$ is $C(CH_3)$, $X^3$ is C(H), $R^1$ is $CH_3$, $R^5$ is $CH_3$, and $R^2$ is

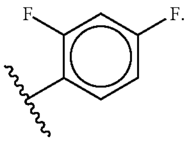

In some embodiments, $X^2$ is N, $X^1$ is $C(CH_3)$, $X^3$ is C(H), $R^1$ is $CH_2OH$, $R^5$ is $CH_3$, and $R^2$ is

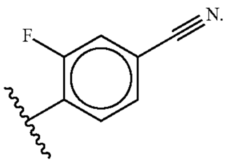

In some embodiments, $X^2$ is N, $X^1$ is $C(CH_3)$, $X^3$ is C(H), $R^1$ is $CH_2OH$, $R^5$ is $CH_3$, and $R^2$ is

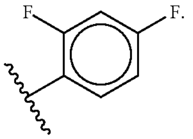

In certain embodiments, for a compound or salt of Formula (I) or Formula (I'), $X^2$ is N, $X^1$ is C(CN), and $X^3$ is C(R). In some embodiments, $X^2$ is N, $X^1$ is C(CN), and $X^3$ is C(H). In some embodiments, $X^2$ is N, $X^1$ is C(CN), $X^3$ is C(H), and $R^5$ is $CH_3$. In some embodiments, $X^2$ is N, $X^1$ is C(CN), $X^3$ is C(H), and $R^6$ is H. In some embodiments, $X^2$ is N, $X^1$ is C(CN), $X^3$ is C(H), $R^4$ is H, and $R^{4'}$ is H. In some embodiments, $X^2$ is N, $X^1$ is C(CN), $X^3$ is C(H), and $R^3$ is H. In some embodiments, $X^2$ is N, $X^1$ is C(CN), $X^3$ is C(H), and $R^1$ is $CH_3$. In some embodiments, $X^2$ is N, $X^1$ is C(CN), $X^3$ is C(H), and $R^1$ is $CH_2OH$. In some embodiments, $X^2$ is N, $X^1$ is C(CN), $X^3$ is C(H), and $R^2$ is

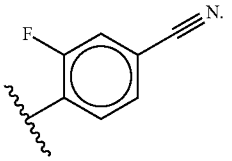

In some embodiments, $X^2$ is N, $X^1$ is C(CN), $X^3$ is C(H), and $R^2$ is

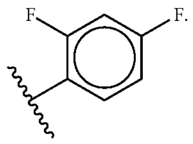

In some embodiments, $X^2$ is N, $X^1$ is C(CN), $X^3$ is C(H), $R^1$ is $CH_3$, and $R^2$ is

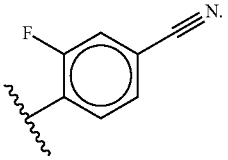

In some embodiments, $X^2$ is N, $X^1$ is C(CN), $X^3$ is C(H), $R^1$ is $CH_3$, and $R^2$ is

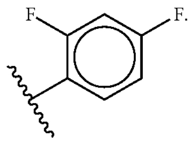

In some embodiments, $X^2$ is N, $X^1$ is C(CN), $X^3$ is C(H), $R^1$ is $CH_2OH$, and $R^2$ is

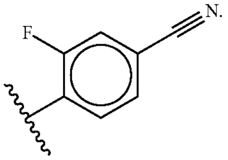

In some embodiments, $X^2$ is N, $X^1$ is C(CN), $X^3$ is C(H), $R^1$ is $CH_2OH$, and $R^2$ is

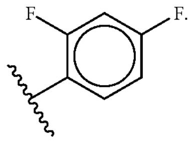

In some embodiments, $X^2$ is N, $X^1$ is C(CN), $X^3$ is C(H), $R^5$ is $CH_3$, and $R^2$ is

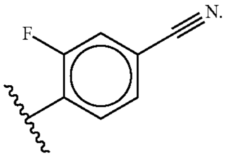

In some embodiments, $X^2$ is N, $X^1$ is C(CN), $X^3$ is C(H), $R^5$ is $CH_3$, and $R^2$ is

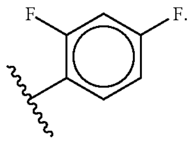

In some embodiments, $X^2$ is N, $X^1$ is C(CN), $X^3$ is C(H), $R^1$ is $CH_3$, $R^5$ is $CH_3$, and $R^2$ is

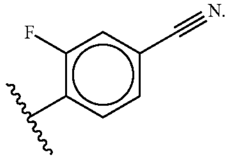

In some embodiments, $X^2$ is N, $X^1$ is C(CN), $X^3$ is C(H), $R^1$ is $CH_3$, $R^5$ is $CH_3$, and $R^2$ is

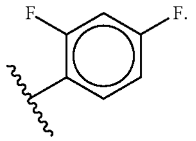

In some embodiments, $X^2$ is N, $X^1$ is C(CN), $X^3$ is C(H), $R^1$ is $CH_2OH$, $R^5$ is $CH_3$, and $R^2$ is

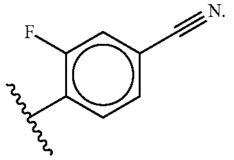

In some embodiments, $X^2$ is N, $X^1$ is C(CN), $X^3$ is C(H), $R^1$ is $CH_2OH$, $R^5$ is $CH_3$, and $R^2$ is

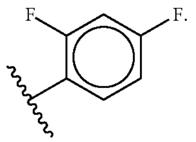

In some embodiments, a compound of Formula (I) or Formula (I') is selected from compound 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 3001, 3002, 3003, 3004, 3005, 3006, 3007, 3008, 3009, 3010, 3011, 3012, 3013, 3502, 3503, 3504, 3505, 3506, 3507, 3508, 3509, 3510, 3511, 3512, 3513, 3514, 3515, 3516, 3517, 3518, and 3519.

In some embodiments, a compound of Formula (I) or Formula (I') is selected from compound 147, 209, 274, 283, 373, 402, 409, 152, 168, 382, 391, 401, 149, 150, 177, 357, 370, 377, 380, 385, 439, 305, 355, 139, 170, 174, 185, 225, 256, 288, 492, 227, 242, 332, 374, 172, 381, 406, 407, 187, 196, 202, 230, 359, 420, 3514, 219, 386, 145, 160, 162, 246, 392, 351, 353, 366, 387, 3009, 405, 433, 469, 3502, 376, 414, 154, 167, 365, 262, 384, 173, 3508, 3515, 266, 447, 281, 375, 394, 285, 264, 369, 195, 181, 198, 156, 183, 161, 348, 138, 3509, 217, 363, 464, 430, 158, 151, 3510, 193, 204, 232, 419, 3516, 146, 243, 3511, 192, 434, 448, 456, 241, 3010, 179, 389, 349, 3504, 458, 468, 248, 399, 163, 347, 3519, 143, 350, 489, 169, 3012, 308, 388, 221, 3517, 444, 364, 159, 396, 189, 477, 276, 3001, 361, 255, 428, 476, 411, 473, 486, 460, 282, 400, 491, 3512, 368, 395, 191, 3505, 166, 424, 148, 3518, 484, 354, 208, 415, 367, 445, 438, 379, 186, 343, 260, 188, 393, 273, 164, 427, 250, 3507, 352, 418, 398, 3011, 165, 197, 200, 371, 459, 275, 176, 327, 441, 3503, 342, 483, 472, 463, 178, 284, 239, 426, 3513, 410, 478, 194, 155, 224, 211, 455, 454, 226, 190, 229, 245, 238, 182, 338, 453, 362, 344, 417, 3004, 299, 345, 431, 306, 488, 223, 157, 212, 432, 278, 304, 254, 153, 413, 171, 358, 289, 482, 210, 457, 435, 440, 247, 340, 236, 403, 286, 485, 452, 462, 336, 412, 279, 296, 437, 461, and 425.

In some embodiments, a compound of Formula (I) or Formula (I') is selected from compound 147, 209, 274, 283, 373, 402, 409, 152, 168, 382, 391, 401, 149, 150, 177, 357, 370, 377, 380, 385, 439, 305, 355, 139, 170, 174, 185, 225, 256, 288, 492, 227, 242, 332, 374, 172, 381, 406, 407, 187, 196, 202, 230, 359, 420, 3514, 219, 386, 145, 160, 162, 246, 392, 351, 353, 366, 387, 3009, 405, 433, 469, 3502, 376, 414, 154, 167, 365, 262, 384, 173, 3508, 3515, 266, 447, 281, 375, 394,285, 264, 369, 195, 181, 198, 156, 183, 161, 348, 138, 3509, 217, 363, 464, 430, 158, 151, 3510, 193, 204, 232, 419, 3516, 146, 243, 3511, 192, 434, 448, 456, 241, 3010, 179, 389, 349, 3504, 458, 468, 248, 399, 163, 347, 3519, 143, 350, 489, 169, 3012, 308, 388, 221, 3517, 444, 364, 159, 396, 189, 477, 276, 3001, 361, 255,428, 476, 411, 473, 486, 460, 282, 400, 491, 3512, 368, 395, 191, 3505, 166, 424, 148, 3518, 484, 354, 208, 415, 367, 445, 438, 379, 186, 343, 260, 188, 393, 273, 164, 427, 250, 3507, 352, 418, 398, 3011, 165, 197, 200, 371, 459, 275, 176, 327, 441, 3503, 342, 483,472, 463, 178, 284, 239, 426, 3513, 410, 478, 194, 155, 224, 211, 455, 454, 226, 190, 229, 245, 238, 182, 338, 453, 362, 344, and 417.

In some embodiments, a compound of Formula (I) or Formula (I') is selected from compound 147, 209, 274, 283, 373, 402, 409, 152, 168, 382, 391, 401, 149, 150, 177, 357, 370, 377, 380, 385, 439, 305, 355, 139, 170, 174, 185, 225, 256, 288, 492, 227, 242, 332, 374, 172, 381, 406, 407, 187, 196, 202, 230, 359, 420, 3514, 219, 386, 145, 160, 162, 246, 392, 351, 353, 366, 387, 3009, 405, 433, 469, 3502, 376, 414, 154, 167, 365, 262, 384, 173, 3508, 3515, 266, 447, 281, 375, 394, 285, 264, 369, 195, 181, 198, 156, 183, 161, 348, 138, 3509, 217, 363, 464, 430, 158, 151, 3510, 193, 204, 232, 419, 3516, 146, 243, 3511, 192, 434, 448, 456, 241, 3010, 179, 389, 349, 3504, 458, 468, 248, 399, 163, 347, 3519, 143, and 350.

In some embodiments, a compound of Formula (I) or Formula (I') is selected from compound 147, 209, 274, 283, 373, 402, 409, 152, 168, 382, 391, 401, 149, 150, 177, 357, 370, 377, 380, 385, 439, 305, 355, 139, 170, 174, 185, 225, 256, 288, 492, 227, 242, 332, 374, 172, 381, 406, and 407.

In some embodiments, a compound of Formula (I) or Formula (I') is selected from compound 185, 152, 177, 283, 149, 162, 147, 373, 274, 3514, 209, 355, 246, 285, 139, 198, 464, 402, 256, 401, 332, 288, 382, 3515, 391, 377, 3508, 173, 357, 381, 353, 3502, 492, 385,407, 374, 406, 393,439, 3509, 242, 394, 154, 174, 305, 489, 409, 227, 433, 262, 150, 146, 380, 476, 202, 151, 365, 230, 351, 170, 266, 405, 167, 282, 138, 161, 3510, 376, 187, 486, 366, 468, 3516, 386, 469, 255, 158, 428, 350, 403, 3517, 179, 3009, 243, 160, 420, 225, 181, 477, 392, 3511, 264, 232, 363, 195, 248, 148, 156, 396, 487, 3010, 168, 361, 456, 172, 434, 273, 241, 196, 375, 364, 3504, 488, 349, 281, 3503, 3007, 379, 472, 193, 159, 183, 348, 143, 473, 217, 219, 448, 438, 204, 327, 245, 417, 343, 208, 145, 447, 169, 284, 239, 238, 491, 430, 384, 308, 415, 3505, 189, 414, 192, 276, 461, 483, 3519, 424, 3001, 399, 3507, 435, 176, 178, 347, 445, 444, 164, 427, 254, 157, 463, 460, 352, 397, 478, 269, 229, 212, 182, 367, 388, 188, 475, 404, 368, 390, 190, 221, 395, 370, 418, 354, 197, 431, 345, 342, 454, 211, 358, 3012, 398, 369, 223, 3513, 155, 482, 258, 426, 199, 471, 432, 250, 277, and 344.

In some embodiments, a compound of Formula (I) or Formula (I') is selected from compound 185, 152, 177, 283, 149, 162, 147, 373, 274, 3514, 209, 355, 246, 285, 139, 198, 464, 402, 256, 401, 332, 288, 382, 3515, 391, 377, 3508, 173, 357, 381, 353, 3502, 492, 385, 407, 374, 406, 393, 439, 3509, 242, 394, 154, 174, 305, 489, 409, 227, 433, 262, 150, 146, 380, 476, 202, 151, 365, 230, 351, 170, 266, 405, 167, 282, 138, 161, 3510, 376, 187, 486, 366, 468, 3516, 386, 469, 255, 158, 428, 350, 403, 3517, 179, 3009, 243, 160, 420, 225, 181, 477, 392, 3511, 264, 232, 363, 195, 248, 148, 156, 396, 487, 3010, 168, 361, 456, 172, 434, 273, 241, 196, 375, 364, 3504, 488, 349, 281, 3503, 3007, 379, 472, 193, 159, 183, 348, 143, 473, 217, 219, 448, 438, 204, 327, 245, 417, 343, and 208.

In some embodiments, a compound of Formula (I) or Formula (I') is selected from compound In some embodiments, a compound of Formula (I) or Formula (I') is selected from compound 185, 152, 177, 283, 149, 162, 147, 373, 274, 3514, 209, 355, 246, 285, 139, 198, 464, 402, 256, 401, 332, 288, 382, 3515, 391, 377, 3508, 173, 357, 381, 353, 3502, 492, 385, 407, 374, 406, 393, 439, 3509, 242, 394, 154, 174, 305, 489, 409, 227, 433, 262, 150, 146, 380, 476, 202, 151, 365, 230, and 351.

In some embodiments, a compound of Formula (I) or Formula (I') is selected from compound 185, 152, and 177.

In some embodiments, a compound of Formula (I) or Formula (I') is selected from compound 152, 283, 373, 209, 355, 382, 391, 377, 381, 380, 185, 177, 149, 162, 274, 285, 139, 198, 402, 256, 401, 288, 173, 407, 374, 406, 393, 242, 305, 230, 232, 246, 464, 385, 394, 409, 433, 365, 170, 167, 376, 386, 160, 225, 361, 414, 422, 332, 154, 405, 366, 363, 172, 384, 359, 3514, 187, 447, 360, 147, 3515, 357, 353, 351, 158, 350, 3508, 227, 392, 204, 3502, 174, 395, 150, 428, 181, 439, 168, 202, 151, 161, 195, 159, 262, 179, 434, 349, 415, 219, 276, 3509, 208, 169, 3510, 243, 248, 241, 375, 448, 417, 444, 196, 352, 403, 420, 354, 387, 419, 200, 486, 421, 266, 156, 476, 398, 344, 3516, 430, 389, 489, 3511, 226, 492, 367, 473, 399, 281, 423, 282, 347, 404, 411, 379, 400, 224, 371, 3517, 435, 383, 472, 362, 206, 445, 368, 364, 416, 432, 284, 348, 370, 456, 469, 396, 192, 264, 236, 438, 143, 157, 3010, 239, 327, 388, 255, 217, 3512, 193, 183, 410, 431, 189, 3503, 245, 273, 201, 3504, 203, 164, 176, 488, 194, 429, 155, 437, 279, 425, 207, 443, 343, 304, 325, 372, 182, 477, 254, 308, 345, 178, 397, 441, 427, 146, 418, 186, 212, 221, 275, 346, 269, 289, 148, 3012, 278, 440, 138, 238, 475, 153, 378, 166, 487, 145, 265, 468, 191, 3001, 229, 197, 454, 424, 446, 247, 3505, 306, 233, 455, 3513, 3004, 210, 390, 483, 491, 213, 286, 141, 453, 3518, 463, 470, 458, 413, 342, 163, 442, 426, 436, 408, 199, 218, 171, 369, 474, 467, 223, 250, 299, 234, 211, 214, 280, 335, 188, 261, 338, 318, 484, 180, 260, 480, 320, 303, 140, 490, 465, 165, 3011, 478, 293 and 277.

In some embodiments, a compound of Formula (I) or Formula (I') is selected from compound 152, 283, 373, 209, 355, 382, 391, 377, 381, 380, 185, 177, 149, 162, 274, 285, 139, 198, 402, 256, 401, 288, 173, 407, 374, 406, 393, 242, 305, 230, 232, 246, 464, 385, 394, 409, 433, 365, 170, 167, 376, 386, 160, 225, 361, 414, 422, 332, 154, 405, 366, 363, 172, 384, 359, 3514, 187, 447, 360, 147, 3515, 357, 353, 351, 158, 350, 3508, 227, 392, 204, 3502, 174, 395, 150, 428, 181, 439, 168, 202, 151, 161, 195, 159, 262, 179, 434, 349, 415, 219, 276, 3509, 208, 169, 3510, 243, 248, 241, 375, 448, 417, 444, 196, 352, 403, 420, 354, 387, 419, 200, 486, 421, 266, 156, 476, 398, 344, 3516, 430, 389, 489, 3511, 226, 492, 367, 473, 399, 281, 423, 282, 347, 404, 411, 379, 400, 224, 371, 3517, 435, 383, 472, 362, 206, 445, 368, 364, 416, 432, 284, 348, 370, 456, 469, 396, 192, 264, 236, 438, 143, 157, 3010, 239, 327, 388, 255, 217, 3512, 193, 183, 410, 431, 189, 3503, 245, 273, 201, 3504, 203, 164, 176, 488, 194, 429, 155, 437, 279, 425, 207, 443, 343, 304, 325, 372, 182, 477, 254, 308, 345, 178, 397, 441,427, 146, 418, 186, 212, 221, 275, 346, 269, 289, 148, 3012, 278, 440, 138, 238, 475, 153, 378, 166, 487, 145, 265, 468, 191, 3001, 229, 197, 454, 424, 446, 247, 3505, 306, 233, 455, 3513, 3004, 210, 390, 483, 491, 213, 286, 141, 453, 3518, 463, and 470.

In some embodiments, a compound of Formula (I) or Formula (I') is selected from compound 152, 283, 373, 209, 355, 382, 391, 377, 381, 380, 185, 177, 149, 162, 274, 285, 139, 198, 402, 256, 401, 288, 173, 407, 374, 406, 393, 242, 305, 230, 232, 246, 464, 385, 394, 409, 433, 365, 170, 167, 376, 386, 160, 225, 361, 414, 422, 332, 154, 405, 366, 363, 172, 384, 359, 3514, 187, 447, 360, 147, 3515, 357, 353, 351, 158, 350, 3508, 227, 392, 204, 3502, 174, 395, 150, 428, 181, 439, 168, 202, 151, 161, 195, 159, 262, 179, 434, 349, 415, 219, 276, 3509, 208, 169, 3510, 243, 248, 241, 375, 448, 417, 444, 196, 352, 403, 420, 354, 387, 419, 200, 486, 421, 266, 156, 476, 398, 344, 3516, 430, 389, 489, 3511, 226, 492, 367, 473, 399, 281, 423, 282, 347, 404, 411, 379, 400, 224, 371, 3517, 435, 383, 472, 362, 206, 445, 368, 364, 416, 432, 284, 348, 370, 456, 469, 396, 192, 264, 236, 438, 143, 157, 3010, 239, 327, 388, 255, 217, 3512, 193, 183, 410, 431, 189, 3503, 245, and 273.

In some embodiments, a compound of Formula (I) or Formula (I') is selected from compound 152, 283, 373, 209, 355, 382, 391, 377, 381, 380, 185, 177, 149, 162, 274, 285, 139, 198, 402, 256, 401, 288, 173, 407, 374, 406, 393, 242, 305, 230, 232, 246, 464, 385, 394, 409, 433, 365, 170, 167, 376, 386, 160, 225, 361, 414, 422, 332, 154, 405, 366, 363, 172, 384, 359, 3514, 187, 447, 360, 147, 3515, 357, 353, 351, 158, 350, 3508, 227, 392, 204, 3502, 174, 395, 150, 428, and 181.

In one aspect, disclosed herein is a compound represented by Formula (I-ep):

(I-ep)

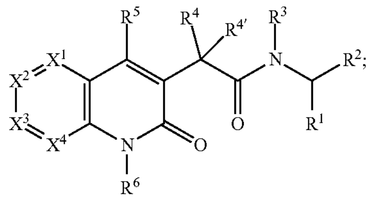

or a salt thereof, wherein:

$X^1$ is selected from C(R) and N;

$X^2$ is selected from C(R) and N;

$X^3$ is selected from C(R) and N;

$X^4$ is selected from C(R) and N;

wherein at least one of $X^1$, $X^2$, and $X^3$ is N and no more than two of $X^1$, $X^2$, and $X^3$ are N;

$X^4$ is selected from C(R);

each R is independently selected from:

hydrogen; halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; and $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{1-6}$ haloalkyl, and $C_{1-6}$ alkyl;

$R^1$ is selected from:

hydrogen;

$C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{1-6}$ alkyl, and $C_{1-6}$ haloalkyl; or $R^1$ together with $R^2$ form a $C_{3-10}$ carbocycle, or 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl;

$R^2$ is selected from:

hydrogen;

$C_{1-6}$ alkyl, $C_{2-6}$ alkenyl, and $C_{2-6}$ alkynyl, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{1-6}$alkyl, and $C_{1-6}$ haloalkyl; or $R^1$ together with $R^2$ form a $C_{3-10}$ carbocycle, or 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, and $C_{1-6}$ alkyl;

$R^3$ is selected from:

hydrogen;

$R^4$ is selected from:

hydrogen, halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$;

$C_{1-6}$ alkyl optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$C_{3-10}$ carbocycle and 3- to 10-membered heterocycle, wherein the $C_{3-10}$ carbocycle and 3- to 10-membered heterocycle are each optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$R^{4'}$ is selected from:

hydrogen, halogen;

$C_{1-3}$ alkyl optionally substituted with one or more substituents independently selected from halogen, —CN, —OH, —O($C_{1-3}$ alkyl), —O($C_{1-3}$ haloalkyl), —$NH_2$, —NH($C_{1-6}$ alkyl), and —N($C_{1-6}$ alkyl)$_2$;

$C_{3-10}$ carbocycle and 3- to 10-membered heterocycle, wherein the $C_{3-10}$ carbocycle and 3- to 10-membered heterocycle are each optionally substituted with one or more substituents independently selected from halogen, —CN, —OH, —O($C_{1-3}$ alkyl), —O($C_{1-3}$ haloalkyl), —$NH_2$, —NH($C_{1-6}$ alkyl), and —N($C_{1-6}$ alkyl)$_2$;

or $R^4$ and $R^{4'}$ together form a form a $C_{3-10}$ carbocycle or 3- to 10-membered heterocycle, each of which is optionally substituted with one or more substituents independently selected from: halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl;

$R^5$ is selected from:

hydrogen, halogen, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, —$NO_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$R^6$ is selected from:

hydrogen.

In one aspect, disclosed herein is a compound represented by Formula (II):

or a salt thereof, wherein:

(II)

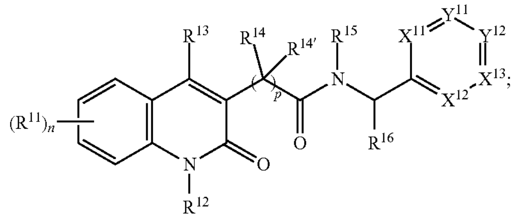

n is 1, 2, 3, or 4;

p is 1, 2, or 3;

$X^{11}$ is selected from C($R^{17a}$) and N;

$X^{12}$ is selected from C($R^{17b}$) and N;

$X^{13}$ is selected from C($R^{17c}$) and N;

$Y^{11}$ is selected from C($R^{17d}$);

$Y^{12}$ is selected from C($R^{17e}$);

each $R^{11}$ is independently selected from:

halogen, —$NO_2$, —CN, —$N_3$, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —N($R^{19a}$)C(O)N($R^{19a}$)$_2$, —OC(O)N($R^{19a}$)$_2$, —N($R^{19a}$)C(O)O$R^{19a}$, —C(O)O$R^{19a}$, —OC(O)$R^{19a}$, —S(O)$R^{19a}$, and —S(O)$_2R^{19a}$;

$C_{1-6}$ alkyl, $C_{2-6}$ alkenyl, and $C_{2-6}$ alkynyl, each of which is optionally substituted with one or more substituents independently selected from halogen, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —C(O)O$R^{19a}$, —OC(O)$R^{19a}$, —N($R^{19a}$)C(O)N($R^{19a}$)$_2$, —OC(O)N($R^{19a}$)$_2$, —N($R^{19a}$)C(O)O$R^{19a}$, —S(O)$R^{19a}$, —S(O)$_2R^{19a}$, —$NO_2$, =O, =S, =N($R^{19a}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{18a}$; and $C_{3-10}$ carbocycle and 3- to 10-membered heterocycle, each of which is optionally substituted with one or more substituents independently selected from halogen, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —N($R^{19a}$)C(O)N($R^{19a}$)$_2$, —OC(O)N($R^{19a}$)$_2$, —N($R^{19a}$)C(O)O$R^{19a}$, —C(O)O$R^{19a}$, —OC(O)$R^{19a}$, —S(O)$R^{19a}$, —S(O)$_2R^{19a}$, —$NO_2$, =O—, =S, =N($R^{19a}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{18a}$;

$R^{12}$ is selected from:

hydrogen, halogen, —$NO_2$, —$N_3$, —CN, —$OR^{19b}$, —$SR^{19b}$, —N($R^{19b}$)$_2$, —C(O)$R^{19b}$, —C(O)N($R^{19b}$)$_2$, —N($R^{19b}$)C(O)$R^{19b}$, —N($R^{19b}$)C(O)N($R^{19b}$)$_2$, —OC(O)N($R^{19b}$)$_2$, —N($R^{19b}$)C(O)O$R^{19b}$, —C(O)O$R^{19b}$, —OC(O)$R^{19b}$, —S(O)$R^{19b}$, and —S(O)$_2R^{19b}$;

$C_{1-6}$ alkyl, $C_{2-6}$ alkenyl, and $C_{2-6}$ alkynyl, each of which is optionally substituted with one or more substituents independently selected from halogen, —$OR^{19b}$, —$SR^{19b}$, —N($R^{19b}$)$_2$, —C(O)$R^{19b}$, —C(O)N($R^{19b}$)$_2$, —N($R^{19b}$)C(O)$R^{19b}$, —C(O)O$R^{19b}$, —OC(O)$R^{19b}$, —N($R^{19b}$)C(O)N($R^{19b}$)$_2$, —OC(O)N($R^{19b}$)$_2$, —N($R^{19b}$)C(O)O$R^{19b}$, —S(O)$R^{19b}$, —S(O)$_2R^{19b}$, —$NO_2$, =O, =S, =N($R^{19b}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{18b}$; and $C_{3-10}$ carbocycle and 3- to 10-membered heterocycle, each of which is optionally substituted with one or more substituents independently selected from halogen, —$OR^{19b}$, —$SR^{19b}$, —N($R^{19b}$)$_2$, —C(O)$R^{19b}$, —C(O)N($R^{19b}$)$_2$, —N($R^{19b}$)C(O)$R^{19b}$, —N($R^{19b}$)C(O)N($R^{19b}$)$_2$, —OC(O)N($R^{19b}$)$_2$, —N($R^{19b}$)C(O)O$R^{19b}$, —C(O)O$R^{19b}$, —OC(O)$R^{19b}$, —S(O)$R^{19b}$, —S(O)$_2R^{19b}$, —$NO_2$, =O—, =S, =N($R^{19b}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{18b}$;

$R^{13}$ is selected from:

hydrogen, halogen, —$OR^{19c}$, —$SR^{19c}$, —N($R^{19c}$)$_2$, —$N_3$, —$NO_2$, and —CN; and $C_{1-6}$ alkyl optionally substituted with one or more substituents independently selected from halogen, —$OR^{19c}$, —$SR^{19c}$, —N($R^{19c}$)$_2$, —$N_3$, —$NO_2$, and —CN; and $C_{3-10}$ carbocycle and 3- to 10-membered heterocycle, each of which is optionally substituted with one or more substituents independently selected from halogen, —$OR^{19c}$, —$SR^{19c}$, —N($R^{19c}$)$_2$, —C(O)$R^{19c}$, —C(O)N($R^{19c}$)$_2$, —N($R^{19c}$)C(O)$R^{19c}$, —N($R^{19c}$)C(O)N($R^{19c}$)$_2$, —OC(O)N($R^{19c}$)$_2$, —N($R^{19c}$)C(O)O$R^{19c}$, —C(O)O$R^{19c}$, —OC(O)$R^{19}$, —S(O)$R^{19c}$, —S(O)$_2R^{19c}$, —$NO_2$, —$N_3$, =O—, =S, =N($R^{19c}$), and —CN;

$R^{14}$ is selected from:

hydrogen, halogen, —$OR^{19d}$, —$SR^{19d}$, —N($R^{19d}$)$_2$, —$N_3$, —$NO_2$, and —CN; and $C_{1-6}$ alkyl which is optionally substituted with one or more substituents independently selected from halogen, —$OR^{19d}$, —$SR^{19d}$, —N($R^{19d}$)$_2$, —$N_3$, —$NO_2$, and —CN; and $C_{3-10}$ carbocycle and 3- to 10-membered heterocycle, each of which is optionally substituted with one or more substituents independently selected from halogen, —$OR^{19d}$, —$SR^{19d}$, —N($R^{19d}$)$_2$, —C(O)$R^{19d}$, —C(O)N($R^{19d}$)$_2$, —N($R^{19d}$)C(O)$R^{19d}$, —N($R^{19d}$)C(O)N($R^{19d}$)$_2$, —OC(O)N($R^{19d}$)$_2$, —N($R^{19d}$)C(O)O$R^{19d}$, —C(O)O$R^{19d}$, —OC(O)$R^{19d}$, —S(O)$R^{19d}$, —S(O)$_2R^{19d}$, —$NO_2$, —$N_3$, =O—, =S, =N($R^{19d}$), and —CN; or $R^{13}$ together with $R^{14}$ form a $C_{3-10}$ carbocycle, or 3- to 10-membered heterocycle, wherein the $C_{3-10}$ carbocycle, or 3- to 10-membered heterocycle, is optionally substituted with one or more $R^{18c}$;

$R^{14'}$ is selected from:

hydrogen, halogen, —$OR^{19d}$, —$SR^{19d}$, —N($R^{19d}$)$_2$, —$N_3$, —$NO_2$, and —CN; and $C_{1-6}$ alkyl which is optionally substituted with one or more substituents independently selected from halogen, —$OR^{19d}$, —$SR^{19d}$, —$N(R^{19d})_2$, —$N_3$, —$NO_2$, and —CN; and $C_{3-10}$ carbocycle and 3- to 10-membered heterocycle, each of which is optionally substituted with one or more substituents independently selected from halogen, —$OR^{19d}$, —$SR^{19d}$, —$N(R^{19d})_2$, —$C(O)R^{19d}$, —$C(O)N(R^{19d})_2$, —$N(R^{19d})C(O)R^{19d}$, —$N(R^{19d})C(O)N(R^{19d})_2$, —$OC(O)N(R^{19d})_2$, —$N(R^{19d})C(O)OR^{19d}$, —$C(O)OR^{19d}$, —$OC(O)R^{19d}$, —$S(O)R^{19d}$, —$S(O)_2R^{19d}$, —$NO_2$, —$N_3$, ═O—, ═S, ═$N(R^{19d})$, and —CN; or $R^{13}$ together with $R^{14'}$ form a $C_{3-10}$ carbocycle, or 3- to 10-membered heterocycle, wherein the $C_{3-10}$ carbocycle, or 3- to 10-membered heterocycle, is optionally substituted with one or more $R^{18c}$;

$R^{15}$ is selected from:

hydrogen, halogen, —$OR^{19e}$, —$SR^{19e}$, —$N(R^{19e})_2$, —$N_3$, —$NO_2$, and —CN; and $C_{1-6}$ alkyl optionally substituted with one or more $R^{18d}$; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$;

$R^{16}$ is selected from:

hydrogen, halogen, —$OR^{19f}$, —$SR^{19f}$, —$N(R^{19f})_2$, —$N_3$, —$NO_2$, and —CN; and $C_{1-6}$ alkyl optionally substituted with one or more $R^{18d}$; or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$;

each $R^{17a}$ is independently selected from:

hydrogen, halogen, —$OR^{19g}$, —$SR^{19g}$, —$N(R^{19g})_2$, —$N_3$, —$NO_2$, —CN, —$N_3$; and $C_{1-6}$ alkyl, $C_{2-6}$ alkenyl, and $C_{2-6}$ alkynyl, each of which is optionally substituted with one or more $R^{18f}$; or $R^{15}$ together with $R^{17a}$ form a 3- to 10-membered heterocycle, wherein the 3- to 10-membered heterocycle is optionally substituted with one or more $R^{18f}$; or $R^{16}$ together with $R^{17a}$ form a 3- to 10-membered heterocycle, wherein the 3- to 10-membered heterocycle is optionally substituted with one or more $R^{18f}$;

each $R^{17b}$ is independently selected from:

hydrogen, halogen, —$OR^{19g}$, —$SR^{19g}$, —$N(R^{19g})_2$, —$N_3$, —$NO_2$, —CN, —$N_3$; and $C_{1-6}$ alkyl, $C_{2-6}$ alkenyl, and $C_{2-6}$ alkynyl, each of which is optionally substituted with one or more $R^{18f}$; or $R^5$ together with $R^{17b}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$;

each $R^{17c}$ is independently selected from:

hydrogen, halogen, —$OR^{19g}$, —$SR^{19g}$, —$N(R^{19g})_2$, —$N_3$, —$NO_2$, —CN, —$N_3$; and $C_{1-6}$ alkyl, $C_{2-6}$ alkenyl, and $C_{2-6}$ alkynyl, each of which is optionally substituted with one or more $R^{18f}$;

each $R^{17d}$ is independently selected from:

hydrogen, halogen, —$OR^{19g}$, —$SR^{19g}$, —$N(R^{19g})_2$, —$N_3$, —$NO_2$, —CN, —$N_3$; and $C_{1-6}$ alkyl, $C_{2-6}$ alkenyl, and $C_{2-6}$ alkynyl, each of which is optionally substituted with one or more $R^{18f}$;

each $R^{17e}$ is independently selected from:

hydrogen, halogen, —$OR^{19g}$, —$SR^{19g}$, —$N(R^{19g})_2$, —$N_3$, —$NO_2$, —CN, —$N_3$; and $C_{1-6}$ alkyl, $C_{2-6}$ alkenyl, and $C_{2-6}$ alkynyl, each of which is optionally substituted with one or more $R^{18f}$.

each $R^{18a}$ is independently selected from:

halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$N_3$, —$NO_2$, ═O, ═S, ═$N(R^{19h})$, and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$N_3$, —$NO_2$, ═O, ═S, ═$N(R^{19h})$, and —CN;

each $R^{18b}$ is independently selected from:

halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19}$, —$S(O)R^{19h}$, —$S(O)_2R^{19h}$, —$NO_2$, —$N_3$, ═O, ═S, ═$N(R^{19h})$, and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, —$N_3$, ═O, ═S, ═$N(R^{19h})$, and —CN;

each $R^{18c}$ is independently selected from:

halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, —$N_3$, ═O, ═S, ═$N(R^{19h})$, and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, —$N_3$, ═O, ═S, ═$N(R^{19h})$, and —CN;

each $R^{18d}$ is independently selected from:

halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, —$N_3$, =O, =S, =$N(R^{19h})$, and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, —$N_3$, =O, =S, =$N(R^{19h})$, and —CN;

each $R^{18e}$ is independently selected from:

halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, —$N_3$, =O, =S, =$N(R^{19h})$, and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, —$N_3$, =O, =S, =$N(R^{19h})$, and —CN;

each $R^{18f}$ is independently selected from:

halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, $C(O)OR^{19h}$, —$OC(O)R^{19h}$, —$S(O)R^{19h}$, —$S(O)_2R^{19h}$, —$NO_2$, =O, =S, =$N(R^{19h})$, and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, —$N_3$, =O, =S, =$N(R^{19h})$, and —CN;

each $R^{19a}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{19b}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{19c}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{19d}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, —$N_3$, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$alkynyl, $C_{3-10}$ carbocycle, 3- to 10-membered heterocycle, and $C_{1-6}$haloalkyl;

each $R^{19e}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —$N_3$, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$alkynyl, $C_{3-10}$ carbocycle, 3- to 10-membered heterocycle, and $C_{1-6}$ haloalkyl;

each $R^{19f}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, —$N_3$, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{19g}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, —$N_3$, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; and each $R^{19h}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, —$N_3$, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$haloalkyl;

wherein when at least one $R^{11}$ is OMe, then:

$R^{16}$ is selected from:

halogen, —$OR^{19f}$, —$SR^{19f}$, —N($R^{19f}$)$_2$, —$N_3$, —$NO_2$, and —CN; and $C_{1-6}$ alkyl optionally substituted with one or more $R^{18c}$; or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$;

$R^{15}$ and $R^{17a}$ do not come together to form a ring;

$R^{15}$ and $R^{17b}$ do not come together to form a ring;

$R^{16}$ and $R^{17a}$ do not come together to form a ring; and $R^{16}$ and $R^{17b}$ do not come together to form a ring.

In one aspect, disclosed herein is a compound represented by Formula (II):

(II)

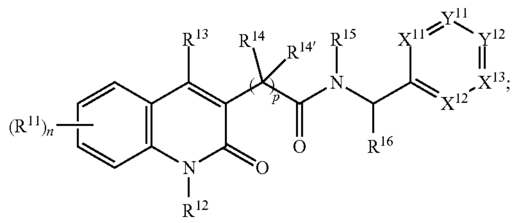

or a salt thereof, wherein:

n is 1, 2, 3, or 4;

p is 1;

$X^{11}$ is selected from C($R^{17a}$) and N;

$X^{12}$ is selected from C($R^{17b}$) and N;

$X^{13}$ is selected from C($R^{17c}$) and N;

$Y^{11}$ is selected from C($R^{17d}$);

$Y^{12}$ is selected from C($R^{17e}$);

each $R^{11}$ is independently selected from:

halogen, —$NO_2$, —CN, —$N_3$, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —N($R^{19a}$)C(O)N($R^{19a}$)$_2$, —OC(O)N($R^{19a}$)$_2$, —N($R^{19a}$)C(O)O$R^{19a}$, —C(O)O$R^{19a}$, —OC(O)$R^{19a}$, —S(O)$R^{19a}$, and —S(O)$_2R^{19a}$;

$C_{1-6}$ alkyl, $C_{2-6}$ alkenyl, and $C_{2-6}$ alkynyl, each of which is optionally substituted with one or more substituents independently selected from halogen, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —C(O)O$R^{19a}$, —OC(O)$R^{19a}$, —N($R^{19a}$)C(O)N($R^{19a}$)$_2$, —OC(O)N($R^{19a}$)$_2$, —N($R^{19a}$)C(O)O$R^{19a}$, —S(O)$R^{19a}$, —S(O)$_2R^{19a}$, —$NO_2$, =O, =S, =N($R^{19a}$), —CN, $C_{3-10}$ carbocycle and 3- to 10-membered heterocycle, wherein the $C_{3-10}$ carbocycle and 3- to 10-membered heterocycle are each optionally substituted with one or more $R^{18a}$; and $C_{3-10}$ carbocycle and 3- to 10-membered heterocycle, each of which is optionally substituted with one or more substituents independently selected from halogen, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —N($R^{19a}$)C(O)N($R^{19a}$)$_2$, —OC(O)N($R^{19a}$)$_2$, —N($R^{19a}$)C(O)O$R^{19a}$, —C(O)O$R^{19a}$, —OC(O)$R^{19a}$, —S(O)$R^{19a}$, —S(O)$_2R^{19a}$, —$NO_2$, =O—, =S, =N($R^{19a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{18a}$.

$R^{12}$ is selected from:

hydrogen, halogen, —$NO_2$, —CN, —$OR^{19b}$, —$SR^{19b}$, —N($R^{19b}$)$_2$, —C(O)$R^{19b}$, —C(O)N($R^{19b}$)$_2$, —N($R^{19b}$)C(O)$R^{19b}$, —N($R^{19b}$)C(O)N($R^{19b}$)$_2$, —OC(O)N($R^{19b}$)$_2$, —N($R^{19b}$)C(O)O$R^{19b}$, —C(O)O$R^{19b}$, —OC(O)$R^{19b}$, —S(O)$R^{19b}$, and —S(O)$_2R^{19b}$;

$C_{1-6}$ alkyl, $C_{2-6}$ alkenyl, and $C_{2-6}$ alkynyl, each of which is optionally substituted with one or more substituents independently selected from halogen, —$OR^{19b}$, —$SR^{19b}$, —N($R^{19b}$)$_2$, —C(O)$R^{19b}$, —C(O)N($R^{19b}$)$_2$, —N($R^{19b}$)C(O)$R^{19b}$, —C(O)

$OR^{19b}$, —OC(O)$R^{19b}$, —N($R^{19b}$)C(O)N($R^{19b}$)$_2$, —OC(O)N($R^{19b}$)$_2$, —N($R^{19b}$)C(O)O$R^{19b}$, —S(O)$R^{19b}$, —S(O)$_2R^{19b}$, —$NO_2$, =O, =S, =N($R^{19b}$), —CN, $C_{3-10}$ carbocycle and 3- to 10-membered heterocycle, wherein the $C_{3-10}$ carbocycle and 3- to 10-membered heterocycle are each optionally substituted with one or more $R^{18b}$; and $C_{3-10}$ carbocycle and 3- to 10-membered heterocycle, each of which is optionally substituted with one or more substituents independently selected from halogen, —$OR^{19b}$, —$SR^{19b}$, —N($R^{19b}$)$_2$, —C(O)$R^{19b}$, —C(O)N($R^{19b}$)$_2$, —N($R^{19b}$)C(O)$R^{19b}$, —N($R^{19b}$)C(O)N($R^{19b}$)$_2$, —OC(O)N($R^{19b}$)$_2$, —N($R^{19b}$)C(O)O$R^{19b}$, —C(O)O$R^{19b}$, —OC(O)$R^{19b}$, —S(O)$R^{19b}$, —S(O)$_2R^{19b}$, —$NO_2$, =O—, =S, =N($R^{19b}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{18b}$;

$R^{13}$ is selected from:

hydrogen, halogen, —$OR^{19c}$, —$SR^{19c}$, —N($R^{19c}$)$_2$, —$NO_2$, and —CN; and $C_{1-6}$ alkyl optionally substituted with one or more substituents independently selected from halogen, —$OR^{19c}$, —$SR^{19c}$, —N($R^{19c}$)$_2$, —$NO_2$, and —CN; and $C_{3-10}$ carbocycle and 3- to 10-membered heterocycle, each of which is optionally substituted with one or more substituents independently selected from halogen, —$OR^{19c}$, —$SR^{19c}$, —N($R^{19c}$)$_2$, —C(O)$R^{19c}$, —C(O)N($R^{19c}$)$_2$, —N($R^{19c}$)C(O)$R^{19c}$, —N($R^{19c}$)C(O)N($R^{19c}$)$_2$, —OC(O)N($R^{19c}$)$_2$, —N($R^{19c}$)C(O)O$R^{19c}$, —C(O)O$R^{19c}$, —OC(O)$R^{19c}$, —S(O)$R^{19c}$, —S(O)$_2R^{19c}$, —$NO_2$, =O—, =S, =N($R^{19c}$), and —CN;

$R^{14}$ is selected from:

hydrogen, halogen, —$OR^{19d}$, —$SR^{19d}$, —N($R^{19d}$)$_2$, —$NO_2$, and —CN; and $C_{1-6}$ alkyl which is optionally substituted with one or more substituents independently selected from halogen, —$OR^{19d}$, —$SR^{19d}$, —N($R^{19d}$)$_2$, —$NO_2$, and —CN; and $C_{3-10}$ carbocycle and 3- to 10-membered heterocycle, each of which is optionally substituted with one or more substituents independently selected from halogen, —$OR^{19d}$, —$SR^{19d}$, —N($R^{19d}$)$_2$, —C(O)$R^{19d}$, —C(O)N($R^{19d}$)$_2$, —N($R^{19d}$)C(O)$R^{19d}$, —N($R^{19d}$)C(O)N($R^{19d}$)$_2$, —OC(O)N($R^{19d}$)$_2$, —N($R^{19d}$)C(O)O$R^{19d}$, —C(O)O$R^{19d}$, —OC(O)$R^{19d}$, —S(O)$R^{19d}$, —S(O)$_2R^{19d}$, —$NO_2$, =O—, =S, =N($R^{19d}$), and —CN; or $R^{13}$ together with $R^{14}$ form a $C_{3-10}$ carbocycle, or 3- to 10-membered heterocycle, wherein the $C_{3-10}$ carbocycle, or 3- to 10-membered heterocycle, is optionally substituted with one or more $R^{18c}$;

$R^{14'}$ is selected from:

hydrogen, halogen, —$OR^{19d}$, —$SR^{19d}$, —N($R^{19d}$)$_2$, —$NO_2$, and —CN; and $C_{1-6}$ alkyl which is optionally substituted with one or more substituents independently selected from halogen, —$OR^{19d}$, —$SR^{19d}$, —N($R^{19d}$)$_2$, —$NO_2$, and —CN; and $C_{3-10}$ carbocycle and 3- to 10-membered heterocycle, each of which is optionally substituted with one or more substituents independently selected from halogen, —$OR^{19d}$, —$SR^{19d}$, —N($R^{19d}$)$_2$, —C(O)$R^{19d}$, —C(O)N($R^{19d}$)$_2$, —N($R^{19d}$)C(O)$R^{19d}$, —N($R^{19d}$)C(O)N($R^{19d}$)$_2$, —OC(O)N($R^{19d}$)$_2$, —N($R^{19d}$)C(O)O$R^{19d}$, —C(O)O$R^{19d}$, —OC(O)$R^{19d}$, —S(O)$R^{19d}$, —S(O)$_2R^{19d}$, —$NO_2$, =O—, =S, =N($R^{19d}$), and —CN; or $R^{13}$ together with $R^{14'}$ form a $C_{3-10}$ carbocycle, or 3- to 10-membered heterocycle, wherein the $C_{3-10}$ carbocycle, or 3- to 10-membered heterocycle, is optionally substituted with one or more $R^{18c}$;

$R^{15}$ is selected from:

hydrogen, halogen, —$OR^{19e}$, —$SR^{19e}$, —N($R^{19e}$)$_2$, —$NO_2$, and —CN; and $C_{1-6}$ alkyl optionally substituted with one or more $R^{18d}$; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$.

$R^{16}$ is selected from:

hydrogen, halogen, —$OR^{19f}$, —$SR^{19f}$—N($R^{19f}$)$_2$, —$NO_2$, and —CN; and $C_{1-6}$ alkyl optionally substituted with one or more $R^{18e}$; or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$;

each $R^{17a}$, $R^{17b}$, $R^{17c}$, $R^{17d}$, and $R^{17e}$ is independently selected from:

hydrogen, halogen, —$OR^{19g}$, —$SR^{19g}$, —N($R^{19g}$)$_2$, —$NO_2$, —CN, —$N_3$; and $C_{1-6}$ alkyl, $C_{2-6}$ alkenyl, and $C_{2-6}$ alkynyl, each of which is optionally substituted with one or more $R^{18f}$; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{17a}$ form a 3- to 10-membered heterocycle, wherein the 3- to 10-membered heterocycle is optionally substituted with one or more $R^{18f}$;

$R^{16}$ together with $R^{17b}$ form a 3- to 10-membered heterocycle, wherein the 3- to 10-membered heterocycle is optionally substituted with one or more $R^{18f}$; each $R^{18a}$ is independently selected from:

halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2R^{19h}$, —$NO_2$, =O, =S, =N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)

$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN;

each $R^{18b}$ is independently selected from:

halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN;

each $R^{18c}$ is independently selected from:

halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN;

each $R^{18d}$ is independently selected from:

halogen, —$OR^{19h}$, —$SR^{19h}$, N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN;

each $R^{18e}$ is independently selected from:

halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN;

each $R^{18f}$ is independently selected from:

halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN;

each $R^{19a}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$alkynyl, $C_{3-10}$ carbocycle, 3- to 10-membered heterocycle, and $C_{1-6}$ haloalkyl;

each $R^{19b}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{19e}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{19d}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$alkynyl, $C_{3-10}$ carbocycle, 3- to 10-membered heterocycle, and $C_{1-6}$ haloalkyl;

each $R^{19e}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$alkenyl, $C_{2-6}$ alkynyl, $C_{3-10}$ carbocycle, 3- to 10-membered heterocycle, and $C_{1-6}$ haloalkyl;

each $R^{19f}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_1$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{19g}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; and each $R^{19h}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$haloalkyl;

wherein when at least one $R^{11}$ is OMe, then $R^{16}$ is not hydrogen;

$R^{15}$ and $R^{17a}$ do not come together to form a ring;

$R^{15}$ and $R^{17b}$ do not come together to form a ring;

$R^{16}$ and $R^{17a}$ do not come together to form a ring; and $R^{16}$ and $R^{17b}$ do not come together to form a ring;

wherein when $R^{16}$ is selected from: halogen, —$OR^{19f}$, —$SR^{19f}$ —N($R^{19f}$)$_2$, —$NO_2$, and —CN; and $C_{1-6}$ alkyl optionally substituted with one or more $R^{18c}$; then $Y^{11}$ is additionally selected from N; and $Y^{12}$ is additionally selected from N;

wherein when $R^{16}$ together with $R^{17a}$ form a 3- to 10-membered heterocycle, wherein the 3- to 10-membered heterocycle is optionally substituted with one or more $R^{18f}$; then $Y^{11}$ is additionally selected from N; and $Y^{12}$ is additionally selected from N; and wherein when $R^{16}$ together with $R^{17b}$ form a 3- to 10-membered heterocycle, wherein the 3- to 10-membered heterocycle is optionally substituted with one or more $R^{18f}$; then $Y^{11}$ is additionally selected from N; and $Y^{12}$ is additionally selected from N.

In some embodiments, a compound of Formula (II) or Formula (II'), the variables n and p can each be any suitable variable known by one of skill in the art. In some embodiments, n is 1, 2, 3, or 4. In some embodiments, n is 0, 1, 2, 3, or 4. In some embodiments, n is 1, 2, or 3. In some embodiments, n is 1. In some embodiments, n is 2. In some embodiments, n is 3. In some embodiments, n is 4. In some embodiments, n is 1 or 2. In some embodiments, n is 0 or 1. In some embodiments, n is 0 or 2. In some embodiments, n is 0 or 3. In some embodiments, n is 0 or 4. In some embodiments, n is 1 or 2. In some embodiments, n is 1 or 3. In some embodiments, n is 1 or 4. In some embodiments, n is 2 or 3. In some embodiments, n is 2 or 4. In some embodiments, n is 3 or 4. In some embodiments, n is 0, 1, or 2. In some embodiments, n is 0, 1, or 3. In some embodiments, n is 0, 1, or 4. In some embodiments, n is 0, 2, or 3. In some embodiments, n is 0, 2, or 4. In some embodiments, n is 0, 3, or 4. In some embodiments, n is 1, 2 or 3. In some embodiments, n is 1, 2 or 4. In some embodiments, n is 2, 3, or 4. In some embodiments, n is 0, 1, 2, or 3. In some embodiments, n is 0, 1, 2, or 4. In some embodiments, n is 1, 2, 3, or 4. In some embodiments, p is 1. In some embodiments, p is 0. In some embodiments, p is 2. In some embodiments, p is 3. In some embodiments, p is 0 or 1. In some embodiments, p is 0 or 2. In some embodiments, p is 0 or 3. In some embodiments, p is 1 or 2. In some embodiments, p is 1 or 3. In some embodiments, p is 2 or 3. In some embodiments, p is 4. In some embodiments, p is 1 or 4. In some embodiments, p is 1, 2, or 3. In some embodiments, p is 0, 1, or 2. In some embodiments, p is 0, 1, or 3.

In certain embodiments, for a compound or salt of Formula (II) or Formula (II'), each $R^{11}$ is independently selected from halogen, $—NO_2$, $—N_3$, —CN, $—OR^{19a}$, $—SR^{19a}$, $—N(R^{19a})_2$, $—C(O)R^{19a}$; $C_{1-6}$ alkyl, which is optionally substituted with one or more substituents independently selected from halogen, $—OR^{19a}$, $—SR^{19a}$, $—N(R^{19a})_2$, $—C(O)R^{19a}$, $—C(O)N(R^{19a})_2$, $—N(R^{19a})C(O)R^{19a}$, $—C(O)OR^{19a}$, $—OC(O)R^{19a}$, $—N(R^{19a})C(O)N(R^{19a})_2$, $—OC(O)N(R^{19a})_2$, $—N(R^{19a})C(O)OR^{19a}$, $—S(O)R^{19a}$, $—S(O)_2R^{19a}$, $—NO_2$, =O, =S, $=N(R^{19a})$, —CN, $C_{3-10}$ carbocycle and 3- to 10-membered heterocycle; and $C_{3-10}$ carbocycle which is optionally substituted with one or more substituents independently selected from halogen, $—OR^{19a}$, $—SR^{19a}$, $—N(R^{19a})_2$, $—C(O)R^{19a}$, $—C(O)N(R^{19a})_2$, $—N(R^{19a})C(O)R^{19a}$, $—N(R^{19a})C(O)N(R^{19a})_2$, $—OC(O)N(R^{19a})_2$, $—N(R^{19a})C(O)OR^{19a}$, $—C(O)OR^{19a}$, $—OC(O)R^{19a}$, $—S(O)R^{19a}$, $—S(O)_2R^{19a}$, $—NO_2$, =O—, =S, $=N(R^{19a})$, —CN, $—N_3$, $C_{1-6}$ alkyl, $C_{2-6}$ alkenyl, and $C_{2-6}$ alkynyl. In some embodiments, each $R^{11}$ is independently selected from halogen, $—N_3$, —CN, $—OR^{19a}$, $—N(R^{19a})_2$, $—C(O)R^{19a}$; $C_{1-6}$ alkyl; and $C_{3-10}$ carbocycle. In some embodiments, each $R^{11}$ is independently selected from: halogen, $—N_3$, —CN, $—OR^{19a}$, $C_{1-6}$ alkyl, and $C_{3-10}$ carbocycle. In some embodiments, each $R^{11}$ is —Cl, —F, —Br, $—N_3$, —CN, —OH, —OMe, methyl, or cyclopropyl. In some embodiments, each $R^{11}$ is independently selected from —Cl, —F, —CN, methyl, and cyclopropyl. In some embodiments, each $R^{11}$ is independently selected from —F, —CN, and methyl. In some embodiments, each $R^{11}$ is independently selected from —F and —CN. In some embodiments, $R^{11}$ is selected from halogen. In some embodiments, $R^{11}$ is selected from halogen, and $Y^{12}$ is selected from C(CN), C(H), and C(F). In some embodiments, $R^{11}$ is selected from halogen, and $Y^{12}$ is selected from C(CN). In some embodiments, $R^{11}$ is selected from halogen, and $Y^{11}$ is selected from C(H). In some embodiments, $R^{11}$ is selected from halogen, and $X^{13}$ is selected from N and C(H). In some embodiments, $R^{11}$ is selected from halogen, and $X^1$ and $X^2$ are N. In some embodiments, $R^{11}$ is selected from halogen, and $X^{11}$ is selected from N, C(H), and C(F). In some embodiments, $R^{11}$ is selected from halogen, and $X^{12}$ is selected from N, C(H), and C(F).

In some embodiments, $R^{11}$ is selected from F. In some embodiments, $R^{11}$ is selected from F, and $Y^{12}$ is selected from C(CN), C(H), and C(F). In some embodiments, $R^{11}$ is selected from F, and $Y^{12}$ is selected from C(CN). In some embodiments, $R^{11}$ is selected from F, and $Y^{11}$ is selected from C(H). In some embodiments, $R^{11}$ is selected from F, and $X^{13}$ is selected from N and C(H). In some embodiments, $R^{11}$ is selected from F, and $X^1$ and $X^2$ are N. In some embodiments, $R^{11}$ is selected from F, and $X^{11}$ is selected from N, C(H), and C(F). In some embodiments, $R^{11}$ is selected from F, and $X^{12}$ is selected from N, C(H), and C(F).

In certain embodiments, for a compound or salt of Formula (II) or Formula (II'), $X^{11}$ is N, $X^{12}$ is N, $X^{13}$ is C(H), $Y^{11}$ is C(H), and $Y^{12}$ is C(CN). In some embodiments, $X^{11}$ is N, $X^{12}$ is N, $X^{13}$ is C(H), $Y^{11}$ is C(H), and $Y^{12}$ is C(CN), and $R^{16}$ is optionally substituted $C_1$ alkyl. In some embodiments, $X^{11}$ is N, $X^{12}$ is N, $X^{13}$ is C(H), $Y^{11}$ is C(H), and $Y^{12}$ is C(CN), and $R^{16}$ ia $—CH_3$. In some embodiments, $X^{11}$ is N, $X^{12}$ is N, $X^{13}$ is C(H), $Y^{11}$ is C(H), and $Y^{12}$ is C(CN), and $R^5$ is H. In some embodiments, $X^{11}$ is N, $X^{12}$ is N, $X^{13}$ is C(H), $Y^{11}$ is C(H), and $Y^{12}$ is C(CN), $R^{14}$ is H, and $R^{14'}$ is H. In some embodiments, $X^{11}$ is N, $X^{12}$ is N, $X^{13}$ is C(H), $Y^{11}$ is C(H), and $Y^{12}$ is C(CN), and $R^{12}$ is H. In some embodiments, $X^{11}$ is N, $X^{12}$ is N, $X^{13}$ is C(H), $Y^{11}$ is C(H), and $Y^{12}$ is C(CN), and $R^{13}$ is selected from $CH_3$, H, and cyclopropyl. In some embodiments, $X^{11}$ is N, $X^{12}$ is N, $X^{13}$ is C(H), $Y^{11}$ is C(H), and $Y^{12}$ is C(CN), and $R^{13}$ is selected from $CH_3$. In some embodiments, $X^{11}$ is N, $X^{12}$ is N, $X^{13}$ is C(H), $Y^{11}$ is C(H), and $Y^{12}$ is C(CN), and $R^{13}$ is selected from cyclopropyl. In some embodiments, $X^{11}$ is N, $X^{12}$ is N, $X^{13}$ is C(H), $Y^{11}$ is C(H), and $Y^{12}$ is C(CN), and $R^{13}$ is selected from H. In some embodiments, $X^{11}$ is N, $X^{12}$ is N, $X^{13}$ is C(H), $Y^{11}$ is C(H), and $Y^{12}$ is C(CN), and $R^{11}$ is selected from $CH_3$, cyclopropyl, F, Cl, Br, $CF_3$, CN, $N_3$, OH, and OMe. In some embodiments, $X^{11}$ is N, $X^{12}$ is N, $X^{13}$ is C(H), $Y^{11}$ is C(H), and $Y^{12}$ is C(CN), and $R^{11}$ is selected from $CH_3$, F, Cl, Br, $CF_3$, and CN. In some embodiments, $X^{11}$ is N, $X^{12}$ is N, $X^{13}$ is C(H), $Y^{11}$ is C(H), and $Y^{12}$ is C(CN), and $R^{11}$ is selected from F, Cl and CN. In some embodiments, $X^{11}$ is N, $X^{12}$ is N, $X^{13}$ is C(H), $Y^{11}$ is C(H), and $Y^{12}$ is C(CN), and $R^{11}$ is selected from F and CN. In some embodiments, $X^{11}$ is N, $X^{12}$ is N, $X^{13}$ is C(H), $Y^{11}$ is C(H), and $Y^{12}$ is C(CN), and $R^{11}$ is selected from F. In some embodiments, $X^{11}$ is N, $X^{12}$ is N, $X^{13}$ is C(H), $Y^{11}$ is C(H), and $Y^{12}$ is C(CN), and $R^{11}$ is selected from CN. In some embodiments, $X^{11}$ is N, $X^{12}$ is N, $X^{13}$ is C(H), $Y^{11}$ is C(H), and $Y^{12}$ is C(CN), and n is 1 or 2. In some embodiments, $X^{11}$ is N, $X^{12}$ is N, $X^{13}$ is C(H), $Y^{11}$ is C(H), and $Y^{12}$ is C(CN), and n is 1. In some embodiments, $X^{11}$ is N, $X^{12}$ is N, $X^{13}$ is C(H), $Y^{11}$ is C(H), and $Y^{12}$ is C(CN), and n is 2. In some embodiments, $X^{11}$ is N, $X^{12}$ is N, $X^{13}$ is C(H), $Y^{11}$ is C(H), and $Y^{12}$ is C(CN), n is 1 or 2, and $R^{11}$ is selected from CN and F. In some embodiments, $X^{11}$ is N, $X^{12}$ is N, $X^{13}$ is C(H), $Y^{11}$ is C(H), and $Y^{12}$ is C(CN), n is 1 or 2, and $R^{11}$ is selected from CN. In some embodiments, $X^{11}$ is N, $X^{12}$ is N, $X^{13}$ is C(H), $Y^{11}$ is C(H), and $Y^{12}$ is C(CN), n is 1 or 2, and $R^{11}$ is selected from CN. In some embodiments, $X^{11}$ is N, $X^{12}$ is N, $X^{13}$ is C(H), $Y^{11}$ is C(H), and $Y^{12}$ is C(CN), n is 1 or 2, and $R^{11}$ is selected from F. In some embodiments, $X^{11}$ is N, $X^{12}$ is N, $X^{13}$ is C(H), $Y^{11}$ is C(H), and $Y^{12}$ is C(CN), n is 2, and $R^{11}$ is selected from CN and F. In some embodiments, $X^{11}$ is N, $X^{12}$ is N, $X^{13}$ is C(H), $Y^{11}$ is C(H), and $Y^{12}$ is C(CN), n is 2, and $R^{11}$ is selected from CN. In some embodiments, $X^1$ is N, $X^{12}$ is N, $X^{13}$ is C(H), $Y^{11}$ is C(H), and $Y^2$ is C(CN), n is 2, and $R^{11}$ is selected from F. In some embodiments, $X^{11}$ is N, $X^{12}$ is C(H), $X^{13}$ is N, $Y^{11}$ is C(H), and $Y^{12}$ is C(CN). In some embodiments, $X^{11}$ is N, $X^{12}$ is C(H), $X^{13}$ is N, $Y^{11}$ is C(H), and $Y^{12}$ is C(CN). In some embodiments, $X^{11}$ is N, $X^{12}$ is C(H), $X^{13}$ is N, $Y^{11}$ is C(H), and $Y^{12}$ is C(CN), and $R^{16}$ is optionally substituted $C_1$ alkyl. In some embodiments, $X^{11}$ is N, $X^{12}$ is C(H), $X^{13}$ is N, $Y^{11}$ is C(H), and $Y^{12}$ is C(CN), and $R^{16}$ ia $—CH_3$. In some embodiments, $X^{11}$ is N, $X^{12}$ is C(H), $X^{13}$ is N, $Y^{11}$ is C(H), and $Y^{12}$ is C(CN), and $R^{15}$ is H. In some embodiments, $X^{11}$ is N, $X^{12}$ is C(H), $X^{13}$ is N, $Y^{11}$ is C(H), and $Y^{11}$ is C(CN), $R^{14}$ is H, and $R^{14}$ is H. In some embodiments, $X^{11}$ is N, $X^{12}$ is C(H), $X^{13}$ is N, $Y^{11}$ is C(H), and $Y^{12}$ is C(CN), and $R^{12}$ is H. In some embodiments, $X^{11}$ is N, $X^{12}$ is C(H), $X^{13}$ is N, $Y^{11}$ is C(H), and $Y^{12}$ is C(CN), and $R^{13}$ is selected from $CH_3$, H, and cyclopropyl. In some embodiments, $X^{11}$ is N, $X^{12}$ is C(H), $X^{11}$ is N, $Y^{11}$ is C(H), and $Y^{12}$ is C(CN), and $R^{13}$ is selected from $CH_3$. In some embodiments, $X^{11}$ is N, $X^{12}$ is C(H), $X^{13}$ is N, $Y^{11}$ is C(H), and $Y^{12}$ is C(CN), and $R^{13}$ is selected from cyclopropyl. In some embodiments, $X^{11}$ is N, $X^{12}$ is C(H), $X^{11}$ is N, $Y^{11}$ is C(H), and $Y^{12}$ is C(CN), and $R^{13}$ is selected from H. In some embodiments, $X^{11}$ is N, $X^{12}$ is C(H), $X^{13}$ is N, $Y^{11}$ is C(H), and $Y^{12}$ is C(CN), and $R^{11}$ is selected from $CH_3$, cyclopropyl, F, Cl, Br, $CF_3$, CN, $N_3$, OH, and OMe. In some embodiments, $X^{11}$ is N, $X^{12}$ is C(H), $X^{13}$ is N, $Y^{11}$ is C(H), and $Y^{12}$ is C(CN), and $R^{11}$ is selected from $CH_3$, F, Cl, Br, $CF_3$, and CN. In some embodiments, $X^{11}$ is N, $X^{12}$ is C(H), $X^{13}$ is N, $Y^{11}$ is C(H), and $Y^{12}$ is C(CN), and $R^{11}$ is selected from F, Cl and CN. In some embodiments, $X^{11}$ is N, $X^{12}$ is C(H), $X^{13}$ is N, $Y^{11}$ is C(H), and $Y^{12}$ is C(CN), and $R^{11}$ is selected from F and CN. In some embodiments, $X^{11}$ is N, $X^{12}$ is C(H), $X^{13}$ is N, $Y^{11}$ is C(H), and $Y^{12}$ is C(CN), and $R^{11}$ is selected from F. In some embodiments, $X^{11}$ is N, $X^{12}$ is C(H), $X^{13}$ is N, $Y^{11}$ is C(H), and $Y^{12}$ is C(CN), and $R^{11}$ is selected from CN. In some embodiments, $X^{11}$ is N, $X^{12}$ is C(H), $X^{13}$ is N, $Y^{11}$ is C(H), and $Y^{12}$ is C(CN), and n is 1 or 2. In some embodiments, $X^{11}$ is N, $X^{12}$ is C(H), $X^{13}$ is N, $Y^{11}$ is C(H), and $Y^{12}$ is C(CN), and n is 1. In some embodiments, $X^{11}$ is N, $X^{12}$ is C(H), $X^{13}$ is N, $Y^{11}$ is C(H), and $Y^{12}$ is C(CN), and n is 2. In some embodiments, $X^{11}$ is N, $X^{12}$ is C(H), $X^{13}$ is N, $Y^{11}$ is C(H), and $Y^{12}$ is C(CN), n is 1 or 2, and $R^{11}$ is selected from CN and F. In some embodiments, $X^{11}$ is N, $X^{12}$ is C(H), $X^{13}$ is N, $Y^{11}$ is C(H), and $Y^{12}$ is C(CN), n is 1 or 2, and $R^{11}$ is selected from CN. In some embodiments, $X^{11}$ is N, $X^{12}$ is C(H), $X^{13}$ is N, $Y^{11}$ is C(H), and $Y^{12}$ is C(CN), n is 1 or 2, and $R^{11}$ is selected from CN. In some embodiments, $X^{11}$ is N, $X^{12}$ is C(H), $X^{13}$ is N, $Y^{11}$ is C(H), and $Y^{12}$ is C(CN), n is 1 or 2, and $R^{11}$ is selected from F. In some embodiments, $X^{11}$ is N, $X^{12}$ is C(H), $X^{13}$ is N, $Y^{11}$ is C(H), and $Y^{12}$ is C(CN), n is 2, and $R^{11}$ is selected from CN and F. In some embodiments, $X^{11}$ is N, $X^{12}$ is C(H), $X^{13}$ is N, $Y^{11}$ is C(H), and $Y^{12}$ is C(CN), n is 2, and $R^{11}$ is selected from CN. In some embodiments, $X^{11}$ is N, $X^{12}$ is C(H), $X^{13}$ is N, $Y^{11}$ is C(H), and $Y^{12}$ is C(CN), n is 2, and $R^{11}$ is selected from F. In some embodiments, $X^{11}$ is C(F), $X^{12}$ is N, $X^{13}$ is C(H), $Y^{11}$ is C(H), and $Y^{12}$ is C(CN). In some embodiments, $X^{11}$ is C(F), $X^{12}$ is N, $X^{13}$ is C(H), $Y^{11}$ is C(H), and $Y^{12}$ is C(CN). In some embodiments, $X^{11}$ is C(F), $X^{12}$ is N, $X^{13}$ is C(H), $Y^{11}$ is C(H), and $Y^{12}$ is C(CN), and $R^{16}$ is optionally substituted $C_1$ alkyl. In some embodiments, $X^{11}$ is C(F), $X^{12}$ is N, $X^{13}$ is C(H), $Y^{11}$ is C(H), and $Y^{12}$ is C(CN), and $R^{16}$ ia —$CH_3$. In some embodiments, $X^{11}$ is C(F), $X^{12}$ is N, $X^{13}$ is C(H), $Y^{11}$ is C(H), and $Y^{12}$ is C(CN), and $R^{15}$ is H. In some embodiments, $X^{11}$ is C(F), $X^{12}$ is N, $X^{13}$ is C(H), $Y^{11}$ is C(H), and $Y^{12}$ is C(CN), $R^{14}$ is H, and $R^{14'}$ is H. In some embodiments, $X^{11}$ is C(F), $X^{12}$ is N, $X^{13}$ is C(H), $Y^{11}$ is C(H), and $Y^{12}$ is C(CN), and $R^{12}$ is H. In some embodiments, $X^{11}$ is C(F), $X^{12}$ is N, $X^{13}$ is C(H), $Y^{11}$ is C(H), and $Y^{12}$ is C(CN), and $R^{13}$ is selected from $CH_3$, H, and cyclopropyl. In some embodiments, $X^{11}$ is C(F), $X^{12}$ is N, $X^{13}$ is C(H), $Y^{11}$ is C(H), and $Y^{12}$ is C(CN), and $R^{13}$ is selected from $CH_3$. In some embodiments, $X^{11}$ is C(F), $X^{12}$ is N, $X^{13}$ is C(H), $Y^{11}$ is C(H), and $Y^{12}$ is C(CN), and $R^{13}$ is selected from cyclopropyl. In some embodiments, $X^{11}$ is C(F), $X^{12}$ is N, $X^{13}$ is C(H), $Y^{11}$ is C(H), and $Y^{12}$ is C(CN), and $R^{13}$ is selected from H. In some embodiments, $X^{11}$ is C(F), $X^{12}$ is N, $X^{13}$ is C(H), $Y^{11}$ is C(H), and $Y^{12}$ is C(CN), and $R^{11}$ is selected from $CH_3$, cyclopropyl, F, Cl, Br, $CF_3$, CN, $N_3$, OH, and OMe. In some embodiments, $X^{11}$ is C(F), $X^{12}$ is N, $X^{13}$ is C(H), $Y^{11}$ is C(H), and $Y^{12}$ is C(CN), and $R^{11}$ is selected from $CH_3$, F, Cl, Br, $CF_3$, and CN. In some embodiments, $X^{11}$ is C(F), $X^{12}$ is N, $X^{13}$ is C(H), $Y^{11}$ is C(H), and $Y^{12}$ is C(CN), and $R^{11}$ is selected from F, Cl and CN. In some embodiments, $X^{11}$ is C(F), $X^{12}$ is N, $X^{13}$ is C(H), $Y^{11}$ is C(H), and $Y^{12}$ is C(CN), and $R^{11}$ is selected from F and CN. In some embodiments, $X^{11}$ is C(F), $X^{12}$ is N, $X^{13}$ is C(H), $Y^{11}$ is C(H), and $Y^{12}$ is C(CN), and $R^{11}$ is selected from F. In some embodiments, $X^{11}$ is C(F), $X^{12}$ is N, $X^{13}$ is C(H), $Y^{11}$ is C(H), and $Y^{12}$ is C(CN), and $R^{11}$ is selected from CN. In some embodiments, $X^{11}$ is C(F), $X^{12}$ is N, $X^{13}$ is C(H), $Y^{11}$ is C(H), and $Y^{12}$ is C(CN), and n is 1 or 2. In some embodiments, $X^{11}$ is C(F), $X^{12}$ is N, $X^{13}$ is C(H), $Y^{11}$ is C(H), and $Y^{12}$ is C(CN), and n is 1. In some embodiments, $X^{11}$ is C(F), $X^{12}$ is N, $X^{13}$ is C(H), $Y^{11}$ is C(H), and $Y^{12}$ is C(CN), and n is 2. In some embodiments, $X^{11}$ is C(F), $X^{12}$ is N, $X^{13}$ is C(H), $Y^{11}$ is C(H), and $Y^{12}$ is C(CN), n is 1 or 2, and $R^{11}$ is selected from CN and F. In some embodiments, $X^{11}$ is C(F), $X^{12}$ is N, $X^{13}$ is C(H), $Y^{11}$ is C(H), and $Y^{12}$ is C(CN), n is 1 or 2, and $R^{11}$ is selected from CN. In some embodiments, $X^{11}$ is C(F), $X^{12}$ is N, $X^{13}$ is C(H), $Y^{11}$ is C(H), and $Y^{12}$ is C(CN), n is 1 or 2, and $R^{11}$ is selected from CN. In some embodiments, $X^{11}$ is C(F), $X^{12}$ is N, $X^{13}$ is C(H), $Y^{11}$ is C(H), and $Y^{12}$ is C(CN), n is 1 or 2, and $R^{11}$ is selected from F. In some embodiments, $X^{11}$ is C(F), $X^{12}$ is N, $X^{13}$ is C(H), $Y^{11}$ is C(H), and $Y^{12}$ is C(CN), n is 2, and $R^{11}$ is selected from CN and F. In some embodiments, $X^{11}$ is C(F), $X^{12}$ is N, $X^{13}$ is C(H), $Y^{11}$ is C(H), and $Y^{12}$ is C(CN), n is 2, and $R^{11}$ is selected from CN. In some embodiments, $X^{11}$ is C(F), $X^{12}$ is N, $X^{13}$ is C(H), $Y^{11}$ is C(H), and $Y^{12}$ is C(CN), n is 2, and $R^{11}$ is selected from F.

In certain embodiments, for a compound of Formula (II) or Formula (II'),

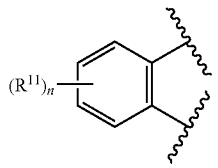

is not

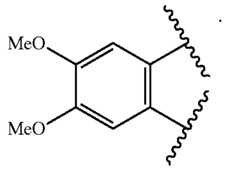 [SMILES: *c1cc(OC)c(OC)cc1*]

In certain embodiments, for a compound of Formula (II) or Formula (II'), n is 1 or 2.

In certain embodiments, for a compound of Formula (II) or Formula (II'), n is 1 or 2; and

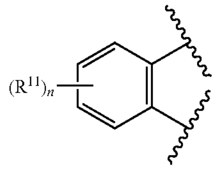

is not

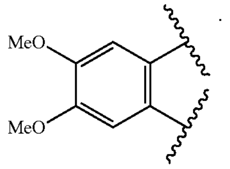 [SMILES: *c1cc(OC)c(OC)cc1*]

In one aspect, disclosed herein is a compound represented by Formula (II-A):

(II-A)

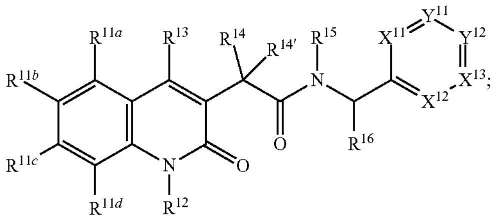

or a salt thereof, wherein:

$X^{11}$ is selected from $C(R^{17a})$ and N;

$X^{12}$ is selected from $C(R^{17b})$ and N;

$X^{13}$ is selected from $C(R^{17c})$ and N;

$Y^{11}$ is selected from $C(R^{17d})$ and N;

$Y^{12}$ is selected from $C(R^{17e})$ and N;

each $R^{11a}$, $R^{11b}$, $R^{11c}$, and $R^{11d}$ is independently selected from:

hydrogen, halogen, —$NO_2$, —CN, —$N_3$, —$OR^{19a}$, —$SR^{19a}$, —$N(R^{19a})_2$, —$C(O)R^{19a}$, —$C(O)N(R^{19a})_2$, —$N(R^{19a})C(O)R^{19a}$, —$N(R^{19a})C(O)N(R^{19a})_2$, —$OC(O)N(R^{19a})_2$, —$N(R^{19a})C(O)OR^{19a}$, —$C(O)OR^{19a}$, —$OC(O)R^{19a}$, —$S(O)R^{19a}$, and —$S(O)_2R^{19a}$;

$C_{1-6}$ alkyl, $C_{2-6}$ alkenyl, and $C_{2-6}$ alkynyl, each of which is optionally substituted with one or more substituents independently selected from halogen, —$OR^{19a}$, —$SR^{19a}$, $N(R^{19a})_2$, —$C(O)R^{19a}$, —$C(O)N(R^{19a})_2$, —$N(R^{19a})C(O)R^{19a}$, —$C(O)OR^{19a}$, $OC(O)R^{19a}$, —$N(R^{19a})C(O)N(R^{19a})_2$, —$OC(O)N(R^{19a})_2$, —$N(R^{19a})C(O)OR^{19a}$, —$S(O)R^{19a}$, —$S(O)_2R^{19a}$, —$NO_2$, =O, =S, =$N(R^{19a})$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{18a}$; and $C_{3-10}$ carbocycle and 3- to 10-membered heterocycle, each of which is optionally substituted with one or more substituents independently selected from halogen, —$OR^{19a}$, —$SR^{19a}$, —$N(R^{19a})_2$, —$C(O)R^{19a}$, —$C(O)N(R^{19a})_2$, —$N(R^{19a})C(O)R^{19a}$, —$N(R^{19a})C(O)N(R^{19a})_2$, —$OC(O)N(R^{19a})_2$, —$N(R^{19a})C(O)OR^{19a}$, —$C(O)OR^{19a}$, —$OC(O)R^{19a}$, —$S(O)R^{19a}$, —$S(O)_2R^{19a}$, —$NO_2$, =O—, =S, =$N(R^{19a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{18a}$;

wherein when $R^{11a}$, $R^{11b}$, and $R^{11}$ are each hydrogen; then $R^{11d}$ is not hydrogen;

wherein when $R^{11b}$ is —$OCH_3$; then $R^{11c}$ is not —OMe;

$R^{12}$ is selected from:

hydrogen, halogen, —$NO_2$, —CN, —$OR^{19b}$, —$SR^{19b}$, —$N(R^{19b})_2$, —$C(O)R^{19b}$, —$C(O)N(R^{19b})_2$, —$N(R^{19b})C(O)R^{19b}$, —$N(R^{19b})C(O)N(R^{19b})_2$, —$OC(O)N(R^{19b})_2$, —$N(R^{19b})C(O)OR^{19b}$, —$C(O)OR^{19b}$, —$OC(O)R^{19b}$, —$S(O)R^{19b}$, and —$S(O)_2R^{19b}$;

$C_{1-6}$ alkyl, $C_{2-6}$ alkenyl, and $C_{2-6}$ alkynyl, each of which is optionally substituted with one or more substituents independently selected from halogen, —$OR^{19b}$, —$SR^{19b}$, —$N(R^{19b})_2$, —$C(O)R^{19b}$, —$C(O)N(R^{19b})_2$, —$N(R^{19b})C(O)R^{19b}$, —$C(O)OR^{19b}$, —$OC(O)R^{19b}$, —$N(R^{19b})C(O)N(R^{19b})_2$, —$OC(O)N(R^{19b})_2$, —$N(R^{19b})C(O)OR^{19b}$, —$S(O)R^{19b}$, —$S(O)_2R^{19b}$, —$NO_2$, =O, =S, =$N(R^{19b})$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{18b}$; and $C_{3-10}$ carbocycle and 3- to 10-membered heterocycle, each of which is optionally substituted with one or more substituents independently selected from halogen, —$OR^{19b}$, —$SR^{19b}$, —$N(R^{19b})_2$, —$C(O)R^{19b}$, —$C(O)N(R^{19b})_2$, —$N(R^{19b})C(O)R^{19b}$, —$N(R^{19b})C(O)N(R^{19b})_2$, —$OC(O)N(R^{19b})_2$, —$N(R^{19b})C(O)OR^{19b}$, —$C(O)OR^{19b}$, —$OC(O)R^{19b}$, —$S(O)R^{19b}$, —$S(O)_2R^{19b}$, —$NO_2$, =O—, =S, =$N(R^{19b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{18b}$;

$R^{13}$ is selected from:

hydrogen, halogen, —$OR^{19c}$, —$SR^{19c}$, —$N(R^{19c})_2$, —$NO_2$, and —CN; and $C_{1-6}$ alkyl optionally substituted with one or more substituents independently selected from halogen, —$OR^{19c}$, —$SR^{19c}$, —$N(R^{19c})_2$, —$NO_2$, and —CN; and $C_{3-10}$ carbocycle and 3- to 10-membered heterocycle, each of which is optionally substituted with one or more substituents independently selected from halogen, —$OR^{19c}$, —$SR^{19c}$, —$N(R^{19c})_2$, —$C(O)R^{19c}$, —$C(O)N(R^{19c})_2$, —$N(R^{19c})C(O)R^{19c}$, —$N(R^{19c})C(O)N(R^{19c})_2$, —$OC(O)N(R^{19c})_2$, —$N(R^{19c})C(O)OR^{19c}$, —$C(O)OR^{19c}$, —$OC(O)R^{19}$, —$S(O)R^{19c}$, —$S(O)_2R^{19c}$, —$NO_2$, and —CN;

$R^{14}$ is selected from:

hydrogen, halogen, —$OR^{19d}$, —$SR^{19d}$, —$N(R^{19d})_2$, —$NO_2$, and —CN; and $C_{1-6}$ alkyl which is optionally substituted with one or more substituents independently selected from halogen, —$OR^{19d}$, —$SR^{19d}$, —$N(R^{19d})_2$, —$NO_2$, and —CN; and $C_{3-10}$ carbocycle and 3- to 10-membered heterocycle, each of which is optionally substituted with one or more substituents independently selected from halogen, —$OR^{19d}$, —$SR^{19d}$, —$N(R^{19d})_2$, —$C(O)R^{19d}$, —$C(O)N(R^{19d})_2$, —$N(R^{19d})C(O)R^{19d}$, —$N(R^{19d})C(O)N(R^{19d})_2$, —$OC(O)N(R^{19d})_2$, —$N(R^{19d})C(O)OR^{19d}$, —$C(O)OR^{19d}$, —$OC(O)R^{19d}$, —$S(O)R^{19d}$, —$S(O)_2R^{19d}$, —$NO_2$, =O—, =S, =$N(R^{19d})$, and —CN;

$R^{14'}$ is selected from:

hydrogen, halogen, —$OR^{19d}$, —$SR^{19d}$, —$N(R^{19d})_2$, —$NO_2$, and —CN; and $C_{1-6}$ alkyl which is optionally substituted with one or more substituents independently selected from halogen, —$OR^{19d}$, —$SR^{19d}$, —$N(R^{19d})_2$, —$NO_2$, and —CN; and $C_{3-10}$ carbocycle and 3- to 10-membered heterocycle, each of which is optionally substituted with one or more substituents independently selected from halogen, —$OR^{19d}$, —$SR^{19d}$, —$N(R^{19d})_2$, —$C(O)R^{19d}$, —$C(O)N(R^{19d})_2$, —$N(R^{19d})C(O)R^{19d}$, —$N(R^{19d})C(O)N(R^{19d})_2$, —$OC(O)N(R^{19d})_2$, —$N(R^{19d})C(O)

$OR^{19d}$, —C(O)$OR^{19d}$, —OC(O)$R^{19d}$, —S(O)$R^{19d}$, —S(O)$_2R^{19d}$, —$NO_2$, =O—, =S, =N($R^{19d}$), and —CN; or $R^{14}$ together with $R^{14'}$ form a $C_{3-10}$ carbocycle, or 3- to 10-membered heterocycle, wherein the $C_{3-10}$ carbocycle, or 3- to 10-membered heterocycle, is optionally substituted with one or more substituents independently selected from $R^{18c}$;

$R^{15}$ is selected from:

hydrogen, halogen, —$OR^{19e}$, —$SR^{19e}$, —N($R^{19e}$)$_2$, —$NO_2$, and —CN; and $C_{1-6}$ alkyl optionally substituted with one or more substituents independently selected from $R^{18d}$; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more substituents independently selected from $R^{18f}$;

$R^{16}$ is selected from:

hydrogen, halogen, —$OR^{19f}$, —$SR^{19f}$—N($R^{19f}$)$_2$, —$NO_2$, and —CN; and $C_{1-6}$ alkyl optionally substituted with one or more $R^{18e}$; or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$;

each $R^{17a}$, $R^{17b}$, $R^{17c}$, $R^{17d}$, and $R^{17e}$ is independently selected from:

hydrogen, halogen, —$OR^{19g}$, —$SR^{19g}$, —N($R^{19g}$)$_2$, —$NO_2$, —CN, —$N_3$; and $C_{1-6}$ alkyl, $C_{2-6}$ alkenyl, and $C_{2-6}$ alkynyl, each of which is optionally substituted with one or more $R^{18f}$; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$; or $R^{15}$, $R^{16}$, and $R^{17b}$ together form a bridged heterocycle, wherein the bridged heterocycle is optionally substituted with one or more $R^{18f}$.

each $R^{18a}$, $R^{18b}$, $R^{18c}$, $R^{18d}$, $R^{18e}$, and $R^{18f}$ is independently selected from:

halogen, —$OR^{19h}$, —$SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, $SR^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)$OR^{19h}$, —C(O)$OR^{19h}$, —OC(O)$R^{19h}$, —S(O)$R^{19h}$, —S(O)$_2R^{19h}$, —$NO_2$, =O, =S, =N($R^{19h}$), and —CN;

each $R^{19a}$, $R^{19b}$, $R^{19c}$, $R^{19d}$, $R^{19e}$, $R^{19f}$, $R^{19g}$, and $R^{19h}$ is independently selected from:

hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In certain embodiments, for a compound or salt of Formula (II), Formula (II'), or Formula (II-A), $X^{11}$ is selected from C($R^{17a}$) and N. In some embodiments, $X^{11}$ is selected from C($R^{17a}$). In some embodiments, $X^{11}$ is selected from N. In certain embodiments, for a compound or salt of Formula (II), $X^{12}$ is selected from C($R^{17b}$) and N. In some embodiments, $X^{12}$ is selected from C($R^{17b}$). In some embodiments, $X^{12}$ is selected from N. In certain embodiments, for a compound or salt of Formula (II), $X^{13}$ is selected from C($R^{17c}$) and N. In some embodiments, $X^{13}$ is selected from C($R^{17c}$). In some embodiments, $X^{13}$ is selected from N.

In certain embodiments, for a compound or salt of Formula (II), Formula (II-A), or Formula (II'), $Y^{11}$ is selected from C($R^{17d}$). In some embodiments, $Y^{11}$ is selected from C($R^{17d}$) and N. In some embodiments, $Y^{11}$ is selected from N. In certain embodiments, for a compound or salt of Formula (II), $Y^{12}$ is selected from C($R^{17c}$). In some embodiments, $Y^{12}$ is selected from C($R^{17c}$) and N.

In certain embodiments, for a compound or salt of Formula (II), Formula (II-A), or Formula (II'), each $R^{11}$ can be any suitable functional group known by one of skill in the art. In some embodiments, each $R^{11}$ is independently selected from: halogen, —$NO_2$, —$N_3$, —CN, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —N($R^{19a}$)C(O)N($R^{19a}$)$_2$, —OC(O)N($R^{19a}$)$_2$, —N($R^{19a}$)C(O)$OR^{19a}$, —C(O)$OR^{19a}$, —OC(O)$R^{19a}$, —S(O)$R^{19a}$, and —S(O)$_2R^{19a}$; $C_{1-6}$ alkyl, $C_{2-6}$ alkenyl, and $C_{2-6}$ alkynyl, each of which is optionally substituted with one or more substituents independently selected from halogen, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —C(O)$OR^{19a}$, —OC(O)$R^{19a}$, —N($R^{19a}$)C(O)N($R^{19a}$)$_2$, —OC(O)N($R^{19a}$)$_2$, —N($R^{19a}$)C(O)$OR^{19a}$, —S(O)$R^{19a}$, —S(O)$_2R^{19a}$, —$NO_2$, =O, =S, =N($R^{19a}$), —CN, $C_{3-10}$ carbocycle and 3- to 10-membered heterocycle, wherein the $C_{3-10}$ carbocycle and 3- to 10-membered heterocycle are each optionally substituted with one or more $R^{18a}$; and $C_{3-10}$ carbocycle and 3- to 10-membered heterocycle, each of which is optionally substituted with one or more substituents independently selected from halogen, —$OR^{19a}$, —$SR^{19a}$, —N($R^{19a}$)$_2$, —C(O)$R^{19a}$, —C(O)N($R^{19a}$)$_2$, —N($R^{19a}$)C(O)

$R^{19a}$, —N($R^{19a}$)C(O)N($R^{19a}$)$_2$, —OC(O)N($R^{19a}$)$_2$, —N($R^{19a}$)C(O)O$R^{19a}$, —C(O)O$R^{19a}$, —OC(O)$R^{19a}$, —S(O)$R^{19a}$, —S(O)$_2R^{19a}$, —$NO_2$, ═O—, ═S, ═N($R^{19a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{18a}$.

In certain embodiments, for a compound or salt of Formula (II-A), each $R^{11a}$, $R^{11b}$, $R^{11c}$, and $R^{11d}$ is independently selected from hydrogen, halogen, —$NO_2$, —$N_3$, —CN, —O$R^{19a}$, —S$R^{19a}$, —N($R^{19a}$)$_2$, —C(O)$R^{19a}$; $C_{1-6}$ alkyl, which is optionally substituted with one or more substituents independently selected from halogen, —O$R^{19a}$, —S$R^{19a}$, —N($R^{19a}$)$_2$, —C(O)$R^{19a}$, —C(O)N($R^{19a}$)$_2$, —N($R^{19a}$)C(O)$R^{19a}$, —C(O)O$R^{19a}$, —OC(O)$R^{19a}$, —N($R^{19a}$)C(O)N($R^{19a}$)$_2$, —OC(O)N($R^{19a}$)$_2$, —N($R^{19a}$)C(O)O$R^{19a}$, —S(O)$R^{19a}$, —S(O)$_2R^{19a}$, —$NO_2$, ═O, ═S, ═N($R^{19a}$), —CN, $C_{3-10}$ carbocycle and 3- to 10-membered heterocycle; and $C_{3-10}$ carbocycle which is optionally substituted with one or more substituents independently selected from halogen, —O$R^{19a}$, —S$R^9$a, —N($R^{19a}$)$_2$, —C(O)$R^{19a}$, —C(O)N($R^{19a}$)$_2$, —N($R^{19a}$)C(O)$R^{19a}$, —N($R^{19a}$)C(O)N($R^{19a}$)$_2$, —OC(O)N($R^{19a}$)$_2$, —N($R^{19a}$)C(O)O$R^{19a}$, —C(O)O$R^{19a}$, —OC(O)$R^{19a}$, —S(O)$R^{19a}$, —S(O)$_2R^{19a}$, —$NO_2$, ═O—, ═S, ═N($R^{19a}$), —CN, —$N_3$, $C_{1-6}$ alkyl, $C_{2-6}$ alkenyl, and $C_{2-6}$ alkynyl. In some embodiments, each $R^{11a}$, $R^{11b}$, $R^{11c}$, and $R^{11d}$ is independently selected from hydrogen, halogen, —$N_3$, —CN, —O$R^{19a}$, —N($R^{19a}$)$_2$, —C(O)$R^{19a}$; $C_{1-6}$ alkyl; and $C_{3-10}$ carbocycle. In some embodiments, each $R^{11a}$, $R^{11b}$, $R^{11c}$, and $R^{11d}$ is independently selected from: hydrogen, halogen, —$N_3$, —CN, —O$R^{19a}$, $C_{1-6}$ alkyl, and $C_{3-10}$ carbocycle. In some embodiments, each $R^{11a}$, $R^{11b}$, $R^{11c}$, and $R^{11d}$ is —H, —Cl, —F, —Br, —$N_3$, —CN, —OH, —OMe, methyl, or cyclopropyl. In some embodiments, each $R^{11a}$, $R^{11b}$, $R^{11c}$, and $R^{11d}$ is independently selected from —H, —Cl, —F, —CN, methyl, and cyclopropyl. In some embodiments, each $R^{11a}$, $R^{11b}$, $R^{11c}$, and $R^{11d}$ is independently selected from —H, —F, —CN, and methyl. In some embodiments, each $R^{11a}$, $R^{11b}$, $R^{11c}$, and $R^{11d}$ is independently selected from —H, —F, and —CN. In some embodiments, when $R^{11a}$, $R^{11b}$, and $R^{11c}$ are each hydrogen; then $R^{11d}$ is not hydrogen. In some embodiments, when $R^{11b}$ is —$OCH_3$; then $R^{11c}$ is not —OMe. In some embodiments, when $R^{11a}$, $R^{11b}$, and $R^{11c}$ are each hydrogen; then $R^{11d}$ is not hydrogen; and when $R^{11b}$ is —$OCH_3$; then $R^{11c}$ is not —OMe. In some embodiments, $R^{11a}$, $R^{11b}$, $R^{11c}$, and $R^{11d}$ are each independently selected from hydrogen, —Cl, —F, —Br, —CN, $N_3$, —OH, —OMe, methyl, cyclopropyl, —$CH_2N(CH_3)_2$, $CF_3$, and

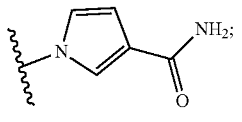 [SMILES: *n1ccc(C(N)=O)c1]

wherein when $R^{11a}$, $R^{11b}$, and $R^{11c}$ are each hydrogen; then $R^{11d}$ is selected from —Cl, —F, —Br, —CN, $N_3$, —OH, —OMe, methyl, cyclopropyl, —$CH_2N(CH_3)_2$, and $CF_3$; wherein when $R^{11b}$ is —$OCH_3$; then $R^{11c}$ is independently selected from hydrogen, —Cl, —F, —Br, —CN, $N_3$, —OH, methyl, cyclopropyl, —$CH_2N(CH_3)_2$, and $CF_3$. In some embodiments, $R^{11a}$, $R^{11b}$, $R^{11c}$, and $R^{11d}$ are each independently selected from hydrogen, —F, —CN, and methyl; wherein when $R^{11a}$, $R^{11b}$, and $R^{11c}$ are each hydrogen; then $R^{11d}$ is selected from —F, —CN, and methyl.

In certain embodiments, for a compound or salt of Formula (II), Formula (II-A), or Formula (II'), $R^{12}$ can be any suitable functional group known by one of skill in the art. In some embodiments, $R^{12}$ is selected from: hydrogen, halogen, —$NO_2$, —$N_3$, —CN, —O$R^{19b}$, —S$R^{19b}$, —N($R^{19b}$)$_2$, —C(O)$R^{19b}$, —C(O)N($R^{19b}$)$_2$, —N($R^{19b}$)C(O)$R^{19b}$, —N($R^{19b}$)C(O)N($R^{19b}$)$_2$, —OC(O)N($R^{19b}$)$_2$, —N($R^{19b}$)C(O)O$R^{19b}$, —C(O)O$R^{19b}$, —OC(O)$R^{19b}$, —S(O)$R^{19b}$, and —S(O)$_2R^{19b}$; $C_{1-6}$ alkyl, $C_{2-6}$alkenyl, and $C_{2-6}$ alkynyl, each of which is optionally substituted with one or more substituents independently selected from halogen, —O$R^{19b}$, —S$R^{19b}$, —N($R^{19b}$)$_2$, —C(O)$R^{19b}$, —C(O)N($R^{19b}$)$_2$, —N($R^{19b}$)C(O)$R^{19b}$, —C(O)O$R^{19b}$, —OC(O)$R^{19b}$, —N($R^{19b}$)C(O)N($R^{19b}$)$_2$, —OC(O)N($R^{19b}$)$_2$, —N($R^{19b}$)C(O)O$R^{19b}$, —S(O)$R^{19b}$, —S(O)$_2R^{19b}$, —$NO_2$, ═O, ═S, ═N($R^{19b}$), —CN, $C_{3-10}$ carbocycle and 3- to 10-membered heterocycle, wherein the $C_{3-10}$ carbocycle and 3- to 10-membered heterocycle are each optionally substituted with one or more $R^{18b}$; and $C_{3-10}$ carbocycle and 3- to 10-membered heterocycle, each of which is optionally substituted with one or more substituents independently selected from halogen, —O$R^{19b}$, —S$R^{19b}$, —N($R^{19b}$)$_2$, —C(O)$R^{19b}$, —C(O)N($R^{19b}$)$_2$, —N($R^{19b}$)C(O)$R^{19b}$, —N($R^{19b}$)C(O)N($R^{19b}$)$_2$, —OC(O)N($R^{19b}$)$_2$, —N($R^{19b}$)C(O)O$R^{19b}$, —C(O)O$R^{19b}$, —OC(O)$R^{19b}$, —S(O)$R^{19b}$, —S(O)$_2R^{19b}$, —$NO_2$, ═O—, ═S, ═N($R^{19b}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{18b}$. In some embodiments, $R^{12}$ is selected from: hydrogen, halogen, —$NO_2$, —CN, —O$R^{19b}$, —S$R^{19b}$, —N($R^{19b}$)$_2$, —C(O)$R^{19b}$; and $C_{1-6}$ alkyl, which is optionally substituted with one or more substituents independently selected from halogen, —O$R^{19b}$, —S$R^{19b}$, —N($R^{19b}$)$_2$, —C(O)$R^{19b}$, —C(O)N($R^{19b}$)$_2$, —N($R^{19b}$)C(O)$R^{19b}$, —C(O)O$R^{19b}$, —OC(O)$R^{19b}$, —N($R^{19b}$)C(O)N($R^{19b}$)$_2$, —OC(O)N($R^{19b}$)$_2$, —N($R^{19b}$)C(O)O$R^{19b}$, —S(O)$R^{19b}$, —S(O)$_2R^{19b}$, —$NO_2$, ═O, ═S, ═N($R^{19b}$), —CN, $C_{3-10}$ carbocycle and 3- to 10-membered heterocycle. In some embodiments, $R^{12}$ is selected from hydrogen, halogen, —O$R^{19b}$, and $C_{1-6}$ alkyl. In some embodiments, $R^{12}$ is hydrogen or $C_{1-6}$ alkyl. In some embodiments, $R^{12}$ is hydrogen.

In certain embodiments, for a compound or salt of Formula (II), Formula (II-A), or Formula (II'), $R^{13}$ can be any suitable functional group known by one of skill in the art. In some embodiments, $R^{13}$ is selected from: hydrogen, halogen, —O$R^{19c}$, —S$R^{19c}$, —N($R^{19c}$)$_2$, —$NO_2$, and —CN; and $C_{1-6}$ alkyl optionally substituted with one or more substituents independently selected from halogen, —O$R^{19c}$, —S$R^{19c}$, —N($R^{19c}$)$_2$, —$NO_2$, and —CN; and $C_{3-10}$ carbocycle and 3- to 10-membered heterocycle, each of which is optionally substituted with one or more substituents independently selected from halogen, —O$R^{19c}$, —S$R^{19c}$, —N($R^{19c}$)$_2$, —C(O)$R^{19c}$, —C(O)N($R^{19c}$)$_2$, —N($R^{19c}$)C(O)$R^{19c}$, —N($R^{19c}$)C(O)N($R^{19c}$)$_2$, —OC(O)N($R^{19c}$)$_2$, —N($R^{19c}$)C(O)O$R^{19c}$, —C(O)O$R^{19c}$, —OC(O)$R^{19c}$, —S(O)$R^{19c}$, —S(O)$_2R^{19c}$, —$NO_2$, ═O—, ═S, ═N($R^{19c}$), and —CN; or $R^{13}$ together with $R^{14}$ form a $C_{3-10}$ carbocycle, or 3- to 10-membered heterocycle, wherein the $C_{3-10}$ carbocycle, or 3- to 10-membered heterocycle, is optionally substituted with one or more $R^{18c}$. In some embodiments, $R^{13}$ is selected from: hydrogen, halogen, —O$R^{19c}$, —S$R^{19c}$, —N($R^{19c}$)$_2$; and $C_{1-6}$ alkyl which is optionally substituted with one or more substituents independently selected from halogen, —O$R^{19c}$, —S$R^{19c}$, —N($R^{19c}$)$_2$, —$NO_2$, and —CN; and $C_{3-10}$ carbocycle which is optionally substituted with one or more substituents independently selected from halogen, —O$R^{19c}$, —S$R^{19c}$, —N($R^{19c}$)$_2$, —C(O)$R^{19c}$, —C(O)

$N(R^{19c})_2$, —$N(R^{19c})C(O)R^{19c}$, —$N(R^{19c})C(O)N(R^{19c})_2$, —$OC(O)N(R^{19c})_2$, —$N(R^{19c})C(O)OR^{19c}$, —$C(O)OR^{19c}$, —$OC(O)R^{19c}$, —$S(O)R^{19c}$, —$S(O)_2R^{19c}$, —$NO_2$, =O—, =S, =$N(R^{19c})$, and —CN; or $R^{13}$ together with $R^{14}$ form a 3- to 10-membered heterocycle, wherein the 3- to 10-membered heterocycle is optionally substituted with one or more $R^{18c}$.

In certain embodiments, for a compound or salt of Formula (II), Formula (II-A), or Formula (II'), $R^{13}$ is selected from: hydrogen, halogen, —$OR^{19c}$, $C_{1-6}$ alkyl, and $C_{3-10}$ carbocycle; or $R^{13}$ together with $R^{14}$ form a 3- to 10-membered heterocycle, wherein the 3- to 10-membered heterocycle is optionally substituted with one or more $R^{18c}$. In some embodiments, $R^{13}$ is selected from: hydrogen, —$OR^{19c}$, $C_{1-6}$ alkyl and $C_{3-10}$ carbocycle; or $R^{13}$ together with $R^{14}$ form a 3- to 10-membered heterocycle. In some embodiments, $R^{13}$ is hydrogen, —OH, —OMe, methyl, cyclopropyl, or $R^{13}$ together with $R^{14}$ form a pyridinyl. In some embodiments, $R^{13}$ is hydrogen, —OH, —OMe, methyl, or cyclopropyl. In some embodiments, $R^{13}$ is selected from hydrogen, methyl, ethyl, —OH, —OMe, —$CF_3$, —$C(H)F_2$, —N(H)Me, and cyclopropyl. In some embodiments, $R^{13}$ is selected from hydrogen. In some embodiments, $R^{13}$ is selected from methyl.

In certain embodiments, for a compound or salt of Formula (II) or Formula (II-A), $R^{14}$ can be any suitable functional group known by one of skill in the art. In some embodiments, $R^{14}$ is independently selected from: hydrogen, halogen, —$OR^{19d}$, —$SR^{19d}$, —$N(R^{19d})_2$, —$NO_2$, and —CN; and $C_{1-6}$ alkyl which is optionally substituted with one or more substituents independently selected from halogen, —$OR^{19d}$, —$SR^{19d}$, —$N(R^{19d})_2$, —$NO_2$, and —CN; and $C_{3-10}$ carbocycle and 3- to 10-membered heterocycle, each of which is optionally substituted with one or more substituents independently selected from halogen, —$OR^{11d}$, —$SR^{11d}$, —$N(R^{19d})_2$, —$C(O)R^{19d}$, —$C(O)N(R^{19d})_2$, —$N(R^{19d})C(O)R^{19d}$, —$N(R^{19d})C(O)N(R^{19d})_2$, —$OC(O)N(R^{19d})_2$, —$N(R^{19d})C(O)OR^{19d}$, —$C(O)OR^{19d}$, —$OC(O)R^{19d}$, —$S(O)R^{19d}$, —$S(O)_2R^{19d}$, —$NO_2$, =O—, =S, =$N(R^{19d})$, and —CN; or $R^{13}$ together with $R^{14}$ form a $C_{3-10}$ carbocycle, or 3- to 10-membered heterocycle, wherein the $C_{3-10}$ carbocycle, or 3- to 10-membered heterocycle, is optionally substituted with one or more $R^{18c}$. In some embodiments, $R^{14}$ is independently selected from: hydrogen, halogen, —$OR^{19d}$, —$SR^{19d}$, —$N(R^{19d})_2$, —$NO_2$, and —CN; and $C_{1-6}$ alkyl which is optionally substituted with one or more substituents independently selected from halogen, —$OR^{19d}$, —$SR^{19d}$, —$N(R^{19d})_2$, —$NO_2$, and —CN; and $C_{3-10}$ carbocycle and 3- to 10-membered heterocycle, each of which is optionally substituted with one or more substituents independently selected from halogen, —$OR^{19a}$, —$SR^{19d}$, —$N(R^{19d})_2$, —$C(O)R^{19d}$, —$C(O)N(R^{19d})_2$, —$N(R^{19d})C(O)R^{19d}$, —$N(R^{19d})C(O)N(R^{19d})_2$, —$OC(O)N(R^{19d})_2$, —$N(R^{19d})C(O)OR^{19d}$, —$C(O)OR^{19d}$, —$OC(O)R^{19d}$, —$S(O)R^{19d}$, —$S(O)_2R^{19d}$, —$NO_2$, =O—, =S, =$N(R^{19d})$, and —CN.

In certain embodiments, for a compound or salt of Formula (II) or Formula (II-A), $R^{14}$ is selected from: hydrogen, halogen, —$OR^{19d}$, —$SR^{19d}$, —$N(R^{19d})_2$; and $C_{1-6}$ alkyl which is optionally substituted with one or more substituents independently selected from halogen, —$OR^{19d}$, —$SR^{19d}$, —$N(R^{19d})_2$, —$NO_2$, and —CN; or $R^{13}$ together with $R^{14}$ form a $C_{3-10}$ carbocycle, or 3- to 10-membered heterocycle, wherein the $C_{3-10}$ carbocycle, or 3- to 10-membered heterocycle, is optionally substituted with one or more $R^{18c}$. In some embodiments, $R^{14}$ is selected from: hydrogen, halogen, —$OR^{19d}$, —$SR^{19d}$, —$N(R^{19d})_2$; and $C_{1-6}$ alkyl which is optionally substituted with one or more substituents independently selected from halogen, —$OR^{19d}$, —$SR^{19d}$, —$N(R^{19d})_2$, —$NO_2$, and —CN. In some embodiments, $R^{14}$ is selected from: hydrogen, halogen, —$OR^{19d}$, and $C_{1-6}$ alkyl; or $R^{13}$ together with $R^{14}$ form a $C_{3-10}$ carbocycle, or 3- to 10-membered heterocycle. In some embodiments, $R^{14}$ is selected from: hydrogen, halogen, —$OR^{19d}$, and $C_{1-6}$ alkyl. In some embodiments, $R^{14}$ is hydrogen, $C_{1-6}$ alkyl, or $R^{13}$ together with $R^{14}$ form a $C_{3-10}$ carbocycle, or 3- to 10-membered heterocycle. In some embodiments, $R^{14}$ is hydrogen or $C_{1-6}$ alkyl. In some embodiments, $R^{14}$ is hydrogen, methyl, or $R^{13}$ together with $R^{14}$ form a pyridinyl. In some embodiments, $R^{14}$ is hydrogen or methyl. In some embodiments, $R^{14}$ is selected from hydrogen, methyl, and fluoro. In some embodiments, $R^{14}$ is selected from hydrogen. In some embodiments, $R^{14}$ is selected from hydrogen and methyl. In some embodiments, $R^{14}$ is selected from hydrogen and fluoro. In some embodiments, $R^{14}$ is selected from methyl and fluoro. In some embodiments, $R^{14}$ is selected from hydrogen and cyano. In some embodiments, $R^{14}$ is selected from cyano. In some embodiments, $R^{14}$ and $R^{14'}$ together form a cyclopropane ring optionally substituted with one or more substituents selected from —F and —$CH_3$.

In certain embodiments, for a compound or salt of Formula (II) or Formula (II-A), $R^{14'}$ can be any suitable functional group known by one of skill in the art. In some embodiments, $R^{14'}$ is independently selected from: hydrogen, halogen, —$OR^{19d}$, —$SR^{19d}$, —$N(R^{19d})_2$, —$NO_2$, and —CN; and $C_{1-6}$ alkyl which is optionally substituted with one or more substituents independently selected from halogen, —$OR^{19d}$, —$SR^{19d}$, —$N(R^{19d})_2$, —$NO_2$, and —CN; and $C_{3-10}$ carbocycle and 3- to 10-membered heterocycle, each of which is optionally substituted with one or more substituents independently selected from halogen, —$OR^{19d}$, —$SR^{19d}$, —$N(R^{19d})_2$, —$C(O)R^{19d}$, —$C(O)N(R^{19d})_2$, —$N(R^{19d})C(O)R^{19d}$, —$N(R^{19d})C(O)N(R^{19d})_2$, —$OC(O)N(R^{19d})_2$, —$N(R^{19d})C(O)OR^{19d}$, —$C(O)OR^{19d}$, —$OC(O)R^{19d}$, —$S(O)R^{19d}$, —$S(O)_2R^{19d}$, —$NO_2$, =O—, =S, =$N(R^{19d})$, and —CN; or $R^{13}$ together with $R^{14'}$ form a $C_{3-10}$ carbocycle, or 3- to 10-membered heterocycle, wherein the $C_{3-10}$ carbocycle, or 3- to 10-membered heterocycle, is optionally substituted with one or more $R^{18c}$. In some embodiments, $R^{14'}$ is independently selected from: hydrogen, halogen, —$OR^{19d}$, —$SR^{19d}$, —$N(R^{19d})_2$, —$NO_2$, and —CN; and $C_{1-6}$ alkyl which is optionally substituted with one or more substituents independently selected from halogen, —$OR^{19a}$, —$SR^{19d}$, —$N(R^{19d})_2$, —$NO_2$, and —CN; and $C_{3-10}$ carbocycle and 3- to 10-membered heterocycle, each of which is optionally substituted with one or more substituents independently selected from halogen, —$OR^{19d}$, —$SR^{19d}$, —$N(R^{19d})_2$, —$C(O)R^{19d}$, —$C(O)N(R^{19d})_2$, —$N(R^{19d})C(O)R^{19d}$, —$N(R^{19d})C(O)N(R^{19d})_2$, —$OC(O)N(R^{19d})_2$, —$N(R^{19d})C(O)OR^{19d}$, —$C(O)OR^{19d}$, —$OC(O)R^{19d}$, —$S(O)R^{19d}$, —$S(O)_2R^{19d}$, —$NO_2$, =O—, =S, =$N(R^{19d})$, and —CN.

In certain embodiments, for a compound or salt of Formula (II) or Formula (II-A), $R^{14'}$ is selected from: hydrogen, halogen, —$OR^{19d}$, —$SR^{19d}$, —$N(R^{19d})_2$; and $C_{1-6}$ alkyl which is optionally substituted with one or more substituents independently selected from halogen, —$OR^{19d}$, —$SR^{19d}$, —$N(R^{19d})_2$, —$NO_2$, and —CN; or $R^{13}$ together with $R^{14'}$ form a $C_{3-10}$ carbocycle, or 3- to 10-membered heterocycle, wherein the $C_{3-10}$ carbocycle, or 3- to 10-membered heterocycle, is optionally substituted with one or more $R^{18c}$. In some embodiments, $R^{14'}$ is selected from: hydrogen, halogen, —$OR^{19d}$, —$SR^{19d}$, —$N(R^{19a})_2$; and $C_{1-6}$ alkyl which is optionally substituted with one or more substituents independently selected from halogen, —$OR^{19d}$, —$SR^{19d}$, —$N(R^{19d})_2$, —$NO_2$, and —CN. In some embodiments, $R^{14'}$ is selected from: hydrogen, halogen, —$OR^{19d}$, and $C_{1-6}$ alkyl; or $R^{13}$ together with $R^{14'}$ form a $C_{3-10}$ carbocycle, or 3- to 10-membered heterocycle. In some embodiments, $R^{14'}$ is selected from: hydrogen, halogen, —$OR^{19d}$, and $C_{1-6}$ alkyl. In some embodiments, $R^{14'}$ is hydrogen, $C_{1-6}$ alkyl, or $R^{13}$ together with $R^{14'}$ form a $C_{3-10}$ carbocycle, or 3- to 10-membered heterocycle. In some embodiments, $R^{14'}$ is hydrogen or $C_{1-6}$ alkyl. In some embodiments, $R^{14'}$ is hydrogen, methyl, or $R^{13}$ together with $R^{14'}$ form a pyridinyl. In some embodiments, $R^{14'}$ is hydrogen or methyl. In some embodiments, $R^{14'}$ is selected from hydrogen, methyl, and fluoro. In some embodiments, $R^{14'}$ is selected from hydrogen. In some embodiments, $R^{14'}$ is selected from hydrogen and methyl. In some embodiments, $R^{14'}$ is selected from hydrogen and fluoro. In some embodiments, $R^{14'}$ is selected from methyl and fluoro. In some embodiments, $R^{14'}$ is selected from hydrogen and cyano. In some embodiments, $R^{14'}$ is selected from cyano. In some embodiments,

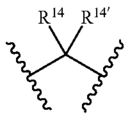

is selected from:

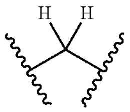, 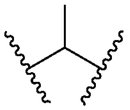, 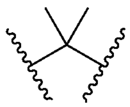,

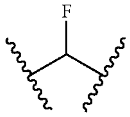, 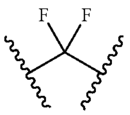, 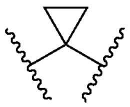,

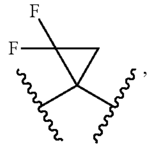, and 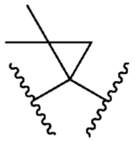.

In some embodiments,

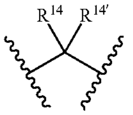

is selected from

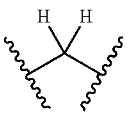, 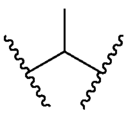,

-continued

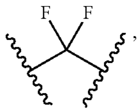, and 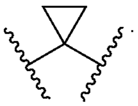.

In some embodiments,

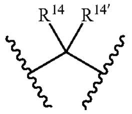

is selected from:

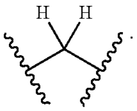 [SMILES: *C*].

In some embodiments,

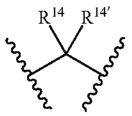

is selected from:

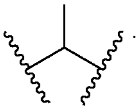 [SMILES: *C(*)C].

In some embodiments

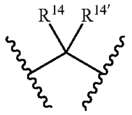

is selected from:

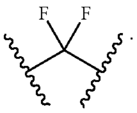 [SMILES: *C(*)(F)F].

In some embodiments,

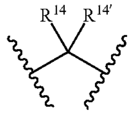

is selected from:

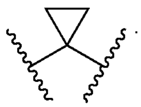 [SMILES: *C1(*)CC1]

.

In certain embodiments, for a compound or salt of Formula (II), Formula (II-A), or Formula (II'), $R^{15}$ can be any suitable functional group known by one of skill in the art. In some embodiments, $R^{15}$ is selected from: hydrogen, halogen, —$OR^{19e}$, —$SR^{19e}$, —$N(R^{19e})_2$, —$NO_2$, and —CN; and $C_{1-6}$ alkyl optionally substituted with one or more $R^{18d}$; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$. In some embodiments, $R^{15}$ is selected from: hydrogen, —$OR^{19e}$, —$SR^{19e}$, —$N(R^{19e})_2$, and $C_{1-6}$ alkyl optionally substituted with one or more $R^{18d}$; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$. In some embodiments, $R^{15}$ is selected from: hydrogen and $C_{1-6}$ alkyl; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$. In some embodiments, $R^{15}$ is hydrogen, $C_{1-6}$ alkyl; or $R^{15}$ together with $R^{17a}$ form a 3- to 10-membered heterocycle, wherein the 3- to 10-membered heterocycle is optionally substituted with one or more —$OR^{19h}$ or $C_{1-3}$ alkyl; or $R^{15}$ together with $R^{17b}$ form a 3- to 10-membered heterocycle, wherein the 3- to 10-membered heterocycle is optionally substituted with one or more —$OR^{19h}$ or $C_{1-3}$ alkyl. In some embodiments, $R^{15}$ is hydrogen; or $R^{15}$ together with $R^{17a}$ is tetrahydroisoquinoline optionally substituted with —OH or methyl. In some embodiments, $R^{15}$ together with $R^{17b}$ is tetrahydroisoquinoline optionally substituted with —OH or methyl. In some embodiments, $R^{15}$ is hydrogen.

In certain embodiments, for a compound or salt of Formula (II), Formula (II-A), or Formula (II'), $R^{16}$ can be any suitable functional group known by one of skill in the art. In some embodiments, $R^{16}$ is selected from: hydrogen, halogen, —$OR^{19f}$, —$SR^{19f}$, —$N(R^{19f})_2$, —$NO_2$, and —CN; and $C_{1-6}$ alkyl optionally substituted with one or more $R^{18e}$; or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$. In some embodiments, $R^{16}$ is selected from: hydrogen, halogen, —$OR^{19f}$, —$SR^{19f}$, —$N(R^{19f})_2$; and $C_{1-6}$ alkyl optionally substituted with one or more $R^{18e}$; or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$. In some embodiments, $R^{16}$ is hydrogen, $C_{1-3}$ alkyl optionally substituted with —$OR^{19h}$; or $R^{16}$ together with $R^{17a}$ form a 3- to 10-membered heterocycle, wherein the 3- to 10-membered heterocycle is optionally substituted with one or more substituents independently selected halogen, —$OR^{19h}$, —$SR^{19h}$, —$N(R^{19h})_2$, and —CN; or $R^{16}$ together with $R^{17b}$ form a 3- to 10-membered heterocycle, wherein the 3- to 10-membered heterocycle is optionally substituted with one or more substituents independently selected halogen, —$OR^{19h}$, —$SR^{19h}$, —$N(R^{19'})_2$, and —CN. In some embodiments, $R^{16}$ is hydrogen, $C_1$ alkyl, optionally substituted with —OH, or $R^{16}$ together with $R^{17a}$ form a dihydrobenzofuranyl or dihydrofuropyridinyl optionally substituted with one or more —F or —CN. In some embodiments, $R^{16}$ is hydrogen, $C_1$ alkyl, optionally substituted with —OH, or $R^{16}$ together with $R^{17b}$ form a dihydrobenzofuranyl or dihydrofuropyridinyl optionally substituted with one or more —F or —CN. In some embodiments, $R^{16}$ is hydrogen or methyl. In some embodiments, $R^{16}$ is methyl. In some embodiments, $R^{16}$ together with $R^{17a}$ form:

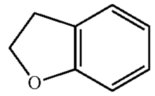

, which is optionally substituted with one or more —F or —CN In some embodiments, $R^{16}$ together with $R^{17a}$ form:

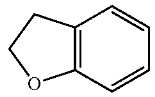

, which is optionally substituted with one or more —CN. In some embodiments, $R^{16}$ together with $R^{17a}$ form:

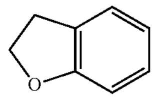

, which is optionally substituted with one or more —F. In some embodiments, $R^{16}$ together with $R^{17b}$ form:

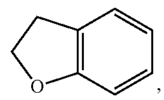

, which is optionally substituted with one or more —F or —CN In some embodiments, $R^{16}$ together with $R^{17b}$ form:

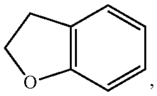

which is optionally substituted with one or more —CN. In some embodiments, $R^{16}$ together with $R^{17b}$ form:

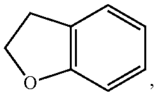

which is optionally substituted with one or more —F. In some embodiments, $R^{16}$ is hydrogen, $C_1$ alkyl, optionally substituted with —OH. In some embodiments, $R^{16}$ is hydrogen, methyl, or $CH_2OH$. In some embodiments, $R^{16}$ is methyl, or $CH_2OH$. In some embodiments, $R^{16}$ is methyl.

In certain embodiments, for a compound or salt of Formula (II), Formula (II-A), or Formula (II'), $R^{16}$ and $R^{17a}$ are taken together to form a 3- to 10-membered heterocycle selected from

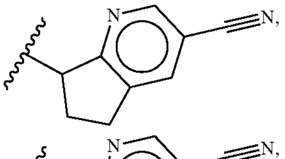

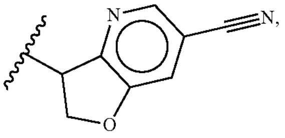

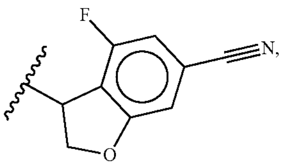

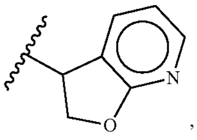

,

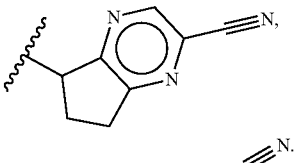

and

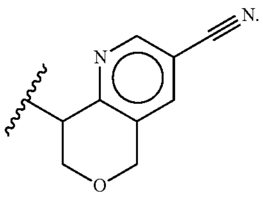

In certain embodiments, for a compound or salt of Formula (II), Formula (II-A), or Formula (II'),

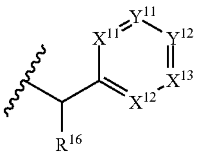

is selected from

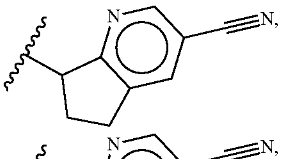

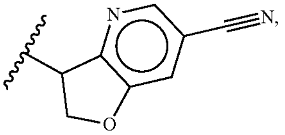

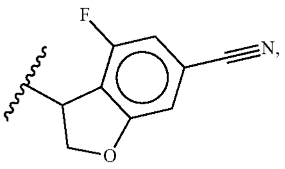

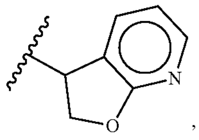

,

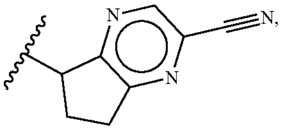

and

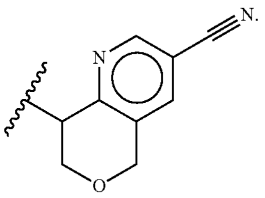

In some embodiments, $R^{16}$ and $R^{17a}$ are taken together to form a 3- to 10-membered heterocycle selected from

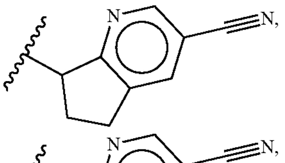

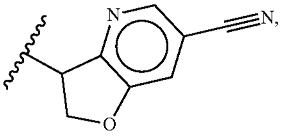

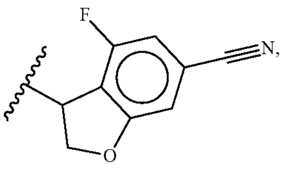

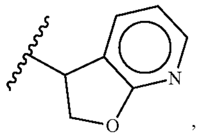

,

-continued

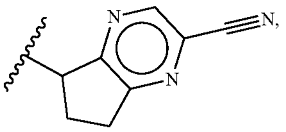

and

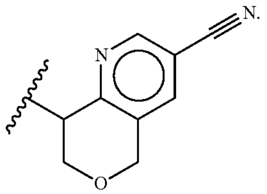

In some embodiments, $R^{16}$ and $R^{17b}$ are taken together to form a 3- to 10-membered heterocycle selected from

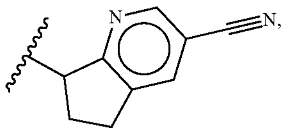

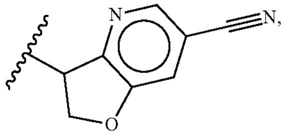

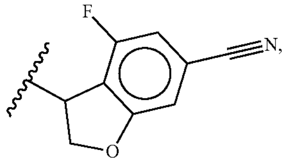

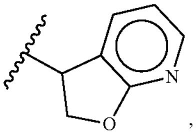

,

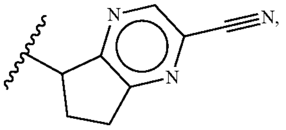

and

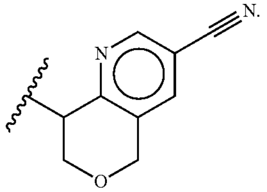

In some embodiments, $R^{16}$ and $R^{17b}$ are taken together to form a 3- to 10-membered heterocycle selected from

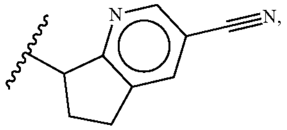

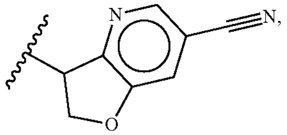

-continued

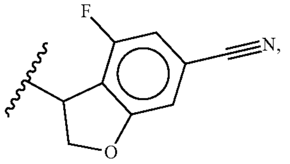

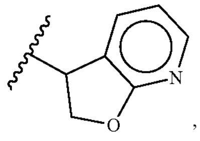

,

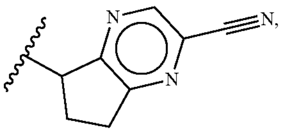

and

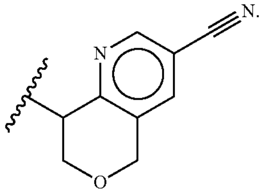

In certain embodiments, for a compound or salt of Formula (II), Formula (II-A), or Formula (II'), each $R^{17a}$, $R^{17b}$, $R^{17c}$, $R^{17d}$, and $R^{17e}$ can be any suitable functional group known by one of skill in the art. In some embodiments, each $R^{17a}$, $R^{17b}$, $R^{17c}$, $R^{17d}$, and $R^{17e}$ is independently selected from: hydrogen, halogen, —$OR^{19g}$, —$SR^{19g}$, —$N(R^{19g})_2$, —$NO_2$, and —CN; and $C_{1-6}$ alkyl optionally substituted with one or more $R^{18f}$ or $R^{15}$ together with $R^{17a}$ form a 3- to 10-membered heterocycle, wherein the 3- to 10-membered heterocycle is optionally substituted with one or more $R^{18f}$; or $R^{16}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$. In some embodiments, each $R^{17a}$, $R^{17b}$, $R^{17c}$, $R^{17d}$, and $R^{17e}$ is independently selected from: hydrogen, halogen, —$OR^{19g}$, —$N(R^{19g})_2$, and —CN; and $C_{1-6}$ alkyl optionally substituted with one or more $R^{18f}$; or $R^{15}$ together with $R^{17a}$ form a 3- to 10-membered heterocycle, wherein the 3- to 10-membered heterocycle is optionally substituted with one or more $R^{18f}$; or $R^{16}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$.

In certain embodiments, for a compound or salt of Formula (II), Formula (II-A), or Formula (II'), each $R^{17a}$, $R^{17b}$, $R^{17c}$, $R^{17d}$, and $R^{17e}$ is independently selected from: hydrogen, halogen, —$OR^{19g}$, and —CN; and $C_{1-6}$ alkyl optionally substituted with one or more $R^{18f}$; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$;

or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$. In some embodiments, each $R^{17a}$, $R^{17b}$, $R^{17c}$, $R^{17d}$, and $R^{17e}$ is independently halogen, —CN, or $R^{15}$ together with $R^{17a}$ form a 3- to 10-membered heterocycle, wherein the 3- to 10-membered heterocycle is optionally substituted with one or more $R^{18f}$; or $R^{16}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$. In some embodiments, each $R^{17a}$, $R^{17b}$, $R^{17c}$, $R^{17d}$, and $R^{17e}$ is independently —F, —CN; or $R^{15}$ together with $R^{17a}$ is tetrahydroisoquinoline optionally substituted with —OH or methyl; or $R^{16}$ together with $R^{17a}$ form a dihydrobenzofuranyl or dihydrofuropyridinyl optionally substituted with one or more —F or —CN; or $R^{15}$ together with $R^{17b}$ is tetrahydroisoquinoline optionally substituted with —OH or methyl; or $R^{16}$ together with $R^{17b}$ form a dihydrobenzofuranyl or dihydrofuropyridinyl optionally substituted with one or more —F or —CN. In some embodiments, each $R^{17a}$, $R^{17b}$, $R^{17c}$, $R^{17d}$, and $R^{17e}$ is independently —F or —CN.

In certain embodiments, for a compound or salt of Formula (II), Formula (II-A), or Formula (II'), $R^{17a}$ together with $R^{16}$ form:

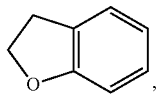

which is optionally substituted with one or more substituents independently selected from —F and —CN. In some embodiments, $R^{17b}$ together with $R^{16}$ form:

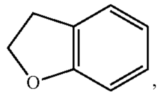

which is optionally substituted with one or more substituents independently selected from —F and —CN.

In certain embodiments, for a compound or salt of Formula (II), Formula (II-A), or Formula (II'), each $R^{17a}$ is independently selected from:

- hydrogen, halogen, $—OR^{19g}$, $—SR^{19g}$, $—N(R^{19g})_2$, $—NO_2$, —CN, and $—N_3$; and
- $C_{1-6}$ alkyl, $C_{2-6}$ alkenyl, and $C_{2-6}$ alkynyl, each of which is optionally substituted with one or more $R^{18f}$; or
- $R^{15}$ together with $R^{17a}$ form a 3- to 10-membered heterocycle, wherein the 3- to 10-membered heterocycle is optionally substituted with one or more $R^{18f}$; or
- $R^{16}$ together with $R^{17a}$ form a 3- to 10-membered heterocycle, wherein the 3- to 10-membered heterocycle is optionally substituted with one or more $R^{18f}$.

In some embodiments, each $R^{17a}$ is independently selected from:

- hydrogen, halogen, and —CN; and
- $C_{1-6}$ alkyl, $C_{2-6}$ alkenyl, and $C_{2-6}$ alkynyl, each of which is optionally substituted with one or more substituents independently selected from —F and —CN; or
- $R^{15}$ together with $R^{17a}$ form a 3- to 10-membered heterocycle, wherein the 3- to 10-membered heterocycle is optionally substituted with one or more $R^{18f}$; or
- $R^{16}$ together with $R^{17a}$ form a 3- to 10-membered heterocycle, wherein the 3- to 10-membered heterocycle is optionally substituted with one or more $R^{18f}$.

In some embodiments, each $R^{17a}$ is independently selected from:

- hydrogen, —F, and —CN; and
- $C_1$ alkyl and $C_2$ alkynyl, each of which is optionally substituted with one or more substituents independently selected from —F and —CN; or
- $R^{15}$ together with $R^{17a}$ form a 3- to 10-membered heterocycle, wherein the 3- to 10-membered heterocycle is optionally substituted with one or more $R^{18f}$; or
- $R^{16}$ together with $R^{17a}$ form a 3- to 10-membered heterocycle, wherein the 3- to 10-membered heterocycle is optionally substituted with one or more $R^{18f}$.

In some embodiments, each $R^{17a}$ is independently selected from: hydrogen, —F, —CN, $—CH_3$, and —CCH; or

- $R^{15}$ together with $R^{17a}$ form a 3- to 10-membered heterocycle, wherein the 3- to 10-membered heterocycle is optionally substituted with one or more $R^{18f}$; or
- $R^{16}$ together with $R^{17a}$ form a 3- to 10-membered heterocycle, wherein the 3- to 10-membered heterocycle is optionally substituted with one or more $R^{18f}$.

In some embodiments, each $R^{17a}$ is independently selected from: hydrogen, —F, —CN, $—CH_3$, and —CCH; or

- $R^{15}$ together with $R^{17a}$ form a 3- to 10-membered heterocycle, wherein the 3- to 10-membered heterocycle is optionally substituted with one or more substituents independently selected from —F and —CN; or
- $R^{16}$ together with $R^{17a}$ form a 3- to 10-membered heterocycle, wherein the 3- to 10-membered heterocycle is optionally substituted with one or more substituents independently selected from —F and —CN.

In some embodiments, each $R^{17a}$ is independently selected from: hydrogen, —F, —CN, $—CH_3$, and —CCH; or

- $R^{15}$ together with $R^{17a}$ form a 3- to 10-membered heterocycle, wherein the 3- to 10-membered heterocycle is optionally substituted with one or more substituents independently selected from —F; or
- $R^{16}$ together with $R^{17a}$ form a 3- to 10-membered heterocycle, wherein the 3- to 10-membered heterocycle is optionally substituted with one or more substituents independently selected from —F.

In some embodiments, each $R^{17a}$ is independently selected from: hydrogen, —F, —CN, $—CH_3$, and —CCH; or

- $R^{15}$ together with $R^{17a}$ form a 3- to 10-membered heterocycle, wherein the 3- to 10-membered heterocycle is optionally substituted with one or more substituents independently selected from —CN; or
- $R^{16}$ together with $R^{17a}$ form a 3- to 10-membered heterocycle, wherein the 3- to 10-membered heterocycle is optionally substituted with one or more substituents independently selected from —CN.

In some embodiments, each $R^{17a}$ is independently selected from: hydrogen, —F, —CN, $—CH_3$, and —CCH; or $R^{16}$ together with $R^{17a}$ form a 3- to 10-membered heterocycle, wherein the 3- to 10-membered heterocycle is optionally substituted with one or more $R^{18f}$. In some embodiments, each $R^{17a}$ is independently selected from: hydrogen, —F, —CN, —$CH_3$, and —CCH; or $R^{16}$ together with $R^{17a}$ form a 3- to 10-membered heterocycle, wherein the 3- to 10-membered heterocycle is optionally substituted with one or more substituents independently selected from halogen, —CN, —OH, —$OCH_3$, —SH, —$NH_2$, —$NO_2$, —$N_3$, $C_{1-6}$ alkyl, and $C_{2-6}$ alkynyl. In some embodiments, each $R^{17a}$ is independently selected from: hydrogen, —F, —CN, —$CH_3$, and —CCH; or $R^{16}$ together with $R^{17a}$ form a 3- to 10-membered heterocycle, wherein the 3- to 10-membered heterocycle is optionally substituted with one or more substituents independently selected from halogen, —CN, $C_{1-6}$ alkyl, and $C_{2-6}$ alkynyl. In some embodiments, each $R^{17a}$ is independently selected from: hydrogen, —F, —CN, —$CH_3$, and —CCH; or $R^{16}$ together with $R^{17a}$ form a 3- to 10-membered heterocycle, wherein the 3- to 10-membered heterocycle is optionally substituted with one or more substituents independently selected from halogen, —CN, $C_1$ alkyl, and $C_2$ alkynyl. In some embodiments, each $R^{17a}$ is independently selected from: hydrogen, —F, —CN, —$CH_3$, and —CCH; or $R^{16}$ together with $R^{17a}$ form a 3- to 10-membered heterocycle, wherein the 3- to 10-membered heterocycle is optionally substituted with one or more substituents independently selected from —F, —CN, —$CH_3$, and —CCH. In some embodiments, each $R^{17a}$ is independently selected from: hydrogen, —F, —CN, —$CH_3$, and —CCH; or $R^{16}$ together with $R^{17a}$ form a 3- to 10-membered heterocycle, wherein the 3- to 10-membered heterocycle is optionally substituted with one or more substituents independently selected from —F and —CN. In some embodiments, each $R^{17a}$ is independently selected from: hydrogen, —F, —CN, —$CH_3$, and —CCH; or $R^{16}$ together with $R^{17a}$ form a 3- to 10-membered heterocycle, wherein the 3- to 10-membered heterocycle is optionally substituted with one or more substituents independently selected from —F. In some embodiments, each $R^{17a}$ is independently selected from: hydrogen, —F, —CN, —$CH_3$, and —CCH; or $R^{16}$ together with $R^{17a}$ form a 3- to 10-membered heterocycle, wherein the 3- to 10-membered heterocycle is optionally substituted with one or more substituents independently selected from —CN.

In certain embodiments, for a compound or salt of Formula (II), Formula (II-A), or Formula (II'), $R^{16}$ together with $R^{17a}$ form a 3- to 10-membered heterocycle, wherein the 3- to 10-membered heterocycle is optionally substituted with one or more $R^{18f}$. In some embodiments, $R^{16}$ together with $R^{17a}$ form a 3- to 10-membered heterocycle, wherein the 3- to 10-membered heterocycle is optionally substituted with one or more substituents independently selected from halogen, —CN, —OH, —$OCH_3$, —SH, —$NH_2$, —$NO_2$, —$N_3$, $C_{1-6}$ alkyl, and $C_{2-6}$ alkynyl. In some embodiments, $R^{16}$ together with $R^{17a}$ form a 3- to 10-membered heterocycle, wherein the 3- to 10-membered heterocycle is optionally substituted with one or more substituents independently selected from halogen, —CN, $C_{1-6}$ alkyl, and $C_{2-6}$ alkynyl. In some embodiments, $R^{16}$ together with $R^{17a}$ form a 3- to 10-membered heterocycle, wherein the 3- to 10-membered heterocycle is optionally substituted with one or more substituents independently selected from halogen, —CN, $C_1$ alkyl, and $C_2$ alkynyl. In some embodiments, $R^{16}$ together with $R^{17a}$ form a 3- to 10-membered heterocycle, wherein the 3- to 10-membered heterocycle is optionally substituted with one or more substituents independently selected from —F, —CN, —$CH_3$, and —CCH. In some embodiments, $R^{16}$ together with $R^{17a}$ form a 3- to 10-membered heterocycle, wherein the 3- to 10-membered heterocycle is optionally substituted with one or more substituents independently selected from —F and —CN. In some embodiments, $R^{16}$ together with $R^{17a}$ form a 3- to 10-membered heterocycle, wherein the 3- to 10-membered heterocycle is optionally substituted with one or more substituents independently selected from —F. In some embodiments, $R^{16}$ together with $R^{17a}$ form a 3- to 10-membered heterocycle, wherein the 3- to 10-membered heterocycle is optionally substituted with one or more substituents independently selected from —CN.

In some embodiments, each $R^{17a}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl, $C_{2-6}$ alkenyl, and $C_{2-6}$ alkynyl, each of which is optionally substituted with one or more $R^{18f}$.

In some embodiments, each $R^{17a}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl and $C_{2-6}$ alkynyl, each of which is optionally substituted with one or more $R^{18f}$.

In some embodiments, each $R^{17a}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl and $C_{2-6}$ alkynyl, each of which is optionally substituted with one or more substituents independently selected from halogen or CN.

In some embodiments, each $R^{17a}$ is independently selected from:

hydrogen, halogen, —$OR^{19g}$, —$N(R^{19g})_2$, —CN, and —$N_3$; and $C_{1-6}$ alkyl and $C_{2-6}$ alkynyl, each of which is optionally substituted with one or more substituents independently selected from halogen or CN.

In some embodiments, each $R^{17a}$ is independently selected from:

hydrogen, halogen, —$OR^{19g}$, —CN, and —$N_3$; and $C_{1-6}$ alkyl and $C_{2-6}$ alkynyl, each of which is optionally substituted with one or more substituents independently selected from halogen or CN.

In some embodiments, each $R^{17a}$ is independently selected from:

hydrogen, halogen, and —CN; and $C_{1-6}$ alkyl and $C_{2-6}$ alkynyl, each of which is optionally substituted with one or more substituents independently selected from halogen or CN.

In some embodiments, each $R^{17a}$ is independently selected from:

hydrogen, halogen, and —CN; and $C_{1-3}$ alkyl and $C_{2-3}$ alkynyl, each of which is optionally substituted with one or more substituents independently selected from halogen or CN.

In some embodiments, each $R^{17a}$ is independently selected from:

hydrogen, halogen, and —CN; and $C_1$ alkyl and $C_{2-3}$ alkynyl, each of which is optionally substituted with one or more substituents independently selected from halogen or CN.

In some embodiments, each $R^{17a}$ is independently selected from:

hydrogen, halogen, and —CN; and $C_{1-6}$alkyl and $C_{2-6}$ alkynyl.

In some embodiments, each $R^{17a}$ is independently selected from:

hydrogen, halogen, and —CN; and $C_{1-3}$ alkyl and $C_{2-6}$ alkynyl.

In some embodiments, each $R^{17a}$ is independently selected from:

hydrogen, halogen, and —CN; and $C_1$ alkyl and $C_{2-3}$ alkynyl.

In some embodiments, each $R^{17a}$ is independently selected from:

hydrogen, halogen, and —CN; and $C_1$ alkyl and $C_2$ alkynyl.

In some embodiments, each $R^{17a}$ is independently selected from:

hydrogen, —F, and —CN; and $C_1$ alkyl and $C_2$ alkynyl.

In some embodiments, each $R^{17a}$ is independently selected from: hydrogen, —CN, —F, —$CH_3$, and —CCH.

In some embodiments, each $R^{17a}$ is independently selected from: hydrogen, —CN, —F, and —$CH_3$. In some embodiments, each $R^{17a}$ is independently selected from: hydrogen, —CN, —F, and —CCH. In some embodiments, each $R^{17a}$ is independently selected from: hydrogen, —CN, —CCH, and —$CH_3$. In some embodiments, each $R^{17a}$ is independently selected from: hydrogen, —CCH, —F, and —$CH_3$. In some embodiments, each $R^{17a}$ is independently selected from: hydrogen, —CCH, —F, and —$CH_3$.

In some embodiments, each $R^{17a}$ is independently selected from: hydrogen, —CN, and —F. In some embodiments, each $R^{17a}$ is independently selected from: hydrogen, —$CH_3$, and —F. In some embodiments, each $R^{17a}$ is independently selected from: hydrogen, —$CH_3$, and —CN. In some embodiments, each $R^{17a}$ is independently selected from: hydrogen, —CCH, and —F. In some embodiments, each $R^{17a}$ is independently selected from: hydrogen, —CCH, and —CN.

In some embodiments, each $R^{17a}$ is independently selected from: hydrogen and —CN. In some embodiments, each $R^{17a}$ is independently selected from: hydrogen and —F. In some embodiments, each $R^{17a}$ is independently selected from: hydrogen and —$CH_3$. In some embodiments, each $R^{17a}$ is independently selected from: hydrogen and —CCH.

In some embodiments, each $R^{17a}$ is independently selected from: hydrogen. In some embodiments, each $R^{17a}$ is independently selected from: —F. In some embodiments, each $R^{17a}$ is independently selected from: —CN. In some embodiments, each $R^{17a}$ is independently selected from: —$CH_3$. In some embodiments, each $R^{17a}$ is independently selected from: —CCH.

In certain embodiments, for a compound or salt of Formula (II), Formula (II-A), or Formula (II'), each $R^{17b}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl, $C_{2-6}$ alkenyl, and $C_{2-6}$ alkynyl, each of which is optionally substituted with one or more $R^{18f}$; or $R^{15}$ together with $R^{17b}$ form a 3- to 10-membered heterocycle, wherein the 3- to 10-membered heterocycle is optionally substituted with one or more $R^1$Sf; or $R^{16}$ together with $R^{17b}$ form a 3- to 10-membered heterocycle, wherein the 3- to 10-membered heterocycle is optionally substituted with one or more $R^{18f}$.

In some embodiments, each $R^{17b}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl, $C_{2-6}$ alkenyl, and $C_{2-6}$ alkynyl, each of which is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$.

In some embodiments, each $R^{17b}$ is independently selected from:

hydrogen, halogen, and —CN; and $C_{1-6}$ alkyl, $C_{2-6}$ alkenyl, and $C_{2-6}$ alkynyl, each of which is optionally substituted with one or more substituents independently selected from —F and —CN; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$.

In some embodiments, each $R^{17b}$ is independently selected from:

hydrogen, —F, and —CN; and $C_1$ alkyl and $C_2$ alkynyl, each of which is optionally substituted with one or more substituents independently selected from —F and —CN; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$.

In some embodiments, each $R^{17b}$ is independently selected from: hydrogen, —F, —CN, —$CH_3$, and —CCH; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$.

In some embodiments, each $R^{17b}$ is independently selected from: hydrogen, —F, —CN, —$CH_3$, and —CCH; or $R^{15}$ together with $R^{17b}$ form a 3- to 10-membered heterocycle, wherein the 3- to 10-membered heterocycle is optionally substituted with one or more substituents independently selected from —F and —CN; or $R^{16}$ together with $R^{17b}$ form a 3- to 10-membered heterocycle, wherein the 3- to 10-membered heterocycle is optionally substituted with one or more substituents independently selected from —F and —CN.

In some embodiments, each $R^{17b}$ is independently selected from: hydrogen, —F, —CN, —$CH_3$, and —CCH; or $R^{15}$ together with $R^{17b}$ form a 3- to 10-membered heterocycle, wherein the 3- to 10-membered heterocycle is optionally substituted with one or more substituents independently selected from —F; or $R^{16}$ together with $R^{17b}$ form a 3- to 10-membered heterocycle, wherein the 3- to 10-membered heterocycle is optionally substituted with one or more substituents independently selected from —F.

In some embodiments, each $R^{17b}$ is independently selected from: hydrogen, —F, —CN, —$CH_3$, and —CCH; or $R^{15}$ together with $R^{17b}$ form a 3- to 10-membered heterocycle, wherein the 3- to 10-membered heterocycle is optionally substituted with one or more substituents independently selected from —CN; or $R^{16}$ together with $R^{17b}$ form a 3- to 10-membered heterocycle, wherein the 3- to 10-membered heterocycle is optionally substituted with one or more substituents independently selected from —CN.

In some embodiments, each $R^{17b}$ is independently selected from: hydrogen, —F, —CN, —$CH_3$, and —CCH; or $R^{16}$ together with $R^{17b}$ form a 3- to 10-membered heterocycle, wherein the 3- to 10-membered heterocycle is optionally substituted with one or more $R^{18f}$. In some embodiments, each $R^{17b}$ is independently selected from: hydrogen, —F, —CN, —$CH_3$, and —CCH; or $R^{16}$ together with $R^{17b}$ form a 3- to 10-membered heterocycle, wherein the 3- to 10-membered heterocycle is optionally substituted with one or more substituents independently selected from halogen, —CN, —OH, —$OCH_3$, —SH, —$NH_2$, —$NO_2$, —$N_3$, $C_{1-6}$ alkyl, and $C_{2-6}$ alkynyl. In some embodiments, each $R^{17b}$ is independently selected from: hydrogen, —F, —CN, —$CH_3$, and —CCH; or $R^{16}$ together with $R^{17b}$ form a 3- to 10-membered heterocycle, wherein the 3- to 10-membered heterocycle is optionally substituted with one or more substituents independently selected from halogen, —CN, $C_{1-6}$ alkyl, and $C_{2-6}$ alkynyl. In some embodiments, each $R^{17b}$ is independently selected from: hydrogen, —F, —CN, —$CH_3$, and —CCH; or $R^{16}$ together with $R^{17b}$ form a 3- to 10-membered heterocycle, wherein the 3- to 10-membered heterocycle is optionally substituted with one or more substituents independently selected from halogen, —CN, $C_1$ alkyl, and $C_2$ alkynyl. In some embodiments, each $R^{17b}$ is independently selected from: hydrogen, —F, —CN, —$CH_3$, and —CCH; or $R^{16}$ together with $R^{17b}$ form a 3- to 10-membered heterocycle, wherein the 3- to 10-membered heterocycle is optionally substituted with one or more substituents independently selected from —F, —CN, —$CH_3$, and —CCH. In some embodiments, each $R^{17b}$ is independently selected from: hydrogen, —F, —CN, —$CH_3$, and —CCH; or $R^{16}$ together with $R^{17b}$ form a 3- to 10-membered heterocycle, wherein the 3- to 10-membered heterocycle is optionally substituted with one or more substituents independently selected from —F and —CN. In some embodiments, each $R^{17b}$ is independently selected from: hydrogen, —F, —CN, —$CH_3$, and —CCH; or $R^{16}$ together with $R^{17b}$ form a 3- to 10-membered heterocycle, wherein the 3- to 10-membered heterocycle is optionally substituted with one or more substituents independently selected from —F. In some embodiments, each $R^{17b}$ is independently selected from: hydrogen, —F, —CN, —$CH_3$, and —CCH; or $R^{16}$ together with $R^{17b}$ form a 3- to 10-membered heterocycle, wherein the 3- to 10-membered heterocycle is optionally substituted with one or more substituents independently selected from —CN.

In certain embodiments, for a compound or salt of Formula (II), Formula (II-A), or Formula (II'), $R^{16}$ together with $R^{17b}$ form a 3- to 10-membered heterocycle, wherein the 3- to 10-membered heterocycle is optionally substituted with one or more $R^{18f}$. In some embodiments, $R^{16}$ together with $R^{17b}$ form a 3- to 10-membered heterocycle, wherein the 3- to 10-membered heterocycle is optionally substituted with one or more substituents independently selected from halogen, —CN, —OH, —$OCH_3$, —SH, —$NH_2$, —$NO_2$, —$N_3$, $C_{1-6}$ alkyl, and $C_{2-6}$ alkynyl. In some embodiments, $R^{16}$ together with $R^{17b}$ form a 3- to 10-membered heterocycle, wherein the 3- to 10-membered heterocycle is optionally substituted with one or more substituents independently selected from halogen, —CN, $C_{1-6}$ alkyl, and $C_{2-6}$ alkynyl. In some embodiments, $R^{16}$ together with $R^{17b}$ form a 3- to 10-membered heterocycle, wherein the 3- to 10-membered heterocycle is optionally substituted with one or more substituents independently selected from halogen, —CN, $C_1$ alkyl, and $C_2$ alkynyl. In some embodiments, $R^{16}$ together with $R^{17b}$ form a 3- to 10-membered heterocycle, wherein the 3- to 10-membered heterocycle is optionally substituted with one or more substituents independently selected from —F, —CN, —$CH_3$, and —CCH. In some embodiments, $R^{16}$ together with $R^{17b}$ form a 3- to 10-membered heterocycle, wherein the 3- to 10-membered heterocycle is optionally substituted with one or more substituents independently selected from —F and —CN. In some embodiments, $R^{16}$ together with $R^{17b}$ form a 3- to 10-membered heterocycle, wherein the 3- to 10-membered heterocycle is optionally substituted with one or more substituents independently selected from —F. In some embodiments, $R^{16}$ together with $R^{17b}$ form a 3- to 10-membered heterocycle, wherein the 3- to 10-membered heterocycle is optionally substituted with one or more substituents independently selected from —CN.

In some embodiments, each $R^{17b}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl, $C_{2-6}$ alkenyl, and $C_{2-6}$ alkynyl, each of which is optionally substituted with one or more $R^{18f}$.

In some embodiments, each $R^{17b}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl and $C_{2-6}$ alkynyl, each of which is optionally substituted with one or more $R^{18f}$.

In some embodiments, each $R^{17b}$ is independently selected from:

hydrogen, halogen, —$OR^{19g}$, —$SR^{19g}$, —$N(R^{19g})_2$, —$NO_2$, —CN, —$N_3$; and $C_{1-6}$ alkyl and $C_{2-6}$ alkynyl, each of which is optionally substituted with one or more substituents independently selected from halogen or CN.

In some embodiments, each $R^{17b}$ is independently selected from:

hydrogen, halogen, —$OR^{19g}$, —$N(R^{19g})_2$, —CN, and —$N_3$; and $C_{1-6}$ alkyl and $C_{2-6}$ alkynyl, each of which is optionally substituted with one or more substituents independently selected from halogen or CN.

In some embodiments, each $R^{17b}$ is independently selected from:

hydrogen, halogen, —$OR^{19g}$, —CN, and —$N_3$; and $C_{1-6}$ alkyl and $C_{2-6}$ alkynyl, each of which is optionally substituted with one or more substituents independently selected from halogen or CN.

In some embodiments, each $R^{17b}$ is independently selected from:

hydrogen, halogen, and —CN; and $C_{1-6}$ alkyl and $C_{2-6}$ alkynyl, each of which is optionally substituted with one or more substituents independently selected from halogen or CN.

In some embodiments, each $R^{17b}$ is independently selected from:

hydrogen, halogen, and —CN; and $C_{1-3}$ alkyl and $C_{2-3}$ alkynyl, each of which is optionally substituted with one or more substituents independently selected from halogen or CN.

In some embodiments, each $R^{17b}$ is independently selected from:

hydrogen, halogen, and —CN; and $C_1$ alkyl and $C_{2-3}$ alkynyl, each of which is optionally substituted with one or more substituents independently selected from halogen or CN.

In some embodiments, each $R^{17b}$ is independently selected from:

hydrogen, halogen, and —CN; and $C_{1-6}$alkyl and $C_{2-6}$ alkynyl.

In some embodiments, each $R^{17b}$ is independently selected from:

hydrogen, halogen, and —CN; and $C_{1-3}$ alkyl and $C_{2-6}$ alkynyl.

In some embodiments, each $R^{17b}$ is independently selected from:

hydrogen, halogen, and —CN; and $C_1$ alkyl and $C_{2-3}$ alkynyl.

In some embodiments, each $R^{17b}$ is independently selected from:

hydrogen, halogen, and —CN; and $C_1$ alkyl and $C_2$ alkynyl.

In some embodiments, each $R^{17b}$ is independently selected from:

hydrogen, —F, and —CN; and $C_1$ alkyl and $C_2$ alkynyl.

In some embodiments, each $R^{17b}$ is independently selected from: hydrogen, —CN, —F, —$CH_3$, and —CCH.

In some embodiments, each $R^{17b}$ is independently selected from: hydrogen, —CN, —F, and —$CH_3$. In some embodiments, each $R^{17b}$ is independently selected from: hydrogen, —CN, —F, and —CCH. In some embodiments, each $R^{17b}$ is independently selected from: hydrogen, —CN, —CCH, and —$CH_3$. In some embodiments, each $R^{17b}$ is independently selected from: hydrogen, —CCH, —F, and —$CH_3$. In some embodiments, each $R^{17b}$ is independently selected from: hydrogen, —CCH, —F, and —$CH_3$.

In some embodiments, each $R^{17b}$ is independently selected from: hydrogen, —CN, and —F. In some embodiments, each $R^{17b}$ is independently selected from: hydrogen, —$CH_3$, and —F. In some embodiments, each $R^{17b}$ is independently selected from: hydrogen, —$CH_3$, and —CN. In some embodiments, each $R^{17b}$ is independently selected from: hydrogen, —CCH, and —F. In some embodiments, each $R^{17b}$ is independently selected from: hydrogen, —CCH, and —CN.

In some embodiments, each $R^{17b}$ is independently selected from: hydrogen and —CN. In some embodiments, each $R^{17b}$ is independently selected from: hydrogen and —F. In some embodiments, each $R^{17b}$ is independently selected from: hydrogen and —$CH_3$. In some embodiments, each $R^{17b}$ is independently selected from: hydrogen and —CCH.

In some embodiments, each $R^{17b}$ is independently selected from: hydrogen. In some embodiments, each $R^{17b}$ is independently selected from: —F. In some embodiments, each $R^{17b}$ is independently selected from: —CN. In some embodiments, each $R^{17b}$ is independently selected from: —$CH_3$. In some embodiments, each $R^{17b}$ is independently selected from: —CCH.

In certain embodiments, for a compound or salt of Formula (II), Formula (II-A), or Formula (II'), each $R^{17c}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl, $C_{2-6}$ alkenyl, and $C_{2-6}$ alkynyl, each of which is optionally substituted with one or more $R^{18f}$.

In some embodiments, each $R^{17c}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl, $C_{2-6}$ alkenyl, and $C_{2-6}$ alkynyl, each of which is optionally substituted with one or more $R^{18f}$.

In some embodiments, each $R^{17c}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl and $C_{2-6}$ alkynyl, each of which is optionally substituted with one or more $R^{18f}$.

In some embodiments, each $R^{17c}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl and $C_{2-6}$ alkynyl, each of which is optionally substituted with one or more substituents independently selected from halogen or CN.

In some embodiments, each $R^{17c}$ is independently selected from:

hydrogen, halogen, —$OR^{19g}$, —$N(R^{19g})_2$, —CN, and —$N_3$; and $C_{1-6}$ alkyl and $C_{2-6}$ alkynyl, each of which is optionally substituted with one or more substituents independently selected from halogen or CN.

In some embodiments, each $R^{17c}$ is independently selected from:

hydrogen, halogen, —$OR^{19g}$, —CN, and —$N_3$; and $C_{1-6}$ alkyl and $C_{2-6}$ alkynyl, each of which is optionally substituted with one or more substituents independently selected from halogen or CN.

In some embodiments, each $R^{17c}$ is independently selected from:

hydrogen, halogen, and —CN; and $C_{1-6}$ alkyl and $C_{2-6}$ alkynyl, each of which is optionally substituted with one or more substituents independently selected from halogen or CN.

In some embodiments, each $R^{17c}$ is independently selected from:

hydrogen, halogen, and —CN; and $C_{1-3}$ alkyl and $C_{2-3}$ alkynyl, each of which is optionally substituted with one or more substituents independently selected from halogen or CN.

In some embodiments, each $R^{17c}$ is independently selected from:

hydrogen, halogen, and —CN; and $C_1$ alkyl and $C_{2-3}$ alkynyl, each of which is optionally substituted with one or more substituents independently selected from halogen or CN.

In some embodiments, each $R^{17c}$ is independently selected from:

hydrogen, halogen, and —CN; and $C_{1-6}$ alkyl and $C_{2-6}$ alkynyl.

In some embodiments, each $R^{17c}$ is independently selected from:

hydrogen, halogen, and —CN; and $C_{1-3}$ alkyl and $C_{2-6}$ alkynyl.

In some embodiments, each $R^{17c}$ is independently selected from:

hydrogen, halogen, and —CN; and $C_1$ alkyl and $C_{2-3}$ alkynyl.

In some embodiments, each $R^{7c}$ is independently selected from:

hydrogen, halogen, and —CN; and $C_1$ alkyl and $C_2$ alkynyl.

In some embodiments, each $R^{17c}$ is independently selected from:

hydrogen, —F, and —CN; and $C_1$ alkyl and $C_2$ alkynyl.

In some embodiments, each $R^{17c}$ is independently selected from: hydrogen, —CN, —F, —$CH_3$, and —CCH.

In some embodiments, each $R^{17c}$ is independently selected from: hydrogen, —CN, —F, and —$CH_3$. In some embodiments, each $R^{17c}$ is independently selected from:

hydrogen, —CN, —F, and —CCH. In some embodiments, each $R^{17c}$ is independently selected from: hydrogen, —CN, —CCH, and —$CH_3$. In some embodiments, each $R^{17c}$ is independently selected from: hydrogen, —CCH, —F, and —$CH_3$. In some embodiments, each $R^{17c}$ is independently selected from: hydrogen, —CCH, —F, and —$CH_3$.

In some embodiments, each $R^{17c}$ is independently selected from: hydrogen, —CN, and —F. In some embodiments, each $R^{17c}$ is independently selected from: hydrogen, —$CH_3$, and —F. In some embodiments, each $R^{17c}$ is independently selected from: hydrogen, —$CH_3$, and —CN. In some embodiments, each $R^{17c}$ is independently selected from: hydrogen, —CCH, and —F. In some embodiments, each $R^{17c}$ is independently selected from: hydrogen, —CCH, and —CN.

In some embodiments, each $R^{17c}$ is independently selected from: hydrogen and —CN. In some embodiments, each $R^{17c}$ is independently selected from: hydrogen and —F. In some embodiments, each $R^{17c}$ is independently selected from: hydrogen and —$CH_3$. In some embodiments, each $R^{17c}$ is independently selected from: hydrogen and —CCH.

In some embodiments, each $R^{17c}$ is independently selected from: hydrogen. In some embodiments, each $R^{17c}$ is independently selected from: —F. In some embodiments, each $R^{17c}$ is independently selected from: —CN. In some embodiments, each $R^{17c}$ is independently selected from: —$CH_3$. In some embodiments, each $R^{17c}$ is independently selected from: —CCH.

In certain embodiments, for a compound or salt of Formula (II), Formula (II-A), or Formula (II'), each $R^{17d}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl, $C_{2-6}$ alkenyl, and $C_{2-6}$ alkynyl, each of which is optionally substituted with one or more $R^{18f}$.

In some embodiments, each $R^{17d}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl, $C_{2-6}$ alkenyl, and $C_{2-6}$ alkynyl, each of which is optionally substituted with one or more $R^{18f}$.

In some embodiments, each $R^{17d}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl and $C_{2-6}$ alkynyl, each of which is optionally substituted with one or more $R^{18f}$.

In some embodiments, each $R^{17d}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl and $C_{2-6}$ alkynyl, each of which is optionally substituted with one or more substituents independently selected from halogen or CN.

In some embodiments, each $R^{17d}$ is independently selected from:

hydrogen, halogen, —$OR^{19g}$, —$N(R^{19g})_2$, —CN, and —$N_3$; and $C_{1-6}$ alkyl and $C_{2-6}$ alkynyl, each of which is optionally substituted with one or more substituents independently selected from halogen or CN.

In some embodiments, each $R^{17d}$ is independently selected from:

hydrogen, halogen, —$OR^{19g}$, —CN, and —$N_3$; and $C_{1-6}$ alkyl and $C_{2-6}$ alkynyl, each of which is optionally substituted with one or more substituents independently selected from halogen or CN.

In some embodiments, each $R^{17d}$ is independently selected from:

hydrogen, halogen, and —CN; and $C_{1-6}$ alkyl and $C_{2-6}$ alkynyl, each of which is optionally substituted with one or more substituents independently selected from halogen or CN.

In some embodiments, each $R^{17d}$ is independently selected from:

hydrogen, halogen, and —CN; and $C_{1-3}$ alkyl and $C_{2-3}$ alkynyl, each of which is optionally substituted with one or more substituents independently selected from halogen or CN.

In some embodiments, each $R^{17d}$ is independently selected from:

hydrogen, halogen, and —CN; and $C_1$ alkyl and $C_{2-3}$ alkynyl, each of which is optionally substituted with one or more substituents independently selected from halogen or CN.

In some embodiments, each $R^{17d}$ is independently selected from:

hydrogen, halogen, and —CN; and $C_{1-6}$ alkyl and $C_{2-6}$ alkynyl.

In some embodiments, each $R^{17d}$ is independently selected from:

hydrogen, halogen, and —CN; and $C_{1-3}$ alkyl and $C_{2-6}$ alkynyl.

In some embodiments, each $R^{17d}$ is independently selected from:

hydrogen, halogen, and —CN; and $C_1$ alkyl and $C_{2-3}$ alkynyl.

In some embodiments, each $R^{17d}$ is independently selected from:

hydrogen, halogen, and —CN; and $C_1$ alkyl and $C_2$ alkynyl.

In some embodiments, each $R^{17d}$ is independently selected from:

hydrogen, —F, and —CN; and $C_1$ alkyl and $C_2$ alkynyl.

In some embodiments, each $R^{17d}$ is independently selected from: hydrogen, —CN, —F, —$CH_3$, and —CCH.

In some embodiments, each $R^{17d}$ is independently selected from: hydrogen, —CN, —F, and —$CH_3$. In some embodiments, each $R^{17d}$ is independently selected from: hydrogen, —CN, —F, and —CCH. In some embodiments, each $R^{17d}$ is independently selected from: hydrogen, —CN, —CCH, and —$CH_3$. In some embodiments, each $R^{17d}$ is independently selected from: hydrogen, —CCH, —F, and —$CH_3$. In some embodiments, each $R^{17d}$ is independently selected from: hydrogen, —CCH, —F, and —$CH_3$.

In some embodiments, each $R^{17d}$ is independently selected from: hydrogen, —CN, and —F. In some embodiments, each $R^{17d}$ is independently selected from: hydrogen, —$CH_3$, and —F. In some embodiments, each $R^{17d}$ is independently selected from: hydrogen, —$CH_3$, and —CN. In some embodiments, each $R^{17d}$ is independently selected from: hydrogen, —CCH, and —F. In some embodiments, each $R^{17d}$ is independently selected from: hydrogen, —CCH, and —CN.

In some embodiments, each $R^{17d}$ is independently selected from: hydrogen and —CN. In some embodiments, each $R^{17d}$ is independently selected from: hydrogen and —F. In some embodiments, each $R^{17d}$ is independently selected from: hydrogen and —$CH_3$. In some embodiments, each $R^{17d}$ is independently selected from: hydrogen and —CCH.

In some embodiments, each $R^{17d}$ is independently selected from: hydrogen. In some embodiments, each $R^{17d}$ is independently selected from: —F. In some embodiments, each $R^{17d}$ is independently selected from: —CN. In some embodiments, each $R^{17d}$ is independently selected from: —$CH_3$. In some embodiments, each $R^{17d}$ is independently selected from: —CCH.

In certain embodiments, for a compound or salt of Formula (II), Formula (II-A), or Formula (II'), each $R^{17e}$, is independently selected from:

hydrogen, halogen, —$OR^{19g}$, —$SR^{19g}$, —$N(R^{19g})_2$, —$NO_2$, —CN, and —$N_3$; and $C_{1-6}$ alkyl, $C_{2-6}$ alkenyl, and $C_{2-6}$ alkynyl, each of which is optionally substituted with one or more $R^{18f}$.

In some embodiments, each $R^{17}$, is independently selected from:

hydrogen, halogen, —$OR^{19g}$, —$SR^{19g}$, —$N(R^{19g})_2$, —$NO_2$, —CN, and —$N_3$; and $C_{1-6}$ alkyl, $C_{2-6}$ alkenyl, and $C_{2-6}$ alkynyl, each of which is optionally substituted with one or more $R^{18f}$.

In some embodiments, each $R^{17e}$, is independently selected from:

hydrogen, halogen, —$OR^{19g}$, —$SR^{19g}$, —$N(R^{19g})_2$, —$NO_2$, —CN, and —$N_3$; and $C_{1-6}$ alkyl and $C_{2-6}$ alkynyl, each of which is optionally substituted with one or more $R^{18f}$.

In some embodiments, each $R^{17e}$ is independently selected from:

hydrogen, halogen, —$OR^{19g}$, —$SR^{19g}$, —$N(R^{19g})_2$, —$NO_2$, —CN, and —$N_3$; and $C_{1-6}$ alkyl and $C_{2-6}$ alkynyl, each of which is optionally substituted with one or more substituents independently selected from halogen or CN.

In some embodiments, each $R^{17e}$ is independently selected from:

hydrogen, halogen, —$OR^{19g}$, —$N(R^{19g})_2$, —CN, and —$N_3$; and $C_{1-6}$ alkyl and $C_{2-6}$ alkynyl, each of which is optionally substituted with one or more substituents independently selected from halogen or CN.

In some embodiments, each $R^{17e}$ is independently selected from:

hydrogen, halogen, —$OR^{19g}$, —CN, and —$N_3$; and $C_{1-6}$ alkyl and $C_{2-6}$ alkynyl, each of which is optionally substituted with one or more substituents independently selected from halogen or CN.

In some embodiments, each $R^{17e}$ is independently selected from:

hydrogen, halogen, and —CN; and $C_{1-6}$ alkyl and $C_{2-6}$ alkynyl, each of which is optionally substituted with one or more substituents independently selected from halogen or CN.

In some embodiments, each $R^{17e}$ is independently selected from:

hydrogen, halogen, and —CN; and $C_{1-3}$ alkyl and $C_{2-3}$ alkynyl, each of which is optionally substituted with one or more substituents independently selected from halogen or CN.

In some embodiments, each $R^{17e}$ is independently selected from:

hydrogen, halogen, and —CN; and $C_1$ alkyl and $C_{2-3}$ alkynyl, each of which is optionally substituted with one or more substituents independently selected from halogen or CN.

In some embodiments, each $R^{17e}$ is independently selected from:

hydrogen, halogen, and —CN; and $C_{1-6}$ alkyl and $C_{2-6}$ alkynyl.

In some embodiments, each $R^{17e}$ is independently selected from:

hydrogen, halogen, and —CN; and $C_{1-3}$ alkyl and $C_{2-6}$ alkynyl.

In some embodiments, each $R^{17e}$ is independently selected from:

hydrogen, halogen, and —CN; and $C_1$ alkyl and $C_{2-3}$ alkynyl.

In some embodiments, each $R^{17e}$ is independently selected from:

hydrogen, halogen, and —CN; and $C_1$ alkyl and $C_2$ alkynyl.

In some embodiments, each $R^{17e}$ is independently selected from:

hydrogen, —F, and —CN; and $C_1$ alkyl and $C_2$ alkynyl.

In some embodiments, each $R^{17e}$ is independently selected from: hydrogen, —CN, —F, —$CH_3$, and —CCH.

In some embodiments, each $R^{17e}$ is independently selected from: hydrogen, —CN, —F, and —$CH_3$. In some embodiments, each $R^{17e}$ is independently selected from: hydrogen, —CN, —F, and —CCH. In some embodiments, each $R^{17e}$ is independently selected from: hydrogen, —CN, —CCH, and —$CH_3$. In some embodiments, each $R^{17e}$ is independently selected from: hydrogen, —CCH, —F, and —$CH_3$. In some embodiments, each $R^{17e}$ is independently selected from: hydrogen, —CCH, —F, and —$CH_3$.

In some embodiments, each $R^{17e}$ is independently selected from: hydrogen, —CN, and —F. In some embodiments, each $R^{17e}$ is independently selected from: hydrogen, —$CH_3$, and —F. In some embodiments, each $R^{17e}$ is independently selected from: hydrogen, —$CH_3$, and —CN. In some embodiments, each $R^{17e}$ is independently selected from: hydrogen, —CCH, and —F. In some embodiments, each $R^{17e}$ is independently selected from: hydrogen, —CCH, and —CN.

In some embodiments, each $R^{17e}$ is independently selected from: hydrogen and —CN. In some embodiments, each $R^{17e}$ is independently selected from: hydrogen and —F. In some embodiments, each $R^{17e}$ is independently selected from: hydrogen and —$CH_3$. In some embodiments, each $R^{17e}$ is independently selected from: hydrogen and —CCH.

In some embodiments, each $R^{17e}$ is independently selected from: hydrogen. In some embodiments, each $R^{17e}$ is independently selected from: —F. In some embodiments, each $R^{17e}$ is independently selected from: —CN. In some embodiments, each $R^{17e}$ is independently selected from: —$CH_3$. In some embodiments, each $R^{17e}$ is independently selected from: —CCH.

In certain embodiments, for a compound or salt of Formula (II), Formula (II-A), or Formula (II'), each of $R^{18a}$, $R^{18b}$, $R^{18c}$, $R^{18d}$, $R^{18e}$, and $R^{18f}$ can be any suitable functional group known by one of skill in the art. In some embodiments, each of $R^{18a}$, $R^{18b}$, $R^{18c}$, $R^{18d}$, $R^{18e}$, and $R^{18f}$ are independently selected from: halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, =O, =S, =$N(R^{19h})$, and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19b})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, =O, =S, =$N(R^{19h})$, and —CN. In some embodiments, each $R^{18a}$ is independently selected from halogen, —$OR^{19h}$, —$SR^{19h}$, —$N(R^{19h})_2$, —$C(O)R^{19h}$, —CN, and $C_{1-3}$ alkyl. In some embodiments, each $R^{18a}$ is independently selected from halogen, —$OR^{19h}$, —$N(R^{19h})_2$, —CN, and $C_{1-3}$ alkyl. In some embodiments, each $R^{18a}$ is independently selected from halogen, —$OR^{19h}$, and —CN. In some embodiments, each $R^{18b}$ is independently selected from halogen, —$OR^{19h}$, —$SR^{19h}$, —$N(R^{19h})_2$, —$C(O)R^{19h}$, —CN, and $C_{1-3}$ alkyl. In some embodiments, each $R^{18b}$ is independently selected from halogen, —$OR^{19h}$, —$N(R^{19h})_2$, —CN, and $C_{1-3}$ alkyl. In some embodiments, each $R^{18b}$ is independently selected from halogen, —$OR^{19h}$, and —CN. In some embodiments, each $R^{18c}$ is independently selected from halogen, —$OR^{19h}$, —$SR^{19h}$, —$N(R^{19h})_2$, —$C(O)R^{19h}$, —CN, and $C_{1-3}$ alkyl. In some embodiments, each $R^{18c}$ is independently selected from halogen, —$OR^{19h}$, —$N(R^{19h})_2$, —CN, and $C_{1-3}$ alkyl. In some embodiments, each $R^{18c}$ is independently selected from halogen, —$OR^{19h}$, and —CN. In some embodiments, each $R^{18d}$ is independently selected from halogen, —$OR^{19h}$, —$SR^{19h}$, —$N(R^{19h})_2$, —$C(O)R^{19h}$, —CN, and $C_{1-3}$ alkyl. In some embodiments, each $R^{18d}$ is independently selected from halogen, —$OR^{19h}$, —$N(R^{19h})_2$, —CN, and $C_{1-3}$ alkyl. In some embodiments, each $R^{18d}$ is independently selected from halogen, —$OR^{19h}$, and —CN. In some embodiments, each $R^{18e}$ is independently selected from halogen, —$OR^{19h}$, —$SR^{19h}$, —$N(R^{19h})_2$, —$C(O)R^{19h}$, —CN, and $C_{1-3}$ alkyl. In some embodiments, each $R^{18e}$ is independently selected from halogen, —$OR^{19h}$, —$N(R^{19h})_2$, —CN, and $C_{1-3}$ alkyl. In some embodiments, each $R^{18e}$ is independently selected from halogen, —$OR^{19h}$, and —CN. In some embodiments, each $R^{18c}$ is independently —$OR^{19h}$. In some embodiments, each $R^{18c}$ is independently —OH. In some embodiments, each $R^{18f}$ is independently selected from halogen, —$OR^{19h}$, —$SR^{19h}$, —$N(R^{19h})_2$, —$C(O)R^{19h}$, —CN, and $C_{1-3}$ alkyl. In some embodiments, each $R^{18f}$ is independently selected from halogen, —$OR^{19h}$, —$N(R^{19h})_2$, —CN, and $C_{1-3}$ alkyl. In some embodiments, each $R^{18f}$ is independently selected from halogen, —$OR^{19h}$, and —CN. In some embodiments, each $R^{18f}$ is independently halogen or —CN. In some embodiments, each $R^{18f}$ is independently fluoro or —CN.

In certain embodiments, for a compound or salt of Formula (II), Formula (II-A), or Formula (II'), each of $R^{19a}$, $R^{19b}$, $R^{19c}$, $R^{19d}$, $R^{19e}$, $R^{19f}$, $R^{19g}$, and $R^{19h}$ can be any suitable functional group known by one of skill in the art. In some embodiments, each of $R^{19a}$, $R^{19b}$, $R^{19C}$, $R^{19d}$, $R^{19e}$, $R^{19f}$, $R^{19g}$, and $R^{19h}$ are independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}\ alkyl)_2$, —$NH(C_{1-6}\ alkyl)$, $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}\ alkyl)_2$, —$NH(C_{1-6}\ alkyl)$, $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{19a}$ is independently selected from hydrogen, $C_{1-6}$ alkyl, $C_{2-6}$ alkenyl, $C_{2-6}$ alkynyl, $C_{3-10}$ carbocycle, and 3- to 10-membered heterocycle. In some embodiments, each $R^{19a}$ is independently selected from hydrogen, $C_{1-6}$ alkyl, $C_{2-6}$ alkenyl, and $C_{2-6}$ alkynyl. In some embodiments, each $R^{19a}$ is independently selected from hydrogen and $C_{1-6}$ alkyl. In some embodiments, each $R^{19a}$ is independently selected from hydrogen and methyl. In some embodiments, each $R^{19a}$ is independently selected from hydrogen. In some embodiments, each $R^{19b}$ is independently selected from hydrogen, $C_{1-6}$ alkyl, $C_{2-6}$ alkenyl, $C_{2-6}$ alkynyl, $C_{3-10}$ carbocycle, and 3- to 10-membered heterocycle. In some embodiments, each $R^{19b}$ is independently selected from hydrogen, $C_{1-6}$ alkyl, $C_{2-6}$ alkenyl, and $C_{2-6}$ alkynyl. In some embodiments, each $R^{19b}$ is independently selected from hydrogen and $C_{1-6}$ alkyl. In some embodiments, each $R^{19b}$ is independently selected from hydrogen and methyl. In some embodiments, each $R^{19b}$ is independently selected from hydrogen. In some embodiments, each $R^{19c}$ is independently selected from hydrogen, $C_{1-6}$ alkyl, $C_{2-6}$ alkenyl, $C_{2-6}$ alkynyl, $C_{3-10}$ carbocycle, and 3- to 10-membered heterocycle. In some embodiments, each $R^{19c}$ is independently selected from hydrogen, $C_{1-6}$ alkyl, $C_{2-6}$ alkenyl, and $C_{2-6}$ alkynyl. In some embodiments, each $R^{19c}$ is independently selected from hydrogen and $C_{1-6}$ alkyl. In some embodiments, each $R^{19c}$ is independently selected from hydrogen and methyl. In some embodiments, each $R^{19c}$ is independently selected from hydrogen. In some embodiments, each $R^{19d}$ is independently selected from hydrogen, $C_{1-6}$ alkyl, $C_{2-6}$ alkenyl, $C_{2-6}$ alkynyl, $C_{3-10}$ carbocycle, and 3- to 10-membered heterocycle. In some embodiments, each $R^{19d}$ is independently selected from hydrogen, $C_{1-6}$ alkyl, $C_{2-6}$ alkenyl, and $C_{2-6}$ alkynyl. In some embodiments, each $R^{19d}$ is independently selected from hydrogen and $C_{1-6}$ alkyl. In some embodiments, each $R^{19d}$ is independently selected from hydrogen and methyl. In some embodiments, each $R^{19d}$ is independently selected from hydrogen. In some embodiments, each $R^{19e}$ is independently selected from hydrogen, $C_{1-6}$ alkyl, $C_{2-6}$ alkenyl, $C_{2-6}$ alkynyl, $C_{3-10}$ carbocycle, and 3- to 10-membered heterocycle. In some embodiments, each $R^{19e}$ is independently selected from hydrogen, $C_{1-6}$ alkyl, $C_{2-6}$ alkenyl, and $C_{2-6}$ alkynyl. In some embodiments, each $R^{19c}$ is independently selected from hydrogen and $C_{1-6}$ alkyl. In some embodiments, each $R^{19c}$ is independently selected from hydrogen and methyl. In some embodiments, each $R^{19e}$ is independently selected from hydrogen. In some embodiments, each $R^{19f}$ is independently selected from hydrogen, $C_{1-6}$ alkyl, $C_{2-6}$ alkenyl, $C_{2-6}$ alkynyl, $C_{3-10}$ carbocycle, and 3- to 10-membered heterocycle. In some embodiments, each $R^{19f}$ is independently selected from hydrogen, $C_{1-6}$ alkyl, $C_{2-6}$ alkenyl, and $C_{2-6}$ alkynyl. In some embodiments, each $R^{19f}$ is independently selected from hydrogen and $C_{1-6}$ alkyl. In some embodiments, each $R^{19f}$ is independently selected from hydrogen and methyl. In some embodiments, each $R^{19f}$ is independently selected from hydrogen. In some embodiments, each $R^{19g}$ is independently selected from hydrogen, $C_{1-6}$ alkyl, $C_{2-6}$ alkenyl, $C_{2-6}$ alkynyl, $C_{3-10}$ carbocycle, and 3- to 10-membered heterocycle. In some embodiments, each $R^{19g}$ is independently selected from hydrogen, $C_{1-6}$ alkyl, $C_{2-6}$ alkenyl, and $C_{2-6}$ alkynyl. In some embodiments, each $R^{19g}$ is independently selected from hydrogen and $C_{1-6}$ alkyl. In some embodiments, each $R^{19g}$ is independently selected from hydrogen and methyl. In some embodiments, each $R^{19g}$ is independently selected from hydrogen. In some embodiments, each $R^{19h}$ is independently selected from hydrogen, $C_{1-6}$ alkyl, $C_{2-6}$ alkenyl, $C_{2-6}$ alkynyl, $C_{3-10}$ carbocycle, and 3- to 10-membered heterocycle. In some embodiments, each $R^{19h}$ is independently selected from hydrogen, $C_{1-6}$ alkyl, $C_{2-6}$ alkenyl, and $C_{2-6}$ alkynyl. In some embodiments, each $R^{19h}$ is independently selected from hydrogen and $C_{1-6}$ alkyl. In some embodiments, each $R^{19h}$ is independently selected from hydrogen. In some embodiments, each $R^{19h}$ is independently selected from hydrogen and methyl. In some embodiments, each $R^{19h}$ is independently selected from hydrogen.

In certain embodiments, for a compound or salt of Formula (II), Formula (II-A), or Formula (II'), $Y^{12}$ is selected from C(CN), C(H), and C(F). In some embodiments, $Y^{12}$ is selected from C(CN). In some embodiments, $Y^{11}$ is selected from C(H). In some embodiments, $X^{13}$ is selected from N and C(H). In some embodiments, $X^{12}$ and $X^{12}$ are N. In some embodiments, $X^{11}$ is selected from N, C(H), and C(F). In some embodiments, $X^{12}$ is selected from N, C(H), and C(F).

In certain embodiments, for a compound or salt of Formula (II), Formula (II-A), or Formula (II'), $X^{11}$ is N, $X^{12}$ is N, $X^{13}$ is C(H), $Y^{11}$ is C(H), and $Y^{12}$ is C(CN). In some embodiments, $X^{11}$ is N, $X^{12}$ is N, $X^{13}$ is C(H), $Y^{11}$ is C(H), and $Y^{12}$ is C(CN), and $R^{16}$ is optionally substituted $C_1$ alkyl. In some embodiments, $X^{11}$ is N, $X^{12}$ is N, $X^{13}$ is C(H), $Y^{11}$ is C(H), and $Y^{12}$ is C(CN), and $R^{16}$ ia —$CH_3$. In some embodiments, $X^{11}$ is N, $X^{12}$ is N, $X^{13}$ is C(H), $Y^{11}$ is C(H), and $Y^{12}$ is C(CN), and $R^{15}$ is H. In some embodiments, $X^{11}$ is N, $X^{12}$ is N, $X^{13}$ is C(H), $Y^{11}$ is C(H), and $Y^{12}$ is C(CN), $R^{14}$ is H, and $R^{14'}$ is H. In some embodiments, $X^{11}$ is N, $X^{12}$ is N, $X^{13}$ is C(H), $Y^{11}$ is C(H), and $Y^{12}$ is C(CN), and $R^{12}$ is H. In some embodiments, $X^{11}$ is N, $X^{12}$ is N, $X^{13}$ is C(H), $Y^{11}$ is C(H), and $Y^{12}$ is C(CN), and $R^{13}$ is selected from $CH_3$, H, and cyclopropyl. In some embodiments, $X^{11}$ is N, $X^{12}$ is N, $X^{13}$ is C(H), $Y^{11}$ is C(H), and $Y^{12}$ is C(CN), and $R^{13}$ is selected from $CH_3$. In some embodiments, $X^{11}$ is N, $X^{12}$ is N, $X^{13}$ is C(H), $Y^{11}$ is C(H), and $Y^{12}$ is C(CN), and $R^{13}$ is selected from cyclopropyl. In some embodiments, $X^{11}$ is N, $X^{12}$ is N, $X^{13}$ is C(H), $Y^{11}$ is C(H), and $Y^{12}$ is C(CN), and $R^{13}$ is selected from H. In some embodiments, $X^{11}$ is N, $X^{12}$ is N, $X^{13}$ is C(H), $Y^{11}$ is C(H), and $Y^{12}$ is C(CN), and $R^{11}$ is selected from $CH_3$, cyclopropyl, F, Cl, Br, $CF_3$, CN, $N_3$, OH, and OMe. In some embodiments, $X^{11}$ is N, $X^{12}$ is N, $X^{13}$ is C(H), $Y^{11}$ is C(H), and $Y^{12}$ is C(CN), and $R^{11}$ is selected from $CH_3$, F, Cl, Br, $CF_3$, and CN. In some embodiments, $X^{11}$ is N, $X^{12}$ is N, $X^{13}$ is C(H), $Y^{11}$ is C(H), and $Y^{12}$ is C(CN), and $R^{11}$ is selected from F, Cl and CN. In some embodiments, $X^{11}$ is N, $X^{12}$ is N, $X^{13}$ is C(H), $Y^{11}$ is C(H), and $Y^{12}$ is C(CN), and $R^{11}$ is selected from F and CN. In some embodiments, $X^{11}$ is N, $X^{12}$ is N, $X^{13}$ is C(H), $Y^{11}$ is C(H), and $Y^{12}$ is C(CN), and $R^{11}$ is selected from F. In some embodiments, $X^{11}$ is N, $X^{12}$ is N, $X^{13}$ is C(H), $Y^{11}$ is C(H), and $Y^{12}$ is C(CN), and $R^{11}$ is selected from CN. In some embodiments, $X^{11}$ is N, $X^{12}$ is C(H), $X^{13}$ is N, $Y^{11}$ is C(H), and $Y^{12}$ is C(CN). In some embodiments, $X^{11}$ is N, $X^{12}$ is C(H), $X^{13}$ is N, $Y^{11}$ is C(H), and $Y^{12}$ is C(CN). In some embodiments, $X^{11}$ is N, $X^{12}$ is C(H), $X^{13}$ is N, $Y^{11}$ is C(H), and $Y^{12}$ is C(CN), and $R^{16}$ is optionally substituted $C_1$ alkyl. In some embodiments, $X^{11}$ is N, $X^{12}$ is C(H), $X^{13}$ is N, $Y^{11}$ is C(H), and $Y^{12}$ is C(CN), and $R^{16}$ ia —$CH_3$. In some embodiments, $X^{11}$ is N, $X^{12}$ is C(H), $X^{13}$ is N, $Y^{11}$ is C(H), and $Y^{12}$ is C(CN), and $R^{15}$ is H. In some embodiments, $X^{11}$ is N, $X^{12}$ is C(H), $X^{13}$ is N, $Y^{11}$ is C(H), and $Y^{12}$ is C(CN), $R^{14}$ is H, and $R^{14'}$ is H. In some embodiments, $X^{11}$ is N, $X^{12}$ is C(H), $X^{13}$ is N, $Y^{11}$ is C(H), and $Y^{12}$ is C(CN), and $R^{12}$ is H. In some embodiments, $X^{11}$ is N, $X^{12}$ is C(H), $X^{13}$ is N, $Y^{11}$ is C(H), and $Y^{12}$ is C(CN), and $R^{13}$ is selected from $CH_3$, H, and cyclopropyl. In some embodiments, $X^{11}$ is N, $X^{12}$ is C(H), $X^{13}$ is N, $Y^{11}$ is C(H), and $Y^{12}$ is C(CN), and $R^{13}$ is selected from $CH_3$. In some embodiments, $X^{11}$ is N, $X^{12}$ is C(H), $X^{13}$ is N, $Y^{11}$ is C(H), and $Y^{12}$ is C(CN), and $R^{13}$ is selected from cyclopropyl. In some embodiments, $X^{11}$ is N, $X^{12}$ is C(H), $X^{13}$ is N, $Y^{11}$ is C(H), and $Y^{12}$ is C(CN), and $R^{13}$ is selected from H. In some embodiments, $X^{11}$ is N, $X^{12}$ is C(H), $X^{13}$ is N, $Y^{11}$ is C(H), and $Y^{12}$ is C(CN), and $R^{11}$ is selected from $CH_3$, cyclopropyl, F, Cl, Br, $CF_3$, CN, $N_3$, OH, and OMe. In some embodiments, $X^{11}$ is N, $X^{12}$ is C(H), $X^{13}$ is N, $Y^{11}$ is C(H), and $Y^{12}$ is C(CN), and $R^{11}$ is selected from $CH_3$, F, Cl, Br, $CF_3$, and CN. In some embodiments, $X^{11}$ is N, $X^{12}$ is C(H), $X^{13}$ is N, $Y^{11}$ is C(H), and $Y^{12}$ is C(CN), and $R^{11}$ is selected from F, Cl and CN. In some embodiments, $X^{11}$ is N, $X^{12}$ is C(H), $X^{13}$ is N, $Y^{11}$ is C(H), and $Y^{12}$ is C(CN), and $R^{11}$ is selected from F and CN. In some embodiments, $X^{11}$ is N, $X^{12}$ is C(H), $X^{13}$ is N, $Y^{11}$ is C(H), and $Y^{12}$ is C(CN), and $R^{11}$ is selected from F. In some embodiments, $X^{11}$ is N, $X^{12}$ is C(H), $X^{13}$ is N, $Y^{11}$ is C(H), and $Y^{12}$ is C(CN), and $R^{11}$ is selected from CN. In some embodiments, $X^{11}$ is C(F), $X^{12}$ is N, $X^{13}$ is C(H), $Y^{11}$ is C(H), and $Y^{12}$ is C(CN). In some embodiments, $X^{11}$ is C(F), $X^{12}$ is N, $X^{13}$ is C(H), $Y^{11}$ is C(H), and $Y^{12}$ is C(CN). In some embodiments, $X^{11}$ is C(F), $X^{12}$ is N, $X^{13}$ is C(H), $Y^{11}$ is C(H), and $Y^{12}$ is C(CN), and $R^{16}$ is optionally substituted $C_1$ alkyl. In some embodiments, $X^{11}$ is C(F), $X^{12}$ is N, $X^{13}$ is C(H), Yu is C(H), and $Y^{12}$ is C(CN), and $R^{16}$ ia —$CH_3$. In some embodiments, $X^{11}$ is C(F), $X^{12}$ is N, $X^{13}$ is C(H), $Y^{11}$ is C(H), and $Y^{12}$ is C(CN), and $R^{15}$ is H. In some embodiments, $X^{11}$ is C(F), $X^{12}$ is N, $X^{13}$ is C(H), $Y^{11}$ is C(H), and $Y^{12}$ is C(CN), $R^{14}$ is H, and $R^{14'}$ is H. In some embodiments, $X^{11}$ is C(F), $X^{12}$ is N, $X^{13}$ is C(H), $Y^{11}$ is C(H), and $Y^{12}$ is C(CN), and $R^{12}$ is H. In some embodiments, $X^{11}$ is C(F), $X^{12}$ is N, $X^{13}$ is C(H), $Y^{11}$ is C(H), and $Y^{12}$ is C(CN), and $R^{13}$ is selected from $CH_3$, H, and cyclopropyl. In some embodiments, $X^{11}$ is C(F), $X^{12}$ is N, $X^{13}$ is C(H), $Y^{11}$ is C(H), and $Y^{12}$ is C(CN), and $R^{13}$ is selected from $CH_3$. In some embodiments, $X^{11}$ is C(F), $X^{12}$ is N, $X^{13}$ is C(H), $Y^{11}$ is C(H), and $Y^{12}$ is C(CN), and $R^{13}$ is selected from cyclopropyl. In some embodiments, $X^{11}$ is C(F), $X^{12}$ is N, $X^{13}$ is C(H), $Y^{11}$ is C(H), and $Y^{12}$ is C(CN), and $R^{13}$ is selected from H. In some embodiments, $X^{11}$ is C(F), $X^{12}$ is N, $X^{13}$ is C(H), $Y^{11}$ is C(H), and $Y^{12}$ is C(CN), and $R^{11}$ is selected from $CH_3$, cyclopropyl, F, Cl, Br, $CF_3$, CN, $N_3$, OH, and OMe. In some embodiments, $X^{11}$ is C(F), $X^{12}$ is N, $X^{13}$ is C(H), $Y^{11}$ is C(H), and $Y^{12}$ is C(CN), and $R^{11}$ is selected from $CH_3$, F, Cl, Br, $CF_3$, and CN. In some embodiments, $X^{11}$ is C(F), $X^{12}$ is N, $X^{13}$ is C(H), $Y^{11}$ is C(H), and $Y^{12}$ is C(CN), and $R^{11}$ is selected from F, Cl and CN. In some embodiments, $X^{11}$ is C(F), $X^{12}$ is N, $X^{13}$ is C(H), $Y^{11}$ is C(H), and $Y^{12}$ is C(CN), and $R^{11}$ is selected from F and CN. In some embodiments, $X^{11}$ is C(F), $X^{12}$ is N, $X^{13}$ is C(H), $Y^{11}$ is C(H), and $Y^{12}$ is C(CN), and $R^{11}$ is selected from F. In some embodiments, $X^{11}$ is C(F), $X^{12}$ is N, $X^{13}$ is C(H), $Y^{11}$ is C(H), and $Y^{12}$ is C(CN), and $R^{11}$ is selected from CN.

In some embodiments, the compound of Formula (II) is a compound of Formula (IIa):

(IIa)

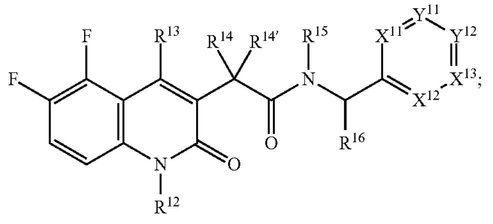

or a salt thereof.

In some embodiments, the compound of Formula (II) is a compound of Formula (IIb):

(IIb)

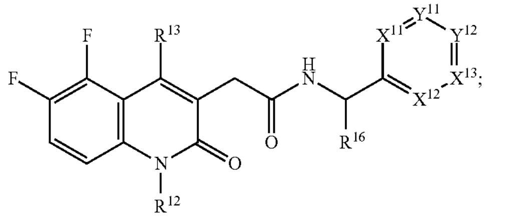

or a salt thereof.

In some embodiments, the compound of Formula (II) is a compound of Formula (IIc):

(IIc)

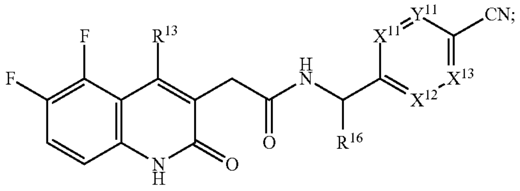

or a salt thereof.

In some embodiments, the compound of Formula (II) is a compound of Formula (IId):

(IId)

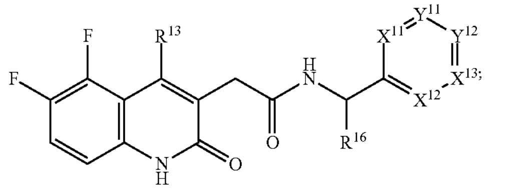

or a salt thereof. In some embodiments, the compound of Formula (II) is a compound of Formula (IIe):

(IIe)

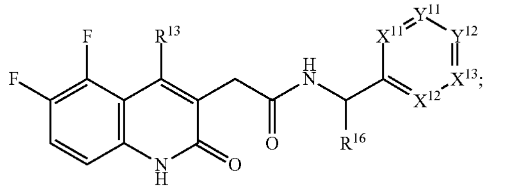

or a salt thereof.

In certain aspects, the disclosure provides a compound represented by Formula (IIf)

(IIf)

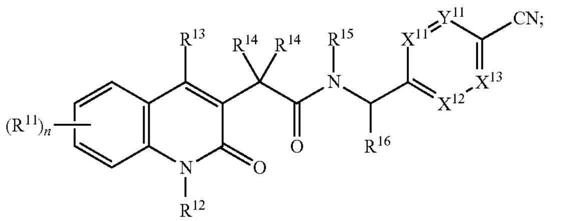

or a salt thereof, wherein:

$R^{14}$ is selected from:

hydrogen, halogen, —$OR^{19d}$, —$SR^{19d}$, —$N(R^{19d})_2$, —$NO_2$, and —CN; and $C_{1-6}$ alkyl which is optionally substituted with one or more substituents independently selected from halogen, —$OR^{19d}$, —$SR^{19d}$, —$N(R^{19d})_2$, —$NO_2$, and —CN; and $C_{3-10}$ carbocycle and 3- to 10-membered heterocycle, each of which is optionally substituted with one or more substituents independently selected from halogen, —$OR^{19d}$, —$SR^{19d}$, —$N(R^{19d})_2$, —$C(O)R^{19d}$, —$C(O)N(R^{19d})_2$, —$N(R^{19d})C(O)R^{19d}$, —$N(R^{19d})C(O)N(R^{19d})_2$, —$OC(O)N(R^{19d})_2$, —$N(R^{19d})C(O)OR^{19d}$, —$C(O)OR^{19d}$, —$OC(O)R^{19d}$, —$S(O)R^{19d}$, —$S(O)_2R^{19d}$, —$NO_2$, ═O—, ═S, ═$N(R^{19d})$, and —CN.

In some embodiments, the compound of Formula (IIa) is a compound of Formula (II).

In some embodiments, the compound of Formula (IIb) is a compound of Formula (II).

In some embodiments, the compound of Formula (IIc) is a compound of Formula (II).

In some embodiments, the compound of Formula (IId) is a compound of Formula (II).

In some embodiments, the compound of Formula (IIe) is a compound of Formula (II).

In some embodiments, the compound of Formula (IIf) is a compound of Formula (II).

In some embodiments, the compound of Formula (IIa) is a compound of Formula (II-A).

In some embodiments, the compound of Formula (IIb) is a compound of Formula (II-A).

In some embodiments, the compound of Formula (IIc) is a compound of Formula (II-A).

In some embodiments, the compound of Formula (IId) is a compound of Formula (II-A).

In some embodiments, the compound of Formula (IIe) is a compound of Formula (II-A).

In some embodiments, the compound of Formula (IIf) is a compound of Formula (II-A).

In some embodiments, the compound is

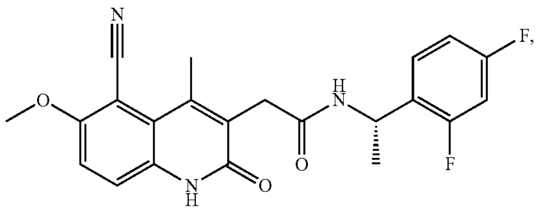 [SMILES: COc1ccc2[nH]c(=O)c(CC(=O)N[C@@H](C)c3ccc(F)cc3F)c(C)c2c1C#N]

or a salt thereof.

In some embodiments, a compound of Formula (II), Formula (II-A), or Formula (II') is selected from compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 2001, 2002, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 1153, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2590, 2591, 2592, 2593, 2594, 2595, 2596, 2597, 2598, 2599, 2600, 2601, 2602, 2603, 2604, 2605, 2606, 2607, 2608, 4502, 4503, 4504, and 4505.

In some embodiments, a compound of Formula (II), Formula (II-A), or Formula (II') is selected from compound 22, 34, 36, 130, 12, 21, 38, 69, 85, 107, 28, 37, 83, 101, 108, 109, 116, 120, 2052, 2069, 2589, 2601, 11, 24, 32, 50, 60, 61, 66, 89, 106, 115, 1150, 2046, 2602, 52, 58, 68, 100, 112, 118, 126, 1046, 1145, 1148, 2055, 2603, 1, 16, 45, 96, 104, 131, 1068, 1124, 2075, 2607, 35, 42, 72, 95, 1140, 2606, 2, 17, 18, 59, 1133, 2050, 2502, 2554, 2597, 15, 31, 111, 113, 135, 1129, 1132, 54, 67, 2056, 2596, 1053, 1081, 1107, 2016, 2604, 41, 99, 1059, 2079, 2533, 2592, 1051, 1104, 1136, 1139, 1146, 2520, 57, 62, 2049, 2562, 2563, 10, 1063, 1109, 2524, 33, 1101, 2501, 2538, 2552, 49, 1095, 97, 127, 2523, 2593, 1069, 2530, 2546, 14, 20, 44, 129, 1080, 2063, 133, 1050, 1070, 27, 51, 65, 2054, 2078, 2561, 2594, 46, 2529, 2542, 119, 1048, 1144, 2002, 2022, 2070, 2519, 13, 2521, 2522, 2001, 2541, 2567, 105, 1131, 2023, 2595, 1103, 2551, 2605, 63, 1142, 2051, 2513, 2590, 1079, 2060, 40, 1119, 1123, 1077, 1111, 2015, 1065, 2553, 2564, 110, 1084, 1128, 98, 1106, 2042, 1118, 2568, 1135, 2040, 2514, 2598, 1052, 2057, 2600, 2072, 74, 1130, 1127, 2543, 2511, 1100, 2516, 6, 1153, 2532, 128, 2048, 4504, 1113, 2549, 2061, 2043, 1134, 2066, 2071, 71, 1097, 137, 103, 1092, 93, 2041, 2021, 2010, 2029, 4502, 55, 2531, 2039, 91, 2550, 1143, 5, 2027, 2077, 2591, 2512, 48, 2586, 2585, 1138, 123, 2030, 1076, 1149, 1058, 30, 53, 1086, 2017, 2599, 1064, 2035, 2024, 1141, 56, 1061, 84, 1078, 1120, 2539, 1147, 2518, 2037, 4505, 9, 3, 2020, 2517, 1062, 2555, 2557, 1066, 7, 114, 1110, 2507, 2583, 4, 2528, 47, 2544, 2580, 2011, 2527, 2569, 1112, 2515, 1071, 1137, 2587, 1067, 1088, 1090, 1083, 26, 1102, 1089, 1108, 2556, 94, 2062, 1098, 78, 1099, 2510, 1114, 2074, 1122, 2044, 4503, 2025, 1060, 2565, 2534, 2013, 2575, 1075, 1072, 1125, 1054, 2577, 1151, 2067, 2019, 90, 2047, 1115, 92, 2536, 2558, 1096, 2576, 2571, 1085, 2548, 2068, 1091, 1073, 75, 1152, 125, 2064, and 88.

In some embodiments, a compound of Formula (II), Formula (II-A), or Formula (II') is selected from compound 22, 34, 36, 130, 12, 21, 38, 69, 85, 107, 28, 37, 83, 101, 108, 109, 116, 120, 2052, 2069, 2589, 2601, 11, 24, 32, 50, 60, 61, 66, 89, 106, 115, 1150, 2046, 2602, 52, 58, 68, 100, 112, 118, 126, 1046, 1145, 1148, 2055, 2603, 1, 16, 45, 96, 104, 131, 1068, 1124, 2075, 2607, 35, 42, 72, 95, 1140, 2606, 2, 17, 18, 59, 1133, 2050, 2502, 2554, 2597, 15, 31, 111, 113, 135, 1129, 1132, 54, 67, 2056, 2596, 1053, 1081, 1107, 2016, 2604, 41, 99, 1059, 2079, 2533, 2592, 1051, 1104, 1136, 1139, 1146, 2520, 57, 62, 2049, 2562, 2563, 10, 1063, 1109, 2524, 33, 1101, 2501, 2538, 2552, 49, 1095, 97, 127, 2523, 2593, 1069, 2530, 2546, 14, 20, 44, 129, 1080, 2063, 133, 1050, 1070, 27, 51, 65, 2054, 2078, 2561, 2594, 46, 2529, 2542, 119, 1048, 1144, 2002, 2022, 2070, 2519, 13, 2521, 2522, 2001, 2541, 2567, 105, 1131, 2023, 2595, 1103, 2551, 2605, 63, 1142, 2051, 2513, 2590, 1079, 2060, 40, 1119, 1123, 1077, 1111, 2015, 1065, 2553, 2564, 110, 1084, 1128, 98, 1106, 2042, 1118, 2568, 1135, 2040, 2514, 2598, 1052, 2057, 2600, 2072, 74, 1130, 1127, 2543, 2511, 1100, 2516, 6, 1153, 2532, 128, 2048, 4504, 1113, 2549, 2061, 2043, 1134, 2066, 2071, 71, 1097, 137, 103, 1092, 93, 2041, 2021, 2010, 2029, 4502, 55, 2531, 2039, 91, 2550, 1143, 5, 2027, 2077, 2591, 2512, 48, 2586, 2585, 1138, 123, 2030, 1076, 1149, 1058, 30, 53, 1086, 2017, 2599, 1064, 2035, 2024, 1141, 56, 1061, 84, 1078, 1120, 2539, 1147, 2518, 2037, 4505, 9, 3, 2020, 2517, 1062, 2555, 2557, 1066, 7, 114, 1110, 2507, 2583, 4, 2528, 47, 2544, 2580, 2011, 2527, 2569, 1112, 2515, 1071, 1137, 2587, 1067, 1088, 1090, 1083, 26, 1102, 1089, 1108, 2556, 94, 2062, 1098, 78, 1099, 2510, 1114, 2074, 1122, and 2044.

In some embodiments, a compound of Formula (II), Formula (II-A), or Formula (II') is selected from compound 22, 34, 36, 130, 12, 21, 38, 69, 85, 107, 28, 37, 83, 101, 108, 109, 116, 120, 2052, 2069, 2589, 2601, 11, 24, 32, 50, 60, 61, 66, 89, 106, 115, 1150, 2046, 2602, 52, 58, 68, 100, 112, 118, 126, 1046, 1145, 1148, 2055, 2603, 1, 16, 45, 96, 104, 131, 1068, 1124, 2075, 2607, 35, 42, 72, 95, 1140, 2606, 2, 17, 18, 59, 1133, 2050, 2502, 2554, 2597, 15, 31, 111, 113, 135, 1129, 1132, 54, 67, 2056, 2596, 1053, 1081, 1107, 2016, 2604, 41, 99, 1059, 2079, 2533, 2592, 1051, 1104, 1136, 1139, 1146, 2520, 57, 62, 2049, 2562, 2563, 10, 1063, 1109, 2524, 33, 1101, 2501, 2538, 2552, 49, 1095, 97, 127, 2523, 2593, 1069, 2530, 2546, 14, 20, 44, 129, 1080, 2063, 133, 1050, 1070, 27, 51, 65, 2054, 2078, 2561, 2594, 46, 2529, 2542, 119, 1048, 1144, 2002, 2022, 2070, 2519, 13, 2521, 2522, 2001, 2541, 2567, 105, 1131, 2023, 2595, 1103, 2551, 2605, 63, 1142, 2051, 2513, 2590, 1079, 2060, 40, 1119, 1123, 1077, 1111, 2015, 1065, 2553, 2564, 110, 1084, 1128, 98, 1106, 2042, 1118, 2568, 1135, 2040, 2514, 2598, 1052, 2057, 2600, 2072, 74, 1130, 1127, 2543, 2511, 1100, 2516, 6, 1153, 2532, 128, 2048, 4504, 1113, 2549, and 2061.

In some embodiments, a compound of Formula (II), Formula (II-A), or Formula (II') is selected from compound 22, 34, 36, 130, 12, 21, 38, 69, 85, 107, 28, 37, 83, 101, 108, 109, 116, 120, 2052, 2069, 2589, 2601, 11, 24, 32, 50, 60, 61, 66, 89, 106, 115, 1150, 2046, 2602, 52, 58, 68, 100, 112, 118, 126, 1046, 1145, 1148, 2055, 2603, 1, 16, 45, 96, 104, 131, 1068, 1124, 2075, 2607, 35, 42, 72, 95, 1140, 2606, 2, 17, 18, 59, 1133, 2050, 2502, 2554, and 2597.

In some embodiments, a compound of Formula (II), Formula (II-A), or Formula (II') is selected from compound 22, 32, 42, 34, 36, 37, 1150, 1129, 1132, 38, 28, 66, 1068, 1140, 85, 2601, 68, 1145, 59, 2079, 61, 2602, 2, 107, 2052, 2589, 1148, 13, 83, 2046, 52, 12, 69, 101, 1136, 46, 21, 109, 116, 16, 96, 15, 2533, 1046, 1, 1133, 1139, 130, 11, 35, 1107, 1142, 1149, 31, 1059, 2607, 2050, 2538, 1146, 106, 2502, 2554, 24, 2603, 1104, 2520, 62, 2530, 2002, 1053, 2552, 65, 50, 2049, 27, 120, 2055, 18, 67, 1051, 108, 1081, 2056, 2016, 118, 112, 2524, 1101, 20, 1077, 3, 89, 115, 2594, 1124, 72, 14, 2529, 1109, 1080, 95, 2597, 10, 135, 51, 2542, 40, 45, 1095, 41, 2501, 2595, 33, 74, 2592, 4504, 30, 126, 2001, 1106, 2075, 2563, 2596, 2568, 2051, 75, 60, 4502, 49, 100, 2541, 1128, 2522, 2523, 2604, 2562, 129, 1063, 2606, 2561, 1065, 131, 1144, 1131, 2564, 2078, 9, 1141, 2057, 1147, 6, 4, 2040, 2593, 19, 2567, 1103, 2598, 1047, 1119, 2519, 23, 2545, 1138, 2546, 1118, 133, 7, 58, 1134, 1123, 26, 1108, 2015, 2605, 1076, 2041, 54, 2514, 17, 1097, 1127, 104, 113, 2513, 1070, 1048, 2023, 2521, 119, 44, 2074, 1066, 1120, and 2048.

In some embodiments, a compound of Formula (II), Formula (II-A), or Formula (II') is selected from compound 22, 32, 42, 34, 36, 37, 1150, 1129, 1132, 38, 28, 66, 1068, 1140, 85, 2601, 68, 1145, 59, 2079, 61, 2602, 2, 107, 2052, 2589, 1148, 13, 83, 2046, 52, 12, 69, 101, 1136, 46, 21, 109, 116, 16, 96, 15, 2533, 1046, 1, 1133, 1139, 130, 11, 35, 1107, 1142, 1149, 31, 1059, 2607, 2050, 2538, 1146, 106, 2502, 2554, 24, 2603, 1104, 2520, 62, 2530, 2002, 1053, 2552, 65, 50, 2049, 27, 120, 2055, 18, 67, 1051, 108, 1081, 2056, 2016, 118, 112, 2524, 1101, 20, 1077, 3, 89, 115, 2594, 1124, 72, 14, 2529, 1109, 1080, 95, 2597, 10, 135, 51, 2542, 40, 45, 1095, 41, 2501, 2595, 33, 74, 2592, 4504, 30, 126, 2001, 1106, 2075, 2563, 2596, 2568, 2051, 75, 60, 4502, 49, 100, 2541, 1128, 2522, 2523, 2604, 2562, 129, 1063, 2606, 2561, 1065, 131, 1144, 1131, 2564, 2078, 9, 1141, 2057, 1147, 6, 4, 2040, 2593, 19, 2567, 1103, 2598, 1047, 1119, 2519, 23, 2545, 1138, 2546, 1118, 133, 7, 58, 1134, 1123, 26, 1108, 2015, 2605, 1076, 2041, 54, 2514, 17, 1097, 1127, 104, 113, 2513, 1070, 1048, 2023, 2521, 119, and 44.

In some embodiments, a compound of Formula (II), Formula (II-A), or Formula (II') is selected from compound 22, 32, 42, 34, 36, 37, 1150, 1129, 1132, 38, 28, 66, 1068, 1140, 85, 2601, 68, 1145, 59, 2079, 61, 2602, 2, 107, 2052, 2589, 1148, 13, 83, 2046, 52, 12, 69, 101, 1136, 46, 21, 109, 116, 16, 96, 15, 2533, 1046, 1, 1133, 1139, 130, 11, 35, 1107, 1142, 1149, 31, 1059, 2607, 2050, 2538, 1146, 106, 2502, 2554, 24, 2603, 1104, 2520, 62, 2530, 2002, 1053, 2552, 65, 50, 2049, 27, 120, 2055, 18, 67, 1051, 108, 1081, 2056, 2016, 118, 112, 2524, 1101, 20, 1077, 3, 89, 115, 2594, 1124, 72, 14, 2529, 1109, 1080, 95, 2597, 10, 135, 51, 2542, 40, 45, 1095, 41, 2501, 2595, 33, 74, 2592, 4504, 30, 126, 2001, 1106, 2075, 2563, 2596, 2568, 2051, 75, 60, 4502, 49, 100, 2541, 1128, 2522, 2523, 2604, 2562, 129, 1063, 2606, 2561, 1065, 131, 1144, 1131, 2564, 2078, 9, 1141, 2057, 1147, 6, 4, and 2040.

In some embodiments, a compound of Formula (II), Formula (II-A), or Formula (II') is selected from compound 22, 32, 42, 34, 36, 37, 1150, 1129, 1132, 38, 28, 66, 1068, 1140, 85, 2601, 68, 1145, 59, 2079, 61, 2602, 2, 107, 2052, 2589, 1148, and 13.

In some embodiments, a compound of Formula (II), Formula (II-A), or Formula (II') is selected from compound 22, 1140, 32, 42, 36, 1129, 66, 68, 61, 83, 69, 109, 96, 1142, 74, 30, 34, 37, 1132, 38, 28, 85, 59, 2602, 2, 107, 52, 46, 116, 65, 50, 115, 72, 95, 40, 131, 73, 1145, 2079, 12, 16, 1139, 130, 1107, 2502, 2603, 1104, 67, 1081, 118, 112, 135, 126, 70, 1150, 2601, 21, 1133, 2607, 2050, 106, 24, 89, 2075, 100, 129, 1138, 54, 113, 2589, 1148, 13, 1136, 120, 108, 2016, 1109, 10, 44, 2070, 2533, 31, 2056, 1101, 51, 1095, 49, 1103, 98, 114, 11, 2520, 14, 41, 57, 2052, 2530, 18, 133, 35, 1128, 1144, 99, 2606, 1, 2538, 2002, 2055, 1077, 2568, 119, 111, 1068, 1080, 2597, 45, 2563, 56, 2524, 2545, 27, 1124, 2522, 1079, 2552, 2501, 4, 58, 2015, 1097, 2054, 2066, 2596, 2051, 2514, 2045, 2595, 127, 128, 2546, 137, 1146, 26, 1063, 1119, 104, 2023, 94, 101, 48, 97, 71, 2529, 1127, 2561, 62, 1111, 2060, 2064, 2001, 60, 2057, 2562, 2511, 15, 33, 2077, 4504, 6, 53, 2542, 1130, 2022, 2594, 2567, 2513, 1076, 2072, 1092, 1106, 1108, 2067, 1102, 1059, 2605, 2521, 17, 47, 2017, 1141, 1149, 1113, 2564, 1118, 2069, 2061, 4502, 23, 2063, 20, 1134, 2519, 1131, 1100, 2604, 2078, 1123, 9, 1153, 2010, 2516, 2553, 2037, 2555, 7, 2543, 2541, 2068, 2547, 2540, 2049, 1065, 1147, 29, 2059, 2065, 123, 2593, 55, 2550, 2011, 2048, 90, 122, 4503, 2590, 1105, 2532, 63, 1084, 103, 25, 1143, 2531, 2040, 2009, 1094, 2544, 1078, 1110, 3, 2042, 2024, 1070, 2076, 92, 2517, 1120, 1135, 19, 2071, 2585, 2518, 2058, 2029, 2021, 2592, 91, 5, 121, 1152, 1112, 102, 2020, 2074, 1083, 1099, 2508, 2556, 1137, 105, 2587, 2035, 2557, 117, 78, 1122, 2043, 84, 2551, 2549, 134, 2062, 1075, 1064, 1062, 1067, 1151, 2586, 4505, 1115, 1096, 2053, 136, 2013, 2575, 43, 75, 1098, 80, 2507, 1114, 2033, 125, 1058, 2044, 2025, 2047, 2019, 2027, 124, 77, 81, 1066, 2026, 88, 2576, and 64.

In some embodiments, a compound of Formula (II), Formula (II-A), or Formula (II') is selected from compound 22, 1140, 32, 42, 36, 1129, 66, 68, 61, 83, 69, 109, 96, 1142, 74, 30, 34, 37, 1132, 38, 28, 85, 59, 2602, 2, 107, 52, 46, 116, 65, 50, 115, 72, 95, 40, 131, 73, 1145, 2079, 12, 16, 1139, 130, 1107, 2502, 2603, 1104, 67, 1081, 118, 112, 135, 126, 70, 1150, 2601, 21, 1133, 2607, 2050, 106, 24, 89, 2075, 100, 129, 1138, 54, 113, 2589, 1148, 13, 1136, 120, 108, 2016, 1109, 10, 44, 2070, 2533, 31, 2056, 1101, 51, 1095, 49, 1103, 98, 114, 11, 2520, 14, 41, 57, 2052, 2530, 18, 133, 35, 1128, 1144, 99, 2606, 1, 2538, 2002, 2055, 1077, 2568, 119, 111, 1068, 1080, 2597, 45, 2563, 56, 2524, 2545, 27, 1124, 2522, 1079, 2552, 2501, 4, 58, 2015, 1097, 2054, 2066, 2596, 2051, 2514, 2045, 2595, 127, 128, 2546, 137, 1146, 26, 1063, 1119, 104, 2023, 94, 101, 48, 97, 71, 2529, 1127, 2561, 62, 1111, 2060, 2064, 2001, 60, 2057, 2562, 2511, 15, 33, 2077, 4504, 6, 53, 2542, 1130, 2022, 2594, 2567, 2513, 1076, 2072, 1092, 1106, 1108, 2067, 1102, 1059, 2605, 2521, 17, 47, 2017, 1141, 1149, 1113, 2564, 1118, 2069, 2061, 4502, 23, 2063, 20, 1134, 2519, 1131, 1100, 2604, 2078, 1123, 9, 1153, 2010, 2516, 2553, 2037, 2555, 7, 2543, 2541, 2068, 2547, 2540, 2049, 1065, 1147, 29, 2059, 2065, 123, 2593, 55, 2550, 2011, 2048, 90, 122, 4503, 2590, 1105, 2532, 63, 1084, 103, 25, 1143, 2531, 2040, 2009, 1094, 2544, 1078, 1110, 3, 2042, 2024, 1070, 2076, 92, 2517, 1120, 1135, 19, 2071, 2585, 2518, 2058, 2029, 2021, 2592, 91, 5, 121, 1152, 1112, 102, 2020, 2074, 1083, 1099, 2508, 2556, 1137, 105, 2587, 2035, 2557, 117, 78, 1122, 2043, 84, 2551, 2549, 134, 2062, 1075, 1064, and 1062.

In some embodiments, a compound of Formula (II), Formula (II-A), or Formula (II') is selected from compound 22, 1140, 32, 42, 36, 1129, 66, 68, 61, 83, 69, 109, 96, 1142, 74, 30, 34, 37, 1132, 38, 28, 85, 59, 2602, 2, 107, 52, 46, 116, 65, 50, 115, 72, 95, 40, 131, 73, 1145, 2079, 12, 16, 1139, 130, 1107, 2502, 2603, 1104, 67, 1081, 118, 112, 135, 126, 70, 1150, 2601, 21, 1133, 2607, 2050, 106, 24, 89, 2075, 100, 129, 1138, 54, 113, 2589, 1148, 13, 1136, 120, 108, 2016, 1109, 10, 44, 2070, 2533, 31, 2056, 1101, 51, 1095, 49, 1103, 98, 114, 11, 2520, 14, 41, 57, 2052, 2530, 18, 133, 35, 1128, 1144, 99, 2606, 1, 2538, 2002, 2055, 1077, 2568, 119, 111, 1068, 1080, 2597, 45, 2563, 56, 2524, 2545, 27, 1124, 2522, 1079, 2552, 2501, 4, 58, 2015, 1097, 2054, 2066, 2596, 2051, 2514, 2045, 2595, 127, 128, 2546, 137, 1146, 26, 1063, 1119, 104, 2023, 94, 101, 48, 97, 71, 2529, 1127, 2561, 62, 1111, 2060, 2064, 2001, 60, 2057, 2562, 2511, 15, 33, 2077, 4504, 6, 53, 2542, 1130, 2022, 2594, 2567, 2513, 1076, 2072, 1092, 1106, 1108, 2067, 1102, 1059, 2605, 2521, 17, 47, 2017, 1141, 1149, 1113, 2564, 1118, 2069, 2061, 4502, 23, 2063, 20, 1134, 2519, 1131, 1100, 2604, 2078, 1123, 9, 1153, 2010, 2516, 2553, 2037, 2555, 7, 2543, 2541, 2068, 2547, and 2540.

In some embodiments, a compound of Formula (II), Formula (II-A), or Formula (II') is selected from compound 22, 1140, 32, 42, 36, 1129, 66, 68, 61, 83, 69, 109, 96, 1142, 74, 30, 34, 37, 1132, 38, 28, 85, 59, 2602, 2, 107, 52, 46, 116, 65, 50, 115, 72, 95, 40, 131, 73, 1145, 2079, 12, 16, 1139, 130, 1107, 2502, 2603, 1104, 67, 1081, 118, 112, 135, 126, 70, 1150, 2601, 21, 1133, 2607, 2050, 106, 24, 89, 2075, 100, 129, 1138, 54, 113, 2589, 1148, 13, 1136, 120, 108, 2016, 1109, 10, 44, 2070, 2533, 31, 2056, 1101, 51, 1095, 49, 1103, 98, 114, 11, 2520, 14, 41, 57, 2052, 2530, 18, 133, 35, 1128, 1144, and 99.

In one aspect, disclosed herein is a compound represented by Formula (II-A-ep):

(II-A-ep)

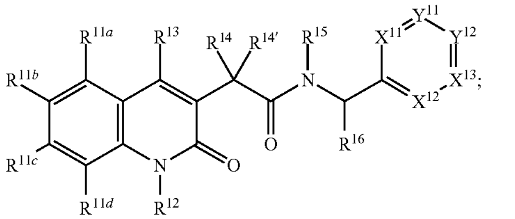

or a salt thereof, wherein:

$X^{11}$ is selected from $C(R^{17a})$ and N;

$X^{12}$ is selected from $C(R^{17b})$ and N;

$X^{13}$ is selected from $C(R^{17c})$ and N;

$Y^{11}$ is selected from $C(R^{17d})$ and N;

$Y^{12}$ is selected from $C(R^{17e})$ and N;

each $R^{11a}$, $R^{11b}$, $R^{11c}$, and $R^{11d}$ is independently selected from:

hydrogen; halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; and $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{1-6}$ haloalkyl, and $C_{1-6}$ alkyl;

wherein when $R^{11a}$, $R^{11b}$, and $R^{11c}$ are each hydrogen; then $R^{11d}$ is not hydrogen;

wherein when $R^{11b}$ is —$OCH_3$; then $R^{11c}$ is not —OMe;

$R^{12}$ is selected from:

hydrogen;

$R^{13}$ is selected from:

hydrogen, halogen, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, —$NO_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$R^{14}$ is selected from:

hydrogen, halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$;

$C_{1-6}$ alkyl optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$C_{3-10}$ carbocycle and 3- to 10-membered heterocycle, wherein the $C_{3-10}$ carbocycle and 3- to 10-membered heterocycle are each optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$R^{14'}$ is selected from:

hydrogen, halogen;

$C_{1-3}$ alkyl optionally substituted with one or more substituents independently selected from halogen, —CN, —OH, —O($C_{1-3}$ alkyl), —O($C_{1-3}$ haloalkyl), —$NH_2$, —NH($C_{1-6}$ alkyl), and —N($C_{1-6}$ alkyl)$_2$;

$C_{3-10}$ carbocycle and 3- to 10-membered heterocycle, wherein the $C_{3-10}$ carbocycle and 3- to 10-membered heterocycle are each optionally substituted with one or more substituents independently selected from halogen, —CN, —OH, —O($C_{1-3}$ alkyl), —O($C_{1-3}$ haloalkyl), —$NH_2$, —NH($C_{1-6}$ alkyl), and —N($C_{1-6}$ alkyl)$_2$;

or $R^{14}$ and $R^{14'}$ together form a form a $C_{3-10}$ carbocycle or 3- to 10-membered heterocycle, each of which is optionally substituted with one or more substituents independently selected from: halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl;

$R^{15}$ is selected from:

hydrogen;

$R^{16}$ is selected from:

hydrogen;

$C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, and $C_{1-6}$ alkyl; or $R^{16}$ together with $R^{17a}$ form a $C_{3-10}$ carbocycle, or 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl;

each $R^{17a}$, $R^{17b}$, $R^{17c}$, $R^{17d}$, and $R^{17e}$ is independently selected from:

hydrogen, halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{1-6}$ alkyl, $C_{1-6}$ haloalkyl, $C_{3-5}$ carbocycle and 3- to 5-membered heterocycle, or $R^{15}$ together with $R^{17a}$ form a 3- to 10-membered heterocycle, wherein the 3- to 10-membered heterocycle is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl; or $R^{15}$ together with $R^{17b}$ form a 3- to 10-membered heterocycle, wherein the 3- to 10-membered heterocycle is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl; or $R^{16}$ together with $R^{17a}$ form a 3- to 10-membered heterocycle, wherein the 3- to 10-membered heterocycle is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl; or $R^{16}$ together with $R^{17b}$ form a 3- to 10-membered heterocycle, wherein the 3- to 10-membered heterocycle is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl; or $R^{15}$, $R^{16}$, and $R^{17b}$ together form a bridged heterocycle, wherein the bridged heterocycle is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl.

In one aspect, disclosed herein is a compound represented by Formula (IV):

(IV)

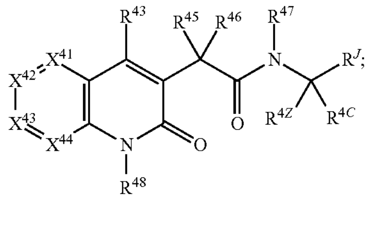

or a salt thereof, wherein:

$R^J$ is a 3- to 10-membered heterocycle, wherein the 3- to 10-membered heterocycle is optionally substituted with one or more substituents independently selected from halogen, —$OR^{410b}$, —$SR^{410b}$, —N($R^{410b}$)$_2$, —C(O)$R^{410b}$, —C(O)N($R^{410b}$)$_2$, —N($R^{410b}$)C(O)$R^{410b}$, —N($R^{410b}$)C(O)N($R^{410b}$)$_2$, —OC(O)N($R^{410b}$)$_2$, —N($R^{410b}$)C(O)O$R^{410b}$, —C(O)O$R^{410b}$, —OC(O)$R^{410b}$, —S(O)$R^{410b}$, —S(O)$_2R^{410b}$, —$NO_2$, =O, =S, =N($R^{410b}$), —$N_3$, —CN, $C_{1-6}$alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49a}$;

$X^{41}$ is selected from C($R^{41a}$) and N;

$X^{42}$ is selected from C($R^{41b}$) and N;

$X^{43}$ is selected from C($R^{41c}$) and N;

$X^{44}$ is selected from C($R^{41d}$) and N;

wherein no more than two of $X^{41}$, $X^{42}$, $X^{43}$, and $X^{44}$ are N;

$R^{41a}$, $R^{41b}$, $R^{41c}$, and $R^{41d}$ are each independently selected from:

hydrogen;

halogen, —$NO_2$, —$N_3$, —CN, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$a)$_2$, —N($R^{410a}$)C(O)O$R^{410a}$, —C(O)O$R^{410a}$, —OC(O)$R^{410a}$, —S(O)$R^{410a}$, and —S(O)$_2R^{410a}$;

$C_{1-6}$ alkyl, $C_{2-6}$ alkenyl, and $C_{2-6}$ alkynyl, each of which is optionally substituted with one or more substituents independently selected from halogen, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —C(O)O$R^{410a}$, —OC(O)$R^{410a}$, —N($R^{410a}$)C(O)N($R^{410a}$)$_2$, —OC(O)N($R^{410a}$)$_2$, —N($R^{410a}$)C(O)O$R^{410a}$, —S(O)$R^{410a}$, —S(O)$_2R^{410a}$, —$NO_2$, =O, =S, =N($R^{410a}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49a}$; and $C_{3-10}$ carbocycle and 3- to 10-membered heterocycle, each of which is optionally substituted with one or more substituents independently selected from halogen, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$)C(O)O$R^{410a}$, —C(O)O$R^{410a}$, —OC(O)$R^{410a}$, —S(O)$R^{410a}$, —S(O)$_2R^{410a}$, —$NO_2$, =O, =S, =N($R^{410a}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49a}$;

wherein when $X^{41}$ is C(H), $X^{42}$ is C(H), and $X^{43}$ is C(H); then $R^{41d}$ is not hydrogen;

$R^{43}$ is selected from:

hydrogen, halogen, —$OR^{410x}$, —$SR^{410x}$, —N($R^{410x}$)$_2$, —$NO_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more substituents independently selected from $R^{47e}$;

$R^{4Z}$ is selected from:

—C(O)$R^{410z}$, —C(O)N($R^{410z}$)$_2$, —C(O)O$R^{410z}$, and —CN;

$C_{1-6}$ alkyl, $C_{2-6}$ alkenyl, and $C_{2-6}$ alkynyl, each of which is optionally substituted with one or more substituents independently selected from halogen, —$OR^{410z}$, —$SR^{410z}$, —N($R^{410z}$)$_2$, —C(O)$R^{410z}$, —C(O)N($R^{410z}$)$_2$, —N($R^{410z}$)C(O)$R^{410z}$, —C(O)O$R^{410z}$, —OC(O)$R^{410z}$, —N($R^{410z}$)C(O)N($R^{410z}$)$_2$, —OC(O)N($R^{410z}$)$_2$, —N($R^{410z}$)C(O)O$R^{410z}$, —S(O)$R^{410z}$, —S(O)$_2R^{410z}$, —NO$_2$, =O, =S, =N($R^{410z}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49z}$; and $C_{3-10}$ carbocycle and 3- to 10-membered heterocycle, each of which is optionally substituted with one or more substituents independently selected from halogen, —O$R^{410z}$, —S$R^{410z}$, —N($R^{410z}$)$_2$, —C(O)$R^{410z}$, —C(O)N($R^{410z}$)$_2$, —N($R^{410z}$)C(O)$R^{410z}$, —N($R^{410z}$)C(O)N($R^{410z}$)$_2$, —OC(O)N($R^{410z}$)$_2$, —N($R^{410z}$)C(O)O$R^{410z}$, —C(O)O$R^{410z}$, —OC(O)$R^{410z}$, —S(O)$R^{410z}$, —S(O)$_2R^{410z}$, —NO$_2$, =O, =S, =N($R^{410z}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49z}$.

$R^{4C}$ is selected from:

hydrogen;

—C(O)$R^{410c}$, —C(O)N($R^{410c}$)$_2$, —C(O)O$R^{410c}$, and —CN;

$C_{1-6}$ alkyl, $C_{2-6}$ alkenyl, and $C_{2-6}$ alkynyl, each of which is optionally substituted with one or more substituents independently selected from halogen, —O$R^{410c}$, —S$R^{410c}$, —N($R^{410c}$)$_2$, —C(O)$R^{410c}$, —C(O)N($R^{410c}$)$_2$, —N($R^{410c}$)C(O)$R^{410c}$, —C(O)O$R^{410c}$, —OC(O)$R^{410c}$, —N($R^{410c}$)C(O)N($R^{410c}$)$_2$, —OC(O)N($R^{410c}$)$_2$, —N($R^{410c}$)C(O)O$R^{410c}$, —S(O)$R^{410c}$, —S(O)$_2R^{410c}$, —NO$_2$, =O, =S, =N($R^{410c}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49c}$; and $C_{3-10}$ carbocycle and 3- to 10-membered heterocycle, each of which is optionally substituted with one or more substituents independently selected from halogen, —O$R^{410c}$, —S$R^{410c}$, —N($R^{410c}$)$_2$, —C(O)$R^{410c}$, —C(O)N($R^{410c}$)$_2$, —N($R^{410c}$)C(O)$R^{410c}$, —N($R^{410c}$)C(O)N($R^{410c}$)$_2$, —OC(O)N($R^{410c}$)$_2$, —N($R^{410c}$)C(O)O$R^{410c}$, —C(O)O$R^{410c}$, —OC(O)$R^{410c}$, —S(O)$R^{410c}$, —S(O)$_2R^{410c}$, —NO$_2$, =O, =S, =N($R^{410c}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49c}$; —

$R^{45}$ is selected from:

hydrogen;

halogen, —O$R^{410d}$, —S$R^{410d}$, —N($R^{410d}$)$_2$, —C(O)$R^{410a}$, —C(O)N($R^{410d}$)$_2$, —N($R^{410a}$)C(O)$R^{410d}$, —C(O)O$R^{410d}$, —OC(O)$R^{410d}$, —N($R^{410a}$)C(O)N($R^{41a}$)$_2$, —OC(O)N($R^{410d}$)$_2$, —N($R^{410d}$)C(O)O$R^{410d}$, —S(O)$R^{410d}$, —S(O)$_2R^{410d}$, —NO$_2$, —N$_3$, and —CN;

$C_{1-6}$ alkyl, $C_{2-6}$ alkenyl, and $C_{2-6}$ alkynyl, each of which is optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —C(O)O$R^{410d}$, —OC(O)$R^{410d}$, —N($R^{410a}$)C(O)N($R^{410d}$)$_2$, —OC(O)N($R^{410d}$)$_2$, —N($R^{410d}$)C(O)O$R^{410d}$, —S(O)$R^{410d}$, —S(O)$_2R^{410a}$, —NO$_2$, =O, =S, =N($R^{41a}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49d}$; and $C_{3-10}$ carbocycle and 3- to 10-membered heterocycle, each of which is optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410a}$)C(O)$R^{410d}$, —N($R^{410d}$)C(O)N($R^{410d}$)$_2$, —OC(O)N($R^{410d}$)$_2$, —N($R^{410d}$)C(O)O$R^{410d}$, —C(O)O$R^{410d}$, —OC(O)$R^{410d}$, —S(O)$R^{410d}$, —S(O)$_2R^{410d}$, —NO$_2$, =O, =S, =N($R^{410d}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49d}$; or $R^{45}$ together with $R^{46}$ form a 3- to 10-membered heterocycle or $C_{3-10}$ carbocycle, wherein the 3- to 10-membered heterocycle or $C_{3-10}$ carbocycle is optionally substituted with one or more $R^{49d}$;

$R^{46}$ is selected from:

hydrogen;

halogen, —O$R^{410c}$, —S$R^{410c}$, —N($R^{410e}$)$_2$, —C(O)$R^{410e}$, —C(O)N($R^{410e}$)$_2$, —N($R^{410e}$)C(O)$R^{410e}$, —C(O)O$R^{410e}$, —OC(O)$R^{410e}$, —N($R^{410e}$)C(O)N($R^{410e}$)$_2$, —OC(O)N($R^{410e}$)$_2$, —N($R^{410e}$)C(O)O$R^{410e}$, —S(O)$R^{410c}$, —S(O)$_2R^{410e}$, —NO$_2$, —N$_3$, and —CN;

$C_{1-6}$ alkyl, $C_{2-6}$ alkenyl, and $C_{2-6}$ alkynyl, each of which is optionally substituted with one or more substituents independently selected from halogen, —O$R^{410e}$, —S$R^{410e}$, —N($R^{410e}$)$_2$, —C(O)$R^{410e}$, —C(O)N($R^{410e}$)$_2$, —N($R^{410e}$)C(O)$R^{410e}$, —C(O)O$R^{410e}$, —OC(O)$R^{410e}$, —N($R^{410e}$)C(O)N($R^{410e}$)$_2$, —OC(O)N($R^{410e}$)$_2$, —N($R^{410e}$)C(O)O$R^{410e}$, —S(O)$R^{410e}$, —S(O)$_2R^{410e}$, —NO$_2$, =O, =S, =N($R^{410e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49e}$; and $C_{3-10}$ carbocycle and 3- to 10-membered heterocycle, each of which is optionally substituted with one or more substituents independently selected from halogen, —O$R^{410e}$, —S$R^{410e}$, —N($R^{410e}$)$_2$, —C(O)$R^{410e}$, —C(O)N($R^{410e}$)$_2$, —N($R^{410e}$)C(O)$R^{410e}$, —N($R^{410e}$)C(O)N($R^{410e}$)$_2$, —OC(O)N($R^{410e}$)$_2$, —N($R^{410e}$)C(O)O$R^{410e}$, —C(O)O$R^{410e}$, —OC(O)$R^{410e}$, —S(O)$R^{410e}$, —S(O)$_2R^{410e}$, —NO$_2$, =O, =S, =N($R^{410e}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49e}$.

$R^{47}$ is selected from:

hydrogen;

—C(O)$R^{410f}$, —C(O)N($R^{410f}$)$_2$, —C(O)O$R^{410f}$, —S(O)$R^{410f}$, and —S(O)$_2R^{410f}$;

$C_{1-6}$ alkyl optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —C(O)O$R^{410f}$, —OC(O)$R^{410f}$, —N($R^{410f}$)C(O)N($R^{410f}$)$_2$, —OC(O)N($R^{410f}$)$_2$, —N($R^{410f}$)C(O)O$R^{410f}$, —S(O)$R^{410f}$, —S(O)$_2R^{410f}$, —NO$_2$, =O, =S, =N($R^{410f}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49f}$; and $C_{3-10}$ carbocycle and 3- to 10-membered heterocycle, each of which is optionally substituted with one or more substituents independently selected from halogen, —OR$^{410f}$, —SR$^{410f}$, —N(R$^{410f}$)$_2$, —C(O)R$^{410f}$, —C(O)N(R$^{410f}$)$_2$, —N(R$^{410f}$)C(O)R$^{410f}$, —N(R$^{410f}$)C(O)N(R$^{410f}$)$_2$, —OC(O)N(R$^{410f}$)$_2$, —N(R$^{410f}$)C(O)OR$^{410f}$, —C(O)OR$^{410f}$, —OC(O)R$^{410f}$, —S(O)R$^{410f}$, —S(O)$_2$R$^{410f}$, —NO$_2$, =O, =S, =N(R$^{410f}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{49f}$;

each R$^{47e}$ is independently selected from:

halogen, —OR$^{410y}$, —SR$^{410y}$, —N(R$^{410y}$)$_2$, —C(O)R$^{410y}$, —C(O)N(R$^{410y}$)$_2$, —N(R$^{410y}$)C(O)R$^{410y}$, —N(R$^{410y}$)C(O)N(R$^{410y}$)$_2$, —OC(O)N(R$^{410y}$)$_2$, —N(R$^{410y}$)C(O)OR$^{410y}$, —C(O)OR$^{410y}$, —OC(O)R$^{410y}$, —S(O)R$^{410y}$, —S(O)$_2$R$^{410y}$, —NO$_2$, =O, =S, =N(R$^{410y}$), and —CN; and C$_{1-3}$ alkyl, C$_{2-3}$ alkenyl, and C$_{2-3}$ alkynyl, each of which is optionally substituted with one or more substituents independently selected from halogen, —OR$^{410y}$, —SR$^{410y}$, —N(R$^{410y}$)$_2$, —C(O)R$^{410y}$, —C(O)N(R$^{410y}$)$_2$, —N(R$^{410y}$)C(O)R$^{410y}$, —N(R$^{410y}$)C(O)N(R$^{410y}$)$_2$, —OC(O)N(R$^{410y}$)$_2$, —N(R$^{410y}$)C(O)OR$^{410y}$, —C(O)OR$^{410y}$, —OC(O)R$^{410y}$, —S(O)R$^{410y}$, —S(O)$_2$R$^{410y}$, —NO$_2$, =O, =S, =N(R$^{410y}$), and —CN;

R$^{48}$ is selected from:

hydrogen;

—C(O)R$^{410g}$, —C(O)N(R$^{410g}$)$_2$, —C(O)OR$^{410g}$, —S(O)R$^{410g}$, and —S(O)$_2$R$^{410g}$;

C$_{1-6}$ alkyl optionally substituted with one or more substituents independently selected from halogen, —OR$^{410g}$, —SR$^{410g}$, N(R$^{410g}$)$_2$, —C(O)R$^{410g}$, —C(O)N(R$^{410g}$)$_2$, —N(R$^{410g}$)C(O)R$^{410g}$, —C(O)OR$^{410g}$, —OC(O)R$^{410g}$, —N(R$^{410g}$)C(O)N(R$^{410g}$)$_2$, —OC(O)N(R$^{410g}$)$_2$, —N(R$^{410g}$)C(O)OR$^{410g}$, —S(O)R$^{410g}$, —S(O)$_2$R$^{410g}$, —NO$_2$, =O, =S, =N(R$^{410g}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{49g}$; and C$_{3-10}$ carbocycle and 3- to 10-membered heterocycle, each of which is optionally substituted with one or more substituents independently selected from halogen, —OR$^{410g}$, —SR$^{410g}$, —N(R$^{410g}$)$_2$, —C(O)R$^{410g}$, —C(O)N(R$^{410g}$)$_2$, —N(R$^{410g}$)C(O)R$^{410g}$, —N(R$^{410g}$)C(O)N(R$^{410g}$)$_2$, —OC(O)N(R$^{410g}$)$_2$, —N(R$^{410g}$)C(O)OR$^{410g}$, —C(O)OR$^{410g}$, —OC(O)R$^{410g}$, —S(O)R$^{410g}$, —S(O)$_2$R$^{410g}$, —NO$_2$, =O, =S, =N(R$^{410g}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{49g}$;

each R$^{49a}$ is independently selected from:

halogen, —OR$^{410a}$, —SR$^{410a}$, —N(R$^{410a}$)$_2$, —C(O)R$^{410a}$, —C(O)N(R$^{410a}$)$_2$, —N(R$^{410a}$)C(O)R$^{410a}$, —N(R$^{410a}$)C(O)N(R$^{410a}$)$_2$, —OC(O)N(R$^{410a}$)$_2$, —N(R$^{410a}$)C(O)OR$^{410a}$, —C(O)OR$^{410a}$, —OC(O)R$^{410a}$, —S(O)R$^{410a}$, —S(O)$_2$R$^{410a}$, —NO$_2$, =O, =S, =N(R$^{410a}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{410a}$, —SR$^{410a}$, —N(R$^{410a}$)$_2$, —C(O)R$^{410a}$, —C(O)N(R$^{410a}$)$_2$, —N(R$^{410a}$)C(O)R$^{410a}$, —N(R$^{410a}$)C(O)N(R$^{410a}$)$_2$, —OC(O)N(R$^{410a}$)$_2$, —N(R$^{410a}$)C(O)OR$^{410a}$, —C(O)OR$^{410a}$, —OC(O)R$^{410a}$, —S(O)R$^{410a}$, —S(O)$_2$R$^{410a}$, —NO$_2$, =O, =S, =N(R$^{410a}$), —N$_3$, and —CN;

each R$^{49z}$ is independently selected from:

halogen, —OR$^{410z}$, —SR$^{410z}$, —N(R$^{410z}$)$_2$, —C(O)R$^{410z}$, —C(O)N(R$^{410z}$)$_2$, —N(R$^{410z}$)C(O)R$^{410z}$, —N(R$^{410z}$)C(O)N(R$^{410z}$)$_2$, —OC(O)N(R$^{410z}$)$_2$, —N(R$^{410z}$)C(O)OR$^{410z}$, —C(O)OR$^{410z}$, OC(O)R$^{410z}$, —S(O)R$^{410z}$, —S(O)$_2$R$^{410z}$, —NO$_2$, =O, =S, =N(R$^{410z}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{410z}$, —SR$^{410z}$, —N(R$^{410z}$)$_2$, —C(O)R$^{410z}$, —C(O)N(R$^{410z}$)$_2$, —N(R$^{410z}$)C(O)R$^{410z}$, —N(R$^{410z}$)C(O)N(R$^{410z}$)$_2$, —OC(O)N(R$^{410z}$)$_2$, —N(R$^{410z}$)C(O)OR$^{410z}$, —C(O)OR$^{410z}$, —OC(O)R$^{410z}$, —S(O)R$^{410z}$, —S(O)$_2$R$^{410z}$, —NO$_2$, =O, =S, =N(R$^{410z}$), —N$_3$, and —CN;

each R$^{49c}$ is independently selected from:

halogen, —OR$^{410c}$, —SR$^{410c}$, —N(R$^{410c}$)$_2$, —C(O)R$^{410c}$, —C(O)N(R$^{410c}$)$_2$, —N(R$^{410c}$)C(O)R$^{410c}$, —N(R$^{410c}$)C(O)N(R$^{410c}$)$_2$, —OC(O)N(R$^{410c}$)$_2$, —N(R$^{410c}$)C(O)OR$^{410c}$, —C(O)OR$^{410c}$, —OC(O)R$^{410c}$, —S(O)R$^{410c}$, —S(O)$_2$R$^{410c}$, —NO$_2$, =O, =S, =N(R$^{410c}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{410c}$, —SR$^{410c}$, —N(R$^{410c}$)$_2$, —C(O)R$^{410c}$, —C(O)N(R$^{410c}$)$_2$, —N(R$^{410c}$)C(O)R$^{410c}$, —N(R$^{410c}$)C(O)N(R$^{410c}$)$_2$, —OC(O)N(R$^{410c}$)$_2$, —N(R$^{410c}$)C(O)OR$^{410c}$, —C(O)OR$^{410c}$, —OC(O)R$^{410c}$, —S(O)R$^{410c}$, —S(O)$_2$R$^{410c}$, —NO$_2$, =O, =S, =N(R$^{410c}$), —N$_3$, and —CN;

each R$^{49d}$ is independently selected from:

halogen, —OR$^{410d}$, —SR$^{410d}$, —N(R$^{410d}$)$_2$, —C(O)R$^{410d}$, —C(O)N(R$^{410d}$)$_2$, —N(R$^{410d}$)C(O)R$^{410d}$, —N(R$^{410d}$)C(O)N(R$^{410d}$)$_2$, —OC(O)N(R$^{410d}$)$_2$, —N(R$^{410d}$)C(O)OR$^{410d}$, —C(O)OR$^{410d}$, —OC(O)R$^{410d}$, —S(O)R$^{410d}$, —S(O)$_2$R$^{410d}$, —NO$_2$, =O, =S, =N(R$^{410d}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{410d}$, —SR$^{410d}$, —N(R$^{410d}$)$_2$, —C(O)R$^{410d}$, —C(O)N(R$^{410d}$)$_2$, —N(R$^{410d}$)C(O)R$^{410d}$, —N(R$^{410d}$)C(O)N(R$^{410d}$)$_2$, —OC(O)N(R$^{410d}$)$_2$—N(R$^{410d}$)C(O)OR$^{410d}$, —C(O)OR$^{410d}$, —OC(O)R$^{410d}$, —S(O)R$^{410d}$, —S(O)$_2$R$^{410d}$, —NO$_2$, =O, =S, =N(R$^{410d}$), —N$_3$, and —CN;

each R$^{49e}$ is independently selected from:

halogen, —OR$^{410e}$, —SR$^{410e}$, —N(R$^{410e}$)$_2$, —C(O)R$^{410e}$, —C(O)N(R$^{410e}$)$_2$, —N(R$^{410e}$)C(O)R$^{410e}$, —N(R$^{410e}$)C(O)N(R$^{410e}$)$_2$, —OC(O)N(R$^{410e}$)$_2$, —N(R$^{410e}$)C(O)OR$^{410e}$, —C(O)OR$^{410e}$, —OC(O)R$^{410e}$, —S(O)R$^{410e}$, —S(O)$_2$R$^{410e}$, —NO$_2$, =O, =S, =N(R$^{410e}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{410c}$, —SR$^{410c}$, —N(R$^{410e}$)$_2$, —C(O)R$^{410e}$, —C(O)N(R$^{410e}$)$_2$, —N(R$^{410e}$)C(O)R$^{410e}$, —N(R$^{410e}$)C(O)N(R$^{410e}$)$_2$, —OC(O)N(R$^{410e}$)$_2$, —N(R$^{410e}$)C(O)OR$^{410e}$, —C(O)OR$^{410e}$, —OC(O)R$^{410e}$, —S(O)R$^{410e}$, —S(O)$_2$R$^{410e}$, —NO$_2$, =O, =S, =N(R$^{410e}$), —N$_3$, and —CN;

each $R^{49f}$ is independently selected from:

halogen, $—OR^{410f}$, $—SR^{410f}$, $—N(R^{410f})_2$, $—C(O)R^{410f}$, $—C(O)N(R^{410f})_2$, $—N(R^{410f})C(O)R^{410f}$, $—N(R^{410f})C(O)N(R^{410f})_2$, $—OC(O)N(R^{410f})_2$, $—N(R^{410f})C(O)OR^{410f}$, $—C(O)OR^{410f}$, $—OC(O)R^{410f}$, $—S(O)R^{410f}$, $—S(O)_2R^{410f}$, $—NO_2$, =O, =S, $=N(R^{410f})$, $—N_3$, and —CN; and $C_{1-3}$ alkyl, $C_{2-3}$ alkenyl, and $C_{2-3}$ alkynyl, each of which is optionally substituted with one or more substituents independently selected from halogen, $—OR^{410f}$, $—SR^{410f}$, $—N(R^{410f})_2$, $—C(O)R^{410f}$, $—C(O)N(R^{410f})_2$, $—N(R^{410f})C(O)R^{410f}$, $—N(R^{410f})C(O)N(R^{410f})_2$, $—OC(O)N(R^{410f})_2$, $—N(R^{410f})C(O)OR^{410f}$, $—C(O)OR^{410f}$, $—OC(O)R^{410f}$, $—S(O)R^{410f}$, $—S(O)_2R^{410f}$, $—NO_2$, =O, =S, $=N(R^{410f})$, $—N_3$, and —CN;

each $R^{49g}$ is independently selected from:

halogen, $—OR^{410g}$, $—SR^{410g}$, $—N(R^{410g})_2$, $—C(O)R^{410g}$, $—C(O)N(R^{410g})_2$, $—N(R^{410g})C(O)R^{410g}$, $—N(R^{410g})C(O)N(R^{410g})_2$, $—OC(O)N(R^{410g})_2$, $—N(R^{410g})C(O)OR^{410g}$, $—C(O)OR^{410g}$, $—OC(O)R^{410g}$, $—S(O)R^{410g}$, $—S(O)_2R^{410g}$, $—NO_2$, =O, =S, $=N(R^{410g})$, $—N_3$, and —CN; and $C_{1-3}$ alkyl, $C_{2-3}$ alkenyl, and $C_{2-3}$ alkynyl, each of which is optionally substituted with one or more substituents independently selected from halogen, $—OR^{410g}$, $—SR^{410g}$, $—N(R^{410g})_2$, $—C(O)R^{410g}$, $—C(O)N(R^{410g})_2$, $—N(R^{410g})C(O)R^{410g}$, $—N(R^{410g})C(O)N(R^{410g})_2$, $—OC(O)N(R^{410g})_2$, $—N(R^{410g})C(O)OR^{410g}$, $—C(O)OR^{410g}$, $—OC(O)R^{410g}$, $—S(O)R^{410g}$, $—S(O)_2R^{410g}$, $—NO_2$, =O, =S, $=N(R^{410g})$, $—N_3$, and —CN; and each $R^{410a}$, $R^{410b}$, $R^{410c}$, $R^{410d}$, $R^{410e}$, $R^{410f}$, $R^{410g}$, $R^{410x}$, $R^{410y}$ and $R^{410z}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, $—NO_2$, $—NH_2$, =O, =S, $—O—C_{1-6}$ alkyl, $—S—C_{1-6}$ alkyl, $—N(C_{1-6}$ alkyl$)_2$, $—NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, $—NO_2$, $—NH_2$, =O, =S, $—O—C_{1-6}$ alkyl, $—S—C_{1-6}$ alkyl, $—N(C_{1-6}$ alkyl$)_2$, $—NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$haloalkyl.

In certain embodiments, for a compound or salt of Formula (II), Formula (II-A), or Formula (II'), $X^{41}$ is N.

In certain embodiments, for a compound or salt of Formula (II), Formula (II-A), or Formula (II'), $X^{42}$ is N.

In certain embodiments, for a compound or salt of Formula (II), Formula (II-A), or Formula (II'), $X^{43}$ is N.

In certain embodiments, for a compound or salt of Formula (II), Formula (II-A), or Formula (II'), $X^{44}$ is N.

In certain embodiments, for a compound or salt of Formula (II), Formula (II-A), or Formula (II'), $X^{41}$ is $C(R^{41a})$; $X^{42}$ is $C(R^{41b})$; $X^{43}$ is $C(R^{41c})$; $X^{44}$ is $C(R^{41d})$.

In some embodiments, $R^{41a}$, $R^{41b}$, $R^{41c}$, and $R^{41d}$ are each independently selected from:

hydrogen, halogen, $—N_3$, —CN, $—OR^{410a}$, $—SR^{410a}$, $—N(R^{410a})_2$, $—C(O)R^{410a}$, $—C(O)N(R^{410a})_2$, $—N(R^{410a})C(O)R^{410a}$, $—N(R^{410a})C(O)N(R^{410a})_2$, $—C(O)OR^{410a}$;

$C_{1-6}$ alkyl, $C_{2-6}$ alkenyl, and $C_{2-6}$ alkynyl, each of which is optionally substituted with one or more substituents independently selected from halogen, $—OR^{410a}$, $—SR^{410a}$, $—N(R^{410a})_2$, =O, =S, $=N(R^{410a})$;

$C_{3-10}$ carbocycle and 3- to 10-membered heterocycle, each of which is optionally substituted with one or more substituents independently selected from —F, —Cl, —CN, —OH, $—C(O)NH_2$, and $C_{1-6}$ alkyl.

In some embodiments, $R^{41a}$, $R^{41b}$, $R^{41c}$, and $R^{41d}$ are each independently selected from: hydrogen, —F, —Cl, —Br, —I, —CN, $—N_3$, —OH, —OMe, —OEt, —O(n-Pr), —O(iPr), —O(i-Bu),

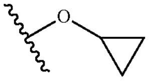, $—OCF_3$,

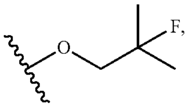 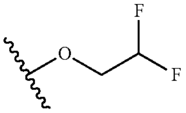,

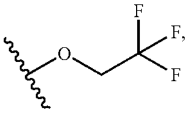

$—NH_2$, —NH(Me), —NH(Et), $—N(Et)_2$, —NH(i-Bu), —NH(Ph), —NHBn,

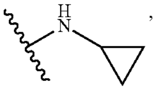, 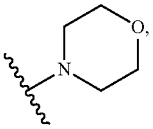 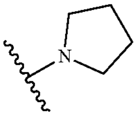,

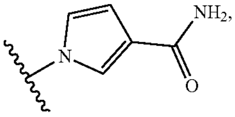

$—CF_3$, methyl, -ethyl, cyclopropyl, $—CH_2N(CH_3)_2$, —CCMe, —CCH, phenyl, N-morpholinyl, and N-pyrrolidinyl.

In some embodiments, $R^{41a}$, $R^{41b}$, $R^{41c}$, and $R^{41d}$ are each independently selected from: hydrogen, —F, —CN, —OH, —OMe, —OEt, —O(n-Pr), —O(iPr), $—OCF_3$, $—NH_2$, —NH(Me), —NH(Et), $—N(Et)_2$, —NH(i-Bu), —NH(Ph), —NHBn,

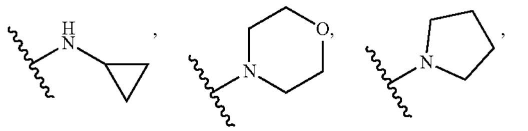 [SMILES: *NC1CC1 ; *N1CCOCC1 ; *N1CCCC1]

$—CF_3$, -methyl, -ethyl, and cyclopropyl. In some embodiments, $R^{41a}$, $R^{41b}$, $R^{41c}$, and $R^{41d}$ are each independently selected from: hydrogen, —F, —Cl, —OH, and —CN.

In some embodiments, for a compound or salt of Formula (II), Formula (II-A), or Formula (II'), each $R^{410a}$, $R^{410b}$, $R^{410c}$, $R^{410d}$, $R^{410e}$, $R^{410f}$, $R^{410g}$, $R^{410x}$, $R^{410y}$, and $R^{410z}$ is independently selected from: hydrogen, methyl, ethyl, propyl, isopropyl, cyclopropyl, isobutyl, $—CF_3$, $—CH_2CF_3$, $—CH_2CHF_2$, $—CH_2C(F)(Me)_2$, and $—CH_2$-phenyl. In some embodiments, two $R^{410a}$ are taken together to form a $C_{3-10}$ carbocycle or 3- to 10-membered heterocycle.

In some embodiments, for a compound or salt of Formula (II), Formula (II-A), or Formula (II'), $R^{4Z}$ is selected from: methyl, ethyl, propyl, isopropyl, cyclopropyl, isobutyl, $—CF_3$, $—CH_2CF_3$, $—CH_2CHF_2$, $—CH_2C(F)(Me)_2$, and $—CH_2$-phenyl. In some embodiments, $R^{4Z}$ is methyl, $—CH_2OH$, $—CH_2CH_2OH$, $C(Me)_2OH$, or $—CH_2OMe$. $R^{4Z}$ is methyl.

In some embodiments, for a compound or salt of Formula (II), Formula (II-A), or Formula (II'), $R^{4C}$ is hydrogen.

In some embodiments, for a compound or salt of Formula (II), Formula (II-A), or Formula (II'), $R^J$ is a 5- to 10-membered heteroaryl optionally substituted with one or more substituents independently selected from halogen, $—OR^{410b}$, $—SR^{410b}$, $—N(R^{410b})_2$, $—C(O)R^{410b}$, $—C(O)N(R^{410b})_2$, $—N(R^{410b})C(O)R^{410b}$, $—N(R^{410b})C(O)N(R^{410b})_2$, $—OC(O)N(R^{410b})_2$, $—N(R^{410b})C(O)OR^{410b}$, $—C(O)OR^{410b}$, $—OC(O)R^{410b}$, $—S(O)R^{410b}$, $—S(O)_2R^{410b}$, $—NO_2$, =O, =S, $=N(R^{410b})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49a}$. In some embodiments, $R^J$ is a 5-membered heteroaryl optionally substituted with one or more substituents independently selected from halogen, $—OR^{410b}$, $—SR^{410b}$, $—N(R^{410b})_2$, $—C(O)R^{410b}$, $—C(O)N(R^{410b})_2$, $—N(R^{410b})C(O)R^{410b}$, $—N(R^{410b})C(O)N(R^{410b})_2$, $—OC(O)N(R^{410b})_2$, $—N(R^{410b})C(O)OR^{410b}$, $—C(O)OR^{410b}$, $—OC(O)R^{410b}$, $—S(O)R^{410b}$, $—S(O)_2R^{410b}$, $—NO_2$, =O, =S, $=N(R^{410b})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49a}$. In some embodiments, $R^J$ is a thiophene, thiazole, thiadiazole, furan, isoxazole, oxazole, oxadiazole, pyrrole, pyrazole, imidazole, or triazole optionally substituted with one or more substituents independently selected from halogen, $—OR^{410b}$, $—N(R^{410b})_2$, $—C(O)R^{410b}$, $—C(O)N(R^{410b})_2$, $—N(R^{410b})C(O)R^{410b}$, $—OC(O)N(R^{410b})_2$, $—C(O)OR^{410b}$, $—OC(O)R^{410b}$, =O, =S, $=N(R^{410b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49a}$. In some embodiments, $R^J$ is a thiophene, thiazole, or oxazole optionally substituted with one or more substituents independently selected from halogen, $—OR^{410b}$, $—N(R^{410b})_2$, $—C(O)R^{410b}$, $—C(O)N(R^{410b})_2$, $—N(R^{410b})C(O)R^{410b}$, $—OC(O)N(R^{410b})_2$, $—C(O)OR^{410b}$, $—OC(O)R^{410b}$, =O, =S, $=N(R^{410b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49a}$. In some embodiments, $R^J$ is a thiophene, thiazole, or oxazole optionally substituted with one or more substituents independently selected from halogen, —Cl, —F, —Br, —CN, $N_3$, —OH, —OMe, methyl, cyclopropyl, and $CF_3$.

In some embodiments, for a compound or salt of Formula (II), Formula (II-A), or Formula (II'), $R^{47}$ is hydrogen.

In some embodiments, for a compound or salt of Formula (II), Formula (II-A), or Formula (II'), $R^{43}$ is selected from: hydrogen, —F, —Cl, —OH, —NHMe, —CN, $C_{1-3}$ alkyl, and cyclopropyl, wherein the $C_{1-3}$ alkyl and cyclopropyl are each optionally substituted with one or more —F. In some embodiments, $R^{43}$ is selected from: hydrogen, $—CH_3$, cyclopropyl, —F, —Cl, —CN, and $CF_3$. In some embodiments, $R^{43}$ is selected from: hydrogen and $CH_3$. In some embodiments, $R^{43}$ is hydrogen. In some embodiments, $R^{43}$ is $—CH_3$.

In some embodiments, for a compound or salt of Formula (II), Formula (II-A), or Formula (II'), $R^{48}$ is selected from: hydrogen and methyl. In some embodiments, $R^{48}$ is hydrogen. In some embodiments, $R^{48}$ is methyl.

In some embodiments, for a compound or salt of Formula (II), Formula (II-A), or Formula (II'), $R^{45}$ is selected from: hydrogen, halogen, and $C_{1-6}$ alkyl optionally substituted with one or more substituents independently selected from halogen, $—OR^{410d}$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{49d}$; $R^{46}$ is selected from: hydrogen, halogen, $C_{1-6}$ alkyl optionally substituted with one or more substituents independently selected from halogen, $—OR^{410d}$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{49d}$; or $R^{45}$ together with $R^{46}$ form a 3- to 10-membered heterocycle or $C_{3-10}$ carbocycle, wherein the 3- to 10-membered heterocycle or $C_{3-10}$ carbocycle is optionally substituted with one or more $R^{49d}$. In some embodiments, $R^{45}$ is selected from: hydrogen, halogen, and $C_{1-6}$ alkyl optionally substituted with one or more substituents independently selected from halogen, $—OR^{410d}$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{49d}$; $R^{46}$ is selected from: hydrogen, halogen, $C_{1-6}$ alkyl optionally substituted with one or more substituents independently selected from halogen, $—OR^{410d}$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{49d}$. In some embodiments, $R^{45}$ together with $R^{46}$ form a 3- to 10-membered heterocycle or $C_{3-10}$ carbocycle, wherein the 3- to 10-membered heterocycle or $C_{3-10}$ carbocycle is optionally substituted with one or more $R^{49d}$. In some embodiments, $R^{45}$ is selected from: hydrogen, methyl, ethyl, cyclopropyl, and fluoro; $R^{46}$ is selected from hydrogen and fluoro. In some embodiments, $R^{45}$ together with $R^{46}$ form a cyclopropyl optionally substituted with one or more —F or $—CH_3$. In some embodiments,

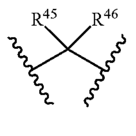

is selected from:
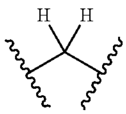, 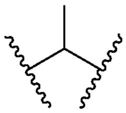, 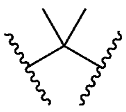, 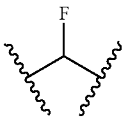,
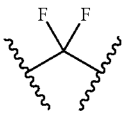, 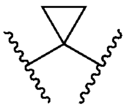, 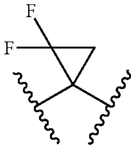, and
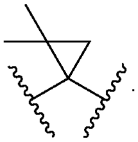.
In some embodiments,
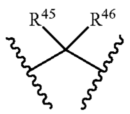
is selected from:
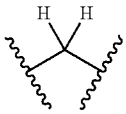, 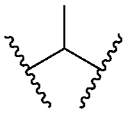, 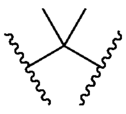, 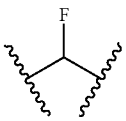,
and
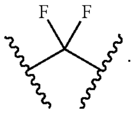.
In some embodiments,
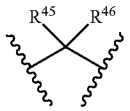
is selected from:
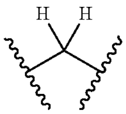, 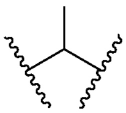, and 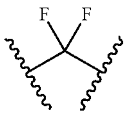.
In some embodiments,
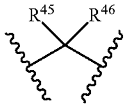
is selected from:
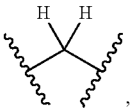, 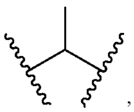, 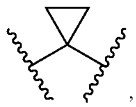, and
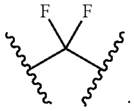.
In some embodiments,
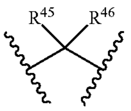
is
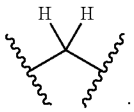.
In some embodiments,
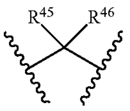 is 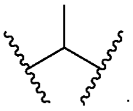.
In some embodiments,
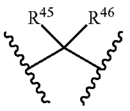 is 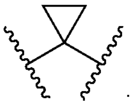.
In some embodiments,
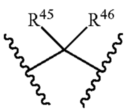 is 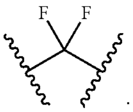.
In some embodiments, a compound of Formula (II), Formula (II-A), or Formula (II') is selected from compound 4001, 4002, 4003, 4004, 4005, 4006, 4007, 4008, 4009, and 4010.

In some embodiments, a compound of Formula (II), Formula (II-A), or Formula (II') is selected from compound 4001, 4004, 4006, 4010, 4002, 4008, 4009, and 4005.

In some embodiments, a compound of Formula (II), Formula (II-A), or Formula (II') is selected from compound 4001, 4004, 4006, and 4010.

In some embodiments, a compound of Formula (II), Formula (II-A), or Formula (II') is selected from compound 4004, 4001, 4009, 4005, 4008, 4006, 4010, and 4002.

In some embodiments, a compound of Formula (II), Formula (II-A), or Formula (II') is selected from compound 4004, 4001, 4009, 4005, 4008, and 4006.

In some embodiments, a compound of Formula (II), Formula (II-A), or Formula (II') is selected from compound 4004, 4001, and 4009.

In some embodiments, a compound of Formula (II), Formula (II-A), or Formula (II') is selected from compound 4004, 4001, 4003, 4006, 4009, 4005, 4010, 4002, and 4008.

In some embodiments, a compound of Formula (II), Formula (II-A), or Formula (II') is selected from compound 4004, and 4001.

In one aspect, disclosed herein is a compound represented by Formula (IV-ep):

(IV-ep)

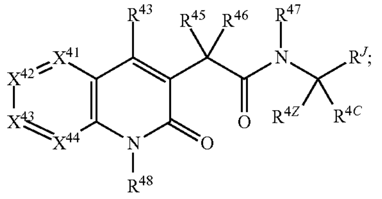

or a salt thereof, wherein:

$R^J$ is a 5- to 10-membered heteroaryl, wherein the 5- to 10-membered heteroaryl is optionally substituted with one or more substituents independently selected from hydrogen, halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{1-6}$ alkyl, $C_{1-6}$ haloalkyl;

$X^{41}$ is selected from C($R^{41a}$) and N;

$X^{42}$ is selected from C($R^{41b}$) and N;

$X^{43}$ is selected from C($R^{41c}$) and N;

$X^{44}$ is selected from C($R^{41d}$) and N;

wherein no more than two of $X^{41}$, $X^{42}$, $X^{43}$, and $X^{44}$ are N;

$R^{41a}$, $R^{41b}$, $R^{41c}$, and $R^{41d}$ are each independently selected from:

hydrogen; halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH ($C_{1-6}$ alkyl), and —N($C_{1-6}$ alkyl)$_2$; and $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{1-6}$ haloalkyl, and $C_{1-6}$ alkyl;

wherein when $X^{41}$ is C(H), $X^{42}$ is C(H), and $X^{43}$ is C(H); then $R^{41d}$ is not hydrogen;

$R^{43}$ is selected from:

hydrogen, halogen, —OH, —O($C_{1-6}$ alkyl), —O($C_{1-6}$ haloalkyl), —SH, —S($C_{1-6}$ alkyl), —$NH_2$, —NH ($C_{1-6}$ alkyl), —N($C_{1-6}$ alkyl)$_2$, —$NO_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$R^{4Z}$ is selected from:

$C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH ($C_{1-6}$ alkyl), —N($C_{1-6}$ alkyl)$_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, and $C_{1-6}$ alkyl;

$R^{4C}$ is selected from:

hydrogen;

$C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH ($C_{1-6}$ alkyl), —N($C_{1-6}$ alkyl)$_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, and $C_{1-6}$ alkyl;

$R^{45}$ is selected from:

hydrogen, halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$;

$C_{1-6}$ alkyl optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH ($C_{1-6}$ alkyl), and —N($C_{1-6}$ alkyl)$_2$;

$C_{3-10}$ carbocycle and 3- to 10-membered heterocycle, wherein the $C_{3-10}$ carbocycle and 3- to 10-membered heterocycle are each optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$R^{46}$ is selected from:

hydrogen, halogen;

$C_{1-3}$ alkyl optionally substituted with one or more substituents independently selected from halogen, —CN, —OH, —O($C_{1-3}$ alkyl), —O($C_{1-3}$ haloalkyl), —$NH_2$, —NH($C_{1-6}$ alkyl), and —N($C_{1-6}$ alkyl)$_2$;

$C_{3-10}$ carbocycle and 3- to 10-membered heterocycle, wherein the $C_{3-10}$ carbocycle and 3- to 10-membered heterocycle are each optionally substituted with one or more substituents independently selected from halogen, —CN, —OH, —O($C_{1-3}$ alkyl), —O($C_{1-3}$ haloalkyl), —$NH_2$, —NH($C_{1-6}$ alkyl), and —N($C_{1-6}$ alkyl)$_2$;

or $R^{14}$ and $R^{14'}$ together form a form a $C_{3-10}$ carbocycle or 3- to 10-membered heterocycle, each of which is optionally substituted with one or more substituents independently selected from: halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl;

$R^{47}$ is selected from:

hydrogen;

$R^{48}$ is selected from:

hydrogen.

In one aspect, disclosed herein is a compound represented by Formula (III):

(III)

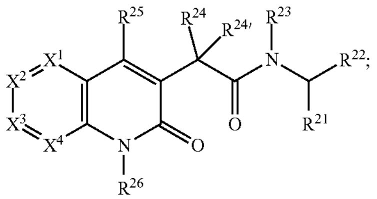

or a salt thereof, wherein:

$X^1$, $X^2$, $X^3$, and $X^4$ are independently selected from C(R) and N wherein no more than two of $X^1$, $X^2$, $X^3$, and $X^4$ are N;

each R is independently selected from:

hydrogen, halogen, —$NO_2$, —CN, —$N_3$, —$OR^{28}$, —$SR^{28}$, —$N(R^{28})_2$, —$C(O)R^{28}$, —$C(O)N(R^{28})_2$, —$N(R^{28})C(O)R^{28}$, —$N(R^{28})C(O)N(R^{28})_2$, —$OC(O)N(R^{28})_2$, —$N(R^{28})C(O)OR^{28}$, —$C(O)OR^{28}$, —$OC(O)R^{28}$, —$S(O)R^{28}$, and —$S(O)_2R^{28}$;

$C_{1-6}$ alkyl, $C_{2-6}$ alkenyl, and $C_{2-6}$ alkynyl, each of which is optionally substituted with one or more substituents independently selected from halogen, —$OR^{28}$, —$SR^{28}$, —$N(R^{28})_2$, —$C(O)R^{28}$, —$C(O)N(R^{28})_2$, —$N(R^{28})C(O)R^{28}$, —$C(O)OR^{28}$, —$OC(O)R^{28}$, —$N(R^{28})C(O)N(R^{28})_2$, —$OC(O)N(R^{28})_2$, —$N(R^{28})C(O)OR^{28}$, —$S(O)R^{28}$, —$S(O)_2R^{28}$, —$NO_2$, =O, =S, =$N(R^{28})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{27}$; and $C_{3-10}$ carbocycle and 3- to 10-membered heterocycle, each of which is optionally substituted with one or more substituents independently selected from halogen, —$OR^{28}$, —$SR^{28}$, —$N(R^{28})_2$, —$C(O)R^{28}$, —$C(O)N(R^{28})_2$, —$N(R^{28})C(O)R^{28}$, —$N(R^{28})C(O)N(R^{28})_2$, —$OC(O)N(R^{28})_2$, —$N(R^{28})C(O)OR^{28}$, —$C(O)OR^{28}$, —$OC(O)R^{28}$, —$S(O)R^{28}$, —$S(O)_2R^{28}$, —$NO_2$, =O—, =S, =$N(R^{28})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27}$;

$R^{21}$ is selected from:

hydrogen, $C_{1-6}$ alkyl, $C_{2-6}$ alkenyl, and $C_{2-6}$ alkynyl, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$C(O)OR^{28a}$, —$OC(O)R^{28a}$, —$N(R^{28a})C(O)N(R^{28a})_2$, —$OC(O)N(R^{28a})_2$, —$N(R^{28a})C(O)OR^{28a}$, —$S(O)R^{28a}$, —$S(O)_2R^{28a}$, —$NO_2$, =O, =S, =$N(R^{28a})$, —$N_3$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{27a}$; and $C_{3-10}$ carbocycle, and 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, =O—, =S, =$N(R^{28a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27a}$.

$R^{22}$ is selected from:

hydrogen, $C_{1-6}$ alkyl, $C_{2-6}$ alkenyl, and $C_{2-6}$ alkynyl, each of which is optionally substituted with one or more substituents independently selected from halogen, —$OR^{28b}$, $SR^{28b}$, —$N(R^{28b})_2$, —$C(O)R^{28b}$, —$C(O)N(R^{28b})_2$, —$N(R^{28b})C(O)R^{28b}$, —$C(O)OR^{28b}$, —$OC(O)R^{28b}$, —$N(R^{28b})C(O)N(R^{28b})_2$, —$OC(O)N(R^{28b})_2$, —$N(R^{28b})C(O)OR^{28b}$, —$S(O)R^{28b}$, —$S(O)_2R^{28b}$, —$NO_2$, =O, =S, =$N(R^{28b})$, —$N_3$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{27b}$; and $C_{3-10}$ carbocycle, and 3- to 10-membered heterocycle, each of which is optionally substituted with one or more substituents independently selected from halogen, —$OR^{28b}$, —$SR^{28b}$, —$N(R^{28b})_2$, —$C(O)R^{28b}$, —$C(O)N(R^{28b})_2$, —$N(R^{28b})C(O)R^{28b}$, —$N(R^{28b})C(O)N(R^{28b})_2$, —$OC(O)N(R^{28b})_2$, —$N(R^{28b})C(O)OR^{28b}$, —$C(O)OR^{28b}$, —$OC(O)R^{28b}$, —$S(O)R^{28b}$, —$S(O)_2R^{28b}$, —$NO_2$, =O—, =S, =$N(R^{28b})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27b}$; or $R^{21}$ together with $R^{22}$ form a $C_{3-10}$ carbocycle, or 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, =O—, =S, =$N(R^{28a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27b}$;

$R^{23}$ is selected from:

hydrogen, halogen, —$OR^{28c}$, —$SR^{28c}$, —$N(R^{28c})_2$, —$N_3$, —$NO_2$, and —CN; and $C_{1-6}$ alkyl optionally substituted with one or more one or more $R^{27c}$; or $R^{21}$ together with $R^{23}$ form a 3- to 10-membered heterocycle, which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —N($R^{28a}$)C(O)O$R^{28a}$, —C(O)O$R^{28a}$, —OC(O)$R^{28a}$, —S(O)$R^{28a}$, —S(O)$_2R^{28a}$, —$NO_2$, ═O—, ═S, ═N($R^{28a}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27c}$;

or $R^{22}$ together with $R^{23}$ form a $C_{3-10}$ carbocycle, or 3- to 10-membered heterocycle, each of which is optionally substituted with one or more substituents independently selected from halogen, —O$R^{28a}$, —S$R^{28a}$, —N($R^{28a}$)$_2$, —C(O)$R^{28a}$, —C(O)N($R^{28a}$)$_2$, —N($R^{28a}$)C(O)$R^{28a}$, —N($R^{28a}$)C(O)N($R^{28a}$)$_2$, —OC(O)N($R^{28a}$)$_2$, —N($R^{28a}$)C(O)O$R^{28a}$, —C(O)O$R^{28a}$, —OC(O)$R^{28a}$, —S(O)$R^{28a}$, —S(O)$_2R^{28a}$, —$NO_2$, ═O—, ═S, ═N($R^{28a}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27c}$;

or $R^{21}$, $R^{22}$, and $R^{23}$ together form a bicyclic heterocycle which is optionally substituted with one or more substituents independently selected from halogen, —O$R^{28a}$, —S$R^{28a}$, —N($R^{28a}$)$_2$, —C(O)$R^{28a}$, —C(O)N($R^{28a}$)$_2$, —N($R^{28a}$)C(O)$R^{28a}$, —N($R^{28a}$)C(O)N($R^{28a}$)$_2$, —OC(O)N($R^{28a}$)$_2$, —N($R^{28a}$)C(O)O$R^{28a}$, —C(O)O$R^{28a}$, —OC(O)$R^{28a}$, —S(O)$R^{28a}$, —S(O)$_2R^{28a}$, —$NO_2$, ═O—, ═S, ═N($R^{28a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{27c}$;

$R^{24}$ is independently selected from:

hydrogen, halogen, —O$R^{28d}$, —S$R^{28d}$, —N($R^{28d}$)$_2$, —$N_3$, —$NO_2$, and —CN; and $C_{1-6}$ alkyl optionally substituted with one or more substituents independently selected from halogen, —O$R^{28d}$, —S$R^{28d}$, —N($R^{28d}$)$_2$, —$NO_2$, and —$N_3$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{27d}$;

$R^{24'}$ is independently selected from:

hydrogen, halogen, —O$R^{28d}$, —S$R^{28d}$, —N($R^{28d}$)$_2$, —$N_3$, —$NO_2$, and —CN; and $C_{1-6}$ alkyl optionally substituted with one or more substituents independently selected from halogen, —O$R^{28d}$, —S$R^{28d}$, —N($R^{28d}$)$_2$, —$NO_2$, and —$N_3$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{27d}$ $R^{25}$ is selected from:

hydrogen, halogen, —O$R^{28e}$, —S$R^{28e}$, —N($R^{28e}$)$_2$, —$NO_2$, —$N_3$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more $R^{27e}$; or $R^{24}$ together with $R^{25}$ form a 3- to 10-membered heterocycle, wherein the 3- to 10-membered heterocycle is optionally substituted with one or more $R^{27e}$;

$R^{26}$ is selected from:

hydrogen, halogen, —O$R^{28f}$, —S$R^{28f}$, —N($R^{28f}$)$_2$, —$N_3$, —$NO_2$, and —CN; and $C_{1-6}$ alkyl optionally substituted with one or more $R^{27f}$;

each $R^{27}$ is independently selected from:

halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2R^{28g}$, —$NO_2$, —$N_3$, ═O, ═S, ═N($R^{28g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2R^{28g}$, —$NO_2$, —$N_3$, ═O, ═S, ═N($R^{28g}$), and —CN;

each $R^{27a}$ is independently selected from:

halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2R^{28g}$, —$NO_2$, —$N_3$, ═O, ═S, ═N($R^{28g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2R^{28g}$, —$NO_2$, —$N_3$, ═O, ═S, ═N($R^{28g}$), and —CN;

each $R^{27b}$ is independently selected from:

halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2R^{28g}$, —$NO_2$, —$N_3$, ═O, ═S, ═N($R^{28g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{28g}$, —S$R^{28g}$, N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2R^{28g}$, —$NO_2$, —$N_3$, ═O, ═S, ═N($R^{28g}$), and —CN;

each $R^{27}$, is independently selected from:

halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2R^{28g}$, —$NO_2$, —$N_3$, ═O, ═S, ═N($R^{28g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2R^{28g}$, —$NO_2$, —$N_3$, ═O, ═S, ═N($R^{28g}$), and —CN;

each $R^{27d}$ is independently selected from:

halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)

$OR^{28g}$, —C(O)$OR^{28g}$, —OC(O)$R^{28g}$, —S(O)$R^{28g}$, —S(O)$_2R^{28g}$, —$NO_2$, —$N_3$, =O, =S, =N($R^{28g}$), and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)$OR^{28g}$, —C(O)$OR^{28g}$, —OC(O)$R^{28g}$, —S(O)$R^{28g}$, —S(O)$_2R^{28g}$, —1 $NO_2$, —$N_3$, =O, =S, =N($R^{28g}$), and —CN;

each $R^{27e}$ is independently selected from:

halogen, —$OR^{28g}$, —$SR^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)$OR^{28g}$, —C(O)$OR^{28g}$, —OC(O)$R^{28g}$, —S(O)$R^{28g}$, —S(O)$_2R^{28g}$, —$NO_2$, —$N_3$, =O, =S, =N($R^{28g}$), and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)$OR^{28g}$, —C(O)$OR^{28g}$, —OC(O)$R^{28g}$, —S(O)$R^{28g}$, —S(O)$_2R^{28g}$, —$NO_2$, —$N_3$, =O, =S, =N($R^{28g}$), and —CN;

each $R^{27f}$ is independently selected from:

halogen, —$OR^{28g}$, —$SR^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)$OR^{28g}$, —C(O)$OR^{28g}$, —OC(O)$R^{28g}$, —S(O)$R^{28g}$, —S(O)$_2R^{28g}$, —$NO_2$, —$N_3$, =O, =S, =N($R^{28g}$), and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)$OR^{28g}$, —C(O)$OR^{28g}$, —OC(O)$R^{28g}$, —S(O)$R^{28g}$, —S(O)$_2R^{28g}$, —$NO_2$, —$N_3$, =O, =S, =N($R^{28g}$), and —CN;

each $R^{28}$ is independently selected from:

hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28a}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28b}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28c}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28d}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28e}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28f}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; and each $R^{28g}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, —$N_3$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In some embodiments, the compound of Formula (III) is not

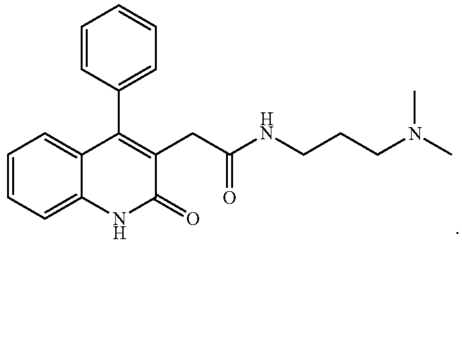 [SMILES: CN(C)CCCNC(=O)Cc1c(-c2ccccc2)c2ccccc2[nH]c1=O]

.

In some embodiments, for a compound or salt of Formula (III), $R^{21}$ is selected from:

hydrogen, $C_{1-6}$ alkyl, $C_{2-6}$ alkenyl, and $C_{2-6}$ alkynyl, each of which is optionally substituted with one or more substituents independently selected from halogen, —$OR^{28a}$, —$SR^{28a}$, —C(O)$R^{28a}$, —C(O)N($R^{28a}$)$_2$, —N($R^{28a}$)C(O)$R^{28a}$, —C(O)O$R^{28a}$, —OC(O)$R^{28a}$, —N($R^{28a}$)C(O)N($R^{28a}$)$_2$, —OC(O)N($R^{28a}$)$_2$, —N($R^{28a}$)C(O)O$R^{28a}$, —S(O)$R^{28a}$, —S(O)$_2R^{28a}$, —$NO_2$, =O, =S, =N($R^{28a}$), —CN, $C_{3-10}$ carbocycle, and 3- to 10-membered heterocycle, wherein the $C_{3-10}$ carbocycle, and 3- to 10-membered heterocycle, are each optionally substituted with one or more substituents independently selected from $R^{27a}$; and $C_{3-10}$ carbocycle, and 3- to 10-membered heterocycle, each of which is optionally substituted with one or more substituents independently selected from halogen, —$OR^{28a}$, —$SR^{28a}$, —N($R^{28a}$)$_2$, —C(O)$R^{28a}$, —C(O)N($R^{28a}$)$_2$, —N($R^{28a}$)C(O)$R^{28a}$, —N($R^{28a}$)C(O)N($R^{28a}$)$_2$, —OC(O)N($R^{28a}$)$_2$, —N($R^{28a}$)C(O)O$R^{28a}$, —C(O)O$R^{28a}$, —OC(O)$R^{28a}$, —S(O)$R^{28a}$, —S(O)$_2R^{28a}$, —$NO_2$, =O—, =S, =N($R^{28a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{27a}$;

$R^{22}$ is selected from:

hydrogen, $C_{1-6}$ alkyl, $C_{2-6}$ alkenyl, and $C_{2-6}$ alkynyl, each of which is optionally substituted with one or more substituents independently selected from halogen, —$OR^{28b}$, —$SR^{28b}$, —C(O)$R^{28b}$, —C(O)N($R^{28b}$)$_2$, —N($R^{28b}$)C(O)$R^{28b}$, —C(O)O$R^{28b}$, —OC(O)$R^{28b}$, —N($R^{28b}$)C(O)N($R^{28b}$)$_2$, —OC(O)N($R^{28b}$)$_2$, —N($R^{28b}$)C(O)O$R^{28b}$, —S(O)$R^{28b}$, —S(O)$_2R^{28b}$, —$NO_2$, =O, =S, =N($R^{28b}$), —CN, $C_{3-10}$ carbocycle, and 3- to 10-membered heterocycle, wherein the $C_{3-10}$ carbocycle, and 3- to 10-membered heterocycle, are each optionally substituted with one or more substituents independently selected from $R^{27b}$; and $C_{3-10}$ carbocycle, and 3- to 10-membered heterocycle, each of which is optionally substituted with one or more substituents independently selected from halogen, —$OR^{28b}$, —$SR^{28b}$, —N($R^{28b}$)$_2$, —C(O)$R^{28b}$, —C(O)N($R^{28b}$)$_2$, —N($R^{28b}$)C(O)$R^{28b}$, —N($R^{28b}$)C(O)N($R^{28b}$)$_2$, —OC(O)N($R^{28b}$)$_2$, —N($R^{28b}$)C(O)O$R^{28b}$, —C(O)O$R^{28b}$, OC(O)$R^{28b}$, —S(O)$R^{28b}$, —S(O)$_2R^{28b}$, —$NO_2$, =O—, =S, =N($R^{28b}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{27b}$; or $R^{21}$ together with $R^{22}$ form a $C_{3-10}$ carbocycle, or 3- to 10-membered heterocycle, each of which is optionally substituted with one or more substituents independently selected from halogen, —$OR^{28a}$, —$SR^{28a}$, —N($R^{28a}$)$_2$, —C(O)$R^{28a}$, —C(O)N($R^{28a}$)$_2$, —N($R^{28a}$)C(O)$R^{28a}$, —N($R^{28a}$)C(O)N($R^{28a}$)$_2$, —OC(O)N($R^{28a}$)$_2$, —N($R^{28a}$)C(O)O$R^{28a}$, —C(O)O$R^{28a}$, —OC(O)$R^{28a}$, —S(O)$R^{28a}$, —S(O)$_2R^{28a}$, —$NO_2$, =O—, =S, =N($R^{28a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{27b}$.

In some embodiments, for a compound or salt of Formula (III), $R^{25}$ is selected from:

hydrogen, halogen, —$OR^{28e}$, —$SR^{28e}$, —$N(R^{28e})_2$, —$NO_2$, —CN, and $C_{1-6}$ alkyl, wherein the $C_{1-6}$ alkyl is optionally substituted with one or more $R^{27e}$.

In one aspect, disclosed herein is a method of treating a cardiac disease in an individual in need thereof, the method comprising administering a therapeutically effective amount of a compound of Formula (III-ep):

Formula (III-ep)

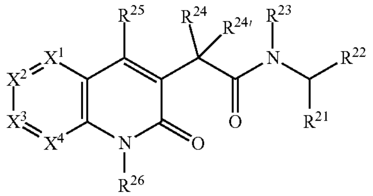

or a salt thereof, wherein:

$X^1$ is selected from C(R) and N, $X^2$ is selected from C(R) and N, $X^3$ is selected from C(R) and N, $X^4$ is selected from C(R) and N, wherein no more than two of $X^1$, $X^2$, $X^3$, and $X^4$ are N;

each R is independently selected from:

hydrogen; halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH ($C_{1-6}$ alkyl), and —N($C_{1-6}$ alkyl)$_2$; and $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{1-6}$ haloalkyl, and $C_{1-6}$alkyl;

$R^{21}$ is selected from:

hydrogen;

$C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH ($C_{1-6}$ alkyl), $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{1-6}$ alkyl, and $C_{1-6}$ haloalkyl;

$R^{22}$ is selected from:

hydrogen;

$C_{1-6}$ alkyl, $C_{2-6}$ alkenyl, and $C_{2-6}$ alkynyl, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH ($C_{1-6}$ alkyl), $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, $C_{1-6}$ alkyl, and $C_{1-6}$ haloalkyl; or $R^{21}$ together with $R^{22}$ form a $C_{3-10}$ carbocycle, or 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, and $C_{1-6}$ alkyl;

$R^{23}$ is selected from:

hydrogen; or $R^{22}$ together with $R^{23}$ form a $C_{3-10}$ carbocycle, or 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$, and $C_{1-6}$ alkyl;

or $R^{21}$, $R^{22}$, and $R^{23}$ together form a bridged heterocycle, wherein the bridged heterocycle is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl.

$R^{24}$ is selected from:

hydrogen, halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), —N($C_{1-6}$ alkyl)$_2$;

$C_{1-6}$ alkyl optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH ($C_{1-6}$ alkyl), and —N($C_{1-6}$ alkyl)$_2$;

$C_{3-10}$ carbocycle and 3- to 10-membered heterocycle, wherein the $C_{3-10}$ carbocycle and 3- to 10-membered heterocycle are each optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$R^{24'}$ is selected from:

hydrogen, halogen;

$C_{1-3}$ alkyl optionally substituted with one or more substituents independently selected from halogen, —CN, —OH, —O($C_{1-3}$ alkyl), —O($C_{1-3}$ haloalkyl), —$NH_2$, —NH($C_{1-6}$ alkyl), and —N($C_{1-6}$ alkyl)$_2$;

$C_{3-10}$ carbocycle and 3- to 10-membered heterocycle, wherein the $C_{3-10}$ carbocycle and 3- to 10-membered heterocycle are each optionally substituted with one or more substituents independently selected from halogen, —CN, —OH, —O($C_{1-3}$ alkyl), —O($C_{1-3}$ haloalkyl), —$NH_2$, —NH($C_{1-6}$ alkyl), and —N($C_{1-6}$ alkyl)$_2$;

or $R^{24}$ and $R^{24'}$ together form a $C_{3-10}$ carbocycle or 3- to 10-membered heterocycle, each of which is optionally substituted with one or more substituents independently selected from: halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl;

$R^{25}$ is selected from:

hydrogen, halogen, —OH, —O($C_{1-6}$ alkyl), —O($C_{1-6}$ haloalkyl), —SH, —S($C_{1-6}$ alkyl), —$NH_2$, —NH ($C_{1-6}$ alkyl), —N($C_{1-6}$ alkyl)$_2$, —$NO_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$;

$R^{26}$ is selected from:

hydrogen.

In some embodiments, for a compound of Formula (III-ep), $R^{25}$ is selected from:

hydrogen, halogen, —OH, —O($C_{1-6}$ alkyl), —O($C_{1-6}$ haloalkyl), —SH, —S($C_{1-6}$ alkyl), —$NH_2$, —NH ($C_{1-6}$ alkyl), —N($C_{1-6}$ alkyl)$_2$, —$NO_2$, —CN, $C_{1-6}$ alkyl, wherein the $C_{1-6}$ alkyl is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$.

Therapeutic Applications

Methods of administration of a compound or salt of Formula (I), (II-A), (IV), or (III) discussed herein may be used for the treatment of cardiac diseases and disorders. Examples of cardiac diseases and disorders include but are not limited to heart attack, heart failure, heart infection, endocarditis, myocarditis, pericarditis, arrhythmia, abnormal heart rhythms, aorta disease, Marfan syndrome, vascular disease, stroke, congenital heart disease, coronary artery disease, rhematic heart disease, peripheral vascular disease, heart valve disease, pericardial disease, heart muscle disease, cardiomyopathy, and deep vein thrombosis and pulmonary embolism. Examples of heart infections include but are not limited to endocarditis, myocarditis, and pericarditis.

Methods of administration of a compound or salt of Formula (I), (II-A), (IV), or (III) discussed herein may be used for the treatment of diseases and disorders resulting from the dysfunction of muscle myosin. Methods of administration of a compound or salt of Formula (I), (II-A), (IV), or (III) discussed herein may be used for the treatment of diseases and disorders through the modulation of muscle myosin. In some embodiments, the muscle myosin is cardiac muscle myosin (e.g., of ventricular or atrial tissue). In some embodiments, the muscle myosin is skeletal muscle myosin.

Methods of administration of a compound or salt of Formula (I), (II-A), (IV), or (III) discussed herein may be used for the treatment of diseases and disorders through the modulation of myosin cross-bridge cycling.

Cardiac Muscle Myosin

Methods of administration of a compound or salt of Formula (I), (II-A), (IV), or (III) discussed herein may be used for the modulation of cardiac muscle myosin. Methods of administration of a compound or salt of Formula (I), (II-A), (IV), or (III) discussed herein may be used for the treatment of cardiac diseases and disorders. Examples of cardiac diseases and disorders include but are not limited to heart attack, heart failure, heart infection, endocarditis, myocarditis, pericarditis, arrhythmia, abnormal heart rhythms, aorta disease, Marfan syndrome, vascular disease, stroke, congenital heart disease, coronary artery disease, rhematic heart disease, peripheral vascular disease, heart valve disease, pericardial disease, heart muscle disease, cardiomyopathy, deep vein thrombosis, and embolism (e.g., pulmonary embolism). Examples of heart infections include but are not limited to endocarditis, myocarditis, and pericarditis.

Methods of administration of a compound or salt of Formula (I), (II-A), (IV), or (III) discussed herein may be used for the treatment of one or more myopathy (myopathies).

In some embodiments, the myopathy is a cardiac myopathy. In some embodiments, the present disclosure provides a method of treating a condition selected from hypertrophic cardiomyopathy (HCM). In some embodiments, the present disclosure provides a method of treating a condition selected from hypertrophic cardiomyopathy (HCM); heart failure with preserved ejection fraction (HFpEF); disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; ischemia; and angina. In some embodiments, the present disclosure provides a compound for use in treating one or more condition(s) selected from: hypertrophic cardiomyopathy (HCM); heart failure with preserved ejection fraction (HFpEF); disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; ischemia; and angina. In some embodiments, said heart failure with preserved ejection fraction (HFpEF) comprises one or more disorders selected from disorders of relaxation and disorders of chamber stiffness (diabetic HFpEF). In some embodiments, said heart failure with preserved ejection fraction (HFpEF) comprises HFpEF related to hypertension. In some embodiments, said heart failure with preserved ejection fraction (HFpEF) comprises HFpEF related to aortic valvular disease. In some embodiments, said left ventricular (LV) hypertrophy is malignant left ventricular (LV) hypertrophy. In some embodiments, said restrictive cardiomyopathy comprises one or more subgroups selected from inflammatory subgroups, infiltrative subgroups, storage subgroups, idiopathic/inherited subgroups, congenital heart disease subgroups. In some embodiments, said inflammatory subgroups comprise one or more subgroups selected from Loefilers and EMF. In some embodiments, said inflammatory subgroups comprise one or more subgroups selected from amyloid, sarcoid, and XRT. In some embodiments, said storage subgroups comprise one or more subgroups selected from hemochromatosis, Fabry, and glycogen storage disease. In some embodiments, said idiopathic/inherited subgroups comprise one or more subgroups selected from Trop I (beta myosin HC), Trop T (alpha cardiac actin), and desmin related subgroups. In some embodiments, said congenital heart disease subgroups comprise one or more subgroups selected from pressure-overloaded RV, Tetralogy of Fallot, and pulmonic stenosis. In an aspect, the present disclosure provides a method of treating hypertrophic cardiomyopathy or a related condition comprising administering to a subject in need thereof a compound or salt disclosed herein (e.g., a compound or salt of Formula (I), (II-A), (IV), or (III)). In an aspect, the present disclosure provides a method of treating obstructive hypertrophic cardiomyopathy comprising administering to a subject in need thereof a compound or salt disclosed herein. In an aspect, the present disclosure provides a method of treating non-obstructive hypertrophic cardiomyopathy comprising administering to a subject in need thereof a compound or salt of disclosed herein. In an aspect, the present disclosure provides a method of treating heart failure with preserved ejection fraction comprising administering to a subject in need thereof a compound or disclosed herein. In an aspect, the present disclosure provides a method of treating left ventricle stiffness comprising administering to a subject in need thereof a compound or salt disclosed herein. In an aspect, the present disclosure provides a method of treating a condition selected from hypertrophic cardiomyopathy (HCM); disorders of relaxation; ischemic cardiomyopathy; cardiac transplant allograft vasculopathy; restrictive cardiomyopathy; left ventricular (LV) hypertrophy; ischemia; and andangin, the method comprising administering a ventricular-selective agent.

In an aspect, the present disclosure provides methods of treating atrial cardiopathy, Heart failure with ejection fraction (e.g., Heart failure with preserved ejection fraction (HFpEF), Heart failure with reduced ejection fraction (HFrEF)), arrhythmia (e.g., Atrial fibrillation), stroke (e.g., Cardioembolic stroke, Cryptogenic stroke), valve disease (e.g., Mitral valve disease, or Tricuspid valve disease), comprises administering an atrial-selective agent. In an aspect, the present disclosure provides methods of treating atrial cardiopathy, Heart failure with preserved ejection fraction (HFpEF), Heart failure with reduced ejection fraction (HFrEF), Atrial fibrillation, Cardioembolic stroke, Cryptogenic stroke, Mitral valve disease, or Tricuspid valve disease. In some embodiments, the method comprises administering an atrial-selective agent. In an aspect, the present disclosure provides methods of treating atrial cardiopathy. In some embodiments, the present disclosure provides a method of treating HFpEF. In some embodiments, the present disclosure provides a method of treating HFrEF. In some embodiments, the present disclosure provides a method of treating Atrial fibrillation. In some embodiments, the present disclosure provides a method of treating Cardioembolic stroke. In some embodiments, the present disclosure provides a method of treating Cryptogenic stroke. In some embodiments, the present disclosure provides a method of treating Mitral valve disease. In some embodiments, the present disclosure provides a method of treating Tricuspid valve disease. In some embodiments, the present disclosure provides a method of treating one or more diseases selected from atrial cardiopathy, HFpEF, HFrEF, Atrial fibrillation, Cardioembolic stroke, Cryptogenic stroke, Mitral valve disease, and Tricuspid valve disease. In some embodiments, the method comprises administering a compound of Formula (I), (II-A), (IV), or (III). In some embodiments, the compound of Formula (I), (II-A), (IV), or (III) is for use in treating one or more diseases selected from atrial cardiopathy, HFpEF, HFrEF, Atrial fibrillation, Cardioembolic stroke, Cryptogenic stroke, Mitral valve disease, and Tricuspid valve disease, comprises an atrial-selective agent. In some embodiments, the atrial-selective agent selectively inhibits atrial myosin relative to ventricular myosin or relative to skeletal myosin. In some embodiments, the atrial-selective agent selectively inhibits atrial myosin regulatory light chain relative to ventricular myosin regulatory light chain, or relative to skeletal myosin regulatory light chain, or relative to both atrial myosin regulatory light chain and skeletal myosin regulatory light chain.

In an aspect, disclosed herein are methods to treat a disease by the administration of a compound or salt of Formula (I), (II-A), (IV), or (III).

In an aspect, disclosed herein are methods to treat cardiac disease by the administration of a compound or salt of Formula (I), (II-A), (IV), or (III).

In an aspect, disclosed herein are methods to treat cardiovascular disease or a related condition by the administration of a compound or salt of Formula (I), (II-A), (IV), or (III). In an aspect, disclosed herein are methods to treat cardiovascular disease or a related condition by the administration of a compound or salt of Formula (I), (II-A), (IV), or (III).

In an aspect, the present disclosure provides a method of treating a condition selected from hypertrophic cardiomyopathy (HCM); heart failure with preserved ejection fraction (HFpEF); disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; ischemia; angina; and myocarditis. In some embodiments, the condition is cardiac dysfunction related to acute or chronic myocarditis. In some embodiments, the myocarditis is parasitic, bacterial, viral, or non-infectious. In some embodiments, the myocarditis is auto-immune myocarditis. In some embodiments, the myocarditis is eosinophilic myocarditis. In some embodiments, the condition is a myopathy. In some embodiments, the condition is a cardiomyopathy. In some embodiments, the cardiomyopathy is a toxic cardiomyopathy. In some embodiments, the toxic cardiomyopathy is related to exposure to chemotherapeutic agents, ethanol, cocaine, other toxic substances, or any combination thereof. In some embodiments, said heart failure with preserved ejection fraction (HFpEF) comprises one or more disorders selected from disorders of relaxation and disorders of chamber stiffness (diabetic HFpEF). In some embodiments, said left ventricular (LV) hypertrophy is malignant left ventricular (LV) hypertrophy. In some embodiments, said restrictive cardiomyopathy comprises one or more subgroups selected from inflammatory subgroups, infiltrative subgroups, storage subgroups, idiopathic subgroups, inherited subgroups, congenital heart disease subgroups. In some embodiments, said inflammatory subgroups comprise one or more subgroups selected from Loefilers and EMF. In some embodiments, said inflammatory subgroups comprise one or more subgroups selected from amyloid, sarcoid, and radiation (e.g., XRT, radiation therapy, or radiation injury). In some embodiments, said storage subgroups comprise one or more subgroups selected from hemochromatosis, Fabry, and glycogen storage disease. In some embodiments, said inherited subgroups is related to conditions associated with Troponin I (beta myosin Heavy Chain), Troponin T (e.g. alpha cardiac actin), or desmin. In some embodiments, said congenital heart disease subgroups comprises one or more subgroups selected from pressure-overloaded right ventricle (RV), Tetralogy of Fallot, and pulmonic stenosis. In an aspect, the present disclosure provides a method of treating hypertrophic cardiomyopathy or a related condition comprising administering to a subject in need thereof a compound or salt disclosed herein.

In an aspect, the present disclosure provides a method of treating obstructive hypertrophic cardiomyopathy comprising administering to a subject in need thereof a compound or salt disclosed herein. In an aspect, the present disclosure provides a method of treating non-obstructive hypertrophic cardiomyopathy comprising administering to a subject in need thereof a compound or salt of disclosed herein. In an aspect, the present disclosure provides a method of treating heart failure with preserved ejection fraction comprising administering to a subject in need thereof a compound or disclosed herein. In an aspect, the present disclosure provides a method of treating left ventricle stiffness comprising administering to a subject in need thereof a compound or salt disclosed herein.

In some embodiments, the present disclosure provides a method of treating dilated (DCM) cardiomyopathy. In some embodiments, the present disclosure provides a method of treating sudden cardiac death.

In an aspect, the present disclosure provides a method of treating a cardiac disease or disorder, the method comprising administering a compound or salt of any one of Formula (I), (II-A), (IV), or (III) to a subject in need thereof. In some embodiments, administering the compound or salt of any one of Formula (I), (II-A), (IV), or (III) modulates the subject's heart rate (HR), end diastolic volume (EDV), or fractional shortening (FS). In some embodiments, the administering the compound or salt increases the subject's HR. In some embodiments, the administering the compound or salt increases the subject's FS. In some embodiments, the administering the compound or salt increases the subject's EDV. In some embodiments, the administering the compound or salt decreases the subject's HR. In some embodiments, the administering the compound or salt decreases the subject's FS. In some embodiments, the administering the compound or salt decreases the subject's EDV. In some embodiments the administering the compound or salt does not change (e.g., does not significantly change) the subject's HR. In some embodiments the administering the compound or salt does not change (e.g., does not significantly change) the subject's FS. In some embodiments the administering the compound or salt does not change (e.g., does not significantly change) the subject's EDV. In some embodiments, the administering the compound or salt modulates an index of left-ventricular fractional shortening (FS) and systolic wall-thickening index (SWT). In some embodiments, the administering the compound or salt modulates an index of left-ventricular fractional shortening (FS). In some embodiments, the administering the compound or salt modulates an index of systolic wall-thickening index (SWT). In some embodiments, administering the compound or salt of any one of Formula (I), (II-A), (IV), or (III) modulates the subject's isovolumic contraction time (IVCT), or Pre-ejection period, or isovolumic relaxation time (IVRT), or ejection fraction (EF). In some embodiments, the administering the compound or salt increases the subject's IVCT. In some embodiments, the administering the compound or salt increases the subject's Pre-ejection period. In some embodiments, the administering the compound or salt increases the subject's IVRT. In some embodiments, the administering the compound or salt increases the subject's EF. In some embodiments, the administering the compound or salt decreases the subject's IVCT. In some embodiments, the administering the compound or salt decreases the subject's Pre-ejection period. In some embodiments, the administering the compound or salt decreases the subject's IVRT. In some embodiments, the administering the compound or salt decreases the subject's EF. In some embodiments, the administering the compound or salt does not change (e.g., does not significantly change) the subject's IVCT. In some embodiments, the administering the compound or salt does not change (e.g., does not significantly change) the subject's Pre-ejection period. In some embodiments, the administering the compound or salt does not change (e.g., does not significantly change) the subject's IVRT. In some embodiments, the administering the compound or salt does not change (e.g., does not significantly change) the subject's EF. In some embodiments, the administering the compound or salt modulates actomyosin cycling rates. In some embodiments, the administering the compound or salt modulates peak E-wave velocity (E). In some embodiments, the administering the compound or salt modulates peak A-wave velocity (A). In some embodiments, the administering the compound or salt modulates peak early diastolic mitral annular velocity (e'). In some embodiments, E-wave and A-wave may refer two distinct periods of filling of the ventricle (e.g., left ventricle) with blood from the atrium (e.g., left atrium), e.g., wherein the E-wave may occur early in diastole, and e.g., wherein the A-wave may occur late in diastole, e.g., when the atrium contracts. In some embodiments, the change in HR, FS, SWT, IVCT, IVRT, EF, or pre-ejection period is from about 1% from baseline to about 30% from baseline.

In some embodiments, the method comprising administering a compound of Formula (III) further comprises further comprising administering an additional active agent.

In an aspect, the present disclosure provides a pharmaceutical composition comprising the compound or salt of Formula (I), (II-A), (IV), or (III) and one or more excipient(s) (e.g., a pharmaceutically acceptable excipient).

In an aspect, the present disclosure provides a method of modulating a light chain (e.g., a myosin light chain). Alternatively, or in addition, in some embodiments, the present disclosure provides a method of modulating a heavy chain (e.g., a myosin heavy chain). In some embodiments, a compound or salt of the present disclosure (e.g., Formula (I), (II-A), (IV), or (III)) modulates a light chain. In some embodiments, a compound or salt of the present disclosure modulates a regulatory light chain (RLC) (e.g., a myosin regulatory light chain). In some embodiments, a compound or salt of the present disclosure modulates an essential light chain (ELC) (e.g., a myosin essential light chain). In some embodiments, the regulatory light chain is a cardiac myosin regulatory light chain. In some embodiments, the modulating the regulatory light chain is inhibiting the regulatory light chain (e.g., inhibiting the function of the RLC). Alternatively, or in addition, in some embodiments, the modulating the rlc is activating the RLC (e.g., activating the function of the RLC). In some embodiments, the method changes the ability of a myosin lever arm to develop force. In some embodiments, the method modulates cross bridge cycling. In some embodiments, administering the compound or salt overcomes a disturbance in an interaction between myosin regulatory light chain and myosin heavy chain. In some embodiments, the disturbance is caused by a genetic mutation. In some embodiments, the method of modulating an RLC is for use in treating hypertrophic cardiomyopathy. In some embodiments, a compound or salt of the present disclosure directly binds myosin RLC. Alternatively, on in addition, in some embodiments, a compound or salt of the present disclosure indirectly modulates one or more other protein(s) (e.g., other sarcomeric protein(s), or e.g., protein(s) other than myosin RLC). In some embodiments, a compound or salt of the present disclosure indirectly modulates myosin or myosin binding protein C, or one or more thin-filament protein(s).

In some embodiments, the compound or salt is an inhibitor of myosin ATP-ase. In some embodiments, administering a compound of the present disclosure modulates ATP cycling rates of one or more sarcomeric protein(s) (e.g., actomyosin cycling). In some embodiments, administering a compound of the present disclosure activates ATP cycling rates of sarcomeric proteins. Alternatively, in some embodiments, administering a compound of the present disclosure inhibits ATP cycling rates of sarcomeric proteins. In some embodiments, the modulating ATP cycling rates of sarcomeric proteiens is through interactions (e.g., binding) with one or more sarcomere protein(s) (e.g., myosin, myosin regulatory light chain, myosin essential light chain, or myosin binding protein-c).

In some embodiments, administering a compound or salt of the present disclosure modulates actin floating on myosin. In some embodiments, administering a compound or salt of the present disclosure modulates actin floating on myosin in a different way than a direct myosin inhibitor modulates actin floating on myosin (e.g., as shown in a Motility assay).

In an aspect, administering a compound or salt of the disclosure (e.g., a compound or salt of any one of Formula (I), (II-A), (IV), or (III) modulates one or more sarcomeric protein(s). In an aspect, administering a compound or salt of the disclosure (e.g., a compound or salt of any one of Formula (I), (II-A), (IV), or (III)) modulates a myosin (e.g., myosin in cardiac muscle, myosin in skeletal muscle). In an aspect, administering a compound or salt of the disclosure (e.g., a compound or salt of any one Formula (I), Formula (II-A), Formula (IV), or Formula (III)) modulates a myosin light chain (e.g., essential myosin light chain, regulatory myosin light chain). In some embodiments, administering a compound or salt of the disclosure (e.g., a compound or salt of any one of Formula (I), (II-A), (IV), or (III)) modulates a regulatory light chain (e.g., myosin regulatory light chain). In some embodiments, the compound or salt of the disclosure (e.g., a compound or salt of any one of Formula (I), (II-A), (IV), or (III)) inhibits a regulatory light chain. Alternatively, in some embodiments, the compound or salt of the disclosure (e.g., a compound or salt of any one of Formula (I), (II-A), (IV), or (III)) activates a myosin regulatory light chain.

In an aspect, administering a compound of the present disclosure treats a patient (e.g., with HCM) through modulation of a myosin regulatory light chain (e.g., cardiac myosin regulatory light chain).

In some embodiments, the patient to which a compound of the present disclosure is administered exhibits a myosin heavy chain mutation (e.g., on chromosome 14 g11.2-3, e.g., MYH7). In some embodiments, the patient exhibits a β-myosin heavy chain mutation (e.g., on chromosome 14 q11.2-3, e.g., MYH7). In some embodiments, the patient exhibits an insertion/deletion polymorphism in the gene encoding for angiotensin converting enzyme (e.g., ACE). In some embodiments, the patient with the insertion/deletion polymorphism in the gene encoding for ACE exhibits more marked hypertrophy of the left ventricle. In some embodiments, the patient exhibits a troponin mutation (e.g., troponin T or troponin C). In some embodiments, the patient exhibits a myosin binding protein C (MYBPC) mutation. In some embodiments, the patient exhibits a myosin 7 mutation. In some embodiments, the patient exhibits multiple mutations selected from troponin, RLC, MYBPC, myosin 7, myosin heavy chain, and ACE. In some embodiments, the patient exhibits multiple mutations selected from troponin, RLC, MYBPC, and myosin 7.

In some embodiments, the patient to which a compound of the present disclosure is administered exhibits a myosin regulatory light chain mutation (e.g., E22K mutation). In some embodiments, the myosin regulatory light chain mutation disturbs the interaction of myosin regulatory light chain with myosin heavy chain. In some embodiments, the disturbance in the interaction between myosin regulatory light chain and myosin heavy chain leads to structural abnormalities in the myosin cross bridge (e.g., in the myosin cross bridge, e.g., in the lever arm of the myosin cross bridge). In some embodiments, the mutation in the myosin regulatory light chain leads to reduced contractility. In some embodiments, the mutation in the myosin regulatory light chain leads to decreased cardiac output.

In some embodiments, modulation of the myosin regulatory light chain overcomes a disturbance in an interaction between myosin regulatory light chain and myosin heavy chain (e.g., which leads to structural abnormalities in the myosin cross bridge, e.g., in the lever arm of the myosin cross bridge). In some embodiments, administering a compound of the present disclosure (e.g., to a patient with an RLC mutation) changes a myosin lever arm's ability to develop force. In some embodiments, the myosin lever arm's changed ability to develop force results in slowed contraction. In some embodiments, the myosin lever arm's changed ability to develop force results in accelerated relaxation. In some embodiments, the myosin lever arm's changed ability to develop force results in slowed contraction and accelerated relaxation. In some embodiments, this helps overcome mutations (e.g., that enhance the proportion of force-developing myosin heads, e.g., HCM mutations). In some embodiments, this action (e.g., slowed contraction or accelerated relaxation) is greater at low calcium (e.g., diastolic) compared to high calcium (e.g., systolic) (e.g., which may modulate its inhibitory action as the heart contracts and relaxes). In some embodiments, modulation of the myosin regulatory light chain leads to reduced contractility. In some embodiments, modulation of the myosin regulatory light chain leads to decreased cardiac output. In some embodiments, modulation of the myosin regulatory light chain leads to slowing of early contraction (e.g., resulting from slower walking of myosin heads along actin). In some embodiments, the slowing of early contraction is used to treat HCM (e.g., obstructive HCM, oHCM). In some embodiments, treatment through this mechanism is administered for genetic HCM or non-genetic HCM.

In some embodiments, one or more cardiac mutation(s) (e.g., a mutation in the myosin regulatory light chain) in a patient (e.g., a patient with HCM) modulate(s) a spatial gradient of myosin regulatory light chain phosphorylation (e.g., modulate relative to that in the heart of a patient without HCM). In some embodiments, a mutation in the myosin regulatory light chain modulates the spatial gradient of myosin regulatory light chain phosphorylation. In some embodiments, a mutation in the myosin regulatory light chain decreases cardiac torsion (e.g., so that blood is less efficiently wrung out of the heart). In some embodiments, a mutation in the myosin regulatory light chain decreases cardiac torsion by altering the mechanism by which the spatial gradient of myosin light chain phosphorylation across the heart inversely alters tension production. In some embodiments, a mutation in the myosin regulatory light chain decreases cardiac torsion by altering the mechanism by which the spatial gradient of myosin light chain phosphorylation across the heart inversely alters the stretch activation response. In some embodiments, a mutation in the myosin regulatory light chain decreases cardiac torsion by modulating a mechanism by which the spatial gradient of myosin light chain phosphorylation across the heart inversely alters tension production and the stretch activation response. In some embodiments, treatment through this mechanism is administered for genetic HCM or non-genetic HCM.

In some embodiments, modulation of the myosin regulatory light chain increases cardiac torsion in a patient (e.g., with HCM) relative to a patient without HCM. In some embodiments, modulation of myosin regulatory light chain increases torsion by modulating the spatial gradient of myosin light chain phosphorylation across the heart.

In some embodiments, the myosin regulatory light chain mutation decreases calcium-activated tension. In some embodiments, the myosin regulatory light chain mutation decreases calcium-activated stiffness. In some embodiments, the myosin regulatory light chain mutation reduces myofilament $Ca^{2+}$ sensitivity. In some embodiments, modulation of the myosin regulatory light chain increases calcium-activated tension. In some embodiments, modulation of the myosin regulatory light chain increases calcium-activated stiffness. In some embodiments, modulation of the myosin regulatory light chain increases myofilament $Ca^{2+}$ sensitivity. In some embodiments, upon administration of a compound or salt of the present disclosure, changes in calcium sensitivity are length dependent. In some embodiments, upon administration of a compound or salt of the present disclosure, changes in calcium sensitivity are length dependent (e.g., except with decreases in calcium sensitivity at long sarcomere lengths). In some embodiments, administering a compound of the present disclosure changes calcium sensitivity. In some embodiments, administering a compound of the present disclosure changes calcium sensitivity when the sarcomere is stretched. In some embodiments, treatment through this mechanism is administered for genetic HCM or non-genetic HCM.

In an aspect, a compound of the present disclosure (e.g., a compound of Formula (I), (II-A), (IV), or (III)) selectively inhibits function of ventricular myosin. In some embodiments, a compound of the present disclosure selectively inhibits function of atrial myosin. In some embodiments, a compound of the present disclosure selectively inhibits function of skeletal myosin. In some embodiments, a compound of the present disclosure selectively inhibits function of ventricular myosin relative to atrial myosin. In some embodiments, a compound of the present disclosure selectively inhibits function of ventricular myosin relative to skeletal myosin. In some embodiments, a compound of the present disclosure selectively inhibits function of ventricular myosin relative to atrial myosin and skeletal myosin. In some embodiments, a compound of the present disclosure selectively inhibits function of atrial myosin relative to ventricular myosin. In some embodiments, a compound of the present disclosure selectively inhibits function of atrial myosin relative to skeletal myosin. In some embodiments, a compound of the present disclosure selectively inhibits function of atrial myosin relative to ventricular myosin and skeletal myosin. In some embodiments, a compound of the present disclosure selectively inhibits function of skeletal myosin relative to atrial myosin. In some embodiments, a compound of the present disclosure selectively inhibits function of skeletal myosin relative to ventricular myosin. In some embodiments, a compound of the present disclosure selectively inhibits function of skeletal myosin relative to atrial myosin and ventricular myosin.

In an aspect, a compound of the present disclosure (e.g., a compound of Formula (I), (II-A), (IV), or (III)) selectively activates function of ventricular myosin. In some embodiments, a compound of the present disclosure selectively activates function of atrial myosin. In some embodiments, a compound of the present disclosure selectively activates function of skeletal myosin. In some embodiments, a compound of the present disclosure selectively activates function of ventricular myosin relative to atrial myosin. In some embodiments, a compound of the present disclosure selectively activates function of ventricular myosin relative to skeletal myosin. In some embodiments, a compound of the present disclosure selectively activates function of ventricular myosin relative to atrial myosin and skeletal myosin. In some embodiments, a compound of the present disclosure selectively activates function of atrial myosin relative to ventricular myosin. In some embodiments, a compound of the present disclosure selectively activates function of atrial myosin relative to skeletal myosin. In some embodiments, a compound of the present disclosure selectively activates function of atrial myosin relative to ventricular myosin and skeletal myosin. In some embodiments, a compound of the present disclosure selectively activates function of skeletal myosin relative to atrial myosin. In some embodiments, a compound of the present disclosure selectively activates function of skeletal myosin relative to ventricular myosin. In some embodiments, a compound of the present disclosure selectively activates function of skeletal myosin relative to atrial myosin and ventricular myosin.

In some embodiments, administering a compound or salt of the present disclosure does not modulate myosin heavy chain. In some embodiments, the compound or salt of the present disclosure does not bind myosin heavy chain. In some embodiments, the compound or salt of the present disclosure does not inhibit myosin heavy chain. In some embodiments, the compound or salt of the present disclosure does not activate myosin heavy chain.

In some embodiments, the term selective inhibition refers to a 10-fold decrease in activity (e.g., in some embodiments, selective inhibition of ventricular myosin relative to atrial myosin refers to a state wherein the $EC_{25}$ value for ventricular myosin is 10-times lower than that of atrial myosin). In some embodiments, the term selective inhibition refers to a decrease in activity that is at least about 2-fold, at least about 3-fold, at least about 4-fold, at least about 5-fold, at least about 7-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold, at least about 125-fold, at least about 150-fold, at least about 175-fold, at least about 200-fold, at least about 300-fold, at least about 400-fold, at least about 500-fold, at least about 600-fold, at least about 700-fold, at least about 800-fold, at least about 900-fold, at least about 1000-fold, at least about 2000-fold, at least about 10,000-fold, or more. Alternatively, or in addition, in some embodiments, the term selective inhibition refers to a decrease in activity that is at most about 2-fold, at most about 3-fold, at most about 4-fold, at most about 5-fold, at most about 7-fold, at most about 10-fold, at most about 15-fold, at most about 20-fold, at most about 30-fold, at most about 40-fold, at most about 50-fold, at most about 60-fold, at most about 70-fold, at most about 80-fold, at most about 90-fold, at most about 100-fold, at most about 125-fold, at most about 150-fold, at most about 175-fold, at most about 200-fold, at most about 300-fold, at most about 400-fold, at most about 500-fold, at most about 600-fold, at most about 700-fold, at most about 800-fold, at most about 900-fold, at most about 1000-fold, at most about 2000-fold, at most about 10,000-fold, or less. In some embodiments, the term selective inhibition refers to a decrease in activity that is about 1-fold to about 5,000-fold. In some embodiments, the term selective inhibition refers to a decrease in activity that is at least about 1-fold. In some embodiments, the term selective inhibition refers to a decrease in activity that is at most about 5,000-fold. In some embodiments, the term selective inhibition refers to a decrease in activity that is about 1-fold to about 2-fold, about 1-fold to about 5-fold, about 1-fold to about 10-fold, about 1-fold to about 25-fold, about 1-fold to about 50-fold, about 1-fold to about 75-fold, about 1-fold to about 100-fold, about 1-fold to about 200-fold, about 1-fold to about 500-fold, about 1-fold to about 1,000-fold, about 1-fold to about 5,000-fold, about 2-fold to about 5-fold, about 2-fold to about 10-fold, about 2-fold to about 25-fold, about 2-fold to about 50-fold, about 2-fold to about 75-fold, about 2-fold to about 100-fold, about 2-fold to about 200-fold, about 2-fold to about 500-fold, about 2-fold to about 1,000-fold, about 2-fold to about 5,000-fold, about 5-fold to about 10-fold, about 5-fold to about 25-fold, about 5-fold to about 50-fold, about 5-fold to about 75-fold, about 5-fold to about 100-fold, about 5-fold to about 200-fold, about 5-fold to about 500-fold, about 5-fold to about 1,000-fold, about 5-fold to about 5,000-fold, about 10-fold to about 25-fold, about 10-fold to about 50-fold, about 10-fold to about 75-fold, about 10-fold to about 100-fold, about 10-fold to about 200-fold, about 10-fold to about 500-fold, about 10-fold to about 1,000-fold, about 10-fold to about 5,000-fold, about 25-fold to about 50-fold, about 25-fold to about 75-fold, about 25-fold to about 100-fold, about 25-fold to about 200-fold, about 25-fold to about 500-fold, about 25-fold to about 1,000-fold, about 25-fold to about 5,000-fold, about 50-fold to about 75-fold, about 50-fold to about 100-fold, about 50-fold to about 200-fold, about 50-fold to about 500-fold, about 50-fold to about 1,000-fold, about 50-fold to about 5,000-fold, about 75-fold to about 100-fold, about 75-fold to about 200-fold, about 75-fold to about 500-fold, about 75-fold to about 1,000-fold, about 75-fold to about 5,000-fold, about 100-fold to about 200-fold, about 100-fold to about 500-fold, about 100-fold to about 1,000-fold, about 100-fold to about 5,000-fold, about 200-fold to about 500-fold, about 200-fold to about 1,000-fold, about 200-fold to about 5,000-fold, about 500-fold to about 1,000-fold, about 500-fold to about 5,000-fold, or about 1,000-fold to about 5,000-fold, or about 2-fold to about 10,000 fold. In some embodiments, the term selective inhibition refers to a decrease in activity that is about 1-fold, about 2-fold, about 5-fold, about 10-fold, about 25-fold, about 50-fold, about 75-fold, about 100-fold, about 200-fold, about 500-fold, about 1,000-fold, about 5,000-fold, about 10,000-fold, or 100,000-fold.

In some embodiments, the term selective activation refers to a 10-fold increase in activity (e.g., in some embodiments, selective activation of ventricular myosin relative to atrial myosin refers to a state wherein the $EC_{25}$ value for ventricular myosin is 10-times higher than that of atrial myosin). In some embodiments, the term selective activation refers to an increase in activity that is at least about 2-fold, at least about 3-fold, at least about 4-fold, at least about 5-fold, at least about 7-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold, at least about 125-fold, at least about 150-fold, at least about 175-fold, at least about 200-fold, at least about 300-fold, at least about 400-fold, at least about 500-fold, at least about 600-fold, at least about 700-fold, at least about 800-fold, at least about 900-fold, at least about 1000-fold, at least about 2000-fold, at least about 10,000-fold, or more. Alternatively, or in addition, in some embodiments, the term selective activation refers to an increase in activity that is at most about 2-fold, at most about 3-fold, at most about 4-fold, at most about 5-fold, at most about 7-fold, at most about 10-fold, at most about 15-fold, at most about 20-fold, at most about 30-fold, at most about 40-fold, at most about 50-fold, at most about 60-fold, at most about 70-fold, at most about 80-fold, at most about 90-fold, at most about 100-fold, at most about 125-fold, at most about 150-fold, at most about 175-fold, at most about 200-fold, at most about 300-fold, at most about 400-fold, at most about 500-fold, at most about 600-fold, at most about 700-fold, at most about 800-fold, at most about 900-fold, at most about 1000-fold, at most about 2000-fold, at most about 10,000-fold, or less. In some embodiments, the term selective activation refers to an increase in activity that is about 1-fold to about 5,000-fold. In some embodiments, the term selective activation refers to an increase in activity that is at least about 1-fold. In some embodiments, the term selective activation refers to an increase in activity that is at most about 5,000-fold. In some embodiments, the term selective activation refers to an increase in activity that is about 1-fold to about 2-fold, about 1-fold to about 5-fold, about 1-fold to about 10-fold, about 1-fold to about 25-fold, about 1-fold to about 50-fold, about 1-fold to about 75-fold, about 1-fold to about 100-fold, about 1-fold to about 200-fold, about 1-fold to about 500-fold, about 1-fold to about 1,000-fold, about 1-fold to about 5,000-fold, about 2-fold to about 5-fold, about 2-fold to about 10-fold, about 2-fold to about 25-fold, about 2-fold to about 50-fold, about 2-fold to about 75-fold, about 2-fold to about 100-fold, about 2-fold to about 200-fold, about 2-fold to about 500-fold, about 2-fold to about 1,000-fold, about 2-fold to about 5,000-fold, about 5-fold to about 10-fold, about 5-fold to about 25-fold, about 5-fold to about 50-fold, about 5-fold to about 75-fold, about 5-fold to about 100-fold, about 5-fold to about 200-fold, about 5-fold to about 500-fold, about 5-fold to about 1,000-fold, about 5-fold to about 5,000-fold, about 10-fold to about 25-fold, about 10-fold to about 50-fold, about 10-fold to about 75-fold, about 10-fold to about 100-fold, about 10-fold to about 200-fold, about 10-fold to about 500-fold, about 10-fold to about 1,000-fold, about 10-fold to about 5,000-fold, about 25-fold to about 50-fold, about 25-fold to about 75-fold, about 25-fold to about 100-fold, about 25-fold to about 200-fold, about 25-fold to about 500-fold, about 25-fold to about 1,000-fold, about 25-fold to about 5,000-fold, about 50-fold to about 75-fold, about 50-fold to about 100-fold, about 50-fold to about 200-fold, about 50-fold to about 500-fold, about 50-fold to about 1,000-fold, about 50-fold to about 5,000-fold, about 75-fold to about 100-fold, about 75-fold to about 200-fold, about 75-fold to about 500-fold, about 75-fold to about 1,000-fold, about 75-fold to about 5,000-fold, about 100-fold to about 200-fold, about 100-fold to about 500-fold, about 100-fold to about 1,000-fold, about 100-fold to about 5,000-fold, about 200-fold to about 500-fold, about 200-fold to about 1,000-fold, about 200-fold to about 5,000-fold, about 500-fold to about 1,000-fold, about 500-fold to about 5,000-fold, or about 1,000-fold to about 5,000-fold, or about 2-fold to about 10,000 fold. In some embodiments, the term selective activation refers to an increase in activity that is about 1-fold, about 2-fold, about 5-fold, about 10-fold, about 25-fold, about 50-fold, about 75-fold, about 100-fold, about 200-fold, about 500-fold, about 1,000-fold, or about 5,000-fold.

In an aspect, the present disclosure provides methods of treating atrial cardiopathy, Heart failure with ejection fraction (e.g., Heart failure with preserved ejection fraction (HFpEF), Heart failure with reduced ejection fraction (HFrEF)), arrhythmia (e.g., Atrial fibrillation), stroke (e.g., Cardioembolic stroke, Cryptogenic stroke), valve disease (e.g., Mitral valve disease, or Tricuspid valve disease), comprises administering an atrial-selective agent. In an aspect, the present disclosure provides methods of treating atrial cardiopathy, Heart failure with preserved ejection fraction (HFpEF), Heart failure with reduced ejection fraction (HFrEF), Atrial fibrillation, Cardioembolic stroke, Cryptogenic stroke, Mitral valve disease, or Tricuspid valve disease, comprises administering an atrial-selective agent. In an aspect, the present disclosure provides methods of treating atrial cardiopathy. In some embodiments, the present disclosure provides a method of treating HFpEF. In some embodiments, the present disclosure provides a method of treating HFrEF. In some embodiments, the present disclosure provides a method of treating Atrial fibrillation. In some embodiments, the present disclosure provides a method of treating Cardioembolic stroke. In some embodiments, the present disclosure provides a method of treating Cryptogenic stroke. In some embodiments, the present disclosure provides a method of treating Mitral valve disease. In some embodiments, the present disclosure provides a method of treating Tricuspid valve disease.

In some embodiments, the present disclosure provides a method of treating one or more diseases selected from atrial cardiopathy, HFpEF, HFrEF, Atrial fibrillation, Cardioembolic stroke, Cryptogenic stroke, Mitral valve disease, and Tricuspid valve disease. In some embodiments, the method comprises administering a compound of Formula (I), (II-A), (IV), or (III). In some embodiments, the compound of Formula (I), (II-A), (IV), or (III) for use in treating one or more diseases selected from atrial cardiopathy, HFpEF, HFrEF, Atrial fibrillation, Cardioembolic stroke, Cryptogenic stroke, Mitral valve disease, and Tricuspid valve disease, comprises an atrial-selective agent. In some embodiments, the atrial-selective agent selectively inhibits atrial myosin relative to ventricular myosin or relative to skeletal myosin. In some embodiments, the atrial-selective agent selectively inhibits atrial myosin regulatory light chain relative to ventricular myosin regulatory light chain, or relative to skeletal myosin regulatory light chain, or relative to both atrial myosin regulatory light chain and skeletal myosin regulatory light chain. In an aspect, the present disclosure provides a method of treating activity-induced muscle damage, a movement disorder, a neuromuscular condition, or a metabolic myopathy, the method comprising administering a compound or salt of any one of Formula (I), (II-A), (IV), or (III) to a subject in need thereof. In some embodiments, the compound or salt of any one of Formula (I), (II-A), (IV), or (III) inhibits skeletal muscle myosin II. In some embodiments, said movement disorder comprises muscle spasticity. In some embodiments, said muscle spasticity may be selected from spasticity associated with multiple sclerosis, Parkinson's disease, Alzheimer's disease, or cerebral palsy, or injury, or a traumatic event such as stroke, traumatic brain injury, spinal cord injury, hypoxia, meningitis, encephalitis, phenylketonuria, or amyotrophic lateral sclerosis.

Methods of administration of a compound or salt of Formula (I), (II-A), (IV), or (III) discussed herein may be used for the treatment of cardiac conditions. In an aspect, the present disclosure provides a method of treating a condition selected from hypertrophic cardiomyopathy (HCM); heart failure with preserved ejection fraction (HFpEF); disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; ischemia; and angina. In some embodiments, said heart failure with preserved ejection fraction (HFpEF) comprises one or more disorders selected from disorders of relaxation and disorders of chamber stiffness (diabetic HFpEF). In some embodiments, said left ventricular (LV) hypertrophy is malignant left ventricular (LV) hypertrophy. In some embodiments, said restrictive cardiomyopathy comprises one or more subgroups selected from inflammatory subgroups, infiltrative subgroups, storage subgroups, idiopathic/inherited subgroups, congenital heart disease subgroups. In some embodiments, said inflammatory subgroups comprise one or more subgroups selected from Loefilers and EMF. In some embodiments, said inflammatory subgroups comprise one or more subgroups selected from amyloid, sarcoid, and XRT. In some embodiments, said storage subgroups comprise one or more subgroups selected from hemochromatosis, Fabry, and glycogen storage disease. In some embodiments, said idiopathic/inherited subgroups comprise one or more subgroups selected from Trop I (beta myosin HC), Trop T (alpha cardiac actin), and desmin related subgroups. In some embodiments, said congenital heart disease subgroups comprise one or more subgroups selected from pressure-overloaded RV, Tetralogy of Fallot, and pulmonic stenosis. In an aspect, the present disclosure provides a method of treating hypertrophic cardiomyopathy or a related condition comprising administering to a subject in need thereof a compound or salt disclosed herein.

In an aspect, the present disclosure provides a method of treating obstructive hypertrophic cardiomyopathy comprising administering to a subject in need thereof a compound or salt disclosed herein. In an aspect, the present disclosure provides a method of treating non-obstructive hypertrophic cardiomyopathy comprising administering to a subject in need thereof a compound or salt of disclosed herein. In an aspect, the present disclosure provides a method of treating heart failure with preserved ejection fraction comprising administering to a subject in need thereof a compound or disclosed herein. In an aspect, the present disclosure provides a method of treating left ventricle stiffness comprising administering to a subject in need thereof a compound or salt disclosed herein.

In an aspect, the present disclosure provides a method of administering to a subject in need thereof a compound or salt disclosed herein. In an aspect, the present disclosure provides a method of treating non-obstructive hypertrophic cardiomyopathy comprising administering to a subject in need thereof a compound or salt of disclosed herein. In an aspect, the present disclosure provides a method of treating heart failure with preserved ejection fraction comprising administering to a subject in need thereof a compound or disclosed herein. In an aspect, the present disclosure provides a method of treating left ventricle stiffness comprising administering to a subject in need thereof a compound or salt disclosed herein.

Skeletal Muscle Myosin

In an aspect, methods of administration of a compound or salt of Formula (I), (II-A), (IV), or (III) discussed herein may be used for the modulation of skeletal muscle myosin. In some embodiments, the modulation of skeletal muscle myosin is inhibition of skeletal muscle myosin. In an aspect, methods of administration of a compound or salt of Formula (I), (II-A), (IV), or (III) discussed herein may be used for the treatment of one or more neuromuscular condition(s) or movement disorder(s) or activity-induced muscle damage or one or more metabolic myopathy (myopathies). In an aspect, the present disclosure provides a method of treating a myopathy of skeletal muscle.

In some embodiments, the present disclosure provides a method of modulating certain aspects of cardiac myopathy (e.g., HR, FS, EDV, IVRT, EF, IVCT, Pre-ejection period, E, A, or e') in a patient who also has one or more condition(s) that include(s) a cardiac myopathy (e.g. BMD, or DMD, or other neuromuscular conditions).

In some embodiments, skeletal muscle is mainly composed of two types of fibers, slow-twitch muscle fiber (e.g. type I) and fast-twitch muscle fiber (e.g. type II). In each muscle, the two types of fibers may be configured in a mosaic-like arrangement, e.g., with differences in fiber type composition in different muscles and at different points in growth and development. Slow-twitch muscle fibers may have excellent aerobic energy production ability. Contraction rate of the slow-twitch muscle fiber may be low. but tolerance to fatigue may be high. Slow-twitch muscle fibers may have a higher concentration of mitochondria and myoglobin than do fast-twitch fibers and may be surrounded by more capillaries than are fast-twitch fibers. Slow-twitch fibers may contract at a slower rate due to lower myosin ATPase activity and produce less power compared to fast-twitch fibers, but they may be able to maintain contractile function over longer-terms, such as in stabilization, postural control, and endurance exercises.

Fast twitch muscle fibers in humans may be further divided into two main fiber types depending on the specific fast skeletal myosin they express (Type IIa, IIx/d). A third type of fast fiber (Type IIb) exists in other mammals but may be rarely identified in human muscle. Fast-twitch muscle fibers may have excellent anaerobic energy production ability and are able to generate high amounts of tension over a short period of time. Typically, fast-twitch muscle fibers may have lower concentrations of mitochondria, myoglobin, and capillaries compared to slow-twitch fibers, and thus can fatigue more quickly. Fast-twitch muscles may produce quicker force required for power and resistance activities.

The proportion of the type I and type II can vary in different individuals. For example, non-athletic individuals can have close to 50% of each muscle fiber types. Power athletes can have a higher ratio of fast-twitch fibers, e.g., 70-75% type II in sprinters. Endurance athletes can have a higher ratio of slow-twitch fibers, e.g., 70-80% in distance runners. The proportion of the type I and type II fibers can also vary depending on the age of an individual. The proportion of type II fibers, especially the type IIx, can decline as an individual ages, resulting in a loss in lean muscle mass. The proportion of type II fibers can also increase with fat mass.

The contractile action of skeletal muscle may lead to muscle damage in subjects with neuromuscular disease, e.g., DMD, and this damage may be more prevalent in fast fibers. It has been observed that acute force drop after lengthening injury may be greater in predominantly fast type II fiber muscles compared to predominantly slow type I fiber muscles in dystrophy mouse models. The degree of acute force drop and histological damage in dystrophy mouse models may be proportional to peak force development during lengthening injury. Excessive contraction-induced injuries, which may precede the inflammation and irreversible fibrosis that may characterize late-stage DMD pathology. Contraction-induced muscle damage in these patients may be reduced by limiting peak force generation in type II fibers and possibly increasing reliance on healthier type I fibers.

When healthy muscle is subjected to excessive, unaccustomed exercise, it develops soreness and sustained reductions in strength and range of motion. Proteins also leak from injured muscle fibers into circulation, including creatine kinase (CK), lactate dehydrogenase and myoglobin. These biomarkers are not unique to either fast or slow fibers and so do not provide detail regarding differences in fiber responses to injury. Troponin I (TNNI) is a component of the troponin complex that controls initiation of contraction of muscle by calcium. It is distinct in that there is a different isoform for each type of striated muscle: TNNI1 in slow skeletal muscle, TNNI2 in fast skeletal muscle and TNNI3 in cardiac muscle. Selective enzyme-linked immunosorbent assays (ELISAs) have been used to demonstrate that TNNI2 but not TNNI1 is elevated in circulation after injurious exercise, even under extreme conditions.

DMD and BMD are caused by an absence (DMD) or truncation (BMD) of the dystrophin protein. Dystrophin provides a structural link between the actin cytoskeleton and the basement membrane through the dystrophin-glycoprotein complex. When dystrophin is absent or truncated, contraction of muscle leads to heightened muscle stress and injury with normal use. While the sensitivity to injury is much higher in DMD muscle than in BMD or healthy muscle, fast fibers still appear to be more susceptible than slow fibers, with young DMD patients exhibiting histological evidence of disruption in fast fibers and early loss of type IIx fibers. These fibers may leak muscle contents, such as troponin, creatine kinase, or myoglobin.

Methods of administration of a compound or salt of Formula (Formula (I), (II-A), (IV), or (III) discussed herein may be used for inhibiting or activating muscle myosin II (e.g., skeletal muscle myosin II). In some embodiments, the compounds and salts thereof may be used to treat activity-induced muscle damage. In some embodiments, the compounds may be used to treat neuromuscular conditions and movement disorders (which may comprise spasticity).

Methods of administration of a compound or salt of Formula (I), (II-A), (IV), or (III) discussed herein may be used for the treatment of activity-induced muscle damage, neuromuscular conditions, movement disorders, or metabolic myopathies. In some embodiments, activity-induced muscle damage, neuromuscular conditions, movement disorders, or metabolic myopathies are treated through administration of a skeletal inhibitor. Examples of neuromuscular conditions include but are not limited to Duchenne muscular dystrophy, Becker muscular dystrophy, myotonic dystrophy 1, myotonic dystrophy 2, facioscapulohumeral muscular dystrophy, oculopharyngeal muscular dystrophy, limb girdle muscular dystrophies, tendinitis and carpal tunnel syndrome. Examples of movement disorders include but are not limited to muscle spasticity disorders, spasticity associated with multiple sclerosis, Parkinson's disease, Alzheimer's disease, or cerebral palsy, or injury or a traumatic event such as stroke, traumatic brain injury, spinal cord injury, hypoxia, meningitis, encephalitis, phenylketonuria, or amyotrophic lateral sclerosis. Also included are other conditions that may respond to the inhibition or activation of skeletal myosin II, skeletal troponin C, skeletal troponin I, skeletal tropomyosin, skeletal troponin T, skeletal regulatory light chains, skeletal myosin binding protein C or skeletal actin. In some embodiments, neuromuscular conditions and movement disorders are selected from muscular dystrophies and myopathies. In some embodiments, muscular dystrophies are diseases that cause progressive weakness and loss of muscle mass where abnormal genes (mutations) interfere with the production of proteins needed to form healthy muscle. In some embodiments, muscular dystrophies are selected from Becker muscular dystrophy (BMD), Congenital muscular dystrophies (CMD), Duchenne muscular dystrophy (DMD), Emery-Dreifuss muscular dystrophy (EDMD), Facioscapulohumeral muscular dystrophy (FSHD), Limb-girdle muscular dystrophies (LGMD), Myotonic dystrophy (DM), and Oculopharyngeal muscular dystrophy (OPMD). In some embodiments, Congenital muscular dystrophies (CMD) is selected from Bethlem CMD, Fukuyama CMD, Muscle-eye-brain diseases (MEBs), Rigid spine syndromes, Ullrich CMD, and Walker-Warburg syndromes (WWS). In some embodiments, myopathies are diseases of muscle that are not caused by nerve disorders. Myopathies may cause the muscles to become weak or shrunken (atrophied). In some embodiments, myopathies are selected from congenital myopathies, distal myopathies, endocrine myopathies, inflammatory myopathies, metabolic myopathies, myofibrillar myopathies (MFM), scapuloperoneal myopathy, and cardiomyopathies. In some embodiments, congenital myopathies are selected from cap myopathies, centronuclear myopathies, congenital myopathies with fiber type disproportion, core myopathies, central core disease, multiminicore myopathies, myosin storage myopathies, myotubular myopathy, and nemaline myopathies. In some embodiments, distal myopathies are selected from, gne myopathy/Nonaka myopathy/hereditary inclusion-body myopathy (HIBM), laing distal myopathy, Markesbery-Griggs late-onset distal myopathy, Miyoshi myopathy, Udd myopathy/tibial muscular dystrophy, VCP myopathy/IBMPFD, vocal cord and pharyngeal distal myopathy, and Welander distal myopathy. In some embodiments, endocrine myopathies are selected from, hyperthyroid myopathy, and hypothyroid myopathy. In some embodiments, inflammatory myopathies are selected from, dermatomyositis, inclusion-body myositis, and polymyositis. In some embodiments, metabolic myopathies are selected from, von Gierke's disease, Anderson disease, Fanconi-Bickel syndrome, aldolase A deficiency, acid maltase deficiency (Pompe disease), carnitine deficiency, carnitine palmitoyltransferase deficiency, debrancher enzyme deficiency (Cori disease, Forbes disease), lactate dehydrogenase deficiency, myoadenylate deaminase deficiency, phosphofructokinase deficiency (Tarui disease), phosphoglycerate kinase deficiency, phosphoglycerate mutase deficiency (Her's disease), and phosphorylase deficiency (e.g. McArdle's disease). In some embodiments, metabolic myopathies are selected from McArdle's disease. In some embodiments, cardiomyopathies are selected from intrinsic cardiomyopathies and extrinsic cardiomyopathies. In some embodiments, intrinsic cardiomyopathies are selected from genetic myopathies and acquired myopathies. In some embodiments, genetic myopathies are selected from Hypertrophic cardiomyopathy, arrhythmogenic right ventricular cardiomyopathy (ARVC), LV non-compaction, ion channelopathies, dilated cardiomyopathy (DCM), and restrictive cardiomyopathy (RCM). In some embodiments, acquired myopathies are selected from stress cardiomyopathy, myocarditis, eosinophilic myocarditis, and ischemic cardiomyopathy. In some embodiments, extrinsic cardiomyopathies are selected from metabolic cardiomyopathies, endomyocardial cardiomyopathies, endocrine cardiomyopathies, and cardiofacial cardiomyopathies. In some embodiments, metabolic cardiomyopathies are selected from Fabry's disease and hemochromatosis. In some embodiments, endomyocardial cardiomyopathies are selected from endomyocardial fibrosis and Hypereosinophilic syndrome. In some embodiments, endocrine cardiomyopathies are selected from diabetes mellitus, hyperthyroidism, and acromegaly. In some embodiments, the Cardiofacial cardiomyopathy is Noonan syndrome.

In some embodiments, the disease (e.g., activity-induced muscle damage, neuromuscular condition, movement disorder, or metabolic myopathy) comprises muscle wasting. In some embodiments, the muscle wasting comprises Cachexia. In some embodiments, the Cachexia is associated with one or more cancer(s). In some embodiments, the one or more cancer(s) is selected from renal cell carcinoma. In some embodiments, the muscle wasting arises from inactivity. In some embodiments, the muscle wasting comprises acute quadriplegic myopathy. In some embodiments, the muscle wasting arises from a reaction against anesthetics. In some embodiments, the muscle wasting comprises rhabdomyolysis. In some embodiments, the muscle wasting comprises Compartment syndrome. In some embodiments, the disease comprises muscle pain. In some embodiments, the disease comprises back pain. In some embodiments, the disease comprises lower-back pain. In some embodiments, the disease comprises chronic back pain. In some embodiments, the disease comprises insomnia. In some embodiments, the disease is insomnia. In some embodiments, the compound or salt is administered in a low dose. In some embodiments, the disease is insomnia, and the compound or salt is administered in a low dose. In some embodiments, the subject in need thereof experiences enhanced strength and enhanced fatiguability. In some embodiments, the subject in need thereof does not experience muscle leakiness.

In some embodiments, the present disclosure provides methods of treating a cardiomyopathy in a patient with a neuromuscular condition (e.g., Duchenne Muscular Dystrophy, Becker Muscular Dystrophy, Limb-Girdle Muscular Dystrophy, e.g., susceptible LGMD), the methods comprising administering a compound or salt of the present disclosure.

In an aspect, methods of administration of a compound or salt of Formula (I), (II-A), (IV), or (III) discussed herein may be used for the modulation of skeletal muscle myosin. In some embodiments, the modulation of skeletal muscle myosin is activation of skeletal muscle myosin. In some embodiments, the compound or salt of the present disclosure (e.g., compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof) is an activator of myosin ATP-ase. Methods of administration of a compound or salt of Formula (I), (II-A), (IV), or (III) discussed herein may be used for the treatment of metabolic diseases and disorders. Examples of metabolic diseases and disorders include but are not limited to: obesity, morbid obesity, super morbid obesity, pre-diabetes, diabetes, (e.g., type 1 diabetes, type 2 diabetes), or metabolic syndrome (e.g., comprising one or more of the following: high blood pressure, high blood sugar, too much body fat around the waist, or irregular cholesterol levels). In some embodiments, the subject's blood pressure exceeds about 130/85 mmHg. In some embodiments, the subject's fasting blood sugar levels exceeds about 100 mg/dL. In some embodiments, the subject's triglyceride levels exceeds about 150 mg/dL. In some embodiments, the subject's HDL cholesterol levels is lower than about 50 mg/dL for men or about 40 mg/dL for women. In some embodiments, the subject's waist circumference exceeds about 40 in for men or 35 inches for women.

In an aspect, the present disclosure provides a method of treating a metabolic condition or a related condition, in a subject in need thereof, the method comprising administering a compound or salt of the present disclosure (e.g., a compound or salt of Formula (I), (II-A), (IV), or (III)), e.g., compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof). In an aspect, the present disclosure provides a method of treating obesity or a related condition, in a subject in need thereof, the method comprising administering a compound or salt of the present disclosure. In some embodiments, the method comprises administering compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof. In some embodiments, compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof is an activator of myosin (e.g., skeletal myosin, ventricular myosin, or atrial myosin). In some embodiments, compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof is an activator of skeletal myosin.

In some embodiments, the present disclosure provides a method of inducing fast fiber ATPase activation in a patient in need thereof.

In an aspect, the present disclosure provides a method of inducing weight loss, in a subject in need thereof, the method comprising administering a compound or salt of the present disclosure (e.g., a compound or salt of Formula (I), (II-A), (IV), or (III)). In some embodiments, the method comprises administering compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof. In some embodiments, the present disclosure provides a method of inducing weight loss without necessarily increasing muscle mass by increasing basal metabolic rate, the method comprising administering a compound or salt of the present disclosure. Alternatively, in some embodiments, muscle mass is increased. In some embodiments, the present disclosure provides a method of inducing weight loss without necessarily increasing muscle mass by increasing basal metabolic rate, the method comprising administering a compound or salt of the present disclosure. In some embodiments, the present disclosure provides a method of preventing muscle loss in the background of one or more other weight loss strategie(s) (e.g., diet, exercise, or incretin therapeutics). In some embodiments, the method comprises administering compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof. In some embodiments, the compound of the present disclosure activates skeletal muscle myosin. In some embodiments, compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof activates skeletal muscle myosin. In some embodiments, the compound of the present disclosure has a Rabbit Psoas Y125 value (e.g., a value corresponding to 125% activity relative to activity in the absence of exogenous compound) in Table 5, Table 6, or Table 7. In some embodiments, the compound of the present disclosure does not have Rabbit Psoas Y75 value in Table 5, Table 6, or Table 7 (e.g., because it does not inhibit skeletal muscle myosin). In some embodiments, the activation of skeletal muscle myosin increases baseline metabolic rate. In some embodiments, the activation of skeletal muscle myosin increases daily ATP consumption. In some embodiments, the activation of skeletal muscle myosin increases daily ATP consumption without necessarily increasing muscle mass. In some embodiments, the activation of skeletal muscle myosin increases daily ATP consumption, without necessarily increasing muscle mass, and decreases body fat. In some embodiments, the method comprises administering a compound or salt that is an activator of skeletal muscle myosin. In some embodiments, the method comprises administering a compound or salt that has a Rabbit Psoas Y125 value in Table 5, Table 6, or Table 7. In some embodiments, the method comprises administering a compound or salt that does not have a Rabbit Psoas Y75 value in Table 5, Table 6, or Table 7.

In some embodiments, the subject in need thereof is overweight, obese, morbidly obese, or super morbidly obese. In some embodiments, the subject in need thereof exhibits Class I, Class II, or Class III obesity. In some embodiments, obesity of the subject is linked to genetic factors.

In some embodiments, administering a compound or salt of the present disclosure does not change muscle mass. In some embodiments, administering a compound or salt of the present disclosure increases resting fast muscle ATP turnover without changes in baseline tension. In some embodiments, administering a compound or salt of the present disclosure prevents muscle loss that occurs with obesity treatments (e.g., diet, exercise, SGLT2/GLP1/bariatric surgery, other surgeries)

In some embodiments, increases to baseline energy consumption in skeletal muscle leads to weight loss in a patient in need there of. In some embodiments, increases to baseline energy consumption in skeletal muscle leads leads to positive health impacts other than weight loss (e.g., in addition to weight loss), such as, for example, glycemic control (e.g., in T2D) or aliviation of another condition. In some embodiments, the subject exhibits one or more condition(s) (or exhibits elevated risk of the one or more condition(s)), and administration of a compound or salt of the present disclosure alleviates or treats one or more of condition(s) (or alleviates risk of the one or more condition(s)), selected from: cardiovascular disease, pre-diabetes, diabetes (e.g., type 2 diabetes, type 1 diabetes), osteoarthritis, polycystic ovary syndrome, infertility, sleep apnea (e.g., obstructive sleep apnoea), breathing problems, asthma, a substance abuse disorder (e.g., alcoholism or addiction), peripheral vascular disease, venous thromboembolism, fatty liver (e.g., Nonalcoholic steatohepatitis (NASH), or nonalcoholic fatty liver disease (NAFLD)), high blood pressure, high LDL cholesterol, low HDL cholesterol, high levels of triglycerides, coronary heart disease, gallbladder disease, cancer, mental illness (e.g., depression, anxiety), addiction (e.g., alcoholism), chronic pain, long COVID, difficulty with physical functioning, stroke, and paralysis (e.g., full or partial paralysis). In some embodiments, the subject has experienced weight gain as a result of treatment for one or more diseases (e.g., through administration of certain psychiatric medications).

In some embodiments, the subject in need thereof has a BMI of at least about 15 kg/$m^2$, at least about 16 kg/$m^2$, at least about 17 kg/$m^2$, at least about 18 kg/$m^2$, at least about 19 kg/$m^2$, at least about 20 kg/$m^2$, at least about 21 kg/$m^2$, at least about 22 kg/$m^2$, at least about 23 kg/$m^2$, at least about 24 kg/$m^2$, at least about 25 kg/$m^2$, at least about 26 kg/$m^2$, at least about 27 kg/$m^2$, at least about 28 kg/$m^2$, at least about 29 kg/$m^2$, at least about 30 kg/$m^2$, at least about 31 kg/$m^2$, at least about 32 kg/$m^2$, at least about 33 kg/$m^2$, at least about 34 kg/$m^2$, at least about 35 kg/$m^2$, at least about 36 kg/$m^2$, at least about 37 kg/$m^2$, at least about 38 kg/$m^2$, at least about 39 kg/$m^2$, at least about 40 kg/$m^2$, at least about 41 kg/$m^2$, at least about 42 kg/$m^2$, at least about 43 kg/$m^2$, at least about 44 kg/$m^2$, at least about 45 kg/$m^2$, at least about 46 kg/$m^2$, at least about 47 kg/$m^2$, at least about 48 kg/$m^2$, at least about 49 kg/$m^2$, at least about 50 kg/$m^2$, at least about 51 kg/$m^2$, at least about 52 kg/$m^2$, at least about 53 kg/$m^2$, at least about 54 kg/$m^2$, at least about 55 kg/$m^2$, at least about 56 kg/$m^2$, at least about 57 kg/$m^2$, at least about 58 kg/$m^2$, at least about 59 kg/$m^2$, at least about 60 kg/$m^2$, at least about 65 kg/$m^2$, at least about 70 kg/$m^2$, at least about 75 kg/$m^2$, at least about 80 kg/$m^2$, or more. Alternatively, or in addition, in some embodiments, the subject has a BMI of at most about 15, at most about 16, at most about 17, at most about 18, at most about 19, at most about 20, at most about 21, at most about 22, at most about 23, at most about 24, at most about 25, at most about 26, at most about 27, at most about 28, at most about 29, at most about 30, at most about 31, at most about 32, at most about 33, at most about 34, at most about 35, at most about 36, at most about 37, at most about 38, at most about 39, at most about 40, at most about 41, at most about 42, at most about 43, at most about 44, at most about 45, at most about 46, at most about 47, at most about 48, at most about 49, at most about 50, at most about 51, at most about 52, at most about 53, at most about 54, at most about 55, at most about 56, at most about 57, at most about 58, at most about 59, at most about 60, at most about 65, at most about 70, at most about 75, at most about 80, or less. In some embodiments, the subject has a BMI of about 24 to about 55. In some embodiments, the subject has a BMI of at least about 24. In some embodiments, the subject has a BMI of at most about 55. In some embodiments, the subject has a BMI of about 24 to about 26, about 24 to about 28, about 24 to about 30, about 24 to about 32, about 24 to about 34, about 24 to about 36, about 24 to about 38, about 24 to about 40, about 24 to about 45, about 24 to about 50, about 24 to about 55, about 26 to about 28, about 26 to about 30, about 26 to about 32, about 26 to about 34, about 26 to about 36, about 26 to about 38, about 26 to about 40, about 26 to about 45, about 26 to about 50, about 26 to about 55, about 28 to about 30, about 28 to about 32, about 28 to about 34, about 28 to about 36, about 28 to about 38, about 28 to about 40, about 28 to about 45, about 28 to about 50, about 28 to about 55, about 30 to about 32, about 30 to about 34, about 30 to about 36, about 30 to about 38, about 30 to about 40, about 30 to about 45, about 30 to about 50, about 30 to about 55, about 32 to about 34, about 32 to about 36, about 32 to about 38, about 32 to about 40, about 32 to about 45, about 32 to about 50, about 32 to about 55, about 34 to about 36, about 34 to about 38, about 34 to about 40, about 34 to about 45, about 34 to about 50, about 34 to about 55, about 36 to about 38, about 36 to about 40, about 36 to about 45, about 36 to about 50, about 36 to about 55, about 38 to about 40, about 38 to about 45, about 38 to about 50, about 38 to about 55, about 40 to about 45, about 40 to about 50, about 40 to about 55, about 45 to about 50, about 45 to about 55, or about 50 to about 55. In some embodiments, the subject has a BMI of about 24, about 26, about 28, about 30, about 32, about 34, about 36, about 38, about 40, about 45, about 50, or about 55, wherein the units are kg/$m^2$. In some embodiments, the subject in need thereof has a BMI of about 18.5-24.9 kg/$m^2$.

In some embodiments, the subject in need thereof has a body fat percentage of at least about 10%, at least about 15%, at least about 20%, at least about 21%, at least about 22%, at least about 23%, at least about 24%, at least about 25%, at least about 26%, at least about 27%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, or more. Alternatively, or in addition, in some embodiments, the subject has a body fat percentage of at most about 10%, at most about 15%, at most about 20%, at most about 21%, at most about 22%, at most about 23%, at most about 24%, at most about 25%, at most about 26%, at most about 27%, at most about 29%, at most about 30%, at most about 31%, at most about 32%, at most about 33%, at most about 34%, at most about 35%, at most about 36%, at most about 37%, at most about 38%, at most about 39%, at most about 40%, at most about 41%, at most about 42%, at most about 43%, at most about 44%, at most about 45%, at most about 46%, at most about 47%, at most about 48%, at most about 49%, at most about 50%, at most about 51%, at most about 52%, at most about 53%, at most about 54%, at most about 55%, at most about 56%, at most about 57%, at most about 58%, at most about 59%, at most about 60%, at most about 61%, at most about 62%, at most about 63%, at most about 64%, at most about 65%, at most about 66%, at most about 67%, at most about 68%, at most about 69%, at most about 70%, at most about 71%, at most about 72%, at most about 73%, at most about 74%, at most about 75%, or less. In some embodiments, the subject has a body fat percentage of about 15% to about 70%. In some embodiments, the subject has a body fat percentage of at least about 15%. In some embodiments, the subject has a body fat percentage of at most about 70%. In some embodiments, the subject has a body fat percentage of about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 30% to about 35%, about 30% to about 40%, about 30% to about 45%, about 30% to about 50%, about 30% to about 55%, about 30% to about 60%, about 30% to about 65%, about 30% to about 70%, about 35% to about 40%, about 35% to about 45%, about 35% to about 50%, about 35% to about 55%, about 35% to about 60%, about 35% to about 65%, about 35% to about 70%, about 40% to about 45%, about 40% to about 50%, about 40% to about 55%, about 40% to about 60%, about 40% to about 65%, about 40% to about 70%, about 45% to about 50%, about 45% to about 55%, about 45% to about 60%, about 45% to about 65%, about 45% to about 70%, about 50% to about 55%, about 50% to about 60%, about 50% to about 65%, about 50% to about 70%, about 55% to about 60%, about 55% to about 65%, about 55% to about 70%, about 60% to about 65%, about 60% to about 70%, or about 65% to about 70%. In some embodiments, the subject has a body fat percentage of about 15%, about 20%, about 25%, about 30%, about 35%, about 40%, about 45%, about 50%, about 55%, about 60%, about 65%, or about 70%.

In some embodiments, compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof is an activator of skeletal myosin.

In some embodiments, compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof modulates skeletal myosin RLC. In some embodiments, the modulation of RLC is allosteric.

Myosin hydrolyses ATP to drive conformational change and cyclic binding to muscle actin which regulates force of contraction. In resting (relaxed) muscle, myosin also exists in at least two additional energy states. These include a low energy state (super-relaxed or SRX) and a high energy state (disordered-relaxed or DRX). Both resting states of myosin are not engaged with actin but consume different levels of ATP. Research suggests that DRX myosin consumes approximately 5-10 times more ATP than SRX myosin.

Basal metabolic rate and skeletal muscle health can be benefited by either increasing muscle metabolic rate (e.g., increasing basal energy consumption in skeletal muscle by altering calcium or myosin ATPase) or increasing muscle turnover (e.g., increasing protein synthesis and/or degradation) by administering a compound or salt of the present disclosure. Such benefits can include an increase in protein synthesis and a decrease in fat.

In some embodiments, administering a compound or salt of the present disclosure increases basal energy states. In some embodiments, administering a compound or salt of the present disclosure modulates the population of skeletal myosin in the SRX, DRX, and actin-bound states. In some embodiments, administering a compound or salt of the present disclosure modulates the rate of ATP conversion to ADP of skeletal myosin in the SRX, DRX, and actin-bound states. In some embodiments, transition of myosin from SRX to DRX states does not change baseline tension but increases ATP consumption.

In some embodiments, compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof modulator of skeletal myosin. In some embodiments, compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof is an activator of skeletal myosin (e.g., skeletal myosin ATP-ase). In some embodiments, compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof is an inhibitor of skeletal myosin. In some embodiments, compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof is a modulator of skeletal myosin RLC. In some embodiments, compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof is an activator of skeletal myosin RLC. In some embodiments, compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof is an inhibitor of skeletal myosin RLC. In some embodiments, the modulation of RLC is allosteric.

In some embodiments, administering a compound or salt of the present disclosure modulates the population of skeletal myosin in the SRX and DRX states, thereby increasing ATP consumption without changing baseline tension. In some embodiments, administering a compound or salt of the present disclosure increases the population of muscle myosin (e.g., skeletal muscle myosin, e.g., fast muscle myosin) in the DRX state and decreases the population in the SRX state. In some embodiments, administering a compound or salt of the present disclosure increases the population of muscle myosin (e.g., skeletal muscle myosin, e.g., fast muscle myosin) in the DRX state by at least about 1%, at least about 2%, at least about 3%, at least about 5%, at least about 10%, at least about 12.5%, at least about 15%, at least about 17.5%, at least about 20%, at least about 25%, at least about 27.5%, at least about 30%, at least about 35%, at least about 40%, at least about 50%, or more. Alternatively, or in addition, in some embodiments, administering a compound or salt of the present disclosure decreases the population of muscle myosin (e.g., skeletal muscle myosin, e.g., fast muscle myosin) in the DRX state by at most about 1%, at most about 2%, at most about 3%, at most about 5%, at most about 10%, at most about 12.5%, at most about 15%, at most about 17.5%, at most about 20%, at most about 25%, at most about 27.5%, at most about 30%, at most about 35%, at most about 40%, at most about 50%, or less. In some embodiments, administering a compound or salt of the present disclosure increases the population of muscle myosin (e.g., skeletal muscle myosin, e.g., fast muscle myosin) in the DRX state (e.g., from the population in the SRX state) by about 1% to about 50%. In some embodiments, administering a compound or salt of the present disclosure increases the population of muscle myosin (e.g., skeletal muscle myosin, e.g., fast muscle myosin) in the DRX state (e.g., from the population in the SRX state) by at least about 1%. In some embodiments, administering a compound or salt of the present disclosure increases the population of muscle myosin (e.g., skeletal muscle myosin, e.g., fast muscle myosin) in the DRX state (e.g., from the population in the SRX state) by at most about 50%. In some embodiments, administering a compound or salt of the present disclosure increases the population of muscle myosin (e.g., skeletal muscle myosin, e.g., fast muscle myosin) in the DRX state (e.g., from the population in the SRX state) by about 1% to about 3%, about 1% to about 5%, about 1% to about 7.5%, about 1% to about 10%, about 1% to about 15%, about 1% to about 20%, about 1% to about 25%, about 1% to about 30%, about 1% to about 35%, about 1% to about 40%, about 1% to about 50%, about 3% to about 5%, about 3% to about 7.5%, about 3% to about 10%, about 3% to about 15%, about 3% to about 20%, about 3% to about 25%, about 3% to about 30%, about 3% to about 35%, about 3% to about 40%, about 3% to about 50%, about 5% to about 7.5%, about 5% to about 10%, about 5% to about 15%, about 5% to about 20%, about 5% to about 25%, about 5% to about 30%, about 5% to about 35%, about 5% to about 40%, about 5% to about 50%, about 7.5% to about 10%, about 7.5% to about 15%, about 7.5% to about 20%, about 7.5% to about 25%, about 7.5% to about 30%, about 7.5% to about 35%, about 7.5% to about 40%, about 7.5% to about 50%, about 10% to about 15%, about 10% to about 20%, about 10% to about 25%, about 10% to about 30%, about 10% to about 35%, about 10% to about 40%, about 10% to about 50%, about 15% to about 20%, about 15% to about 25%, about 15% to about 30%, about 15% to about 35%, about 15% to about 40%, about 15% to about 50%, about 20% to about 25%, about 20% to about 30%, about 20% to about 35%, about 20% to about 40%, about 20% to about 50%, about 25% to about 30%, about 25% to about 35%, about 25% to about 40%, about 25% to about 50%, about 30% to about 35%, about 30% to about 40%, about 30% to about 50%, about 35% to about 40%, about 35% to about 50%, or about 40% to about 50%. In some embodiments, administering a compound or salt of the present disclosure increases the population of muscle myosin (e.g., skeletal muscle myosin, e.g., fast muscle myosin) in the DRX state (e.g., from the population in the SRX state) by about 1%, about 3%, about 5%, about 7.5%, about 10%, about 15%, about 20%, about 25%, about 30%, about 35%, about 40%, or about 50%.

In some embodiments, increasing the population of muscle myosin (e.g., skeletal muscle myosin, e.g., fast muscle myosin) from an SRX to a DRX state would increase resting energy consumption (REC) (e.g., in some embodiments, increasing DRX by 30% would increase REC by approx. 154 kCal/day, e.g., assuming approximately 50% of total muscle can be fast skeletal fibers, 40% of muscle weight can be myosin, 1 ATP can bind to 1 myosin head, and that the ATPase activity of DRX myosin can be 0.03 ATP/sec, 7.3 kcal·mol-1 ATP consumed, and e.g., in some embodiments this would translate to 7.3 kg fat mass, wherein, e.g., 1 kg fat may equal 7700 kcal).

In some embodiments, administering a compound or salt of the present disclosure change(s) the rate of myosin (e.g., skeletal myosin) entering the DRX state, e.g., from the SRX state.

In some embodiments, phosphorylation of myosin RLC can increase with preconditioning contractions in both fast and slow fibers. In some embodiments, RLC phosphorylation can increase the population of myosin in the DRX state, e.g., disrupting the SRX helical organization. In some embodiments, such disrupting may only occur in fast fibers. In some embodiments, temperature regulation may be independent of phosphorylation, and, e.g., may inhibit phosphorylation effects on twitch potentiation of fast muscle in mammals and humans.

In some embodiments, administering a compound or salt of the present disclosure (e.g., compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof) increases contraction-induced stress (e.g., in normal skeletal muscle, e.g., muscle in a patient that does not have a neuromuscular condition, or e.g., in a patient that does not have a muscular dystrophy). In some embodiments, the contraction induced stress comprises membrane stress. In some embodiments, the contraction induced stress leads to skeletal muscle adaptation (e.g., similar to a response to exercise training). In some embodiments, membrane stress activates stem cells. In some embodiments, stress (e.g., contraction induced, membrane) leads to protein synthesis or degradation or controlled muscle injury. In some embodiments, contraction stress causes increases in muscle injury biomarkers (e.g., creatine kinase, e.g., fsTnl, myoglobin, or ssTNL). In some embodiments, contraction induced stress leads to higher baseline VO2max.

In some embodiments, MLCK phosphorylates RLC to transiently increase the proportion of DRX heads, e.g., with genetic variation in MLCK-coding genes possibly altering efficiency of phosphorylation.

In some embodiments, a compound or salt of the present disclosure is a selective (or partially selective) myosin activator. In some embodiments, a compound or salt of the present disclosure activates myosin ATPase in both native muscle and purified motor-domain preparations. In some embodiments, a compound or salt of the present disclosure increases calcium sensitivity and maximal force output, e.g., in isolated single permeabilized fast skeletal muscle fibers, e.g., from rabbit muscle (e.g., rabbit psoas). In some embodiments, administering a compound or salt of the present disclosure increases the fraction of the myosin filament in a DRX state in single fibers from rabbit skeletal muscle. In some embodiments, administering a compound or salt of the present disclosure increases the ATPase rate of all myosin in the DRX, SRX, or actin bound state (e.g., by at least about 1%, at least about 10%, at least about 20%, at least about 50%, at least about 75%, at least about 100%, at least about 150%, or more, or, alternatively or in addition, by at most about 1%, at most about 10%, at most about 20%, at most about 50%, at most about 75%, at most about 100%, at most about 150%, or less). In some embodiments, administering a compound or salt of the present disclosure increases submaximal force with enhanced injury force drop, e.g., relative to a control molecule. In some embodiments, administering a compound or salt of the present disclosure accelerates force drop in muscles undergoing eccentric exercise (e.g., in healthy mouse muscle with changing maximal force development), e.g., relative to a control molecule. In some embodiments, eccentric (e.g., lengthening) contractions stress healthy muscle. In some embodiments, the stress leads to accentuated force drop compared to fixed-length contractions (e.g., isometric).

In some embodiments, a compound or salt of the present disclosure is an activator that is skeletal selective and/or is a non-myosin activator. In some embodiments, administering a compound or salt of the present disclosure increases calcium sensitivity. In some embodiments, administering a compound or salt of the present disclosure increases the rate of force development. In some embodiments, administering a compound or salt of the present disclosure decreases relaxation velocity.

In some embodiments, administering a compound or salt of the present disclosure increases both the extent (e.g., the fraction) and the rate of DRX myosin (e.g., in APT/sec). In some embodiments, administering a compound or salt of the present disclosure increases the fraction of the myosin filament in a DRX state in single fibers, e.g., from rabbit skeletal muscle. In some embodiments, administering a compound or salt of the present disclosure increases the ATPase rate of all myosin in the DRX state. In some embodiments, administering a compound or salt of the present disclosure mildly sensitizes force without injury enhancement (e.g., in EDL muscle ex vivo). In some embodiments, the compound or salt increases force at low frequencies, e.g., in an ex vivo assay, (e.g., by at least about 1%, at least about 5%, at least about 10%, at least about 25%, at least about 30%, at least about 50% or more). In some embodiments, the compound or salt increases relaxation time. In some embodiments, the compound or salt of the present disclosure increases 02 consumption. In some embodiments, the compound or salt of the present disclosure increases respiratory rate, body temperature, or activity. In some embodiments, the compound or salt of the present disclosure does not one or more of: change respiratory rate, body temperature, and activity.

In some embodiments, the compound or salt of the present disclosure increases insulin resistance, insulin sensitivity, glucose uptake (e.g., from circulation), oxidation potential, or a combination thereof.

In some embodiments, a patient is administered a compound or salt of the present disclosure in combination with a GLP-1 agonist, and the patient exhibits diminished skeletal muscle loss relative to a patient to whom a compound or salt of the present disclosure was not administered.

In some embodiments, skeletal muscle has two major fiber types (e.g., Type 1—slow, Type IIa—fast fatigue-resistance, type II x/d—fast fatigable). In some embodiments, type 1 fibers are injury resistant, and exhibit high oxidative capacity and high turnover. In some embodiments, type II fibers are injury susceptible, and exhibit low oxidative capacity and low turnover. In some embodiments, slow fibers have high protein overlap with cardiac muscle. In some embodiments, obesity drives fast fibers and shifts energy consumption. In some embodiments, as body fat percentage decreases, the percentage of type 1 fibers increase. In some embodiments, the compound or salt of the present disclosure targets slow fibers. In some embodiments, slow fibers are more present in obese patients than in healthy patients.

Methods of administration of a compound or salt of Formula (I), (II-A), (IV), or (III) discussed herein may be used for the treatment of obesity, sarcopenia, wasting syndrome, frailty, cachexia, muscle spasm, post-surgical and post-traumatic muscle weakness, neuromuscular disease, and other indications in a mammal.

In some embodiments, "obesity" means having a body mass index (BMI) greater than or equal to 30 $kg/m^2$.

In some embodiments, BMI refers to weight (kg) divided by height ($m^2$).

In some embodiments, the term "obesity" may encompasse hyperplastic obesity, (e.g., an increase in the number of fat cells relative to a non-obese person). In some embodiments, the term "obesity" encompasses hypertrophic obesity (e.g., an increase in the size of the fat cells relative to a non-obese person).

In some embodiments, "overweight" may be defined as having a BMI from 25 to 30 $kg/m^2$. In some embodiments, severe (e.g., morbid) obesity is defined as a BMI greater than or equal to 40 $kg/m^2$.

In some embodiments, "sarcopenia" may mean a loss of skeletal muscle mass, quality, and strength. Sarcopenia may attributed to ageing or HIV infection or other causes. Sarcopenia may lead to frailty, for example, in the elderly.

In some embodiments, "wasting syndrome" may mean a condition characterized by involuntary weight loss and may be associated with chronic fever and diarrhea. In some embodiments, patients with wasting syndrome lose 10% of baseline body weight within one month.

In some embodiments, abnormal contraction of skeletal muscle may be a pathogenetic cause of several disorders, including obesity, sarcopenia, wasting syndrome, frailty, cachexia, muscle spasm, post-surgical and post-traumatic muscle weakness, and neuromuscular disease, which pose serious health problems as adult diseases. In some embodiments, the contraction and relaxation of skeletal muscle are mainly controlled by increases and decreases of intracellular calcium. In some embodiments, intracellular calcium may bind with calmodulin, e.g., to activate myosin light chain phosphorylation enzyme. In some embodiments, the activation of myosin light chain phosphorylation enzyme results in phosphorylation of the myosin light chain. In some embodiments, the phosphorylation of myosin light chain causes contraction of skeletal muscles.

In some embodiments, a compound or salt of the present disclosure modulates (e.g., reduces or increases) intracellular calcium. In some embodiments, a compound or salt of the present disclosure distends blood vessels. In some embodiments, when a compound or salt of the present disclosure decreases intracellular calcium, then blood vessels are distended.

Alternatively, or in addition, in some embodiments, skeletal muscle contraction is independent of intracellular calcium level. In some embodiments, pharmaceutical agents which only reduce intracellular calcium may be insufficient to treat diseases caused by abnormal skeletal muscle contraction.

In some embodiments, disclosed herein are methods to treat cardiac disease by the administration of a compound or salt of Formula (I), (II-A), (IV), or (III). In some embodiments, disclosed herein is a method of treating cardiac disease in an individual in need thereof, the method comprising administering a therapeutically effective amount of a compound of Formula (III):

Formula (III)

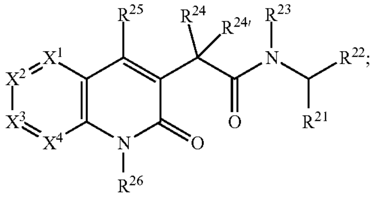

or a salt thereof, wherein:

$X^1$, $X^2$, $X^3$, and $X^4$ are independently selected from C(R) and N wherein no more than two of $X^1$, $X^2$, $X^3$, and $X^4$ are N;

each R is independently selected from:

hydrogen, halogen, —$NO_2$, —CN, —$N_3$, —$OR^{28}$, —$SR^{28}$, —$N(R^{28})_2$, —$C(O)R^{28}$, —$C(O)N(R^{28})_2$, —$N(R^{28})C(O)R^{28}$, —$N(R^{28})C(O)N(R^{28})_2$, —$OC(O)N(R^{28})_2$, —$N(R^{28})C(O)OR^{28}$, —$C(O)OR^{28}$, —$OC(O)R^{28}$, —$S(O)R^{28}$, and —$S(O)_2R^{28}$;

$C_{1-6}$ alkyl, $C_{2-6}$ alkenyl, and $C_{2-6}$ alkynyl, each of which is optionally substituted with one or more substituents independently selected from halogen, —$OR^{28}$, —$SR^{28}$, —$N(R^{28})_2$, —$C(O)R^{28}$, —$C(O)N(R^{28})_2$, —$N(R^{28})C(O)R^{28}$, —$C(O)OR^{28}$, —$OC(O)R^{28}$, —$N(R^{28})C(O)N(R^{28})_2$, —$OC(O)N(R^{28})_2$, —$N(R^{28})C(O)OR^{28}$, —$S(O)R^{28}$, —$S(O)_2R^{28}$, —$NO_2$, ═O, ═S, ═$N(R^{28})$, —CN, $C_{3-10}$ carbocycle and 3- to 10-membered heterocycle, wherein the $C_{3-10}$ carbocycle and 3- to 10-membered heterocycle are each optionally substituted with one or more $R^{27}$; and $C_{3-10}$ carbocycle and 3- to 10-membered heterocycle, each of which is optionally substituted with one or more substituents independently selected from halogen, —$OR^{28}$, —$SR^{28}$, —$N(R^{28})_2$, —$C(O)R^{28}$, —$C(O)N(R^{28})_2$, —$N(R^{28})C(O)R^{28}$. —$N(R^{28})C(O)N(R^{28})_2$, —$OC(O)N(R^{28})_2$, —$N(R^{28})C(O)OR^{28}$, —$C(O)OR^{28}$, —$OC(O)R^{28}$, —$S(O)R^{28}$, —$S(O)_2R^{28}$, —$NO_2$, ═O—, ═S, ═$N(R^{28})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27}$;

$R^{21}$ is selected from:

hydrogen, $C_{1-6}$ alkyl, $C_{2-6}$ alkenyl, and $C_{2-6}$ alkynyl, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$C(O)OR^{28a}$, —$OC(O)R^{28a}$, —$N(R^{28a})C(O)N(R^{28a})_2$, —$OC(O)N(R^{28a})_2$, —$N(R^{28a})C(O)OR^{28a}$, —$S(O)R^{28a}$, —$S(O)_2R^{28a}$, —$NO_2$, ═O, ═S, ═$N(R^{28a})$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{27a}$; and $C_{3-10}$ carbocycle, and 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27a}$;

$R^{22}$ is selected from:

hydrogen, $C_{1-6}$ alkyl, $C_{2-6}$ alkenyl, and $C_{2-6}$ alkynyl, each of which is optionally substituted with one or more substituents independently selected from halogen, —$OR^{28b}$, —$SR^{28b}$, —$N(R^{28b})_2$, —$C(O)R^{28b}$, —$C(O)N(R^{28b})_2$, —$N(R^{28b})C(O)R^{28b}$, —$C(O)OR^{28b}$, —$OC(O)R^{28b}$, —$N(R^{28b})C(O)N(R^{28b})_2$, —$OC(O)N(R^{28b})_2$, —$N(R^{28b})C(O)OR^{28b}$, —$S(O)R^{28b}$, —$S(O)_2R^{28b}$, —$NO_2$, ═O, ═S, ═$N(R^{28b})$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{27b}$; and $C_{3-10}$ carbocycle, and 3- to 10-membered heterocycle, each of which is optionally substituted with one or more substituents independently selected from halogen, —$OR^{28b}$, —$SR^{28b}$, —$N(R^{28b})_2$, —$C(O)R^{28b}$, —$C(O)N(R^{28b})_2$, —$N(R^{28b})C(O)R^{28b}$, —$N(R^{28b})C(O)N(R^{28b})_2$, —$OC(O)N(R^{28b})_2$, —$N(R^{28b})C(O)OR^{28b}$, —$C(O)OR^{28b}$, —$OC(O)R^{28b}$, —$S(O)R^{28b}$, —$S(O)_2R^{28b}$, —$NO_2$, ═O—, ═S, ═$N(R^{28b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27b}$; or $R^{21}$ together with $R^{22}$ form a $C_{3-10}$ carbocycle, or 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27b}$;

$R^{23}$ is selected from:

hydrogen, halogen, —$OR^{28c}$, —$SR^{28c}$, —$N(R^{28c})_2$, —$NO_2$, and —CN; and $C_{1-6}$ alkyl optionally substituted with one or more one or more $R^{27c}$; or $R^{21}$ together with $R^{23}$ form a 3- to 10-membered heterocycle, which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27c}$ $R^{22}$ together with $R^{23}$ form a $C_{3-10}$ carbocycle, or 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$ alkyl, $C_{2-6}$ alkenyl, and $C_{2-6}$alkynyl, wherein $C_{1-6}$ alkyl, $C_{2-6}$ alkenyl, and $C_{2-6}$ alkynyl are each optionally substituted with one or more $R^{27e}$;

or $R^{21}$, $R^{22}$ and $R^{23}$ together form a bicyclic heterocycle which is optionally substituted with one or more substituents independently selected from halogen, —$OR^{28a}$, $SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{27c}$;

$R^{24}$ is independently selected from:

hydrogen, halogen, —$OR^{28d}$, —$SR^{28d}$, —$N(R^{28d})_2$, —$NO_2$, and —CN; and $C_{1-6}$ alkyl optionally substituted with one or more substituents independently selected from halogen, —$OR^{28d}$, —$SR^{28d}$, —$N(R^{28d})_2$, —$NO_2$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{27d}$;

$R^{24'}$ is independently selected from:

hydrogen, halogen, —$OR^{28d}$, —$SR^{28d}$, —$N(R^{28d})_2$, —$NO_2$, and —CN; and $C_{1-6}$ alkyl optionally substituted with one or more substituents independently selected from halogen, —$OR^{28d}$, —$SR^{28d}$, —$N(R^{28d})_2$, —$NO_2$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{27d}$;

$R^{25}$ is selected from:

hydrogen, halogen, —$OR^{28e}$, —$SR^{28e}$, —$N(R^{28e})_2$, —$NO_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more $R^{27e}$; or $R^{24}$ together with $R^{25}$ form a 3- to 10-membered heterocycle, wherein the 3- to 10-membered heterocycle is optionally substituted with one or more $R^{27e}$;

$R^{26}$ is selected from:

hydrogen, halogen, —$OR^{28f}$, —$SR^{28f}$, —$N(R^{28f})_2$, —$NO_2$, and —CN; and $C_{1-6}$ alkyl optionally substituted with one or more $R^{27f}$;

each $R^{27}$ is independently selected from:

halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN;

each $R^{27a}$ is independently selected from:

halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN;

each $R^{27b}$ is independently selected from:

halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN;

each $R^{27c}$ is independently selected from:

halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN;

each $R^{27d}$ is independently selected from:

halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN;

each $R^{27e}$ is independently selected from:

halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN;

each $R^{27f}$ is independently selected from:

halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)

$OR^{28g}$, —C(O)$OR^{28g}$, —OC(O)$R^{28g}$, —S(O)$R^{28g}$, —S(O)$_2R^{28g}$, —$NO_2$, =O, =S, =N($R^{28g}$), and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)$OR^{28g}$, —C(O)$OR^{28g}$, —OC(O)$R^{28g}$, —S(O)$R^{28g}$, —S(O)$_2R^{28g}$, —$NO_2$, =O, =S, =N($R^{28g}$), and —CN;

each $R^{28}$ is independently selected from:

hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28a}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28b}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28c}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28d}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28e}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

each $R^{28f}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; and each $R^{28g}$ is independently selected from:

hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In certain embodiments, for a compound or salt of Formula (III), $X^1$, $X^2$, $X^3$, and $X^4$ are independently selected from C(R) and N wherein no more than two of $X^1$, $X^2$, $X^3$, and $X^4$ are N. In some embodiments, $X^1$ is N. In some embodiments, $X^1$ is C(R). In some embodiments, $X^2$ is N. In some embodiments, $X^2$ is C(R). In some embodiments, $X^3$ is N. In some embodiments, $X^3$ is C(R). In some embodiments, $X^4$ is N. In some embodiments, $X^4$ is C(R). In some embodiments, $X^1$ is N, $X^2$ is C(R), $X^3$ is C(R), and $X^4$ is C(R). In some embodiments, $X^1$ is C(R), $X^2$ is N, $X^3$ is C(R), and $X^4$ is C(R). In some embodiments, $X^1$ is C(R), $X^2$ is C(R), $X^3$ is N, and $X^4$ is C(R). In some embodiments, $X^1$ is N, $X^2$ is C(R), $X^3$ is N, and $X^4$ is C(R). In some embodiments, $X^1$ is C(R), $X^2$ is N, $X^3$ is N, and $X^4$ is C(R).

In some embodiments, for a compound or salt of Formula (III), R can be any suitable functional group known by one of skill in the art. In some embodiments, each R is independently selected from: hydrogen, halogen, —$NO_2$, —CN, —$N_3$, —$OR^8$, —$SR^8$, —N($R^8$)$_2$, —C(O)$R^8$, —C(O)N(R)$_2$, —N($R^8$)C(O)$R^8$, —N($R^8$)C(O)N($R^8$)$_2$, —OC(O)N($R^8$)$_2$, —N($R^8$)C(O)O$R^8$, —C(O)O$R^8$, —OC(O)$R^8$, —S(O)$R^8$, and —S(O)$_2R^8$; $C_{1-6}$ alkyl, $C_{2-6}$ alkenyl, and $C_{2-6}$ alkynyl, each of which is optionally substituted with one or more substituents independently selected from halogen, —$OR^8$, —$SR^8$, —N($R^8$)$_2$, —C(O)$R^8$, —C(O)N($R^8$)$_2$, —N($R^8$)C(O)$R^8$, —C(O)O$R^8$, —OC(O)$R^8$, —N($R^8$)C(O)N($R^8$)$_2$, —OC(O)N($R^8$)$_2$, —N($R^8$)C(O)O$R^8$, —S(O)$R^8$, —S(O)$_2R^8$, —$NO_2$, ═O, ═S, ═N($R^8$), —CN, $C_{3-10}$ carbocycle and 3- to 10-membered heterocycle, wherein the $C_{3-10}$ carbocycle and 3- to 10-membered heterocycle are each optionally substituted with one or more $R^7$; and $C_{3-10}$ carbocycle and 3- to 10-membered heterocycle, each of which is optionally substituted with one or more substituents independently selected from halogen, —$OR^8$, —$SR^8$, —N($R^8$)$_2$, —C(O)$R^8$, —C(O)N($R^8$)$_2$, —N($R^8$)C(O)$R^8$, —N($R^8$)C(O)N(R)$_2$, —OC(O)N($R^8$)$_2$, —N($R^8$)C(O)O$R^8$, —C(O)O$R^8$, —OC(O)$R^8$, —S(O)$R^8$, —S(O)$_2R^8$, —$NO_2$, ═O—, ═S, ═N($R^8$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^7$.

In some embodiments, for a compound or salt of Formula (III), each R is independently selected from: hydrogen, halogen, —$NO_2$, —CN, —$N_3$, —$OR^8$, —$SR^8$, —N($R^8$)$_2$, —C(O)$R^8$, —C(O)N(R)$_2$, —N($R^8$)C(O)$R^8$, and —N($R^8$)C(O)N($R^8$)$_2$; $C_{1-6}$ alkyl, $C_{2-6}$ alkenyl, and $C_{2-6}$ alkynyl, each of which is optionally substituted with one or more substituents independently selected from halogen, —$OR^8$, —$SR^8$, —N($R^8$)$_2$, —$NO_2$, ═O, ═S, ═N(R); and $C_{3-10}$ carbocycle and 3- to 10-membered heterocycle. In some embodiments, each R is independently selected from hydrogen, halogen, —CN, —$N_3$, —$OR^8$, —$SR^8$, —N($R^8$)$_2$, —C(O)$R^8$, —C(O)N($R^8$)$_2$, and —N($R^8$)C(O)$R^8$; $C_{1-6}$ alkyl, $C_{2-6}$ alkenyl, and $C_{2-6}$ alkynyl, each of which is optionally substituted with one or more substituents independently selected from halogen, —$OR^8$; and $C_{3-10}$ carbocycle and 3- to 10-membered heterocycle. In some embodiments, each R is independently selected from: hydrogen, halogen, —CN, —$N_3$, —$OR^8$, —$SR^8$, —N($R^8$)$_2$; $C_{1-6}$ alkyl and $C_{2-6}$ alkynyl, each of which is optionally substituted with one or more substituents independently selected from halogen; and $C_{3-10}$ carbocycle and 3- to 10-membered heterocycle. In some embodiments, each R is independently selected from: —F, —Cl, —Br, —I, —CN, —$N_3$, —$OR^8$, —$SR^8$, —N($R^8$)$_2$, —$CF_3$, methyl, ethyl, cyclopropyl, —CCMe, phenyl, morpholinyl, and pyrrolidinyl. In some embodiments, each R is independently selected from: —F, —Cl, —Br, —I, —CN, —$N_3$, —$OR^8$, —$SR^8$, —N($R^8$)$_2$, —$CF_3$, methyl, ethyl, cyclopropyl, —CCMe, phenyl, morpholinyl, and pyrrolidinyl, wherein each $R^8$ is independently selected from the group consisting of hydrogen, methyl, ethyl, propyl, isopropyl, cyclopropyl, isobutyl, —$CF_3$, —$CH_2CF_3$, —$CH_2CHF_2$, —$CH_2$CF(Me)$_2$, —$CH_2CHMe_2$, —$CH_2$-phenyl. In some embodiments, each R is independently selected from: —H, —F, Cl, —Br, —I, —CN, —$N_3$, —OH, —OMe, —OEt, —O-propyl, —O-isopropyl, —O-butyl, —O-isobutyl, —$OCF_3$, —$OCH_2CFMe_2$, —$OCH_2CHF_2$, —$OCH_2CF_3$, —$OCH_2$CF($CH_3$)$_2$, —O-cyclopropyl, —SMe, —SEt, —$NH_2$, —NHMe, —NHEt, —NH-propyl, —NH-cyclopropyl, —NH-butyl, —NH-isobutyl, —NH-cyclobutyl, —$NMe_2$, —$NEt_2$, —NH-phenyl, -Me, -Et, -cyclopropyl, -n-propyl, isopropyl, —$CF_3$, —CCMe, -morpholinyl, and pyrrolidinyl. In some embodiments, each R is independently selected from: —H, —F, Cl, —Br, —I, —OH, -Me, -Et, —$OCH_2CF_3$, —$OCH_2CHF_2$, —OMe, -cyclopropyl, —CN, —OEt, —$CF_3$, —O—$CF_3$, —O-cyclopropyl, -n-propyl, isopropyl, —$OCH_2$CF($CH_3$)$_2$, —O— propyl, —O-isopropyl, —$OCH_2CFMe_2$, —SMe, —NHMe, —$NH_2$, —NHEt, —CCMe, —$NMe_2$, —$NEt_2$, —$N_3$, —NH— cyclopropyl, —NH-isobutyl, —NH-phenyl, -morpholinyl, pyrrolidinyl In some embodiments, each R is independently selected from: —H, —F, Cl, —Br, —I, —CN, —$N_3$, —OH, —OMe, —OEt, —O-propyl, —O— isopropyl, —$OCF_3$, —$OCH_2CFMe_2$, —$OCH_2CHF_2$, —$OCH_2CF_3$, —$OCH_2$CF($CH_3$)$_2$, —O-cyclopropyl, —SMe, —$NH_2$, —NHMe, —NHEt, —NH-cyclopropyl, —NH-isobutyl, —$NMe_2$, —$NEt_2$, —NH-phenyl, -Me, -Et, -cyclopropyl, -n-propyl, isopropyl, —$CF_3$, —CCMe, -morpholinyl, and pyrrolidinyl. In some embodiments, each R is independently selected from: —H, —F, Cl, —Br, —I, —CN, —$N_3$, —OH, —OMe, —OEt, —O-propyl, —O-isopropyl, —$OCF_3$, —$OCH_2CFMe_2$, —$OCH_2CHF_2$, —$OCH_2CF_3$, —$OCH_2$CF($CH_3$)$_2$, —O— cyclopropyl, —SMe, —$NH_2$, —NHMe, —NHEt, —$NEt_2$, -Me, -Et, -cyclopropyl, -n-propyl, isopropyl, —$CF_3$, and —CCMe.

In some embodiments, for a compound or salt of Formula (III), $R^{21}$ can be any suitable functional group known by one of skill in the art. In some embodiments, $R^{21}$ is selected from: hydrogen; $C_{1-6}$ alkyl, $C_{2-6}$ alkenyl, and $C_{2-6}$ alkynyl, each of which is optionally substituted with one or more substituents independently selected from halogen, —$OR^{28a}$, —$SR^{28a}$, —N($R^{28a}$)$_2$, —C(O)$R^{28a}$, C(O)N($R^{28a}$)$_2$, —N($R^{28a}$)C(O)$R^{28a}$, —C(O)O$R^{28a}$, —OC(O)$R^{28a}$, —N($R^{28a}$)C(O)N($R^{28a}$)$_2$, —OC(O)N($R^{28a}$)$_2$, —N($R^{28a}$)C(O)O$R^{28a}$, —S(O)$R^{28a}$, —S(O)$_2R^{28a}$, —$NO_2$, ═O, ═S, ═N($R^{28a}$), —CN, $C_{3-10}$ carbocycle, and 3- to 10-membered heterocycle, wherein the $C_{3-10}$ carbocycle, and 3- to 10-membered heterocycle, are each optionally substituted with one or more $R^{27a}$; and $C_{3-10}$ carbocycle, and 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27a}$; or $R^{21}$ together with $R^{22}$ form a $C_{3-10}$ carbocycle, or 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27b}$. In some embodiments, $R^{21}$ is selected from: hydrogen; $C_{1-6}$ alkyl, $C_{2-6}$ alkenyl, and $C_{2-6}$ alkynyl, each of which is optionally substituted with one or more substituents independently selected from halogen, —$OR^{28a}$, —$SR^{28a}$, —$N(R^{28a})_2$, —$C(O)R^{28a}$, —$S(O)R^{28a}$, —$S(O)_2R^{28a}$, —$NO_2$, and —CN; and $C_{3-10}$ carbocycle, and 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27a}$, or $R^{21}$ together with $R^{22}$ form a $C_{3-10}$ carbocycle, or 3- to 10-membered heterocycle, each of which is optionally substituted with one or more substituents independently selected from halogen, —$OR^{28a}$, —$SR^{8a}$, —$N(R^{8a})_2$, —$C(O)R^{8a}$, —$S(O)R^{8a}$, —$S(O)_2R^{8a}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$. In some embodiments, $R^{21}$ is selected from hydrogen; $C_{1-6}$ alkyl, $C_{2-6}$ alkenyl, and $C_{2-6}$ alkynyl, each of which is optionally substituted with one or more substituents independently selected from halogen, —$OR^{28a}$, —$SR^{28a}$, —$N(R^{28a})_2$, —$C(O)R^{28a}$, —$S(O)R^{28a}$, —$S(O)_2R^{28a}$, —$NO_2$, and —CN; and $C_{3-10}$ carbocycle, and 3- to 10-membered heterocycle, each of which is optionally substituted with one or more substituents independently selected from halogen, —$C(O)R^{8a}$, —CN, $C_{1-6}$ alkyl, or $R^{21}$ together with $R^{22}$ form a $C_{3-10}$ carbocycle, or 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$NO_2$, —CN, and $C_{1-6}$ alkyl, wherein $C_{1-6}$ alkyl is optionally substituted with one or more $R^{27b}$. In some embodiments, $R^{21}$ is hydrogen, methyl, —$CH_2OH$, —$CH_2CH_2OH$, $C(Me)_2OH$, —$CH_2OMe$, or $R^{21}$ together with $R^{22}$ form a $C_{3-10}$ carbocycle, or 3- to 10-membered heterocycle, each of which is optionally substituted with one or more substituents independently selected from —F, —COMe, —CN, and methyl. In some embodiments, $R^{21}$ is hydrogen, methyl, —$CH_2OH$, —$CH_2CH_2OH$, $C(Me)_2OH$, —$CH_2OMe$, or $R^{21}$ together with $R^{22}$ form:

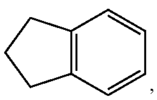,
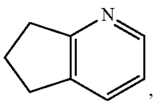,
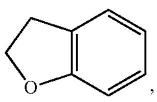,

-continued

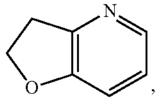,
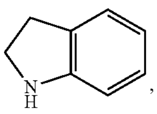, or
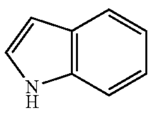

each of which are optionally substituted with one or more fluoro, —C(O)Me, —CN, and methyl.

In some embodiments, for a compound or salt of Formula (III), $R^{22}$ can be any suitable functional group known by one of skill in the art. In some embodiments, $R^{22}$ is selected from: hydrogen; $C_{1-6}$ alkyl, $C_{2-6}$ alkenyl, and $C_{2-6}$ alkynyl, each of which is optionally substituted with one or more substituents independently selected from halogen, —$OR^{28b}$, —$SR^{28b}$, —$N(R^{28b})_2$, —$C(O)R^{28b}$, —$C(O)N(R^{28b})_2$, —$N(R^{28b})C(O)R^{28b}$, —$C(O)OR^{28b}$, —$OC(O)R^{28b}$, —$N(R^{28b})C(O)N(R^{28b})_2$, —$OC(O)N(R^{28b})_2$, —$N(R^{28b})C(O)OR^{28b}$, —$S(O)R^{28b}$, —$S(O)_2R^{28b}$, —$NO_2$, ═O, ═S, ═$N(R^{28b})$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{28b}$; and $C_{3-10}$ carbocycle, and 3- to 10-membered heterocycle, each of which is optionally substituted with one or more substituents independently selected from halogen, —$OR^{28b}$, —$SR^{28b}$, —$N(R^{28b})_2$, —$C(O)R^{28b}$, —$C(O)N(R^{28b})_2$, —$N(R^{28b})C(O)R^{28b}$, —$N(R^{28b})C(O)N(R^{28b})_2$, —$OC(O)N(R^{28b})_2$, —$N(R^{28b})C(O)OR^{28b}$, —$C(O)OR^{28b}$, —$OC(O)R^{28b}$, —$S(O)R^{28b}$ $S(O)_2R^{28b}$, —$NO_2$, ═O—, ═S, ═$N(R^{28b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27b}$; or $R^{21}$ together with $R^{22}$ form a $C_{3-10}$ carbocycle, or 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27b}$.

In some embodiments, for a compound or salt of Formula (III), $R^{22}$ is selected from: hydrogen, $C_{1-6}$ alkyl, and $C_{2-6}$ alkenyl, each of which is optionally substituted with one or more substituents independently selected from halogen, —$OR^{28b}$, —$SR^{28b}$, —$N(R^{28b})_2$, —$C(O)R^{28b}$, —$S(O)R^{28b}$, —$S(O)_2R^{28b}$, —$NO_2$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{27b}$; and $C_{3-10}$ carbocycle, and 3- to 10-membered heterocycle, each of which is optionally substituted with one or more substituents independently selected from halogen, —$OR^{28b}$, —$SR^{28b}$, —$N(R^{28b})_2$, —$C(O)R^{28b}$, —$S(O)R^{28b}$, —$S(O)_2R^{28b}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27b}$; or $R^{21}$ together with $R^{22}$ form a $C_{3-10}$ carbocycle, or 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$S(O)R^{28a}$, —$S(O)_2R^{28a}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27b}$. In some embodiments, $R^{22}$ is selected from: hydrogen, $C_{1-6}$ alkyl, and $C_{2-6}$ alkenyl, each of which is optionally substituted with one or more substituents independently selected from halogen, —$OR^{28b}$, —$SR^{28b}$, —$N(R^{28b})_2$, —$C(O)R^{28b}$, —$S(O)R^{28b}$, —$S(O)_2R^{28b}$, —$NO_2$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{27b}$; and $C_{3-10}$ carbocycle, and 3- to 10-membered heterocycle, each of which is optionally substituted with one or more substituents independently selected from halogen, —$OR^{28b}$, —$C(O)R^{28b}$, —$S(O)_2R^{28b}$, —CN, and $C_{1-6}$ alkyl, wherein $C_{1-6}$ alkyl is optionally substituted with one or more $R^{27b}$; or $R^{21}$ together with $R^{22}$ form a $C_{3-10}$ carbocycle, or 3- to 10-membered heterocycle, each of which is optionally substituted with one or more substituents independently selected from halogen, —$C(O)R^{28a}$, —CN, and $C_{1-6}$ alkyl, wherein $C_{1-6}$ alkyl is optionally substituted with one or more $R^{27b}$. In some embodiments, $R^{22}$ is selected from hydrogen, $C_{1-6}$ alkyl, and $C_{2-6}$ alkenyl, each of which is optionally substituted with one or more substituents independently selected from halogen, —$OR^{28b}$, $C_{3-10}$ carbocycle, and 3- to 10-membered heterocycle; and $C_{3-10}$ carbocycle, and 3- to 10-membered heterocycle, each of which is optionally substituted with one or more substituents independently selected from halogen, —$OR^{28b}$, —$C(O)R^{28b}$, $S(O)_2R^{28b}$, —CN, and $C_{1-6}$ alkyl; or $R^{21}$ together with $R^{22}$ form a $C_{3-10}$ carbocycle, or 3- to 10-membered heterocycle, each of which is optionally substituted with one or more substituents independently selected from halogen, —$C(O)R^{28a}$, —CN, and $C_{1-6}$ alkyl, wherein $C_{1-6}$ alkyl is optionally substituted with one or more $R^{27b}$. In some embodiments, $R^{22}$ is hydrogen, $C_{1-2}$ alkyl, phenyl, or pyridinyl, wherein the $C_{1-2}$ alkyl is optionally substituted with one or more substituents independently selected from —OH and phenyl, and wherein the phenyl or pyridinyl is optionally substituted with one or more substituents independently selected from —F, —OH, —OMe, —COMe, —$SO_2Me$, —CN, and methyl. In some embodiments, $R^{22}$ is phenyl, or pyridinyl, wherein the phenyl or pyridinyl is optionally substituted with one or more substituents independently selected from —F, —OH, —OMe, —COMe, —$SO_2Me$, —CN, and methyl. In some embodiments, $R^{22}$ together with $R^{21}$ form:

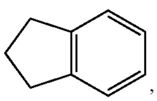, 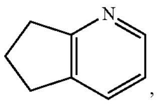, 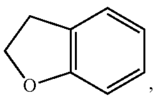,

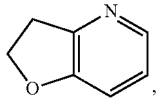, 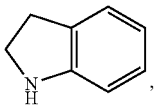, or 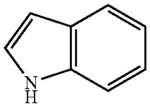

each of which are optionally substituted with one or more fluoro, —C(O)Me, —CN, and methyl.

In some embodiments, for a compound or salt of Formula (III), $R^{23}$ can be any suitable functional group known by one of skill in the art. In some embodiments, $R^{23}$ is selected from: hydrogen, halogen, —$OR^{28c}$, —$SR^{28c}$, —$N(R^{28c})_2$, —$NO_2$, and —CN; and $C_{1-6}$ alkyl optionally substituted with one or more one or more $R^{27c}$; or $R^{21}$ together with $R^{23}$ form a 3- to 10-membered heterocycle, which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, =O—, =S, =$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27c}$; $R^{22}$ together with $R^{23}$ form a $C_{3-10}$ carbocycle, or 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, =O—, =S, =$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27c}$. In some embodiments, $R^{23}$ is selected from: hydrogen, halogen, —$OR^{28c}$, —$SR^{28c}$, —$N(R^{28c})_2$, —$NO_2$, and —CN; and $C_{1-6}$ alkyl optionally substituted with one or more one or more $R^{27c}$. In some embodiments, $R^{23}$ is selected from: hydrogen, halogen, —$OR^{28c}$, —CN, and $C_{1-6}$ alkyl. In some embodiments, $R^{23}$ is selected from hydrogen and $C_{1-6}$ alkyl. In some embodiments, $R^{23}$ is selected from hydrogen and $C_{1-3}$ alkyl. In some embodiments, $R^{23}$ is hydrogen.

In some embodiments, for a compound or salt of Formula (III), $R^{24}$ can be any suitable functional group known by one of skill in the art. In some embodiments, each $R^{24}$ is independently selected from hydrogen, halogen, —$OR^{28d}$, —$SR^{28d}$, —$N(R^{28d})_2$, —$NO_2$, and —CN; and $C_{1-6}$ alkyl optionally substituted with one or more substituents independently selected from halogen, —$OR^{28d}$, —$SR^{28d}$, —$N(R^{28d})_2$, —$NO_2$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{27d}$; or $R^{24}$ together with $R^{25}$ form a 3- to 10-membered heterocycle, wherein the 3- to 10-membered heterocycle is optionally substituted with one or more $R^{27e}$. In some embodiments each $R^{24}$ is independently selected from hydrogen, halogen, —$OR^{28d}$, and —CN; and $C_{1-6}$ alkyl optionally substituted with one or more substituents independently selected from halogen, —$OR^{28d}$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{27d}$. In some embodiments, $R^{24}$ is independently selected from hydrogen, halogen, —$OR^{28d}$, —$SR^{28d}$, —$N(R^{28d})_2$, —$NO_2$, and —CN; and $C_{1-6}$ alkyl optionally substituted with one or more substituents independently selected from $C_{3-10}$ carbocycle. In some embodiments, $R^{24}$ is independently selected from hydrogen, halogen; and $C_{1-6}$ alkyl optionally substituted with one or more substituents independently selected from $C_{3-10}$ carbocycle. In some embodiments, $R^{24}$ is independently selected from hydrogen, —F, and $C_1$ alkyl optionally substituted with phenyl. In some embodiments, $R^{24}$ is independently hydrogen or methyl. In some embodiments, $R^{24}$ is hydrogen. In some embodiments, each $R^{24}$ is methyl.

In some embodiments, for a compound or salt of Formula (III), $R^{24'}$ can be any suitable functional group known by one of skill in the art. In some embodiments, each $R^{24'}$ is independently selected from hydrogen, halogen, —$OR^{28d}$, —$SR^{28d}$, —$N(R^{28d})_2$, —$NO_2$, and —CN; and $C_{1-6}$ alkyl optionally substituted with one or more substituents independently selected from halogen, —$OR^{28d}$, —$SR^{28d}$, —$N(R^{28d})_2$, —$NO_2$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{27d}$; or $R^{24'}$ together with $R^{25}$ form a 3- to 10-membered heterocycle, wherein the 3- to 10-membered heterocycle is optionally substituted with one or more $R^{27e}$. In some embodiments each $R^{24'}$ is independently selected from hydrogen, halogen, —$OR^{28d}$, and —CN; and $C_{1-6}$ alkyl optionally substituted with one or more substituents independently selected from halogen, —$OR^{28d}$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{27d}$. In some embodiments, $R^{24'}$ is independently selected from hydrogen, halogen, —$OR^{28d}$, —$SR^{28d}$, —$N(R^{28d})_2$, —$NO_2$, and —CN; and $C_{1-6}$ alkyl optionally substituted with one or more substituents independently selected from $C_{3-10}$ carbocycle. In some embodiments, $R^{24'}$ is independently selected from hydrogen, halogen; and $C_{1-6}$ alkyl optionally substituted with one or more substituents independently selected from $C_{3-10}$ carbocycle. In some embodiments, $R^{24'}$ is independently selected from hydrogen, —F, and $C_1$ alkyl optionally substituted with phenyl. In some embodiments, $R^{24'}$ is independently hydrogen or methyl. In some embodiments, $R^{24'}$ is hydrogen. In some embodiments, each $R^{24'}$ is methyl.

In some embodiments, for a compound or salt of Formula (III), $R^{25}$ can be any suitable functional group known by one of skill in the art. In some embodiments, for a compound or salt of Formula (III), $R^{25}$ is selected from: hydrogen, halogen, —$OR^{28e}$, —$SR^{28e}$, —$N(R^{28e})_2$, —$NO_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more $R^{27e}$; or $R^{24}$ together with $R^{25}$ form a 3- to 10-membered heterocycle, wherein the 3- to 10-membered heterocycle is optionally substituted with one or more $R^{27e}$. In some embodiments, for a compound or salt of Formula (III), $R^{25}$ is selected from: hydrogen, halogen, —$OR^{28c}$, —$SR^{28c}$, —$N(R^{28e})_2$, —$NO_2$, —CN, $C_{1-6}$ alkyl, $C_{3-5}$ carbocycle, $C_{7-10}$ carbocycle, and 3- to 10-membered heterocycle, wherein the $C_{1-6}$ alkyl, $C_{3-10}$ carbocycle, and 3- to 10-membered heterocycle are each optionally substituted with one or more $R^{27e}$; or $R^{24}$ together with $R^{25}$ form a 3- to 10-membered heterocycle, wherein the 3- to 10-membered heterocycle is optionally substituted with one or more $R^{27e}$. In some embodiments, $R^{25}$ is selected from hydrogen, halogen, —$OR^{8e}$, —$SR^{8e}$, —$N(R^{8e})_2$, —$NO_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more $R^{27e}$; or $R^{24}$ together with $R^{25}$ form a 3- to 10-membered heterocycle, wherein the 3- to 10-membered heterocycle is optionally substituted with one or more $R^{27e}$. In some embodiments, $R^{25}$ is selected from: hydrogen, halogen, —$OR^{28e}$, —$N(R^{28e})_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more $R^{27e}$. In some embodiments, $R^{25}$ is selected from: hydrogen, halogen, —$OR^{28e}$, —$N(R^{28e})_2$, —CN, $C_{1-6}$ alkyl, and $C_{3-10}$ carbocycle, wherein the $C_{1-6}$ alkyl, and $C_{3-10}$ carbocycle, are each optionally substituted with one or more $R^{27c}$. In some embodiments, hydrogen, halogen, —$OR^{28e}$, —$N(R^{28e})_2$, —CN, $C_{1-3}$ alkyl, and $C_{3-6}$ carbocycle, wherein the $C_{1-6}$ alkyl, and $C_{3-10}$ carbocycle, are each optionally substituted with one or more $R^{28e}$. In some embodiments, $R^{25}$ is selected from hydrogen, —Cl, —OH, —OMe, —NHMe, —CN, $C_{1-2}$ alkyl, and cyclopropyl, wherein the $C_{1-2}$ alkyl and cyclopropyl are each optionally substituted with one or more —F. In some embodiments, $R^{25}$ is selected from hydrogen, —Cl, —OH, —OMe, —NHMe, —CN, methyl, ethyl, —$CF_3$, —$CHF_2$, and cyclopropyl.

In some embodiments, for a compound or salt of Formula (III), $R^{26}$ can be any suitable functional group known by one of skill in the art. In some embodiments, $R^{26}$ is selected from: hydrogen, halogen, —$OR^{28f}$, —$SR^{28f}$, —$N(R^{28f})_2$, —$NO_2$, and —CN; and $C_{1-6}$ alkyl optionally substituted with one or more $R^{27f}$. In some embodiments, $R^{26}$ is selected from: hydrogen, halogen, —$OR^{28f}$; and $C_{1-6}$ alkyl optionally substituted with one or more $R^{27f}$. In some embodiments, $R^{26}$ is selected from: hydrogen, halogen, —$OR^{28f}$, and $C_{1-6}$ alkyl. In some embodiments, $R^{26}$ is selected from hydrogen and $C_{1-6}$ alkyl. In some embodiments, $R^{26}$ is selected from hydrogen and $C_{1-3}$ alkyl. In some embodiments, $R^{26}$ is hydrogen.

In some embodiments, for a compound or salt of Formula (III), each of $R^{27}$, $R^{27a}$, $R^{27b}$, $R^{27c}$, $R^{27a}$, $R^{27e}$, and $R^{27f}$ can be any suitable functional group known by one of skill in the art. In some embodiments, each of $R^{27}$, $R^{27a}$, $R^{27b}$, $R^{27c}$, $R^{27a}$, $R^{27e}$, and $R^{27f}$ are independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, =O, =S, =$N(R^{28g})$, and —CN.

In some embodiments, for a compound or salt of Formula (III), each $R^{27}$ is independently selected from: halogen, —$OR^{28g}$, —$N(R^{28g})_2$, —$C(O)R^{28g}$, and $C_{1-3}$ alkyl. In some embodiments, each $R^{27}$ is independently selected from: halogen, —$OR^{28g}$, and $C_{1-3}$ alkyl. In some embodiments, each $R^{27}$ is independently selected from: halogen, —OH, and —OMe.

In some embodiments, for a compound or salt of Formula (III), each $R^{27a}$ is independently selected from: halogen, —$OR^{28g}$, —$N(R^{28g})_2$, —$C(O)R^{28g}$, and $C_{1-3}$ alkyl. In some embodiments, each $R^{27a}$ is independently selected from: halogen, —$OR^{28g}$, and $C_{1-3}$ alkyl. In some embodiments, each $R^{27a}$ is independently selected from: halogen, —OH, and —OMe.

In some embodiments, for a compound or salt of Formula (III), each $R^{27b}$ is independently selected from: halogen, —$OR^{28g}$, —$N(R^{28g})_2$, —$C(O)R^{28g}$, and $C_{1-3}$ alkyl. In some embodiments, each $R^{27b}$ is independently selected from: halogen, —$OR^{8g}$, and $C_{1-3}$ alkyl. In some embodiments, each $R^{27b}$ is independently selected from: halogen, —OH, and —OMe.

In some embodiments, for a compound or salt of Formula (III), each $R^{27c}$ is independently selected from: halogen, —$OR^{28g}$, —$N(R^{28g})_2$, —$C(O)R^{28g}$, and $C_{1-3}$ alkyl. In some embodiments, each $R^{27c}$ is independently selected from: halogen, —$OR^{28g}$, and $C_{1-3}$ alkyl. In some embodiments, each $R^{27c}$ is independently selected from: halogen, —OH, and —OMe.

In some embodiments, for a compound or salt of Formula (III), each $R^{27d}$ is independently selected from: halogen, —$OR^{28g}$, —$N(R^{28g})_2$, —$C(O)R^{28g}$, and $C_{1-3}$ alkyl. In some embodiments, each $R^{27d}$ is independently selected from: halogen, —$OR^{28g}$, and $C_{1-3}$ alkyl. In some embodiments, each $R^{27d}$ is independently selected from: halogen, —OH, and —OMe.

In some embodiments, for a compound or salt of Formula (III), each $R^{27e}$ is independently selected from: halogen, —$OR^{28g}$, —$N(R^{28g})_2$, —$C(O)R^{28g}$, and $C_{1-3}$ alkyl. In some embodiments, each $R^{27e}$ is independently selected from: halogen, —$OR^{8g}$, and $C_{1-3}$ alkyl. In some embodiments, each $R^{27e}$ is independently selected from: halogen, —OH, and —OMe. In some embodiments, each $R^{27e}$ is fluoro.

In some embodiments, for a compound or salt of Formula (III), each $R^{27f}$ is independently selected from: halogen, —$OR^{28g}$, —$N(R^{28g})_2$, —$C(O)R^{28g}$, and $C_{1-3}$ alkyl. In some embodiments, each $R^{27f}$ is independently selected from: halogen, —$OR^{8g}$, and $C_{1-3}$ alkyl. In some embodiments, each $R^{27f}$ is independently selected from: halogen, —OH, and —OMe.

In some embodiments, for a compound or salt of Formula (III), Each of $R^{28}$, $R^{28a}$, $R^{28b}$, $R^{28c}$, $R^{28d}$, $R^{28c}$, $R^{28f}$, and $R^{28g}$ can be any suitable functional group known by one of skill in the art. In some embodiments, each of $R^{28}$, $R^{28a}$, $R^{28b}$, $R^{28c}$, $R^{28d}$, $R^{28e}$, $R^{28f}$, and $R^{28g}$ are independently selected from hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$haloalkyl.

In some embodiments, for a compound or salt of Formula (III), each $R^{28}$ is independently selected from: hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —SH, —$NO_2$, —$NH_2$, $C_{3-10}$ carbocycle, 3- to 10-membered heterocycle; and $C_{3-10}$ carbocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, each $R^{28}$ is independently selected from: hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —$NH_2$, $C_{3-10}$ carbocycle, and $C_{3-10}$ carbocycle, each of which is optionally substituted with one or more substituents independently selected from halogen, —CN, —OH, —O—$C_{1-6}$ alkyl, —S—$C_{1-6}$ alkyl, —$SO_2$—$C_{1-6}$ alkyl, —$N(C_{1-6}$ alkyl$)_2$, —$NH(C_{1-6}$ alkyl), $C_{1-6}$ alkyl, $C_{2-6}$ alkenyl, and $C_{2-6}$alkynyl. In some embodiments, each $R^{28}$ is independently selected from: hydrogen; and $C_{1-6}$ alkyl, and $C_{3-10}$ carbocycle, each of which is optionally substituted with one or more substituents independently selected from halogen, $C_{3-10}$ carbocycle; and $C_{3-10}$ carbocycle, each of which is optionally substituted with —OH. In some embodiments, each $R^{28}$ is hydrogen, methyl, ethyl, propyl, isopropyl, cyclopropyl, isobutyl, —$CF_3$, —$CH_2CF_3$, —$CH_2CHF_2$, —$CH_2CF(Me)_2$, —$CH_2CHMe_2$, or —$CH_2$-phenyl.

In some embodiments, for a compound or salt of Formula (III), each $R^{28a}$ is independently selected from: hydrogen, halogen, $C_{1-6}$ alkyl, $C_{2-6}$ alkenyl, and $C_{2-6}$ alkynyl. In some embodiments, each $R^{28a}$ is independently selected from: hydrogen and $C_{1-6}$ alkyl. In some embodiments, each $R^{28a}$ is independently selected from: hydrogen and methyl.

In some embodiments, for a compound or salt of Formula (III), each $R^{28b}$ is independently selected from: hydrogen, halogen, $C_{1-6}$ alkyl, $C_{2-6}$ alkenyl, and $C_{2-6}$ alkynyl. In some embodiments, each $R^{28b}$ is independently selected from: hydrogen and $C_{1-6}$ alkyl. In some embodiments, each $R^{28b}$ is independently selected from: hydrogen and methyl.

In some embodiments, for a compound or salt of Formula (III), each $R^{28c}$ is independently selected from: hydrogen, halogen, $C_{1-6}$ alkyl, $C_{2-6}$ alkenyl, and $C_{2-6}$ alkynyl. In some embodiments, each $R^{28c}$ is independently selected from: hydrogen and $C_{1-6}$ alkyl. In some embodiments, each $R^{28c}$ is independently selected from: hydrogen and methyl.

In some embodiments, for a compound or salt of Formula (III), each $R^{28d}$ is independently selected from: hydrogen, halogen, $C_{1-6}$ alkyl, $C_{2-6}$ alkenyl, and $C_{2-6}$ alkynyl. In some embodiments, each $R^{28d}$ is independently selected from: hydrogen and $C_{1-6}$ alkyl. In some embodiments, each $R^{28a}$ is independently selected from: hydrogen and methyl.

In some embodiments, for a compound or salt of Formula (III), each $R^{28e}$ is independently selected from: hydrogen, halogen, $C_{1-6}$ alkyl, $C_{2-6}$ alkenyl, and $C_{2-6}$ alkynyl. In some embodiments, each $R^{28e}$ is independently selected from: hydrogen and $C_{1-6}$ alkyl. In some embodiments, each $R^{28e}$ is independently selected from: hydrogen and methyl. In some embodiments, each $R^{28e}$ is independently hydrogen.

In some embodiments, for a compound or salt of Formula (III), each $R^{28f}$ is independently selected from: hydrogen, halogen, $C_{1-6}$ alkyl, $C_{2-6}$ alkenyl, and $C_{2-6}$ alkynyl. In some embodiments, each $R^{28f}$ is independently selected from: hydrogen and $C_{1-6}$ alkyl. In some embodiments, each $R^{28f}$ is independently selected from: hydrogen and methyl.

In some embodiments, for a compound or salt of Formula (III), each $R^{28g}$ is independently selected from: hydrogen, halogen, $C_{1-6}$ alkyl, $C_{2-6}$ alkenyl, and $C_{2-6}$ alkynyl. In some embodiments, each $R^{28g}$ is independently selected from: hydrogen and $C_{1-6}$ alkyl. In some embodiments, each $R^{28g}$ is independently selected from: hydrogen and methyl.

In some embodiments, a compound of Formula (III) is selected from compound 22, 34, 36, 130, 12, 21, 38, 69, 85, 107, 28, 37, 83, 101, 108, 109, 116, 120, 2052, 2069, 2589, 2601, 11, 24, 32, 50, 60, 61, 66, 89, 106, 115, 1150, 2046, 2602, 52, 58, 68, 100, 112, 118, 126, 1046, 1145, 1148, 2055, 2603, 1, 16, 45, 96, 104, 131, 1068, 1124, 2075, 2607, 35, 42, 72, 95, 1140, 2606, 2, 17, 18, 59, 1133, 2050, 2502, 2554, 2597, 15, 31, 111, 113, 135, 1129, 1132, 54, 67, 2056, 2596, 1053, 1081, 1107, 2016, 2604, 41, 99, 1059, 2079, 2533, 2592, 1051, 1104, 1136, 1139, 1146, 2520, 57, 62, 2049, 2562, 2563, 10, 1063, 1109, 2524, 33, 1101, 2501, 2538, 2552, 49, 1095, 97, 127, 2523, 2593, 1069, 2530, 2546, 14, 20, 44, 129, 1080, 2063, 133, 1050, 1070, 27, 51, 65, 2054, 2078, 2561, 2594, 46, 2529, 2542, 119, 1048, 1144, 2002, 2022, 2070, 2519, 13, 2521, 2522, 2001, 2541, 2567, 105, 1131, 2023, 2595, 1103, 2551, 2605, 63, 1142, 2051, 2513, 2590, 1079, 2060, 40, 1119, 1123, 1077, 1111, 2015, 1065, 2553, 2564, 110, 1084, 1128, 98, 1106, 2042, 1118, 2568, 1135, 2040, 2514, 2598, 1052, 2057, 2600, 2072, 74, 1130, 1127, 2543, 2511, 1100, 2516, 6, 1153, 2532, 128, 2048, 4504, 1113, 2549, 2061, 2043, 1134, 2066, 2071, 71, 1097, 137, 103, 1092, 93, 2041, 2021, 2010, 2029, 4502, 55, 2531, 2039, 91, 2550, 1143, 5, 2027, 2077, 2591, 2512, 48, 2586, 2585, 1138, 123, 2030, 1076, 1149, 1058, 30, 53, 1086, 2017, 2599, 1064, 2035, 2024, 1141, 56, 1061, 84, 1078, 1120, 2539, 1147, 2518, 2037, 4505, 9, 3, 2020, 2517, 1062, 2555, 2557, 1066, 7, 114, 1110, 2507, 2583, 4, 2528, 47, 2544, 2580, 2011, 2527, 2569, 1112, 2515, 1071, 1137, 2587, 1067, 1088, 1090, 1083, 26, 1102, 1089, 1108, 2556, 94, 2062, 1098, 78, 1099, 2510, 1114, 2074, 1122, 2044, 4503, 2025, 1060, 2565, 2534, 2013, 2575, 1075, 1072, 1125, 1054, 2577, 1151, 2067, 2019, 90, 2047, 1115, 92, 2536, 2558, 1096, 2576, 2571, 1085, 2548, 2068, 1091, 1073, 75, 1152, 125, 2064, 88, 147, 209, 274, 283, 373, 402, 409, 152, 168, 382, 391, 401, 149, 150, 177, 357, 370, 377, 380, 385, 439, 305, 355, 139, 170, 174, 185, 225, 256, 288, 492, 227, 242, 332, 374, 172, 381, 406, 407, 187, 196, 202, 230, 359, 420, 3514, 219, 386, 145, 160, 162, 246, 392, 351, 353, 366, 387, 3009, 405, 433, 469, 3502, 376, 414, 154, 167, 365, 262, 384, 173, 3508, 3515, 266, 447, 281, 375, 394, 285, 264, 369, 195, 181, 198, 156, 183, 161, 348, 138, 3509, 217, 363, 464, 430, 158, 151, 3510, 193, 204, 232, 419, 3516, 146, 243, 3511, 192, 434, 448, 456, 241, 3010, 179, 389, 349, 3504, 458, 468, 248, 399, 163, 347, 3519, 143, 350, 489, 169, 3012, 308, 388, 221, 3517, 444, 364, 159, 396, 189, 477, 276, 3001, 361, 255, 428, 476, 411, 473, 486, 460, 282, 400, 491, 3512, 368, 395, 191, 3505, 166, 424, 148, 3518, 484, 354, 208, 415, 367, 445, 438, 379, 186, 343, 260, 188, 393, 273, 164, 427, 250, 3507, 352, 418, 398, 3011, 165, 197, 200, 371, 459, 275, 176, 327, 441, 3503, 342, 483, 472, 463, 178, 284, 239, 426, 3513, 410, 478, 194, 155, 224, 211, 455, 454, 226, 190, 229, 245, 238, 182, 338, 453, 362, 344, 417, 3004, 299, 345, 431, 306, 488, 223, 157, 212, 432, 278, 304, 254, 153, 413, 171, 358, 289, 482, 210, 457, 435, 440, 247, 340, 236, 403, 286, 485, 452, 462, 336, 412, 279, 296, 437, 461, 425, 4001, 4004, 4006, 4010, 4002, 4008, 4009, and 4005.

In some embodiments, a compound of Formula (III) is selected from compound 22, 34, 36, 130, 12, 21, 38, 69, 85, 107, 28, 37, 83, 101, 108, 109, 116, 120, 2052, 2069, 2589, 2601, 11, 24, 32, 50, 60, 61, 66, 89, 106, 115, 1150, 2046, 2602, 52, 58, 68, 100, 112, 118, 126, 1046, 1145, 1148, 2055, 2603, 1, 16, 45, 96, 104, 131, 1068, 1124, 2075, 2607, 35, 42, 72, 95, 1140, 2606, 2, 17, 18, 59, 1133, 2050, 2502, 2554, 2597, 15, 31, 111, 113, 135, 1129, 1132, 54, 67, 2056, 2596, 1053, 1081, 1107, 2016, 2604, 41, 99, 1059, 2079, 2533, 2592, 1051, 1104, 1136, 1139, 1146, 2520, 57, 62, 2049, 2562, 2563, 10, 1063, 1109, 2524, 33, 1101, 2501, 2538, 2552, 49, 1095, 97, 127, 2523, 2593, 1069, 2530, 2546, 14, 20, 44, 129, 1080, 2063, 133, 1050, 1070, 27, 51, 65, 2054, 2078, 2561, 2594, 46, 2529, 2542, 119, 1048, 1144, 2002, 2022, 2070, 2519, 13, 2521, 2522, 2001, 2541, 2567, 105, 1131, 2023, 2595, 1103, 2551, 2605, 63, 1142, 2051, 2513, 2590, 1079, 2060, 40, 1119, 1123, 1077, 1111, 2015, 1065, 2553, 2564, 110, 1084, 1128, 98, 1106, 2042, 1118, 2568, 1135, 2040, 2514, 2598, 1052, 2057, 2600, 2072, 74, 1130, 1127, 2543, 2511, 1100, 2516, 6, 1153, 2532, 128, 2048, 4504, 1113, 2549, 2061, 2043, 1134, 2066, 2071, 71, 1097, 137, 103, 1092, 93, 2041, 2021, 2010, 2029, 4502, 55, 2531, 2039, 91, 2550, 1143, 5, 2027, 2077, 2591, 2512, 48, 2586, 2585, 1138, 123, 2030, 1076, 1149, 1058, 30, 53, 1086, 2017, 2599, 1064, 2035, 2024, 1141, 56, 1061, 84, 1078, 1120, 2539, 1147, 2518, 2037, 4505, 9, 3, 2020, 2517, 1062, 2555, 2557, 1066, 7, 114, 1110, 2507, 2583, 4, 2528, 47, 2544, 2580, 2011, 2527, 2569, 1112, 2515, 1071, 1137, 2587, 1067, 1088, 1090, 1083, 26, 1102, 1089, 1108, 2556, 94, 2062, 1098, 78, 1099, 2510, 1114, 2074, 1122, 2044, 147, 209, 274, 283, 373, 402, 409, 152, 168, 382, 391, 401, 149, 150, 177, 357, 370, 377, 380, 385, 439, 305, 355, 139, 170, 174, 185, 225, 256, 288, 492, 227, 242, 332, 374, 172, 381, 406, 407, 187, 196, 202, 230, 359, 420, 3514, 219, 386, 145, 160, 162, 246, 392, 351, 353, 366, 387, 3009, 405, 433, 469, 3502, 376, 414, 154, 167, 365, 262, 384, 173, 3508, 3515, 266, 447, 281, 375, 394, 285, 264, 369, 195, 181, 198, 156, 183, 161, 348, 138, 3509, 217, 363, 464, 430, 158, 151, 3510, 193, 204, 232, 419, 3516, 146, 243, 3511, 192, 434, 448, 456, 241, 3010, 179, 389, 349, 3504, 458, 468, 248, 399, 163, 347, 3519, 143, 350, 489, 169, 3012, 308, 388, 221, 3517, 444, 364, 159, 396, 189, 477, 276, 3001, 361, 255, 428, 476, 411, 473, 486, 460, 282, 400, 491, 3512, 368, 395, 191, 3505, 166, 424, 148, 3518, 484, 354, 208, 415, 367, 445, 438, 379, 186, 343, 260, 188, 393, 273, 164, 427, 250, 3507, 352, 418, 398, 3011, 165, 197, 200, 371, 459, 275, 176, 327, 441, 3503, 342, 483, 472, 463, 178, 284, 239, 426, 3513, 410,478, 194, 155, 224, 211,455, 454, 226, 190, 229, 245, 238, 182, 338, 453, 362, 344, 417, 4001, 4004, 4006, 4010, 4002, 4008, 4009, and 4005.

In some embodiments, a compound of Formula (III) is selected from compound 22, 34, 36, 130, 12, 21, 38, 69, 85, 107, 28, 37, 83, 101, 108, 109, 116, 120, 2052, 2069, 2589, 2601, 11, 24, 32, 50, 60, 61, 66, 89, 106, 115, 1150, 2046, 2602, 52, 58, 68, 100, 112, 118, 126, 1046, 1145, 1148, 2055, 2603, 1, 16, 45, 96, 104, 131, 1068, 1124, 2075, 2607, 35, 42, 72, 95, 1140, 2606, 2, 17, 18, 59, 1133, 2050, 2502, 2554, 2597, 15, 31, 111, 113, 135, 1129, 1132, 54, 67, 2056, 2596, 1053, 1081, 1107, 2016, 2604, 41, 99, 1059, 2079, 2533, 2592, 1051, 1104, 1136, 1139, 1146, 2520, 57, 62, 2049, 2562, 2563, 10, 1063, 1109, 2524, 33, 1101, 2501, 2538, 2552, 49, 1095, 97, 127, 2523, 2593, 1069, 2530, 2546, 14, 20, 44, 129, 1080, 2063, 133, 1050, 1070, 27, 51, 65, 2054, 2078, 2561, 2594, 46, 2529, 2542, 119, 1048, 1144, 2002, 2022, 2070, 2519, 13, 2521, 2522, 2001, 2541, 2567, 105, 1131, 2023, 2595, 1103, 2551, 2605, 63, 1142, 2051, 2513, 2590, 1079, 2060, 40, 1119, 1123, 1077, 1111, 2015, 1065, 2553, 2564, 110, 1084, 1128, 98, 1106, 2042, 1118, 2568, 1135, 2040, 2514, 2598, 1052, 2057, 2600, 2072, 74, 1130, 1127, 2543, 2511, 1100, 2516, 6, 1153, 2532, 128, 2048, 4504, 1113, 2549, 2061, 147, 209, 274, 283, 373, 402, 409, 152, 168, 382, 391, 401, 149, 150, 177, 357, 370, 377, 380, 385, 439, 305, 355, 139, 170, 174, 185, 225, 256, 288, 492, 227, 242, 332, 374, 172, 381, 406, 407, 187, 196, 202, 230, 359, 420, 3514, 219, 386, 145, 160, 162, 246, 392, 351, 353, 366, 387, 3009, 405, 433, 469, 3502, 376, 414, 154, 167, 365, 262, 384, 173, 3508, 3515, 266, 447, 281, 375, 394, 285, 264, 369, 195, 181, 198, 156, 183, 161, 348, 138, 3509, 217, 363, 464, 430, 158, 151, 3510, 193, 204, 232, 419, 3516, 146, 243, 3511, 192, 434, 448, 456, 241, 3010, 179, 389, 349, 3504, 458, 468, 248, 399, 163, 347, 3519, 143, 350, 4001, 4004, 4006, and 4010.

In some embodiments, a compound of Formula (III) is selected from compound 22, 34, 36, 130, 12, 21, 38, 69, 85, 107, 28, 37, 83, 101, 108, 109, 116, 120, 2052, 2069, 2589, 2601, 11, 24, 32, 50, 60, 61, 66, 89, 106, 115, 1150, 2046, 2602, 52, 58, 68, 100, 112, 118, 126, 1046, 1145, 1148, 2055, 2603, 1, 16, 45, 96, 104, 131, 1068, 1124, 2075, 2607, 35, 42, 72, 95, 1140, 2606, 2, 17, 18, 59, 1133, 2050, 2502, 2554, 2597, 147, 209, 274, 283, 373, 402, 409, 152, 168, 382, 391, 401, 149, 150, 177, 357, 370, 377, 380, 385, 439, 305, 355, 139, 170, 174, 185, 225, 256, 288, 492, 227, 242, 332, 374, 172, 381, 406, and 407.

In some embodiments, a compound of Formula (III) is selected from compound 22, 32, 42, 34, 36, 37, 1150, 1129, 1132, 38, 28, 66, 1068, 1140, 85, 2601, 68, 1145, 59, 2079, 61, 2602, 2, 107, 2052, 2589, 1148, 13, 83, 2046, 52, 12, 69, 101, 1136, 46, 21, 109, 116, 16, 96, 15, 2533, 1046, 1, 1133, 1139, 130, 11, 35, 1107, 1142, 1149, 31, 1059, 2607, 2050, 2538, 1146, 106, 2502, 2554, 24, 2603, 1104, 2520, 62, 2530, 2002, 1053, 2552, 65, 50, 2049, 27, 120, 2055, 18, 67, 1051, 108, 1081, 2056, 2016, 118, 112, 2524, 1101, 20, 1077, 3, 89, 115, 2594, 1124, 72, 14, 2529, 1109, 1080, 95, 2597, 10, 135, 51, 2542, 40, 45, 1095, 41, 2501, 2595, 33, 74, 2592, 4504, 30, 126, 2001, 1106, 2075, 2563, 2596, 2568, 2051, 75, 60, 4502, 49, 100, 2541, 1128, 2522, 2523, 2604, 2562, 129, 1063, 2606, 2561, 1065, 131, 1144, 1131, 2564, 2078, 9, 1141, 2057, 1147, 6, 4, 2040, 2593, 19, 2567, 1103, 2598, 1047, 1119, 2519, 23, 2545, 1138, 2546, 1118, 133, 7, 58, 1134, 1123, 26, 1108, 2015, 2605, 1076, 2041, 54, 2514, 17, 1097, 1127, 104, 113, 2513, 1070, 1048, 2023, 2521, 119, 44, 2074, 1066, 1120, 2048, 185, 152, 177, 283, 149, 162, 147, 373, 274, 3514, 209, 355, 246, 285, 139, 198, 464, 402, 256, 401, 332, 288, 382, 3515, 391, 377, 3508, 173, 357, 381, 353, 3502, 492, 385, 407, 374, 406, 393, 439, 3509, 242, 394, 154, 174, 305, 489, 409, 227, 433, 262, 150, 146, 380, 476, 202, 151, 365, 230, 351, 170, 266, 405, 167, 282, 138, 161, 3510, 376, 187, 486, 366, 468, 3516, 386, 469, 255, 158, 428, 350, 403, 3517, 179, 3009, 243, 160, 420, 225, 181, 477, 392, 3511, 264, 232, 363, 195, 248, 148, 156, 396, 487, 3010, 168, 361, 456, 172, 434, 273, 241, 196, 375, 364, 3504, 488, 349, 281, 3503, 3007, 379, 472, 193, 159, 183, 348, 143, 473, 217, 219, 448, 438, 204, 327, 245, 417, 343, 208, 145, 447, 169, 284, 239, 238, 491, 430, 384, 308, 415, 3505, 189, 414, 192, 276, 461, 483, 3519, 424, 3001, 399, 3507, 435, 176, 178, 347, 445, 444, 164, 427, 254, 157, 463, 460, 352, 397, 478, 269, 229, 212, 182, 367, 388, 188, 475, 404, 368, 390, 190, 221, 395, 370, 418, 354, 197, 431, 345, 342, 454, 211, 358, 3012, 398, 369, 223, 3513, 155, 482, 258, 426, 199, 471, 432, 250, 277, 344, 4004, 4001, 4009, 4005, 4008, 4006, 4010, and 4002.

In some embodiments, a compound of Formula (III) is selected from compound 22, 32, 42, 34, 36, 37, 1150, 1129, 1132, 38, 28, 66, 1068, 1140, 85, 2601, 68, 1145, 59, 2079, 61, 2602, 2, 107, 2052, 2589, 1148, 13, 83, 2046, 52, 12, 69, 101, 1136, 46, 21, 109, 116, 16, 96, 15, 2533, 1046, 1, 1133, 1139, 130, 11, 35, 1107, 1142, 1149, 31, 1059, 2607, 2050, 2538, 1146, 106, 2502, 2554, 24, 2603, 1104, 2520, 62, 2530, 2002, 1053, 2552, 65, 50, 2049, 27, 120, 2055, 18, 67, 1051, 108, 1081, 2056, 2016, 118, 112, 2524, 1101, 20, 1077, 3, 89, 115, 2594, 1124, 72, 14, 2529, 1109, 1080, 95, 2597, 10, 135, 51, 2542, 40, 45, 1095, 41, 2501, 2595, 33, 74, 2592, 4504, 30, 126, 2001, 1106, 2075, 2563, 2596, 2568, 2051, 75, 60, 4502, 49, 100, 2541, 1128, 2522, 2523, 2604, 2562, 129, 1063, 2606, 2561, 1065, 131, 1144, 1131, 2564, 2078, 9, 1141, 2057, 1147, 6, 4, 2040, 2593, 19, 2567, 1103, 2598, 1047, 1119, 2519, 23, 2545, 1138, 2546, 1118, 133, 7, 58, 1134, 1123, 26, 1108, 2015, 2605, 1076, 2041, 54, 2514, 17, 1097, 1127, 104, 113, 2513, 1070, 1048, 2023, 2521, 119, 44, 185, 152, 177, 283, 149, 162, 147, 373, 274, 3514, 209, 355, 246, 285, 139, 198, 464, 402, 256, 401, 332, 288, 382, 3515, 391, 377, 3508, 173, 357, 381, 353, 3502, 492, 385, 407, 374, 406, 393, 439, 3509, 242, 394, 154, 174, 305, 489, 409, 227, 433, 262, 150, 146, 380, 476, 202, 151, 365, 230, 351, 170, 266, 405, 167, 282, 138, 161, 3510, 376, 187, 486, 366, 468, 3516, 386, 469, 255, 158, 428, 350, 403, 3517, 179, 3009, 243, 160, 420, 225, 181, 477, 392, 3511, 264, 232, 363, 195, 248, 148, 156, 396, 487, 3010, 168, 361, 456, 172, 434, 273, 241, 196, 375, 364, 3504, 488, 349, 281, 3503, 3007, 379, 472, 193, 159, 183, 348, 143, 473, 217, 219, 448, 438, 204, 327, 245, 417, 343, 208, 4004, 4001, 4009, 4005, 4008, and 4006.

In some embodiments, a compound of Formula (III) is selected from compound 22, 32, 42, 34, 36, 37, 1150, 1129, 1132, 38, 28, 66, 1068, 1140, 85, 2601, 68, 1145, 59, 2079, 61, 2602, 2, 107, 2052, 2589, 1148, 13, 83, 2046, 52, 12, 69, 101, 1136, 46, 21, 109, 116, 16, 96, 15, 2533, 1046, 1, 1133, 1139, 130, 11, 35, 1107, 1142, 1149, 31, 1059, 2607, 2050, 2538, 1146, 106, 2502, 2554, 24, 2603, 1104, 2520, 62, 2530, 2002, 1053, 2552, 65, 50, 2049, 27, 120, 2055, 18, 67, 1051, 108, 1081, 2056, 2016, 118, 112, 2524, 1101, 20, 1077, 3, 89, 115, 2594, 1124, 72, 14, 2529, 1109, 1080, 95, 2597, 10, 135, 51, 2542, 40, 45, 1095, 41, 2501, 2595, 33, 74, 2592, 4504, 30, 126, 2001, 1106, 2075, 2563, 2596, 2568, 2051, 75, 60, 4502, 49, 100, 2541, 1128, 2522, 2523, 2604, 2562, 129, 1063, 2606, 2561, 1065, 131, 1144, 1131, 2564, 2078, 9, 1141, 2057, 1147, 6, 4, 2040, 185, 152, 177, 283, 149, 162, 147, 373, 274, 3514, 209, 355, 246, 285, 139, 198, 464, 402, 256, 401, 332, 288, 382, 3515, 391, 377, 3508, 173, 357, 381, 353, 3502, 492, 385, 407, 374, 406, 393, 439, 3509, 242, 394, 154, 174, 305, 489, 409, 227, 433, 262, 150, 146, 380, 476, 202, 151, 365, 230, 351, 4004, 4001, and 4009.

In some embodiments, a compound of Formula (III) is selected from compound 22, 32, 42, 34, 36, 37, 1150, 1129, 1132, 38, 28, 66, 1068, 1140, 85, 2601, 68, 1145, 59, 2079, 61, 2602, 2, 107, 2052, 2589, 1148, 13, 185, 152, and 177.

In some embodiments, a compound of Formula (III) is selected from compound 22, 1140, 32, 42, 36, 1129, 66, 68, 61, 83, 69, 109, 96, 1142, 74, 30, 34, 37, 1132, 38, 28, 85, 59, 2602, 2, 107, 52, 46, 116, 65, 50, 115, 72, 95, 40, 131, 73, 1145, 2079, 12, 16, 1139, 130, 1107, 2502, 2603, 1104, 67, 1081, 118, 112, 135, 126, 70, 1150, 2601, 21, 1133, 2607, 2050, 106, 24, 89, 2075, 100, 129, 1138, 54, 113, 2589, 1148, 13, 1136, 120, 108, 2016, 1109, 10, 44, 2070, 2533, 31, 2056, 1101, 51, 1095, 49, 1103, 98, 114, 11, 2520, 14, 41, 57, 2052, 2530, 18, 133, 35, 1128, 1144, 99, 2606, 1, 2538, 2002, 2055, 1077, 2568, 119, 111, 1068, 1080, 2597, 45, 2563, 56, 2524, 2545, 27, 1124, 2522, 1079, 2552, 2501, 4, 58, 2015, 1097, 2054, 2066, 2596, 2051, 2514, 2045, 2595, 127, 128, 2546, 137, 1146, 26, 1063, 1119, 104, 2023, 94, 101, 48, 97, 71, 2529, 1127, 2561, 62, 1111, 2060, 2064, 2001, 60, 2057, 2562, 2511, 15, 33, 2077, 4504, 6, 53, 2542, 1130, 2022, 2594, 2567, 2513, 1076, 2072, 1092, 1106, 1108, 2067, 1102, 1059, 2605, 2521, 17, 47, 2017, 1141, 1149, 1113, 2564, 1118, 2069, 2061, 4502, 23, 2063, 20, 1134, 2519, 1131, 1100, 2604, 2078, 1123, 9, 1153, 2010, 2516, 2553, 2037, 2555, 7, 2543, 2541, 2068, 2547, 2540, 2049, 1065, 1147, 29, 2059, 2065, 123, 2593, 55, 2550, 2011, 2048, 90, 122, 4503, 2590, 1105, 2532, 63, 1084, 103, 25, 1143, 2531, 2040, 2009, 1094, 2544, 1078, 1110, 3, 2042, 2024, 1070, 2076, 92, 2517, 1120, 1135, 19, 2071, 2585, 2518, 2058, 2029, 2021, 2592, 91, 5, 121, 1152, 1112, 102, 2020, 2074, 1083, 1099, 2508, 2556, 1137, 105, 2587, 2035, 2557, 117, 78, 1122, 2043, 84, 2551, 2549, 134, 2062, 1075, 1064, 1062, 1067, 1151, 2586, 4505, 1115, 1096, 2053, 136, 2013, 2575, 43, 75, 1098, 80, 2507, 1114, 2033, 125, 1058, 2044, 2025, 2047, 2019, 2027, 124, 77, 81, 1066, 2026, 88, 2576, 64, 152, 283, 373, 209, 355, 382, 391, 377, 381, 380, 185, 177, 149, 162, 274, 285, 139, 198, 402, 256, 401, 288, 173, 407, 374, 406, 393, 242, 305, 230, 232, 246, 464, 385, 394, 409, 433, 365, 170, 167, 376, 386, 160, 225, 361, 414, 422, 332, 154, 405, 366, 363, 172, 384, 359, 3514, 187, 447, 360, 147, 3515, 357, 353, 351, 158, 350, 3508, 227, 392, 204, 3502, 174, 395, 150, 428, 181, 439, 168, 202, 151, 161, 195, 159, 262, 179, 434, 349, 415, 219, 276, 3509, 208, 169, 3510, 243, 248, 241, 375, 448, 417, 444, 196, 352, 403, 420, 354, 387, 419, 200, 486, 421, 266, 156, 476, 398, 344, 3516, 430, 389, 489, 3511, 226, 492, 367, 473, 399, 281, 423, 282, 347, 404, 411, 379, 400, 224, 371, 3517, 435, 383, 472, 362, 206, 445, 368, 364, 416, 432, 284, 348, 370, 456, 469, 396, 192, 264, 236, 438, 143, 157, 3010, 239, 327, 388, 255, 217, 3512, 193, 183, 410, 431, 189, 3503, 245, 273, 201, 3504, 203, 164, 176, 488, 194, 429, 155, 437, 279, 425, 207, 443, 343, 304, 325, 372, 182, 477, 254, 308, 345, 178, 397, 441, 427, 146, 418, 186, 212, 221, 275, 346, 269, 289, 148, 3012, 278, 440, 138, 238, 475, 153, 378, 166, 487, 145, 265, 468, 191, 3001, 229, 197, 454, 424, 446, 247, 3505, 306, 233, 455, 3513, 3004, 210, 390, 483, 491, 213, 286, 141, 453, 3518, 463, 470, 458, 413, 342, 163, 442, 426, 436, 408, 199, 218, 171, 369, 474, 467, 223, 250, 299, 234, 211, 214, 280, 335, 188, 261, 338, 318, 484, 180, 260, 480, 320, 303, 140, 490, 465, 165, 3011, 478, 293, 277, 4004, 4001, 4003, 4006, 4009, 4005, 4010, 4002, and 4008.

In some embodiments, a compound of Formula (III) is selected from compound 22, 1140, 32, 42, 36, 1129, 66, 68, 61, 83, 69, 109, 96, 1142, 74, 30, 34, 37, 1132, 38, 28, 85, 59, 2602, 2, 107, 52, 46, 116, 65, 50, 115, 72, 95, 40, 131, 73, 1145, 2079, 12, 16, 1139, 130, 1107, 2502, 2603, 1104, 67, 1081, 118, 112, 135, 126, 70, 1150, 2601, 21, 1133, 2607, 2050, 106, 24, 89, 2075, 100, 129, 1138, 54, 113, 2589, 1148, 13, 1136, 120, 108, 2016, 1109, 10, 44, 2070, 2533, 31, 2056, 1101, 51, 1095, 49, 1103, 98, 114, 11, 2520, 14, 41, 57, 2052, 2530, 18, 133, 35, 1128, 1144, 99, 2606, 1, 2538, 2002, 2055, 1077, 2568, 119, 111, 1068, 1080, 2597, 45, 2563, 56, 2524, 2545, 27, 1124, 2522, 1079, 2552, 2501, 4, 58, 2015, 1097, 2054, 2066, 2596, 2051, 2514, 2045, 2595, 127, 128, 2546, 137, 1146, 26, 1063, 1119, 104, 2023, 94, 101, 48, 97, 71, 2529, 1127, 2561, 62, 1111, 2060, 2064, 2001, 60, 2057, 2562, 2511, 15, 33, 2077, 4504, 6, 53, 2542, 1130, 2022, 2594, 2567, 2513, 1076, 2072, 1092, 1106, 1108, 2067, 1102, 1059, 2605, 2521, 17, 47, 2017, 1141, 1149, 1113, 2564, 1118, 2069, 2061, 4502, 23, 2063, 20, 1134, 2519, 1131, 1100, 2604, 2078, 1123, 9, 1153, 2010, 2516, 2553, 2037, 2555, 7, 2543, 2541, 2068, 2547, 2540, 2049, 1065, 1147, 29, 2059, 2065, 123, 2593, 55, 2550, 2011, 2048, 90, 122, 4503, 2590, 1105, 2532, 63, 1084, 103, 25, 1143, 2531, 2040, 2009, 1094, 2544, 1078, 1110, 3, 2042, 2024, 1070, 2076, 92, 2517, 1120, 1135, 19, 2071, 2585, 2518, 2058, 2029, 2021, 2592, 91, 5, 121, 1152, 1112, 102, 2020, 2074, 1083, 1099, 2508, 2556, 1137, 105, 2587, 2035, 2557, 117, 78, 1122, 2043, 84, 2551, 2549, 134, 2062, 1075, 1064, 1062, 152, 283, 373, 209, 355, 382, 391, 377, 381, 380, 185, 177, 149, 162, 274, 285, 139, 198, 402, 256, 401, 288, 173, 407, 374, 406, 393, 242, 305, 230, 232, 246, 464, 385, 394, 409, 433, 365, 170, 167, 376, 386, 160, 225, 361, 414, 422, 332, 154, 405, 366, 363, 172, 384, 359, 3514, 187, 447, 360, 147, 3515, 357, 353, 351, 158, 350, 3508, 227, 392, 204, 3502, 174, 395, 150, 428, 181, 439, 168, 202, 151, 161, 195, 159, 262, 179, 434, 349, 415, 219, 276, 3509, 208, 169, 3510, 243, 248, 241, 375, 448, 417, 444, 196, 352, 403, 420, 354, 387, 419, 200, 486, 421, 266, 156, 476, 398, 344, 3516, 430, 389, 489, 3511, 226, 492, 367, 473, 399, 281, 423, 282, 347, 404, 411, 379, 400, 224, 371, 3517, 435, 383, 472, 362, 206, 445, 368, 364, 416, 432, 284, 348, 370, 456, 469, 396, 192, 264, 236, 438, 143, 157, 3010, 239, 327, 388, 255, 217, 3512, 193, 183, 410, 431, 189, 3503, 245, 273, 201, 3504, 203, 164, 176, 488, 194, 429, 155, 437, 279, 425, 207, 443, 343, 304, 325, 372, 182, 477, 254, 308, 345, 178, 397, 441, 427, 146, 418, 186, 212, 221, 275, 346, 269, 289, 148, 3012, 278, 440, 138, 238, 475, 153, 378, 166, 487, 145, 265, 468, 191, 3001, 229, 197, 454, 424, 446, 247, 3505, 306, 233, 455, 3513, 3004, 210, 390, 483, 491, 213, 286, 141, 453, 3518, 463, 470, 4004, 4001, 4003, 4006, 4009, 4005, 4010, 4002, and 4008.

In some embodiments, a compound of Formula (III) is selected from compound 22, 1140, 32, 42, 36, 1129, 66, 68, 61, 83, 69, 109, 96, 1142, 74, 30, 34, 37, 1132, 38, 28, 85, 59, 2602, 2, 107, 52, 46, 116, 65, 50, 115, 72, 95, 40, 131, 73, 1145, 2079, 12, 16, 1139, 130, 1107, 2502, 2603, 1104, 67, 1081, 118, 112, 135, 126, 70, 1150, 2601, 21, 1133, 2607, 2050, 106, 24, 89, 2075, 100, 129, 1138, 54, 113, 2589, 1148, 13, 1136, 120, 108, 2016, 1109, 10, 44, 2070, 2533, 31, 2056, 1101, 51, 1095, 49, 1103, 98, 114, 11, 2520, 14, 41, 57, 2052, 2530, 18, 133, 35, 1128, 1144, 99, 2606, 1, 2538, 2002, 2055, 1077, 2568, 119, 111, 1068, 1080, 2597, 45, 2563, 56, 2524, 2545, 27, 1124, 2522, 1079, 2552, 2501, 4, 58, 2015, 1097, 2054, 2066, 2596, 2051, 2514, 2045, 2595, 127, 128, 2546, 137, 1146, 26, 1063, 1119, 104, 2023, 94, 101, 48, 97, 71, 2529, 1127, 2561, 62, 1111, 2060, 2064, 2001, 60, 2057, 2562, 2511, 15, 33, 2077, 4504, 6, 53, 2542, 1130, 2022, 2594, 2567, 2513, 1076, 2072, 1092, 1106, 1108, 2067, 1102, 1059, 2605, 2521, 17, 47, 2017, 1141, 1149, 1113, 2564, 1118, 2069, 2061, 4502, 23, 2063, 20, 1134, 2519, 1131, 1100, 2604, 2078, 1123, 9, 1153, 2010, 2516, 2553, 2037, 2555, 7, 2543, 2541, 2068, 2547, 2540, 152, 283, 373, 209, 355, 382, 391, 377, 381, 380, 185, 177, 149, 162, 274, 285, 139, 198, 402, 256, 401, 288, 173, 407, 374, 406, 393, 242, 305, 230, 232, 246, 464, 385, 394, 409, 433, 365, 170, 167, 376, 386, 160, 225, 361, 414, 422, 332, 154, 405, 366, 363, 172, 384, 359, 3514, 187, 447, 360, 147, 3515, 357, 353, 351, 158, 350, 3508, 227, 392, 204, 3502, 174, 395, 150, 428, 181, 439, 168, 202, 151, 161, 195, 159, 262, 179, 434, 349, 415, 219, 276, 3509, 208, 169, 3510, 243, 248, 241, 375, 448, 417, 444, 196, 352, 403, 420, 354, 387, 419, 200, 486, 421, 266, 156, 476, 398, 344, 3516, 430, 389, 489, 3511, 226, 492, 367, 473, 399, 281, 423, 282, 347, 404, 411, 379, 400, 224, 371, 3517, 435, 383, 472, 362, 206, 445, 368, 364, 416, 432, 284, 348, 370, 456, 469, 396, 192, 264, 236, 438, 143, 157, 3010, 239, 327, 388, 255, 217, 3512, 193, 183, 410, 431, 189, 3503, 245, 273, 4004, and 4001.

In some embodiments, a compound of Formula (III) is selected from compound 22, 1140, 32, 42, 36, 1129, 66, 68, 61, 83, 69, 109, 96, 1142, 74, 30, 34, 37, 1132, 38, 28, 85, 59, 2602, 2, 107, 52, 46, 116, 65, 50, 115, 72, 95, 40, 131, 73, 1145, 2079, 12, 16, 1139, 130, 1107, 2502, 2603, 1104, 67, 1081, 118, 112, 135, 126, 70, 1150, 2601, 21, 1133, 2607, 2050, 106, 24, 89, 2075, 100, 129, 1138, 54, 113, 2589, 1148, 13, 1136, 120, 108, 2016, 1109, 10, 44, 2070, 2533, 31, 2056, 1101, 51, 1095, 49, 1103, 98, 114, 11, 2520, 14, 41, 57, 2052, 2530, 18, 133, 35, 1128, 1144, 99, 152, 283, 373, 209, 355, 382, 391, 377, 381, 380, 185, 177, 149, 162, 274, 285, 139, 198, 402, 256, 401, 288, 173, 407, 374, 406, 393, 242, 305, 230, 232, 246, 464, 385, 394, 409, 433, 365, 170, 167, 376, 386, 160, 225, 361, 414, 422, 332, 154, 405, 366, 363, 172, 384, 359, 3514, 187, 447, 360, 147, 3515, 357, 353, 351, 158, 350, 3508, 227, 392, 204, 3502, 174, 395, 150, 428, and 181.

Methods of administration of a compound or salt of Formula (I), (II-A), (IV), or (III) discussed herein may be used for the treatment of cardiac conditions. In an aspect, the present disclosure provides a method of treating a condition selected from hypertrophic cardiomyopathy (HCM); heart failure with preserved ejection fraction (HFpEF); disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; ischemia; and andangina. In some embodiments, said heart failure with preserved ejection fraction (HFpEF) comprises one or more disorders selected from disorders of relaxation and disorders of chamber stiffness (diabetic HFpEF). In some embodiments, said left ventricular (LV) hypertrophy is malignant left ventricular (LV) hypertrophy. In some embodiments, said restrictive cardiomyopathy comprises one or more subgroups selected from inflammatory subgroups, infiltrative subgroups, storage subgroups, idiopathic/inherited subgroups, congenital heart disease subgroups. In some embodiments, said inflammatory subgroups comprise one or more subgroups selected from Loefllers and EMF. In some embodiments, said inflammatory subgroups comprise one or more subgroups selected from amyloid, sarcoid, and XRT. In some embodiments, said storage subgroups comprise one or more subgroups selected from hemochromatosis, Fabry, and glycogen storage disease. In some embodiments, said idiopathic/inherited subgroups comprise one or more subgroups selected from Trop I (beta myosin HC), Trop T (alpha cardiac actin), and desmin related subgroups. In some embodiments, said congenital heart disease subgroups comprise one or more subgroups selected from pressure-overloaded RV, Tetralogy of Fallot, and pulmonic stenosis. In an aspect, the present disclosure provides a method of treating hypertrophic cardiomyopathy or a related condition comprising administering to a subject in need thereof a compound or salt disclosed herein.

In an aspect, the present disclosure provides a method of treating obstructive hypertrophic cardiomyopathy comprising administering to a subject in need thereof a compound or salt disclosed herein. In an aspect, the present disclosure provides a method of treating non-obstructive hypertrophic cardiomyopathy comprising administering to a subject in need thereof a compound or salt of disclosed herein. In an aspect, the present disclosure provides a method of treating heart failure with preserved ejection fraction comprising administering to a subject in need thereof a compound or disclosed herein. In an aspect, the present disclosure provides a method of treating left ventricle stiffness comprising administering to a subject in need thereof a compound or salt disclosed herein.

Pharmaceutical Compositions

In aspect, the disclosed herein is a pharmaceutical composition comprising any compound or salt thereof disclosed herein and a pharmaceutically acceptable excipient. In aspect, disclosed herein is a pharmaceutical composition comprising a compound or salt of any one of Formula (I), Formula (II-A), Formula (IV), or Formula (III). In aspect, the disclosed herein is a pharmaceutical composition comprising a compound or salt of any one of Formula (I), Formula (II-A), Formula (IV), or Formula (III). In aspect, the disclosed herein is a pharmaceutical composition comprising a compound or salt of any one of formula (I). In aspect, the disclosed herein is a pharmaceutical composition comprising a compound or salt of any one of formula (II-A). In aspect, the disclosed herein is a pharmaceutical composition comprising a compound or salt of any one of formula (IV). In aspect, the disclosed herein is a pharmaceutical composition comprising a compound or salt of any one of formula (III).

Combination Therapies

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually hours, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

The chemical entities described herein (e.g., a compound or salt of Formula (I), (II-A), (IV), or (III)) can be co-administered with, and the pharmaceutical compositions can include, the additional active agent (e.g., pharmaceutical agents, adjuvants, and the like).

In certain embodiments, a compound or salt of the disclosure may be administered in combination with a corticosteroid. In certain embodiments, a compound or salt of the disclosure is administered in combination with deflazacort. In certain embodiments, a compound or salt of the disclosure is administered in combination with prednisone. In certain embodiments, a compound or salt of the disclosure is administered in combination with a morpholino antisense oligomer. In certain embodiments, a compound or salt of the disclosure is administered in combination with and exon skipping therapy. In certain embodiments, the additional therapeutic agent is eteplirsen or ataluren. In certain embodiments, a compound or salt of the disclosure is administered in combination with givinostat.

In certain embodiments, a compound or salt of the disclosure is used in combination with a gene therapy. In certain embodiments, the compound or salt of the disclosure is used in combination with adeno-associated virus (AAV) containing genes encoding replacement proteins, e.g., dystrophin, or truncated version thereof, e.g., microdystrophin. In certain embodiments, a compound or salt of the disclosure is administered in combination with vamorolone.

In certain embodiments, a compound or salt of the disclosure is administered in combination with one or more incretin therapeutic(s).

In certain embodiments, a compound or salt of the disclosure (such as compound 2014, 2018, 2028, 2034, 2045, 2059, 2508, 2509, 2510, 2512, 2523, 2527, 2528, 2534, 2535, 2536, 2537, 2540, 2547, 2548, 2551, 2560, 2566, 2570, 2572, 2578, 2580, 2582, 2584, 2588, 2598, 2599, 2608, 3003, 3006, 3506, 3512, 3519, 4007, or a salt thereof), or a compound or salt with a Y125 value in Table 5, Table 6, or Table 7, may be administered in combination with one or more agents selected from a GLP-1 (e.g., Glucagon-like peptide-1) modulator (e.g., a GLP-1 agonist). In some embodiments, a compound or salt of the present disclosure may be administered in combination with a GLP-1 agonist. In some embodiments, a compound or salt of the present disclosure may be administered in combination with an SGLT2 inhibitor. In some embodiments, a compound or salt of the present disclosure may be administered in combination with a GIP agonist. In some embodiments, a compound or salt of the present disclosure may be administered in combination with a lipase inhibitor (e.g., orlistat). In certain embodiments, a compound or salt of the disclosure may be administered in combination with one or more agents selected from a GIP (e.g., glucose-dependent insulinotropic polypeptide) modulator (e.g., a GIP agonist). In certain embodiments, a compound or salt of the disclosure may be administered in combination with one or more antidiabetic medication(s). In certain embodiments, a compound or salt of the disclosure may be administered in combination with one or more agents selected from Dulaglutide, Exenatide, Semaglutide, Liraglutide, Lixisenatide, and Tirzepatide. In certain embodiments, a compound or salt of the disclosure may be administered in combination with one or more SGLT2 inhibitors (e.g., Dapagliflozin, Canagliflozin, Empagliflozin, or Remogliflozin). In certain embodiments, a compound or salt of the disclosure may be administered in combination with one or more insulin sensitizers, such as a buiguanide (e.g., such as metformin, phenformin, or buformin), a thiazolidinedione (e.g., Rosiglitazone, Pioglitazone, or Troglitazone), or a Lyn kinase activator, such as tolimidone. In certain embodiments, a compound or salt of the disclosure may be administered in combination with one or more Secretagogues (e.g., one or more stimulators of beta cells), such as a "sulfonylureas" type secretagogue (e.g., a First-generation agent, such as tolbutamide, acetohexamide, tolazamide, chlorpropamide; or a Second-generation agent, such as glipizide, glyburide or glibenclamide, glimepiride, gliclazide, glyclopyramide, or gliquidone); or a "Meglitinides-type" secretagogue (e.g., repaglinide, nateglinide). In certain embodiments, a compound or salt of the disclosure may be administered in combination with one or more Alpha-glucosidase inhibitors (e.g., decreasing the rate at which glucose is absorbed from the gastrointestinal tract), such as miglitol, acarbose, or voglibose.

In certain embodiments, a compound or salt of the disclosure may be administered in combination with a modulator of one or more targets selected from: skeletal myosin, skeletal actin, skeletal tropomyosin, skeletal troponin C, skeletal troponin I, skeletal troponin T, and skeletal muscle, including fragments and isoforms thereof, and the skeletal sarcomere. In certain embodiments, a compound or salt of the disclosure may be administered in combination with one or more therapeutic agent(s) useful in the treatment of the aforementioned disorders including: anti-obesity agents, anti-sarcopenia agents, anti-wasting syndrome agents, anti-frailty agents, anti-cachexia agents, anti-muscle spasm agents, agents against post-surgical and post-traumatic muscle weakness, and anti-neuromuscular disease agents.

EXAMPLES

The invention now being generally described, it will be more readily understood by reference to the following examples which are included merely for purposes of illustration of certain aspects and embodiments of the present invention, and are not intended to limit the invention in any way.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

In some embodiments, compounds of the disclosure are below in Table 1, Table 2, and Table 3.

In some embodiments, compounds of the disclosure are below in Table 1, Table 2, Table 3, and Table 4.

In some embodiments, compounds of the disclosure are below in Table 1. In some embodiments, compounds of the disclosure are below in Table 2. In some embodiments, compounds of the disclosure are below in Table 3. In some embodiments, compounds of the disclosure are below in Table 4.

In some embodiments, compounds of the disclosure are selected from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116,117, 118, 119, 120, 121, 122, 123, 124, 125, 126, 127, 128, 129, 130, 131, 132, 133, 134, 135, 136, 137, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 2001, 2002, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 1153, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2590, 2591, 2592, 2593, 2594, 2595, 2596, 2597, 2598, 2599, 2600, 2601, 2602, 2603, 2604, 2605, 2606, 2607, 2608, 4502, 4503, 4504, 4505, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 3001, 3002, 3003, 3004, 3005, 3006, 3007, 3008, 3009, 3010, 3011, 3012, 3013, 3502, 3503, 3504, 3505, 3506, 3507, 3508, 3509, 3510, 3511, 3512, 3513, 3514, 3515, 3516, 3517, 3518, 3519, 4001, 4002, 4003, 4004, 4005, 4006, 4007, 4008, 4009, 4010, 7001, 7002, 7003, 7004, 7005, 7006, 7007, 7008, 7009, 7010, 7011, 7012, 7013, 7014, 7015, 7016, 7017, 7018, 7019, 7020, 7021, 7022, 7023, 7024, 7025, 7026, 7027, 7028, 7029, 7030, 7031, 7032, 7033, 7034, 7035, 7036, 7037, 7038, 7039, 7040, 7041, 7042, 7043, 7044, 7045, 7046, 7047, 7048, 7049, 7050, 7051, 7052, 7053, 7054, 7055, 7056, 7057, 7058, 7059, 7060, 7061, 7062, 7063, 7064, 7065, 7066, 7067, 7068, 7069, 7070, 7071, 7072, 7073, 7074, 7075, 7076, 7077, 7078, 7079, 7080, 7081, 7082, 7083, 7084, 7085, 7086, 7087, 7088, 7089, 7090, 7091, 7092, 7093, 7094, 4801, 4802, 4803, 4804, 4805, 4806, 4807, 4808, 4809, 4810, 4811, 4812, 4813, 4814, 4815, 4816, 4817, 4818, 4819, 4820, 4821, 4822, 4823, 4824, 4825, 4826, 4827, 4828, 4829, 4830, 4831, 4832, 4833, 4834, 4835, 4836, 4837, 4838, 4839, 4840, 4841, 4842, 4843, 4844, 4845, 4846, 4847, 4848, 4849, 4850, 3520, 3521, 3522, and 3523.

In some embodiments, compounds of the disclosure are selected from compound: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 2001, 2002, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 1153, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2590, 2591, 2592, 2593, 2594, 2595, 2596, 2597, 2598, 2599, 2600, 2601, 2602, 2603, 2604, 2605, 2606, 2607, 2608, 4502, 4503, 4504, 4505, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 3001, 3002, 3003, 3004, 3005, 3006, 3007, 3008, 3009, 3010, 3011, 3012, 3013, 3502, 3503, 3504, 3505, 3506, 3507, 3508, 3509, 3510, 3511, 3512, 3513, 3514, 3515, 3516, 3517, 3518, 3519, 4001, 4002, 4003, 4004, 4005, 4006, 4007, 4008, 4009, 4010, 4801, 4802, 4803, 4804, 4805, 4806, 4807, 4808, 4809, 4810, 4811, 4812, 4813, 4814, 4815, 4816, 4817, 4818, 4819, 4820, 4821, 4822, 4823, 4824, 4825, 4826, 4827, 4828, 4829, 4830, 4831, 4832, 4833, 4834, 4835, 4836, 4837, 4838, 4839, 4840, 4841, 4842, 4843, 4844, 4845, 4846, 4847, 4848, 4849, 4850, 3520, 3521, 3522, and 3523.

TABLE 1
| Cmpd No. | Structure |
| --- | --- |
| 1 | 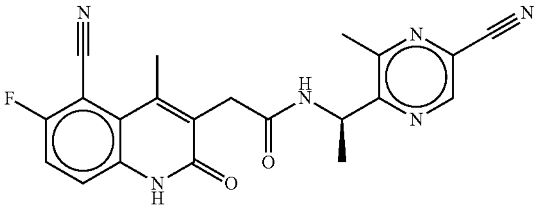 |
| 2 | 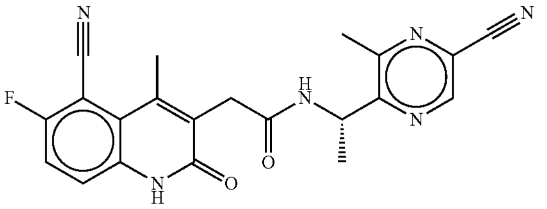 |
| 3 | 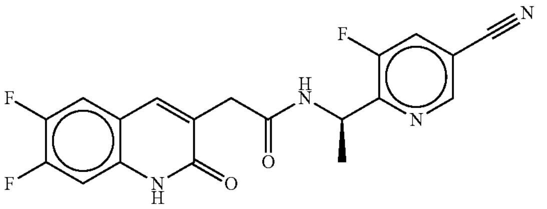 |
| 4 | 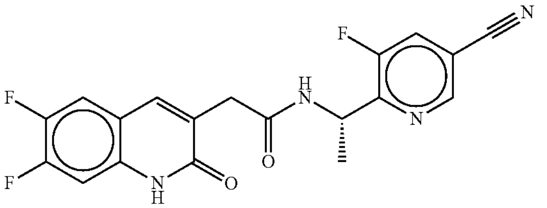 |
| 5 | 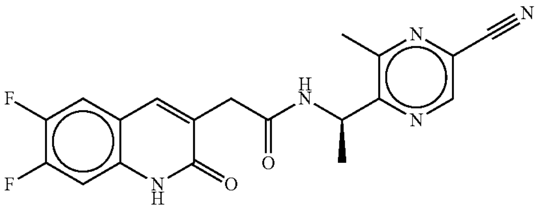 |
| 6 | 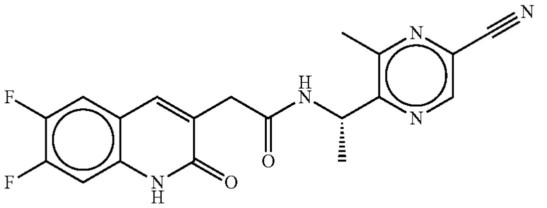 |
| 7 | 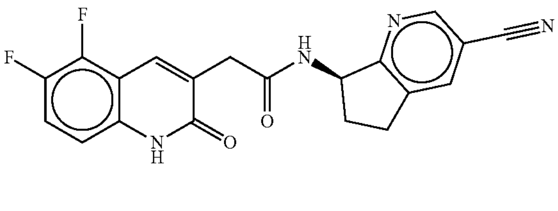 |

TABLE 1-continued
| Cmpd No. | Structure |
|---|---|
| 8 | 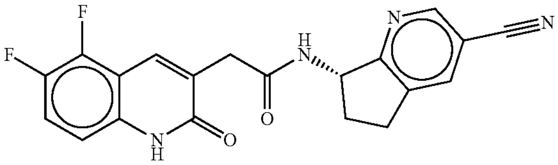 |
| 9 | 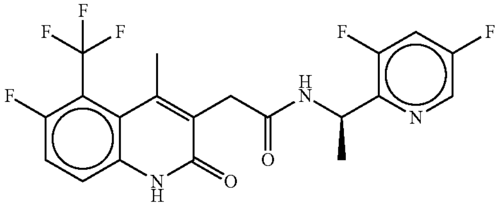 |
| 10 | 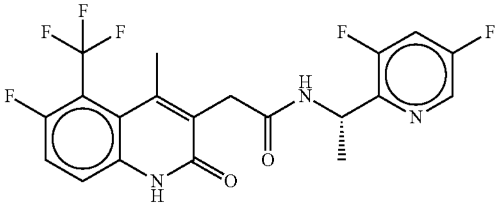 |
| 11 | 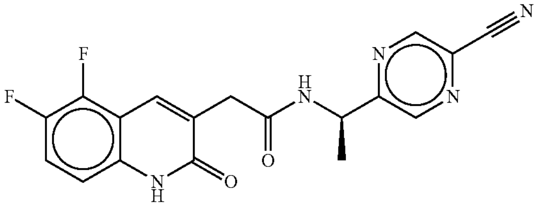 |
| 12 | 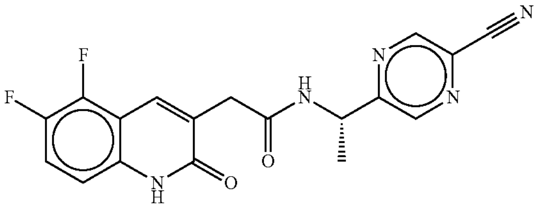 |
| 13 | 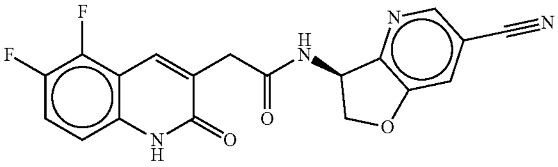 |
| 14 | 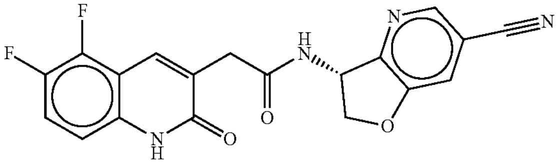 |

TABLE 1-continued
| Cmpd No. | Structure |
| --- | --- |
| 15 | 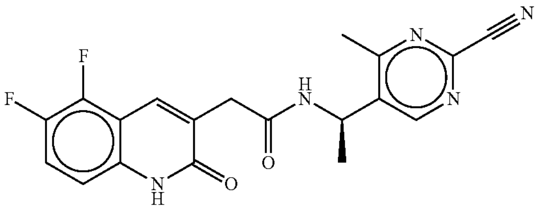 |
| 16 | 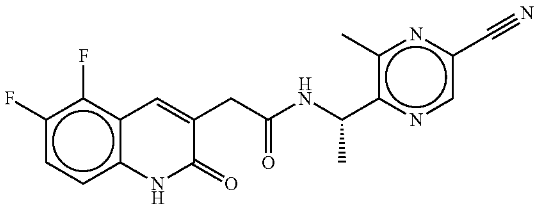 |
| 17 | 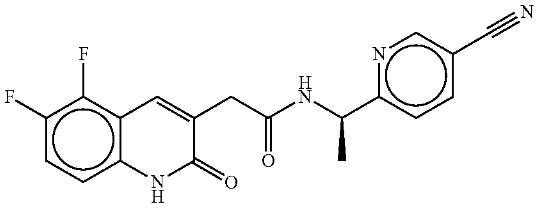 |
| 18 | 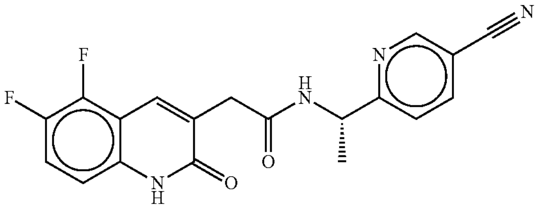 |
| 19 | 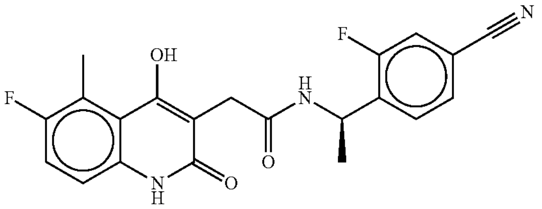 |
| 20 | 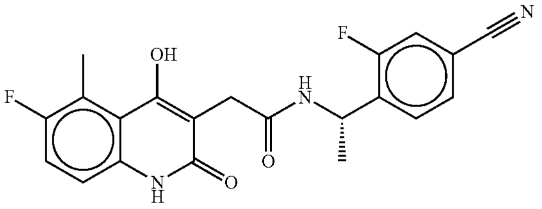 |
| 21 | 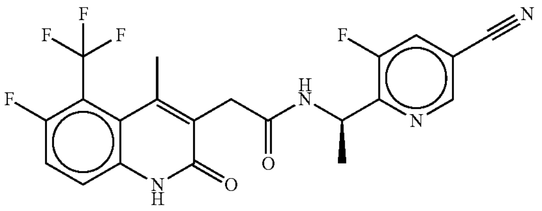 |

TABLE 1-continued
| Cmpd No. | Structure |
| --- | --- |
| 22 | 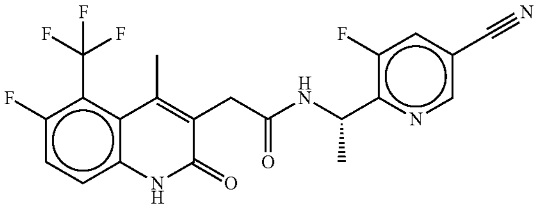 |
| 23 | 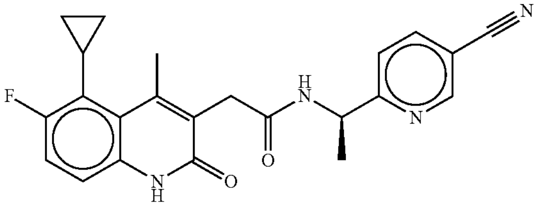 |
| 24 | 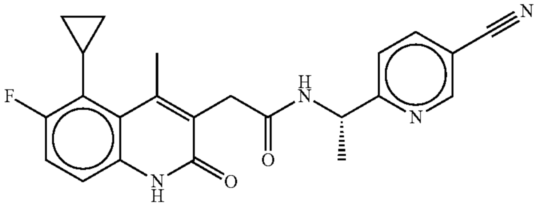 |
| 25 | 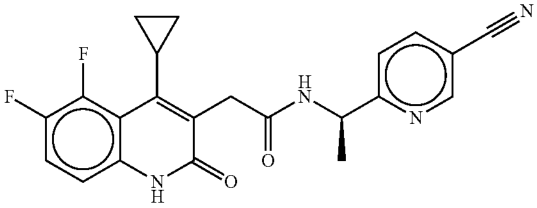 |
| 26 | 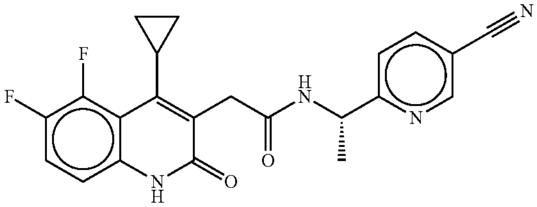 |
| 27 | 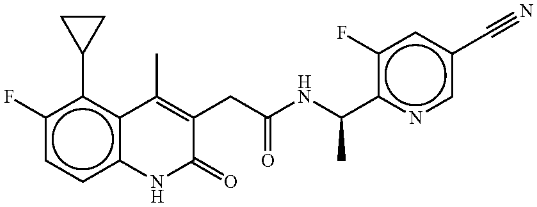 |
| 28 | 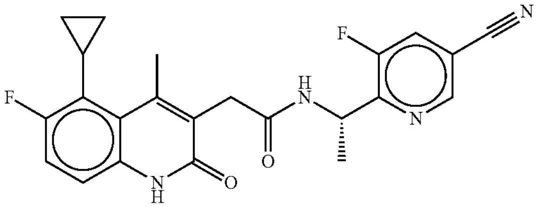 |

TABLE 1-continued
| Cmpd No. | Structure |
|---|---|
| 29 | 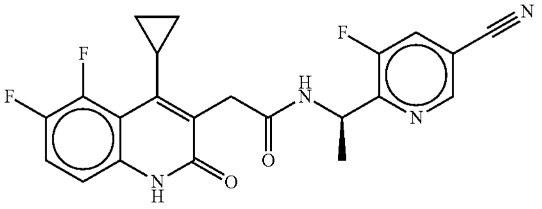 |
| 30 | 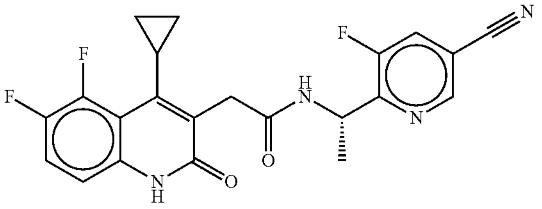 |
| 31 | 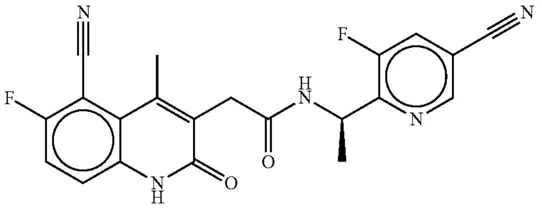 |
| 32 | 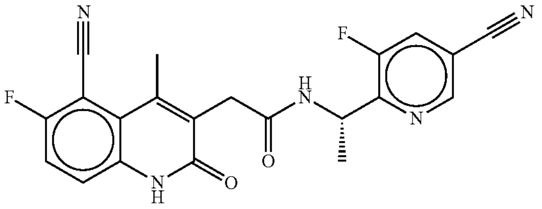 |
| 33 | 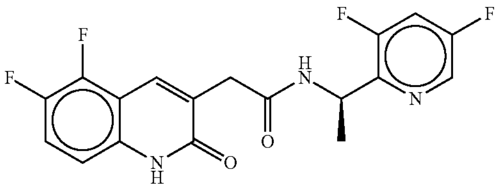 |
| 34 | 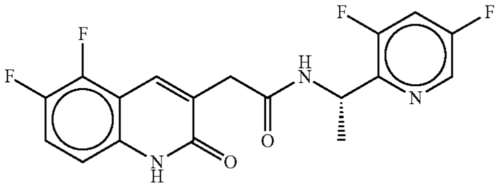 |
| 35 | 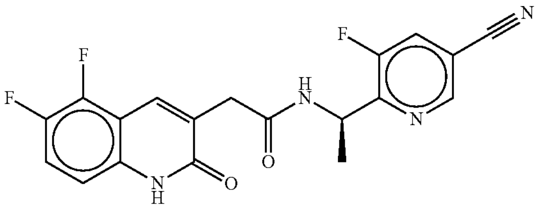 |

TABLE 1-continued
| Cmpd No. | Structure |
| --- | --- |
| 36 | 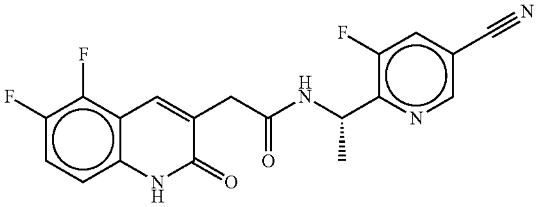 |
| 37 | 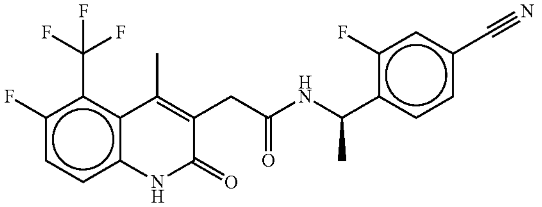 |
| 38 | 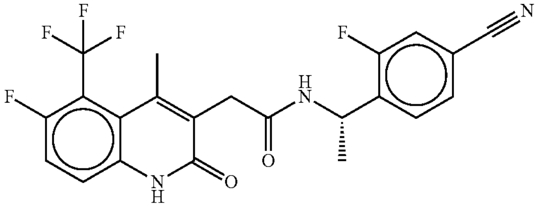 |
| 39 | 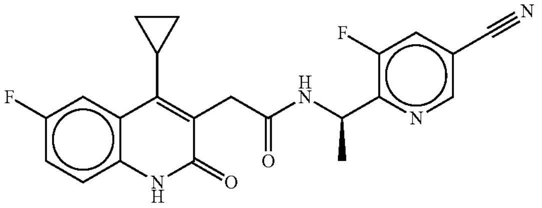 |
| 40 | 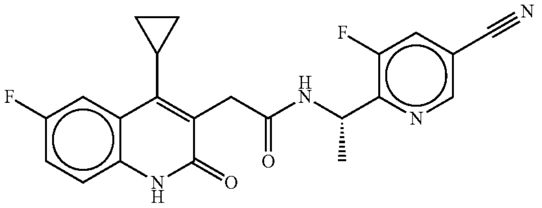 |
| 41 | 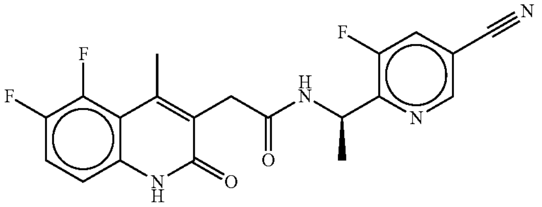 |
| 42 | 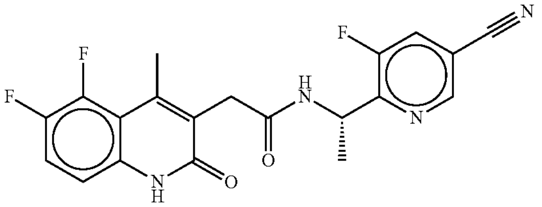 |

TABLE 1-continued
| Cmpd No. | Structure |
|---|---|
| 43 | 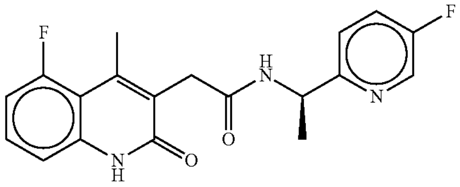 |
| 44 | 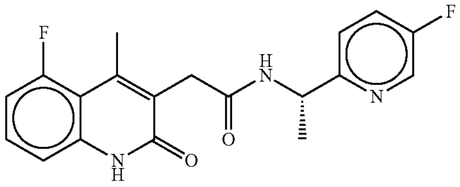 |
| 45 | 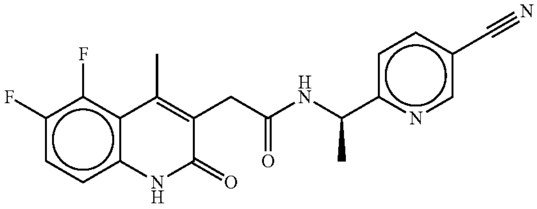 |
| 46 | 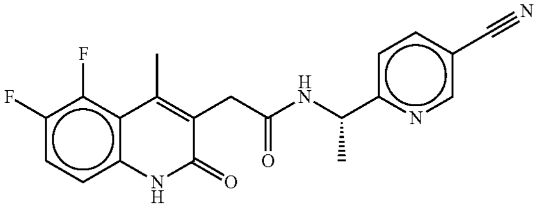 |
| 47 | 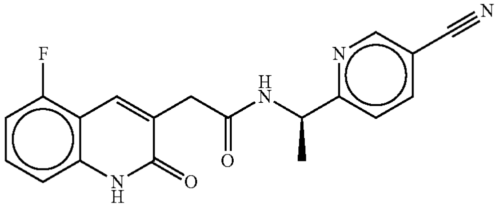 |
| 48 | 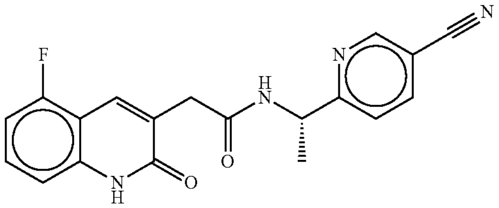 |
| 49 | 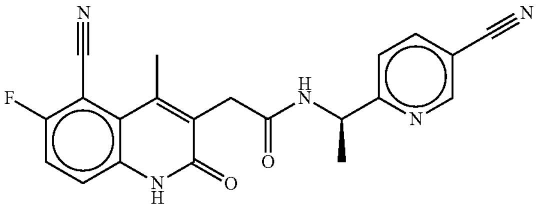 |

TABLE 1-continued
| Cmpd No. | Structure |
|---|---|
| 50 | 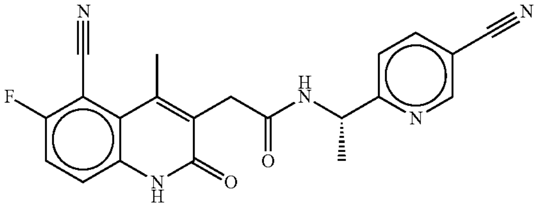 |
| 51 | 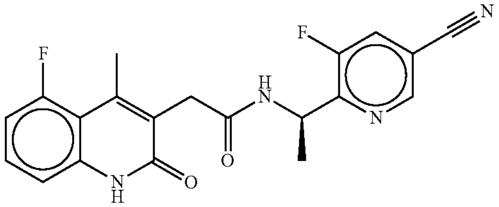 |
| 52 | 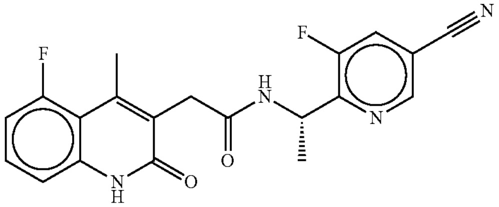 |
| 53 | 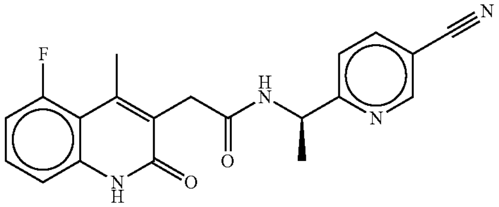 |
| 54 | 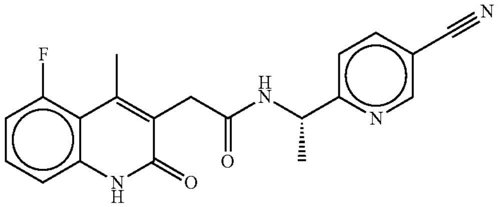 |
| 55 | 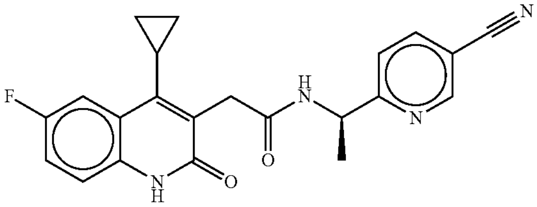 |
| 56 | 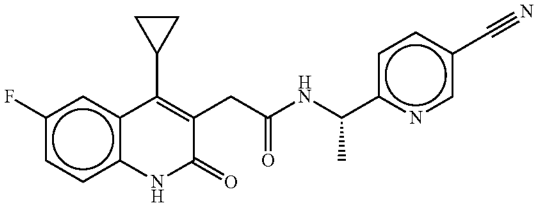 |

TABLE 1-continued
| Cmpd No. | Structure |
| --- | --- |
| 57 | 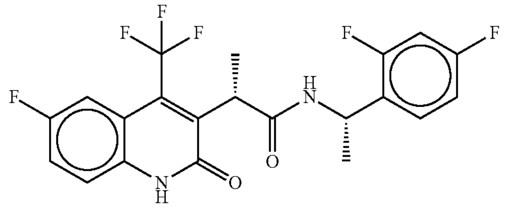 |
| 58 | 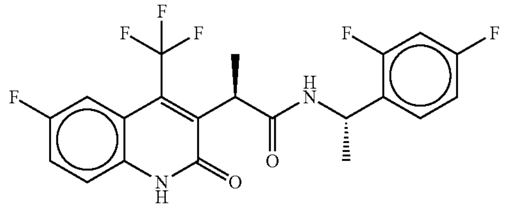 |
| 59 | 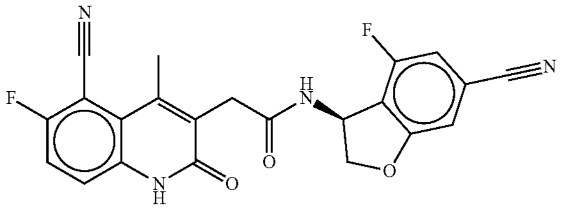 |
| 60 | 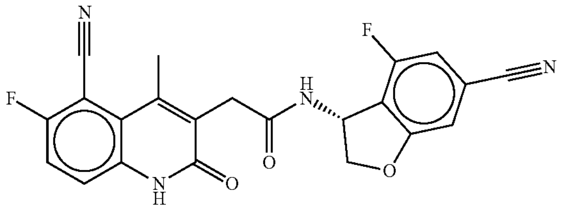 |
| 61 | 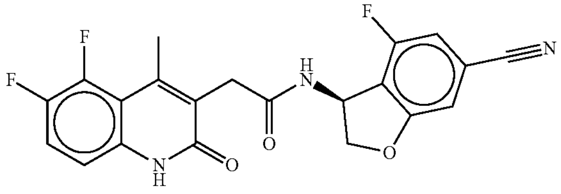 |
| 62 | 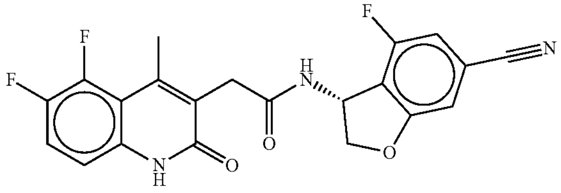 |
| 63 | 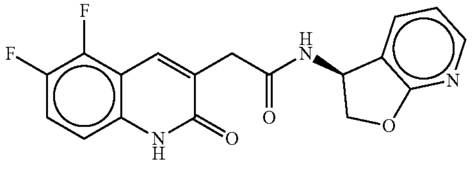 |

TABLE 1-continued
| Cmpd No. | Structure |
|---|---|
| 64 | 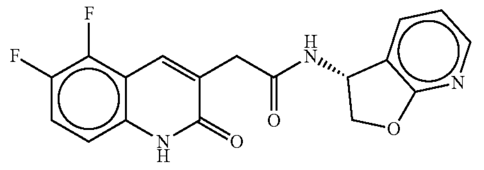 |
| 65 | 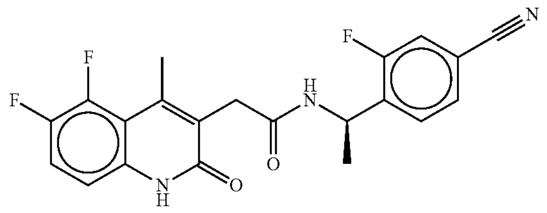 |
| 66 | 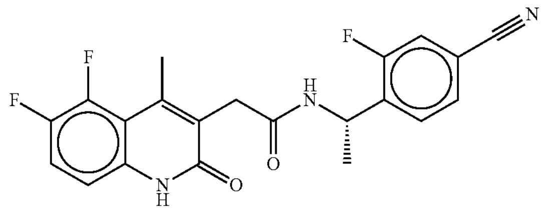 |
| 67 | 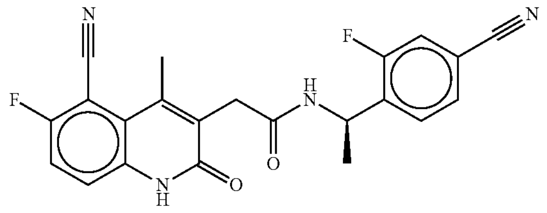 |
| 68 | 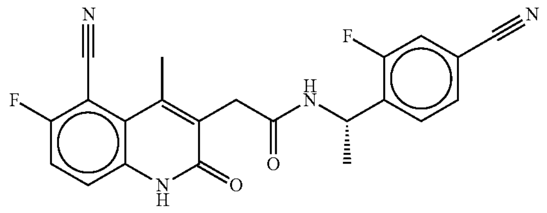 |
| 69 | 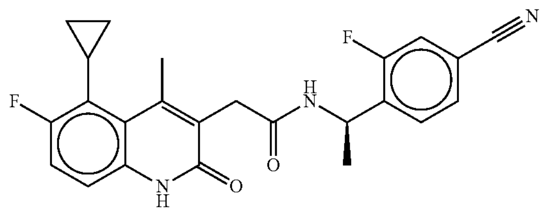 |
| 70 | 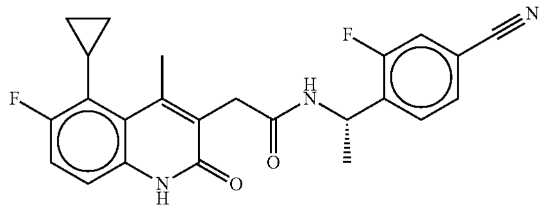 |

TABLE 1-continued
| Cmpd No. | Structure |
|---|---|
| 71 | 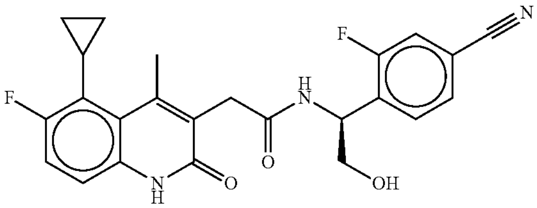 |
| 72 | 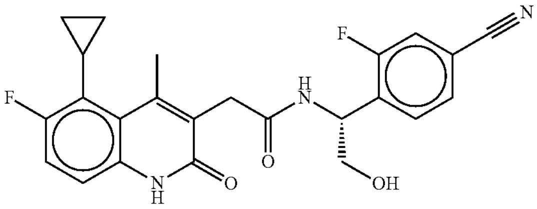 |
| 73 | 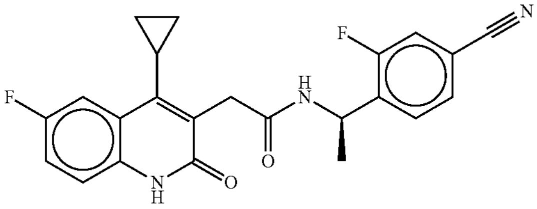 |
| 74 | 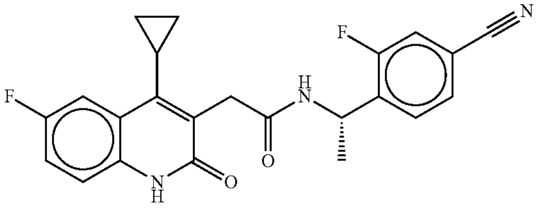 |
| 75 | 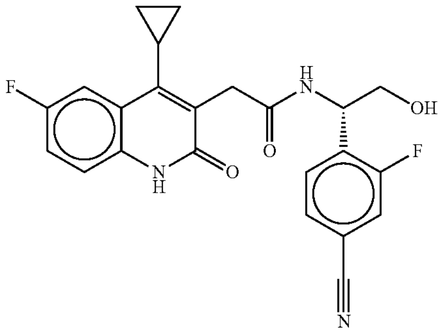 |
| 76 | 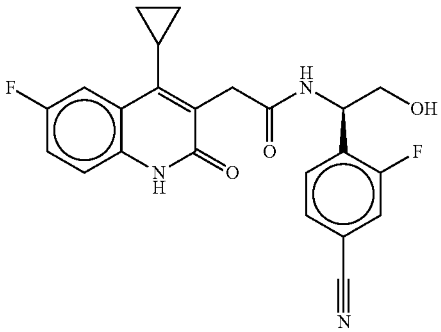 |

TABLE 1-continued
| Cmpd No. | Structure |
|---|---|
| 77 | 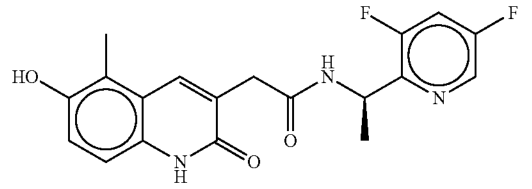 |
| 78 | 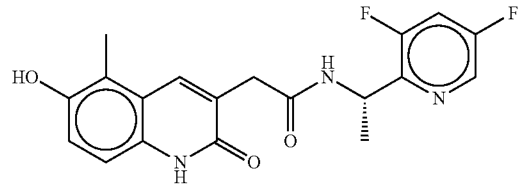 |
| 79 | 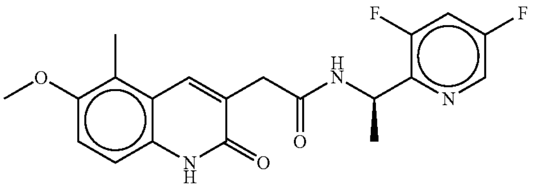 |
| 80 | 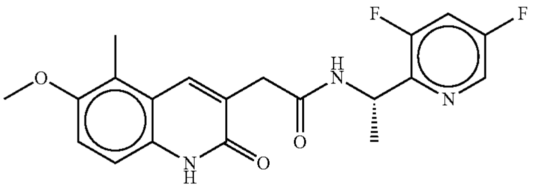 |
| 81 | 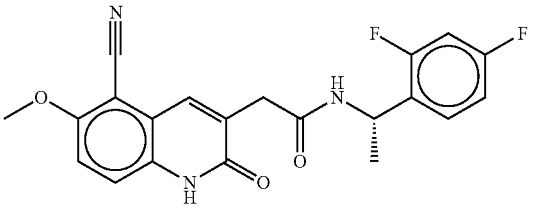 |
| 82 | 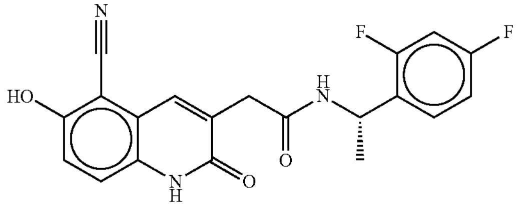 |
| 83 | 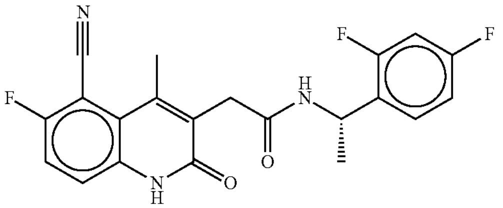 |

TABLE 1-continued
| Cmpd No. | Structure |
|---|---|
| 84 | 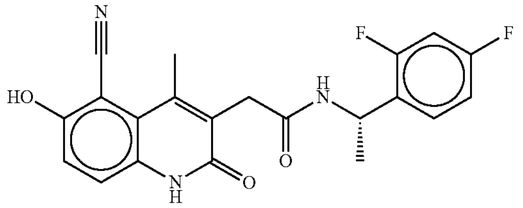 |
| 85 | 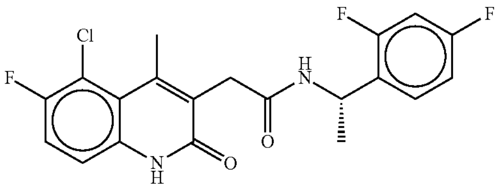 |
| 86 | 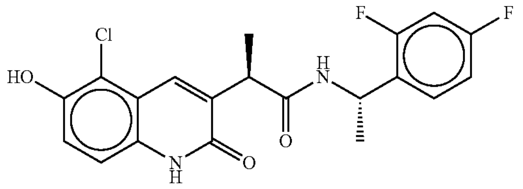 |
| 87 | 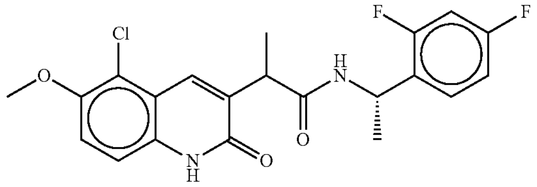 |
| 88 | 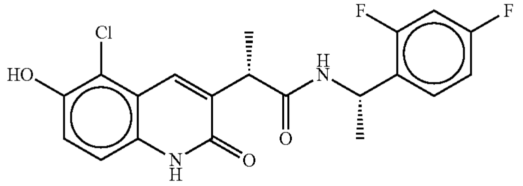 |
| 89 | 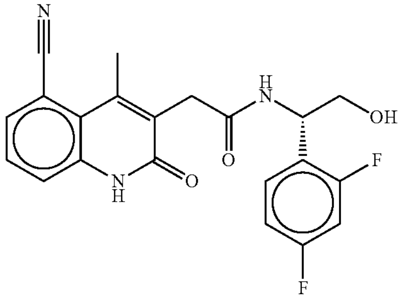 |

TABLE 1-continued
| Cmpd No. | Structure |
| --- | --- |
| 90 | 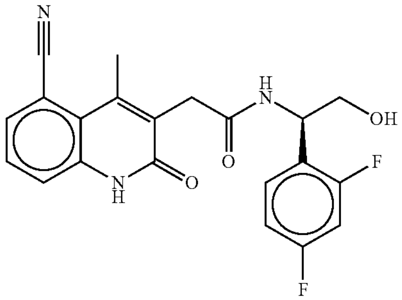 |
| 91 | 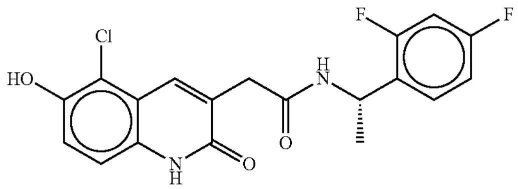 |
| 92 | 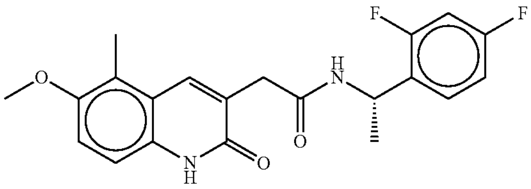 |
| 93 | 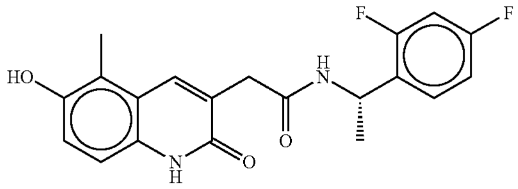 |
| 94 | 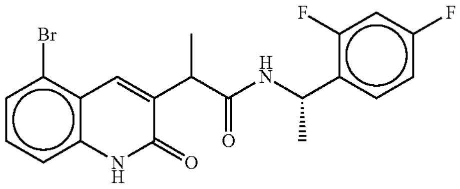 |
| 95 | 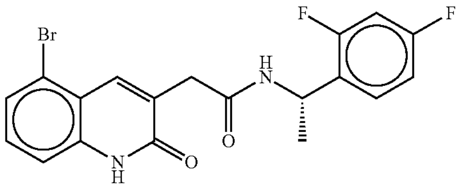 |
| 96 | 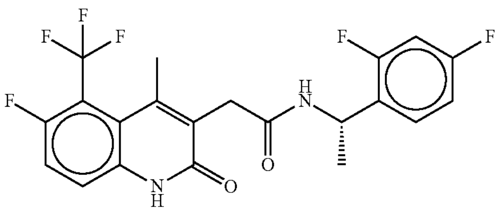 |

TABLE 1-continued
| Cmpd No. | Structure |
|---|---|
| 97 | 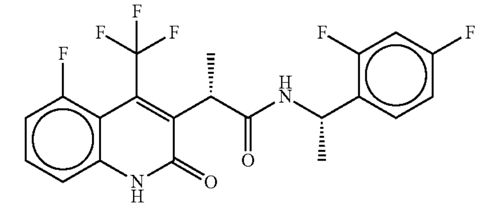 |
| 98 | 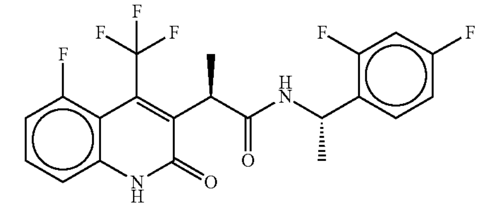 |
| 99 | 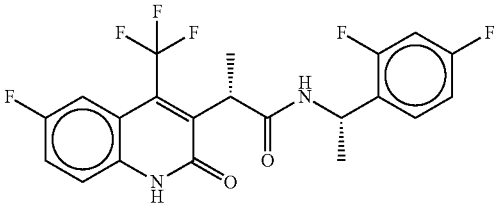 |
| 100 | 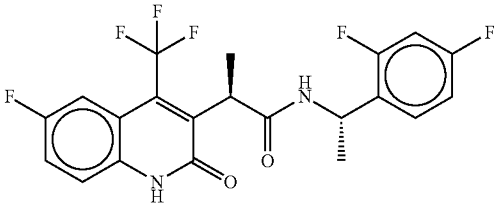 |
| 101 | 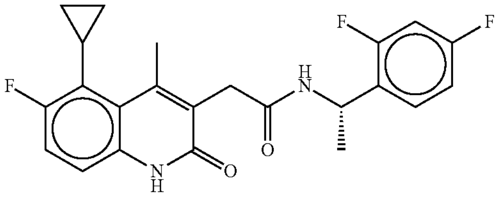 |
| 102 | 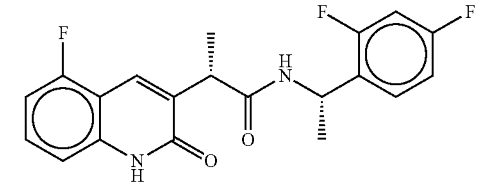 |
| 103 | 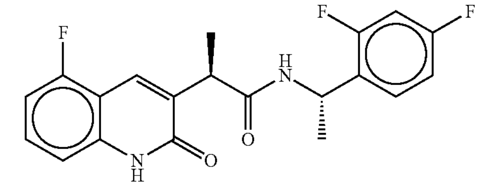 |

TABLE 1-continued
| Cmpd No. | Structure |
| --- | --- |
| 104 | 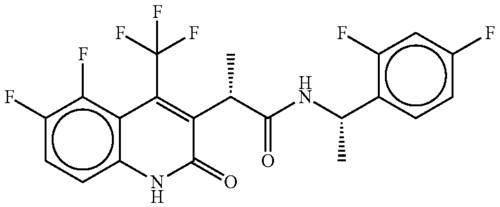 |
| 105 | 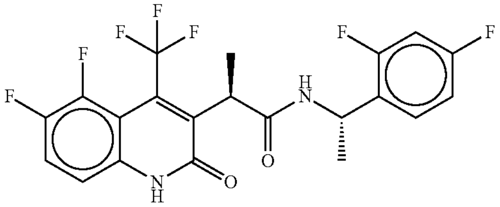 |
| 106 | 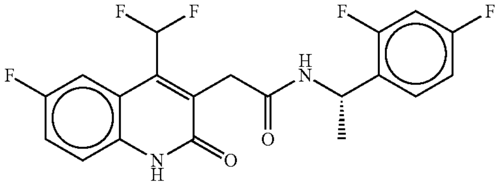 |
| 107 | 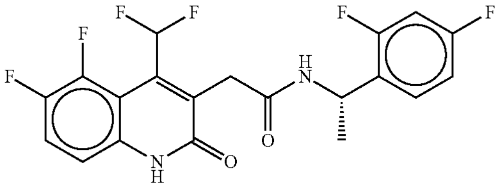 |
| 108 | 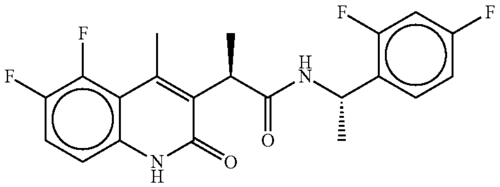 |
| 109 | 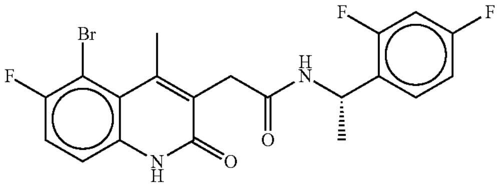 |
| 110 | 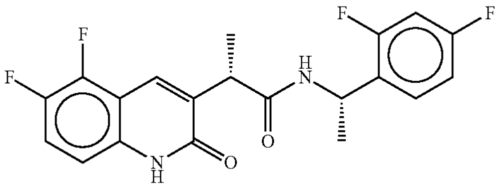 |

TABLE 1-continued
| Cmpd No. | Structure |
|---|---|
| 111 | 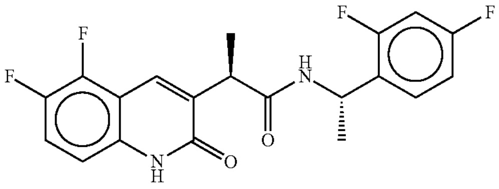 |
| 112 | 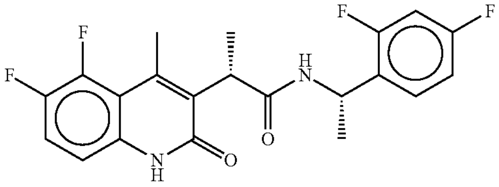 |
| 113 | 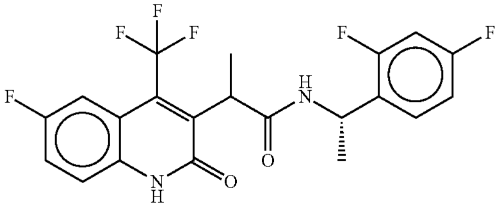 |
| 114 | 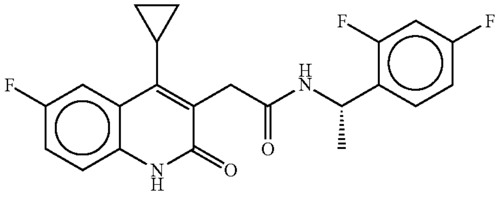 |
| 115 | 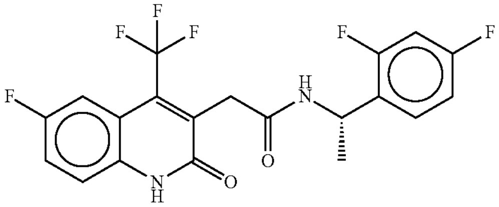 |
| 116 | 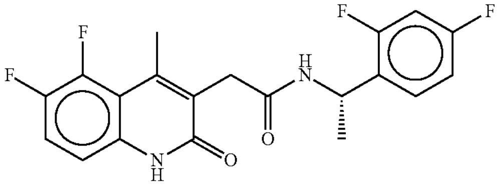 |
| 117 | 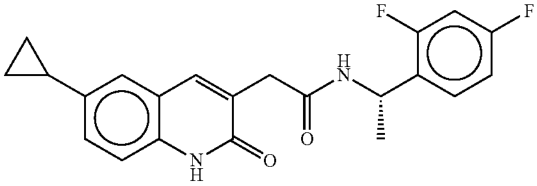 |

TABLE 1-continued
| Cmpd No. | Structure |
|---|---|
| 118 | 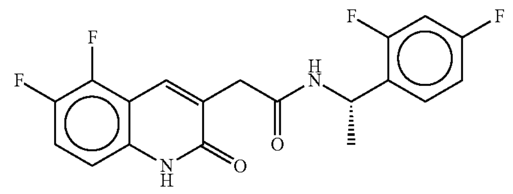 |
| 119 | 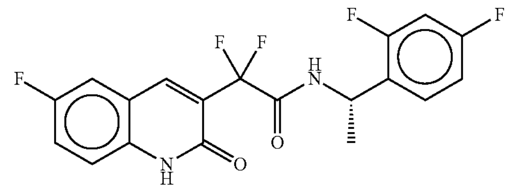 |
| 120 | 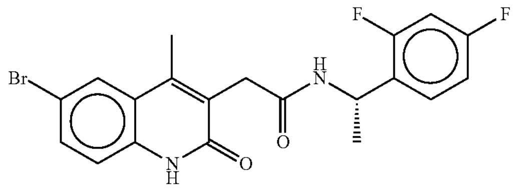 |
| 121 | 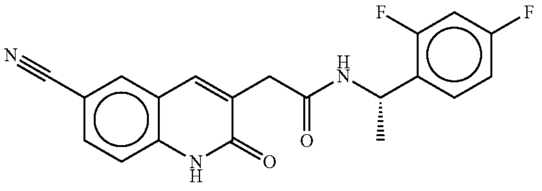 |
| 122 | 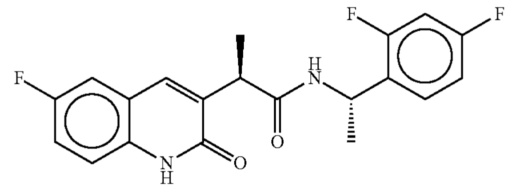 |
| 123 | 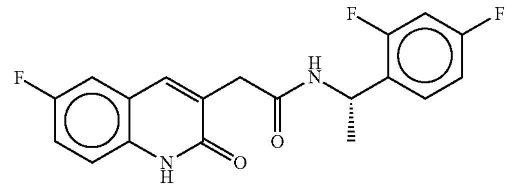 |
| 124 | 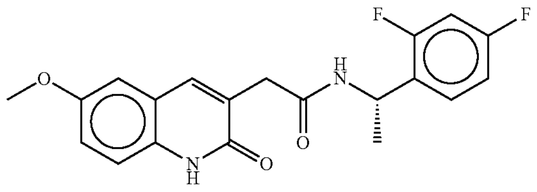 |
| 125 | 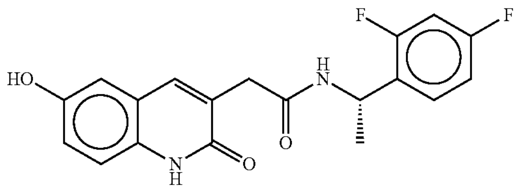

TABLE 1-continued
| Cmpd No. | Structure |
|---|---|
| 126 | 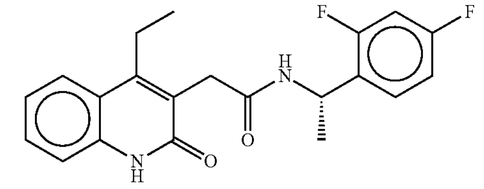 |
| 127 | 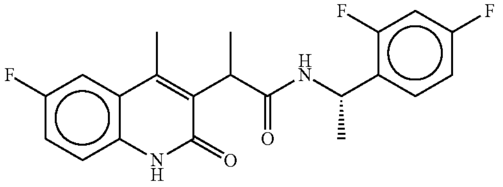 |
| 128 | 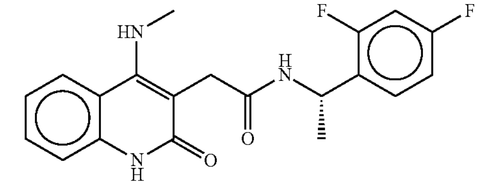 |
| 129 | 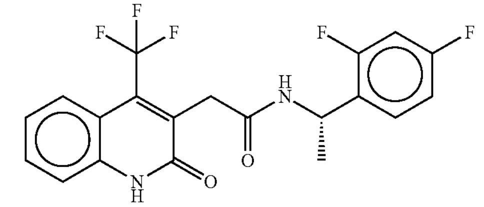 |
| 130 | 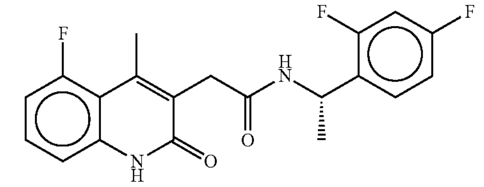 |
| 131 | 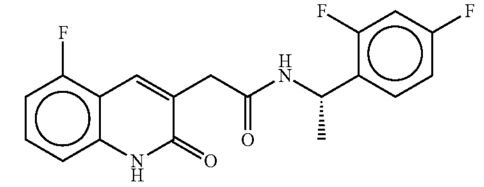 |
| 132 | 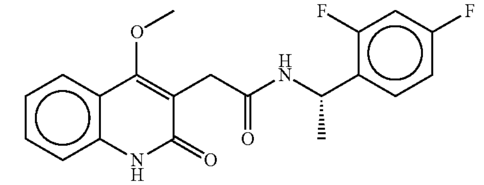 |
| 133 | 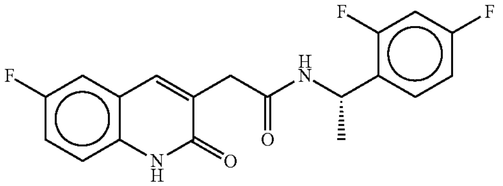 |

TABLE 1-continued
| Cmpd No. | Structure |
|---|---|
| 134 | 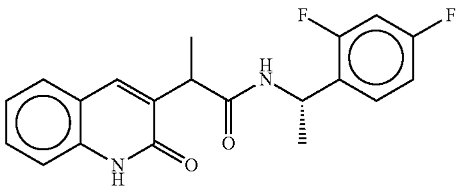 |
| 135 | 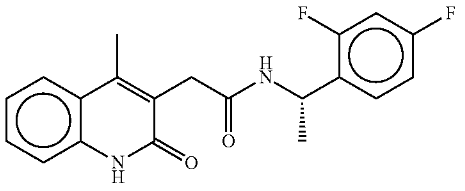 |
| 136 | 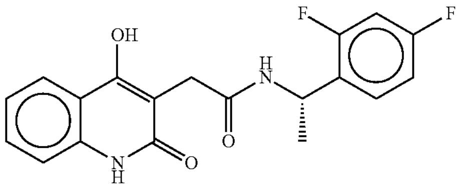 |
| 137 | 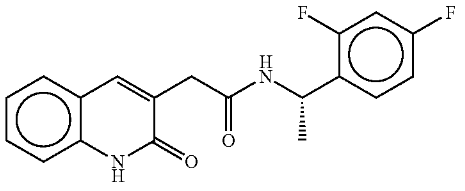 |
| 1038 | 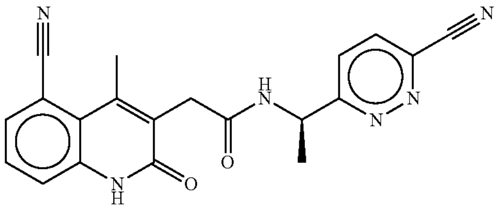 |
| 1039 | 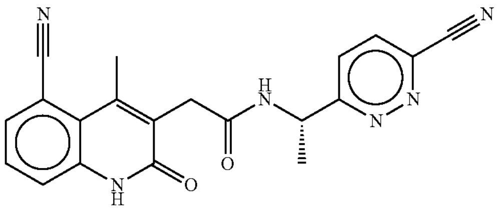 |
| 1040 | 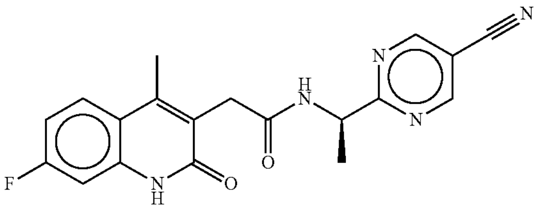 |

TABLE 1-continued
| Cmpd No. | Structure |
|---|---|
| 1041 | 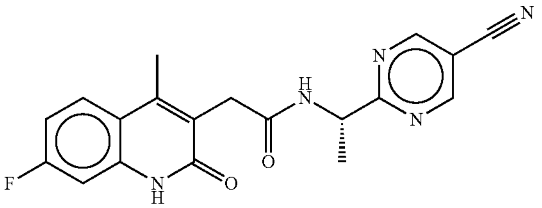 |
| 1042 | 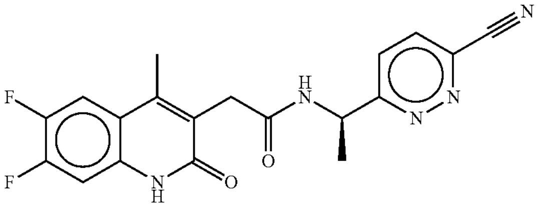 |
| 1043 | 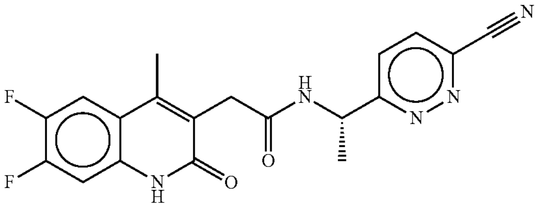 |
| 1044 | 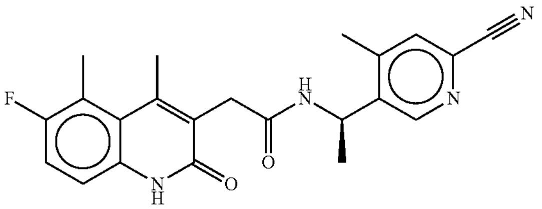 |
| 1045 | 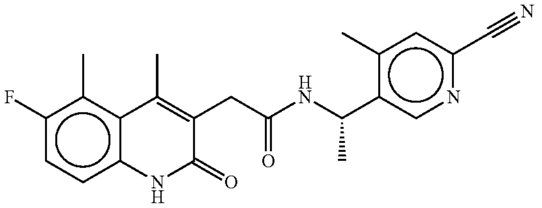 |
| 1046 | 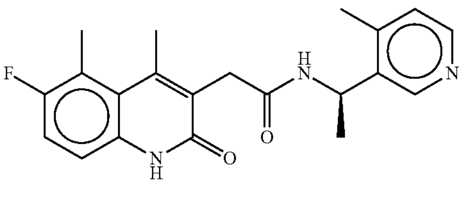 |
| 1047 | 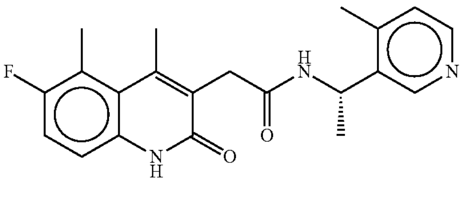 |

TABLE 1-continued
| Cmpd No. | Structure |
|---|---|
| 1048 | 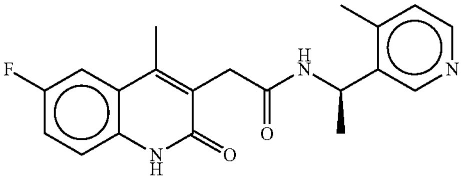 |
| 1049 | 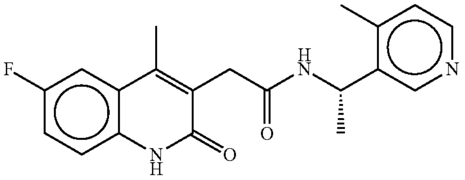 |
| 1050 | 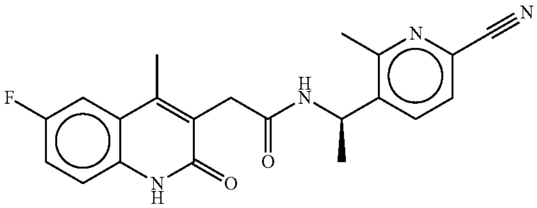 |
| 1051 | 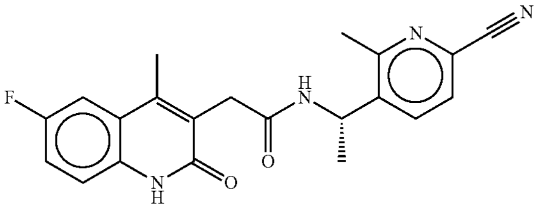 |
| 1052 | 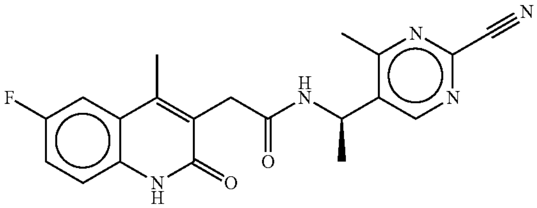 |
| 1053 | 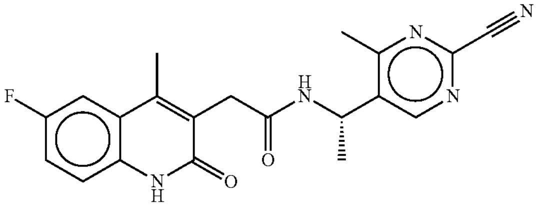 |
| 1054 | 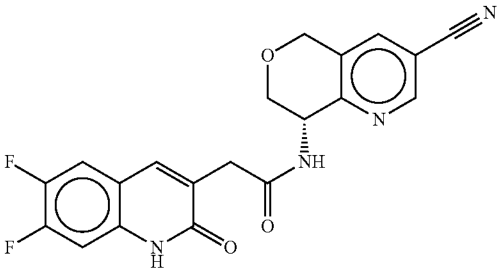 |

TABLE 1-continued
| Cmpd No. | Structure |
|---|---|
| 1055 | 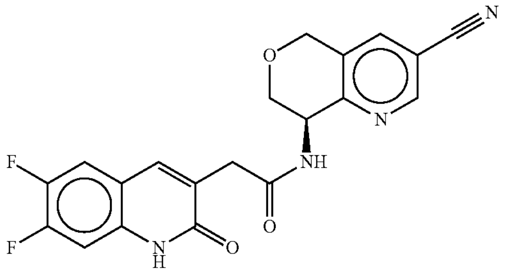 |
| 1056 | 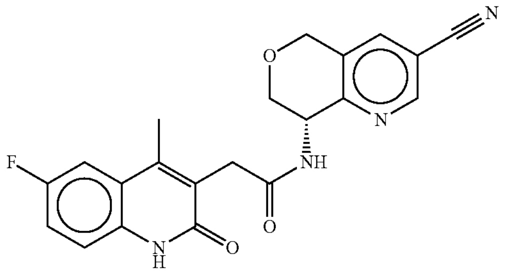 |
| 1057 | 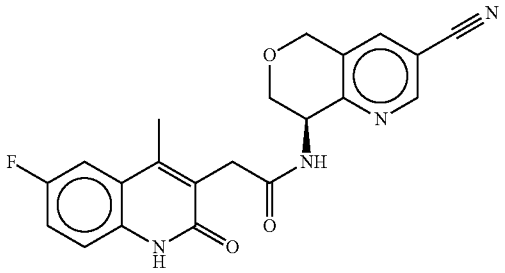 |
| 1058 | 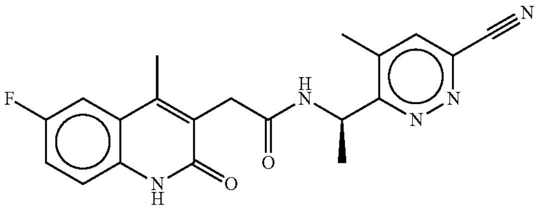 |
| 1059 | 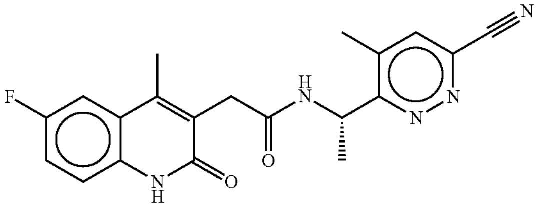 |
| 1060 | 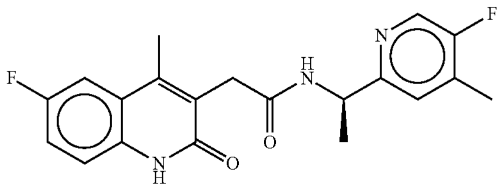 |

TABLE 1-continued
| Cmpd No. | Structure |
| --- | --- |
| 1061 | 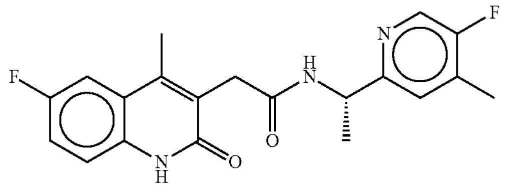 |
| 1062 | 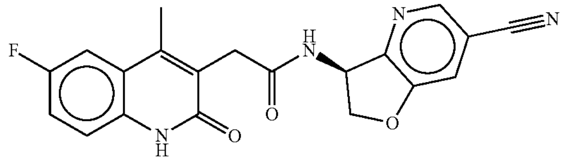 |
| 1063 | 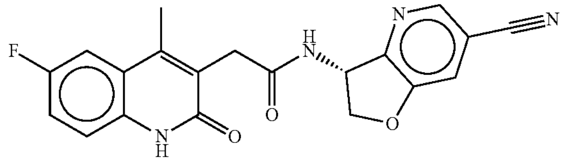 |
| 1064 | 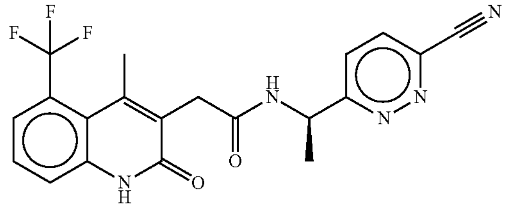 |
| 1065 | 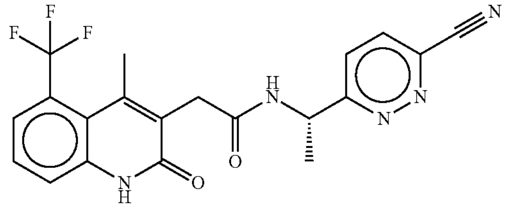 |
| 1066 | 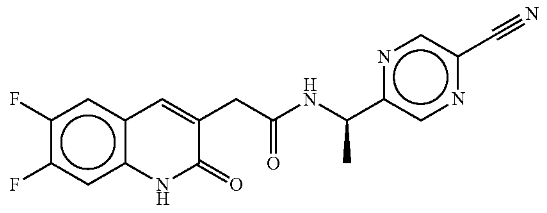 |
| 1067 | 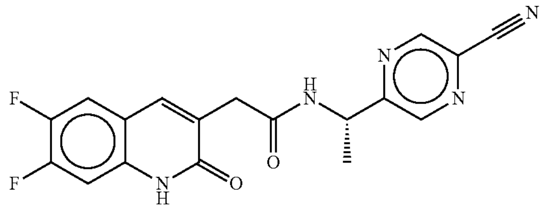 |

TABLE 1-continued
| Cmpd No. | Structure |
| --- | --- |
| 1068 | 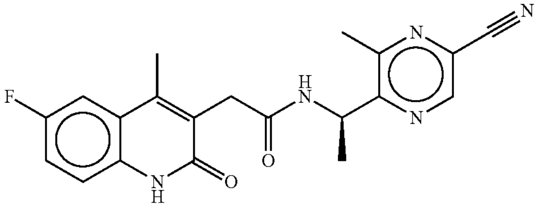 |
| 1069 | 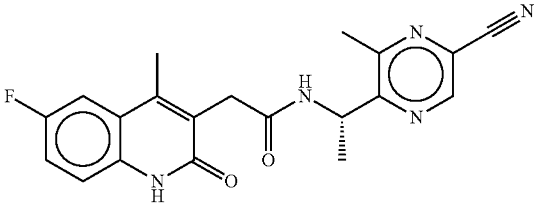 |
| 1070 | 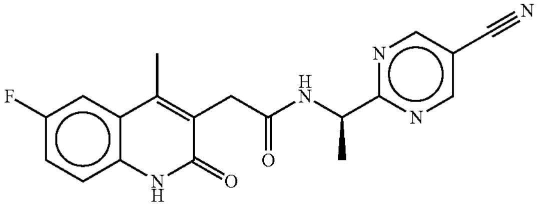 |
| 1071 | 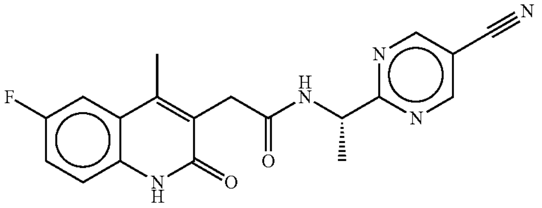 |
| 1072 | 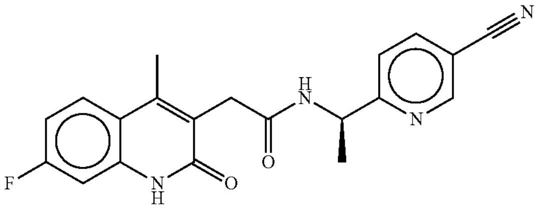 |
| 1073 | 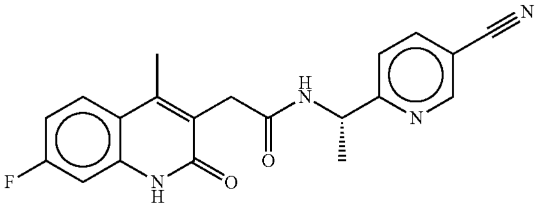 |
| 1074 | 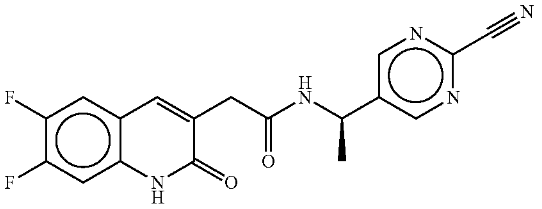 |

TABLE 1-continued
| Cmpd No. | Structure |
|---|---|
| 1075 | 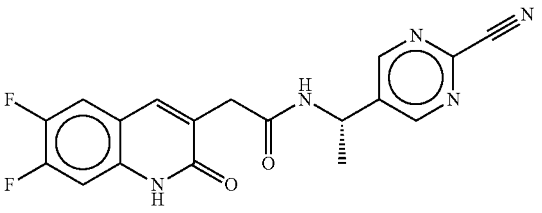 |
| 1076 | 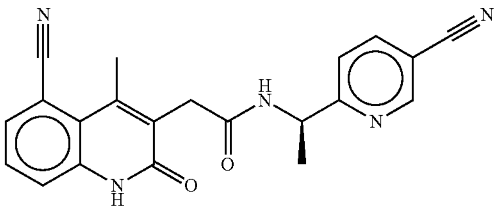 |
| 1077 | 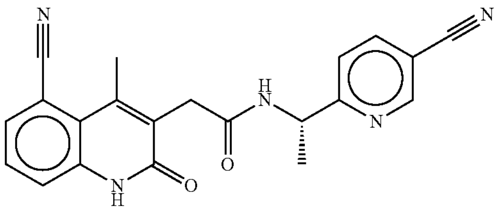 |
| 1078 | 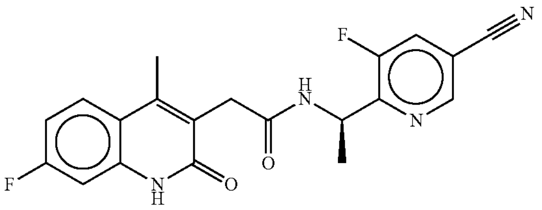 |
| 1079 | 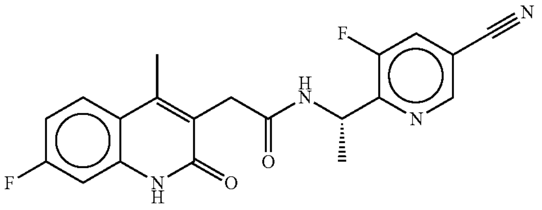 |
| 1080 | 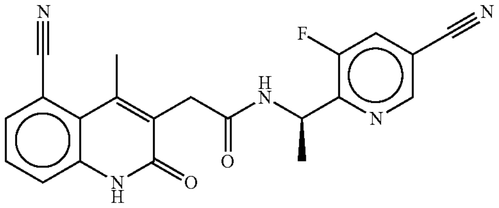 |
| 1081 | 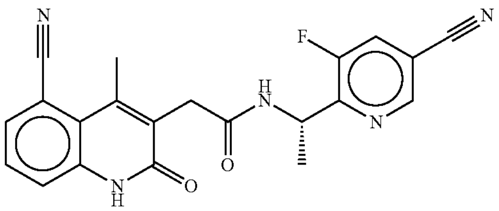 |

TABLE 1-continued
| Cmpd No. | Structure |
|---|---|
| 1082 | 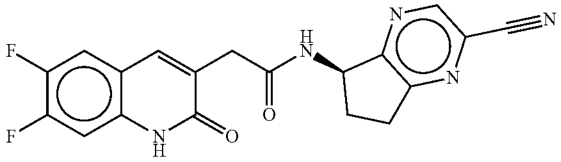 |
| 1083 | 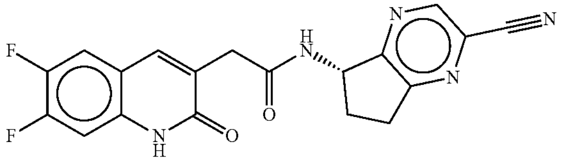 |
| 1084 | 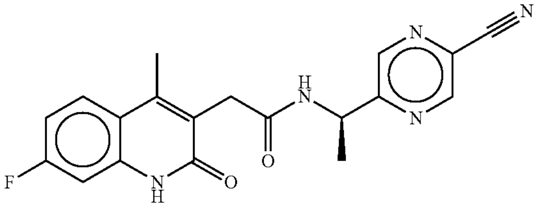 |
| 1085 | 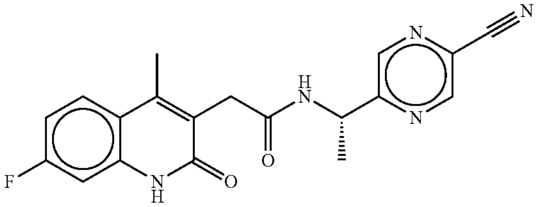 |
| 1086 | 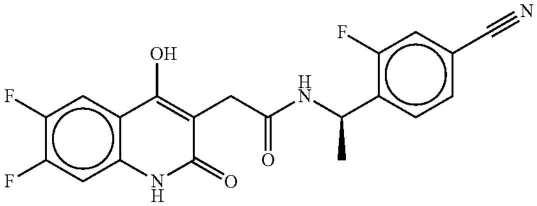 |
| 1087 | 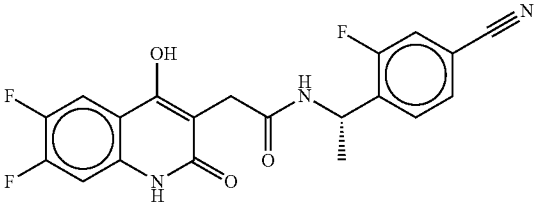 |
| 1088 | 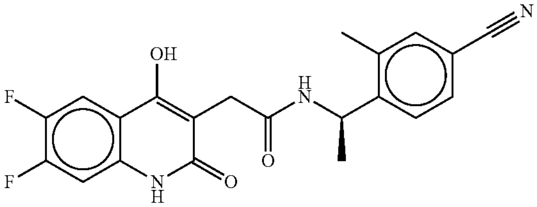 |

TABLE 1-continued
| Cmpd No. | Structure |
|---|---|
| 1089 | 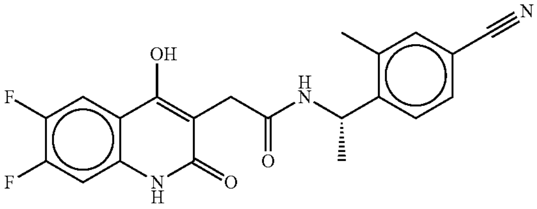 |
| 1090 | 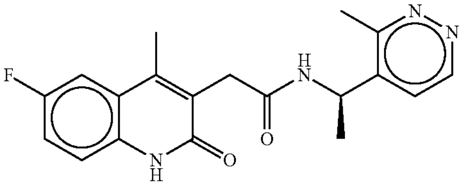 |
| 1091 | 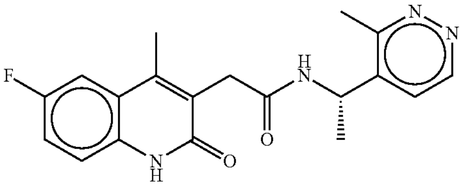 |
| 1092 | 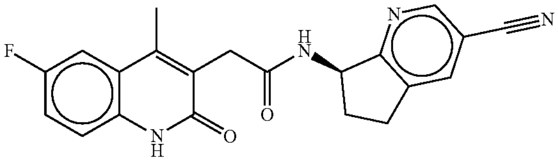 |
| 1093 | 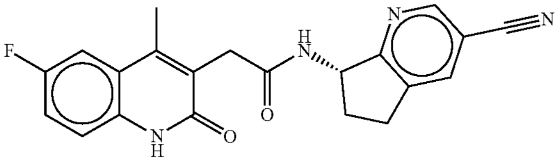 |
| 1094 | 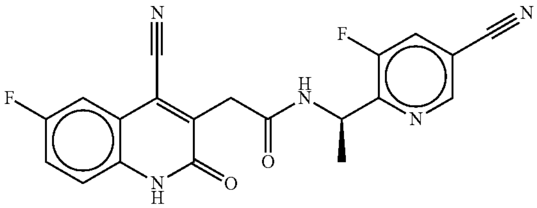 |
| 1095 | 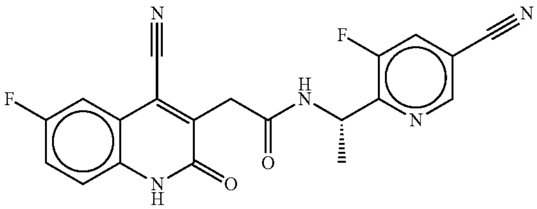 |

TABLE 1-continued
| Cmpd No. | Structure |
|---|---|
| 1096 | 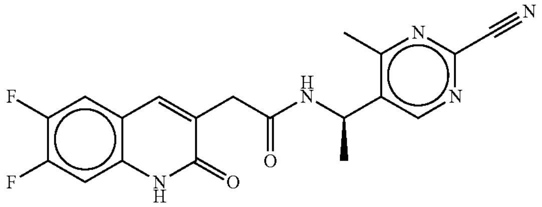 |
| 1097 | 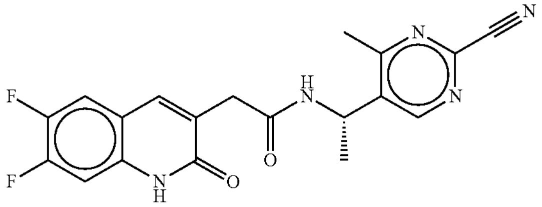 |
| 1098 | 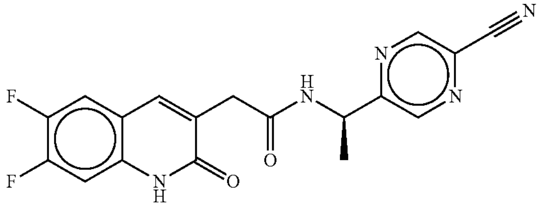 |
| 1099 | 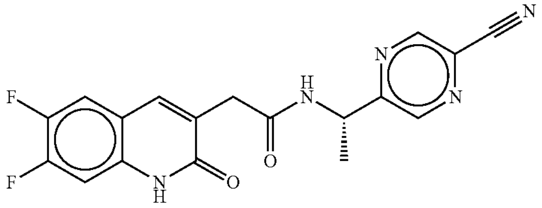 |
| 1100 | 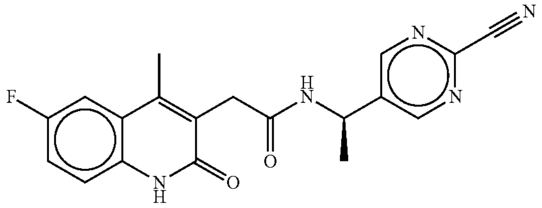 |
| 1101 | 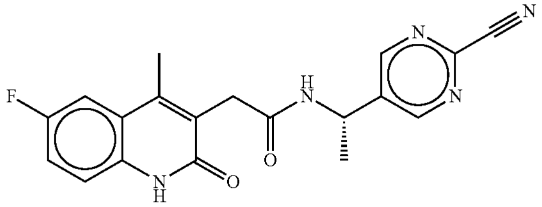 |
| 1102 | 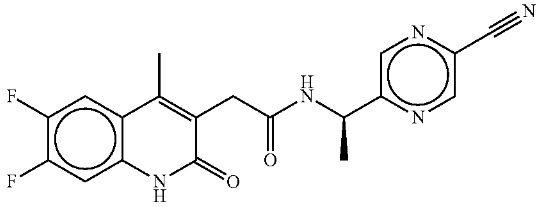 |

TABLE 1-continued
| Cmpd No. | Structure |
|---|---|
| 1103 | 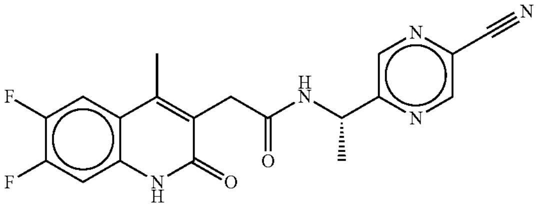 |
| 1104 | 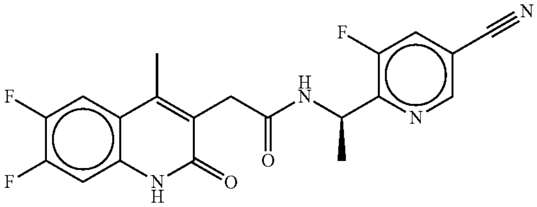 |
| 1105 | 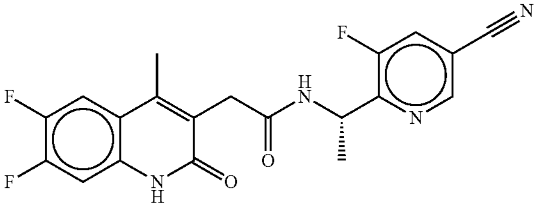 |
| 1106 | 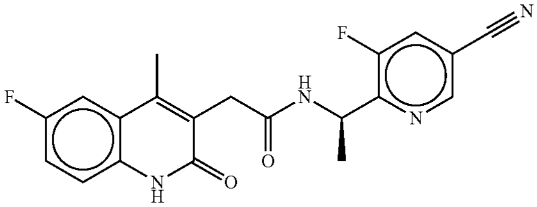 |
| 1107 | 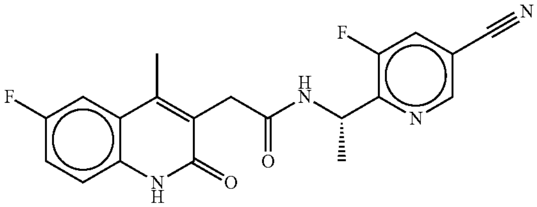 |
| 1108 | 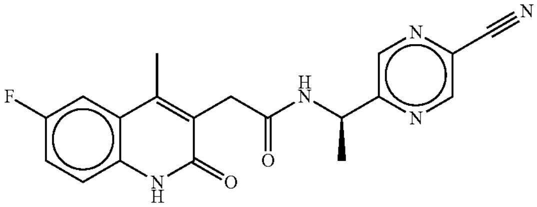 |
| 1109 | 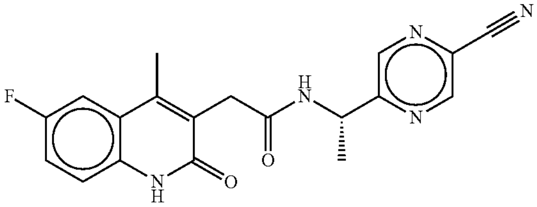 |

TABLE 1-continued
| Cmpd No. | Structure |
|---|---|
| 1110 | 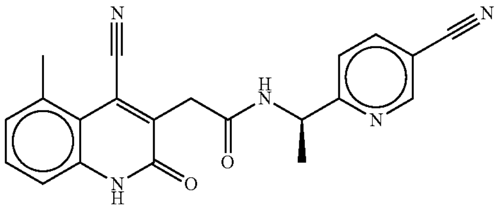 |
| 1111 | 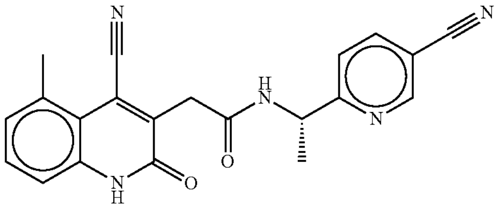 |
| 1112 | 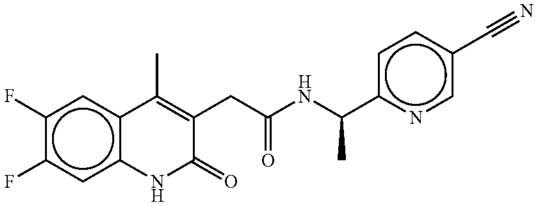 |
| 1113 | 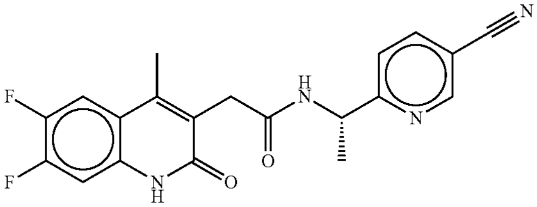 |
| 1114 | 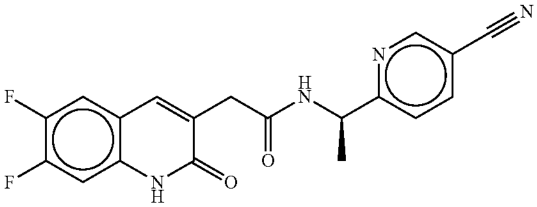 |
| 1115 | 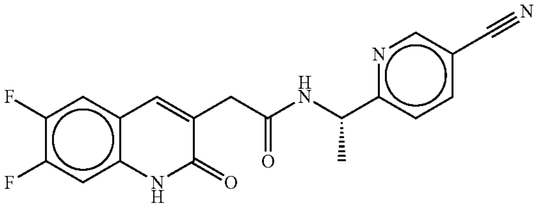 |
| 1116 | 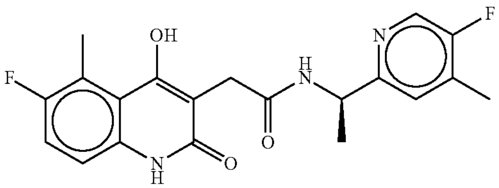 |

TABLE 1-continued
| Cmpd No. | Structure |
|---|---|
| 1117 | 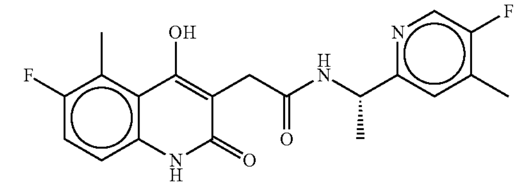 |
| 1118 | 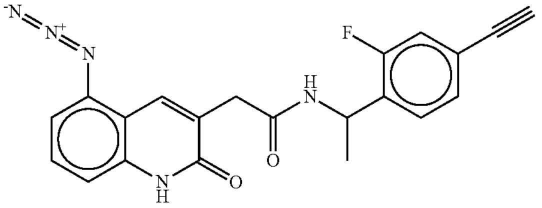 |
| 1119 | 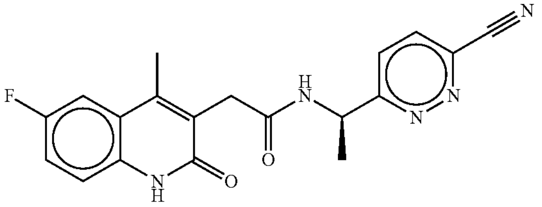 |
| 1120 | 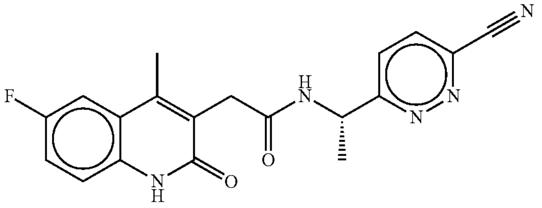 |
| 1121 | 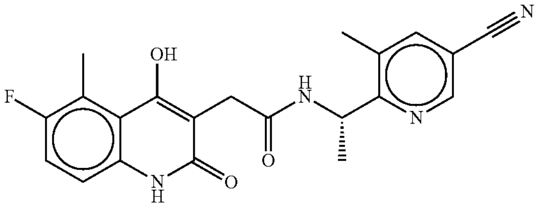 |
| 1122 | 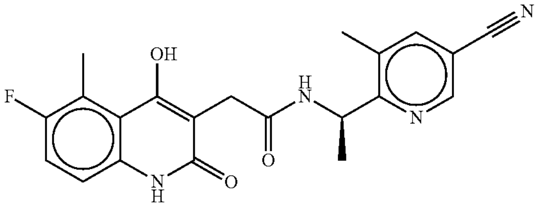 |
| 1123 | 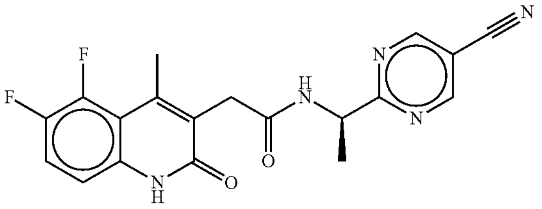 |

TABLE 1-continued
| Cmpd No. | Structure |
|---|---|
| 1124 | 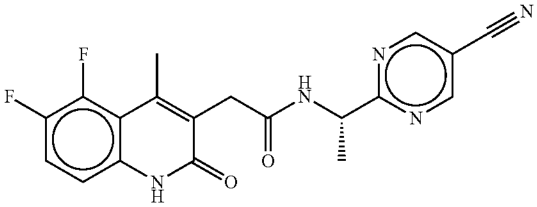 |
| 1125 | 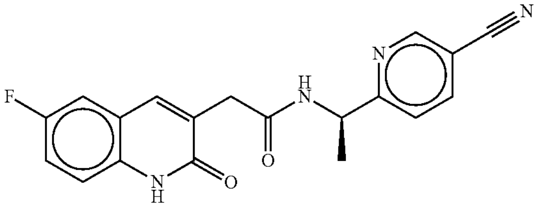 |
| 1126 | 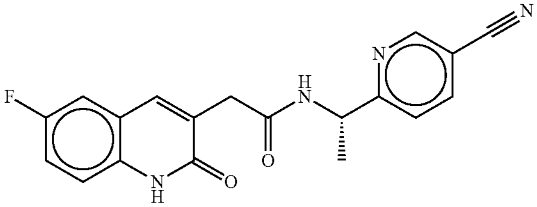 |
| 1127 | 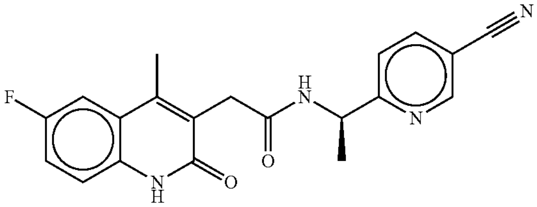 |
| 1128 | 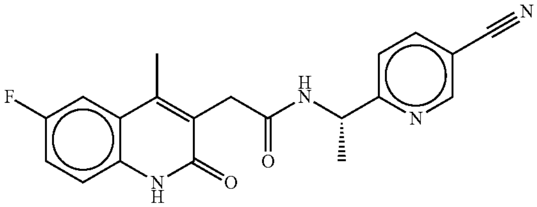 |
| 1129 | 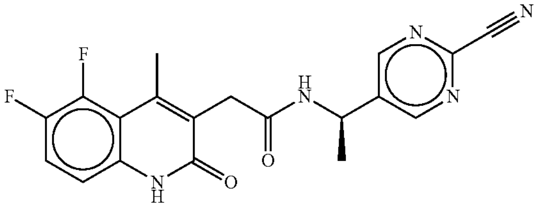 |
| 1130 | 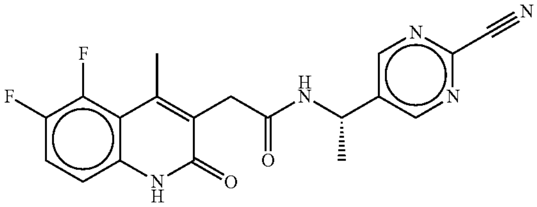 |

TABLE 1-continued
| Cmpd No. | Structure |
|---|---|
| 1131 | 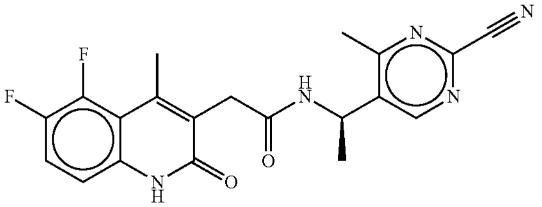 |
| 1132 | 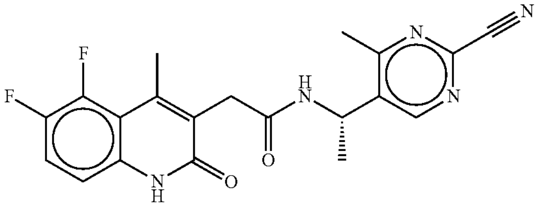 |
| 1133 | 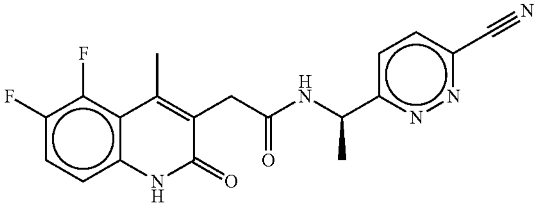 |
| 1134 | 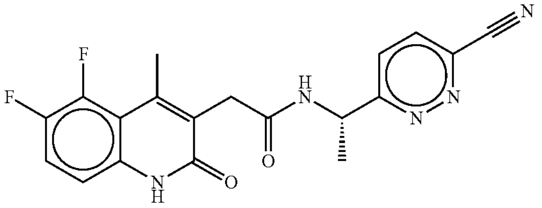 |
| 1135 | 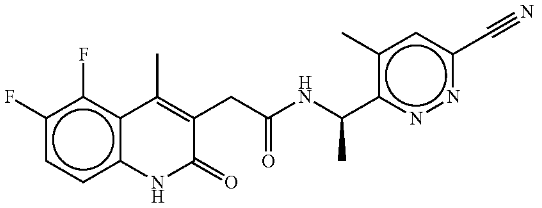 |
| 1136 | 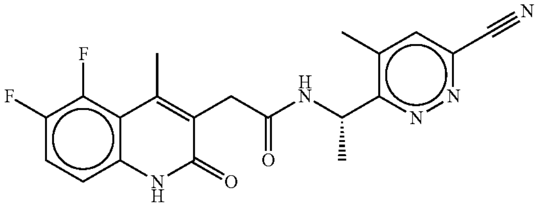 |
| 1137 | 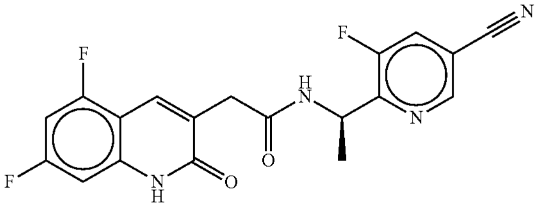 |

TABLE 1-continued
| Cmpd No. | Structure |
| --- | --- |
| 1138 | 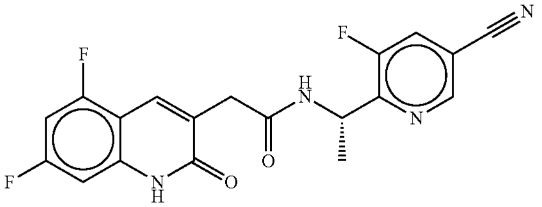 |
| 1139 | 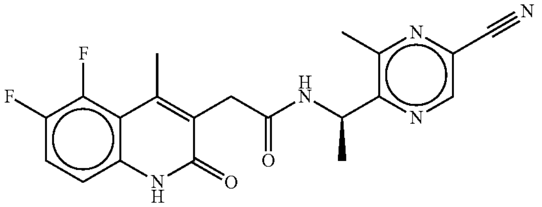 |
| 1140 | 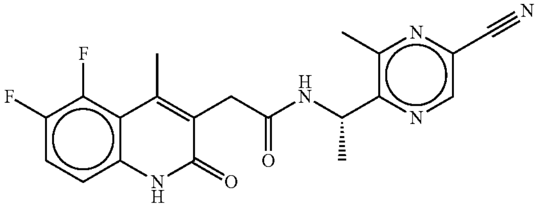 |
| 1141 | 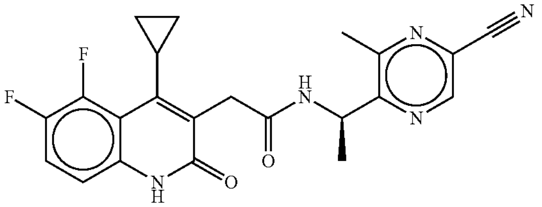 |
| 1142 | 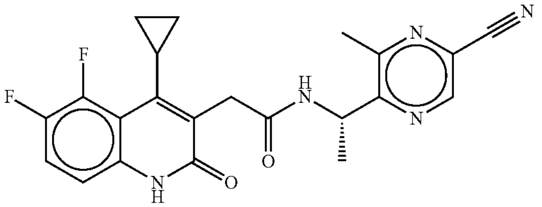 |
| 1143 | 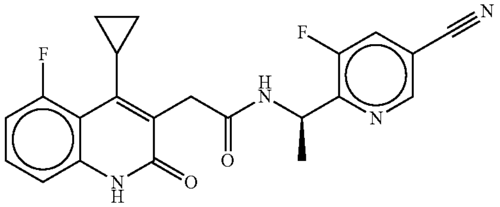 |
| 1144 | 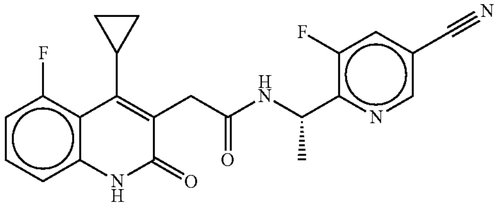 |

TABLE 1-continued
| Cmpd No. | Structure |
|---|---|
| 1145 | 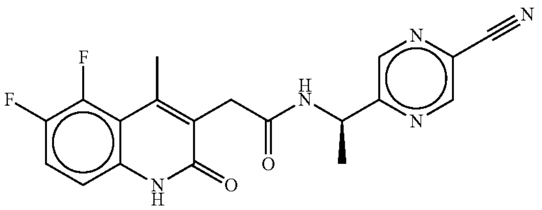 |
| 1146 | 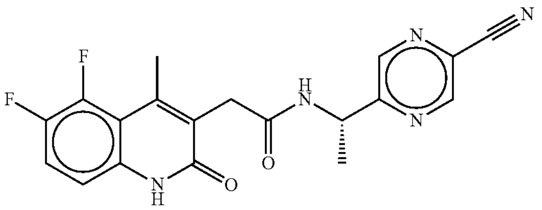 |
| 1147 | 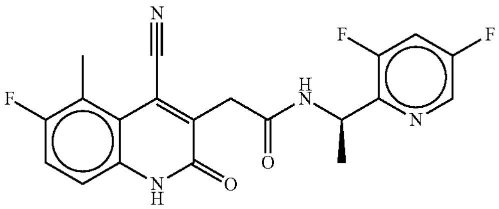 |
| 1148 | 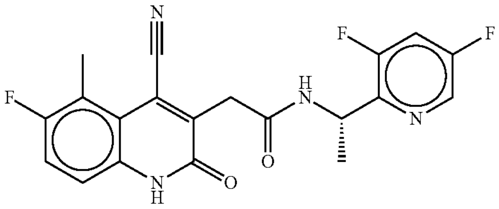 |
| 1149 | 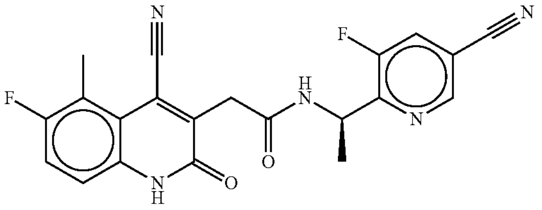 |
| 1150 | 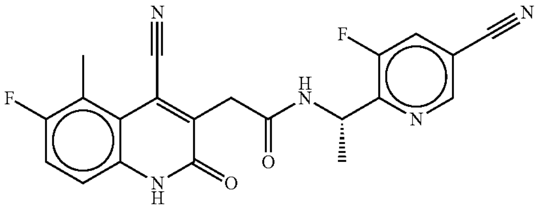 |
| 1151 | 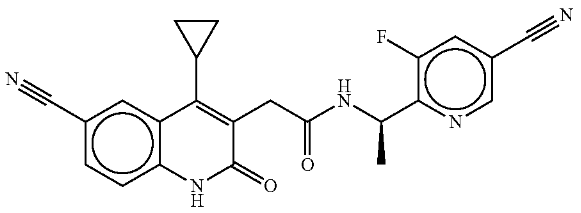 |

TABLE 1-continued
| Cmpd No. | Structure |
|---|---|
| 1152 | 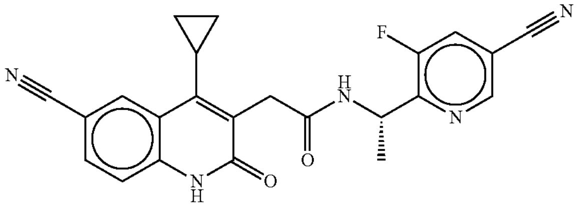 |
| 1153 | 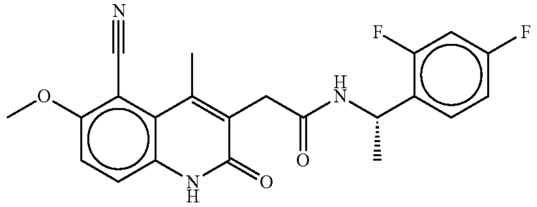 |
| 2001 | 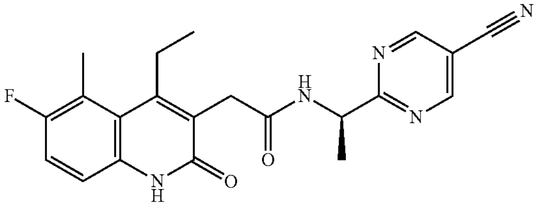 [SMILES: CCc1c(CC(=O)N[C@H](C)c2ncc(C#N)cn2)c(=O)[nH]c2ccc(F)c(C)c12] |
| 2002 | 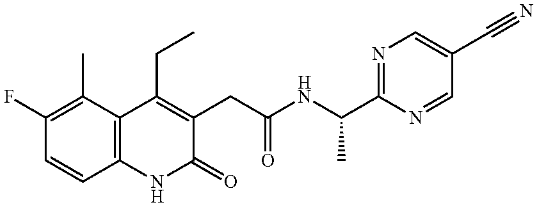 [SMILES: CCc1c(CC(=O)N[C@@H](C)c2ncc(C#N)cn2)c(=O)[nH]c2ccc(F)c(C)c12] |
| 2009 | 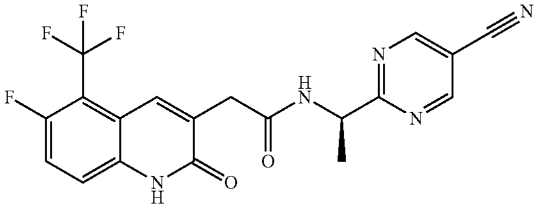 [SMILES: C[C@@H](NC(=O)Cc1cc2c(C(F)(F)F)c(F)ccc2[nH]c1=O)c1ncc(C#N)cn1] |
| 2010 | 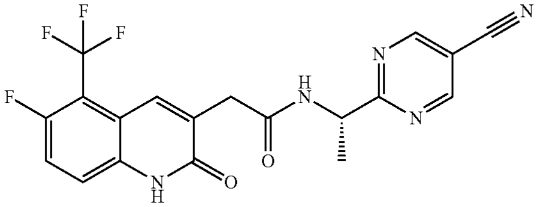 [SMILES: C[C@H](NC(=O)Cc1cc2c(C(F)(F)F)c(F)ccc2[nH]c1=O)c1ncc(C#N)cn1] |
| 2011 | 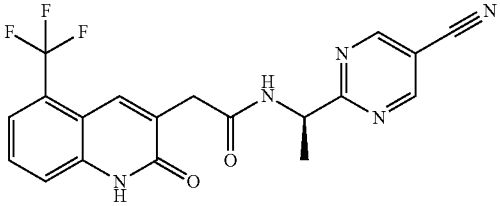 [SMILES: C[C@@H](NC(=O)Cc1cc2c(C(F)(F)F)cccc2[nH]c1=O)c1ncc(C#N)cn1] |

TABLE 1-continued
| Cmpd No. | Structure |
|---|---|
| 2012 | 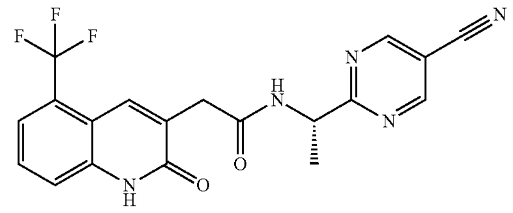 [SMILES: C[C@H](NC(=O)Cc1cc2c(C(F)(F)F)cccc2[nH]c1=O)c1ncc(C#N)cn1] |
| 2013 | 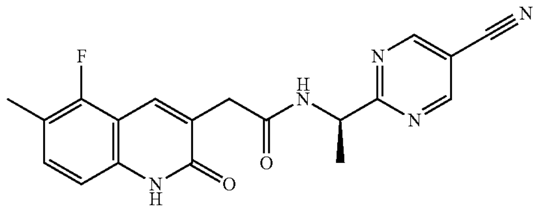 [SMILES: Cc1ccc2[nH]c(=O)c(CC(=O)N[C@H](C)c3ncc(C#N)cn3)cc2c1F] |
| 2014 | 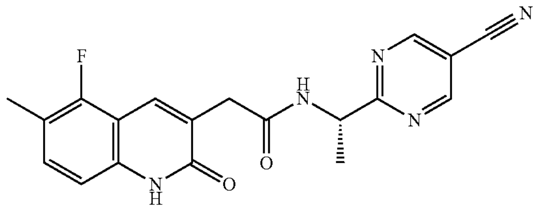 [SMILES: Cc1ccc2[nH]c(=O)c(CC(=O)N[C@@H](C)c3ncc(C#N)cn3)cc2c1F] |
| 2015 | 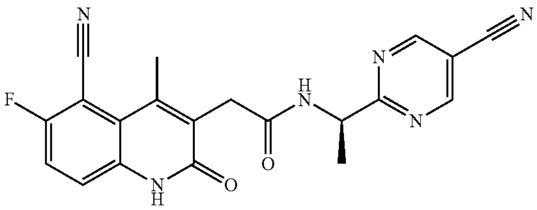 [SMILES: Cc1c(CC(=O)N[C@H](C)c2ncc(C#N)cn2)c(=O)[nH]c2ccc(F)c(C#N)c12] |
| 2016 | 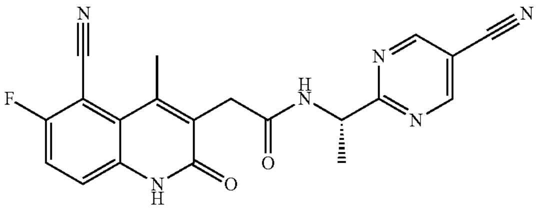 [SMILES: Cc1c(CC(=O)N[C@@H](C)c2ncc(C#N)cn2)c(=O)[nH]c2ccc(F)c(C#N)c12] |
| 2017 | 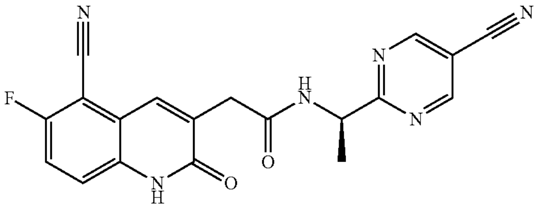 [SMILES: C[C@@H](NC(=O)Cc1cc2c(C#N)c(F)ccc2[nH]c1=O)c1ncc(C#N)cn1] |
| 2018 | 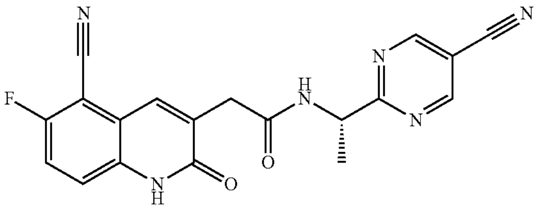 [SMILES: C[C@H](NC(=O)Cc1cc2c(C#N)c(F)ccc2[nH]c1=O)c1ncc(C#N)cn1] |

TABLE 1-continued
| Cmpd No. | Structure |
| --- | --- |
| 2019 | 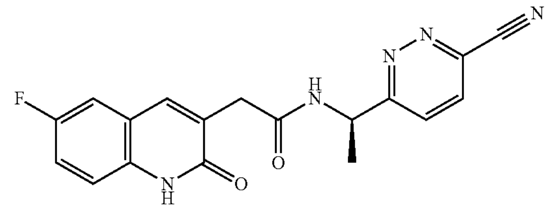 [SMILES: C[C@@H](NC(=O)Cc1cc2cc(F)ccc2[nH]c1=O)c1ccc(C#N)nn1] |
| 2020 | 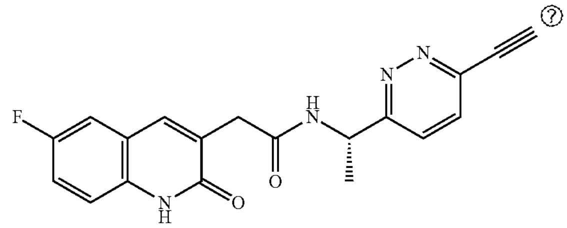 [SMILES: C#Cc1ccc([C@H](C)NC(=O)Cc2cc3cc(F)ccc3[nH]c2=O)nn1] |
| 2021 | 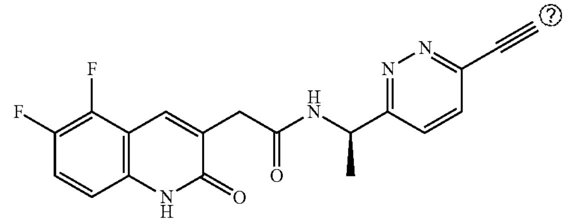 [SMILES: C#Cc1ccc([C@@H](C)NC(=O)Cc2cc3c(F)c(F)ccc3[nH]c2=O)nn1] |
| 2022 | 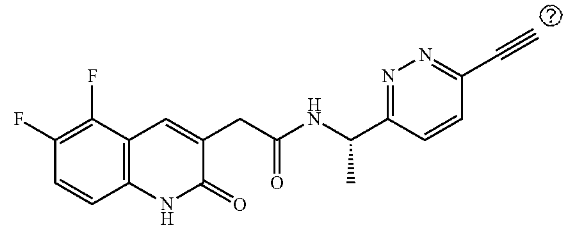 [SMILES: C#Cc1ccc([C@H](C)NC(=O)Cc2cc3c(F)c(F)ccc3[nH]c2=O)nn1] |
| 2023 | 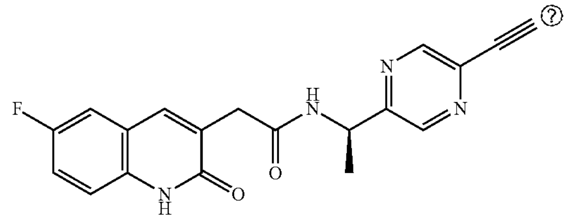 [SMILES: C#Cc1cnc([C@@H](C)NC(=O)Cc2cc3cc(F)ccc3[nH]c2=O)cn1] |
| 2024 | 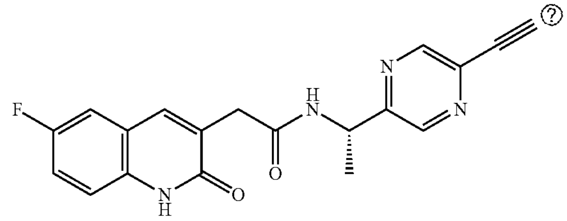 [SMILES: C#Cc1cnc([C@H](C)NC(=O)Cc2cc3cc(F)ccc3[nH]c2=O)cn1] |

TABLE 1-continued
| Cmpd No. | Structure |
| --- | --- |
| 2025 | 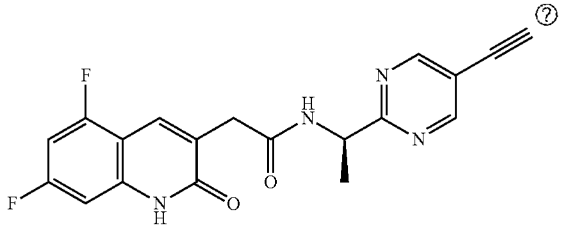 [SMILES: C#Cc1cnc([C@@H](C)NC(=O)Cc2cc3c(F)cc(F)cc3[nH]c2=O)nc1] |
| 2026 | 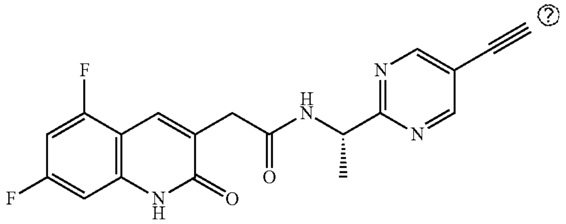 [SMILES: C#Cc1cnc([C@H](C)NC(=O)Cc2cc3c(F)cc(F)cc3[nH]c2=O)nc1] |
| 2027 | 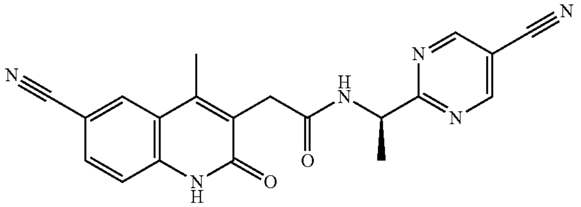 [SMILES: Cc1c(CC(=O)N[C@H](C)c2ncc(C#N)cn2)c(=O)[nH]c2ccc(C#N)cc12] |
| 2028 | 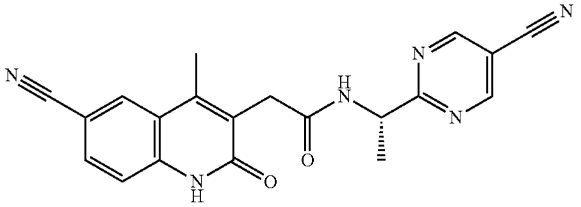 [SMILES: Cc1c(CC(=O)N[C@@H](C)c2ncc(C#N)cn2)c(=O)[nH]c2ccc(C#N)cc12] |
| 2029 | 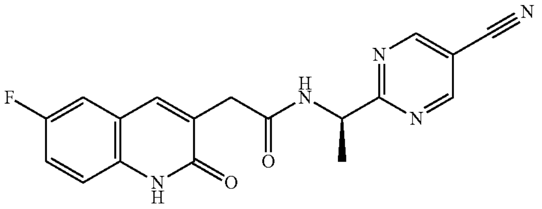 [SMILES: C[C@@H](NC(=O)Cc1cc2cc(F)ccc2[nH]c1=O)c1ncc(C#N)cn1] |
| 2030 | 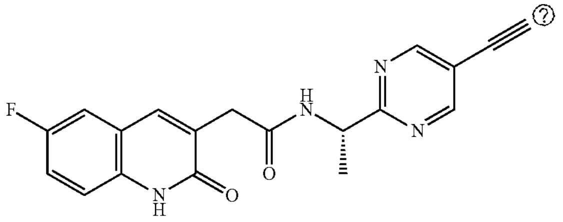 [SMILES: C#Cc1cnc([C@H](C)NC(=O)Cc2cc3cc(F)ccc3[nH]c2=O)nc1] |
| 2033 | 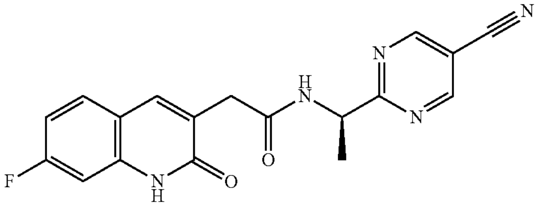 [SMILES: C[C@@H](NC(=O)Cc1cc2ccc(F)cc2[nH]c1=O)c1ncc(C#N)cn1] |

TABLE 1-continued
| Cmpd No. | Structure |
| --- | --- |
| 2034 | 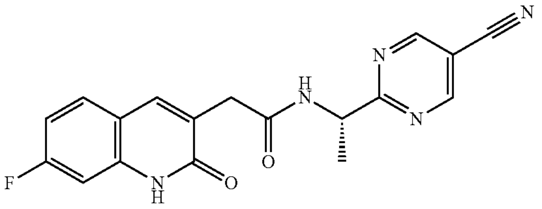 [SMILES: C[C@H](NC(=O)Cc1cc2ccc(F)cc2[nH]c1=O)c1ncc(C#N)cn1] |
| 2035 | 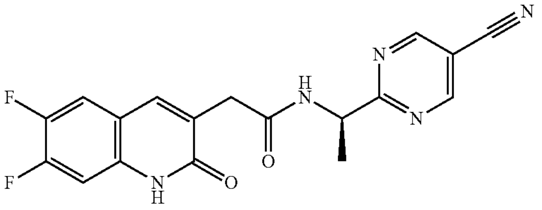 [SMILES: C[C@@H](NC(=O)Cc1cc2cc(F)c(F)cc2[nH]c1=O)c1ncc(C#N)cn1] |
| 2036 | 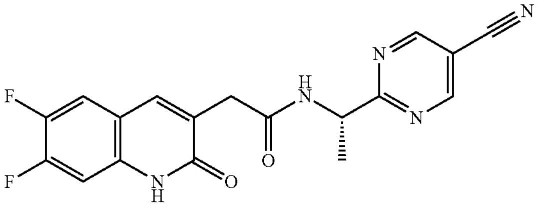 [SMILES: C[C@H](NC(=O)Cc1cc2cc(F)c(F)cc2[nH]c1=O)c1ncc(C#N)cn1] |
| 2037 | 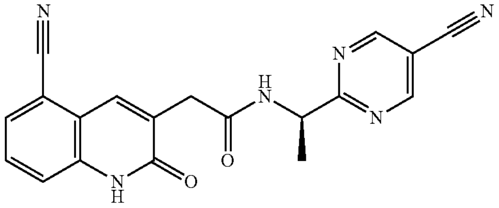 [SMILES: C[C@@H](NC(=O)Cc1cc2c(C#N)cccc2[nH]c1=O)c1ncc(C#N)cn1] |
| 2038 | 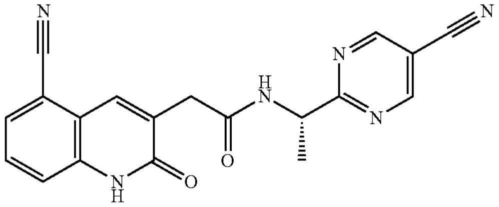 [SMILES: C[C@H](NC(=O)Cc1cc2c(C#N)cccc2[nH]c1=O)c1ncc(C#N)cn1] |
| 2039 | 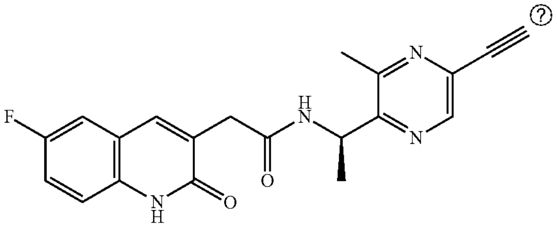 [SMILES: C#Cc1cnc([C@@H](C)NC(=O)Cc2cc3cc(F)ccc3[nH]c2=O)c(C)n1] |
| 2040 | 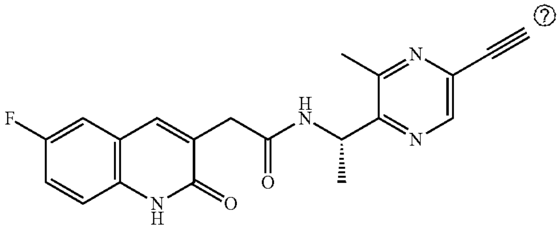 [SMILES: C#Cc1cnc([C@H](C)NC(=O)Cc2cc3cc(F)ccc3[nH]c2=O)c(C)n1] |

TABLE 1-continued
| Cmpd No. | Structure |
| --- | --- |
| 2041 | 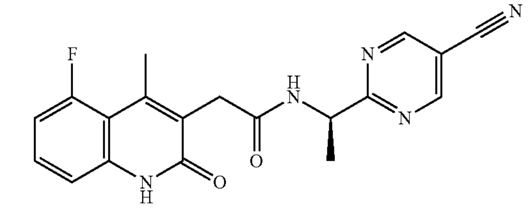 [SMILES: Cc1c(CC(=O)N[C@H](C)c2ncc(C#N)cn2)c(=O)[nH]c2cccc(F)c12] |
| 2042 | 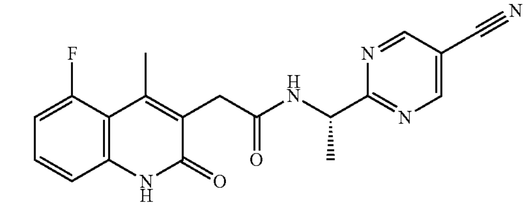 [SMILES: Cc1c(CC(=O)N[C@@H](C)c2ncc(C#N)cn2)c(=O)[nH]c2cccc(F)c12] |
| 2043 | 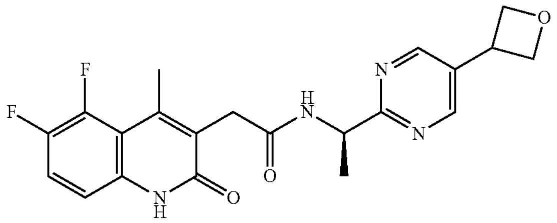 [SMILES: Cc1c(CC(=O)N[C@H](C)c2ncc(C3COC3)cn2)c(=O)[nH]c2ccc(F)c(F)c12] |
| 2044 | 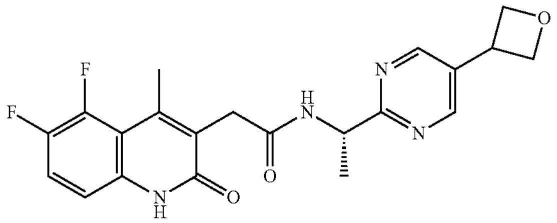 [SMILES: Cc1c(CC(=O)N[C@@H](C)c2ncc(C3COC3)cn2)c(=O)[nH]c2ccc(F)c(F)c12] |
| 2045 | 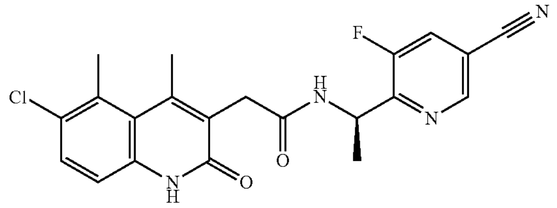 [SMILES: Cc1c(Cl)ccc2[nH]c(=O)c(CC(=O)N[C@H](C)c3ncc(C#N)cc3F)c(C)c12] |
| 2046 | 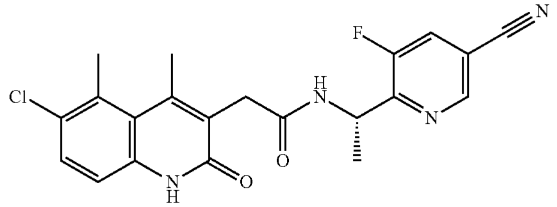 [SMILES: Cc1c(Cl)ccc2[nH]c(=O)c(CC(=O)N[C@@H](C)c3ncc(C#N)cc3F)c(C)c12] |
| 2047 | 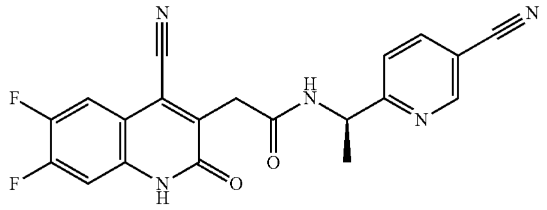 [SMILES: C[C@@H](NC(=O)Cc1c(C#N)c2cc(F)c(F)cc2[nH]c1=O)c1ccc(C#N)cn1] |

TABLE 1-continued
| Cmpd No. | Structure |
|---|---|
| 2048 | 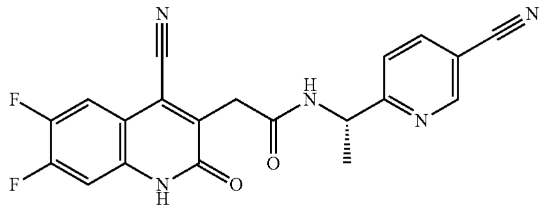 [SMILES: C[C@H](NC(=O)Cc1c(C#N)c2cc(F)c(F)cc2[nH]c1=O)c1ccc(C#N)cn1] |
| 2049 | 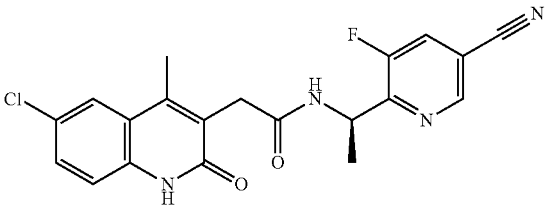 [SMILES: Cc1c(CC(=O)N[C@H](C)c2ncc(C#N)cc2F)c(=O)[nH]c2ccc(Cl)cc12] |
| 2050 | 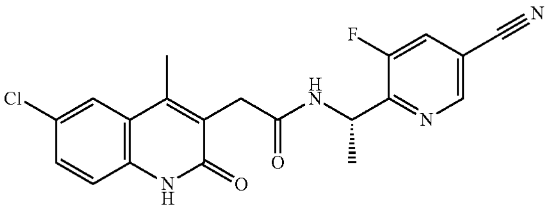 [SMILES: Cc1c(CC(=O)N[C@@H](C)c2ncc(C#N)cc2F)c(=O)[nH]c2ccc(Cl)cc12] |
| 2051 | 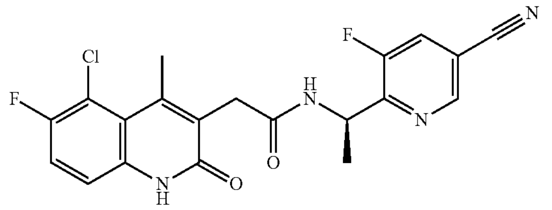 [SMILES: Cc1c(CC(=O)N[C@H](C)c2ncc(C#N)cc2F)c(=O)[nH]c2ccc(F)c(Cl)c12] |
| 2052 | 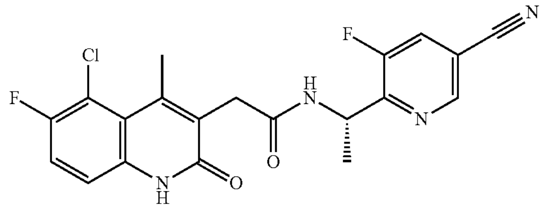 [SMILES: Cc1c(CC(=O)N[C@@H](C)c2ncc(C#N)cc2F)c(=O)[nH]c2ccc(F)c(Cl)c12] |
| 2053 | 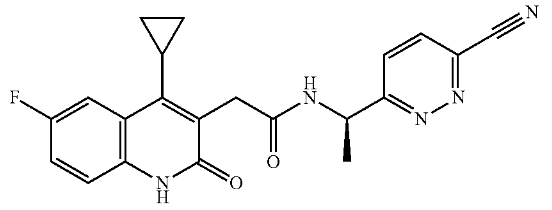 [SMILES: C[C@@H](NC(=O)Cc1c(C2CC2)c2cc(F)ccc2[nH]c1=O)c1ccc(C#N)nn1] |
| 2054 | 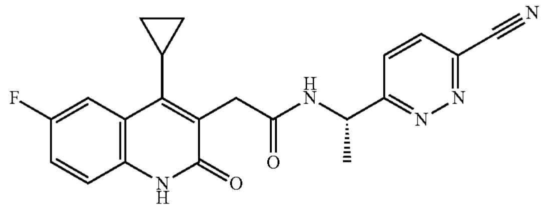 [SMILES: C[C@H](NC(=O)Cc1c(C2CC2)c2cc(F)ccc2[nH]c1=O)c1ccc(C#N)nn1] |

TABLE 1-continued
| Cmpd No. | Structure |
|---|---|
| 2055 | 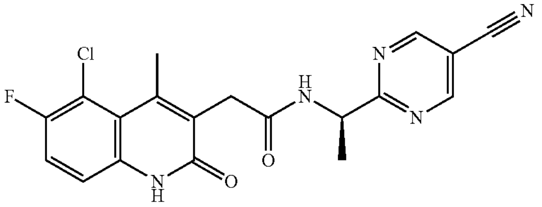 [SMILES: Cc1c(CC(=O)N[C@H](C)c2ncc(C#N)cn2)c(=O)[nH]c2ccc(F)c(Cl)c12] |
| 2056 | 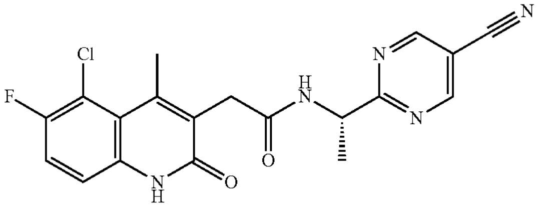 [SMILES: Cc1c(CC(=O)N[C@@H](C)c2ncc(C#N)cn2)c(=O)[nH]c2ccc(F)c(Cl)c12] |
| 2057 | 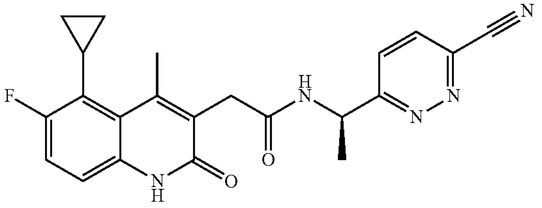 [SMILES: Cc1c(CC(=O)N[C@H](C)c2ccc(C#N)nn2)c(=O)[nH]c2ccc(F)c(C3CC3)c12] |
| 2058 | 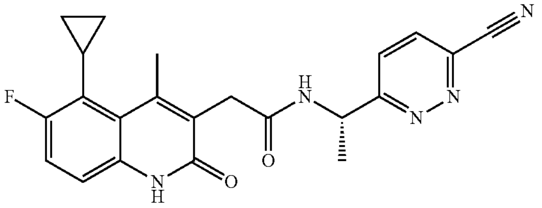 [SMILES: Cc1c(CC(=O)N[C@@H](C)c2ccc(C#N)nn2)c(=O)[nH]c2ccc(F)c(C3CC3)c12] |
| 2059 | 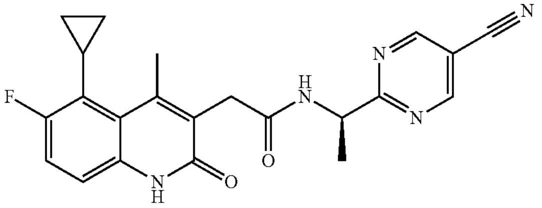 [SMILES: Cc1c(CC(=O)N[C@H](C)c2ncc(C#N)cn2)c(=O)[nH]c2ccc(F)c(C3CC3)c12] |
| 2060 | 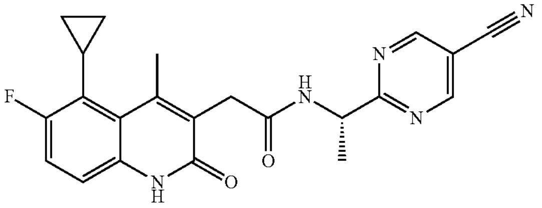 [SMILES: Cc1c(CC(=O)N[C@@H](C)c2ncc(C#N)cn2)c(=O)[nH]c2ccc(F)c(C3CC3)c12] |
| 2061 | 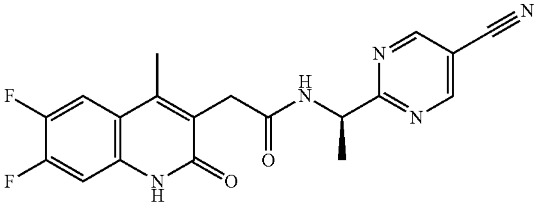 [SMILES: Cc1c(CC(=O)N[C@H](C)c2ncc(C#N)cn2)c(=O)[nH]c2cc(F)c(F)cc12] |

TABLE 1-continued
| Cmpd No. | Structure |
| --- | --- |
| 2062 | 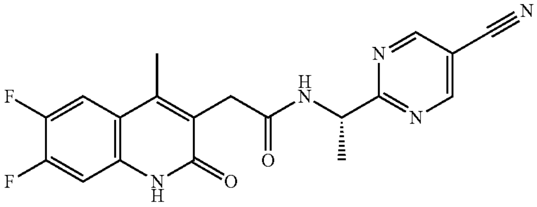 [SMILES: Cc1c(CC(=O)N[C@@H](C)c2ncc(C#N)cn2)c(=O)[nH]c2cc(F)c(F)cc12] |
| 2063 | 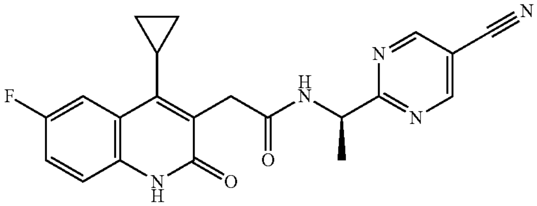 [SMILES: C[C@@H](NC(=O)Cc1c(C2CC2)c2cc(F)ccc2[nH]c1=O)c1ncc(C#N)cn1] |
| 2064 | 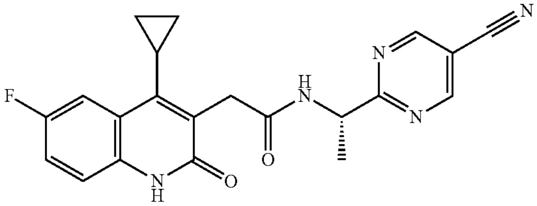 [SMILES: C[C@H](NC(=O)Cc1c(C2CC2)c2cc(F)ccc2[nH]c1=O)c1ncc(C#N)cn1] |
| 2065 | 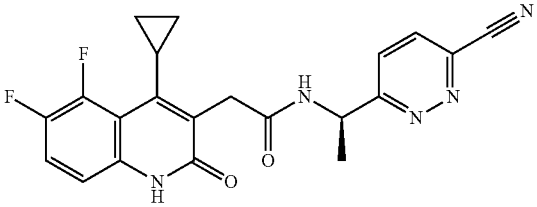 [SMILES: C[C@@H](NC(=O)Cc1c(C2CC2)c2c(F)c(F)ccc2[nH]c1=O)c1ccc(C#N)nn1] |
| 2066 | 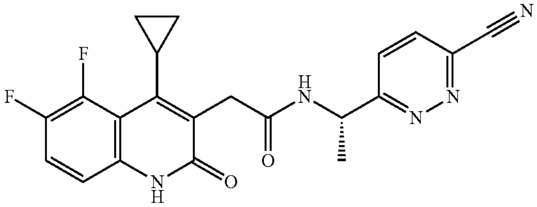 [SMILES: C[C@H](NC(=O)Cc1c(C2CC2)c2c(F)c(F)ccc2[nH]c1=O)c1ccc(C#N)nn1] |
| 2067 | 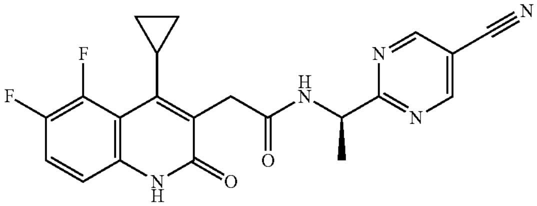 [SMILES: C[C@@H](NC(=O)Cc1c(C2CC2)c2c(F)c(F)ccc2[nH]c1=O)c1ncc(C#N)cn1] |
| 2068 | 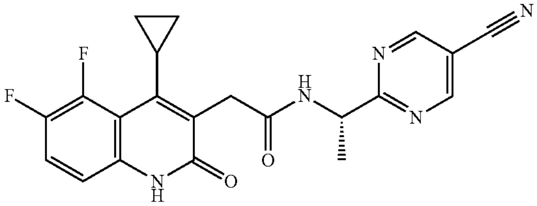 [SMILES: C[C@H](NC(=O)Cc1c(C2CC2)c2c(F)c(F)ccc2[nH]c1=O)c1ncc(C#N)cn1] |

TABLE 1-continued
| Cmpd No. | Structure |
|---|---|
| 2069 | 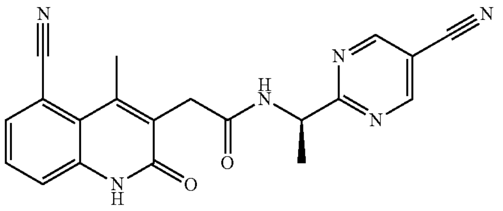 [SMILES: Cc1c(CC(=O)N[C@H](C)c2ncc(C#N)cn2)c(=O)[nH]c2cccc(C#N)c12] |
| 2070 | 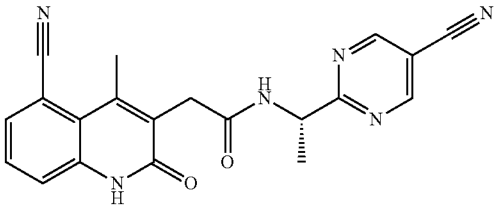 [SMILES: Cc1c(CC(=O)N[C@@H](C)c2ncc(C#N)cn2)c(=O)[nH]c2cccc(C#N)c12] |
| 2071 | 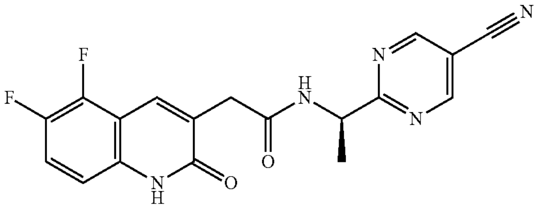 [SMILES: C[C@@H](NC(=O)Cc1cc2c(F)c(F)ccc2[nH]c1=O)c1ncc(C#N)cn1] |
| 2072 | 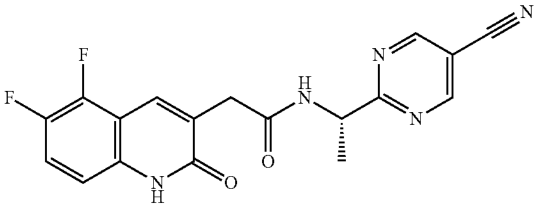 [SMILES: C[C@H](NC(=O)Cc1cc2c(F)c(F)ccc2[nH]c1=O)c1ncc(C#N)cn1] |
| 2073 | 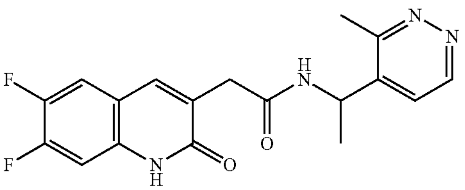 [SMILES: Cc1nnccc1C(C)NC(=O)Cc1cc2cc(F)c(F)cc2[nH]c1=O] |
| 2074 | 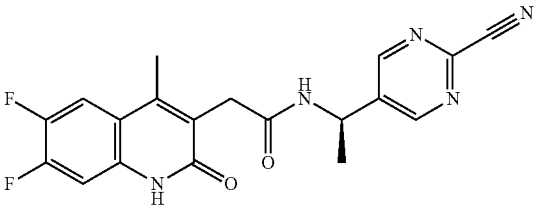 [SMILES: Cc1c(CC(=O)N[C@H](C)c2cnc(C#N)nc2)c(=O)[nH]c2cc(F)c(F)cc12] |
| 2075 | 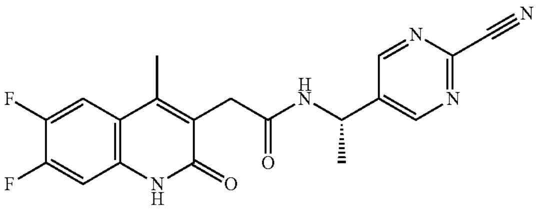 [SMILES: Cc1c(CC(=O)N[C@@H](C)c2cnc(C#N)nc2)c(=O)[nH]c2cc(F)c(F)cc12] |

TABLE 1-continued
| Cmpd No. | Structure |
|---|---|
| 2076 | 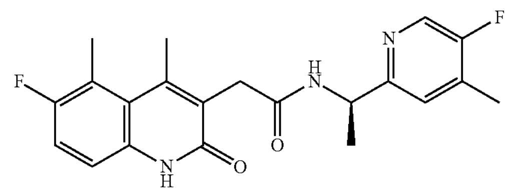 [SMILES: Cc1cc([C@@H](C)NC(=O)Cc2c(C)c3c(C)c(F)ccc3[nH]c2=O)ncc1F] |
| 2077 | 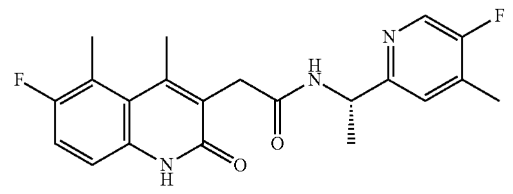 [SMILES: Cc1cc([C@H](C)NC(=O)Cc2c(C)c3c(C)c(F)ccc3[nH]c2=O)ncc1F] |
| 2078 | 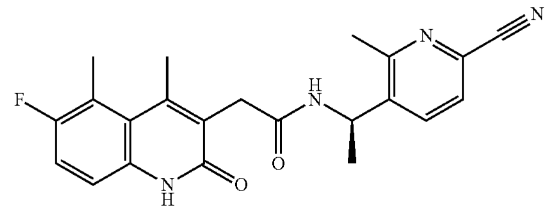 [SMILES: Cc1nc(C#N)ccc1[C@@H](C)NC(=O)Cc1c(C)c2c(C)c(F)ccc2[nH]c1=O] |
| 2079 | 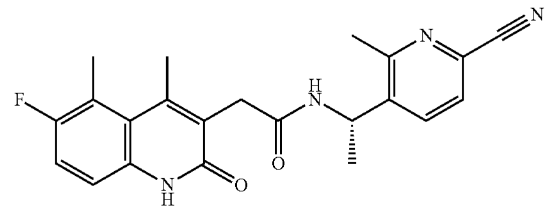 [SMILES: Cc1nc(C#N)ccc1[C@H](C)NC(=O)Cc1c(C)c2c(C)c(F)ccc2[nH]c1=O] |
| 2501 | 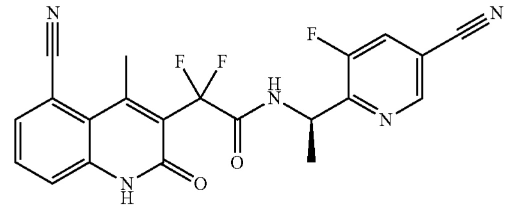 [SMILES: Cc1c(C(F)(F)C(=O)N[C@H](C)c2ncc(C#N)cc2F)c(=O)[nH]c2cccc(C#N)c12] |
| 2502 | 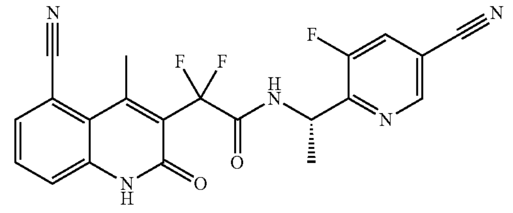 [SMILES: Cc1c(C(F)(F)C(=O)N[C@@H](C)c2ncc(C#N)cc2F)c(=O)[nH]c2cccc(C#N)c12] |
| 2503 | 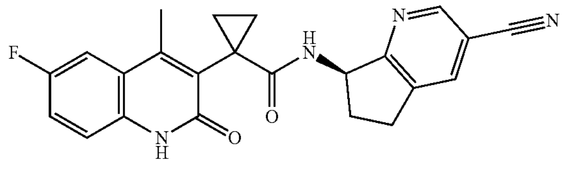 [SMILES: Cc1c(C2(C(=O)N[C@@H]3CCc4cc(C#N)cnc43)CC2)c(=O)[nH]c2ccc(F)cc12] |

TABLE 1-continued
| Cmpd No. | Structure |
|---|---|
| 2504 | 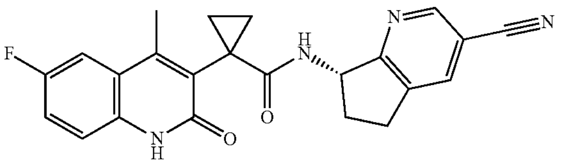 [SMILES: Cc1c(C2(C(=O)N[C@H]3CCc4cc(C#N)cnc43)CC2)c(=O)[nH]c2ccc(F)cc12] |
| 2505 | 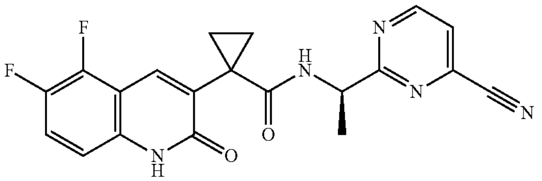 [SMILES: C[C@@H](NC(=O)C1(c2cc3c(F)c(F)ccc3[nH]c2=O)CC1)c1nccc(C#N)n1] |
| 2506 | 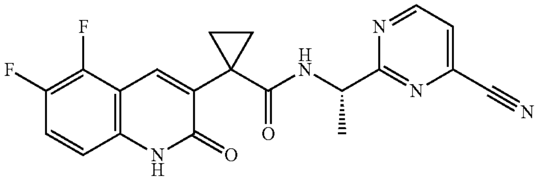 [SMILES: C[C@H](NC(=O)C1(c2cc3c(F)c(F)ccc3[nH]c2=O)CC1)c1nccc(C#N)n1] |
| 2507 | 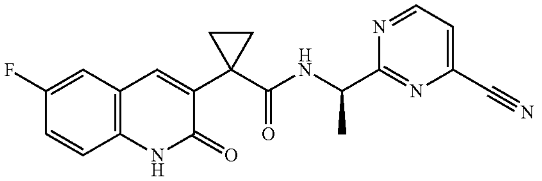 [SMILES: C[C@@H](NC(=O)C1(c2cc3cc(F)ccc3[nH]c2=O)CC1)c1nccc(C#N)n1] |
| 2508 | 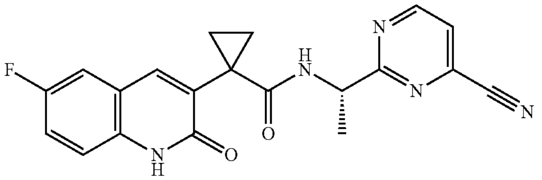 [SMILES: C[C@H](NC(=O)C1(c2cc3cc(F)ccc3[nH]c2=O)CC1)c1nccc(C#N)n1] |
| 2509 | 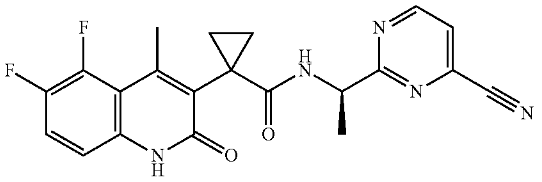 [SMILES: Cc1c(C2(C(=O)N[C@H](C)c3nccc(C#N)n3)CC2)c(=O)[nH]c2ccc(F)c(F)c12] |
| 2510 | 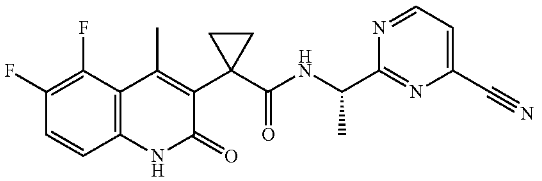 [SMILES: Cc1c(C2(C(=O)N[C@@H](C)c3nccc(C#N)n3)CC2)c(=O)[nH]c2ccc(F)c(F)c12] |
| 2511 | 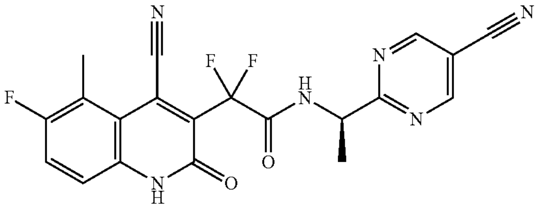 [SMILES: Cc1c(F)ccc2[nH]c(=O)c(C(F)(F)C(=O)N[C@H](C)c3ncc(C#N)cn3)c(C#N)c12] |

TABLE 1-continued
| Cmpd No. | Structure |
|---|---|
| 2512 | 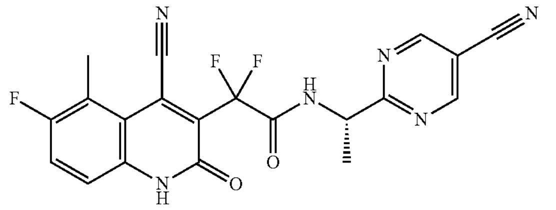 [SMILES: Cc1c(F)ccc2[nH]c(=O)c(C(F)(F)C(=O)N[C@@H](C)c3ncc(C#N)cn3)c(C#N)c12] |
| 2513 | 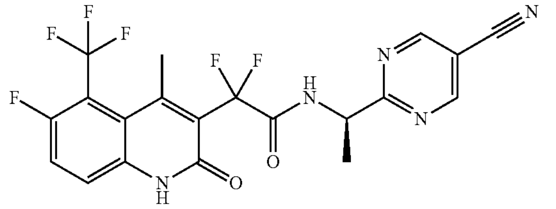 [SMILES: Cc1c(C(F)(F)C(=O)N[C@H](C)c2ncc(C#N)cn2)c(=O)[nH]c2ccc(F)c(C(F)(F)F)c12] |
| 2514 | 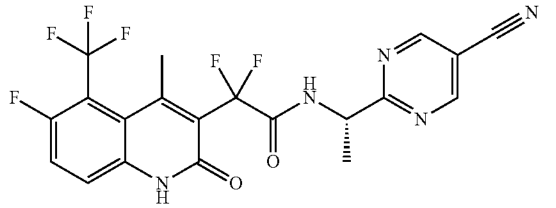 [SMILES: Cc1c(C(F)(F)C(=O)N[C@@H](C)c2ncc(C#N)cn2)c(=O)[nH]c2ccc(F)c(C(F)(F)F)c12] |
| 2515 | 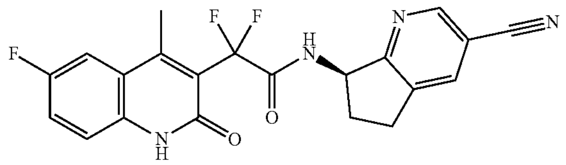 [SMILES: Cc1c(C(F)(F)C(=O)N[C@@H]2CCc3cc(C#N)cnc32)c(=O)[nH]c2ccc(F)cc12] |
| 2516 | 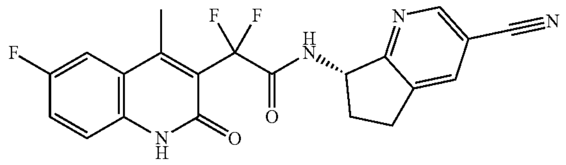 [SMILES: Cc1c(C(F)(F)C(=O)N[C@H]2CCc3cc(C#N)cnc32)c(=O)[nH]c2ccc(F)cc12] |
| 2517 | 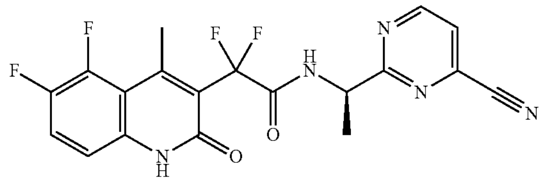 [SMILES: Cc1c(C(F)(F)C(=O)N[C@H](C)c2nccc(C#N)n2)c(=O)[nH]c2ccc(F)c(F)c12] |
| 2518 | 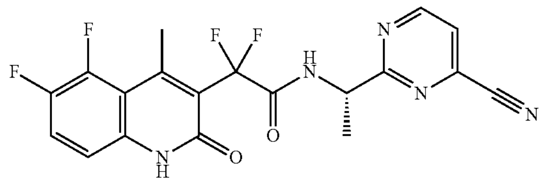 [SMILES: Cc1c(C(F)(F)C(=O)N[C@@H](C)c2nccc(C#N)n2)c(=O)[nH]c2ccc(F)c(F)c12] |

TABLE 1-continued
| Cmpd No. | Structure |
|---|---|
| 2519 | 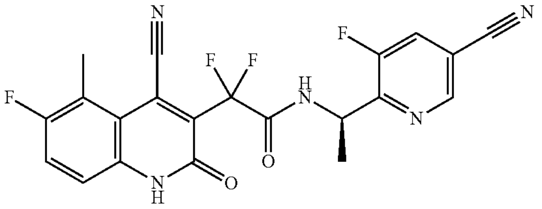 [SMILES: Cc1c(F)ccc2[nH]c(=O)c(C(F)(F)C(=O)N[C@H](C)c3ncc(C#N)cc3F)c(C#N)c12] |
| 2520 | 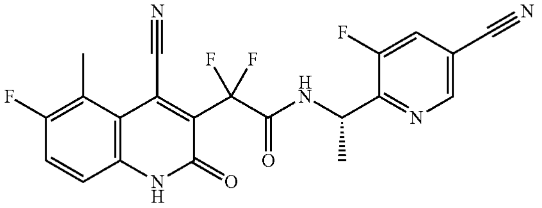 [SMILES: Cc1c(F)ccc2[nH]c(=O)c(C(F)(F)C(=O)N[C@@H](C)c3ncc(C#N)cc3F)c(C#N)c12] |
| 2521 | 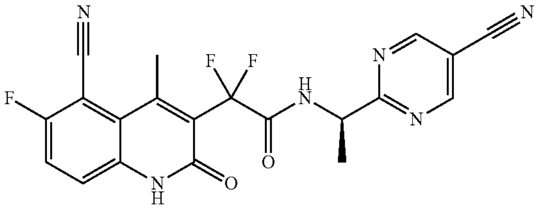 [SMILES: Cc1c(C(F)(F)C(=O)N[C@H](C)c2ncc(C#N)cn2)c(=O)[nH]c2ccc(F)c(C#N)c12] |
| 2522 | 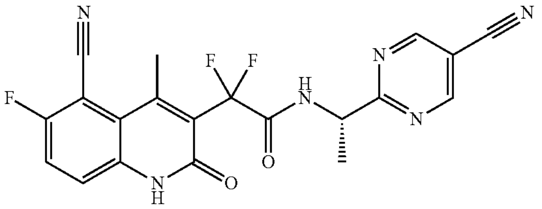 [SMILES: Cc1c(C(F)(F)C(=O)N[C@@H](C)c2ncc(C#N)cn2)c(=O)[nH]c2ccc(F)c(C#N)c12] |
| 2523 | 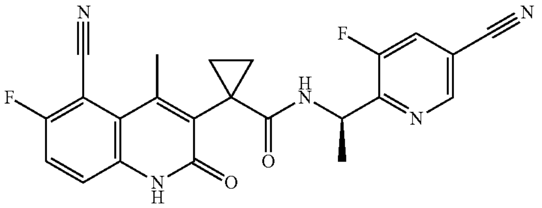 [SMILES: Cc1c(C2(C(=O)N[C@H](C)c3ncc(C#N)cc3F)CC2)c(=O)[nH]c2ccc(F)c(C#N)c12] |
| 2524 | 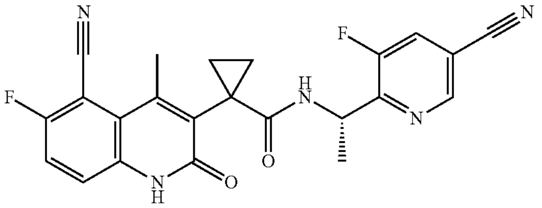 [SMILES: Cc1c(C2(C(=O)N[C@@H](C)c3ncc(C#N)cc3F)CC2)c(=O)[nH]c2ccc(F)c(C#N)c12] |
| 2527 | 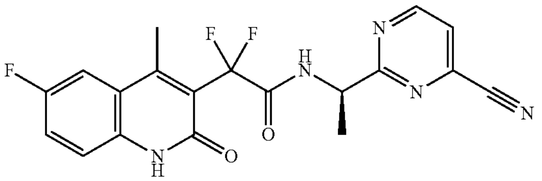 [SMILES: Cc1c(C(F)(F)C(=O)N[C@H](C)c2nccc(C#N)n2)c(=O)[nH]c2ccc(F)cc12] |

TABLE 1-continued
| Cmpd No. | Structure |
|---|---|
| 2528 | 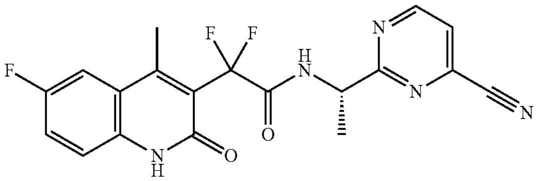 [SMILES: Cc1c(C(F)(F)C(=O)N[C@@H](C)c2nccc(C#N)n2)c(=O)[nH]c2ccc(F)cc12] |
| 2529 | 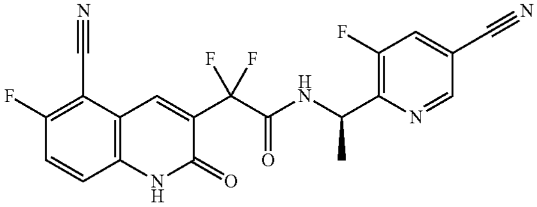 [SMILES: C[C@@H](NC(=O)C(F)(F)c1cc2c(C#N)c(F)ccc2[nH]c1=O)c1ncc(C#N)cc1F] |
| 2530 | 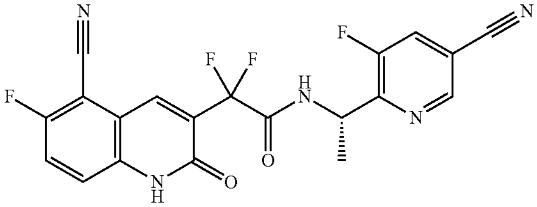 [SMILES: C[C@H](NC(=O)C(F)(F)c1cc2c(C#N)c(F)ccc2[nH]c1=O)c1ncc(C#N)cc1F] |
| 2531 | 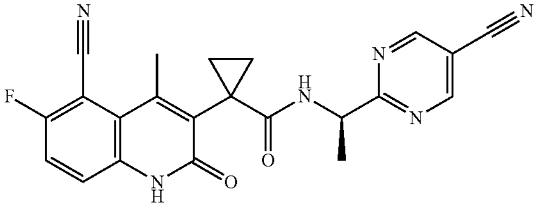 [SMILES: Cc1c(C2(C(=O)N[C@H](C)c3ncc(C#N)cn3)CC2)c(=O)[nH]c2ccc(F)c(C#N)c12] |
| 2532 | 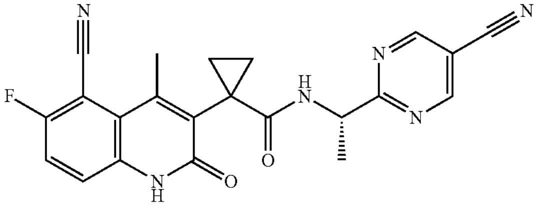 [SMILES: Cc1c(C2(C(=O)N[C@@H](C)c3ncc(C#N)cn3)CC2)c(=O)[nH]c2ccc(F)c(C#N)c12] |
| 2533 | 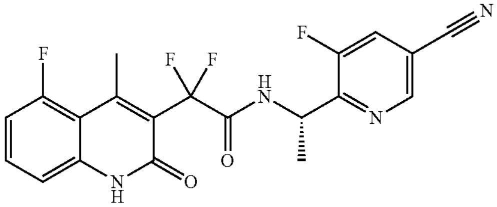 [SMILES: Cc1c(C(F)(F)C(=O)N[C@@H](C)c2ncc(C#N)cc2F)c(=O)[nH]c2cccc(F)c12] |
| 2534 | 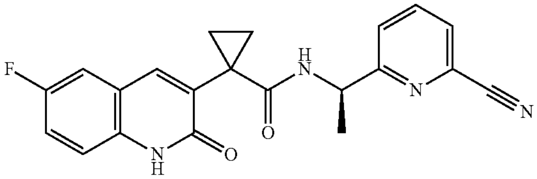 [SMILES: C[C@@H](NC(=O)C1(c2cc3cc(F)ccc3[nH]c2=O)CC1)c1cccc(C#N)n1] |

TABLE 1-continued
| Cmpd No. | Structure |
|---|---|
| 2535 | 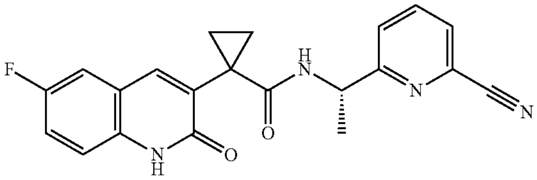 |
| 2536 | 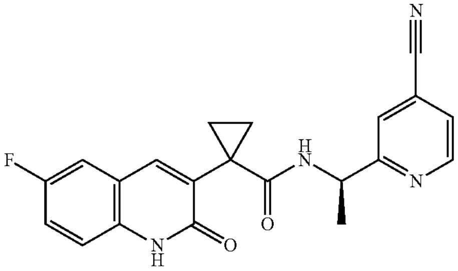 [SMILES: C[C@@H](NC(=O)C1(c2cc3cc(F)ccc3[nH]c2=O)CC1)c1cc(C#N)ccn1] |
| 2537 | 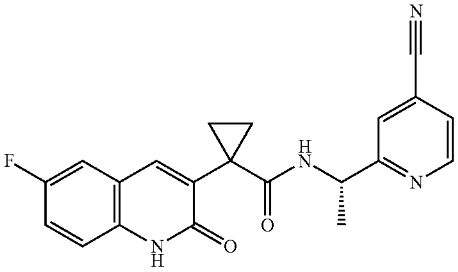 [SMILES: C[C@H](NC(=O)C1(c2cc3cc(F)ccc3[nH]c2=O)CC1)c1cc(C#N)ccn1] |
| 2538 | 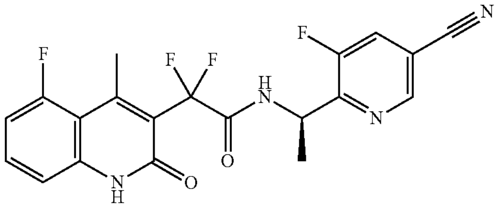 [SMILES: Cc1c(C(F)(F)C(=O)N[C@H](C)c2ncc(C#N)cc2F)c(=O)[nH]c2cccc(F)c12] |
| 2539 | 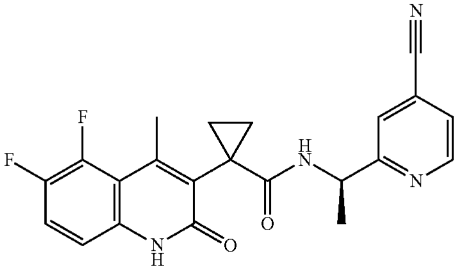 [SMILES: Cc1c(C2(C(=O)N[C@H](C)c3cc(C#N)ccn3)CC2)c(=O)[nH]c2ccc(F)c(F)c12] |
| 2540 | 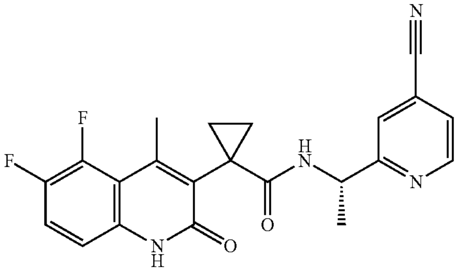 [SMILES: Cc1c(C2(C(=O)N[C@@H](C)c3cc(C#N)ccn3)CC2)c(=O)[nH]c2ccc(F)c(F)c12] |

TABLE 1-continued
| Cmpd No. | Structure |
|---|---|
| 2541 | 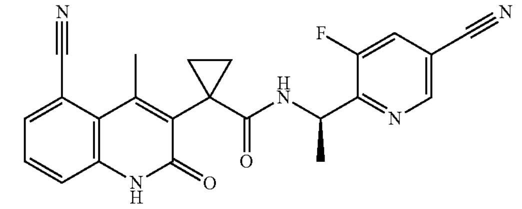 [SMILES: Cc1c(C2(C(=O)N[C@H](C)c3ncc(C#N)cc3F)CC2)c(=O)[nH]c2cccc(C#N)c12] |
| 2542 | 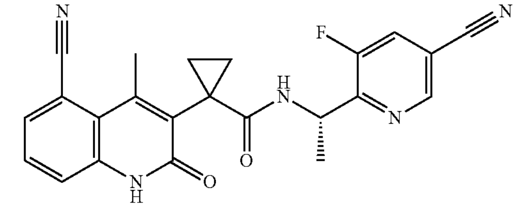 [SMILES: Cc1c(C2(C(=O)N[C@@H](C)c3ncc(C#N)cc3F)CC2)c(=O)[nH]c2cccc(C#N)c12] |
| 2543 | 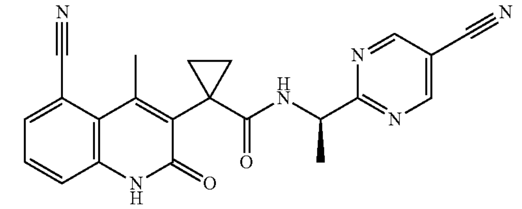 [SMILES: Cc1c(C2(C(=O)N[C@H](C)c3ncc(C#N)cn3)CC2)c(=O)[nH]c2cccc(C#N)c12] |
| 2544 | 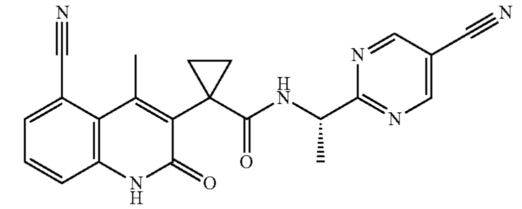 [SMILES: Cc1c(C2(C(=O)N[C@@H](C)c3ncc(C#N)cn3)CC2)c(=O)[nH]c2cccc(C#N)c12] |
| 2545 | 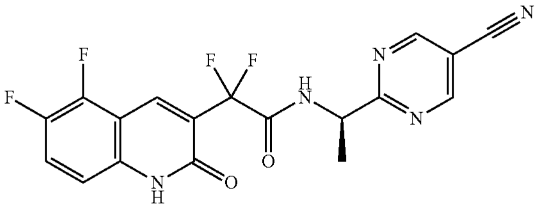 [SMILES: C[C@@H](NC(=O)C(F)(F)c1cc2c(F)c(F)ccc2[nH]c1=O)c1ncc(C#N)cn1] |
| 2546 | 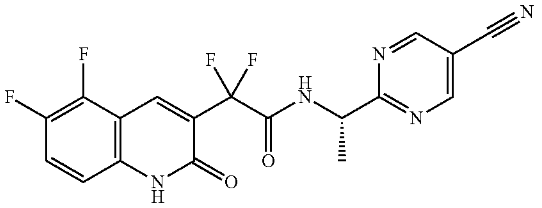 |
| 2547 | 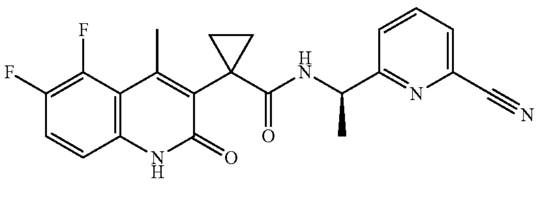 [SMILES: Cc1c(C2(C(=O)N[C@H](C)c3cccc(C#N)n3)CC2)c(=O)[nH]c2ccc(F)c(F)c12] |

TABLE 1-continued
| Cmpd No. | Structure |
| --- | --- |
| 2548 | 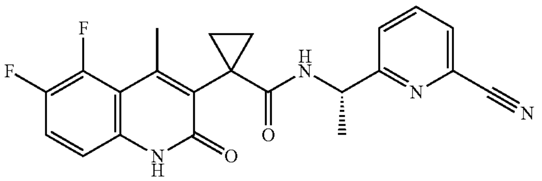 [SMILES: Cc1c(C2(C(=O)N[C@@H](C)c3cccc(C#N)n3)CC2)c(=O)[nH]c2ccc(F)c(F)c12] |
| 2549 | 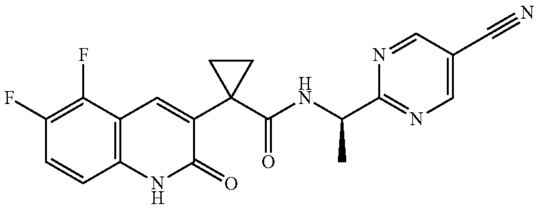 [SMILES: C[C@@H](NC(=O)C1(c2cc3c(F)c(F)ccc3[nH]c2=O)CC1)c1ncc(C#N)cn1] |
| 2550 | 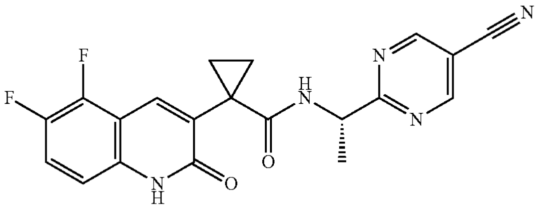 [SMILES: C[C@H](NC(=O)C1(c2cc3c(F)c(F)ccc3[nH]c2=O)CC1)c1ncc(C#N)cn1] |
| 2551 | 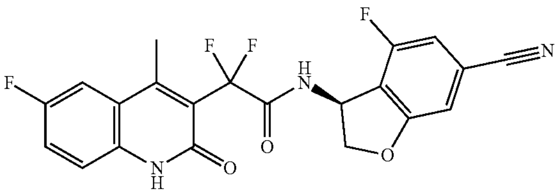 [SMILES: Cc1c(C(F)(F)C(=O)N[C@@H]2COc3cc(C#N)cc(F)c32)c(=O)[nH]c2ccc(F)cc12] |
| 2552 | 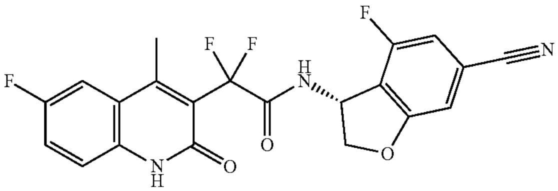 [SMILES: Cc1c(C(F)(F)C(=O)N[C@H]2COc3cc(C#N)cc(F)c32)c(=O)[nH]c2ccc(F)cc12] |
| 2553 | 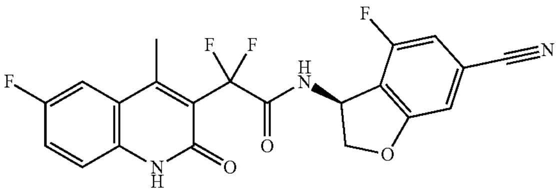 [SMILES: Cc1c(C(F)(F)C(=O)N[C@@H]2COc3cc(C#N)cc(F)c32)c(=O)[nH]c2ccc(F)cc12] |
| 2554 | 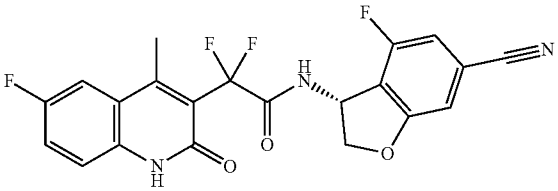 [SMILES: Cc1c(C(F)(F)C(=O)N[C@H]2COc3cc(C#N)cc(F)c32)c(=O)[nH]c2ccc(F)cc12] |

TABLE 1-continued
| Cmpd No. | Structure |
|---|---|
| 2555 | 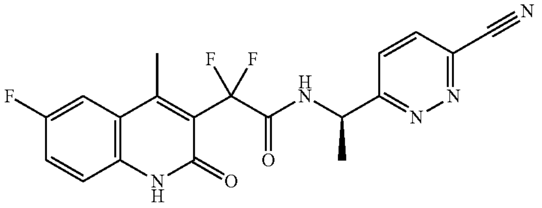 [SMILES: Cc1c(C(F)(F)C(=O)N[C@H](C)c2ccc(C#N)nn2)c(=O)[nH]c2ccc(F)cc12] |
| 2556 | 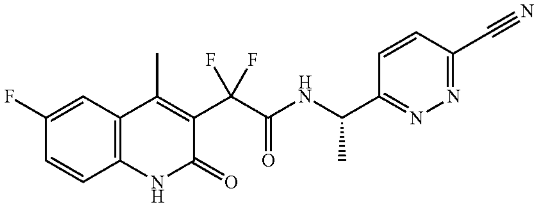 [SMILES: Cc1c(C(F)(F)C(=O)N[C@@H](C)c2ccc(C#N)nn2)c(=O)[nH]c2ccc(F)cc12] |
| 2557 | 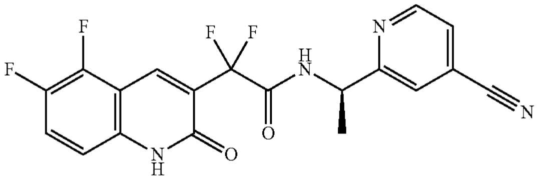 [SMILES: C[C@@H](NC(=O)C(F)(F)c1cc2c(F)c(F)ccc2[nH]c1=O)c1cc(C#N)ccn1] |
| 2558 | 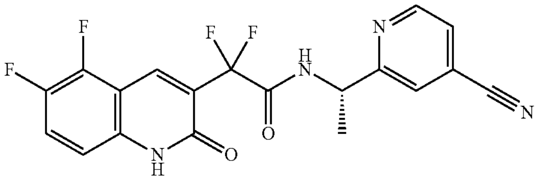 [SMILES: C[C@H](NC(=O)C(F)(F)c1cc2c(F)c(F)ccc2[nH]c1=O)c1cc(C#N)ccn1] |
| 2559 | 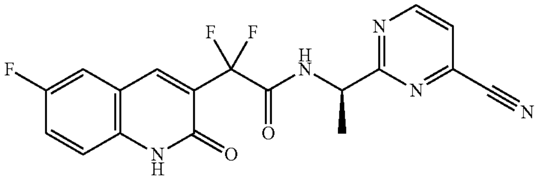 [SMILES: C[C@@H](NC(=O)C(F)(F)c1cc2cc(F)ccc2[nH]c1=O)c1nccc(C#N)n1] |
| 2560 | 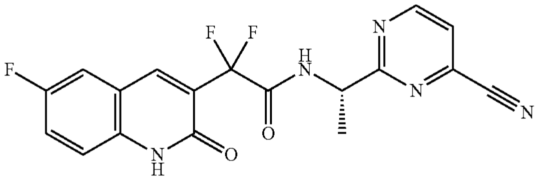 [SMILES: C[C@H](NC(=O)C(F)(F)c1cc2cc(F)ccc2[nH]c1=O)c1nccc(C#N)n1] |
| 2561 | 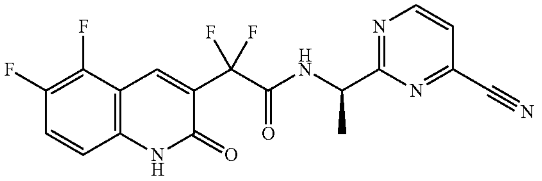 [SMILES: C[C@@H](NC(=O)C(F)(F)c1cc2c(F)c(F)ccc2[nH]c1=O)c1nccc(C#N)n1] |
| 2562 | 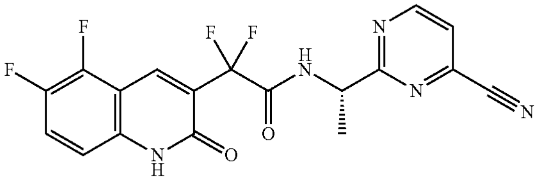 [SMILES: C[C@H](NC(=O)C(F)(F)c1cc2c(F)c(F)ccc2[nH]c1=O)c1nccc(C#N)n1] |

TABLE 1-continued
| Cmpd No. | Structure |
| --- | --- |
| 2563 | 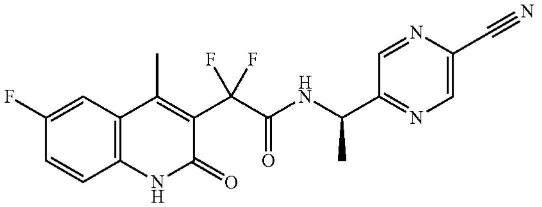 [SMILES: Cc1c(C(F)(F)C(=O)N[C@H](C)c2cnc(C#N)cn2)c(=O)[nH]c2ccc(F)cc12] |
| 2564 | 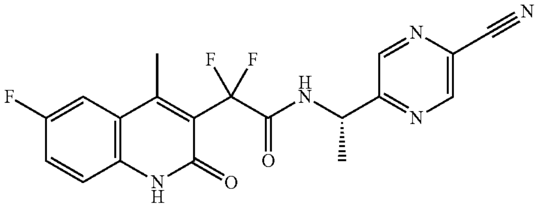 [SMILES: Cc1c(C(F)(F)C(=O)N[C@@H](C)c2cnc(C#N)cn2)c(=O)[nH]c2ccc(F)cc12] |
| 2565 | 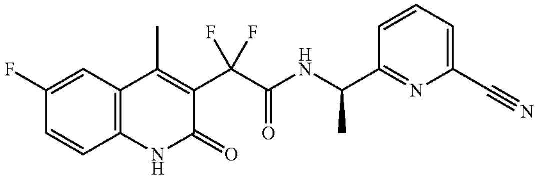 [SMILES: Cc1c(C(F)(F)C(=O)N[C@H](C)c2cccc(C#N)n2)c(=O)[nH]c2ccc(F)cc12] |
| 2566 | 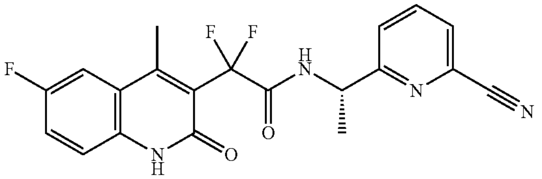 [SMILES: Cc1c(C(F)(F)C(=O)N[C@@H](C)c2cccc(C#N)n2)c(=O)[nH]c2ccc(F)cc12] |
| 2567 | 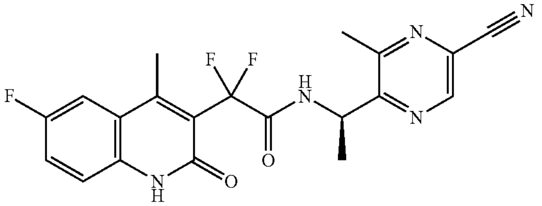 [SMILES: Cc1nc(C#N)cnc1[C@@H](C)NC(=O)C(F)(F)c1c(C)c2cc(F)ccc2[nH]c1=O] |
| 2568 | 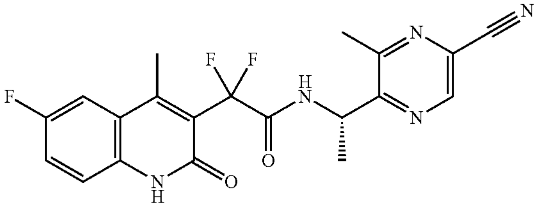 [SMILES: Cc1nc(C#N)cnc1[C@H](C)NC(=O)C(F)(F)c1c(C)c2cc(F)ccc2[nH]c1=O] |
| 2569 | 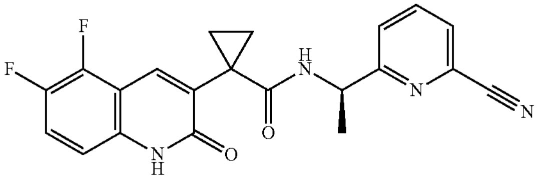 [SMILES: C[C@@H](NC(=O)C1(c2cc3c(F)c(F)ccc3[nH]c2=O)CC1)c1cccc(C#N)n1] |

TABLE 1-continued
| Cmpd No. | Structure |
|---|---|
| 2570 | 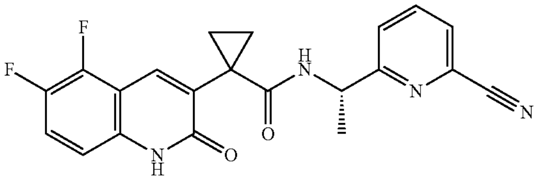 [SMILES: C[C@H](NC(=O)C1(c2cc3c(F)c(F)ccc3[nH]c2=O)CC1)c1cccc(C#N)n1] |
| 2571 | 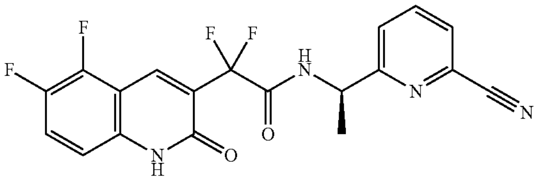 [SMILES: C[C@@H](NC(=O)C(F)(F)c1cc2c(F)c(F)ccc2[nH]c1=O)c1cccc(C#N)n1] |
| 2572 | 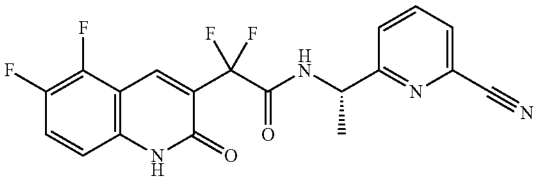 [SMILES: C[C@H](NC(=O)C(F)(F)c1cc2c(F)c(F)ccc2[nH]c1=O)c1cccc(C#N)n1] |
| 2573 | 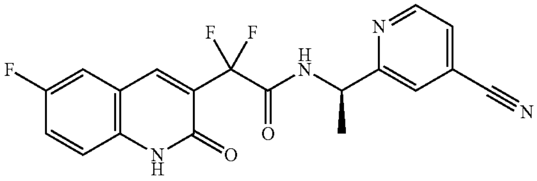 [SMILES: C[C@@H](NC(=O)C(F)(F)c1cc2cc(F)ccc2[nH]c1=O)c1cc(C#N)ccn1] |
| 2574 | 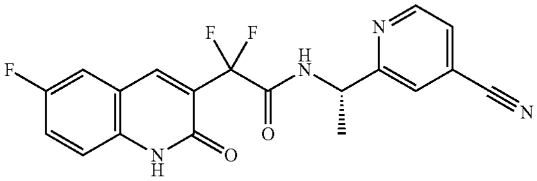 [SMILES: C[C@H](NC(=O)C(F)(F)c1cc2cc(F)ccc2[nH]c1=O)c1cc(C#N)ccn1] |
| 2575 | 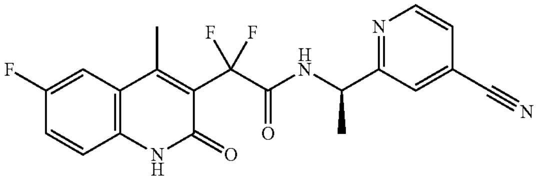 [SMILES: Cc1c(C(F)(F)C(=O)N[C@H](C)c2cc(C#N)ccn2)c(=O)[nH]c2ccc(F)cc12] |
| 2576 | 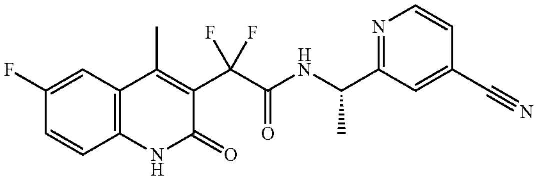 [SMILES: Cc1c(C(F)(F)C(=O)N[C@@H](C)c2cc(C#N)ccn2)c(=O)[nH]c2ccc(F)cc12] |

TABLE 1-continued
| Cmpd No. | Structure |
| --- | --- |
| 2577 | 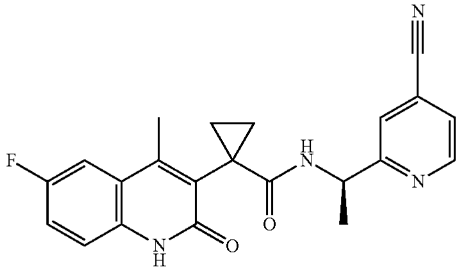 [SMILES: Cc1c(C2(C(=O)N[C@H](C)c3cc(C#N)ccn3)CC2)c(=O)[nH]c2ccc(F)cc12] |
| 2578 | 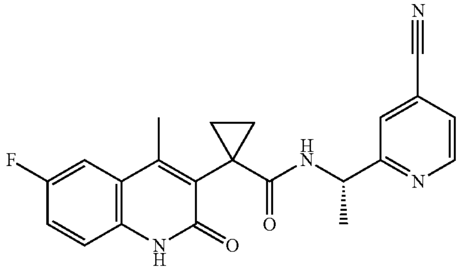 [SMILES: Cc1c(C2(C(=O)N[C@@H](C)c3cc(C#N)ccn3)CC2)c(=O)[nH]c2ccc(F)cc12] |
| 2579 | 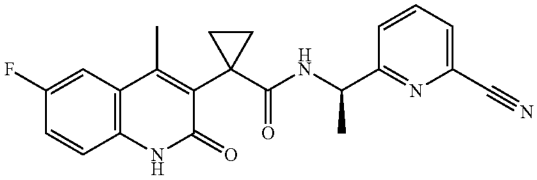 [SMILES: Cc1c(C2(C(=O)N[C@H](C)c3cccc(C#N)n3)CC2)c(=O)[nH]c2ccc(F)cc12] |
| 2580 | 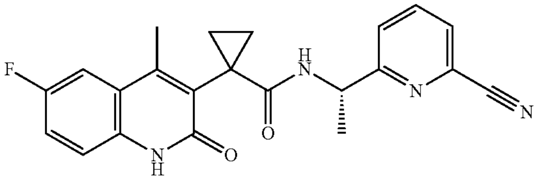 [SMILES: Cc1c(C2(C(=O)N[C@@H](C)c3cccc(C#N)n3)CC2)c(=O)[nH]c2ccc(F)cc12] |
| 2581 | 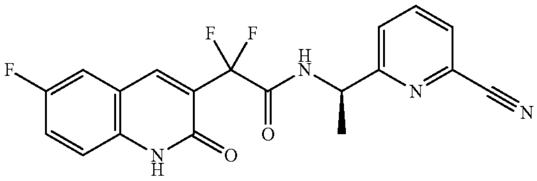 [SMILES: C[C@@H](NC(=O)C(F)(F)c1cc2cc(F)ccc2[nH]c1=O)c1cccc(C#N)n1] |
| 2582 | 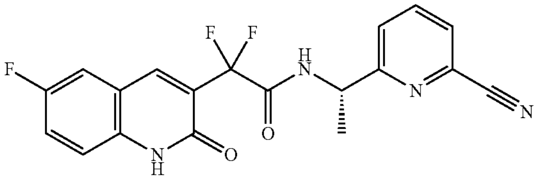 [SMILES: C[C@H](NC(=O)C(F)(F)c1cc2cc(F)ccc2[nH]c1=O)c1cccc(C#N)n1] |

TABLE 1-continued
| Cmpd No. | Structure |
|---|---|
| 2583 | 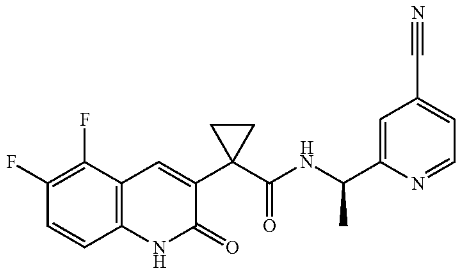 [SMILES: C[C@@H](NC(=O)C1(c2cc3c(F)c(F)ccc3[nH]c2=O)CC1)c1cc(C#N)ccn1] |
| 2584 | 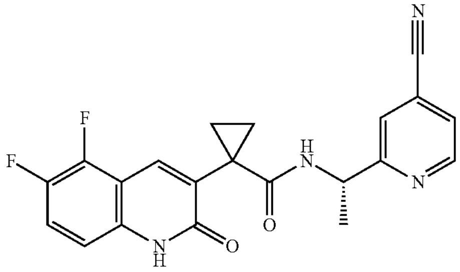 [SMILES: C[C@H](NC(=O)C1(c2cc3c(F)c(F)ccc3[nH]c2=O)CC1)c1cc(C#N)ccn1] |
| 2585 | 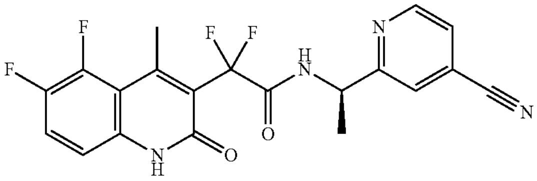 [SMILES: Cc1c(C(F)(F)C(=O)N[C@H](C)c2cc(C#N)ccn2)c(=O)[nH]c2ccc(F)c(F)c12] |
| 2586 | 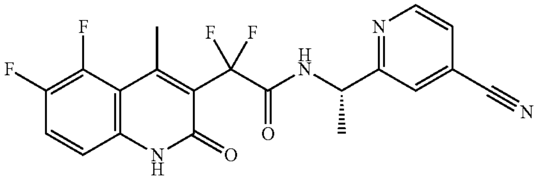 [SMILES: Cc1c(C(F)(F)C(=O)N[C@@H](C)c2cc(C#N)ccn2)c(=O)[nH]c2ccc(F)c(F)c12] |
| 2587 | 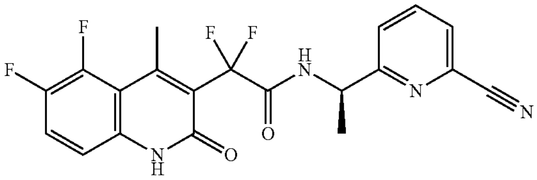 [SMILES: Cc1c(C(F)(F)C(=O)N[C@H](C)c2cccc(C#N)n2)c(=O)[nH]c2ccc(F)c(F)c12] |
| 2588 | 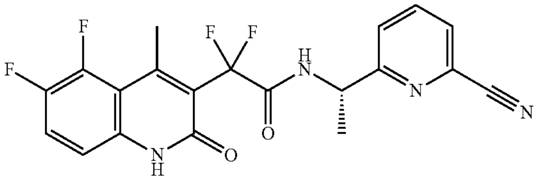 [SMILES: Cc1c(C(F)(F)C(=O)N[C@@H](C)c2cccc(C#N)n2)c(=O)[nH]c2ccc(F)c(F)c12] |
| 2590 | 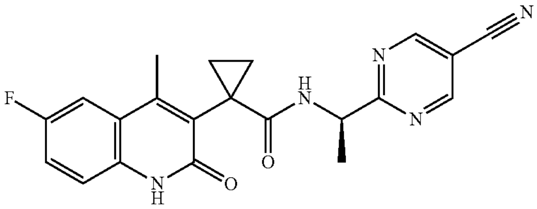 [SMILES: Cc1c(C2(C(=O)N[C@H](C)c3ncc(C#N)cn3)CC2)c(=O)[nH]c2ccc(F)cc12] |

TABLE 1-continued
| Cmpd No. | Structure |
| --- | --- |
| 2591 | 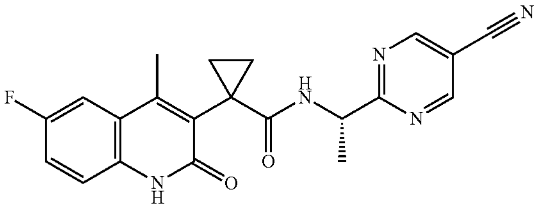 [SMILES: Cc1c(C2(C(=O)N[C@@H](C)c3ncc(C#N)cn3)CC2)c(=O)[nH]c2ccc(F)cc12] |
| 2592 | 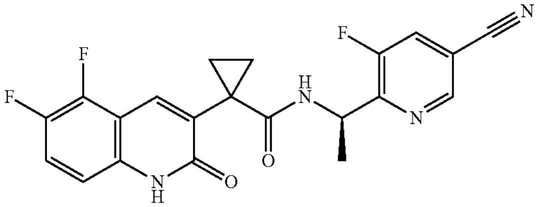 [SMILES: C[C@@H](NC(=O)C1(c2cc3c(F)c(F)ccc3[nH]c2=O)CC1)c1ncc(C#N)cc1F] |
| 2593 | 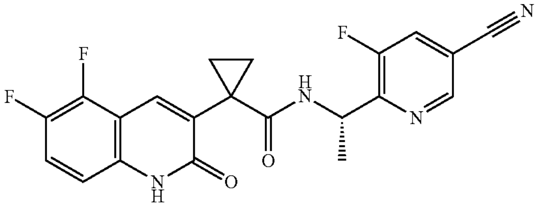 [SMILES: C[C@H](NC(=O)C1(c2cc3c(F)c(F)ccc3[nH]c2=O)CC1)c1ncc(C#N)cc1F] |
| 2594 | 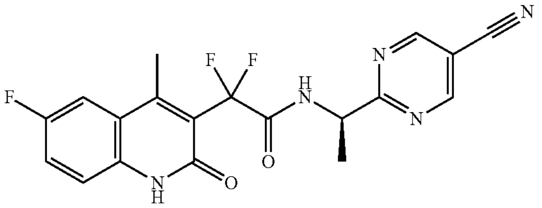 [SMILES: Cc1c(C(F)(F)C(=O)N[C@H](C)c2ncc(C#N)cn2)c(=O)[nH]c2ccc(F)cc12] |
| 2595 | 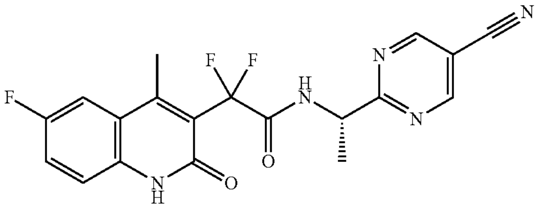 [SMILES: Cc1c(C(F)(F)C(=O)N[C@@H](C)c2ncc(C#N)cn2)c(=O)[nH]c2ccc(F)cc12] |
| 2596 | 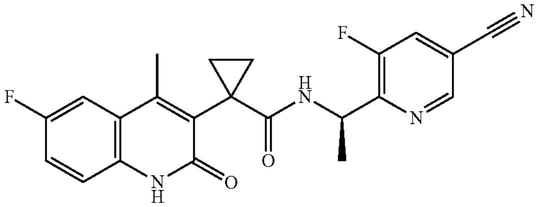 [SMILES: Cc1c(C2(C(=O)N[C@H](C)c3ncc(C#N)cc3F)CC2)c(=O)[nH]c2ccc(F)cc12] |
| 2597 | 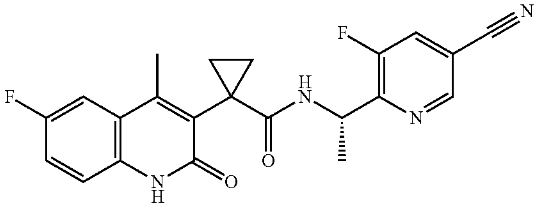 [SMILES: Cc1c(C2(C(=O)N[C@@H](C)c3ncc(C#N)cc3F)CC2)c(=O)[nH]c2ccc(F)cc12] |

TABLE 1-continued
| Cmpd No. | Structure |
| --- | --- |
| 2598 | 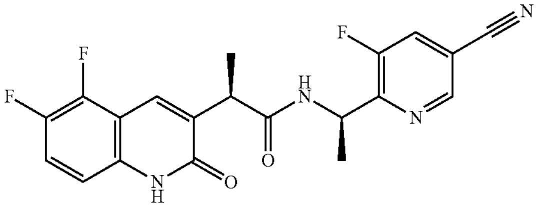 [SMILES: C[C@@H](NC(=O)[C@H](C)c1cc2c(F)c(F)ccc2[nH]c1=O)c1ncc(C#N)cc1F] |
| 2599 | 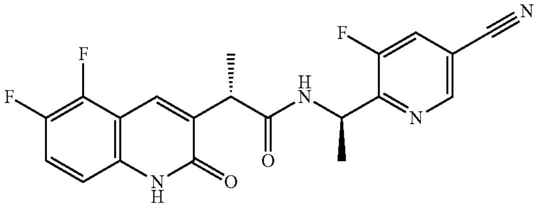 [SMILES: C[C@H](C(=O)N[C@H](C)c1ncc(C#N)cc1F)c1cc2c(F)c(F)ccc2[nH]c1=O] |
| 2600 | 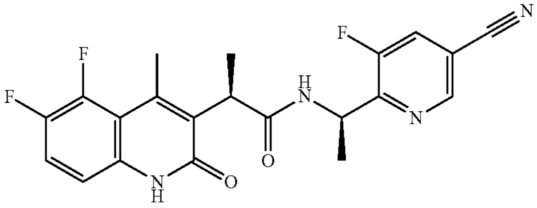 [SMILES: Cc1c([C@@H](C)C(=O)N[C@H](C)c2ncc(C#N)cc2F)c(=O)[nH]c2ccc(F)c(F)c12] |
| 2601 | 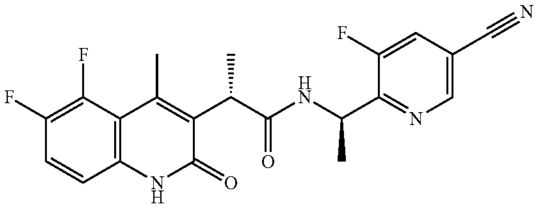 [SMILES: Cc1c([C@H](C)C(=O)N[C@H](C)c2ncc(C#N)cc2F)c(=O)[nH]c2ccc(F)c(F)c12] |
| 2602 | 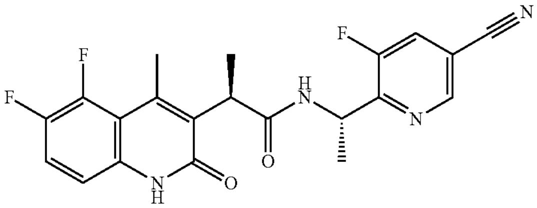 [SMILES: Cc1c([C@@H](C)C(=O)N[C@@H](C)c2ncc(C#N)cc2F)c(=O)[nH]c2ccc(F)c(F)c12] |
| 2603 | 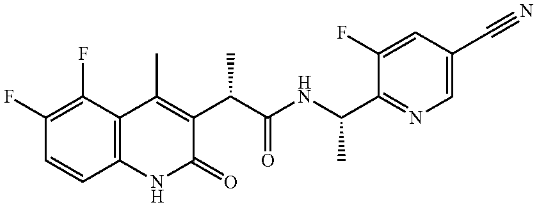 [SMILES: Cc1c([C@H](C)C(=O)N[C@@H](C)c2ncc(C#N)cc2F)c(=O)[nH]c2ccc(F)c(F)c12] |
| 2604 | 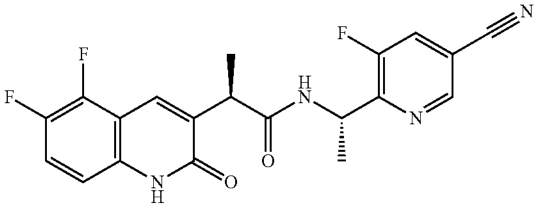 [SMILES: C[C@H](NC(=O)[C@H](C)c1cc2c(F)c(F)ccc2[nH]c1=O)c1ncc(C#N)cc1F] |

TABLE 1-continued
| Cmpd No. | Structure |
|---|---|
| 2605 | 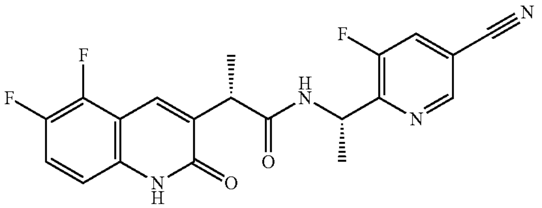 [SMILES: C[C@H](NC(=O)[C@@H](C)c1cc2c(F)c(F)ccc2[nH]c1=O)c1ncc(C#N)cc1F] |
| 2606 | 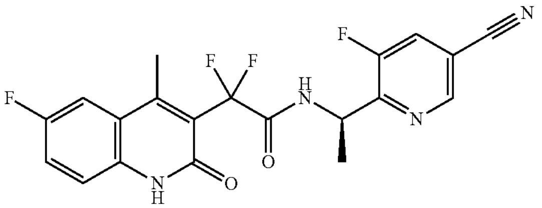 [SMILES: Cc1c(C(F)(F)C(=O)N[C@H](C)c2ncc(C#N)cc2F)c(=O)[nH]c2ccc(F)cc12] |
| 2607 | 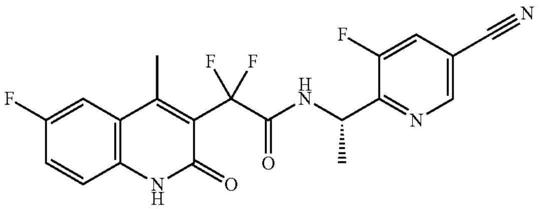 [SMILES: Cc1c(C(F)(F)C(=O)N[C@@H](C)c2ncc(C#N)cc2F)c(=O)[nH]c2ccc(F)cc12] |
| 2608 | 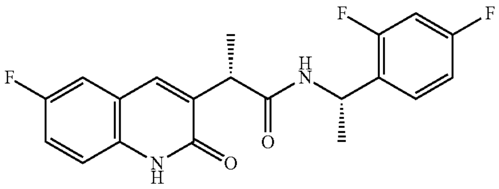 [SMILES: C[C@H](NC(=O)[C@@H](C)c1cc2cc(F)ccc2[nH]c1=O)c1ccc(F)cc1F] |
| 4502 | 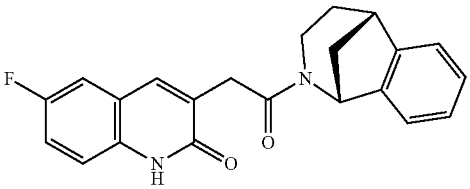 [SMILES: O=C(Cc1cc2cc(F)ccc2[nH]c1=O)N1CC[C@H]2C[C@@H]1c1ccccc12] |
| 4503 | 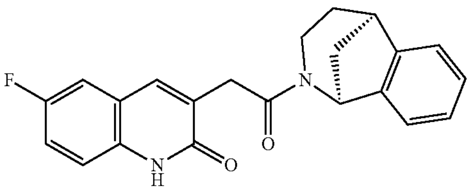 [SMILES: O=C(Cc1cc2cc(F)ccc2[nH]c1=O)N1CC[C@@H]2C[C@H]1c1ccccc12] |
| 4504 | 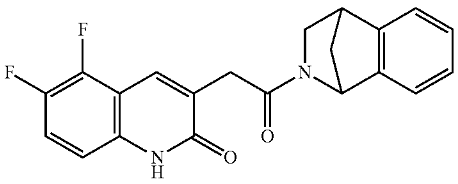 [SMILES: O=C(Cc1cc2c(F)c(F)ccc2[nH]c1=O)N1CC2CC1c1ccccc12] |

TABLE 1-continued
| Cmpd No. | Structure |
|---|---|
| 4505 | 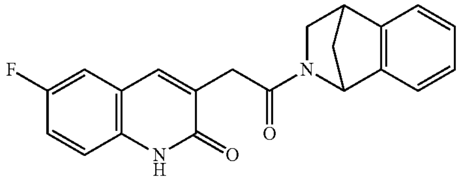 [SMILES: O=C(Cc1cc2cc(F)ccc2[nH]c1=O)N1CC2CC1c1ccccc12] |
| 4801 | 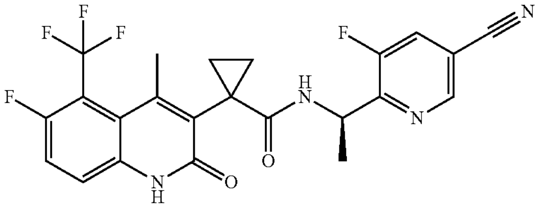 [SMILES: Cc1c(C2(C(=O)N[C@H](C)c3ncc(C#N)cc3F)CC2)c(=O)[nH]c2ccc(F)c(C(F)(F)F)c12] |
| 4802 | 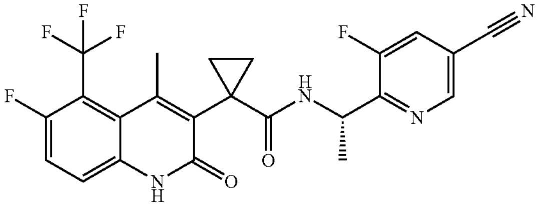 [SMILES: Cc1c(C2(C(=O)N[C@@H](C)c3ncc(C#N)cc3F)CC2)c(=O)[nH]c2ccc(F)c(C(F)(F)F)c12] |
| 4803 | 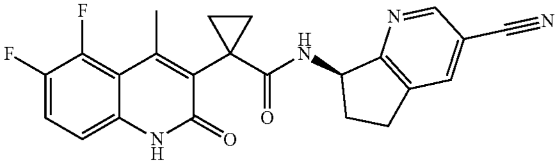 [SMILES: Cc1c(C2(C(=O)N[C@@H]3CCc4cc(C#N)cnc43)CC2)c(=O)[nH]c2ccc(F)c(F)c12] |
| 4804 | 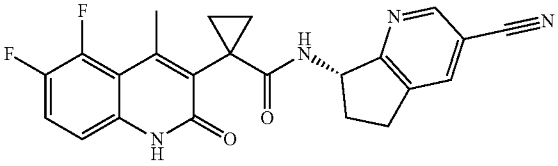 [SMILES: Cc1c(C2(C(=O)N[C@H]3CCc4cc(C#N)cnc43)CC2)c(=O)[nH]c2ccc(F)c(F)c12] |
| 4805 | 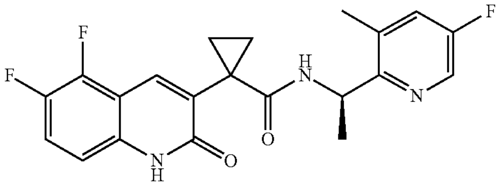 [SMILES: Cc1cc(F)cnc1[C@@H](C)NC(=O)C1(c2cc3c(F)c(F)ccc3[nH]c2=O)CC1] |
| 4806 | 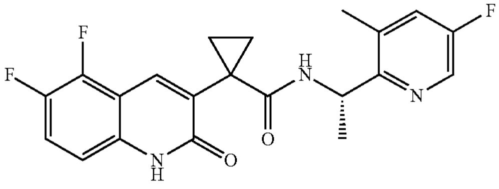 [SMILES: Cc1cc(F)cnc1[C@H](C)NC(=O)C1(c2cc3c(F)c(F)ccc3[nH]c2=O)CC1] |
| 4807 | 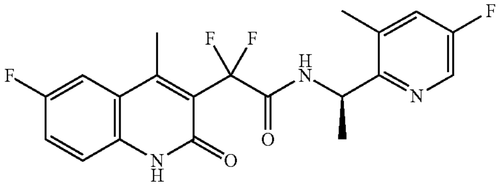 [SMILES: Cc1cc(F)cnc1[C@@H](C)NC(=O)C(F)(F)c1c(C)c2cc(F)ccc2[nH]c1=O] |

TABLE 1-continued
| Cmpd No. | Structure |
| --- | --- |
| 4808 | 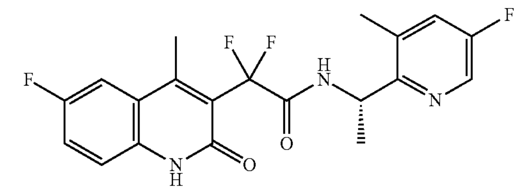 [SMILES: Cc1cc(F)cnc1[C@H](C)NC(=O)C(F)(F)c1c(C)c2cc(F)ccc2[nH]c1=O] |
| 4809 | 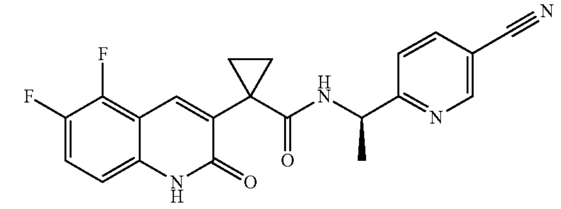 [SMILES: C[C@@H](NC(=O)C1(c2cc3c(F)c(F)ccc3[nH]c2=O)CC1)c1ccc(C#N)cn1] |
| 4810 | 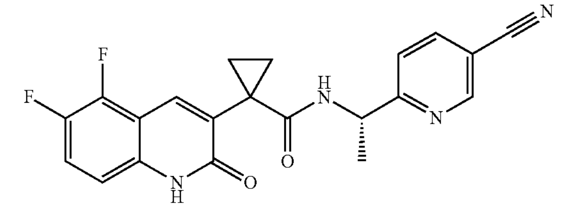 [SMILES: C[C@H](NC(=O)C1(c2cc3c(F)c(F)ccc3[nH]c2=O)CC1)c1ccc(C#N)cn1] |
| 4811 | 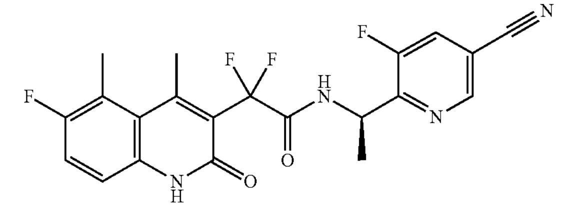 [SMILES: Cc1c(F)ccc2[nH]c(=O)c(C(F)(F)C(=O)N[C@H](C)c3ncc(C#N)cc3F)c(C)c12] |
| 4812 | 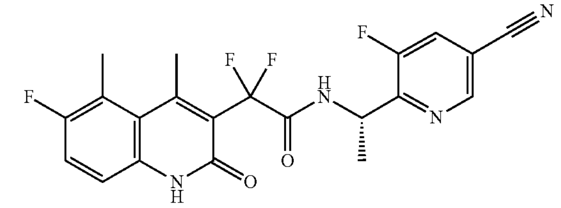 [SMILES: Cc1c(F)ccc2[nH]c(=O)c(C(F)(F)C(=O)N[C@@H](C)c3ncc(C#N)cc3F)c(C)c12] |
| 4813 | 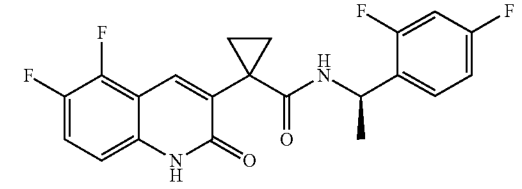 [SMILES: C[C@@H](NC(=O)C1(c2cc3c(F)c(F)ccc3[nH]c2=O)CC1)c1ccc(F)cc1F] |
| 4814 | 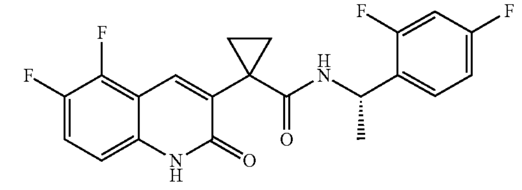 [SMILES: C[C@H](NC(=O)C1(c2cc3c(F)c(F)ccc3[nH]c2=O)CC1)c1ccc(F)cc1F] |

TABLE 1-continued
| Cmpd No. | Structure |
|---|---|
| 4815 | 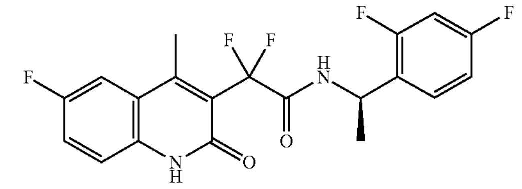 [SMILES: Cc1c(C(F)(F)C(=O)N[C@H](C)c2ccc(F)cc2F)c(=O)[nH]c2ccc(F)cc12] |
| 4816 | 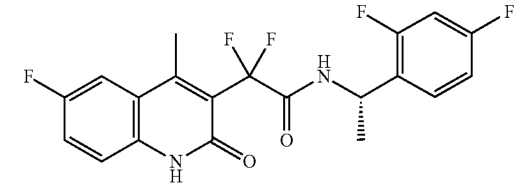 [SMILES: Cc1c(C(F)(F)C(=O)N[C@@H](C)c2ccc(F)cc2F)c(=O)[nH]c2ccc(F)cc12] |
| 4817 | 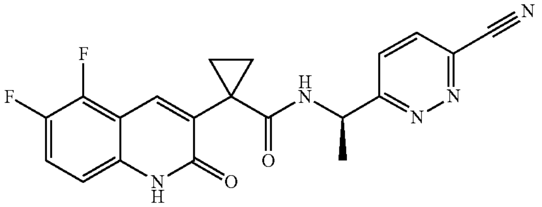 |
| 4818 | 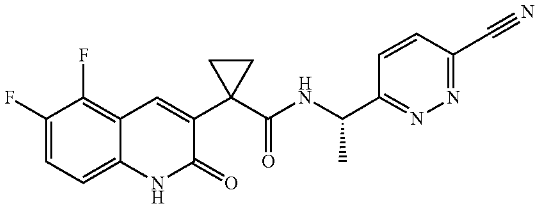 |
| 4819 | 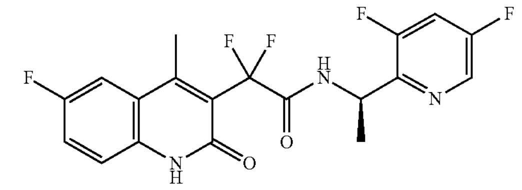 [SMILES: Cc1c(C(F)(F)C(=O)N[C@H](C)c2ncc(F)cc2F)c(=O)[nH]c2ccc(F)cc12] |
| 4820 | 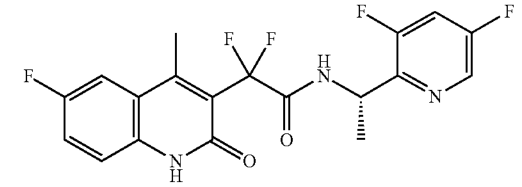 [SMILES: Cc1c(C(F)(F)C(=O)N[C@@H](C)c2ncc(F)cc2F)c(=O)[nH]c2ccc(F)cc12] |
| 4821 | 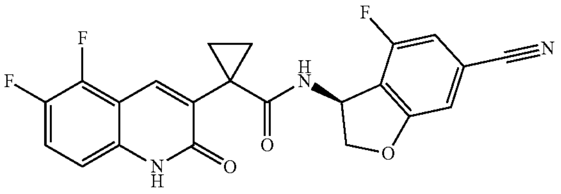 [SMILES: N#Cc1cc(F)c2c(c1)OC[C@H]2NC(=O)C1(c2cc3c(F)c(F)ccc3[nH]c2=O)CC1] |

TABLE 1-continued
| Cmpd No. | Structure |
|---|---|
| 4822 | 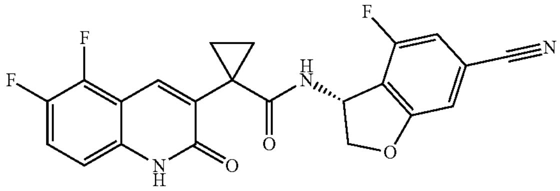 [SMILES: N#Cc1cc(F)c2c(c1)OC[C@@H]2NC(=O)C1(c2cc3c(F)c(F)ccc3[nH]c2=O)CC1] |
| 4823 | 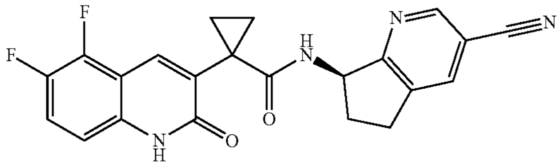 [SMILES: N#Cc1cnc2c(c1)CC[C@H]2NC(=O)C1(c2cc3c(F)c(F)ccc3[nH]c2=O)CC1] |
| 4824 | 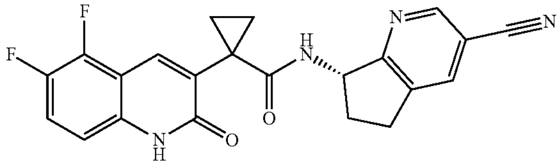 [SMILES: N#Cc1cnc2c(c1)CC[C@@H]2NC(=O)C1(c2cc3c(F)c(F)ccc3[nH]c2=O)CC1] |
| 4825 | 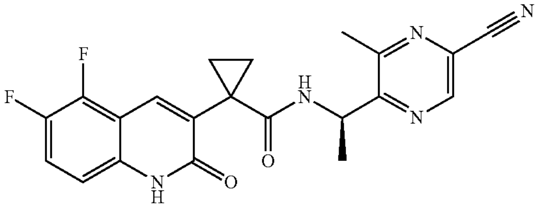 [SMILES: Cc1nc(C#N)cnc1[C@@H](C)NC(=O)C1(c2cc3c(F)c(F)ccc3[nH]c2=O)CC1] |
| 4826 | 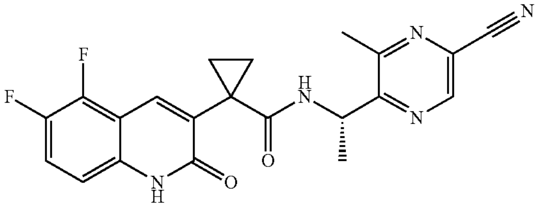 [SMILES: Cc1nc(C#N)cnc1[C@H](C)NC(=O)C1(c2cc3c(F)c(F)ccc3[nH]c2=O)CC1] |
| 4827 | 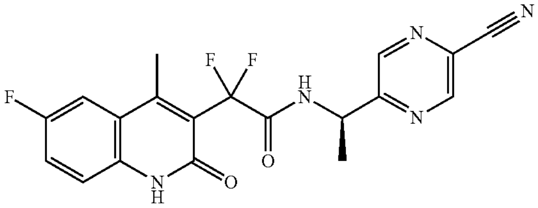 [SMILES: Cc1c(C(F)(F)C(=O)N[C@H](C)c2cnc(C#N)cn2)c(=O)[nH]c2ccc(F)cc12] |
| 4828 | 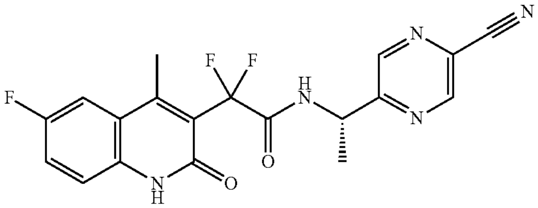 [SMILES: Cc1c(C(F)(F)C(=O)N[C@@H](C)c2cnc(C#N)cn2)c(=O)[nH]c2ccc(F)cc12] |

TABLE 1-continued
| Cmpd No. | Structure |
|---|---|
| 4829 | 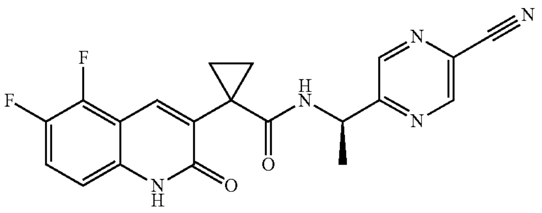 [SMILES: C[C@@H](NC(=O)C1(c2cc3c(F)c(F)ccc3[nH]c2=O)CC1)c1cnc(C#N)cn1] |
| 4830 | 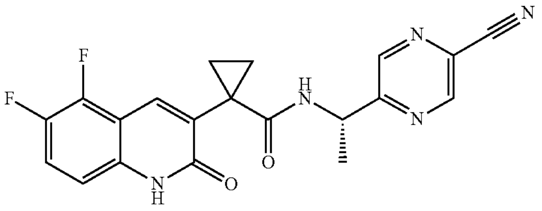 [SMILES: C[C@H](NC(=O)C1(c2cc3c(F)c(F)ccc3[nH]c2=O)CC1)c1cnc(C#N)cn1] |
| 4831 | 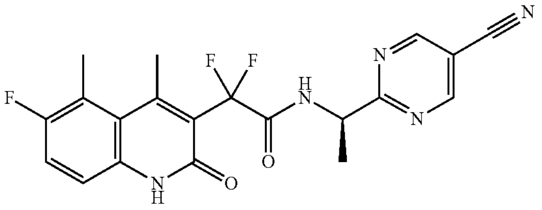 [SMILES: Cc1c(F)ccc2[nH]c(=O)c(C(F)(F)C(=O)N[C@H](C)c3ncc(C#N)cn3)c(C)c12] |
| 4832 | 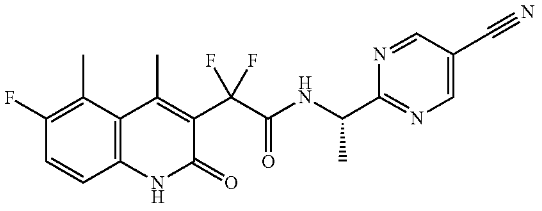 [SMILES: Cc1c(F)ccc2[nH]c(=O)c(C(F)(F)C(=O)N[C@@H](C)c3ncc(C#N)cn3)c(C)c12] |
| 4833 | 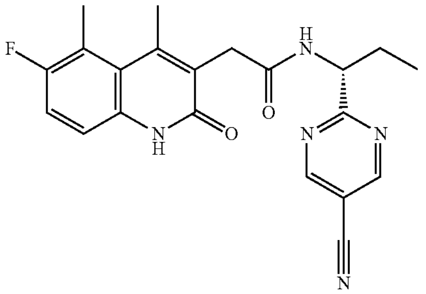 [SMILES: CC[C@@H](NC(=O)Cc1c(C)c2c(C)c(F)ccc2[nH]c1=O)c1ncc(C#N)cn1] |
| 4834 | 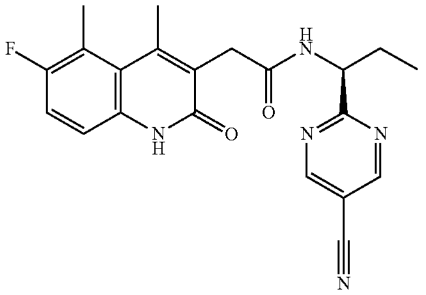 [SMILES: CC[C@H](NC(=O)Cc1c(C)c2c(C)c(F)ccc2[nH]c1=O)c1ncc(C#N)cn1] |

TABLE 1-continued
| Cmpd No. | Structure |
|---|---|
| 4835 | 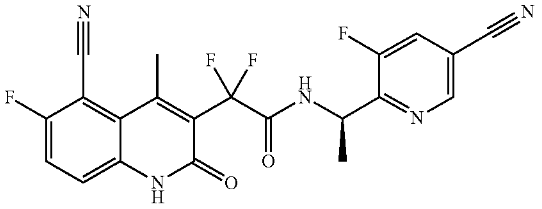 [SMILES: Cc1c(C(F)(F)C(=O)N[C@H](C)c2ncc(C#N)cc2F)c(=O)[nH]c2ccc(F)c(C#N)c12] |
| 4836 | 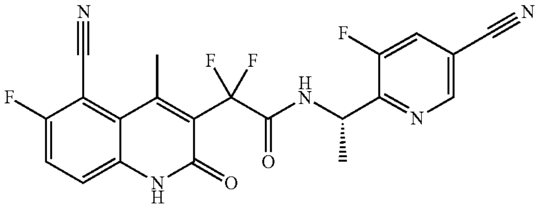 [SMILES: Cc1c(C(F)(F)C(=O)N[C@@H](C)c2ncc(C#N)cc2F)c(=O)[nH]c2ccc(F)c(C#N)c12] |
| 4837 | 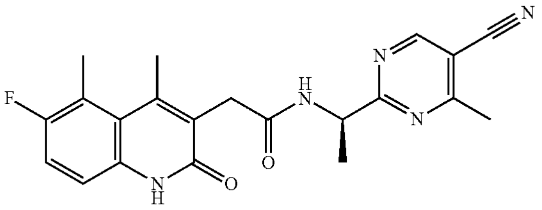 [SMILES: Cc1nc([C@@H](C)NC(=O)Cc2c(C)c3c(C)c(F)ccc3[nH]c2=O)ncc1C#N] |
| 4838 | 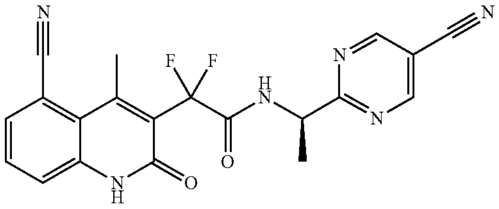 [SMILES: Cc1c(C(F)(F)C(=O)N[C@H](C)c2ncc(C#N)cn2)c(=O)[nH]c2cccc(C#N)c12] |
| 4839 | 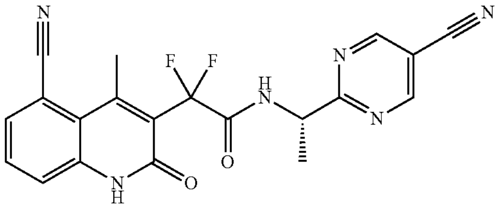 [SMILES: Cc1c(C(F)(F)C(=O)N[C@@H](C)c2ncc(C#N)cn2)c(=O)[nH]c2cccc(C#N)c12] |
| 4840 | 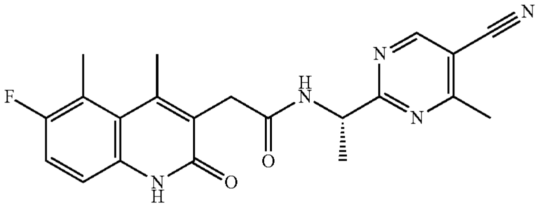 [SMILES: Cc1nc([C@H](C)NC(=O)Cc2c(C)c3c(C)c(F)ccc3[nH]c2=O)ncc1C#N] |
| 4841 | 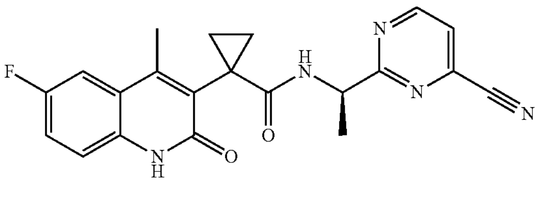 [SMILES: Cc1c(C2(C(=O)N[C@H](C)c3nccc(C#N)n3)CC2)c(=O)[nH]c2ccc(F)cc12] |

TABLE 1-continued
| Cmpd No. | Structure |
| --- | --- |
| 4842 | 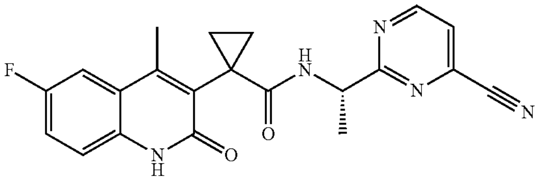 [SMILES: Cc1c(C2(C(=O)N[C@@H](C)c3nccc(C#N)n3)CC2)c(=O)[nH]c2ccc(F)cc12] |
| 4843 | 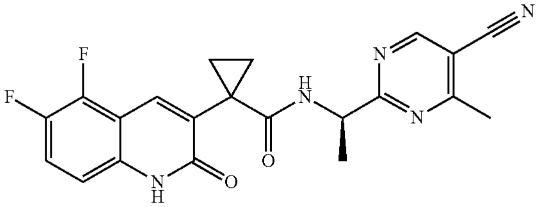 [SMILES: Cc1nc([C@@H](C)NC(=O)C2(c3cc4c(F)c(F)ccc4[nH]c3=O)CC2)ncc1C#N] |
| 4844 | 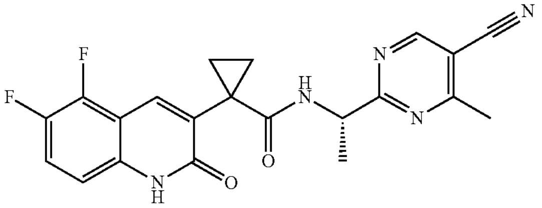 [SMILES: Cc1nc([C@H](C)NC(=O)C2(c3cc4c(F)c(F)ccc4[nH]c3=O)CC2)ncc1C#N] |
| 4845 | 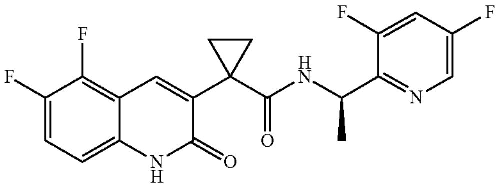 [SMILES: C[C@@H](NC(=O)C1(c2cc3c(F)c(F)ccc3[nH]c2=O)CC1)c1ncc(F)cc1F] |
| 4846 | 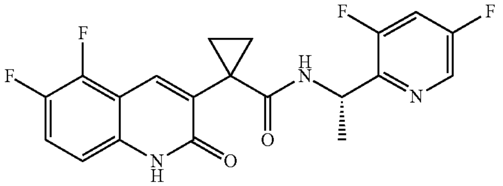 [SMILES: C[C@H](NC(=O)C1(c2cc3c(F)c(F)ccc3[nH]c2=O)CC1)c1ncc(F)cc1F] |
| 4847 | 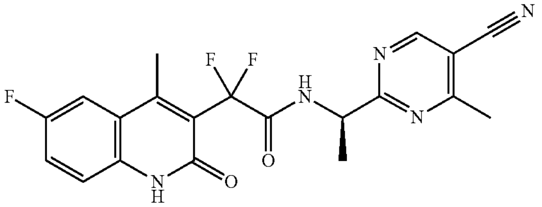 [SMILES: Cc1nc([C@@H](C)NC(=O)C(F)(F)c2c(C)c3cc(F)ccc3[nH]c2=O)ncc1C#N] |
| 4848 | 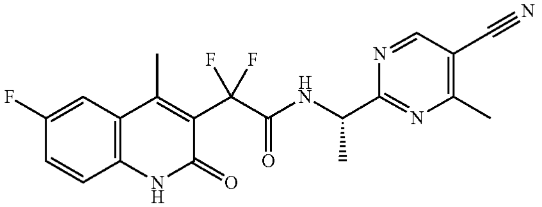 [SMILES: Cc1nc([C@H](C)NC(=O)C(F)(F)c2c(C)c3cc(F)ccc3[nH]c2=O)ncc1C#N] |

TABLE 1-continued
| Cmpd No. | Structure |
|---|---|
| 4849 | 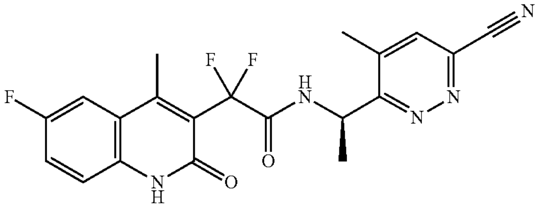 [SMILES: Cc1cc(C#N)nnc1[C@@H](C)NC(=O)C(F)(F)c1c(C)c2cc(F)ccc2[nH]c1=O] |
| 4850 | 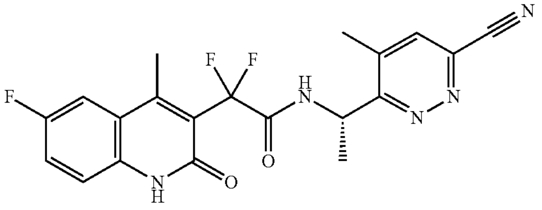 [SMILES: Cc1cc(C#N)nnc1[C@H](C)NC(=O)C(F)(F)c1c(C)c2cc(F)ccc2[nH]c1=O] |
| 4851 | 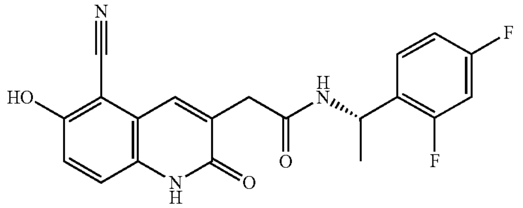 [SMILES: C[C@H](NC(=O)Cc1cc2c(C#N)c(O)ccc2[nH]c1=O)c1ccc(F)cc1F] |
TABLE 1-A
| MS | |
|---|---|
| Cmpd No. | Mass Spec |
| 1 | 405.1 |
| 2 | 405.1 |
| 3 | 387.1 |
| 4 | 387.1 |
| 5 | 384.15 |
| 6 | 384.15 |
| 7 | 381.1 |
| 8 | 381.1 |
| 9 | 444.05 |
| 10 | 444.05 |
| 11 | 370 |
| 12 | 370 |
| 13 | 383.05 |
| 14 | 383.05 |
| 15 | 381.95 |
| 16 | 381.95 |
| 17 | 369 |
| 18 | 369.05 |
| 19 | 398.1 |
| 20 | 398.2 |
| 21 | 450.95 |
| 22 | 450.95 |
| 23 | 405.05 |
| 24 | 405.05 |
| 25 | 409 |
| 26 | 409 |
| 27 | 423.1 |
| 28 | 423 |
| 29 | 425.1 |
| 30 | 425.05 |
| 31 | 408 |
| 32 | 408 |
| 33 | 379.95 |
| 34 | 379.9 |
| 35 | 387.1 |
| 36 | 387.1 |
TABLE 1-A-continued
| MS | |
|---|---|
| Cmpd No. | Mass Spec |
| 37 | 450.05 |
| 38 | 450 |
| 39 | 409 |
| 40 | 409.15 |
| 41 | 401.05 |
| 42 | 401.05 |
| 43 | 358.05 |
| 44 | 358.15 |
| 45 | 383.1 |
| 46 | 383 |
| 47 | 351.05 |
| 48 | 351.1 |
| 49 | 390.15 |
| 50 | 390.15 |
| 51 | 383 |
| 52 | 383.05 |
| 53 | 365.05 |
| 54 | 365.05 |
| 55 | 391.05 |
| 56 | 391.05 |
| 57 | 443.15 |
| 58 | 443.05 |
| 59 | 418.95 |
| 60 | 421.05 |
| 61 | 412 |
| 62 | 412 |
| 63 | 358.1 |
| 64 | 358.15 |
| 65 | 399.95 |
| 66 | 399.95 |
| 67 | 407.15 |
| 68 | 407.15 |
| 69 | 422.4 |
| 70 | 422.4 |
| 71 | 438.4 |
| 72 | 438.35 |

TABLE 1-A-continued

| MS | |
|---|---|
| Cmpd No. | Mass Spec |
| 73 | 408.35 |
| 74 | 408.15 |
| 75 | 424.35 |
| 76 | 424.35 |
| 77 | 374.1 |
| 78 | 374.05 |
| 79 | 388.15 |
| 80 | 388.05 |
| 81 | 398.1 |
| 82 | 384 |
| 83 | 400.1 |
| 84 | 398.2 |
| 85 | 409.1 |
| 86 | 407.05 |
| 87 | 421 |
| 88 | 407.05 |
| 89 | 398.15 |
| 90 | 398.15 |
| 91 | 393.15 |
| 92 | 387.05 |
| 93 | 371.05 |
| 94 | |
| 95 | 452.95 |
| 96 | 443.05 |
| 97 | 443 |
| 98 | 443 |
| 99 | 443.1 |
| 100 | 443.1 |
| 101 | 415.2 |
| 102 | 375.2 |
| 103 | 375.2 |
| 104 | 460.1 |
| 105 | 460.1 |
| 106 | 410.95 |
| 107 | 429.2 |
| 108 | 407 |
| 109 | 453 |
| 110 | 393.05 |
| 111 | 393.15 |
| 112 | 407 |
| 113 | 443.1 |
| 114 | 401.15 |
| 115 | 428.9 |
| 116 | 392.9 |
| 117 | 383.1 |
| 118 | 379.1 |
| 119 | 396.9 |
| 120 | 437 |
| 121 | 368.15 |
| 122 | 373 |
| 123 | 362.05 |
| 124 | 373.1 |
| 125 | 359.15 |
| 126 | 371.05 |
| 127 | 389 |
| 128 | 372.15 |
| 129 | 411.05 |
| 130 | 375.25 |
| 131 | 361.2 |
| 132 | 395.05 |
| 133 | 344 |
| 134 | 357.1 |
| 135 | 357.1 |
| 136 | 356.9 |
| 137 | 343.25 |
| 1038 | 373.1 |
| 1039 | 373.05 |
| 1040 | 366 |
| 1041 | 366 |
| 1042 | 384.1 |
| 1043 | 384 |
| 1044 | 393.2 |
| 1045 | 393.2 |
| 1046 | 368.2 |
| 1047 | 368.2 |

TABLE 1-A-continued

| MS | |
|---|---|
| Cmpd No. | Mass Spec |
| 1048 | 354.2 |
| 1049 | 354.2 |
| 1050 | 379.25 |
| 1051 | 379.25 |
| 1052 | 380.2 |
| 1053 | 380.2 |
| 1054 | 395.15 |
| 1055 | 397.2 |
| 1056 | 393.1 |
| 1057 | 393.1 |
| 1058 | 380.1 |
| 1059 | 380.1 |
| 1060 | 372.05 |
| 1061 | 372.05 |
| 1062 | 379.2 |
| 1063 | 379.1 |
| 1064 | 414.2 |
| 1065 | 414.2 |
| 1066 | 368.15 |
| 1067 | 368.15 |
| 1068 | 380.1 |
| 1069 | 378.15 |
| 1070 | 366.05 |
| 1071 | 366.2 |
| 1072 | 365.05 |
| 1073 | 365.05 |
| 1074 | 370 |
| 1075 | 370 |
| 1076 | 372 |
| 1077 | 370.05 |
| 1078 | 383 |
| 1079 | 383 |
| 1080 | 390.05 |
| 1081 | 390.2 |
| 1082 | 382 |
| 1083 | 382 |
| 1084 | 364.1 |
| 1085 | 364.1 |
| 1086 | 402 |
| 1087 | 398.1 |
| 1088 | 398.1 |
| 1089 | 398.1 |
| 1090 | 355.05 |
| 1091 | 355.05 |
| 1092 | 377.1 |
| 1093 | 377.1 |
| 1094 | 394.05 |
| 1095 | 394.1 |
| 1096 | 384.2 |
| 1097 | 384 |
| 1098 | 370 |
| 1099 | 370 |
| 1100 | 366.15 |
| 1101 | 366.15 |
| 1102 | 382 |
| 1103 | 384.1 |
| 1104 | 401.1 |
| 1105 | 401.1 |
| 1106 | 383.1 |
| 1107 | 383.15 |
| 1108 | 366.1 |
| 1109 | 366.1 |
| 1110 | 370.05 |
| 1111 | 372.15 |
| 1112 | 383.1 |
| 1113 | 383.1 |
| 1114 | 369.15 |
| 1115 | 369.15 |
| 1116 | 388.2 |
| 1117 | 388.2 |
| 1118 | 390.05 |
| 1119 | 366.05 |
| 1120 | 366.1 |
| 1121 | 395.1 |
| 1122 | 395.1 |

TABLE 1-A-continued

| MS | |
|---|---|
| Cmpd No. | Mass Spec |
| 1123 | 384.05 |
| 1124 | 384.15 |
| 1125 | 351.1 |
| 1126 | 351.1 |
| 1127 | 365.05 |
| 1128 | 365.1 |
| 1129 | 382.15 |
| 1130 | 382.05 |
| 1131 | 398.2 |
| 1132 | 398.2 |
| 1133 | 384.11 |
| 1134 | 382.1 |
| 1135 | 398.05 |
| 1136 | 398.05 |
| 1137 | 387.05 |
| 1138 | 387.1 |
| 1139 | 398.15 |
| 1140 | 398.15 |
| 1141 | 422 |
| 1142 | 422 |
| 1143 | 409.05 |
| 1144 | 408.95 |
| 1145 | 384.1 |
| 1146 | 384.1 |
| 1147 | 401.05 |
| 1148 | 401.05 |
| 1149 | 408.05 |
| 1150 | 408.05 |
| 1151 | 416 |
| 1152 | 416.15 |
| 1153 | 412.1 |
| 2001 | 394.15 |
| 2002 | 394.15 |
| 2009 | 420.1 |
| 2010 | 420.1 |
| 2011 | 400.1 |
| 2012 | 400.1 |
| 2013 | 366.05 |
| 2014 | 366.05 |
| 2015 | 391.1 |
| 2016 | 391.1 |
| 2017 | 375 |
| 2018 | 377.1 |
| 2019 | 350.15 |
| 2020 | 350.15 |
| 2021 | 370.1 |
| 2022 | 370.1 |
| 2023 | 352.05 |
| 2024 | 352.05 |
| 2025 | 370.1 |
| 2026 | 370.1 |
| 2027 | 373.05 |
| 2028 | 373.15 |
| 2029 | 352.1 |
| 2030 | 352.1 |
| 2033 | 352.1 |
| 2034 | 352.1 |
| 2035 | 370.1 |
| 2036 | 370.1 |
| 2037 | 359.1 |
| 2038 | 359.05 |
| 2039 | 366.1 |
| 2040 | 366.1 |
| 2041 | 366.05 |
| 2042 | 366.05 |
| 2043 | 415.1 |
| 2044 | 415.1 |
| 2045 | 431.05 |
| 2046 | 413.05 |
| 2047 | 394.15 |
| 2048 | 394.05 |
| 2049 | 399.15 |
| 2050 | 399.1 |
| 2051 | 417.1 |
| 2052 | 417.05 |

TABLE 1-A-continued

| MS | |
|---|---|
| Cmpd No. | Mass Spec |
| 2053 | 392.15 |
| 2054 | 392.15 |
| 2055 | 400.1 |
| 2056 | 400.1 |
| 2057 | 406.1 |
| 2058 | 406.1 |
| 2059 | 406.1 |
| 2060 | 406.05 |
| 2061 | 382 |
| 2062 | 382 |
| 2063 | 392.1 |
| 2064 | 392.15 |
| 2065 | 41.05 |
| 2066 | 410.05 |
| 2067 | 408.15 |
| 2068 | 408.15 |
| 2069 | 373.1 |
| 2070 | 371.05 |
| 2071 | 370.2 |
| 2072 | 370.2 |
| 2073 | 359.15 |
| 2074 | 384.05 |
| 2075 | |
| | 384 |
| 2076 | 386.05 |
| 2077 | 386.05 |
| 2078 | 391.05 |
| 2079 | 393.01 |
| 2501 | 426.1 |
| 2502 | 426.1 |
| 2503 | 403 |
| 2504 | 403 |
| 2505 | 396.1 |
| 2506 | 396.15 |
| 2507 | 378.05 |
| 2508 | 378.05 |
| 2509 | 410.05 |
| 2510 | 410.05 |
| 2511 | 427.1 |
| 2512 | 427.1 |
| 2513 | 470.1 |
| 2514 | 470.1 |
| 2515 | 413.1 |
| 2516 | 413.1 |
| 2517 | 418.05 |
| 2518 | 418.05 |
| 2519 | 444.1 |
| 2520 | 444.1 |
| 2521 | 427.1 |
| 2522 | 427.1 |
| 2523 | 434.15 |
| 2524 | 434.15 |
| 2527 | 402.15 |
| 2528 | 402.1 |
| 2529 | 430.1 |
| 2530 | 430.05 |
| 2531 | 417.1 |
| 2532 | 417.1 |
| 2533 | 419.1 |
| 2534 | 377.05 |
| 2535 | 377 |
| 2536 | 377.15 |
| 2537 | 377.15 |
| 2538 | 419.1 |
| 2539 | 409.2 |
| 2540 | 409.15 |
| 2541 | 416.1 |
| 2542 | 416.1 |
| 2543 | 399.1 |
| 2544 | 399.1 |
| 2545 | 406 |
| 2546 | 406 |
| 2547 | 409.15 |
| 2548 | 409.15 |
| 2549 | 396.05 |

TABLE 1-A-continued

| MS | |
|---|---|
| Cmpd No. | Mass Spec |
| 2550 | 396.05 |
| 2551 | 422 |
| 2552 | 422 |
| 2553 | 432.05 |
| 2554 | 432.05 |
| 2555 | 402 |
| 2556 | 402 |
| 2557 | 405.1 |
| 2558 | 405.15 |
| 2559 | 388 |
| 2560 | 388.1 |
| 2561 | 406.1 |
| 2562 | 406.1 |
| 2563 | 401.95 |
| 2564 | 402 |
| 2565 | 401.15 |
| 2566 | 401.1 |
| 2567 | 416.1 |
| 2568 | 416.1 |
| 2569 | 395.05 |
| 2570 | 395.05 |
| 2571 | 405.15 |
| 2572 | 405.15 |
| 2573 | 387.1 |
| 2574 | 387.1 |
| 2575 | 401.15 |
| 2576 | 401.15 |
| 2577 | 391.1 |
| 2578 | 391.1 |
| 2579 | 391.1 |
| 2580 | 391.1 |
| 2581 | 387.15 |
| 2582 | 387.1 |
| 2583 | 395.05 |
| 2584 | 395.1 |
| 2585 | 419 |
| 2586 | 491.05 |
| 2587 | 419.05 |
| 2588 | 419.05 |
| 2590 | 392.2 |
| 2591 | 392.2 |
| 2592 | 413.1 |
| 2593 | 413.1 |
| 2594 | 402.15 |
| 2595 | 402.15 |
| 2596 | 409.1 |
| 2597 | 409.1 |
| 2598 | 401.05 |
| 2599 | 401.05 |
| 2600 | 415.05 |
| 2601 | 415.05 |
| 2602 | 415.05 |
| 2603 | 415.05 |
| 2604 | 401.05 |
| 2605 | 399 |
| 2606 | 419.05 |
| 2607 | 419.1 |

TABLE 1-A-continued

| MS | |
|---|---|
| Cmpd No. | Mass Spec |
| 2608 | 375.05 |
| 4502 | 363.1 |
| 4503 | 363.3 |
| 4504 | 367.1 |
| 4505 | 491.1 |
| 4801 | 477.1 |
| 4802 | 477.1 |
| 4803 | 421.15 |
| 4804 | 421.15 |
| 4805 | 402.05 |
| 4806 | 402.05 |
| 4807 | 408 |
| 4808 | 408.15 |
| 4809 | 395.05 |
| 4810 | 395.05 |
| 4811 | 433.15 |
| 4812 | 433.1 |
| 4813 | 405.05 |
| 4814 | 405 |
| 4815 | 411.05 |
| 4816 | 411.05 |
| 4817 | 394 |
| 4818 | 394 |
| 4819 | 412 |
| 4820 | 412.1 |
| 4821 | 426.05 |
| 4822 | 426.05 |
| 4823 | 407.15 |
| 4824 | 407.1 |
| 4825 | 410.1 |
| 4826 | 410.1 |
| 4827 | 402.05 |
| 4828 | 402.05 |
| 4829 | 396.05 |
| 4830 | 396.05 |
| 4831 | 416.1 |
| 4832 | 416.1 |
| 4833 | 394.15 |
| 4834 | 394.15 |
| 4835 | 444.05 |
| 4836 | 444 |
| 4837 | 394.1 |
| 4838 | 409.05 |
| 4839 | 409.05 |
| 4840 | 394.1 |
| 4841 | 392.05 |
| 4842 | 392.05 |
| 4843 | 410.1 |
| 4844 | 410.15 |
| 4845 | 406.1 |
| 4846 | 406.15 |
| 4847 | 416.1 |
| 4848 | 416.1 |
| 4849 | 416.05 |
| 4850 | 416.05 |

TABLE 1-A

| NMR | |
|---|---|
| Cmpd No. | NMR |
| 1 | $^{1}$H NMR (300 MHz, DMSO-d6) δ 12.17 (s, 1H), 9.04 (s, 1H), 8.64 (d, J = 7.2 Hz, 1H), 7.75-7.58 (m, 2H), 5.22-5.17 (m, 1H), 3.72 (d, J = 15.9 Hz, 1H), 3.63 (d, J = 15.9 Hz, 1H), 2.65-2.59 (m, 6H), 1.41 (d, J = 6.9 Hz, 3H). |
| 2 | $^{1}$H NMR (300 MHz, DMSO-d6) δ 12.06 (s, 1H), 9.04 (s, 1H), 8.64 (d, J = 7.2 Hz, 1H), 7.72-7.61 (m, 2H), 5.22-5.17 (m, 1H), 3.71 (d, J = 15.6 Hz, 1H), 3.63 (d, J = 15.9 Hz, 1H), 2.62 (d, J = 1.8 Hz, 6H), 1.41 (d, J = 6.9 Hz, 3H). |
| 8 | $^{1}$H NMR (400 MHz, DMSO-$d_6$) δ 12.05 (s, 1H), 8.82 (s, 1H), 8.51 (d, J = 8.4 Hz, 1H), 8.17 (s, 1H), 8.05 (s, 1H), 7.62-7.55 (m, 1H), 7.14-7.11 (m, 1H), 5.35-5.27 (m, 1H), 3.48 (s, 2H), 3.02-2.95 (m, 1H), 2.95-2.84 (m, 1H), 2.50-2.45 (m, 1H), 1.85-1.95 (m, 1H). |

TABLE 1-A-continued

| Cmpd No. | NMR |
|---|---|
| 11 | $^1$H NMR (300 MHz, DMSO-d6) δ 12.11 (s, 1H), 9.16 (d, J = 1.5 Hz, 1H), 8.93 (d, J = 1.5 Hz, 1H), 8.79 (d, J = 6.9 Hz, 1H), 7.95 (s, 1H), 7.62-7.53 (m, 1H), 7.16-7.06 (m, 1H), 5.08-4.98 (m, 1H), 3.62-3.44 (m, 2H), 1.46 (d, J = 7.1 Hz, 3H). |
| 12 | $^1$H NMR (300 MHz, DMSO-d6) δ 12.12 (s, 1H), 9.16 (d, J = 1.5 Hz, 1H), 8.93 (d, J = 1.5 Hz, 1H), 8.79 (d, J = 6.9 Hz, 1H), 7.95 (s, 1H), 7.62-7.53 (m, 1H), 7.11 (d, J = 9.3 Hz, 1H), 5.07-4.98 (m, 1H), 3.62-3.44 (m, 2H), 1.46 (d, J = 7.1 Hz, 3H). |
| 13 | $^1$H NMR (300 MHz, DMSO-$d_6$) δ 12.06 (s, 1H), 8.81 (d, J = 7.5 Hz, 1H), 8.53 (d, J = 1.8 Hz, 1H), 7.98 (s, 1H), 7.81 (d, J = 1.5 Hz, 1H), 7.62-7.53 (m, 1H), 7.12 (dd, J = 9.3, 3.3 Hz, 1H), 5.54-5.45 (m, 1H), 4.89 (t, J = 9.3 Hz, 1H), 4.38 (dd, J = 9.6, 5.7 Hz, 1H), 3.47 (t, J = 1.5 Hz, 2H).. |
| 14 | $^1$H NMR (300 MHz, DMSO-$d_6$) δ 12.06 (s, 1H), 8.81 (d, J = 7.5 Hz, 1H), 8.53 (d, J = 1.8 Hz, 1H), 7.98 (s, 1H), 7.81 (d, J = 1.5 Hz, 1H), 7.62-7.53 (m, 1H), 7.12 (dd, J = 9.3, 3.3 Hz, 1H), 5.54-5.45 (m, 1H), 4.92-4.86 (m, 1H), 4.38 (dd, J = 9.6, 5.7 Hz, 1H), 3.52-3.41 (m, 2H).. |
| 19 | $^1$H NMR (400 MHz, DMSO-$d_6$) δ 12.05 (s, 1H), 11.43 (s, 1H), 9.33 (d, J = 7.6 Hz, 1H), 8.15-7.80 (m, 1H), 7.80-7.69 (m, 1H), 7.69-7.58 (m, 1H), 7.35-7.29 (m, 1H), 7.14-7.11 (m, 1H), 5.19-5.12 (m, 1H), 3.75-3.62 (m, 2H), 2.59 (d, J = 2.4 Hz, 3H), 1.39 (d, J = 6.8 Hz, 3H). |
| 20 | $^1$H NMR (400 MHz, DMSO-$d_6$) δ 12.02 (s, 1H), 11.39 (s, 1H), 9.35 (d, J = 7.6 Hz, 1H), 8.02-7.80 (m, 1H), 7.80-7.68 (m, 1H), 7.67-7.49 (m, 1H), 7.48-7.25 (m, 1H), 7.23-6.99 (m, 1H), 5.33-5.01 (m, 1H), 3.75-3.60 (m, 2H), 2.60 (d, J = 2.4 Hz, 3H), 1.39 (d, J = 6.8 Hz, 3H). |
| 39 | $^1$H NMR (400 MHz, DMSO-$d_6$) δ 11.75 (s, 1H), 8.88 (s, 1H), 8.57 (d, J = 7.2 Hz, 1H), 8.37 (dd, J = 10.6, 1.6 Hz, 1H), 7.81 (dd, J = 10.6, 2.8 Hz, 1H), 7.38-7.27 (m, 2H), 5.26-5.21 (m, 1H), 3.71 (s, 2H), 1.83-1.76 (m, 1H), 1.40 (d, J = 6.8 Hz, 3H), 1.15-1.10 (m, 2H), 0.59-0.51 (m, 2H). |
| 40 | $^1$H NMR (400 MHz, DMSO-$d_6$) δ 11.73 (s, 1H), 8.88 (s, 1H), 8.57 (d, J = 7.2 Hz, 1H), 8.37 (dd, J = 9.6, 1.6 Hz, 1H), 7.81 (dd, J = 10.6, 2.8 Hz, 1H), 7.38-7.27 (m, 2H), 5.26-5.19 (m, 1H), 3.71 (s, 2H), 1.84-1.76 (m, 1H), 1.40 (d, J = 6.8 Hz, 3H), 1.15-1.09 (m, 2H), 0.59-0.51 (m, 2H). |
| 59 | $^1$H NMR (400 MHz, DMSO-$d_6$) δ 12.17 (s, 1H), 8.76 (d, J = 7.8 Hz, 1H), 7.71-7.63 (m, 2H), 7.40-7.37 (m, 1H), 7.29 (d, J = 1.2 Hz, 1H), 5.75-5.69 (m, 1H), 4.82-4.77 (m, 1H), 4.38-4.35 (m, 1H), 3.66 (s, 2H), 2.66 (s, 3H). |
| 60 | $^1$H NMR (300 MHz, DMSO-$d_6$): δ 12.17 (s, 1H), 8.77 (d, J = 7.8 Hz, 1H), 7.73-7.66 (m, 2H), 7.39 (d, J = 8.4 Hz, 1H), 7.30 (s, 1H), 5.73 (s, 1H), 4.83-4.77 (m, 1H), 4.40-4.35 (m, 1H), 3.66 (s, 2H), 2.67 (s, 3H). |
| 67 | $^1$H NMR (400 MHz, DMSO-$d_6$) δ 12.18 (s, 1H), 8.67 (d, J = 7.2 Hz, 1H), 7.82-7.79 (m, 1H), 7.71-7.60 (m, 4H), 5.12-5.08 (m, 1H), 3.75-3.70 (m, 2H), 2.63 (s, 3H), 1.37 (d, J = 7.2 Hz, 3H). |
| 68 | $^1$H NMR (400 MHz, DMSO-$d_6$) δ 12.18 (s, 1H), 8.67 (d, J = 7.6 Hz, 1H), 7.82-7.79 (m, 1H), 7.71-7.60 (m, 4H), 5.12-5.08 (m, 1H), 3.71 (s, 2H), 2.63 (s, 3H), 1.37 (d, J = 7.2 Hz, 3H). |
| 77 | $^1$H NMR (300 MHz, DMSO-$d_6$) δ 11.59 (s, 1H), 9.19 (s, 1H), 8.56 (d, J = 7.0 Hz, 1H), 8.48 (d, J = 2.5 Hz, 1H), 7.91 (s, 1H), 7.83 (s, 1H), 7.01 (s, 2H), 5.30-5.20 (m, 1H), 3.41 (d, J = 8.7 Hz, 2H), 2.25 (s, 3H), 1.38 (d, J = 6.9 Hz, 4H). $^{19}$F NMR (282 MHz, DMSO-$d_6$) δ −122.68 (1F), −126.05 (1F). |
| 78 | $^1$H NMR (300 MHz, DMSO-$d_6$) δ 11.59 (s, 1H), 9.20 (s, 1H), 8.56 (d, J = 7.6 Hz, 1H), 8.48 (d, J = 2.4 Hz, 1H), 7.91 (dd, J = 10.2 Hz, 2.4 Hz, 1H), 7.83 (s, 1H), 7.01 (s, 2H), 5.24 (q, J = 7.1 Hz, 1H), 3.51-3.37 (m, 2H), 2.25 (s, 3H), 1.38 (d, J = 6.9 Hz, 3H). $^{19}$F NMR (282 MHz, DMSO-$d_6$) δ −122.68 (1F), −126.05 (1F). |
| 81 | $^1$H NMR (300 MHz, DMSO-$d_6$) δ 12.07 (s, 1H), 8.63 (d, J = 7.6 Hz, 1H), 7.82 (s, 1H), 7.57-7.42 (m, 3H), 7.17 (s, 1H), 7.04 (t, J = 9.0 Hz, 1H), 5.09 (t, J = 7.2 Hz, 1H), 3.95 (s, 3H), 3.53 (s, 2H), 1.35 (d, J = 7.0 Hz, 3H). $^{19}$F NMR (376 MHz, DMSO-$d_6$) δ −112.79 (1F), −115.42 (1F). |
| 82 | $^1$H NMR (300 MHz, DMSO-$d_6$) δ 11.99 (s, 1H), 8.61 (d, J = 7.7 Hz, 1H), 7.76 (s, 1H), 7.46 (dd, J = 19.7, 8.1 Hz, 2H), 7.18 (t, J = 9.6 Hz, 2H), 7.03 (t, J = 9.6 Hz, 1H), 5.09 (t, J = 7.2 Hz, 1H), 3.50 (s, 2H), 2.54 (s, 1H), 1.35 (d, J = 7.0 Hz, 3H). $^{19}$F NMR (376 MHz, DMSO-$d_6$) δ −112.81(1F), −115.42 (1F). |
| 83 | $^1$H NMR (300 MHz, DMSO-$d_6$) δ 12.18 (s, 1H), 8.55 (d, J = 7.5 Hz, 1H), 7.72-7.59 (m, 2H), 7.51-7.43 (m, 1H), 7.22-7.21 (m, 1H), 7.12-7.01 (m, 1H), 5.12-5.03 (m, 1H), 3.70 (s, 2H), 2.64 (s, 3H), 1.36 (d, J = 6.9 Hz, 3H). |
| 84 | $^1$H NMR (400 MHz, DMSO-d6) δ 11.89 (s, 1H), 11.39-11.38 (m, 1H), 8.49 (d, J = 7.6 Hz, 1H), 7.49-7.43 (m, 2H), 7.22-7.14 (m, 2H), 7.07-7.02 (m, 1H), 5.11-5.03 (m, 1H), 3.66 (s, 2H), 2.60 (s, 3H), 1.35 (d, J = 6.8 Hz, 3H). |
| 85 | $^1$H NMR (300 MHz, DMSO-d6) δ 11.90 (s, 1H), 8.51 (d, J = 7.8 Hz, 1H), 7.59-7.50 (m, 1H), 7.48-7.42 (m, 1H), 7.33 (dd, J = 9.0, 5.1 Hz, 1H), 7.21-7.15 (m, 1H), 7.14-7.02 (m, 1H), 5.13-5.03 (m, 1H), 3.68 (s, 2H), 2.62 (s, 3H), 1.35 (d, J = 6.9 Hz, 3H). |
| 87 | $^1$H NMR (400 MHz, DMSO-$d_6$) δ 11.94 (brs, 1H), 8.66 (d, J = 7.4 Hz, 1H), 7.96 (s, 1H), 7.51-7.32 (m, 2H), 7.27 (t, J = 9.2 Hz, 1H), 7.23-7.03 (m, 2H), 5.08 (t, J = 7.2 Hz, 1H), 3.96 (q, J = 7.0 Hz, 1H), 3.87 (d, J = 4.2 Hz, 3H), 1.31 (t, J = 7.2 Hz, 6H). $^{19}$F NMR (376 MHz, DMSO-$d_6$) δ −112.99 (1F), −115.60 (1F). |
| 96 | $^1$H NMR (300 MHz, DMSO-d6) δ 12.08 (s, 1H), 8.55 (d, J = 7.8 Hz, 1H), 7.61-7.58 (m, 2H), 7.57-7.45 (m, 1H), 7.25-7.11 (m, 1H), 7.11-7.00 (m, 1H), 5.09-5.06 (m, 1H), 3.64 (s, 2H), 2.30 (d, J = 2.7 Hz, 3H), 1.35 (d, J = 6.9 Hz, 3H). |
| 101 | $^1$HNMR (300 MHz, DMSO-d6) δ 11.70 (s, 1H), 8.45 (d, J = 7.8 Hz, 1H), 7.51-7.43 (m, 1H), 7.30-7.13 (m, 3H), 7.08-7.01 (m, 1H), 5.14-5.04 (m, 1H), 3.68-3.57 (m, 2H), 2.62 (s, 3H), 2.18-2.08 (m, 1H), 1.35 (d, J = 6.9 Hz, 3H), 1.24 (s, 2H), 0.48-0.42 (m, 2H). |
| 104 | $^1$H NMR (400 MHz, DMSO-$d_6$): 12.56 (s, 1H), 7.80-7.71 (m, 2H), 7.41-7.35(m, 1H), 7.26 (d, J = 2.4, 1H), 7.16-7.10(m, 1H), 7.00-6.96 (m, 1H), 5.18-5.12 (m, 1H), 4.23-4.19 (m, 1H), 1.41(d, J = 8.0, 3H), 1.34(d, J = 7.2, 3H). |
| 105 | $^1$H NMR (400 MHz, DMSO-$d_6$): 12.56 (s, 1H), 7.80-7.71 (m, 2H), 7.41-7.35(m, 1H), 7.26 (d, J = 2.4, 1H), 7.16-7.10(m, 1H), 7.00-6.96 (m, 1H), 5.18-5.12 (m, 1H), 4.23-4.19 (m, 1H), 1.41(d, J = 8.0, 3H), 1.34(d, J = 7.2, 3H). |

TABLE 1-A-continued

| NMR | |
|---|---|
| Cmpd No. | NMR |
| 106 | $^1$H NMR (300 MHz, DMSO-d6) δ 12.22 (s, 1H), 8.70 (d, J = 7.5 Hz, 1H), 7.50-7.49 (m, 1H), 7.47-7.39 (m, 2H), 7.17-7.15 (m, 1H), 7.04-7.03 (m, 1H), 5.07-5.02 (m, 1H), 3.83 (s, 2H), 1.35 (d, J = 6.9 Hz, 3H).. |
| 107 | : $^1$H NMR (400 MHz, DMSO-d6) δ 12.37 (s, 1H), 8.66-8.68 (d, J = 8 Hz, 1H), 7.70-7.73 (m, 1H), 7.14-7.68 (m, 3H), 7.02-7.07(m, 1H), 5.02-5.04 (m, 1H), 3.32-3.88 (m, 2H), 1.34-1.36 (d, J = 8 Hz, 3H). |
| 108 | $^1$H NMR (400 MHz, DMSO-$d_6$) δ 11.91 (s, 1H), 7.82 (d, J = 7.6 Hz, 1H), 7.69-7.51 (m, 1H), 7.50-7.28 (m, 1H), 7.28-6.28 (m, 3H), 5.35-5.04 (m, 1H), 4.17 (d, J = 6.8 Hz, 1H), 2.43 (d, J = 6.8 Hz, 3H), 1.38-1.11 (m, 6H). |
| 110 | $^1$H NMR (400 MHz, DMSO-d6) δ 12.09 (s, 1H), 8.57-8.59 (d, J = 8 Hz, 1H), 7.85 (s, 1H), 8.57-8.59 (m, 1H), 7.08-7.11 (m, 1H), 6.89-6.93 (m, 3H), 5.08-5.10 (m, 1H), 3.94-3.96 (m, 1H), 1.31-1.33 (m, 6H). |
| 111 | $^1$H NMR (400 MHz, DMSO-d6) δ 12.09 (s, 1H), 8.54-8.56 (d, J = 8 Hz, 1H), 7.85 (s, 1H), 7.56-7.61 (m, 1H), 7.54-7.57 (m, 1H), 7.06-7.20 (m, 3H), 5.01-5.02 (m, 1H), 3.77-4.01 (m, 1H), 1.29-1.32 (m, 6H). 393.15 |
| 112 | $^1$H NMR (400 MHz, DMSO-$d_6$) δ 11.94 (s, 1H), 7.87 (d, J = 8.0 Hz, 1H), 7.71-7.52 (m, 1H), 7.38-7.25 (m, 1H), 7.22-7.08 (m, 2H), 7.01-6.85 (m, 1H), 5.38-5.08 (m, 1H), 4.42-4.02 (m, 1H), 2.18 (d, J = 6.8 Hz, 3H), 1.29 (d, J = 7.2 Hz, 3H), 1.23 (d, J = 7.2 Hz, 3H). |
| 114 | $^1$H NMR (400 MHz, DMSO-$d_6$) δ 11.77 (s, 1H), 8.50 (d, J = 7.6 Hz, 1H), 7.82 (dd, J = 10.8, 2.8 Hz, 1H), 7.56-7.50 (m, 1H), 7.44-7.28(m, 2H), 7.28-7.14 (m, 1H), 7.03 (dd, J = 9.6, 7.2 Hz, 1H), 5.10-5.05 (m, 1H), 3.78-3.68 (m, 2H), 1.86-1.83 (m, 1H), 1.35 (d, J = 7.2 Hz, 3H), 1.12 (d, J = 8.8 Hz, 2H), 0.65-0.50 (m, 2H). |
| 115 | $^1$H NMR (400 MHz, DMSO-d6) δ 12.44 (s, 1H), 8.59 (d, J = 6.8 Hz, 1H), 7.56-7.52 (m, 1H), 7.46-7.41 (m, 3H), 7.20-7.05 (m, 2H), 5.08-5.05 (m, 1H), 3.89 (s, 2H), 1.35 (d, J = 6.8 Hz, 3H). |
| 116 | $^1$H NMR (400 MHz, DMSO-d6) δ 11.92 (s, 1H), 8.49 (d, J = 7.6 Hz, 1H), 7.60-7.53 (m, 1H), 7.49-7.43 (m, 1H), 7.19-7.03 (m, 3H), 5.11-5.03 (m, 1H), 3.65 (s, 2H), 2.44 (d, J = 6.0 Hz, 3H), 1.35 (d, J = 6.8 Hz, 3H). |
| 119 | $^1$H NMR (300 MHz, DMSO-$d_6$) δ 12.27 (s, 1H), 9.25 (d, J = 7.8 Hz, 1H), 8.37 (s, 1H), 7.77-7.73 (m, 1H), 7.63-7.50 (m, 2H), 7.39-7.35 (m, 1H), 7.23-7.15 (m, 1H), 7.08-7.03 (m, 1H), 5.18 (t, J = 7.2 Hz, 1H), 1.45 (d, J = 6.9 Hz, 3H). |
| 127 | $^1$H NMR (400 MHz, DMSO-d6) δ 11.74 (s, 1H), 7.85-7.81 (m, 1H), 7.58-7.51 (m, 1H), 7.49-7.26 (m, 3H), 7.28-7.12 (m, 1H), 7.03-6.93 (m, 1H), 5.20-5.14 (m, 1H), 4.22-4.12 (m, 1H), 2.23 (s, 3H), 1.29-1.23 (m, 6H). |
| 129 | $^1$H NMR (300 MHz, DMSO-$d_6$) δ 12.38 (s, 1H), 8.58 (d, J = 7.5 Hz, 1H), 7.75-7.74 (m, 1H), 7.72-7.71 (m, 1H), 7.62-7.39 (m, 2H), 7.32-7.26 (m, 1H), 7.22-7.16 (m, 1H), 7.13-7.01 (m, 1H), 5.0--5.05 (m, 1H), 3.90-3.89 (m, 2H), 1.35 (d, J = 6.9 Hz, 3H). |
| 130 | $^1$H NMR (300 MHz, DMSO-$d_6$) δ 11.92 (s, 1H), 8.49 (d, J = 7.5 Hz, 1H), 7.51-7.40 (m, 2H), 7.20-7.03 (m, 3H), 6.99-6.92 (m, 1H), 5.10-5.03 (m, 1H), 3.63 (s, 2H), 2.43 (d, J = 6.3 Hz, 3H), 1.34 (d, J = 6.9 Hz, 3H). |
| 131 | $^1$H NMR (400 MHz, DMSO-d6) δ 12.03 (s, 1H), 8.58 (d, J = 7.6 Hz, 1H), 7.86 (s, 1H), 7.55-7.41 (m, 2H), 7.22-7.09 (m, 2H), 7.08-6.95 (m, 2H), 5.14-5.07 (m, 1H), 1.36 (d, J = 7.2 Hz, 3H). |
| 133 | $^1$H NMR (300 MHz, DMSO-$d_6$) δ 11.88 (s, 1H), 8.56 (d, J = 7.5 Hz, 1H), 7.74 (s, 1H), 7.53-7.45 (m, 2H), 7.39-7.27 (m, 2H), 7.21-7.13 (m, 1H), 7.07-7.00 (m, 1H), 5.14-5.04 (m, 1H), 3.41 (s, 2H), 1.35 (d, J = 7.2 Hz, 3H). |
| 135 | $^1$H NMR (300 MHz, DMSO-$d_6$) δ 11.70 (s, 1H), 8.45 (d, J = 7.5 Hz, 1H), 7.96-7.73 (m, 1H), 7.59-7.44 (m, 2H), 7.30-7.28 (m, 1H), 7.22-7.12 (m, 2H), 7.07-7.01 (m, 1H), 5.12-5.03 (m, 1H), 3.62 (s, 2H), 2.35 (s, 3H), 1.35 (d, J = 6.9 Hz, 3H). |
| 136 | $^1$H NMR (300 MHz, DMSO-$d_6$) δ 11.85 (d, J = 7.2 Hz, 1H), 8.53-8.49 (m, 1H), 7.68(s, 1H), 7.61 (d, J = 7.8 Hz, 1H), 7.57-4-7.40 (m, 2H), 7.37(t, J = 7.5 Hz, 1H), 7.31-7.18 (m, 2H), 7.03-6.90 (m, 1H), 5.11-5.04 (m, 1H), 3.95-3.88 (m, 1H), 1.35-1.24 (m, 6H). |
| 137 | $^1$H NMR (400 MHz, DMSO-$d_6$) δ 11.82 (s, 1H), 8.57 (d, J = 7.6 Hz, 1H), 7.75 (s, 1H), 7.59 (dd, J = 8.0, 1.6 Hz, 1H), 7.52-7.50 (m, 1H), 7.48-7.43 (m, 1H), 7.30-7.14 (m, 2H), 7.06-7.02 (m, 1H), 5.13-5.06 (m, 1H), 3.45 (s, 2H), 1.35 (d, J = 6.8 Hz, 3H). |
| 1092 | $^1$H NMR (400 MHz, DMSO-$d_6$) δ 11.70 (s, 1H), 8.75 (s, 1H), 8.27 (d, J = 8.4 Hz, 1H), 8.07 (s, 1H), 7.52-7.49 (m, 1H), 7.32-7.23 (m, 2H), 5.20-5.18 (m, 1H), 3.57 (s, 2H), 2.92-2.74 (m, 2H), 2.43-2.31 (m, 2H), 2.26 (s, 3H), 1.86-1.76 (m, 1H). |
| 1093 | $^1$H NMR (400 MHz, DMSO-$d_6$) δ 11.77 (s, 1H), 8.82 (d, J = 1.9 Hz, 1H), 8.33 (d, J = 8.0 Hz, 1H), 8.15 (s, 1H), 7.59-7.56 (m, 1H), 7.40-7.30 (m, 2H), 5.29-5.25 (m, 1H), 3.64 (s, 2H), 2.99-2.81 (m, 2H), 2.50-2.42 (m, 1H), 2.38 (s, 3H), 1.93-1.83 (m, 1H). |
| 1096 | $^1$H NMR (300 MHz, DMSO-$d_6$) δ 11.95 (s, 1H), 8.87 (s, 1H), 8.72 (d, J = 6.9 Hz, 1H), 7.82-7.74 (m, 2H), 7.24-7.17 (m, 1H), 5.07-4.98 (m, 1H), 3.83-3.38 (m, 2H), 2.73 (s, 3H), 1.42 (d, J = 7.2 Hz, 3H). $^{19}$F NMR (282 MHz, DMSO-$d_6$) δ −134.21 (1F), −145.62 (1F). |
| 1097 | $^1$H NMR (300 MHz, DMSO-$d_6$) δ 11.95 (s, 1H), 8.87 (s, 1H), 8.72 (d, J = 6.9 Hz, 1H), 7.82-7.74 (m, 2H), 7.24-7.17 (m, 1H), 5.07-4.98 (m, 1H), 3.83-3.38 (m, 2H), 2.73 (s, 3H), 1.42 (d, J = 7.2 Hz 3H). $^{19}$F NMR (282 MHz, DMSO-$d_6$) δ −134.30 (1F), −145.62 (1F). |
| 1098 | $^1$H NMR (400 MHz, DMSO-$d_6$) δ 11.98 (s, 1H), 9.16 (d, J = 1.2 Hz, 1H), 8.93 (d, J = 1.2 Hz, 1H), 8.76 (d, J = 6.8 Hz, 1H), 7.81-7.76 (m, 2H), 7.22 (dd, J = 11.6, 7.2 Hz, 1H), 5.06-4.99 (m, 1H), 3.45 (dd, J = 28.8, 15.2 Hz, 2H), 1.45 (d, J = 7.2 Hz, 3H). $^{19}$F NMR (376 MHz, DMSO-$d_6$) δ −134.35 (1F), −145.61 (1F). |
| 1099 | $^1$H NMR (400 MHz, DMSO-$d_6$) δ 11.98 (s, 1H), 9.16 (d, J = 1.2 Hz, 1H), 8.93 (d, J = 1.2 Hz, 1H), 8.76 (d, J = 6.8 Hz, 1H), 7.81-7.76 (m, 2H), 7.22 (dd, J = 11.6, 7.2 Hz, 1H), 5.06-4.99 (m, 1H), 3.45 (dd, J = 28.8, 15.2 Hz, 2H), 1.45 (d, J = 7.2 Hz, 3H). $^{19}$F NMR (377 MHz, DMSO-$d_6$) δ −134.35 (1F), −145.61 (1F). |
| 1100 | $^1$H NMR (400 MHz, DMSO-$d_6$) δ 11.83 (s, 1H), 9.01 (s, 2H), 8.64 (d, J = 7.2 Hz, 1H), 7.58 (dd, J = 10.8, 2.8 Hz, 1H), 7.41-7.27 (m, 2H), 5.04-4.99 (m, 1H), 3.63 (d, J = 2.4 Hz, 2H), 2.36 (s, 3H), 1.46 (d, J = 7.2 Hz, 3H). |

TABLE 1-A-continued

| Cmpd No. | NMR |
|---|---|
| 1101 | $^1$H NMR (400 MHz, DMSO-$d_6$) δ 11.83 (s, 1H), 9.01 (s, 2H), 8.64 (d, J = 7.2 Hz, 1H), 7.58 (dd, J = 10.4, 2.8 Hz, 1H), 7.41-7.27 (m, 2H), 5.00 (t, J = 7.2 Hz, 1H), 3.63 (d, J = 2.4 Hz, 2H), 2.36 (s, 3H), 1.45 (d, J = 7.2 Hz, 3H). |
| 1108 | $^1$H NMR (400 MHz, DMSO-d6) δ 11.82 (s, 1H), 9.15 (d, J = 1.6 Hz, 1H), 8.90 (d, J = 1.6 Hz, 1H), 8.69 (d, J = 6.8 Hz, 1H), 7.59-7.55 (m, 1H), 7.40-7.29 (m, 2H), 5.05-4.98 (m, 1H), 3.70-3.61 (m, 2H), 2.36 (s, 3H), 1.45 (d, J = 7.2 Hz, 3H). |
| 1109 | $^1$H NMR (400 MHz, DMSO-d6) δ 11.82 (s, 1H), 9.15 (d, J = 1.6 Hz, 1H), 8.90 (d, J = 1.6 Hz, 1H), 8.69 (d, J = 7.2 Hz, 1H), 7.58-7.55 (m, 1H), 7.40-7.29 (m, 2H), 5.05-4.98 (m, 1H), 3.70-3.61 (m, 2H), 2.35 (s, 3H), 1.45 (d, J = 7.2 Hz, 3H). |
| 1110 | $^1$H NMR (300 MHz, DMSO-d6) δ 12.40 (s, 1H), 8.97 (d, J = 2.1 Hz, 1H), 8.82 (d, J = 7.2 Hz, 1H), 8.28-8.25 (m, 1H), 7.64 (d, J = 8.1 Hz, 1H), 7.49-7.43 (m, 1H), 7.27 (d, J = 8.1 Hz, 1H), 7.11 (d, J = 7.5 Hz, 1H), 5.03-4.93(m, 1H), 3.83 (s, 2H), 2.82 (s, 3H), 1.43 (d, J = 7.2 Hz, 3H). |
| 1111 | $^1$H NMR (300 MHz, DMSO-d6) δ 12.39 (d, J = 7.8 Hz, 1H), 8.98 (d, J = 1.2, 1H), 8.83 (d, J = 7.2 Hz, 1H), 8.28-8.25 (m, 1H), 7.64 (d, J = 8.1 Hz, 1H), 7.49-7.44 (m, 1H), 7.27 (d, J = 8.1 Hz, 1H), 7.12 (d, J = 7.5 Hz, 1H), 5.00-4.95 (m, 1H), 3.83 (s, 2H), 2.83 (s, 3H), 1.43 (d, J = 7.2 Hz, 3H). |
| 1112 | $^1$H NMR (300 MHz, DMSO-d6) δ 11.84(s, 1H), 8.95 (d, J = 1.5, 1H), 8.65 (d, J = 7.5 Hz, 1H), 8.25 (dd, J = 8.4, 2.1 Hz, 1H), 7.87-7.80 (m, 2H), 7.61 (d, J = 8.4 Hz, 1H), 7.22 (dd, J = 11.4, 7.2 Hz, 1H), 4.98-4.03 (m, 1H), 3.63 (s, 2H), 2.33 (s, 3 H) 1.41 (d, J = 6.9 Hz, 3H). |
| 1113 | $^1$H NMR (300 MHz, DMSO-d6) δ 11.84(s, 1H), 8.95 (d, J = 1.5, 1H), 8.65 (d, J = 7.5 Hz, 1H), 8.25 (dd, J = 8.4, 2.1 Hz, 1H), 7.87-7.80 (m, 2H), 7.61 (d, J = 8.4 Hz, 1H), 7.22 (dd, J = 11.4, 7.2 Hz, 1H), 4.98-4.03 (m, 1H), 3.63 (s, 2H), 2.33 (s, 3 H) 1.41 (d, J = 6.9 Hz, 3H). |
| 1114 | $^1$H NMR (400 MHz, DMSO-d6) δ 11.95 (s, 1H), 8.96 (d, J = 1.6 Hz, 1H), 8.64 (d, J = 7.2 Hz, 1H), 8.25 (dd, J = 8.4, 2.4 Hz, 1H), 7.81-7.76 (m, 2H), 7.65 (d, J = 8.4 Hz, 1H), 7.24-7.19 (m, 1H), 4.99-4.95 (m, 1H), 3.45 (s, 2H), 1.41 (d, J = 7.2 Hz, 3H). |
| 1115 | $^1$H NMR (400 MHz, DMSO-d6) δ 11.95 (s, 1H), 8.96 (d, J = 1.6 Hz, 1H), 8.64 (d, J = 7.2 Hz, 1H), 8.25 (dd, J = 8.4, 2.0 Hz, 1H), 7.81-7.76 (m, 2H), 7.65-7.63 (m, 1H), 7.24-7.19 (m, 1H), 4.99-4.95 (m, 1H), 3.45 (s, 2H), 1.41 (d, J = 7.2 Hz, 3H). |
| 1116 | $^1$H NMR (300 MHz, DMSO-$d_6$) δ 10.59 (s, 1H), 9.44 (s, 1H), 8.32 (d, J = 1.5 Hz, 1H), 7.26 (d, J = 6.3 Hz, 1H), 7.17-7.11 (m, 1H), 7.01 (dd, J = 9.0, 5.1 Hz, 1H), 4.87-4.82 (m, 1H), 3.47 (s, 2H), 2.69 (d, J = 2.7 Hz, 3H), 2.12 (d, J = 1.5 Hz, 3H), 1.33 (d, J = 6.9 Hz, 3H). |
| 1117 | $^1$H NMR (300 MHz, DMSO-$d_6$) δ 10.59 (s, 1H), 9.44 (s, 1H), 8.32 (d, J = 1.5 Hz, 1H), 7.26 (d, J = 6.3 Hz, 1H), 7.17-7.11 (m, 1H), 7.01 (dd, J = 9.0, 5.1 Hz, 1H), 4.87-4.82 (m, 1H), 3.47 (s, 2H), 2.69 (d, J = 2.7 Hz, 3H), 2.12 (d, J = 1.5 Hz, 3H), 1.33 (d, J = 6.9 Hz, 3H). |
| 1119 | $^1$H NMR (400 MHz, DMSO-d6) δ 11.81 (s, 1H), 8.73 (d, J = 7.2 Hz, 1H), 8.31 (d, J = 8.8 Hz, 1H), 7.96 (d, J = 8.8 Hz, 1H), 7.58-7.55 (m, 1H), 7.38-7.29 (m, 2H), 5.20-5.16 (m, 1H), 3.67-3.65 (m, 2H), 2.34 (s, 3H), 1.51 (d, J = 7.2 Hz, 3H). |
| 1120 | $^1$H NMR (400 MHz, DMSO-d6) δ 11.81 (s, 1H), 8.73 (d, J = 7.2 Hz, 1H), 8.31 (d, J = 8.8 Hz, 1H), 7.96 (d, J = 8.8 Hz, 1H), 7.58-7.55 (m, 1H), 7.38-7.29 (m, 2H), 5.20-5.16 (m, 1H), 3.67-3.65 (m, 2H), 2.34 (s, 3H), 1.51 (d, J = 7.2 Hz, 3H). |
| 1123 | $^1$H NMR (400 MHz, DMSO, ppm) δ 11.92 (s, 1H), 9.27 (s, 2H), 8.58 (d, J = 7.1 Hz, 1H), 7.61 (q, J = 9.2 Hz, 1H), 7.13-7.10 (m, 1H), 5.03-4.96 (m, 1H), 3.76-3.62 (m, 2H), 2.47 (d, J = 6.2 Hz, 3H), 1.44 (d, J = 7.1 Hz, 3H).<br>FNMR (400 MHz, DMSO, ppm) δ −139.22-−139.27 (m, 1F), −146.99-−147.04 (m, 1F). |
| 1124 | $^1$H NMR (300 MHz, DMSO-$d_6$) δ 11.93 (s, 1H), 9.27 (s, 2H), 8.59 (d, J = 7.2 Hz, 1H), 7.62-7.52 (m, 1H), 7.13-7.09 (m, 1H), 4.99 (t, J = 7.2 Hz, 1H), 3.76-3.61 (m, 2H), 2.51-2.44 (m, 3H), 1.43 (d, J = 6.9 Hz, 3H). $^{19}$F NMR (282 MHz, DMSO-$d_6$) δ −139.20 (1F), −147.04 (1F). |
| 1131 | $^1$H NMR (400 MHz, DMSO-$d_6$) δ 11.95 (s, 1H), 8.85 (s, 1H), 8.67 (d, J = 6.8 Hz, 1H), 7.61-7.55 (m, 1H), 7.13-7.06 (m, 1H), 5.05-4.98 (m, 1H), 3.63 (d, J = 3.2 Hz, 2H), 2.57 (s, 3H), 2.45 (d, J = 6.4 Hz, 2H), 1.42 (d, J = 7.2 Hz, 3H). |
| 1132 | $^1$H NMR (400 MHz, DMSO-$d_6$) δ 11.95 (s, 1H), 8.85 (s, 1H), 8.67 (d, J = 6.8 Hz, 1H), 7.61-7.55 (m, 1H), 7.12-7.08 (m, 1H), 5.05-4.98 (m, 1H), 3.63 (d, J = 3.2 Hz, 2H), 2.57 (s, 3H), 2.45 (d, J = 6.4 Hz, 3H), 1.42 (d, J = 7.2 Hz, 3H). |
| 1135 | $^1$H NMR (300 MHz, DMSO-d6) δ 11.91 (s, 1H), 8.73 (d, J = 7.5 Hz, 1H), 8.18 (d, J = 0.6 Hz, 1H), 7.62-7.52 (m, 1H), 7.12-7.08 (m, 1H), 5.35-5.27 (m, 1H), 3.70-3.56 (m, 2H), 2.41 (d, J = 8.4 Hz, 6H), 1.49 (d, J = 6.9 Hz, 3H).. |
| 1136 | $^1$H NMR (300 MHz, DMSO-d6) δ 11.91 (s, 1H), 8.73 (d, J = 7.5 Hz, 1H), 8.18 (s, 1H), 7.61-7.52 (m, 1H), 7.11-7.07 (m, 1H), 5.35-5.26 (m, 1H), 3.69-3.56 (m, 2H), 2.41 (d, J = 15.9 Hz, 6H), 1.49 (d, J = 6.9 Hz, 3H). |
| 1137 | $^1$H NMR (400 MHz, DMSO-$d_6$) δ 12.09 (s, 1H), 8.87 (t, J = 1.2 Hz, 1H), 8.70 (d, J = 7.0 Hz, 1H), 8.39 (dd, J = 9.9, 1.7 Hz, 1H), 7.79 (s, 1H), 7.16-7.06 (m, 1H), 6.90 (dd, J = 9.8, 2.3 Hz, 1H), 5.30-5.19 (m, 1H), 3.43-3.39 (m, J = 2H), 1.40 (d, J = 7.0 Hz, 3H). $^{19}$F NMR (376 MHz, DMSO-$d_6$) δ −106.92 (1F), δ −117.64 (1F), δ −124.74 (1F). |
| 1138 | $^1$H NMR (400 MHz, DMSO-$d_6$) δ 12.09 (s, 1H), 8.87 (s, 1H), 8.71 (d, J = 7.0 Hz, 1H), 8.39 (dd, J = 10.0, 1.7 Hz, 1H), 7.79 (s, 1H), 7.16-7.06 (m, 1H), 6.94-6.87 (m, 1H), 5.26 (q, J = 6.9 Hz, 1H), 3.49-3.39 (m, 2H), 1.40 (d, J = 7.0 Hz, 3H). $^{19}$F NMR (376 MHz, DMSO-$d_6$) δ −106.93 (1F), δ −117.64 (1F), δ −124.74 (1F). |
| 1141 | $^1$H NMR (300 MHz, DMSO-$d_6$) δ 11.87 (s, 1H), 9.04 (s, 1H), 8.56 (d, J = 7.2 Hz, 1H), 7.59-7.50 (m, 1H), 7.09-7.05 (m, 1H), 5.24-5.19 (m, 1H), 3.75-3.60 (m, 2H), 2.63 (s, 3H), 2.00-1.97 (m, 1H), 1.42 (d, J = 6.9 Hz, 3H), 1.01 (d, J = 8.4 Hz, 2H), 0.60-0.53 (m, 2H) |
| 1142 | $^1$H NMR (300 MHz, DMSO-$d_6$) δ 11.87 (s, 1H), 9.04 (s, 1H), 8.56 (d, J = 7.5 Hz, 1H), 7.53-7.50 (m, 1H), 7.10-7.05 (m, 1H), 5.26-5.17 (m, 1H), 3.75-3.60 (m, 2H), 2.64 (s, 3H), 1.99-1.97 (m, 1H), 1.42 (d, J = 6.6 Hz, 3H), 1.02-0.99 (m, 2H), 0.60-0.53 (m, 2H) |
| 1143 | $^1$H NMR (300 MHz, DMSO-$d_6$) δ 11.82 (s, 1H), 8.88 (s, 1H), 8.56 (d, J = 7.2 Hz, 1H), 8.39-8.35 (m, 1H), 7.45-7.37 (m, 1H), 7.09 (d, J = 7.8 Hz, 1H), 6.98-6.91 (m, 1H), 5.23 (t, J = 7.5 Hz, 1H), 3.70 (s, 2H), 1.96 (s, 1H), 1.40 (d, J = 6.9 Hz, 3H), 0.98 (t, J = 7.5 Hz, 2H), 0.51 (s, 2H). $^{19}$F NMR (282 MHz, DMSO-$d_6$) δ −106.88 (1F), −124.67 (1F). |

TABLE 1-A-continued

| NMR | |
|---|---|
| Cmpd No. | NMR |
| 1144 | $^1$H NMR (300 MHz, DMSO-$d_6$) δ 11.82 (s, 1H), 8.88 (s, 1H), 8.56 (d, J = 7.2 Hz, 1H), 8.39-8.35 (m, 1H), 7.45-7.38 (m, 1H), 7.09 (d, J = 7.8 Hz, 1H), 6.98-6.91 (m, 1H), 5.23 (t, J = 7.5 Hz, 1H), 3.70 (s, 2H), 1.96 (s, 1H), 1.40 (d, J = 6.9 Hz, 3H), 0.98 (t, J = 7.5 Hz, 2H), 0.51 (s, 2H). $^{19}$F NMR (282 MHz, DMSO-$d_6$) δ −106.88 (1F), −124.67 (1F). |
| 1146 | $^1$H NMR (400 MHz, DMSO-$d_6$) δ 11.96 (s, 1H), 9.16 (d, J = 1.2 Hz, 1H), 8.88 (d, J = 1.6 Hz, 1H), 8.70 (d, J = 6.8 Hz, 1H), 7.61-7.54 (m, 1H), 7.12-7.09 (m, 1H), 5.04-5.00 (m, 1H), 3.73-3.63 (m, 2H), 2.47 (s, 3H), 1.45 (d, J = 7.2 Hz, 3H). |
| 1147 | $^1$H NMR (300 MHz, DMSO-$d_6$) δ 12.42 (s, 1H), 8.71 (d, J = 7.5 Hz, 1H), 8.50 (d, J = 2.4 Hz, 1H), 7.95-7.87 (m, 1H), 7.57-7.42 (m, 1H), 7.35-7.21 (m, 1H), 5.34-5.15 (m, 1H), 3.83-3.71 (m, 2H), 2.70 (d, J = 2.1 Hz, 3H), 1.40 (d, J = 6.9 Hz, 3H). |
| 1148 | $^1$H NMR (300 MHz, DMSO-$d_6$) δ 12.42 (s, 1H), 8.72 (d, J = 7.5 Hz, 1H), 8.50 (d, J = 2.4 Hz, 1H), 7.95-7.87 (m, 1H), 7.59-7.36 (m, 1H), 7.34-7.21 (m, 1H), 5.35-5.23 (m, 1H), 3.83-3.71 (m, 2H), 2.70 (d, J = 2.1 Hz, 3H), 1.39 (d, J = 7.2 Hz, 3H). |
| 1151 | $^1$H NMR (300 MHz, DMSO-$d_6$) δ 12.08 (s, 1H), 8.88 (d, J = 1.6 Hz, 1H), 8.59 (d, J = 7.2 Hz, 1H), 8.49 (d, J = 1.8 Hz, 1H), 8.37 (dd, J = 10.0, 1.7 Hz, 1H), 7.84 (dd, J = 8.5, 1.8 Hz, 1H), 7.38 (d, J = 8.5 Hz, 1H), 5.23 (p, J = 6.9 Hz, 1H), 3.72 (s, 2H), 1.84 (q, J = 7.8, 7.3 Hz, 1H), 1.40 (d, J = 7.0 Hz, 3H), 1.14 (p, J = 9.4 Hz, 2H), 0.59-0.51 (m, 2H). $^{19}$F NMR (282 MHz, DMSO-$d_6$) δ −124.52 (1F). |
| 1152 | $^1$H NMR (300 MHz, DMSO-$d_6$) δ 12.06 (s, 1H), 8.89 (s, 1H), 8.59 (d, J = 7.2 Hz, 1H), 8.49 (d, J = 1.8 Hz, 1H), 8.37 (dd, J = 9.9, 1.7 Hz, 1H), 7.84 (dd, J = 8.5, 1.8 Hz, 1H), 7.38 (d, J = 8.5 Hz, 1H), 5.23 (t, J = 7.0 Hz, 1H), 3.72 (s, 2H), 1.85 (t, J = 7.0 Hz, 1H), 1.40 (d, J = 7.0 Hz, 3H), 1.14 (p, J = 9.4 Hz, 2H), 0.55 (d, J = 6.0 Hz, 2H). $^{19}$F NMR (282 MHz, DMSO-$d_6$) δ −124.70 (1F). |
| 2043 | $^1$H NMR (300 MHz, DMSO-$d_6$) δ 11.20 (s, 1H), 8.83 (s, 2H), 8.42 (d, J = 7.8 Hz, 1H), 7.62-7.53 (m, 1H), 7.14-7.09 (m, 1H), 5.04-4.90 (m, 3H), 4.68 (t, J = 6.6 Hz, 2H), 4.35-4.25 (m, 1H), 3.69-3.62 (m, 2H), 2.47 (d, J = 6.3 Hz, 3H), 1.40 (d, J = 6.9 Hz, 3H). |
| 2044 | $^1$H NMR (300 MHz, DMSO-$d_6$) δ 11.93 (s, 1H), 8.86 (s, 2H), 8.42 (d, J = 7.8 Hz, 1H), 7.62-7.52 (m, 1H), 7.13-7.08 (m, 1H), 5.04-4.91 (m, 3H), 4.68 (t, J = 6.6 Hz, 2H), 4.30-4.24 (m, 1H), 3.74-3.62 (m, 2H), 2.47 (d, J = 6.6 Hz, 3H), 1.40 (d, J = 6.9 Hz, 3H). |
| 2071 | $^1$H-NMR: (300 MHz, DMSO-$d_6$, ppm) δ 12.06 (s, 1H), 9.28 (s, 2H), 8.74 (d, J = 7.2 Hz, 1H), 7.95 (s, 1H), 7.63-7.53(m, 1H), 7.14 (dd, J = 9.3, 3.0 Hz, 1H), 5.08-4.99 (m, 1H), 3.56-3.44 (m, 2H), 1.46 (d, J = 7.2 Hz, 3H). $^{19}$F-NMR: (282 MHz, DMSO-$d_6$, ppm), δ −147.5 (d, J = 21.7 Hz, 1F), 147.6 (d, J = 21.1 Hz, 1F). |
| 2511 | $^1$H NMR (400 MHz, DMSO-$d_6$) δ 12.81 (s, 1H), 9.32 (s, 2H), 9.30 (t, J = 5.6 Hz, 1H), 7.63 (t, J = 9.2 Hz, 1H), 7.34-7.31 (m, 1H), 5.14-5.07 (m, 1H), 2.75 (d, J = 2.0 Hz, 3H), 1.52 (d, J = 7.2 Hz, 3H). $^{19}$F NMR (377 MHz, DMSO-$d_6$) δ −101.00 (2F), −118.83 (1F). |
| 2512 | $^1$H NMR (400 MHz, DMSO-$d_6$) δ 12.82 (s, 1H), 9.31 (s, 2H), 9.26 (d, J = 7.2 Hz, 1H), 7.65 (t, J = 9.2 Hz, 1H), 7.35-7.32 (m, 1H), 5.14-5.09 (m, 1H), 2.76 (d, J = 2.0 Hz, 3H), 1.52 (d, J = 7.2 Hz, 3H). $^{19}$F NMR (377 MHz, DMSO-$d_6$) δ −101.07 (2F), −118.62 (1F). |
| 2513 | $^1$H NMR (300 MHz, DMSO-$d_6$) δ 12.34 (s, 1H), 9.31 (s, 2H), 8.99 (d, J = 7.5 Hz, 1H), 7.76-7.70 (m, 1H), 7.66-7.61 (m, 1H), 5.14-5.09 (m, 1H), 2.54-2.50 (m, 3H), 1.54 (d, J = 7.2 Hz, 3H). |
| 2514 | $^1$H NMR (300 MHz, DMSO-$d_6$) δ 12.35 (s, 1H), 9.32 (s, 2H), 9.00 (d, J = 7.5 Hz, 1H), 7.77-7.70 (m, 1H), 7.66-7.61 (m, 1H), 5.17-5.07 (m, 1H), 2.55-2.50 (m, 3H), 1.54 (d, J = 7.2 Hz, 3H). |
| 2529 | $^1$H NMR (400 MHz, DMSO-d6) δ 12.67 (s, 1H), 9.27 (d, J = 7.2 Hz, 1H), 8.90 (s, 1H), 8.41 (d, J = 1.6 Hz, 1H), 8.11 (s, 1H), 7.83 (t, J = 9.2 Hz, 1H), 7.72-7.68 (m, 1H), 5.35-5.28 (m, 1H), 1.49 (d, J = 6.8 Hz, 3H). |
| 2530 | $^1$H NMR (400 MHz, DMSO-d6) δ 12.51 (s, 1H), 9.27 (d, J = 6.8 Hz, 1H), 8.90 (s, 1H), 8.41 (d, J = 9.2 Hz, 1H), 8.11 (s, 1H), 7.83 (t, J = 9.2 Hz, 1H), 7.72-7.68 (m, 1H), 5.35-5.28 (m, 1H), 1.49 (d, J = 6.8 Hz, 3H). |
| 2531 | $^1$H NMR (300 MHz, DMSO-d6) δ 12.08 (s, 1H), 9.25 (s, 2H), 7.72-7.67 (m, 3H), 5.06 (s, 1H), 2.84 (s, 3H), 1.52 (s, 2H), 1.37 (d, J = 6.9 Hz, 3H), 0.93 (s, 2H). |
| 2532 | $^1$H NMR (300 MHz, DMSO-d6) δ 12.09 (s, 1H), 9.32 (s, 2H), 7.75-7.65 (m, 3H), 5.05 (d, J = 5.7 Hz, 1H), 2.84 (s, 3H), 1.53-1.49 (m, 2H), 1.38 (d, J = 6.9 Hz, 3H), 0.93 (s, 2H). |
| 2543 | $^1$H NMR (400 MHz, Methanol-$d_4$) δ 9.04 (s, 2H), 7.74-7.70 (m, 1H), 7.65-7.62 (m, 2H), 5.17 (s, 1H), 3.03 (s, 3H), 1.77-1.68 (m, 2H), 1.46 (d, J = 7.2 Hz, 3H), 1.13-1.05 (m, 2H). |
| 2544 | $^1$H NMR (400 MHz, Methanol-$d_4$) δ 9.08 (s, 2H), 7.72-7.66 (m, 1H), 7.63-7.61 (m, 2H), 5.18-5.17 (m, 1H), 3.03 (s, 4H), 1.77-1.66 (m, 2H), 1.46 (d, J = 7.2 Hz, 3H), 1.12-0.87 (m, 2H). |
| 2569 | $^1$H NMR (400 MHz, DMSO-$d_6$) δ 12.12 (s, 1H), 7.99-7.87 (m, 3H), 7.80-7.77 (m, 2H), 7.60 (d, J = 10.0 Hz, 1H), 7.14-7.11 (m, 1H), 4.98 (t, J = 7.2 Hz, 1H), 1.41-1.37 (m, 1H), 1.34 (d, J = 7.2 Hz, 3H), 1.31-1.28 (m, 1H), 1.14-1.11 (m, 1H), 0.89 (s, 1H). |
| 2570 | $^1$H NMR (400 MHz, DMSO-$d_6$) δ 12.11 (s, 1H), 7.99-7.87 (m, 3H), 7.79 (t, J = 8.0 Hz, 2H), 7.60 (d, J = 10.0 Hz, 1H), 7.14-7.11 (m, 1H), 4.98 (t, J = 7.6 Hz, 1H), 1.40-1.37 (m, 1H), 1.34-1.33 (m, 3H), 1.31-1.29 (m, 1H), 1.13 (s, 1H), 0.87 (d, J = 2.8 Hz, 1H). |
| 2573 | $^1$H NMR (400 MHz, DMSO-$d_6$) δ 12.30 (s, 1H), 9.36 (d, J = 8.0 Hz, 1H), 8.79 (t, J = 4.4 Hz, 1H), 8.43 (s, 1H), 8.02 (s, 1H), 7.78-7.75 (m, 2H), 7.57-7.53 (m, 1H), 7.45-7.41 (m, 1H), 5.11-5.04 (m, 1H), 1.53 (d, J = 7.2 Hz, 3H). |
| 2574 | $^1$H NMR (400 MHz, DMSO-$d_6$) δ 12.30 (s, 1H), 9.36 (d, J = 7.6 Hz, 1H), 8.79 (d, J = 5.2 Hz, 1H), 8.42 (s, 1H), 8.02 (s, 1H), 7.78-7.75 (m, 2H), 7.57-7.53 (m, 1H), 7.44-7.41 (m, 1H), 5.11-5.04 (m, 1H), 1.53 (d, J = 7.2 Hz, 3H). |
| 2579 | $^1$H NMR (300 MHz, DMSO-$d_6$) δ 11.74 (s, 1H), 8.03-8.00 (m, 1H), 7.97-7.90 (m, 1H), 7.87-7.75 (m, 2H), 7.61-7.57 (m, 1H), 7.43-7.37 (m, 1H), 7.32-7.29 (m, 1H), 5.08-4.98 (m, 1H), 2.51-2.49 (m, 3H), 1.55-1.16 (m, 2H), 1.34-1.23 (m, 3H), 0.96-0.87 (m, 2H). |
| 2580 | $^1$H NMR (300 MHz, DMSO-$d_6$) δ 11.74 (s, 1H), 8.03-7.97 (m, 1H), 7.90-7.87 (m, 1H), 7.74-7.61 (m, 2H), 7.60-7.57 (m, 1H), 7.43-7.38 (m, 1H), 7.37-7.30 (m, 1H), 5.08-4.98 (m, 1H), 2.52-2.49 (m, 3H), 1.56-1.51 (m, 2H), 1.34-1.23 (m, 3H), 0.96-0.92 (m, 2H). |

TABLE 1-A-continued

| Cmpd No. | NMR |
|---|---|
| 2587 | $^1$H NMR (400 MHz, DMSO-d6) δ 12.29 (s, 1H), 9.10 (d, J = 8.0 Hz, 1H), 8.03 (t, J = 7.6 Hz, 1H), 7.94-7.91 (m, 2H), 7.75-7.72 (m, 1H), 7.16-7.13 (m, 1H), 5.07-5.03 (m, 1H), 2.76-2.74 (m, 3H), 1.50 (d, J = 7.2 Hz, 3H). |
| 2588 | $^1$H NMR (400 MHz, DMSO-d6) δ 12.29 (s, 1H), 9.10 (d, J = 8.0 Hz, 1H), 8.03 (t, J = 8.0 Hz, 1H), 7.94-7.91 (m, 2H), 7.77-7.70 (m, 1H), 7.16-7.13 (m, 1H), 5.09-5.02 (m, 1H), 2.76-2.74 (m, 3H), 1.51 (d, J = 7.2 Hz, 3H). |
| 2592 | $^1$HNMR- (400 MHz, DMSO-$d_6$, ppm) δ 12.00 (s, 1H), 8.08 (s, 1H), 8.33 (dd, J = 9.9, 1.7 Hz, 1H), 7.86 (s, 1H), 7.73 (d, J = 7.3 Hz, 1H), 7.64-7.54 (m, 1H), 7.1-7.07 (m, 1H), 5.25 (p, J = 7.2 Hz, 1H), 1.38 (ddd, J = 10.1, 6.5, 3.7 Hz, 1H), 1.31 (d, J = 7.0 Hz, 3H), 1.21 (ddd, J = 9.6, 6.8, 4.1 Hz, 1H), 1.03 (ddd, J = 10.8, 6.8, 4.0 Hz, 1H), 0.89 (ddd, J = 9.8, 6.8, 3.9 Hz, 1H). $^{19}$FNMR (376 MHz, DMSO-$d_6$, ppm) δ −124.15, −146.76 (d, J = 22.6 Hz, 1F), −148.08 (d, J = 22.6 Hz, 1F). |
| 2593 | ]$^+$ $^1$H NMR (400 MHz, DMSO-$d_6$, ppm) δ 12.02 (s, 1H), 8.80 (s, 1H), 8.34 (dd, J = 9.9, 1.7 Hz, 1H), 7.87 (s, 1H), 7.74 (d, J = 7.3 Hz, 1H), 7.60 (dt, J = 10.6, 8.8 Hz, 1H), 7.16-7.08 (m, 1H), 5.31-5.20 (m, 1H), 1.42-1.35 (m, 1H), 1.31 (d, J = 7.0 Hz, 3H), 1.26-1.18 (m, 1H), 1.09-0.99 (m, 1H), 0.94-0.85 (m, 1H). $^{19}$F NMR(376 MHz, DMSO-$d_6$, ppm) δ −124.15(s, 1F), −146.77 (d, J = 21.6 Hz, 1F), −148.08 (d, J = 21.8 Hz, 1F). |
| 2596 | $^1$H NMR (300 MHz, DMSO-$d_6$) δ 11.70 (s, 1H), 8.79 (m, 1H), 8.37-8.33 (m, 1H), 7.71 (d, J = 7.5 Hz, 1H), 7.60-7.56 (m, 1H), 7.43-7.36 (m, 1H), 7.33-7.28 (m, 1H), 5.32-5.22 (m, 1H), 2.43 (s, 3H), 1.47-1.39 (m, 2H), 1.31-1.23 (m, 3H), 0.89-0.83 (m, 2H). |
| 2597 | $^1$H NMR (300 MHz, DMSO-$d_6$) δ 11.70 (s, 1H), 8.79 (s, 1H), 8.37-8.33 (m, 1H), 7.71 (d, J = 7.8 Hz, 1H), 7.60-7.56 (m, 1H), 7.43-7.39 (m, 1H), 7.37-7.28 (m, 1H), 5.29-5.24 (m, 1H), 2.43 (s, 3H), 1.48-1.42 (m, 2H), 1.31-1.23 (m, 3H), 0.89-0.83 (m, 2H). |
| 2600 | $^1$H NMR (300 MHz, DMSO-d6) δ 11.88 (s, 1H), 8.78 (s, 1H), 8.38-8.35 (m, 1H), 8.00 (d, J = 7.2 Hz, 1H), 7.62-7.53 (m, 1H), 7.14-7.09 (m, 1H), 5.32-5.27 (m, 1H), 4.30-4.23 (m, 1H), 2.20 (d, J = 7.2 Hz, 3H), 1.34 (d, J = 7.2 Hz, 3H), 1.21 (d, J = 7.2 Hz, 3H). |
| 2602 | $^1$H NMR (300 MHz, DMSO-d6) δ 11.90 (s, 1H), 8.84 (s, 1H), 8.41-8.31 (m, 1H), 8.00 (d, J = 7.2 Hz, 1H), 7.61-7.53 (m, 1H), 7.14-7.09 (m, 1H), 5.33-5.24 (m, 1H), 4.22-4.15 (m, 1H), 2.41 (d, J = 7.2 Hz, 3H), 1.35 (d, J = 7.2 Hz, 3H), 1.22 (d, J = 7.2 Hz, 3H). |
| 2604 | $^1$H NMR (300 MHz, DMSO-$d_6$)) δ 12.09 (s, 1H), 8.72 (t, J = 1.2 Hz, 1H), 8.65 (d, J = 6.9 Hz, 1H), 8.39-8.36 (m, 1H), 7.62-7.59 (m, 1H), 7.516-7.53 (m, 1H), 7.13-7.10 (m, 1H), 5.24-5.15 (m, 1H), 3.98-3.91 (m, 1H), 1.36 (d, J = 7.2 Hz, 3H), 1.26 (d, J = 7.2 Hz, 3H). |
| 2605 | $^1$H NMR (300 MHz, DMSO-$d_6$)) δ 12.08 (s, 1H), 8.72 (t, J = 1.2 Hz, 1H), 8.65 (d, J = 6.9 Hz, 1H), 8.39-8.35 (m, 1H), 7.61-7.55 (m, 1H), 7.51 (s, 1H), 7.12-7.08 (m, 1H), 5.27-5.18 (m, 1H), 3.98-3.91 (m, 1H), 1.37 (d, J = 7.2 Hz, 3H), 1.26 (d, J = 7.2 Hz, 3H). |
| 2606 | $^1$H NMR (300 MHz, DMSO-d6) δ 12.06 (s, 1H), 8.92-8.89 (m, 2H), 8.41 (d, J = 9.9, 1.5 Hz, 1H), 7.80 (dd, J = 10.8, 2.7 Hz, 1H), 7.53 (td, J = 8.7, 2.7 Hz, 1H), 7.34 (dd, J = 9.0, 5.1 Hz, 1H), 5.36-5.26 (m, 1H), 2.62 (t, J = 3.0 Hz, 3H), 1.49 (d, J = 7.2 Hz, 3H). |
| 2607 | $^1$H NMR (300 MHz, DMSO-d6) δ 12.06 (s, 1H), 8.92-8.89 (m, 2H), 8.41 (dd, J = 9.9, 1.5 Hz, 1H), 7.80 (dd, J = 10.8, 2.7 Hz, 1H), 7.53 (td, J = 8.7, 2.7 Hz, 1H), 7.34 (dd, J = 9.0, 5.1 Hz, 1H), 5.31 (p, J = 6.7 Hz, 1H), 2.62 (t, J = 3.0 Hz, 3H), 1.49 (d, J = 7.2 Hz, 3H). |
| 4502 | $^1$H NMR (400 MHz, DMSO-$d_6$) δ 11.90 (d, J = 21.6 Hz, 1H), 7.74 (d, J = 49.2 Hz, 1H), 7.56-7.44 (m, 1H), 7.35-7.22 (m, 6H), 5.56 (dd, J = 143.6, 4.0 Hz, 1H), 4.06-3.65 (m, 2H), 3.57-3.35 (m, 1H), 3.33-3.31 (m, 1H), 2.50-2.38 (m, 1H), 2.27-2.07 (m, 1H), 2.03-1.95 (m, 1H), 1.92-1.76 (m, 1H), 1.58 (d, J = 13.2 Hz, 1H). |
| 4503 | $^1$H NMR (400 MHz, DMSO-$d_6$) δ 11.90 (d, J = 21.6 Hz, 1H), 7.74 (d, J = 49.2 Hz, 1H), 7.56-7.44 (m, 1H), 7.35-7.22 (m, 6H), 5.56 (dd, J = 143.6, 4.0 Hz, 1H), 4.06-3.65 (m, 2H), 3.57-3.35 (m, 1H), 3.33-3.31 (m, 1H), 2.50-2.38 (m, 1H), 2.27-2.07 (m, 1H), 2.03-1.95 (m, 1H), 1.92-1.76 (m, 1H), 1.58 (d, J = 13.2 Hz, 1H). |

TABLE 2

| Cmpd No. | Structure |
|---|---|
| 138 | 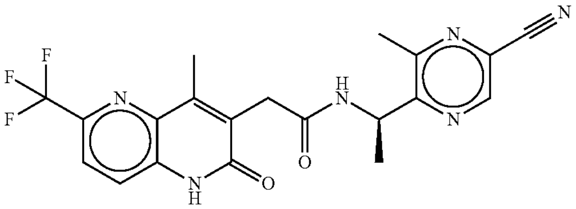 |
| 139 | 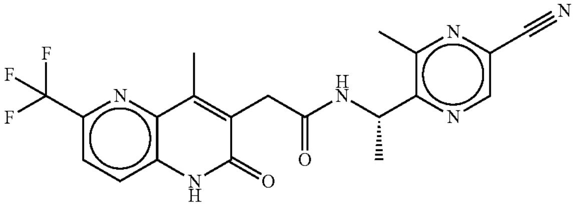 |

TABLE 2-continued
| Cmpd No. | Structure |
| --- | --- |
| 140 | 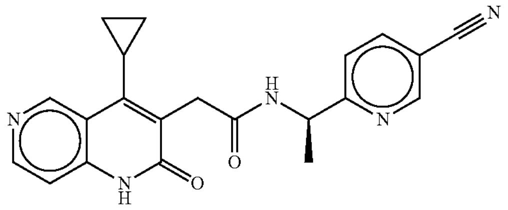 |
| 141 | 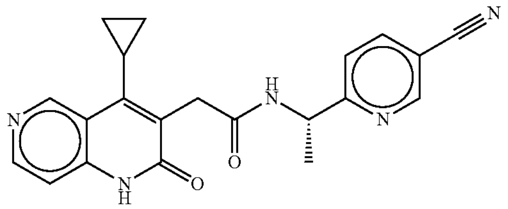 |
| 142 | 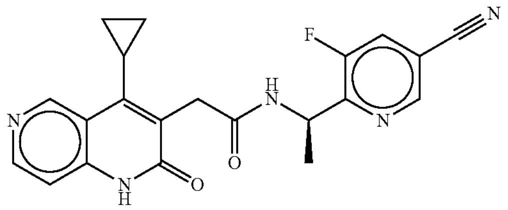 |
| 143 | 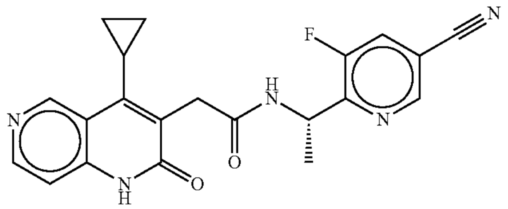 |
| 144 | 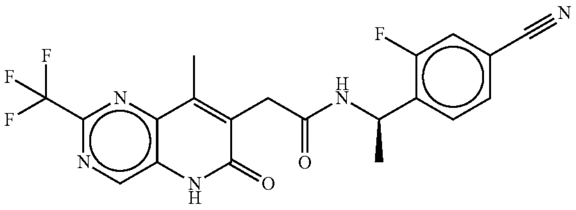 |
| 145 | 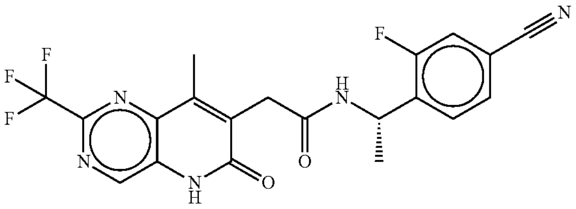 |
| 146 | 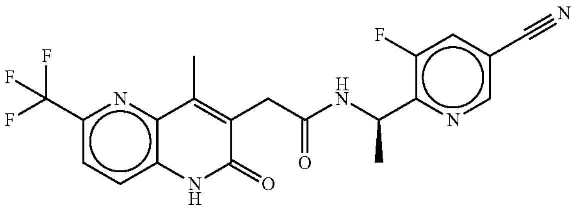 |

TABLE 2-continued
| Cmpd No. | Structure |
| --- | --- |
| 147 | 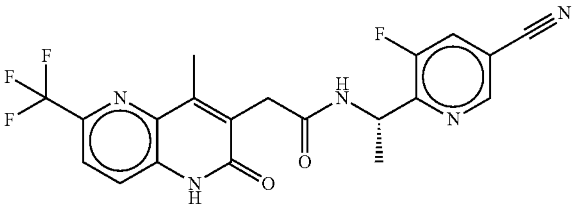 |
| 148 | 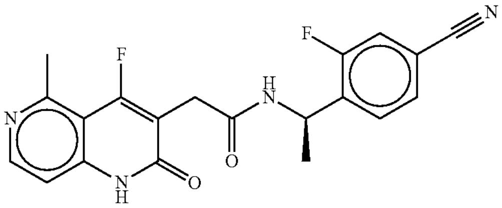 |
| 149 | 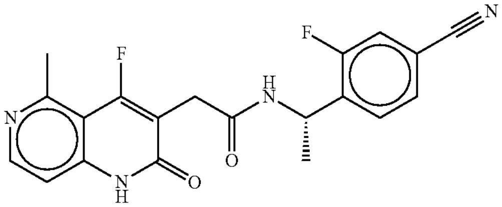 |
| 150 | 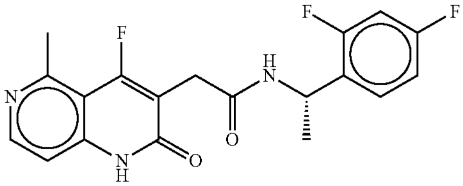 |
| 151 | 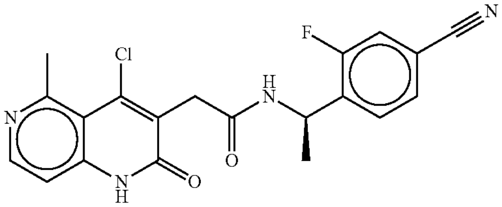 |
| 152 | 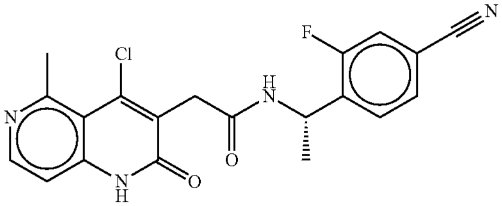 |
| 153 | 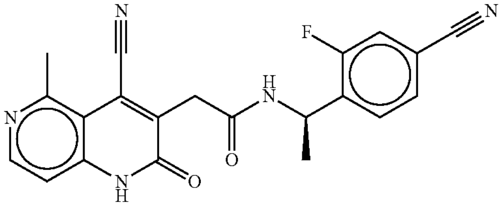 |

TABLE 2-continued
| Cmpd No. | Structure |
| --- | --- |
| 154 | 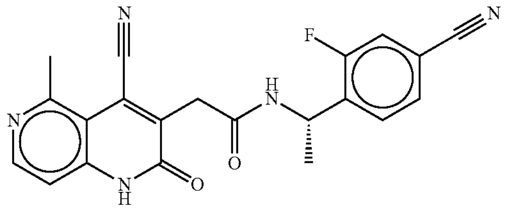 |
| 155 | 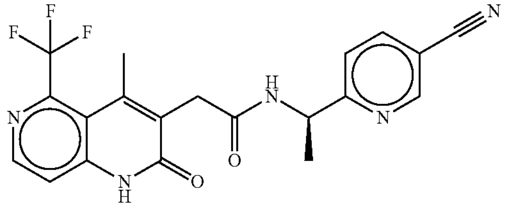 |
| 156 | 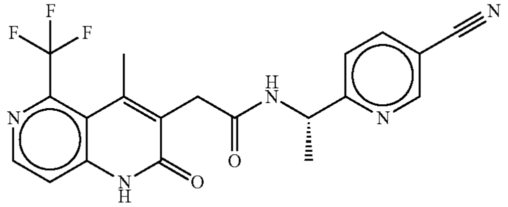 |
| 157 | 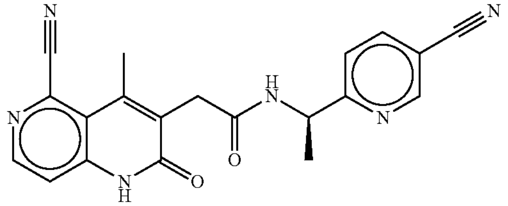 |
| 158 | 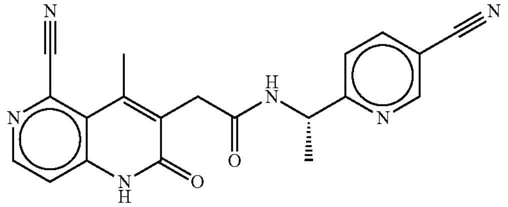 |
| 159 | 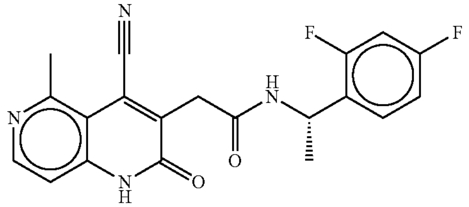 |
| 160 | 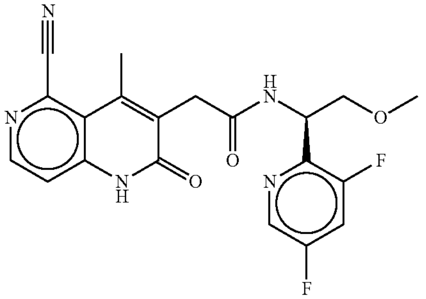 |

TABLE 2-continued
| Cmpd No. | Structure |
| --- | --- |
| 161 | 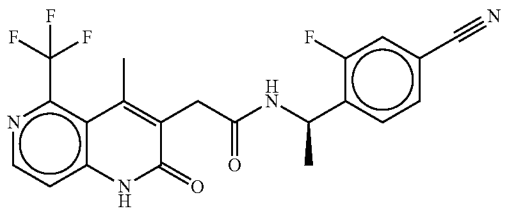 |
| 162 | 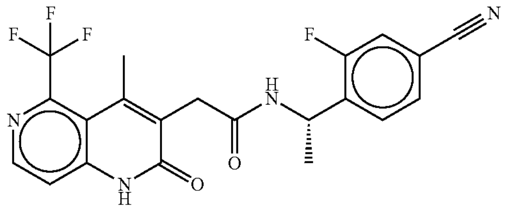 |
| 163 | 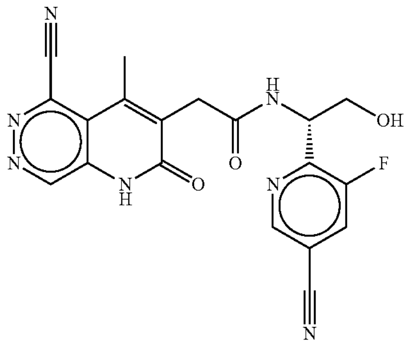 |
| 164 | 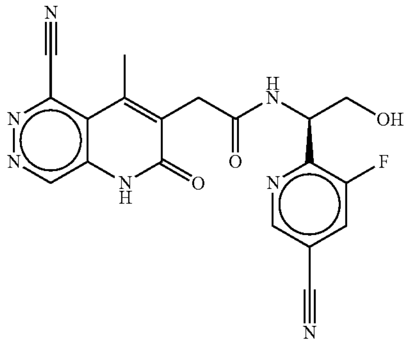 |
| 165 | 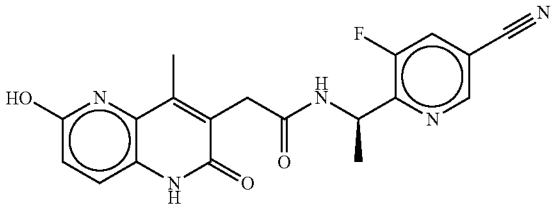 |
| 166 | 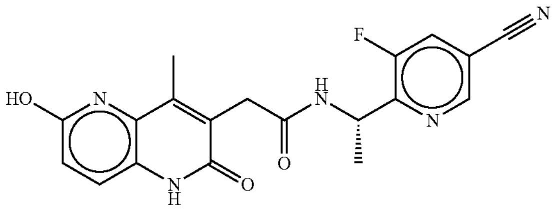 |

TABLE 2-continued
| Cmpd No. | Structure |
| --- | --- |
| 167 | 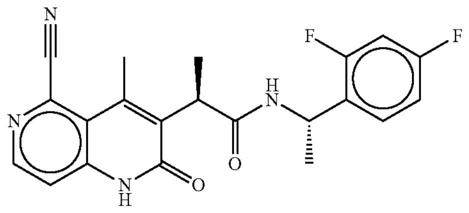 |
| 168 | 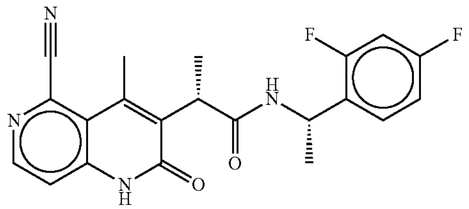 |
| 169 | 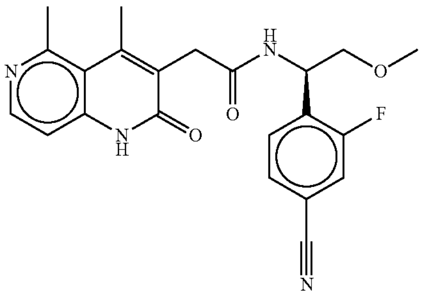 |
| 170 | 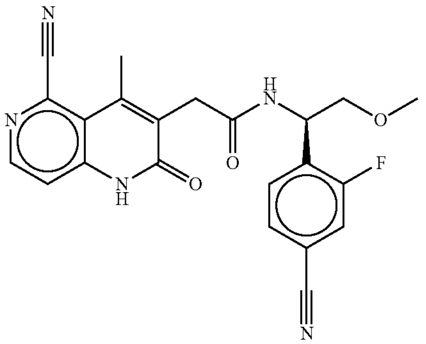 |
| 171 | 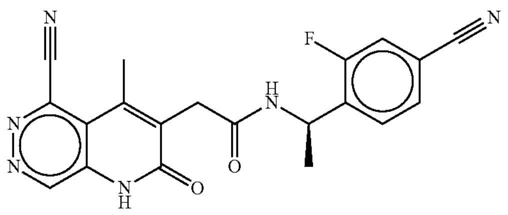 |
| 172 | 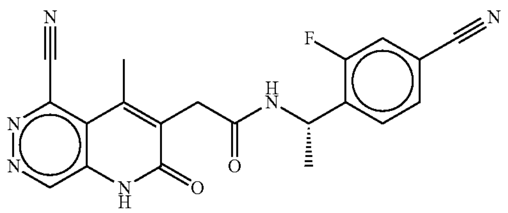 |

TABLE 2-continued
| Cmpd No. | Structure |
| --- | --- |
| 173 | 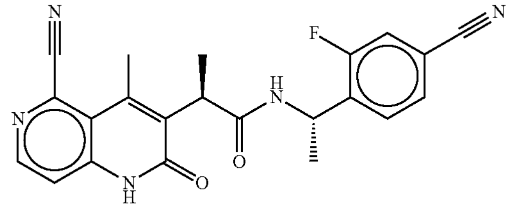 |
| 174 | 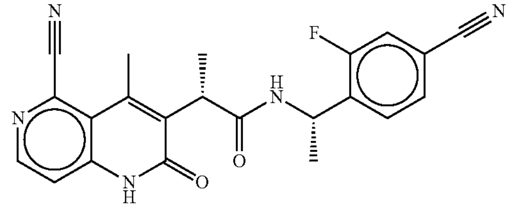 |
| 175 | 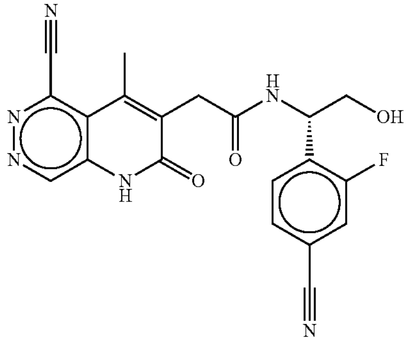 |
| 176 | 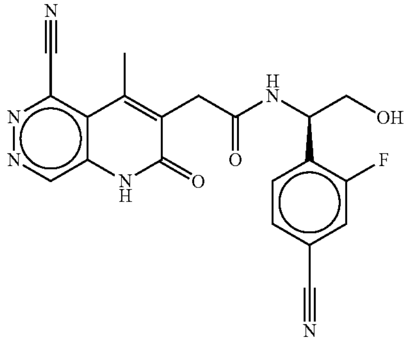 |
| 177 | 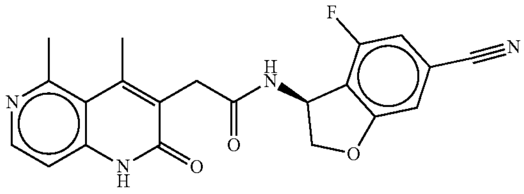 |
| 178 | 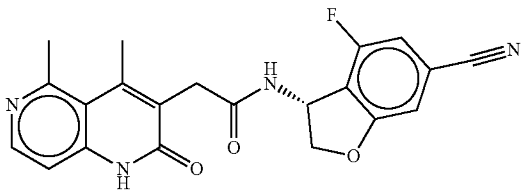 |

TABLE 2-continued
| Cmpd No. | Structure |
|---|---|
| 179 | 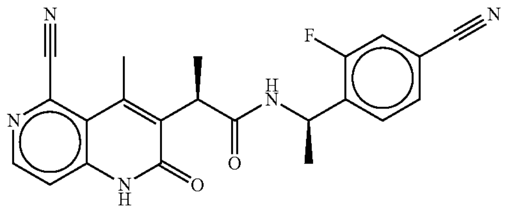 |
| 180 | 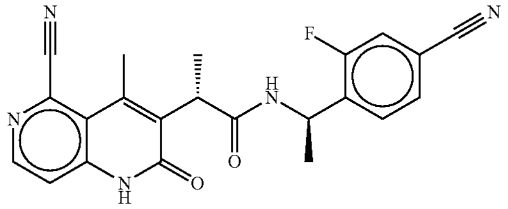 |
| 181 | 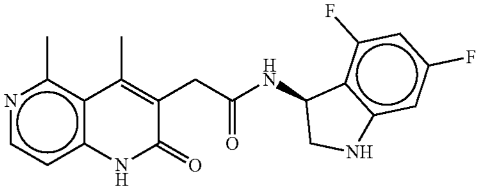 |
| 182 | 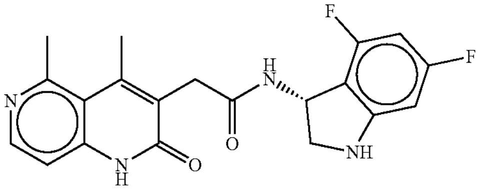 |
| 183 | 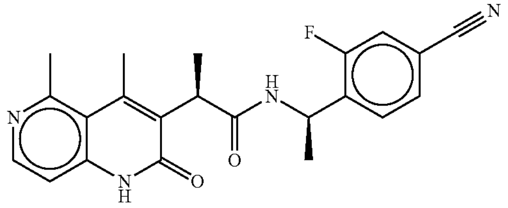 |
| 184 | 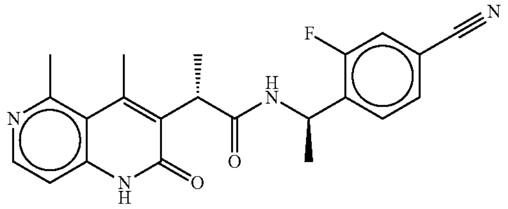 |
| 185 | 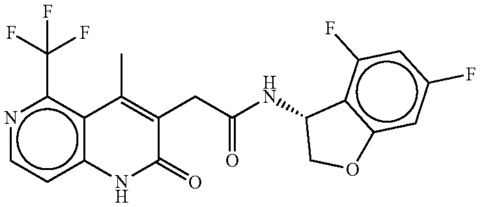 |

TABLE 2-continued
| Cmpd No. | Structure |
| --- | --- |
| 186 | 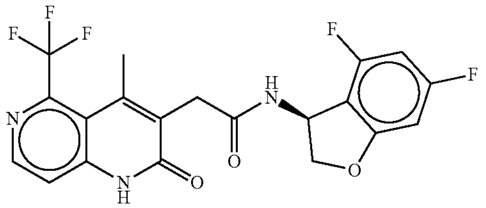 |
| 187 | 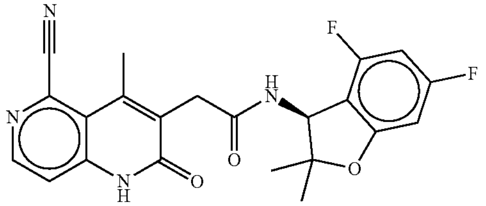 |
| 188 | 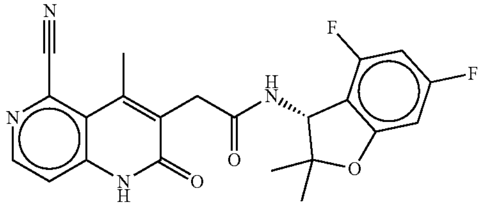 |
| 189 | 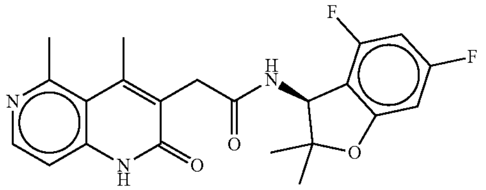 |
| 190 | 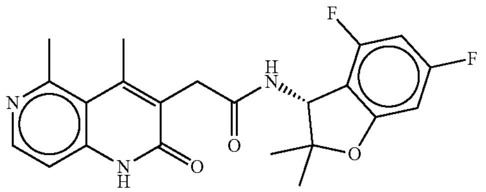 |
| 191 | 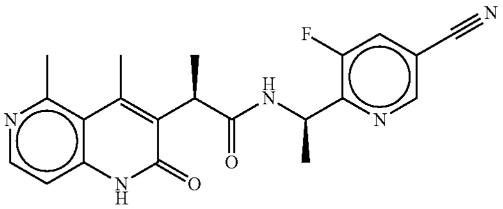 |
| 192 | 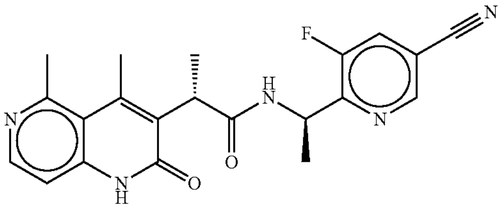 |

TABLE 2-continued
| Cmpd No. | Structure |
|---|---|
| 193 | 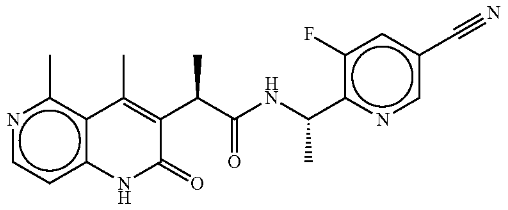 |
| 194 | 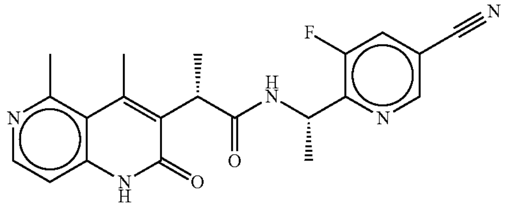 |
| 195 | 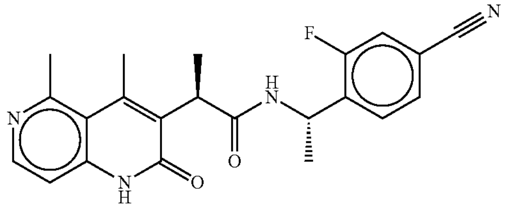 |
| 196 | 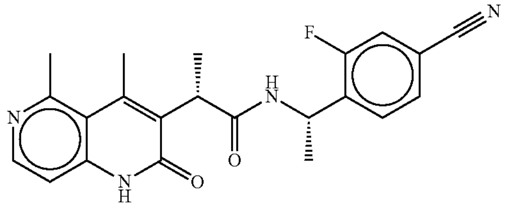 |
| 197 | 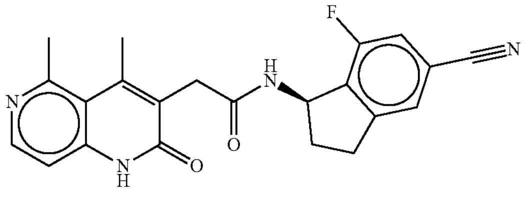 |
| 198 | 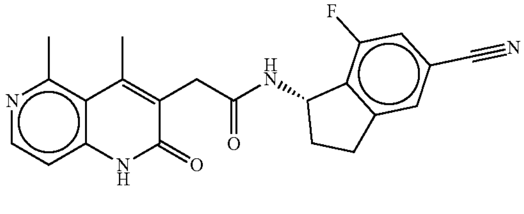 |
| 199 | 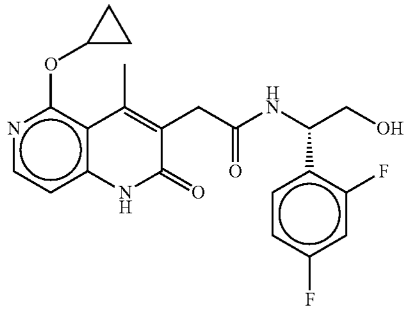 |

TABLE 2-continued
| Cmpd No. | Structure |
|---|---|
| 200 | 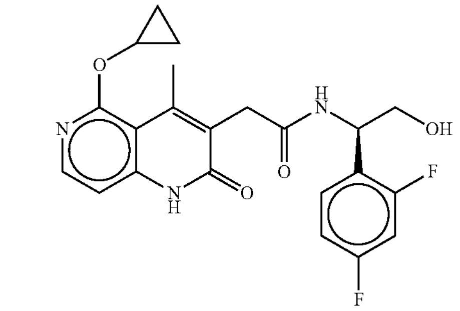 |
| 201 | 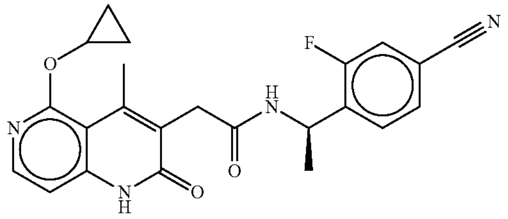 |
| 202 | 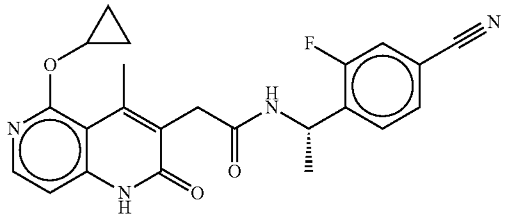 |
| 203 | 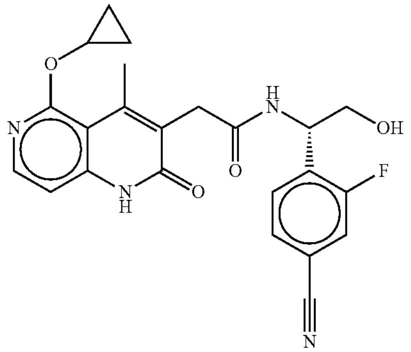 |
| 204 | 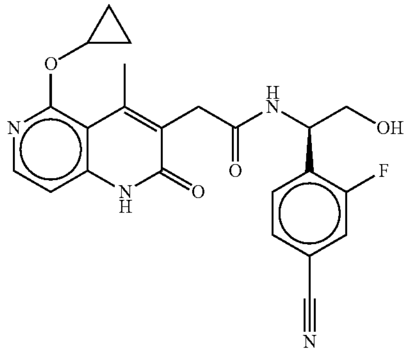 |

TABLE 2-continued
| Cmpd No. | Structure |
| --- | --- |
| 205 | 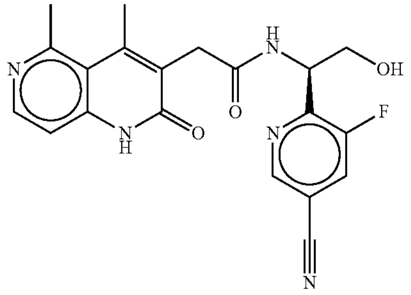 |
| 206 | 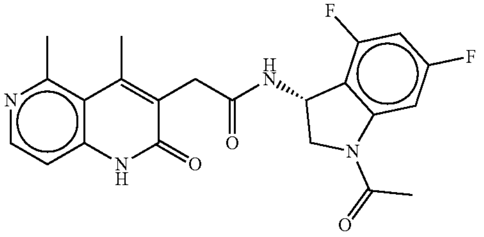 |
| 207 | 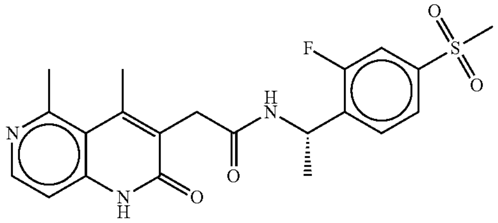 |
| 208 | 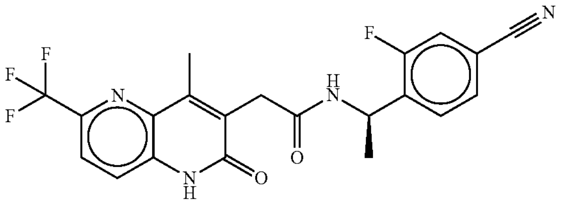 |
| 209 | 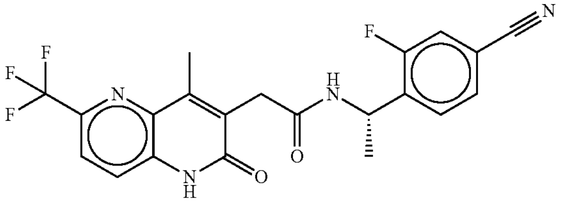 |
| 210 | 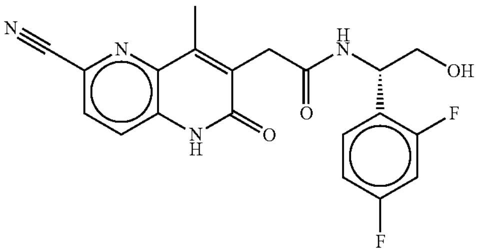 |

TABLE 2-continued
| Cmpd No. | Structure |
|---|---|
| 211 | 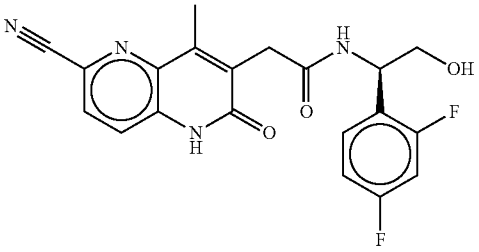 |
| 212 | 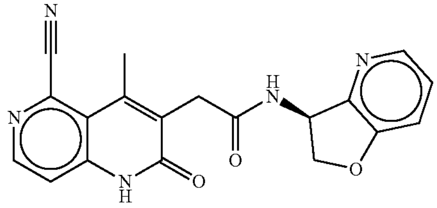 |
| 213 | 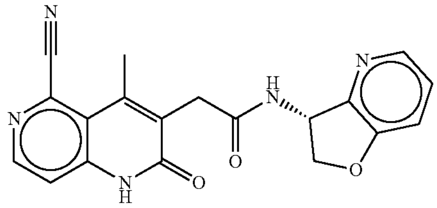 |
| 214 | 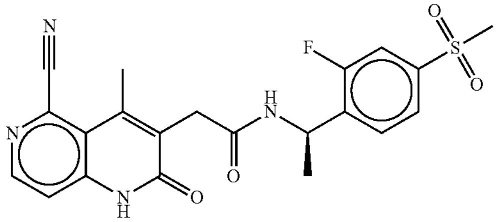 |
| 215 | 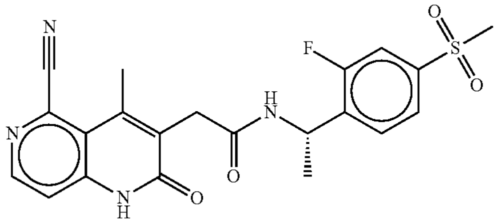 |
| 216 | 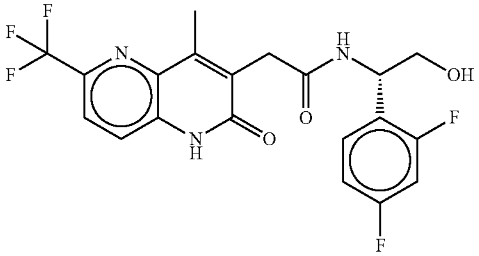 |

TABLE 2-continued
| Cmpd No. | Structure |
| --- | --- |
| 217 | 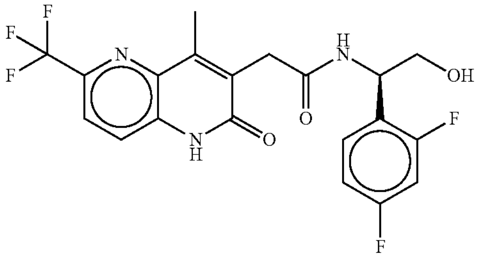 |
| 218 | 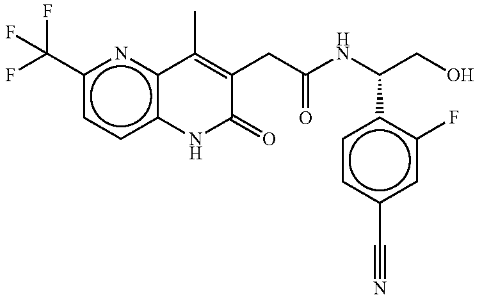 |
| 219 | 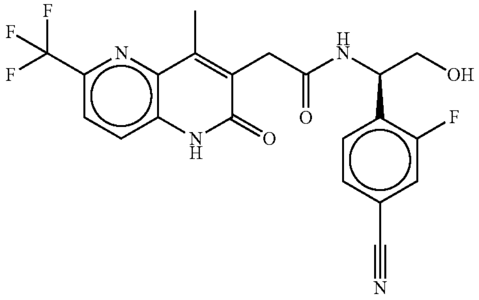 |
| 220 | 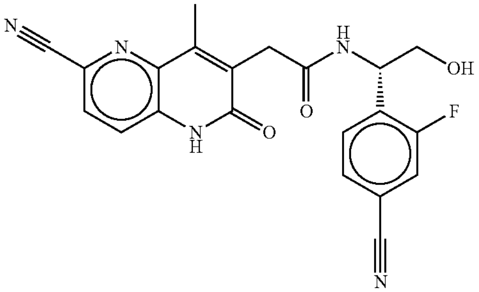 |
| 221 | 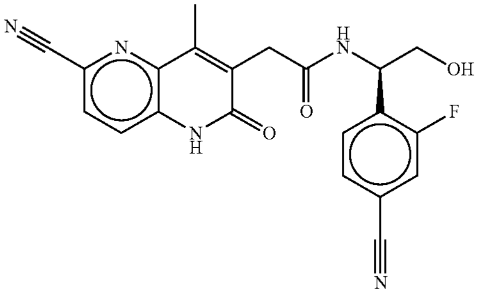 |

TABLE 2-continued
| Cmpd No. | Structure |
| --- | --- |
| 222 | 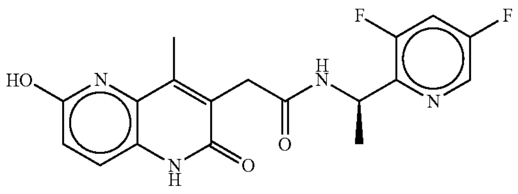 |
| 223 | 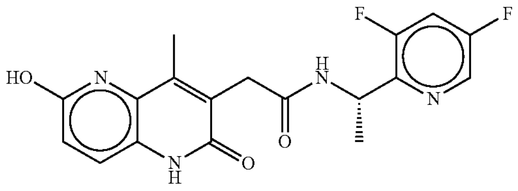 |
| 224 | 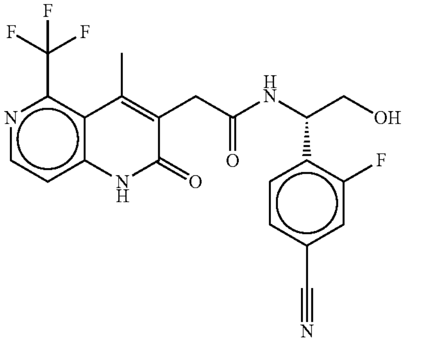 |
| 225 | 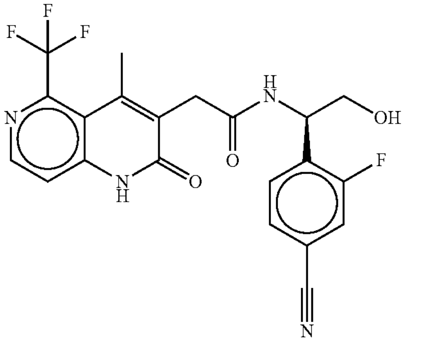 |
| 226 | 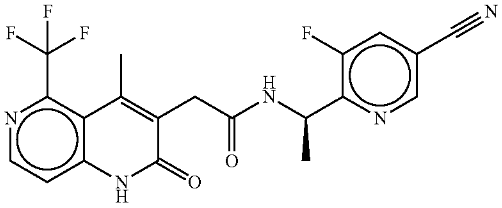 |
| 227 | 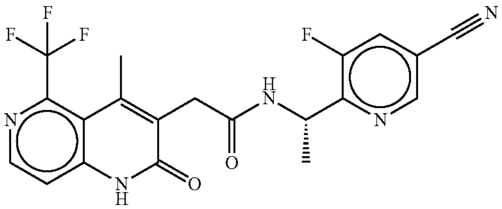 |

TABLE 2-continued
| Cmpd No. | Structure |
| --- | --- |
| 228 | 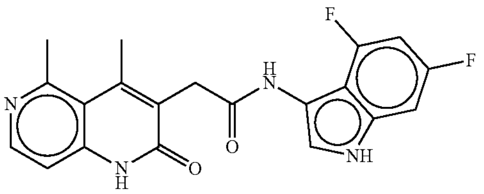 |
| 229 | 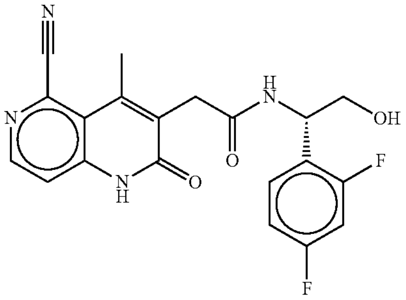 |
| 230 | 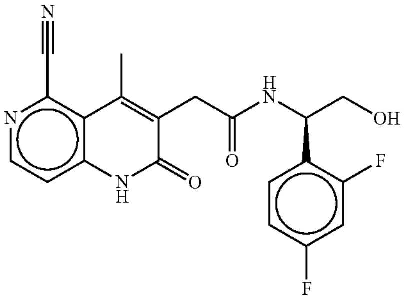 |
| 231 | 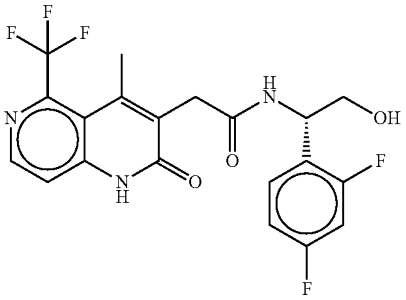 |
| 232 | 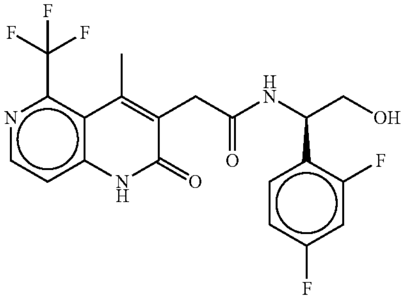 |
| 233 | 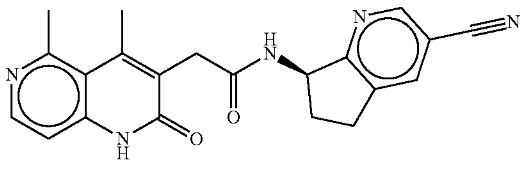 |

TABLE 2-continued
| Cmpd No. | Structure |
|---|---|
| 234 | 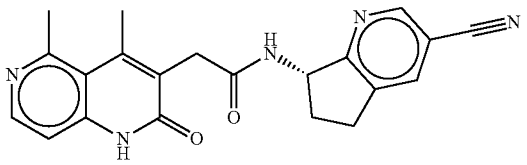 |
| 235 | 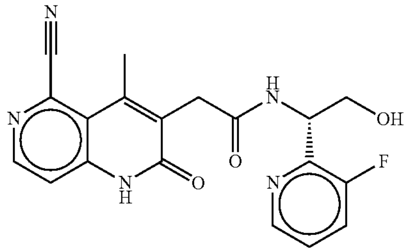 |
| 236 | 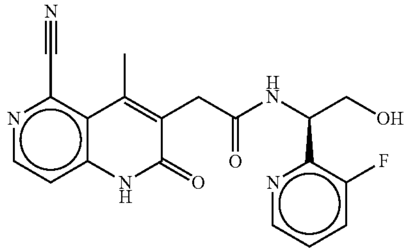 |
| 237 | 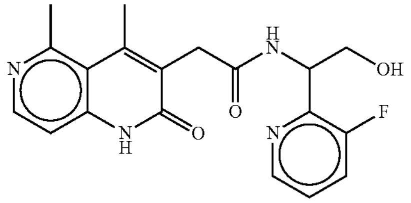 |
| 238 | 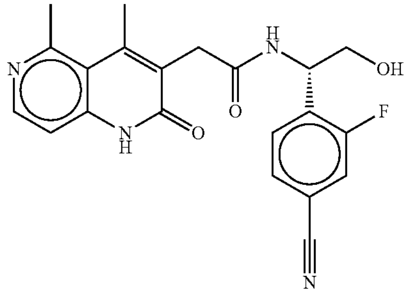 |
| 239 | 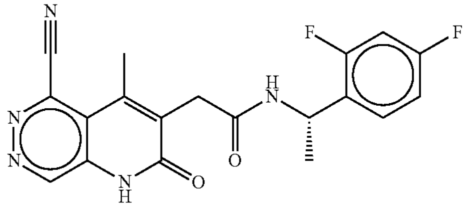 |

TABLE 2-continued
| Cmpd No. | Structure |
|---|---|
| 240 | 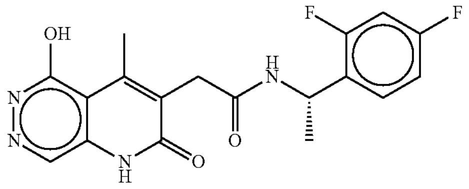 |
| 241 | 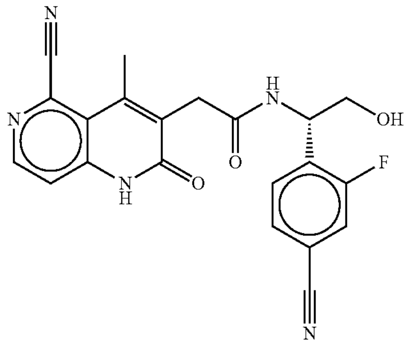 |
| 242 | 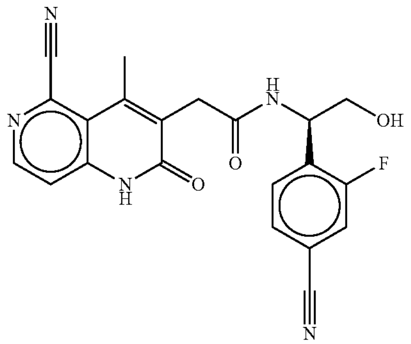 |
| 243 | 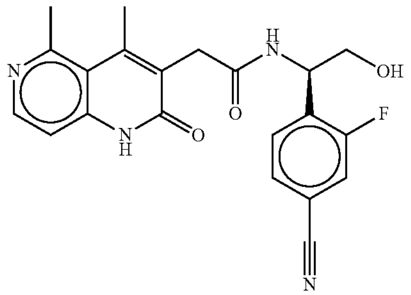 |
| 244 | 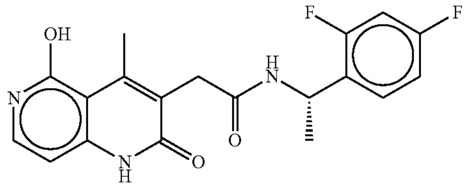 |

TABLE 2-continued
| Cmpd No. | Structure |
| --- | --- |
| 245 | 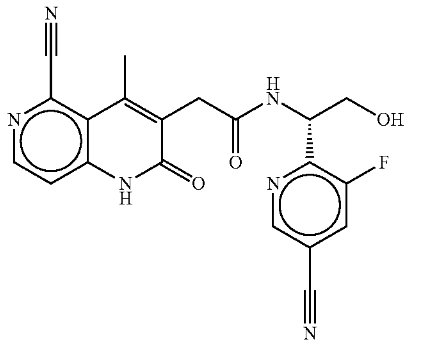 |
| 246 | 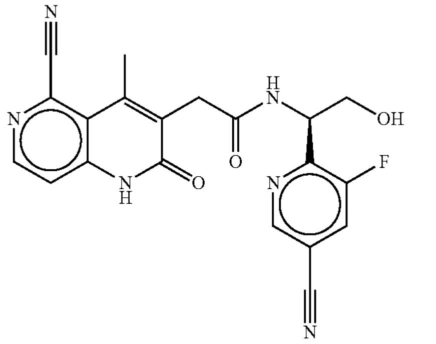 |
| 247 | 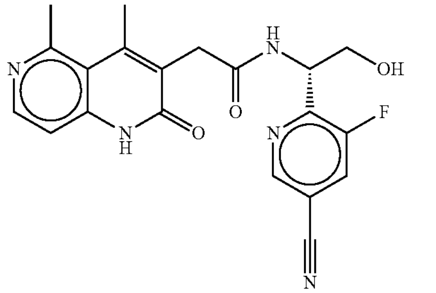 |
| 248 | 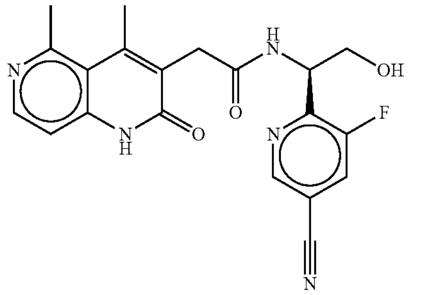 |
| 249 | 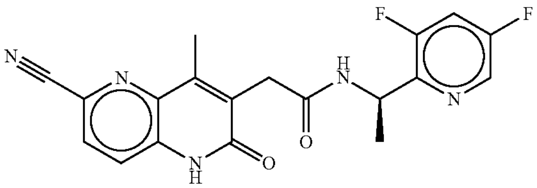 |

TABLE 2-continued
| Cmpd No. | Structure |
| --- | --- |
| 250 | 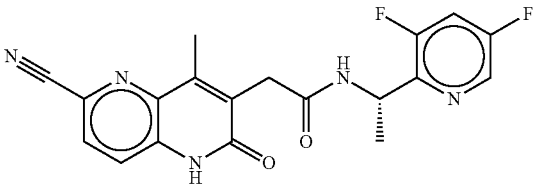 |
| 251 | 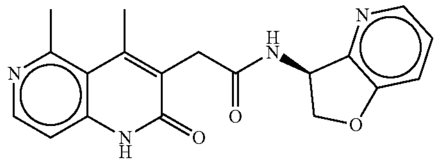 |
| 252 | 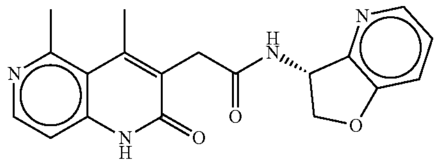 |
| 253 | 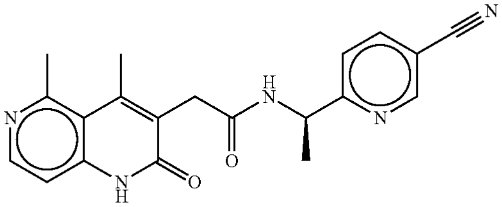 |
| 254 | 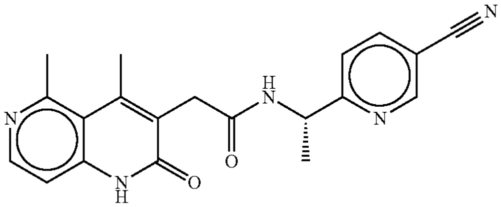 |
| 255 | 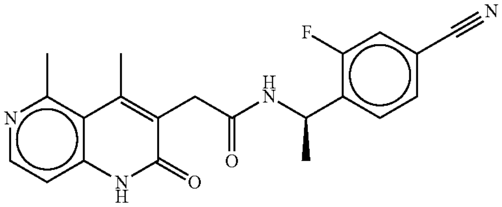 |
| 256 | 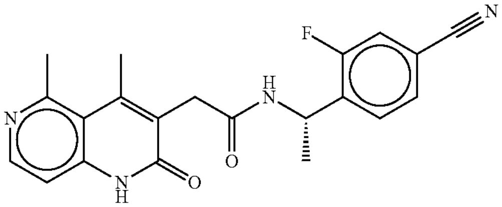 |
| 257 | 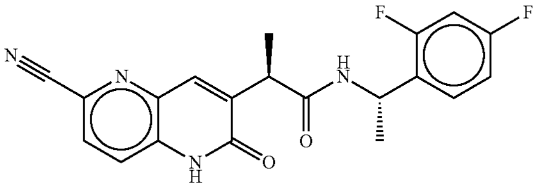 |

TABLE 2-continued
| Cmpd No. | Structure |
| --- | --- |
| 258 | 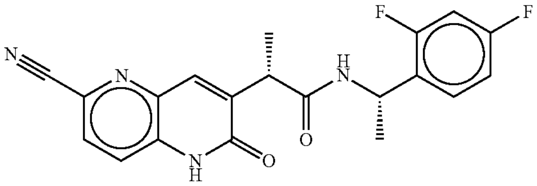 |
| 259 | 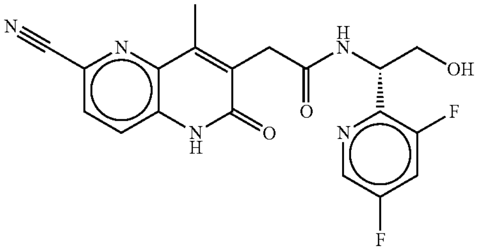 |
| 260 | 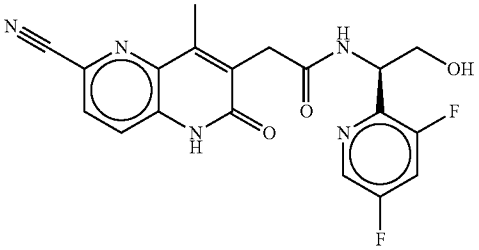 |
| 261 | 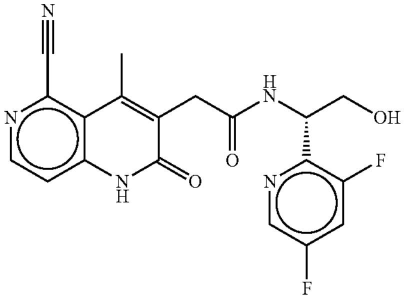 |
| 262 | 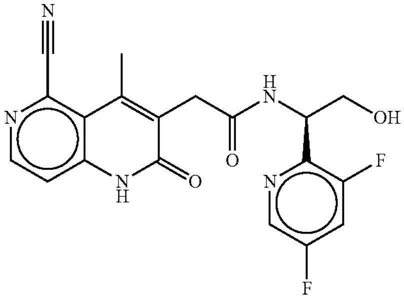 |

TABLE 2-continued
| Cmpd No. | Structure |
|---|---|
| 263 | 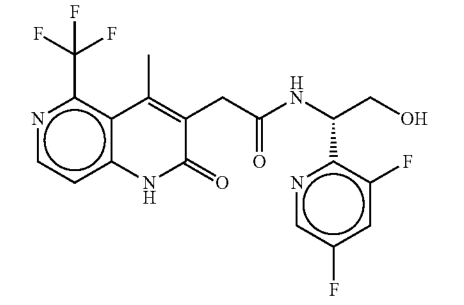 |
| 264 | 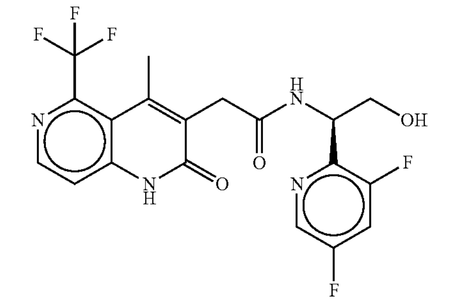 |
| 265 | 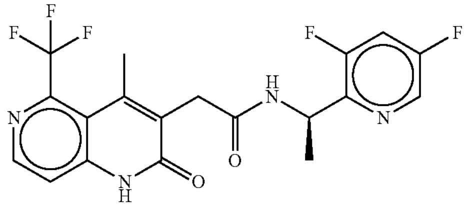 |
| 266 | 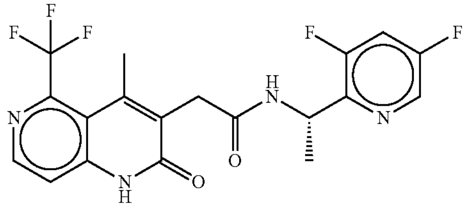 |
| 267 | 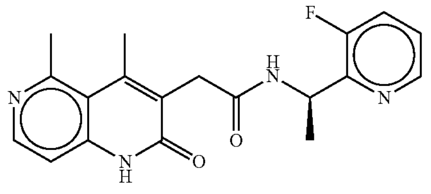 |
| 268 | 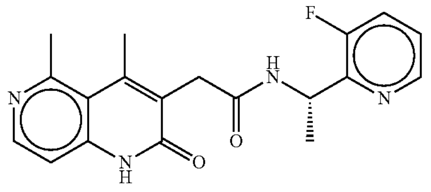 |

TABLE 2-continued
| Cmpd No. | Structure |
| --- | --- |
| 269 | 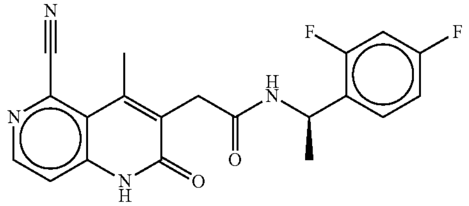 |
| 270 | 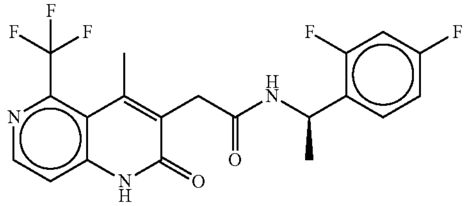 |
| 271 | 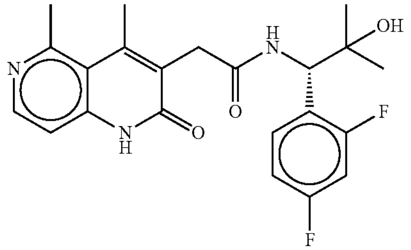 |
| 272 | 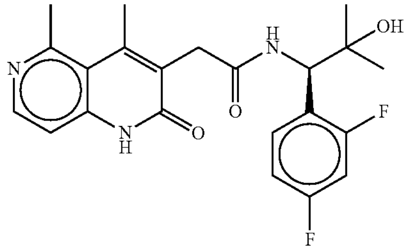 |
| 273 | 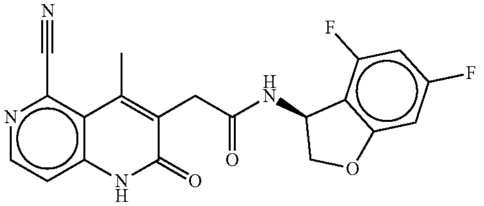 |
| 274 | 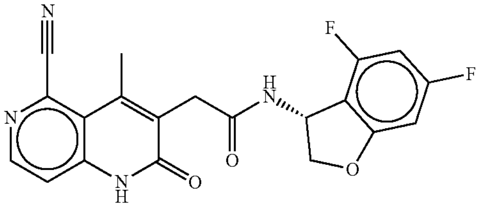 |

TABLE 2-continued
| Cmpd No. | Structure |
|---|---|
| 275 | 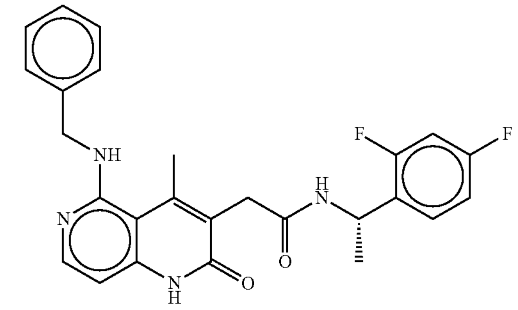 |
| 276 | 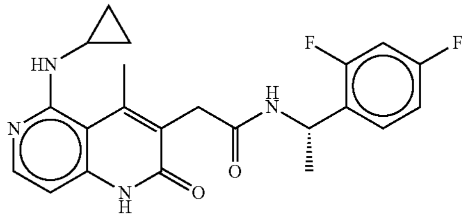 |
| 277 | 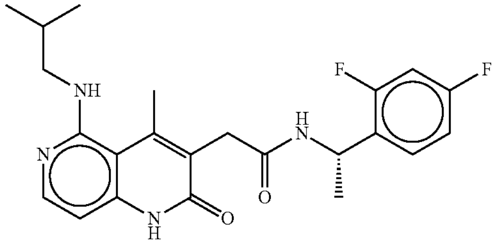 |
| 278 | 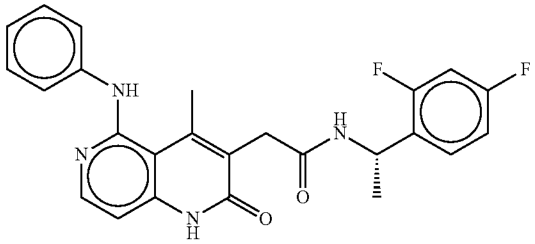 |
| 279 | 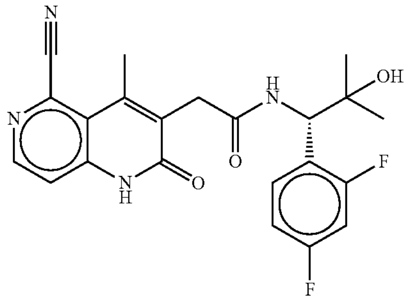 |

TABLE 2-continued
| Cmpd No. | Structure |
| --- | --- |
| 280 | 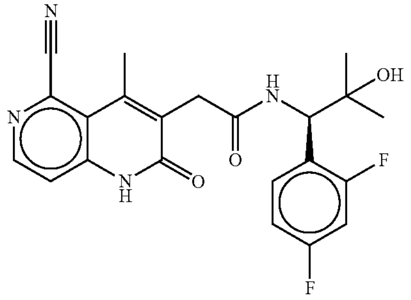 |
| 281 | 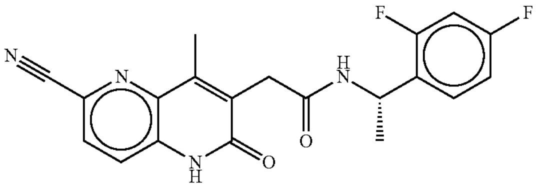 |
| 282 | 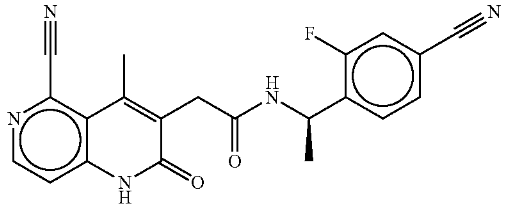 |
| 283 | 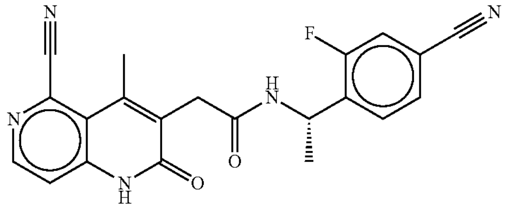 |
| 284 | 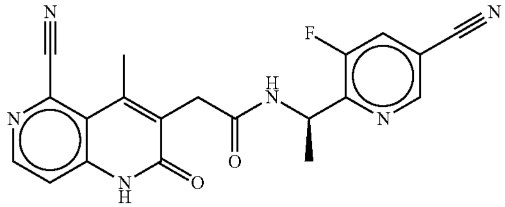 |
| 285 | 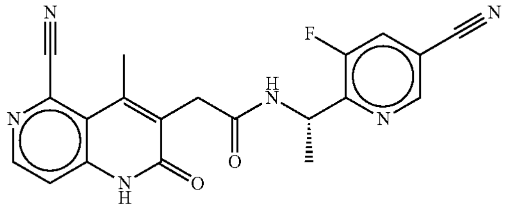 |
| 286 | 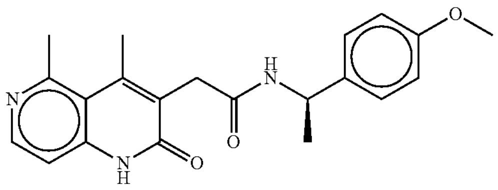 |

TABLE 2-continued
| Cmpd No. | Structure |
| --- | --- |
| 287 | 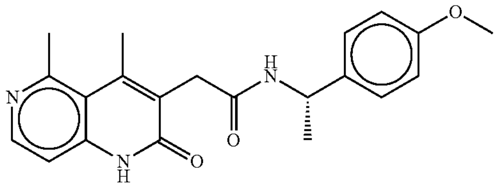 |
| 288 | 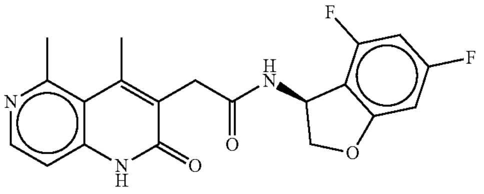 |
| 289 | 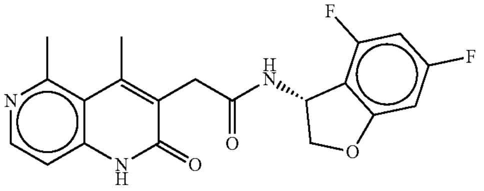 |
| 290 | 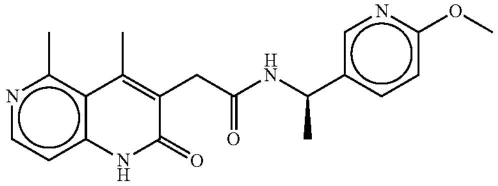 |
| 291 | 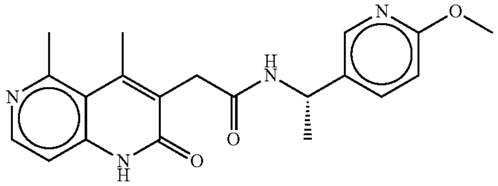 |
| 292 | 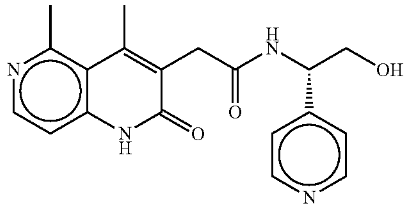 |
| 293 | 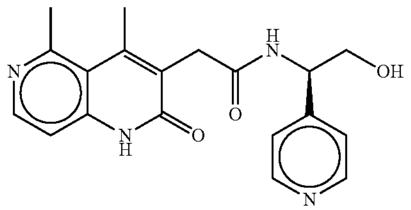 |

TABLE 2-continued
| Cmpd No. | Structure |
|---|---|
| 294 | 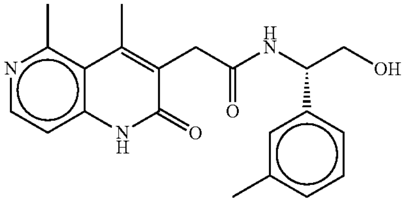 |
| 295 | 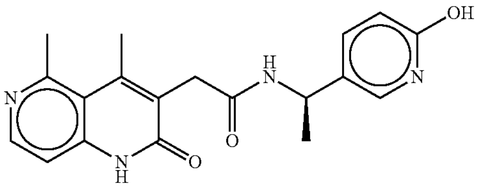 |
| 296 | 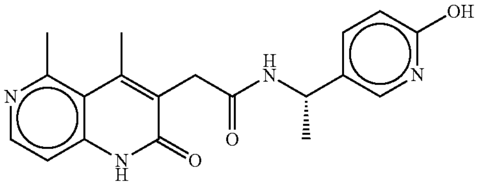 |
| 297 | 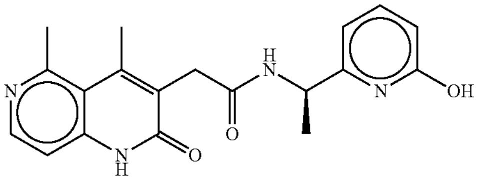 |
| 298 | 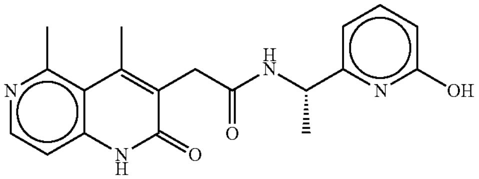 |
| 299 | 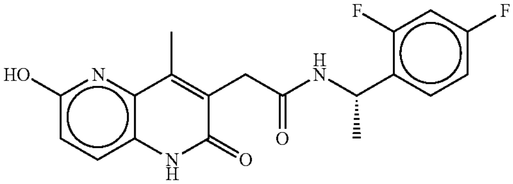 |
| 300 | 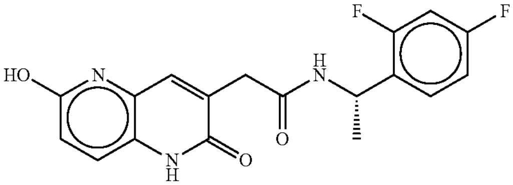 |
| 301 | 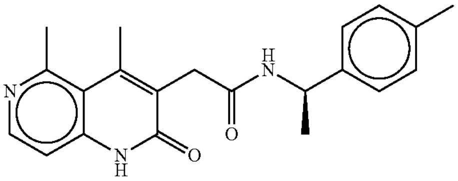 |

TABLE 2-continued
| Cmpd No. | Structure |
|---|---|
| 302 | 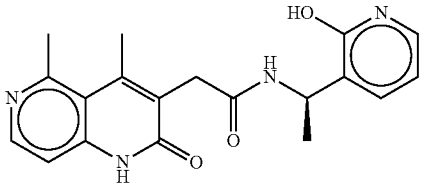 |
| 303 | 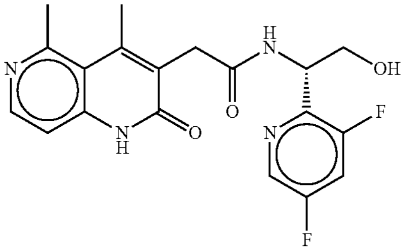 |
| 304 | 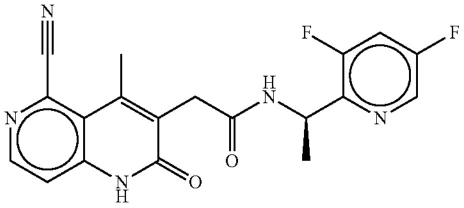 |
| 305 | 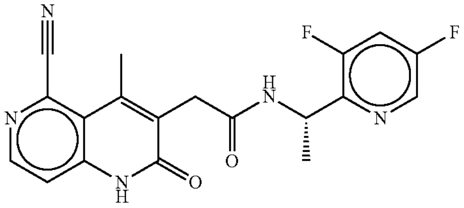 |
| 306 | 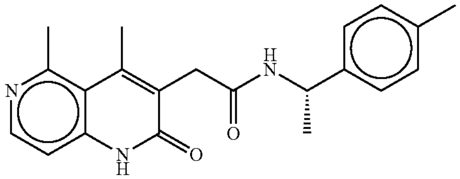 |
| 307 | 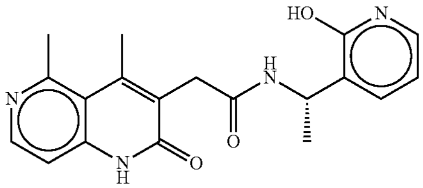 |
| 308 | 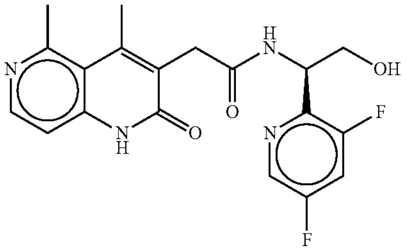 |

TABLE 2-continued
| Cmpd No. | Structure |
| --- | --- |
| 309 | 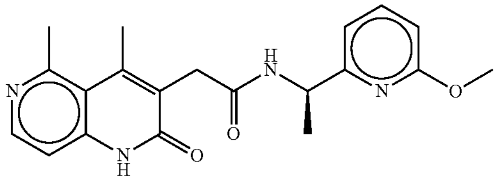 |
| 310 | 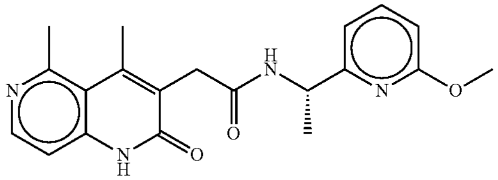 |
| 311 | 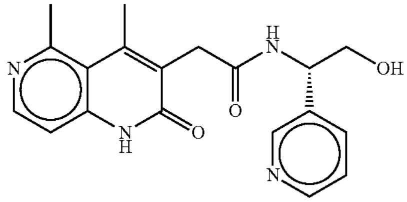 |
| 312 | 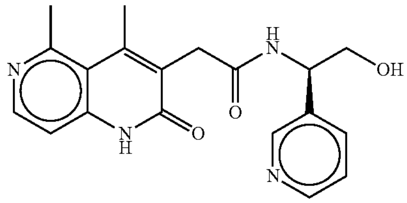 |
| 313 | 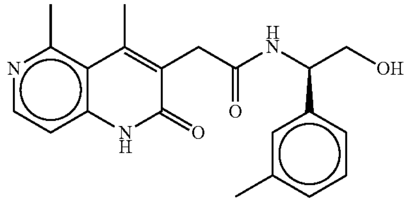 |
| 314 | 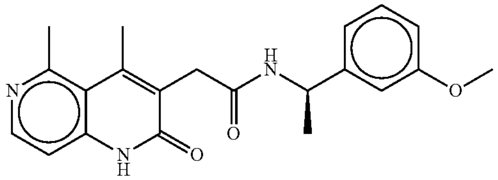 |
| 315 | 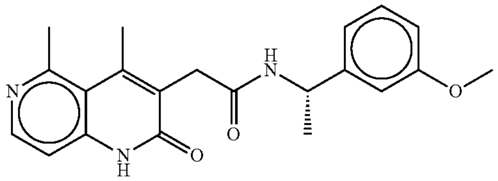 |
| 316 | 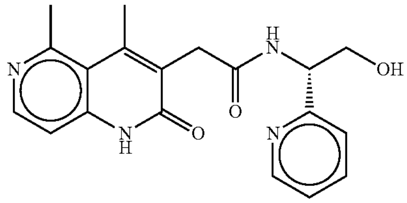 |

TABLE 2-continued
| Cmpd No. | Structure |
| --- | --- |
| 317 | 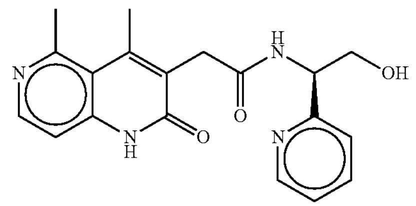 |
| 318 | 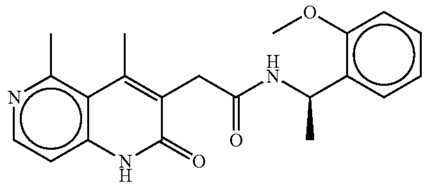 |
| 319 | 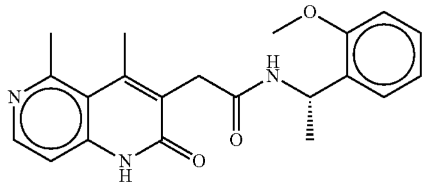 |
| 320 | 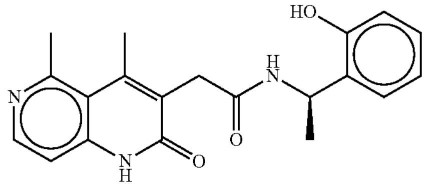 |
| 321 | 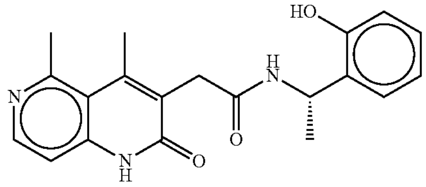 |
| 322 | 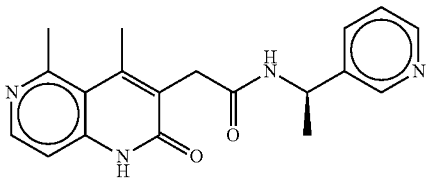 |
| 323 | 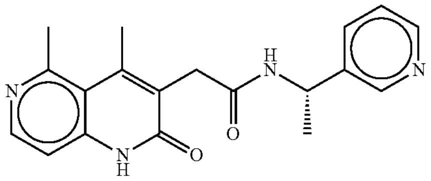 |
| 324 | 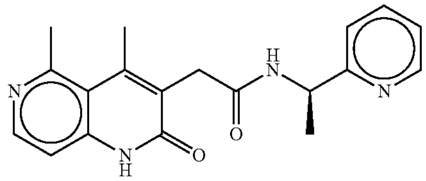 |

TABLE 2-continued
| Cmpd No. | Structure |
|---|---|
| 325 | 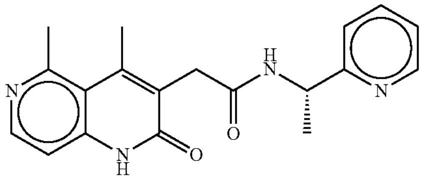 |
| 326 | 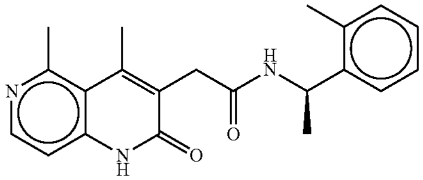 |
| 327 | 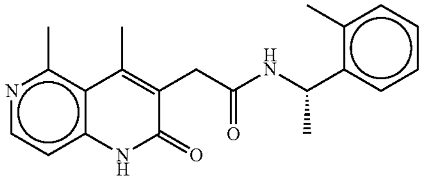 |
| 328 | 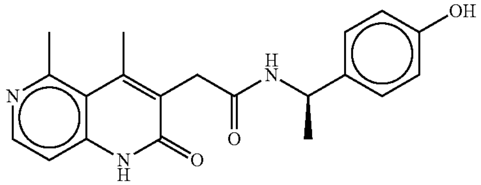 |
| 329 | 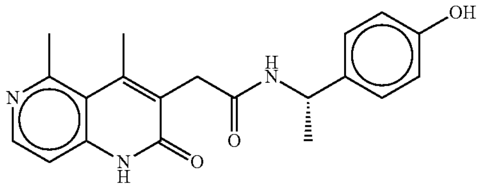 |
| 330 | 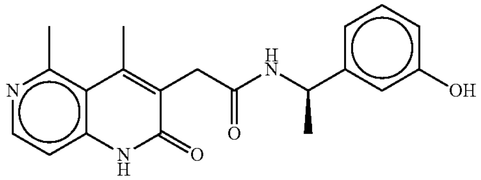 |
| 331 | 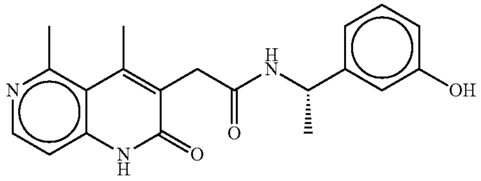 |
| 332 | 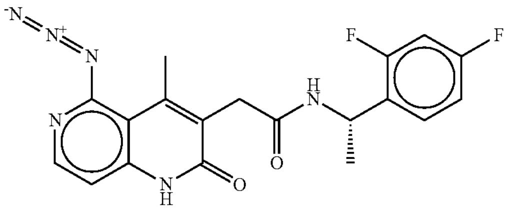 |

TABLE 2-continued
| Cmpd No. | Structure |
| --- | --- |
| 333 | 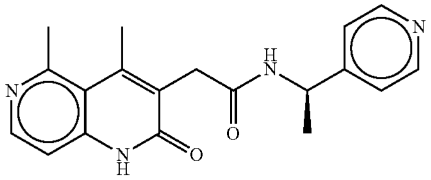 |
| 334 | 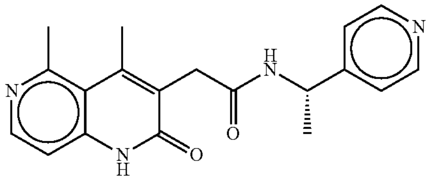 |
| 335 | 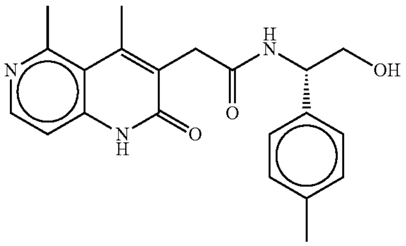 |
| 336 | 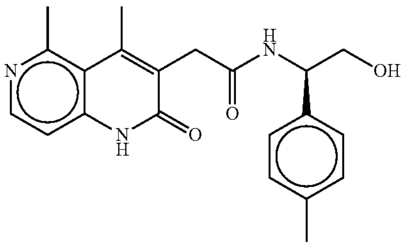 |
| 337 | 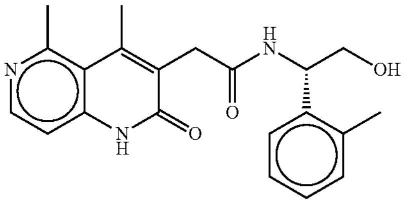 |
| 338 | 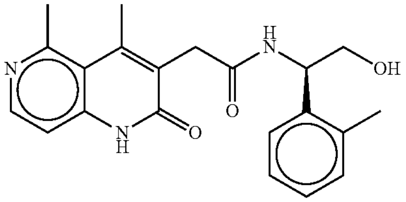 |
| 339 | 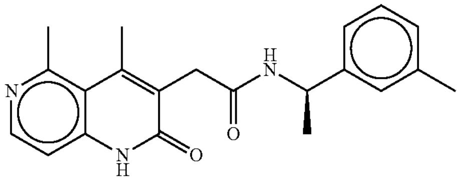 |

TABLE 2-continued
| Cmpd No. | Structure |
|---|---|
| 340 | 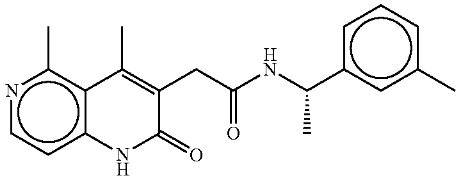 |
| 341 | 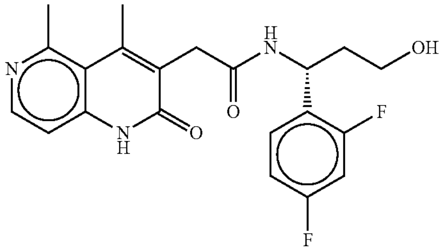 |
| 342 | 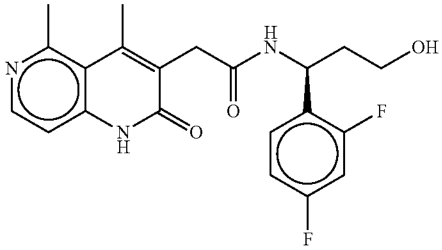 |
| 343 | 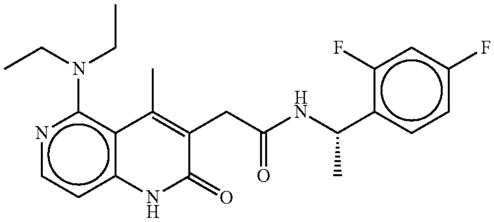 |
| 344 | 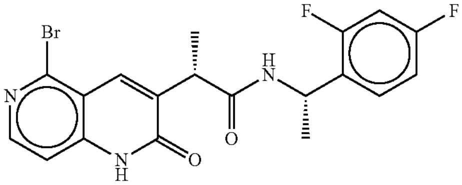 |
| 345 | 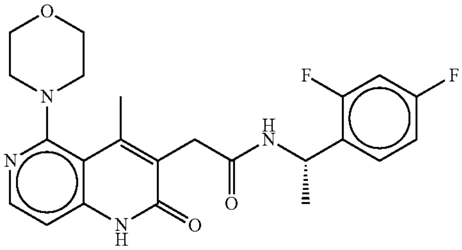 |

TABLE 2-continued
| Cmpd No. | Structure |
|---|---|
| 346 | 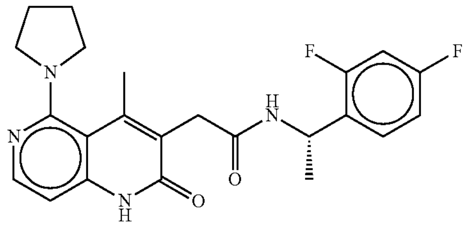 |
| 347 | 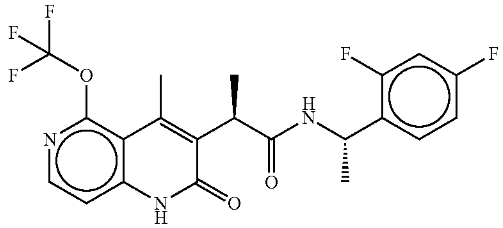 |
| 348 | 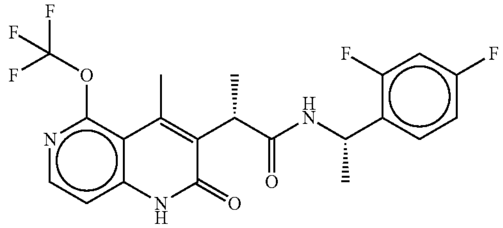 |
| 349 | 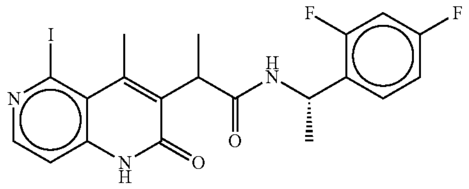 |
| 350 | 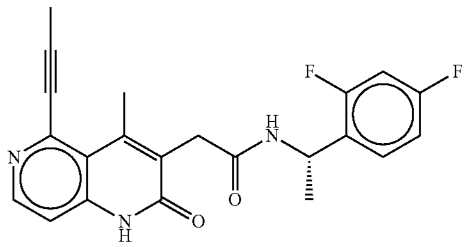 |
| 351 | 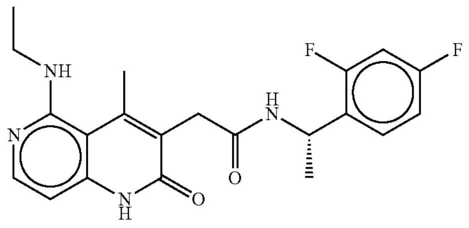 |
| 352 | 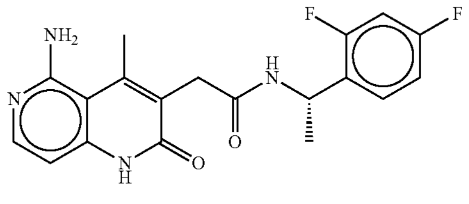 |

TABLE 2-continued
| Cmpd No. | Structure |
| --- | --- |
| 353 | 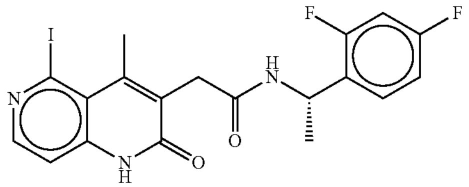 |
| 354 | 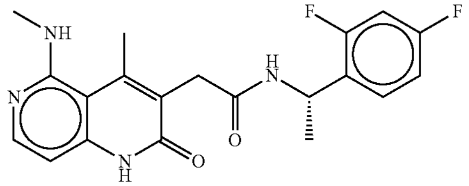 |
| 355 | 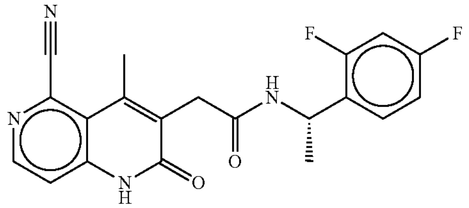 |
| 356 | 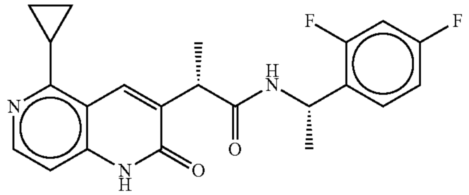 |
| 357 | 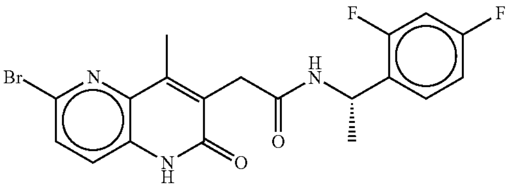 |
| 358 | 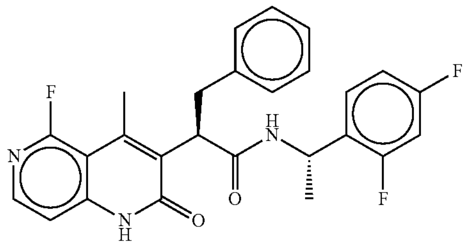 |
| 359 | 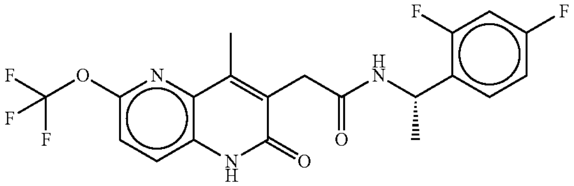 |

TABLE 2-continued
| Cmpd No. | Structure |
|---|---|
| 360 | 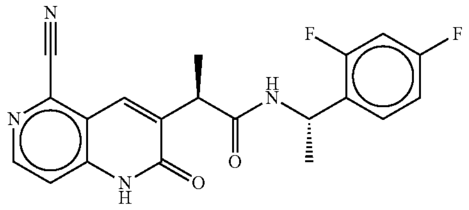 |
| 361 | 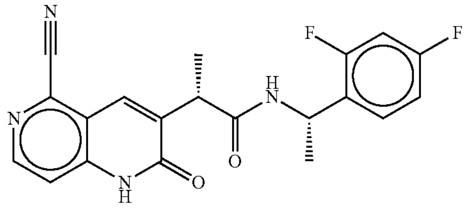 |
| 362 | 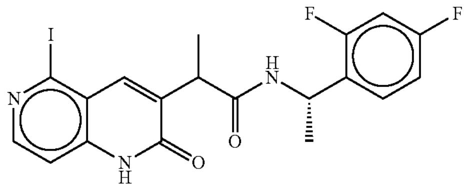 |
| 363 | 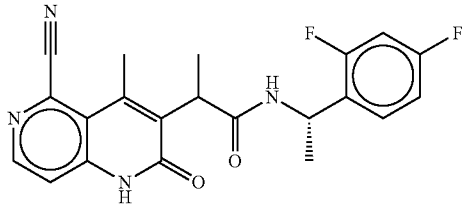 |
| 364 | 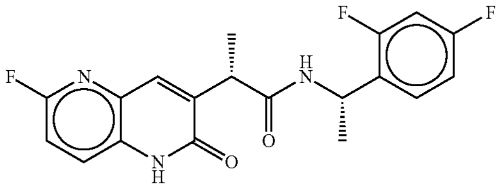 |
| 365 | 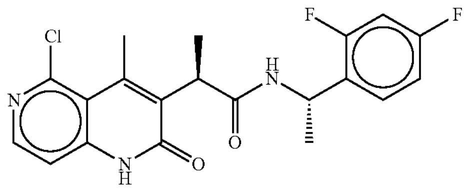 |
| 366 | 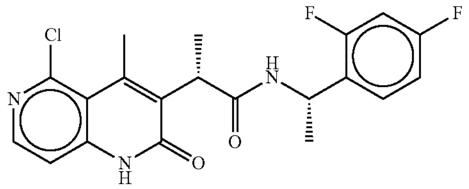 |

TABLE 2-continued
| Cmpd No. | Structure |
|---|---|
| 367 | 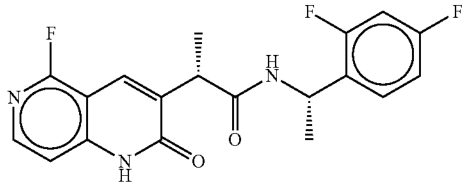 |
| 368 | 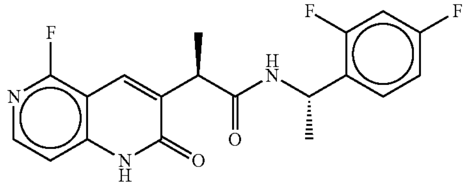 |
| 369 | 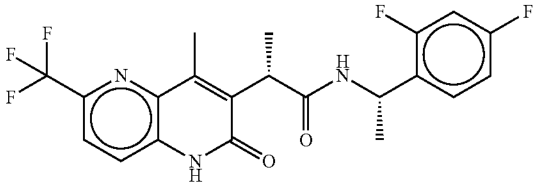 |
| 370 | 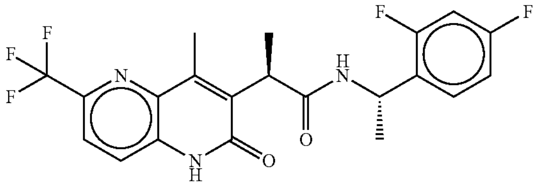 |
| 371 | 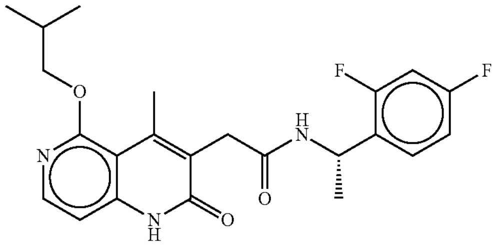 |
| 372 | 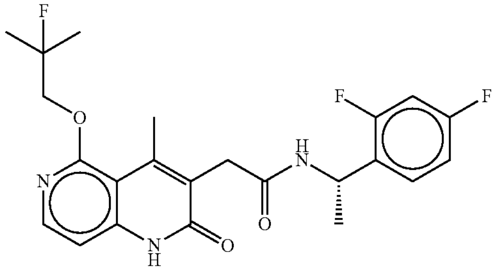 |
| 373 | 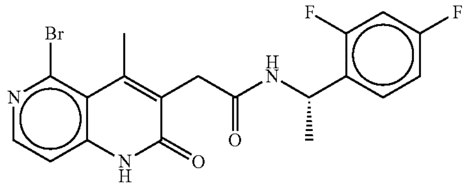 |

TABLE 2-continued
| Cmpd No. | Structure |
|---|---|
| 374 | 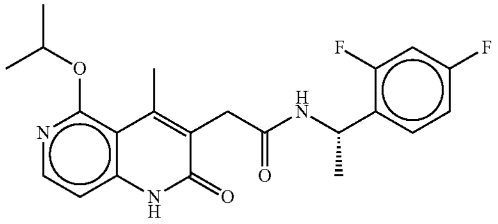 |
| 375 | 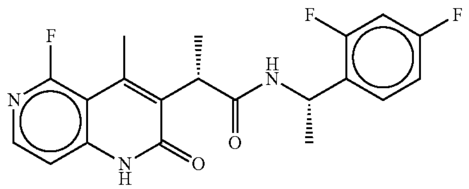 |
| 376 | 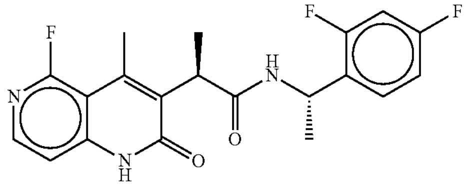 |
| 377 | 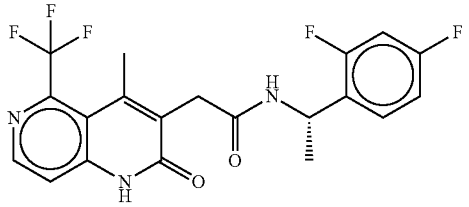 |
| 378 | 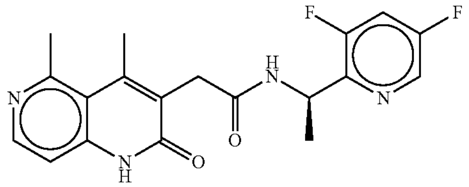 |
| 379 | 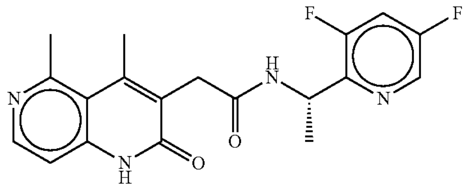 |
| 380 | 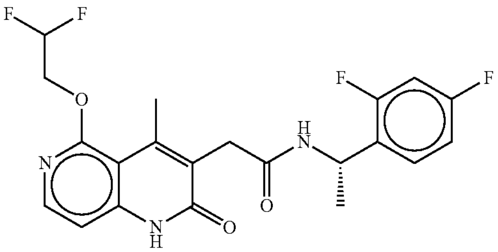 |

TABLE 2-continued
| Cmpd No. | Structure |
|---|---|
| 381 | 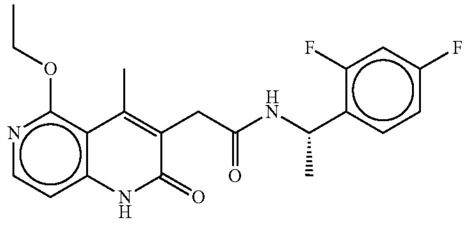 |
| 382 | 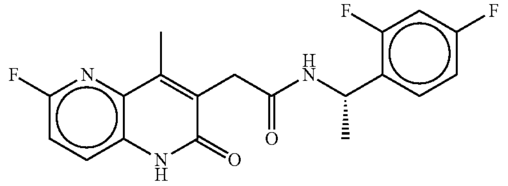 |
| 383 | 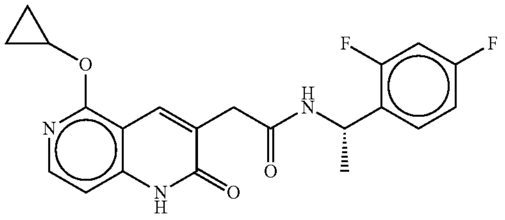 |
| 384 | 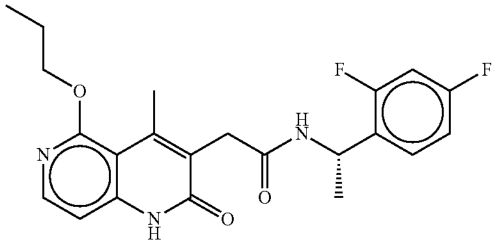 |
| 385 | 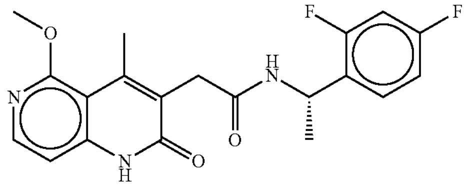 |
| 386 | 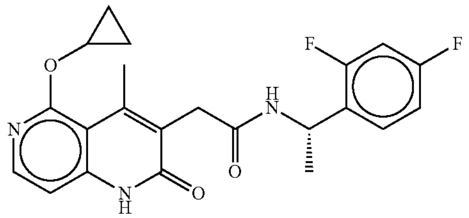 |
| 387 | 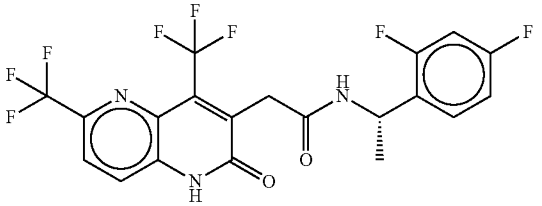 |

TABLE 2-continued
| Cmpd No. | Structure |
|---|---|
| 388 | 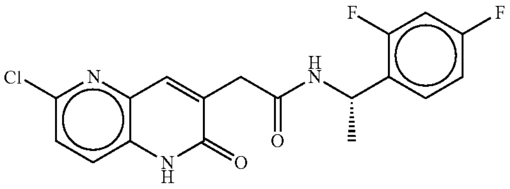 |
| 389 | 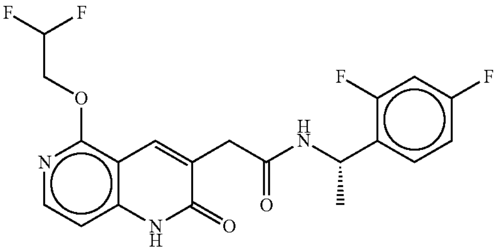 |
| 390 | 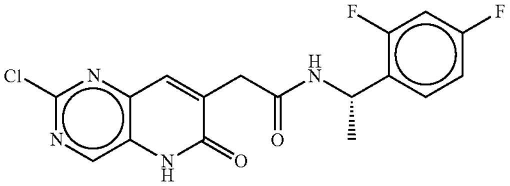 |
| 391 | 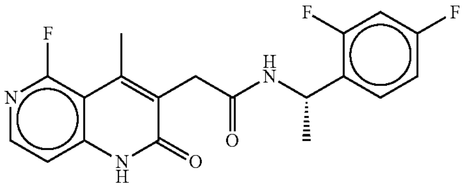 |
| 392 | 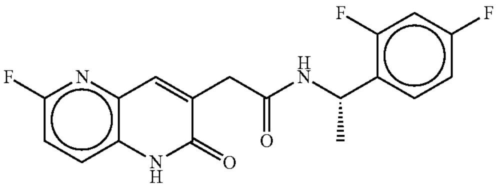 |
| 393 | 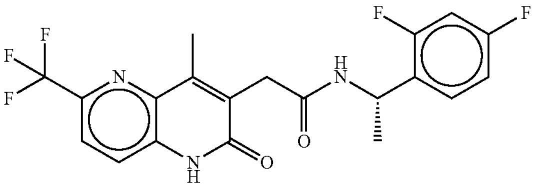 |
| 394 | 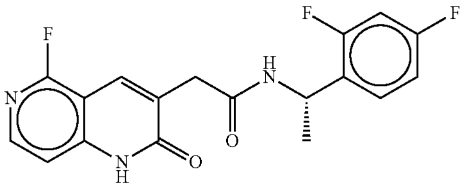 |

TABLE 2-continued
| Cmpd No. | Structure |
|---|---|
| 395 | 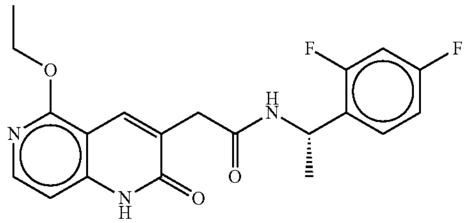 |
| 396 | 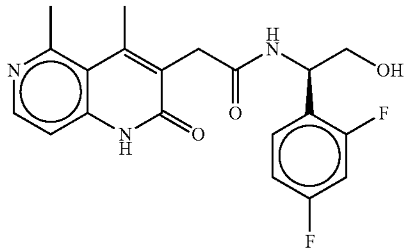 |
| 397 | 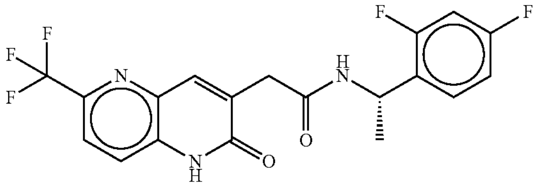 |
| 398 | 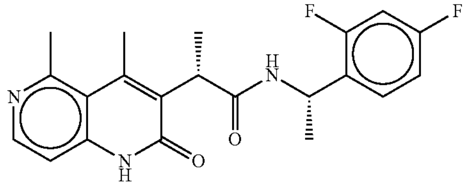 |
| 399 | 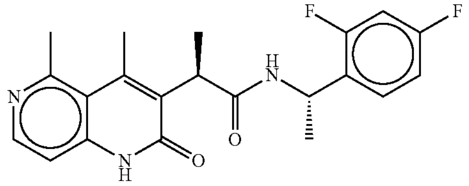 |
| 400 | 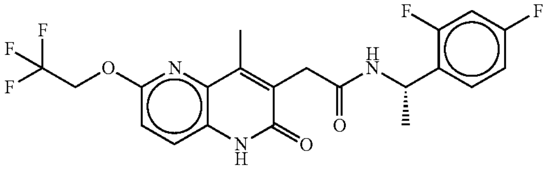 |
| 401 | 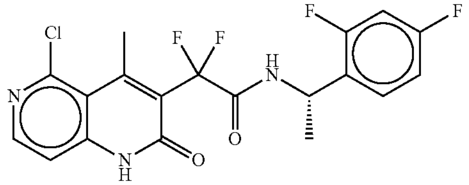 |

TABLE 2-continued
| Cmpd No. | Structure |
|---|---|
| 402 | 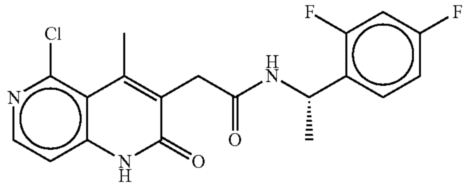 |
| 403 | 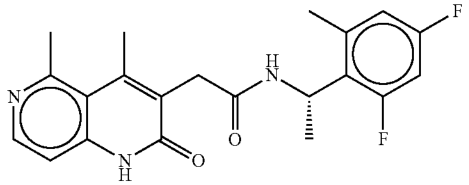 |
| 404 | 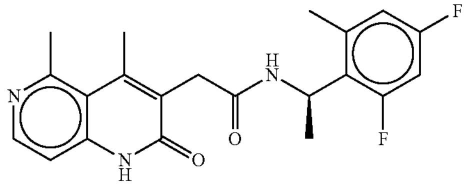 |
| 405 | 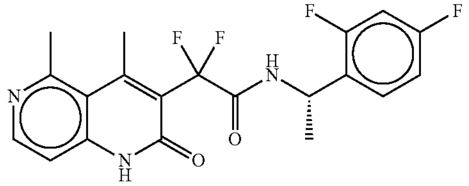 |
| 406 | 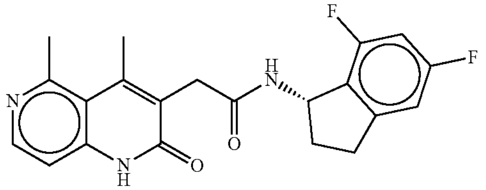 |
| 407 | 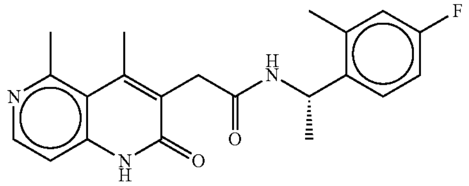 |
| 408 | 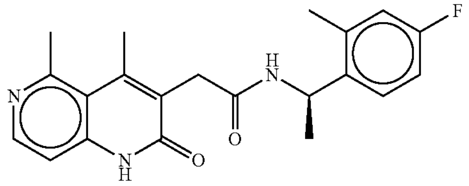 |
| 409 | 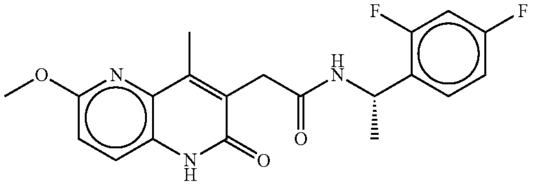 |

TABLE 2-continued
| Cmpd No. | Structure |
| --- | --- |
| 410 | 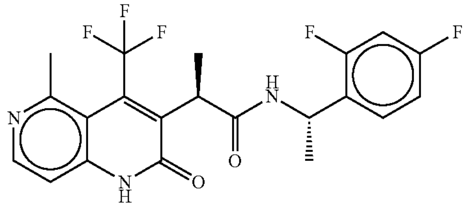 |
| 411 | 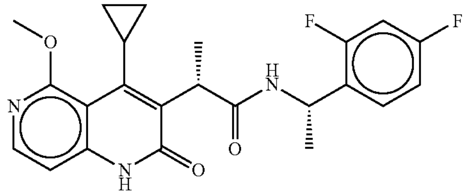 |
| 412 | 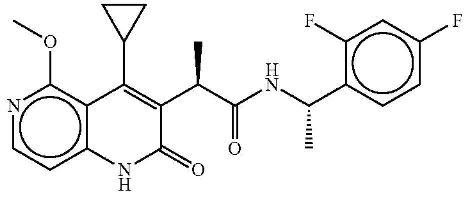 |
| 413 | 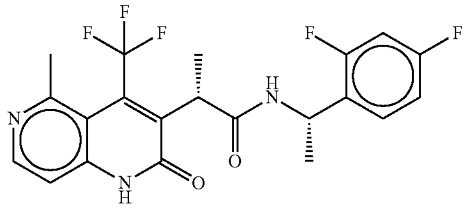 |
| 414 | 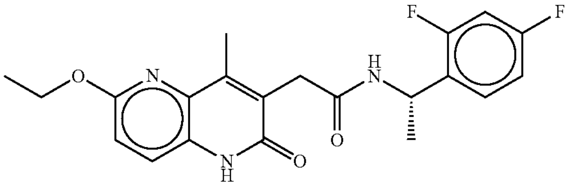 |
| 415 | 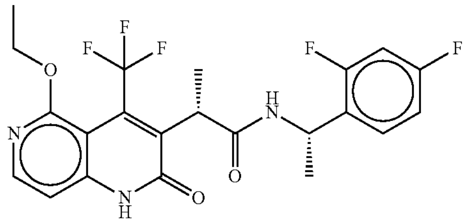 |
| 416 | 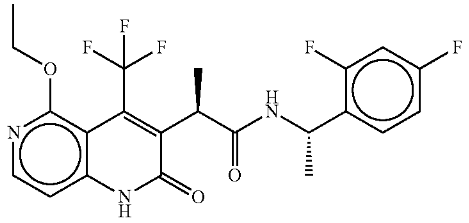 |

TABLE 2-continued
| Cmpd No. | Structure |
| --- | --- |
| 417 | 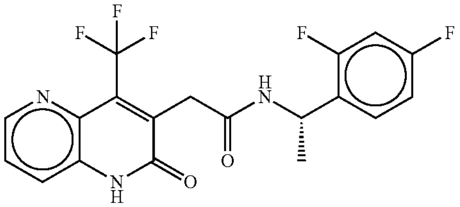 |
| 418 | 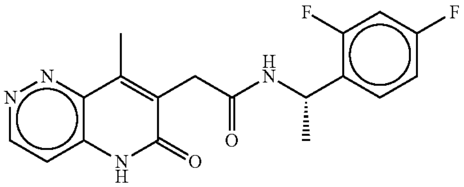 |
| 419 | 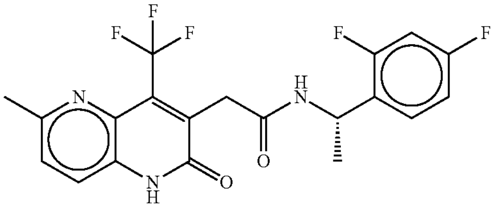 |
| 420 | 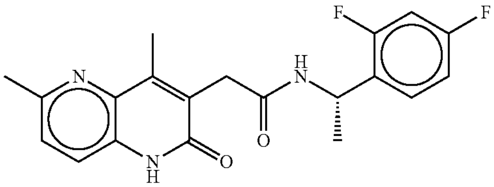 |
| 421 | 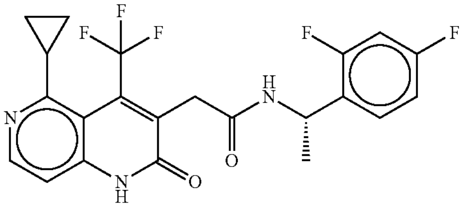 |
| 422 | 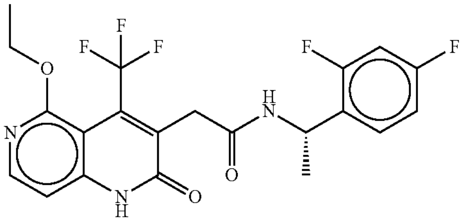 |
| 423 | 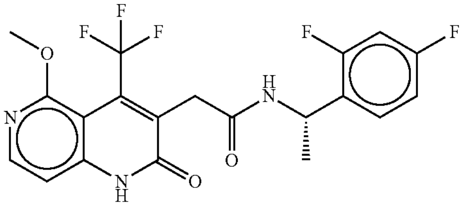 |

TABLE 2-continued
| Cmpd No. | Structure |
| --- | --- |
| 424 | 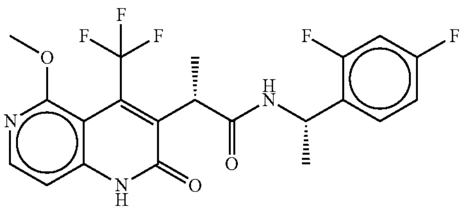 |
| 425 | 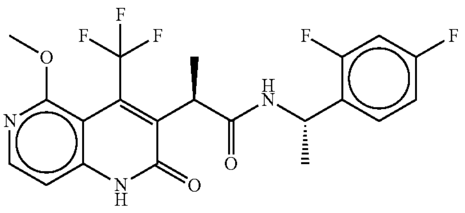 |
| 426 | 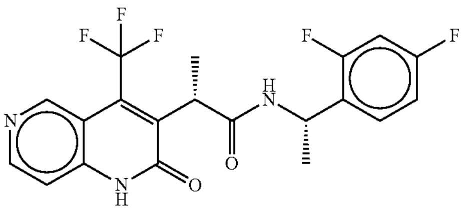 |
| 427 | 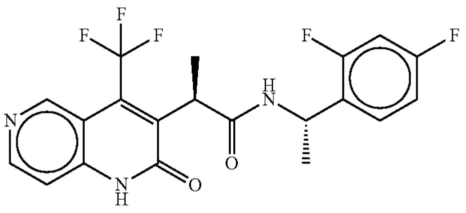 |
| 428 | 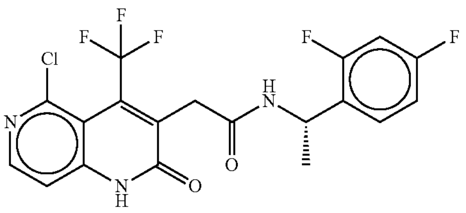 |
| 429 | 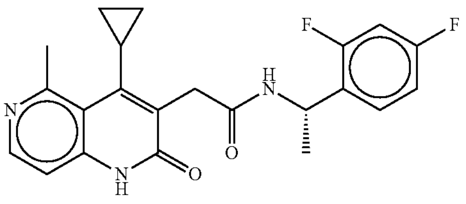 |
| 430 | 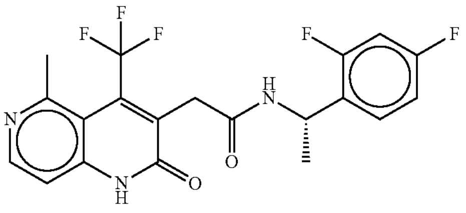 |

TABLE 2-continued
| Cmpd No. | Structure |
|---|---|
| 431 | 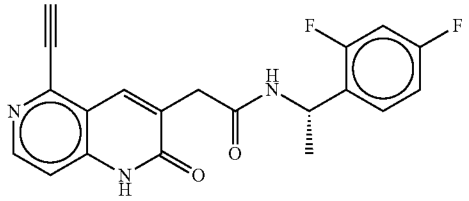 |
| 432 | 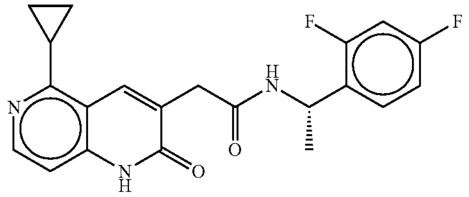 |
| 433 | 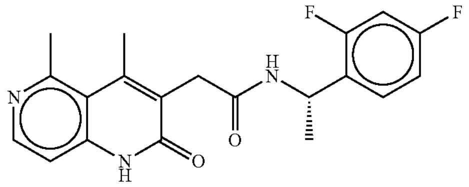 |
| 434 | 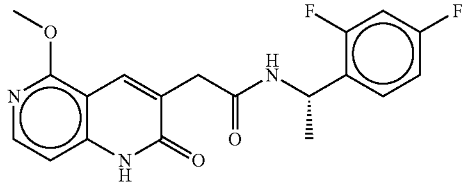 |
| 435 | 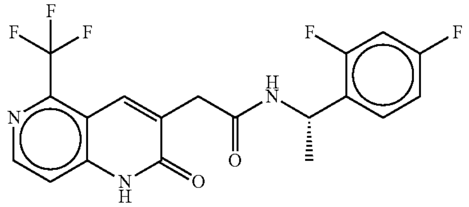 |
| 436 | 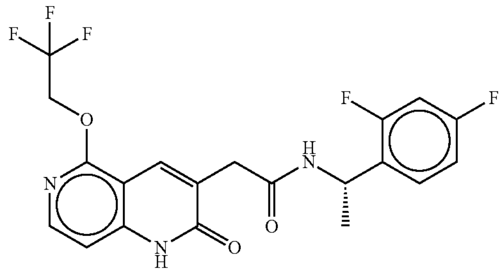 |
| 437 | 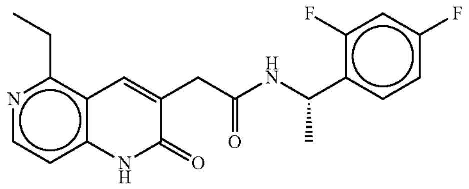 |

TABLE 2-continued
| Cmpd No. | Structure |
| --- | --- |
| 438 | 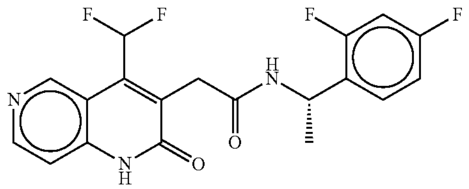 |
| 439 | 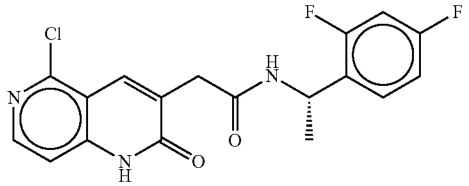 |
| 440 | 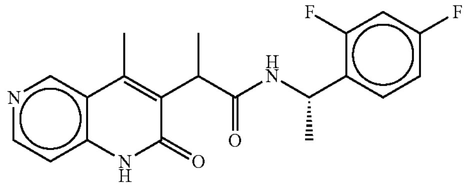 |
| 441 | 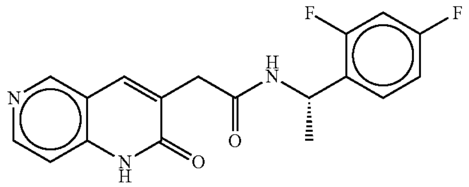 |
| 442 | 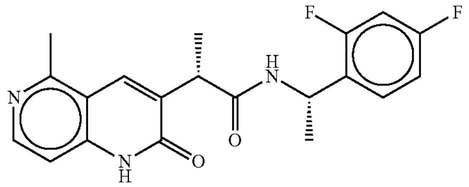 |
| 443 | 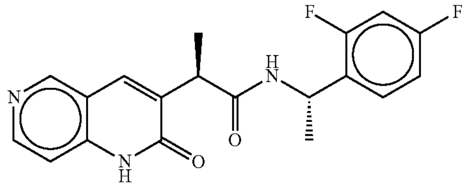 |
| 444 | 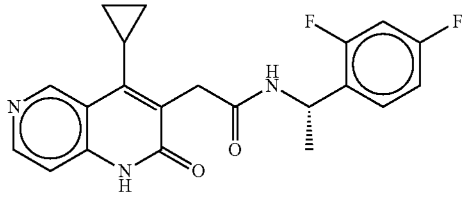 |
| 445 | 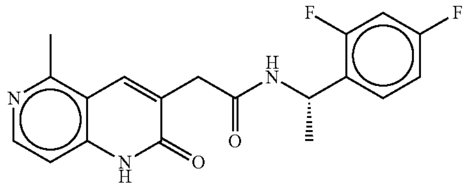 |

TABLE 2-continued
| Cmpd No. | Structure |
| --- | --- |
| 446 | 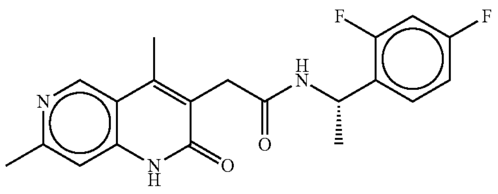 |
| 447 | 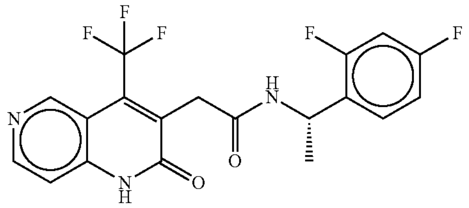 |
| 448 | 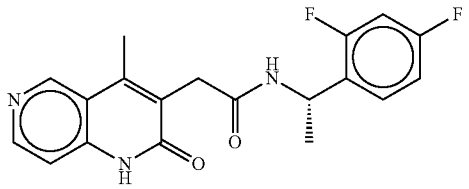 |
| 449 | 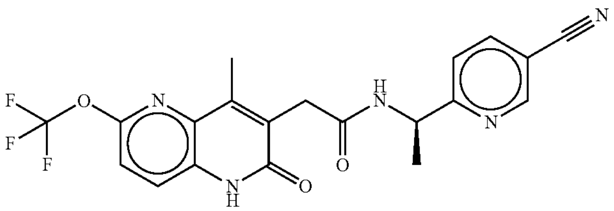 |
| 450 | 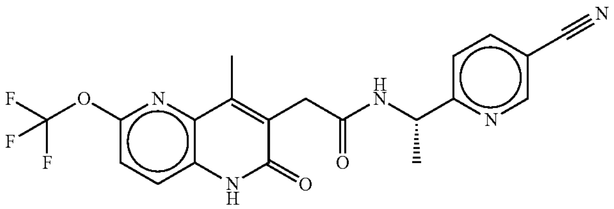 |
| 451 | 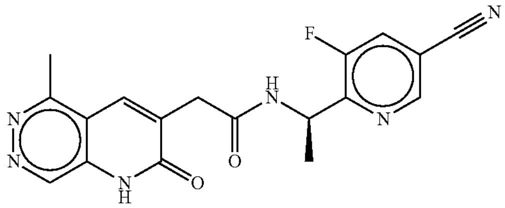 |
| 452 | 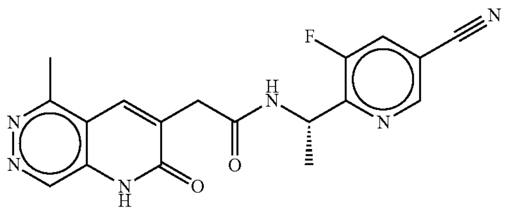 |

TABLE 2-continued
| Cmpd No. | Structure |
|---|---|
| 453 | 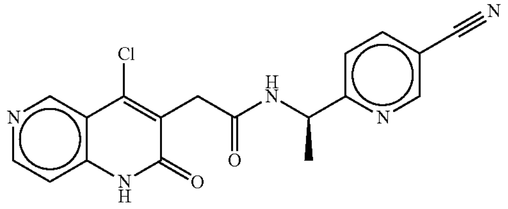 |
| 454 | 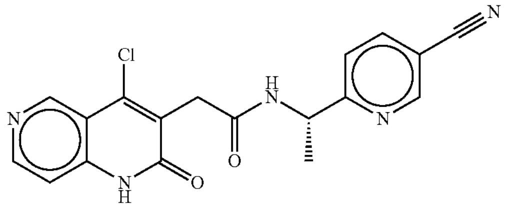 |
| 455 | 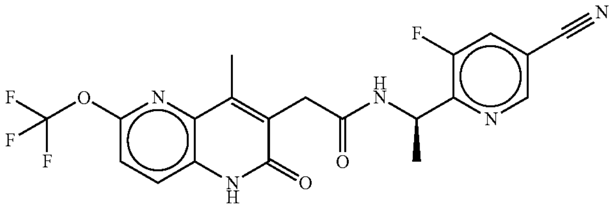 |
| 456 | 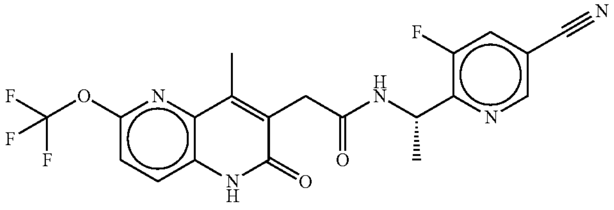 |
| 457 | 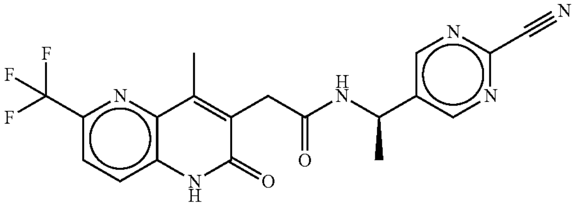 |
| 458 | 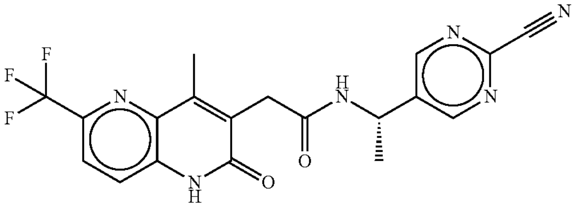 |
| 459 | 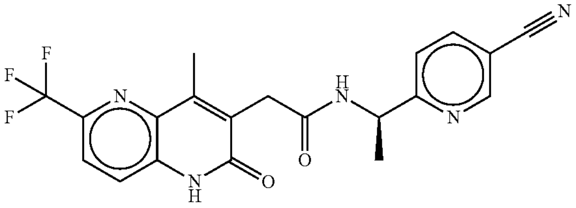 |

TABLE 2-continued
| Cmpd No. | Structure |
|---|---|
| 460 | 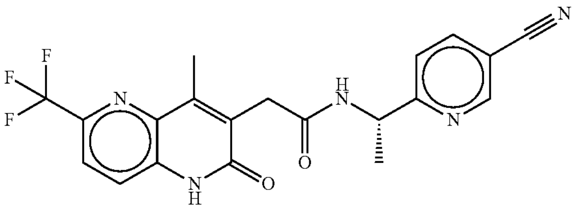 |
| 461 | 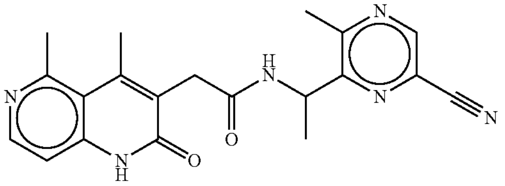 |
| 462 | 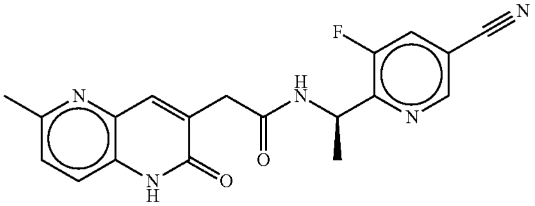 |
| 463 | 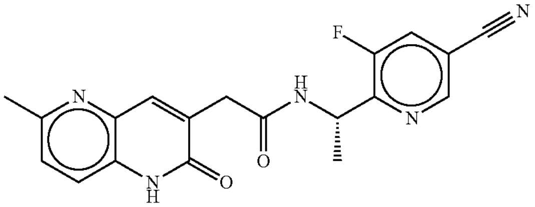 |
| 464 | 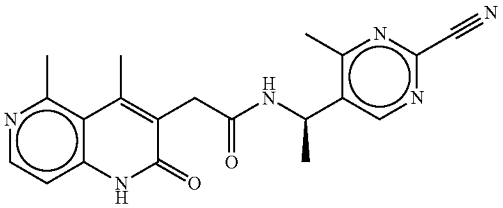 |
| 465 | 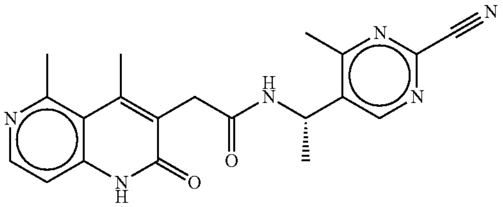 |
| 466 | 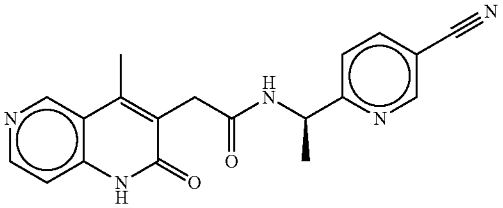 |

TABLE 2-continued
| Cmpd No. | Structure |
|---|---|
| 467 | 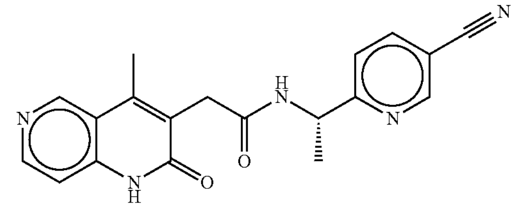 |
| 468 | 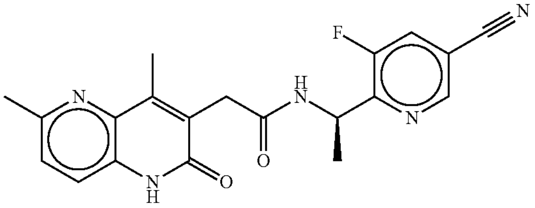 |
| 469 | 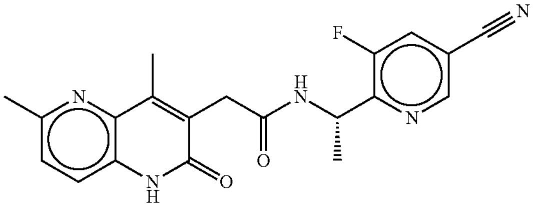 |
| 470 | 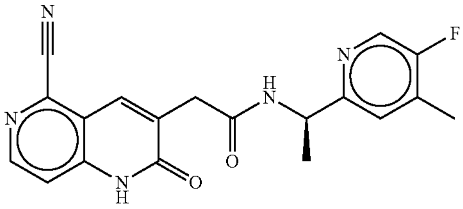 |
| 471 | 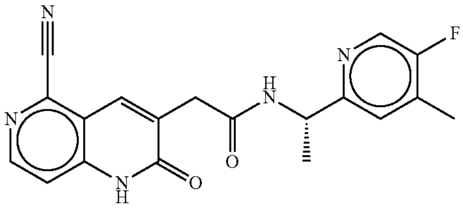 |
| 472 | 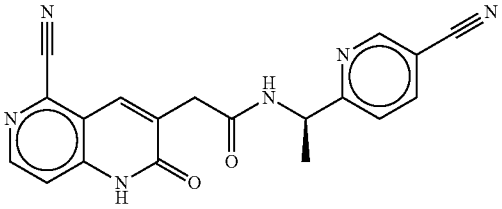 |
| 473 | 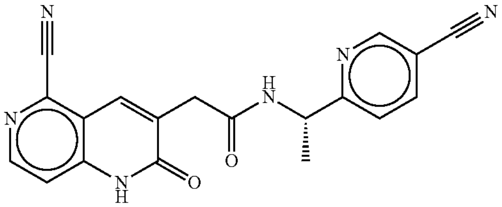 |

TABLE 2-continued
| Cmpd No. | Structure |
| --- | --- |
| 474 | 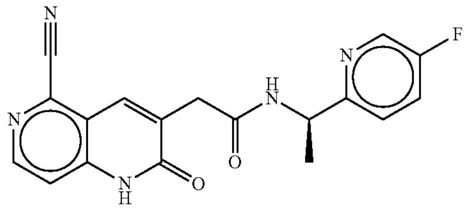 |
| 475 | 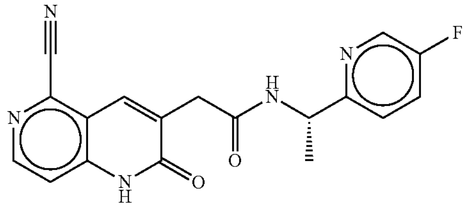 |
| 476 | 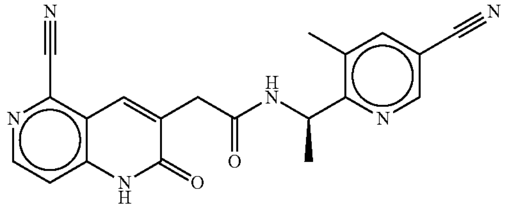 |
| 477 | 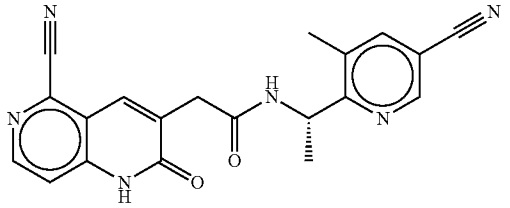 |
| 478 | 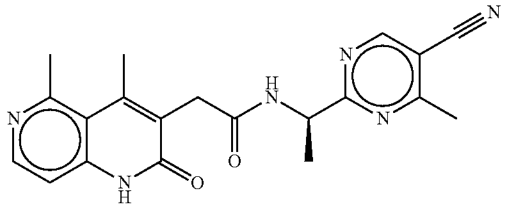 |
| 479 | 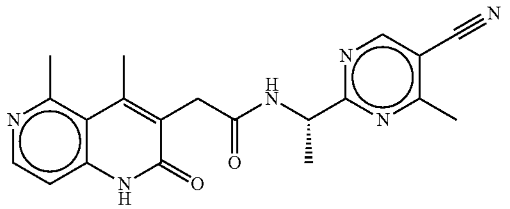 |
| 480 | 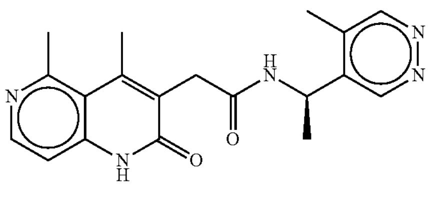 |

TABLE 2-continued
| Cmpd No. | Structure |
| --- | --- |
| 481 | 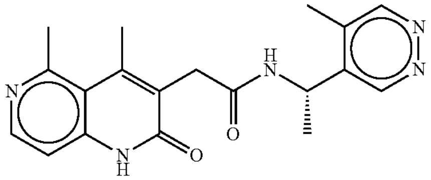 |
| 482 | 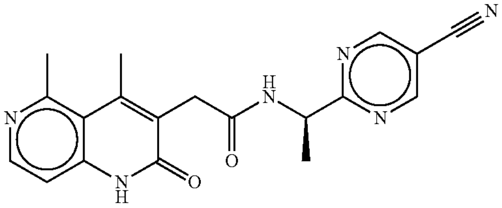 |
| 483 | 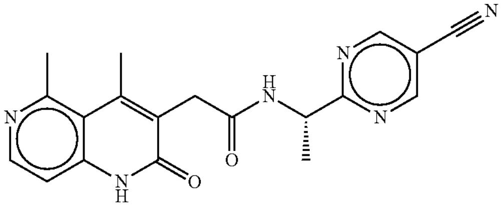 |
| 484 | 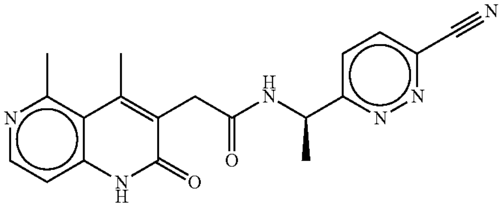 |
| 485 | 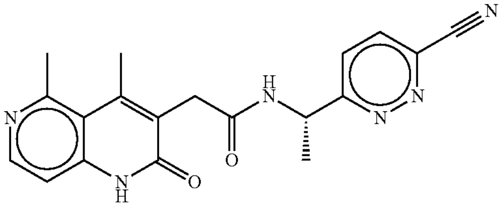 |
| 486 | 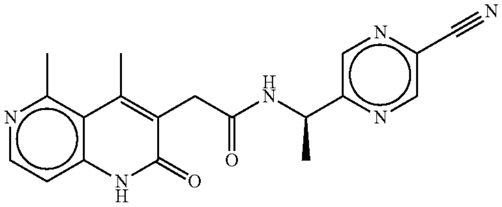 |
| 487 | 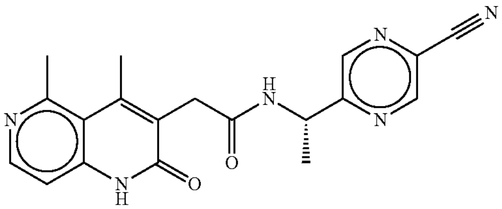 |

TABLE 2-continued
| Cmpd No. | Structure |
| --- | --- |
| 488 | 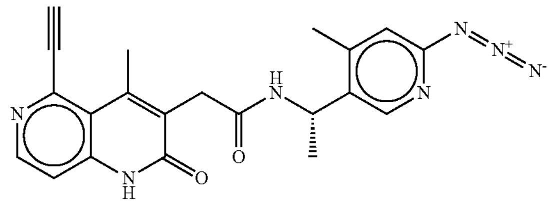 |
| 489 | 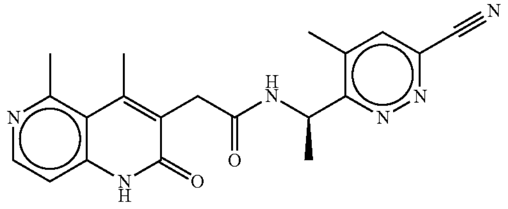 |
| 490 | 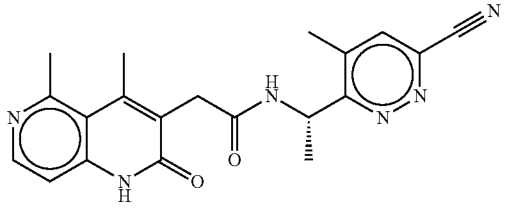 |
| 491 | 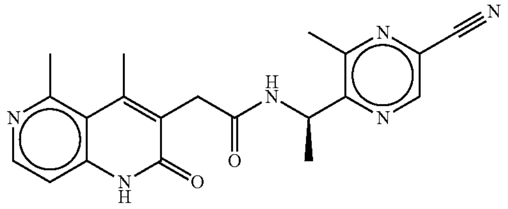 |
| 492 | 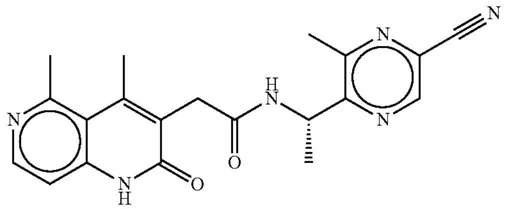 |
| 493 | 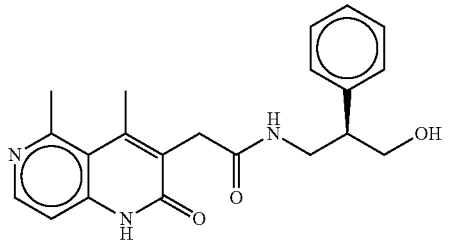 |
| 494 | 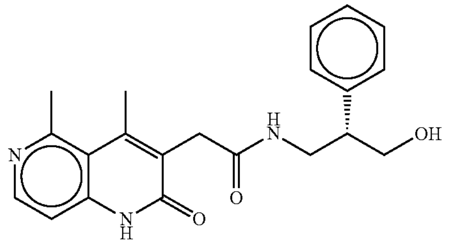 |

TABLE 2-continued
| Cmpd No. | Structure |
| --- | --- |
| 495 | 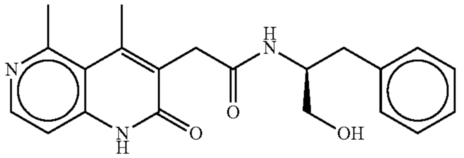 |
| 496 | 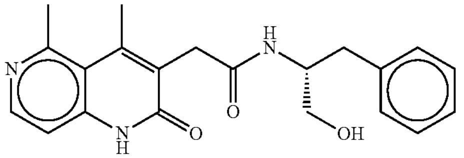 |
| 497 | 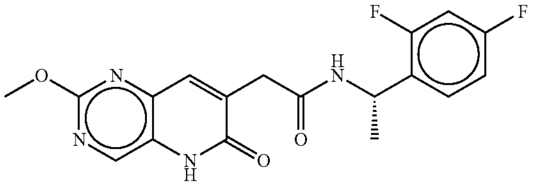 |
| 498 | 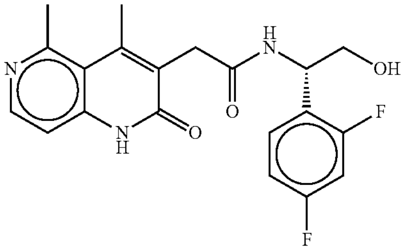 |
| 499 | 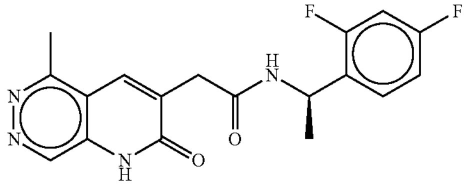 |
| 500 | 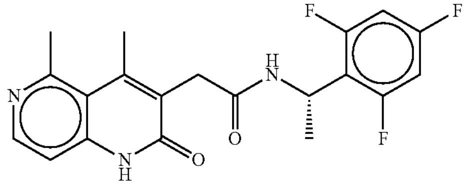 |
| 501 | 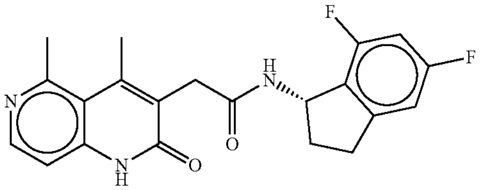 |
| 3001 | 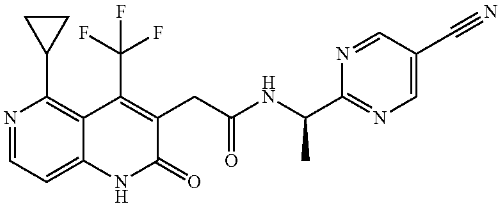 [SMILES: C[C@@H](NC(=O)Cc1c(C(F)(F)F)c2c(C3CC3)nccc2[nH]c1=O)c1ncc(C#N)cn1] |

TABLE 2-continued
| Cmpd No. | Structure |
|---|---|
| 3002 | 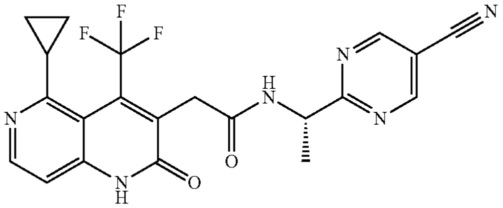 [SMILES: C[C@H](NC(=O)Cc1c(C(F)(F)F)c2c(C3CC3)nccc2[nH]c1=O)c1ncc(C#N)cn1] |
| 3003 | 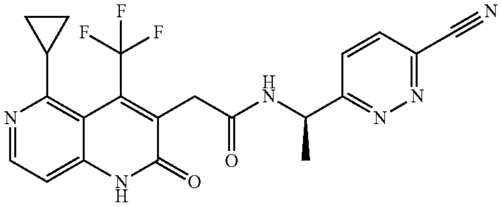 [SMILES: C[C@@H](NC(=O)Cc1c(C(F)(F)F)c2c(C3CC3)nccc2[nH]c1=O)c1ccc(C#N)nn1] |
| 3004 | 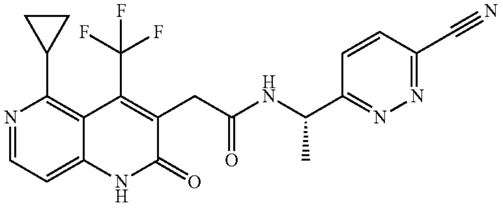 [SMILES: C[C@H](NC(=O)Cc1c(C(F)(F)F)c2c(C3CC3)nccc2[nH]c1=O)c1ccc(C#N)nn1] |
| 3005 | 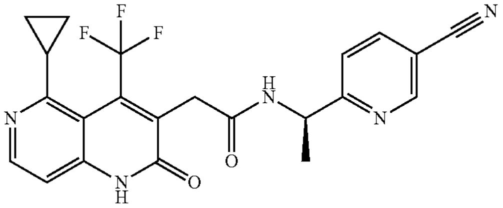 [SMILES: C[C@@H](NC(=O)Cc1c(C(F)(F)F)c2c(C3CC3)nccc2[nH]c1=O)c1ccc(C#N)cn1] |
| 3006 | 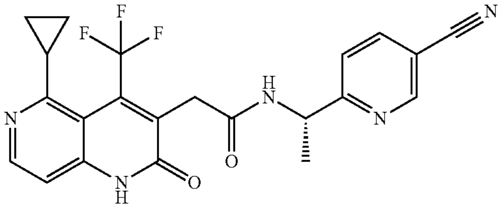 [SMILES: C[C@H](NC(=O)Cc1c(C(F)(F)F)c2c(C3CC3)nccc2[nH]c1=O)c1ccc(C#N)cn1] |
| 3007 | 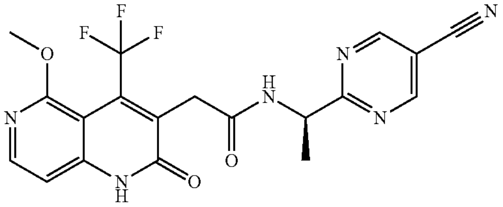 [SMILES: COc1nccc2[nH]c(=O)c(CC(=O)N[C@H](C)c3ncc(C#N)cn3)c(C(F)(F)F)c12] |
| 3008 | 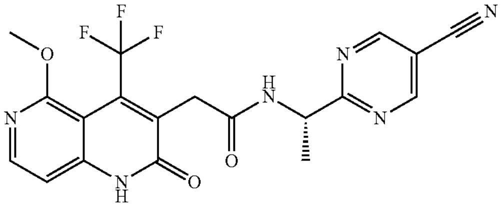 [SMILES: COc1nccc2[nH]c(=O)c(CC(=O)N[C@@H](C)c3ncc(C#N)cn3)c(C(F)(F)F)c12] |

TABLE 2-continued
| Cmpd No. | Structure |
|---|---|
| 3009 | 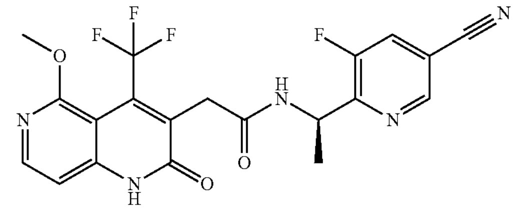 [SMILES: COc1nccc2[nH]c(=O)c(CC(=O)N[C@H](C)c3ncc(C#N)cc3F)c(C(F)(F)F)c12] |
| 3010 | 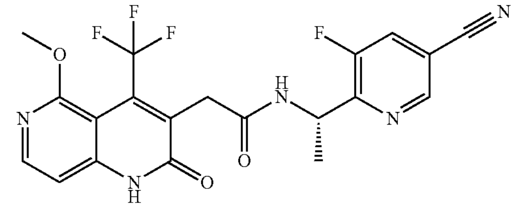 [SMILES: COc1nccc2[nH]c(=O)c(CC(=O)N[C@@H](C)c3ncc(C#N)cc3F)c(C(F)(F)F)c12] |
| 3011 | 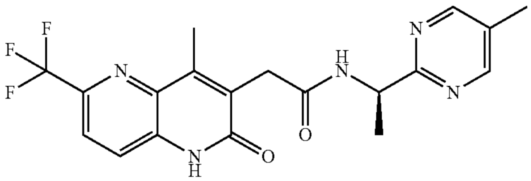 [SMILES: Cc1cnc([C@@H](C)NC(=O)Cc2c(C)c3nc(C(F)(F)F)ccc3[nH]c2=O)nc1] |
| 3012 | 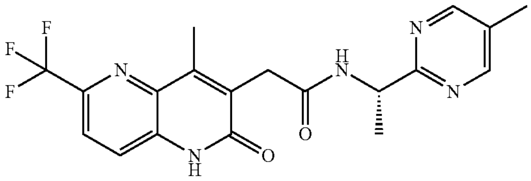 [SMILES: Cc1cnc([C@H](C)NC(=O)Cc2c(C)c3nc(C(F)(F)F)ccc3[nH]c2=O)nc1] |
| 3013 | 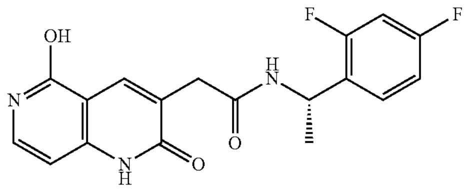 [SMILES: C[C@H](NC(=O)Cc1cc2c(O)nccc2[nH]c1=O)c1ccc(F)cc1F] |
| 3502 | 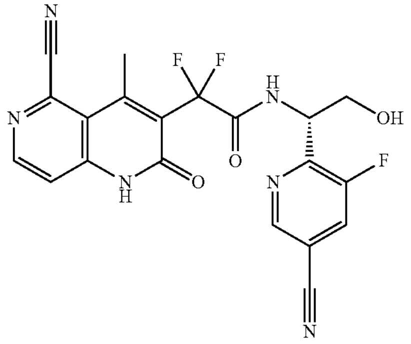 [SMILES: Cc1c(C(F)(F)C(=O)N[C@H](CO)c2ncc(C#N)cc2F)c(=O)[nH]c2ccnc(C#N)c12] |
| 3503 | 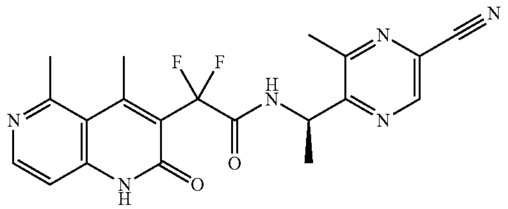 [SMILES: Cc1nc(C#N)cnc1[C@@H](C)NC(=O)C(F)(F)c1c(C)c2c(C)nccc2[nH]c1=O] |

TABLE 2-continued
| Cmpd No. | Structure |
| --- | --- |
| 3504 | 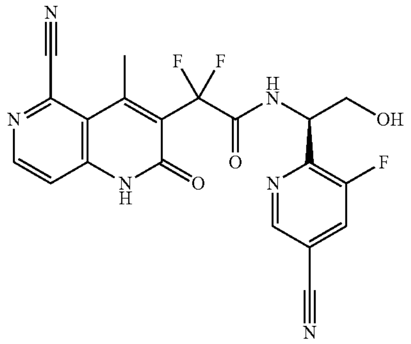 [SMILES: Cc1c(C(F)(F)C(=O)N[C@@H](CO)c2ncc(C#N)cc2F)c(=O)[nH]c2ccnc(C#N)c12] |
| 3505 | 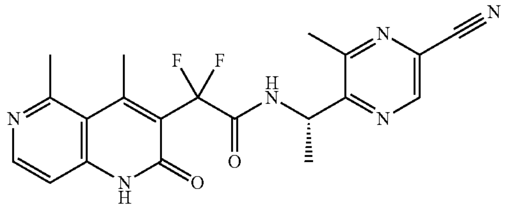 [SMILES: Cc1nc(C#N)cnc1[C@H](C)NC(=O)C(F)(F)c1c(C)c2c(C)nccc2[nH]c1=O] |
| 3506 | 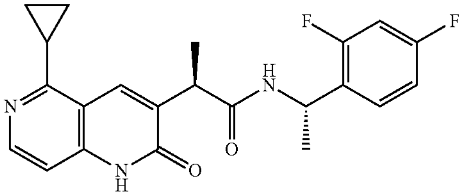 [SMILES: C[C@H](NC(=O)[C@H](C)c1cc2c(C3CC3)nccc2[nH]c1=O)c1ccc(F)cc1F] |
| 3507 | 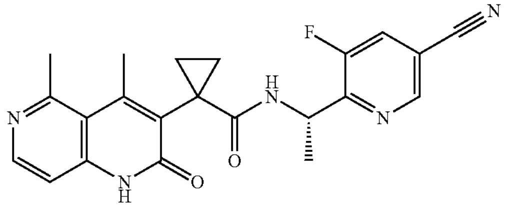 [SMILES: Cc1nccc2[nH]c(=O)c(C3(C(=O)N[C@@H](C)c4ncc(C#N)cc4F)CC3)c(C)c12] |
| 3508 | 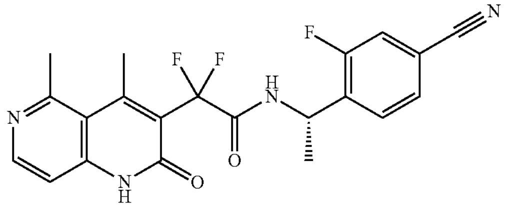 [SMILES: Cc1nccc2[nH]c(=O)c(C(F)(F)C(=O)N[C@@H](C)c3ccc(C#N)cc3F)c(C)c12] |
| 3509 | 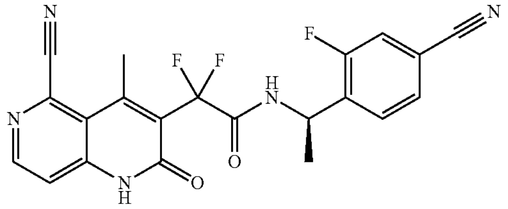 [SMILES: Cc1c(C(F)(F)C(=O)N[C@H](C)c2ccc(C#N)cc2F)c(=O)[nH]c2ccnc(C#N)c12] |

TABLE 2-continued
| Cmpd No. | Structure |
|---|---|
| 3510 | 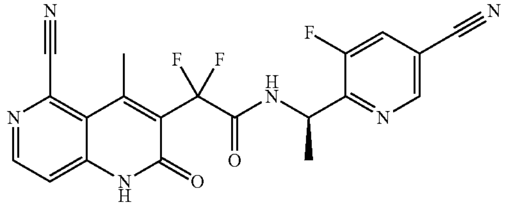 [SMILES: Cc1c(C(F)(F)C(=O)N[C@H](C)c2ncc(C#N)cc2F)c(=O)[nH]c2ccnc(C#N)c12] |
| 3511 | 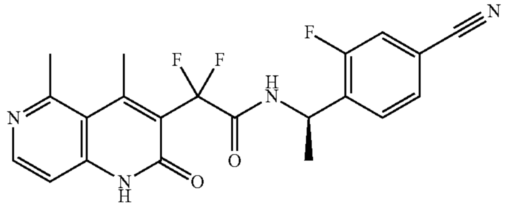 [SMILES: Cc1nccc2[nH]c(=O)c(C(F)(F)C(=O)N[C@H](C)c3ccc(C#N)cc3F)c(C)c12] |
| 3512 | 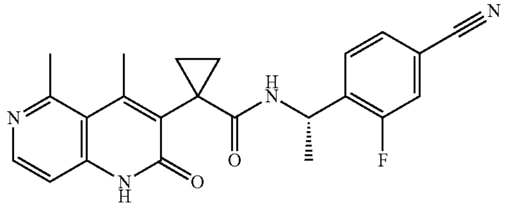 [SMILES: Cc1nccc2[nH]c(=O)c(C3(C(=O)N[C@@H](C)c4ccc(C#N)cc4F)CC3)c(C)c12] |
| 3513 | 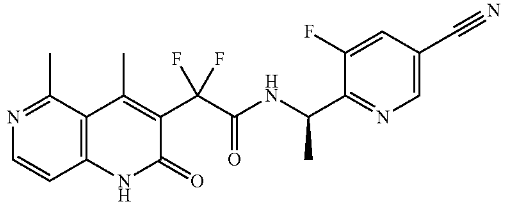 [SMILES: Cc1nccc2[nH]c(=O)c(C(F)(F)C(=O)N[C@H](C)c3ncc(C#N)cc3F)c(C)c12] |
| 3514 | 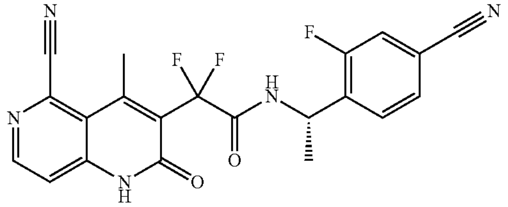 [SMILES: Cc1c(C(F)(F)C(=O)N[C@@H](C)c2ccc(C#N)cc2F)c(=O)[nH]c2ccnc(C#N)c12] |
| 3515 | 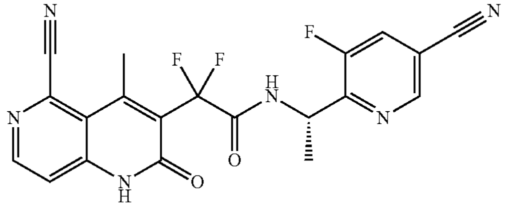 [SMILES: Cc1c(C(F)(F)C(=O)N[C@@H](C)c2ncc(C#N)cc2F)c(=O)[nH]c2ccnc(C#N)c12] |
| 3516 | 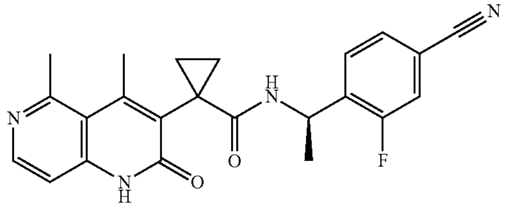 [SMILES: Cc1nccc2[nH]c(=O)c(C3(C(=O)N[C@H](C)c4ccc(C#N)cc4F)CC3)c(C)c12] |

TABLE 2-continued
| Cmpd No. | Structure |
| --- | --- |
| 3517 | 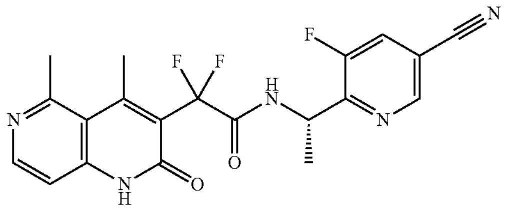 [SMILES: Cc1nccc2[nH]c(=O)c(C(F)(F)C(=O)N[C@@H](C)c3ncc(C#N)cc3F)c(C)c12] |
| 3518 | 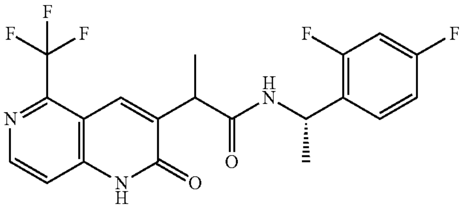 [SMILES: CC(C(=O)N[C@@H](C)c1ccc(F)cc1F)c1cc2c(C(F)(F)F)nccc2[nH]c1=O] |
| 3519 | 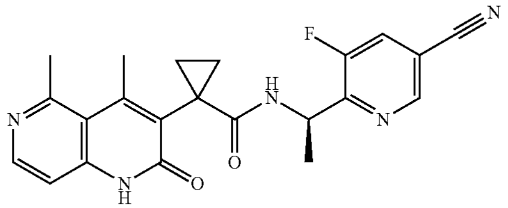 [SMILES: Cc1nccc2[nH]c(=O)c(C3(C(=O)N[C@H](C)c4ncc(C#N)cc4F)CC3)c(C)c12] |
| 3520 | 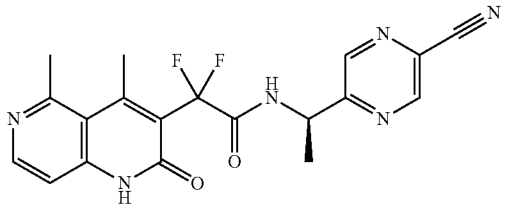 [SMILES: Cc1nccc2[nH]c(=O)c(C(F)(F)C(=O)N[C@H](C)c3cnc(C#N)cn3)c(C)c12] |
| 3521 | 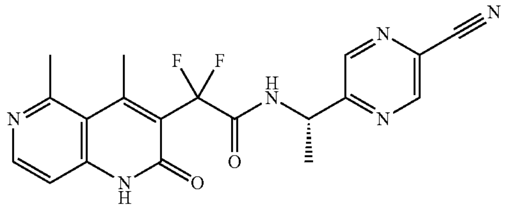 [SMILES: Cc1nccc2[nH]c(=O)c(C(F)(F)C(=O)N[C@@H](C)c3cnc(C#N)cn3)c(C)c12] |
| 3522 | 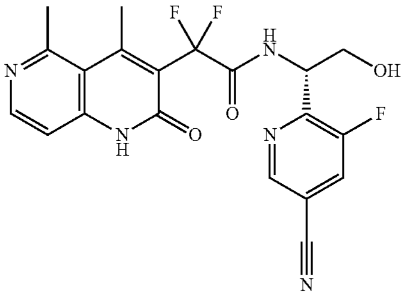 [SMILES: Cc1nccc2[nH]c(=O)c(C(F)(F)C(=O)N[C@H](CO)c3ncc(C#N)cc3F)c(C)c12] |

TABLE 2-continued
| Cmpd No. | Structure |
|---|---|
| 3523 | 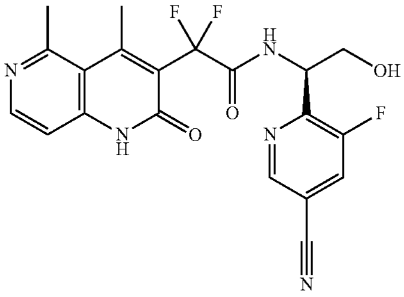 [SMILES: Cc1nccc2[nH]c(=O)c(C(F)(F)C(=O)N[C@@H](CO)c3ncc(C#N)cc3F)c(C)c12] |
TABLE 2-A
| MS | |
|---|---|
| Cmpd No. | Mass Spec |
| 138 | 431.1 |
| 139 | 431.05 |
| 140 | 374.2 |
| 141 | 374.15 |
| 142 | 392.05 |
| 143 | 392.05 |
| 144 | 432.05 |
| 145 | 432.05 |
| 146 | 453.95 |
| 147 | |
| 148 | 383.05 |
| 149 | 383.05 |
| 150 | 376.05 |
| 151 | 399.15 |
| 152 | 399.1 |
| 153 | 390 |
| 154 | 390 |
| 155 | 416.1 |
| 156 | 416.1 |
| 157 | 373.1 |
| 158 | 373.05 |
| 159 | 383.05 |
| 160 | 414.2 |
| 161 | 433.05 |
| 162 | 433.05 |
| 163 | 408.15 |
| 164 | 408.2 |
| 165 | 382.05 |
| 166 | 382.05 |
| 167 | 395.2 |
| 168 | 395.2 |
| 169 | 409.2 |
| 170 | 420.05 |
| 171 | 391.05 |
| 172 | 391.2 |
| 173 | 404.1 |
| 174 | 404.1 |
| 175 | 407.05 |
| 176 | 405.15 |
| 177 | 393.05 |
| 178 | 393.05 |
| 179 | 402.15 |
| 180 | 402.15 |
| 181 | 385.1 |
| 182 | 384.95 |
| 183 | 393.25 |
| 184 | 393.25 |
| 185 | 340.05 |
| 186 | 340.1 |
| 187 | 425.05 |
| 188 | 425.1 |
| 189 | 414.2 |
| 190 | 414.15 |
| 191 | 394.05 |
TABLE 2-A-continued
| MS | |
|---|---|
| Cmpd No. | Mass Spec |
| 192 | 394.05 |
| 193 | 394.2 |
| 194 | 394.1 |
| 195 | 393.1 |
| 196 | 393.1 |
| 197 | 391.1 |
| 198 | 391.15 |
| 199 | 430.1 |
| 200 | 430.1 |
| 201 | 421.2 |
| 202 | 421.3 |
| 203 | 437.2 |
| 204 | 437.2 |
| 205 | 396.2 |
| 206 | 427.3 |
| 207 | 432.1 |
| 208 | 433.35 |
| 209 | 433.35 |
| 210 | 399.2 |
| 211 | 399.2 |
| 212 | 362 |
| 213 | 362 |
| 214 | 443.1 |
| 215 | 443.1 |
| 216 | 442.05 |
| 217 | 442.1 |
| 218 | 449.15 |
| 219 | 449 |
| 220 | 406.1 |
| 221 | 406.1 |
| 222 | 375.2 |
| 223 | 375.2 |
| 224 | 449 |
| 225 | 449 |
| 226 | 434.1 |
| 227 | 434.1 |
| 228 | 383.1 |
| 229 | 399.2 |
| 230 | 399.2 |
| 231 | 442.15 |
| 232 | 442.15 |
| 233 | 374.2 |
| 234 | 374.1 |
| 235 | 382.15 |
| 236 | 382.15 |
| 237 | 371.15 |
| 238 | 395.1 |
| 239 | 382.2 |
| 240 | 375.1 |
| 241 | 406 |
| 242 | 406 |
| 243 | 395.1 |
| 244 | 372.15 |
| 245 | 407.1 |

TABLE 2-A-continued

| MS | |
|---|---|
| Cmpd No. | Mass Spec |
| 246 | 407.35 |
| 247 | 396.1 |
| 248 | 396.2 |
| 249 | 384.3 |
| 250 | 384.3 |
| 251 | 351.1 |
| 252 | 351.05 |
| 253 | 362.1 |
| 254 | 362.1 |
| 255 | 379.2 |
| 256 | 379.1 |
| 257 | 383.1 |
| 258 | 383.1 |
| 259 | 400.1 |
| 260 | 400.1 |
| 261 | 400.2 |
| 262 | 400.2 |
| 263 | 443 |
| 264 | 443.1 |
| 265 | 427.15 |
| 266 | 427.15 |
| 267 | 355.2 |
| 268 | 355.2 |
| 269 | 383 |
| 270 | 425.85 |
| 271 | 416.1 |
| 272 | 416.1 |
| 273 | 397.1 |
| 274 | 397.1 |
| 275 | 426.49 |
| 276 | 412.81 |
| 277 | 428.99 |
| 278 | 448.93 |
| 279 | 427.1 |
| 280 | 427.1 |
| 281 | 383.15 |
| 282 | 390.2 |
| 283 | 390.1 |
| 284 | 391.1 |
| 285 | 391.1 |
| 286 | 366.2 |
| 287 | 366.3 |
| 288 | 386.1 |
| 289 | 386.1 |
| 290 | 367.2 |
| 291 | 367.2 |
| 292 | 353.2 |
| 293 | 353.2 |
| 294 | 366.2 |
| 295 | 353.2 |
| 296 | 353.2 |
| 297 | 353.1 |
| 298 | 353.1 |
| 299 | 373.8 |
| 300 | 360.2 |
| 301 | 350.2 |
| 302 | 353.2 |
| 303 | 389.05 |
| 304 | 384.15 |
| 305 | 384.15 |
| 306 | 350.2 |
| 307 | 353.1 |
| 308 | 389.1 |
| 309 | 367.1 |
| 310 | 367 |
| 311 | 353.15 |
| 312 | 353.15 |
| 313 | 366.2 |
| 314 | 366.2 |
| 315 | 366.2 |
| 316 | 352.9 |
| 317 | 352.85 |
| 318 | 366.2 |
| 319 | 366.2 |
| 320 | 352.2 |

TABLE 2-A-continued

| MS | |
|---|---|
| Cmpd No. | Mass Spec |
| 321 | 352.2 |
| 322 | 337.2 |
| 323 | 336.9 |
| 324 | 337.2 |
| 325 | 337.2 |
| 326 | 350.2 |
| 327 | 350.2 |
| 328 | 352.1 |
| 329 | 352.2 |
| 330 | 352.2 |
| 331 | 352.2 |
| 332 | 398.95 |
| 333 | 337.45 |
| 334 | 337.45 |
| 335 | 366.2 |
| 336 | 366.2 |
| 337 | 366.05 |
| 338 | 366.05 |
| 339 | 350.2 |
| 340 | 350.2 |
| 341 | 402.2 |
| 342 | 402.2 |
| 343 | 428.98 |
| 344 | |
| 345 | 442.8 |
| 346 | 426.76 |
| 347 | 456.15 |
| 348 | 456.15 |
| 349 | |
| 350 | 395.87 |
| 351 | 400.92 |
| 352 | 372.88 |
| 353 | 483.79 |
| 354 | 387.05 |
| 355 | 383 |
| 356 | 398.25 |
| 357 | 438.05 |
| 358 | 466.25 |
| 359 | 442.1 |
| 360 | 383 |
| 361 | 383.15 |
| 362 | 483.95 |
| 363 | 397 |
| 364 | 376.2 |
| 365 | 406.2 |
| 366 | 406.1 |
| 367 | 376.15 |
| 368 | 376.1 |
| 369 | 440.2 |
| 370 | 440.1 |
| 371 | 429.95 |
| 372 | 447.92 |
| 373 | 534.86 |
| 374 | 415.43 |
| 375 | 390.2 |
| 376 | 390.1 |
| 377 | 426.2 |
| 378 | 373.05 |
| 379 | 373 |
| 380 | 438.42 |
| 381 | 402.21 |
| 382 | 375.1 |
| 383 | 414.15 |
| 384 | 415.82 |
| 385 | 388.14 |
| 386 | 414.15 |
| 387 | 479.1 |
| 388 | 378.05 |
| 389 | 424.2 |
| 390 | 378.95 |
| 391 | 376 |
| 392 | 362.05 |
| 393 | 426 |
| 394 | 362 |
| 395 | 378.95 |

TABLE 2-A-continued

| MS | |
|---|---|
| Cmpd No. | Mass Spec |
| 396 | 388 |
| 397 | 412 |
| 398 | 386.2 |
| 399 | 386.15 |
| 400 | 456.15 |
| 401 | 428.05 |
| 402 | 392.1 |
| 403 | 386.15 |
| 404 | 386.25 |
| 405 | 407.95 |
| 406 | 384 |
| 407 | 368.2 |
| 408 | 372.1 |
| 409 | 388.15 |
| 410 | 440 |
| 411 | 258.1 |
| 412 | 258.1 |
| 413 | 440 |
| 414 | 402.2 |
| 415 | 469.8 |
| 416 | 469.75 |
| 417 | 411.75 |
| 418 | 359.1 |
| 419 | 426.1 |
| 420 | 372 |
| 421 | 451.95 |
| 422 | 455.75 |
| 423 | 442.15 |
| 424 | 455.95 |
| 425 | 455.95 |
| 426 | 426.1 |
| 427 | 426.05 |
| 428 | 446.05 |
| 429 | 258.1 |
| 430 | 426.1 |
| 431 | 368.1 |
| 432 | 384.05 |
| 433 | 372.1 |
| 434 | 374 |
| 435 | 412 |
| 436 | 442.2 |
| 437 | 371.95 |
| 438 | 394.1 |
| 439 | 378 |
| 440 | 372 |
| 441 | 344 |
| 442 | 372.1 |
| 443 | 357.95 |
| 444 | 384.1 |
| 445 | 357.85 |
| 446 | 372 |
| 447 | 412.25 |
| 448 | 358.05 |
| 449 | 432.05 |
| 450 | 432.05 |
| 451 | 367.05 |
| 452 | 367 |
| 453 | 367.95 |
| 454 | 368 |
| 455 | 450 |
| 456 | 449.95 |
| 457 | 417.05 |
| 458 | 417.05 |
| 459 | 416.05 |
| 460 | 416.05 |
| 461 | 377.25 |
| 462 | 366.05 |
| 463 | 366.1 |
| 464 | 377.25 |
| 465 | 377.1 |
| 466 | 348.05 |
| 467 | 348.2 |
| 468 | 380.15 |
| 469 | 380.2 |
| 470 | 366.05 |

TABLE 2-A-continued

| MS | |
|---|---|
| Cmpd No. | Mass Spec |
| 471 | 366.05 |
| 472 | 359.26 |
| 473 | 359.05 |
| 474 | 352.05 |
| 475 | 352 |
| 476 | 371 |
| 477 | 371 |
| 478 | 377.2 |
| 479 | 377.25 |
| 480 | 352.1 |
| 481 | 352.1 |
| 482 | 363.15 |
| 483 | 363.1 |
| 484 | 361.15 |
| 485 | 363.2 |
| 486 | 363.25 |
| 487 | 363 |
| 488 | 402.2 |
| 489 | 377.25 |
| 490 | 377.25 |
| 491 | 377.15 |
| 492 | 377.2 |
| 493 | 366.2 |
| 494 | 366.2 |
| 495 | 366.3 |
| 496 | 366.1 |
| 497 | 375.25 |
| 498 | 388 |
| 499 | 358.8 |
| 500 | 390.05 |
| 501 | 384.1 |
| 3001 | 443.1 |
| 3002 | 443.1 |
| 3003 | 443.05 |
| 3004 | 443.05 |
| 3005 | 442.05 |
| 3006 | 442 |
| 3007 | 433.1 |
| 3008 | 433.1 |
| 3009 | 450.1 |
| 3010 | 450 |
| 3011 | 417.05 |
| 3012 | 417.05 |
| 3013 | 359.8 |
| 3502 | 443.05 |
| 3503 | 413 |
| 3504 | 443.05 |
| 3505 | 413 |
| 3506 | 398.2 |
| 3507 | 406.15 |
| 3508 | 415.05 |
| 3509 | 424 |
| 3510 | 427.1 |
| 3511 | 415.1 |
| 3512 | 405.15 |
| 3513 | 416.05 |
| 3514 | 424 |
| 3515 | 472.1 |
| 3516 | 405.15 |
| 3517 | 416.1 |
| 3518 | 426 |
| 3519 | 406.15 |
| 3520 | 399.15 |
| 3521 | 399.1 |
| 3522 | 432.1 |
| 3523 | 432 |

TABLE 2-A

| NMR | |
|---|---|
| Cmpd No. | NMR |
| 138 | $^1$H NMR (300 MHz, DMSO-$d_6$) δ 12.17 (s, 1H), 9.05 (s, 1H), 8.62 (d, J = 7.2 Hz, 1H), 7.97 (d, J = 8.7 Hz, 1H), 7.84 (d, J = 8.4 Hz, 1H), 5.25-5.16 (m, 1H), 3.74-3.48 (m, 2H), 2.62 (s, 3H), 2.42 (s, 3H), 1.41 (d, J = 6.9 Hz, 3H). |
| 139 | $^1$H NMR (300 MHz, DMSO-$d_6$) δ 12.17 (s, 1H), 9.04 (s, 1H), 8.62 (d, J = 7.2 Hz, 1H), 7.96 (d, J = 8.7 Hz, 1H), 7.83 (d, J = 8.4 Hz, 1H), 5.25-5.16 (m, 1H), 3.70-3.48 (m, 2H), 2.62 (s, 3H), 2.42 (s, 3H), 1.41 (d, J = 6.9 Hz, 3H). |
| 144 | $^1$H NMR (300 MHz, DMSO-$d_6$) δ 12.47 (s, 1H), 8.90 (s, 1H), 8.72 (d, J = 7.2 Hz, 1H), 7.82-7.78 (m, 1H), 7.70-7.67 (m, 1H), 7.64-7.59 (m, 1H), 5.14-5.05 (m, 1H), 3.71 (d, J = 2.7 Hz, 2H), 2.43 (s, 3H), 1.37 (d, J = 7.2 Hz, 3H). |
| 145 | $^1$H NMR (300 MHz, DMSO-d6) δ 12.46 (s, 1H), 8.90 (s, 1H), 8.72 (d, J = 7.2 Hz, 1H), 7.82-7.78 (m, 1H), 7.71-7.64 (m, 1H), 7.62 (t, J = 7.5 Hz, 1H), 5.12-5.07 (m, 1H), 3.77-3.66 (d, J = 2.7 Hz, 2H), 2.43 (s, 3H), 1.37 (d, J = 7.2 Hz, 3H). |
| 148 | $^1$H NMR (400 MHz, DMSO-$d_6$) δ 12.23 (s, 1H), 8.73 (d, J = 6.4 Hz, 1H), 8.36 (t, J = 4 Hz, 1H), 7.81-7.78 (m, 1H), 7.70-7.60 (m, 1H), 7.15-7.07 (m, 1H), 5.14-5.03 (m, 1H), 2.75 (t, J = 6.8 Hz, 3H), 1.38 (d, J = 6.8 Hz, 3H). |
| 149 | $^1$H NMR (300 MHz, DMSO-$d_6$) δ 12.25 (s, 1H), 8.73 (d, J = 7.2 Hz, 1H), 8.36 (d, J = 5.7 Hz, 1H), 7.82-7.70 (m, 1H), 7.69-7.67 (m, 1H), 7.62 (t, J = 7.2 Hz, 1H), 7.15-7.12 (m, 1H), 5.15-5.05 (m, 1H), 3.48 (s, 2H), 2.75 (d, J = 6.9 Hz, 3H), 1.37 (d, J = 6.9 Hz, 3H). |
| 151 | $^1$H NMR (400 MHz, DMSO-$d_6$) δ 12.31 (s, 1H), 8.68 (d, J = 7.2 Hz, 1H), 8.33 (d, J = 5.6 Hz, 1H), 7.82-7.79 (m, 1H), 7.72-7.69 (m, 1H), 7.61 (t, J = 8.0 Hz, 1H), 7.16 (d, J = 5.6 Hz, 1H), 5.15-5.07 (m, 1H), 3.77-3.67 (m, 2H), 2.97 (s, 3H), 1.37 (d, J = 7.2 Hz, 3H). |
| 152 | $^1$H NMR (400 MHz, DMSO-$d_6$) δ 12.31 (s, 1H), 8.68 (d, J = 7.6 Hz, 1H), 8.33 (d, J = 5.6 Hz, 1H), 7.82-7.79 (m, 1H), 7.71-7.69 (m, 1H), 7.61 (t, J = 7.6 Hz, 1H), 7.16 (d, J = 5.6 Hz, 1H), 5.14-5.07 (m, 1H), 3.77-3.67 (m, 2H), 2.97 (s, 3H), 1.37 (d, J = 6.8 Hz, 3H). |
| 153 | $^1$H NMR (300 MHz, DMSO-$d_6$) δ 12.61 (s, 1H), 8.88 (d, J = 7.2 Hz, 1H), 8.38 (d, J = 5.7 Hz, 1H), 7.84-7.80 (m, 1H), 7.71-7.61 (m, 2H), 7.17 (d, J = 5.7 Hz, 1H), 5.16-5.06 (m, 1H), 3.80 (s, 2H), 2.99 (s, 3H), 1.39 (d, J = 6.9 Hz, 3H). |
| 154 | $^1$H NMR (300 MHz, DMSO-$d_6$) δ 12.61 (s, 1H), 8.87 (d, J = 7.2 Hz, 1H), 8.38 (d, J = 6.3 Hz, 1H), 7.83-7.80 (m, 1H), 7.71-7.61 (m, 2H), 7.17 (d, J = 5.7 Hz, 1H), 5.16-5.07 (m, 1H), 3.80 (s, 2H), 2.99 (s, 3H), 1.40 (d, J = 6.9 Hz, 3H). |
| 167 | $^1$H NMR (300 MHz, Methanol-d4) δ 12.43 (s, 1H), 8.59 (d, J = 3.0 Hz, 1H), 7.91 (d, J = 9.0 Hz, 1H), 7.50 (d, J = 9.0 Hz, 1H), 7.32-7.24 (m, 1H), 7.18-7.10 (m, 1H), 6.88-6.91 (m, 1H), 5.26-5.17 (m, 1H), 4.27-4.20 (m, 1H), 2.40 (s, 3H), 1.31-1.23 (m, 6H). |
| 168 | $^1$H NMR (300 MHz, Methanol-$d_4$) δ 12.41 (s, 1H), 8.58 (d, J = 6.0 Hz, 1H), 7.82 (d, J = 9.0 Hz, 1H), 7.49 (d, J = 3.0 Hz, 1H), 7.46-7.38 (m, 1H), 7.18-7.16 (m, 1H), 7.09-7.02 (m, 1H), 5.22-5.12 (m, 1H), 4.18-4.11 (m, 1H), 2.69 (s, 3H), 1.29-1.26 (m, 6.0 H). |
| 185 | $^1$H NMR (300 MHz, Methanol-$d_4$) δ 12.40 (s, 1H), 8.74 (d, J = 6.0 Hz, 1H), 8.54z (d, J = 6.0 Hz, 1H), 7.47 (d, J = 6.0 Hz, 1H), 6.78-6.69 (m, 2H), 5.64-5.59 (m, 1H), 4.79-4.74 (m, 1H), 4.34-4.31 (m, 1H), 3.64 (s, 2H), 2.42 (d, J = 3.0 Hz, 3H). |
| 186 | $^1$H NMR (300 MHz, Methanol-$d_4$) δ 12.40 (s, 1H), 8.74 (d, J = 6.0 Hz, 1H), 8.54z (d, J = 6.0 Hz, 1H), 7.47 (d, J = 6.0 Hz, 1H), 6.78-6.69 (m, 2H), 5.64-5.59 (m, 1H), 4.79-4.74 (m, 1H), 4.34-4.31 (m, 1H), 3.64 (s, 2H), 2.42-2.31 (m, 3H). |
| 231 | $^1$H NMR (400 MHz, DMSO-$d_6$) δ 12.38 (s, 1H), 8.53-8.47 (m, 2H), 7.48-7.42 (m, 2H), 7.20-7.03 (m, 2H), 5.10-4.97 (m, 2H), 3.71 (s, 2H), 3.55 (s, 2H), 2.38 (s, 3H). |
| 239 | $^1$H NMR (300 MHz, DMSO-$d_6$) δ 9.31 (s, 1H), 8.67 (d, J = 7.2 Hz, 1H), 7.55-7.53 (m, 1H), 7.28-7.21 (m, 1H), 7.16-7.14 (m, 1H), 5.14 (t, J = 6.9 Hz, 1H), 3.79 (s, 2H), 2.74 (s, 3H), 1.43 (d, J = 6.9 Hz, 3H). |
| 240 | $^1$H NMR (400 MHz, DMSO-d6) δ 12.74 (s, 1H), 12.26 (s, 1H), 8.47 (d, J = 7.6 Hz, 1H), 7.87 (s, 1H), 7.46-7.42 (m, 1H), 7.19-7.14 (m, 1H), 7.07-7.05 (m, 1H), 5.08-5.04 (m, 1H), 3.63-3.47 (m, 2H), 2.54 (s, 3H), 1.34 (d, J = 7.2 Hz, 3H). |
| 249 | $^1$H NMR (300 MHz, DMSO-d6) δ 12.22 (s, 1H), 8.54-8.49 (m, 2H), 8.04 (d, J = 8.4 Hz, 1H), 7.93-7.86 (m, 1H), 7.76 (d, J = 8.4 Hz, 1H), 5.24-5.17 (m, 1H), 3.76-3.57 (m, 2H), 2.39 (s, 3H), 1.38 (d, J = 7.2 Hz, 3H). |
| 250 | $^1$H NMR (300 MHz, DMSO-d6) δ 12.22 (s, 1H), 8.54-8.49 (m, 2H), 8.04 (d, J = 8.4 Hz, 1H), 7.93-7.86 (m, 1H), 7.76 (d, J = 8.4 Hz, 1H), 5.24-5.17 (m, 1H), 3.76-3.57 (m, 2H), 2.39 (s, 3H), 1.38 (d, J = 7.2 Hz, 3H). |
| 256 | $^1$H NMR (300 MHz, DMSO-$d_6$) δ 11.92 (s, 1H), 8.74-8.52 (m, 1H), 8.33-8.19 (m, 1H), 7.88-7.73 (m, 1H), 7.73-7.53 (m, 2H), 7.18-6.91 (m, 1H), 5.32-5.01 (m, 1H), 3.66 (s, 2H), 2.86 (s, 3H), 1.50-1.17 (m, 3H). |
| 269 | $^1$H NMR (300 MHz, DMSO-d6) δ 12.38 (s, 1H), 8.57-8.54 (m, 2H), 7.51-7.43 (m, 2H), 7.21-7.14 (m, 1H), 7.10-7.04 (m, 1H), 5.10-5.06 (m, 1H), 3.69 (s, 2H), 2.67 (s, 3H), 1.36 (d, J = 6.9 Hz, 3H) |
| 270 | $^1$H NMR (300 MHz, DMSO-d6) δ 12.38 (s, 1H), 8.56-8.52 (m, 2H), 7.50-7.42 (m, 2H), 7.22-7.14 (m, 1H), 7.09-7.03 (m, 1H), 5.11-5.06 (m, 1H), 3.68 (s, 2H), 2.38 (d, J = 2.4 Hz, 4H), 1.35 (d, J = 7.2 Hz, 3H). |
| 347 | $^1$H NMR (300 MHz, DMSO-$d_6$) δ 12.34 (s, 1H), 8.15 (d, J = 5.6 Hz, 1H), 7.89 (d, J = 8.2 Hz, 1H), 7.33-7.22 (m, 1H), 7.23 (d, J = 5.6 Hz, 1H), 7.13-7.10 (m, 1H), 6.90-6.84 (m, 1H), 5.30-5.20 (m, 1H), 4.27-4.20 (m, 1H), 2.07 (s, 3H), 1.29 (d, J = 7.1 Hz, 3H), 1.22 (d, J = 7.1 Hz, 3H). |
| 348 | $^1$H NMR (300 MHz, DMSO-$d_6$) δ 12.30 (s, 1H), 8.15 (d, J = 5.6 Hz, 1H), 7.81 (d, J = 7.7 Hz, 1H), 7.45-7.37 (m, 1H), 7.22 (d, J = 5.6 Hz, 1H), 7.23-7.11 (m, 1H), 7.08-7.01 (m, 1H), 5.22-5.13 (m, 1H), 4.18-4.11 (m, 1H), 2.41 (s, 3H), 1.26 (d, J = 7.1 Hz, 6H). |
| 355 | $^1$HNMR (300 MHz, DMSO-d6, ppm): δ 12.39 (s, 1H), 8.57-8.52 (m, 2H), 7.51-7.43 (m, 2H), 7.21-7.14 (m, 2H), 7.09-7.03 (m, 2H), 5.13-5.03 (m, 1H), 3.69 (s, 2H), 2.72 (s, 3H), 1.37-1.23 (m, 3H). |
| 359 | $^1$H NMR (300 MHz, DMSO-$d_6$): δ 12.08 (s, 1H), 8.59 (d, J = 7.7 Hz, 1H), 7.88 (d, J = 8.7 Hz, 1H), 7.60-7.35 (m, 2H), 7.26-6.99 (m, 2H), 5.03-5.13 (m, 1H), 3.74-3.56 (m, 2H), 2.36 (s, 3H), 1.35 (d, J = 7.0 Hz, 3H). |
| 360 | $^1$H NMR (300 MHz, DMSO-$d_6$) δ 12.55 (s, 1H), 8.62-8.57 (m, 2H), 7.90 (s, 1H), 7.45 (d, J = 6.0 Hz, 2H), 7.28-7.98 (m, 2H), 5.18-5.01 (m, 1H), 4.08-3.87 (m, 1H), 1.39-1.28 (m, 6H). |

TABLE 2-A-continued

| NMR | |
|---|---|
| Cmpd No. | NMR |
| 361 | $^1$H NMR (300 MHz, DMSO-$d_6$) δ 12.56 (s, 1H), 8.62-8.57 (m, 2H), 7.69 (s, 1H), 7.45 (d, J = 6.0 Hz, 1H), 7.40-7.32 (m, 1H), 7.17-7.10 (m, 1H), 6.96-6.89 (m, 1H), 5.13-5.14 (m, 1H), 4.01-3.94 (m, 1H), 1.37-1.33 (m, 6H). |
| 363 | $^1$H NMR (400 MHz, Methanol-$d_4$) δ 8.52 (dd, J = 5.6, 2.4 Hz, 1H), 7.47-7.35 (m, 1H), 7.30-7.28 (m, 1H), 6.91-6.84 (m, 2H), 5.27-5.24 (m 1H), 4.31-4.24(m 1H), 2.83 (s, 1H), 2.67 (s, 2H), 1.48-1.35 (m, 6H); |
| 367 | $^1$H NMR (400 MHz, DMSO-$d_6$) δ 12.44 (s, 1H), 8.55 (d, J = 6.8 Hz, 1H), 8.07 (d, J = 6.0 Hz, 1H), 7.57 (s, 1H), 7.41-7.35 (m, 1H), 7.16-7.11 (m, 2H), 6.94-6.90 (m, 1H), 5.10-5.03 (m, 1H), 3.93-3.88 (m, 1H), 1.34-1.23 (m, 6H). |
| 368 | $^1$H NMR (400 MHz, DMSO-$d_6$) δ 12.44 (s, 1H), 8.57 (d, J = 7.2 Hz, 1H), 8.07 (d, J = 6.0 Hz, 1H), 7.57 (s, 1H), 7.41-7.35 (m, 1H), 7.16-7.11 (m, 2H), 6.94-6.90 (m, 1H), 5.10-5.03 (m, 1H), 3.93-3.88 (m, 1H), 1.34-1.23 (m, 6H). |
| 369 | $^1$H NMR (300 MHz, DMSO-d6) δ 12.20 (s, 1H), 7.98 (d, J = 8.4 Hz, 1H), 7.87-7.80 (m, 2H), 7.31-7.23 (m, 1H), 7.17-7.09 (m, 1H), 6.89-6.83 (m, 1H), 5.21-5.16 (m, 1H), 4.14-4.07 (m, 1H), 2.30 (s, 3H), 1.29-1.05 (m, 6H). |
| 370 | $^1$H NMR (300 MHz, DMSO-d6) δ 12.18-12.08 (m, 1H), 7.98 (d, J = 8.4 Hz, 1H), 7.85-7.82 (m, 2H), 7.45-7.37 (m, 1H), 7.19-7.01 (m, 2H), 5.20-5.14 (m, 1H), 4.09-4.01 (m, 1H), 2.50 (s, 3H), 1.30-1.22 (m, 6H). |
| 375 | $^1$H NMR (400 MHz, DMSO-$d_6$) δ 12.27 (s, 1H), 8.05-8.03 (m, 1H), 7.81 (d, J = 8.0 Hz, 1H), 7.43-7.37 (m, 1H), 7.18-7.12 (m, 2H), 7.06-7.02 (m, 1H), 5.18-5.15 (m, 1H), 4.14-4.09 (m, 1H), 2.41 (d, J = 6.4 Hz, 3H), 1.25-1.23 (m, 6H). |
| 376 | $^1$H NMR (400 MHz, DMSO-$d_6$) δ 12.27 (s, 1H), 8.05 (dd, J = 5.6, 1.2 Hz, 1H), 7.86 (d, J = 8.0 Hz, 1H), 7.31-7.25 (m, 1H), 7.18-7.11 (m, 2H), 6.95-6.90 (m, 1H), 5.22-5.20 (m, 1H), 4.22-4.17 (m, 1H), 2.15 (s, 3H), 1.29 (d, J = 8.0 Hz, 3H), 1.23 (d, J = 7.2 Hz, 3H). |
| 377 | $^1$H NMR (300 MHz, DMSO-$d_6$): δ 12.04 (s, 1H), 8.59-8.49 (m, 2H), 7.51-7.43 (m, 2H), 7.17-7.01 (m, 2H), 5.14-5.05 (m, 1H), 3.69 (s, 2H), 2.38 (s, 3H), 1.36-1.34 (d, J = 7.04 Hz, 3H). |
| 382 | $^1$H NMR (300 MHz, DMSO-$d_6$): 11.98(s, 1H), 8.52 (d, J = 7.5, 1H), 7.85-7.80(m, 1H), 7.52-7.49(m, 1H), 7.47-7.44(m, 1H), 7.34-7.21(m, 1H), 7.20-7.02(m, 1H), 5.12-5.05(m, 1H), 3.63(s, 2H), 2.37(s, 3H), 1.40(s, 3H) |
| 383 | $^1$H NMR (300 MHz, DMSO-$d_6$) δ 12.08 (s, 1H), 8.56 (d, J = 7.8 Hz, 1H), 8.05 (d, J = 6.0 Hz, 1H), 7.75 (s, 1H), 7.51-7.43 (m, 1H), 7.17-7.13 (m, 1H), 7.07-7.00 (m, 1H), 6.87 (d, J = 6.0 Hz, 1H), 5.11-5.06 (m, 1H), 4.43-4.36 (m, 1H), 3.35 (s, 2H), 1.34 (d, J = 7.2 Hz, 3H), 0.80-0.76 (m, 2H), 0.72-0.69 (m, 2H). |
| 386 | $^1$H NMR (400 MHz, DMSO-$d_6$) δ 11.96 (s, 1H), 8.43 (d, J = 7.6 Hz, 1H), 8.01 (d, J = 5.6 Hz, 1H), 7.47-7.41 (m, 1H), 7.19-7.14 (m, 1H), 7.07-7.02 (m, 1H), 6.87 (d, J = 5.6 Hz, 1H), 5.10-5.03 (m, 1H), 4.42-4.37 (m, 1H), 3.32 (s, 1H), 2.36 (s, 3H), 1.34 (d, J = 6.8 Hz, 3H), 0.80-0.78 (m, 2H), 0.77-0.76 (m, 2H). |
| 387 | $^1$H NMR (300 MHz, DMSO-$d_6$): 8.61 (d, J = 7.5, 1H), 8.06 (d, J = 8.7, 1H), 7.93 (d, J = 8.7, 1H), 7.44 (d, J = 6.9, 1H), 7.20-7.08(m, 2H), 5.07 (t, J = 7.2, 1H), 3.93(s, 2H), 1.36(d, J = 6.9, 3H) |
| 391 | $^1$H NMR (400 MHz, DMSO-$d_6$) δ 12.28 (s, 1H), 8.49 (d, J = 7.6 Hz, 1H), 8.04-8.03 (m, 1H), 7.49-7.43 (m, 1H), 7.20-7.13 (m, 2H), 7.08-7.03 (m, 1H), 5.10-5.06 (m, 1H), 3.63 (d, J = 2.4 Hz, 2H), 2.41 (d, J = 6.0 Hz, 3H), 1.35 (d, J = 7.2 Hz, 3H). |
| 392 | $^1$H NMR (300 MHz, DMSO-$d_6$) δ 12.10 (s, 1H), 8.60 (d, J = 7.8 Hz, 1H), 7.84 (dd, J = 8.7, 7.5 Hz, 1H), 7.73 (s, 1H), 7.53-7.45 (m, 1H), 7.31 (dd, J = 8.7, 2.7 Hz, 1H), 7.21-7.13 (m, 1H), 7.07-7.01 (m, 1H), 5.14-5.05 (m, 1H), 3.49 (s, 2H), 1.36-1.34 (m, 3H). |
| 394 | $^1$H NMR (400 MHz, DMSO-$d_6$) δ12.39 (s, 1H), 8.58 (d, J = 7.6 Hz, 1H), 8.07 (d, J = 5.6 Hz, 1H), 7.85 (s, 1H), 7.53-7.43 (m, 1H), 7.23-7.12 (m, 2H), 7.09-7.00 (m, 1H), 5.21-5.02 (m, 1H), 3.48 (s, 2H), 1.36 (d, J = 7.0 Hz, 3H). |
| 398 | $^1$H NMR (300 MHz, DMSO-$d_6$) δ 11.98 (s, 1H), 8.27 (d, J = 5.2 Hz, 1H), 7.90 (d, J = 8.0 Hz, 1H), 7.37-7.29 (m, 1H), 7.21-7.12 (m, 2H), 7.01-6.96 (m, 1H), 5.26-5.21 (m, 1H), 4.26-4.21 (m, 1H), 2.78 (d, J = 2.8 Hz, 3H), 2.22 (s, 3H), 1.27 (m, 6H). |
| 399 | $^1$H NMR (400 MHz, DMSO-$d_6$): $^1$H NMR (300 MHz, DMSO-$d_6$) δ 11.94 (s, 1H), 8.25 (d, J = 5.5 Hz, 1H), 7.83 (d, J = 7.8 Hz, 1H), 7.47-7.39 (m, 1H), 7.20-7.02 (m, 3H), 5.23-5.13 (m, 1H), 4.19-4.12 (m, 1H), 2.88 (s, 3H), 2.50 (s, 3H), 1.28-1.26 (m, 6H). |
| 405 | $^1$H NMR (400 MHz, DMSO-$d_6$) δ 12.19 (s, 1H), 9.00 (d, J = 8.0 Hz, 1H), 8.34 (d, J = 5.6 Hz, 1H), 7.77-7.57 (m, 1H), 7.21-7.15 (m, 1H), 7.08-7.03 (m, 2H), 5.21-5.14 (m, 1H), 2.87 (s, 3H), 2.74 (d, J = 4.0 Hz, 3H), 1.43 (d, J = 7.2 Hz, 3H). |
| 410 | $^1$H NMR (400 MHz, Methanol-$d_4$) δ 8.33 (d, J = 5.6 Hz, 1H), 7.83 (d, J = 7.2 Hz, 1H), 7.40-7.34 (m, 1H), 7.17 (d, J = 5.6 Hz, 1H), 6.90-6.84 (m, 2H), 5.25-5.21 (m, 1H), 3.99-3.94 (m, 1H), 2.74-2.72 (m, 3H), 1.62-1.60 (m, 3H), 1.45 (d, J = 7.2 Hz, 3H). |
| 411 | $^1$H NMR (300 MHz, DMSO-$d_6$): 11.88 (s, 1H), 7.96(d, J = 5.4, 1H), 7.56-7.45(m, 2H), 7.17-6.98(m, 2H), 6.81 ((d, J = 5.7, 1H), 5.18-5.13(m, 1H), 4.26-4.19(m, 1H), 3.96 (s, 3H), 2.13-2.10 (m, 1H), 1.36 (d, J = 6.9, 2H), 1.06 (d, J = 6.6, 3H), 1.03 (d, J = 3.9, 3H), 0.67-0.63 (m, 1H), 0.49-0.46 (m, 1H). |
| 412 | $^1$H NMR (300 MHz, DMSO-$d_6$): 11.88 (s, 1H), 7.96(d, J = 5.4, 1H), 7.56-7.45(m, 2H), 7.17-6.98(m, 2H), 6.81 ((d, J = 5.7, 1H), 5.18-5.13(m, 1H), 4.26-4.19(m, 1H), 3.96 (s, 3H), 2.13-2.10 (m, 1H), 1.36 (d, J = 6.9, 2H), 1.06 (d, J = 6.6, 3H), 1.03 (d, J = 3.9, 3H), 0.67-0.63 (m, 1H), 0.49-0.46 (m, 1H) |
| 413 | $^1$H NMR (400 MHz, Methanol-$d_4$) δ 8.29 (d, J = 5.6 Hz, 1H), 7.85 (d, J = 7.6 Hz, 1H), 7.48-7.42 (m, 1H), 7.08 (d, J = 5.6 Hz, 1H), 6.90-6.84 (m, 2H), 5.27-5.20 (m, 1H), 4.00-3.94 (m, 1H), 2.71-2.70 (m, 3H), 1.63-1.61 (m, 3H), 1.41 (d, J = 7.2 Hz, 3H). |
| 418 | $^1$H NMR (400 MHz, DMSO-$d_6$) δ 12.09 (s, 1H), 9.11 (d, J = 6.0, 1H), 8.55 (d, J = 7.6 Hz, 1H), 7.50-7.44 (m, 1H), 7.36 (d, J = 6.0, 1H), 7.19-7.14 (m, 1H), 7.08-7.04 (m, 1H), 5.10-5.06 (m, 1H), 3.66 (s, 2H), 2.57 (s, 3H), 1.36 (d, J = 6.8 Hz, 3H). |
| 419 | $^1$H NMR (400 MHz, DMSO-$d_6$) δ 12.38 (s, 1H), 8.57 (d, J = 7.6 Hz, 1H), 7.64 (d, J = 8.4 Hz, 1H), 7.48-7.41 (m, 2H), 7.21-7.15 (m, 1H), 7.10-7.05 (m, 1H), 5.09-5.05 (m, 1H), 3.89 (s, 2H), 2.52 (s, 3H), 1.35 (d, J = 7.1 Hz, 3H). |
| 420 | $^1$H NMR (400 MHz, DMSO-d6) δ 11.74 (s, 1H), 8.48 (d, J = 7.6 Hz, 1H), 7.56-7.03 (m, 5H), 5.05-5.09 (m, 1H), 3.60 (s, 2H), 2.53 (s, 3H), 2.45 (s, 3H), 1.35 (m, 3H). |
| 421 | $^1$H NMR (400 MHz, DMSO-$d_6$) δ 12.23 (s, 1H), δ 8.57 (d, J = 7.6 Hz, 1H), 8.26 (d, J = 5.2 Hz, 1H), 7.46 (q, J = 8.0 Hz, 1H), 7.21-7.15 (m, 1H), 7.09-7.04 (m, 1H), 6.98 (d, J = 5.2 Hz, 1H), 5.08-5.02 (m, 1H), 3.73 (s, 2H), 2.10 (s, 1H), 1.34 (d, J = 6.8 Hz, 3H), 1.13 (s, 2H), 1.02 (dd, J = 7.6, 3.2 Hz, 2H). |

TABLE 2-A-continued

| NMR | |
|---|---|
| Cmpd No. | NMR |
| 423 | $^1$H NMR (400 MHz, DMSO-$d_6$) δ 12.50 (s, 1H), 8.50 (d, J = 7.6 Hz, 1H), 8.09 (d, J = 5.6 Hz, 1H), 7.44 (dd, J = 15.2, 8.8 Hz, 1H), 7.20-7.14 (m, 1H), 7.17-7.04 (m, 1H), 6.91 (d, J = 6.0 Hz, 1H), 5.07-5.02 (m, 1H), 3.93 (s, 3H), 3.82-3.71 (m, 2H), 1.34 (d, J = 6.8 Hz, 3H). |
| 426 | $^1$H NMR (400 MHz, DMSO-$d_6$) δ 12.63 (s, 1H), 8.92 (d, J = 2.4 Hz, 1H), 8.56 (d, J = 5.6 Hz, 1H), 7.80 (d, J = 7.6 Hz, 1H), 7.41-7.35 (m, 1H), 7.32 (d, J = 5.6 Hz, 1H), 7.18-7.12 (m, 1H), 7.17-7.00 (m, 1H), 5.17-5.10 (m, 1H), 4.30-4.25 m, 1H), 1.37 (d, J = 6.8 Hz, 3H), 1.26 (d, J = 7.2 Hz, 3H). |
| 427 | $^1$H NMR (400 MHz, DMSO-$d_6$) δ 12.65 (s, 1H), 8.91 (d, J = 2.4 Hz, 1H), 8.56 (d, J = 5.6 Hz, 1H), 7.77 (d, J = 8.0 Hz, 1H), 7.39-7.33 (m, 2H), 7.16-7.11 (m, 1H), 7.01-6.96 (m, 1H), 5.20-5.12 (m, 1H), 4.29-4.24 (m, 1H), 1.37 (d, J = 6.8 Hz, 3H), 1.30 (d, J = 7.2 Hz, 3H). |
| 429 | $^1$H NMR (300 MHz, DMSO-$d_6$): 11.85 (s, 1H), 8.5 (d, J = 5.4, 1H), 8.2 (d, J = 7.5, 1H), 7.57-7.49(m, 1H), 7.20-7.08(m, 1H), 7.07-7.00 (m, 1H), 5.09 (t, J = 7.2, 1H), 3.73 (d, J = 1.2, 2H), 2.92 (s, 3H), 2.17-2.13 (m, 1H), 1.36 (d, J = 6.9, 2H), 1.12-1.09 (m, 2H) |
| 430 | $^1$H NMR (400 MHz, Methanol-$d_4$) δ 8.30 (d, J = 5.6 Hz, 1H), 7.46-7.30 (m, 1H), 7.11 (d, J = 5.6 Hz, 1H), 6.94-6.93 (m, 1H), 6.91-6.86 (m, 1H), 5.20-5.14 (m, 1H), 3.94-3.83 (m, 2H), 2.70 (s, 3H), 1.46 (d, J = 7.2 Hz, 3H). |
| 431 | $^1$H NMR (400 MHz, DMSO-$d_6$) δ 12.04 (s, 1H), 8.62 (d, J = 7.6 Hz, 1H), 8.40 (d, J = 5.6 Hz, 1H), 8.01 (s, 1H), 7.51-7.44 (m, 1H), 7.21-7.14 (m, 2H), 7.06-7.02 (m, 1H), 5.11-5.08 (m, 1H), 4.75 (s, 1H), 3.49 (s, 2H), 1.35 (d, J = 7.2 Hz, 3H). |
| 432 | $^1$H NMR (300 MHz, DMSO-$d_6$) δ 12.00 (s, 1H), 8.58 (d, J = 7.5 Hz, 1H), 8.29-8.21 (m, 2H), 7.50 (d, J = 6.6 Hz, 1H), 7.11-6.98 (m, 1H), 6.97-6.95 (m, 2H), 5.10 (s, 1H), 3.46 (s, 2H), 2.51-2.50 (m, 1H), 1.36 (d, J = 6.9 Hz, 3H), 1.05-0.99 (m, 4H). |
| 434 | $^1$H NMR (300 MHz, DMSO-d6) δ 12.09 (s, 1H), 8.57 (d, J = 7.5 Hz, 1H), 8.02 (d, J = 5.7 Hz, 1H), 7.85 (s, 1H), 7.51-7.43 (m, 1H), 7.21-7.17 (m, 1H), 7.15-7.14 (m, 1H), 6.85 (d, J = 6.0 Hz, 1H), 5.11-5.06 (m, 1H), 3.96 (s, 3H), 1.35 (d, J = 7.2 Hz, 3H). |
| 435 | $^1$H NMR (300 MHz, DMSO-$d_6$) δ 12.49 (s, 1H), 8.64 (d, J = 7.5 Hz, 1H), 8.55 (d, J = 5.7 Hz, 1H), 7.96 (s, 1H), 7.52-7.44 (m, 2H), 7.21-7.14 (m, 1H), 7.07-7.04 (m, 1H), 5.12-5.07 (m, 1H), 3.54 (s, 2H), 1.36 (d, J = 7.2 Hz, 3H). |
| 438 | $^1$H NMR (300 MHz, DMSO-$d_6$) δ 12.41 (s, 1H), 9.08 (s, 1H), 8.73 (d, J = 7.8 Hz, 1H), 8.50 (d, J = 5.7 Hz, 1H), 7.61-7.26 (m, 3H), 7.21-7.13 (m, 1H), 7.08-7.01 (m, 1H), 5.09-5.04 (m, 1H), 3.82 (s, 2H), 1.35 (d, J = 6.9 Hz, 3H). |
| 440 | $^1$H NMR (300 MHz, DMSO-$d_6$) δ 11.96 (s, 1H), 9.02-8.85 (m, 1H), 8.57-8.38 (m, 1H), 7.95-7.72 (m, 1H), 7.56-7.29 (m, 1H), 7.28-7.17 (m, 2H), 7.16-6.94 (m, 1H), 5.33-5.01 (m, 1H), 4.28-4.02 (m, 1H), 2.49 (s, 2H), 2.29 (s, 1H), 1.40-1.28 (m, 6H). |
| 441 | $^1$H NMR (400 MHz, DMSO-$d_6$) δ 12.07 (s, 1H), 8.78 (s, 1H), 8.57 (d, J = 7.6 Hz, 1H), 8.43 (d, J = 5.6 Hz, 1H), 7.84 (s, 1H), 7.51-7.45 (m, 1H), 7.20-7.14 (m, 2H), 7.07-7.02 (m, 1H), 5.11-5.07 (m, 1H), 3.43 (s, 2H), 1.35 (d, J = 6.8 Hz, 3H). |
| 442 | $^1$H NMR (400 MHz, DMSO-$d_6$) δ 12.07 (s, 1H), 8.52 (d, J = 7.6 Hz, 1H), 8.29 (d, J = 5.6 Hz, 1H), 7.90 (s, 1H), 7.49-7.43 (m, 1H), 7.20-7.15 (m, 1H), 7.09-7.06 (m, 2H), 5.13-5.06 (m, 1H), 3.93-3.88 (m, 1H), 2.67 (s, 3H), 1.33-1.23 (m, 6H). |
| 443 | $^1$H NMR (400 MHz, DMSO-$d_6$) δ 12.10 (s, 1H), 8.76 (s, 1H), 8.54 (d, J = 7.6 Hz, 1H), 8.43 (d, J = 5.6 Hz, 1H), 7.72 (s, 1H), 7.45-7.39 (td, J = 8.7, 6.6 Hz, 1H), 7.18-7.12 (m, 2H), 6.95-6.90 (m, 1H), 5.09-5.02 (m, 1H), 3.93-3.87 (m, 1H), 1.36-1.32 (m, 6H). |
| 444 | $^1$H NMR (300 MHz, Methanol-$d_4$) δ 9.34 (s, 1H), 8.41 (d, J = 5.7 Hz, 1H), 7.48-7.43 (m, 1H), 7.24 (d, J = 5.7 Hz, 1H), 6.94-6.86 (m, 2H), 5.20-5.18 (m, 1H), 3.90 (s, 2H), 2.12-1.90 (m, 1H), 1.47 (d, J = 6.9 Hz, 3H), 1.25-1.22 (m, 2H), 0.75-0.70 (m, 2H). |
| 445 | $^1$H NMR (400 MHz, DMSO-$d_6$) δ 12.03 (s, 1H), 8.57 (d, J = 7.6 Hz, 1H), 8.28 (d, J = 5.7 Hz, 1H), 7.97 (s, 1H), 7.49 (td, J = 8.7, 6.5 Hz, 1H), 7.18 (ddd, J = 11.4, 9.2, 2.5 Hz, 1H), 7.05 (dd, J = 8.6, 5.9 Hz, 2H), 5.11 (q, J = 7.2 Hz, 1H), 3.46 (s, 2H), 2.63 (s, 3H), 2.54-2.48 (m, 2H), 1.36 (d, J = 7.0 Hz, 3H). |
| 446 | $^1$H NMR (400 MHz, DMSO-d6) δ 11.91 (s, 1H), 8.82 (s, 1H), 8.48 (d, J = 7.7 Hz, 1H), 7.75-7.44 (m, 1H), 7.19-7.13 (m, 1H), 7.07-6.97 (m, 2H), 5.08-5.04 (m, 1H), 3.59 (d, J = 3.0 Hz, 2H), 2.50 (s, 3H), 2.38 (s, 3H), 1.34 (d, J = 7.0 Hz, 3H). |
| 447 | $^1$H NMR (400 MHz, DMSO-$d_6$) δ 12.62 (s, 1H), 8.88-8.86 (m, 1H), 8.62 (d, J = 7.6 Hz, 1H), 8.55 (d, J = 5.6 Hz, 1H), 7.47-7.43 (m, 1H), 7.32 (d, J = 5.6 Hz, 1H), 7.31-7.15 (m, 1H), 7.10-7.05 (m, 1H), 5.10-5.03 (m, 1H), 3.93-3.82 (m, 2H), 1.35 (d, J = 7.2 Hz, 3H). |
| 448 | $^1$H NMR (300 MHz, DMSO-$d_6$) δ 8.98 (s, 1H), 8.45 (d, J = 5.7 Hz, 1H), 7.48-7.43 (m, 1H), 7.27 (d, J = 5.7 Hz, 1H), 6.95-6.88 (m, 2H), 5.24-5.17 (m, 1H), 3.78 (s, 2H), 2.55 (s, 3H), 1.48 (d, J = 7.2 Hz, 3H). |
| 462 | $^1$H NMR (300 MHz, DMSO-$d_6$) δ 11.84 (s, 1H), 8.88 (s, 1H), 8.69 (d, J = 7.2 Hz, 1H), 8.40-8.37 (m, 1H), 7.73 (s, 1H), 7.56 (d, J = 8.4 Hz, 1H), 7.34 (d, J = 8.4 Hz, 1H), 5.34-5.19 (m, 1H), 3.53-3.39 (m, 2H), 2.51-2.49 (m, 3H), 1.40 (d, J = 6.9 Hz, 3H). |
| 463 | $^1$H NMR (300 MHz, DMSO-$d_6$) δ 11.84 (s, 1H), 8.88 (s, 1H), 8.69 (d, J = 7.2 Hz, 1H), 8.40-8.37 (m, 1H), 7.73 (s, 1H), 7.56 (d, J = 8.4 Hz, 1H), 7.34 (d, J = 8.4 Hz, 1H), 5.34-5.19 (m, 1H), 3.53-3.39 (m, 2H), 2.51-2.49 (m, 3H), 1.40 (d, J = 6.9 Hz, 3H). |
| 466 | $^1$H NMR (300 MHz, DMSO-d6) δ 11.97 (s, 1H), 8.96 (d, J = 1.2 Hz, 2H), 8.56 (d, J = 7.5 Hz, 1H), 8.45 (d, J = 5.7 Hz, 1H), 8.26 (dd, J = 8.1, 2.1 Hz, 1H), 7.61 (dd, J = 8.4, 0.9 Hz, 1H), 7.19 (dd, J = 5.7, 0.6 Hz, 1H), 4.97 (m, 1H), 3.66 (d, J = 3.0 Hz, 2H), 2.44 (s, 3H), 1.41 (d, J = 7.2 Hz, 3H). |
| 467 | $^1$H NMR (300 MHz, DMSO-d6) δ 11.99 (s, 1H), 8.96 (d, J = 1.5 Hz, 2H), 8.57 (d, J = 7.5 Hz, 1H), 8.45 (d, J = 5.7 Hz, 1H), 8.26 (m, 1H), 7.65-7.57 (m, 1H), 7.18 (d, J = 5.7 Hz, 1H), 4.96 (m, 1H), 3.65 (d, J = 3.0 Hz, 2H), 2.44 (s, 3H), 1.40 (d, J = 7.2 Hz, 3H). |
| 470 | $^1$H NMR (300 MHz, DMSO-d6) δ 12.49 (s, 1H), 8.67-8.50 (m, 2H), 8.36 (d, J = 1.5 Hz, 1H), 7.99 (s, 1H), 7.43 (dd, J = 24.3, 6.0 Hz, 2H), 4.91 (m, 1H), 3.60 (s, 2H), 2.27 (d, J = 1.5 Hz, 3H), 1.39 (d, J = 6.9 Hz, 3H). |
| 471 | $^1$H NMR (300 MHz, DMSO-d6) δ 8.65-8.50 (m, 2H), 8.36 (d, J = 1.5 Hz, 1H), 7.98 (s, 1H), 7.42 (m, 2H), 4.91 (m, 1H), 3.59 (s, 2H), 2.27 (d, J = 1.5 Hz, 3H), 1.39 (d, J = 6.9 Hz, 3H). |
| 474 | $^1$H NMR (300 MHz, DMSO-d6) δ 12.54 (s, 1H), 8.61-8.56 (m, 2H), 8.50 (d, J = 2.7 Hz, 1H), 7.98 (s, 1H), 7.70-7.63 (m, 1H), 7.51-7.45 (m, 2H), 4.98 (p, J = 7.2 Hz, 1H), 3.59 (s, 2H), 1.40 (d, J = 7.2 Hz, 3H). |

TABLE 2-A-continued

| NMR | |
|---|---|
| Cmpd No. | NMR |
| 475 | $^1$H NMR (300 MHz, DMSO-d6) δ 12.55 (s, 1H), δ 8.59 (t, J = 7.5 Hz, 2H), 8.50 (d, J = 2.7 Hz, 1H), 7.98 (s, 1H), 7.70-7.63 (m, 1H), 7.51-7.45 (m, 2H), 4.98 (p, J = 7.2 Hz, 1H), 3.59 (s, 2H), 1.40 (d, J = 7.2 Hz, 3H). |
| 476 | $^1$H NMR (300 MHz, DMSO-d6) δ 12.47 (s, 1H), 8.84 (d, J = 2.1 Hz, 1H), 8.63-8.56 (m, 2H), 8.11 (d, J = 1.5 Hz, 1H), 7.92 (s, 1H), 7.45 (d, J = 5.7 Hz, 1H), 5.25-5.20 (m, 1H), 3.58-3.52 (m, 2H), 2.40 (s, 3H), 1.37 (d, J = 6.9 Hz, 3H). |
| 477 | $^1$H NMR (300 MHz, DMSO-d6) δ 12.47 (s, 1H), 8.84 (d, J = 2.1 Hz, 1H), 8.63-8.55 (m, 2H), 8.11 (d, J = 2.1 Hz, 1H), 7.92 (s, 1H), 7.44 (d, J = 5.7 Hz, 1H), 5.23 (t, J = 6.9 Hz, 1H), 3.53 (d, J = 3.0 Hz, 2H), 2.40 (s, 3H), 1.37 (d, J = 6.8 Hz, 3H). |
| 3510 | $^1$H NMR (400 MHz, DMSO-d6) δ 12.64 (s, 1H), 9.01 (d, J = 7.2 Hz, 1H), 8.90 (s, 1H), 8.65 (d, J = 5.2 Hz, 1H), 8.42-8.39 (m, 1H), 7.48 (d, J = 5.6 Hz, 1H), 5.35-5.28 (m, 1H), 2.94 (t, J = 2.8 Hz, 3H), 1.48 (d, J = 6.8 Hz, 3H). |
| 3513 | $^1$H NMR (400 MHz, Methanol-d4) δ 8.76 (s, 1H), 8.30 (d, J = 5.6 Hz, 1H), 8.09-8.06 (m, 1H), 7.11 (d, J = 5.6 Hz, 1H), 5.51-5.45 (m, 1H), 2.94 (s, 3H), 2.85-2.83 (m, 3H), 1.58 (d, J = 6.8 Hz, 3H), 1.28 (s, 1H), 0.90-0.85 (m, 1H). |
| 3515 | $^1$H NMR (300 MHz, DMSO-d6) δ 12.64 (s, 1H), 9.02 (d, J = 7.5 Hz, 1H), 8.91 (s, 1H), 8.65 (d, J = 6.0 Hz, 1H), 8.43-8.39 (m, 1H), 7.48 (d, J = 5.4 Hz, 1H), 5.32 (s, 1H), 2.94 (t, J = 3.0 Hz, 3H), 1.49 (d, J = 7.2 Hz, 3H). |
| 3517 | $^1$H NMR (400 MHz, Methanol-d4) δ 8.76-8.75 (m, 1H), 8.30 (d, J = 5.6 Hz, 1H), 8.09-8.06 (m, 1H), 7.11 (d, J = 5.6 Hz, 1H), 5.50-5.45 (m, 1H), 2.94 (s, 3H), 2.84 (d, J = 4.4 Hz, 3H), 1.58 (d, J = 7.2 Hz, 3H), 1.28 (s, 1H), 0.91-0.85 (m, 1H). |
| 3518 | $^1$H NMR (300 MHz, DMSO-$d_6$) δ 12.54 (s, 1H), 8.63-8.60 (m, 1H), 8.57-8.54 (m, 1H), 7.93-7.78 (m, 1H), 7.51-7.33 (m, 2H), 7.23-6.89 (m, 2H), 5.11-5.08 (m, 1H), 3.99-3.97 (m, 1H), 1.35-1.27 (m, 6H). |

TABLE 3

| Cmpd No. | Structure |
|---|---|
| 4001 | 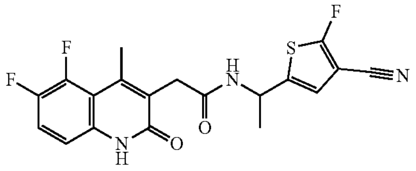 [SMILES: Cc1c(CC(=O)NC(C)c2cc(C#N)c(F)s2)c(=O)[nH]c2ccc(F)c(F)c12] |
| 4002 | 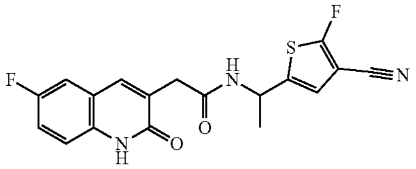 [SMILES: CC(NC(=O)Cc1cc2cc(F)ccc2[nH]c1=O)c1cc(C#N)c(F)s1] |
| 4003 | 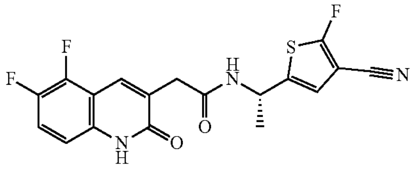 [SMILES: C[C@H](NC(=O)Cc1cc2c(F)c(F)ccc2[nH]c1=O)c1cc(C#N)c(F)s1] |
| 4004 | 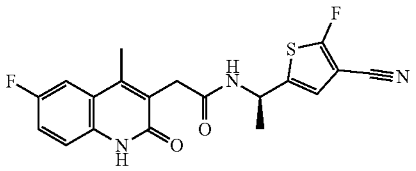 [SMILES: Cc1c(CC(=O)N[C@H](C)c2cc(C#N)c(F)s2)c(=O)[nH]c2ccc(F)cc12] |
| 4005 | 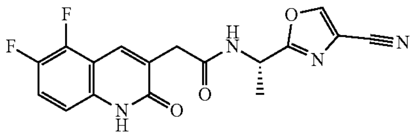 [SMILES: C[C@H](NC(=O)Cc1cc2c(F)c(F)ccc2[nH]c1=O)c1nc(C#N)co1] |

TABLE 3-continued

| Cmpd No. | Structure |
|---|---|
| 4006 | 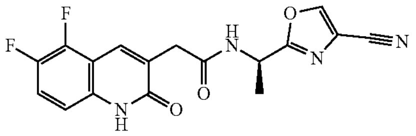 [SMILES: C[C@@H](NC(=O)Cc1cc2c(F)c(F)ccc2[nH]c1=O)c1nc(C#N)co1] |
| 4007 | 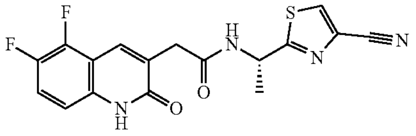 [SMILES: C[C@H](NC(=O)Cc1cc2c(F)c(F)ccc2[nH]c1=O)c1nc(C#N)cs1] |
| 4008 | 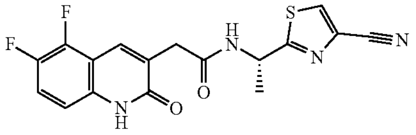 [SMILES: C[C@H](NC(=O)Cc1cc2c(F)c(F)ccc2[nH]c1=O)c1nc(C#N)cs1] |
| 4009 | 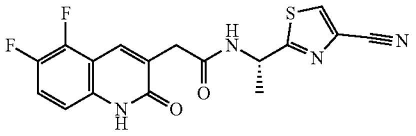 [SMILES: C[C@H](NC(=O)Cc1cc2c(F)c(F)ccc2[nH]c1=O)c1nc(C#N)cs1] |
| 4010 | 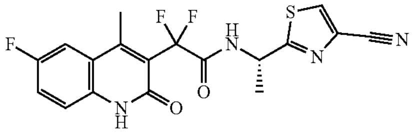 [SMILES: Cc1c(C(F)(F)C(=O)N[C@@H](C)c2nc(C#N)cs2)c(=O)[nH]c2ccc(F)cc12] |

TABLE 3A

| Cmpd No. | NMR | Mass Spec |
|---|---|---|
| 4001 | | 406 |
| 4002 | | 373.95 |
| 4003 | | 392 |
| 4004 | | 386.0 |
| 4005 | | 386.0 |
| 4006 | $^{1}$H NMR (400 MHz, DMSO-$d_6$) δ 11.95 (s, 1H), 9.05 (s, 1H), 8.75 (d, J = 7.5 Hz, 1H), 7.95 (s, 1H), 7.58 (q, J = 9.4 Hz, 1H), 7.12 (dd, J = 9.2, 3.2 Hz, 1H), 5.09 (p, J = 7.2 Hz, 1H), 3.47 (s, 2H), 1.47 (d, J = 7.2 Hz, 3H). $^{19}$F NMR (376 MHz, DMSO-$d_6$) δ −147.49 (q, J = 21.8 Hz). | 359.0 |
| 4007 | $^{1}$H NMR (400 MHz, DMSO-$d_6$) δ 12.04 (s, 1H), 9.06 (s, 1H), 8.75 (d, J = 7.6 Hz, 1H), 7.96 (s, 1H), 7.58 (dt, J = 10.4, 9.0 Hz, 1H), 7.12 (dd, J = 9.2, 3.4 Hz, 1H), 5.09 (p, J = 7.2 Hz, 1H), 3.53-3.42 (m, 2H), 1.47 (d, J = 7.2 Hz, 3H). $^{19}$F NMR (376 MHz, DMSO-$d_6$) δ −147.49 (q, J = 21.6 Hz). $^{19}$F NMR (376 MHz, DMSO-$d_6$) δ −147.49 (q, J = 21.6 Hz). | 359.1 |
| 4008 | $^{1}$H NMR (300 MHz, DMSO-$d_6$) δ 12.07 (s, 1H), 8.94 (d, J = 7.2 Hz, 1H), 8.77 (s, 1H), 7.97 (s, 1H), 7.62-7.53 (m, 1H), 7.13-7.09 (m, 1H), 5.24-5.15 (m, 1H), 3.52 (d, J = 26.7 Hz, 2H), 1.53-1.17 (m, 3H). $^{19}$F NMR (282 MHz, DMSO-d6) δ −147.37-−147.58 (2F). | 375.0 |
| 4009 | 1H NMR (300 MHz, DMSO-$d_6$) δ 12.06 (s, 1H), 8.94 (d, J = 7.5 Hz, 1H), 8.77 (s, 1H), 7.96 (s, 1H), 7.62-7.53 (m, 1H), 7.11 (d, J = 8.7 Hz, 1H), 5.24-5.14 (m, 1H), 3.52 (s, 2H), 1.53-1.23 (m, 3H). $^{19}$F NMR (282 MHz, DMSO-d6) δ −147.37-−147.58 (2F). | 375.0 |
| 4010 | $^{1}$H NMR (400 MHz, DMSO-$d_6$) δ 12.14 (s, 1H), 9.35 (d, J = 8.0 Hz, 1H), 8.80 (s, 1H), 7.82 (dd, J = 10.6, 2.8 Hz, 1H), 7.54 (td, J = 8.6, 2.4 Hz, 1H), 7.35 (dd, J = 9.0, 5.2 Hz, 1H), 5.28 (p, J = 7.2 Hz, 1H), 2.65 (t, J = 3.2 Hz, 3H), 1.60 (d, J = 7.0 Hz, 3H). $^{19}$F NMR (376 MHz, DMSO-$d_6$) δ −97.34, −119.54. | 407.0 |

TABLE 4

| Cmpd No. | Structure |
|---|---|
| 7001 | 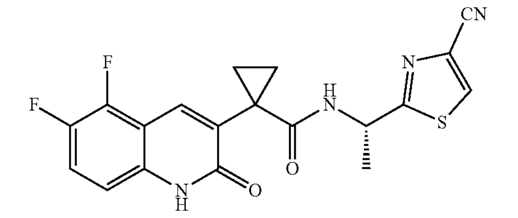 [SMILES: C[C@H](NC(=O)C1(c2cc3c(F)c(F)ccc3[nH]c2=O)CC1)c1nc(C#N)cs1] |
| 7002 | 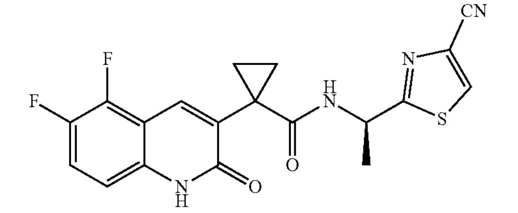 [SMILES: C[C@@H](NC(=O)C1(c2cc3c(F)c(F)ccc3[nH]c2=O)CC1)c1nc(C#N)cs1] |
| 7003 | 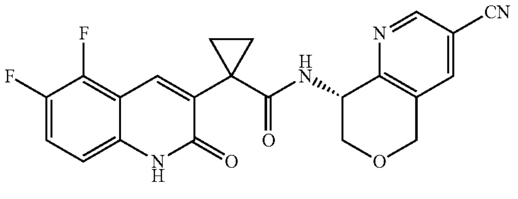 [SMILES: N#Cc1cnc2c(c1)COC[C@@H]2NC(=O)C1(c2cc3c(F)c(F)ccc3[nH]c2=O)CC1] |
| 7004 | 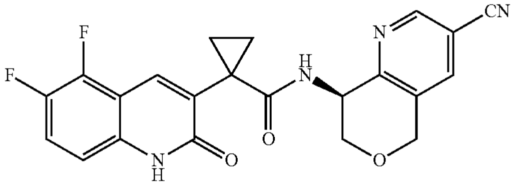 [SMILES: N#Cc1cnc2c(c1)COC[C@H]2NC(=O)C1(c2cc3c(F)c(F)ccc3[nH]c2=O)CC1] |

TABLE 4-continued

| Cmpd No. | Structure |
|---|---|
| 7005 | 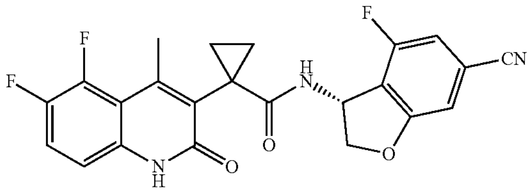 [SMILES: Cc1c(C2(C(=O)N[C@H]3COc4cc(C#N)cc(F)c43)CC2)c(=O)[nH]c2ccc(F)c(F)c12] |
| 7006 | 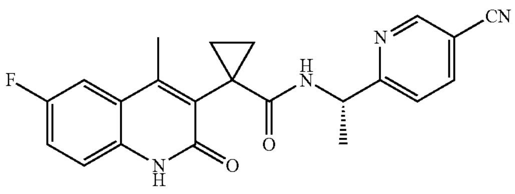 [SMILES: Cc1c(C2(C(=O)N[C@@H](C)c3ccc(C#N)cn3)CC2)c(=O)[nH]c2ccc(F)cc12] |
| 7007 | 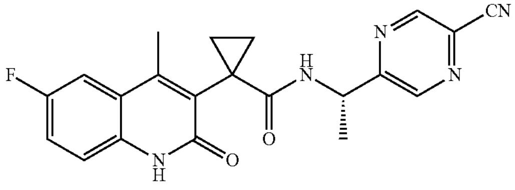 [SMILES: Cc1c(C2(C(=O)N[C@@H](C)c3cnc(C#N)cn3)CC2)c(=O)[nH]c2ccc(F)cc12] |
| 7008 | 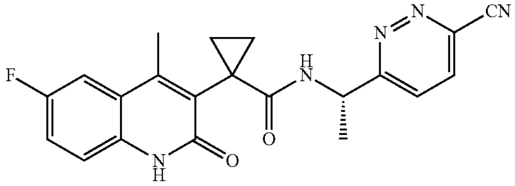 [SMILES: Cc1c(C2(C(=O)N[C@@H](C)c3ccc(C#N)nn3)CC2)c(=O)[nH]c2ccc(F)cc12] |

TABLE 4-continued
| Cmpd No. | Structure |
|---|---|
| 7009 | 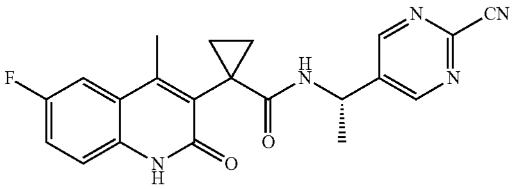 [SMILES: Cc1c(C2(C(=O)N[C@@H](C)c3cnc(C#N)nc3)CC2)c(=O)[nH]c2ccc(F)cc12] |
| 7010 | 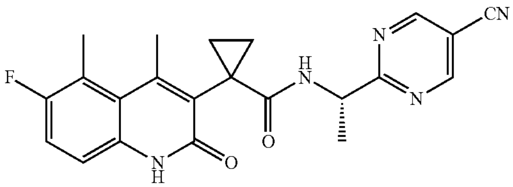 [SMILES: Cc1c(F)ccc2[nH]c(=O)c(C3(C(=O)N[C@@H](C)c4ncc(C#N)cn4)CC3)c(C)c12] |
| 7011 | 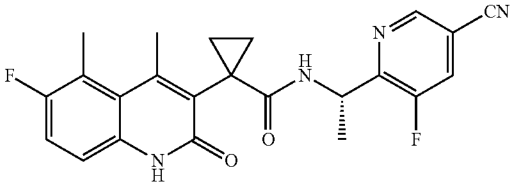 [SMILES: Cc1c(F)ccc2[nH]c(=O)c(C3(C(=O)N[C@@H](C)c4ncc(C#N)cc4F)CC3)c(C)c12] |
| 7012 | 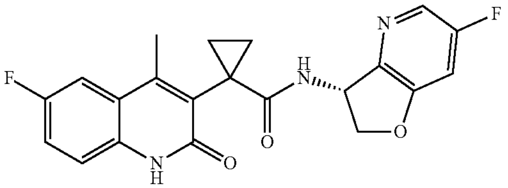 [SMILES: Cc1c(C2(C(=O)N[C@H]3COc4cc(F)cnc43)CC2)c(=O)[nH]c2ccc(F)cc12] |
| 7013 | 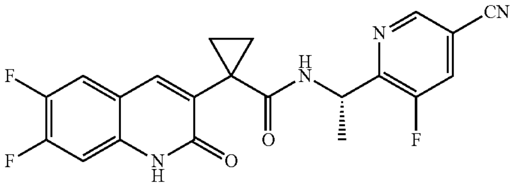 [SMILES: C[C@H](NC(=O)C1(c2cc3cc(F)c(F)cc3[nH]c2=O)CC1)c1ncc(C#N)cc1F] |
| 7014 | 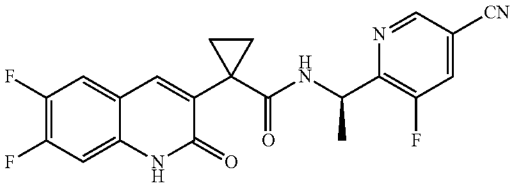 [SMILES: C[C@@H](NC(=O)C1(c2cc3cc(F)c(F)cc3[nH]c2=O)CC1)c1ncc(C#N)cc1F] |
| 7015 | 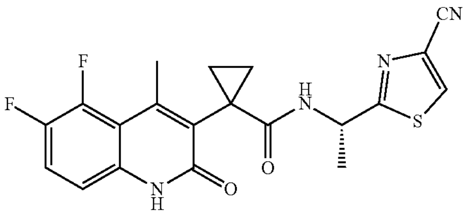 [SMILES: Cc1c(C2(C(=O)N[C@@H](C)c3nc(C#N)cs3)CC2)c(=O)[nH]c2ccc(F)c(F)c12] |
TABLE 4-continued
| Cmpd No. | Structure |
|---|---|
| 7016 | 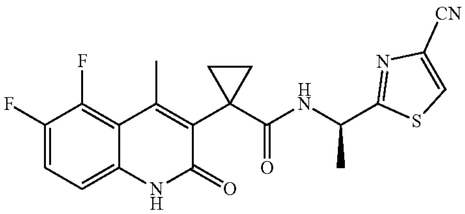 [SMILES: Cc1c(C2(C(=O)N[C@H](C)c3nc(C#N)cs3)CC2)c(=O)[nH]c2ccc(F)c(F)c12] |
| 7017 | 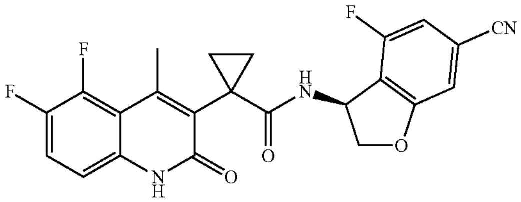 [SMILES: Cc1c(C2(C(=O)N[C@@H]3COc4cc(C#N)cc(F)c43)CC2)c(=O)[nH]c2ccc(F)c(F)c12] |
| 7018 | 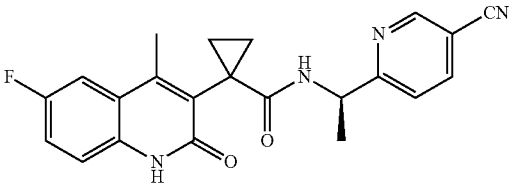 |
| 7019 | 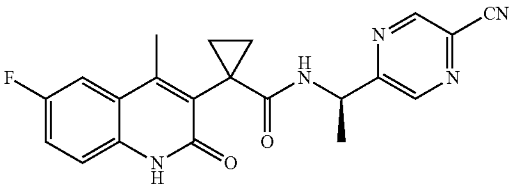 [SMILES: Cc1c(C2(C(=O)N[C@H](C)c3cnc(C#N)cn3)CC2)c(=O)[nH]c2ccc(F)cc12] |
| 7020 | 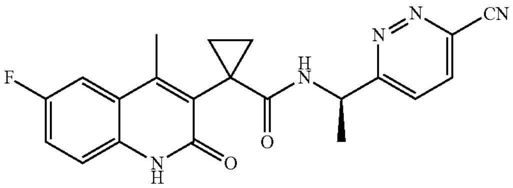 |
| 7021 | 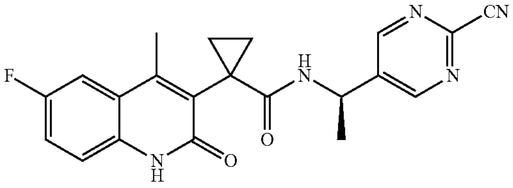 [SMILES: Cc1c(C2(C(=O)N[C@H](C)c3cnc(C#N)nc3)CC2)c(=O)[nH]c2ccc(F)cc12] |
| 7022 | 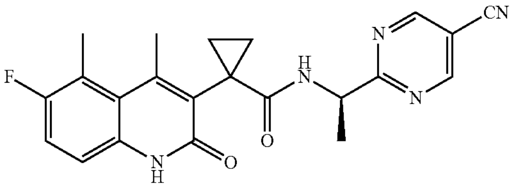 |

TABLE 4-continued
| Cmpd No. | Structure |
|---|---|
| 7023 | 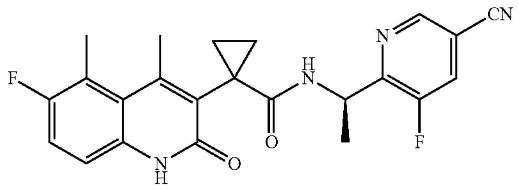 [SMILES: Cc1c(F)ccc2[nH]c(=O)c(C3(C(=O)N[C@H](C)c4ncc(C#N)cc4F)CC3)c(C)c12] |
| 7024 | 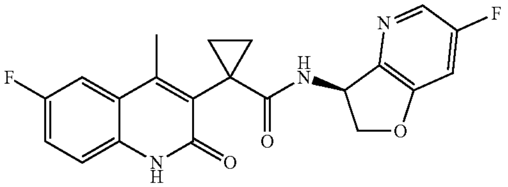 [SMILES: Cc1c(C2(C(=O)N[C@@H]3COc4cc(F)cnc43)CC2)c(=O)[nH]c2ccc(F)cc12] |
| 7025 | 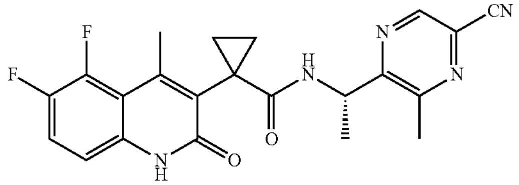 [SMILES: Cc1nc(C#N)cnc1[C@H](C)NC(=O)C1(c2c(C)c3c(F)c(F)ccc3[nH]c2=O)CC1] |
| 7026 | 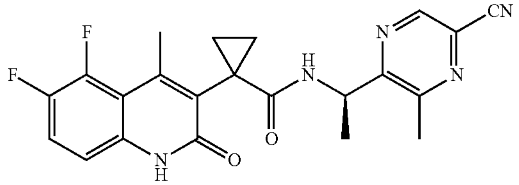 [SMILES: Cc1nc(C#N)cnc1[C@@H](C)NC(=O)C1(c2c(C)c3c(F)c(F)ccc3[nH]c2=O)CC1] |
| 7027 | 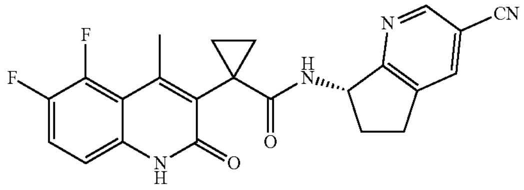 [SMILES: Cc1c(C2(C(=O)N[C@H]3CCc4cc(C#N)cnc43)CC2)c(=O)[nH]c2ccc(F)c(F)c12] |
| 7028 | 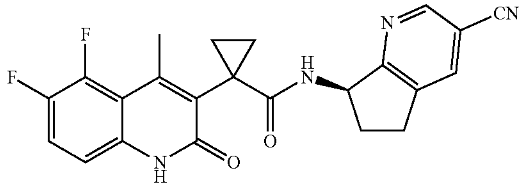 [SMILES: Cc1c(C2(C(=O)N[C@@H]3CCc4cc(C#N)cnc43)CC2)c(=O)[nH]c2ccc(F)c(F)c12] |
| 7029 | 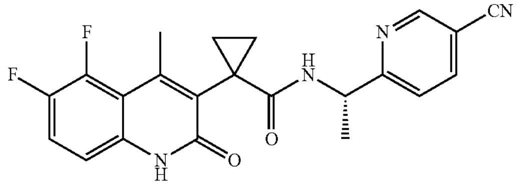 [SMILES: Cc1c(C2(C(=O)N[C@@H](C)c3ccc(C#N)cn3)CC2)c(=O)[nH]c2ccc(F)c(F)c12] |
| 7030 | 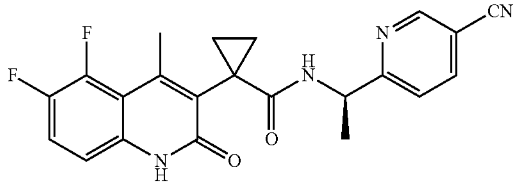 [SMILES: Cc1c(C2(C(=O)N[C@H](C)c3ccc(C#N)cn3)CC2)c(=O)[nH]c2ccc(F)c(F)c12] |
| 7031 | 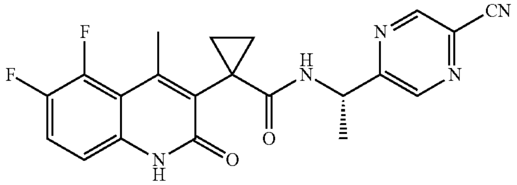 [SMILES: Cc1c(C2(C(=O)N[C@@H](C)c3cnc(C#N)cn3)CC2)c(=O)[nH]c2ccc(F)c(F)c12] |
| 7032 | 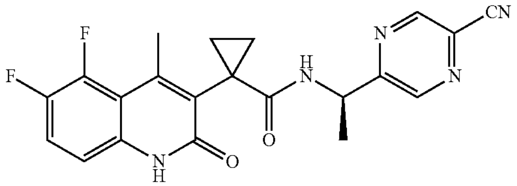 [SMILES: Cc1c(C2(C(=O)N[C@H](C)c3cnc(C#N)cn3)CC2)c(=O)[nH]c2ccc(F)c(F)c12] |
| 7033 | 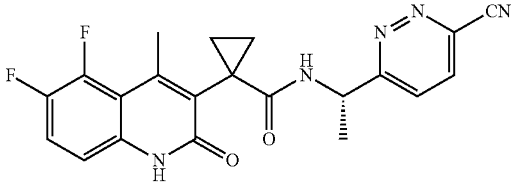 [SMILES: Cc1c(C2(C(=O)N[C@@H](C)c3ccc(C#N)nn3)CC2)c(=O)[nH]c2ccc(F)c(F)c12] |
| 7034 | 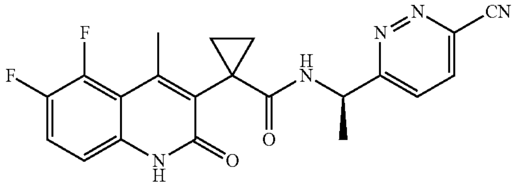 [SMILES: Cc1c(C2(C(=O)N[C@H](C)c3ccc(C#N)nn3)CC2)c(=O)[nH]c2ccc(F)c(F)c12] |
| 7035 | 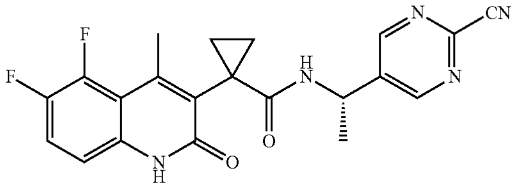 |
| 7036 | 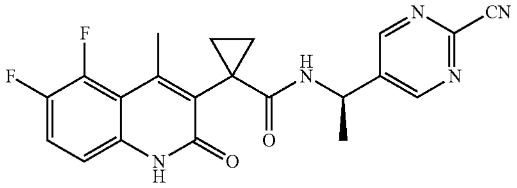 [SMILES: Cc1c(C2(C(=O)N[C@H](C)c3cnc(C#N)nc3)CC2)c(=O)[nH]c2ccc(F)c(F)c12] |
| 7037 | 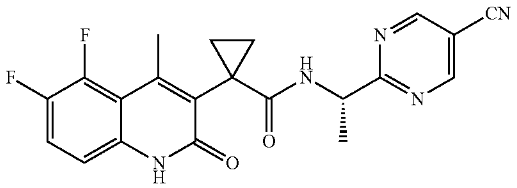 |
| 7038 | 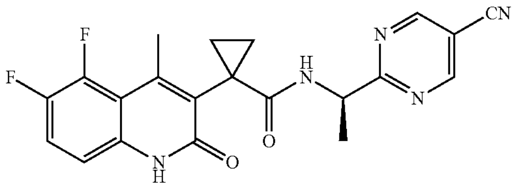 |

TABLE 4-continued
| Cmpd No. | Structure |
|---|---|
| 7039 | 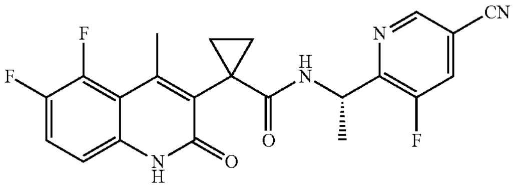 |
| 7040 | 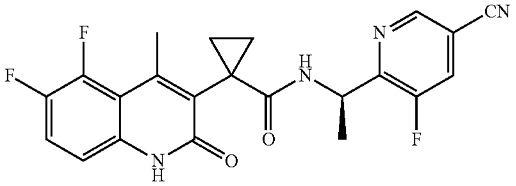 [SMILES: Cc1c(C2(C(=O)N[C@H](C)c3ncc(C#N)cc3F)CC2)c(=O)[nH]c2ccc(F)c(F)c12] |
| 7041 | 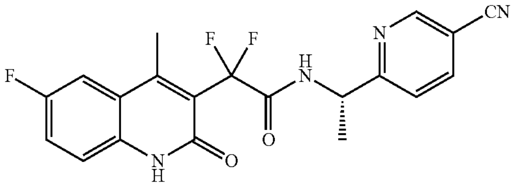 [SMILES: Cc1c(C(F)(F)C(=O)N[C@@H](C)c2ccc(C#N)cn2)c(=O)[nH]c2ccc(F)cc12] |
| 7042 | 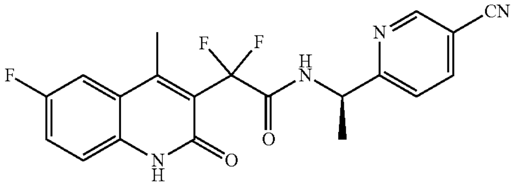 [SMILES: Cc1c(C(F)(F)C(=O)N[C@H](C)c2ccc(C#N)cn2)c(=O)[nH]c2ccc(F)cc12] |
| 7043 | 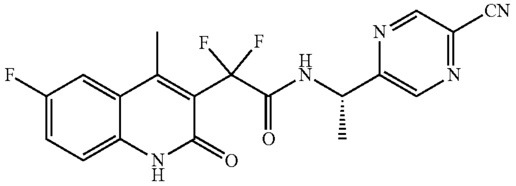 [SMILES: Cc1c(C(F)(F)C(=O)N[C@@H](C)c2cnc(C#N)cn2)c(=O)[nH]c2ccc(F)cc12] |
| 7044 | 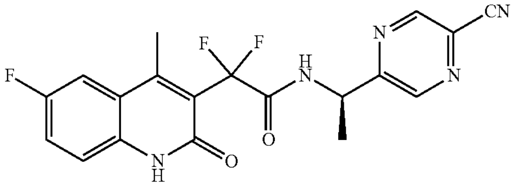 [SMILES: Cc1c(C(F)(F)C(=O)N[C@H](C)c2cnc(C#N)cn2)c(=O)[nH]c2ccc(F)cc12] |
| 7045 | 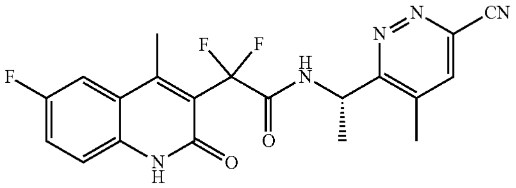 [SMILES: Cc1cc(C#N)nnc1[C@H](C)NC(=O)C(F)(F)c1c(C)c2cc(F)ccc2[nH]c1=O] |
| 7046 | 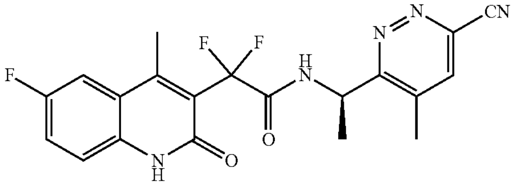 [SMILES: Cc1cc(C#N)nnc1[C@@H](C)NC(=O)C(F)(F)c1c(C)c2cc(F)ccc2[nH]c1=O] |
TABLE 4-continued
| Cmpd No. | Structure |
|---|---|
| 7047 | 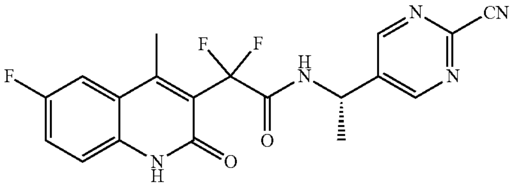 [SMILES: Cc1c(C(F)(F)C(=O)N[C@@H](C)c2cnc(C#N)nc2)c(=O)[nH]c2ccc(F)cc12] |
| 7048 | 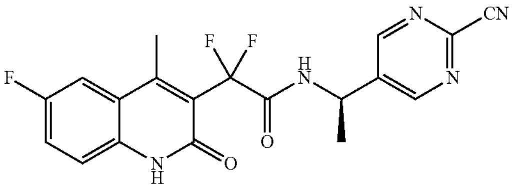 [SMILES: Cc1c(C(F)(F)C(=O)N[C@H](C)c2cnc(C#N)nc2)c(=O)[nH]c2ccc(F)cc12] |
| 7049 | 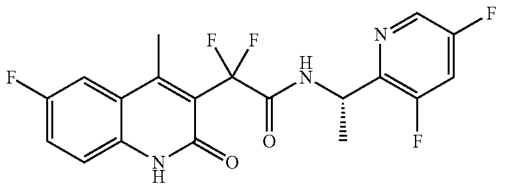 |
| 7050 | 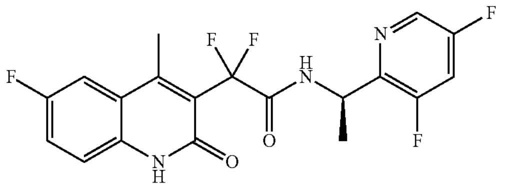 |
| 7051 | 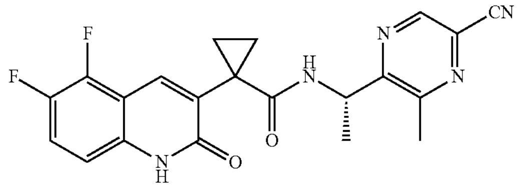 [SMILES: Cc1nc(C#N)cnc1[C@H](C)NC(=O)C1(c2cc3c(F)c(F)ccc3[nH]c2=O)CC1] |
| 7052 | 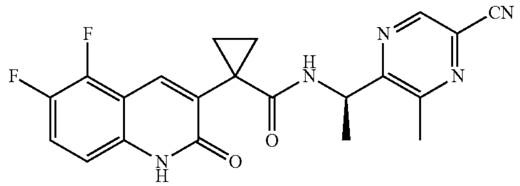 [SMILES: Cc1nc(C#N)cnc1[C@@H](C)NC(=O)C1(c2cc3c(F)c(F)ccc3[nH]c2=O)CC1] |
| 7053 | 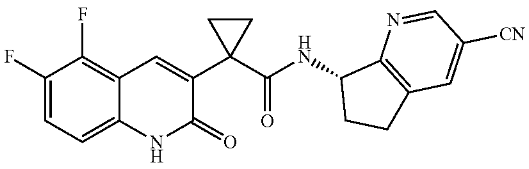 [SMILES: N#Cc1cnc2c(c1)CC[C@@H]2NC(=O)C1(c2cc3c(F)c(F)ccc3[nH]c2=O)CC1] |
| 7054 | 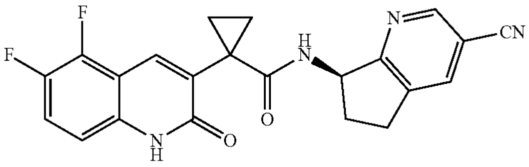 [SMILES: N#Cc1cnc2c(c1)CC[C@H]2NC(=O)C1(c2cc3c(F)c(F)ccc3[nH]c2=O)CC1] |

TABLE 4-continued
| Cmpd No. | Structure |
| --- | --- |
| 7055 | 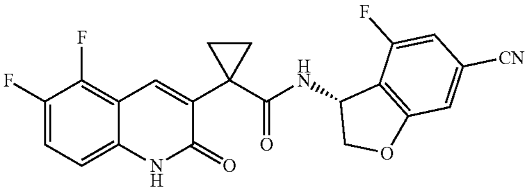 [SMILES: N#Cc1cc(F)c2c(c1)OC[C@@H]2NC(=O)C1(c2cc3c(F)c(F)ccc3[nH]c2=O)CC1] |
| 7056 | 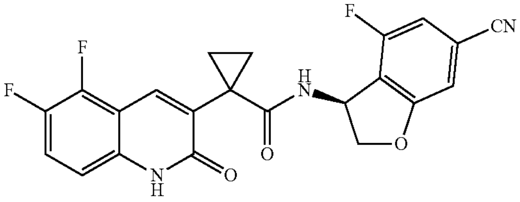 [SMILES: N#Cc1cc(F)c2c(c1)OC[C@H]2NC(=O)C1(c2cc3c(F)c(F)ccc3[nH]c2=O)CC1] |
| 7057 | 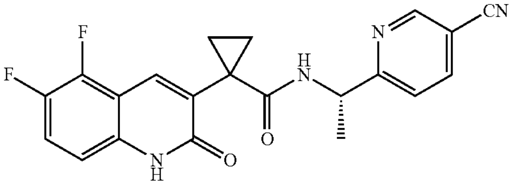 [SMILES: C[C@H](NC(=O)C1(c2cc3c(F)c(F)ccc3[nH]c2=O)CC1)c1ccc(C#N)cn1] |
| 7058 | 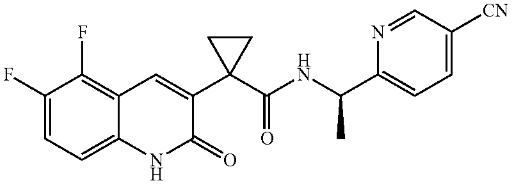 [SMILES: C[C@@H](NC(=O)C1(c2cc3c(F)c(F)ccc3[nH]c2=O)CC1)c1ccc(C#N)cn1] |
| 7059 | 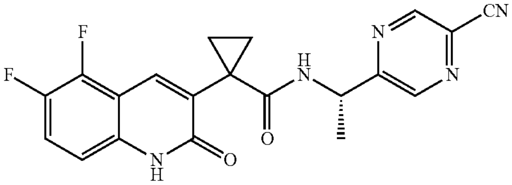 [SMILES: C[C@H](NC(=O)C1(c2cc3c(F)c(F)ccc3[nH]c2=O)CC1)c1cnc(C#N)cn1] |
| 7060 | 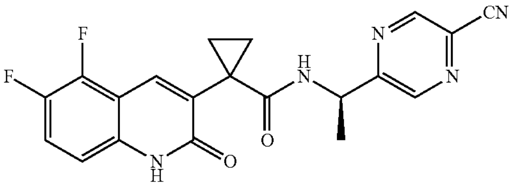 [SMILES: C[C@@H](NC(=O)C1(c2cc3c(F)c(F)ccc3[nH]c2=O)CC1)c1cnc(C#N)cn1] |
| 7061 | 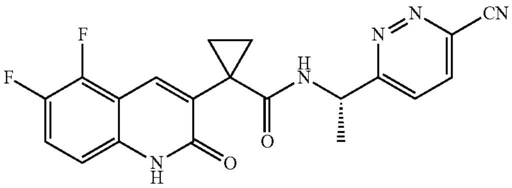 [SMILES: C[C@H](NC(=O)C1(c2cc3c(F)c(F)ccc3[nH]c2=O)CC1)c1ccc(C#N)nn1] |
| 7062 | 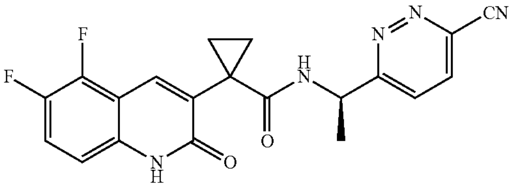 [SMILES: C[C@@H](NC(=O)C1(c2cc3c(F)c(F)ccc3[nH]c2=O)CC1)c1ccc(C#N)nn1] |
TABLE 4-continued
| Cmpd No. | Structure |
| --- | --- |
| 7063 | 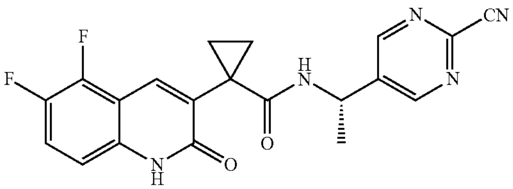 [SMILES: C[C@H](NC(=O)C1(c2cc3c(F)c(F)ccc3[nH]c2=O)CC1)c1cnc(C#N)nc1] |
| 7064 | 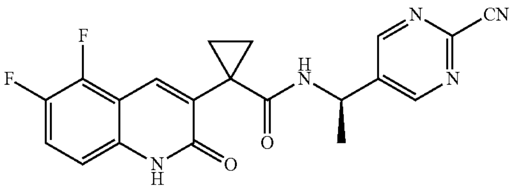 [SMILES: C[C@@H](NC(=O)C1(c2cc3c(F)c(F)ccc3[nH]c2=O)CC1)c1cnc(C#N)nc1] |
| 7065 | 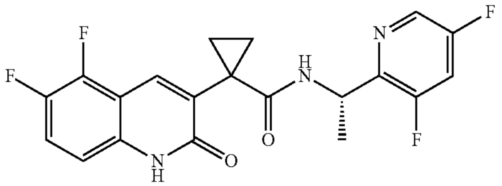 [SMILES: C[C@H](NC(=O)C1(c2cc3c(F)c(F)ccc3[nH]c2=O)CC1)c1ncc(F)cc1F] |
| 7066 | 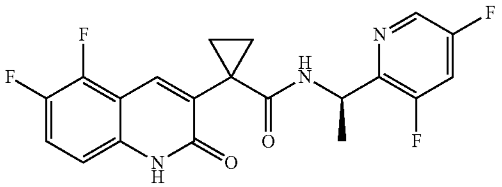 [SMILES: C[C@@H](NC(=O)C1(c2cc3c(F)c(F)ccc3[nH]c2=O)CC1)c1ncc(F)cc1F] |
| 7067 | 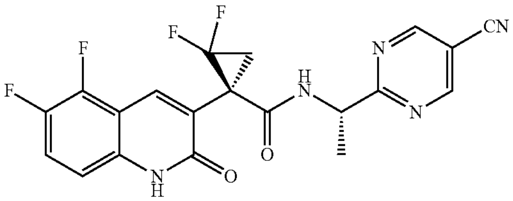 [SMILES: C[C@H](NC(=O)[C@]1(c2cc3c(F)c(F)ccc3[nH]c2=O)CC1(F)F)c1ncc(C#N)cn1] |
| 7068 | 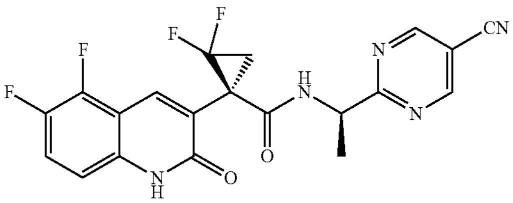 [SMILES: C[C@@H](NC(=O)[C@]1(c2cc3c(F)c(F)ccc3[nH]c2=O)CC1(F)F)c1ncc(C#N)cn1] |
| 7069 | 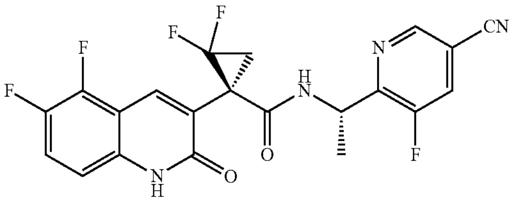 [SMILES: C[C@H](NC(=O)[C@]1(c2cc3c(F)c(F)ccc3[nH]c2=O)CC1(F)F)c1ncc(C#N)cc1F] |

TABLE 4-continued
| Cmpd No. | Structure |
|---|---|
| 7070 | 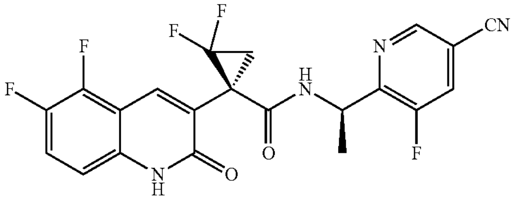 [SMILES: C[C@@H](NC(=O)[C@]1(c2cc3c(F)c(F)ccc3[nH]c2=O)CC1(F)F)c1ncc(C#N)cc1F] |
| 7071 | 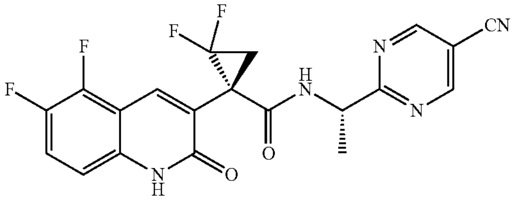 [SMILES: C[C@H](NC(=O)[C@@]1(c2cc3c(F)c(F)ccc3[nH]c2=O)CC1(F)F)c1ncc(C#N)cn1] |
| 7072 | 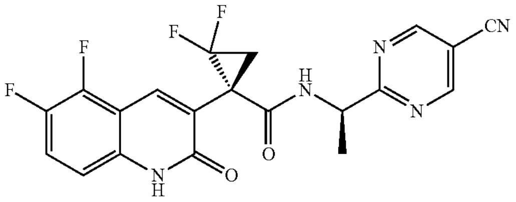 [SMILES: C[C@@H](NC(=O)[C@@]1(c2cc3c(F)c(F)ccc3[nH]c2=O)CC1(F)F)c1ncc(C#N)cn1] |
| 7073 | 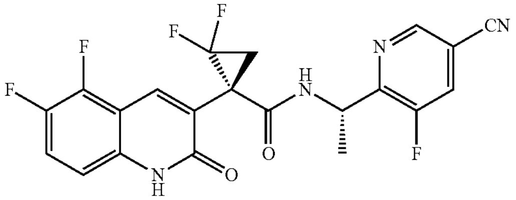 [SMILES: C[C@H](NC(=O)[C@@]1(c2cc3c(F)c(F)ccc3[nH]c2=O)CC1(F)F)c1ncc(C#N)cc1F] |
| 7074 | 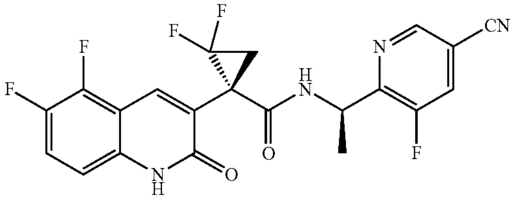 [SMILES: C[C@@H](NC(=O)[C@@]1(c2cc3c(F)c(F)ccc3[nH]c2=O)CC1(F)F)c1ncc(C#N)cc1F] |
| 7075 | 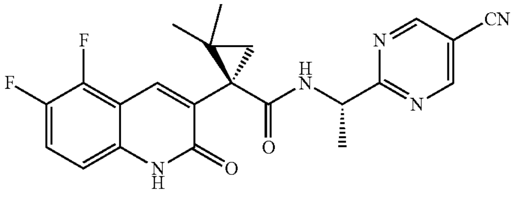 [SMILES: C[C@H](NC(=O)[C@]1(c2cc3c(F)c(F)ccc3[nH]c2=O)CC1(C)C)c1ncc(C#N)cn1] |
| 7076 | 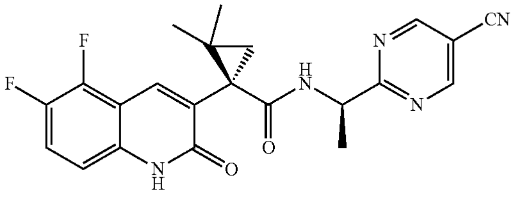 [SMILES: C[C@@H](NC(=O)[C@]1(c2cc3c(F)c(F)ccc3[nH]c2=O)CC1(C)C)c1ncc(C#N)cn1] |
TABLE 4-continued
| Cmpd No. | Structure |
|---|---|
| 7077 | 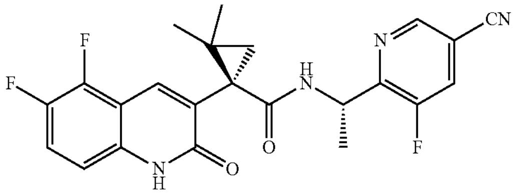 [SMILES: C[C@H](NC(=O)[C@]1(c2cc3c(F)c(F)ccc3[nH]c2=O)CC1(C)C)c1ncc(C#N)cc1F] |
| 7078 | 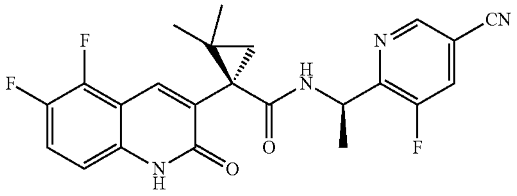 [SMILES: C[C@@H](NC(=O)[C@]1(c2cc3c(F)c(F)ccc3[nH]c2=O)CC1(C)C)c1ncc(C#N)cc1F] |
| 7079 | 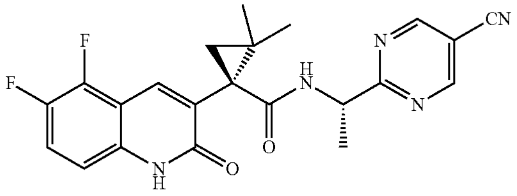 [SMILES: C[C@H](NC(=O)[C@@]1(c2cc3c(F)c(F)ccc3[nH]c2=O)CC1(C)C)c1ncc(C#N)cn1] |
| 7080 | 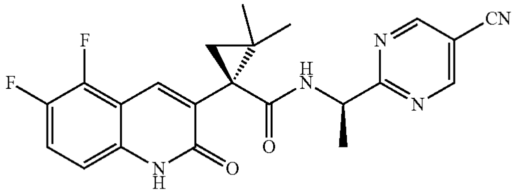 [SMILES: C[C@@H](NC(=O)[C@@]1(c2cc3c(F)c(F)ccc3[nH]c2=O)CC1(C)C)c1ncc(C#N)cn1] |
| 7081 | 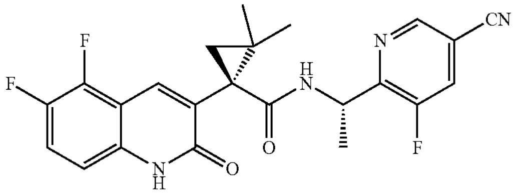 [SMILES: C[C@H](NC(=O)[C@@]1(c2cc3c(F)c(F)ccc3[nH]c2=O)CC1(C)C)c1ncc(C#N)cc1F] |
| 7082 | 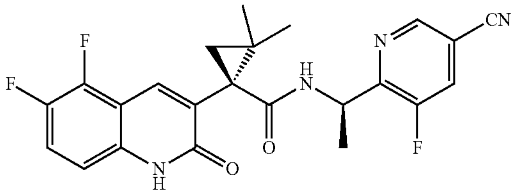 [SMILES: C[C@@H](NC(=O)[C@@]1(c2cc3c(F)c(F)ccc3[nH]c2=O)CC1(C)C)c1ncc(C#N)cc1F] |
| 7083 | 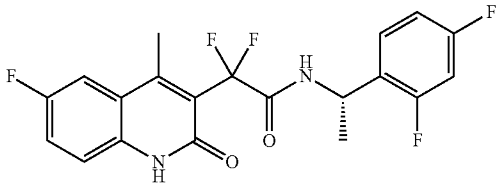 [SMILES: Cc1c(C(F)(F)C(=O)N[C@@H](C)c2ccc(F)cc2F)c(=O)[nH]c2ccc(F)cc12] |

TABLE 4-continued

| Cmpd No. | Structure |
|---|---|
| 7084 | 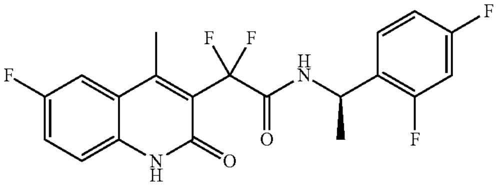 [SMILES: Cc1c(C(F)(F)C(=O)N[C@H](C)c2ccc(F)cc2F)c(=O)[nH]c2ccc(F)cc12] |
| 7085 | 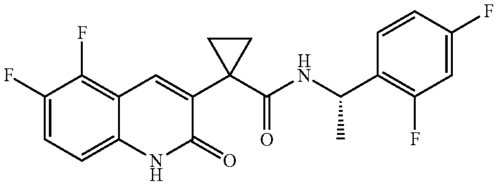 |
| 7086 | 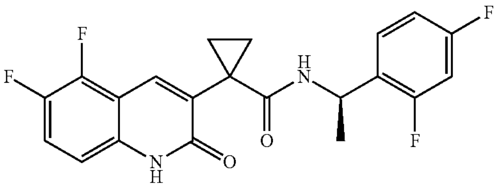 |
| 7087 | 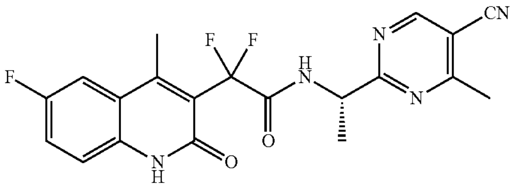 [SMILES: Cc1nc([C@H](C)NC(=O)C(F)(F)c2c(C)c3cc(F)ccc3[nH]c2=O)ncc1C#N] |
| 7088 | 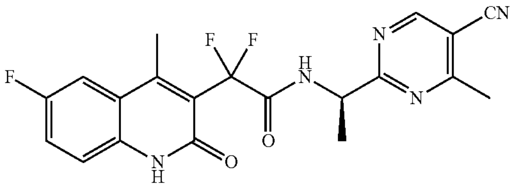 [SMILES: Cc1nc([C@@H](C)NC(=O)C(F)(F)c2c(C)c3cc(F)ccc3[nH]c2=O)ncc1C#N] |
| 7089 | 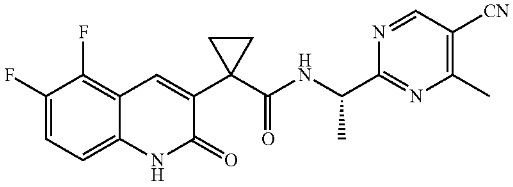 [SMILES: Cc1nc([C@H](C)NC(=O)C2(c3cc4c(F)c(F)ccc4[nH]c3=O)CC2)ncc1C#N] |
| 7090 | 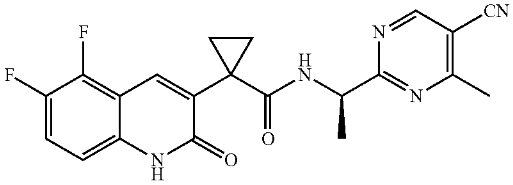 [SMILES: Cc1nc([C@@H](C)NC(=O)C2(c3cc4c(F)c(F)ccc4[nH]c3=O)CC2)ncc1C#N] |
| 7091 | 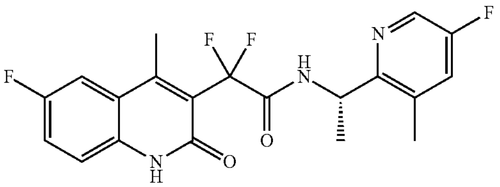 [SMILES: Cc1cc(F)cnc1[C@H](C)NC(=O)C(F)(F)c1c(C)c2cc(F)ccc2[nH]c1=O] |
| 7092 | 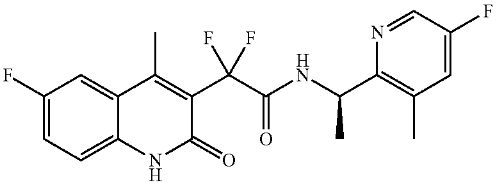 [SMILES: Cc1cc(F)cnc1[C@@H](C)NC(=O)C(F)(F)c1c(C)c2cc(F)ccc2[nH]c1=O] |
| 7093 | 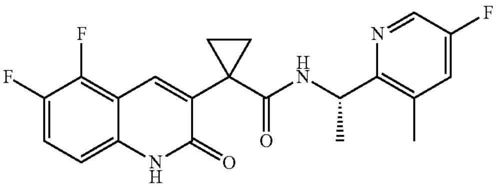 [SMILES: Cc1cc(F)cnc1[C@H](C)NC(=O)C1(c2cc3c(F)c(F)ccc3[nH]c2=O)CC1] |
| 7094 | 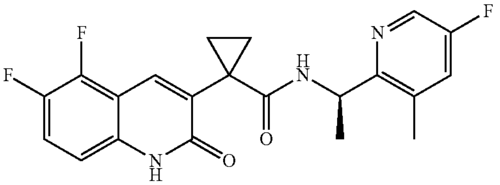 [SMILES: Cc1cc(F)cnc1[C@@H](C)NC(=O)C1(c2cc3c(F)c(F)ccc3[nH]c2=O)CC1] |

Example 1. Myofibril ATPase Assay

Myofibril ATPase assays are known in the art to be useful in evaluating small molecules for the treatment of HCM and other cardiac indications. Myosin ATPase activity is assessed by using a coupled reaction system, in which ADP generated by the myosin ATPase function is coupled to the disappearance of NADH through the pyruvate kinase/lactate dehydrogenase (PK-LDH) system. ATPase activity produces ADP, which is used as a substrate for PK to produce pyruvate and regenerate ATP. The pyruvate is then used as a substrate by LDH to oxidize NADH to NAD+. The rate of the reaction is monitored through the time-dependent disappearance of NADH using absorbance at 340 nm, which, when the couple system is in stoichiometric excess, is directly correlated to the ATPase activity of the myosin. Inhibition of ATPase activity by the assayed compounds is indicated by a reduced rate of NADH loss, relative to vehicle-treated controls, over the experimental time window. Activation of ATPase activity by the assayed compounds is indicated by an increased rate of NADH loss, relative to vehicle-treated controls, over the experimental time window. Rabbit Psoas, Porcine atria, and Porcine ventricle are the primary sources of myofibril material. The results are shown in Table 5, Table 6, and Table 7.

Materials: The following stock solutions and reagents were used in the Myofibril ATPase Assay:

| Stock Solutions |
|---|
| PIPES, 200 mM and 120 mM in $H_2O$, pH 7.0 |
| $MgCl_2$ in $H_2O$, 200 mM |
| PM12 Buffer, 10X: 120 mM PIPES (from 200 mM stock), 20 mM $MgCl_2$ (from 200 mM stock) |
| PBS Buffer, 1X: 135 mM NaCl, 27 mM KCl, 10 mM $Na(PO_4)_2$, 1.8 mM $K_2(PO_4)$, pH 7.4 |
| EGTA in $H_2O$, 250 mM |

-continued

| Stock Solutions |
|---|
| $CaCl_2$ in $H_2O$, 500 mM |
| DTT in $H_2O$, 1M |
| BSA in $H_2O$, 10 mg/mL |
| ATP in 1X PBS, 50 mM |
| NADH in 1X PM12 and 1 mM DTT, 26 mM |
| PEP in 1X PM12, 78 mM, pH 7.0 |

Stock Solutions of pCa buffer. Combine PIPES, $CaCl_2$, and EGTA solutions with water. Adjust pH to 7.0 and bring final volume to 100 mL.

-continued

| Preparation of Stocks Solutions for 100 mL of pCa buffer | | | | |
|---|---|---|---|---|
| pCA | 120 mM PIPES (mL) | Approx. Water (mL) | $CaCl_2$ (mL) | EGTA (mL) |
| 8.0 | 10 | 68.905 | 1.095 | 20 |
| 10.0 | 10 | 69.988 | 0.012 | 20 |

Buffer A & Buffer B. Prepare buffers A and B according to the table below.

| Total Well Volume (µL) | 50 | Component | Stock Concentrations Value | Unit | Final Concentrations in Specific Buffer | Reaction Concentrations | Volume per well (µL) | Number of Wells Total Volume (µL) | 400 | 1200 |
|---|---|---|---|---|---|---|---|---|---|---|
| | | PM12 Buffer | 10 | × | 1.00× | 1.00× | 2.50 | 1000.00 | 1300.00 | PM12 Buffer (1×) |
| | | KCl | 2000 | mM | 0.00 mM | 0.00 mM | 0.00 | 0.00 | 0.00 | KCl (0 mM) |
| | | pCa Solution | 10 | × | 0.00× | 0.00× | 0.00 | 0.00 | 0.00 | pCa Solution (0.×) |
| | | Compound | 100 | % | 0.00% | 0.00% | 0.00 | 0.00 | 0.00 | Compound (0%) |
| Buffer A (µL) | 25 | BSA | 10 | mg/mL | 0.10 mg/mL | 0.10 mg/mL | 0.25 | 100.00 | 130.00 | BSA (0.1 mg/mL) |
| | | DTT | 1000 | mM | 1.00 mM | 1.00 mM | 0.03 | 10.00 | 13.00 | DTT (1 mM) |
| | | PK/LDH | 200 | × | 2.00× | 1.00× | 0.25 | 100.00 | 130.00 | PK/LDH (1×) |
| | | Ventricle Prep 18 | 8.2 | mg/mL | 1.00 mg/mL | 0.50 mg/mL | 3.05 | 1219.51 | 1585.37 | Ventricle Prep 18 (0.5 mg/mL) |
| | | Antifoam | 1.00 | % | 0.01% | 0.01% | 0.25 | 100.00 | 130.00 | Antifoam (0.01%) |
| | | Water | | | | | 18.68 | 7470.49 | 9711.63 | Water |
| | | | | | | | 25.00 | 10000.00 | 13000.00 | Total |
| | | PM12 Buffer | 10 | × | 1.00× | 1.00× | 2.50 | 1000.00 | 1300.00 | PM12 Buffer (1×) |
| | | KCl | 1000 | mM | 0.00 mM | 30.00 mM | 0.00 | 0.00 | 0.00 | KCl (30 m M) |
| | | Compound | 100 | % | 0.00% | 0.00% | 0.00 | 0.00 | 0.00 | Compound (0%) |
| | | pCa Solution | 10 | × | 2.00× | 1.00× | 5.00 | 2000.00 | 2600.00 | pCa Solution (1×) |
| Buffer B (µL) | 25 | BSA | 10 | mg/mL | 0.10 mg/mL | 0.10 mg/mL | 0.25 | 100.00 | 130.00 | BSA (0.1 mg/mL) |
| | | DTT | 1000 | mM | 1.00 mM | 1.00 mM | 0.03 | 10.00 | 13.00 | DTT (1 mM) |
| | | ATP | 50 | mM | 0.50 mM | 0.25 mM | 0.25 | 100.00 | 130.00 | ATP (0.25 mM) |
| | | NADH | 26 | mM | 1.00 mM | 0.50 mM | 0.96 | 384.62 | 500.00 | NADH (0.5 mM) |
| | | PEP | 78 | mM | 3.00 mM | 1.50 mM | 0.96 | 384.62 | 500.00 | PEP (1.5 mM) |
| | | Antifoam | 1.00 | % | 0.01% | 0.01% | 0.25 | 100.00 | 130.00 | Antifoam (0.01%) |
| | | Water | | | | | 14.80 | 5920.77 | 7697.00 | Water |
| | | | | | | | 25.00 | 10000.00 | 13000.00 | |

| Preparation of Stocks Solutions for 100 mL of pCa buffer | | | | |
|---|---|---|---|---|
| pCA | 120 mM PIPES (mL) | Approx. Water (mL) | $CaCl_2$ (mL) | EGTA (mL) |
| 4.0 | 10 | 59.797 | 10.203 | 20 |
| 4.5 | 10 | 59.959 | 10.041 | 20 |
| 5.0 | 10 | 60.060 | 9.940 | 20 |
| 5.5 | 10 | 60.244 | 9.756 | 20 |
| 5.75 | 10 | 60.434 | 9.566 | 20 |
| 6.0 | 10 | 60.750 | 9.250 | 20 |
| 6.25 | 10 | 61.262 | 8.738 | 20 |
| 6.5 | 10 | 62.045 | 7.955 | 20 |
| 6.75 | 10 | 63.138 | 6.862 | 20 |
| 7.0 | 10 | 64.484 | 5.516 | 20 |

Myofibril ATPase Assay Procedure: BSA, ATP, NADH, PEP, and DTT solutions were thawed at room temperature, then transferred to ice. Pellet-frozen myofibrils were transferred with approximately twice the required volume into a sufficiently large tube and capped. Myofibrils were thawed by rolling in a water bath for approximately 15 min at room temperature and cooled on ice. Buffers A and B were prepared by adjusting volumes as necessary for required number of wells and stored on ice. 0.5 µL of the compounds to be assayed were added into wells. 25 µL of Buffer A was dispensed into the wells, followed by 25 µL of Buffer B. The wells were measured for absorbance at 340 nm, using a kinetic protocol in which the wells are read every 1.5-2 min for 75 min. Assay data analysis was performed using a python script that filtered the raw data to retain those points falling between a starting and ending time and between a maximum and minimum absorbance, then used the filtered time-domain 340 nm absorbance data in each well to calculate a slope via linear regression analysis in units of mAU/min. Compound slopes were normalized between 100% and 0% activity, where 100% represented the slope of wells containing only compound vehicle, and fit to a 4-parameter logistic model. In addition to the fit parameters, the $EC_{25\%}$ values were calculated, relative to the 100% normalized value. Additionally, the Y125 values were calculated for compounds that increased myosin ATP-ase activity. Fit parameters, calculated effective concentrations, filtered raw data, and calculated slopes were exported, in addition to compound-specific graphs of normalized ATPase activity versus concentration in μM. Each value reported in Table 5, Table 6, and Table 7 is either a Y75 value or a Y125 value. Values without a double cross sign, ‡, are Y75 values, which reflect the concentration required to reduce myosin ATP-ase activity by 25% (e.g., Y-axis activity value is 75% of initial value), relative to myosin ATP-ase activity in the absence of exogenous compound. Values with a double cross sign, ‡, next to the value, are Y125 values, which reflect the concentration required to increase myosin ATP-ase activity by 25% (e.g., Y-axis activity value is 125% of initial value), relative to myosin ATP-ase activity in the absence of exogenous compound. The results are shown in Table 5, Table 6, and Table 7.

Skeletal Myofibril Isolation:

Myofibrils from various animals and tissue types were acquired from a variety of sources: rabbit psoas muscle was purchased from Pel-Freez Biologicals (Rogers, AR) and porcine cardiac muscle was purchased from Exemplar Genetics. All myofibrils were prepared using a method based upon those described in Herrmann et al. (1993) and summarized here. Minced tissue was homogenized for 50 sec with a Polytron homogenizer into 10 volumes (relative to weight in grams) of Isolation Buffer A (50 mM Tris, pH 8.0, 0.1 M potassium acetate, 5 mM KCl, 2 mM DTT, 5 mM EDTA, 0.5% v/v Triton X-100) supplemented with 0.1 mM PMSF, 10 μM leupeptin, 5 μM pepstatin, and 0.5 mM sodium azide. The myofibrils were recovered by centrifugation (Beckman Allegra 6R, 1200 g, 10 min) and resuspended in 10 volumes Isolation Buffer B (Buffer A above without protease inhibitors or sodium azide). The myofibrils were further homogenized as before and recovered by centrifugation. Cellular membranes and debris were removed by 2 washes in Isolation Buffer B, centrifuging each as before. The myofibrils were then suspended in Isolation Buffer C (Tris, potassium acetate, KCl, and DTT as above, supplemented with 2 mM magnesium acetate) and homogenized as described above. The myofibrils were collected by centrifugation and washed 3 times with Isolation Buffer C before being passed through a 100 μM nylon mesh sheet (Spectrum Laboratories) to remove the larger particles. The sieved myofibrils were centrifuged at 1200 g for 15 min and resuspended in 2 to 3 volumes of PM12-60 buffer (12 mM PIPES, pH 6.8, 2 mM $MgCl_2$, 60 mM KCl, 1 mM DTT). D-sucrose was added to 10% and the myofibril suspension was drop-frozen into liquid nitrogen at stored at −80° C.

Cardiac Myofibril Isolation:

Myofibrils from porcine cardiac muscle was isolated from the left ventricle of Yucatan minipigs. Myofibrils were prepared using a method based upon those described in Herrmann et al. (1993) and summarized here. Minced tissue was homogenized for 50 sec with a Polytron homogenizer into 10 volumes (relative to weight in grams) of Isolation Buffer A (75 mM KCl, 10 mM Imidazole, 2 mM $MgCl_2$, 2 mM EGTA, 1 mM $NaN_3$, 1% v/v Triton X-100) supplemented with 4 mM Phosphocreatine, 1 mM ATP, 50 mM BDM, 1 mM DTT, 1 mM Benzamide HCl, 0.1 mM PMSF, 10 μM leupeptin, 5 μM pepstatin, and 10 mM EDTA. The myofibrils were recovered by centrifugation (Beckman Allegra 6R, 1200 g, 15 min) and resuspended in 10 volumes Isolation Buffer B (Buffer A above without supplemental reagents). The myofibrils were further homogenized described above and recovered by centrifugation for 7 mins. Cellular membranes and debris were removed by 3 washes in Isolation Buffer B, centrifuging each as before. The myofibrils were then suspended in Isolation Buffer C (Buffer A above without supplemental reagents and Triton) and homogenized as described above. The myofibrils were collected by centrifugation and washed 3 times with Isolation Buffer C before being passed through a 100 μM nylon mesh sheet (Spectrum Laboratories) to remove the larger particles. The sieved myofibrils were centrifuged at 1200 g for 15 min and resuspended in 2 to 3 volumes of PM12-60 buffer (12 mM PIPES, pH 6.8, 2 mM $MgCl_2$, 60 mM KCl, 1 mM DTT). D-sucrose was added to 10% and the myofibril suspension was drop-frozen into liquid nitrogen at stored at −80° C. Certain compounds of the disclosure have ventricle and atrial $EC_{25}$ values as in Table 5, Table 6, and Table 7. Skeletal EC25 refers to, e.g., Rabbit Psoas $EC_{25}$ (μM) (Rabbit Psoas Prep pCa 25 GEOM_MEAN). Atrial EC25 refers to, e.g., Porcine Atrial $EC_{25}$ (μM) (Porcine Atria Prep pCa 25 GEOM_MEAN), Ventricular EC25 refers to, e.g., Porcine Ventricular $EC_{25}$ (μM)

(Porcine Ventricle Prep pCa 25 GEOM_MEAN).

Certain compounds of the disclosure have cardiac ventricle $EC_{25}$ values as in Table 5, 6, and 7.

Example 2. Echocardiogram Data

Experiments were performed to evaluate the in vivo ability of the compounds of the disclosure to modulate systolic cardiac performance. Non-invasively echocardiography was used to assess cardiac indicators in isoflurane-anesthetized SD rats. A set of conscious rats were treated with either vehicle control (0 mg/kg PO; n=78) or a single dose of a test compound (10 mg/kg PO, n=2 to 6/compound) via oral gavage. Cardiac function/geometry were recorded at two separate time-points/days: once prior to dosing (e.g., at baseline, day −2) and at ~2 hrs post-dosing (day 0). In these experiments, heart rate (HR), echocardiography-derived indices of left-ventricular systolic performance, as well as dimensions/volumes were measured using a high-frequency transducer and parasternal long-axis transthoracic views (Vevo3100, VisualSonic). LV fractional shortening (FS), an index of systolic function, was defined as the end-diastole normalized change in internal dimensions divided by the difference in diameter (LVid) of the left ventricle between end-systole (LVids) and end-diastole (LVidd) (e.g., FS=100·[LVidd−LVids]/LVidd). LV volumes were derived using the Teichholz formula (LVV=[7·LVid^3]/[2.4+LVid]). In addition, a systolic wall-thickening index (SWT) was also evaluated. SWT is defined as the relative ratio (end-diastole normalized) of left-ventricular (anterior and posterior) wall-thickness change during systole; e.g., SWT={[(anterior LV wall thickness in systole−anterior LV wall thickness in diastole)]+[(posterior LV wall thickness in systole−posterior LV wall thickness in diastole)]}/{2*diastolic thickness}. In all cases, blood samples were taken (via either tail-vein micro-sampling or cardiac-puncture) at the time of each echocardiographic examination in order to establish pharmacokinetic (PK)/pharmacodynamics (PD) relationships. The results are shown in Table A below.

TABLE A

| Compound No. | HR % vs. VEH | EDV % vs. VEH | FS % vs. VEH | SWT % vs. VEH |
|---|---|---|---|---|
| 355 | + | + | ++ | + |
| 83 | + | − | ++ | ++ |
| 256 | + | − | − | − |
| 27 | − | ++ | ++ | +++ |
| 42 | 0 | + | −− | +++ |
| 41 | − | − | − | +++ |
| 1146 | + | − | −− | −− |
| 36 | ++ | + | −−− | −− |
| 1123 | + | −− | −− | −−− |
| 1106 | + | + | −− | −− |
| 1124 | + | + | −− | − |
| 2071 | − | − | − | ++ |
| 35 | + | ++ | − | 0 |
| 13035 | − | − | − | −− |
| 13034 | + | − | − | −− |
| 9631 | + | ++ | −− | −− |
| 9630 | + | ++ | −− | −− |
| 11434 | + | − | − | − |
| 11042 | + | + | −− | −− |
| 9522 | − | ++ | −− | −− |
| 8603 | − | +++ | −−− | −−− |

+ is 1% to 10% increase; ++ is 11% to 20% increase; +++ is 21% increase and above; − is 1% to 20% decrease; −− is 21% to 40% decrease; −−− is 41% to 60% decrease; and −−−− is 61% decrease and below.

TABLE 5

| Cmpd No. | Atrial $EC_{25}$ (μM) | Ventricular $EC_{25}$ (μM) | Skeletal $EC_{25}$ (μM) |
|---|---|---|---|
| 1* | 0.07 | 0.14 | 0.11 |
| 2* | 0.09 | 0.08 | 0.02 |
| 3* | 3.40 | 0.31 | 2.33 |
| 4* | 4.38 | 0.96 | 0.15 |
| 5* | 1.45 | 4.13 | 3.60 |
| 6* | 0.81 | 0.95 | 0.30 |
| 7* | 3.80 | 1.27 | 0.81 |
| 8* | 100.00 | 100.00 | 100.00 |
| 9 | 3.29 | 0.92 | 0.65 |
| 10 | 0.16 | 0.39 | 0.05 |
| 11* | 0.05 | 0.15 | 0.07 |
| 12* | 0.03 | 0.11 | 0.03 |
| 13* | 0.32 | 0.09 | 0.05 |
| 14* | 0.21 | 0.34 | 0.07 |
| 15* | 0.10 | 0.13 | 0.29 |
| 16* | 0.07 | 0.13 | 0.03 |
| 17 | 0.09 | 1.56 | 0.43 |
| 18 | 0.09 | 0.26 | 0.08 |
| 19 | 100.00 | 1.01 | 2.92 |
| 20 | 0.21 | 0.31 | 0.51 |
| 21 | 0.03 | 0.13 | 0.04 |
| 22 | 0.02 | 0.02 | 0.00 |
| 23 | 100.00 | 1.19 | 0.50 |
| 24 | 0.05 | 0.21 | 0.04 |
| 25 | 100.00 | 100.00 | 1.68 |
| 26 | 6.13 | 1.40 | 0.21 |
| 27 | 0.23 | 0.24 | 0.14 |
| 28 | 0.04 | 0.06 | 0.02 |
| 29 | 100.00 | 100.00 | 1.06 |
| 30 | 1.93 | 0.48 | 0.01 |
| 31 | 0.10 | 0.16 | 0.06 |
| 32 | 0.05 | 0.04 | 0.01 |
| 33 | 0.17 | 0.46 | 0.29 |
| 34 | 0.02 | 0.05 | 0.02 |
| 35 | 0.08 | 0.15 | 0.09 |
| 36 | 0.02 | 0.05 | 0.01 |
| 37 | 0.04 | 0.05 | 0.02 |
| 38 | 0.03 | 0.06 | 0.02 |
| 39 | 100.00 | 100.00 | 100.00 |
| 40 | 0.47 | 0.41 | 0.02 |
| 41 | 0.13 | 0.45 | 0.07 |
| 42 | 0.08 | 0.04 | 0.01 |

TABLE 5-continued

| Cmpd No. | Atrial $EC_{25}$ (μM) | Ventricular $EC_{25}$ (μM) | Skeletal $EC_{25}$ (μM) |
|---|---|---|---|
| 43 | 100.00 | 100.00 | 14.83 |
| 44 | 0.21 | 1.97 | 0.05 |
| 45 | 0.07 | 0.42 | 0.12 |
| 46 | 0.24 | 0.12 | 0.02 |
| 47 | 4.48 | 4.80 | 0.43 |
| 48 | 1.55 | 4.14 | 0.23 |
| 49 | 0.18 | 0.68 | 0.06 |
| 50 | 0.05 | 0.23 | 0.02 |
| 51 | 0.23 | 0.40 | 0.06 |
| 52 | 0.06 | 0.10 | 0.02 |
| 53 | 1.93 | 6.53 | 0.31 |
| 54 | 0.11 | 1.53 | 0.04 |
| 55 | 1.29 | 100.00 | 1.20 |
| 56 | 2.47 | 3.98 | 0.12 |
| 57** | 0.15 | 100.00 | 0.07 |
| 58** | 0.06 | 1.32 | 0.15 |
| 59* | 0.09 | 0.07 | 0.02 |
| 60* | 0.05 | 0.62 | 0.27 |
| 61* | 0.05 | 0.08 | 0.01 |
| 62* | 0.15 | 0.21 | 0.26 |
| 63* | 0.42 | 62.72 | 1.55 |
| 64* | 100.00 | 100.00 | 83.26 |
| 65 | 0.23 | 0.22 | 0.02 |
| 66 | 0.05 | 0.06 | 0.01 |
| 67 | 0.11 | 0.26 | 0.03 |
| 68 | 0.06 | 0.07 | 0.01 |
| 69 | 0.03 | 0.11 | 0.01 |
| 70 | 100.00 | 100.00 | 0.03 |
| 71 | 1.10 | 8.50 | 0.23 |
| 72 | 0.08 | 0.34 | 0.02 |
| 73 | 100.00 | 100.00 | 0.02 |
| 74 | 0.69 | 0.46 | 0.01 |
| 75 | 59.37 | 0.61 | 15.21 |
| 76 | 100.00 | 100.00 | 100.00 |
| 77* | 100.00 | 100.00 | 47.84 |
| 78* | 7.08 | 100.00 | 6.60 |
| 79* | 100.00 | 100.00 | 100.00 |
| 80* | 100.00 | 100.00 | 18.54 |
| 81 | 100.00 | 100.00 | 51.89 |
| 82 | 100.00 | 100.00 | 100.00 |
| 83 | 0.04 | 0.10 | 0.01 |
| 84 | 2.52 | 55.56 | 7.24 |
| 85 | 0.03 | 0.07 | 0.02 |
| 86** | 100.00 | 100.00 | 100.00 |
| 87 | 100.00 | 100.00 | 100.00 |
| 88** | 83.97 | 88.39 | 74.46 |
| 89* | 0.05 | 0.32 | 0.04 |
| 90* | 23.51 | 100.00 | 1.26 |
| 91 | 1.38 | 100.00 | 3.55 |
| 92 | 29.94 | 100.00 | 2.83 |
| 93 | 1.18 | 22.97 | 100.00 |
| 94 | 6.81 | 100.00 | 0.22 |
| 95 | 0.08 | 0.39 | 0.02 |
| 96 | 0.07 | 0.13 | 0.01 |
| 97* | 0.19 | 5.34 | 0.23 |
| 98* | 0.53 | 4.12 | 0.06 |
| 99* | 0.13 | 100.00 | 0.09 |
| 100* | 0.06 | 0.69 | 0.04 |
| 101 | 0.04 | 0.11 | 0.23 |
| 102* | 100.00 | 100.00 | 3.90 |
| 103* | 1.13 | 100.00 | 1.64 |
| 104* | 0.07 | 1.60 | 0.22 |
| 105* | 0.35 | 6.41 | 5.34 |
| 106 | 0.05 | 0.20 | 0.04 |
| 107 | 0.03 | 0.09 | 0.02 |
| 108* | 0.04 | 0.28 | 0.05 |
| 109 | 0.04 | 0.13 | 0.01 |
| 110* | 0.52 | 42.60 | 100.00 |
| 111* | 0.10 | 100.00 | 0.11 |
| 112* | 0.06 | 0.31 | 0.03 |
| 113 | 0.10 | 1.61 | 0.04 |
| 114 | 3.86 | 4.54 | 0.06 |
| 115 | 0.05 | 0.32 | 0.02 |
| 116 | 0.04 | 0.13 | 0.02 |
| 117 | 100.00 | 100.00 | 6.32 |
| 118 | 0.06 | 0.30 | 0.03 |
| 119 | 0.26 | 1.96 | 0.11 |

TABLE 5-continued

| Cmpd No. | Atrial $EC_{25}$ (μM) | Ventricular $EC_{25}$ (μM) | Skeletal $EC_{25}$ (μM) |
|---|---|---|---|
| 120 | 0.04 | 0.25 | 0.05 |
| 121 | 100.00 | 100.00 | 3.75 |
| 122* | 100.00 | 100.00 | 1.26 |
| 123**** | 1.75 | 15.08 | 1.14 |
| 124 | 100.00 | 100.00 | 42.44 |
| 125 | 64.80 | 20.89 | 25.67 |
| 126 | 0.06 | 0.49 | 0.03 |
| 127 | 0.19 | 3.12 | 0.17 |
| 128 | 0.90 | 9.83 | 0.17 |
| 129 | 0.21 | 0.75 | 0.04 |
| 130 | 0.02 | 0.15 | 0.03 |
| 131 | 0.07 | 0.81 | 0.02 |
| 132 | 100.00 | 100.00 | 100.00 |
| 133 | 0.22 | 1.27 | 0.08 |
| 134 | 100.00 | 100.00 | 7.99 |
| 135 | 0.10 | 0.40 | 0.03 |
| 136 | 100.00 | 100.00 | 12.53 |
| 137 | 1.12 | 3.33 | 0.19 |
| 1038 | 0.42 | 2.7 | 0.34 |
| 1039 | 0.22 | 0.67 | 0.08 |
| 1040 | 6.01 | 12 | 52 |
| 1041 | 18.0 | 76 | 7.39 |
| 1042 | 0.89 | 24 | 1.88 |
| 1043 | 1.28 | 3.5 | 0.41 |
| 1044 | 0.06 | 0.10 | 0.02 |
| 1045 | 1.5 | 1.7 | 0.44 |
| 1046 | 0.06 | 0.14 | 0.04 |
| 1047 | 100.00 | 1.13 | 100 |
| 1048 | 0.29 | 1.73 | 2.2 |
| 1049 | 100.00 | 100.00 | 29 |
| 1050 | 0.22 | 2.36 | 3.4 |
| 1051 | 0.14 | 0.26 | 0.03 |
| 1052 | 0.65 | 7.05 | 0.78 |
| 1053 | 0.12 | 0.22 | 0.04 |
| 1054 | 19.09 | 100.00 | 100 |
| 1055 | 100.00 | 100.00 | 18 |
| 1056 | 100.00 | 100.00 | 100 |
| 1057 | 100.00 | 100.00 | 21 |
| 1058 | 1.92 | 6.86 | 29.21 |
| 1059 | 0.13 | 0.16 | 0.39 |
| 1060 | 13.11 | 100.00 | 100.00 |
| 1061 | 2.49 | 100.00 | 100.00 |
| 1062 | 3.49 | 6.56 | 9.26 |
| 1063 | 0.16 | 0.76 | 0.22 |
| 1064 | 2.17 | 14.07 | 9.09 |
| 1065 | 0.51 | 0.80 | 1.00 |
| 1066 | 3.79 | 10.31 | 62.54 |
| 1067 | 5.67 | 31.71 | 10.01 |
| 1068 | 0.07 | 0.06 | 0.12 |
| 1069 | 0.20 | 2.10 | 100.00 |
| 1070 | 0.22 | 1.72 | 2.50 |
| 1071 | 5.29 | 11.94 | 100.00 |
| 1072 | 17.57 | 36.86 | 100.00 |
| 1073 | 53.69 | 89.23 | 100.00 |
| 1074 | 100.00 | 100.00 | 100.00 |
| 1075 | 16.51 | 15.41 | 8.39 |
| 1076 | 1.89 | 1.49 | 0.35 |
| 1077 | 0.49 | 0.31 | 0.11 |
| 1078 | 2.57 | 2.05 | 2.27 |
| 1079 | 0.44 | 3.04 | 0.14 |
| 1080 | 0.21 | 0.36 | 0.12 |
| 1081 | 0.12 | 0.28 | 0.03 |
| 1082 | 100.00 | 100.00 | 100.00 |
| 1083 | 5.80 | 100.00 | 4.15 |
| 1084 | 0.52 | 16.13 | 1.63 |
| 1085 | 44.26 | 100.00 | 100.00 |
| 1086 | 1.94 | 100.00 | 100.00 |
| 1087 | 100.00 | 100.00 | 100.00 |
| 1088 | 5.78 | 100.00 | 100.00 |
| 1089 | 6.41 | 42.07 | 100.00 |
| 1090 | 5.79 | 100.00 | 100.00 |
| 1091 | 53.30 | 80.11 | 100.00 |
| 1092 | 1.13 | 2.41 | 0.36 |
| 1093 | 100.00 | 100.00 | 100.00 |
| 1094 | 100.00 | 100.00 | 2.26 |
| 1095 | 0.18 | 0.42 | 0.06 |
| 1096 | 31.81 | 100.00 | 12.10 |
| 1097 | 1.11 | 1.56 | 0.15 |
| 1098 | 7.06 | 17.06 | 17.72 |
| 1099 | 7.61 | 49.75 | 4.41 |
| 1100 | 0.77 | 2.27 | 0.53 |
| 1101 | 0.17 | 0.31 | 0.06 |
| 1102 | 6.15 | 6.45 | 0.37 |
| 1103 | 0.40 | 1.07 | 0.06 |
| 1104 | 0.14 | 0.21 | 0.03 |
| 1105 | 100.00 | 4.47 | 1.36 |
| 1106 | 0.54 | 0.49 | 0.37 |
| 1107 | 0.12 | 0.15 | 0.03 |
| 1108 | 6.47 | 1.44 | 0.37 |
| 1109 | 0.16 | 0.36 | 0.05 |
| 1110 | 4.08 | 100.00 | 2.28 |
| 1111 | 0.49 | 2.28 | 0.26 |
| 1112 | 5.01 | 2.09 | 3.86 |
| 1113 | 0.97 | 2.55 | 0.47 |
| 1114 | 8.40 | 8.08 | 22.82 |
| 1115 | 27.67 | 69.62 | 11.40 |
| 1116 | 100.00 | 100.00 | 100.00 |
| 1117 | 100.00 | 46.61 | 100.00 |
| 1118 | 0.57 | 1.26 | 0.49 |
| 1119 | 0.48 | 1.18 | 0.22 |
| 1120 | 2.58 | 10.61 | 2.90 |
| 1121 | 100.00 | 100.00 | 100.00 |
| 1122 | 9.16 | 38.45 | 6.95 |
| 1123 | 0.48 | 1.37 | 0.58 |
| 1124 | 0.07 | 0.34 | 0.14 |
| 1125 | 18.28 | 100.00 | 100.00 |
| 1126 | 100.00 | 100.00 | 100.00 |
| 1127 | 0.72 | 1.57 | 0.24 |
| 1128 | 0.52 | 0.70 | 0.09 |
| 1129 | 0.10 | 0.05 | 0.01 |
| 1130 | 0.71 | 2.74 | 0.32 |
| 1131 | 0.35 | 0.89 | 0.53 |
| 1132 | 0.10 | 0.05 | 0.02 |
| 1133 | 0.09 | 0.14 | 0.04 |
| 1134 | 1.02 | 1.35 | 0.51 |
| 1135 | 0.59 | 5.94 | 2.90 |
| 1136 | 0.14 | 0.12 | 0.05 |
| 1137 | 5.32 | 2.51 | 5.34 |
| 1138 | 1.64 | 1.22 | 0.04 |
| 1139 | 0.14 | 0.14 | 0.03 |
| 1140 | 0.08 | 0.06 | 0.00 |
| 1141 | 2.35 | 0.93 | 0.45 |
| 1142 | 0.42 | 0.15 | 0.01 |
| 1143 | 1.44 | 4.45 | 1.78 |
| 1144 | 0.29 | 0.84 | 0.09 |
| 1145 | 0.06 | 0.07 | 0.03 |
| 1146 | 0.14 | 0.19 | 0.21 |
| 1147 | 2.84 | 0.94 | 1.01 |
| 1148 | 0.06 | 0.09 | 0.05 |
| 1149 | 1.90 | 0.15 | 0.47 |
| 1150 | 0.05 | 0.05 | 0.04 |
| 1151 | 21.52 | 21.67 | 10.08 |
| 1152 | 59.91 | 7.78 | 3.82 |
| 1153 | 0.89 | 2.86 | 0.66 |
| 2001* | 0.33 | 0.49 | 0.27 |
| 2002* | 0.29 | 0.21 | 0.11 |
| 2009* | 100.00 | 100.00 | 2.25 |
| 2010* | 1.25 | 3.45 | 0.66 |
| 2011* | 4.71 | 25.68 | 1.24 |
| 2012* | 100.00 | 100.00 | 100.00 |
| 2013* | 16.08 | 100.00 | 13.05 |
| 2014* | 100.00 | 100.00‡ | 100.00 |
| 2015* | 0.49 | 1.45 | 0.15 |
| 2016* | 0.12 | 0.29 | 0.05 |
| 2017* | 2.02 | 5.12 | 0.43 |
| 2018* | 100.00‡ | 100.00‡ | 100.00‡ |
| 2019* | 22.98 | 100.00 | 39.98 |
| 2020* | 3.46 | 40.64 | 3.96 |
| 2021* | 1.22 | 19.02 | 3.44 |
| 2022* | 0.30 | 4.08 | 0.32 |
| 2023* | 0.36 | 1.79 | 0.22 |
| 2024* | 2.30 | 5.67 | 2.46 |
| 2025* | 12.69 | 100.00 | 30.27 |
| 2026* | 100.00 | 100.00 | 70.11 |

TABLE 5-continued

| Cmpd No. | Atrial EC$_{25}$ (μM) | Ventricular EC$_{25}$ (μM) | Skeletal EC$_{25}$ (μM) |
|---|---|---|---|
| 2027* | 1.48 | 100.00 | 41.80 |
| 2028* | 100.00 | 100.00‡ | 73.42‡ |
| 2029* | 1.26 | 18.01 | 3.21 |
| 2030* | 1.84 | 100.00 | 100.00 |
| 2033* | 100.00 | 100.00 | 24.12 |
| 2034* | 100.00 | 100.00 | 100.00‡ |
| 2035* | 2.19 | 38.21 | 5.70 |
| 2036* | 100.00 | 100.00 | 100.00 |
| 2037* | 2.88 | 5.31 | 0.79 |
| 2038* | 100.00 | 100.00 | 100.00 |
| 2039* | 1.33 | 2.38 | 100.00 |
| 2040* | 0.60 | 0.99 | 2.12 |
| 2041* | 1.18 | 1.50 | 100.00 |
| 2042* | 0.55 | 2.11 | 2.39 |
| 2043* | 1.01 | 4.16 | 7.03 |
| 2044* | 9.19 | 5.84 | 29.36 |
| 2045* | 100.00‡ | 100.00‡ | 0.16 |
| 2046* | 0.05 | 0.10 | |
| 2047* | 25.33 | 47.78 | 30.48 |
| 2048* | 0.90 | 10.98 | 1.25 |
| 2049* | 0.15 | 0.23 | 1.00 |
| 2050* | 0.09 | 0.18 | 0.04 |
| 2051* | 0.43 | 0.60 | 0.16 |
| 2052* | 0.04 | 0.09 | 0.08 |
| 2053* | 100.00 | 100.00 | 12.45 |
| 2054* | 0.23 | 3.72 | 0.15 |
| 2055* | 0.06 | 0.26 | 0.11 |
| 2056* | 0.11 | 0.29 | 0.06 |
| 2057* | 0.65 | 0.94 | 0.27 |
| 2058* | 100.00 | 68.08 | 3.15 |
| 2059* | 100.00‡ | 56.97 | 1.09 |
| 2060* | 0.45 | 3.02 | 0.26 |
| 2061* | 0.98 | 6.96 | 0.49 |
| 2062* | 6.95 | 62.53 | 8.36 |
| 2063* | 0.21 | 100.00 | 0.50 |
| 2064* | 77.71 | 32.11 | 0.26 |
| 2065* | 100.00 | 100.00 | 1.10 |
| 2066* | 1.06 | 7.88 | 0.15 |
| 2067* | 22.93 | 100.00 | 0.37 |
| 2068* | 47.17 | 93.24 | 0.87 |
| 2069* | 0.04 | 2.76 | 0.49 |
| 2070* | 0.30 | 2.11 | 0.05 |
| 2071* | 1.07 | 2.62 | 2.93 |
| 2072* | 0.68 | 11.13 | 0.35 |
| 2073* | 100.00 | 100.00 | 100.00 |
| 2074* | 9.01 | 10.13 | 4.03 |
| 2075* | 0.07 | 0.52 | 0.04 |
| 2076* | 100.00 | 46.49 | 2.56 |
| 2077* | 1.50 | 100.00 | 0.29 |
| 2078* | 0.23 | 0.91 | 0.56 |
| 2079* | 0.13 | 0.07 | 0.03 |
| 2501* | 0.17 | 0.45 | 0.15 |
| 2502* | 0.09 | 0.20 | 0.03 |
| 2503* | 100.00 | 100.00 | 100.00 |
| 2504* | 100.00 | 100.00 | 100.00 |
| 2505* | 100.00 | 100.00 | 100.00 |
| 2506* | 100.00 | 100.00 | 100.00 |
| 2507* | 4.10 | 100.00 | 19.51 |
| 2508* | 100.00 | 70.50‡ | 5.03 |
| 2509* | 100.00‡ | 77.92‡ | 94.41‡ |
| 2510* | 7.78 | 77.57‡ | 85.63‡ |
| 2511* | 0.76 | 2.64 | 0.28 |
| 2512* | 1.53 | 33.47 | 100.00‡ |
| 2513* | 0.43 | 1.62 | 0.34 |
| 2514* | 0.60 | 1.53 | 0.16 |
| 2515* | 5.06 | 100.00 | 100.00 |
| 2516* | 0.79 | 100.00 | 0.67 |
| 2517* | 3.47 | 24.94 | 2.86 |
| 2518* | 2.85 | 100.00 | 3.14 |
| 2519* | 0.31 | 1.19 | 0.52 |
| 2520* | 0.14 | 0.21 | 0.07 |
| 2521* | 0.32 | 1.83 | 0.41 |
| 2522* | 0.32 | 0.72 | 0.14 |
| 2523* | 0.19 | 0.74 | 100.00‡ |
| 2524* | 0.16 | 0.31 | 0.13 |
| 2527* | 4.73 | 100.00 | 100.00‡ |
| 2528* | 4.45 | 100.00 | 93.23‡ |

TABLE 5-continued

| Cmpd No. | Atrial EC$_{25}$ (μM) | Ventricular EC$_{25}$ (μM) | Skeletal EC$_{25}$ (μM) |
|---|---|---|---|
| 2529* | 0.24 | 0.35 | 0.24 |
| 2530* | 0.20 | 0.21 | 0.08 |
| 2531* | 1.29 | 15.11 | 2.08 |
| 2532* | 0.89 | 45.96 | 1.49 |
| 2533* | 0.13 | 0.13 | 0.06 |
| 2534* | 15.93 | 100.00 | 37.90‡ |
| 2535* | 100.00 | 85.38‡ | 51.07‡ |
| 2536* | 30.59 | 100.00 | 77.37‡ |
| 2537* | 100.00 | 100.00‡ | 100.00‡ |
| 2538* | 0.17 | 0.18 | 0.11 |
| 2539* | 2.76 | 100.00 | 100.00 |
| 2540* | 100.00‡ | 100.00 | 0.96 |
| 2541* | 0.33 | 0.70 | 0.85 |
| 2542* | 0.24 | 0.40 | 0.32 |
| 2543* | 0.73 | 4.00 | 0.83 |
| 2544* | 4.48 | 18.26 | 2.27 |
| 2545* | 7.98 | 1.22 | 0.13 |
| 2546* | 0.20 | 1.23 | 0.19 |
| 2547* | 100.00‡ | 58.38‡ | 0.91 |
| 2548* | 45.39 | 100.00 | 45.96‡ |
| 2549* | 0.97 | 100.00 | 7.56 |
| 2550* | 1.39 | 77.93 | 1.22 |
| 2551* | 0.40 | 27.43‡ | 7.28 |
| 2552* | 0.17 | 0.22 | 0.15 |
| 2553* | 0.51 | 34.88 | 0.79 |
| 2554* | 0.09 | 0.20 | |
| 2555* | 3.65 | 6.70 | 0.80 |
| 2556* | 6.56 | 16.01 | 5.17 |
| 2557* | 3.66 | 7.27 | 6.04 |
| 2558* | 31.66 | 81.97 | 100.00 |
| 2559* | 100.00 | 100.00 | 100.00 |
| 2560* | 100.00 | 100.00 | 61.98‡ |
| 2561* | 0.23 | 0.79 | 0.25 |
| 2562* | 0.15 | 0.75 | 0.28 |
| 2563* | 0.15 | 0.54 | 0.12 |
| 2564* | 0.51 | 0.89 | 0.49 |
| 2565* | 14.39 | 100.00 | 100.00 |
| 2566* | 100.00 | 100.00‡ | 100.00‡ |
| 2567* | 0.34 | 1.07 | 0.33 |
| 2568* | 0.57 | 0.58 | 0.11 |
| 2569* | 4.84 | 100.00 | 100.00 |
| 2570* | 100.00‡ | 63.85‡ | 26.03‡ |
| 2571* | 40.54 | 8.06 | 100.00 |
| 2572* | 100.00 | 100.00‡ | 100.00 |
| 2573* | 100.00 | 100.00 | 100.00 |
| 2574* | 100.00 | 100.00 | 100.00 |
| 2575* | 16.13 | 20.79 | 14.65 |
| 2576* | 38.95 | 100.00 | 76.36 |
| 2577* | 19.55 | 100.00 | 100.00 |
| 2578* | 100.00‡ | 100.00‡ | 100.00‡ |
| 2579* | 100.00 | 100.00 | 100.00 |
| 2580* | 4.52 | 100.00 | 17.17‡ |
| 2581* | 100.00 | 100.00 | 100.00 |
| 2582* | 100.00‡ | 68.39‡ | 75.10‡ |
| 2583* | 4.31 | 100.00 | 100.00 |
| 2584* | 100.00 | 100.00‡ | 100.00‡ |
| 2585* | 1.59 | 7.05 | 3.04 |
| 2586* | 1.58 | 15.70 | 10.30 |
| 2587* | 5.60 | 100.00 | 5.65 |
| 2588* | 100.00 | 67.27‡ | 19.03‡ |
| 2589* | 0.04 | 0.09 | 0.05 |
| 2590* | 0.43 | 3.41 | 1.30 |
| 2591* | 1.52 | 18.78 | 100.00 |
| 2592* | 0.13 | 0.47 | 3.54 |
| 2593* | 0.19 | 1.00 | 1.15 |
| 2594* | 0.23 | 0.33 | 0.33 |
| 2595* | 0.36 | 0.45 | 0.17 |
| 2596* | 0.11 | 0.55 | 0.16 |
| 2597* | 0.09 | 0.39 | 0.12 |
| 2598** | 0.60 | 1.10 | 100.00‡ |
| 2599** | 2.16 | 16.66 | 100.00‡ |
| 2600** | 0.67 | 100.00 | 100.00 |
| 2601** | 0.04 | 0.07 | 0.04 |
| 2602** | 0.05 | 0.08 | 0.02 |
| 2603** | 0.06 | 0.21 | 0.03 |
| 2604** | 0.12 | 0.75 | 0.54 |
| 2605** | 0.40 | 1.47 | 0.40 |

TABLE 5-continued

| Cmpd No. | Atrial $EC_{25}$ (μM) | Ventricular $EC_{25}$ (μM) | Skeletal $EC_{25}$ (μM) |
|---|---|---|---|
| 2606* | 0.08 | 0.77 | 0.10 |
| 2607* | 0.07 | 0.17 | 0.04 |
| 2608* | 100.00 | 44.26‡ | 100.00 |
| 4502* | 1.28 | 0.63 | 0.50 |
| 4503* | 11.52 | 2.98 | 1.29 |
| 4504* | 0.92 | 0.47 | 0.30 |
| 4505* | 3.02 | 31.63 | 11.19 |
| 4801* | 0.28 | 100.00 | 0.28 |
| 4802* | 0.20 | 1.00 | 0.14 |
| 4803* | 100.00 | 100.00 | 0.27 |
| 4804* | 4.71 | 100.00 | 100.00 |
| 4805* | 1.66 | 100.00 | 1.91 |
| 4806* | 0.71 | 33.85 | 2.39 |
| 4807* | | 1.39 | 0.82 |
| 4808* | | 100.00 | 100.00 |
| 4809* | 3.07 | 31.20 | 1.34 |
| 4810* | 1.90 | 100.00 | 100.00 |
| 4811* | 0.73 | 0.46 | 0.59 |
| 4812* | 0.19 | 0.18 | 0.05 |
| 4813 | 0.37 | 100.00 | 0.91 |
| 4814 | 0.23 | 1.31 | 0.19 |
| 4815 | 1.05 | 100.00 | 1.04 |
| 4816 | 0.15 | 0.26 | 0.15 |
| 4817* | 2.48 | 65.71 | 10.40 |
| 4818* | 15.59 | 100.00 | 25.37 |
| 4819* | 0.28 | 2.65 | 1.02 |
| 4820* | 0.12 | 0.61 | 0.11 |
| 4821* | 0.44 | 100.00 | 20.88 |
| 4822* | 0.16 | 0.48 | 0.08 |
| 4823* | 8.47 | 100.00 | 42.66 |
| 4824* | 100.00 | 100.00 | 8.80 |
| 4825* | 0.43 | 100.00 | 100.00 |
| 4826* | 0.67 | 10.09 | 1.00 |
| 4827* | 0.23 | 0.71 | 0.08 |
| 4828* | 0.30 | 1.13 | 0.24 |
| 4829* | 0.45 | 6.13 | 1.15 |
| 4830* | 0.46 | 100.00 | 1.34 |
| 4831* | 0.12 | 0.39 | 0.06 |
| 4832* | 0.12 | 0.58 | 0.17 |
| 4833* | 0.52 | 1.04 | 0.25 |
| 4834* | 0.49 | 0.64 | 0.15 |
| 4835* | 0.18 | 0.77 | 0.11 |
| 4836* | 0.17 | 0.15 | 0.02 |
| 4837* | 1.90 | 3.67 | 0.21 |
| 4838* | 0.92 | 3.58 | 0.28 |
| 4839* | 1.67 | 1.85 | 0.13 |
| 4840* | 1.44 | 1.62 | 0.29 |
| 4841* | 97.50 | 100.00 | 100.00 |
| 4842* | 100.00 | 100.00 | 37.46 |

*denotes that absolute stereochemistry is not yet known. Associated $EC_{25}$ values are to a single enantiomer with unknown absolute configuration.
**denotes that absolute stereochemistry is not yet known. Associated $EC_{25}$ values are to a single diastereomer with unknown absolute configuration.
*** denotes a mixture of diasteromers.
****denotes a racemic mixture.
‡denotes that the number is a Y125 value, not a Y75 value.

TABLE 6

| Cmpd No. | Atrial $EC_{25}$ (μM) | Ventricular $EC_{25}$ (μM) | Skeletal $EC_{25}$ (μM) |
|---|---|---|---|
| 138* | 0.35 | 1.17 | 2.85 |
| 139* | 0.08 | 0.18 | 0.02 |
| 140 | 100.00 | 100.00 | 42.18 |
| 141 | 100.00 | 100.00 | 8.74 |
| 142 | 100.00 | 100.00 | 100.00 |
| 143 | 0.96 | 6.56 | 0.61 |
| 144 | 100.00 | 100.00 | 100.00 |
| 145 | 0.13 | 10.15 | 3.46 |
| 146 | 0.54 | 0.68 | 2.05 |
| 147 | 0.02 | 0.12 | 0.06 |
| 148 | 1.99 | 3.02 | 2.55 |
| 149 | 0.06 | 0.10 | 0.02 |
| 150 | 0.06 | 0.68 | 0.09 |

TABLE 6-continued

| Cmpd No. | Atrial $EC_{25}$ (μM) | Ventricular $EC_{25}$ (μM) | Skeletal $EC_{25}$ (μM) |
|---|---|---|---|
| 151 | 0.44 | 0.87 | 0.11 |
| 152 | 0.05 | 0.09 | 0.01 |
| 153 | 19.40 | 100.00 | 3.09 |
| 154 | 0.18 | 0.54 | 0.04 |
| 155 | 6.06 | 62.81 | 1.24 |
| 156 | 0.33 | 3.12 | 0.21 |
| 157 | 13.10 | 26.29 | 0.62 |
| 158 | 0.43 | 1.80 | 0.06 |
| 159 | 1.17 | 6.35 | 0.11 |
| 160 | 0.13 | 2.23 | 0.03 |
| 161 | 0.34 | 1.19 | 0.11 |
| 162 | 0.13 | 0.11 | 0.02 |
| 163 | 0.94 | 100.00 | 12.34 |
| 164 | 2.51 | 22.06 | 1.12 |
| 165 | 2.77 | 100.00 | 47.80 |
| 166 | 1.91 | 100.00 | 3.22 |
| 167 | 0.18 | 1.13 | 0.03 |
| 168* | 0.05 | 3.63 | 0.10 |
| 169 | 1.06 | 10.52 | 0.15 |
| 170 | 0.08 | 1.02 | 0.03 |
| 171 | 22.46 | 100.00 | 15.02 |
| 172 | 0.10 | 3.78 | 0.04 |
| 173** | 0.22 | 0.30 | 0.02 |
| 174** | 0.08 | 0.55 | 0.08 |
| 175 | 100.00 | 100.00 | 100.00 |
| 176 | 3.29 | 19.33 | 1.13 |
| 177* | 0.06 | 0.09 | 0.02 |
| 178* | 4.55 | 20.24 | 1.84 |
| 179* | 0.71 | 2.15 | 0.13 |
| 180* | 100.00 | 100.00 | 28.17 |
| 181* | 0.31 | 2.51 | 0.09 |
| 182* | 8.60 | 35.91 | 1.76 |
| 183* | 0.33 | 6.37 | 0.75 |
| 184* | 100.00 | 100.00 | 100.00 |
| 185* | 0.08 | 0.08 | 0.02 |
| 186* | 2.39 | 100.00 | 2.19 |
| 187* | 0.11 | 1.36 | 0.05 |
| 188* | 2.43 | 39.56 | 26.50 |
| 189* | 1.22 | 13.14 | 0.87 |
| 190* | 8.11 | 45.62 | 100.00 |
| 191* | 1.73 | 100.00 | 4.04 |
| 192* | 0.59 | 14.65 | 0.55 |
| 193* | 0.47 | 5.94 | 0.75 |
| 194* | 5.87 | 100.00 | 1.22 |
| 195* | 0.30 | 2.97 | 0.11 |
| 196* | 0.11 | 4.23 | 0.18 |
| 197* | 2.80 | 49.43 | 4.23 |
| 198* | 0.31 | 0.18 | 0.02 |
| 199 | 100.00 | 67.50 | 13.03 |
| 200 | 3.03 | 100.00 | 0.19 |
| 201 | 100.00 | 100.00 | 1.02 |
| 202 | 0.11 | 0.83 | 0.11 |
| 203 | 100.00 | 100.00 | 1.10 |
| 204 | 0.47 | 7.78 | 0.07 |
| 205 | | | |
| 206 | 100.00 | 100.00 | 0.40 |
| 207* | 100.00 | 100.00 | 1.32 |
| 208* | 2.16 | 9.68 | 0.15 |
| 209* | 0.03 | 0.14 | 0.01 |
| 210 | 30.20 | 100.00 | 7.04 |
| 211 | 7.02 | 53.99 | 22.09 |
| 212* | 14.71 | 35.35 | 2.21 |
| 213* | 100.00 | 100.00 | 7.67 |
| 214* | 100.00 | 100.00 | 23.30 |
| 215* | 100.00 | 100.00 | 100.00 |
| 216 | 100.00 | 100.00 | 100.00 |
| 217 | 0.36 | 6.79 | 0.71 |
| 218 | 100.00 | 100.00 | 14.86 |
| 219 | 0.12 | 7.16 | 0.14 |
| 220 | 100.00 | 100.00 | 100.00 |
| 221 | 1.12 | 45.66 | 2.27 |
| 222* | 100.00 | 100.00 | 100.00 |
| 223* | 12.99 | 61.19 | 16.17 |
| 224* | 6.57 | 100.00 | 0.36 |
| 225* | 0.08 | 2.46 | 0.03 |
| 226* | 7.58 | 100.00 | 0.27 |
| 227* | 0.09 | 0.62 | 0.07 |

TABLE 6-continued

| Cmpd No. | Atrial $EC_{25}$ (μM) | Ventricular $EC_{25}$ (μM) | Skeletal $EC_{25}$ (μM) |
|---|---|---|---|
| 228 | 100.00 | 100.00 | 100.00 |
| 229 | 8.21 | 34.95 | 4.20 |
| 230 | 0.11 | 0.96 | 0.02 |
| 231 | 100.00 | 100.00 | 100.00 |
| 232 | 0.47 | 2.74 | 0.02 |
| 233* | 100.00 | 100.00 | 5.72 |
| 234* | 100.00 | 100.00 | 20.28 |
| 235* | 100.00 | 100.00 | 100.00 |
| 236* | 38.11 | 100.00 | 0.59 |
| 237 | 100.00 | 100.00 | 100.00 |
| 238* | 8.52 | 11.53 | 2.87 |
| 239 | 4.64 | 10.80 | 0.65 |
| 240 | 100.00 | 100.00 | 100.00 |
| 241* | 0.69 | 4.21 | 0.17 |
| 242* | 0.09 | 0.52 | 0.02 |
| 243* | 0.56 | 2.20 | 0.17 |
| 244 | 100.00 | 100.00 | 100.00 |
| 245* | 8.37 | 9.46 | 0.93 |
| 246* | 0.13 | 0.15 | 0.03 |
| 247* | 34.93 | 100.00 | 4.60 |
| 248* | 0.86 | 3.01 | 0.17 |
| 249* | 100.00 | 100.00 | 100.00 |
| 250* | 2.60 | 80.59 | 16.64 |
| 251* | 100.00 | 100.00 | 100.00 |
| 252* | 100.00 | 100.00 | 100.00 |
| 253* | 100.00 | 100.00 | 100.00 |
| 254* | 18.17 | 23.41 | 1.78 |
| 255* | 1.30 | 1.77 | 0.71 |
| 256* | 0.08 | 0.19 | 0.02 |
| 257** | 100.00 | 100.00 | 100.00 |
| 258** | 100.00 | 63.55 | 100.00 |
| 259 | 100.00 | 100.00 | 100.00 |
| 260 | 2.40 | 100.00 | 33.76 |
| 261 | 100.00 | 100.00 | 26.68 |
| 262 | 0.19 | 0.67 | 0.13 |
| 263 | 100.00 | 100.00 | 100.00 |
| 264 | 0.29 | 2.73 | 0.57 |
| 265* | 100.00 | 100.00 | 3.86 |
| 266* | 0.25 | 1.11 | 0.21 |
| 267* | 100.00 | 100.00 | 100.00 |
| 268* | 100.00 | 100.00 | 100.00 |
| 269 | 100.00 | 34.76 | 2.47 |
| 270 | 100.00 | 100.00 | 100.00 |
| 271* | 100.00 | 100.00 | 100.00 |
| 272* | 100.00 | 100.00 | 100.00 |
| 273* | 2.50 | 4.08 | 0.97 |
| 274* | 0.04 | 0.13 | 0.02 |
| 275 | 3.24 | 100.00 | 2.30 |
| 276 | 1.25 | 15.06 | 0.14 |
| 277 | 100.00 | 84.29 | 82.10 |
| 278 | 17.26 | 100.00 | 2.73 |
| 279* | 78.18 | 100.00 | 1.29 |
| 280* | 100.00 | 100.00 | 24.76 |
| 281 | 0.27 | 5.52 | 0.34 |
| 282* | 1.55 | 1.16 | 0.35 |
| 283* | 0.04 | 0.10 | 0.01 |
| 284* | 4.56 | 10.63 | 0.49 |
| 285* | 0.28 | 0.16 | 0.02 |
| 286* | 45.61 | 100.00 | 8.58 |
| 287* | 100.00 | 100.00 | 100.00 |
| 288* | 0.08 | 0.27 | 0.02 |
| 289* | 28.00 | 100.00 | 2.54 |
| 290* | 100.00 | 100.00 | 100.00 |
| 291* | 100.00 | 100.00 | 100.00 |
| 292 | 100.00 | 100.00 | 100.00 |
| 293 | 100.00 | 100.00 | 73.40 |
| 294* | 100.00 | 100.00 | 100.00 |
| 295* | 100.00 | 100.00 | 100.00 |
| 296* | 88.12 | 100.00 | 100.00 |
| 297* | 100.00 | 100.00 | 100.00 |
| 298* | 100.00 | 100.00 | 100.00 |
| 299 | 10.21 | 100.00 | 17.50 |
| 300 | 100.00 | 100.00 | 100.00 |
| 301* | 100.00 | 100.00 | 100.00 |
| 302* | 100.00 | 100.00 | 100.00 |
| 303* | 100.00 | 100.00 | 40.83 |
| 304* | 17.26 | 100.00 | 1.57 |

TABLE 6-continued

| Cmpd No. | Atrial $EC_{25}$ (μM) | Ventricular $EC_{25}$ (μM) | Skeletal $EC_{25}$ (μM) |
|---|---|---|---|
| 305* | 0.07 | 0.57 | 0.02 |
| 306* | 11.75 | 100.00 | 5.05 |
| 307* | 100.00 | 100.00 | 100.00 |
| 308* | 1.07 | 12.24 | 1.82 |
| 309* | 100.00 | 100.00 | 100.00 |
| 310* | 100.00 | 100.00 | 100.00 |
| 311* | 100.00 | 100.00 | 100.00 |
| 312* | 100.00 | 100.00 | 100.00 |
| 313* | 100.00 | 100.00 | 100.00 |
| 314* | 100.00 | 100.00 | 100.00 |
| 315* | 100.00 | 100.00 | 100.00 |
| 316* | 100.00 | 100.00 | 100.00 |
| 317* | 100.00 | 100.00 | 100.00 |
| 318* | 100.00 | 100.00 | 27.68 |
| 319* | 100.00 | 100.00 | 100.00 |
| 320* | 100.00 | 100.00 | 34.09 |
| 321* | 100.00 | 100.00 | 100.00 |
| 322* | 100.00 | 100.00 | 100.00 |
| 323* | 100.00 | 100.00 | 100.00 |
| 324* | 100.00 | 100.00 | 100.00 |
| 325* | 100.00 | 100.00 | 1.57 |
| 326* | 100.00 | 100.00 | 100.00 |
| 327* | 3.29 | 9.24 | 0.67 |
| 328* | 100.00 | 100.00 | 100.00 |
| 329* | 100.00 | 100.00 | 100.00 |
| 330* | 100.00 | 100.00 | 100.00 |
| 331* | 100.00 | 100.00 | 100.00 |
| 332 | 0.09 | 0.20 | 0.04 |
| 333* | 100.00 | 100.00 | 100.00 |
| 334* | 100.00 | 100.00 | 100.00 |
| 335* | 100.00 | 100.00 | 26.39 |
| 336* | 69.32 | 100.00 | 100.00 |
| 337* | 100.00 | 100.00 | 100.00 |
| 338* | 8.69 | 100.00 | 27.39 |
| 339* | 100.00 | 100.00 | 100.00 |
| 340* | 36.97 | 100.00 | 100.00 |
| 341* | 100.00 | 100.00 | 100.00 |
| 342* | 3.65 | 52.00 | 11.14 |
| 343 | 2.39 | 9.62 | 1.55 |
| 344* | 9.52 | 90.74 | 0.23 |
| 345 | 10.74 | 51.73 | 1.83 |
| 346 | 100.00 | 100.00 | 2.37 |
| 347* | 0.94 | 20.36 | 0.35 |
| 348* | 0.34 | 6.44 | 0.51 |
| 349 | 0.76 | 5.41 | 0.13 |
| 350 | 0.99 | 1.99 | 0.06 |
| 351 | 0.14 | 0.97 | 0.06 |
| 352 | 2.64 | 31.62 | 0.18 |
| 353 | 0.14 | 0.31 | 0.06 |
| 354 | 2.11 | 49.13 | 0.19 |
| 355 | 0.07 | 0.14 | 0.01 |
| 356* | 100.00 | 100.00 | 157.50 |
| 357 | 0.06 | 0.31 | 0.06 |
| 358* | 23.89 | 54.71 | 100.00 |
| 359 | 0.11 | 100.00 | 0.04 |
| 360* | 100.00 | 100.00 | 0.05 |
| 361* | 1.29 | 3.68 | 0.03 |
| 362 | 9.38 | 100.00 | 0.40 |
| 363 | 0.36 | 2.83 | 0.04 |
| 364* | 1.16 | 4.71 | 0.44 |
| 365* | 0.18 | 0.92 | 0.03 |
| 366* | 0.14 | 1.48 | 0.04 |
| 367* | 2.23 | 36.08 | 0.29 |
| 368* | 1.66 | 43.64 | 0.43 |
| 369* | 0.29 | 60.83 | 15.36 |
| 370* | 0.06 | 48.16 | 0.51 |
| 371 | 3.04 | 100.00 | 0.37 |
| 372 | 100.00 | 100.00 | 1.61 |
| 373 | 0.04 | 0.12 | 0.01 |
| 374 | 0.09 | 0.37 | 0.02 |
| 375* | 0.27 | 4.58 | 0.17 |
| 376* | 0.16 | 1.33 | 0.03 |
| 377 | 0.06 | 0.29 | 0.01 |
| 378* | 100.00 | 100.00 | 3.18 |
| 379* | 2.36 | 5.81 | 0.36 |
| 380 | 0.06 | 0.77 | 0.01 |
| 381 | 0.10 | 0.31 | 0.01 |

TABLE 6-continued

| Cmpd No. | Atrial $EC_{25}$ (μM) | Ventricular $EC_{25}$ (μM) | Skeletal $EC_{25}$ (μM) |
|---|---|---|---|
| 382 | 0.05 | 0.28 | 0.01 |
| 383 | 100.00 | 100.00 | 0.39 |
| 384 | 0.21 | 11.67 | 0.04 |
| 385 | 0.06 | 0.33 | 0.03 |
| 386 | 0.12 | 1.51 | 0.03 |
| 387 | 0.14 | 100.00 | 0.19 |
| 388 | 1.08 | 38.06 | 0.67 |
| 389 | 0.71 | 100.00 | 0.25 |
| 390 | 100.00 | 44.80 | 7.06 |
| 391 | 0.05 | 0.29 | 0.01 |
| 392 | 0.13 | 2.65 | 0.07 |
| 393 | 2.46 | 0.42 | 0.02 |
| 394 | 0.27 | 0.53 | 0.03 |
| 395 | 1.69 | 47.49 | 0.08 |
| 396* | 1.18 | 3.32 | 0.55 |
| 397 | 100.00 | 32.40 | 1.87 |
| 398* | 2.73 | 59.63 | 0.23 |
| 399* | 0.91 | 18.33 | 0.30 |
| 400 | 1.55 | 100.00 | 0.36 |
| 401 | 0.05 | 0.20 | 0.02 |
| 402 | 0.04 | 0.19 | 0.02 |
| 403* | 40.23 | 2.08 | 0.19 |
| 404* | 100.00 | 42.84 | 0.35 |
| 405 | 0.15 | 1.12 | 0.04 |
| 406 | 0.10 | 0.38 | 0.02 |
| 407 | 0.10 | 0.33 | 0.02 |
| 408 | 100.00 | 100.00 | 13.02 |
| 409 | 0.04 | 0.59 | 0.03 |
| 410* | 5.46 | 100.00 | 0.76 |
| 411* | 1.41 | 100.00 | 0.35 |
| 412* | 76.17 | 100.00 | 100.00 |
| 413* | 20.63 | 100.00 | 10.76 |
| 414 | 0.16 | 13.93 | 0.03 |
| 415* | 2.22 | 12.58 | 0.13 |
| 416* | 100.00 | 100.00 | 0.46 |
| 417 | 9.70 | 9.50 | 0.17 |
| 418 | 2.66 | 48.43 | 2.19 |
| 419 | 0.49 | 100.00 | 0.19 |
| 420 | 0.11 | 2.34 | 0.19 |
| 421 | 100.00 | 100.00 | 0.20 |
| 422 | 100.00 | 100.00 | 0.03 |
| 423 | 100.00 | 100.00 | 0.34 |
| 424* | 1.91 | 17.24 | 4.49 |
| 425* | 94.54 | 100.00 | 1.31 |
| 426* | 4.84 | 66.84 | 12.74 |
| 427* | 2.53 | 22.60 | 2.02 |
| 428 | 1.35 | 1.94 | 0.09 |
| 429 | 100.00 | 100.00 | 1.22 |
| 430 | 0.38 | 11.63 | 0.25 |
| 431 | 11.13 | 50.88 | 0.80 |
| 432 | 16.07 | 80.53 | 0.47 |
| 433 | 0.15 | 0.64 | 0.03 |
| 434 | 0.65 | 3.84 | 0.13 |
| 435 | 32.52 | 19.10 | 0.38 |
| 436 | 100.00 | 100.00 | 12.92 |
| 437 | 91.43 | 100.00 | 1.28 |
| 438 | 2.35 | 7.68 | 0.60 |
| 439 | 0.06 | 0.47 | 0.10 |
| 440 | 34.65 | 100.00 | 2.78 |
| 441 | 3.48 | 100.00 | 1.88 |
| 442* | 100.00 | 100.00 | 12.41 |
| 443* | 100.00 | 100.00 | 1.34 |
| 444 | 1.14 | 20.82 | 0.17 |
| 445 | 2.32 | 20.53 | 0.43 |
| 446 | 100.00 | 100.00 | 4.59 |
| 447 | 0.25 | 10.16 | 0.05 |
| 448 | 0.65 | 7.29 | 0.17 |
| 449 | 100.00 | 100.00 | 100.00 |
| 450 | 100.00 | 100.00 | 100.00 |
| 451 | 100.00 | 100.00 | 100.00 |
| 452 | 63.47 | 100.00 | 100.00 |
| 453 | 8.79 | 100.00 | 9.12 |
| 454 | 7.21 | 52.30 | 4.25 |
| 455 | 7.11 | 100.00 | 5.74 |
| 456 | 0.66 | 3.69 | 0.53 |
| 457 | 30.66 | 100.00 | 100.00 |
| 458 | 0.79 | 100.00 | 10.51 |

TABLE 6-continued

| Cmpd No. | Atrial $EC_{25}$ (μM) | Ventricular $EC_{25}$ (μM) | Skeletal $EC_{25}$ (μM) |
|---|---|---|---|
| 459 | 3.13 | 100.00 | 100.00 |
| 460 | 1.53 | 30.78 | 100.00 |
| 461 | 94.45 | 15.98 | 100.00 |
| 462 | 65.72 | 100.00 | 100.00 |
| 463 | 4.39 | 26.99 | 9.72 |
| 464 | 0.37 | 0.18 | 0.03 |
| 465 | 100.00 | 100.00 | 47.72 |
| 466 | 100.00 | 100.00 | 100.00 |
| 467 | 100.00 | 100.00 | 16.00 |
| 468 | 0.80 | 1.48 | 4.03 |
| 469 | 0.15 | 1.66 | 0.55 |
| 470 | 100.00 | 100.00 | 9.89 |
| 471 | 100.00 | 67.58 | 100.00 |
| 472 | 4.05 | 5.93 | 0.40 |
| 473 | 1.44 | 6.63 | 0.30 |
| 474 | 100.00 | 100.00 | 15.42 |
| 475 | 100.00 | 39.76 | 2.98 |
| 476 | 1.38 | 0.77 | 0.23 |
| 477 | 1.23 | 2.64 | 1.78 |
| 478 | 5.84 | 33.12 | 65.26 |
| 479 | 100.00 | 100.00 | 100.00 |
| 480 | 100.00 | 100.00 | 33.82 |
| 481 | 100.00 | 100.00 | 100.00 |
| 482 | 28.27 | 63.17 | 100.00 |
| 483 | 4.03 | 16.67 | 7.32 |
| 484 | 2.09 | 100.00 | 27.88 |
| 485 | 48.27 | 100.00 | 100.00 |
| 486 | 1.49 | 1.47 | 0.20 |
| 487 | 100.00 | 3.42 | 3.42 |
| 488 | 12.56 | 4.94 | 1.15 |
| 489 | 1.00 | 0.57 | 0.26 |
| 490 | 100.00 | 100.00 | 45.80 |
| 491 | 1.57 | 11.59 | 7.59 |
| 492 | 0.08 | 0.32 | 0.28 |
| 493 | 100.00 | 100.00 | 100.00 |
| 494 | 100.00 | 100.00 | 100.00 |
| 495 | 100.00 | 100.00 | 100.00 |
| 496 | 100.00 | 100.00 | 100.00 |
| 497 | 73.3 | 100 | 100 |
| 498 | 100 | 100 | 7.2 |
| 499 | 100 | 100 | 100 |
| 500 | 43 | 70 | 2.3 |
| 501 | 76 | 78 | 3.4 |
| 3001* | 1.25 | 17.65 | 4.13 |
| 3002* | 100.00 | 100.00 | 100.00 |
| 3003* | 92.51‡ | 100.00 | 94.25‡ |
| 3004* | 10.04 | 100.00 | 5.99 |
| 3005* | 100.00 | 100.00 | 100.00 |
| 3006* | 77.22‡ | 100.00 | 100.00 |
| 3007* | 100.00 | 5.73 | 100.00 |
| 3009* | 0.14 | 2.17 | 100.00 |
| 3010* | 0.70 | 3.57 | 0.63 |
| 3011* | 2.74 | 100.00 | 63.42 |
| 3012* | 1.06 | 58.99 | 2.71 |
| 3013 | | 100.00 | 100.00 |
| 3502* | 0.15 | 0.31 | 0.08 |
| 3503* | 3.50 | 5.70 | 0.89 |
| 3504* | 0.77 | 4.90 | 1.04 |
| 3505* | 1.90 | 13.00 | 4.70 |
| 3506* | | 100.00 | 108.50‡ |
| 3507* | 2.61 | 18.82 | 100.00 |
| 3508* | 0.22 | 0.29 | 0.07 |
| 3509* | 0.35 | 0.50 | 0.15 |
| 3510* | 0.44 | 1.30 | 0.16 |
| 3511* | 0.56 | 2.65 | 0.26 |
| 3512* | 1.65 | 100.00‡ | 0.71 |
| 3513* | 4.94 | 62.33 | 5.80 |
| 3514* | 0.11 | 0.13 | 0.05 |
| 3515* | 0.24 | 0.28 | 0.06 |
| 3516* | 0.51 | 1.49 | 0.24 |
| 3517* | 1.12 | 2.11 | 0.38 |
| 3518* | 2.05 | 100.00 | 9.37 |
| 3519* | 0.94 | 17.07 | 97.12‡ |
| 3520* | 2.38 | 4.50 | 0.25 |

TABLE 6-continued

| Cmpd No. | Atrial $EC_{25}$ (μM) | Ventricular $EC_{25}$ (μM) | Skeletal $EC_{25}$ (μM) |
|---|---|---|---|
| 3521* | 14.61 | 34.58 | 2.68 |
| 3522* | 1.10 | 2.90 | 0.28 |
| 3523* | 9.76 | 21.66 | 8.73 |

*denotes that absolute stereochemistry is not yet known. Associated $EC_{25}$ values are to a single enantiomer with unknown absolute configuration.
**denotes that absolute stereochemistry is not yet known. Associated $EC_{25}$ values are to a single diastereomer with unknown absolute configuration.
*** denotes a mixture of diasteromers.
**** denotes a racemic mixture.
‡denotes that the number is a Y125 value, not a Y75 value.

TABLE 7

| Cmpd No. | Atrial $EC_{25}$ (μM) | Ventricular $EC_{25}$ (μM) | Skeletal $EC_{25}$ (μM) |
|---|---|---|---|
| 4001* | 0.26 | 0.58 | 0.16 |
| 4002* | 1.60 | 100.00 | 4.10 |
| 4003* | 100.00 | 100.00 | 1.06 |
| 4004* | 0.41 | 0.31 | 0.16 |
| 4005* | 3.02 | 2.05 | 1.77 |
| 4006* | 0.74 | 6.66 | 1.11 |
| 4007* | 100.00 | 100.00 | 100.00‡ |
| 4008* | 2.24 | 2.08 | 4.42 |
| 4009* | 2.28 | 0.91 | 1.49 |
| 4010* | 0.74 | 19.76 | 2.38 |

*denotes that absolute stereochemistry is not yet known. Associated $EC_{25}$ values are to a single enantiomer with unknown absolute configuration.
** denotes that absolute stereochemistry is not yet known. Associated $EC_{25}$ values are to a single diastereomer with unknown absolute configuration.
*** denotes a mixture of diasteromers.
**** denotes a racemic mixture.
‡denotes that the number is a Y125 value, not a Y75 value.

(Compound 434)

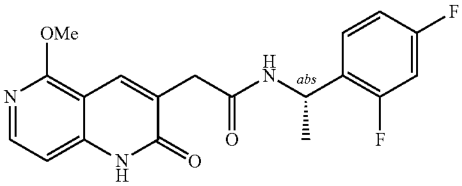

N-[(1S)-1-(2,4-difluorophenyl)ethyl]-2-(5-methoxy-2-oxo-1H-1,6-naphthyridin-3-yl)acetamide Methyl 2-(5-chloro-2-oxo-1H-1,6-naphthyridin-3-yl)acetate. Into a 100-mL round-bottom flask, was placed (5-chloro-2-oxo-1H-1,6-naphthyridin-3-yl)acetic acid (900.00 mg, 3.77 mmol, 1.00 equiv), MeOH (40 mL), $SOCl_2$ (2243 mg, 19 mmol, 5 equiv). The reaction mixture was stirred for 120 min at 50° C. The residue was purified using silica gel column chromatography. The collected fractions were combined and concentrated under vacuum resulting in 700 mg (73.46%) of methyl 2-(5-chloro-2-oxo-1H-1,6-naphthyridin-3-yl)acetate. LCMS (ES, m/z): 253 $[M+H]^+$.

Methyl 2-(5-methoxy-2-oxo-1H-1,6-naphthyridin-3-yl) acetate. Into a 20-mL round-bottom flask purged and maintained with an inert atmosphere of nitrogen, was placed methyl 2-(5-chloro-2-oxo-1H-1,6-naphthyridin-3-yl)acetate (200.00 mg, 0.79 mmol, 1.00 equiv), $Cs_2CO_3$ (773.77 mg, 2.38 mmol, 3.00 equiv), MeOH (5.00 mL). The reaction mixture was stirred for 46 h at 105° C. The reaction was then quenched by the addition of 30 mL of water and The reaction mixture reaction mixture was extracted with of ethyl acetate and the organic layers combined and concentrated under vacuum. The residue was purified using column chromatography and resulted in 150 mg (76.33%) of methyl 2-(5-methoxy-2-oxo-1H-1,6-naphthyridin-3-yl)acetate. LCMS (ES, m/z): 249 $[M+H]^+$.

N-[(1S)-1-(2,4-difluorophenyl)ethyl]-2-(5-methoxy-2-oxo-1H-1,6-naphthyridin-3-yl)acetamide. A mixture of methyl 2-(5-methoxy-2-oxo-1H-1,6-naphthyridin-3-yl)acetate(120.00 mg, 0.48 mmol, 1.00 equiv), HATU (220.57 mg, 0.58 mmol, 1.20 equiv), DIEA(187.43 mg, 1.45 mmol, 3.00 equiv) and (1S)-1-(2,4-difluorophenyl)ethanamine (91.17 mg, 0.58 mmol, 1.20 equiv) in DMF (5.00 mL) was stirred for 2 h at room temperature. The reaction was quenched with water at room temperature and the precipitated solids were collected by filtration and washed. The crude product (100 mg) was purified by Prep-HPLC with the following conditions (Column: XBridge Prep C18 OBD Column, 5 um, 19*150 mm; Mobile Phase A: Water(10 MMOL/L $NH_4HCO_3$), Mobile Phase B: ACN; Flow rate: 25 mL/min; Gradient: 25 B to 37 B in 8 min; 254 nm; RT1:7.42; RT2; Injection Volume: ml) to afford N-[(1S)-1-(2,4-difluorophenyl)ethyl]-2-(5-methoxy-2-oxo-1H-1,6-naphthyridin-3-yl)acetamide (12.8 mg, 7.09%). LCMS (ES, m/z): 374.00 $[M+H]^-$. $^1H$ NMR (300 MHz, DMSO-d6) δ 12.09 (s, $^1H$), 8.57 (d, J=7.5 Hz, $^1H$), 8.02 (d, J=5.7 Hz, $^1H$), 7.85 (s, $^1H$), 7.51-7.43 (m, $^1H$), 7.21-7.17 (m, $^1H$), 7.15-7.14 (m, $^1H$), 6.85 (d, J=6.0 Hz, $^1H$), 5.11-5.06 (m, $^1H$), 3.96 (s, $^3H$), 1.35 (d, J=7.2 Hz, $^3H$)

(Compound 432)

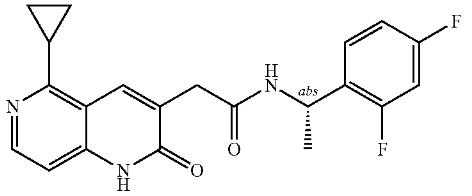

2-(5-Cyclopropyl-2-oxo-1H-1,6-naphthyridin-3-yl)-N-[(1S)-1-(2,4-difluorophenyl)ethyl]acetamide Methyl 2-(5-chloro-2-oxo-1H-1,6-naphthyridin-3-yl) acetate. Into a 100-mL round-bottom flask, was placed (5-chloro-2-oxo-1H-1,6-naphthyridin-3-yl) acetic acid (900.00 mg, 3.77 mmol, 1.00 equiv), MeOH (40 mL), $SOCl_2$ (2243.49 mg, 18.86 mmol, 5 equiv). The reaction mixture was stirred for 120 min at 50° C. The resulting mixture was concentrated under reduced pressure and the residue was purified using silica gel column chromatography with ethyl acetate/petroleum ether (1:1). The collected fractions were combined and concentrated under vacuum resulting in 700 mg (73.46%) of methyl 2-(5-chloro-2-oxo-1H-1,6-naphthyridin-3-yl) acetate. LCMS (ES, m/z): 253 $[M+H]^+$.

Methyl 2-(5-cyclopropyl-2-oxo-1H-1,6-naphthyridin-3-yl) acetate. Into a 10-mL round-bottom flask, was placed methyl 2-(5-chloro-2-oxo-1H-1,6-naphthyridin-3-yl) acetate (300 mg, 1.19 mmol, 1 equiv), dioxane (4 mL), $K_2CO_3$ (820.53 mg, 5.935 mmol, 5 equiv), cyclopropylboronic acid (306.0 mg, 3.561 mmol, 3 equiv), Pd(dppf)$Cl_2$ (86.88 mg, 0.119 mmol, 0.1 equiv). The reaction mixture was stirred for 3 h at 120° C. The resulting mixture was diluted with water. The resulting mixture was extracted with EtOAc and the resulting mixture was concentrated under reduced pressure and the residue was purified by silica gel column chromatography, to afford methyl 2-(5-cyclopropyl-2-oxo-1H-1,6-naphthyridin-3-yl) acetate (180 mg, 58.69%).

LCMS (ES, m/z): 259 $[M+H]^+$. (5-Cyclopropyl-2-oxo-1H-1,6-naphthyridin-3-yl) acetic acid. A solution of methyl 2-(5-cyclopropyl-2-oxo-1H-1,6-naphthyridin-3-yl) acetate (180.00 mg, 0.697 mmol, 1.00 equiv) and LiOH (50.07 mg, 2.09 mmol, 3.00 equiv) in $H_2O$ (2.00 mL) and MeOH (2.00 mL) was stirred for 2 h at room temperature. The resulting mixture was concentrated under reduced pressure and the residue was dissolved in water (10 mL) and acidified to pH 5 with HCl (aq.). The resulting mixture was concentrated under vacuum and purified by reverse flash chromatography with the following conditions: column, C18 silica gel; mobile phase, MeCN in water, 5% to 5.3% gradient in 10 min; detector, UV 254 nm. to afford (5-cyclopropyl-2-oxo-1H-1,6-naphthyridin-3-yl) acetic acid (130 mg, 76.37%). LCMS (ES, m/z): 245 $[M+H]^+$.

2-(5-Cyclopropyl-2-oxo-1H-1,6-naphthyridin-3-yl)-N-[(1S)-1-(2,4-difluorophenyl) ethyl]acetamide. To a stirred mixture of (5-cyclopropyl-2-oxo-1H-1,6-naphthyridin-3-yl) acetic acid (100.00 mg, 0.409 mmol, 1.00 equiv) and HATU (186.81 mg, 0.491 mmol, 1.20 equiv) in DMF (5.00 mL) were added DIEA (211.66 mg, 1.638 mmol, 4.00 equiv) and (1S)-1-(2,4-difluorophenyl) ethanamine (96.52 mg, 0.614 mmol, 1.50 equiv) in portions at room temperature under nitrogen atmosphere. The resulting mixture was stirred for 2 h at room temperature under nitrogen atmosphere. The residue was dissolved in water. The resulting mixture was extracted with EtOAc. The combined organic layers were washed with brine and dried over anhydrous $Na_2SO_4$. The filtrate was concentrated under reduced pressure and the pressure and the residue was purified by reverse flash chromatography with the following conditions: column, C18; mobile phase, ACN in water, 10% to 50% gradient in 30 min; detector, UV 254 nm resulting in 2-(5-cyclopropyl-2-oxo-1H-1,6-naphthyridin-3-yl)-N-[(1S)-1-(2,4-difluorophenyl) ethyl]acetamide (47.5 mg, 30.26%). LCMS (ES, m/z): 384.05 $[M+H]^+$. $^1H$ NMR (300 MHz, DMSO-$d_6$) δ 12.00 (s, $^1H$), 8.58 (d, J=7.5 Hz, $^1H$), 8.29-8.21 (m, $^2H$), 7.50 (d, J=6.6 Hz, $^1H$), 7.11-6.98 (m, $^1H$), 6.97-6.95 (m, $^2H$), 5.10 (s, $^1H$), 3.46 (s, 2H), 2.51-2.50 (m, $^1H$), 1.36 (d, J=6.9 Hz, 3H), 1.05-0.99 (m, $^4H$).

(Compound 431)

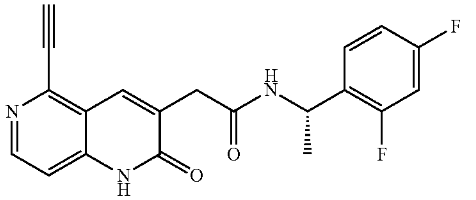

N-[(1S)-1-(2,4-Difluorophenyl)ethyl]-2-(5-ethynyl-2-oxo-1H-1,6-naphthyridin-3-yl)acetamide N-(3-Bromo-2-chloropyridin-4-yl)-2,2-dimethylpropanamide. To a stirred solution of 3-bromo-2-chloropyridin-4-amine (8 g, 39 mmol, 1 equiv) and TEA (7.80 g, 77.1 mmol, 2 equiv) in DCM (100 mL) was added 2,2-dimethylpropanoyl chloride (6.04 g, 50.1 mmol, 1.3 equiv) dropwise at 0° C. under air atmosphere. The resulting mixture was stirred for 3 h at room temperature under air atmosphere and then diluted with water, extracted with $CH_2Cl_2$ and the combined organic layers were washed with brine and dried over anhydrous $Na_2SO_4$. The filtrate was concentrated under reduced pressure and the residue was purified by silica gel column chromatography to afford N-(3-bromo-2-chloropyridin-4-yl)-2,2-dimethylpropanamide (7.5 g, 66.71%). LCMS (ES, m/z): 291 $[M+H]^+$.

N-(2-Chloro-3-formylpyridin-4-yl)-2,2-dimethylpropanamide. To a stirred solution of N-(3-bromo-2-chloropyridin-4-yl)-2,2-dimethylpropanamide (7 g, 24 mmol, 1 equiv) in THF (100 mL) was added NaH (0.63 g, 26.4 mmol, 1.1 equiv) in portions at 0° C. under argon atmosphere. The resulting mixture was stirred for 20 min at 0° C. under argon atmosphere. To the above mixture was added n-BuLi (11.52 mL, 28.81 mmol, 1.2 equiv) dropwise over 5 min at −78° C. The resulting mixture was stirred for additional 30 min at −78° C. and DMF (7.02 g, 96.0 mmol, 4 equiv) was added dropwise over 5 min at −78° C. The resulting mixture was stirred for additional 2 h at −78° C. The reaction was quenched with sat. $NH_4Cl$ (aq.) at −78° C. and then was diluted with water (100 mL). The resulting mixture was extracted with EtOAc and the combined organic layers were washed with brine and dried over anhydrous $Na_2SO_4$. The filtrate was concentrated under reduced pressure and the residue was purified by silica gel column chromatography to afford N-(2-chloro-3-formylpyridin-4-yl)-2,2-dimethylpropanamide (5.0 g, 86.53%)LCMS (ES, m/z): 241 $[M+H]^+$.

1,4-Di-tert-butyl 2-{[2-chloro-4-(2,2-dimethylpropanamido)pyridin-3-yl](hydroxy)methyl}butanedioate. To a stirred solution of 1,4-di-tert-butyl butanedioate (9.57 g, 41.548 mmol, 2 equiv) in THF (100 mL) was added LDA (31.16 mL, 62.322 mmol, 3 equiv) dropwise at −78° C. under argon atmosphere. The resulting mixture was stirred for 30 min at −78° C. under argon atmosphere. To the mixture was added N-(2-chloro-3-formylpyridin-4-yl)-2,2-dimethylpropanamide (5 g, 21 mmol, 1 equiv) and $ZnCl_2$ (29.68 mL, 20.77 mmol, I equiv) dropwise over 5 min at −78° C. The resulting mixture was stirred for additional 2 h at −78° C. The reaction was quenched with sat. $NH_4Cl$ (aq.) at −78° C. The resulting mixture was diluted with water (100 mL) extracted with EtOAc. The combined organic layers were washed with brine and dried over anhydrous $Na_2SO_4$. The filtrate was concentrated under reduced pressure and the residue was purified by silica gel column chromatography to afford 1,4-di-tert-butyl 2-{[2-chloro-4-(2,2-dimethylpropanamido)pyridin-3-yl](hydroxy)methyl}butanedioate (5.2 g, 53.15%). LCMS (ES, m/z): 471 $[M+H]^+$. (5-Chloro-2-oxo-1H-1,6-naphthyridin-3-yl)acetic acid. A solution of 1,4-di-tert-butyl 2-{[2-chloro-4-(2,2-dimethylpropanamido) pyridin-3-yl](hydroxy)methyl}butanedioate (5 g, 10 mmol, 1 equiv) and KOH (2.98 g, 53.1 mmol, 5 equiv) in EtOH (70 mL) was stirred for overnight at 80° C. under air atmosphere. The mixture was cooled to room temperature and acidified to pH 3-4 with HCl (aq. 3 M). The precipitated solids were collected by filtration and washed with MeCN to afford (5-chloro-2-oxo-1H-1,6-naphthyridin-3-yl)acetic acid (2.0 g, 78.95%). LCMS (ES, m/z): 239 $[M+H]^+$.

Methyl 2-(5-chloro-2-oxo-1H-1,6-naphthyridin-3-yl)acetate. To a stirred solution of (5-chloro-2-oxo-1H-1,6-naphthyridin-3-yl)acetic acid (2 g, 8 mmol, 1 equiv) in MeOH (30 mL), $SOCl_2$ (4.99 g, 41.9 mmol, 5 equiv) was added dropwise at 0° C. under air atmosphere. The resulting mixture was stirred for 2 h at 50° C. under air atmosphere. The mixture was cooled to room temperature. The resulting mixture was concentrated under reduced pressure and the crude product was used in the next step directly without further purification to afford methyl 2-(5-chloro-2-oxo-1H-1,6-naphthyridin-3-yl)acetate (2 g, 94.45%) . . . LCMS (ES, m/z): 253 $[M+H]^+$.

Methyl 2-(5-iodo-2-oxo-1H-1,6-naphthyridin-3-yl)acetate.

To a stirred solution of methyl 2-(5-chloro-2-oxo-1H-1,6-naphthyridin-3-yl) acetate (2 g, 8 mmol, 1 equiv) and NaI (5.93 g, 39.6 mmol, 5.0 equiv) in MeCN (20 mL) was added TMSC1 (2.58 g, 23.7 mmol, 3.0 equiv) dropwise at 0° C. under argon atmosphere. The final reaction mixture was irradiated with microwave radiation for 40 min at 60° C. The resulting mixture was diluted with water (30 mL). The resulting mixture was extracted with $CH_2Cl_2$. The combined organic layers were washed with brine (2×30 mL), dried over anhydrous $Na_2SO_4$. The filtrate was concentrated under reduced pressure and the residue was purified by silica gel column chromatography to afford methyl 2-(5-iodo-2-oxo-1H-1,6-naphthyridin-3-yl)acetate (1.1 g, 40.38%). LCMS (ES, m/z): 345 $[M+H]^+$.

Methyl 2-{2-oxo-5-[2-(trimethylsilyl)ethynyl]-1H-1,6-naphthyridin-3-yl}acetate. To a stirred solution of methyl 2-(5-iodo-2-oxo-1H-1,6-naphthyridin-3-yl)acetate (1 g, 3 mmol, 1 equiv) and trimethylsilylacetylene (1.43 g, 14.5 mmol, 5 equiv) in THF (15 mL) were added $Pd(PPh_3)_2Cl_2$ (0.41 g, 0.58 mmol, 0.2 equiv) and CuI (0.06 g, 0.29 mmol, 0.1 equiv) and TEA (0.59 g, 5.8 mmol, 2 equiv) in portions at room temperature under argon atmosphere. The resulting mixture was stirred for 3 h at room temperature under argon atmosphere. The resulting mixture was concentrated under reduced pressure and the residue was purified by silica gel column chromatography, to afford methyl 2-{2-oxo-5-[2-(trimethylsilyl)ethynyl]-1H-1,6-naphthyridin-3-yl}acetate (400 mg, 43.78%). LCMS (ES, m/z): 315 $[M+H]^+$.

(5-Ethynyl-2-oxo-1H-1,6-naphthyridin-3-yl)acetic acid. A solution of methyl 2-{2-oxo-5-[2-(trimethylsilyl)ethynyl]-1H-1,6-naphthyridin-3-yl}acetate (400 mg, 1.27 mmol, 1 equiv) and LiOH (60.94 mg, 2.54 mmol, 2 equiv) in MeCOH (5 mL, 123.5 mmol, 97.07 equiv) and $H_2O$ (5 mL, 278 mmol, 218.16 equiv) was stirred for 2 h at 40° C. under air atmosphere. The mixture was cooled to room temperature. The resulting mixture was concentrated under reduced pressure and the crude product was used in the next step directly without further purification, to afford (5-ethynyl-2-oxo-1H-1,6-naphthyridin-3-yl) acetic acid (380 mg, 91.62%). LCMS (ES, m/z): 229 $[M+H]^+$.

N-[(1S)-1-(2,4-difluorophenyl)ethyl]-2-(5-ethynyl-2-oxo-1H-1,6-naphthyridin-3-yl)acetamide. To a stirred solution of (5-ethynyl-2-oxo-1H-1,6-naphthyridin-3-yl) acetic acid (90 mg, 0.4 mmol, 1 equiv) and (1S)-1-(2,4-difluorophenyl) ethanamine (80.6 mg, 0.512 mmol, 1.3 equiv) in DMF (3 mL) were added HATU (179.95 mg, 0.473 mmol, 1.2 equiv) and DIEA (102 mg, 0.788 mmol, 2 equiv) in portions at room temperature under air atmosphere. The resulting mixture was stirred for 3 h at room temperature under air atmosphere. The resulting mixture was diluted with water (15 mL) and extracted with EtOAc. The combined organic layers were washed with brine and dried over anhydrous $Na_2SO_4$. The filtrate was concentrated under reduced pressure and the crude product (100 mg) was purified by Prep-HPLC with the following conditions (Column: XBridge Shield RP18 OBD Column, 19*150 mm, 5 μm; Mobile Phase A: Water(10 mmoL/L $NH_4HCO_3$), Mobile Phase B: ACN; Flow rate: 25 mL/min; Gradient: 20% B to 40% B in 8 min; Wave Length: 254 nm; $RT_1$(min): 7.00) to afford N-[(1S)-1-(2,4-difluorophenyl)ethyl]-2-(5-ethynyl-2-oxo-1H-1,6-naphthyridin-3-yl)acetamide (40 mg, 27.61%). LCMS (ES, m/z): 368.10 $[M+H]^+$. $^1H$ NMR (400 MHz, DMSO-$d_6$) δ 12.04 (s, $^1H$), 8.62 (d, J=7.6 Hz, $^1H$), 8.40 (d, J=5.6 Hz, $^1H$), 8.01 (s, $^1H$), 7.51-7.44 (m, $^1H$), 7.21-7.14 (m, $^2H$), 7.06-7.02 (m, $^1H$), 5.11-5.08 (m, $^1H$), 4.75 (s, $^1H$), 3.49 (s, $^2H$), 1.35 (d, J=7.2 Hz, $^3H$).

(Compound) 440)

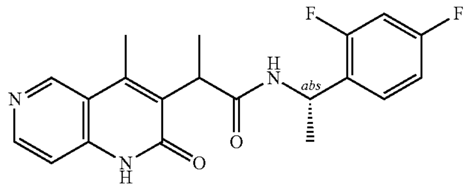

(2R*)-2-(5,6-difluoro-4-methyl-2-oxo-1H-quinolin-3-yl)-N-[(1S)-1-(2,4-difluorophenyl)ethyl]propenamide N-(3-acetylpyridin-4-yl)-2,2-dimethylpropanamide. A mixture of 1-(4-aminopyridin-3-yl) ethanone (1.5 g, 11.017 mmol, 1.00 equiv) and TEA (3.34 g, 33.1 mmol, 3.00 equiv) in DCM (20 mL) was stirred for 2 h at room temperature under air atmosphere. The resulting mixture was diluted with water (20 mL) and extracted with $CH_2Cl_2$. The resulting mixture was concentrated under reduced pressure and the residue was purified by silica gel column chromatography to afford N-(3-acetylpyridin-4-yl)-2,2-dimethylpropanamide (2 g, 82.42%). LCMS (ES, m/z): 221$[M+H]^+$.

1,4-Di-tert-butyl 2-[1-[4-(2,2-dimethylpropanamido)pyridin-3-yl]-1-hydroxyethyl]butanedioate. To a solution of 1,4-di-tert-butyl butanedioate (1.67 g, 7.26 mmol, 2.00 equiv) in THF (20 mL) was added LDA (2 M in THF) (3.63 mL, 7.26 mmol, 2.00 equiv) at −78° C. The mixture was stirred for 30 min. N-(3-acetylpyridin-4-yl)-2,2-dimethylpropanamide (800.00 mg, 3.632 mmol, 1.00 equiv) and $ZnCl_2$ (1 M in THF) (3.63 mL, 3.63 mmol, 1.00 equiv) were added at −78° C. and stirred for 1 h. The reaction was quenched by the addition of saturated $NH_4Cl$ (aq.) (10 mL) at 0° C. The resulting mixture was diluted with water and extracted with EtOAc. The resulting mixture was concentrated under reduced pressure and the residue was purified by silica gel column chromatography to afford 1,4-di-tert-butyl 2-[1-[4-(2,2-dimethylpropanamido)pyridin-3-yl]-1-hydroxyethyl]butanedioate (1.57 g, 95.70%). LCMS (ES, m/z): 451$[M+H]^+$.

(4-Methyl-2-oxo-1H-1,6-naphthyridin-3-yl)acetic acid. Into a 100 mL round-bottom flask, 1,4-di-tert-butyl 2-[1-[4-(2,2-dimethylpropanamido)pyridin-3-yl]-1-hydroxyethyl] butanedioate (1.57 g, 3.48 mmol, 1.00 equiv), Dioxane (10.50 mL), and HCl (3 M in $H_2O$) (10.50 mL) were placed. The reaction mixture was stirred for 12 h at 100° C. The resulting mixture was concentrated under vacuum. The product was precipitated by the addition of ACN. The solids were collected by filtration resulting in (4-methyl-2-oxo-1H-1,6-naphthyridin-3-yl) acetic acid (700 mg, 92.01%). LCMS (ES, m/z): 219$[M+H]^+$.

Methyl 2-(4-methyl-2-oxo-1H-1,6-naphthyridin-3-yl)acetate. A mixture of (4-methyl-2-oxo-1H-1,6-naphthyridin-3-yl)acetic acid (700 mg, 3.21 mmol, 1.00 equiv) and thionyl chloride (3.82 g, 32.1 mmol, 10.00 equiv) in MeOH (10 mL) was stirred for h at 80° C. under air atmosphere. The mixture was cooled to room temperature. The resulting mixture was concentrated under reduced pressure and the residue was purified by trituration with ACN (5 mL) resulting in methyl 2-(4-methyl-2-oxo-1H-1,6-naphthyridin-3-yl) acetate (600 mg, 72.48%). LCMS (ES, m/z): 233$[M+H]^+$.

Methyl 2-(4-methyl-2-oxo-1H-1,6-naphthyridin-3-yl) propanoate. To a solution of methyl 2-(4-methyl-2-oxo-1H-

1,6-naphthyridin-3-yl)acetate (420 mg, 1.81 mmol, 1.00 equiv) in THF (8 mL) was added LiHMDS (1 M in THF) (3.48 mL, 4.52 mmol, 2.50 equiv) at 0° C. The mixture was stirred for 30 min. $CH_3I$ (0.12 mL, 0.83 mmol, 1.05 equiv) was added and the mixture was warmed to room temperature and stirred for 1 h. The reaction was quenched by the addition of saturated $NH_4Cl$ (aq.) (5 mL) at 0° C. The resulting mixture was diluted with water (20 mL). The aqueous layer was extracted with EtOAc. The resulting mixture was concentrated under reduced pressure and the residue was purified by silica gel column chromatography to afford methyl 2-(4-methyl-2-oxo-1H-1,6-naphthyridin-3-yl) propanoate (200 mg, 44.91%). LCMS (ES, m/z): 247[M+H]$^+$.

2-(4-Methyl-2-oxo-1H-1,6-naphthyridin-3-yl)propanoic acid. A mixture of methyl 2-(4-methyl-2-oxo-1H-1,6-naphthyridin-3-yl) propanoate (200 mg, 0.812 mmol, 1 equiv) and LiOH (38.90 mg, 1.624 mmol, 2 equiv) in MeOH (2 mL) and $H_2O$ (2 mL) was stirred for 2 h at room temperature under normal atmospheric pressure. The resulting mixture was concentrated under reduced pressure and the resulting mixture was diluted with water (5 mL). The mixture was acidified to pH 5 with HCl (aq.)(1 M). The precipitated solids were collected by filtration and washed with water resulting in 2-(4-methyl-2-oxo-1H-1,6-naphthyridin-3-yl) propanoic acid (100 mg, 53.02%). LCMS (ES, m/z): 233 [M+H]$^+$.

N-[(1S)-1-(2,4-Difluorophenyl)ethyl]-2-(4-methyl-2-oxo-1H-1,6-naphthyridin-3-yl)propanamide. A mixture of 2-(4-methyl-2-oxo-1H-1,6-naphthyridin-3-yl)propanoic acid (40.00 mg, 0.172 mmol, 1.00 equiv), HATU (72.04 mg, 0.19 mmol, 1.1 equiv) and DIEA (66.78 mg, 0.517 mmol, 3 equiv) in DMF (1.00 mL) was stirred for 2 h at room temperature under air atmosphere. The residue was purified by reversed-phase flash chromatography with the following conditions: column, C18; mobile phase, ACN in Water (0.1% FA), 10% to 50% gradient in 40 min; detector, UV 254 nm resulting in N-[(1S)-1-(2,4-difluorophenyl)ethyl]-2-(4-methyl-2-oxo-1H-1,6-naphthyridin-3-yl)propanamide (16.6 mg, 25.95%). LCMS (ES, m/z): 372 [M+H]$^+$. $^1$H NMR (300 MHz, DMSO-$d_6$) δ 11.96 (s, $^1$H), 9.02-8.85 (m, $^1$H), 8.57-8.38 (m, $^1$H), 7.95-7.72 (m, $^1$H), 7.56-7.29 (m, $^1$H), 7.28-7.17 (m, $^2$H), 7.16-6.94 (m, $^1$H), 5.33-5.01 (m, $^1$H), 4.28-4.02 (m, $^1$H), 2.49 (s, $^2$H), 2.29 (s, $^1$H), 1.40-1.28 (m, $^6$H).

(Compound 430)

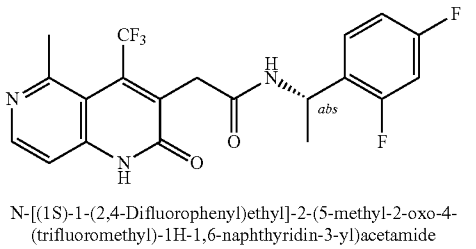

N-[(1S)-1-(2,4-Difluorophenyl)ethyl]-2-(5-methyl-2-oxo-4-(trifluoromethyl)-1H-1,6-naphthyridin-3-yl)acetamide 1-(2,4-Dichloropyridin-3-yl)-2,2,2-trifluoroethanol. Into a 250-mL round-bottom flask, was placed 2,4-dichloropyridine-3-carbaldehyde (4.00 g, 22.73 mmol, 1.00 equiv), THF (80.00 mL), then $TMSCF_3$ (4847.56 mg, 34.09 mmol, 1.50 equiv) was added dropwise at 0° C. in a water/ice bath, and the solution of TBAF (8913.48 mg, 34.091 mmol, 1.50 equiv) in THF (20 mL) was added. The reaction mixture was stirred for 30 min at 0° C. in a water/ice bath. The reaction mixture was allowed to react, with stirring, for an additional 3 hr at 25° C. LCMS showed the desired MS was detected, and most of the starting material was consumed. The reaction was then quenched by the addition of 80 mL of water. The reaction mixture was extracted with ethyl acetate and the organic layers combined and concentrated under vacuum. The residue was purified using silica gel column chromatography resulting in 3.2 g (57.23%) of 1-(2,4-dichloropyridin-3-yl)-2,2,2-trifluoroethanol. LC-MS: (ESI, m/z): 246 [M+H]$^+$.

1-(2,4-Dichloropyridin-3-yl)-2,2,2-trifluoroethanone. Into a 250-mL round-bottom flask, was placed 1-(2,4-dichloropyridin-3-yl)-2,2,2-trifluoroethanol (3.15 g, 12.804 mmol, 1.00 equiv), DCM (80.00 mL, 1258.404 mmol, 98.28 equiv), then Dess-Martin (10861.73 mg, 25.608 mmol, 2.00 equiv) was added slowly. The reaction mixture was stirred for 30 min at 0° C. in a water/ice bath. The reaction mixture was allowed to react, with stirring, for an additional 3 h at 25° C. the resulting mixture was concentrated under vacuum. The residue was purified using silica gel column chromatography resulting in 2.5 g (72.02%) of 1-(2,4-dichloropyridin-3-yl)-2,2,2-trifluoroethanone.

LC-MS: (ESI, m/z): 244 [M+H]$^-$.

1-(4-Azido-2-chloropyridin-3-yl)-2,2,2-trifluoroethanone. Into a 100-mL round-bottom flask, 1-(2,4-dichloropyridin-3-yl)-2,2,2-trifluoroethanone (1.66 g, 6.804 mmol, 1.00 equiv), dimethylformamide (15.00 mL), and azidosodium (663.46 mg, 0.011 mmol, 1.50 equiv) were placed. The reaction mixture was stirred for 16 h at 50° C. in an oil bath. The reaction was then quenched by the addition of 20 mL of water. The reaction mixture was extracted and the organic layers combined and dried over anhydrous sodium sulfate and concentrated under vacuum. resulting in 1230 mg (64.94%) of 1-(4-azido-2-chloropyridin-3-yl)-2,2,2-trifluoroethanone and the crude product was used for the next step. LC-MS: (ESI, m/z): 251 [M+H]$^+$ 1-(4-Amino-2-chloropyridin-3-yl)-2,2,2-trifluoroethanone. To a solution of 1-(4-azido-2-chloropyridin-3-yl)-2,2,2-trifluoroethanone (2.30 g, 9.18 mmol, 1.00 equiv) in EtOAc (40.00 mL), Pd/C (230.00 mg, wet) was added in a pressure tank. The mixture was hydrogenated at room temperature under 1 atm of hydrogen pressure for 3 hours. The reaction was filtered through a Celite pad and concentrated under reduced pressure and the residue was purified by silica gel column chromatography to afford 1-(4-amino-2-chloropyridin-3-yl)-2,2,2-trifluoroethanone (1.3 g, 56.76%).

LC-MS: (ESI, m/z): 225 [M+H]$^+$

2-[l-(4-Amino-2-chloropyridin-3-yl)-2,2,2-trifluoro-1-hydroxyethyl]butanedioate. Into a 100-mL 3-necked round-bottom flask, 1,4-di-tert-butyl butanedioate (1230.64 mg, 5.34 mmol, 2.00 equiv), tetrahydrofuran (15.00 mL), was placed, then LDA (858.62 mg, 8.02 mmol, 3.00 equiv) was added dropwise at −78° C. in a liquid nitrogen bath, the reaction mixture was stirred for 30 min at −78° C. in a liquid nitrogen bath. Then the solution of 1-(4-amino-2-chloropyridin-3-yl)-2,2,2-trifluoroethanone (600.00 mg, 2.67 mmol, 1.00 equiv) in THF (5 mL) was added dropwise, and zinc chloride (364.11 mg, 2.672 mmol, 1.00 equiv) was added. The reaction mixture reacted with stirring, for an additional 1 h while the temperature was maintained at −78° C. in a liquid nitrogen bath. The reaction was quenched by the addition of 10 mL of $NH_4Cl$ (saturated) and diluted with 15 mL of $H_2O$. The reaction mixture was extracted with ethyl acetate and the organic layers combined and concentrated under vacuum. The residue was purified by reversed-phase flash chromatography with the following conditions: (column, C18 silica gel; mobile phase, 0.5% $NH_4HCO_3$ in ACN, 0% to 100% gradient in 60 min; detector, UV 254 nm) to afford 1,4-di-tert-butyl 2-[1-(4-amino-2-chloropyridin-3-yl)-2,2,2-trifluoro-1-hydroxyethyl]butanedioate (460 mg, 34.07%). LC-MS: (ESI, m/z): 455 $[M+H]^+$

[5-Chloro-2-oxo-4-(trifluoromethyl)-1H-1,6-naphthyridin-3-yl]acetic acid. Into a 20-mL vial, was placed 1,4-di-tert-butyl 2-[1-(4-amino-2-chloropyridin-3-yl)-2,2,2-trifluoro-1-hydroxyethyl]butanedioate (460.00 mg, 1.01 mmol, 1.00 equiv), KOH (283.69 mg, 5.06 mmol, 5.00 equiv), ethylene glycol (10.00 mL). The final reaction mixture was irradiated with microwave radiation for 50 min at 80° C. The reaction mixture was diluted with $H_2O$ and the pH value of the solution was adjusted to 3 with HCl (1 mol/L). The residue was purified by reversed-phase flash chromatography with the following conditions: (column, C18 silica gel; mobile phase, 0.1% FA in ACN, 0% to 100% gradient in 60 min; detector, UV 254 nm) to afford [5-Chloro-2-oxo-4-(trifluoromethyl)-1H-1,6-naphthyridin-3-yl]acetic acid (200 mg, 64.50%). LC-MS: (ESI, m/z): 307 $[M+H]^+$ Methyl 2-[5-chloro-2-oxo-4-(trifluoromethyl)-1H-1,6-naphthyridin-3-yl]acetate. Into a 25-mL round-bottom flask, was placed [5-chloro-2-oxo-4-(trifluoromethyl)-1H-1,6-naphthyridin-3-yl]acetic acid (235.00 mg, 0.77 mmol, 1.00 equiv), methanol (10.00 mL), thionyl chloride (911.70 mg, 7.66 mmol, 10.00 equiv). The reaction mixture was stirred for 2 hr at 70° C. in an oil bath. The resulting mixture was concentrated under vacuum. The residue was purified by silica gel column chromatography to afford methyl 2-[5-chloro-2-oxo-4-(trifluoromethyl)-1H-1,6-naphthyridin-3-yl]acetate (120 mg, 43.95%). LC-MS: (ESI, m/z): 321 $[M+H]^+$ Methyl 2-[5-methyl-2-oxo-4-(trifluoromethyl)-1H-1,6-naphthyridin-3-yl]acetate To a solution of methyl 2-[5-chloro-2-oxo-4-(trifluoromethyl)-1H-1,6-naphthyridin-3-yl]acetate (100 mg, 0.3 mmol, 1.00 equiv) and tetramethyltin (557.77 mg, 3.12 mmol, 10.00 equiv) in water (0.40 mL) and Dioxane (4.00 mL) were added lithium chloride (13.22 mg, 0.31 mmol, 1.00 equiv) and tetrakis(triphenylphosphine)palladium(0) (36.04 mg, 0.031 mmol, 0.10 equiv). After stirring for 4 h at 110° C. under 1 atm nitrogen, the resulting mixture was concentrated under reduced pressure and the residue was purified by Prep-TLC, eluted with DCM/MeOH (20/1) to afford methyl 2-[5-methyl-2-oxo-4-(trifluoromethyl)-1H-1,6-naphthyridin-3-yl]acetate (55 mg, 52.87%). LC-MS: (ESI, m/z): 301 $[M+H]^+$

[5-Methyl-2-oxo-4-(trifluoromethyl)-1H-1,6-naphthyridin-3-yl]acetic acid Into a 8-mL vial, was placed methyl 2-[5-methyl-2-oxo-4-(trifluoromethyl)-1H-1,6-naphthyridin-3-yl]acetate (54.00 mg, 0.18 mmol, 1.00 equiv), MeOH (4.00 mL), $H_2O$ (0.80 mL), then $LiOH \cdot H_2O$ (75.48 mg, 1.80 mmol, 10.00 equiv) was added. The reaction mixture was stirred for 4 h at 25° C. The resulting mixture was concentrated under vacuum. The reaction mixture was diluted with 1 mL of $H_2O$ and the pH value of the solution was adjusted to 3 with HCl (1 mol/L). The solids were collected by filtration resulting in 100 mg (90.91%) of [5-methyl-2-oxo-4-(trifluoromethyl)-1H-1,6-naphthyridin-3-yl]acetic acid. LC-MS: (ESI, m/z): 287 $[M+H]^+$ N-[(1S)-1-(2,4-difluorophenyl)ethyl]-2-[5-methyl-2-oxo-4-(trifluoromethyl)-1H-1,6-naphthyridin-3-yl]acetamide. Into a 8-mL vial, was placed N-[(1S)-1-(2,4-difluorophenyl) ethyl]-2-[5-methyl-2-oxo-4-(trifluoromethyl)-1H-1,6-naphthyridin-3-yl]acetamide (28.00 mg, 0.06 mmol, 1.00 equiv), DMF (3.00 mL), PyBOP (37.68 mg, 0.07 mmol, 1.10 equiv), DIEA (25.52 mg, 0.20 mmol, 3.00 equiv), (1S)-1-(2,4-difluorophenyl)ethanamine (15.52 mg, 0.10 mmol, 1.50 equiv). The reaction mixture was stirred for 8 hr at 20° C. The residue was purified by reversed-phase flash chromatography with the following conditions: (column, C18 silica gel; mobile phase, 0.5% $NH_4HCO_3$ in ACN, 0% to 100% gradient in 60 min; detector, UV 254 nm). to afford N-[(1S)-1-(2,4-difluorophenyl)ethyl]-2-[5-methyl-2-oxo-4-(trifluoromethyl)-1H-1,6-naphthyridin-3-yl]acetamide (12 mg, 42.64%). LC-MS: (ESI, m/z): 426.10 $[M+H]^+$ $^1H$ NMR (400 MHz, Methanol-$d_4$) δ 8.30 (d, J=5.6 Hz, 1H), 7.46-7.30 (m, $^1H$), 7.11 (d, J=5.6 Hz, $^1H$), 6.94-6.93 (in, $^1H$), 6.91-6.86 (m, $^1H$), 5.20-5.14 (m, 1H), 3.94-3.83 (m, 2H), 2.70 (s, $^3H$), 1.46 (d, J=7.2 Hz, 3H).

(Compound 394)

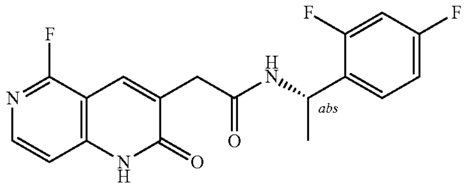

N-[(1S)-1-(2,4-difluorophenyl)ethyl]-2-(5-fluoro-2-oxo-1H-1,6-naphthyridin-3-yl)acetamide tert-butyl N-(3-bromo-2-fluoropyridin-4-yl)carbamate. To a solution of 3-bromo-2-fluoropyridin-4-amine (30 g, 157 mmol, 1.00 equiv) in THF (300 mL) was added LiHMDS (1 M in THF) (315.79 mL, 314.13 mmol, 2 equiv) at 0° C. The mixture was stirred for 30 min. $(Boc)_2O$ (35.31 g, 161.78 mmol, 1.03 equiv) was added and the mixture was allowed to warm to room temperature and stirred for 1 h. The reaction was quenched with saturated $NH_4Cl$ (aq.) (200 mL) at room temperature. The resulting mixture was extracted with EtOAc. The combined organic layers were washed with brine and dried over anhydrous $Na_2SO_4$. The filtrate was concentrated under reduced pressure and the residue was purified by silica gel column chromatography to afford tert-butyl N-(3-bromo-2-fluoropyridin-4-yl) carbamate (35 g, 76.54%). LCMS (ES, m/z): 291$[M+H]^+$.

tert-butyl N-(2-fluoro-3-formylpyridin-4-yl) carbamate. To a solution of tert-butyl N-(3-bromo-2-fluoropyridin-4-yl) carbamate (30 g, 103 mmol, 1.00 equiv) in THF (300 mL) was added NaH (2.97 g, 123.66 mmol, 1.2 equiv) at 0° C. The mixture was stirred for 30 min. n-BuLi (1 M in THF) (62.07 mL, 123.66 mmol, 1.2 equiv) was added and the mixture was cooled to −78° C. and stirred for 30 min. DMF (30.13 g, 412.20 mmol, 4 equiv) was added to the mixture in portions at −78° C. The resulting mixture was stirred for additional 2 h at −78° C. The reaction was quenched with sat. $NH_4Cl$ (aq.) (100 mL) at 0° C. The resulting mixture was extracted with EtOAc. The combined organic layers were washed with brine and dried over anhydrous $Na_2SO_4$. The filtrate was concentrated under reduced pressure and the residue was purified by silica gel column chromatography to afford tert-butyl N-(2-fluoro-3-formylpyridin-4-yl)carbamate (20 g, 80.79%). LCMS (ES, m/z): 241 [M+H]. 4-Amino-2-fluoropyridine-3-carbaldehyde. A solution of tert-butyl N-(2-fluoro-3-formylpyridin-4-yl)carbamate (30 g, 125 mmol, 1.00 equiv) in HCl (gas) in 1,4-dioxane (300 mL) was stirred for 2 h at room temperature under air atmosphere. The resulting mixture was concentrated under reduced pressure and the resulting mixture was diluted with water. The mixture was basified to pH 8 with saturated $NaHCO_3$ (aq.).

The precipitated solids were collected by filtration and washed with water. The residue was purified by silica gel column chromatography to afford 4-amino-2-fluoropyridine-3-carbaldehyde (15 g, 85.73%). LCMS (ES, m/z): 141[M+H]$^+$.

3-[(4-Amino-2-fluoropyridin-3-yl)(hydroxy)methyl]-1-[(1S)-1-(2,4-difluorophenyl)ethyl]pyrrolidine-2,5-dione. LDA (2 M in THF) (53.57 mL, 107.05 mmol, 3 equiv) was added to a solution of 1-[(1S)-1-(2,4-difluorophenyl)ethyl] pyrrolidine-2,5-dione (17.07 g, 71.37 mmol, 2 equiv) in THF (100 mL) at −78° C. The mixture was stirred for 30 min. 4-amino-2-fluoropyridine-3-carbaldehyde (5 g, 36 mmol, 1.00 equiv) and $ZnCl_2$ (1 M in THF) (35.71 mL, 35.68 mmol, 1 equiv) was added and the mixture was allowed to −78° C. and stirred for 1 h. The reaction was quenched with saturated $NH_4Cl$ (aq.) (100 mL) at 0° C. The resulting mixture was extracted with EtOAc. The combined organic layers were washed with brine and dried over anhydrous $Na_2SO_4$. The filtrate was concentrated under reduced pressure and the residue was purified by silica gel column chromatography to afford 3-[(4-amino-2-fluoropyridin-3-yl)(hydroxy)methyl]-1-[(1S)-1-(2,4-difluorophenyl) ethyl]pyrrolidine-2,5-dione (5 g, 36.94%). LCMS (ES, m/z): 380[M+H]$^+$.

N-[(1S)-1-(2,4-difluorophenyl)ethyl]-2-(5-fluoro-2-oxo-1H-1,6-naphthyridin-3-yl)acetamide. A mixture of 3-[(4-amino-2-fluoropyridin-3-yl)(hydroxy)methyl]-1-[(1S)-1-(2,4-difluorophenyl)ethyl]pyrrolidine-2,5-dione (10 g, 26 mmol, 1.00 equiv) and $K_2CO_3$ (18.22 g, 131.81 mmol, 5 equiv) in EtOH (100 mL) was stirred overnight at room temperature under air atmosphere. The resulting mixture was diluted with water (1 L). The precipitated solids were collected by filtration and washed with water resulting in N-[(1S)-1-(2,4-difluorophenyl)ethyl]-2-(5-fluoro-2-oxo-1H-1,6-naphthyridin-3-yl)acetamide (5 g, 52.49%). LCMS (ES, m/z): 362[M+H]$^+$.

$^1$H NMR (400 MHz, DMSO-$d_6$) δ12.39 (s, $^1$H), 8.58 (d, J=7.6 Hz, $^1$H), 8.07 (d, J=5.6 Hz, $^1$H), 7.85 (s, $^1$H), 7.53-7.43 (m, $^1$H), 7.23-7.12 (m, $^2$H), 7.09-7.00 (m, $^1$H), 5.21-5.02 (m, $^1$H), 3.48 (s, $^2$H), 1.36 (d, J=7.0 Hz, $^3$H).

(Compound 426 and 427)

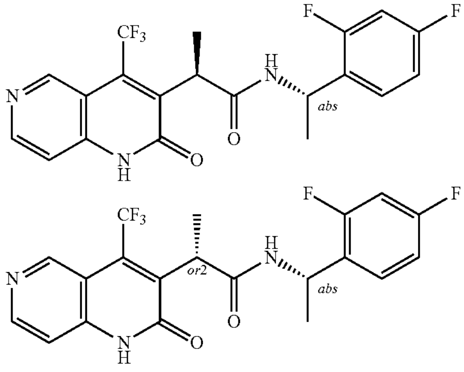

(2R*)-N-[(1S)-1-(2,4-difluorophenyl)ethyl]-2-[2-oxo-4-(trifluoromethyl)-1H-1,6-naphthyridin-3-yl]propanamide and (2S*)-N-[1S)-1-(2,4-difluorophenyl)ethyl]-2-[2-oxo-4-(trifluoromethyl)-1H-1,6-naphthyridin-3-yl]propanamide tert-butyl 4-(4-aminopyridin-3-yl)-3-[(tert-butylperoxy) methyl]-5,5,5-trifluoro-4-hydroxy-2-methylpentanoate. To a stirred solution of 1,4-di-tert-butyl 2-methylbutanedioate (1413.62 mg, 5.79 mmol, 2.00 equiv) in THF (10 mL) was added LDA (2M, 4.34 mL, 8.68 mmol, 3.00 equiv) at −78° C. under argon atmosphere. The resulting mixture was stirred for 0.5 h at −78° C., followed by the addition of 1-(4-aminopyridin-3-yl)-2,2,2-trifluoroethanone (550 mg, 2.9 mmol, 1.00 equiv) in THF (3 mL) and zinc chloride (0.7M solution in THF) (4.13 mL, 2.89 mmol, 1.00 equiv) at −78° C. The resulting mixture was stirred for 1 h at −78° C. The reaction was added $H_2O$ and extracted with EtOAc. The combined organic layers were washed with brine and dried over anhydrous $Na_2SO_4$. The filtrate was concentrated under reduced pressure and the residue was purified by Prep-TLC (PE/EA 1:1) to afford tert-butyl 4-(4-aminopyridin-3-yl)-3-[(tert-butylperoxy)methyl]-5,5,5-trifluoro-4-hydroxy-2-methylpentanoate (900 mg, 64.15%). LC-MS: (ESI, m/z): 437 [M+H]$^+$ 2-[2-Oxo-4-(trifluoromethyl)-1H-1,6-naphthyridin-3-yl] propanoic acid. Hydrogen chloride solution (6.87 mL, 20.62 mmol, 10.00 equiv, 3 M) was added to a stirred solution of tert-butyl 4-(4-aminopyridin-3-yl)-3-[(tert-butylperoxy) methyl]-5,5,5-trifluoro-4-hydroxy-2-methylpentanoate (900.00 mg, 2.06 mmol, 1.00 equiv) in dioxane (4 mL). The resulting mixture was stirred for 5 h at 95° C. The reaction was concentrated under reduced pressure and the residue was added ACN (5 mL) and filtrated to afford 2-[2-oxo-4-(trifluoromethyl)-1H-1,6-naphthyridin-3-yl]propanoic acid (400 mg, 61.00%). LC-MS: (ESI, m/z): 287 [M+H]$^+$ N-[(1S)-1-(2,4-Difluorophenyl)ethyl]-2-[6-fluoro-2-oxo-4-(trifluoromethyl)-1H-quinolin-3-yl]propanamide. PyBop (566.37 mg, 1.09 mmol, 1.10 equiv) and DIEA (255.75 mg, 1.98 mmol, 2.00 equiv) was added to a stirred solution of 2-[6-fluoro-2-oxo-4-(trifluoromethyl)-1H-quinolin-3-yl] propanoic acid (300.00 mg, 0.99 mmol, 1.00 equiv) in DCM (5 mL) was added. The resulting mixture was stirred for 0.5 h at room temperature, followed by the addition of (1S)-1-(2,4-difluorophenyl)ethanamine (171.05 mg, 1.09 mmol, 1.10 equiv). The resulting mixture was stirred for 16 h at room temperature. The reaction was concentrated under reduced pressure and the residue was purified by Prep-TLC ($CH_2Cl_2$/MeOH 30:1) to afford the crude product. Then the crude product was further purified by reverse flash chromatography with the following conditions: (column, C18 silica gel; mobile phase, ACN in water, 10% to 60% gradient in 20 min; detector, UV 254 nm), to afford N-[(1S)-1-(2,4-difluorophenyl)ethyl]-2-[6-fluoro-2-oxo-4-(trifluoromethyl)-1H-quinolin-3-yl]propanamide (200 mg, 45.70%). LC-MS: (ESI, m/z): 426 [M+H]$^+$ (2R*)-N-[(1S)-1-(2,4-difluorophenyl)ethyl]-2-[2-oxo-4-(trifluoromethyl)-1H-1,6-naphthyridin-3-yl]propanamide. The compound of N-[(1S)-1-(2,4-difluorophenyl)ethyl]-2-[2-oxo-4-(trifluoromethyl)-1H-1,6-naphthyridin-3-yl]propanamide (150.00 mg, 0.35 mmol, 1.00 equiv) was separated by Chiral-HPLC, (Column: CHIRAL ART Amylose-C Neo, Mobile Phase: Hex(0.1% FA):EtOH=85:15, Flow rate: 1.0 ml/min) to afford (2R*)-N-[(1S)-1-(2,4-difluorophenyl) ethyl]-2-[2-oxo-4-(trifluoromethyl)-1H-1,6-naphthyridin-3-yl]propanamide (35 mg, 23.33%). LC-MS: (ESI, m/z): 426.05 [M+H]$^1$H NMR (400 MHz, DMSO-$d_6$) δ 12.65 (s, $^1$H), 8.91 (d, J=2.4 Hz, $^1$H), 8.56 (d, J=5.6 Hz, $^1$H), 7.77 (d, J=8.0 Hz, $^1$H), 7.39-7.33 (m, $^2$H), 7.16-7.11 (m, $^1$H), 7.01-6.96 (m, $^1$H), 5.20-5.12 (m, $^1$H), 4.29-4.24 (m, $^1$H), 1.37 (d, J=6.8 Hz, $^3$H), 1.30 (d, J=7.2 Hz, $^3$H).

(2S*)-N-[(1S)-1-(2,4-difluorophenyl)ethyl]-2-[2-oxo-4-(trifluoromethyl)-1H-1,6-naphthyridin-3-yl]propanamide The compound of N-[(1S)-1-(2,4-difluorophenyl)ethyl]-2-[2-oxo-4-(trifluoromethyl)-1H-1,6-naphthyridin-3-yl]propanamide (150.00 mg, 0.353 mmol, 1.00 equiv) was separated by Chiral-HPLC, (Column: CHIRAL ART Amylose-C Neo, Mobile Phase: Hex(0.1% FA):EtOH=85:15, Flow rate: 1.0 ml/min) to afford (2S*)-N-[(1S)-1-(2,4-difluorophenyl) ethyl]-2-[2-oxo-4-(trifluoromethyl)-1H-1,6-naphthyridin-3-yl]propanamide (90 mg, 60.00%). LC-MS: (ESI, m/z): 426.10 $[M+H]^+$ $^1H$ NMR (400 MHz, DMSO-$d_6$) δ 12.63 (s, $^1H$), 8.92 (d, J=2.4 Hz, $^1H$), 8.56 (d, J=5.6 Hz, $^1H$), 7.80 (d, J=7.6 Hz, $^1H$), 7.41-7.35 (m, $^1H$), 7.32 (d, J=5.6 Hz, $^1H$), 7.18-7.12 (m, $^1H$), 7.17-7.00 (m, $^1H$), 5.17-5.10 (m, $^1H$), 4.30-4.25 m, $^1H$), 1.37 (d, J=6.8 Hz, $^3H$), 1.26 (d, J=7.2 Hz, $^3H$).

(Compound 421)

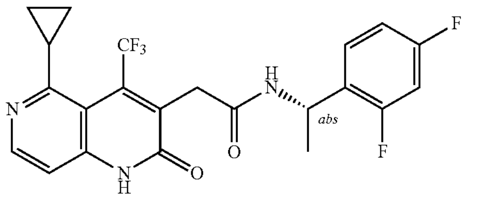

2-[5-cyclopropyl-2-oxo-4-(trifluoromethyl)-1H-1,6-naphthyridin-3-yl]-N-[(1S)-1-(2,4-difluorophenyl)ethyl]acetamide 1,4-Di-tert-butyl 2-[1-(4-amino-2-chloropyridin-3-yl)-2,2,2-trifluoro-1-hydroxyethyl]-3-methylbutanedioate. In a 100-mL three-necks bottom flask, LDA (13.36 mL, 26.72 mmol, 3.00 equiv) was added dropwise to a solution of 1,4-di-tert-butyl 2-methylbutanedioate (4.35 g, 17.81 mmol, 2.00 equiv) in THF (40 mL) at −78° C. under argon atmosphere. The reaction mixture was stirred at −78° C. for 30 mins. Then a solution of 1-(4-amino-2-chloropyridin-3-yl)-2,2,2-trifluoroethanone (2.00 g, 8.91 mmol, 1.00 equiv) in 40 mL THF and $ZnCl_2$ (8.91 mL, 8.91 mmol, 1.00 equiv) were added dropwise and the mixture was stirred for another 1 h. 40% The reaction was quenched with saturated $NH_4Cl$ (150 mL), and then the mixture was extracted with EtOAc. The combined organic extracts were washed with saturated brine (100 mL), dried over anhydrous $Na_2SO_4$, and concentrated under vacuum to yield a crude product which was purified by silica gel column chromatography to afford 1,4-Di-tert-butyl 2-[1-(4-amino-2-chloropyridin-3-yl)-2,2,2-trifluoro-1-hydroxyethyl]-3-methylbutanedioate (400 mg, 9.58%). LC-MS: (ESI, m/z): $[M+H]^+$=455.

2-[5-Chloro-2-oxo-4-(trifluoromethyl)-1H-1,6-naphthyridin-3-yl]propanoic acid. Into a 50-mL sealed tube, was placed 1,4-di-tert-butyl 2-[1-(4-amino-2-chloropyridin-3-yl)-2,2,2-trifluoro-1-hydroxyethyl]-3-methylbutanedioate (465.00 mg, 0.992 mmol, 1.00 equiv), KOH (278.19 mg, 4.96 mmol, 5.00 equiv), ethylene glycol (10.00 mL). The final reaction mixture was irradiated with microwave radiation for 50 min at 80 degrees C. The pH of the solution was adjusted to 3 with HCl (1 mol/L). The resulting mixture was concentrated. The crude product (800 mg) was purified by Flash-Prep-HPLC with the following conditions (IntelFlash-1): Column, silica gel; mobile phase, $NH_4HCO_3$; Detector. 10 mL product was obtained. The resulting mixture was concentrated to afford 2-[5-chloro-2-oxo-4-(trifluoromethyl)-1H-1,6-naphthyridin-3-yl]propanoic acid (138 mg, 43.40%).

LC-MS: (ESI, m/z): $[M+H]^+$=307.

2-[5-Chloro-2-oxo-4-(trifluoromethyl)-1H-1,6-naphthyridin-3-yl]-N-[(1S)-1-(2,4-difluorophenyl) ethyl]acetamide. Into a 40-mL vial, [5-chloro-2-oxo-4-(trifluoromethyl)-1H-1,6-naphthyridin-3-yl]acetic acid (145.00 mg, 0.47 mmol, 1.00 equiv), EDCI (108.78 mg, 0.57 mmol, 1.20 equiv), DMAP (11.55 mg, 0.10 mmol, 0.20 equiv), and DCM (6.00 mL), (1S)-1-(2,4-difluorophenyl)ethanamine (34.93 mg, 0.22 mmol, 0.47 equiv) was placed. The reaction mixture was stirred for 4 h at 25 degrees C. The resulting mixture was concentrated under vacuum. The residue was purified using silica gel column chromatography resulting in 140 mg (66.41%) of 2-[5-chloro-2-oxo-4-(trifluoromethyl)-1H-1,6-naphthyridin-3-yl]-N-[(1S)-1-(2,4-difluorophenyl)ethyl]acetamide.

LC-MS: (ESI, m/z): [M+H]J=446.

2-[5-Cyclopropyl-2-oxo-4-(trifluoromethyl)-1H-1,6-naphthyridin-3-yl]-N-[(1S)-1-(2,4-difluorophenyl)ethyl]acetamide. A mixture of 2-[5-chloro-2-oxo-4-(trifluoromethyl)-1H-1,6-naphthyridin-3-yl]-N-[(1S)-1-(2,4-difluorophenyl)ethyl]acetamide (100 mg, 0.22 mmol, 1 equiv), $Pd_2(dba)_3$ (20.54 mg, 0.02 mmol, 0.1 equiv), P(t-Bu)$_3$ (4.54 mg, 0.02 mmol, 0.1 equiv), $ZnCl_2$ (152.86 mg, 1.12 mmol, 5 equiv) and cyclopropylboronic acid (96.35 mg, 1.12 mmol, 5 equiv) in THF (2 mL) was stirred for 2 h at 70° C. under argon atmosphere. The resulting mixture was concentrated under reduced pressure and the residue was purified by silica gel column chromatography to afford crude product. The resulting mixture was concentrated under reduced pressure and the residue was purified by reversed-phase flash chromatography with the following conditions: (column, C18 silica gel; mobile phase, MeCN in Water (0.1% FA), 0% to 60% gradient in 50 min; detector, UV 254 nm). The resulting mixture was concentrated under reduced pressure to afford 2-[5-cyclopropyl-2-oxo-4-(trifluoromethyl)-1H-1,6-naphthyridin-3-yl]-N-[(1S)-1-(2,4-difluorophenyl)ethyl]acetamide (40 mg, 39.50%). LC-MS: (ESI, m/z): $[M+H]^+$=451.95. $^1H$ NMR (400 MHz, DMSO-$d_6$) δ 12.23 (s, $^1H$), δ 8.57 (d, J=7.6 Hz, $^1H$), 8.26 (d, J=5.2 Hz, $^1H$), 7.46 (q, J=8.0 Hz, $^1H$), 7.21-7.15 (m, $^1H$), 7.09-7.04 (m, $^1H$), 6.98 (d, J=5.2 Hz, $^1H$), 5.08-5.02 (m, $^1H$), 3.73 (s, $^2H$), 2.10 (s, $^1H$), 1.34 (d, J=6.8 Hz, $^3H$), 1.13 (s, $^2H$), 1.02 (dd, J=7.6, 3.2 Hz, $^2H$).

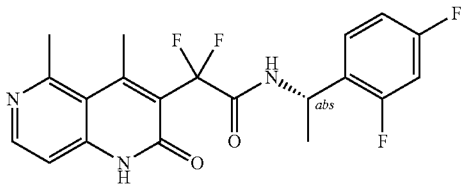

N-[(1S)-1-(2,4-Difluorophenyl)ethyl]-2-(4,5-dimethyl-2-oxo-1H-1,6-naphthyridin-3-yl)-2,2-difluoroacetamide tert-Butyl 3-(4-amino-2-chloropyridin-3-yl)-3-hydroxybutanoate. tert-Butyl 2-(bromoacetate (3816.53 mg, 14.655 mmol, 5.00 equiv) was added to a stirred solution of 1-(4-amino-2-chloropyridin-3-yl)ethanone (500.00 mg, 2.931 mmol, 1.00 equiv) in THF (30.00 mL). After stirring for 4 h at 70° C., the reaction was quenched by the addition of saturated $NH_4Cl$ (aq. 30 mL) at r.t. The resulting mixture was extracted with EtOAc. The combined organic layers were dried over anhydrous $Na_2SO_4$, The filtrate was concentrated under reduced pressure and the residue was purified by silica gel column chromatography to afford the product tert-butyl 3-(4-amino-2-chloropyridin-3-yl)-3-hydroxybutanoate (570 mg, 67.82%). LC-MS: (ESI, m/z): 287 $[M+H]^+$ 5-Chloro-4-methyl-1H-1,6-naphthyridin-2-one. KOH (293.48 mg, 5.230 mmol, 5.00 equiv) was added to a stirred solution of tert-butyl 3-(4-amino-2-chloropyridin-3-yl)-3-hydroxybutanoate (300.00 mg, 1.046 mmol, 1.00 equiv) in EtOH (50.00 mL). After stirring for 4 h at 80 degrees C., the reaction was quenched by the addition of $H_2O$ (50 mL) at room temperature. After removal of EtOH under reduced pressure, and water (10 mL) was added, the PH of the solution was adjusted to 5 with HCl (1 M). Then the resulting mixture was extracted with EtOAc. The combined organic layers were dried over anhydrous $Na_2SO_4$. The filtrate was concentrated under reduced pressure and the residue was purified by silica gel column chromatography to afford the product 5-chloro-4-methyl-1H-1,6-naphthyridin-2-one (150 mg, 73.67%). LC-MS: (ESI, m/z): 195 $[M+H]^+$ Ethyl 2-(5-chloro-4-methyl-2-oxo-1H-1,6-naphthyridin-3-yl)-2,2-difluoroacetate. To a stirred solution of 5-chloro-4-methyl-111-1,6-naphthyridin-2-one (150.00 mg, 0.77 mmol, 1.00 equiv) in DMF (5.00 mL) and acetone (5.00 mL) was added ethyl 2,2-difluoro-2-iodoacetate (578.01 mg, 2.31 mmol, 3.00 equiv) and $Na_2CO_3$ (245.07 mg, 2.31 mmol, 3.00 equiv). After stirring for 24 h at room temperature with light irradiation (450 nm), the reaction was quenched by the addition of saturated $NH_4Cl$ (aq, 50 mL) at room temperature. The resulting mixture was extracted with EtOAc, the combined organic layers were dried over anhydrous $Na_2SO_4$, an the filtrate was concentrated under reduced pressure. The residue was purified by silica gel column chromatography to afford ethyl 2-(5-chloro-4-methyl-2-oxo-1H-1,6-naphthyridin-3-yl)-2,2-difluoroacetate (130 mg, 53.26%). LC-MS: (ESI, m/z): 317 $[M+H]^+$ (5-Chloro-4-methyl-2-oxo-1H-1,6-naphthyridin-3-yl)difluoroacetic acid. To a stirred solution of ethyl 2-(5-chloro-4-methyl-2-oxo-1H-1,6-naphthyridin-3-yl)-2,2-difluoroacetate (150.00 mg, 0.47 mmol, 1.00 equiv) in MeOH (5.00 mL) and $H_2O$ (5.00 mL) was added LiOH (56.71 mg, 2.37 mmol, 5.00 equiv). After stirring for 4 h at room temperature, the solvent was concentrated under reduced pressure and water (2 mL) was added, to adjust the PH to 6 with HCl (1 M). The residue was further purified by reverse flash chromatography with the following conditions: (column, C18 silica gel; mobile phase, MeOH in water, 5% to 20% gradient in 30 min; detector, UV 254 nm). After removal of the solvent, the product (5-chloro-4-methyl-2-oxo-1H-1,6-naphthyridin-3-yl)difluoroacetic acid (100 mg, 73.15%) was collected. LC-MS: (ESI, m/z): 289 $[M+H]^+$ 2-(5-Chloro-4-methyl-2-oxo-1H-1,6-naphthyridin-3-yl)-N-[(1S)-1-(2,4-difluorophenyl)ethyl]-2,2-difluoroacetamide. Into a 40-mL vial, (5-chloro-4-methyl-2-oxo-1H-1,6-naphthyridin-3-yl)difluoroacetic acid (100.00 mg, 0.346 mmol, 1.00 equiv), DCM (8.00 mL), $T_3P$ (83.20 mg, 2.079 mmol, 6.00 equiv), DIEA (179.11 mg, 1.386 mmol, 4.00 equiv), and (1S)-1-(2,4-difluorophenyl)ethanamine (81.68 mg, 0.520 mmol, 1.50 equiv) was placed. The reaction mixture was stirred for 12 h at 30° C. The resulting mixture was concentrated under vacuum and the residue purified by silica gel column chromatography resulting in 95 mg (64.10%) of 2-(5-chloro-4-methyl-2-oxo-1H-1,6-naphthyridin-3-yl)-N-[(1S)-1-(2,4-difluorophenyl)ethyl]-2,2-difluoroacetamide. LC-MS: (ESI, m/z): 426 $[M+H]^+$ N-[(1S)-1-(2,4-Difluorophenyl)ethyl]-2-(4,5-dimethyl-2-oxo-1H-1,6-naphthyridin-3-yl)-2,2-difluoroacetamide. Into a 8-mL vial, 2-(5-chloro-4-methyl-2-oxo-1H-1,6-naphthyridin-3-yl)-N-[(1S)-1-(2,4-difluorophenyl)ethyl]-2,2-difluoroacetamide (80.00 mg, 0.19 mmol, 1.00 equiv), lithium chloride (7.93 mg, 0.19 mmol, 1.00 equiv), water (0.3 mL), and Dioxane (3.0 mL) was placed, then tetrakis(triphenylphosphine)palladium(0) (21.61 mg, 0.019 mmol, 0.10 equiv) was added in Ar atmosphere, and tetramethyltin (334.47 mg, 1.870 mmol, 10.00 equiv) was injected into the mixture. The reaction mixture was stirred for 4 h at 100° C. in an oil bath under Ar atmosphere. The resulting mixture was concentrated under vacuum. The crude product (100 mg, crude) was purified by Flash-Prep-HPLC with the following conditions (IntelFlash-1): (Column, C18 silica gel; mobile phase, 0.05% $NH_4HCO_3$ in ACN; Detector, 220 nm) resulting in 43 mg (56.44%) of N-[(1 S)-1-(2,4-difluorophenyl)ethyl]-2-(4,5-dimethyl-2-oxo-1H-1,6-naphthyridin-3-yl)-2,2-difluoroacetamide. LC-MS: (ESI, m/z): 407.95 $[M+H]^+$ $^1H$ NMR (400 MHz, DMSO-$d_6$) δ 12.19 (s, $^1H$), 9.00 (d, J=8.0 Hz, $^1H$), 8.34 (d, J=5.6 Hz, $^1H$), 7.77-7.57 (m, $^1H$), 7.21-7.15 (m, $^1H$), 7.08-7.03 (m, $^2H$), 5.21-5.14 (in, H), 2.87 (s, $^3H$), 2.74 (d, J=4.0 Hz, $^3H$), 1.43 (d, J=7.2 Hz, $^3H$).

(Compound 420)

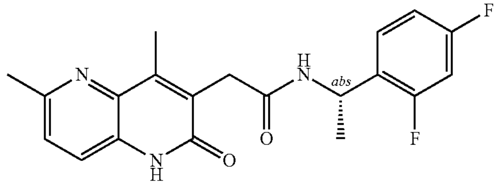

N-[(1S)-1-(2,4-Difluorophenyl)ethyl]-2-(4,6-dimethyl-2-oxo-1H-1,5-naphthyridin-3-yl)acetamide N-(2-bromo-6-methylpyridin-3-yl)-2,2-dimethylpropanamide. 2,2-dimethylpropanoyl chloride (2.90 g, 24.059 mmol, 1.5 equiv) was added to a stirred solution of 2-bromo-6-methylpyridin-3-amine (3 g, 16.039 mmol, 1 equiv) and TEA (4.87 g, 48.117 mmol, 3 equiv) in DCM (50 mL) dropwise at 0° C. The resulting mixture was concentrated under vacuum. The residue was purified by silica gel column chromatography to afford N-(2-bromo-6-methylpyridin-3-yl)-2,2-dimethylpropanamide (3.5 g, 80.47%). LCMS (ES, m/z): 271 [M+H]+

N-(2-Acetyl-6-methylpyridin-3-yl)-2,2-dimethylpropanamide. N-(2-bromo-6-methylpyridin-3-yl)-2,2-dimethylpropanamide (1.00 g, 3.69 mmol, 1.00 equiv), THF (20.00 mL), NaH(60%) (0.27 g, 5.53 mmol, 1.50 equiv) was added into a 100-mL 3-necked round-bottom flask purged and maintained with an inert atmosphere of argon, was placed at 0° C. and stirred for 0.5 h. n-BuLi (2.5M) (2.30 mL, 3.69 mmol, 1.00 equiv) was added at −78° C. and stirred for 0.5 h, then N-methoxy-N-methylacetamide (1.14 g, 11.06 mmol, 3.00 equiv) was added at −78° C. and stirred for 0.5 h. The reaction mixture was stirred for 30 min at −78° C. The reaction was then quenched by the addition of 100 mL of $NH_4Cl$(aq.). The reaction mixture was extracted with ethyl acetate and concentrated. The residue was purified using silica gel column chromotography with ethyl acetate/petroleum ether (1:10) resulting in 700 mg (81.01%) of N-(2-acetyl-6-methylpyridin-3-yl)-2,2-dimethylpropanamide. LCMS (ES, m/z): 235 [M+H]+

1,4-Di-tert-butyl 2-[1-[3-(2,2-dimethylpropanamido)-6-methylpyridin-2-yl]-hydroxyethyl]butanedioate. 1,4-di-tert-butyl butanedioate (1376.13 mg, 5.976 mmol, 2.00 equiv), THF (15 mL), LDA (3.00 mL, 5.976 mmol, 2.00 equiv, 2M in THF) was placed into a 100-mL 3-necked round-bottom flask purged and maintained with an inert atmosphere of argon at −78° C. and stirred for 0.5 hr. Then N-(2-acetyl-6-methylpyridin-3-yl)-2,2-dimethylpropanamide (700.00 mg, 2.988 mmol, 1.00 equiv), $ZnCl_2$(4.30 mL, 2.988 mmol, 1 equiv, 0.7M in THF) was added at −78° C. The reaction mixture was stirred for 30 min at −78° C. The reaction was then quenched by the addition of 100 mL of $NH_4Cl$ (aq.) (100 mL). The reaction mixture was extracted with ethyl acetate and concentrated. The residue was purified using silica gel column chromatography resulting in 950 mg (68.44%) of 1,4-di-tert-butyl 2-[1-[3-(2,2-dimethylpropanamido)-6-methylpyridin-2-yl]-1-hydroxyethyl]butanedioate. LCMS (ES, m/z): 465 $[M+H]^+$ (4,6-Dimethyl-2-oxo-1H-1,5-naphthyridin-3-yl)acetic acid. 1,4-di-tert-butyl 2-[1-[3-(2,2-dimethylpropanamido)-6-methylpyridin-2-yl]-1-hydroxyethyl]butanedioate (900.00 mg, 1.937 mmol, 1.00 equiv), Dioxane (6.00 mL), HCl(6M, 6.00 mL) was placed into a 50-mL pressure tank reactor purged and maintained with an inert atmosphere of argon. The reaction mixture was stirred for 12 hr at 95° C. The resulting mixture was concentrated. The crude product was purified by re-crystallization from MeCN resulting in 200 mg (44.46%) of (4,6-dimethyl-2-oxo-1H-1,5-naphthyridin-3-yl)acetic acid. LCMS (ES, m/z): 233 [M+H]+

N-[(1S)-1-(2,4-Difluorophenyl)ethyl]-2-(4,6-dimethyl-2-oxo-1H-1,5-naphthyridin-3-yl)acetamide. (4,6-dimethyl-2-oxo-1H-1,5-naphthyridin-3-yl) acetic acid (100.00 mg, 0.43 mmol, 1.00 equiv), DCM (2.00 mL), EDCI (99.05 mg, 0.52 mmol, 1.20 equiv), (1S)-1-(2,4-difluorophenyl)ethanamine (81.21 mg, 0.52 mmol, 1.20 equiv), DMAP (26.30 mg, 0.22 mmol, 0.50 equiv) was placed into a 50-mL round-bottom flask purged and maintained with an inert atmosphere of argon, was placed. The reaction mixture was stirred for 2 hr at 25° C. The reaction was then quenched by the addition of 5 mL of water. The solids were collected by filtration. The crude product was purified by re-crystallization from MeCN resulting in 121.2 mg (75.79%) of N-[(1S)-1-(2,4-difluorophenyl)ethyl]-2-(4,6-dimethyl-2-oxo-1H-1,5-naphthyridin-3-yl)acetamide. LCMS (ES, m/z): $372[M+H]^+$ $^1H$ NMR (400 MHz, DMSO-d6) δ 11.74 (s, 1H), 8.48 (d, J=7.6 Hz, 1H), 7.56-7.03 (m, 5H), 5.05-5.09 (m, 1H), 3.60 (s, 2H), 2.53 (s, 3H), 2.45 (s, 3H), 1.35 (m, 3H).

(Compound 412 and 411)

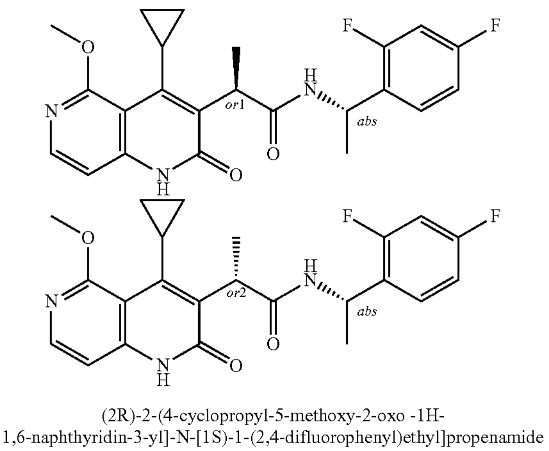

(2R)-2-(4-cyclopropyl-5-methoxy-2-oxo -1H-1,6-naphthyridin-3-yl]-N-[1S)-1-(2,4-difluorophenyl)ethyl]propenamide and ((2S)-2-(4-cyclopropyl-5-methoxy-2-oxo-1H-1,6-naphthyridin-3-yl)-N-[(1S)-1-(2,4-difluorophenyl)ethyl]propenamide 3-Iodo-2-methoxypyridin-4-amine. NIS (906.15 mg, 0.000 mmol, 1.00 equiv) in portions was added to a stirred solution of 2-methoxypyridin-4-amine (500.00 mg, 4.028 mmol, 1.00 equiv) in acetonitrile (5 mL) at 0° C. under nitrogen atmosphere. The reaction mixture was stirred at 10° C. overnight.

The reaction was quenched by the addition of Water/Ice (20 mL) at 0° C. The resulting mixture was extracted with EtOAc (3×50 mL). The combined organic layers were washed with saturated (1×30 mL), then dried over anhydrous $Na_2SO_4$. The filtrate was concentrated under reduced pressure and the residue was purified by silica gel column chromatography to afford 3-iodo-2-methoxypyridin-4-amine (800 mg, 79.44%). LCMS (ES, m/z): $250.1[M+H]^+$.

Methyl 4-amino-2-methoxypyridine-3-carboxylate.

$Pd_2(dba)_3$(10.62 g, 11.598 mmol, 0.2 equiv) and DIEA (14.99 g, 115.982 mmol, 2.0 equiv) were added to a solution of 3-iodo-2-methoxypyridin-4-amine(14.50 g, 57.991 mmol, 1.00 equiv) in 200 mL MeOH at room temperature in a pressure tank. The mixture was purged with nitrogen for 30 min and then was pressurized to 20 atm with carbon monoxide at 100° C. for overnight. The reaction mixture was cooled to room temperature and filtered to remove insoluble solids. The filtrate was concentrated under reduced pressure and the residue was purified by silica gel column chromatography to afford methyl 4-amino-2-methoxypyridine-3-carboxylate (7.7 g, 72.88%). LCMS (ES, m/z): $181.9[M+H]^+$.

Methyl 2-methoxy-4-(4-methoxy-2-methyl-4-oxobutanamido)pyridine-3-carboxylate. Methyl 4-chloro-3-methyl-4-oxobutanoate (5.78 g, 35.13 mmol, 2.00 equiv) was added dropwise to a stirred solution of methyl 4-amino-2-methoxypyridine-3-carboxylate(3.20 g, 17.57 mmol, 1.00 equiv) and TEA(8.89 g, 87.83 mmol, 5.00 equiv) in DCM(60. 00 mL) was added dropwise at 0 degrees C. under argon atmosphere. The reaction mixture was stirred at room temperature under argon atmosphere for 3.5 h. The reaction was quenched by the addition of Water/Ice at room temperature. The resulting mixture was extracted with EtOAc. The combined organic layers were washed with saturated brine, dried over anhydrous $Na_2SO_4$. The filtrate was concentrated under reduced pressure and purified by silica gel column chromatography to afford methyl 2-methoxy-4-(4-methoxy-2-methyl-4-oxobutanamido)pyridine-3-carboxylate(1.2 g, 22.02%). LCMS (ES, m/z): 324.0 $[M+H]^+$.

Methyl 6-methoxy-3-methyl-2,5-dioxo-2,3,4,5-tetrahydro-1H-pyrido[4,3-b]azepine-4-carboxylate. t-BuOK (6.51 g, 58.01 mmol, 6.00 equiv) was added to a stirred mixture of methyl 2-methoxy-4-(4-methoxy-2-methyl-4-oxobutanamido)pyridine-3-carboxylate (3.00 g, 9.67 mmol, 1.00 equiv) in THF (60 mL) at 0° C. under argon atmosphere. The mixture was stirred at room temperature under argon atmosphere for 30 min. 60% The reaction mixture was concentrated under reduced pressure and the residue was used directly to the next step without further purification.

LCMS (ES, m/z): 278.0 $[M+H]^+$.

2-(4-Hydroxy-5-methoxy-2-oxo-1H-1,6-naphthyridin-3-yl)propanoic acid. $Cs_2CO_3$ (10.54 g, 32.34 mmol, 3.00 equiv) was added to a stirred mixture of methyl 6-methoxy-3-methyl-2,5-dioxo-1H,3H,4H-pyrido[4,3-b]azepine-4-carboxylate (3.00 g, 10.78 mmol, 1.00 equiv) in $H_2O$ (60 mL) was added at room temperature under air atmosphere. The mixture was stirred at 95° C. under air atmosphere for 3.5 h. The mixture was acidified to pH 3 with HCl (aq.). The precipitated solids were collected by filtration and washed with acetonitrile (2×50 mL) to afford 2-(4-hydroxy-5-methoxy-2-oxo-1H-1,6-naphthyridin-3-yl)propanoic acid (1.1 g, 38.61%) . . . LCMS (ES, m/z): 264.1 $[M+H]^+$.

Methyl 2-(4-hydroxy-5-methoxy-2-oxo-1H-1,6-naphthyridin-3-yl)propanoate.

$TMSCHN_2$(0.71 g, 6.24 mmol, 1.10 equiv) was added dropwise to a stirred solution of 2-(4-hydroxy-5-methoxy-2-oxo-1H-1,6-naphthyridin-3-yl)propanoic acid(1.50 g, 5.68 mmol, 1.00 equiv) in DMF (15 mL) at 0° C. under argon atmosphere. The mixture was stirred at 0° C. for 1 h. 65% The reaction was quenched by the addition of saturated $NH_4Cl$ (aq.) (50 mL) at 0° C. The resulting mixture was extracted with EtOAc (5×50 mL). The combined organic layers were washed with saturated brine (1×50 mL), dried over anhydrous $Na_2SO_4$. The filtrate was concentrated under reduced pressure and the residue was purified by reverse flash chromatography with the following conditions: (column, C18; mobile phase, MeCN in water, 10% to 80% gradient in 40 min; detector, UV 254 nm) to afford methyl 2-(4-hydroxy-5-methoxy-2-oxo-1H-1,6-naphthyridin-3-yl) propanoate (700 mg, 44.31%). LCMS (ES, m/z): 278.0 $[M+H]^+$.

Methyl 2-[5-methoxy-2-oxo-4-(trifluoromethanesulfonyloxy)-1H-1,6-naphthyridin-3-yl]propanoate. 1,1,1-trifluoro-N-phenyl-N-trifluoromethanesulfonylmethanesulfonamide (847.32 mg, 2.37 mmol, 1.10 equiv) was added to a stirred mixture of methyl 2-(4-hydroxy-5-methoxy-2-oxo-1H-1,6-naphthyridin-3-yl)propanoate (600.00 mg, 2.16 mmol, 1.00 equiv) and DIEA (557.36 mg, 4.31 mmol, 2.00 equiv) in DMF (10 mL) was added at room temperature under air atmosphere. The mixture was stirred at room temperature overnight. The reaction mixture was purified by reverse flash chromatography with the following conditions: (column, C18 silica gel; mobile phase, $CH_3CN$ in water, 10% to 80% gradient in 40 min; detector, UV 254 nm) to afford methyl 2-[5-methoxy-2-oxo-4-(trifluoromethanesulfonyloxy)-1H-1,6-naphthyridin-3-yl]propanoate (400 mg, 45.21%). LCMS (ES, m/z): 410.0 $[M+H]^+$.

Methyl 2-(4-cyclopropyl-5-methoxy-2-oxo-1H-1,6-naphthyridin-3-yl)propanoate. $K_2CO_3$ (404.19 mg, 2.93 mmol, 6 equiv) and $Pd(dppf)Cl_2$ (71.33 mg, 0.10 mmol, 0.2 equiv) was added to a stirred mixture of methyl 2-[5-methoxy-2-oxo-4-(trifluoromethanesulfonyloxy)-1H-1,6-naphthyridin-3-yl]propanoate (200 mg, 0.5 mmol, 1.00 equiv) and cyclopropylboronic acid (251.22 mg, 2.92 mmol, 6 equiv) in 1,4-dioxane (10 mL) was added at room temperature under argon atmosphere. The mixture was stirred at 70° C. for 2 h under argon atmosphere. 65% 70% The resulting mixture was concentrated under reduced pressure and the residue was purified by silica gel column chromatography to afford methyl 2-(4-cyclopropyl-5-methoxy-2-oxo-1H-1,6-naphthyridin-3-yl)propanoate (90 mg, 61.07%). LCMS (ES, m/z): 302.1 $[M+H]^+$. 2-(4-Cyclopropyl-5-methoxy-2-oxo-1, 2-dihydro-1,6-naphthyridin-3-yl)propanoic acid. A stirred solution of methyl 2-(4-cyclopropyl-5-methoxy-2-oxo-1H-1,6-naphthyridin-3-yl)propanoate (180 mg) and TFA (1 mL) in DCM (5 mL) was prepared at room temperature under argon atmosphere 70%. The reaction mixture was concentrated under reduced pressure and then the residue was purified by Prep-TLC ($CH_2Cl_2$/MeOH 20:1) to afford 2-(4-cyclopropyl-5-methoxy-2-oxo-1,2-dihydro-1,6-naphthyridin-3-yl)propanoic acid (130 mg, 58.66%). LCMS (ES, m/z): 288.0 $[M+H]^+$.

(2R)-2-(4-Cyclopropyl-5-methoxy-2-oxo-1H-1,6-naphthyridin-3-yl)-N-[(1S)-1-(2,4-difluorophenyl)ethyl]propanamide. (1S)-1-(2,4-difluorophenyl)ethanamine (91.58 mg, 0.58 mmol, 1.2 equiv) and DIPEA (188.28 mg, 1.46 mmol, 3. 0 equiv) was added to a stirred solution of 2-(4-cyclopropyl-5-methoxy-2-oxo-1H-1,6-naphthyridin-3-yl)propanoic acid (140.00 mg, 0.49 mmol, 1.00 equiv) and HATU (221.57 mg, 0.58 mmol, 1.2 equiv) in DMF (10 mL) were added at room temperature under air atmosphere. The reaction was quenched by the addition of Water at room temperature. The resulting mixture was extracted with EtOAc, the combined organic layers were washed with saturated brine and dried over anhydrous $Na_2SO_4$. The filtrate was concentrated under reduced pressure and the residue was purified by reverse flash chromatography with the following conditions: (column, C18 silica gel; mobile phase, $CH_3CN$ in water, 10% to 80% gradient in 40 min; detector, UV 254 nm) to afford (2R)-2-(4-cyclopropyl-5-methoxy-2-oxo-1H-1,6-naphthyridin-3-yl)-N-[(1S)-1-(2,4-difluorophenyl)ethyl]propanamide (58.0 mg, 27.47%). LCMS (ES, m/z): 258.1 $[M+H]^+$. $^1H$ NMR (300 MHz, DMSO-$d_6$): 11.88 (s, $^1H$), 7.96 (d, J=5.4, $^1H$), 7.56-7.45 (m, $^2H$), 7.17-6.98 (m, $^2H$), 6.81 ((d, J=5.7, $^1H$), 5.18-5.13 (m, $^1H$), 4.26-4.19 (m, $^1H$), 3.96 (s, $^3H$), 2.13-2.10 (m, $^1H$), 1.36 (d, J=6.9, $^2H$), 1.06 (d, J=6.6, $^3H$), 1.03 (d, J=3.9, $^3H$), 0.67-0.63 (m, $^1H$), 0.49-0.46 (m, $^1H$)

(2S)-2-(4-Cyclopropyl-5-methoxy-2-oxo-1H-1,6-naphthyridin-3-yl)-N-[(1S)-1-(2,4-difluorophenyl)ethyl]propanamide. (1S)-1-(2,4-Difluorophenyl)ethanamine (91.58 mg, 0.58 mmol, 1.2 equiv) and DIPEA (188.28 mg, 1.46 mmol, 3.0 equiv) was added to a stirred solution of 2-(4-cyclopropyl-5-methoxy-2-oxo-1H-1,6-naphthyridin-3-yl) propanoic acid (140.00 mg, 0.49 mmol, 1.00 equiv) and HATU (221.57 mg, 0.58 mmol, 1.2 equiv) in DMF (3 mL) at room temperature under air atmosphere. 70% The reaction was quenched by the addition of Water at room temperature. The resulting mixture was extracted with EtOAc and the combined organic layers were washed with saturated brine and dried over anhydrous $Na_2SO_4$. The filtrate was concentrated under reduced pressure and the residue was purified by reverse flash chromatography with the following conditions: (column, C18 silica gel; mobile phase, $CH_3CN$ in water, 10% to 80% gradient in 40 min; detector, UV 254 nm) to afford (2S)-2-(4-cyclopropyl-5-methoxy-2-oxo-1H-1,6-naphthyridin-3-yl)-N-[(1S)-1-(2,4-difluorophenyl)ethyl] propanamide (26.8 mg, 12.56%). LCMS (ES, m/z): 258.1 $[M+H]^+$. $^1H$ NMR (300 MHz, DMSO-$d_6$): 11.88 (s, $^1H$), 7.96 (d, J=5.4, $^1H$), 7.56-7.45 (m, $^2H$), 7.17-6.98 (m, $^2H$), 6.81 ((d, J=5.7, $^1H$), 5.18-5.13 (m, $^1H$), 4.26-4.19 (m, $^1H$), 3.96 (s, $^3H$), 2.13-2.10 (m, $^1H$), 1.36 (d, J=6.9, $^2H$), 1.06 (d, J=6.6, $^3H$), 1.03 (d, J=3.9, 3H), 0.67-0.63 (m, $^1H$), 0.49-0.46 (m, $^1H$).

(Compound 398 and 399)

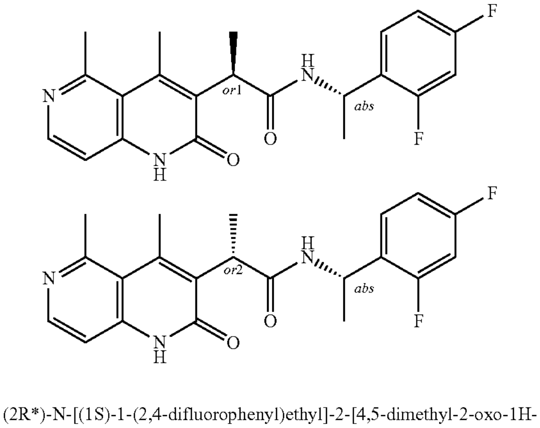

(2R*)-N-[(1S)-1-(2,4-difluorophenyl)ethyl]-2-[4,5-dimethyl-2-oxo-1H-1,6-naphthyridin-3-yl]propanamide and (2S)-N-[1S)-1-(2,4-difluorophenyl)ethyl]-2-(4,5-dimethyl-2-oxo-1H-1,6-naphthyridin-3-yl)propenamide Methyl 2-(5-chloro-4-methyl-2-oxo-1H-1,6-naphthyridin-3-yl)acetate. $SOCl_2$ (3767.11 mg, 31.665 mmol, 5 equiv) was added dropwise to a stirred solution of (5-chloro- 4-methyl-2-oxo-1H-1,6-naphthyridin-3-yl)acetic acid (1600 mg, 6.3 mmol, 1.00 equiv) in MeOH (20.00 mL) at 0 degrees ° C. The resulting mixture was stirred for 2 h at 50° C. The resulting mixture was concentrated under vacuum. The mixture was basified to pH 9 with saturated $NaHCO_3$ (aq.). The aqueous layer was extracted with EtOAc. The combined organic layers were dried over anhydrous $Na_2SO_4$. The filtrate was concentrated under reduced pressure and the residue was purified by silica gel column chromatography to afford methyl 2-(5-chloro-4-methyl-2-oxo-1H-1,6-naphthyridin-3-yl)acetate (1400 mg, 73.78%). LCMS (ES, m/z): 267[M+H]$^+$.

Methyl 2-(5-chloro-4-methyl-2-oxo-1H-1,6-naphthyridin-3-yl)propanoate. A solution of methyl 2-(5-chloro-4-methyl-2-oxo-1H-1,6-naphthyridin-3-yl)acetate (600 mg, 2.250 mmol, 1.00 equiv) in THF (10 mL) was added to LiHMDS (941.16 mg, 5.625 mmol, 2.5 equiv) at −78° C. under argon atmosphere. The resulting mixture was stirred for 20 min at −78° C. under argon atmosphere. $CH_3I$ (351.28 mg, 2.475 mmol, 1.1 equiv) was added dropwise to the above mixture over 2 min at −78° C. The resulting mixture was stirred for additional 1 h at room temperature. The reaction was quenched with saturated $NH_4Cl$ (aq.) at room temperature. The resulting mixture was extracted with EtOAc, the combined organic layers were washed with water, and dried over anhydrous $Na_2SO_4$. The filtrate was concentrated under reduced pressure and purified by silica gel column chromatography to afford methyl 2-(5-chloro-4-methyl-2-oxo-1H-1,6-naphthyridin-3-yl)propanoate (480 mg, 61.79%). LCMS (ES, m/z): 281 [M+H]$^+$.

Methyl 2-(4,5-dimethyl-2-oxo-1H-1,6-naphthyridin-3-yl) propanoate. $K_2CO_3$ (590.81 mg, 4.28 mmol, 3 equiv) and Pd(dppf)$Cl_2$(104.26 mg, 0.14 mmol, 0.1 equiv) was added to a solution of methyl 2-(5-chloro-4-methyl-2-oxo-1H-1,6-naphthyridin-3-yl)propanoate(400.00 mg, 1.43 mmol, 1.00 equiv) and methylboronic acid(852.98 mg, 14.25 mmol, 10 equiv) in dioxane(10.00 mL). After stirring for 3 h at 100° C. under a nitrogen atmosphere. The resulting mixture was concentrated under reduced pressure and the residue was purified by Prep-TLC ($CH_2Cl_2$/MeOH 20:1) to afford methyl 2-(4,5-dimethyl-2-oxo-1H-1,6-naphthyridin-3-yl) propanoate(300 mg, 75.14%). LCMS (ES, m/z): 261 [M+H]$^+$.

2-(4,5-Dimethyl-2-oxo-1H-1,6-naphthyridin-3-yl)propanoic acid. Into a 20 mL vial were added methyl 2-(4,5-dimethyl-2-oxo-1H-1,6-naphthyridin-3-yl) propanoate (250 mg, 0.96 mmol, 1.00 equiv) and LiOH (115.01 mg, 4.80 mmol, 5.00 equiv) in MeOH(1.00 mL)/THF(1.00 mL)/$H_2O$ (1.00 mL) at degrees C. The resulting mixture was stirred for 1 h at 80° C. The mixture was acidified to pH 4 with HCl (aq.) and concentrated under reduced pressure and the residue was purified by Prep-TLC ($CH_2Cl_2$/MeOH 4:1) to afford 2-(4,5-dimethyl-2-oxo-1H-1,6-naphthyridin-3-yl) propanoic acid (210 mg, 81.95%). LCMS (ES, m/z): 247 [M+H]$^+$.

N-[(1S)-1-(2,4-Difluorophenyl)ethyl]-2-(4,5-dimethyl-2-oxo-1H-1,6-naphthyridin-3-yl)propanamide. EDCI (186.82 mg, 0.97 mmol, 1.2 equiv), (1S)-1-(2,4-difluorophenyl) ethanamine (153.17 mg, 0.97 mmol, 1.2 equiv) was added dropwise to a stirred solution of 2-(4,5-dimethyl-2-oxo-1H-1,6-naphthyridin-3-yl)propanoic acid (200 mg, 0.8 mmol, 1.00 equiv) and DMAP (49.61 mg, 0.41 mmol, 0.5 equiv) in DMF(3.00 mL) at room temperature. The resulting mixture was stirred for 3 h at room temperature. The resulting mixture was purified by reverse flash chromatography with the following conditions: (column, silica gel; mobile phase, MeCN in water, 0% to 100% gradient in 50 min; detector, UV 254 nm) to afford N-[(1S)-1-(2,4-difluorophenyl)ethyl]-2-(4,5-dimethyl-2-oxo-1H-1,6-naphthyridin-3-yl)propanamide (200 mg, 61.47%). LCMS (ES, m/z): 386[M+H]$^+$.

(2R*)-N-[(1S)-1-(2,4-Difluorophenyl)ethyl]-2-(4,5-dimethyl-2-oxo-1H-1,6-naphthyridin-3-yl)propanamide. The N-[(1S)-1-(2,4-difluorophenyl)ethyl]-2-(4,5-dimethyl-2-oxo-1H-1,6-naphthyridin-3-yl)propanamide (40 mg, 0.1 mmol, 1.00 equiv) was separated by Chiral-HPLC, Column: CHIRALPAK IG, Mobile Phase: Hex(0.1% DEA): EtOH=50:50, Flow rate: 1.0 ml/min, to afford (2R*)-N-[(1S)-1-(2,4-difluorophenyl)ethyl]-2-(4,5-dimethyl-2-oxo-1H-1,6-naphthyridin-3-yl)propanamide (20 mg, 50%). LCMS (ES, m/z): 386.15 [M+H]+$^1$H NMR (400 MHz, DMSO-$d_6$): $^1$H NMR (300 MHz, DMSO-$d_6$) δ 11.94 (s, $^1$H), 8.25 (d, J=5.5 Hz, $^1$H), 7.83 (d, J=7.8 Hz, $^1$H), 7.47-7.39 (m, $^1$H), 7.20-7.02 (m, $^3$H), 5.23-5.13 (m, $^1$H), 4.19-4.12 (m, $^1$H), 2.88 (s, $^3$H), 2.50 (s, 3H), 1.28-1.26 (m, $^6$H).

(2S)—N-[(1S)-1-(2,4-Difluorophenyl)ethyl]-2-(4,5-dimethyl-2-oxo-1H-1,6-naphthyridin-3-yl)propanamide. The N-[(1S)-1-(2,4-difluorophenyl)ethyl]-2-(4,5-dimethyl-2-oxo-1H-1,6-naphthyridin-3-yl)propanamide (40 mg, 0.1 mmol, 1.00 equiv) was separated by Chiral-HPLC, Column: CHIRALPAK IG, Mobile Phase: Hex(0.1% DEA): EtOH=50:50, Flow rate: 1.0 ml/min, to afford (2S)—N-[(1S)-1-(2,4-difluorophenyl)ethyl]-2-(4,5-dimethyl-2-oxo-1H-1,6-naphthyridin-3-yl)propanamide (15.9 mg, 39.75%). LCMS (ES, m/z): 386.20 [M+H]+$^1$H NMR (300 MHz, DMSO-$d_6$) δ 11.98 (s, $^1$H), 8.27 (d, J=5.2 Hz, $^1$H), 7.90 (d, J=8.0 Hz, $^1$H), 7.37-7.29 (m, $^1$H), 7.21-7.12 (m, $^2$H), 7.01-6.96 (m, $^1$H), 5.26-5.21 (m, $^1$H), 4.26-4.21 (m, $^1$H), 2.78 (d, J=2.8 Hz, $^3$H), 2.22 (s, $^3$H), 1.27 (m, $^6$H).

(Compound 391)

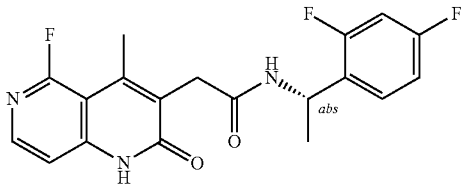

N-[(1S)-1-(2,4-difluorophenyl)ethyl]-2-(5-fluoro-4-methyl-2-oxo-1H-1,6-naphthyridin-3-yl)acetamide 3-(1-butoxyethenyl)-2-chloropyridin-4-amine. Potassium methaneperoxoate potassium (21.88 g, 157.20 mmol, 2 equiv) and DPPP (6.48 g, 15.72 mmol, 0.2 equiv) were added to a solution of 2-chloro-3-iodopyridin-4-amine (20 g, 79 mmol, 1.00 equiv) and butyl vinyl ether (39.36 g, 392.99 mmol, 5 equiv) in Dioxane (300 mL) were added, then $Pd_2(dba)_3$ (7.20 g, 7.86 mmol, 0.1 equiv) was added in Ar atmosphere. After stirring for 16 hours at 110° C. under an Ar atmosphere. Then the resulting mixture was filtered, the filter cake was washed with dioxane. The filtrate was used directly for the next step, to afford 3-(1-butoxyethenyl)-2-chloropyridin-4-amine (30 g, crude).

LCMS (ES, m/z): 227 [M+H]$^+$.

1-(4-amino-2-chloropyridin-3-yl) ethanone. Hydrogen chloride (4 M) was added to a solution of 3-(1-butoxyethenyl)-2-chloropyridin-4-amine (30 g, 132 mmol, 1.00 equiv) in dioxane (200 mL) was added at room temperature, until the mixture was acidified to pH 2 with HCl (4 M). The mixture was stirred for 6 hours. Then the aqueous layer was extracted with EtOAc and the water layer was basified to pH 10 with NaOH (6 M), and extracted with EtOAc. The combined organic layers were washed with $H_2O$, dried over anhydrous $Na_2SO_4$. The filtrate was concentrated under reduced pressure and the residue was purified by silica gel column chromatography to afford 1-(4-amino-2-chloropyridin-3-yl)ethanone (8.5 g, 35.77%). LCMS (ES, m/z): 171 $[M+H]^+$.

1,4-Di-tert-butyl 2-[1-(4-amino-2-chloropyridin-3-yl)-1-hydroxyethyl]butanedioate. In a 500-mL round bottom flask, LDA (18.84 g, 175.85 mmol, 3 equiv) solution (2 M in THF) was added dropwise to a solution of 1,4-di-tert-butyl butanedioate (27.00 g, 117.23 mmol, 2 equiv) in THF (150 mL) at −78° C. under Ar atmosphere. The reaction mixture was stirred at −78° C. for 45 mins. Then a solution of 1-(4-amino-2-chloropyridin-3-yl) ethanone (10 g, 59 mmol, 1.00 equiv) in (50 mL) THF was added dropwise, and zinc chloride (7.99 g, 58.62 mmol, 1 equiv) was added dropwise, and the mixture was stirred for another 60 mins at −78° C. Then the mixture was warmed to −50° C. for 60 mins. Then the reaction was quenched with saturated $NH_4Cl$ (30 mL), and then the mixture was extracted with EtOAc. The combined organic extracts were washed with brine, dried over anhydrous $Na_2SO_4$, and concentrated under vacuum to yield a crude product which was directly purified by Prep-HPLC with the following conditions ($NH_4HCO_3$, 0.1%) to afford 1,4-di-tert-butyl 2-[1-(4-amino-2-chloropyridin-3-yl)-1-hydroxyethyl]butanedioate (100 g, 404.27%). LCMS (ES, m/z): 401 $[M+H]^+$.

(5-chloro-4-methyl-2-oxo-1H-1,6-naphthyridin-3-yl)acetic acid. KOH (55.98 mL, 997.75 mmol, 5.00 equiv) was added to a solution of 1,4-di-tert-butyl 2-[1-(4-amino-2-chloropyridin-3-yl)-1-hydroxyethyl]butanedioate (80 g, 200 mmol, 1.00 equiv) in ethyl alcohol (1120 mL). The mixture was stirred for 16 hours at 80° C. Then the resulting mixture was concentrated under reduced pressure, and water (200 mL) was added to the residue. The mixture was acidified to pH 2 with HCl (4 M). The precipitated solids were collected by filtration and washed with water and slurried with ACN to afford (5-chloro-4-methyl-2-oxo-1H-1,6-naphthyridin-3-yl)acetic acid (40 g, 75.37%).

LCMS(ES, m/z): 253 $[M+H]^+$.

2-(5-chloro-4-methyl-2-oxo-1H-1,6-naphthyridin-3-yl)-N-[(1S)-1-(2,4-difluorophenyl)ethyl]acetamide. EDCI (27315.54 mg, 142.49 mmol, 1.2 equiv), (1S)-1-(2,4-difluorophenyl)ethanamine (22.2 g, 142 mmol, 1.2 equiv) and DMAP (2901.27 mg, 23.75 mmol, 0.2 equiv) was added to a solution of (5-chloro-4-methyl-2-oxo-1H-1,6-naphthyridin-3-yl)acetic acid (30 g, 119 mmol, 1.00 equiv) in dimethylformamide (300 mL) at room temperature. The mixture was stirred for 16 hours at room temperature. The reaction mixture was quenched by water (1 L). The precipitated solids were collected by filtration and washed with $H_2O$. The crude product was slurried from ACN (2×500 mL) to afford 2-(5-chloro-4-methyl-2-oxo-1H-1,6-naphthyridin-3-yl)-N-[(1S)-1-(2,4-difluorophenyl)ethyl]acetamide (38 g, 77.60%). LCMS (ES, m/z): 392 $[M+H]^+$.

N-[(1S)-1-(2,4-Difluorophenyl)ethyl]-2-(5-fluoro-4-methyl-2-oxo-1H-1,6-naphthyridin-3-yl)acetamide. Cesium fluoride (7754.15 mg, 51.05 mmol, 2 equiv) was added to a solution of 2-(5-chloro-4-methyl-2-oxo-1H-1,6-naphthyridin-3-yl)-N-[(1S)-1-(2,4-difluorophenyl)ethyl]acetamide (10 g, 26 mmol, 1.00 equiv) in DMSO (120.00 mL) was added in Ar atmosphere. After stirring for 4 hours at 160° C. under Ar atmosphere, water was added to the mixture, and the precipitated solids were collected by filtration and washed with $H_2O$. The solid was added to ACN (200 mL), and the precipitated solids were collected by filtration. The residue was purified by silica gel column chromatography to afford the crude product. The crude product was slurried with ACN to afford N-[(1S)-1-(2,4-difluorophenyl)ethyl]-2-(5-fluoro-4-methyl-2-oxo-1H-1,6-naphthyridin-3-yl)acetamide (17.23 g, 173.20%). LCMS (ES, m/z): 376 $[M+H]^+$ $^1H$ NMR (400 MHz, DMSO-$d_6$) δ 12.28 (s, $^1H$), 8.49 (d, J=7.6 Hz, $^1H$), 8.04-8.03 (m, $^1H$), 7.49-7.43 (m, $^1H$), 7.20-7.13 (m, $^2H$), 7.08-7.03 (m, $^1H$), 5.10-5.06 (m, $^1H$), 3.63 (d, J=2.4 Hz, $^2H$), 2.41 (d, J=6.0 Hz, $^3H$), 1.35 (d, J=7.2 Hz, $^3H$).

(Compound 382)

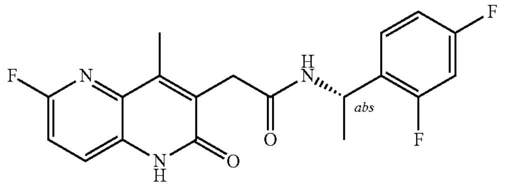

N-[(1S)-1-(2,4-difluorophenyl)ethyl]-2-(6-fluoro-4-methyl-2-oxo-1H-1,5-naphthyridin-3-yl)acetamide 1,4-Di-tert-butyl 2-(1-[3-[(tert-butoxycarbonyl)amino]-6-fluoropyridin-2-yl]-1-hydroxyethyl)butanedioate. LDA (4.96 mL, 9.91 mmol, 3.00 equiv) was added to a stirred solution of 1,4-di-tert-butyl butanedioate(1.52 g, 6.61 mmol, 2.0 equiv) in THF (20 mL) was added at −78° C. under argon atmosphere. The reaction mixture was stirred at −78° C. for 1 h. Tert-butyl N-(2-acetyl-6-fluoropyridin-3-yl) carbamate (840 mg, 3.304 mmol, 1.00 equiv) in THF(20 mL) and $ZnCl_2$ (4.72 mL, 3.304 mmol, 1.00 equiv) was added dropwise at −78° C. under argon atmosphere. The mixture was stirred at −78° C. for 30 min. The reaction was quenched by the addition of saturated $NH_4Cl$ (aq.) (mL) at 0° C. The residue was purified by silica gel column chromatography to afford 1,4-di-tert-butyl 2-(1-[3-[(tert-butoxycarbonyl)amino]-6-fluoropyridin-2-yl]-1-hydroxyethyl) butanedioate (1.2 g, 74.96%). LCMS (ES, m/z): 485.0 $[M+H]^+$.

(6-Fluoro-4-methyl-2-oxo-1H-1,5-naphthyridin-3-yl) acetic acid. A solution of 1,4-di-tert-butyl 2-(1-[3-[(tert-butoxycarbonyl)amino]pyridin-2-yl]-1-hydroxyethyl) butanedioate (800.00 mg, 1.715 mmol, 1.00 equiv) in HCl (6M) (15.00 mL) was stirred at 80° C. for 4 h. 80% The resulting mixture was concentrated under reduced pressure. The residue was purified by trituration with acetonitrile (5 mL) to afford (6-fluoro-4-methyl-2-oxo-1H-1,5-naphthyridin-3-yl) acetic acid (260 mg, 64.20%) LCMS (ES, m/z): 488.0 $[M+H]^+$.

N-[(1S)-1-(2,4-difluorophenyl)ethyl]-2-(6-fluoro-4-methyl-2-oxo-1H-1,5-naphthyridin-3-yl)acetamide. DMAP (12.41 mg, 0.10 mmol, 0.2 equiv) and (1S)-1-(2,4-difluorophenyl) ethanamine (87.83 mg, 0.56 mmol, 1.1 equiv) was added to a stirred mixture of (6-fluoro-4-methyl-2-oxo-1H-1,5-naphthyridin-3-yl)acetic acid (120.00 mg, 0.51 mmol, 1.00 equiv) and EDC.HCl (107.13 mg, 0.56 mmol, 1.1 equiv) in DMF (2 mL) at room temperature under air atmosphere. The mixture was stirred at room temperature under argon atmosphere overnight. The reaction was quenched with water/ice (50) at 0° C. The precipitated solids were collected by filtration and washed with MeCN to give N-[(1S)-1-(2,4-difluorophenyl)ethyl]-2-(6-fluoro-4-methyl-2-oxo-1H-1,5-naphthyridin-3-yl)acetamide (137 mg, 70.19%). LCMS (ES, m/z): 375.1 $[M+H]^+$.

$^1H$ NMR (300 MHz, DMSO-$d_6$): 11.98 (s, $^1H$), 8.52 (d, J=7.5, $^1H$), 7.85-7.80 (m, $^1H$), 7.52-7.49 (m, $^1H$), 7.47-7.44

(m, 1H), 7.34-7.21 (m, 1H), 7.20-7.02 (m, 1H), 5.12-5.05 (m, 1H), 3.63 (s, 2H), 2.37 (s, 3H), 1.40 (s, 3H)

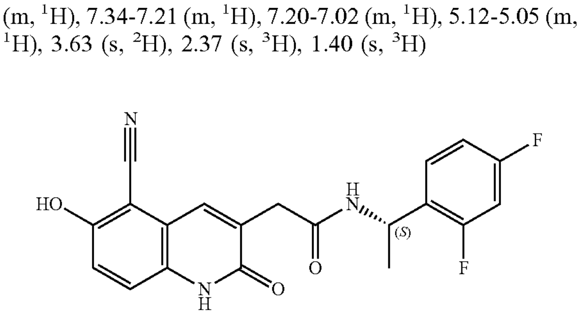

(S)-2-(5-cyano-6-methoxy-2-oxo-1,2-dihydroquinolin-3-yl)-N-(1-(2,4-difluorophenyl)ethyl)acetamide 3-((6-Amino-2-chloro-3-methoxyphenyl)(hydroxy) methyl)-1-((S)-1-(2,4-difluorophenyl)ethyl) pyrrolidine-2,5-dione. LDA (4.00 mL, 2M in THF, 8.08 mmol, 3.00 equiv.) was added to a stirred solution of (S)-1-(1-(2,4-difluorophenyl)ethyl)pyrrolidine-2,5-dione (1.30 g, 5.39 mmol, 2.00 equiv.) in dry THF (15 mL) was added at −78° C. under argon atmosphere. The resulting mixture was stirred for 40 min at −78° C. under argon atmosphere. To the above mixture was added 6-amino-2-chloro-3-methoxybenzaldehyde (500 mg, 2.7 mmol, 1.00 equiv.) and $ZnCl_2$ (3.85 mL, 0.7 M in THF, 2.69 mmol, 1.00 equiv.) at −78° C. The resulting mixture was stirred for additional 1 h at −78° C. The reaction was quenched by the addition of saturated $NH_4Cl$ (aq.) (100 mL) at −30° C. The resulting mixture was extracted with EtOAc (. The combined organic layers were washed with brine and dried over anhydrous $Na_2SO_4$. The filtrate was concentrated under reduced pressure and the residue was purified by silica gel column chromatography to afford 3-[(6-amino-2-chloro-3-methoxyphenyl) (hydroxy) methyl]-1-[(1S)-1-(2,4-difluorophenyl)ethyl]pyrrolidine-2,5-dione (1.75 g, crude). The crude product was used in the next step directly without further purification. LCMS (ES, m/z): 425 $[M+H]^+$ (S)-2-(5-chloro-6-methoxy-2-oxo-1,2-dihydroquinolin-3-yl)-N-(1-(2,4-difluorophenyl)ethyl) acetamide. KOH (1.16 g, 20.59 mmol, 5.00 equiv.) was added to a stirred solution of 3-[(6-amino-2-chloro-3-methoxyphenyl)(hydroxy) methyl]-1-[(1S)-1-(2,4-difluorophenyl)ethyl]pyrrolidine-2,5-dione (1.75 g, 4.12 mmol, 1.00 equiv.) in EtOH (20 mL) was added at room temperature under nitrogen atmosphere. The final reaction mixture was irradiated with microwave radiation for 45 min at 80° C. The mixture/residue was neutralized to pH 7 with 4M HCl (aq.). The resulting mixture was extracted with DCM. The combined organic layers were washed with brine and dried over anhydrous $Na_2SO_4$. The filtrate was concentrated under reduced pressure and the residue was purified by silica gel column chromatography to afford (S)-2-(5-chloro-6-methoxy-2-oxo-1,2-dihydroquinolin-3-yl)-N-(1-(2,4-difluorophenyl) ethyl)acetamide (755 mg, 45.05%). LCMS (ES, m/z): 407 $[M+H]^+$ (S)-2-(5-Cyano-6-methoxy-2-oxo-1,2-dihydroquinolin-3-yl)-N-(1-(2,4-difluorophenyl)ethyl) acetamide (Compound 81). A mixture of 2-(5-chloro-6-methoxy-2-oxo-1,2-dihydroquinolin-3-yl)-N—((S)-1-(2,4-difluorophenyl) ethyl)propanamide (100 mg, 0.2 mmol, 1.00 equiv), $Zn(CN)_2$ (72.16 mg, 0.615 mmol, 2.50 equiv), zinc powder (2.41 mg, 0.04 mmol, 0.15 equiv) and $Pd(dppf)Cl_2$ (26.98 mg, 0.04 mmol, 0.15 equiv) in DMAc (12 mL) was stirred for 30 min at 200° C. under $N_2$ atmosphere. The precipitated solids were collected by filtration and washed with ethyl acetate. The resulting mixture was concentrated under reduced pressure and the crude product (60 mg) was purified by Prep-HPLC with the following conditions (Column: XBridge Prep C18 OBD Column, 19*150 mm, 5 μm; Mobile Phase A: Water(0.1% FA), Mobile Phase B: ACN; Flow rate: 25 mL/min; Gradient: 25% B to 43% B in 7 min, 43% B; Wave Length: 254/220 nm; RT1(min): 6.32) to afford (S)-2-(5-cyano-6-methoxy-2-oxo-1,2-dihydroquinolin-3-yl)-N-(1-(2,4-difluorophenyl)ethyl)acetamide (20 mg, 20.47%). LCMS (ES, m/z): 398 $[M+H]^+$ (S)-2-(5-Cyano-6-hydroxy-2-oxo-1,2-dihydroquinolin-3-yl)-N-(1-(2,4-difluorophenyl)ethyl) acetamide. To a stirred solution/mixture of (S)-2-(5-cyano-6-methoxy-2-oxo-1,2-dihydroquinolin-3-yl)-N-(1-(2,4-difluorophenyl)ethyl)acetamide (150 mg, 0.38 mmol, 1 equiv) in DCM (2 mL) was added $BBr_3$ (283.69 mg, 1.13 mmol, 3.0 equiv) dropwise/in portions at 0° C. The resulting mixture was stirred for overnight at room temperature. The reaction was quenched with water at 0° C. The resulting mixture was concentrated under reduced pressure and the resulting mixture was diluted with MeCN. The precipitated solids were collected by filtration and washed with MeCN. The crude product (60 mg) was purified by Prep-HPLC with the following conditions (Column: XBridge Prep C18 OBD Column, 19*150 mm, 5 μm; Mobile Phase A: Water (0.1% FA), Mobile Phase B: ACN; Flow rate: 25 mL/min; Gradient: 25% B to 43% B in 7 min, 43% B; Wave Length: 254/220 nm; RT1(min): 6.32) to afford (S)-2-(5-cyano-6-hydroxy-2-oxo-1,2-dihydroquinolin-3-yl)-N-(1-(2,4-difluorophenyl)ethyl)acetamide (20.0 mg, 13.82%). LCMS (ES, m/z): 384 $[M+H]^+$ $^1H$ NMR (300 MHz, DMSO-$d_6$) δ 11.99 (s, 1H), 8.61 (d, J=7.7 Hz, 1H), 7.76 (s, 1H), 7.46 (dd, J=19.7, 8.1 Hz, 2H), 7.18 (t, J=9.6 Hz, 2H), 7.03 (t, J=9.6 Hz, 1H), 5.09 (t, J=7.2 Hz, 1H), 3.50 (s, 2H), 2.54 (s, 1H), 1.35 (d, J=7.0 Hz, 3H). $^{19}F$ NMR (376 MHz, DMSO-$d_6$) δ −112.81 (1F), −115.42 (1F).

(Compound 84)

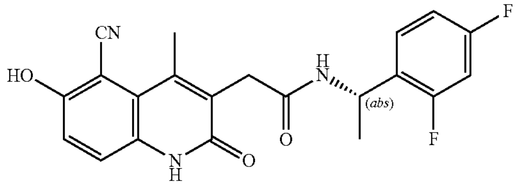

2-(5-Cyano-6-hydroxy-4-methyl-2-oxo-1H-quinolin-3-yl)-N-[(1S)-1-(2,4-difluorophenyl)ethyl]acetamide 1-(2-Chloro-3-fluoro-6-nitrophenyl) ethanone. To a stirred mixture of 1-(2-chloro-3-fluorophenyl) ethanone (20 g, 116 mmol, 1 equiv) in DCM (200 mL) were added $HNO_3$ fuming (80 mL, 1784 mmol, 15.39 equiv) dropwise at 0° C. under argon atmosphere. The resulting mixture was diluted with water. The aqueous layer was extracted with $CH_2Cl_2$. The resulting mixture was concentrated under reduced pressure and the residue was purified by silica gel column chromatography to afford 1-(2-chloro-3-fluoro-6-nitrophenyl) ethanone (9 g, 35.69%). LCMS: (ESI, m/z): $[M+H]^+$=218.

1-(2-chloro-3-methoxy-6-nitrophenyl)ethanone. LiHMDS (69.12 mL, 68.940 mmol, 3 equiv) was added dropwise to a stirred mixture of MeOH (10.00 mL, 247.03 mmol, 10.75 equiv) in THF (50 mL) at 0° C. under air atmosphere. To the above mixture, 1-(2-chloro-3-fluoro-6-nitrophenyl)ethanone (5 g, 23 mmol, 1 equiv) was added in portions over 30 min at 0° C. The resulting mixture was stirred for additional 2 h at room temperature. The reaction was quenched with saturated $NH_4Cl$ (aq.)(50 mL) at 0° C. The aqueous layer was extracted with EtOAc. The resulting mixture was concentrated under reduced pressure and the residue was purified by silica gel column chromatography to afford 1-(2-chloro-3-methoxy-6-nitrophenyl)ethanone (4 g, 75.81%).

LCMS: (ESI, m/z): $[M+H]^+$=230.

1-(6-Amino-2-chloro-3-methoxyphenyl)ethanone. Fe (4.86 g, 87.100 mmol, 5 equiv) was added in portions to a stirred mixture of 1-(2-chloro-3-methoxy-6-nitrophenyl) ethanone (4 g, 17 mmol, 1 equiv) and $NH_4Cl$ (9.32 g, 174.20 mmol, 10 equiv) in MeOH (50 mL) and $H_2O$ (10 mL) at 80° C. under argon atmosphere. The resulting mixture was filtered, the filter cake was washed with MeOH. The filtrate was concentrated under reduced pressure and the residue was purified by silica gel column chromatography to afford 1-(6-amino-2-chloro-3-methoxyphenyl) ethanone (2.4 g, 69.01%). LCMS: (ESI, m/z): $[M+H]^+$=200.

tert-butyl 2-(5-chloro-4-hydroxy-6-methoxy-4-methyl-2-oxo-1,3-dihydroquinolin-3-yl) acetate. A solution of 1,4-di-tert-butyl butanedioate (5.54 g, 24.04 mmol, 2 equiv) in THF (40 mL) was treated with LDA (2 M in THF) (18.09 mL, 36.07 mmol, 3 equiv) for 30 min at −78° C. under nitrogen atmosphere followed by the addition of 1-(6-amino-2-chloro-3-methoxyphenyl) ethanone (2.4 g, 12.02 mmol, 1 equiv) and $ZnCl_2$ (1 M in THF) (12.06 mL, 12.02 mmol, 1 equiv) dropwise at −78° C. The resulting mixture was stirred for 1 h at −78° C. under argon atmosphere. The reaction was quenched by the addition of saturated $NH_4Cl$ (aq.) (20 mL) at 0° C. The aqueous layer was extracted with EtOAc. The resulting mixture was concentrated under reduced pressure and the residue was purified by silica gel column chromatography to afford tert-butyl 2-(5-chloro-4-hydroxy-6-methoxy-4-methyl-2-oxo-1,3-dihydroquinolin-3-yl)acetate (2.3 g, 53.77%). LCMS: (ESI, m/z): $[M+H]^+$=356.

(5-Chloro-6-methoxy-4-methyl-2-oxo-1H-quinolin-3-yl) acetic acid. A mixture of tert-butyl 2-(5-chloro-4-hydroxy-6-methoxy-4-methyl-2-oxo-1,3-dihydroquinolin-3-yl)acetate (2.3 g, 6.5 mmol, 1 equiv) and t-BuOK (1 M in THF) (6.48 mL, 32.32 mmol, 5 equiv) in EtOH (40 mL) was stirred for overnight at room temperature under argon atmosphere. The resulting mixture was concentrated under reduced pressure and the resulting mixture was diluted with water (20 mL). The precipitated solids were collected by filtration and washed with water resulting in (5-chloro-6-methoxy-4-methyl-2-oxo-1H-quinolin-3-yl)acetic acid (1.5 g, 82.38%). LCMS: (ESI, m/z): $[M+H]^+$=282.

Methyl 2-(5-chloro-6-methoxy-4-methyl-2-oxo-1H-quinolin-3-yl)acetate. A mixture of (5-chloro-6-methoxy-4-methyl-2-oxo-1H-quinolin-3-yl)acetic acid (1.8 g, 6.390 mmol, 1 equiv) and $SOCl_2$ (7.60 g, 63.90 mmol, 10 equiv) in MeOH (30 mL) was stirred for 2 h at 50° C. under argon atmosphere. The resulting mixture was concentrated under reduced pressure resulting in methyl 2-(5-chloro-6-methoxy-4-methyl-2-oxo-1H-quinolin-3-yl)acetate (1.4 g, 74.09%). LCMS: (ESI, m/z): $[M+H]^+$=296.

Methyl 2-(5-cyano-6-methoxy-4-methyl-2-oxo-1H-quinolin-3-yl)acetate. CuI (418.61 mg, 2.20 mmol, 1 equiv) was added in portions to a stirred mixture of methyl 2-(5-chloro-6-methoxy-4-methyl-2-oxo-1H-quinolin-3-yl)acetate (650 mg, 2 mmol, 1 equiv) and CuCN (393.73 mg, 4.40 mmol, 2 equiv) in DMSO (10 mL) at room temperature under argon atmosphere. The resulting mixture was stirred for overnight at 150° C. under argon atmosphere. The resulting mixture was diluted with water (50 mL). The aqueous layer was extracted with EtOAc. The residue was purified by silica gel column chromatography to afford methyl 2-(5-cyano-6-methoxy-4-methyl-2-oxo-1H-quinolin-3-yl) acetate (480 mg, 76.28%). LCMS: (ESI, m/z): $[M+H]^+$=287.

(5-Cyano-6-methoxy-4-methyl-2-oxo-1H-quinolin-3-yl) acetic acid. A mixture of methyl 2-(5-cyano-6-methoxy-4-methyl-2-oxo-1H-quinolin-3-yl)acetate (240 mg, 0.8 mmol, 1 equiv) and LiOH (60.23 mg, 2.51 mmol, 3 equiv) in THF (2 mL) and $H_2O$ (2 mL) was stirred for 2 h at room temperature under argon atmosphere. The resulting mixture was concentrated under reduced pressure and the resulting mixture was diluted with water (10 mL). The precipitated solids were collected by filtration and washed with water resulting in (5-cyano-6-methoxy-4-methyl-2-oxo-1H-quinolin-3-yl)acetic acid (200 mg, 87.63%). LCMS: (ESI, m/z): $[M+H]^+$=273.

2-(5-Cyano-6-methoxy-4-methyl-2-oxo-1H-quinolin-3-yl)-N-[(1S)-1-(2,4-difluorophenyl)ethyl]acetamide. HOBT (107.20 mg, 0.79 mmol, 1.2 equiv) and DIEA (256.35 mg, 1.98 mmol, 3 equiv) were added in portions To a stirred mixture of (5-cyano-6-methoxy-4-methyl-2-oxo-1H-quinolin-3-yl) acetic acid (180 mg, 0.6 mmol, 1 equiv), (1S)-1-(2,4-difluorophenyl)ethanamine (124.69 mg, 0.79 mmol, 1.2 equiv) and EDCI (152.09 mg, 0.79 mmol, 1.2 equiv) in DMF (5 mL) at room temperature under argon atmosphere. The resulting mixture was stirred for 2 h at room temperature under argon atmosphere. The residue was purified by reverse flash chromatography with the following conditions: column, C18; mobile phase, MeCN in water, 10% to 50% gradient in 60 min; detector, UV 254 nm resulting in 2-(5-cyano-6-methoxy-4-methyl-2-oxo-1H-quinolin-3-yl)-N-[(1S)-1-(2,4-difluorophenyl)ethyl]acetamide (150 mg, 55.15%). LCMS: (ESI, m/z): $[M+H]^+$=412.

2-(5-cyano-6-hydroxy-4-methyl-2-oxo-1H-quinolin-3-yl)-N-[(1S)-1-(2,4-difluorophenyl)ethyl]acetamide. To a solution of 2-(5-cyano-6-methoxy-4-methyl-2-oxo-1H-quinolin-3-yl)-N-[(1S)-1-(2,4-difluorophenyl)ethyl]acetamide (40 mg, 0.1 mmol, 1 equiv) in DCM (2 mL) was added boron tribromide (121.79 mg, 0.48 mmol, 5 equiv) at 0° C. The mixture was stirred for 15 min at 0° C. Then the mixture was stirred for 16 hours at 50° C. Then 0.1 mL water was added to quench the reaction. The resulting mixture was concentrated under reduced pressure and the residue was purified by reverse flash chromatography with the following conditions: (column, C18 silica gel; mobile phase, MeCN in water, 0.1% HCOOH, 0% to 100% gradient in 40 min; detector, UV 254 nm) to afford 2-(5-cyano-6-hydroxy-4-methyl-2-oxo-1H-quinolin-3-yl)-N-[(1S)-1-(2,4-difluorophenyl)ethyl]acetamide (15 mg, 37.54%). LCMS: (ESI, m/z): $[M+H]^+$=398. $^1H$ NMR (400 MHz, DMSO-d6) δ 11.89 (s, $^1H$), 11.39-11.38 (in, $^1H$), 8.49 (d, J=7.6 Hz, $^1H$), 7.49-7.43 (m, $^2H$), 7.22-7.14 (m, $^2H$), 7.07-7.02 (in, $^1H$), 5.11-5.03 (m, $^1H$), 3.66 (s, $^2H$), 2.60 (s, $^3H$), 1.35 (d, J=6.8 Hz, $^3H$).

(Compound 78 and 77)

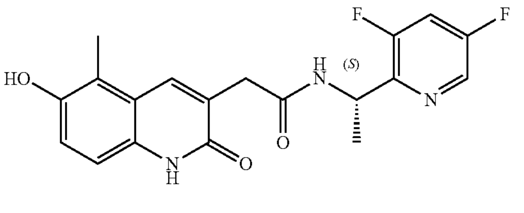

-continued

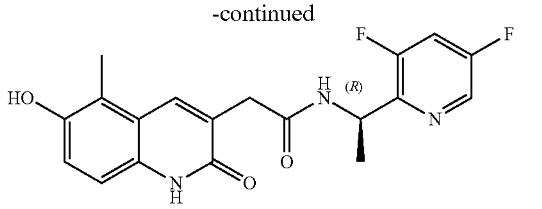

(S)-N-(1-(3,5-difluoropyridin-2-yl)ethyl)-2-(6-hydroxy-5-methyl-2-oxo-1,2-dihydroquin-3-yl)acetamide and (R)-N-(1-(3,5-difluoropyridin-2-yl)ethyl)-2-(6-hydoxy-5-methyl-2-oxo-1,2-dihydroquinolin-3-yl)acetamide 3-Fluoro-2-methyl-6-nitrobenzoic acid. To a stirred solution of 3-fluoro-2-methylbenzoic acid (10.00 g, 64.88 mmol, 1.00 equiv) in con. $H_2SO_4$ (80 mL), then concentrated $HNO_3$ (8 mL) was added dropwise at 0° C. under nitrogen atmosphere. The resulting mixture was stirred for 3 h at room temperature under argon atmosphere. The reaction was quenched with ice water (200 mL). The resulting mixture was extracted with EtOAc. The combined organic layers, dried over anhydrous $Na_2SO_4$. The filtrate was concentrated under reduced pressure and the resulted in 3-fluoro-2-methyl-6-nitrobenzoic acid (8.00 g, 61.92%). LCMS (ES, m/z): 198 $[M-H]^+$ 3-Methoxy-2-methyl-6-nitrobenzoic acid. To a stirred mixture of 3-fluoro-2-methyl-6-nitrobenzoic acid (1.00 g, 5.02 mmol, 1.00 equiv) and NaOMe (0.81 g, 15.06 mmol, 3.00 equiv) in MeOH (15 mL) was stirred for overnight at 70° C. under nitrogen atmosphere. The mixture was allowed to cool to room temperature. The residue was acidified to pH 2 with 6M HCl (aq.). The resulting mixture was extracted with EtOAc and the combined organic layers dried over anhydrous $Na_2SO_4$. The filtrate was concentrated under reduced pressure resulting in 3-methoxy-2-methyl-6-nitrobenzoic acid (3.90 g, 94.30%). LCMS (ES, m/z): 210 $[M-H]^+$ (3-Methoxy-2-methyl-6-nitrophenyl)methanol. Into a 250 mL round-bottom flask were added 3-methoxy-2-methyl-6-nitrobenzoic acid (3.90 g, 18.47 mmol, 1.00 equiv) and $BH_3$-$Me_2S$ (18.4 mL, 184.68 mmol, 10.00 equiv) in THF at 0° C. The reaction was quenched with sat. $NH_4Cl$ (aq.) at 0° C. The resulting mixture was diluted with water (80 mL). The resulting mixture was stirred for 3 h at 60° C. under nitrogen atmosphere. The mixture cooled to room temperature. The resulting mixture was extracted with EtOAc. The combined organic layers were dried over anhydrous $Na_2SO_4$. The filtrate was concentrated under reduced pressure and the residue was purified by silica gel column chromatography to afford (3-methoxy-2-methyl-6-nitrophenyl)methanol (2.90 g, 79.63%). LCMS (ES, m/z): 198 $[M+H]^+$ (6-Amino-3-methoxy-2-methylphenyl)methanol. A mixture of (3-methoxy-2-methyl-6-nitrophenyl) methanol (1.20 g, 6.09 mmol, 1.00 equiv) and 10% Pd/C (0.19 g) in EtOAc (15 mL) was stirred for 1 h at room temperature under hydrogen atmosphere. The resulting mixture was filtered, the filter cake was washed with EtOAc. The filtrate was concentrated under reduced pressure and the residue was purified by silica gel column chromatography to afford (6-amino-3-methoxy-2-methylphenyl)methanol (0.99 g, 97.29%). LCMS (ES, m/z): 168 $[M+H]^+$ 6-Amino-3-methoxy-2-methylbenzaldehyde. A mixture of (3-methoxy-2-methyl-6-nitrophenyl)methanol (800 mg, 4 mmol, 1.00 equiv) and $MnO_2$ (2.47 g, wt: 58%, 28.40 mmol, 7.00 equiv) in DCM (10 mL) was stirred for 1 h at room temperature under air atmosphere. The resulting mixture was filtered, the filter cake was washed with DCM. The filtrate was concentrated under reduced pressure and the residue was purified by silica gel column chromatography to afford 6-amino-3-methoxy-2-methylbenzaldehyde (750 mg, 111.91%). LCMS (ES, m/z): 166 $[M+H]^+$ 1,4-Di-tert-butyl 2-[(6-amino-3-methoxy-2-methylphenyl)(hydroxy)methyl]butanedioate. In a 50-mL round bottom flask, to a solution of 1,4-di-tert-butyl butanedioate (2.10 g, 9.08 mmol, 3.00 equiv) in THF (10 mL) was added dropwise LDA (2 M in THF, 3.0 mL, 6.1 mmol, 2.00 equiv) at −78° C. under $N_2$ atmosphere. The reaction mixture was stirred at −78° C. for 30 mins. Then a solution of 6-amino-3-methoxy-2-methylbenzaldehyde (500 mg, 3 mmol, 1.00 equiv) in 10 mL THF was added dropwise and the mixture was stirred for another 60 mins. The reaction was quenched with saturated $NH_4Cl$ at −78° C., and then the mixture was extracted with EtOAc. The combined organic extracts were washed with brine and dried over anhydrous $Na_2SO_4$, and concentrated under vacuum to the crude product (1.20 g, 70% purity) which was directly used for the next step without further purification. LCMS (ES, m/z): 396 $[M+H]^+$ (6-Methoxy-5-methyl-2-oxo-1H-quinolin-3-yl)acetic acid. A mixture of 1,4-di-tert-butyl 2-[(6-amino-3-methoxy-2-methylphenyl)(hydroxy)methyl]butanedioate (1.20 g, 3.03 mmol, 1.00 equiv) and KOH (851.2 mg, 15.2 mmol, 5.00 equiv) in EtOH (15 mL) was stirred for overnight at 80° C. under $N_2$ atmosphere. The mixture cooled to room temperature. The residue was acidified to pH 2 with 6M HCl (aq.), extracted with EtOAc, dried over anhydrous $Na_2SO_4$, and concentrated under vacuum to the crude product. The crude product (1.4 g) was purified by Prep-HPLC with the following conditions (Column: XBridge Shield RP18 OBD Column, 19*150 mm, 5 μm; Mobile Phase A: Water(0.1% FA), Mobile Phase B: ACN; Flow rate: 25 mL/min; Gradient: 0% B to 100% B in 10 min, 43% B; Wave Length: 254/220 nm; RT1(min): 7.98) to afford (6-methoxy-5-methyl-2-oxo-1H-quinolin-3-yl)acetic acid (400 mg, 53.32%). LCMS (ES, m/z): 248 $[M+H]^+$ (S)—N-(1-(3,5-difluoropyridin-2-yl)ethyl)-2-(6-methoxy-5-methyl-2-oxo-1,2-dihydroquinolin-3-yl)acetamide. To a stirred mixture of (6-methoxy-5-methyl-2-oxo-1H-quinolin-3-yl)acetic acid (100 mg, 0.4 mmol, 1.00 equiv) and (S)-1-(3,5-difluoropyridin-2-yl)ethan-1-amine hydrochloride (76.76 mg, 0.48 mmol, 1.20 equiv) in DMF (1 mL) were added DIEA (313.64 mg, 2.424 mmol, 6.00 equiv), and HATU (230.68 mg, 0.606 mmol, 1.50 equiv) in portions at 0° C. The resulting mixture was stirred for 1 h at room temperature under argon atmosphere. The reaction was quenched with water. The resulting mixture was extracted with EtOAc. The combined organic layers were washed with brine and dried over anhydrous $Na_2SO_4$. The filtrate was concentrated under reduced pressure and the residue was purified by reverse flash chromatography with the following conditions: (column, C18 gel; mobile phase, MeCN in water (with 0.05% FA), 0% to 100% gradient in 10 min; detector, UV 254 nm) resulting in (S)—N-(1-(3,5-difluoropyridin-2-yl)ethyl)-2-(6-methoxy-5-methyl-2-oxo-1,2-dihydroquinolin-3-yl)acetamide (65 mg, 41.49%). LCMS (ES, m/z): 388 $[M+H]^+$ (S)—N-(1-(3,5-Difluoropyridin-2-yl)ethyl)-2-(6-hydroxy-5-methyl-2-oxo-1,2-dihydroquinolin-3-yl) acetamide. $BBr_3$ (1.8 mL, 1 M in DCM solvent, 1.8 mmol, 10.00 equiv) was added dropwise to a solution of (S)—N-(1-(3,5-difluoropyridin-2-yl)ethyl)-2-(6-methoxy-5-methyl-2-oxo-1,2-dihydroquinolin-3-yl) acetamide (70 mg, 0.2 mmol, 1.00 equiv) in DCM (1 mL) and at −10° C. The mixture was stirred for 2 h at room temperature under $N_2$ atmosphere. The reaction was quenched with MeOH (5 mL) at 0° C. The resulting mixture was concentrated under reduced pressure to the crude product. It was purified by trituration with MeCN at 60° C. resulting in (S)—N-(1-(3, 5-difluoropyridin-2-yl)ethyl)-2-(6-hydroxy-5-methyl-2-oxo-1,2-dihydroquinolin-3-yl)acetamide (40 mg, 59.29%). LCMS (ES, m/z): 374 $[M+H]^+$ $^1H$ NMR (300 MHz, DMSO-$d_6$) δ 11.59 (s, $^1H$), 9.20 (s, $^1H$), 8.56 (d, J=7.6 Hz, $^1H$), 8.48 (d, J=2.4 Hz, $^1H$), 7.91 (dd, J=10.2 Hz, 2.4 Hz, $^1H$), 7.83 (s, $^1H$), 7.01 (s, $^2H$), 5.24 (q, J=7.1 Hz, $^1H$), 3.51-3.37 (m, $^2H$), 2.25 (s, $^3H$), 1.38 (d, J=6.9 Hz, $^3H$). $^{19}F$ NMR (282 MHz, DMSO-$d_6$) δ −122.68 ($^1F$), −126.05 ($^1F$).

(R)—N-(1-(3,5-difluoropyridin-2-yl)ethyl)-2-(6-methoxy-5-methyl-2-oxo-1,2-dihydroquinolin-3-yl) acetamide. DIEA (313.64 mg, 2.42 mmol, 6.00 equiv) and HATU (230.68 mg, 0.61 mmol, 1.5 equiv) were added in portions To a stirred mixture of (6-methoxy-5-methyl-2-oxo-1H-quinolin-3-yl) acetic acid (100 mg, 0.4 mmol, 1.00 equiv) and (R)-1-(3,5-difluoropyridin-2-yl)ethan-1-amine hydrochloride (76.76 mg, 0.48 mmol, 1.20 equiv) in DMF (1 mL) at 0° C. The resulting mixture was stirred for 1 h at room temperature under argon atmosphere. The reaction was quenched with water (10 mL). The resulting mixture was extracted with EtOAc. The combined organic layers were washed with brine and dried over anhydrous $Na_2SO_4$. The filtrate was concentrated under reduced pressure and the residue was purified by reverse flash chromatography with the following conditions: (column, C18 gel; mobile phase, MeCN in water (with 0.05% FA), 0% to 100% gradient in 10 min; detector, UV 254 nm) resulting in (R)—N-(1-(3, 5-difluoropyridin-2-yl)ethyl)-2-(6-methoxy-5-methyl-2-oxo-1,2-dihydroquinolin-3-yl)acetamide (65 mg, 41.49%). LCMS (ES, m/z): 388 $[M+H]^+$ (R)—N-(1-(3,5-Difluoropyridin-2-yl)ethyl)-2-(6-hydroxy-5-methyl-2-oxo-1,2-dihydroquinolin-3-yl) acetamide. $BBr_3$ (3.9 mL, 1 M in DCM solvent, 3.9 mmol, 10.00 equiv) was added dropwise to a mixture of (R)—N-(1-(3, 5-difluoropyridin-2-yl) ethyl)-2-(6-methoxy-5-methyl-2-oxo-1,2-dihydroquinolin-3-yl) acetamide (150 mg, 0.39 mmol, 1.00 equiv) in DCM (1.5 mL) and at −10° C. The mixture was stirred for 2 h at room temperature under $N_2$ atmosphere. The reaction was quenched with MeOH at 0° C. The resulting mixture was concentrated under reduced pressure and the crude product (100 mg) was purified by Prep-HPLC with the following conditions (Column: Xselect CSH F-Phenyl OBD column, 19*250 mm, 5 μm; Mobile Phase A: Water(0.1% FA), Mobile Phase B: MeOH-Preparative; Flow rate: 25 mL/min; Gradient: 23% B to 80% B in 12 min, 80% B; Wave Length: 254/220 nm; RT1(min): 9.83) to afford (R)—N-(1-(3,5-difluoropyridin-2-yl)ethyl)-2-(6-hydroxy-5-methyl-2-oxo-1,2-dihydroquinolin-3-yl)acetamide (23.00 mg, 15.91%). LCMS (ES, m/z): 374 $[M+H]^+$ $^1H$ NMR (300 MHz, DMSO-$d_6$) δ 11.59 (s, $^1H$), 9.19 (s, $^1H$), 8.56 (d, J=7.0 Hz, $^1H$), 8.48 (d, J=2.5 Hz, $^1H$), 7.91 (s, $^1H$), 7.83 (s, $^1H$), 7.01 (s, $^2H$), 5.30-5.20 (m, $^1H$), 3.41 (d, J=8.7 Hz, $^2H$), 2.25 (s, $^3H$), 1.38 (d, J=6.9 Hz, $^4H$). $^{19}F$ NMR (282 MHz, DMSO-$d_6$) δ −122.68 ($^1F$), −126.05 ($^1F$).

(Compound 1152 and 1151)

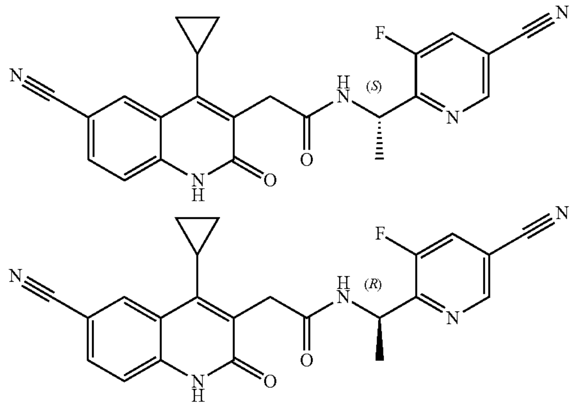

(S)-N-(1-(5-cyano-3-fluoropyridin-2-yl)ethyl)-2-(6-cyano-4-cyclopropyl-2-oxo-1,2-dihydroquinolin-3-yl)acetamide and (R)-N-(1-(5-cyano-3-fluoropyridin-2-yl)ethyl)-2-(6-cyano-4-cyclopropyl-2-oxo-1,2-dihydroquinolin-3-yl)acetamide Methyl 5-bromo-2-(4-ethoxy-4-oxobutanamido) benzoate. To a stirred solution of methyl 2-amino-5-bromobenzoate (23.00 g, 99.97 mmol, 1.00 equiv) in DCM (250 mL) was added DIEA (25.84 g, 199.94 mmol, 2.00 equiv), DMAP (1.22 g, 9.97 mmol, 0.10 equiv), ethyl 4-chloro-4-oxobutanoate (16.45 g, 99.97 mmol, 1.00 equiv). The mixture was stirred at room temperature overnight. The resulting mixture was diluted with water. The organic layer was separated. The aqueous layer was extracted with DCM. The combined organic layers were washed with brine, dried over anhydrous $Na_2SO_4$. The filtrate was concentrated under reduced pressure. The residue was purified by silica gel column chromatography to afford methyl 5-bromo-2-(4-ethoxy-4-oxobutanamido)benzoate (15.44 g, 43.12%). LCMS (ES, m/z): 358 [M+H]+

Ethyl 7-bromo-2,5-dioxo-2,3,4,5-tetrahydro-1H-benzo[b]azepine-4-carboxylate. t-BuOK (9.67 g, 86.20 mmol, 2.00 equiv) was added to a stirred solution of methyl 5-bromo-2-(4-ethoxy-4-oxobutanamido)benzoate (15.44 g, 43.10 mmol, 1.00 equiv) in THF (150 mL). The mixture was stirred at room temperature overnight. The resulting mixture was quenched with water. The aqueous layer was extracted with EtOAc. The combined organic layers were washed with brine, dried over anhydrous $Na_2SO_4$. The filtrate was concentrated under reduced pressure and the residue was purified by silica gel column chromatography to afford ethyl 7-bromo-2,5-dioxo-2,3,4,5-tetrahydro-1H-benzo[b]azepine-4-carboxylate (6.34 g, 45.16%). LCMS (ES, m/z): 326 [M+H]+

2-(6-Bromo-4-hydroxy-2-oxo-1,2-dihydroquinolin-3-yl) acetic acid. KOH (4.36 g, 77.72 mmol, 4.00 equiv) was added to a stirred solution of ethyl 7-bromo-2,5-dioxo-2,3,4,5-tetrahydro-1H-benzo[b]azepine-4-carboxylate (6.34 g, 19.43 mmol, 1.00 equiv) in EtOH (100 mL) was added. The mixture was stirred at 80° C. overnight. The mixture was acidified to pH 6 with 4M HCl (aq.). The solid was filtrated and washed with MeCN to get 2-(6-bromo-4-hydroxy-2-oxo-1, 2-dihydroquinolin-3-yl) acetic acid (5.19 g, 83.60%). LCMS (ES, m/z): 298[M+H]+

Methyl 2-(6-bromo-4-hydroxy-2-oxo-1,2-dihydroquinolin-3-yl)acetate. To a stirred solution of 2-(6-bromo-4-hydroxy-2-oxo-1,2-dihydroquinolin-3-yl) acetic acid (5.19 g, 17.41 mmol, 1.00 equiv) in MeOH (50 mL) was added thionyl chloride (6.21 g, 52.23 mmol, 3.00 equiv) dropwise at 0° C. The mixture was stirred at room temperature for 2 h. The reaction was quenched by the addition of saturated $NaHCO_3$ (aq.). The mixture was extracted with EtOAc. The combined organic layers were washed with brine and dried over anhydrous $Na_2SO_4$. The filtrate was concentrated under reduced pressure and the residue was purified by silica gel column chromatography to afford methyl 2-(6-bromo-4-hydroxy-2-oxo-1,2-dihydroquinolin-3-yl)acetate (4.08 g, 75.15%). LCMS (ES, m/z): 312 [M+H]+

Methyl 2-(6-bromo-2-oxo-4-(((trifluoromethyl)sulfonyl)oxy)-1,2-dihydroquinolin-3-yl) acetate. t-BuOK (7.00 g, 19.60 mmol, 1.50 equiv) was added to a solution of methyl 2-(6-bromo-4-hydroxy-2-oxo-1,2-dihydroquinolin-3-yl) acetate (4.08 g, 13.07 mmol, 1.00 equiv) in DMF (50 mL) was added at 0° C. under argon atmosphere. The mixture was stirred for 15 min at 0° C. under argon atmosphere. 1,1,1-trifluoro-N-phenyl-N-((trifluoromethyl)sulfonyl) methanesulfonamide (7.00 g, 19.60 mmol, 1.50 equiv) dissolved in DMF(50 mL) was added to the mixture at 0° C. and the mixture was allowed to warm to room temperature and stirred for 30 min. The reaction was quenched by the addition of saturated $NH_4Cl$ (aq.) at 0° C. The resulting mixture was extracted with EtOAc. The combined organic layers were washed with brine and dried over anhydrous $Na_2SO_4$. The filtrate was concentrated under reduced pressure and the residue was purified by silica gel column chromatography to afford methyl 2-(6-bromo-2-oxo-4-(((trifluoromethyl)sulfonyl)oxy)-1,2-dihydroquinolin-3-yl)acetate (4.53 g, 78.17%). LCMS (ES, m/z): 444 [M+H]+

Methyl 2-(6-bromo-4-cyclopropyl-2-oxo-1,2-dihydroquinolin-3-yl)acetate. $K_2CO_3$ (4.23 g, 30.60 mmol, 3.00 equiv) and $Pd(dppf)Cl_2$ (1.52 g, 2.04 mmol, 0.20 equiv) were added to a stirred mixture of 2-(6-bromo-2-oxo-4-(((trifluoromethyl)sulfonyl)oxy)-1,2-dihydroquinolin-3-yl) acetate (4.53 g, 10.20 mmol, 1.00 equiv) and cyclopropylboronic acid (5.26 g, 61.20 mmol, 6.00 equiv) in 1,4-dioxane (50 mL) at room temperature under argon atmosphere. The mixture was stirred at 80° C. for 2 h under argon atmosphere. The reaction was quenched by the addition of water. The resulting mixture was extracted with EtOAc. The combined organic layers were washed with brine, dried over anhydrous $Na_2SO_4$. The filtrate was concentrated under reduced pressure and the residue was purified by silica gel column chromatography to afford methyl 2-(6-bromo-4-cyclopropyl-2-oxo-1,2-dihydroquinolin-3-yl)acetate (1.14 g, 33.29%). LCMS (ES, m/z): 336 [M+H]+

Methyl 2-(6-cyano-4-cyclopropyl-2-oxo-1,2-dihydroquinolin-3-yl)acetate. Zinc cyanide (796.11 mg, 6.78 mmol, 2.00 equiv) and $Pd(PPh_3)_4$ (785.78 mg, 0.68 mmol, 0.20 equiv) were added to a stirred solution of methyl 2-(6-bromo-4-cyclopropyl-2-oxo-1, 2-dihydroquinolin-3-yl) acetate (1.14 g, 3.39 mmol, 1.00 equiv) in DMF (15 mL) at room temperature under argon atmosphere. The mixture was stirred at 120° C. overnight. The reaction was quenched by the addition of water. The resulting mixture was extracted with EtOAc. The combined organic layers were washed with brine, dried over anhydrous $Na_2SO_4$. The filtrate was concentrated under reduced pressure and the residue was purified by silica gel column chromatography to afford methyl 2-(6-cyano-4-cyclopropyl-2-oxo-1,2-dihydroquinolin-3-yl) acetate (530 mg, 55.44%). LCMS (ES, m/z): 283 [M+H]+

2-(6-Cyano-4-cyclopropyl-2-oxo-1,2-dihydroquinolin-3-yl)acetic acid. $LiOH{\cdot}H_2O$ (156.93 mg, 3.74 mmol, 2.00 equiv) was added to a stirred solution of methyl 2-(6-cyano-4-cyclopropyl-2-oxo-1,2-dihydroquinolin-3-yl)acetate (530 mg, 2 mmol, 1.00 equiv) in $H_2O$ (5 mL) and THF (5 mL). The mixture was stirred at room temperature under nitrogen atmosphere for 3 h. The resulting mixture was acidified to pH 5 with 1M HCl (aq.) The mixture was filtrated and the solid was washed with MeCN to afford 2-(6-cyano-4-cyclopropyl-2-oxo-1,2-dihydroquinolin-3-yl)acetic acid (276.89 mg, 51.76%). LCMS (ES, m/z): 269 [M+H]+

(S)—N-(1-(5-Cyano-3-fluoropyridin-2-yl)ethyl)-2-(6-cyano-4-cyclopropyl-2-oxo-1,2-dihydroqui nolin-3-yl)acetamide. (S)-6-(1-aminoethyl)-5-fluoronicotinonitrile hydrochloride (30.72 mg, 0.19 mmol, 1.00 equiv), EDCI (49.84 mg, 0.26 mmol, 1.40 equiv), DMAP (9.02 mg, 0.07 mmol, 0.40 equiv) To a stirred solution of 3-(carboxymethyl)-4-cyclopropyl-6-isocyano-1H-quinolin-2-one (50.0 mg, 0.2 mmol, 1.00 equiv) in DMF (2 mL). The mixture was stirred at room temperature overnight. The reaction was quenched by the addition of water and extracted with EtOAc. The combined organic layers were washed with brine and dried over anhydrous $Na_2SO_4$. The filtrate was concentrated under reduced pressure and the residue was dissolved in DMF (1 mL) and purified by reverse flash chromatography with the following conditions: (column, C18 gel; mobile phase, MeCN in water (10 mmol/L $NH_4HCO_3$), 30% to 33% gradient in 5 min; detector, UV 254 nm) to afford (S)—N-(1-(5-cyano-3-fluoropyridin-2-yl)ethyl)-2-(6-cyano-4-cyclopropyl-2-oxo-1,2-dihydroquinolin-3-yl)acetamide(13.7 mg, 17.73%). LCMS (ES, m/z): 416 $[M+H]^+$ $^1H$ NMR (300 MHz, DMSO-$d_6$) δ 12.06 (s, $^1H$), 8.89 (s, $^1H$), 8.59 (d, J=7.2 Hz, $^1H$), 8.49 (d, J=1.8 Hz, $^1H$), 8.37 (dd, J=9.9, 1.7 Hz, $^1H$), 7.84 (dd, J=8.5, 1.8 Hz, $^1H$), 7.38 (d, J=8.5 Hz, $^1H$), 5.23 (t, J=7.0 Hz, $^1H$), 3.72 (s, $^2H$), 1.85 (t, J=7.0 Hz, $^1H$), 1.40 (d, J=7.0 Hz, 3H), 1.14 (p, J=9.4 Hz, $^2H$), 0.55 (d, J=6.0 Hz, $^2H$). $^{19}F$ NMR (282 MHz, DMSO-$d_6$) δ −124.70 ($^1F$).

(R)—N-(1-(5-Cyano-3-fluoropyridin-2-yl)ethyl)-2-(6-cyano-4-cyclopropyl-2-oxo-1,2-dihydroquinolin-3-yl)acetamide (R)-6-(1-aminoethyl)-5-fluoronicotinonitrile hydrochloride (30.72 mg, 0.19 mmol, 1.00 equiv), EDCI (49.84 mg, 0.26 mmol, 1.40 equiv), DMAP (9.02 mg, 0.07 mmol, 0.4 equiv) was added to a stirred solution of 2-(6-cyano-4-cyclopropyl-2-oxo-1,2-dihydroquinolin-3-yl)acetic acid (50.0 mg, 0.19 mmol, 1.00 equiv) in DMF (2 mL)®. The mixture was stirred at room temperature overnight. The reaction was quenched by the addition of water and extracted with EtOAc. The combined organic layers were washed with brine and dried over anhydrous $Na_2SO_4$. The filtrate was concentrated under reduced pressure and the residue was dissolved in DMF(1 mL) and purified by reverse flash chromatography with the following conditions: (column, C18 gel; mobile phase, MeCN in Water (10 mmol/L $NH_4HCO3$), 33% to 36% gradient in 5 min; detector, UV 254 nm) to afford (R)—N-(1-(5-cyano-3-fluoropyridin-2-yl)ethyl)-2-(6-cyano-4-cyclopropyl-2-oxo-1,2-dihydroquinolin-3-yl)acetamide (13.5 mg, 17.47%). LCMS (ES, m/z): 416 $[M+H]^+$ $^1H$ NMR (300 MHz, DMSO-$d_6$) δ 12.08 (s, $^1H$), 8.88 (d, J=1.6 Hz, $^1H$), 8.59 (d, J=7.2 Hz, $^1H$), 8.49 (d, J=1.8 Hz, $^1H$), 8.37 (dd, J=10.0, 1.7 Hz, $^1H$), 7.84 (dd, J=8.5, 1.8 Hz, $^1H$), 7.38 (d, J=8.5 Hz, $^1H$), 5.23 (p, J=6.9 Hz, $^1H$), 3.72 (s, $^2H$), 1.84 (q, J=7.8, 7.3 Hz, $^1H$), 1.40 (d, J=7.0 Hz, $^3H$), 1.14 (p, J=9.4 Hz, $^2H$), 0.59-0.51 (m, $^2H$). $^{19}F$ NMR (282 MHz, DMSO-$d_6$) δ −124.52 ($^1F$).

(Compound 145 and 144)

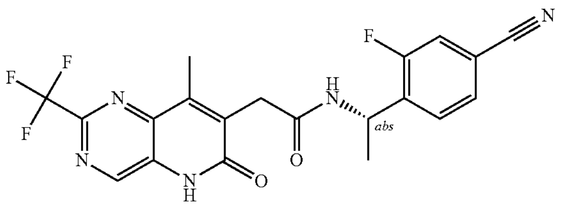

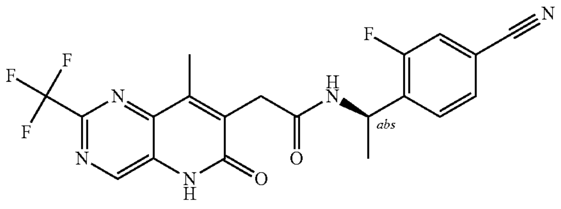

N-[(1S)-1-(4-cyano-2-fluorophenyl)ethyl]-2-[8-methyl-6-oxo-2-(trifluoromethyl)-5H-pyrido[3,2-d]pyrimidin-7-yl]acetamide and N-[(1R)-1-(4-cyano-2-fluorophenyl)ethyl]-2-[8-methyl-6-oxo-2-(trifluoromethyl)-5H-pyrido[3,2-d]pyrimidin-7-yl]acetamide 4-Bromo-2-(trifluoromethyl)pyrimidin-5-amine. A solution of 2-(trifluoromethyl)pyrimidin-5-amine (3.7 g, 22.7 mmol, 1 equiv) and NBS (4.12 g, 23.14 mmol, 1.02 equiv) in MeCN (40 mL) was stirred for 2 h at room temperature under air atmosphere. The resulting mixture was diluted with EtOAc. The resulting mixture was concentrated under reduced pressure and the residue was purified by silica gel column chromatography to afford 4-bromo-2-(trifluoromethyl)pyrimidin-5-amine (3 g, 54.65%). LCMS (ES, m/z): 242 $[Ms+H]^+$.

4-(1-Ethoxyethenyl)-2-(trifluoromethyl)pyrimidin-5-amine. $Pd(PPh_3)_4$(716.28 mg, 0.620 mmol, 0.1 equiv) was added to a stirred solution of 4-bromo-2-(trifluoromethyl)pyrimidin-5-amine (1.5 g, 6.2 mmol, 1 equiv) and tributyl (l-ethoxyethenyl) stannane (2238.59 mg, 6.20 mmol, 1 equiv) in Toluene (30 mL) at 100° C. under argon atmosphere. The resulting mixture was stirred for 4 h at 120° C. under argon atmosphere. The residue was purified by silica gel column chromatography to afford 4-(1-ethoxyethenyl)-2-(trifluoromethyl)pyrimidin-5-amine (1 g, 69.18%). LCMS (ES, m/z): 265 $[Ms+H]^+$.

1-[5-Amino-2-(trifluoromethyl)pyrimidin-4-yl]ethanone. A solution of 4-(1-ethoxyethenyl)-2-(trifluoromethyl)pyrimidin-5-amine (1 g, 4 mmol, 1 equiv) and HCl (10 mL) in dioxane (10 mL) was stirred for 1 h at room temperature under air atmosphere. The aqueous layer was extracted with EtOAc. The resulting mixture was concentrated under reduced pressure and the residue was purified by silica gel column chromatography to afford 1-[5-amino-2-(trifluoromethyl)pyrimidin-4-yl]ethanone (870 mg, 98.90%). LCMS (ES, m/z): 206 $[Ms+H]^+$.

1,4-Di-tert-butyl 2-{1-[5-amino-2-(trifluoromethyl)pyrimidin-4-yl]-1-hydroxyethyl}butanedioate. A solution of 1,4-di-tert-butyl butanedioate (1684.00 mg, 7.31 mmol, 2 equiv) and LDA (1175.01 mg, 10.97 mmol, 3 equiv) in THF (20 mL) was stirred for 0.5 h at −78° C. under argon atmosphere. To the above mixture, 1-[5-amino-2-(trifluoromethyl)pyrimidin-4-yl]ethanone (750 mg, 3.6 mmol, 1 equiv) was added dropwise over 5 min at −78° C. The resulting mixture was stirred for additional 1 h at −78° C. The reaction was quenched with saturated $NH_4Cl$ (aq.) at 0° C. The aqueous layer was extracted with EtOAc. The resulting mixture was concentrated under reduced pressure and the residue was purified by silica gel column chromatography to afford 1,4-di-tert-butyl 2-{1-[5-amino-2-(trifluoromethyl)pyrimidin-4-yl]-1-hydroxyethyl}butanedioate (1.6 g, 100.50%). LCMS (ES, m/z): 436 $[Ms+H]^+$.

[8-Methyl-6-oxo-2-(trifluoromethyl)-5H-pyrido[3,2-d]pyrimidin-7-yl]acetic acid. A solution of 1,4-di-tert-butyl 2-{1-[5-amino-2-(trifluoromethyl)pyrimidin-4-yl]-1-hydroxyethyl}butanedioate (1.5 g, 3.4 mmol, 1 equiv) and HCl/dioxane (v:v=1:1, 30 mL) was stirred for 3 h at room temperature under air atmosphere. The aqueous layer was extracted with EtOAc. The resulting mixture was concentrated under reduced pressure and the residue was purified by silica gel column chromatography to afford [8-methyl-6-oxo-2-(trifluoromethyl)-5H-pyrido[3,2-d]pyrimidin-7-yl]acetic acid (440 mg, 44.47%). LCMS (ES, m/z): 288 $[Ms+H]^+$.

N-[(1S)-1-(4-Cyano-2-fluorophenyl)ethyl]-2-[8-methyl-6-oxo-2-(trifluoromethyl)-5H-pyrido[3,2-d]pyrimidin-7-yl]acetamide. EDCI (64.87 mg, 0.42 mmol, 1.2 equiv) and DMAP (17.02 mg, 0.14 mmol, 0.4 equiv) were added in portions To a stirred solution of [8-methyl-6-oxo-2-(trifluoromethyl)-5H-pyrido[3,2-d]pyrimidin-7-yl]acetic acid (100 mg, 0.3 mmol, 1 equiv) and 4-[(1S)-1-aminoethyl]-3-fluorobenzonitrile (68.60 mg, 0.42 mmol, 1.2 equiv) in DMF (4 mL) at room temperature under air atmosphere. The resulting mixture was stirred for 2 h at room temperature under air atmosphere. The precipitated solids were collected by filtration and washed with water. The crude product (100 mg) was purified by Prep-HPLC with the following conditions (Column: Xselect CSH C18 OBD Column 30*150 mm 5 m, n; Mobile Phase A: Water (0.1% FA), Mobile Phase B: ACN; Flow rate: 60 mL/min; Gradient: 30% B to 55% B in 7 min, 55% B; Wave Length: 254/220 nm; $RT_1$(min): 6.75) to afford N-[(1S)-1-(4-cyano-2-fluorophenyl)ethyl]-2-[8-methyl-6-oxo-2-(trifluoromethyl)-5H-pyrido[3,2-d]pyrimidin-7-yl]acetamide (38.4 mg, 25.45%). LCMS (ES, m/z): 432.05 $[Ms-H]^+$ $^1H$ NMR (300 MHz, DMSO-d6) δ 12.46 (s, $^1H$), 8.90 (s, $^1H$), 8.72 (d, J=7.2 Hz, $^1H$), 7.82-7.78 (m, $^1H$), 7.71-7.64 (in, $^1H$), 7.62 (t, J=7.5 Hz, $^1H$), 5.12-5.07 (in, $^1H$), 3.77-3.66 (d, J=2.7 Hz, $^2H$), 2.43 (s, $^3H$), 1.37 (d, J=7.2 Hz, $^3H$).

N-[(1R)-1-(4-Cyano-2-fluorophenyl)ethyl]-2-[8-methyl-6-oxo-2-(trifluoromethyl)-5H-pyrido[3,2-d]pyrimidin-7-yl]acetamide. EDCI (80.10 mg, 0.418 mmol, 1.2 equiv) and DMAP (17.02 mg, 0.139 mmol, 0.4 equiv) were added in portions To a stirred solution of [8-methyl-6-oxo-2-(trifluoromethyl)-5H-pyrido[3,2-d]pyrimidin-7-yl]acetic acid (100 mg, 0.3 mmol, 1 equiv) and 4-[(IR)-1-aminoethyl]-3-fluorobenzonitrile (68.60 mg, 0.42 mmol, 1.2 equiv) in DMF (3 mL) at room temperature under air atmosphere. The resulting mixture was stirred for 2 h at room temperature under air atmosphere. The precipitated solids were collected by filtration and washed with water. The resulting mixture was concentrated under reduced pressure and the crude product (100 mg) was purified by Prep-HPLC with the following conditions (Column: Xselect CSH C18 OBD Column 30*150 mm 5 μm, n; Mobile Phase A: Water(0.1% FA), Mobile Phase B: ACN; Flow rate: 60 mL/min; Gradient: 30% B to 55% B in 7 min, 55% B; Wave Length: 254/220 nm; $RT_1$(min): 6.77; Number Of Runs: 0) to afford N-[(1R)-1-(4-cyano-2-fluorophenyl)ethyl]-2-[8-methyl-6-oxo-2-(trifluoromethyl)-5H-pyrido[3,2-d]pyrimidin-7-yl]acetamide (31.2 mg, 20.68%). LCMS (ES, m/z): 432.05 $[Ms-H]^+$ $^1H$ NMR (300 MHz, DMSO-$d_6$) δ 12.47 (s, $^1H$), 8.90 (s, $^1H$), 8.72 (d, J=7.2 Hz, $^1H$), 7.82-7.78 (m, $^1H$), 7.70-7.67 (in, $^1H$), 7.64-7.59 (in, $^1$H), 5.14-5.05 (in, $^1$H), 3.71 (d, J=2.7 Hz, $^2$H), 2.43 (s, $^3$H), 1.37 (d, J=7.2 Hz, $^3$H).

(Compound 11 and 12)

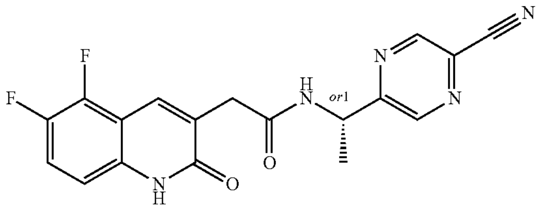

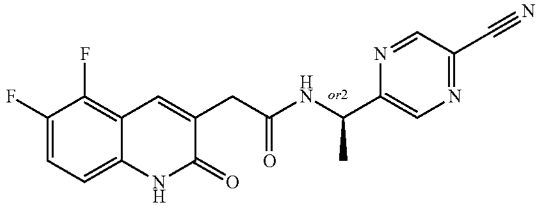

rel-N-[(1R)-1-(5-cyanopyrazin-2-yl)ethyl]-2-(5,6-difluoro-2-oxo-1H-quinolin-3-yl)acetamide and rel-N-[(1S)-1-(5-cyanopyrazin-2-yl)ethyl]-2-(5,6-difluoro-2-oxo-1H-quinolin-3-yl)acetamide Tert-butyl N-(2-bromo-3,4-difluorophenyl)carbamate.

LiHMDS (4.83 g, 28.85 mmol, 2 equiv) was added dropwise To a stirred solution of 2-bromo-3,4-difluoroaniline (3 g, 14 mmol, 1 equiv) in THF (30 mL) was added at 0° C. under argon atmosphere for 0.5 h. $(Boc)_{20}$ (3.46 g, 15.86 mmol, 1.1 equiv) was then added at 0° C. The resulting mixture was stirred for 2 h at room temperature under argon atmosphere. The reaction was quenched with saturated $NH_4Cl$ (100 mL, aq.) at −78° C. The resulting mixture was extracted with EtOAc and combined organic layers were dried over anhydrous $Na_2SO_4$. The filtrate was concentrated under reduced pressure and the residue was purified by silica gel column chromatography to afford tert-butyl N-(2-bromo-3,4-difluorophenyl)carbamate (4 g, 90.01%). LCMS (ES, m/z): 308 $[M+H]^+$.

Tert-butyl N-(3,4-difluoro-2-formylphenyl)carbamate. Tert-butyl N-(2-bromo-3,4-difluorophenyl)carbamate (4 g, 13 mmol, 1 equiv) was added to a stirred solution of NaH (0.37 g, 15.58 mmol, 1.2 equiv) in THF (40 mL) at 0° C. under argon atmosphere for 0.5 h. Followed by addition of n-BuLi (1 M, 1.00 g, 15.58 mmol, 1.2 equiv) at −78° C. and stirred for 0.5 h. To the above mixture was added DMF (3.80 g, 51.93 mmol, 4 equiv) dropwise at −78° C. for 1 h. The reaction was quenched with saturated $NH_4Cl$ (100 mL, aq.) at −78° C. The resulting mixture was extracted with EtOAc and the combined organic layers were dried over anhydrous $Na_2SO_4$. The filtrate was concentrated under reduced pressure and the residue was purified by silica gel column chromatography to afford tert-butyl N-(3,4-difluoro-2-formylphenyl)carbamate (3 g, 89.84%).

LCMS (ES, m/z): 258 $[M+H]^+$.

1,4-Di-tert-butyl2-({6-[(tert-butoxycarbonyl)amino]-2,3-difluorophenyl}(hydroxy)methyl)butanedioate. LDA (2 M, 3.75 g, 34.986 mmol, 3 equiv) was added dropwise to a stirred solution of 1,4-di-tert-butyl butanedioate (5.37 g, 23.324 mmol, 2 equiv) in THF (40 mL) at −78° C. under argon atmosphere for 0.5 h. Then to the above mixture was added tert-butyl N-(3,4-difluoro-2-formylphenyl)carbamate (3 g, 11.662 mmol, 1 equiv) and $ZnCl_2$ (0.7 M, 12 mL, 1 equiv). The resulting mixture was stirred for 2 h at −78° C. under argon atmosphere. The reaction was quenched with saturated $NH_4Cl$ (100 mL, aq.) at −78° C. The resulting mixture was extracted with EtOAc and the combined organic layers were dried over anhydrous $Na_2SO_4$. The filtrate was concentrated under reduced pressure and the residue was purified by silica gel column chromatography to afford 1,4-di-tert-butyl 2-({6-[(tert-butoxycarbonyl)amino]-2,3-difluorophenyl}(hydroxy)methyl)butanedioate (4 g, 70.35%). LCMS (ES, m/z): 488 $[M+H]^+$.

(5,6-difluoro-2-oxo-1H-quinolin-3-yl)acetic acid. HCl (4M, 20 mL) was added dropwise to a stirred solution of 1,4-di-tert-butyl 2-({6-[(tert-butoxycarbonyl)amino]-2,3-difluorophenyl}(hydroxy)methyl)butanedioate (4 g, 8 mmol, 1 equiv) in dioxane (20 mL) at 0° C. under air atmosphere. The resulting mixture was stirred for 2 h at room temperature under air atmosphere, then concentrated under reduced pressure and the residue purified by trituration with ACN, to afford (5,6-difluoro-2-oxo-1H-quinolin-3-yl)acetic acid (1.4 g, 71.34%). LCMS (ES, m/z): 240 $[M+H]^+$.

N-[1-(5-Chloropyrazin-2-yl)ethyl]-2-(5,6-difluoro-2-oxo-1H-quinolin-3-yl) acetamide. 1-(5-Chloropyrazin-2-yl) ethanamine (94.88 mg, 0.60 mmol, 1.2 equiv) was added to a stirred solution of (5,6-difluoro-2-oxo-1H-quinolin-3-yl) acetic acid (120 mg, 0.5 mmol, 1 equiv), EDCI (115.42 mg, 0.60 mmol, 1.2 equiv), DMAP (24.52 mg, 0.20 mmol, 0.4 equiv) in DMF (2 mL) at room temperature under air atmosphere. The resulting mixture was stirred for 2 h at room temperature under air atmosphere and. purified by reversed-phase flash chromatography with the following conditions: (column, C18; mobile phase, MeCN in Water (0.1% FA), 10% to 50% gradient in 10 min; detector, UV 254 nm) to afford N-[1-(5-chloropyrazin-2-yl)ethyl]-2-(5,6-difluoro-2-oxo-1H-quinolin-3-yl)acetamide (150 mg, 78.93%).

N-[1-(5-Cyanopyrazin-2-yl)ethyl]-2-(5,6-difluoro-2-oxo-1H-quinolin-3-yl) acetamide. A stirred solution of N-[1-(5-chloropyrazin-2-yl)ethyl]-2-(5,6-difluoro-2-oxo-1H-quinolin-3-yl) acetamide (150 mg, 0.396 mmol, 1 equiv), Zn (10.36 mg, 0.158 mmol, 0.4 equiv), $Zn(CN)_2$ (93.00 mg, 0.792 mmol, 2 equiv) and $Pd(dppf)Cl_2$ (57.96 mg, 0.079 mmol, 0.2 equiv) in DMF (2 mL) was prepared at 120° C. under argon atmosphere. The resulting mixture was stirred for 2 h at 120° C. under argon atmosphere. The reaction was quenched with $H_2O$ (100 mL, aq.) at room temperature and extracted with $CH_2Cl_2$. The combined organic layers were dried over anhydrous $Na_2SO_4$. The filtrate was concentrated under reduced pressure and the residue was purified by reversed-phase flash chromatography with the following conditions: (column, C18; mobile phase, MeCN in water (0.1% FA), 10% to 50% gradient in 10 min; detector, UV 254 nm) to afford N-[1-(5-cyanopyrazin-2-yl)ethyl]-2-(5,6-difluoro-2-oxo-1H-quinolin-3-yl) acetamide (80 mg, 54.8%). LCMS (ES, m/z): 370[M+H]+.

rel-N-[(1R)-1-(5-cyanopyrazin-2-yl)ethyl]-2-(5,6-difluoro-2-oxo-1H-quinolin-3-yl) acetamide. A solution of N-[1-(5-cyanopyrazin-2-yl)ethyl]-2-(5,6-difluoro-2-oxo-1H-quinolin-3-yl) acetamide (80 mg, 0.230 mmol, 1 equiv) in DMSO (1 mL) was separated by flash chromatography with the following conditions: (Column: CHIRALPAK IA-3, 4.6*50 mm, 3 um; Mobile Phase A: Hex (0.1% DEA):EtOH=50:50; Flow rate: 1 mL/min; Gradient: 0% B to 0% B; Injection Volume: 5 ul mL) to afford rel-N-[(1R)-1-(5-cyanopyrazin-2-yl)ethyl]-2-(5,6-difluoro-2-oxo-1H-quinolin-3-yl) acetamide (21.6 mg, 25.41%). LCMS (ES, m/z): 370.00 $[M+H]^+$. $^1H$ NMR (300 MHz, DMSO-d6) δ 12.12 (s, $^1$H), 9.16 (d, J=1.5 Hz, $^1$H), 8.93 (d, J=1.5 Hz, $^1$H), 8.79 (d, J=6.9 Hz, $^1$H), 7.95 (s, $^1$H), 7.62-7.53 (m, $^1$H), 7.11 (d, J=9.3 Hz, $^1$H), 5.07-4.98 (m, $^1$H), 3.62-3.44 (m, $^2$H), 1.46 (d, J=7.1 Hz, $^3$H).

rel-N-[(1S)-1-(5-cyanopyrazin-2-yl)ethyl]-2-(5,6-difluoro-2-oxo-1H-quinolin-3-yl)acetamide (33.3 mg, 39.18%). LCMS (ES, m/z): 370.00 [M+H]$^+$. $^1$H NMR (300 MHz, DMSO-d6) δ 12.11 (s, $^1$H), 9.16 (d, J=1.5 Hz, $^1$H), 8.93 (d, J=1.5 Hz, $^1$H), 8.79 (d, J=6.9 Hz, $^1$H), 7.95 (s, $^1$H), 7.62-7.53 (m, $^1$H), 7.16-7.06 (m, $^1$H), 5.08-4.98 (m, $^1$H), 3.62-3.44 (m, $^2$H), 1.46 (d, J=7.1 Hz, $^3$H).

(Compound 1146)

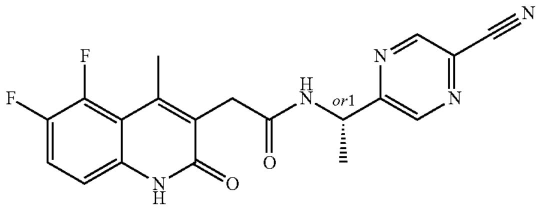

rel-N-[(1R)-1-(5-cyanopyrazin-2-yl)ethyl]-2-(5,6-difluoro-4-methyl-2-oxo-1H-quinolin-3-yl)acetamide 2-Chloro-5-(1-ethoxyethenyl) pyrazine. A mixture of 2-bromo-5-chloropyrazine (20 g, 103 mmol, 1 equiv), tributyl(1-ethoxyethenyl) stannane (37.34 g, 103.40 mmol, 1 equiv), and Pd(dppf)$Cl_2$ (7.57 g, 10.34 mmol, 0.1 equiv) in dioxane (250 mL) was stirred for overnight at 80° C. under argon atmosphere. The mixture was cooled to room temperature. The resulting mixture was concentrated under reduced pressure and the residue was purified by silica gel column chromatography to afford 2-chloro-5-(1-ethoxyethenyl) pyrazine (15 g, 78.58%). LCMS (ES, m/z): 185 [M+H]$^+$.

1-(5-Chloropyrazin-2-yl) ethanone. A mixture of 2-chloro-5-(1-ethoxyethenyl) pyrazine (15 g, 81 mmol, 1 equiv) and HCl (4 M in $H_2O$, 50 mL) in dioxane (150 mL) was stirred for 4 h at room temperature under air atmosphere. The resulting mixture was diluted with water and the PH was adjusted to 8 with $NaHCO_3$ (saturated). The aqueous layer was extracted with EtOAc and the resulting mixture was concentrated under reduced pressure and the residue was purified by silica gel column chromatography to afford 1-(5-chloropyrazin-2-yl) ethanone (10 g, 78.61%). LCMS (ES, m/z): 157 [M+H]$^+$.

(S)—N-[1-(5-Chloropyrazin-2-yl)ethylidene]-2-methylpropane-2-sulfinamide. A mixture of 1-(5-chloropyrazin-2-yl)ethanone (5 g, 31.935 mmol, 1 equiv), (S)-2-methylpropane-2-sulfinamide (5.81 g, 47.902 mmol, 1.5 equiv) and $Ti(OEt)_4$ (14.57 g, 63.870 mmol, 2 equiv) in THF (70 mL) was stirred for 4 h at 60° C. under air atmosphere. The mixture was cooled to room temperature and diluted with water. The resulting mixture was filtered, the filter cake was washed with EtOAc. The aqueous layer was extracted with EtOAc, concentrated under reduced pressure and the residue was purified by silica gel column chromatography to afford (S)—N-[1-(5-chloropyrazin-2-yl)ethylidene]-2-methylpropane-2-sulfinamide (5 g, 60.28%). LCMS (ES, m/z): 260 [M+H]$^+$.

(S)—N-[(1S)-1-(5-chloropyrazin-2-yl)ethyl]-2-methylpropane-2-sulfinamide. A mixture of (S)—N-[1-(5-chloropyrazin-2-yl)ethylidene]-2-methylpropane-2-sulfinamide (5 g, 19.249 mmol, 1 equiv) in MeOH (50 mL) was added $NaBH_4$ (1.46 g, 38.50 mmol, 2 equiv) dropwise. Then the reaction was stirred for 2 h at 0° C. under air atmosphere. The reaction was quenched with water at 0° C. The resulting mixture was concentrated under reduced pressure and the residue was purified by silica gel column chromatography to afford (S)—N-[(1S)-1-(5-chloropyrazin-2-yl)ethyl]-2-methylpropane-2-sulfinamide (3.3 g, 65.49%). LCMS (ES, m/z): 262 [M+H]$^+$.

(S)—N-[(1S)-1-(5-Cyanopyrazin-2-yl)ethyl]-2-methylpropane-2-sulfinamide. A mixture of (S)—N-[(1S)-1-(5-chloropyrazin-2-yl)ethyl]-2-methylpropane-2-sulfinamide (3.3 g, 12.6 mmol, 1 equiv), $Zn(CN)_2$ (2.96 g, 25.21 mmol, 2 equiv), Zn (0.82 g, 12.61 mmol, 1 equiv) and Pd(dppf)$Cl_2$ (1.84 g, 2.52 mmol, 0.2 equiv) in DMSO (40 mL) was stirred for 2 h at 120° C. under argon atmosphere. The mixture was cooled to room temperature, diluted with water and extracted with EtOAc. The combined organic layers were washed with brine and dried over anhydrous $Na_2SO_4$. The filtrate was concentrated under reduced pressure and the residue was purified by silica gel column chromatography to afford (S)—N-[(1S)-1-(5-cyanopyrazin-2-yl)ethyl]-2-methylpropane-2-sulfinamide (1.5 g, 47.15%). LCMS (ES, m/z): 253 [M+H]$^+$.

5-[(1S)-1-Aminoethyl]pyrazine-2-carbonitrile. A mixture of (S)—N-[(1S)-1-(5-cyanopyrazin-2-yl)ethyl]-2-methylpropane-2-sulfinamide (1.2 g, 4.8 mmol, 1 equiv) and HCl (gas, 4M in 1,4-dioxane) (0.52 g, 14.26 mmol, 3 equiv) in dioxane (15 mL) was stirred for 2 h at room temperature under air atmosphere. The resulting mixture was diluted with $CH_2Cl_2$ and concentrated under reduced pressure resulting in 5-[(1S)-1-aminoethyl]pyrazine-2-carbonitrile (700 mg, 99.34%).

LCMS (ES, m/z): 149 [M+H]$^+$.

rel-N-[(1R)-1-(5-Cyanopyrazin-2-yl)ethyl]-2-(5,6-difluoro-4-methyl-2-oxo-1H-quinolin-3-yl)acetamide. A mixture of (5,6-difluoro-4-methyl-2-oxo-1H-quinolin-3-yl) acetic acid (700 mg, 2.765 mmol, 1 equiv), 5-[(1S)-1-aminoethyl]pyrazine-2-carbonitrile (491.55 mg, 3.32 mmol, 1.2 equiv), EDCI (635.96 mg, 3.32 mmol, 1.2 equiv), HOBt (560.35 mg, 4.15 mmol, 1.5 equiv) and DIEA (1071.93 mg, 8.30 mmol, 3 equiv) in DMF (10 mL) was stirred for 2 h at room temperature under air atmosphere. The resulting mixture was diluted with water and the aqueous layer was extracted with EtOAc and concentrated under reduced pressure and the residue was purified by trituration with MeCN resulting in N-[(1S)-1-(5-cyanopyrazin-2-yl)ethyl]-2-(5,6-difluoro-4-methyl-2-oxo-1H-quinolin-3-yl) acetamide (460 mg, 42.45%). LCMS (ES, m/z): 384.05 [M+H]$^+$. $^1$H NMR (400 MHz, DMSO-$d_6$) δ 11.96 (s, $^1$H), 9.16 (d, J=1.2 Hz, $^1$H), 8.88 (d, J=1.6 Hz, $^1$H), 8.70 (d, J=6.8 Hz, $^1$H), 7.61-7.54 (m, $^1$H), 7.12-7.09 (m, $^1$H), 5.04-5.00 (m, $^1$H), 3.73-3.63 (m, $^2$H), 2.47 (s, $^3$H), 1.45 (d, J=7.2 Hz, $^3$H).

(Compound 1124 and 1123)

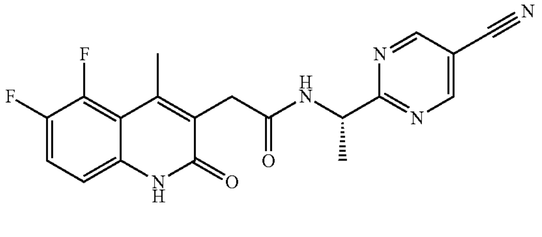

-continued

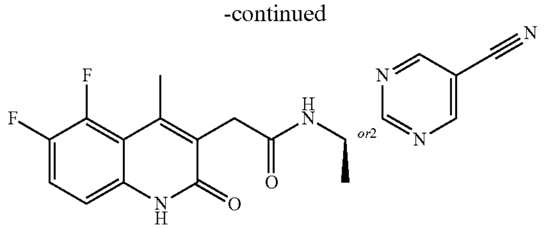

(S)-N-(1-(5-Cyanopyrimidin-2-yl)ethyl]-2-(5,6-difluoro-4-methyl-2-oxo-1,2-dihydroquinolin-3-yl) acetamide and (R)-N-(1-(5-cyanopyrimidin-2-yl)ethyl)-2-(5,6-difluoro-4-methyl-2-oxo-1,2-dihydroquinolin-3-yl)acetamide 2-(1-Ethoxyvinyl)-3,4-difluoroaniline. Tributyl(1-ethoxyvinyl)stannane (6.95 g, 19.23 mmol, 2.00 equiv) was added dropwise To a stirred solution of 2-bromo-3,4-difluoroaniline (2.00 g, 9.62 mmol, 1.00 equiv) and $Pd(PPh_3)_4$ (1.11 g, 0.96 mmol, 0.10 equiv) in 1,4-dioxane (20 mL) at room temperature under nitrogen atmosphere. The resulting mixture was stirred for overnight at 100° C. under nitrogen atmosphere. The resulting mixture was diluted with water. The resulting mixture was extracted with EtOAc. The combined organic layers were washed with brine and dried over anhydrous $Na_2SO_4$. The filtrate was concentrated under reduced pressure and the residue was purified by silica gel column chromatography to afford 2-(1-ethoxyvinyl)-3,4-difluoroaniline (1.00 g, 52.21%). LCMS (ES, m/z): 200[M+H]$^+$ 1-(6-Amino-2,3-difluorophenyl)ethan-1-one. 4M HCl (aq.) (10 mL) was added dropwise to a stirred solution of 2-(1-ethoxyvinyl)-3,4-difluoroaniline (1.00 g, 5.02 mmol, 1.00 equiv) in 1,4-dioxane (10 mL) was added at 0° C. under nitrogen atmosphere. The resulting mixture was stirred for 3 hrs at room temperature under nitrogen atmosphere. The mixture was adjusted to pH 8 with saturated $Na_2CO_3$ (aq.). The resulting mixture was extracted with EtOAc and the combined organic layers were washed with brine and dried over anhydrous $Na_2SO_4$. The filtrate was concentrated under reduced pressure and the residue was purified by silica gel column chromatography to afford 1-(6-amino-2,3-difluorophenyl)ethan-1-one (500 mg, 58.20%). LCMS (ES, m/z): 172[M+H]$^+$ Di-tert-butyl 2-(1-(6-amino-2,3-difluorophenyl)-1-hydroxyethyl)succinate. LDA (2.5 M in THF) (3.50 mL, 8.76 mmol, 3.00 equiv) was added dropwise To a stirred solution of di-tert-butyl succinate (1.35 g, 5.84 mmol, 2.00 equiv) in THF (10 mL) was added at −78° C. under argon atmosphere. The resulting mixture was stirred for 1 h at −78° C. under argon atmosphere. 1-(6-amino-2,3-difluorophenyl)ethan-1-one (500 mg, 2.92 mmol, 1.00 equiv) and $ZnCl_2$ (0.7 M in THF) (4.17 mL, 2.92 mmol, 1.00 equiv) was added dropwise to the above mixture over 10 min at −78° C. The resulting mixture was stirred for additional 1 h at −78° C. The reaction was quenched by the addition of saturated $NH_4Cl$ (aq.) (10 mL) at −78° C. The resulting mixture was extracted with EtOAc. The combined organic layers were washed with EtOAc and dried over anhydrous $Na_2SO_4$. The filtrate was concentrated under reduced pressure and the residue was purified by silica gel column chromatography to afford di-tert-butyl 2-(1-(6-amino-2,3-difluorophenyl)-1-hydroxyethyl)succinate (500 mg, 42.63%). LCMS (ES, m/z): 402 [M+H]$^+$ 2-(5,6-difluoro-4-methyl-2-oxo-1,2-dihydroquinolin-3-yl) acetic acid. 4M HCl (aq.) (2.5 mL) was added dropwise to a stirred solution of di-tert-butyl 2-(1-(6-amino-2,3-difluorophenyl)-1-hydroxyethyl) succinate (500 mg, 1 mmol, 1.00 equiv) in 1,4-dioxane (2.5 mL) at 0° C. under nitrogen atmosphere. The resulting mixture was stirred for overnight at 80° C. under nitrogen atmosphere. The mixture cooled to 0° C. and the precipitated solids were collected by filtration and washed with MeCN. Resulting in 2-(5,6-difluoro-4-methyl-2-oxo-1,2-dihydroquinolin-3-yl) acetic acid (200 mg, 63.42%). LCMS (ES, m/z): 254[M+H]$^+$ N-(1-(5-bromopyrimidin-2-yl)ethylidene)-2-methylpropane-2-sulfinamide. $Ti(OEt)_4$ (6.81 g, 29.85 mmol, 2.00 equiv) was added dropwise to a stirred solution of 1-(5-bromopyrimidin-2-yl) ethan-1-one (3.00 g, 14.92 mmol, 1.00 equiv) and 2-methylpropane-2-sulfinamide (2.17 g, 17.91 mmol, 1.20 equiv) in 2-methyl-THF (30 mL) was added at room temperature under nitrogen atmosphere. The resulting mixture was stirred for 3 hrs at 80° C. under nitrogen atmosphere. The reaction was quenched with water at room temperature. The resulting mixture was filtered, the filter cake was washed with EtOAc and the filtrate was concentrated under reduced pressure and purified by silica gel column chromatography to afford N-(1-(5-bromopyrimidin-2-yl)ethylidene)-2-methylpropane-2-sulfinamide (1.50 g, 33.04%). LCMS (ES, m/z): 304[M+H]$^+$ N-(1-(5-bromopyrimidin-2-yl)ethyl)-2-methylpropane-2-sulfinamide. $NaBH_4$ (746.13 mg, 19.72 mmol, 3.00 equiv) was added dropwise to a stirred solution of (Z)—N-(1-(5-bromopyrimidin-2-yl)ethylidene)-2-methylpropane-2-sulfinamide (2.00 g, 6.57 mmol, 1.00 equiv) in THF (20 mL) at 0° C. under nitrogen atmosphere. The resulting mixture was stirred for 1 h at room temperature under nitrogen atmosphere. The reaction was quenched by the addition of ice-water at 0° C. The resulting mixture was extracted with EtOAc. The combined organic layers were washed with brine and dried over anhydrous $Na_2SO_4$. The filtrate was concentrated under reduced pressure and the residue was purified by silica gel column chromatography to afford N-(1-(5-bromopyrimidin-2-yl)ethyl)-2-methylpropane-2-sulfinamide (600 mg, 29.80%). LCMS (ES, m/z): 306[M+H]$^+$ N-(1-(5-Cyanopyrimidin-2-yl)ethyl)-2-methylpropane-2-sulfinamide. $Zn(CN)_2$ (460.14 mg, 3.92 mmol, 2.00 equiv) was added dropwise To a stirred solution of N-(1-(5-bromopyrimidin-2-yl)ethyl)-2-methylpropane-2-sulfinamide (600 mg, 2 mmol, 1.00 equiv) and zinc powder (25.62 mg, 0.39 mmol, 0.20 equiv) and $Pd(dppf)Cl_2$ (286.74 mg, 0.39 mmol, 0.20 equiv) in DMAc (6 mL) at room temperature under nitrogen atmosphere. The resulting mixture was stirred for 2 hrs at 100° C. under nitrogen atmosphere. The mixture was adjusted to pH 8 with saturated $NaHCO_3$ (aq.). The resulting mixture was extracted with EtOAc. The combined organic layers were dried over anhydrous $Na_2SO_4$. The filtrate was concentrated under reduced pressure and purified by silica gel column chromatography to afford N-(1-(5-cyanopyrimidin-2-yl)ethyl)-2-methylpropane-2-sulfinamide (200 mg, 40.45%). LCMS (ES, m/z): 253[M+H]$^+$ 2-(1-Aminoethyl)pyrimidine-5-carbonitrile. 4M HCl (gas) in 1,4-dioxane (2.00 mL, 65.83 mmol, 83.05 equiv) was added dropwise To a stirred solution of N-(1-(5-cyanopyrimidin-2-yl)ethyl)-2-methylpropane-2-sulfinamide (200 mg, 1 mmol, 1.00 equiv) in DCM (2 mL) at 0° C. under nitrogen atmosphere. The resulting mixture was stirred for 2 h at room temperature under nitrogen atmosphere. The resulting mixture was concentrated under reduced pressure resulting in 2-(1-aminoethyl)pyrimidine-5-carbonitrile (200 mg crude, HCl salt). The crude product was used in the next step directly without further purification. LCMS (ES, m/z): 149[M+H]+

N-(1-(5-Cyanopyrimidin-2-yl)ethyl)-2-(5,6-difluoro-4-methyl-2-oxo-1,2-dihydroquinolin-3-yl) acetamide. DIEA (306.27 mg, 2.37 mmol, 3.00 equiv), 2-(5,6-difluoro-4-methyl-2-oxo-1,2-dihydroquinolin-3-yl) acetic acid (200 mg, 0.79 mmol, 1.00 equiv), EDCI (181.70 mg, 0.95 mmol, 1.20 equiv) and HOBt (128.08 mg, 0.95 mmol, 1.20 equiv) in DMF (2 mL) were added dropwise to a stirred solution of 2-(1-aminoethyl)pyrimidine-5-carbonitrile (117.03 mg, 0.79 mmol, 1.00 equiv) at room temperature under nitrogen atmosphere. The resulting mixture was stirred for 4 hrs at room temperature under nitrogen atmosphere. The reaction was quenched by the addition of water at room temperature. The resulting mixture was extracted with EtOAc. The combined organic layers were washed with EtOAc and dried over anhydrous $Na_2SO_4$. The filtrate was concentrated under reduced pressure and purified by silica gel column chromatography to afford N-(1-(5-cyanopyrimidin-2-yl)ethyl)-2-(5,6-difluoro-4-methyl-2-oxo-1,2-dihydroquinolin-3-yl) acetamide (190 mg, 62.75%).

LCMS (ES, m/z): 384[M+H]+

(S)—N-(1-(5-Cyanopyrimidin-2-yl)ethyl)-2-(5,6-difluoro-4-methyl-2-oxo-1,2-dihydroquinolin-3-yl) acetamide. The crude product (190 mg) was purified by Prep-HPLC with the following conditions ((Column: CHIRAL ART Cellulose-SZ, 0.46*10 cm, 3 μm; Mobile Phase A: Hex (0.1% DEA), Mobile Phase B: EtOH-HPLC; Flow rate: 1.67 mL/min; Gradient: 50% B to 50% B in 4 min; Wave Length: 272/239 nm; RT1(min): 11.0; RT2(min): 14.6; Sample Solvent: MeOH:DCM=1:2; Injection Volume: 1.3 mL; Number Of Runs: 7 min) to afford (S)—N-(1-(5-cyanopyrimidin-2-yl)ethyl)-2-(5,6-difluoro-4-methyl-2-oxo-1,2-dihydroquinolin-3-yl)acetamide (58.7 mg, 30.89%). LCMS (ES, m/z): 384[M+H]+ $^1$H NMR (300 MHz, DMSO-$d_6$) δ 11.93 (s, $^1$H), 9.27 (s, $^2$H), 8.59 (d, J=7.2 Hz, $^1$H), 7.62-7.52 (in, $^1$H), 7.13-7.09 (in, $^1$H), 4.99 (t, J=7.2 Hz, $^1$H), 3.76-3.61 (m, $^2$H), 2.51-2.44 (m, $^3$H), 1.43 (d, J=6.9 Hz, $^3$H). $^{19}$F NMR (282 MHz, DMSO-$d_6$) δ −139.20 ($^1$F), −147.04 ($^1$F).

(R)—N-(1-(5-cyanopyrimidin-2-yl)ethyl)-2-(5,6-difluoro-4-methyl-2-oxo-1,2-dihydroquinolin-3-yl) acetamide. The crude product (190 mg) was purified by Prep-HPLC with the following conditions ((Column: CHIRAL ART Cellulose-SZ, 0.46*10 cm, 3 μm; Mobile Phase A: Hex (0.1% DEA), Mobile Phase B: EtOH-HPLC; Flow rate: 1.67 mL/min; Gradient: 50% B to 50% B in 4 min; Wave Length: 272/239 nm; RT1(min): 11.0; RT2(min): 14.6; Sample Solvent: MeOH:DCM=1:2; Injection Volume: 1.3 mL; Number Of Runs: 7 min) to afford (R)—N-(1-(5-cyanopyrimidin-2-yl)ethyl)-2-(5,6-difluoro-4-methyl-2-oxo-1,2-dihydroquinolin-3-yl)acetamide (64.3 mg, 33.84%). LCMS (ES, m/z): 384[M+H]+ $^1$H NMR (300 MHz, DMSO-$d_6$) δ 11.93 (s, $^1$H), 9.27 (s, $^2$H), 8.59 (d, J=7.2 Hz, $^1$H), 7.62-7.56 (m, $^1$H), 7.13-7.08 (m, $^1$H), 4.99 (t, J=6.9 Hz, $^1$H), 3.76-3.61 (m, $^2$H), 2.51-2.44 (m, $^3$H), 1.42 (d, J=6.9 Hz, $^3$H). $^{19}$F NMR (282 MHz, DMSO-$d_6$) δ −139.20 ($^1$F), −147.04 ($^1$F).

(Compound 1111 and 1110)

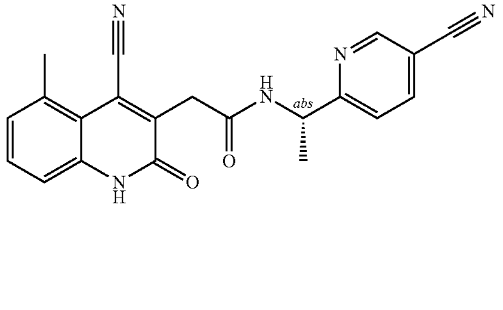

-continued

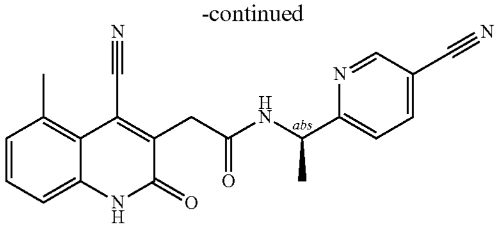

2-(4-cyano-5-methyl-2-oxo-1H-quinolin-3-yl)-N-[(1S)-1-(5-cyanopyridin-2-yl)ethyl]acetamide and 2-(4-cyano-5-methyl-2-oxo-1H-quinolin-3-yl)-N-[(1R)-1-(5-cyanopyridin-2-yl)ethyl]acetamide Methyl 2-methyl-6-nitrobenzoate. A mixture of 2-methyl-6-nitrobenzoic acid (20 g, 110 mmol, 1 equiv), HOBt (22.38 g, 165.61 mmol, 1.5 equiv) and DIEA (42.81 g, 331.22 mmol, 3 equiv) in MeOH (100 mL) was stirred for overnight at 50° C. The resulting mixture was concentrated under reduced pressure and the resulting mixture was diluted with water. The resulting mixture was extracted with EtOAc. The combined organic layers were washed with water, dried over anhydrous $Na_2SO_4$. The filtrate was concentrated under reduced pressure and the resulting mixture was concentrated under reduced pressure and the residue was purified by silica gel column chromatography to afford methyl 2-methyl-6-nitrobenzoate (13.3 g, 61.72%). LCMS (ES, m/z): 196 [M+H]+.

Methyl 2-amino-6-methylbenzoate. A mixture of methyl 2-methyl-6-nitrobenzoate (13.3 g, 68.1 mmol, 1 equiv) and Pd/C (2.6 g, 24.4 mmol, 0.36 equiv) in MeOH (130 mL) was stirred for overnight at room temperature under hydrogen atmosphere. The resulting mixture was filtered, the filter cake was washed with MeOH and the filtrate was concentrated under reduced pressure and the residue was purified by silica gel column chromatography to afford methyl 2-amino-6-methylbenzoate (10.8 g, 95.94%). LCMS (ES, m/z): 166 [M+H]+.

Methyl 2-(4-ethoxy-4-oxobutanamido)-6-methylbenzoate. A mixture of methyl 2-amino-6-methylbenzoate (10.8 g, 65.4 mmol, 1 equiv), ethyl 4-chloro-4-oxobutanoate (11.84 g, 71.92 mmol, 1.1 equiv), DIEA (12.67 g, 98.07 mmol, 1.5 equiv) and DMAP (0.80 g, 6.54 mmol, 0.1 equiv) in DCM (100 mL) was stirred for overnight at room temperature under air atmosphere. The resulting mixture was concentrated under reduced pressure and the residue was purified by silica gel column chromatography to afford methyl 2-(4-ethoxy-4-oxobutanamido)-6-methylbenzoate (18 g, 93.86%).

LCMS (ES, m/z): 294 [M+H]+.

Ethyl 6-methyl-2,5-dioxo-3,4-dihydro-1H-1-benzazepine-4-carboxylate. A mixture of methyl 2-(4-ethoxy-4-oxobutanamido)-6-methylbenzoate (10 g, 34 mmol, 1 equiv) in t-BuOK in THF (1 M) (100 mL) was stirred for overnight at room temperature under argon atmosphere. The crude product was used in the next step directly without further purification. LCMS (ES, m/z): 262 [M+H]+.

(4-Hydroxy-5-methyl-2-oxo-1H-quinolin-3-yl) acetic acid. A mixture of ethyl 6-methyl-2,5-dioxo-3,4-dihydro-1H-1-benzazepine-4-carboxylate (5 g, 19 mmol, 1 equiv) in 1M KOH aqueous (50 mL) was stirred overnight at 100° C. under air atmosphere. The mixture was acidified to pH 3 with HCl (aq.). The precipitated solids were collected by filtration and washed with water. The residue was purified by trituration with MeCN resulting in (4-hydroxy-5-methyl-2-oxo-1H-quinolin-3-yl) acetic acid (2.8 g, 62.74%). LCMS (ES, m/z): 234 $[M+H]^+$.

Methyl 2-(4-hydroxy-5-methyl-2-oxo-1H-quinolin-3-yl) acetate. A mixture of (4-hydroxy-5-methyl-2-oxo-1H-quinolin-3-yl) acetic acid (1.8 g, 7.7 mmol, 1 equiv) and $SOCl_2$ (9.18 g, 77.18 mmol, 10 equiv) in MeOH (18 mL) was stirred for overnight at 50° C. under air atmosphere. The resulting mixture was concentrated under reduced pressure and the residue was purified by trituration with MeCN resulting in methyl 2-(4-hydroxy-5-methyl-2-oxo-1H-quinolin-3-yl) acetate (1.6 g, 83.85%). LCMS (ES, m/z): 248 $[M+H]^+$.

Methyl 2-[5-methyl-2-oxo-4-(trifluoromethanesulfonyloxy)-1H-quinolin-3-yl]acetate. 1,1,1-trifluoro-N-phenyl-N-trifluoromethanesulfonylmethanesulfonamide (2.17 g, 6.07 mmol, 1.5 equiv) was added dropwise to a stirred mixture of methyl 2-(4-hydroxy-5-methyl-2-oxo-1H-quinolin-3-yl)acetate (1 g, 4 mmol, 1 equiv) and t-BuOK (0.91 g, 8.09 mmol, 2 equiv) in DMF (18 mL) at room temperature under argon atmosphere. The resulting mixture was diluted with water. The resulting mixture was extracted with EtOAc. The combined organic layers were washed with water and dried over anhydrous $Na_2SO_4$. The filtrate was concentrated under reduced pressure and the resulting mixture was concentrated under reduced pressure and the residue was purified by silica gel column chromatography to afford methyl 2-[5-methyl-2-oxo-4-(trifluoromethanesulfonyloxy)-1H-quinolin-3-yl] acetate (700 mg, 45.63%). LCMS (ES, m/z): 380 $[M+H]^+$.

Methyl 2-(4-cyano-5-methyl-2-oxo-1H-quinolin-3-yl)acetate. A mixture of methyl 2-[5-methyl-2-oxo-4-(trifluoromethanesulfonyloxy)-1H-quinolin-3-yl]acetate (600 mg, 2 mmol, 1 equiv), $Zn(CN)_2$ (371.47 mg, 3.16 mmol, 2 equiv) and $Pd(dppf)Cl_2$ (231.49 mg, 0.32 mmol, 0.2 equiv) in DMSO (4 mL) was stirred for 2 h at 120° C. under argon atmosphere. The resulting mixture was diluted with water and the resulting mixture was extracted with EtOAc. The combined organic layers were washed with water and dried over anhydrous $Na_2SO_4$. The filtrate was concentrated under reduced pressure and the resulting mixture was concentrated under reduced pressure, then the residue was purified by reversed-phase flash chromatography with the following conditions: (column, C18 silica gel; mobile phase, MeCN in Water (0.1% FA), 10% to 50% gradient in 40 min; detector, UV 254 nm) resulting in methyl 2-(4-cyano-5-methyl-2-oxo-1H-quinolin-3-yl)acetate (300 mg, 74.01%).

LCMS (ES, m/z): 257 $[M+H]^+$.

(4-Cyano-5-methyl-2-oxo-1H-quinolin-3-yl)acetic acid. A mixture of methyl 2-(4-cyano-5-methyl-2-oxo-1H-quinolin-3-yl) acetate (500 mg, 1.95 mmol, 1 equiv) and LiOH (140.19 mg, 5.85 mmol, 3 equiv) in MeOH (5 mL) was stirred for 2 h at room temperature under air atmosphere. The resulting mixture was concentrated under reduced pressure and the residue was purified by trituration with MeCN resulting in (4-cyano-5-methyl-2-oxo-1H-quinolin-3-yl) acetic acid). LCMS (ES, m/z): 243 $[M+H]^+$.

N-[(1S)-1-(5-bromopyridin-2-yl)ethyl]-2-(4-cyano-5-methyl-2-oxo-1H-quinolin-3-yl)acetamide. A mixture of (4-cyano-5-methyl-2-oxo-1H-quinolin-3-yl)acetic acid (100 mg, 0.4 mmol, 1 equiv), (1S)-1-(5-bromopyridin-2-yl) ethanamine (99.61 mg, 0.50 mmol, 1.2 equiv), EDCI (102.88 mg, 0.54 mmol, 1.3 equiv) and DMAP (25.22 mg, 0.21 mmol, 0.5 equiv) in DCM (5 mL) was stirred for overnight at room temperature under air atmosphere. The resulting mixture was concentrated under reduced pressure and the residue was purified by reversed-phase flash chromatography with the following conditions: (column, C18 silica gel; mobile phase, MeCN in water (0.1% FA), 10% to 50% gradient in 40 min; detector, UV 254 nm) resulting in N-[(1S)-1-(5-bromopyridin-2-yl)ethyl]-2-(4-cyano-5-methyl-2-oxo-1H-quinolin-3-yl)acetamide (100 mg, 56.96%). LCMS (ES, m/z): 425 $[M+H]^+$.

2-(4-cyano-5-methyl-2-oxo-1H-quinolin-3-yl)-N-[(1S)-1-(5-cyanopyridin-2-yl)ethyl]acetamide. A mixture of N-[(1S)-1-(5-bromopyridin-2-yl)ethyl]-2-(4-cyano-5-methyl-2-oxo-1H-quinolin-3-yl)acetamide (100 mg, 0.2 mmol, 1 equiv), Zn(CN)2 (55.22 mg, 0.47 mmol, 2 equiv) and $Pd(dppf)Cl_2$ (34.41 mg, 0.05 mmol, 0.2 equiv) in DMSO (5 mL) was stirred for 2 h at 120° C. under argon atmosphere. The resulting mixture was diluted with water. The resulting mixture was extracted with EtOAc. The combined organic layers were washed with water, dried over anhydrous $Na_2SO_4$. The filtrate was concentrated under reduced pressure and the residue was purified by reversed-phase flash chromatography with the following conditions: (column, C18 silica gel; mobile phase, MeCN in water (0.1% FA), 10% to 50% gradient in 40 min; detector, UV 254 nm) resulting in 2-(4-cyano-5-methyl-2-oxo-1H-quinolin-3-yl)-N-[(1S)-1-(5-cyanopyridin-2-yl)ethyl]acetamide (44.1 mg, 50.50%). LCMS (ES, m/z): 372.15 $[M+H]^+$. $^1H$ NMR (300 MHz, DMSO-d6) δ 12.39 (d, J=7.8 Hz, $^1H$), 8.98 (d, J=1.2, $^1H$), 8.83 (d, J=7.2 Hz, $^1H$), 8.28-8.25 (m, $^1H$), 7.64 (d, J=8.1 Hz, $^1H$), 7.49-7.44 (m, $^1H$), 7.27 (d, J=8.1 Hz, $^1H$), 7.12 (d, J=7.5 Hz, $^1H$), 5.00-4.95 (m, $^1H$), 3.83 (s, $^2H$), 2.83 (s, $^3H$), 1.43 (d, J=7.2 Hz, $^3H$).

N-[(1R)-1-(5-Bromopyridin-2-yl)ethyl]-2-(4-cyano-5-methyl-2-oxo-1H-quinolin-3-yl) acetamide. A mixture of (4-cyano-5-methyl-2-oxo-1H-quinolin-3-yl)acetic acid (100 mg, 0.413 mmol, 1 equiv), (1R)-1-(5-bromopyridin-2-yl) ethanamine (99.61 mg, 0.496 mmol, 1.2 equiv), EDCI (94.97 mg, 0.50 mmol, 1.2 equiv) and DMAP (25.22 mg, 0.21 mmol, 0.5 equiv) in DCM (5 mL) was stirred for overnight at room temperature under air atmosphere. The resulting mixture was concentrated under reduced pressure and the residue was purified by reversed-phase flash chromatography with the following conditions: (column, C18 silica gel; mobile phase, MeCN in water (0.1% FA), 10% to 50% gradient in 40 min; detector, UV 254 nm) resulting in N-[(1R)-1-(5-bromopyridin-2-yl)ethyl]-2-(4-cyano-5-methyl-2-oxo-1H-quinolin-3-yl) acetamide (100 mg, 56.96%). LCMS (ES, m/z): 425 $[M+H]^+$.

2-(4-cyano-5-methyl-2-oxo-1H-quinolin-3-yl)-N-[(1R)-1-(5-cyanopyridin-2-yl)ethyl]acetamide. A mixture of N-[(1R)-1-(5-bromopyridin-2-yl)ethyl]-2-(4-cyano-5-methyl-2-oxo-1H-quinolin-3-yl) acetamide (100 mg, 0.2 mmol, 1 equiv), $Zn(CN)_2$ (55.22 mg, 0.47 mmol, 2 equiv) and Pd(dppf) $Cl_2$ (34.41 mg, 0.047 mmol, 0.2 equiv) in DMSO (5 mL) was stirred for 2 h at 120° C. under argon atmosphere. The resulting mixture was diluted with water. The resulting mixture was extracted with EtOAc. The combined organic layers were washed with water and dried over anhydrous $Na_2SO_4$. The filtrate was concentrated under reduced pressure and the residue was purified by reversed-phase flash chromatography with the following conditions: (column, C18 silica gel; mobile phase, MeCN in Water (0.1% FA), 10% to 50% gradient in 40 min; detector, UV 254 nm). resulting in 2-(4-cyano-5-methyl-2-oxo-1H-quinolin-3-yl)-N-[(1R)-1-(5-cyanopyridin-2-yl)ethyl]acetamide (34.3 mg, 39.28%). LCMS (ES, m/z): 370.05 $[M-H]^-$. $^1H$ NMR (300 MHz, DMSO-d6) δ 12.40 (s, $^1H$), 8.97 (d, J=2.1 Hz, $^1H$), 8.82 (d, J=7.2 Hz, $^1H$), 8.28-8.25 (m, $^1H$), 7.64 (d, J=8.1 Hz, $^1H$), 7.49-7.43 (m, $^1H$), 7.27 (d, J=8.1 Hz, $^1H$), 7.11 (d, J=7.5 Hz, $^1H$), 5.03-4.93 (m, $^1H$), 3.83 (s, $^2H$), 2.82 (s, $^3H$), 1.43 (d, J=7.2 Hz, $^3H$).

(Compound 1099 and 1098)

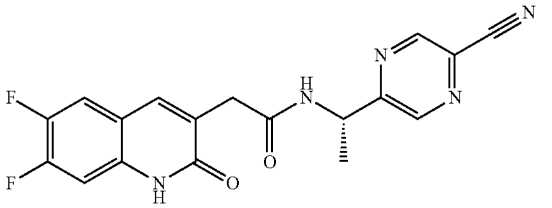

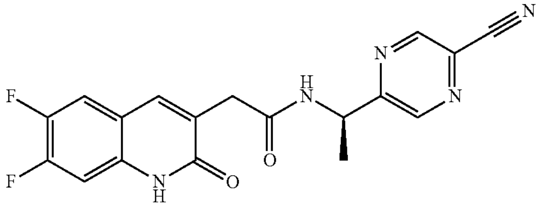

(S)-N-(1-(5-cyanopyrazin-2-yl) ethyl)-2-(6,7-difluoro-2-oxo-1,2-dihydroquinolin-3-yl) acetamide and (R)-N-(1-(5-cyanopyrazin-2-yl)ethyl)-2-(6,7-difluoro-2-oxo-1,2-dihydroquinolin-3-yl)acetamide (2-Amino-4, 5-difluorophenyl) methanol. $BH_3$-THF (54 mL, 1M in THF solvent, 53.434 mmol, 2.00 equiv) was added dropwise to a stirred solution of methyl 2-amino-4, 5-difluorobenzoate (5.00 g, 26.72 mmol, 1.00 equiv) in THF (50 mL) was added at 0° C. under nitrogen atmosphere. The resulting mixture was stirred for 2 hrs at 0° C. under nitrogen atmosphere. The reaction was quenched by the addition of MeOH (100 mL) at 0° C. The residue was purified by silica gel column chromatography to afford (2-amino-4,5-difluorophenyl) methanol (4.05 g, 95.25%). LCMS (ES, m/z): 160 $[M+H]^+$ 2-Amino-4, 5-difluorobenzaldehyde. To a stirred solution of (2-amino-4,5-difluorophenyl) methanol (4.00 g, 25.14 mmol, 1.00 equiv) in DCM (40 mL) was added $MnO_2$ (4.37 g, 50.27 mmol, 2.00 equiv) dropwise at room temperature under nitrogen atmosphere. The resulting mixture was stirred for 4 hrs at 40° C. under nitrogen atmosphere. The resulting mixture was filtered, the filter cake was washed with EtOAc. The filtrate was concentrated under reduced pressure and the residue was purified by silica gel column chromatography to afford 2-amino-4,5-difluorobenzaldehyde (3.00 g, 75.96%). LCMS (ES, m/z): 158 $[M+H]^+$ Di-tert-butyl 2-((2-amino-4,5-difluorophenyl)(hydroxy) methyl) succinate. LDA (19.09 mL, 2M in THF solvent, 38.19 mmol, 3.00 equiv) was added dropwise at To a stirred solution of di-tert-butyl succinate (5.86 g, 25.46 mmol, 2.00 equiv) in THF (30 mL) −78° C. under argon atmosphere. The resulting mixture was stirred for 1 h at −78° C. under argon atmosphere. To the above mixture was added 2-amino-4,5-difluorobenzaldehyde (2.00 g, 12.73 mmol, 1.00 equiv) and $ZnCl_2$ (18.18 mL, 0.7M in THF solvent, 12.73 mmol, 1.00 equiv) dropwise at −78° C. The resulting mixture was stirred for additional 1 h at −78° C. The reaction was quenched by the addition of saturated $NH_4Cl$ (aq.) at −78° C. The resulting mixture was extracted with EtOAc. The combined organic layers were washed with brine and dried over anhydrous $Na_2SO_4$. The filtrate was concentrated under reduced pressure and the residue was purified by silica gel column chromatography to afford di-tert-butyl 2-((2-amino-4,5-difluorophenyl)(hydroxy)methyl)succinate (2.1 g, 42.58%). LCMS (ES, m/z): 388 $[M+H]^+$ 2-(6,7-difluoro-2-oxo-1,2-dihydroquinolin-3-yl) acetic acid. 4M HCl (aq.) (10 mL, 40 mmol) dropwise to a stirred solution of di-tert-butyl 2-((2-amino-4,5-difluorophenyl)(hydroxy)methyl)succinate (2.00 g, 5.16 mmol, 1.00 equiv) in dioxane (10 mL) at room temperature under nitrogen atmosphere. The resulting mixture was stirred for overnight at 80° C. under nitrogen atmosphere. The mixture was basified to pH 5 with saturated $NaHCO_3$ (aq.). The precipitated solids were collected by filtration and washed with MeCN resulting in 2-(6,7-difluoro-2-oxo-1,2-dihydroquinolin-3-yl)acetic acid (1.00 g, 80.99%). LCMS (ES, m/z): 240 $[M+H]^+$ N-(1-(5-cyanopyrazin-2-yl)ethyl)-2-(6,7-difluoro-2-oxo-1,2-dihydroquinolin-3-yl) acetamide. DIEA (202.64 mg, 1.567 mmol, 2.50 equiv) and 5-(1-aminoethyl)pyrazine-2-carbonitrile (200 mg, crude) to a stirred solution of 2-(6,7-difluoro-2-oxo-1,2-dihydroquinolin-3-yl)acetic acid (150 mg, 0.63 mmol, 1.00 equiv) and EDCI (180.34 mg, 0.94 mmol, 1.50 equiv) in DMF (1.5 mL) at 0° C. under nitrogen atmosphere. HOBt (101.69 mg, 0.752 mmol, 1.20 equiv) was added to the above mixture at 0° C. The resulting mixture was stirred for 2 hrs at room temperature under nitrogen atmosphere. The resulting mixture was diluted with water. The resulting mixture was extracted with EtOAc. The combined organic layers were washed with brine, dried over anhydrous $Na_2SO_4$. The filtrate was concentrated under reduced pressure and purified by Prep-TLC (EA) to afford the crude product (200 mg, crude). It was purified by reversed-phase flash chromatography with the following conditions: (Column: C18 spherical 20-35 um, 80 g; Mobile Phase A: Water (0.1% FA), Mobile Phase B: ACN; Flow rate: 40 mL/min; Gradient: 30% B to 70% B in 30 min; 254/220 nm; RT1:20 min) to afford N-(1-(5-cyanopyrazin-2-yl)ethyl)-2-(6,7-difluoro-2-oxo-1,2-dihydroquinolin-3-yl) acetamide (150 mg, 64.76%). LCMS (ES, m/z): 370 $[M+H]^+$ (S)—N-(1-(5-cyanopyrazin-2-yl)ethyl)-2-(6,7-difluoro-2-oxo-1,2-dihydroquinolin-3-yl) acetamide. The N-(1-(5-cyanopyrazin-2-yl)ethyl)-2-(6,7-difluoro-2-oxo-1,2-dihydroquinolin-3-yl)acetamide (140 mg, 0.4 mmol, 1.00 equiv) was purified by Prep-HPLC with the following conditions (Column: CHIRAL ART Cellulose-SZ 3*25 cm, 5 μm; Mobile Phase A: Hex(10 mM $NH_3$-MeOH), Mobile Phase B: EtOH-HPLC; Flow rate: 40 mL/min; Gradient: isocratic 30; Wave Length: 272/230 nm; RT1(min): 11.015; RT2 (min): 13.205; Sample Solvent: DMSO; Injection Volume: 0.35 mL; Number Of Runs: 10 min) to afford (S)—N-(1-(5-cyanopyrazin-2-yl)ethyl)-2-(6,7-difluoro-2-oxo-1,2-dihydroquinolin-3-yl) acetamide (40 mg, 27.74%). LCMS (ES, m/z): 370 $[M+H]+^1H$ NMR (400 MHz, DMSO-$d_6$) δ 11.98 (s, $^1H$), 9.16 (d, J=1.2 Hz, $^1H$), 8.93 (d, J=1.2 Hz, $^1H$), 8.76 (d, J=6.8 Hz, $^1H$), 7.81-7.76 (m, $^2H$), 7.22 (dd, J=11.6, 7.2 Hz, $^1H$), 5.06-4.99 (m, $^1H$), 3.45 (dd, J=28.8, 15.2 Hz, $^2H$), 1.45 (d, J=7.2 Hz, $^3H$). $^{19}F$ NMR (377 MHz, DMSO-$d_6$) δ −134.35 ($^1F$), −145.61 ($^1F$).

(R)—N-(1-(5-cyanopyrazin-2-yl)ethyl)-2-(6,7-difluoro-2-oxo-1,2-dihydroquinolin-3-yl)acetamide. The N-(1-(5-cyanopyrazin-2-yl)ethyl)-2-(6,7-difluoro-2-oxo-1,2-dihydroquinolin-3-yl) acetamide (140 mg, 0.4 mmol, 1.00 equiv) was purified by Prep-HPLC with the following conditions (Column: CHIRAL ART Cellulose-SZ 3*25 cm, 5 μm; Mobile Phase A: Hex(10 mM $NH_3$-MeOH), Mobile Phase B: EtOH-HPLC; Flow rate: 40 mL/min; Gradient: isocratic 30; Wave Length: 272/230 nm; RT1(min): 11.015; RT2 (min): 13.21; Sample Solvent: DMSO; Injection Volume: 0.35 mL; Number Of Runs: 10) to afford (R)—N-(1-(5-cyanopyrazin-2-yl)ethyl)-2-(6,7-difluoro-2-oxo-1,2-dihydroquinolin-3-yl)acetamide (36 mg, 25.35%). LCMS (ES, m/z): 370 $[M+H]^+$ $^1H$ NMR (400 MHz, DMSO-$d_6$) δ 11.98

(s, $^1$H), 9.16 (d, J=1.2 Hz, $^1$H), 8.93 (d, J=1.2 Hz, $^1$H), 8.76 (d, J=6.8 Hz, $^1$H), 7.81-7.76 (m, $^2$H), 7.22 (dd, J=11.6, 7.2 Hz, $^1$H), 5.06-4.99 (m, $^1$H), 3.45 (dd, J=28.8, 15.2 Hz, $^2$H), 1.45 (d, J=7.2 Hz, $^3$H). $^{19}$F NMR (376 MHz, DMSO-$d_6$) δ −134.35 ($^1$F), −145.61 ($^1$F).

(Compound 418)

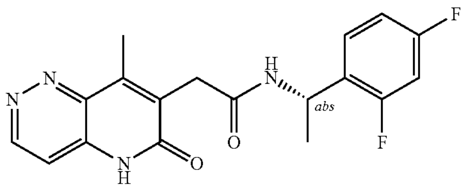

N-[(1S)-1-(2,4-difluorophenyl)ethyl]-2-{8-methyl-6-oxo-5H-pyrido[3,2-c]pyridazin-7-yl}acetamide N-(3-bromopyridazin-4-yl)-2,2-dimethylpropanamide. A solution of 3-bromopyridazin-4-amine (900 mg, 5.172 mmol, 1 equiv) and 2,2-dimethylpropanoyl chloride (623.7 mg, 5.17 mmol, 1 equiv), TEA (785.11 mg, 7.76 mmol, 1.5 equiv) in DCM (10 mL) was stirred for 1.5 h at room temperature under air atmosphere. The resulting mixture was concentrated under reduced pressure and purified by silica gel column chromatography to afford N-(3-bromopyridazin-4-yl)-2,2-dimethylpropanamide (900 mg, 67.41%). LCMS (ES, m/z): 258 [M+H]$^+$ N-(3-acetylpyridazin-4-yl)-2,2-dimethylpropanamide. NaH (125.51 mg, 5.23 mmol, 1.5 equiv) to a stirred solution of N-(3-bromopyridazin-4-yl)-2,2-dimethylpropanamide (900 mg, 3.5 mmol, 1 equiv) in THF (10 mL) was added at 0° C. under argon atmosphere. The resulting mixture was stirred for 30 min at 0° C. under argon atmosphere. To the above mixture was added n-BuLi in hexanes (335.04 mg, 5.23 mmol, 1.5 equiv) dropwise at −78° C. The resulting mixture was stirred for additional 30 min at −78° C. To the above mixture was added N-methoxy-N-methylacetamide (1438.23 mg, 13.95 mmol, 4 equiv) at −78° C. The resulting mixture was stirred for additional 1 h at −78° C. The reaction was quenched with $NH_4Cl$ (aq.) at 0° C. The resulting mixture was extracted with EtOAc. The combined organic layers were concentrated under reduced pressure and purified by silica gel column chromatography to afford N-(3-acetylpyridazin-4-yl)-2,2-dimethylpropanamide (480 mg, 62.22%). LCMS (ES, m/z): 222 [M+H]$^+$ 1,4-Di-tert-butyl 2-{1-[4-(2,2-dimethylpropanamido)pyridazin-3-yl]-1-hydroxyethyl}-butanedioate. LDA (in 2M THF) (697.2 mg, 6.507 mmol, 3 equiv) To a stirred solution of 1,4-di-tert-butyl butanedioate (999.24 mg, 4.338 mmol, 2 equiv) in THF (5 mL) were added dropwise at −78° C. under argon atmosphere. The resulting mixture was stirred for 30 min at −78° C. under argon atmosphere. To the above mixture was added N-(3-acetylpyridazin-4-yl)-2,2-dimethylpropanamide (480 mg, 2.17 mmol, 1 equiv) and $ZnCl_2$ (295.64 mg, 2.17 mmol, 1 equiv) at −78° C. The resulting mixture was stirred for additional 1 h at −78° C. and quenched with saturated $NH_4Cl$ (aq.) at 0° C. The resulting mixture was extracted with EtOAc. The combined organic layers were concentrated under reduced pressure and purified by silica gel column chromatography to afford 1,4-di-tert-butyl 2-{1-[4-(2,2-dimethylpropanamido)pyridazin-3-yl]-1-hydroxyethyl}butanedioate (800 mg, 81.66%). LCMS (ES, m/z): 452[M+H]$^+$ {8-Methyl-6-oxo-5H-pyrido[3,2-c]pyridazin-7-yl}acetic acid. A solution of 1,4-di-tert-butyl 2-{1-[4-(2,2-dimethylpropanamido)pyridazin-3-yl]-1-hydroxyethyl}butanedioate (350 mg, 0.775 mmol, 1 equiv) and HCl (6 M) (3 mL) in dioxane (3 mL) was stirred for overnight at 90° C. under air atmosphere. The resulting mixture was concentrated under vacuum. The crude product was used in the next step directly without further purification. LCMS (ES, m/z): 220 [M+H]+

N-[(1S)-1-(2,4-Difluorophenyl)ethyl]-2-{8-methyl-6-oxo-5H-pyrido[3,2-c]pyridazin-7-yl}acetamide. A solution of {8-methyl-6-oxo-5H-pyrido[3,2-c]pyridazin-7-yl}acetic acid (120 mg, 0.5 mmol, 1 equiv) and (1S)-1-(2,4-difluorophenyl)ethanamine (94.64 mg, 0.6 mmol, 1.1 equiv), EDCI (125.93 mg, 0.66 mmol, 1.2 equiv), HOBT (88.77 mg, 0.66 mmol, 1.2 equiv), and DIEA (283.02 mg, 2.19 mmol, 4 equiv) in DMF (1 mL) was stirred for 2 h at room temperature under air atmosphere. The resulting mixture was diluted with water and extracted with EtOAc. The combined organic layers were concentrated under reduced pressure and purified by Prep-HPLC with the following conditions (Column: XBridge Shield RP18 OBD Column, 19*150 mm, 5 μm; Mobile Phase A: Water(10 mmol/L $NH_4HCO_3$), Mobile Phase B: ACN; Flow rate: 25 mL/min; Gradient: 20% B to 40% B in 8 min, 40% B; Wave Length: 254 nm; $RT_1$(min): 6.18; Number Of Runs: 0) to afford N-[(1S)-1-(2,4-difluorophenyl)ethyl]-2-{8-methyl-6-oxo-5H-pyrido[3,2-c]pyridazin-7-yl}acetamide (33.5 mg, 17.08%). LCMS (ES, m/z): 359.10 [M+H]$^+$ $^1$H NMR (400 MHz, DMSO-$d_6$) δ 12.09 (s, 1H), 9.11 (d, J=6.0, 1H), 8.55 (d, J=7.6 Hz, 1H), 7.50-7.44 (m, 1H), 7.36 (d, J=6.0, 1H), 7.19-7.14 (m, 1H), 7.08-7.04 (m, 1H), 5.10-5.06 (m, 1H), 3.66 (s, 2H), 2.57 (s, 3H), 1.36 (d, J=6.8 Hz, 3H).

(Compound 135)

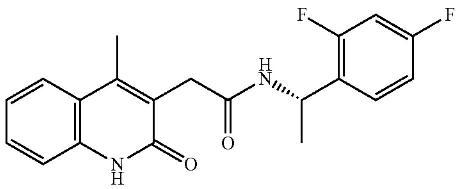

N-[(1S)-1-(2,4-difluorophenyl)ethyl]-2-(4-methyl-2-oxo-1H-quinolin-3-yl)acetamide Acetoacetanilide. Into a 250-mL round-bottom flask, was placed aniline (7.20 g, 77.31 mmol, 1.00 equiv), methyl acetoacetate (8.98 g, 77.31 mmol, 1.00 equiv), Toluene (100 mL). The reaction mixture was stirred for 3 hr at 120 degrees C. The reaction mixture was extracted with ethyl acetate. The residue was purified by silica gel column chromatography to afford 5 g (36.50%) of acetoacetanilide. LCMS (ES, m/z): 178 [M+H]$^+$.

Methyl 4-oxo-3-(phenylcarbamoyl)pentanoate. Into a 100-mL round-bottom flask, was placed acetoacetanilide (2.16 g, 12.19 mmol, 1.00 equiv), methyl 2-bromoacetate (1.77 g, 11.57 mmol, 0.95 equiv), THF (20.00 mL), NaH (877.55 mg, 36.5 mmol, 3.00 equiv). The reaction mixture was stirred for 2 hr at room temperature. The reaction mixture was extracted with ethyl acetate and the residue was purified by silica gel column chromatography to afford 1.8 g (59.24%) of methyl 4-oxo-3-(phenylcarbamoyl)pentanoate. LCMS (ES, m/z): 250 [M+H]$^+$.

Methyl 2-(4-methyl-2-oxo-1H-quinolin-3-yl)acetate. Into a 8-mL vial, was placed methyl 4-oxo-3-(phenylcarbamoyl)

pentanoate (400.00 mg, 1.605 mmol, 1.00 equiv), PPA (4.00 mL, 73.027 mmol, 45.51 equiv). The reaction mixture was stirred for 1 hr at 120 degrees C. The reaction was then quenched by the addition of 20 mL of water/ice. The residue purified by silica gel column chromatography to afford in 200 mg (53.90%) of methyl 2-(4-methyl-2-oxo-1H-quinolin-3-yl)acetate. LCMS (ES, m/z): 232 $[M+H]^+$.

(4-Methyl-2-oxo-1H-quinolin-3-yl)acetic acid. To a stirred solution of methyl 2-(4-methyl-2-oxo-1H-quinolin-3-yl)acetate (750 mg, 3.243 mmol, 1 equiv) and $H_2O$ (4 mL) in MeOH (4 mL) were added LiOH (310.70 mg, 12.972 mmol, 4 equiv) at room temperature under air atmosphere. The resulting mixture was stirred for 3 h at room temperature under air atmosphere. The mixture was adjusted to pH 4 with HCl (aq. 4M). The precipitated solids were collected by filtration and washed with MeCN to afford (4-methyl-2-oxo-1H-quinolin-3-yl)acetic acid (400 mg, 54.51%). LCMS (ES, m/z): 218 $[M+H]^+$.

N-[(1S)-1-(2,4-Difluorophenyl)ethyl]-2-(4-methyl-2-oxo-1H-quinolin-3-yl)acetamide. Into a 40-mL vial, was placed (4-methyl-2-oxo-1H-quinolin-3-yl)acetic acid (200.00 mg, 0.921 mmol, 1.00 equiv), HOBT (161.73 mg, 1.197 mmol, 1.30 equiv), EDCI (229.45 mg, 1.197 mmol, 1.30 equiv), DMF (4.00 mL, 0.055 mmol, 0.06 equiv), DIEA (475.98 mg, 3.683 mmol, 4.00 equiv), (1S)-1-(2,4-difluorophenyl)ethanamine (144.70 mg, 0.921 mmol, 1.00 equiv). The reaction mixture was stirred for 2 hr at room temperature. The residue was purified by silica gel column chromatography to afford in 120 mg (36.57%) of N-[(1S)-1-(2,4-difluorophenyl)ethyl]-2-(4-methyl-2-oxo-1H-quinolin-3-yl)acetamide. LCMS (ES, m/z): $357M+H]^+$. $^1H$ NMR (300 MHz, DMSO-$d_6$) δ 11.70 (s, 1H), 8.45 (d, J=7.5 Hz, 1H), 7.96-7.73 (m, 1H), 7.59-7.44 (m, 2H), 7.30-7.28 (m, 1H), 7.22-7.12 (m, 2H), 7.07-7.01 (m, 1H), 5.12-5.03 (m, 1H), 3.62 (s, 2H), 2.35 (s, 3H), 1.35 (d, J=6.9 Hz, 3H).

(Compound 446)

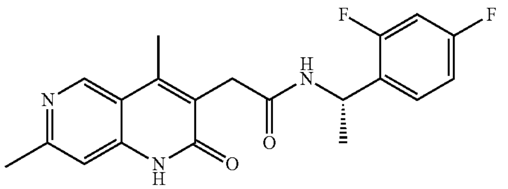

N-[(1S)-1-(2,4-difluorophenyl)ethyl]-2-(4,7-dimethyl-2-oxo-1H-1,6-naphthyridin-3-yl)acetamide Ethyl 4,7-dimethyl-2-oxo-1H-1,6-naphthyridine-3-carboxylate. To a stirred solution of 1-(4-amino-6-methylpyridin-3-yl)ethanone (400 mg, 2.663 mmol, 1 equiv) and diethyl malonate (1279.81 mg, 7.989 mmol, 3 equiv) was added piperidine (56.70 mg, 0.666 mmol, 0.25 equiv) dropwise at room temperature under air atmosphere. The resulting mixture was stirred for 4 h at 180° C. under microwave condition. The resulting mixture was concentrated under reduced pressure and the residue was purified by silica gel column chromatography to afford ethyl 4,7-dimethyl-2-oxo-1H-1,6-naphthyridine-3-carboxylate (400 mg, 60.98%). LCMS (ES, m/z): 247 $[M+H]^+$.

3-(Hydroxymethyl)-4,7-dimethyl-1H-1,6-naphthyridin-2-one.

To a stirred solution of ethyl 4,7-dimethyl-2-oxo-1H-1,6-naphthyridine-3-carboxylate (400 mg, 1.624 mmol, 1 equiv) in THF (4 mL, 49.371 mmol, 30.40 equiv) was added $LiAlH_4$ (67.80 mg, 1.786 mmol, 1.1 equiv) dropwise at 0° C. under air atmosphere. The resulting mixture was stirred for 2 h at room temperature under air atmosphere. The reaction was quenched with MeOH at room temperature. The resulting mixture was concentrated under reduced pressure and purified by silica gel column chromatography to afford 3-(hydroxymethyl)-4,7-dimethyl-1H-1,6-naphthyridin-2-one (220 mg, 66.32%). LCMS (ES, m/z): 205 $[M+H]^+$.

3-(Chloromethyl)-4,7-dimethyl-1H-1,6-naphthyridin-2-one. To a stirred solution of 3-(hydroxymethyl)-4,7-dimethyl-1H-1,6-naphthyridin-2-one (220 mg, 1.077 mmol, 1 equiv) in DCM (3 mL) was added $SOCl_2$ (192.22 mg, 1.615 mmol, 1.5 equiv) dropwise at 0° C. under air atmosphere. The resulting mixture was stirred for 2 h at room temperature under air atmosphere. The resulting mixture was concentrated under reduced pressure and the residue was purified by silica gel column chromatography to afford 3-(chloromethyl)-4,7-dimethyl-1H-1,6-naphthyridin-2-one (200 mg, 83.38%). LCMS (ES, m/z): 223 $[M+H]^+$.

Methyl 2-(4,7-dimethyl-2-oxo-1H-1,6-naphthyridin-3-yl) acetate. To a stirred solution of 3-(chloromethyl)-4,7-dimethyl-1H-1,6-naphthyridin-2-one (200 mg, 0.898 mmol, 1 equiv) and Pd(dppf)$Cl_2$ (65.72 mg, 0.090 mmol, 0.1 equiv) in MeOH (3 mL) was added $Et_3N$ (272.67 mg, 2.694 mmol, 3 equiv) dropwise at room temperature under air atmosphere. The resulting mixture was stirred for 2 h at 100° C. under carbon monoxide (15 atm) atmosphere. The resulting mixture was concentrated under reduced pressure and the residue was purified by silica gel column chromatography to afford methyl 2-(4,7-dimethyl-2-oxo-1H-1,6-naphthyridin-3-yl)acetate (120 mg, 54.25%). LCMS (ES, m/z): 247 $[M+H]^+$.

(4,7-Dimethyl-2-oxo-1H-1,6-naphthyridin-3-yl)acetic acid. To a stirred solution of methyl 2-(4,7-dimethyl-2-oxo-1H-1,6-naphthyridin-3-yl)acetate (120 mg, 0.487 mmol, 1 equiv) in MeOH/$H_2O$ (2 mL) was added LiOH (23.34 mg, 0.974 mmol, 2 equiv) dropwise at room temperature under air atmosphere. The resulting mixture was stirred for 2 h at room temperature under air atmosphere. The mixture was neutralized to pH 6 with HCl (4 M, aq.) and the resulting mixture was filtered, the filter cake was washed with acetonitrile to afford (4,7-dimethyl-2-oxo-1H-1,6-naphthyridin-3-yl)acetic acid (90 mg, 79.53%). LCMS (ES, m/z): 234 $[M+H]^+$.

N-[(1S)-1-(2,4-difluorophenyl)ethyl]-2-(4,7-dimethyl-2-oxo-1H-1,6-naphthyridin-3-yl)acetamide. To a stirred solution of (4,7-dimethyl-2-oxo-1H-1,6-naphthyridin-3-yl)acetic acid (90 mg, 0.388 mmol, 1 equiv) and HATU (176.82 mg, 0.466 mmol, 1.2 equiv) in DMF (1 mL) was added DIEA (200.35 mg, 1.552 mmol, 4 equiv) and (1S)-1-(2,4-difluorophenyl)ethanamine (73.09 mg, 0.466 mmol, 1.2 equiv) at room temperature under air atmosphere. The resulting mixture was stirred for 2 h at room temperature under air atmosphere. The resulting mixture was purified by reversed-phase flash chromatography with the following conditions: column, C18 silica gel; mobile phase, MeCN in Water (0.1% FA), 10% to 50% gradient in 10 min; detector, UV 254 nm. to afford N-[(1S)-1-(2,4-difluorophenyl)ethyl]-2-(4,7-dimethyl-2-oxo-1H-1,6-naphthyridin-3-yl)acetamide (25 mg, 17.37%). LCMS (ES, m/z): 372.00$[M+H]^+$. $^1H$ NMR (400 MHz, DMSO-d6) δ 11.91 (s, 1H), 8.82 (s, 1H), 8.48 (d, J=7.7 Hz, 1H), 7.75-7.44 (m, 1H), 7.19-7.13 (m, 1H), 7.07-6.97 (m, 2H), 5.08-5.04 (m, 1H), 3.59 (d, J=3.0 Hz, 2H), 2.50 (s, 3H), 2.38 (s, 3H), 1.34 (d, J=7.0 Hz, 3H).

(Compound 438)

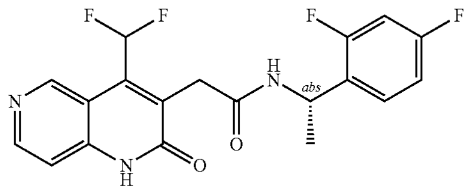

2-[4-(Difluoromethyl)-2-oxo-1H-1,6-naphthyridin-3-yl]-N-[(1S)-1-(2,4-difluorophenyl)ethyl]acetamide N-(3-bromopyridin-4-yl)-2,2-dimethylpropanamide. To a stirred solution of 4-amino-3-bromopyridine (5 g, 28.900 mmol, 1 equiv) in DCM (60 mL) were added 2,2-dimethylpropanoyl chloride (4.18 g, 34.680 mmol, 1.2 equiv) dropwise at 0° C. under air atmosphere. The resulting mixture was stirred for 2 h at room temperature under air atmosphere. The resulting mixture was concentrated under vacuum. The residue was purified by silica gel column chromatography to afford N-(3-bromopyridin-4-yl)-2,2-dimethylpropanamide (6.5 g, 87.47%). LCMS (ES, m/z): 257 $[M+H]^+$ N-[3-(2,2-difluoroacetyl)pyridin-4-yl]-2,2-dimethylpropanamide. To a stirred solution of N-(3-bromopyridin-4-yl)-2,2-dimethylpropanamide (2.5 g, 9.723 mmol, 1 equiv) in THE (40 mL) were added NaH (0.26 g, 10.695 mmol, 1.1 equiv) at 0° C. under argon atmosphere. The resulting mixture was stirred for 30 min at 0° C. under argon atmosphere. To the above mixture was added n-BuLi in hexanes (0.93 g, 14.585 mmol, 1.5 equiv) dropwise at −78° C. The resulting mixture was stirred for additional 30 min at −78° C. To the above mixture was added 2,2-difluoro-N-methoxy-N-methylacetamide (4.06 g, 29.169 mmol, 3 equiv) at −78° C. The resulting mixture was stirred for additional 2 h at −78° C. The reaction was quenched with sat. $NH_4Cl$ (aq.) at 0° C. The resulting mixture was extracted with EtOAc and the combined organic layers were concentrated under reduced pressure and purified by silica gel column chromatography to afford N-[3-(2,2-difluoroacetyl)pyridin-4-yl]-2,2-dimethylpropanamide (1.1 g, 44.15%). LCMS (ES, m/z): 257 $[M+H]^+$ 1,4-di-tert-butyl 2-{1-[4-(2,2-dimethylpropanamido)pyridin-3-yl]-2,2-difluoro-1-hydroxyethyl}butanedioate. To a stirred solution of 1,4-di-tert-butyl butanedioate (1.98 g, 8.586 mmol, 2 equiv) in THE (15 mL) were added LDA (0.92 g, 8.586 mmol, 2 equiv) dropwise at −78° C. under argon atmosphere. The resulting mixture was stirred for 30 min at −78° C. under argon atmosphere. To the above mixture was added N-[3-(2,2-difluoroacetyl)pyridin-4-yl]-2,2-dimethylpropanamide (1.1 g, 4.293 mmol, 1 equiv) and $ZnCl_2$ (0.58 g, 4.293 mmol, 1 equiv) at −78° C. The resulting mixture was stirred for additional 1 h at −78° C. The reaction was quenched with sat. $NH_4Cl$ (aq.) at room temperature. The resulting mixture was extracted with EtOAc. The combined organic layers were concentrated under reduced pressure and the residue was purified by silica gel column chromatography to afford 1,4-di-tert-butyl 2-{1-[4-(2,2-dimethylpropanamido)pyridin-3-yl]-2,2-difluoro-1-hydroxyethyl}butanedioate (1.2 g, 57.45%). LCMS (ES, m/z): 487 $[M+H]^+$

[4-(Difluoromethyl)-2-oxo-1H-1,6-naphthyridin-3-yl] acetic acid. A solution of 1,4-di-tert-butyl 2-{1-[4-(2,2-dimethylpropanamido)pyridin-3-yl]-2,2-difluoro-1-hydroxyethyl}butanedioate (1.2 g, 2.466 mmol, 1 equiv) and HCl (6M) (5 mL) in dioxane (5 mL) was stirred for overnight at 95° C. under air atmosphere. The resulting mixture was concentrated under vacuum. The crude product was used in the next step directly without further purification. LCMS (ES, m/z): 255 $[M+H]^+$ 2-[4-(Difluoromethyl)-2-oxo-1H-1,6-naphthyridin-3-yl]-N-[(1S)-1-(2,4-difluorophenyl)ethyl]acetamide. A solution of [4-(difluoromethyl)-2-oxo-1H-1,6-naphthyridin-3-yl] acetic acid (100 mg, 0.393 mmol, 1 equiv) and (1S)-1-(2,4-difluorophenyl)ethanamine (61.83 mg, 0.393 mmol, 1 equiv), EDCI (98.04 mg, 0.511 mmol, 1.3 equiv), HOBT (69.11 mg, 0.511 mmol, 1.3 equiv), DIEA (152.54 mg, 1.179 mmol, 3 equiv) in DMF (2 mL) was stirred for 2 h at room temperature under air atmosphere. The resulting mixture was diluted with water. The resulting mixture was extracted with EtOAc. The combined organic layers were concentrated under reduced pressure and the crude product was purified by Prep-HPLC with the following conditions (Column: XBridge Prep C18 OBD Column, 19*150 mm, 5 m; Mobile Phase A: Water(10 mmol/L $NH_4HCO_3$), Mobile Phase B: ACN; Flow rate: 25 mL/min; Gradient: 25% B to 43% B in 8 min; Wave Length: 254/220 nm; RT1(min): 6.94) to afford 2-[4-(difluoromethyl)-2-oxo-1H-1,6-naphthyridin-3-yl]-N-[(1S)-1-(2,4-difluorophenyl)ethyl]acetamide (61.7 mg, 39.87%). LCMS (ES, m/z): 394.10$[M+H]^+$ $^1H$ NMR (300 MHz, DMSO-$d_6$) δ 12.41 (s, 1H), 9.08 (s, 1H), 8.73 (d, J=7.8 Hz, 1H), 8.50 (d, J=5.7 Hz, 1H), 7.61-7.26 (m, 3H), 7.21-7.13 (m, 1H), 7.08-7.01 (m, 1H), 5.09-5.04 (m, 1H), 3.82 (s, 2H), 1.35 (d, J=6.9 Hz, 3H).

(Compound 445)

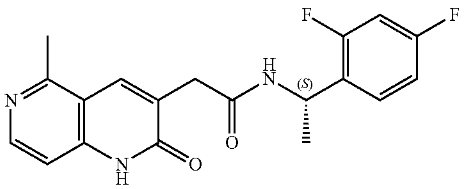

(S)-N(1-(2,4-difluorophenyl)ethyl)-2-(5-methyl-2-oxo-1,2-dihydro-1,6-naphthyridin-3-yl)acetamide 3-[(4-Amino-2-chloropyridin-3-yl)(hydroxy)methyl]-1-[(1S)-1-(2,4-difluorophenyl) ethyl]pyrrolidine-2,5-dione. To a stirred solution of 1-[(1S)-1-(2,4-difluorophenyl)ethyl] pyrrolidine-2,5-dione (4.00 g, 25.641 mmol, 1.00 equiv) in THF (50 mL) was added LDA (15 mL, 2M in THF solvent, 30.769 mmol, 1.20 equiv) at −78° C. The mixture was stirred at −78° C. for 1 h, then 4-amino-2-chloropyridine-3-carbaldehyde (2.62 g, 16.7 mmol, 1.00 equiv) was added, and followed by $ZnCl_2$ (36 mL, 0.7 M in THF solvent, 25.641 mmol, 1.00 equiv). The mixture was stirred at −78° C. for 2 h. After the completion of the reaction, added 200 mL saturated $NH_4Cl$ (aq.) to quench. The aqueous layer was extracted with EtOAc, the organic layer was combined, dried over anhydrous $Na_2SO_4$, filtrated, concentrated under reduced pressure. The residue was purified by flash-column to afford 3-[(4-amino-2-chloropyridin-3-yl)(hydroxy) methyl]-1-[(1S)-1-(2,4-difluorophenyl)ethyl]pyrrolidine-2,5-dione (2.20 g, 21.72%). LCMS (ES, m/z): 396 $[M+H]^+$ 2-(5-Chloro-2-oxo-1H-1,6-naphthyridin-3-yl)-N-[(1S)-1-(2,4-difluorophenyl)ethyl]acetamide. Into a 25 mL pressure tube reactor were added 3-[(4-amino-2-chloropyridin-3-yl)(hydroxy)methyl]-1-[(1S)-1-(2,4-difluorophenyl)ethyl]pyrrolidine-2,5-dione (1.00 g, 2.53 mmol, 1.00 equiv) and KOH (708 mg, 12.6 mmol, 5.0 equiv) EtOH (15 mL). The final reaction mixture was irradiated with microwave radiation for 30 min at 80° C. The mixture cooled to 0° C. The mixture was neutralized to pH 7 with 4M HCl (aq.). The resulting mixture was filtrated to afford 2-(5-chloro-2-oxo-1H-1,6-naphthyridin-3-yl)-N-[(1S)-1-(2,4-difluorophenyl)ethyl]acetamide (600 mg, 53.43%) LCMS (ES, m/z): 378 $[M+H]^+$ N-[(1S)-1-(2, 4-difluorophenyl)ethyl]-2-(5-methyl-2-oxo-1H-1,6-naphthyridin-3-yl)acetamide. To a stirred solution of 2-(5-chloro-2-oxo-1H-1,6-naphthyridin-3-yl)-N-[(1S)-1-(2,4-difluorophenyl)ethyl]acetamide (1.50 g, 3.979 mmol, 1.00 equiv) in dioxane (20 mL) was added trimethyl-1,3,5,2,4,6-trioxatriborinane (3.0 g, 23.874 mmol, 6.00 equiv), $K_2CO_3$ (1.65 g, 11.937 mmol, 3.00 equiv), Pd(dppf)$Cl_2$ (290.86 mg, 0.398 mmol, 0.10 equiv). The mixture was stirred at 80° C. overnight under $N_2$. The solvent was removed under vacuum and the residue was purified by silica gel column chromatography to afford N-[(1S)-1-(2,4-difluorophenyl)ethyl]-2-(5-methyl-2-oxo-1H-1,6-naphthyridin-3-yl)acetamide (705 mg, 49.64%). LCMS (ES, m/z): 358 $[M+H]^+$ $^1$H NMR (400 MHz, DMSO-$d_6$) δ 12.03 (s, 1H), 8.57 (d, J=7.6 Hz, 1H), 8.28 (d, J=5.7 Hz, 1H), 7.97 (s, 1H), 7.49 (td, J=8.7, 6.5 Hz, 1H), 7.18 (ddd, J=11.4, 9.2, 2.5 Hz, 1H), 7.05 (dd, J=8.6, 5.9 Hz, 2H), 5.11 (q, J=7.2 Hz, 1H), 3.46 (s, 2H), 2.63 (s, 3H), 2.54-2.48 (m, 2H), 1.36 (d, J=7.0 Hz, 3H).

(Compound 119)

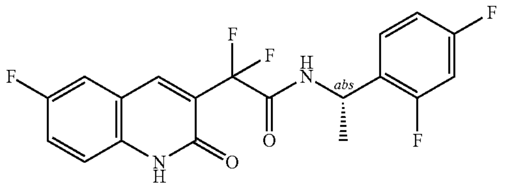

N-[(1S)-1-(2,4-difluorophenyl) ethyl]-2,2-difluoro-2-(6-fluoro-2-oxo-1H-quinolin-3-yl)acetamide Ethyl 2,2-difluoro-2-(6-fluoro-2-oxo-1H-quinolin-3-yl) acetate. Into a 40-mL round-bottomed flask purged and maintained with an inert atmosphere of argon, was placed 6-fluoro-1H-quinolin-2-one (490.00 mg, 3.003 mmol, 1.00 equiv), DMF (10.00 mL), acetone (10.00 mL), $Na_2CO_3$ (636.64 mg, 6.007 mmol, 2.00 equiv), ethyl 2,2-difluoro-2-iodoacetate (2.25 g, 9.010 mmol, 3.00 equiv). The final reaction mixture was irradiated with blue LED for 24 hr at room temperature. The reaction was then quenched by the addition of 50 mL of water. The reaction mixture was extracted with ethyl acetate and the organic layers combined and concentrated under vacuum. The residue purified by silica gel column chromatography to afford in 350 mg (40.86%) of ethyl 2,2-difluoro-2-(6-fluoro-2-oxo-1H-quinolin-3-yl) acetate. LCMS (ES, m/z): 286 $[M+H]^+$.

Difluoro (6-fluoro-2-oxo-1H-quinolin-3-yl) acetic acid. Into a 8 mL vial, was placed ethyl 2,2-difluoro-2-(6-fluoro-2-oxo-1H-quinolin-3-yl) acetate (200.00 mg, 0.701 mmol, 1.00 equiv), MeOH (0.50 mL), $H_2O$ (0.50 mL), LiOH (16.79 mg, 0.701 mmol, 1.00 equiv). The reaction mixture was stirred for 2 hr at room temperature. The resulting mixture was concentrated, water added and the pH of the solution was adjusted to 2 with HCl (1.0 M). The solids were collected by filtration resulting in 150 mg (83.18%) of difluoro (6-fluoro-2-oxo-1H-quinolin-3-yl) acetic acid. LCMS (ES, m/z): 258$[M+H]^+$.

N-[(1S)-1-(2,4-difluorophenyl) ethyl]-2,2-difluoro-2-(6-fluoro-2-oxo-1H-quinolin-3-yl) acetamide. Into a 8-mL vial, was placed difluoro(6-fluoro-2-oxo-1H-quinolin-3-yl) acetic acid (100.00 mg, 0.389 mmol, 1.00 equiv), DMF (1.00 mL), HATU (162.64 mg, 0.428 mmol, 1.1 equiv), (1S)-1-(2,4-difluorophenyl) ethanamine (67.22 mg, 0.428 mmol, 1.10 equiv), DIEA (150.77 mg, 1.167 mmol, 3 equiv). The reaction mixture was stirred for 2 hr at room temperature. The residue was purified by reversed-phase flash chromatography with the following conditions: (column, C18 silica gel; mobile phase, 0.1% HCOOH in ACN, 0% to 100% gradient in 60 min; detector, UV 254 nm) resulting in 50 mg (32.44%) of N-[(1S)-1-(2,4-difluorophenyl) ethyl]-2,2-difluoro-2-(6-fluoro-2-oxo-1H-quinolin-3-yl) acetamide. LCMS (ES, m/z): 396.90 $[M+H]^+$. $^1$H NMR (300 MHz, DMSO-$d_6$) δ 12.27 (s, 1H), 9.25 (d, J=7.8 Hz, 1H), 8.37 (s, 1H), 7.77-7.73 (m, 1H), 7.63-7.50 (m, 2H), 7.39-7.35 (m, 1H), 7.23-7.15 (m, 1H), 7.08-7.03 (m, 1H), 5.18 (t, J=7.2 Hz, 1H), 1.45 (d, J=6.9 Hz, 3H).

(S)-N-(1-(5-cyanopyrimidin-2-yl)ethyl)-2-(5,6-difluoro-4-methyl-2-oxo-1,2-dihydroquinolin-3-yl)acetamide (compound 1124):

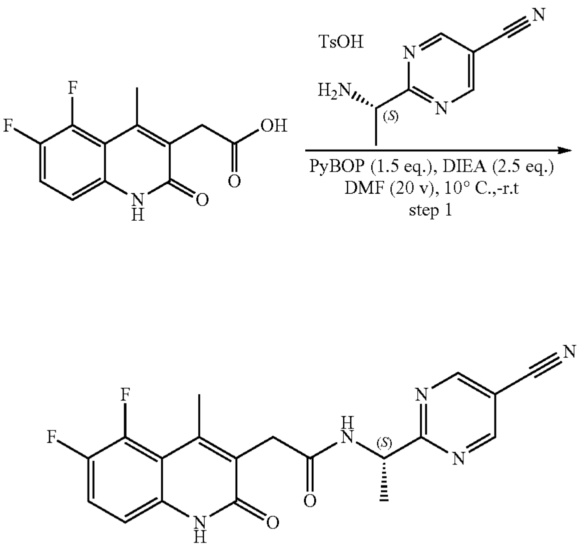

To a 1.0 L 3-necked round-bottom flask (S)-2-(1-aminoethyl)pyrimidine-5-carbonitrile 4-methylbenzenesulfonate (10.6 g, 33.2 mmol, 1.05 eq.), 2-(5,6-difluoro-4-methyl-2-oxo-1,2-dihydroquinolin-3-yl)acetic acid (8.0 g, 31.6 mmol, 1.00 eq.), DIEA (10.2 g, 79.1 mmol, 2.5 eq.), and PyBOP (24.7 g, 47.4 mmol, 1.5 eq.) in DMF (160 mL) at 10° C. The reaction solution was stirred for 3 hours at RT. The crude material was poured into water (800 mL), filtered, and purified by reverse-phasereverse-phase chromatography using a C18 column eluting with MeCN/Water (10 mmol/L $NH_4HCO_3$), followed by chiral SFC to afford (S)—N-(1-(5-cyanopyrimidin-2-yl)ethyl)-2-(5,6-difluoro-4-methyl-2-oxo-1,2-dihydroquinolin-3-yl)acetamide (5.0 g, 41.3%).

LCMS-: (ES, m/z): 384.0 $[M+H]^+$ $^1$H NMR: (300 MHz, DMSO, ppm) δ 11.92 (s, 1H), 9.28 (s, 2H), 8.59 (d, J=6.9 Hz, 1H), 7.62-7.53 (m, 1H), 7.13 (dd, J=9.0, 3.9 Hz, 1H), 5.05-4.95 (m, 1H), 3.80-3.62 (m, 2H), 2.48 (d, J=6.3 Hz, 3H), 1.45 (d, J=7.2 Hz, 3H). $^{19}$F NMR-: (300 MHz, DMSO, ppm), δ −139.21 (d, J=21.3 Hz, 1F), −146.98 (d, J=21.0 Hz, 1F).

(compound 2592 and 2593)

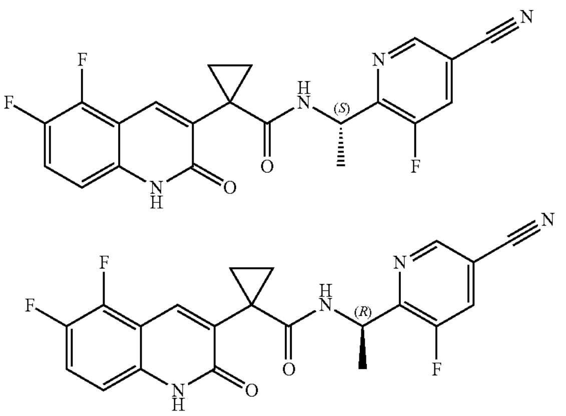

(S)-N-(1-(5-cyano-3-fluoropyridin-2-yl)ethyl)-1-(5,6-difluoro-2-oxo-1,2-dihydroquinolin-3-yl)cyclopane-1-carboxamide and (R)-N-(1-(5-cyano-3-fluoropyridin-2-yl)ethyl)-1-(5,6-difluoro-2-oxo-1,2-dihydroquinolin-3-yl)cyclopropane-1-carboxamide (R)—N-(1-(5-cyano-3-fluoropyridin-2-yl)ethyl)-1-(5,6-difluoro-2-oxo-1,2-dihydroquinolin-3-yl)cyclopropane-1-carboxamide: Under $N_2$, in a flask containing 1-(5,6-difluoro-2-oxo-1,2-dihydroquinolin-3-yl)cyclopropane-1-carboxylic acid (500.0 mg, 1.89 mmol, 1.0 eq.) in DMF, (5 mL) (R)-6-(1-aminoethyl)-5-fluoronicotinonitrile 4-methylbenzenesulfonate (699.63 mg, 2.26 mmol, 1.2 eq.), DIEA (730.0 mg, 5.65 mmol, 3.0 eq.), HOBT (382.1 mg, 2.83 mmol, 1.5 eq.), and EDCI (351.2 mg, 2.26 mmol, 1.2 eq.) were added. The reaction mixture was stirred at RT for 2 hours. The crude material was filtered and the filtrate was directly purified by DAC (0.1 M TFA/MeCN, 10-80%) to afford (R)—N-(1-(5-cyano-3-fluoropyridin-2-yl)ethyl)-1-(5,6-difluoro-2-oxo-1,2-dihydroquinolin-3-yl)cyclopropane-1-carboxamide (240 mg, 30%). LCMS-: (ESI, m/z): $[M+H]^+$=413.1. $^1$HNMR-(400 MHz, DMSO-$d_6$, ppm) δ 12.00 (s, 1H), 8.08 (s, 1H), 8.33 (dd, J=9.9, 1.7 Hz, 1H), 7.86 (s, 11H), 7.73 (d, J=7.3 Hz, 1H), 7.64-7.54 (m, 11H), 7.1-7.07 (m, 1H), 5.25 (p, J=7.2 Hz, 1H), 1.38 (ddd, J=10.1, 6.5, 3.7 Hz, 1H), 1.31 (d, J=7.0 Hz, 3H), 1.21 (ddd, J=9.6, 6.8, 4.1 Hz, 1H), 1.03 (ddd, J=10.8, 6.8, 4.0 Hz, 1H), 0.89 (ddd, J=9.8, 6.8, 3.9 Hz, 1H). $^{19}$FNMR (376 MHz, DMSO-$d_6$, ppm) δ −124.15, −146.76 (d, J=22.6 Hz, 1F), −148.08 (d, J=22.6 Hz, 1F).

N-(3,4-difluorophenyl)-2,2,2-trifluoroacetamide: Under $N_2$ atmosphere, in a 10 L 4-neck RBF 3,4-difluoroaniline (50.0 g, 380.3 mmol, 1.0 eq.) was added in DCM (500 mL). The mixture was cooled in an ice bath for 10 minutes. TFAA (87.86 g, 418.3 mmol, 1.1 eq.) was added dropwise over 60 minutes. The resulting solution was stirred for 2 hours at RT. The reaction mixture was diluted with water. The organic phase was washed with sat. $NaHCO_3$, followed by brine. The organic layer was concentrated under reduced pressure to afford N-(3,4-difluorophenyl)-2,2,2-trifluoroacetamide (83 g, 95%). $^1$H-NMR- (300 MHz, DMSO-$d_6$, ppm) S 11.45 (s, JH), 7.77 (ddd, J=13.6, 7.5, 2.2 Hz, 1H), 7.57-7.42 (m, 2H).

N-(3,4-difluoro-2-formylphenyl)-2,2,2-trifluoroacetamide: Under $N_2$ atmosphere, in a dried 3 L 4-neck RBF to was added N-(3,4-difluorophenyl)-2,2,2-trifluoroacetamide (80.0 g, 345.4 mmol, 1.0 eq.) in 2-MeTHF (800 mL) followed by TMEDA (41.1 g, 345.4 mmol, 1.0 eq.) was added and the reaction mixture was cooled to −70° C. A solution of n-BuLi (345.4 mL, 2.5 eq., 2.5 M in hexane) was added dropwise over 1 h. followed by DMF (50.5 g, 690.8 mmol, 2.0 eq.) dropwise addition over 40 minutes at −70° C. The solution was stirred for 30 minutes then slowly poured into 1 M critic acid (160 mL), diluted with MTBE (80 mL), and separated. The organic layer was washed with water until pH of 3-4 was obtained. The organic layer was washed with sat. $NaHCO_3$ to reach a pH of 8-9. The organic layer was washed with brine followed by n-heptane The suspension was stirred at 0° C. for 1 h to afford N-(3,4-difluoro-2-formylphenyl)-2,2,2-trifluoroacetamide (72.5 g, 80%). Q-NMR (300 MHz, DMSO-$d_6$, ppm) δ 11.90 (s, 1H), 10.19 (s, 1H), 7.90-7.84 (m, 2H), 6.08 (s, 2.87H), 3.71 (s, 8.74H).

Methyl 1-(1-(2,3-difluoro-6-(2,2,2-trifluoroacetamido)phenyl)-1-hydroxy-3-methoxy-3-oxopropan-2-yl)cyclopropane-1-carboxylate: Methyl 1-(2-methoxy-2-oxoethyl)cyclopropane-1-carboxylate (57.14 g, 1.2 eq.,) was dissolved in 2-Me-THF (1.4 L) in a 3 L 4-necks-RBF under $N_2$ atmosphere at −78° C. LDA (414.8 mL, 829.62 mmol, 3.0 eq., 2.0 M in THF) was added dropwise over 2 h and the reaction was stirred at −78° C. for 1 h. N-(3,4-difluoro-2-formylphenyl)-2,2,2-trifluoroacetamide (70.0 g, 276.5 mmol, 1.0 eq.) in THF (420 mL) was added dropwise over 1 h at −78° C.° C. and the resulting solution was stirred at −78° C. for 1 h. The reaction mixture was poured into an ice mixture of 3 M HCl (300 mL). The resulting mixture was extracted with EA. The combined organic layer was washed with brine and condensed to afford methyl 1-(1-(2,3-difluoro-6-(2,2,2-trifluoroacetamido)phenyl)-1-hydroxy-3-methoxy-3-oxopropan-2-yl)cyclopropane-1-carboxylate (70 g, 73%) which was directly used next step.

1-(5,6-Difluoro-2-oxo-1,2-dihydroquinolin-3-yl)cyclopropane-1-carboxylic acid: Methyl 1-(1-(2,3-difluoro-6-(2,2,2-trifluoroacetamido)phenyl)-1-hydroxy-3-methoxy-3-oxopropan-2-yl)cyclopropane-1-carboxylate (70 g, 164 mmol, 1 equiv.) was dissolved in 1,4-dioxane (1.0 L). 3 M HCl (1.0 L, 10 v) was added and the resulting mixture was stirred at 80° C. for 13 hours. The reaction was cooled to rt and poured into ice water (1.5 L) and stirred for 1 h. The crude material was filtered, rinsed with water, diluted with MeCN, and stirred at rt for 2 h. The precipitate was filtered, rinsed with water, and dried in vacuo to afford 1-(5,6-difluoro-2-oxo-1,2-dihydroquinolin-3-yl)cyclopropane-1-carboxylic acid (35.1 g, 80%). LCMS: (ESI, m/z): $[M+H]^+$ =266.0. $^1$H-NMR (400 MHz, DMSO-$d_6$, ppm) δ 12.17 (s, 1H), 11.99 (s, 1H), 7.82 (s, 1H), 7.57 (dt, J=10.6, 8.8 Hz, 1H), 7.11 (dt, J=9.3, 2.5 Hz, 1H), 1.40 (q, J=4.1 Hz, 2H), 1.13 (q, J=4.2 Hz, 2H). $^{19}$F-NMR (376 MHz, DMSO-$d_6$, ppm) δ −146.72 (d, J=21.5 Hz, 1F), −147.74 (d, J=21.5 Hz, 1F).

(S)—N-(1-(5-Cyano-3-fluoropyridin-2-yl)ethyl)-1-(5,6-difluoro-2-oxo-1,2-dihydroquinolin-3-yl)cyclopropane-1-carboxamide (compound 2592 and 2593): 1-(5,6-difluoro-2-oxo-1,2-dihydroquinolin-3-yl)cyclopropane-1-carboxylic acid (34.0 g, 119.1 mmol, 1.0 eq.), (S)-6-(1-aminoethyl)-5-fluoronicotinonitrile hydrochloride(35.8 g, 177.4 mmol, 1.2 eq.), DIEA (46.2 g, 357.3 mmol, 3.0 eq.), HOBT (24.1 g, 178.6 mmol, 1.5 eq.), and EDCI (27.7 g, 178.6 mmol, 1.2 eq.) were dissolved in DMF (340 mL) and the resulting mixture was stirred at RT under $N_2$ for 2 hours. The crude material was filtered and the filtrate was directly purified by DAC (0.1 M TFA/MeCN, 10-80%) to afford (S)—N-(1-(5-cyano-3-fluoropyridin-2-yl)ethyl)-1-(5,6-difluoro-2-oxo-1,2-dihydroquinolin-3-yl)cyclopropane-1-carboxamide (30 g, 56%). LCMS: (ESI, m/z): 463.0 [M+H]+$^1$H NMR (400 MHz, DMSO-$d_6$, ppm) δ 12.02 (s, 1H), 8.80 (s, 1H), 8.34

(dd, J=9.9, 1.7 Hz, 1H), 7.87 (s, 1H), 7.74 (d, J=7.3 Hz, 1H), 7.60 (dt, J=10.6, 8.8 Hz, 1H), 7.16-7.08 (m, 1H), 5.31-5.20 (m, 1H), 1.42-1.35 (m, 1H), 1.31 (d, J=7.0 Hz, 3H), 1.26-1.18 (m, 1H), 1.09-0.99 (m, 1H), 0.94-0.85 (m, 1H). $^{19}$F NMR (376 MHz, DMSO-$d_6$, ppm) δ −124.15 (s, 1F), −146.77 (d, J=21.6 Hz, 1F), −148.08 (d, J=21.8 Hz, 1F).

(compound 2594 and 2595)

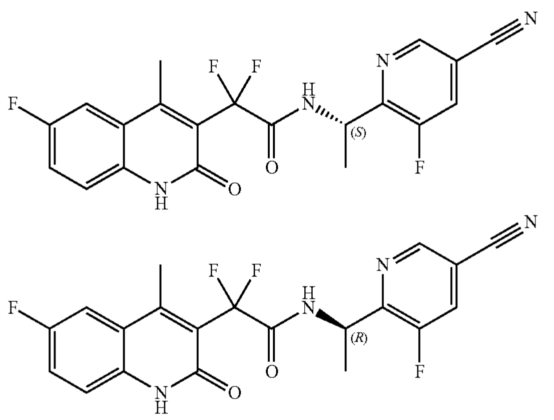

(R)-N-(1-(5-cyano-3-fluoropyridin-2-yl)ethyl)-2,2-difluoro-2-(6-fluoro-4-methyl-2-oxo-1,2-dihydroquinolin-3-yl)acetamide and (S)-N-(1-(5-Cyano-3-fluoropyridin-2-yl)ethyl)-2,2-difluoro-2-(6-fluoro-4-methyl-2-oxo-1,2-dihydroquinolin-3-yl)acetamide:

6-Fluoro-4-hydroxy-4-methyl-3,4-dihydroquinolin-2(1H)-one: To a stirred solution of 1-(2-amino-5-fluorophenyl)ethan-1-one(60.0 g, 0.39 mol, 1.00 eq.) in THF (600.0 mL) was added (2-(tert-butoxy)-2-oxoethyl)zinc(II) bromide (0.6 M) (780 mL, 0.47 mol, 1.2 eq.) dropwise at 25° C. under nitrogen atmosphere. The resulting mixture was stirred for 2 h at 70° C. The reaction mixture was quenched with water (500.0 mL) and stirred for 10 minutes at 0° C. The water layer was extracted with DCM, and the organic layer was washed with brine, dried over anhydrous $Na_2SO_4$, filtered, and concentrated under reduced pressure to afford 6-fluoro-4-hydroxy-4-methyl-3,4-dihydroquinolin-2(1H)-one (50 g, 78.5%). LCMS: (ES, m/z): 196.1 $[M+H]^+$ 6-Fluoro-4-methylquinolin-2(1H)-one: 6-fluoro-4-hydroxy-4-methyl-3,4-dihydroquinolin-2(1H)-one (50.0 g, 0.26 mol, 1.00 eq.) and KOH (72.8 g, 1.3 mol, 5.0 eq.) were dissolved in EtOH (500 mL). The resulting solution was stirred for 2 h at 80° C. The reaction was cooled to RT and quenched with water at 0° C. 2 M HCl was added to the aqueous phase to adjust the pH to 7, and the resulting solution was stirred for 10 minutes at 20° C. The crude material was filtered and the precipitate was washed with $H_2O$ to afford 6-fluoro-4-methylquinolin-2(1H)-one(41 g, 91.1%). LCMS: (ES, m/z): 178.1 $[M+H]^+$ Ethyl 2,2-difluoro-2-(6-fluoro-4-methyl-2-oxo-1,2-dihydroquinolin-3-yl)acetate: 6-fluoro-4-methylquinolin-2(1H)-one (41.0 g, 0.23 mol, 1.00 eq.), ethyl 2-bromo-2,2-difluoroacetate (138.7 g, 0.69 mmol, 3.0 eq.), $K_2HPO_4$ (120 g, 0.69 mmol, 3.0 eq.), CuI (8.74 g, 0.046 mol, 0.2 eq.), and 1,10-Phenanthroline (8.28 g, 0.046 mol, 0.2 eq.) were dissolved in MeCN (820.0 mL) under nitrogen atmosphere. The resulting solution was stirred at 110° C. for 36 hours. The reaction mixture was cooled to 20° C. and filtered. The filtrate was concentrated under reduced pressure and purified by column chromatography to afford ethyl 2,2-difluoro-2-(6-fluoro-4-methyl-2-oxo-1,2-dihydroquinolin-3-yl)acetate (18.0 g, 26%). LCMS: (ES, m/z): 300.1 $[M+H]^+$ 2,2-Difluoro-2-(6-fluoro-4-methyl-2-oxo-1,2-dihydroquinolin-3-yl)acetic acid: Ethyl 2,2-difluoro-2-(6-fluoro-4-methyl-2-oxo-1,2-dihydroquinolin-3-yl)acetate (18 g, 0.06 mol, 1.00 eq.) was dissolved in THF (180.0 mL). LiOH (7.2 g, 0.30 mol, 3.0 eq.) in water (180 mL) was added dropwise at 0° C. The resulting mixture was stirred for 2 h at 30° C. The reaction mixture was quenched with water (360.0 mL) and 2 M HCl to adjust to pH 2-3. The resulting mixture was stirred for 10 min at 20° C., filtered, and the precipitate was washed with $H_2O$ to afford 2,2-difluoro-2-(6-fluoro-4-methyl-2-oxo-1,2-dihydroquinolin-3-yl)acetic acid (15 g, 92.0%). LCMS: (ES, m/z): 272.1 $[M+H]^+$ (S)—N-(1-(5-Cyano-3-fluoropyridin-2-yl)ethyl)-2,2-difluoro-2-(6-fluoro-4-methyl-2-oxo-1,2-dihydroquinolin-3-yl)acetamide (compound 2594 and 2595): 2,2-Difluoro-2-(6-fluoro-4-methyl-2-oxo-1,2-dihydroquinolin-3-yl)acetic acid (2.3 g, 8.5 mmol, 1.00 eq.), (S)-6-(1-aminoethyl)-5-fluoronicotinonitrile hydrochloride (1.88 g, 9.35 mmol, 1.1 eq.), and DIEA (3.29 g, 25.5 mmol, 3.00 eq.) were dissolved in DMF (23.0 mL) at RT under nitrogen atmosphere and stirred for 30 minutes at RT. $T_3P$ (50% in EA) (8.1 g, 12.75 mmol, 1.5 eq.) was added dropwise for 30 min at 0° C. and the reaction was stirred for 1 h at RT under nitrogen atmosphere. The crude material was poured into ice-water, stirred for 30 minutes, filtered, and the precipitate washed with $H_2O$, followed by EA, and dried. The crude residue was purified by column chromatography, followed by an ISCO RPchromatographyWelch-C18-AQ 50*250 10 um column eluting with $CH_3CN$ in $H_2O$ (TFA (0.01%) to afford (S)—N-(1-(5-cyano-3-fluoropyridin-2-yl)ethyl)-2,2-difluoro-2-(6-fluoro-4-methyl-2-oxo-1,2-dihydroquinolin-3-yl)acetamide (2.1 g, 59.2%). LCMS: (ES, m/z): 419.0 $[M+H]^+$ $^1$H NMR (400 MHz, DMSO, ppm) δ 12.05 (s, 1H), 8.90-8.88 (m, 2H), 8.42 (dd, J=9.6, 1.6 Hz, 1H), 7.80 (dd, J=10.8, 2.8 Hz, 1H), 7.55-7.50 (m, 1H), 7.36 (dd, J=9.2, 5.2 Hz, 1H), 5.35-5.28 (m, 1H), 2.61 (d, J=3.2 Hz, 3H), 1.50 (d, J=6.8 Hz, 3H). $^{19}$F NMR (400 MHz, DMSO, ppm) δ −96.24 - −97.88 (m, 2F), −119.67 (s, 1F), 123.78 (s, 1F).

(R)—N-(1-(5-cyano-3-fluoropyridin-2-yl)ethyl)-2,2-difluoro-2-(6-fluoro-4-methyl-2-oxo-1,2-dihydroquinolin-3-yl)acetamide: (R)—N-(1-(5-cyano-3-fluoropyridin-2-yl) ethyl)-2,2-difluoro-2-(6-fluoro-4-methyl-2-oxo-1,2-dihydroquinolin-3-yl)acetamide: 2,2-difluoro-2-(6-fluoro-4-methyl-2-oxo-1,2-dihydroquinolin-3-yl)acetic acid (2.3 g, 8.5 mmol, 1.00 eq.), (R)-6-(1-aminoethyl)-5-fluoronicotinonitrile hydrochloride (3.15 g, 9.35 mmol, 1.1 eq.), and DIEA (3.29 g, 25.5 mmol, 3.00 eq.) were dissolved in DMF (23.0 mL) at RT under nitrogen and stirred for 30 min. $T_3P$ (50% in EA) (8.1 g, 12.75 mmol, 1.5 eq.) was added dropwise over 30 min at 0° C. The resulting solution was stirred for 1 h at RT under nitrogen. The reaction solution was poured into ice-water (50 mL) and stirred for 30 minutes, filtered and the precipitate was washed with $H_2O$, followed by EA, then dried. The crude residue was purified by column chromatography, eluting with PE/THF followed by an ISCO RP Welch-C18-AQ 50*250 10 um column eluting with $CH_3CN$ in $H_2O$+TFA(0.01%) to afford (R)—N-(1-(5-cyano-3-fluoropyridin-2-yl)ethyl)-2,2-difluoro-2-(6-fluoro-4-methyl-2-oxo-1,2-dihydroquinolin-3-yl)acetamide(2.2 g, 62.0%). LCMS: (ES, m/z): 419.0 $[M+H]^+$ $^1$H NMR (400 MHz, DMSO, ppm) δ 12.05 (s, 1H), 8.90-8.88 (m, 2H), 8.42 (dd, J=9.6, 1.6 Hz, 1H), 7.80 (dd, J=10.8, 2.8 Hz, 1H), 7.55-7.50 (m, 1H), 7.36 (dd, J=9.2, 5.2 Hz, 1H), 5.35-5.28 (m, 1H), 2.62 (d, J=3.2 Hz, 3H), 1.50 (d, J=6.8 Hz, 3H). $^{19}F$ NMR (400 MHz, DMSO, ppm) δ −96.24--97.88 (m, 2F), −119.66 (s, 1F), 123.78 (s, 1F).

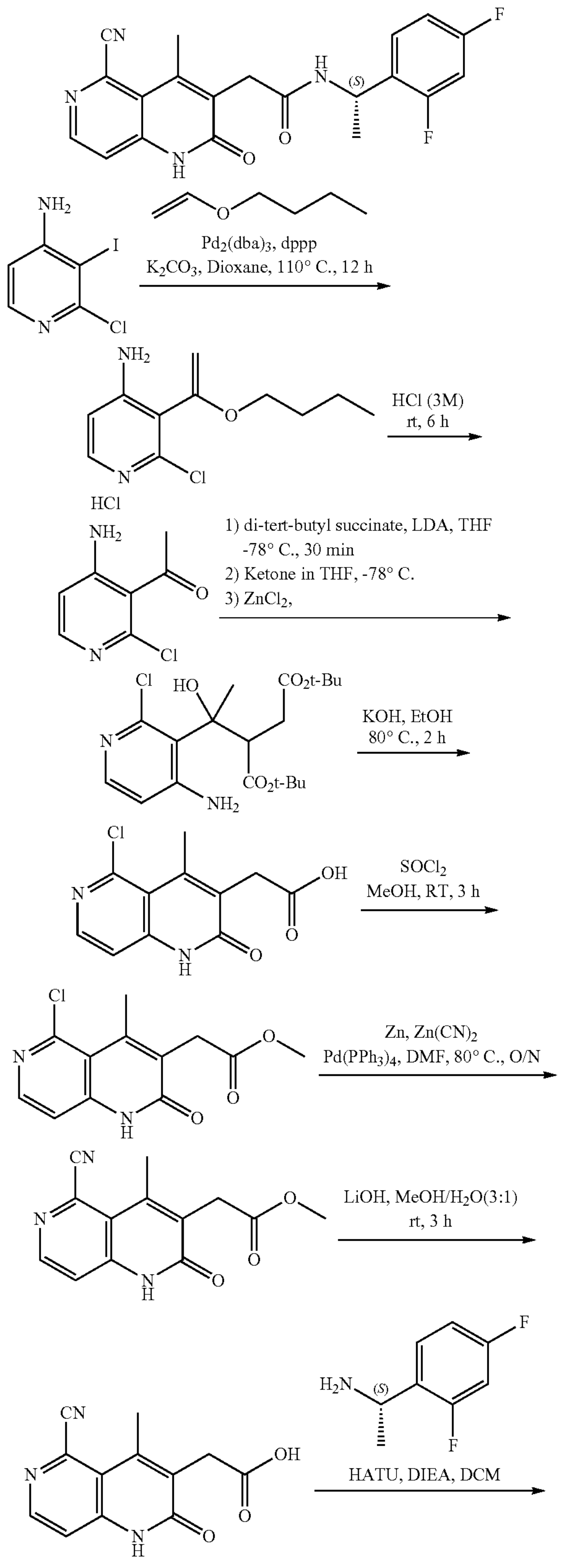

-continued

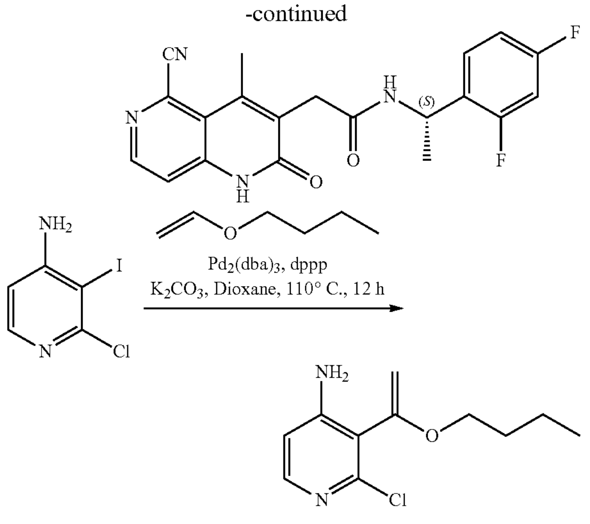

3-(1-butoxyvinyl)-2-chloropyridin-4-amine: 2-chloro-3-iodopyridin-4-amine (650 g, 2554.42 mmol, 1.00 equiv.), 1-(vinyloxy)butane (1279.27 g, 12772.14 mmol, 5.00 equiv.), DPPP (210.72 g, 510.88 mmol, 0.20 equiv.), $K_2CO_3$ (1059.10 g, 7663.25 mmol, 3.00 equiv.) and $Pd_2(dba)_3$ (233.92 g, 255.44 mmol, 0.1 equiv.) were dissolved in dioxane (6 L). The resulting solution was stirred for 12 h at 110° C. under N2. The reaction solution was filtered and the precipitate was washed with EA. The filtrate was washed with brine, dried over anhydrous $Na_2SO_4$, concentrated under reduced pressure to afford 3-(1-butoxyethenyl)-2-chloropyridin-4-amine (700 g, 85%).

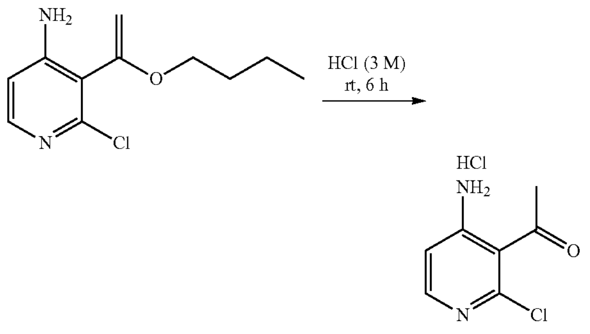

1-(4-amino-2-chloropyridin-3-yl)ethan-1-one hydrochloride: A solution of 3-(1-butoxyethenyl)-2-chloropyridin-4-amine (700 g, 3087.78 mmol, 1.00 equiv.) in HCl (3 M) in 1,4-dioxane (3.5 L) was stirred for 6 h at r.t. The precipitated solids were collected by filtration and washed with EA to afford 1-(4-amino-2-chloropyridin-3-yl) ethanone hydrochloride (326 g, 50.99%).

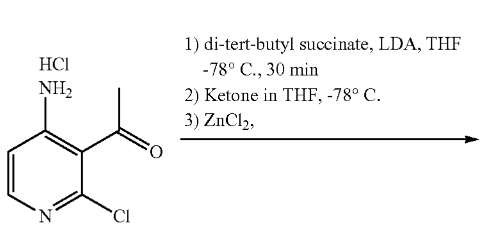

-continued

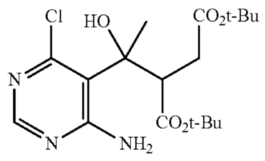

Di-tert-butyl 2-(1-(4-amino-2-chloropyridin-3-yl)-1-hydroxyethyl)succinate: Di-tert-butyl succinate (269.99 g, 1172.34 mmol, 2.00 equiv.) was dissolved in THF (600 mL) under nitrogen. LDA (2 M in THF) (880 mL, 3.00 equiv.) was added dropwise at −78° C. The reaction solution was stirred for 30 minutes at −78° C. A solution of 1-(4-amino-2-chloropyridin-3-yl) ethanone (100 g, 586.16 mmol, 1.00 equiv.) in THF (400 mL) was added to the reaction, followed by the addition of $ZnCl_2$ (1 M) in THF (586 mL, 1.00 equiv.) at −78° C. The reaction was heated to −50° C. The reaction was quenched by the addition of $NH_4Cl$ at 0° C. The crude material was extracted with EA. The combined organic layers were washed with brine, dried over anhydrous $Na_2SO_4$ filtered, and the filtrate was concentrated under reduced pressure to afford 1,4-di-tert-butyl 2-[1-(4-amino-2-chloropyridin-3-yl)-1-hydroxyethyl]butanedioate (200 g, 85.11%).

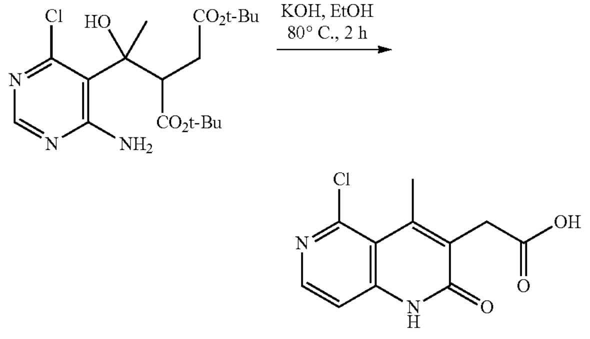

2-(5-chloro-4-methyl-2-oxo-1,2-dihydro-1,6-naphthyridin-3-yl)acetic acid: 1,4-di-tert-butyl 2-[1-(4-amino-2-chloropyridin-3-yl)-1-hydroxyethyl]butanedioate (200 g, 498.87 mmol, 1.00 equiv.) was dissolved in EtOH (2 L), and KOH (139.95 g, 2494.39 mmol, 5.00 equiv.) was added to the reaction solution portionwise at r.t. The solution was stirred for 2 h at 80° C. The residue was dissolved in $H_2O$, extracted with EA, and the aqueous layers were combined. The solution was adjusted to pH=5 with HCl (6 M). The precipitated solids were collected by filtration and washed with $H_2O$ to afford (5-chloro-4-methyl-2-oxo-1H-1,6-naphthyridin-3-yl) acetic acid (60 g, 47.60%).

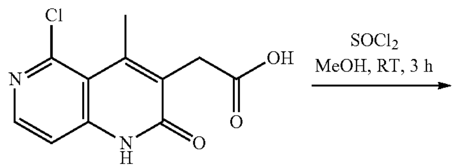

-continued

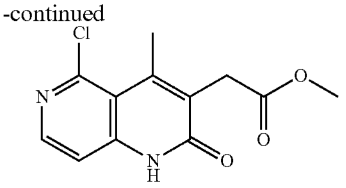

Methyl 2-(5-chloro-4-methyl-2-oxo-1,2-dihydro-1,6-naphthyridin-3-yl)acetate: (5-chloro-4-methyl-2-oxo-1H-1,6-naphthyridin-3-yl) acetic acid (60 g, 237.48 mmol, 1.00 equiv) was dissolved in MeOH (600 mL). $SOCl_2$ (141.25 g, 1187.41 mmol, 5.00 equiv.) was added dropwise at 0° C. The resulting solution was stirred for 3 h at RT. The residue was dissolved in $H_2O$, extracted with DCM, and the combined organic layers were washed with saturated $NaHCO_3$, brine, dried over anhydrous $Na_2SO_4$, filtered, and concentrated under reduced pressure to afford methyl 2-(5-chloro-4-methyl-2-oxo-1H-1,6-naphthyridin-3-yl) acetate (50 g, 78.95%).

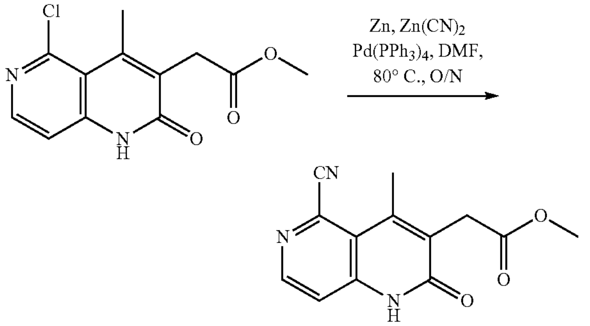

2-(5-cyano-4-methyl-2-oxo-1H-1,6-naphthyridin-3-yl) acetate: Methyl 2-(5-chloro-4-methyl-2-oxo-1H-1,6-naphthyridin-3-yl)acetate (12 g, 44.99 mmol, 1.00 equiv.), $Zn(CN)_2$ (7.93 g, 67.49 mmol, 1.50 equiv.), and $Pd(PPh_3)_4$ (5.20 g, 4.50 mmol, 0.10 equiv.) were dissolved in DMF (120 mL). The solution was stirred for 16 h at 80° C. under N2. The crude material was filtered, and the precipitate was washed with DCM. The filtrate was concentrated under reduced pressure to afford methyl 2-(5-cyano-4-methyl-2-oxo-1H-1,6-naphthyridin-3-yl)acetate (11.6 g, 80.17%).

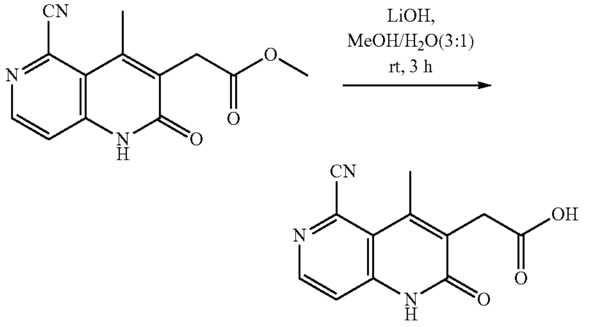

(5-cyano-4-methyl-2-oxo-1H-1,6-naphthyridin-3-yl) acetic acid: Methyl 2-(5-cyano-4-methyl-2-oxo-1H-1,6-naphthyridin-3-yl) acetate (11.6 g, 45.09 mmol, 1.00 equiv.) and LiOH (5.40 g, 225.46 mmol, 5.00 equiv.) were dissolved in MeOH (50 mL) and $H_2O$ (50 mL). The resulting solution was stirred for 3 h at r.t. The crude material was purified by reverse phase chromatography to afford (5-cyano-4-methyl-2-oxo-1H-1,6-naphthyridin-3-yl) acetic acid (5.0391 g, 45.86%).

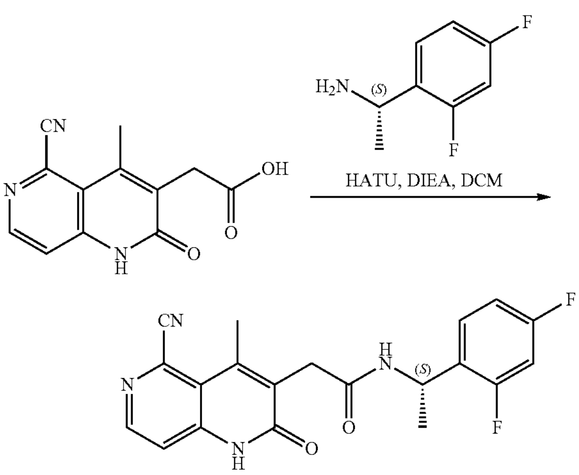

2-(5-cyano-4-methyl-2-oxo-1H-1,6-naphthyridin-3-yl)-N-[(1S)-1-(2,4-difluorophenyl)ethyl]acetamide: (5-cyano-4-methyl-2-oxo-1H-1,6-naphthyridin-3-yl)acetic acid (2.5 g, 10.279 mmol, 1 equiv.), (1S)-1-(2,4-difluorophenyl) ethanamine (1.62 g, 10.279 mmol, 1.0 equiv.), HATU (3.72 g, 15.418 mmol, 1.5 equiv.) and DIEA (3.99 g, 30.837 mmol, 3.0 equiv.) were dissolved in DCM (50 mL) under nitrogen at RT. The resulting solution was stirred for 2 h at RT under nitrogen. The crude material was extracted with $CH_2Cl_2$. The combined organic layers were washed with brine, dried over anhydrous $Na_2SO_4$, filtered, and the filtrate was concentrated under reduced pressure. The crude product was purified by Prep-HPLC to afford 2-(5-cyano-4-methyl-2-oxo-1H-1,6-naphthyridin-3-yl)-N-[(1S)-1-(2,4-difluorophenyl)ethyl]acetamide (1.2 g, 30.53%) (compound 355).

LCMS(ES, m/z): 383 $[M+H]^+$ $^1$HNMR(300 MHz, DMSO-$d_6$, ppm): δ 12.39 (s, 1H), 8.57-8.52 (m, 2H), 7.51-7.43 (m, 2H), 7.21-7.14 (m, 2H), 7.09-7.03 (m, 2H), 5.13-5.03 (m, 1H), 3.69 (s, 2H), 2.72 (s, 3H), 1.37-1.23 (m, 3H).

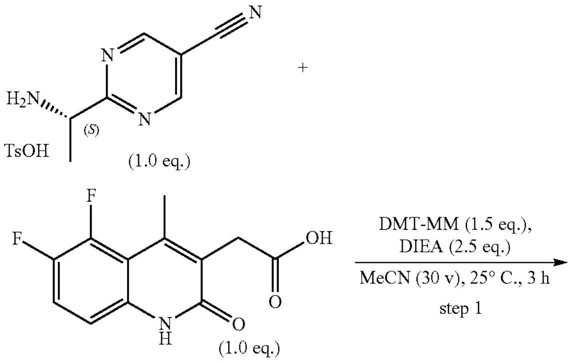

-continued

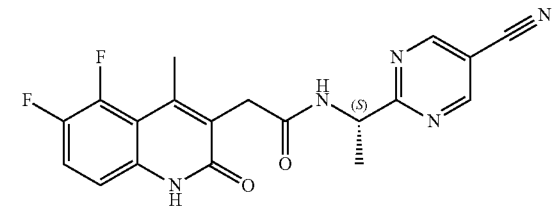

(S)—N-(1-(5-cyanopyrimidin-2-yl)ethyl)-2-(5,6-difluoro-4-methyl-2-oxo-1,2-dihydroquinolin-3-yl)acetamide (compound 1123 and 1124): 2-(5,6-difluoro-4-methyl-2-oxo-1,2-dihydroquinolin-3-yl)acetic acid (2.5 g, 9.9 mmol, 1.0 eq.), (S)-2-(1-aminoethyl)pyrimidine-5-carbonitrile 4-methylbenzenesulfonate (3.4 g, 9.9 mmol, 1.0 eq.), DIEA (3.4 g, 24.6 mmol, 2.5 eq.) was dissolved in MeCN (75 mL) DMT-MM (4.7 g, 14.8 mmol, 1.5 eq.) was added at 25° C. under nitrogen and the resulting solution was stirred for 1 h at 25° C. under nitrogen. The crude residue was purified by DAC, eluting with MeCN/$H_2O$ (0.1% mmol of TFA) to afford (S)—N-(1-(5-cyanopyrimidin-2-yl)ethyl)-2-(5,6-difluoro-4-methyl-2-oxo-1,2-dihydroquinolin-3-yl)acetamide (2.1 g, 55.6%).

LCMS(ES, m/z): 384.1 $[M+H]^+$.

$^1$H-NMR: (300 MHz, DMSO, ppm), δ 11.91 (s, 1H), 9.27 (s, 2H), 8.59 (d, J=7.2 Hz, 1H), 7.62-7.52 (m, 1H), 7.13-7.09 (m, 1H), 5.04-4.97 (m, 1H), 3.77-3.61 (m, 2H), 2.47 (d, J=6.3 Hz, 3H), 1.44 (d, J=7.2 Hz, 3H).

$^{19}$F-NMR: (300 MHz, DMSO, ppm), δ −138.84- −139.28 (m, 1F). −146.70-147.05 (m, 1F).

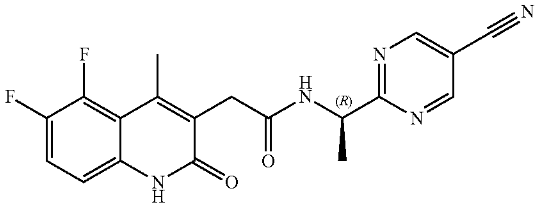

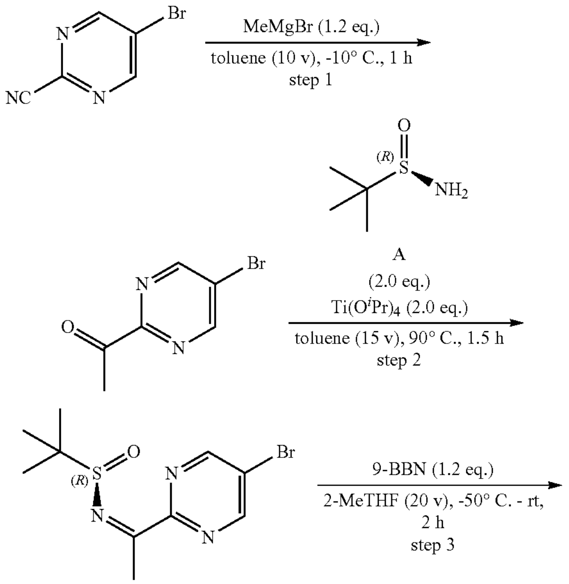

-continued

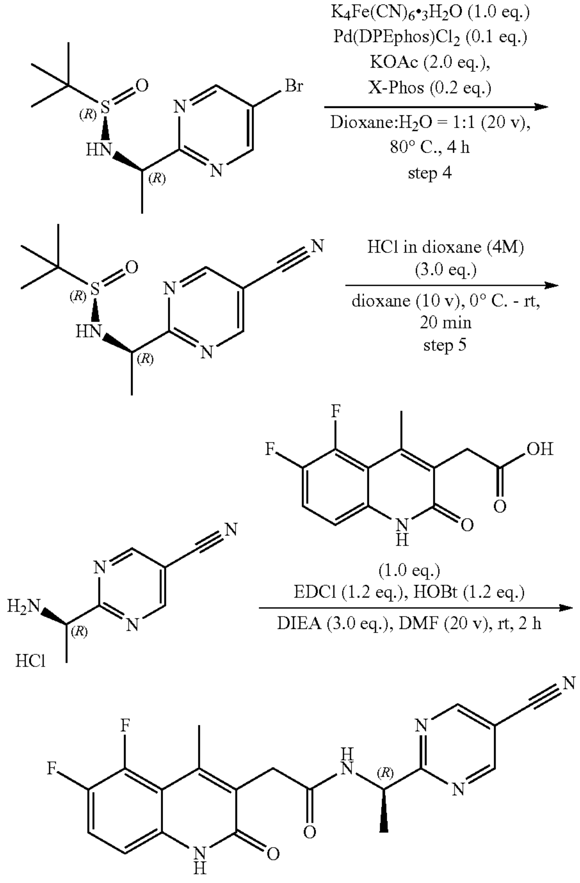

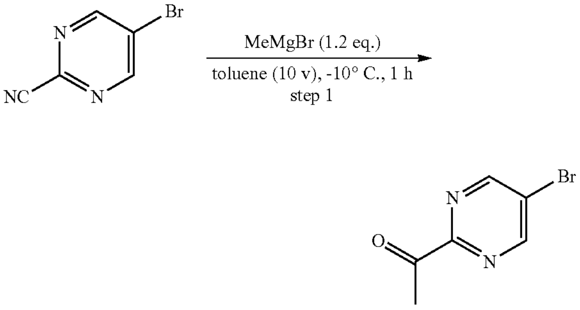

1-(5-bromopyrimidin-2-yl)ethan-1-one: To a stirred solution of 5-bromopyrimidine-2-carbonitrile (90.0 g, 491.8 mmol, 1.0 eq.) in toluene (900 mL) was added MeMgBr (3 mol/L in 2Me-THF) (196.7 mL, 1.2 eq.) slowly dropwise at −10° C. under $N_2$. The resulting solution was stirred for 1 h at −10° C. under nitrogen. The cold reaction solution was slowly added to 3 M HCl (900 mL) at 0° C. while stirring vigorously for 20 min. The crude material was separated and aqueous phase was extracted with DCM. The combined organic layers were washed with brine, dried over anhydrous $Na_2SO_4$, filtered, and concentrated under reduced pressure. The precipitate was added to n-heptane stirred, and filtered to afford 1-(5-bromopyrimidin-2-yl)ethan-1-one(91.0 g, 85.79%).

LCMS: (ES, m/z): 201.1 $[M+H]^+$

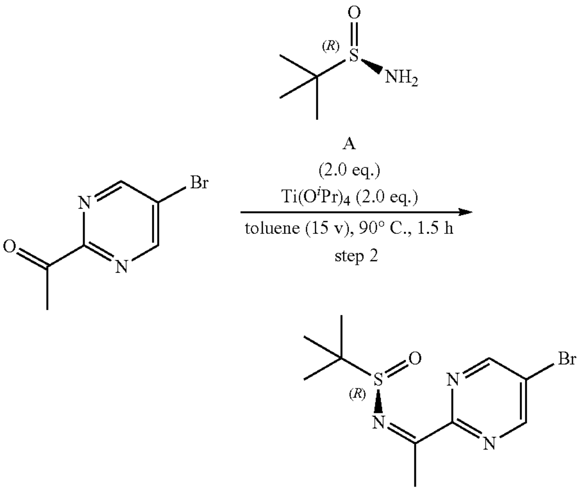

(R,Z)—N-(1-(5-bromopyrimidin-2-yl)ethylidene)-2-methylpropane-2-sulfinamide: A solution of 1-(5-bromopyrimidin-2-yl)ethan-1-one (65.0 g, 325.0 mmol, 1.0 eq.) and (R)-2-methylpropane-2-sulfinamide (78.7 g, 650.0 mmol, 2.0 eq.) in toluene (975 mL) was added $Ti(OPr)_4$ (184.6 g, 650.0 mmol, 2.0 eq.) dropwise at RT under nitrogen. The resulting solution was stirred for 1.5 h at 90° C. under nitrogen. The reaction was cooled to RT. EDTA (2.0 eq.) was added and the solution was stirred for 1 h. The crude material was filtered, and the solids were washed with EA. The organic layer was washed with brine, dried over anhydrous $Na_2SO_4$, filtered and concentrated under reduced pressure to afford (R,Z)—N-(1-(5-bromopyrimidin-2-yl) ethylidene)-2-methylpropane-2-sulfinamide(58.4 g, 59%) which was used in the next step directly without further purification.

LCMS: (ES, m/z): 304.1 $[M+H]^+$

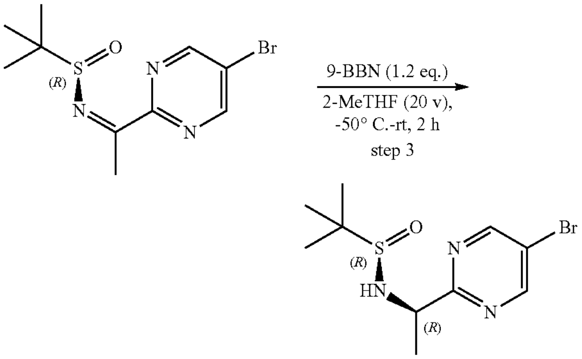

(R)—N—((R)-1-(5-bromopyrimidin-2-yl)ethyl)-2-methylpropane-2-sulfinamide: To a stirred solution of (R,Z)—N-(1-(5-bromopyrimidin-2-yl)ethylidene)-2-methylpropane-2-sulfinamide (58.4 g, 192.7 mmol, 1.0 eq.) in 2-MeTHF (1168 mL) was added 9-BBN (0.5 M in THF) (462.6 mL, 231.2 mmol, 1.2 eq.) dropwise over 30 min at −50° C. under nitrogen. The resulting solution was stirred for 2 h at RT under nitrogen. The reaction was quenched by the addition of $NH_4Cl$ (1.2 L) at 0° C. The crude material was extracted with EA, washed with brine, dried over anhydrous $Na_2SO_4$, filtered, and concentrated under reduced pressure. The crude residue was purified by column chromatography, eluting with PE/EA to afford (R)—N—((R)-1-(5-bromopyrimidin-2-yl)ethyl)-2-methylpropane-2-sulfinamide (11.3 g, 19.5%).

LCMS: (ES, m/z): 306.1 $[M+H]^+$

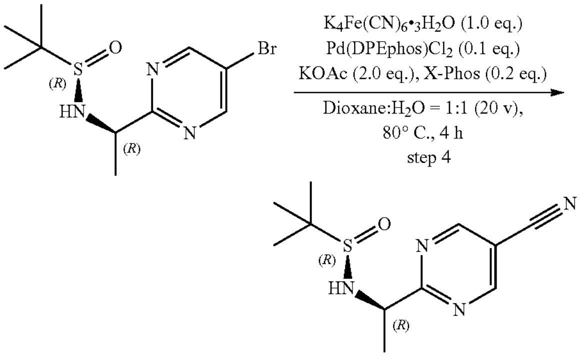

(R)—N—((R)-1-(5-cyanopyrimidin-2-yl)ethyl)-2-methylpropane-2-sulfinamide: (R)—N—((R)-1-(5-bromopyrimidin-2-yl)ethyl)-2-methylpropane-2-sulfinamide (11.3 g, 37.0 mmol, 1.0 eq.), $K_4Fe(CN)_6{\cdot}H_2O$ (15.6 g, 37.0 mmol, 1.0 eq.), $Pd(DPEphos)Cl_2$ (2.7 g, 3.7 mmol, 0.1 eq.), KOAc (7.3 g, 74.1 mmol, 2.0 eq.) and X-Phos (3.5 g, 7.4 mmol, 0.2 eq.) were dissolved in dioxane/$H_2O$ (1:1, 226 mL) under nitrogen. The resulting solution was stirred for 4 h at 80° C. under nitrogen. The reaction was cooled to RT and diluted with water. The crude material was extracted with EA and the organic layers were washed with brine, dried over anhydrous $Na_2SO_4$, filtered, and concentrated under reduced pressure. The crude residue was purified by column chromatography, eluting with PE/EA to afford (R)—N—((R)-1-(5-cyanopyrimidin-2-yl)ethyl)-2-methylpropane-2-sulfinamide (4.7 g, 50.5%).

LCMS: (ES, m/z): 253.1 $[M+]^-$

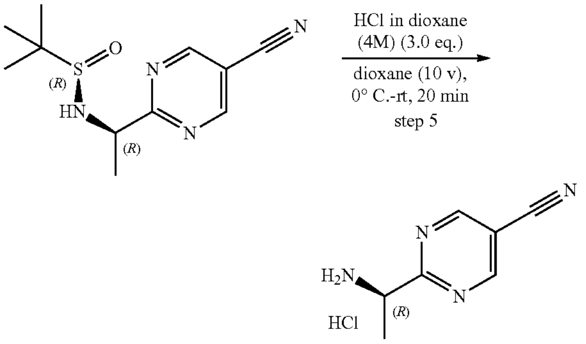

(R)-2-(1-aminoethyl)pyrimidine-5-carbonitrile hydrochloride: (R)—N—((R)-1-(5-cyanopyrimidin-2-yl)ethyl)-2-methylpropane-2-sulfinamide (4.7 g, 18.7 mmol, 1.00 eq.) was dissolved in dioxane (47 mL). 4M HCl in 1,4-dioxane (14.0 mL, 56.0 mmol, 3.0 eq.) was added dropwise at 0° C. under nitrogen. The resulting solution was stirred for 20 min at RT under nitrogen. The crude material was filtered, washed with EA (50 mL), and dried to afford (R)-2-(1-aminoethyl)pyrimidine-5-carbonitrile hydrochloride (2.5 g, 72%).

LCMS: (ES, m/z): 149 $[M+H]^+$

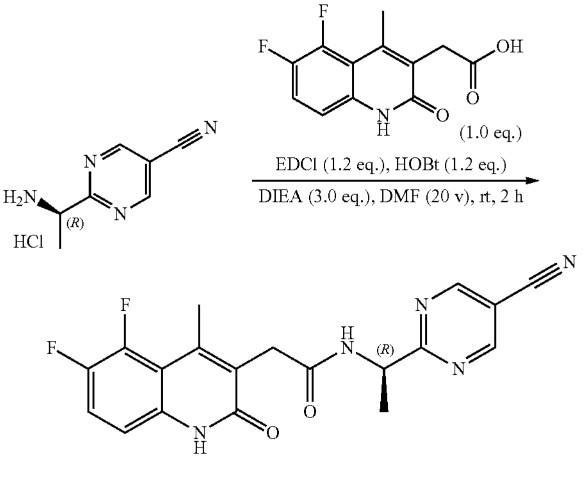

(R)—N-(1-(5-cyanopyrimidin-2-yl)ethyl)-2-(5,6-difluoro-4-methyl-2-oxo-1,2-dihydroquinolin-3-yl)acetamide: (R)-2-(1-aminoethyl)pyrimidine-5-carbonitrile hydrochloride (2.5 g, 13.6 mmol, 1.0 eq.), 2-(5,6-difluoro-4-methyl-2-oxo-1,2-dihydroquinolin-3-yl)acetic acid (3.4 g, 13.6 mmol, 1.0 eq.), EDCI (3.1 g, 16.3 mmol, 1.2 eq.), HOBt (2.2 g, 16.3 mmol, 1.2 eq.) were dissolved in DMF (50 mL) at RT under nitrogen. DIEA (5.3 g, 40.8 mmol, 3.00 eq.) was added dropwise and the resulting solution was stirred for 4 h at RT under nitrogen. The reaction was quenched with water, extracted with DCM and the organic layers were washed with brine, dried over anhydrous $Na_2SO_4$, filtered and concentrated under reduced pressure. Then crude product was washed with EA dried, and purified by SFC with a TMC-SB, 30*250 mm column eluting with Hex and MeOH to afford(R)—N-(1-(5-cyanopyrimidin-2-yl)ethyl)-2-(5,6-difluoro-4-methyl-2-oxo-1,2-dihydroquinolin-3-yl)acetamide (2.07 g, 55%).

LCMS: (ES, m/z): 384.1 $[M+H]^+$ $^1$HNMR: (400 MHz, DMSO, ppm) δ 11.92 (s, 1H), 9.27 (s, 2H), 8.58 (d, J=7.2 Hz, 1H), 7.61-7.54 (m, 1H), 7.13-7.10 (m, 1H), 5.03-4.96 (m, 1H), 3.76-3.62 (m, 2H), 2.47 (d, J=6.4 Hz, 3H), 1.44 (d, J=6.8 Hz, 3H).

$^{19}$FNMR: (400 MHz, DMSO, ppm) δ −139.22-−139.27 (m, 1F), −146.99-−147.04 (m, 1F).

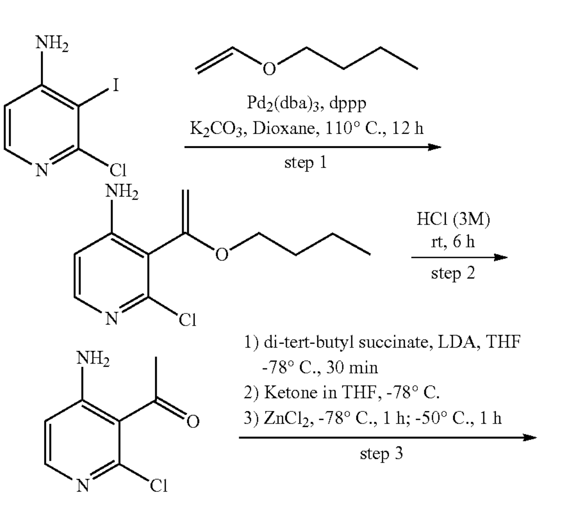

-continued

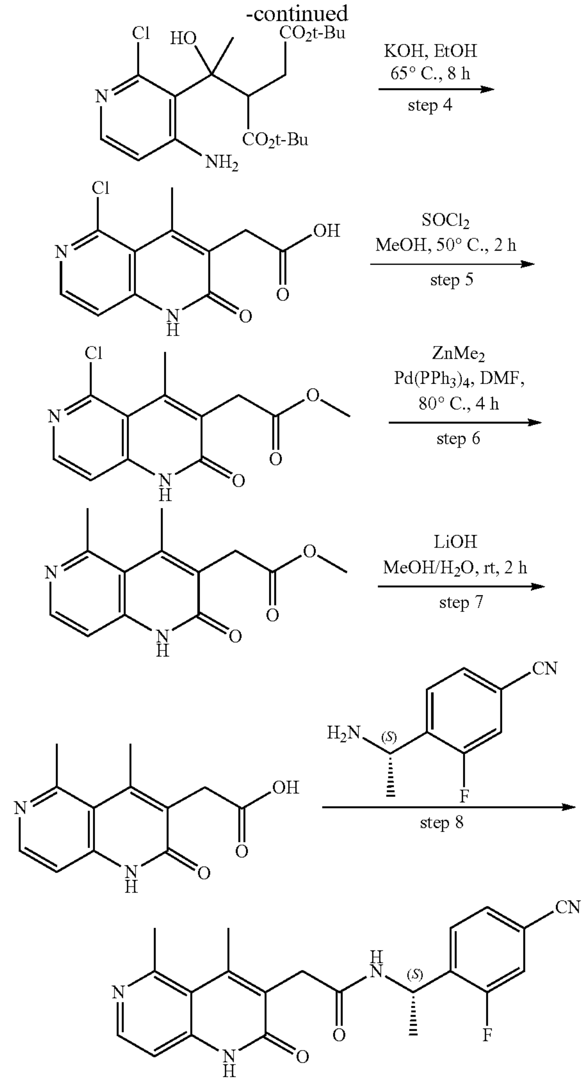

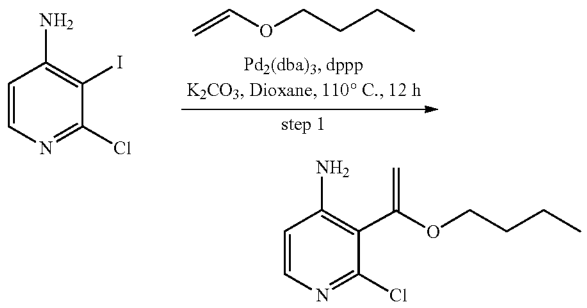

3-(1-butoxyvinyl)-2-chloropyridin-4-amine: 2-chloro-3-iodopyridin-4-amine (50 g, 196.495 mmol, 1 equiv), butyl vinyl ether (98.41 g, 982.475 mmol, 5.00 equiv), DPPP (16.1 g, 39.299 mmol, 0.20 equiv), $K_2CO_3$ (81.34 g, 589.485 mmol, 3.00 equiv) and $Pd_2(dba)_3$ (17.99 g, 19.649 mmol, 0.1 equiv) were dissolved in dioxane(500 mL) in a 1 L 3 necked RBF. The resulting solution was stirred for 12 h at 110° C. under $N_2$. The crude material was filtered, and, the solids were washed with EA, brine, dried over anhydrous $NaSO_4$, filtered and concentrated under reduced pressure to afford 3-(1-butoxyethenyl)-2-chloropyridin-4-amine (44 g, 100%) which was used in the next step directly without further purification.

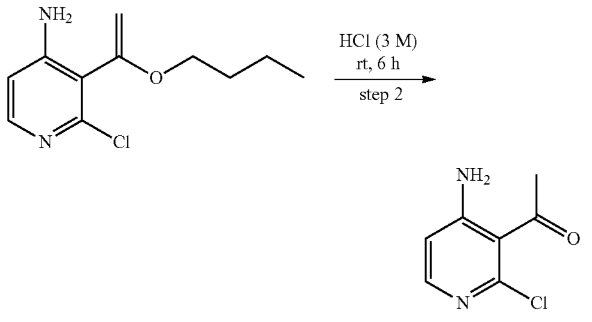

1-(4-amino-2-chloropyridin-3-yl)ethan-1-one: A solution of 3-(1-butoxyethenyl)-2-chloropyridin-4-amine (50 g, 220 mml, 1 equiv.) in HCl/1,4-dioxane (3M, 500 mL) was stirred for 6 h at RT. The precipitate was filtered and washed with EA. The residue was dissolved in water and adjusted to pH 10 with saturated $Na_2CO_3$ (aq.). The aqueous layer was extracted with EA, washed with brine, and dried over anhydrous $Na_2SO_4$, filtered and concentrated to afford 1-(4-amino-2-chloropyridin-3-yl)ethanone (20 g, 43.80%).

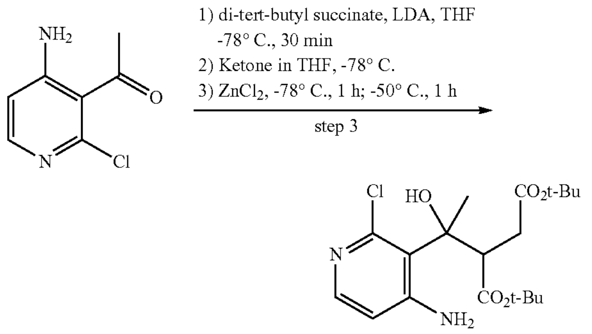

Di-tert-butyl 2-(1-(4-amino-2-chloropyridin-3-yl)-1-hydroxyethyl)succinate: LDA (in 2M THF) (176 mL, 3.00 equiv) was added dropwise at −78° C. to a solution of di-tert-butyl succinate (54.00 g, 234.466 mmol, 2.00 equiv) in THF (150 mL) under $N_2$. The solution was stirred for 30 min at −78° C. Then a solution of 1-(4-amino-2-chloropyridin-3-yl)ethanone (20 g, 117.233 mmol, 1 equiv) in THF (50 mL) followed by $ZnCl_2$(1 M) in THF (117 mL, 1.0 equiv) at −78° C. were added to the solution. The reaction was stirred for 1 h at −50° C. The reaction was quenched by the addition of $NH_4Cl$ at 0° C. The resulting solution was extracted with EA, washed with brine dried over anhydrous $Na_2SO_4$, filtered, and concentrated under reduced pressure to afford di-tert-butyl 2-(1-(4-amino-2-chloropyridin-3-yl)-1-hydroxyethyl)succinate(30 g, 63%) which was used for the next step without purification.

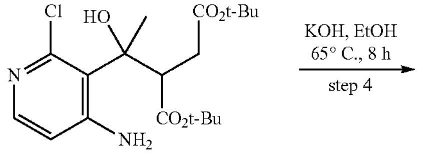

-continued

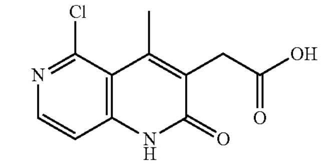

2-(5-chloro-4-methyl-2-oxo-1,2-dihydro-1,6-naphthyridin-3-yl)acetic acid: KOH (20.99 g, 374.160 mmol, 5.0 equiv) was added portionwise at RT to a solution of 1,4-di-tert-butyl 2-[1-(4-amino-2-chloropyridin-3-yl)-1-hydroxyethyl]butanedioate(30 g, 74.832 mmol, 1 equiv) in EtOH (200 mL). The solution was stirred for 8 h at 65° C. The crude material was dissolved in $H_2O$ and extracted with DCM. The aqueous layer was adjusted to pH 5 with HCl (6 M) the precipitated solids were filtered and washed with $H_2O$ to afford (5-chloro-4-methyl-2-oxo-1H-1,6-naphthyridin-3-yl)acetic acid (12 g, 63.47%).

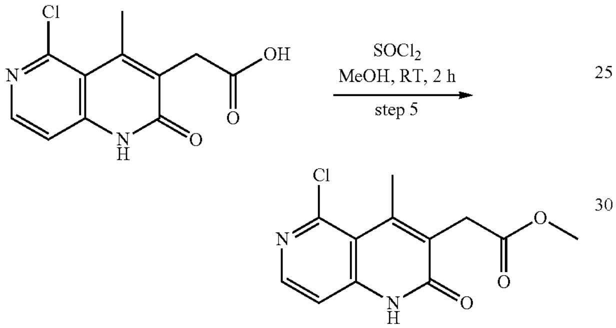

Methyl 2-(5-chloro-4-methyl-2-oxo-1H-1,6-naphthyridin-3-yl)acetate: SOCl2 (28.25 g, 237.485 mmol, 5.0 equiv) was added dropwise at 0° C. to a solution of (5-chloro-4-methyl-2-oxo-1H-1,6-naphthyridin-3-yl)acetic acid (12 g, 47.497 mmol, 1 equiv) in MeOH (200 mL). The resulting solution was stirred for 2 h at RT. The crude solution was adjusted to pH 9 with saturated $Na_2CO_3$ (aq.), extracted with DCM, washed brine, dried over anhydrous $Na_2SO_4$, filtered and concentrated under reduced pressure to affordmethy2-(5-chloro-4-methyl-2-oxo-1H-1,6-naphthyridin-3-yl)acetate (12 g, 94.74%).

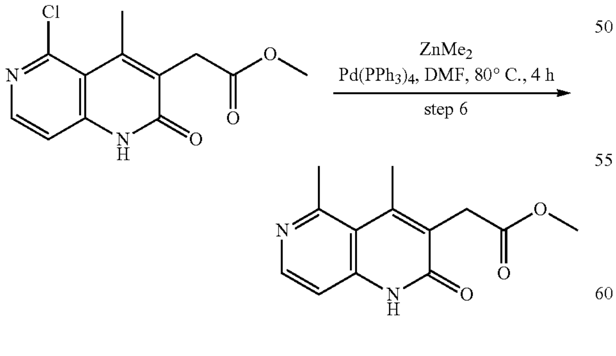

Methyl 2-(4,5-dimethyl-2-oxo-1H-1,6-naphthyridin-3-yl) acetate: $ZnMe_2$ (1 M) in THF (61.6 mL, 61.904 mmol, 1.50 equiv) was added dropwise at RT to a solution of methyl 2-(5-chloro-4-methyl-2-oxo-1H-1,6-naphthyridin-3-yl)acetate (11 g, 41.248 mmol, 1 equiv), $Pd(PPh_3)_4$ (4.33 g, 3.747 mmol, 0.10 equiv) in DMF (100 mL) under $N_2$. The resulting solution was stirred for 4 h at 80° C. The crude reaction was quenched by the addition of MeOH, and filtered. The filtrate was concentrated under reduced pressure and purified by column chromatography to afford methyl 2-(4,5-dimethyl-2-oxo-1H-1,6-naphthyridin-3-yl)acetate (8.0 g, 79.2%).

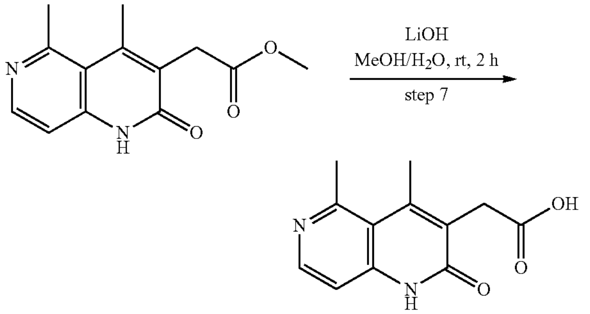

(4,5-dimethyl-2-oxo-1H-1,6-naphthyridin-3-yl)acetic acid: LiOH (3.89 g, 162.083 mmol, 5.00 equiv) was added at RT under $N_2$ to a stirred solution of methyl 2-(4,5-dimethyl-2-oxo-1H-1,6-naphthyridin-3-yl)acetate (8 g, 32.485 mmol, 1 equiv) in MeOH (50 mL) and $H_2O$ (50 mL). The resulting solution was stirred for 3 h at RT. The crude solution was neutralized to pH 7 with HCl (6M) and purified by reverse chromatography with a aC18 column to afford (4,5-dimethyl-2-oxo-1H-1,6-naphthyridin-3-yl)acetic acid (5 g, 66.27%).

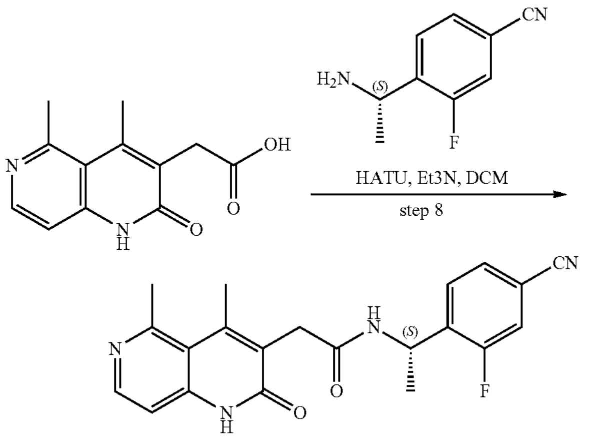

N-[(1S)-1-(4-cyano-2-fluorophenyl)ethyl]-2-(4,5-dimethyl-2-oxo-1H-1,6-naphthyridin-3-yl)acetamide: A solution of (4,5-dimethyl-2-oxo-1H-1,6-naphthyridin-3-yl)acetic acid (5 g, 21.530 mmol, 1 equiv), HATU(12.27 g, 32.295 mmol, 1.5 equiv), $Et_3N$(6.54 g, 64.590 mmol, 3 equiv) and 4-[(1S)-1-aminoethyl]-3-fluorobenzonitrile (3.53 g, 21.500 mmol, 1.00 equiv) in $CH_2Cl_2$(100 mL) was stirred at RT under $N_2$ for 2 h. The crude material was concentrated under vacuum and purified by reverse chromatography with a C18 column to afford N-[(1S)-1-(4-cyano-2-fluorophenyl)ethyl]-2-(4,5-dimethyl-2-oxo-1H-1,6-naphthyridin-3-yl)acetamide (4.8 g, 58.92%) (compound 255 and 256).

LCMS: (ES, m/z): 379$[M+H]^+$

NMR: $^1H$ NMR (300 MHz, DMSO-$d_6$) δ 11.92 (s, 1H), 8.74-8.52 (m, 1H), 8.33-8.19 (m, 1H), 7.88-7.73 (m, 1H), 7.73-7.53 (m, 2H), 7.18-6.91 (m, 1H), 5.32-5.01 (m, 1H), 3.66 (s, 2H), 2.86 (s, 3H), 1.50-1.17 (m, 3H).

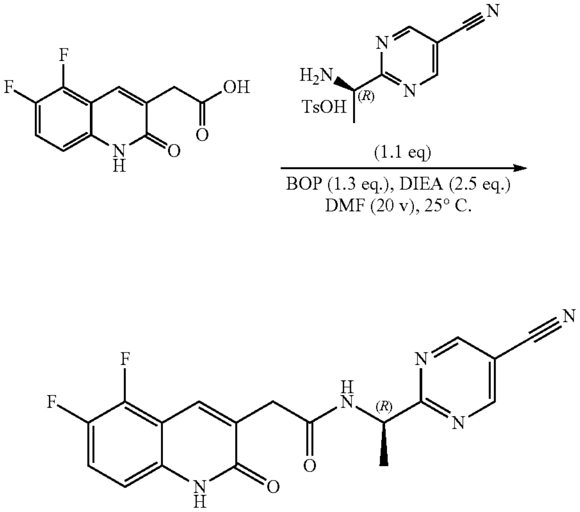

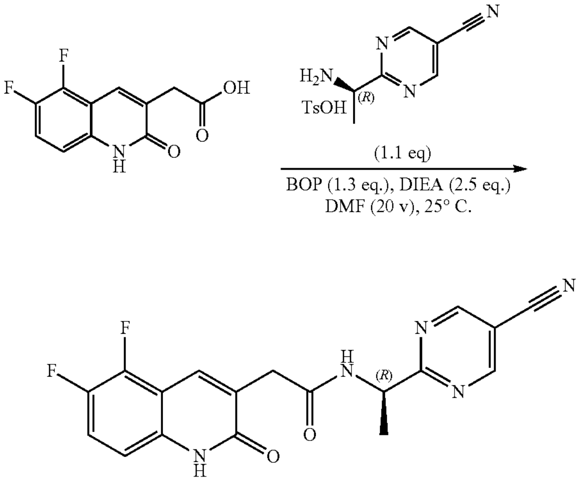

(R)—N-(1-(5-cyanopyrimidin-2-yl)ethyl)-2-(5,6-difluoro-2-oxo-1,2-dihydroquinolin-3-yl)acetamide (Compound 2071 and 2072): 2-(5,6-difluoro-2-oxo-1,2-dihydroquinolin-3-yl)acetic acid (2.0 g, 8.3 mmol, 1.0 eq.), (R)-2-(1-aminoethyl)pyrimidine-5-carbonitrile 4-methylbenzenesulfonate (2.9 g, 9.2 mmol, 1.1 eq.), and DIEA (2.7 g, 20.8 mmol, 2.5 eq.) were dissolved in DMF (40 mL).BOP (4.8 g, 10.8 mmol, 1.3 eq.) was added at 0-5° C. under $N_2$ and the resulting solution was stirred for 1 h at 25° C. under $N_2$. The crude material was directly purified by DAC, eluting with MeCN/$H_2O$ (0.1% mmol of TFA) to afford (R)—N-(1-(5-cyanopyrimidin-2-yl)ethyl)-2-(5,6-difluoro-2-oxo-1,2-dihydroquinolin-3-yl)acetamide (1.26 g, 40.9%).

LCMS (ESI, m/z): $[M+H]^+$=370.2

$^1$H-NMR: (300 MHz, DMSO-$d_6$, ppm) δ 12.06 (s, 1H), 9.28 (s, 2H), 8.74 (d, J=7.2 Hz, 1H), 7.95 (s, 1H), 7.63-7.53 (m, 1H), 7.14 (dd, J=9.3, 3.0 Hz, 1H), 5.08-4.99 (m, 1H), 3.56-3.44 (m, 2H), 1.46 (d, J=7.2 Hz, 3H). $^{19}$F-NMR: (282 MHz, DMSO-$d_6$, ppm), δ −147.5 (d, J=21.7 Hz, 1F), 147.6 (d, J=21.1 Hz, 1F).

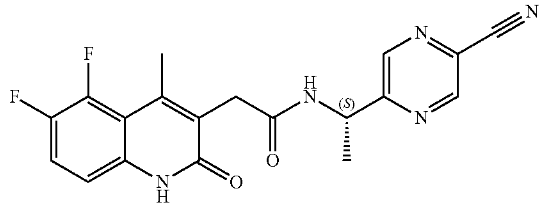

(S)-N-(1-(5-cyanopyrazin-2-yl)ethyl)-2-(5,6-difluoro-4-methyl-2-oxo-1,2-dihydroquinolin-3-yl)acetamide 2-Bromo-5-(1-ethoxyvinyl)pyrazine: 2,5-dibromopyrazine (50.0 g, 211.8 mmol, 1.00 eq.) and $Pd(PPh_3)_2Cl_2$ (7.4 g, 10.6 mmol, 0.05 eq.) were dissolved in DMF (500 mL). Tributyl(1-ethoxyvinyl)stannane (69.0 g, 190.7 mmol, 0.90 eq.) was added dropwise at RT under nitrogen atmosphere. The resulting solution was stirred for 1 h at 100° C. under nitrogen atmosphere. The reaction was cooled to RT, diluted with EA, and aq. KF. The two phase mixture was stirred for 20 min at rt before being filtered through Celite, and separated. The aqueous layer was extracted with EAEA, the organic layers were washed with brine, dried over anhydrous $Na_2SO_4$, filtered and the filtrate was concentrated under reduced pressure. The crude residue was purified by column chromatography, to afford 2-bromo-5-(1-ethoxyvinyl)pyrazine (18.00 g, 37.5%). LCMS: (ES, m/z): 229.1 $[M+H]^+$ 1-(5-Bromopyrazin-2-yl)ethan-1-one: 2-Bromo-5-(1-ethoxyvinyl)pyrazine (18.0 g, 78.9 mmol, 1.00 eq.) was dissolved in THF (180 mL).TFA (72.0 g, 631.6 mmol, 8.00 eq.) was added dropwise at 0° C. and the resulting mixture was stirred for 3 h at RT. The crude solution was adjusted to pH 8 with saturated $NaHCO_3$ (aq.) and extracted with EA. The combined organic layers were washed with brine, dried over anhydrous $Na_2SO_4$, and filtered. The filtrate was concentrated under reduced pressure and purified by column chromatography, to afford 1-(5-bromopyrazin-2-yl)ethan-1-one (14.00 g, 91.2%). LCMS: (ES, m/z): 201.2 $[M+H]^+$ (R,Z)—N-(1-(5-bromopyrazin-2-yl)ethylidene)-2-methylpropane-2-sulfinamide: To a stirred solution of 1-(5-bromopyrazin-2-yl)ethan-1-one (14.0 g, 70.0 mmol, 1.00 eq.) and (R)-2-methylpropane-2-sulfinamide (10.2 g, 84.0 mmol, 1.20 eq.) in toluene (210 mL) was added $Ti(OiPr)_4$ (19.9 g, 70.0 mmol, 1.00 eq.) dropwise at RT under nitrogen atmosphere. The resulting mixture was stirred for 3 h at 90° C. under nitrogen atmosphere. The reaction was cooled to RT, quenched with water (280 mL). The crude material was filtered, the solids were washed with EA, and separated. The aqueous layer was extracted with EA. The combined organic layers were washed with brine, dried over anhydrous $Na_2SO_4$, and filtered. The filtrate was concentrated under reduced pressure and purified by column chromatography to afford (R,Z)—N-(1-(5-bromopyrazin-2-yl)ethylidene)-2-methylpropane-2-sulfinamide (11.00 g, 66.3%). LCMS: (ES, m/z): 304.1$[M+H]^+$ (R)—N—((S)-1-(5-bromopyrazin-2-yl)ethyl)-2-methylpropane-2-sulfinamide: (R,Z)—N-(1-(5-bromopyrazin-2-yl)ethylidene)-2-methylpropane-2-sulfinamide (11.0 g, 36.3 mmol, 1.00 eq.) was dissolved in 2-THF (220 mL). 9-BBN (0.5 M in THF) (87.1 ml, 43.6 mmol, 1.20 eq.) was added dropwise for 10 min at −50° C. under nitrogen atmosphere. The resulting solution was stirred for 1 h at RT under nitrogen atmosphere. The reaction was quenched by the addition of MeOH (11.6 g, 10.0 eq.) at 0° C., and water (150 mL). The crude material was extracted with EA, washed with brine, dried over anhydrous $Na_2SO_4$, and filtered. The filtrate was concentrated under reduced pressure and purified by column chromatography to afford (R)—N—((S)-1-(5-bromopyrazin-2-yl)ethyl)-2-methylpropane-2-sulfinamide (7.20 g, 65.00%). LCMS: (ES, m/z): 306.1 $[M+H]^+$ (R)—N—((S)-1-(5-cyanopyrazin-2-yl)ethyl)-2-methylpropane-2-sulfinamide: (R)—N—((S)-1-(5-bromopyrazin-2-yl)ethyl)-2-methylpropane-2-sulfinamide (7.2 g, 23.6 mmol, 1.00 eq.), $Zn(CN)_2$ (4.16 g, 35.4 mmol, 1.50 eq.) and $Pd(PPh_3)_4$ (2.7 g, 2.4 mmol, 0.1 equiv) were dissolved in DMF (72 mL) under nitrogen atmosphere. The resulting solution was stirred for 2 h at 100° C. under nitrogen atmosphere. The reaction was cooled to RT, and diluted with water. The crude material was extracted with EA, washed with brine, dried over anhydrous $Na_2SO_4$, and filtered. The filtrate was concentrated under reduced pressure and purified by column chromatography, to afford (R)—N—((S)-1-(5-cyanopyrazin-2-yl)ethyl)-2-methylpropane-2-sulfinamide (3.7 g, 65.0%). LCMS: (ES, m/z): 253.1 $[M+H]^+$ (S)-5-(1-aminoethyl)pyrazine-2-carbonitrile: To a stirred solution of (R)—N—((S)-1-(5-cyanopyrazin-2-yl)ethyl)-2-methylpropane-2-sulfinamide (3.7 g, 14.7 mmol, 1.00 eq.) in dioxane (74.0 mL) was added 4M HCl in dioxane (14.7 mL, 58.7 mmol, 4.00 eq.) dropwise at 0° C. under nitrogen atmosphere. The resulting mixture was stirred for 1 h at RT under nitrogen atmosphere. The crude material was filtered and the precipitate was washed with EA, then dried to afford (S)-5-(1-aminoethyl)pyrazine-2-carbonitrile (2.40 g, 90.0%). LCMS: (ES, m/z): 149.1 $[M+H]^+$ (S)—N-(1-(5-cyanopyrazin-2-yl)ethyl)-2-(5,6-difluoro-4-methyl-2-oxo-1,2-dihydroquinolin-3-yl)acetamide (compound 1145 and 1146): To a stirred solution of 2-(5,6-difluoro-4-methyl-2-oxo-1,2-dihydroquinolin-3-yl)acetic acid (2.7 g, 10.9 mmol, 1.00 eq.), (S)-5-(1-aminoethyl) pyrazine-2-carbonitrile hydrochloride (2.00 g, 10.9 mmol, 1.00 eq.), DIEA (4.2 g, 32.6 mmol, 3.00 eq.) and EDCI (3.1 g, 16.3 mmol, 1.50 eq.) was added HOBt (1.76 g, 13.0 mmol, 1.20 eq.) in DMF (54 mL) at RT under nitrogen atmosphere. The resulting mixture was stirred for 2 h at RT under nitrogen atmosphere. The crude material was poured into ice-water (200 mL) and stirred for 0.5 h. The crude was filtered and washed with $H_2O$, and resuspended with EA and filtered again. The precipitate was washed with EA and dried to afford (S)—N-(1-(5-cyanopyrazin-2-yl)ethyl)-2-(5,6-difluoro-4-methyl-2-oxo-1,2-dihydroquinolin-3-yl)acetamide (2.5 g, 60.0%). LCMS: (ES, m/z): 384.1 $[M+H]^+$ H-NMR: (300 MHz, DMSO, ppm) δ 11.97 (s, 1H), 9.16 (s, 1H), 8.89 (s, 1H), 8.71 (d, J=6.9 Hz, 1H), 7.63 (q, J=9.2 Hz, 1H), 7.14-7.10 (m, 1H), 5.07 (t, J=7.0 Hz, 1H), 3.75-3.63 (m, 2H), 2.47 (s, 3H), 1.47 (d, J=7.1 Hz, 3H). FNMR: (300 MHz, DMSO, ppm) δ −139.05-−139.13 (m, 1F), −146.89-−146.96 (m, 1F).

-continued

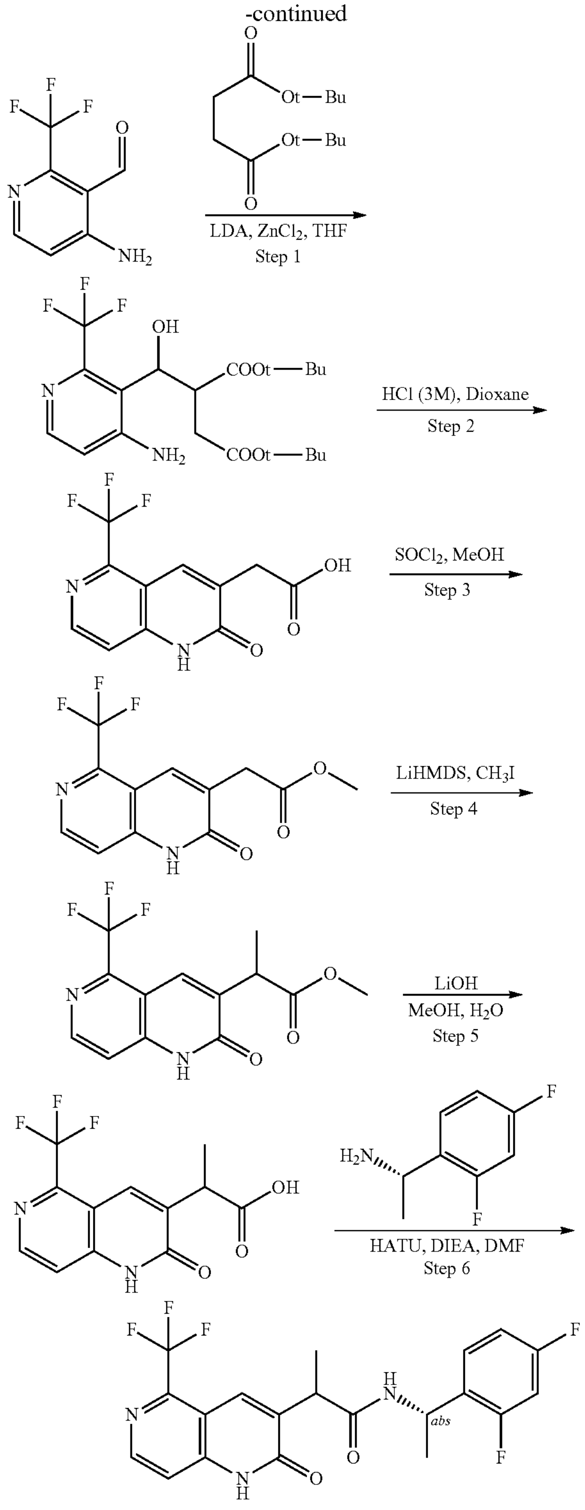

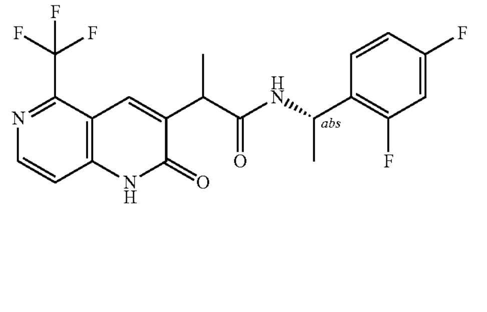

1,4-di-tert-butyl 2-[[4-amino-2-(trifluoromethyl)pyridin-3-yl](hydroxy)methyl]butanedioate: Into a 8-mL vial, was placed tetrahydrofuran (15 mL) in Ar, a solution of 1,4-di-tert-butyl butanedioate (121.13 mg, 0.526 mmol, 2 equiv) was added, followed by LDA (84.52 mg, 0.789 mmol, 3 equiv, 2 M) portionwise at −78° C. in a liquid nitrogen bath, The resulting solution was stirred for 20 min at −78° C. in a liquid nitrogen bath. A solution of 4-amino-2-(trifluoromethyl)pyridine-3-carbaldehyde (50.00 mg, 0.263 mmol, 1.00 equiv, 2M) in THF (2 mL) was added, followed by zinc chloride (35.84 mg, 0.263 mmol, 1 equiv, 0.7M). The resulting solution was stirred, for an additional 1 hr while the temperature was maintained at −78 in a liquid nitrogen bath. The reaction was quenched by the addition of 5 mL of $NH_4Cl$ (sat.), diluted with $H_2O$, and extracted with ethyl acetate. The organic layers were combined, dried over anhydrous sodium sulfate, and concentrated under vacuum. The crude residue was purified with column chromatography eluting with ethyl acetate/petroleum ether to afford 1,4-di-tert-butyl 2-[[4-amino-2-(trifluoromethyl)pyridin-3-yl](hydroxy)methyl]butanedioate (700 mg, 63.34%). LC-MS: (ESI, m/z): 421 $[M+H]^+$

[2-oxo-5-(trifluoromethyl)-1H-1,6-naphthyridin-3-yl] acetic acid: Into a 40-mL vial, was placed 1,4-di-tert-butyl 2-[[4-amino-2-(trifluoromethyl)pyridin-3-yl](hydroxy) methyl]butanedioate (360.00 mg, 0.856 mmol, 1.00 equiv), in Dioxane (2.60 mL), hydrogen chloride (2.60 mL, 3 M). The resulting solution was stirred for 4 h at 100° C. in an oil bath. The resulting mixture was concentrated under vacuum. The resulting mixture was washed with acetonitrile to afford [2-oxo-5-(trifluoromethyl)-1H-1,6-naphthyridin-3-yl]acetic acid (180 mg, 69.51%). LC-MS: (ESI, m/z): 273 $[M+H]^+$ Methyl 2-[2-oxo-5-(trifluoromethyl)-1H-1,6-naphthyridin-3-yl]acetate: To a solution of [2-oxo-5-(trifluoromethyl)-1H-1,6-naphthyridin-3-yl]acetic acid (220.00 mg, 0.808 mmol, 1.00 equiv) in methanol (5.00 mL) was added thionyl chloride (961.53 mg, 8.083 mmol, 10.00 equiv) dropwise. The resulting solution was stirred for 2 h at 80° C. The crude material was concentrated under reduced pressure and purified by column chromatography, eluting with DCM/MeOH to afford methyl 2-[2-oxo-5-(trifluoromethyl)-1H-1,6-naphthyridin-3-yl]acetate (220 mg, 95%). LC-MS: (ESI, m/z): 287 $[M+H]^+$ Methyl 2-[2-oxo-5-(trifluoromethyl)-1H-1,6-naphthyridin-3-yl]propanoate: To a solution of methyl 2-[2-oxo-5-(trifluoromethyl)-1H-1,6-naphthyridin-3-yl]acetate (270.00 mg, 0.943 mmol, 1.00 equiv) in tetrahydrofuran (6.00 mL) was added LiHMDS(1.0 M in THF) (2.17 mL, 2.169 mmol, 2.3 equiv) at −78° C. The resulting solution was stirred for 15 min. Methyl iodide (147.29 mg, 1.038 mmol, 1.10 equiv) was added and the solution was allowed to warm to RT and stirred for 1 h. The crude reaction was quenched by $NH_4Cl$ (sat.) and extracted with EA. The combined organic layers were dried over anhydrous $Na_2SO_4$, filtered, concentrated under reduced pressure, and purified by column chromatography, eluting with DCM/MeOH to afford methyl 2-[2-oxo-5-(trifluoromethyl)-1H-1,6-naphthyridin-3-yl]propanoate (105 mg, 95%). LC-MS: (ESI, m/z): 301 $[M+H]^+$ 2-[2-oxo-5-(trifluoromethyl)-1H-1,6-naphthyridin-3-yl] propanoic acid: To a solution of methyl 2-[2-oxo-5-(trifluoromethyl)-1H-1,6-naphthyridin-3-yl]propanoate (105 mg, 0.350 mmol, 1.00 equiv) in methanol (5.00 mL) and water (1.00 mL) was added lithium hydroxide hydrate (29.35 mg, 0.700 mmol, 2.00 equiv). The resulting solution was stirred for 2 h at RTRT. The resulting solution was concentrated under reduced pressure, diluted with water (3 mL), and adjusted to pH 5 with HCl (1M). The precipitated solids were collected by filtration, washed with water, dried under reduced pressure to afford 2-[2-oxo-5-(trifluoromethyl)-1H-1,6-naphthyridin-3-yl]propanoic acid (70 mg, 95% purity). LC-MS: (ESI, m/z): 287 $[M+H]^+$ N-[(1S)-1-(2,4-difluorophenyl)ethyl]-2-[2-oxo-5-(trifluoromethyl)-1H-1,6-naphthyridin-3-yl]propenamide (Compound 3518): Into a 8-mL vial, was placed 2-[2-oxo-5-(trifluoromethyl)-1H-1,6-naphthyridin-3-yl]propanoic acid (70.00 mg, 0.245 mmol, 1.00 equiv), DMF (3.00 mL), HATU (120.89 mg, 0.318 mmol, 1.3 equiv), DIEA (126.44 mg, 0.978 mmol, 4 equiv), and (1S)-1-(2,4-difluorophenyl) ethanamine (57.66 mg, 0.367 mmol, 1.5 equiv). The resulting solution was stirred for 4 hr at 10° C. The crude reaction was diluted with $H_2O$, extracted with ethyl acetate, and the organic layers combined and concentrated under vacuum. The crude residue was purified by reverse-phase chromatography eluting with water (0.05% $NH_4HCO_3$) and ACN to afford N-[(1S)-1-(2,4-difluorophenyl)ethyl]-2-[2-oxo-5-(trifluoromethyl)-1H-1,6-naphthyridin-3-yl]propanamide (70 mg, 67.02%). LC-MS: (ESI, m/z): 426.0 $[M+H]^+$ $^1H$ NMR (300 MHz, DMSO-$d_6$) δ 12.54 (s, 1H), 8.63-8.60 (m, 1H), 8.57-8.54 (m, 1H), 7.93-7.78 (m, 1H), 7.51-7.33 (m, 2H), 7.23-6.89 (m, 2H), 5.11-5.08 (m, 1H), 3.99-3.97 (m, 1H), 1.35-1.27 (m, 6H).

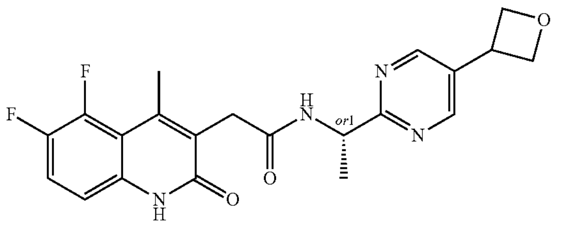

rel-2-(5,6-Difluoro-4-methyl-2-oxo-1H-quinolin-3-yl)-N-[(1R)-1-[5-(oxetan-3-yl)pyrimidin-2-yl]ethyl] acetamide (Compound 2043 and 2044)

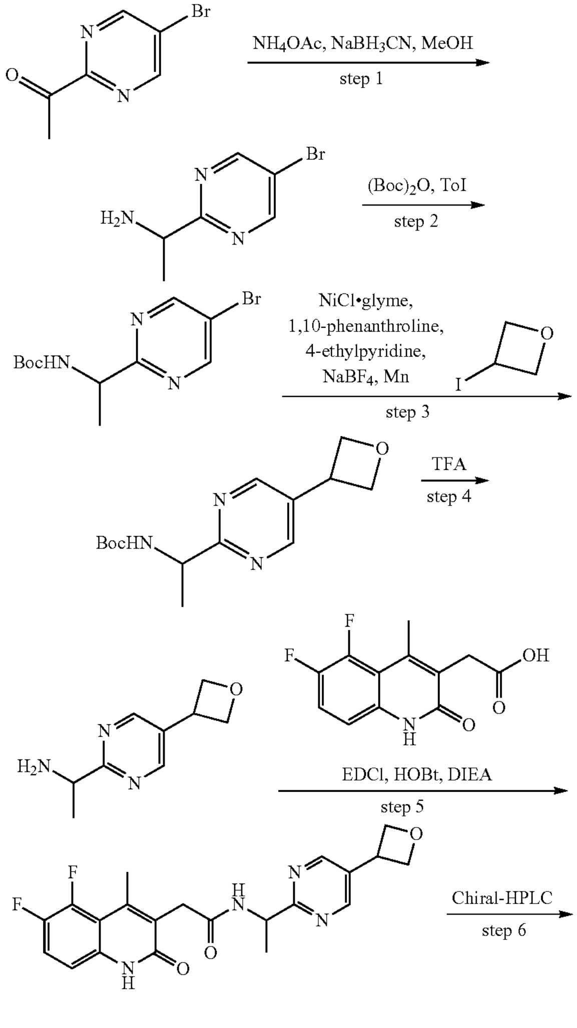

-continued

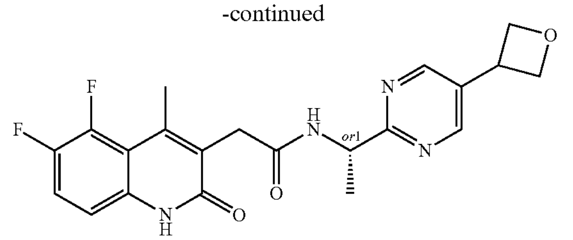

1-(5-bromopyrimidin-2-yl)ethanamine: A solution of 1-(5-bromopyrimidin-2-yl)ethanone (10 g, 49.746 mmol, 1 equiv), $NH_4OAc$ (19.17 g, 248.730 mmol, 5 equiv), and $NaBH_3CN$ (4.69 g, 74.619 mmol, 1.5 equiv) in MeOH (100 mL) was stirred for 2 h at RT. The crude residue was concentrated under vacuum and purified by column chromatography to afford 1-(5-bromopyrimidin-2-yl)ethanamine (6 g, 59.69%). LCMS (ES, m/z): 202 $[M+H]^+$ Tert-butyl N-[1-(5-bromopyrimidin-2-yl)ethyl]carbamate: A solution of 1-(5-bromopyrimidin-2-yl)ethanamine (5.5 g, 27.220 mmol, 1 equiv) and $Boc_2O$ (6.53 g, 29.942 mmol, 1.1 equiv) in Toluene (50 mL) was stirred for 3 h at 110° C. The crude reaction was concentrated under reduced pressure and purified by column chromatography to afford tert-butyl N-[1-(5-bromopyrimidin-2-yl)ethyl]carbamate (6.2 g, 75.38%). LCMS (ES, m/z): $302[M+H]^+$ Tert-butyl N-{1-[5-(oxetan-3-yl)pyrimidin-2-yl]ethyl}carbamate: A solution of tert-butyl N-[1-(5-bromopyridin-2-yl)ethyl]carbamate (1 g, 3.320 mmol, 1 equiv), 3-iodooxetane (0.92 g, 4.980 mmol, 1.5 equiv), (DME) $NiCl_2$ (0.02 g, 0.083 mmol, 0.025 equiv), 1,10-phenanthroline (0.03 g, 0.166 mmol, 0.05 equiv), 4-ethylpyridine (0.18 g, 1.660 mmol, 0.5 equiv), sodium fluoroborate (0.18 g, 1.660 mmol, 0.5 equiv), and Mn (0.36 g, 6.640 mmol, 2 equiv) in MeOH (10 mL) was stirred overnight at 60° C. under argon. The resulting mixture was filtered and the precipitate was washed with methanol. The filtrate was concentrated under reduced pressure and purified by column chromatography to afford tert-butyl N-{1-[5-(oxetan-3-yl)pyrimidin-2-yl]ethyl}carbamate (470 mg, 50.68%). LCMS (ES, m/z): $280[M+H]^+$ 1-[5-(oxetan-3-yl)pyrimidin-2-yl]ethanamine: To a stirred solution of tert-butyl N-{1-[5-(oxetan-3-yl)pyrimidin-2-yl]ethyl}carbamate (470 mg, 1.683 mmol, 1 equiv) in DCM (6 mL) was added TFA (2 mL) dropwise at 0° C. The resulting mixture was stirred overnight at RT. The resulting solution was concentrated under reduced pressure and used in the next step directly without further purification. LCMS (ES, m/z): $180[M+H]^+$ 2-(5,6-difluoro-4-methyl-2-oxo-1H-quinolin-3-yl)-N-{1-[5-(oxetan-3-yl)pyrimidin-2-yl]ethyl}acetamide: A solution of (5,6-difluoro-4-methyl-2-oxo-1H-quinolin-3-yl)acetic acid (250 mg, 0.987 mmol, 1 equiv), 1-[5-(oxetan-3-yl)pyrimidin-2-yl]ethanamine (212.35 mg, 1.184 mmol, 1.2 equiv), EDCI (227.13 mg, 1.184 mmol, 1.2 equiv), HOBT (160.10 mg, 1.184 mmol, 1.2 equiv), and DIEA (382.83 mg, 2.961 mmol, 3 equiv) in DMF (3 mL) was stirred overnight at RT. The resulting solution was diluted with water, extracted with EA, and concentrated under reduced pressure. The crude residue was purified by column chromatography, eluting with $CH_2Cl_2$/MeOH to afford crude product. The crude product was purified by Prep-HPLC with a XBridge Shield RP18 OBD 30*150 mm, 5 μm column eluting with Water(10 mmol/L $NH_4HCO_3$+0.05% $NH_3 \cdot H_2O$) and ACN to afford 2-(5,6-difluoro-4-methyl-2-oxo-1H-quinolin-3-yl)-N-{1-[5-(oxetan-3-yl)pyrimidin-2-yl]ethyl}acetamide (120 mg, 29.33%). LCMS (ES, m/z): $415[M+H]^+$ rel-2-(5,6-difluoro-4-methyl-2-oxo-1H-quinolin-3-yl)-N-[(1R)-1-[5-(oxetan-3-yl)pyrimidin-2-yl]ethyl]acetamide: 2-(5,6-difluoro-4-methyl-2-oxo-1H-quinolin-3-yl)-N-{1-[5-(oxetan-3-yl)pyrimidin-2-yl]ethyl}acetamide (200 mg) was purified by a CHIRAL ART Cellulose-SB, 3*25 cm, 5 μm column eluting with Hex(10 mM $NH_3$-MeOH) and EtOH to afford rel-2-(5,6-difluoro-4-methyl-2-oxo-1H-quinolin-3-yl)-N-[(1R)-1-[5-(oxetan-3-yl)pyrimidin-2-yl]ethyl]acetamide (59.0 mg, 29.50%). LCMS (ES, m/z): 415.10[M+H]+ $^1H$ NMR (300 MHz, DMSO-$d_6$) δ 11.93 (s, 1H), 8.86 (s, 2H), 8.42 (d, J=7.8 Hz, 1H), 7.62-7.52 (m, 11H), 7.13-7.08 (m, 1H), 5.04-4.91 (m, 3H), 4.68 (t, J=6.6 Hz, 211), 4.30-4.24 (m, 1H), 3.74-3.62 (m, 2H), 2.47 (d, J=6.6 Hz, 3H), 1.40 (d, J=6.9 Hz, 3H).

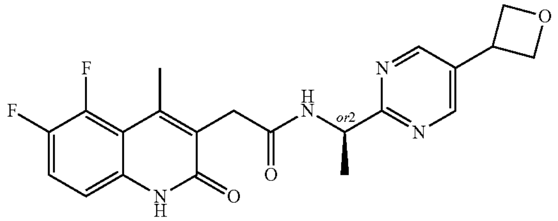

rel-2-(5,6-difluoro-4-methyl-2-oxo-1H-quinolin-3-yl)-N-[(1R)-1-[5-(oxetan-3-yl)pyrimidin-2-yl]ethyl]acetamide

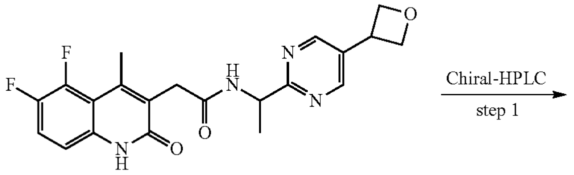

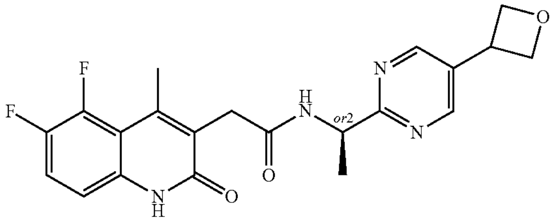

rel-2-(5,6-difluoro-4-methyl-2-oxo-1H-quinolin-3-yl)-N-[(1R)-1-[5-(oxetan-3-yl)pyrimidin-2-yl]ethyl]acetamide 2-(5,6-difluoro-4-methyl-2-oxo-1H-quinolin-3-yl)-N-{1-[5-(oxetan-3-yl)pyrimidin-2-yl]ethyl}acetamide (200 mg) was purified with a CHIRAL ART Cellulose-SB, 3*25 cm, 5 μm eluting with Hex(10 mM $NH_3$-MeOH), and EtOH to afford rel-2-(5,6-difluoro-4-methyl-2-oxo-1H-quinolin-3-yl)-N-[(1R)-1-[5-(oxetan-3-yl)pyrimidin-2-yl]ethyl]acetamide (56.1 mg, 28.05%). LCMS (ES, m/z): $415.10[M+H]^+$ $^1H$ NMR (300 MHz, DMSO-$d_6$) δ 11.20 (s, 111), 8.83 (s, 2H), 8.42 (d, J=7.8 Hz, 111), 7.62-7.53 (m, 1H), 7.14-7.09 (m, 1H), 5.04-4.90 (m, 3H), 4.68 (t, J=6.6 Hz, 2H), 4.35-4.25 (m, 1H), 3.69-3.62 (m, 2H), 2.47 (d, J=6.3 Hz, 3H), 1.40 (d, J=6.9 Hz, 3H).

(Compound 2606 and 2607)

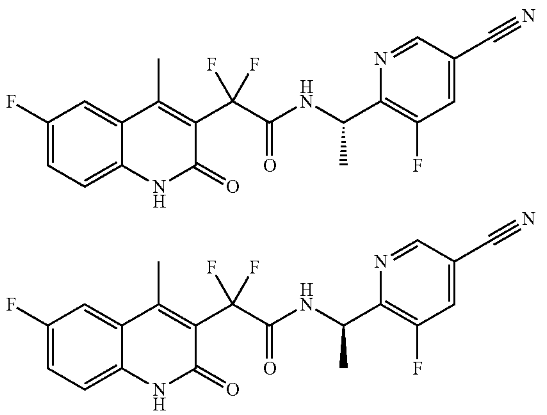

N-[(1S)-1-(5-Cyano-3-fluoropyridin-2-yl)ethyl]-2,2-difluoro-2-(6-fluoro-4-methyl-2-oxo-1H-quinolin-3-yl) acetamide and N-[(1R)-1-(5-Cyano-3-fluoropyridin-2-yl) ethyl]-2,2-difluoro-2-(6-fluoro-4-methyl-2-oxo-1H-quinolin-3-yl) acetamide Tert-butyl 3-(2-amino-5-fluorophenyl)-3-hydroxybutanoate: A solution of 1-(2-amino-5-fluorophenyl) ethanone (5 g, 32.6 mmol, 1 equiv) and tert-butyl 2-(bromozincio) acetate (42.51 g, 163.2 mmol, 5 equiv) in THF (100 mL) was stirred for 2 h at 70° C. under argon. The resulting mixture was concentrated under reduced pressure and purified by column chromatography to afford tert-butyl 3-(2-amino-5-fluorophenyl)-3-hydroxybutanoate (4 g, 45.49%). LCMS (ES, m/z): 270 [M+H]+.

6-Fluoro-4-methyl-1H-quinolin-2-one: A solution of tert-butyl 3-(2-amino-5-fluorophenyl)-3-hydroxybutanoate (4 g, 14.8 mmol, 1 equiv) and KOH (4.17 g, 74.3 mmol, 5 equiv) in EtOH (60 mL) was stirred for 2 h at 80° C. The resulting mixture was concentrated under reduced pressure and purified by column chromatography to afford 6-fluoro-4-methyl-1H-quinolin-2-one (3 g, 95.00%). LCMS (ES, m/z): 178 $[M+H]^+$.

Ethyl 2,2-difluoro-2-(6-fluoro-4-methyl-2-oxo-1H-quinolin-3-yl) acetate: To a stirred solution of 6-fluoro-4-methyl-1H-quinolin-2-one (3 g, 16.9 mmol, 1 equiv) and $Na_2CO_3$ (3.59 g, 33.8 mmol, 2 equiv) in DMF (30 mL) and acetone (30 mL) was added ethyl 2,2-difluoro-2-iodoacetate (12.70 g, 50.8 mmol, 3 equiv) at RT under nitrogen atmosphere. The resulting mixture was filtered and the precipitate was washed with acetone. The filtrate was concentrated under reduced pressure and purified by reverse-phase chromatography with a C18 column eluting with MeCN/Water (0.1% FA) to afford ethyl 2,2-difluoro-2-(6-fluoro-4-methyl-2-oxo-1H-quinolin-3-yl) acetate (1.5 g, 29.60%).

LCMS (ES, m/z): 300 $[M+H]^+$.

2,2-difluoro-2-(6-fluoro-2-hydroxy-4-methyl-decahydroquinolin-3-yl) ethane-1,1-diol: A solution of ethyl 2,2-difluoro-2-(6-fluoro-4-methyl-2-oxo-1H-quinolin-3-yl) acetate (1 g, 3.3 mmol, 1 equiv) and LiOH (0.40 g, 16.7 mmol, 5 equiv) in MeOH (7 mL), $H_2O$ (7 mL) was stirred for 2 h at RT. The resulting mixture was concentrated under reduced pressure and adjusted to pH 5 with HCl (aq.). The precipitated solids were collected by filtration, washed with MeCN, concentrated under reduced pressure, to afford 2,2-difluoro-2-(6-fluoro-2-hydroxy-4-methyl-decahydroquinolin-3-yl) ethane-1,1-diol (800 mg, 84.51%). LCMS (ES, m/z): 272 $[M+H]^+$.

N-[(1S)-1-(5-cyano-3-fluoropyridin-2-yl) ethyl]-2,2-difluoro-2-(6-fluoro-4-methyl-2-oxo-1H-quinolin-3-yl) acetamide: A solution of difluoro(6-fluoro-4-methyl-2-oxo-1H-quinolin-3-yl) acetic acid (100 mg, 0.369 mmol, 1 equiv), EDCI (84.82 mg, 0.443 mmol, 1.2 equiv), DMAP (9.01 mg, 0.074 mmol, 0.2 equiv) and 6-[(1S)-1-aminoethyl]-5-fluoropyridine-3-carbonitrile (60.90 mg, 0.369 mmol, 1 equiv) in DMF (3 mL) was stirred for 4 h at RT. The crude residue was purified by reverse-phase chromatography with a C18 column eluting with MeCN/Water (10 mmol/L $NH_4HCO_3$) to afford N-[(1S)-1-(5-cyano-3-fluoropyridin-2-yl) ethyl]-2,2-difluoro-2-(6-fluoro-4-methyl-2-oxo-1H-quinolin-3-yl) acetamide (66.9 mg, 43.28%). LCMS (ES, m/z): 419.10 $[M+H]^+$. $^1$H NMR (300 MHz, DMSO-d6) δ 12.06 (s, 1H), 8.92-8.89 (m, 2H), 8.41 (dd, J=9.9, 1.5 Hz, 1H), 7.80 (dd, J=10.8, 2.7 Hz, 1H), 7.53 (td, J=8.7, 2.7 Hz, 1H), 7.34 (dd, J=9.0, 5.1 Hz, 1H), 5.31 (p, J=6.7 Hz, 1H), 2.62 (t, J=3.0 Hz, 3H), 1.49 (d, J=7.2 Hz, 3H).

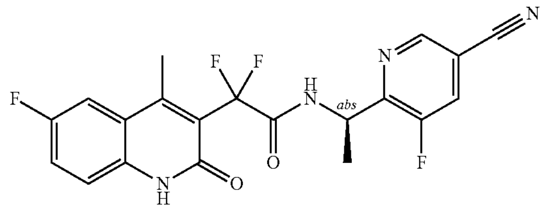 [SMILES: Cc1c(C(F)(F)C(=O)N[C@H](C)c2ncc(C#N)cc2F)c(=O)[nH]c2ccc(F)cc12]

N-[(1R)-1-(5-cyano-3-fluoropyridin-2-yl) ethyl]-2,2-difluoro-2-(6-fluoro-4-methyl-2-oxo-1H-quinolin-3-yl) acetamide: A solution of difluoro(6-fluoro-4-methyl-2-oxo-1H-quinolin-3-yl) acetic acid (100 mg, 0.369 mmol, 1 equiv), EDCI (84.82 mg, 0.443 mmol, 1.2 equiv), DMAP (9.01 mg, 0.074 mmol, 0.2 equiv) and 6-[(1R)-1-aminoethyl]-5-fluoropyridine-3-carbonitrile (60.90 mg, 0.369 mmol, 1 equiv) in DMF (2 mL) was stirred for 4 h at RT. The crude residue was purified by reverse-phase chromatography with a C18 column eluting with MeCN/Water (10 mmol/L $NH_4HCO_3$) to afford N-[(1R)-1-(5-cyano-3-fluoropyridin-2-yl) ethyl]-2,2-difluoro-2-(6-fluoro-4-methyl-2-oxo-1H-quinolin-3-yl) acetamide 8(65.9 mg, 42.63%). LCMS (ES, m/z): 419.05 [M+H]+.

$^1$H NMR (300 MHz, DMSO-d6) δ 12.06 (s, 1H), 8.92-8.89 (m, 2H), 8.41 (d, J=9.9, 1.5 Hz, 1H), 7.80 (dd, J=10.8, 2.7 Hz, 1H), 7.53 (td, J=8.7, 2.7 Hz, 1H), 7.34 (dd, J=9.0, 5.1 Hz, 1H), 5.36-5.26 (m, 1H), 2.62 (t, J=3.0 Hz, 3H), 1.49 (d, J=7.2 Hz, 3H).

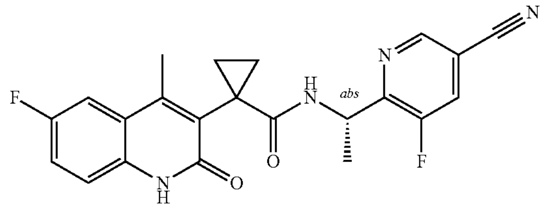

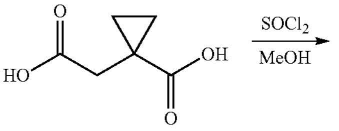

-continued

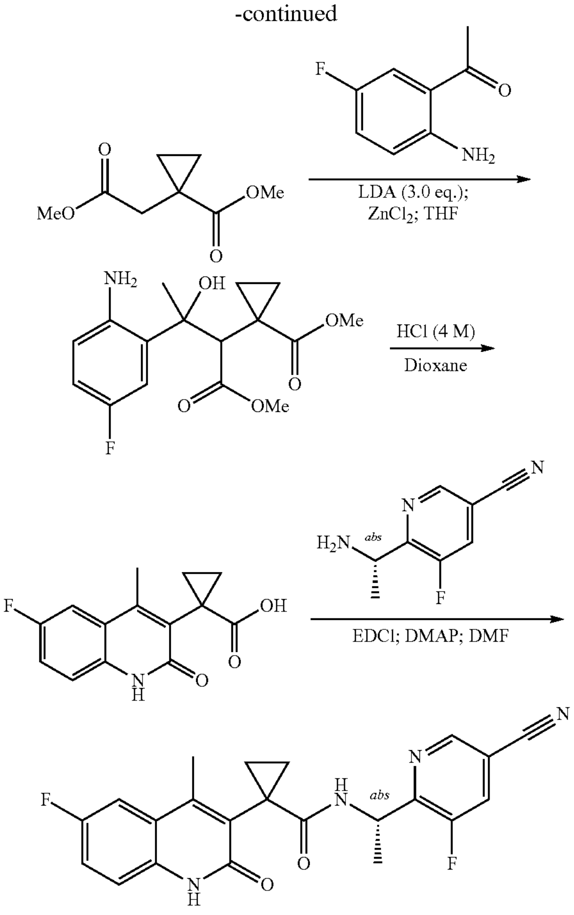

Methyl 1-(2-methoxy-2-oxoethyl)cyclopropane-1-carboxylate: A solution of 1-(carboxymethyl)cyclopropane-1-carboxylic acid (1 g, 6.938 mmol, 1 equiv) and thionyl chloride (8.25 g, 69.380 mmol, 10 equiv) in methanol (15 mL) was stirred overnight at 60° C. The reaction was cooled to RT. The crude reaction was concentrated under reduced pressure, diluted with water and adjusted to pH 8 with saturated $Na_2CO_3$. The aqueous layer was extracted with EA, concentrated under reduced pressure, and purified by column chromatography to afford methyl 1-(2-methoxy-2-oxoethyl)cyclopropane-1-carboxylate (780 mg, 65.29%). LCMS (ES, m/z): 173 $[M+H]^+$.

Methyl 1-[3-(2-amino-5-fluorophenyl)-3-hydroxy-1-methoxy-1-oxobutan-2-yl]cyclopropane-1-carboxylate: To a solution of methyl 1-(2-methoxy-2-oxoethyl)cyclopropane-1-carboxylate (899.37 mg, 5.224 mmol, 2 equiv) in THE (10 mL) was added LDA (7.836 mmol, 3 equiv) at −78° C. The solution was stirred for 30 min. 1-(2-amino-5-fluorophenyl)ethanone (400 mg, 2.612 mmol, 1 equiv) and $ZnCl_2$ (2.612 mmol, 1 equiv) was added at −78° C. and stirred for 1 h. The reaction was quenched with sat. $NH_4Cl$ (aq.) at 0° C. and diluted with water. The aqueous layer was extracted with EA, concentrated under reduced pressure, and purified by column chromatography to afford methyl 1-[3-(2-amino-5-fluorophenyl)-3-hydroxy-1-methoxy-1-oxobutan-2-yl]cyclopropane-1-carboxylate (170 mg, 20.01%). LCMS (ES, m/z): 326 $[M+H]^+$.

1-(6-fluoro-4-methyl-2-oxo-1H-quinolin-3-yl)cyclopropane-1-carboxylic acid: A solution of methyl 1-[3-(2-amino-5-fluorophenyl)-3-hydroxy-1-methoxy-1-oxobutan-2-yl]cyclopropane-1-carboxylate (170 mg, 0.523 mmol, 1 equiv) and hydrogen chloride (2 mL) in dioxane (2 mL) was stirred for 2 h at 80° C. The crude reaction was cooled to RT, concentrated under reduced pressure, and purified by trituration with MeCN to afford 1-(6-fluoro-4-methyl-2-oxo-1H-quinolin-3-yl)cyclopropane-1-carboxylic acid (120 mg, 87.90%). LCMS (ES, m/z): 262 $[M+H]^+$.

N-[(1S)-1-(5-cyano-3-fluoropyridin-2-yl)ethyl]-1-(6-fluoro-4-methyl-2-oxo-1H-quinolin-3-yl)cyclopropane-1-carboxamide (Compound 2596 and 2597): A solution of 1-(6-fluoro-4-methyl-2-oxo-1H-quinolin-3-yl)cyclopropane-1-carboxylic acid (70 mg, 0.268 mmol, 1 equiv), 6-[(1S)-1-aminoethyl]-5-fluoropyridine-3-carbonitrile (53.11 mg, 0.322 mmol, 1.2 equiv), HATU (122.26 mg, 0.322 mmol, 1.2 equiv) and DIEA (103.89 mg, 0.804 mmol, 3 equiv) in DMF (2 mL) was stirred overnight at RT. The crude residue was purified by reverse-phase chromatography with a C18 column eluting with MeCN/Water (0.1% FA) to afford N-[(1S)-1-(5-cyano-3-fluoropyridin-2-yl)ethyl]-1-(6-fluoro-4-methyl-2-oxo-1H-quinolin-3-yl)cyclopropane-1-carboxamide (80 mg, 73.11%). LCMS (ES, m/z): 409.10 $[M+H]^+$. $^1H$ NMR (300 MHz, DMSO-$d_6$) δ 11.70 (s, 1H), 8.79 (s, 1H), 8.37-8.33 (m, 1H), 7.71 (d, J=7.8 Hz, 1H), 7.60-7.56 (m, 1H), 7.43-7.39 (m, 1H), 7.37-7.28 (m, 1H), 5.29-5.24 (m, 1H), 2.43 (s, 3H), 1.48-1.42 (m, 2H), 1.31-1.23 (m, 3H), 0.89-0.83 (m, 2H).

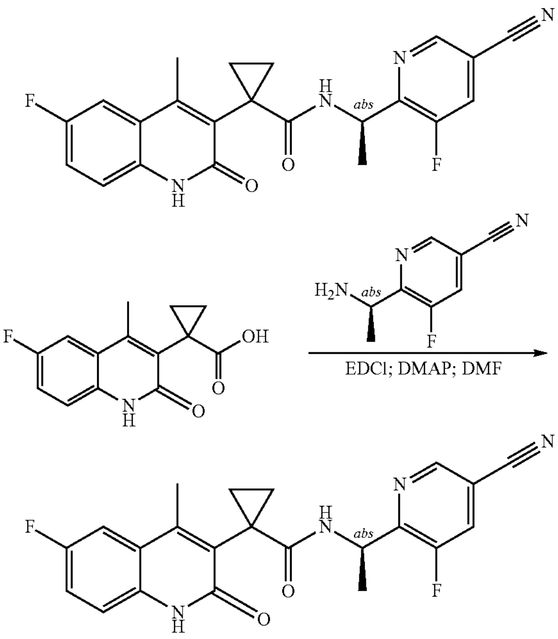

N-[(1R)-1-(5-cyano-3-fluoropyridin-2-yl)ethyl]-1-(6-fluoro-4-methyl-2-oxo-1H-quinolin-3-yl)cyclopropane-1-carboxamide (Compound 2596 and 2597): A solution of 1-(6-fluoro-4-methyl-2-oxo-1H-quinolin-3-yl)cyclopropane-1-carboxylic acid (70 mg, 0.268 mmol, 1 equiv), 6-[(1R)-1-aminoethyl]-5-fluoropyridine-3-carbonitrile (53.11 mg, 0.322 mmol, 1.2 equiv), HATU (122.26 mg, 0.322 mmol, 1.2 equiv) and DIEA (103.89 mg, 0.804 mmol, 3 equiv) in DMF (2 mL) was stirred overnight at RT. The residue was purified by reverse-phase chromatography with a C18 column eluting with MeCN/Water (0.1% FA) to afford N-[(1R)-1-(5-cyano-3-fluoropyridin-2-yl)ethyl]-1-(6-fluoro-4-methyl-2-oxo-1H-quinolin-3-yl)cyclopropane-1-carboxamide (70 mg, 63.97%). LCMS (ES, m/z): 409.10

[M+H]$^+$. $^1$H NMR (300 MHz, DMSO-$d_6$) δ 11.70 (s, 1H), 8.79 (m, 1H), 8.37-8.33 (m, 11H), 7.71 (d, J=7.5 Hz, 1H), 7.60-7.56 (m, 1H), 7.43-7.36 (m, 1H), 7.33-7.28 (m, 1H), 5.32-5.22 (m, 1H), 2.43 (s, 3H), 1.47-1.39 (m, 2H), 1.31-1.23 (m, 3H), 0.89-0.83 (m, 2H).

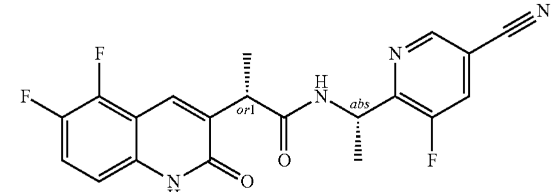

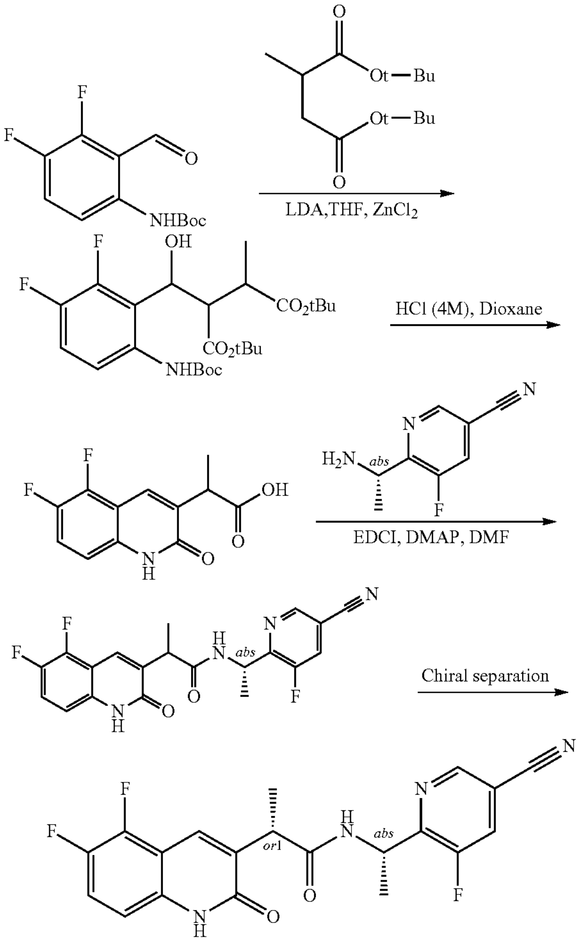

1,4-di-tert-butyl 2-({6-[(tert-butoxycarbonyl)amino]-2,3-difluorophenyl}(hydroxy)methyl)-3-methylbutanedioate: A solution of 1,4-di-tert-butyl 2-methylbutanedioate (3.80 g, 15.550 mmol, 2 equiv) in THF (30 mL) was treated with LDA(in 2M THF) (2.50 g, 23.325 mmol, 3 equiv) for 30 min at −78° C. under argon followed by the addition of tert-butyl N-(3,4-difluoro-2-formylphenyl)carbamate (2 g, 7.775 mmol, 1 equiv) and $ZnCl_2$ (1.06 g, 7.775 mmol, 1 equiv) at −78° C. The resulting mixture was stirred for 1 h at −78° C. under argon. The reaction was quenched with sat. $NH_4Cl$ (aq.) at 0° C. and extracted with EA. The crude residue was concentrated under reduced pressure and purified by column chromatography to afford 1,4-di-tert-butyl 2-({6-[(tert-butoxycarbonyl)amino]-2,3-difluorophenyl}(hydroxy) methyl)-3-methylbutanedioate (2 g, 51.29%). LCMS (ES, m/z): 502 [Ms+H]$^+$.

2-(5,6-difluoro-2-oxo-1H-quinolin-3-yl)propanoic acid: A solution of 1,4-di-tert-butyl 2-({6-[(tert-butoxycarbonyl) amino]-2,3-difluorophenyl}(hydroxy) methyl)-3-methylbutanedioate (2 g, 3.987 mmol, 1 equiv) and HCl (4M) (10 mL) in dioxane (10 mL) was stirred overnight at 80° C. The crude reaction was concentrated under reduced pressure and purified by trituration with MeCN to afford 2-(5,6-difluoro-2-oxo-1H-quinolin-3-yl)propanoic acid (700 mg, 69.33%). LCMS (ES, m/z): 254 [Ms+H]$^+$.

(2R*)-N-[(1S)-1-(5-cyano-3-fluoropyridin-2-yl)ethyl]-2-(5,6-difluoro-2-oxo-1H-quinolin-3-yl)propanamide:

To a stirred solution of rel-(2R)-2-(5,6-difluoro-2-oxo-1H-quinolin-3-yl)propanoic acid (200 mg, 0.790 mmol, 1 equiv) and 6-[(1S)-1-aminoethyl]-5-fluoropyridine-3-carbonitrile (156.56 mg, 0.948 mmol, 1.2 equiv) in DMF (5 mL) was added EDCI (181.70 mg, 0.948 mmol, 1.2 equiv) and DMAP (38.60 mg, 0.316 mmol, 0.4 equiv) at RT. The resulting mixture was stirred for 2 h at RT. The crude residue was purified by reverse-phase chromatography with a C18 column eluting with MeCN/Water (10 mmol/L $NH_4HCO_3$) to afford (2R*)-N-[(1S)-1-(5-cyano-3-fluoropyridin-2-yl) ethyl]-2-(5,6-difluoro-2-oxo-1H-quinolin-3-yl)propanamide (135 mg, 42.69%). LCMS (ES, m/z): 401 [Ms+H]$^+$.

(2S*)-N-[(1S)-1-(5-cyano-3-fluoropyridin-2-yl)ethyl]-2-(5,6-difluoro-2-oxo-1H-quinolin-3-yl)propanamide (Compound 2604 and 2605): (2R*)-N-[(1S)-1-(5-cyano-3-fluoropyridin-2-yl)ethyl]-2-(5,6-difluoro-2-oxo-1H-quinolin-3-yl) propanamide (135 mg) was separated by Chiral-HPLC with a CHIRAL ART Cellulose-SZ (3*25 cm, 5 μm) column eluting with Hex(10 mM $NH_3$-MeOH) and EtOH to afford (2S*)-N-[(1S)-1-(5-cyano-3-fluoropyridin-2-yl)ethyl]-2-(5,6-difluoro-2-oxo-1H-quinolin-3-yl)propanamide (39.6 mg, 29.16%). LCMS (ES, m/z): 399.00 [Ms−H]$^+$. $^1$H NMR (300 MHz, DMSO-$d_6$)) δ 12.08 (s, 1H), 8.72 (t, J=1.2 Hz, 1H), 8.65 (d, J=6.9 Hz, 1H), 8.39-8.35 (m, 1H), 7.61-7.55 (m, 1H), 7.51 (s, 1H), 7.12-7.08 (m, 1H), 5.27-5.18 (m, 1H), 3.98-3.91 (m, 1H), 1.37 (d, J=7.2 Hz, 3H), 1.26 (d, J=7.2 Hz, 3H).

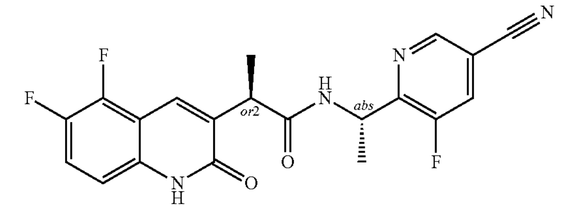

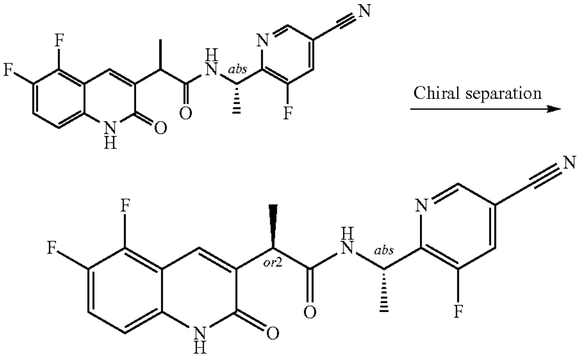

(2R*)-N-[(1S)-1-(5-cyano-3-fluoropyridin-2-yl)ethyl]-2-(5,6-difluoro-2-oxo-1H-quinolin-3-yl)propanamide: (2R*)-N-[(1S)-1-(5-cyano-3-fluoropyridin-2-yl)ethyl]-2-(5,6-difluoro-2-oxo-1H-quinolin-3-yl) propanamide (135 mg) was separated by Chiral-HPLC with a CHIRAL ART Cellulose-SZ (3*25 cm, 5 μm) column eluting with Hex(10 mM $NH_3$-MeOH) and EtOH to afford (2R*)-N-[(1S)-1-(5-cyano-3-fluoropyridin-2-yl)ethyl]-2-(5,6-difluoro-2-oxo-1H-quinolin-3-yl)propanamide (51.6 mg, 36.58. LCMS (ES, m/z): 401.05 $[Ms-H]^+$. $^1H$ NMR (300 MHz, DMSO-$d_6$)) δ 12.09 (s, 1H), 8.72 (t, J=1.2 Hz, 1H), 8.65 (d, J=6.9 Hz, 1H), 8.39-8.36 (m, 1H), 7.62-7.59 (m, 1H), 7.516-7.53 (m, 1H), 7.13-7.10 (m, 1H), 5.24-5.15 (m, 1H), 3.98-3.91 (m, 1H), 1.36 (d, J=7.2 Hz, 3H), 1.26 (d, J=7.2 Hz, 3H).

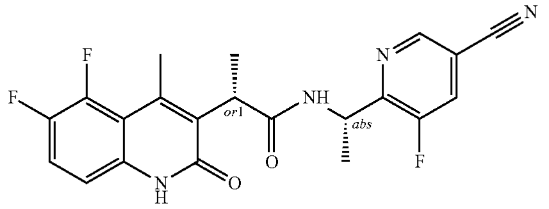

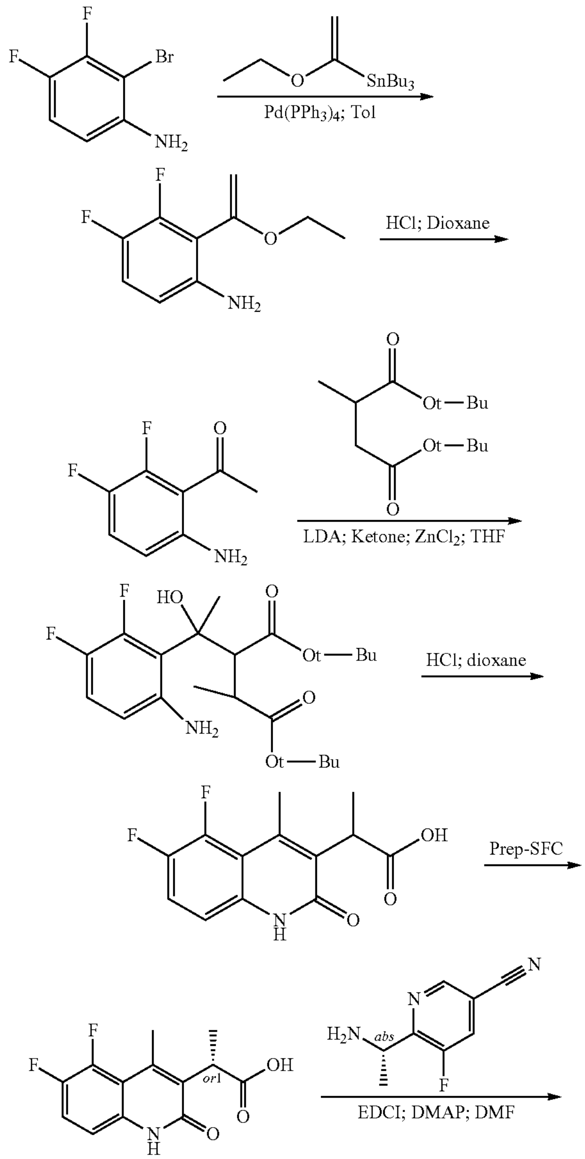

-continued

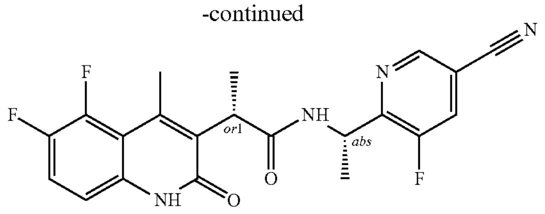

2-(1-ethoxyethenyl)-3,4-difluoroaniline: A solution of 2-bromo-3,4-difluoroaniline (10 g, 48.076 mmol, 1 equiv), tributyl(1-ethoxyethenyl) stannane (34.73 g, 96.152 mmol, 2 equiv) and $Pd(PPh_3)_4$ (5.56 g, 4.808 mmol, 0.1 equiv) in Toluene (50 mL) was stirred overnight at 100° C. under argon. The reaction was quenched with ice water at 0° C. The aqueous layer was extracted with EtOEt and purified by column chromatography to afford 2-(1-ethoxyethenyl)-3,4-difluoroaniline (6.5 g, 67.87%). LCMS (ES, m/z): 200 $[M+H]^+$.

1-(6-amino-2,3-difluorophenyl) ethanone: Into a 40 mL sealed tube were added 2-(1-ethoxyethenyl)-3,4-difluoroaniline (6.4 g, 32.128 mmol, 1 equiv), Dioxane (30 mL, 354.119 mmol) and HCl(4M/L) in 1,4-dioxane (30 mL) at RT. The resulting mixture was stirred for 3 h at RT. The crude reaction was extracted with EA and the aqueous layer was adjusted to pH 8 with saturated $NaHCO_3$ (aq.). The aqueous layer was then extracted with EtOEt, dried over anhydrous $Na_2SO_4$, concentrated under reduced pressure, and purified by column chromatography to afford 1-(6-amino-2,3-difluorophenyl) ethanone (3.2 g, 58.20%). LCMS (ES, m/z): 172 $[M+H]^+$.

1,4-di-tert-butyl 2-[1-(6-amino-2,3-difluorophenyl)-1-hydroxyethyl]-3-methylbutanedioate: To a stirred solution of 1,4-di-tert-butyl 2-methylbutanedioate (5.71 g, 23.372 mmol, 2 equiv) in THF (20 mL) was added LDA (23.37 mL, 46.744 mmol, 4 equiv) dropwise at −78° C. under argon. The resulting mixture was stirred for 30 min at −78° C. under argon. 1-(6-amino-2,3-difluorophenyl) ethanone (2 g, 11.686 mmol, 1 equiv) was added, followed by $ZnCl_2$ (16.69 mL, 11.686 mmol, 1 equiv) dropwise over 10 min at −78° C. The resulting mixture was stirred for an additional 1 h at −78° C. The reaction was quenched by the addition of sat. $NH_4Cl$ (aq.) (1 mL) at 0° C. and extracted with EtOEt. The combined organic layers were washed with brine, dried over anhydrous $Na_2SO_4$, filtered, and the filtrate was concentrated under reduced pressure. The crude residue was purified by column chromatography to afford 1,4-di-tert-butyl 2-[1-(6-amino-2,3-difluorophenyl)-1-hydroxyethyl]-3-methylbutanedioate (1.2 g, 24.72%). LCMS (ES, m/z): 416 $[M+H]^+$.

2-(5,6-difluoro-4-methyl-2-oxo-1H-quinolin-3-yl) propanoic acid: A solution of 1,4-di-tert-butyl 2-[1-(6-amino-2,3-difluorophenyl)-1-hydroxyethyl]-3-methylbutanedioate (1.2 g, 2.888 mmol, 1 equiv) and LiOH (0.35 g, 14.440 mmol, 5 equiv) in MeOH (10 mL) $H_2O$ (10 mL) was stirred for 4 h at 80° C. The resulting solution was concentrated under reduced pressure. The solution was adjusted to pH 5 with HCl (aq.). The precipitated solids were collected by filtration and washed with MeCN. The residue was purified by trituration with MeCN (5 mL) to afford 2-(5,6-difluoro-4-methyl-2-oxo-1H-quinolin-3-yl) propanoic acid (500 mg, 64.78%). LCMS (ES, m/z): 268 $[M+H]^+$.

Rel-(2R)-2-(5,6-difluoro-4-methyl-2-oxo-1H-quinolin-3-yl) propanoic acid: 2-(5,6-difluoro-4-methyl-2-oxo-1H-quinolin-3-yl) propanoic acid (500 mg) was purified by Prep-SFC-HPLC with a CHIRAL ART Cellulose-SC (3*25 cm, 5

µm) column eluting with $CO_2$ and MeOH to afford rel-(2R)-2-(5,6-difluoro-4-methyl-2-oxo-1H-quinolin-3-yl) propanoic acid (220 mg, 44.00%). LCMS (ES, m/z): 268 $[M+H]^+$.

Rel-(2R*)-N-[(1S)-1-(5-cyano-3-fluoropyridin-2-yl) ethyl]-2-(5,6-difluoro-4-methyl-2-oxo-1H-quinolin-3-yl) propenamide (compound 2602): A solution of rel-(2R)-2-(5,6-difluoro-4-methyl-2-oxo-1H-quinolin-3-yl) propanoic acid (100 mg, 0.374 mmol, 1 equiv), DMAP (18.29 mg, 0.150 mmol, 0.4 equiv), EDCI (86.08 mg, 0.449 mmol, 1.2 equiv) and 6-[(1S)-1-aminoethyl]-5-fluoropyridine-3-carbonitrile (61.81 mg, 0.374 mmol, 1 equiv) in DMF (2 mL) was stirred for 2 h at RT. The crude residue was purified by reverse-phasereverse-phase chromatography with a C18 column eluting with MeCN/Water (0.1% FA) to afford rel-(2R*)-N-[(1S)-1-(5-cyano-3-fluoropyridin-2-yl) ethyl]-2-(5,6-difluoro-4-methyl-2-oxo-1H-quinolin-3-yl) propanamide (42.2 mg, 27.22%). LCMS (ES, m/z): 415.05 $[M+H]^+$. $^1H$ NMR (300 MHz, DMSO-d6) δ 11.88 (s, 1H), 8.79 (s, 1H), 8.38-8.35 (m, 1H), 7.99 (d, J=7.2 Hz, 1H), 7.62-7.53 (m, 1H), 7.14-7.09 (m, 1H), 5.34-5.25 (m, 1H), 4.30-4.23 (m, 1H), 2.20 (d, J=7.2 Hz, 3H), 1.34 (d, J=7.2 Hz, 3H), 1.22 (d, J=7.2 Hz, 3H).

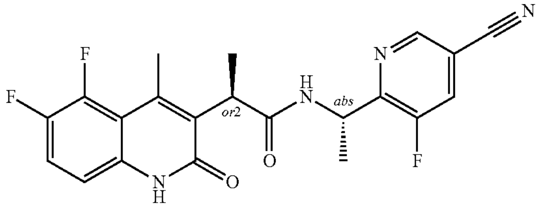

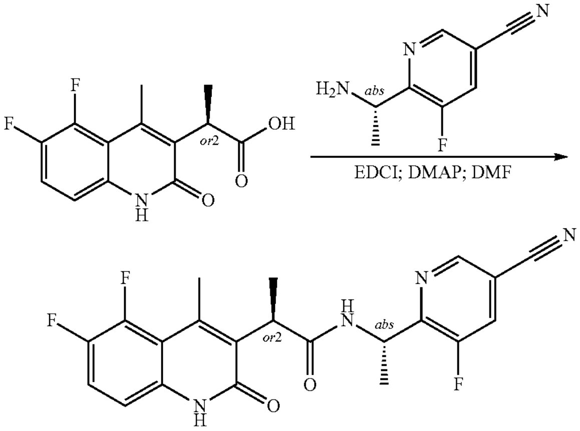

Rel-(2R*)-N-[(1S)-1-(5-cyano-3-fluoropyridin-2-yl) ethyl]-2-(5,6-difluoro-4-methyl-2-oxo-1H-quinolin-3-yl) propanamide: A solution of rel-(2R)-2-(5,6-difluoro-4-methyl-2-oxo-1H-quinolin-3-yl) propanoic acid (100 mg, 0.374 mmol, 1 equiv), DMAP (18.29 mg, 0.150 mmol, 0.4 equiv), EDCI (86.08 mg, 0.449 mmol, 1.2 equiv) and 6-[(1S)-1-aminoethyl]-5-fluoropyridine-3-carbonitrile (61.81 mg, 0.374 mmol, 1 equiv) in DMF (2 mL) was stirred for 2 h at RT. The crude residue was purified by reverse-phase chromatography with a C18 column eluting with MeCN/Water (0.1% FA) to afford rel-(2R*)-N-[(1S)-1-(5-cyano-3-fluoropyridin-2-yl) ethyl]-2-(5,6-difluoro-4-methyl-2-oxo-1H-quinolin-3-yl) propenamide (34.0 mg, 21.94%). LCMS (ES, m/z): 415.05 $[M+H]^1$H NMR (300 MHz, DMSO-d6) δ 11.90 (s, 1H), 8.84 (s, 1H), 8.41-8.31 (m, 1H), 8.00 (d, J=7.2 Hz, 1H), 7.61-7.53 (m, 1H), 7.14-7.09 (m, 1H), 5.33-5.24 (m, 1H), 4.22-4.15 (m, 1H), 2.41 (d, J=7.2 Hz, 3H), 1.35 (d, J=7.2 Hz, 3H), 1.22 (d, J=7.2 Hz, 3H).

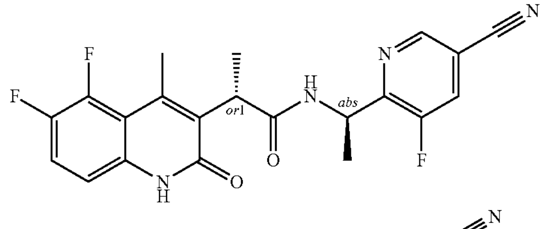

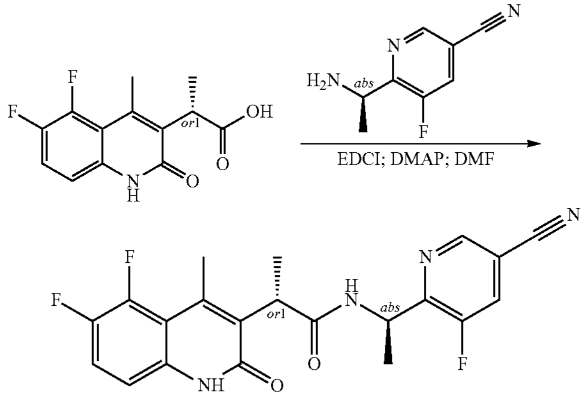

Rel-(2R*)-N-[(1R)-1-(5-cyano-3-fluoropyridin-2-yl) ethyl]-2-(5,6-difluoro-4-methyl-2-oxo-1H-quinolin-3-yl) propanamide (Compound 2600): A solution of rel-(2R)-2-(5,6-difluoro-4-methyl-2-oxo-1H-quinolin-3-yl) propanoic acid (100 mg, 0.374 mmol, 1 equiv), DMAP (18.29 mg, 0.150 mmol, 0.4 equiv), EDCI (86.08 mg, 0.449 mmol, 1.2 equiv) and 6-[(1R)-1-aminoethyl]-5-fluoropyridine-3-carbonitrile (61.81 mg, 0.374 mmol, 1 equiv) in DMF (2 mL) was stirred for 2 h at RTRT. The crude residue was purified by reverse-phase chromatography with a C18 column eluting with MeCN/Water (0.1% FA) to afford rel-(2R*)-N-[(1R)–1-(5-cyano-3-fluoropyridin-2-yl) ethyl]-2-(5,6-difluoro-4-methyl-2-oxo-1H-quinolin-3-yl) propanamide (39.8 mg, 25.68%). LCMS (ES, m/z): 415.05 $[M+H]^+$. $^1H$ NMR (300 MHz, DMSO-d6) δ 11.90 (s, 1H), 8.84 (s, 1H), 8.38-8.34 (m, 1H), 8.00 (d, J=7.2 Hz, 1H), 7.62-7.53 (m, 1H), 7.13-7.09 (m, 1H), 5.33-5.25 (m, 1H), 4.22-4.15 (m, 1H), 2.41 (d, J=7.2 Hz, 3H), 1.30 (d, J=7.2 Hz, 3H), 1.22 (d, J=7.2 Hz, 3H).

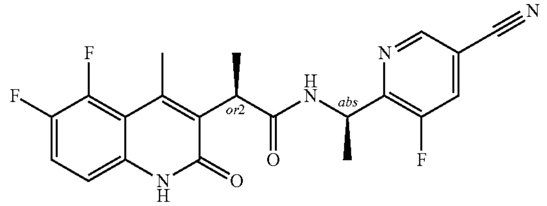

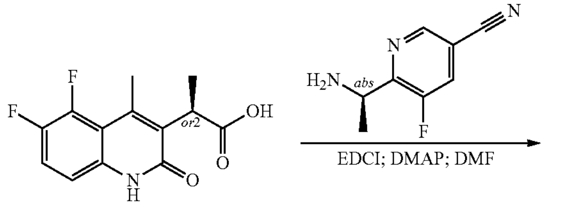

-continued

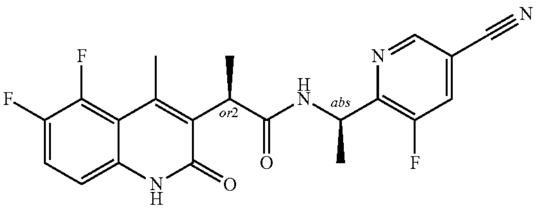

Rel-(2R*)-N-[(1R)-1-(5-cyano-3-fluoropyridin-2-yl) ethyl]-2-(5,6-difluoro-4-methyl-2-oxo-1H-quinolin-3-yl) propanamide: A solution of rel-(2R)-2-(5,6-difluoro-4-methyl-2-oxo-1H-quinolin-3-yl) propanoic acid (100 mg, 0.374 mmol, 1 equiv), DMAP (18.29 mg, 0.150 mmol, 0.4 equiv), EDCI (86.08 mg, 0.449 mmol, 1.2 equiv) and 6-[(1R)-1-aminoethyl]-5-fluoropyridine-3-carbonitrile (61.81 mg, 0.374 mmol, 1 equiv) in DMF (2 mL) was stirred for 2 h at RTRT. The crude residue was purified by reverse-phase chromatography with a C18 column eluting with MeCN/Water (0.1% FA) to afford rel-(2R*)-N-[(IR)-1-(5-cyano-3-fluoropyridin-2-yl) ethyl]-2-(5,6-difluoro-4-methyl-2-oxo-1H-quinolin-3-yl) propanamide (56.5 mg, 36.45%). LCMS (ES, m/z): 415.05 $[M+H]^+$. $^1H$ NMR (300 MHz, DMSO-d6) δ 11.88 (s, 1H), 8.78 (s, 1H), 8.38-8.35 (m, 1H), 8.00 (d, J=7.2 Hz, 1H), 7.62-7.53 (m, 1H), 7.14-7.09 (m, 1H), 5.32-5.27 (m, 1H), 4.30-4.23 (m, 1H), 2.20 (d, J=7.2 Hz, 3H), 1.34 (d, J=7.2 Hz, 3H), 1.21 (d, J=7.2 Hz, 3H).

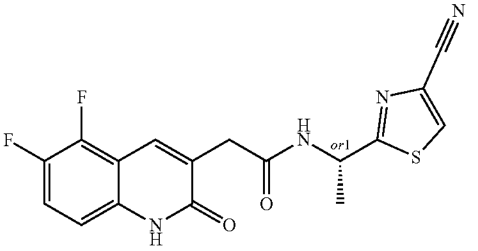

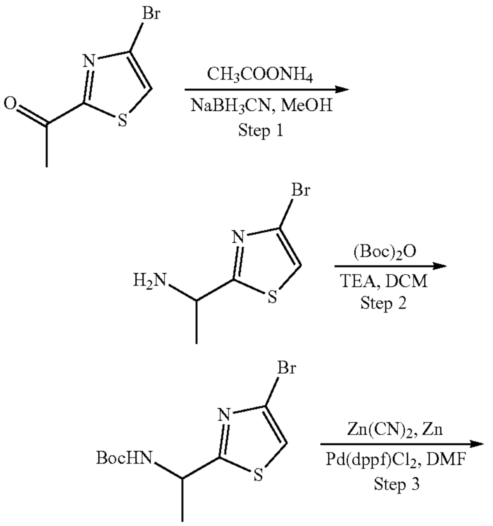

-continued

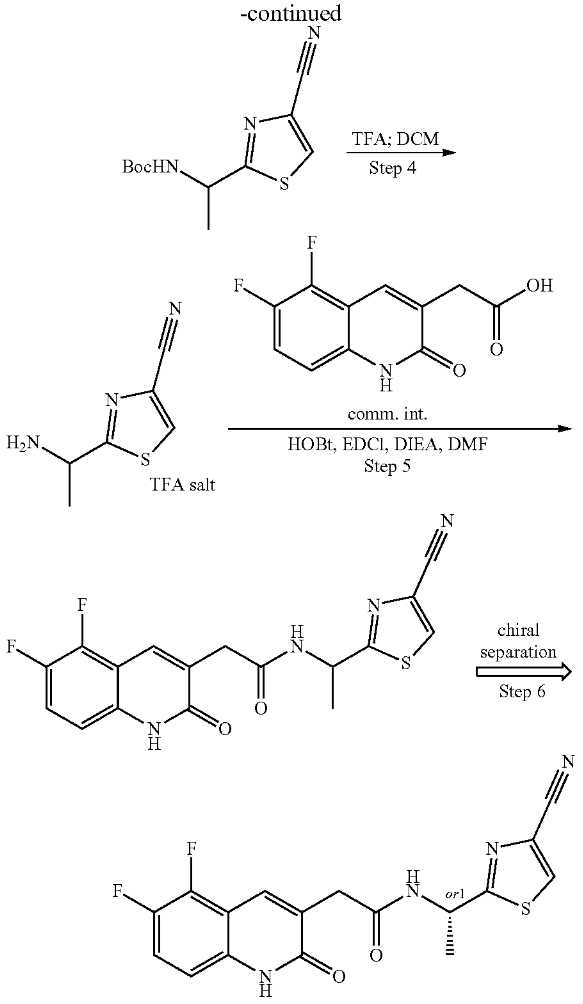

1-(4-bromothiazol-2-yl)ethan-1-amine: A solution of 1-(4-bromo-1,3-thiazol-2-yl)ethanone (4.00 g, 19.4 mmol, 1.00 equiv) in MeOH (40 mL) was treated with ammonium acetate (29.9 g, 388.0 mmol, 20.0 equiv) and $NaHCO_3$ (4.90 g, 58.2 mmol, 3.00 equiv) and stirred overnight at 40° C. under nitrogen. $NaBH_3CN$ (6.10 g, 97.1 mmol, 5.00 equiv) was added dropwise at RT. The reaction was diluted with water and extracted with EA. The combined organic layers were washed with brine, dried over anhydrous $Na_2SO_4$, filtered, and concentrated under reduced pressure. The crude residue was purified by reverse-phase chromatography with a C18 column eluting with MeCN/Water (10 mmol/L $NH_4HCO_3$ to afford 1-(4-bromothiazol-2-yl)ethan-1-amine (800 mg, 19.90%). LCMS (ES, m/z): 207/209 $[M+H]^+$ Tert-butyl (1-(4-bromothiazol-2-yl)ethyl)carbamate: To a stirred solution of 1-(4-bromothiazol-2-yl)ethan-1-amine (800 mg, 3.32 mmol, 1.00 equiv) and $(Boc)_2O$ (868.8 mg, 3.98 mmol, 1.20 equiv) in DCM (10 mL) was added TEA (671.0 mg, 6.64 mmol, 2.00 equiv) and DMAP (20.3 mg, 0.166 mmol, 0.05 equiv) dropwise at R.T under nitrogen. The resulting mixture was stirred for 2 h at RT under nitrogen. The reaction was diluted with water and extracted with EA. The combined organic layers were washed with brine, dried over anhydrous $Na_2SO_4$, filtered, and concentrated under reduced pressure. The crude residue was purified by column chromatography to afford tert-butyl (1-(4-bromothiazol-2-yl)ethyl)carbamate (500 mg, 49.06%). LCMS (ES, m/z): 307/309 $[M+H]^+$ Tert-butyl (1-(4-cyanothiazol-2-yl)ethyl)carbamate: To a stirred solution of tert-butyl (1-(4-bromothiazol-2-yl)ethyl) carbamate (600 mg, 1.95 mmol, 1.00 equiv) and zinc powder (127.7 mg, 1.95 mmol, 1.00 equiv) in DMF (10 mL) was added Pd(dppf)$Cl_2$ (142.9 mg, 0.196 mmol, 0.10 equiv) and $Zn(CN)_2$ (458.7 mg, 3.91 mmol, 2.00 equiv) dropwise at RT under nitrogen. The resulting mixture was stirred for 2 h at 120° C. under argon. The crude reaction was diluted with water and extracted with EA. The combined organic layers were washed with brine, dried over anhydrous $Na_2SO_4$, filtered, and the filtrate was concentrated under reduced pressure. The crude residue was purified by Prep-TLC eluting with PE and EA to afford tert-butyl (1-(4-cyanothiazol-2-yl)ethyl)carbamate (440 mg, 88.93%). LCMS (ES, m/z): 254 $[M+H]^+$ 2-(1-aminoethyl)thiazole-4-carbonitrile: To a stirred solution of tert-butyl (1-(4-cyanothiazol-2-yl)ethyl)carbamate (300 mg, 1.18 mmol, 1.00 equiv) in DCM (4 mL) was added TFA (2 mL, 26.9 mmol, 30.9 equiv) dropwise at RT under nitrogen. The resulting mixture was stirred for 1 h at RT under nitrogen. The crude material was concentrated under reduced pressure to afford 2-(1-aminoethyl)thiazole-4-carbonitrile (300 mg, crude) which was used in the next step directly without further purification.

N-(1-(4-cyanothiazol-2-yl)ethyl)-2-(5,6-difluoro-2-oxo-1,2-dihydroquinolin-3-yl)acetamide (Compound 4009): 2-(6-fluoro-2-oxo-1,2-dihydroquinolin-3-yl)acetic acid (200 mg, 0.836 mmol, 1.00 equiv), EDCI (200.4 mg, 1.05 mmol, 1.25 equiv) and HOBt (141.2 mg, 1.05 mmol, 1.25 equiv) were dissolved in DMF (5 mL). DIEA (270.2 mg, 2.090 mmol, 2.50 equiv) and 2-(1-aminoethyl)thiazole-4-carbonitrile (153.7 mg, 1.00 mmol, 1.2 equiv) was added dropwise at RT under nitrogen. The resulting mixture was stirred for 3 h at RT under nitrogen. The crude reaction was diluted with water and extracted with EA. The combined organic layers were washed with brine, dried over anhydrous $Na_2SO_4$, filtered, and concentrated under reduced pressure. The crude residue was purified by reverse-phase chromatography with a C18 column eluting with MeCN/Water (10 mmol/L $NH_4HCO3$) to afford N-(1-(4-cyanothiazol-2-yl) ethyl)-2-(5,6-difluoro-2-oxo-1,2-dihydroquinolin-3-yl)acetamide (150 mg, 47.92%). LCMS (ES, m/z): 375 $[M+H]^+$ (S)—N-(1-(4-cyanothiazol-2-yl)ethyl)-2-(5,6-difluoro-2-oxo-1,2-dihydroquinolin-3-yl)acetamide (assumed) The racemic product (150 mg) was purified by Prep-HPLC with a CHIRALPAK ID, (3*25 cm, 5 μm) eluting with Hex(0.1% 2M $NH_3$-MeOH) and EtOH to afford (S)—N-(1-(4-cyanothiazol-2-yl)ethyl)-2-(5,6-difluoro-2-oxo-1,2-dihydroquinolin-3-yl)acetamide (42.5 mg, 29.84%). LCMS (ES, m/z): 375.0 $[M+H]^+$1H NMR (300 MHz, DMSO-$d_6$) δ 12.06 (s, 1H), 8.94 (d, J=7.5 Hz, 1H), 8.77 (s, 1H), 7.96 (s, 1H), 7.62-7.53 (m, 1H), 7.11 (d, J=8.7 Hz, 1H), 5.24-5.14 (m, 1H), 3.52 (s, 2H), 1.53-1.23 (m, 3H). $^{19}$F NMR (282 MHz, DMSO-d6) δ −147.37--147.58 (2F).

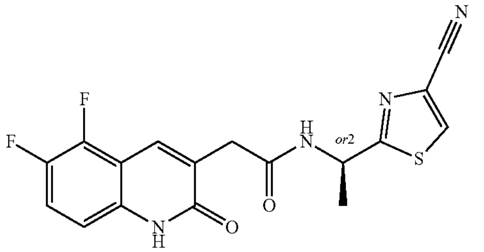

-continued

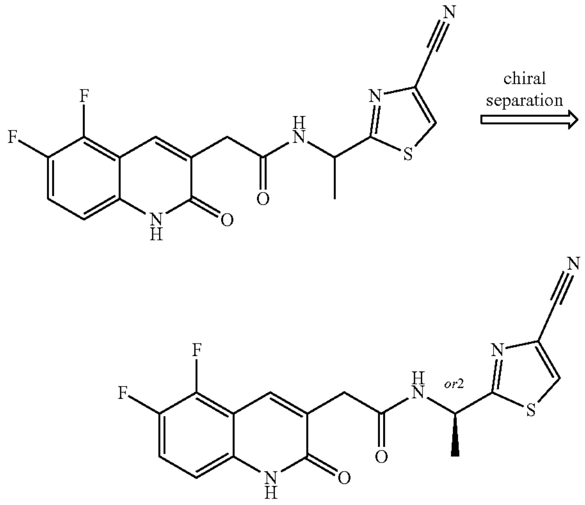

N-[(1R)-1-(4-cyano-1,3-thiazol-2-yl)ethyl]-2-(5,6-difluoro-2-oxo-1H-quinolin-3-yl)acetamide: The racemic product (150 mg) was purified by Prep-HPLC with a CHIRALPAK ID, (3*25 cm, 5 μm) eluting with Hex(0.1% 2M $NH_3$-MeOH) and EtOH to afford N-[(1R)-1-(4-cyano-1,3-thiazol-2-yl)ethyl]-2-(5,6-difluoro-2-oxo-1H-quinolin-3-yl) acetamide (38.5 mg, 27.31%). LCMS (ES, m/z): 375.0 $[M+H]^+$ $^1$H NMR (300 MHz, DMSO-$d_6$) δ 12.07 (s, 1H), 8.94 (d, J=7.2 Hz, 1H), 8.77 (s, 1H), 7.97 (s, 1H), 7.62-7.53 (m, 11H), 7.13-7.09 (m, 1H), 5.24-5.15 (m, 1H), 3.52 (d, J=26.7 Hz, 2H), 1.53-1.17 (m, 3H). $^{19}$F NMR (282 MHz, DMSO-d6) δ −147.37--147.58 (2F).

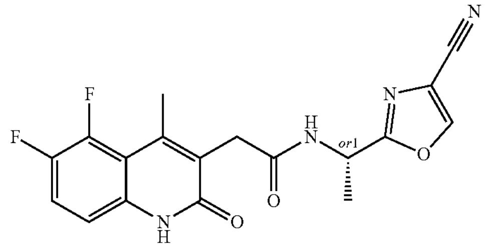

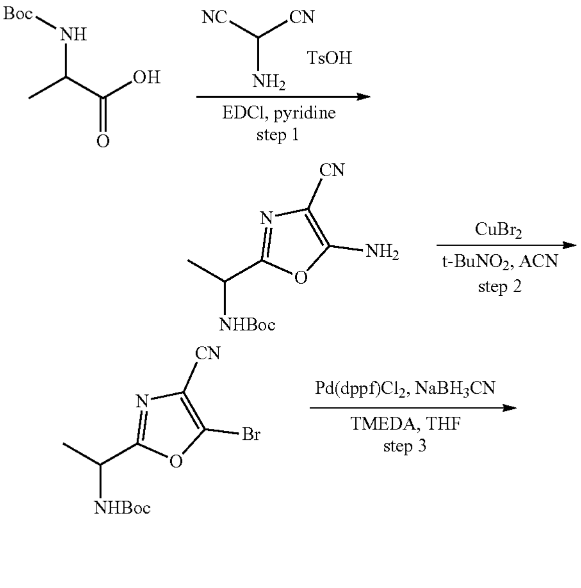

-continued

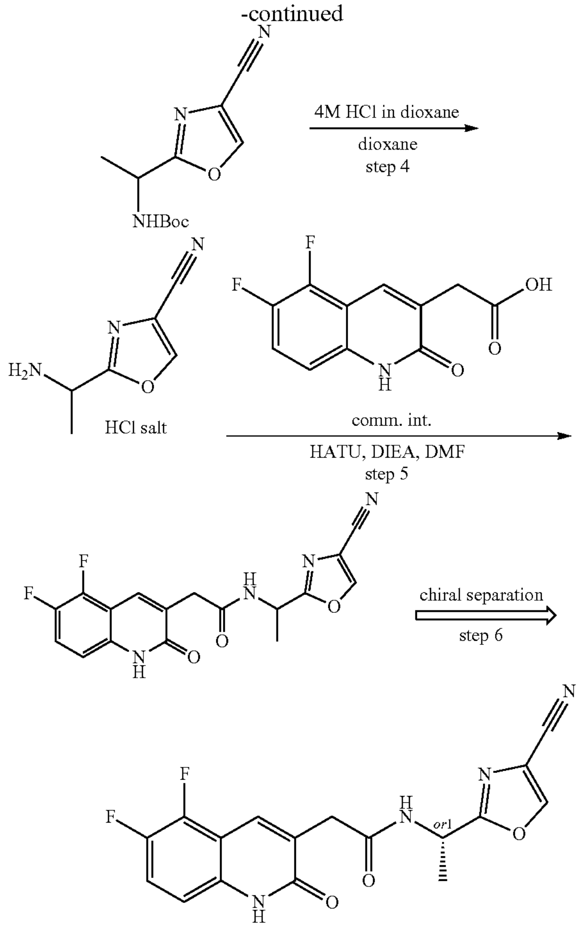

Tert-butyl (1-(5-amino-4-cyanooxazol-2-yl)ethyl)carbamate: To a stirred solution of (tert-butoxycarbonyl)alanine (6.50 g, 34.5 mmol, 1.00 equiv) and 2-aminomalononitrile (9.60 g, 37.8 mmol, 1.10 equiv) in pyridine (100 mL) was added EDCI (7.90 g, 41.2 mmol, 1.20 equiv) portionwise at 25° C. The resulting mixture was stirred for 24 h at 25° C. The reaction was concentrated under reduced pressure and. the crude residue was purified by column chromatography, eluting with PE/EA to afford tert-butyl (1-(5-amino-4-cyanooxazol-2-yl)ethyl)carbamate (6.10 g, 70.37%). LCMS (ES, m/z): 253 $[M+H]^+$ Tert-butyl (1-(5-bromo-4-cyanooxazol-2-yl)ethyl)carbamate: To a stirred solution of tert-butyl (1-(5-amino-4-cyanooxazol-2-yl)ethyl)carbamate (6.10 g, 24.2 mmol, 1.00 equiv) and $CuBr_2$ (8.10 g, 36.3 mmol, 1.50 equiv) in MeCN (80 mL) was added t-$BuNO_2$ (3.00 g, 29.01 mmol, 1.20 equiv) dropwise at 25° C. under argon. The resulting mixture was stirred for 1 h at 25° C. under argon. The reaction was quenched with water at 25° C. The crude material was extracted with EA, dried over $Na_2SO_4$, filtered, concentrated under reduced pressure, and purified by column chromatography to afford tert-butyl (1-(5-bromo-4-cyanooxazol-2-yl)ethyl)carbamate (3.20 g, 42.01%). LCMS (ES, m/z): 316/318 $[M+H]^+$ Tert-butyl (1-(4-cyanooxazol-2-yl)ethyl)carbamate: To a stirred solution of tert-butyl (1-(5-bromo-4-cyanooxazol-2-yl)ethyl)carbamate (2.70 g, 8.54 mmol, 1.00 equiv), $NaBH_3CN$ (1.07 g, 17.1 mmol, 2.00 equiv) and Pd(dppf)$Cl_2$ (1.25 g, 1.71 mmol, 0.20 equiv) in THF (60 mL) was added TMEDA (1.41 mL, 9.39 mmol, 1.10 equiv) dropwise at 0° C. under argon. The resulting mixture was stirred for 2 h at 25° C. The reaction was filtered and the precipitate was washed with EA. The filtrate was concentrated under reduced pressure and purified by reverse-phase chromatography with a C18 column eluting with MeCN/Water (10 mmol/L $NH_4HCO_3$) to afford tert-butyl (1-(4-cyanooxazol-2-yl)ethyl)carbamate (1.70 g, 75.51%). LCMS (ES, m/z): 238 $[M+H]^+$ 2-(1-aminoethyl)oxazole-4-carbonitrile hydrochloride: To a stirred solution of tert-butyl (1-(4-cyanooxazol-2-yl)ethyl)carbamate (1.70 g, 7.17 mmol, 1.00 equiv) in dioxane (15 mL) was added 4 M HCl (gas) in 1,4-dioxane (15 mL) dropwise at 25° C. The resulting crude reaction was concentrated under reduced pressure to afford 2-(1-aminoethyl)oxazole-4-carbonitrile hydrochloride (1.40 g crude, HCl salt) which was used in the next step directly without further purification. LCMS (ES, m/z): 138 $[M+H]^+$ N-(1-(4-cyanooxazol-2-yl)ethyl)-2-(5,6-difluoro-2-oxo-1,2-dihydroquinolin-3-yl)acetamide: A solution of 2-(1-aminoethyl)oxazole-4-carbonitrile hydrochloride (300 mg, 2.19 mmol, 1.00 equiv) and 2-(5,6-difluoro-2-oxo-1,2-dihydroquinolin-3-yl)acetic acid (523.2 mg, 2.19 mmol, 1.00 equiv) in DMF (20 mL) was treated with DIEA (1.19 mL, 10.9 mmol, 5.00 equiv) for 10 min at 25° C. followed by the addition of HATU (998.0 mg, 2.63 mmol, 1.20 equiv) portionwise at 0° C. The resulting mixture was stirred for additional 1.5 h at 25° C. The reaction was quenched by the addition of brine and extracted with EA. The organics were washed with brine, dried over anhydrous $Na_2SO_4$, filtered, and the filtrate was concentrated under reduced pressure and purified by Prep-TLC eluting with $CH_2Cl_2$ and MeOH to afford N-(1-(4-cyanooxazol-2-yl)ethyl)-2-(5,6-difluoro-2-oxo-1,2-dihydroquinolin-3-yl)acetamide (250 mg, 29.98%). LCMS (ES, m/z): 359 $[M+H]^+$ (S)—N-(1-(4-cyanooxazol-2-yl)ethyl)-2-(5,6-difluoro-2-oxo-1,2-dihydroquinolin-3-yl)acetamide (Compound 4007 and 4006): The racemic product (250 mg) was purified by chiral-HPLC with a CHIRALPAK IG, (3*25 cm, 5 μm) eluting with Hex (10 mM $NH_3$-MeOH) and EtOH to afford (S)—N-(1-(4-cyanooxazol-2-yl)ethyl)-2-(5,6-difluoro-2-oxo-1,2-dihydroquinolin-3-yl)acetamide (60 mg, 7.59%). LCMS (ES, m/z): 359.1 $[M+H]$ $^1H$ NMR (400 MHz, DMSO-$d_6$) δ 12.04 (s, 1H), 9.06 (s, 1H), 8.75 (d, J=7.6 Hz, 1H), 7.96 (s, 1H), 7.58 (dt, J=10.4, 9.0 Hz, 1H), 7.12 (dd, J=9.2, 3.4 Hz, 1H), 5.09 (p, J=7.2 Hz, 1H), 3.53-3.42 (m, 2H), 1.47 (d, J=7.2 Hz, 3H). $^{19}F$ NMR (376 MHz, DMSO-$d_6$) δ −147.49 (q, J=21.6 Hz). $^{19}F$ NMR (376 MHz, DMSO-$d_6$) δ −147.49 (q, J=21.6 Hz).

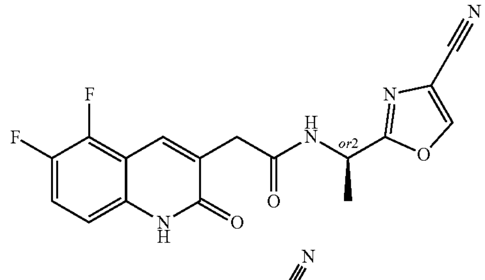

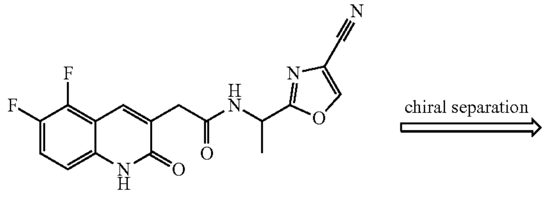

-continued

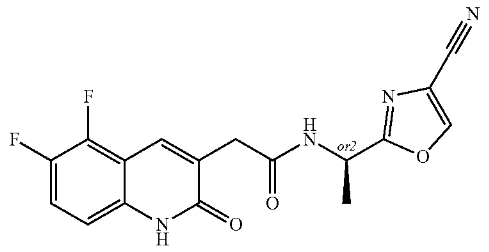

assumed (R)—N-(1-(4-cyanooxazol-2-yl)ethyl)-2-(5,6-difluoro-2-oxo-1,2-dihydroquinolin-3-yl)acetamide (80 mg, 9.79%): The racemic product (250 mg) was separated by chiral-HPLC with a CHIRALPAK IG (3*25 cm, 5 μm) eluting with Hex (10 mM $NH_3$-MeOH) and EtOH to afford (R)—N-(1-(4-cyanooxazol-2-yl)ethyl)-2-(5,6-difluoro-2-oxo-1,2-dihydroquinolin-3-yl)acetamide (80 mg, 9.79%).

LCMS (ES, m/z): 359.0 $[M+H]^-$ $^1H$ NMR (400 MHz, DMSO-d6) δ 11.95 (s, 1H), 9.05 (s, 1H), 8.75 (d, J=7.5 Hz, 1H), 7.95 (s, 1H), 7.58 (q, J=9.4 Hz, 1H), 7.12 (dd, J=9.2, 3.2 Hz, 1H), 5.09 (p, J=7.2 Hz, 1H), 3.47 (s, 2H), 1.47 (d, J=7.2 Hz, 3H). $^{19}F$ NMR (376 MHz, DMSO-$d_6$) δ −147.49 (q, J=21.8 Hz).

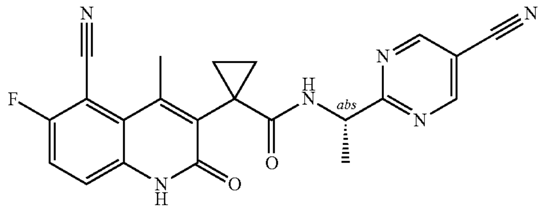

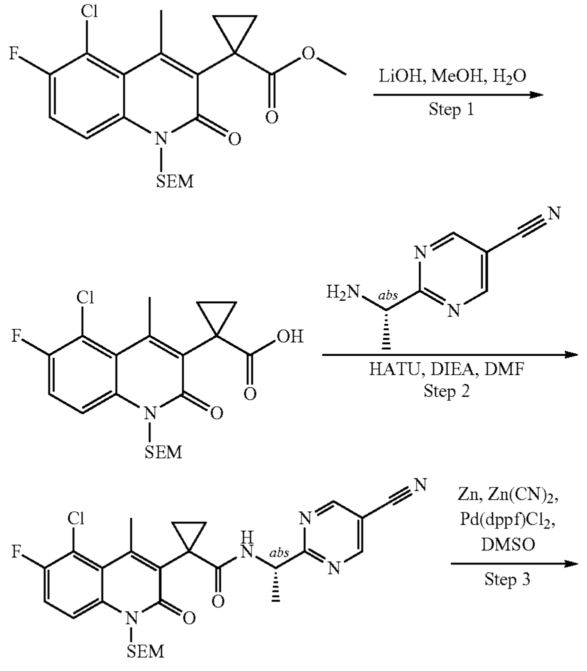

-continued

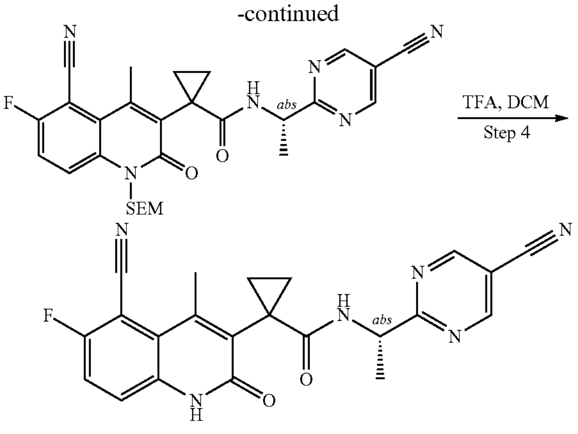

1-(5-chloro-6-fluoro-4-methyl-2-oxo-1-{[2-(trimethylsilyl)ethoxy]methyl}quinolin-3-yl)cyclopropane-1-carboxylic acid: A solution of methyl 1-(5-chloro-6-fluoro-4-methyl-2-oxo-1-{[2-(trimethylsilyl)ethoxy]methyl}quinolin-3-yl)cyclopropane-1-carboxylate (500 mg, 1.136 mmol, 1 equiv) and LiOH (54.43 mg, 2.272 mmol, 2 equiv) in MeOH (1 mL) and $H_2O$ (1 mL) was stirred overnight at RT. The resulting solution was concentrated under reduced pressure and adjusted to pH 6 with conc. HCl. The crude residue was purified by reverse-phase chromatography with a C18 column eluting with MeCN/Water (0.1% FA) to afford 1-(5-chloro-6-fluoro-4-methyl-2-oxo-1-{[2-(trimethylsilyl)ethoxy]methyl}quinolin-3-yl)cyclopropane-1-carboxylic acid (300 mg, 61.97%).

LCMS (ES, m/z): 426 $[M+H]^+$.

1-(5-chloro-6-fluoro-4-methyl-2-oxo-1-{[2-(trimethylsilyl)ethoxy]methyl}quinolin-3-yl)-N-[(1S)-1-(5-cyanopyrimidin-2-yl)ethyl]cyclopropane-1-carboxamide: A solution of 1-(5-chloro-6-fluoro-4-methyl-2-oxo-1-{[2-(trimethylsilyl)ethoxy]methyl}quinolin-3-yl)cyclopropane-1-carboxylic acid (100 mg, 0.235 mmol, 1 equiv), 2-[(1S)-1-aminoethyl]pyrimidine-5-carbonitrile (41.74 mg, 0.282 mmol, 1.2 equiv), HATU (107.12 mg, 0.282 mmol, 1.2 equiv) and DIEA (91.03 mg, 0.705 mmol, 3 equiv) in DMF (5 mL) was stirred overnight at RT. The crude residue was purified by reverse-phase chromatography with a C18 column eluting with MeCN/Water (0.1% FA) to afford 1-(5-chloro-6-fluoro-4-methyl-2-oxo-1-{[2-(trimethylsilyl)ethoxy]methyl}quinolin-3-yl)-N-[(1S)-1-(5-cyanopyrimidin-2-yl)ethyl]cyclopropane-1-carboxamide (60 mg, 45.96%). LCMS (ES, m/z): 556 $[M+H]^+$.

1-(5-cyano-6-fluoro-4-methyl-2-oxo-1-{[2-(trimethylsilyl)ethoxy]methyl}quinolin-3-yl)-N-[(1S)-1-(5-cyanopyrimidin-2-yl)ethyl]cyclopropane-1-carboxamide: A solution of 1-(5-chloro-6-fluoro-4-methyl-2-oxo-1-{[2-(trimethylsilyl)ethoxy]methyl}quinolin-3-yl)-N-[(1S)-1-(5-cyanopyrimidin-2-yl)ethyl]cyclopropane–1-carboxamide (100 mg, 0.180 mmol, 1 equiv), Zn (11.76 mg, 0.180 mmol, 1 equiv), $Zn(CN)_2$ (52.79 mg, 0.450 mmol, 2.5 equiv) and Pd(dppf)$Cl_2$ (13.16 mg, 0.018 mmol, 0.1 equiv) in DMSO (5 mL) was stirred for 2 h at 120° C. under argon. The crude residue was purified by reverse-phase chromatography with a C18 column eluting with MeCN/Water (0.1% FA) to afford 1-(5-cyano-6-fluoro-4-methyl-2-oxo-1-{[2-(trimethylsilyl)ethoxy]methyl}quinolin-3-yl)-N-[(1S)-1-(5-cyanopyrimidin-2-yl)ethyl]cyclopropane-1-carboxamide (60 mg, 61.04%). LCMS (ES, m/z): 547 $[M+H]^+$.

1-(5-cyano-6-fluoro-4-methyl-2-oxo-1H-quinolin-3-yl)-N-[(1S)-1-(5-cyanopyrimidin-2-yl)ethyl]cyclopropane-1-carboxamide (compound 2531 and 2532): A solution of 1-(5-cyano-6-fluoro-4-methyl-2-oxo-1-{[2-(trimethylsilyl)ethoxy]methyl}quinolin-3-yl)-N-[(1S)-1-(5-cyanopyrimidin-2-yl)ethyl]cyclopropane-1-carboxamide (50 mg, 0.091 mmol, 1 equiv) and TFA (0.4 mL, 5.385 mmol, 58.88 equiv) in DCM (1 mL) was stirred for 2 h at RT. The crude reaction was concentrated under reduced pressure and purified by reverse-phase chromatography with aC18 column eluting with MeCN/Water (0.1% FA) to afford 1-(5-cyano-6-fluoro-4-methyl-2-oxo-1H-quinolin-3-yl)-N-[(1S)-1-(5-cyanopyrimidin-2-yl)ethyl]cyclopropane-1-carboxamide (35.8 mg, 94.00%) LCMS (ES, m/z): 417.10 $[M+H]^+$. $^1H$ NMR (300 MHz, DMSO-d6) δ 12.09 (s, 1H), 9.32 (s, 2H), 7.75-7.65 (m, 3H), 5.05 (d, J=5.7 Hz, 1H), 2.84 (s, 3H), 1.53-1.49 (m, 2H), 1.38 (d, J=6.9 Hz, 3H), 0.93 (s, 2H).

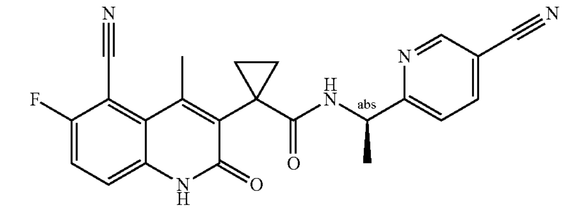

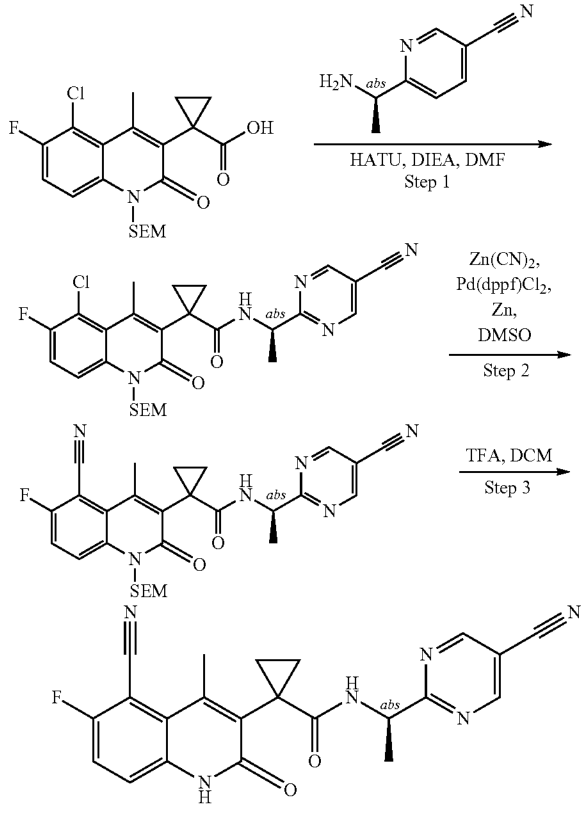

1-(5-chloro-6-fluoro-4-methyl-2-oxo-1-{[2-(trimethylsilyl)ethoxy]methyl}quinolin-3-yl)-N-[(1R)-1-(5-cyanopyrimidin-2-yl)ethyl]cyclopropane-1-carboxamide: A solution of 1-(5-chloro-6-fluoro-4-methyl-2-oxo-1-{[2-(trimethylsilyl)ethoxy]methyl}quinolin-3-yl)cyclopropane-1-carboxylic acid (100 mg, 0.235 mmol, 1 equiv), 2-[(1R)-1-aminoethyl]pyrimidine-5-carbonitrile (41.74 mg, 0.282 mmol, 1.2 equiv), HATU (107.12 mg, 0.282 mmol, 1.2 equiv) and DIEA (91.03 mg, 0.705 mmol, 3 equiv) in DMF (5 mL) was stirred overnight at RT. The crude residue was purified by reverse-phase chromatography with a C18 column MeCN/Water (0.1% FA) to afford 1-(5-chloro-6-fluoro-4-methyl-2-oxo-1-{[2-(trimethylsilyl)ethoxy]methyl}quinolin-3-yl)-N-[(1R)-1-(5-cyanopyrimidin-2-yl)ethyl]cyclopropane-1-carboxamide (80 mg, 61.28%). LCMS (ES, m/z): 556 $[M+H]^+$.

1-(5-cyano-6-fluoro-4-methyl-2-oxo-1-{[2-(trimethylsilyl)ethoxy]methyl}quinolin-3-yl)-N-[(1R)-1-(5-cyanopyrimidin-2-yl)ethyl]cyclopropane-1-carboxamide: A solution of 1-(5-chloro-6-fluoro-4-methyl-2-oxo-1-{[2-(trimethylsilyl)ethoxy]methyl}quinolin-3-yl)-N-[(1R)-1-(5-cyanopyrimidin-2-yl)ethyl]cyclopropane-1-carboxamide (100 mg, 0.180 mmol, 1 equiv), $Zn(CN)_2$ (52.79 mg, 0.450 mmol, 2.5 equiv), $Pd(dppf)Cl_2$ (26.32 mg, 0.036 mmol, 0.2 equiv) and Zn (11.76 mg, 0.180 mmol, 1 equiv) in DMSO (5 mL) was stirred for 3 h at 120° C. under argon. The crude residue was purified by reverse-phase chromatography with a C18 column eluting with MeCN/Water (0.1% FA) to afford 1-(5-cyano-6-fluoro-4-methyl-2-oxo-1-{[2-(trimethylsilyl)ethoxy]methyl}quinolin-3-yl)-N-[(1R)-1-(5-cyanopyrimidin-2-yl)ethyl]cyclopropane-1-carboxamide (60 mg, 61.04%). LCMS (ES, m/z): 547 $[M+H]^+$.

1-(5-cyano-6-fluoro-4-methyl-2-oxo-1H-quinolin-3-yl)-N-[(1R)-1-(5-cyanopyrimidin-2-yl)ethyl]cyclopropane-1-carboxamide (compound 2531 and 2532): A solution of 1-(5-cyano-6-fluoro-4-methyl-2-oxo-1-{[2-(trimethylsilyl)ethoxy]methyl}quinolin-3-yl)-N-[(1R)-1-(5-cyanopyrimidin-2-yl)ethyl]cyclopropane-1-carboxamide (50 mg, 0.091 mmol, 1 equiv) and TFA (0.4 mL, 5.385 mmol, 58.88 equiv) in DCM (1 mL) was stirred for 2 h at RT. The crude reaction was concentrated under reduced pressure and purified by reverse-phase chromatography with a C18 column eluting with MeCN/Water (0.1% FA) to afford 1-(5-cyano-6-fluoro-4-methyl-2-oxo-1H-quinolin-3-yl)-N-[(1R)-1-(5-cyanopyrimidin-2-yl)ethyl]cyclopropane-1-carboxamide (24.1 mg, 63.28%). LCMS (ES, m/z): 417.10 $[M+H]^+$.1H NMR (300 MHz, DMSO-d6) δ 12.08 (s, 1H), 9.25 (s, 2H), 7.72-7.67 (m, 3H), 5.06 (s, 1H), 2.84 (s, 3H), 1.52 (s, 2H), 1.37 (d, J=6.9 Hz, 3H), 0.93 (s, 2H).

(S)-1-(5-cyano-4-methyl-2-oxo-1,2-dihydroquinolin-3-yl)-N-(1-(5-cyanopyrimidin-2-yl)ethyl)cyclopropane-1-carboxamide and (R)-1-(5-cyano-4-methyl-2-oxo-1,2-dihydroquinolin-3-yl)-N-(1-(5-cyanopyrimidin-2-yl)ethyl)cyclopropane-1-carboxamide

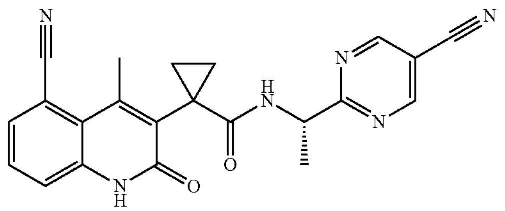

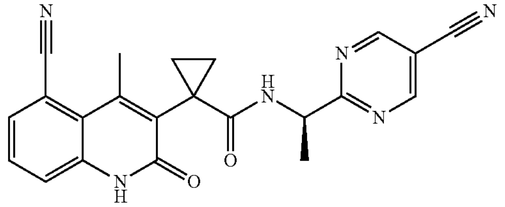

Methyl 2-(5-bromo-4-methyl-2-oxo-1-{[2-(trimethylsilyl)ethoxy]methyl}quinolin-3-yl)acetate: To a solution of methyl 2-(5-bromo-4-methyl-2-oxo-1H-quinolin-3-yl)acetate (309 mg, 0.996 mmol, 1 equiv) in DMF (8 mL) were added $Cs_2CO_3$ (249.86 mg, 1.295 mmol, 1.3 equiv) and [2-(chloromethoxy)ethyl]trimethylsilane (215.93 mg, 1.295 mmol, 1.3 equiv) and the resulting mixture was stirred for 16 h at RTRT. The resulting mixture was diluted with $H_2O$ and extracted with EA. The combined organic layers were washed with $H_2O$, dried over anhydrous $Na_2SO_4$, filtered, and the filtrate was concentrated under reduced pressure. The crude residue was purified by column chromatography to afford methyl 2-(5-bromo-4-methyl-2-oxo-1-{[2-(trimethylsilyl)ethoxy]methyl}quinolin-3-yl)acetate (100 mg, 20.97%). LC-MS: (ESI, m/z): 440 $[M+H]^+$ Methyl 1-(5-bromo-4-methyl-2-oxo-1-{[2-(trimethylsilyl)ethoxy]methyl}420uinoline-3-yl)cyclopropane-1-carboxylate: To a solution of methyl 2-(5-bromo-4-methyl-2-oxo-1-{[2-(trimethylsilyl)ethoxy]methyl}quinolin-3-yl) acetate (650 mg, 1.476 mmol, 1 equiv) and ethenyldiphenylsulfanium (802.27 mg, 2.214 mmol, 1.5 equiv) in DMSO (10 mL) was added DBU (561.73 mg, 3.690 mmol, 2.5 equiv) and the resulting mixture was stirred for 16 h at 25° C. under a nitrogen atmosphere. The reaction was diluted with water and extracted with EA. The organics were washed with water, dried over anhydrous $Na_2SO_4$, filtered, concentrated under reduced pressure, and purified by reverse-phase chromatography with a C18 column eluting with water (0.05% $NH_4HCO_3$) in McCN to afford methyl 1-(5-bromo-4-methyl-2-oxo-1-{[2-(trimethylsilyl)ethoxy]methyl}quinolin-3-yl)cyclopropane-1-carboxylate (280 mg, 38.64%). LC-MS: (ESI, m/z): 466 $[M+H]^+$ Methyl 1-(5-cyano-4-methyl-2-oxo-1-{[2-(trimethylsilyl)ethoxy]methyl}quinolin-3-yl)cyclopropane-1-carboxylate: To a solution of methyl 1-(5-bromo-4-methyl-2-oxo-1-{[2-(trimethylsilyl)ethoxy]methyl}quinolin-3-yl)cyclopropane-1-carboxylate (280 mg, 0.600 mmol, 1 equiv) and zinc cyanide (140.97 mg, 1.200 mmol, 2 equiv) in DMSO (4 mL) was added zinc (15.70 mg, 0.240 mmol, 0.4 equiv) and $Pd(dppf)Cl_2$ (43.92 mg, 0.060 mmol, 0.1 equiv). The resulting mixture was stirred for 2 h at 105° C. under nitrogen atmosphere. The crude reaction was purified by column chromatography to afford methyl 1-(5-cyano-4-methyl-2-oxo-1-{[2-(trimethylsilyl)ethoxy]methyl}quinolin-3-yl)cyclopropane-1-carboxylate (210 mg, 80.56%). LC-MS: (ESI, m/z): 413 $[M+H]^+$ 1-(5-Cyano-4-methyl-2-oxo-1-{[2-(trimethylsilyl)ethoxy]methyl}quinolin-3-yl)cyclopropane-1-carboxylic acid: To a solution of methyl 1-(5-cyano-4-methyl-2-oxo-1-{[2-(trimethylsilyl)ethoxy]methyl}quinolin-3-yl)cyclopropane-1-carboxylate (80 mg, 0.194 mmol, 1 equiv) in MeOH (3 mL) and $H_2O$ (1 mL) was added LiOH (13.93 mg, 0.582 mmol, 3 equiv) and the resulting mixture was stirred for 16 h at 80° C. The crude reaction was concentrated under reduced pressure, diluted with water, and adjusted to pH 5 with HCl (1M). The precipitated solids were collected by filtration, washed with water, and concentrated under reduced pressure to afford 1-(5-cyano-4-methyl-2-oxo-1-{[2-(trimethylsilyl)ethoxy]methyl}quinolin-3-yl)cyclopropane-1-carboxylic acid (67 mg, 81.50%). LC-MS: (ESI, m/z): 399 $[M+H]^+$ (S)-1-(5-cyano-4-methyl-2-oxo-1,2-dihydroquinolin-3-yl)-N-(1-(5-cyanopyrimidin-2-yl)ethyl)cyclopropane-1-carboxamide: To a solution of 1-(5-cyano-4-methyl-2-oxo-1-{[2-(trimethylsilyl)ethoxy]methyl}quinolin-3-yl)-N-[(1S)-1-(5-cyanopyrimidin-2-yl)ethyl]cyclopropane-1-carboxamide (65 mg, 0.123 mmol, 1 equiv) in DCM (2.5 mL) was added TFA (0.6 mL) at 0° C. The resulting mixture was stirred for 3 h at 25° C. The crude reaction mixture was concentrated under reduced pressure and purified by reverse-phase chromatography with a C18 column eluting with 0.1% FA in acetonitrile in water to afford the crude product (60 mg). The crude product was further purification by chiral-HPLC with a CHIRAL ART Amylose-C NEO, (2*25 cm, 5 μm) eluting with Hex(10 mM $NH_3$-MeOH) and EtOH to (S)-1-(5-cyano-4-methyl-2-oxo-1,2-dihydroquinolin-3-yl)-N-(1-(5-cyanopyrimidin-2-yl)ethyl)cyclopropane-1-carboxamide (20.6 mg, 40.83%). LC-MS: (ESI, m/z): 399.10 $[M+H]^+$. $^1H$ NMR (400 MHz, Methanol-$d_4$) δ 9.08 (s, 2H), 7.72-7.66 (m, 1H), 7.63-7.61 (m, 2H), 5.18-5.17 (m, 1H), 3.03 (s, 4H), 1.77-1.66 (m, 2H), 1.46 (d, J=7.2 Hz, 3H), 1.12-0.87 (m, 2H).

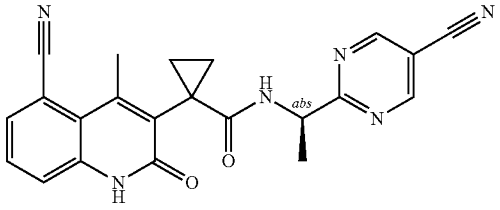 [SMILES: Cc1c(C2(C(=O)N[C@H](C)c3ncc(C#N)cn3)CC2)c(=O)[nH]c2cccc(C#N)c12]

1-(5-cyano-4-methyl-2-oxo-1-{[2-(trimethylsilyl)ethoxy]methyl}quinolin-3-yl)-N-[(1R)-1-(5-cyanopyrimidin-2-yl)ethyl]cyclopropane-1-carboxamide: To a solution of 1-(5-cyano-4-methyl-2-oxo-1-{[2-(trimethylsilyl)ethoxy]methyl}quinolin-3-yl)cyclopropane-1-carboxylic acid (68 mg, 0.171 mmol, 1 equiv) in DMF (2 mL) was added HATU (77.85 mg, 0.205 mmol, 1.2 equiv), DIEA (88.21 mg, 0.684 mmol, 4 equiv) and 2-[(1R)-1-aminoethyl]pyrimidine-5-carbonitrile (30.34 mg, 0.205 mmol, 1.2 equiv). The resulting mixture was stirred for 4 h at 25° C. The crude residue was purified by reverse-phase chromatography with a C18 column eluting with 0.1% FA in MeCN and water to afford 1-(5-cyano-4-methyl-2-oxo-1-{[2-(trimethylsilyl)ethoxy]methyl}quinolin-3-yl)-N-[(1R)-1-(5-cyanopyrimidin-2-yl)ethyl]cyclopropane-1-carboxamide (70 mg, 73.72%). LC-MS: (ESI, m/z): 529 $[M+H]^+$ (R)-1-(5-cyano-4-methyl-2-oxo-1,2-dihydroquinolin-3-yl)-N-(1-(5-cyanopyrimidin-2-yl)ethyl)cyclopropane-1-carboxamide: To a solution of 1-(5-cyano-4-methyl-2-oxo-1-{[2-(trimethylsilyl)ethoxy]methyl}quinolin-3-yl)-N-[(1R)-1-(5-cyanopyrimidin-2-yl)ethyl]cyclopropane-1-carboxamide (70 mg, 0.132 mmol, 1 equiv) in DCM (2 mL) was added TFA (0.5 mL) at 0° C. The resulting mixture was stirred for 3 h at 25° C. The crude reaction was concentrated under reduced pressure and purified by reverse-phase chromatography with a C18 column eluting with water and 0.1% FA in acetonitrile to afford (R)-1-(5-cyano-4-methyl-2-oxo-1,2-dihydroquinolin-3-yl)-N-(1-(5-cyanopyrimidin-2-yl)ethyl)cyclopropane-1-carboxamide (44.2 mg, 83.54%). LC-MS: (ESI, m/z): 399.10 $[M+H]^+$. $^1H$ NMR (400 MHz, Methanol-$d_4$) δ 9.04 (s, 2H), 7.74-7.70 (m, 1H), 7.65-7.62 (m, 2H), 5.17 (s, 1H), 3.03 (s, 3H), 1.77-1.68 (m, 2H), 1.46 (d, J=7.2 Hz, 3H), 1.13-1.05 (m, 2H).

(Compound 4502 and 4503)

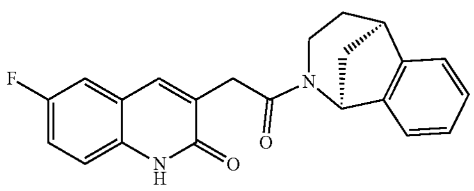

-continued

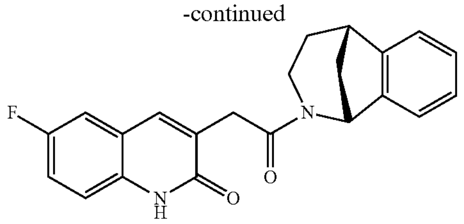

6-Fluoro-3-(2-oxo-2-((1S,5R)-1,3,4,5-tetrahydro-2H-1,5-methanobenzo[c]azepin-2-yl)ethyl)quinolin-2(1H)-one and 6-Fluoro-3-(2-oxo-2-(1S,5S)-1,3,4,5-tetrahydro-2H-1,5-methanobenzo[c]azepin-2-yl)ethyl)quinolin-2(1H)-one (E)-[(2-Bromophenyl)methylidene](prop-2-en-1-yl) amine: To a stirred solution of benzaldehyde, 2-bromo-(10 g, 54.0 mmol, 1 equiv) and allylamine (6.17 g, 108 mmol, 2 equiv) in DCM (300 mL) was added TEA (10.94 g, 108 mmol, 2 equiv) and $MgSO_4$ (13.01 g, 108 mmol, 2 equiv) portion wise at RT. The resulting mixture was stirred overnight at RT. The crude reaction mixture was filtered, and the solids were washed with DCM. The filtrate was concentrated under reduced pressure and purified by column chromatography to afford (E)-[(2-bromophenyl)methylidene](prop-2-en-1-yl)amine (11 g, 90.82%). LCMS (ES, m/z): 224 $[M+H]^+$.

[1-(2-Bromophenyl)but-3-en-1-yl](prop-2-en-1-yl) amine: Into a 500 mL 3-necked round-bottom flask was added (E)-[(2-bromophenyl)methylidene](prop-2-en-1-yl) amine (8 g, 35.698 mmol, 1 equiv) and allylmagnesium bromide (6.74 g, 46.4 mmol, 1.3 equiv) at −78° C. under argon. The resulting mixture was stirred for 3 h at −78° C. under argon. The reaction was quenched with sat. $NH_4Cl$ (aq.) at 0° C. The crude material was extracted with EA, washed with brine, dried over $Na_2SO_4$, filtered, and concentrated under reduced pressure. The crude residue was purified by column chromatography to afford [1-(2-bromophenyl)but-3-en-1-yl](prop-2-en-1-yl)amine (8 g, 84.19%). LCMS (ES, m/z): 266 $[M+H]^+$.

Benzyl N-[1-(2-bromophenyl)but-3-en-1-yl]-N-(prop-2-en-1-yl)carbamate: To a stirred solution of [1-(2-bromophenyl)but-3-en-1-yl](prop-2-en-1-yl)amine (9 g, 33 mmol, 1 equiv) and $K_2CO_3$ (14.02 g, 101 mmol, 3 equiv) in THE (400 mL) was added Cbz-Cl (17.3 g, 101 mmol, 3 equiv) portionwise at RT. The resulting mixture was stirred overnight at 70° C. The reaction was cooled to RT. The crude reaction was diluted with water and extracted with EA. The organic layers were washed with brine, dried over anhydrous $Na_2SO_4$, filtered, and the filtrate was concentrated under reduced pressure. The crude residue was purified by column chromatography to afford benzyl N-[1-(2-bromophenyl)but-3-en-1-yl]-N-(prop-2-en-1-yl)carbamate (9.6 g, 70.93%). LCMS (ES, m/z): 400 $[M+H]^+$.

Benzyl 2-(2-bromophenyl)-3,6-dihydro-2H-pyridine-1-carboxylate: A solution of benzyl N-[1-(2-bromophenyl)but-3-en-1-yl]-N-(prop-2-en-1-yl)carbamate (9 g, 22.4 mmol, 1 equiv) and Grubb's II Gen. Catalyst (1.12 mmol, 0.05 equiv) in Toluene (400 mL) was stirred overnight at 80° C. under argon. The reaction was cooled to RT. The crude material was filtered and the precipitate was washed with $CH_2Cl_2$. The filtrate was concentrated under reduced pressure and purified by column chromatography to afford benzyl 2-(2-bromophenyl)-3,6-dihydro-2H-pyridine-1-carboxylate (5.0 g, 59.74%). LCMS (ES, m/z): 372 $[M+H]^+$.

Benzyl 9-azatricyclo[6.3.1.0{2,7}]dodeca-2(7),3,5,10-tetraene-9-carboxylate: To a stirred solution of benzyl 2-(2-bromophenyl)-3,6-dihydro-2H-pyridine-1-carboxylate (5 g, 13.4 mmol, 1 equiv) and tris(2-methylphenyl)phosphane (0.41 g, 1.3 mmol, 0.1 equiv) in DMF (80 mL) was added $Pd(OAC)_2$ (0.30 g, 1.3 mmol, 0.1 equiv) and TEA (3.40 g, 33.5 mmol, 2.5 equiv) portion wise at RT under argon. The resulting mixture was stirred overnight at 80° C. under argon. The reaction was cooled to RT. The crude material was diluted with water and extracted with EA. The organics were washed with brine, dried over $Na_2SO_4$, filtered and the filtrate was concentrated under reduced pressure. The crude residue was purified by column chromatography to afford benzyl 9-azatricyclo[6.3.1.0{2,7}]dodeca-2(7),3,5,10-tetraene-9-carboxylate (2.4 g, 61.33%). LCMS (ES, m/z): 292 $[M+H]^+$.

9-azatricyclo[6.3.1.0{2,7}]dodeca-2(7),3,5-triene: To a solution of benzyl 9-azatricyclo[6.3.1.0{2,7}]dodeca-2(7),3,5,10-tetraene-9-carboxylate (1.6 g, 5.5 mmol, 1 equiv) in 30 mL MeOH was added Pd/C (10%, 160 mg) in a pressure tube. The solution was hydrogenated at RT under 20 psi of hydrogen pressure for 8 h. The crude reaction was filtered through Celite and concentrated under reduced pressure. The solids were washed with MeOH and the filtrate was concentrated under reduced pressure. The crude residue was purified by column chromatography to afford 9-azatricyclo [6.3.1.0{2,7}]dodeca-2(7),3,5-triene (500 mg, 57.18%). LCMS (ES, m/z): 160 $[M+H]^+$.

3-(2-{9-azatricyclo[6.3.1.0{2,7}]dodeca-2(7),3,5-trien-9-yl}-2-oxoethyl)-6-fluoro-1H-quinolin-2-one: To a stirred solution of 9-azatricyclo[6.3.1.0{2,7}]dodeca-2(7),3,5-triene (100.79 mg, 0.63 mmol, 1.4 equiv) and (6-fluoro-2-oxo-1H-quinolin-3-yl)acetic acid (100 mg, 0.452 mmol, 1.00 equiv) in DMF (5 mL) was added EDCI (112.67 mg, 0.588 mmol, 1.3 equiv) and HOBT (79.42 mg, 0.588 mmol, 1.3 equiv) portion wise at RT. The resulting mixture was stirred for 3 h at RT. The crude reaction was extracted with EA and organics were washed with brine, dried over anhydrous $Na_2SO_4$, and filtered. The filtrate was concentrated under reduced pressure and purified by column chromatography to afford 3-(2-{9-azatricyclo[6.3.1.0{2,7}]dodeca-2(7),3,5-trien-9-yl}-2-oxoethyl)-6-fluoro-1H-quinolin-2-one (50 mg, 30.52%). LCMS (ES, m/z): 363 $[M+H]^+$.

6-Fluoro-3-(2-oxo-2-((1S,5R)-1,3,4,5-tetrahydro-2H-1,5-methanobenzo[c]azepin-2-yl)ethyl)quinolin-2(1H)-one:). The crude product (40 mg) was purified by Prep-HPLC with aLux 5 um Celluloes-3 (3*25 cm, 5 μm) column eluting with Hex(10 mM $NH_3$-MeOH) and EtOH to afford 6-fluoro-3-(2-oxo-2-((1S,5R)-1,3,4,5-tetrahydro-2H-1,5-methanobenzo[c]azepin-2-yl)ethyl)quinolin-2(1H)-one LCMS (ES, m/z): 363.10 $[M+H]^+$. $^1H$ NMR (400 MHz, DMSO-$d_6$) δ 11.90 (d, J=21.6 Hz, 1H), 7.74 (d, J=49.2 Hz, 1H), 7.56-7.44 (m, 1H), 7.35-7.22 (m, 6H), 5.56 (dd, J=143.6, 4.0 Hz, 1H), 4.06-3.65 (m, 2H), 3.57-3.35 (m, 1H), 3.33-3.31 (m, 1H), 2.50-2.38 (m, 1H), 2.27-2.07 (m, 1H), 2.03-1.95 (m, 1H), 1.92-1.76 (m, 1H), 1.58 (d, J=13.2 Hz, 1H).

6-Fluoro-3-(2-oxo-2-((1S,5S)-1,3,4,5-tetrahydro-2H-1,5-methanobenzo[c]azepin-2-yl)ethyl)quinolin-2(1H)-one): The crude product (40 mg) was purified by Prep-HPLC with aLux 5 um Celluloes-3(3*25 cm, 5 μm) eluting with Hex(10 mM $NH_3$-MeOH) and EtOH to afford 6-fluoro-3-(2-oxo-2-((1S,5S)-1,3,4,5-tetrahydro-2H-1,5-methanobenzo[c]azepin-2-yl)ethyl)quinolin-2(1H)-one LCMS (ES, m/z): 363.10 $[M+H]^+$. $^1H$ NMR (400 MHz, DMSO-$d_6$) δ 11.90 (d, J=21.6 Hz, 1H), 7.74 (d, J=49.2 Hz, 1H), 7.56-7.44 (m, 1H), 7.35-7.22 (m, 6H), 5.56 (dd, J=143.6, 4.0 Hz, 1H), 4.06-3.65 (m, 2H), 3.57-3.35 (m, 1H), 3.33-3.31 (m, 1H), 2.50-2.38 (m, 1H), 2.27-2.07 (m, 1H), 2.03-1.95 (m, 1H), 1.92-1.76 (m, 1H), 1.58 (d, J=13.2 Hz, 1H).

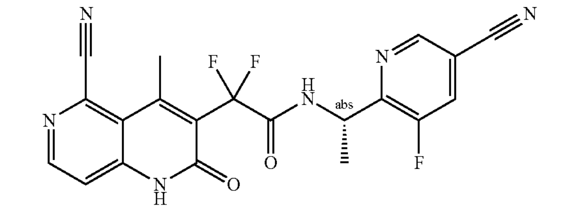

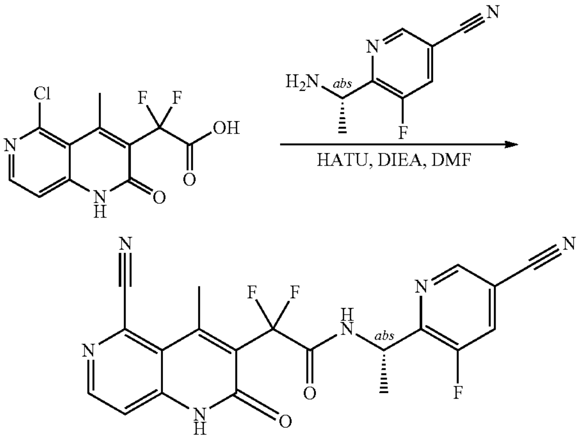

N-[(1S)-1-(5-cyano-3-fluoropyridin-2-yl)ethyl]-2-(5-cyano-4-methyl-2-oxo-1H-1,6-naphthyridin-3-yl)-2,2-difluoroacetamide (Compound 3515): To a stirred solution of (5-cyano-4-methyl-2-oxo-1H-1,6-naphthyridin-3-yl)difluoroacetic acid (50 mg, 0.179 mmol, 1 equiv) and 6-[(1S)-1-aminoethyl]-5-fluoropyridine-3-carbonitrile (35.49 mg, 0.215 mmol, 1.2 equiv) in DMF was added HATU (81.71 mg, 0.215 mmol, 1.2 equiv) and DIEA (69.44 mg, 0.537 mmol, 3 equiv) at RT. The crude residue was purified by reverse-phase chromatography with a C18 column eluting with MeCN/Water (0.1% FA) to afford N-[(1S)-1-(5-cyano-3-fluoropyridin-2-yl)ethyl]-2-(5-cyano-4-methyl-2-oxo-1H-1,6-naphthyridin-3-yl)-2,2-difluoroacetamide (17.1 mg, 22.40%). LCMS (ES, m/z): 427.10 $[M+H]^+$. $^1H$ NMR (300 MHz, DMSO-d6) δ 12.64 (s, 1H), 9.02 (d, J=7.5 Hz, 1H), 8.91 (s, 1H), 8.65 (d, J=6.0 Hz, 1H), 8.43-8.39 (m, 1H), 7.48 (d, J=5.4 Hz, 1H), 5.32 (s, 1H), 2.94 (t, J=3.0 Hz, 3H), 1.49 (d, J=7.2 Hz, 3H).

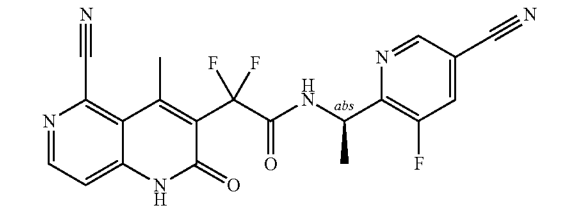

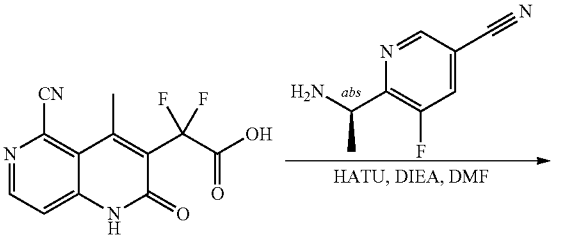

-continued

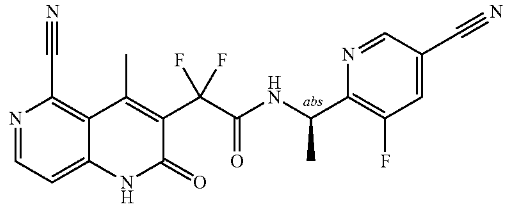

N-[(1R)-1-(5-cyano-3-fluoropyridin-2-yl)ethyl]-2-(5-cyano-4-methyl-2-oxo-1H-1,6-naphthyridin-3-yl)-2,2-difluoroacetamide (Compound 3510): To a stirred solution of (5-cyano-4-methyl-2-oxo-1H-1,6-naphthyridin-3-yl)difluoroacetic acid (50 mg, 0.179 mmol, 1 equiv) and 6-[(1R)-1-aminoethyl]-5-fluoropyridine-3-carbonitrile (35.49 mg, 0.215 mmol, 1.2 equiv) in DMF was added HATU (81.71 mg, 0.215 mmol, 1.2 equiv) and DIEA (69.44 mg, 0.537 mmol, 3 equiv) at RT. The crude residue was purified by reverse-phase chromatography with a C18 column eluting with MeCN/Water (0.1% FA) to afford N-[(1R)-1-(5-cyano-3-fluoropyridin-2-yl)ethyl]-2-(5-cyano-4-methyl-2-oxo-1H-1,6-naphthyridin-3-yl)-2,2-difluoroacetamide (34.0 mg, 44.53%). LCMS (ES, m/z): 427.10 $[M+H]^+$. $^1H$ NMR (400 MHz, DMSO-d6) δ 12.64 (s, 1H), 9.01 (d, J=7.2 Hz, 1H), 8.90 (s, 1H), 8.65 (d, J=5.2 Hz, 1H), 8.42-8.39 (m, 1H), 7.48 (d, J=5.6 Hz, 1H), 5.35-5.28 (m, 1H), 2.94 (t, J=2.8 Hz, 3H), 1.48 (d, J=6.8 Hz, 3H).

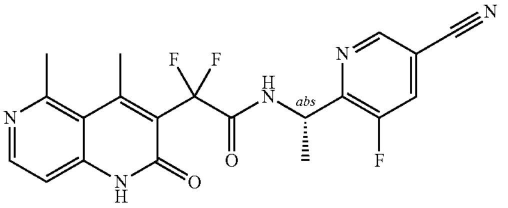

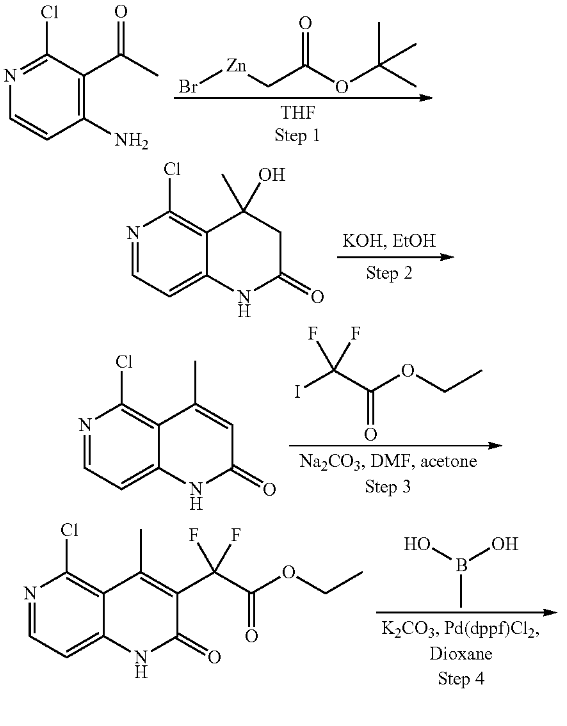

-continued

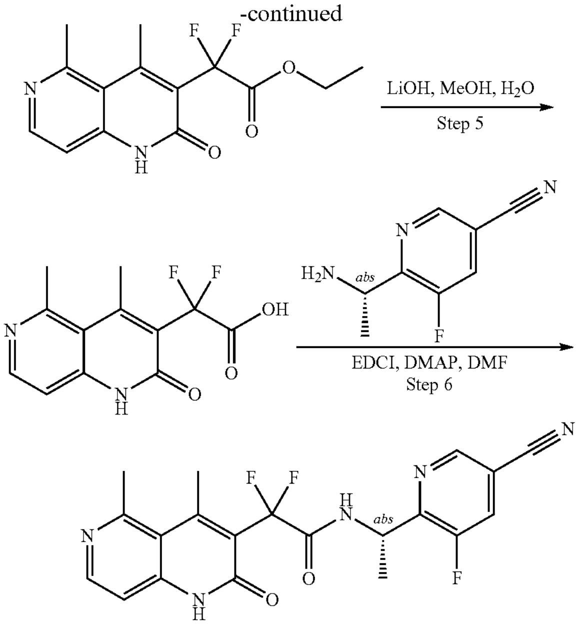

5-chloro-4-hydroxy-4-methyl-1,3-dihydro-1,6-naphthyridin-2-one: A solution of 1-(4-amino-2-chloropyridin-3-yl) ethanone (3 g, 17.585 mmol, 1 equiv) and tert-butyl 2-(bromozincio)acetate (22.90 g, 87.925 mmol, 5 equiv) in THF (30 mL) was stirred overnight at 70° C. The crude reaction was concentrated under reduced pressure and purified by column chromatography, eluting with $CH_2Cl_2$ and MeOH to afford 5-chloro-4-hydroxy-4-methyl-1,3-dihydro-1,6-naphthyridin-2-one (3 g, 80.23%). LCMS (ES, m/z): 213 $[M+H]^+$.

5-chloro-4-methyl-1H-1,6-naphthyridin-2-one: A solution of 5-chloro-4-hydroxy-4-methyl-1,3-dihydro-1,6-naphthyridin-2-one (I g, 4.703 mmol, 1 equiv) and KOH (1.32 g, 23.515 mmol, 5 equiv) in EtOH (10 mL) was stirred for 2 h at 80° C. The crude reaction was concentrated under reduced pressure and purified by trituration with MeCN to afford 5-chloro-4-methyl-1H-1,6-naphthyridin-2-one (600 mg, 65.55%). LCMS (ES, m/z): 195 $[M+H]^+$.

Ethyl 2-(5-chloro-4-methyl-2-oxo-1H-1,6-naphthyridin-3-yl)-2,2-difluoroacetate: A solution of 5-chloro-4-methyl-1H-1,6-naphthyridin-2-one (500 mg, 2.569 mmol, 1 equiv), ethyl 2,2-difluoro-2-iodoacetate (1926.70 mg, 7.707 mmol, 3 equiv) and $Na_2CO_3$ (544.59 mg, 5.138 mmol, 2 equiv) in DMF (6 mL), Acetone (6 mL) was stirred overnight at RT. The reaction was monitored by LCMS. The resulting solution was diluted with water (10 mL). The resulting solution was extracted with EA. The combined organic layers were washed with water, dried over anhydrous $Na_2SO_4$, filtered, and the filtrate was concentrated under reduced pressure. The residue was purified by column chromatography, eluting with PE/EA to afford ethyl 2-(5-chloro-4-methyl-2-oxo-1H-1,6-naphthyridin-3-yl)-2,2-difluoroacetate (400 mg, 49.16%). LCMS (ES, m/z): 317 $[M+H]^+$.

Ethyl 2-(4,5-dimethyl-2-oxo-1H-1,6-naphthyridin-3-yl)-2,2-difluoroacetate: A solution of ethyl 2-(5-chloro-4-methyl-2-oxo-1H-1,6-naphthyridin-3-yl)-2,2-difluoroacetate (300 mg, 0.947 mmol, 1 equiv), methylboronic acid (141.76 mg, 2.367 mmol, 2.5 equiv), $K_2CO_3$ (392.76 mg, 2.841 mmol, 3 equiv) and Pd(dppf)$Cl_2$ (138.63 mg, 0.189 mmol, 0.2 equiv) in Dioxane (5 mL) was stirred overnight at 100° C. under argon. The crude reaction was concentrated under reduced pressure and purified by column chromatography, eluting with PE and EA to afford ethyl 2-(4,5-dimethyl-2-oxo-1H-1,6-naphthyridin-3-yl)-2,2-difluoroacetate (200 mg, 71.26%). LCMS (ES, m/z): 297 $[M+H]^+$.

(4,5-dimethyl-2-oxo-1H-1,6-naphthyridin-3-yl)difluoroacetic acid: A solution of ethyl 2-(4,5-dimethyl-2-oxo-1H-1,6-naphthyridin-3-yl)-2,2-difluoroacetate (200 mg, 0.675 mmol, 1 equiv) and LiOH (32.33 mg, 1.350 mmol, 2 equiv) in MeOH (1 mL) and $H_2O$ (1 mL) was stirred overnight at RT. The crude reaction was concentrated under reduced pressure and was adjusted to pH 5 with conc. HCl. The precipitated solids were filtered, washed with MeCN, and purified by trituration with MeCN to afford (4,5-dimethyl-2-oxo-1H-1,6-naphthyridin-3-yl)difluoroacetic acid (150 mg, 82.84%). LCMS (ES, m/z): 269 $[M+H]^+$.

N-[(1S)-1-(5-cyano-3-fluoropyridin-2-yl)ethyl]-2-(4,5-dimethyl-2-oxo-1H-1,6-naphthyridin-3-yl)-2,2-difluoroacetamide (Compound 3517): A solution of (4,5-dimethyl-2-oxo-1H-1,6-naphthyridin-3-yl)difluoroacetic acid (35 mg, 0.130 mmol, 1 equiv), 6-[(1S)-1-aminoethyl]-5-fluoropyridine-3-carbonitrile (25.86 mg, 0.156 mmol, 1.2 equiv), EDCI (30.02 mg, 0.156 mmol, 1.2 equiv) and DMAP (19.13 mg, 0.156 mmol, 1.2 equiv) in DMF (1 mL) was stirred overnight at RT under argon. The crude material was purified by reverse-phase chromatography with a C18 column eluting with MeCN/Water (0.1% FA) to afford N-[(1S)-1-(5-cyano-3-fluoropyridin-2-yl)ethyl]-2-(4,5-dimethyl-2-oxo-1H-1,6-naphthyridin-3-yl)-2,2-difluoroacetamide (13.4 mg, 24.72%). LCMS (ES, m/z): 416.10 $[M+H]^+$. $^1H$ NMR (400 MHz, Methanol-d4) δ 8.76-8.75 (m, 1H), 8.30 (d, J=5.6 Hz, 1H), 8.09-8.06 (m, 1H), 7.11 (d, J=5.6 Hz, 1H), 5.50-5.45 (m, 1H), 2.94 (s, 3H), 2.84 (d, J=4.4 Hz, 3H), 1.58 (d, J=7.2 Hz, 3H), 1.28 (s, 1H), 0.91-0.85 (m, 1H).

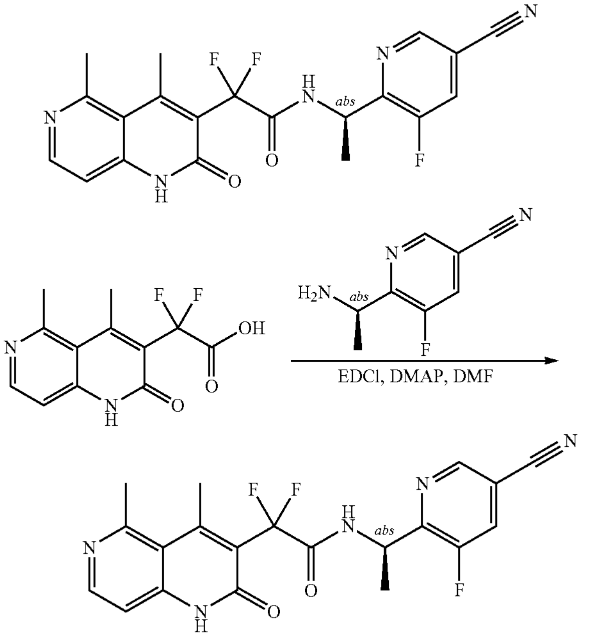

N-[(1R)-1-(5-cyano-3-fluoropyridin-2-yl)ethyl]-2-(4,5-dimethyl-2-oxo-1H-1,6-naphthyridin-3-yl)-2,2-difluoroacetamide (Compound 3513): A solution of (4,5-dimethyl-2-oxo-1H-1,6-naphthyridin-3-yl)difluoroacetic acid (40 mg, 0.149 mmol, 1 equiv), 6-[(1R)-1-aminoethyl]-5-fluoropyridine-3-carbonitrile (29.56 mg, 0.179 mmol, 1.2 equiv), EDCI (34.31 mg, 0.179 mmol, 1.2 equiv) and DMAP (1.82 mg, 0.015 mmol, 0.1 equiv) in DMF (5 mL) was stirred overnight at RT under argon. The crude residue was purified by reverse-phase chromatography with a C18 column eluting with MeCN/Water (0.1% FA) to afford N-[(1R)-1-(5-cyano-3-fluoropyridin-2-yl)ethyl]-2-(4,5-dimethyl-2-oxo-1H-1,6-naphthyridin-3-yl)-2,2-difluoroacetamide (15.4 mg, 24.86%). LCMS (ES, m/z): 416.05 $[M+H]^+$. $^1$H NMR (400 MHz, Methanol-d4) δ 8.76 (s, 1H), 8.30 (d, J=5.6 Hz, 1H), 8.09-8.06 (m, 1H), 7.11 (d, J=5.6 Hz, 1H), 5.51-5.45 (m, 1H), 2.94 (s, 3H), 2.85-2.83 (m, 3H), 1.58 (d, J=6.8 Hz, 3H), 1.28 (s, 1H), 0.90-0.85 (m, 1H).

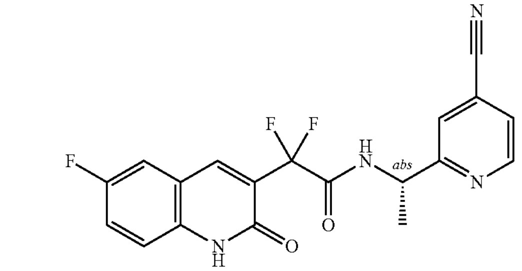

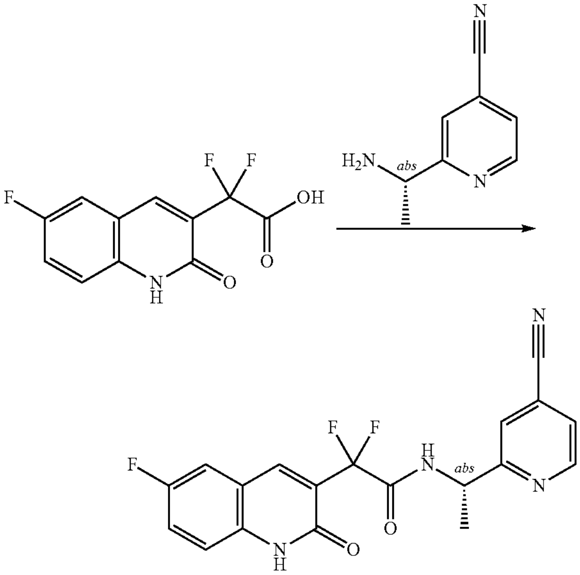

N-[(1S)-1-(4-cyanopyrimidin-2-yl)ethyl]-2,2-difluoro-2-(6-fluoro-2-oxo-1H-quinolin-3-yl)acetamide (Compound 2574): To a stirred solution of difluoro(6-fluoro-2-oxo-1H-quinolin-3-yl)acetic acid (50 mg, 0.194 mmol, 1 equiv) and 2-[(1S)-1-aminoethyl]pyridine-4-carbonitrile (42.92 mg, 0.291 mmol, 1.5 equiv) in DMF (4 mL) was added EDCI (44.73 mg, 0.233 mmol, 1.2 equiv) and DMAP (11.88 mg, 0.097 mmol, 0.5 equiv) portionwise at RT. The resulting mixture was stirred for 2 h at RT. The crude reaction was diluted with water and extracted with EA. The organics were washed with brine, dried over anhydrous $MgSO_4$, filtered and concentrated under reduced pressure. The crude product was purified by Prep-HPLC with a XBridge Shield RP18 OBD Column, 30*150 mm, 5 μm, eluting with Water(10 mmol/L $NH_4HCO_3$+0.05% $NH_3 \cdot H_2O$) and ACN to afford N-[(1S)-1-(4-cyanopyridin-2-yl)ethyl]-2,2-difluoro-2-(6-fluoro-2-oxo-1H-quinolin-3-yl)acetamide (29.0 mg, 38.61%). LCMS (ES, m/z): 387.10 $[M+H]^+$.

$^1$H NMR (400 MHz, DMSO-$d_6$) δ 12.30 (s, 1H), 9.36 (d, J=7.6 Hz, 1H), 8.79 (d, J=5.2 Hz, 1H), 8.42 (s, 1H), 8.02 (s, 1H), 7.78-7.75 (m, 2H), 7.57-7.53 (m, 1H), 7.44-7.41 (m, 1H), 5.11-5.04 (m, 1H), 1.53 (d, J=7.2 Hz, 3H).

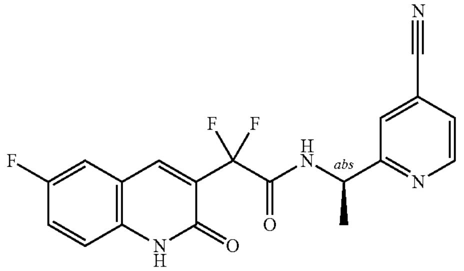

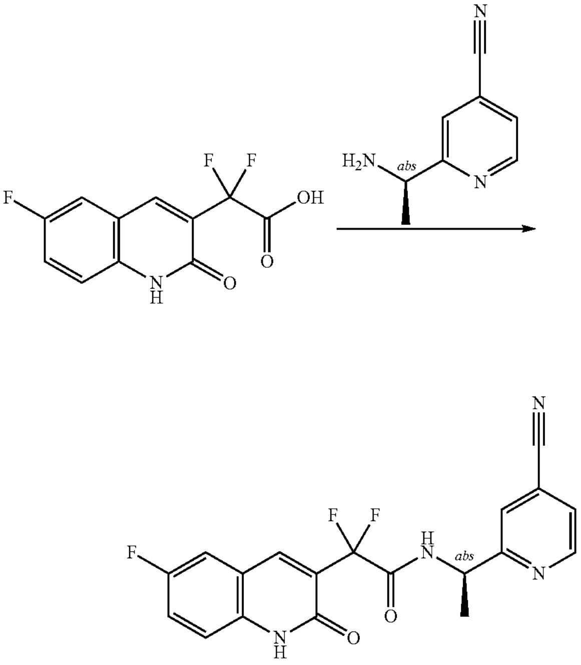

Rel-N-[(1R)-1-(4-cyanopyridin-2-yl)ethyl]-2,2-difluoro-2-(6-fluoro-2-oxo-1H-quinolin-3-yl)acetamide (Compound 2573): To a stirred solution of difluoro(6-fluoro-2-oxo-1H-quinolin-3-yl)acetic acid (50 mg, 0.194 mmol, 1 equiv) and 2-[(1S)-1-aminoethyl]pyridine-4-carbonitrile (42.92 mg, 0.291 mmol, 1.5 equiv) in DMF (4 mL) was added EDCI (44.73 mg, 0.233 mmol, 1.2 equiv) and DMAP (11.88 mg, 0.097 mmol, 0.5 equiv) portionwise at RT. The resulting mixture was stirred for 2 h at RT. The crude reaction was diluted with water and extracted with EA. The organics were washed with brine, dried over $MgSO_4$, filtered and the filtrate was concentrated under reduced pressure. The crude product was purified by Prep-HPLC with a XBridge Shield RP18 OBD Column, 30*150 mm, 5 μm, eluting with Water (10 mmol/L $NH_4HCO_3$+0.05% $NH_3 \cdot H_2O$) and ACN to afford N-[(1S)-1-(4-cyanopyridin-2-yl)ethyl]-2,2-difluoro-2-(6-fluoro-2-oxo-1H-quinolin-3-yl)acetamide (29.0 mg, 38.61%). LCMS (ES, m/z): 387.10 $[M+H]^+$.

$^1$H NMR (400 MHz, DMSO-$d_6$) δ 12.30 (s, 1H), 9.36 (d, J=8.0 Hz, 1H), 8.79 (t, J=4.4 Hz, 1H), 8.43 (s, 1H), 8.02 (s, 1H), 7.78-7.75 (m, 2H), 7.57-7.53 (m, 1H), 7.45-7.41 (m, 1H), 5.11-5.04 (m, 1H), 1.53 (d, J=7.2 Hz, 3H).

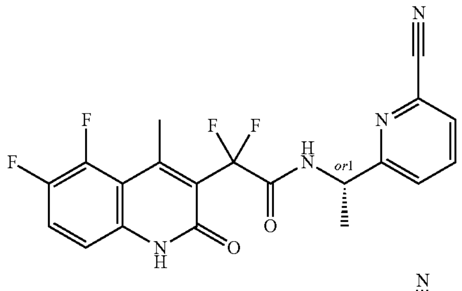

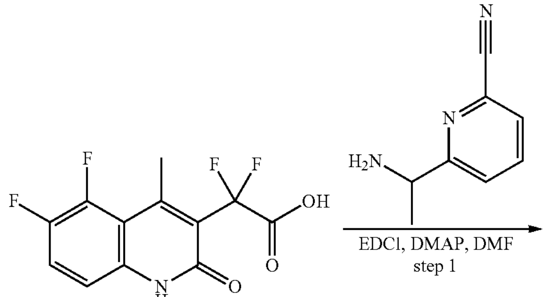

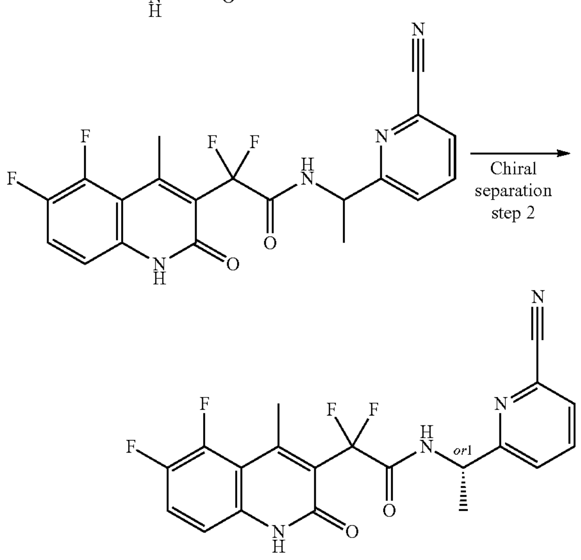

N-[1-(6-cyanopyridin-2-yl)ethyl]-2-(5,6-difluoro-4-methyl-2-oxo-1H-quinolin-3-yl)-2,2-difluoroacetamide: To a stirred solution of (5,6-difluoro-4-methyl-2-oxo-1H-quinolin-3-yl)difluoroacetic acid (150 mg, 0.519 mmol, 1 equiv), EDCI (119.32 mg, 0.623 mmol, 1.2 equiv) and DMAP (25.35 mg, 0.208 mmol, 0.4 equiv) in DMF (2 mL) was added 6-(1-aminoethyl)pyridine-2-carbonitrile (91.61 mg, 0.623 mmol, 1.2 equiv) portionwise at RT. The resulting mixture was stirred overnight at RT. The crude residue was purified by reverse-phase chromatography with a C18 column eluting with MeCN/Water (0.1% FA) to afford N-[1-(6-cyanopyridin-2-yl)ethyl]-2-(5,6-difluoro-4-methyl-2-oxo-1H-quinolin-3-yl)-2,2-difluoroacetamide (100 mg, 46.08%). LC-MS: (ESI, m/z): 419 $[M+H]^+$.

Rel-N-[(1S)-1-(6-cyanopyridin-2-yl)ethyl]-2-(5,6-difluoro-4-methyl-2-oxo-1H-quinolin-3-yl)-2,2-difluoroacetamide (Compound 2588): N-[1-(6-cyanopyridin-2-yl)ethyl]-2-(5,6-difluoro-4-methyl-2-oxo-1H-quinolin-3-yl)-2,2-difluoroacetamide (100 mg, 0.239 mmol, 1 equiv) was purified by chiral separation with a CHIRALPAK IK-3, 4.6*50 mm, 3 um eluting with Hex(10 mM $NH_3$-MeOH) and EtOH to afford rel-N-[(1S)-1-(6-cyanopyridin-2-yl)ethyl]-2-(5,6-difluoro-4-methyl-2-oxo-1H-quinolin-3-yl)-2,2-difluoroacetamide (30 mg, 29.79%). LC-MS: (ESI, m/z): 419.05 $[M+H]^+$.

$^1H$ NMR (400 MHz, DMSO-d6) δ 12.29 (s, 1H), 9.10 (d, J=8.0 Hz, 1H), 8.03 (t, J=8.0 Hz, 1H), 7.94-7.91 (m, 2H), 7.77-7.70 (m, 1H), 7.16-7.13 (m, 1H), 5.09-5.02 (m, 1H), 2.76-2.74 (m, 3H), 1.51 (d, J=7.2 Hz, 3H).

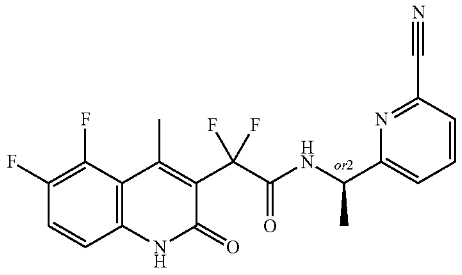

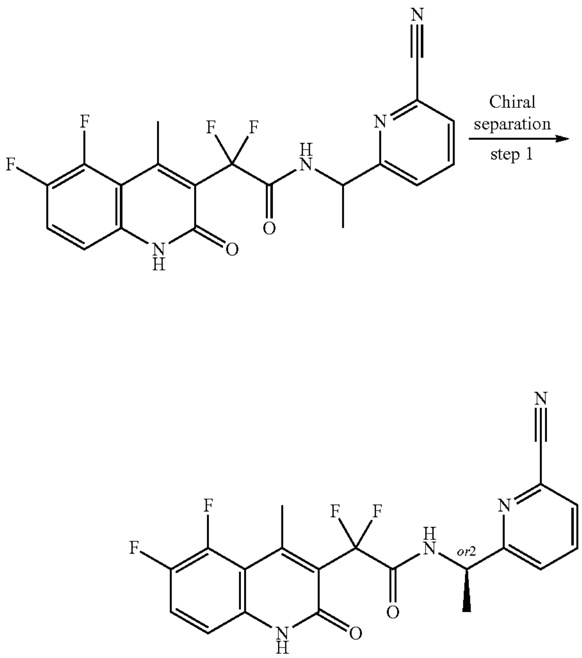

Rel-N-[(1R)-1-(6-cyanopyridin-2-yl)ethyl]-2-(5,6-difluoro-4-methyl-2-oxo-1H-quinolin-3-yl)-2,2-difluoroacetamide (Compound 2587):N-[1-(6-cyanopyridin-2-yl)ethyl]-2-(5,6-difluoro-4-methyl-2-oxo-1H-quinolin-3-yl)-2,2-difluoroacetamide (100 mg, 0.239 mmol, 1 equiv) was purified by chiral separation with a CHIRALPAK IK-3, 4.6*50 mm, 3 um eluting with Hex(10 mM $NH_3$-MeOH) and EtOH to afford rel-N-[(1R)-1-(6-cyanopyridin-2-yl)ethyl]-2-(5,6-difluoro-4-methyl-2-oxo-1H-quinolin-3-yl)-2,2-difluoroacetamide (38.5 mg, 37.54%). LC-MS: (ESI, m/z): 419.05 $[M+H]^+$.

$^1H$ NMR (400 MHz, DMSO-d6) δ 12.29 (s, 1H), 9.10 (d, J=8.0 Hz, 1H), 8.03 (t, J=7.6 Hz, 1H), 7.94-7.91 (m, 2H), 7.75-7.72 (m, 1H), 7.16-7.13 (m, 1H), 5.07-5.03 (m, 1H), 2.76-2.74 (m, 3H), 1.50 (d, J=7.2 Hz, 3H).

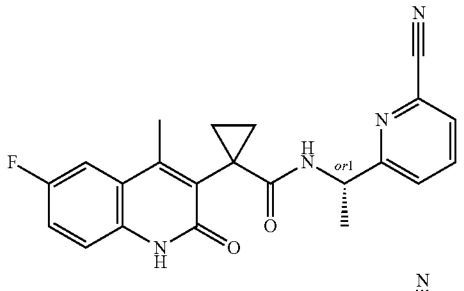

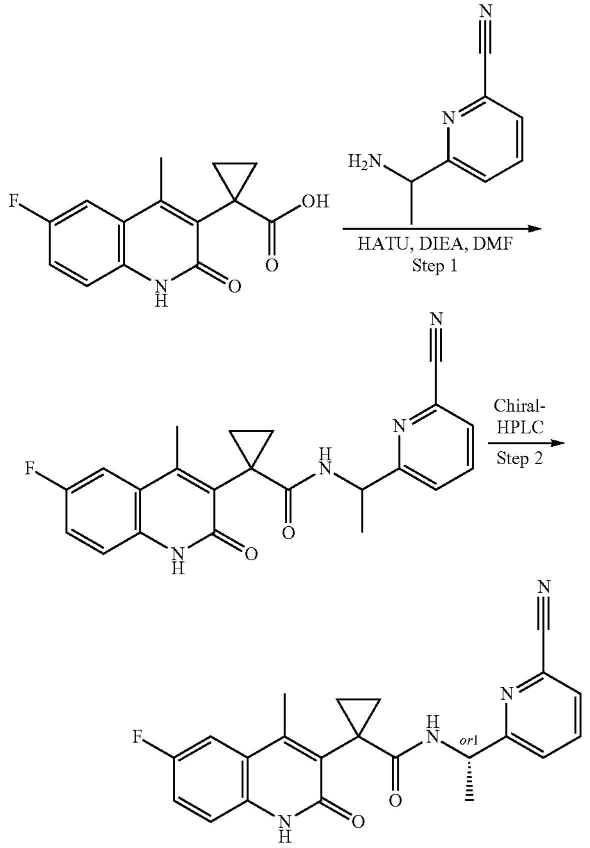

N-[1-(6-cyanopyridin-2-yl)ethyl]-1-(6-fluoro-4-methyl-2-oxo-1H-quinolin-3-yl)cyclopropane-1-carboxamide: A solution of 1-(6-fluoro-4-methyl-2-oxo-1H-quinolin-3-yl) cyclopropane-1-carboxylic acid (200 mg, 0.766 mmol, 1 equiv), 6-(1-aminoethyl)pyridine-2-carbonitrile (135.21 mg, 0.919 mmol, 1.2 equiv), HATU (349.30 mg, 0.919 mmol, 1.2 equiv) and DIEA (296.83 mg, 2.298 mmol, 3 equiv) in DMF (5 mL) was stirred overnight at RT. The crude residue was purified by reverse-phase chromatography with aC18 column eluting with MeCN/Water (0.1% FA) to afford N-[1-(6-cyanopyridin-2-yl)ethyl]-1-(6-fluoro-4-methyl-2-oxo-1H-quinolin-3-yl)cyclopropane-1-carboxamide (90 mg, 30.11%). LCMS (ES, m/z): 391 $[M+H]^+$.

Rel-N-[(1S)-1-(6-cyanopyridin-2-yl)ethyl]-1-(6-fluoro-4-methyl-2-oxo-1H-quinolin-3-yl)cyclopropane-1-carboxamide (Compound 2580): The N-[1-(6-cyanopyridin-2-yl) ethyl]-1-(6-fluoro-4-methyl-2-oxo-1H-quinolin-3-yl) cyclopropane-1-carboxamide (100 mg) was purified by Chiral-HPLC with a CHIRAL ART Cellulose-SZ, 3*25 cm, 5 μm column eluting with Hex(10 mM $NH_3$-MeOH) and EtOH to afford rel-N-[(1S)-1-(6-cyanopyridin-2-yl)ethyl]-1-(6-fluoro-4-methyl-2-oxo-1H-quinolin-3-yl)cyclopropane-1-carboxamide (42.4 mg, 42.40%). LCMS (ES, m/z): 391.10 $[M+H]^+$.

$^1$H NMR (300 MHz, DMSO-$d_6$) δ 11.74 (s, 1H), 8.03-7.97 (m, 1H), 7.90-7.87 (m, 1H), 7.74-7.61 (m, 2H), 7.60-7.57 (m, 1H), 7.43-7.38 (m, 1H), 7.37-7.30 (m, 1H), 5.08-4.98 (m, 1H), 2.52-2.49 (m, 3H), 1.56-1.51 (m, 2H), 1.34-1.23 (m, 3H), 0.96-0.92 (m, 2H).

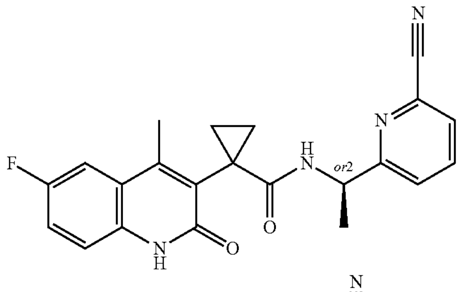

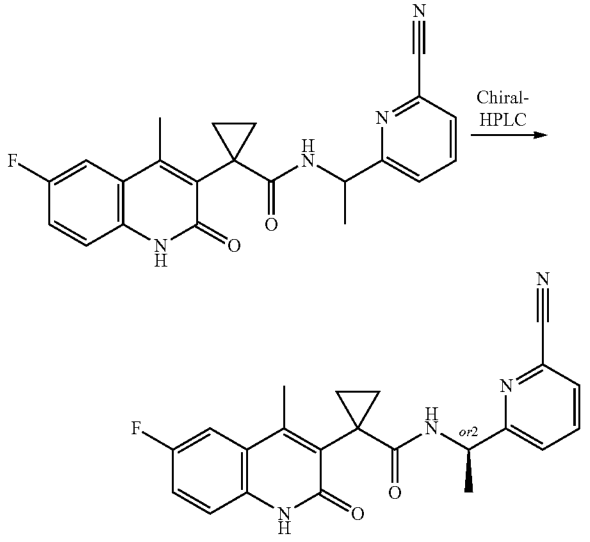

Rel-N-[(1R)-1-(6-cyanopyridin-2-yl)ethyl]-1-(6-fluoro-4-methyl-2-oxo-1H-quinolin-3-yl)cyclopropane-1-carboxamide: The crude product (100 mg) was purified by Chiral-HPLC with a CHIRAL ART Cellulose-SZ, 3*25 cm, 5 μm column eluting with Hex(10 mM $NH_3$-MeOH) and EtOH to afford rel-N-[(1R)-1-(6-cyanopyridin-2-yl)ethyl]-1-(6-fluoro-4-methyl-2-oxo-1H-quinolin-3-yl)cyclopropane-1-carboxamide (35.3 mg, 35.30%). LCMS (ES, m/z): 391.10 $[M+H]^+$. $^1$H NMR (300 MHz, DMSO-$d_6$) δ 11.74 (s, 1H), 8.03-8.00 (m, 1H), 7.97-7.90 (m, 1H), 7.87-7.75 (m, 2H), 7.61-7.57 (m, 1H), 7.43-7.37 (m, 1H), 7.32-7.29 (m, 1H), 5.08-4.98 (m, 1H), 2.51-2.49 (m, 3H), 1.55-1.16 (m, 2H), 1.34-1.23 (m, 3H), 0.96-0.87 (m, 2H).

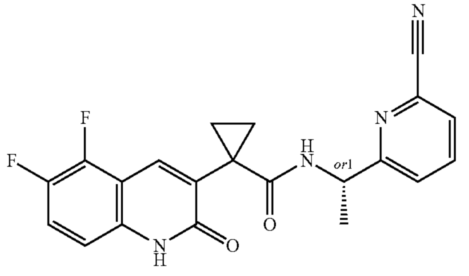

-continued

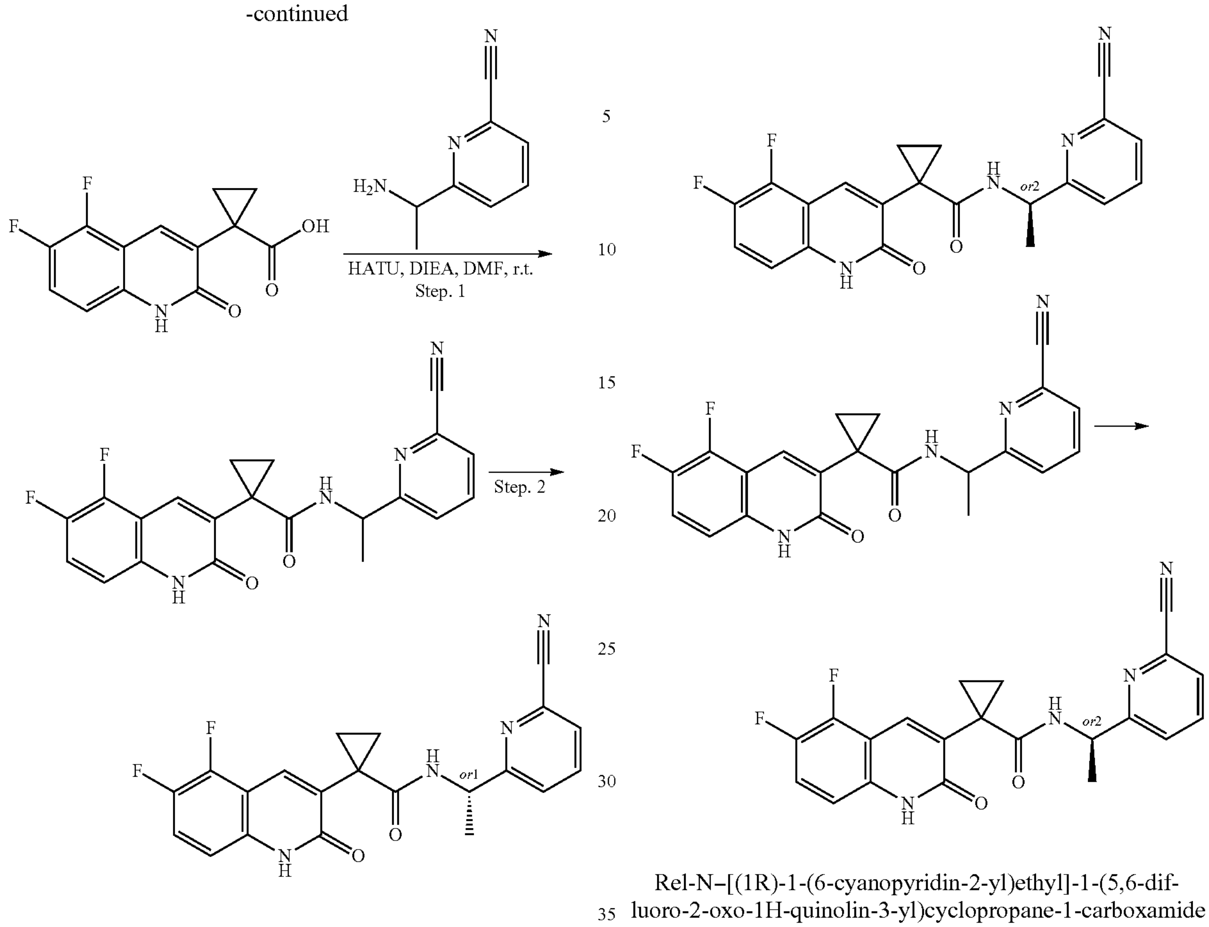

N-[1-(6-cyanopyridin-2-yl)ethyl]-1-(5,6-difluoro-2-oxo-1H-quinolin-3-yl)cyclopropane-1-carboxamide: A solution of 1-(5,6-difluoro-2-oxo-1H-quinolin-3-yl)cyclopropane-1-carboxylic acid (100 mg, 0.377 mmol, 1 equiv), HATU (172.04 mg, 0.452 mmol, 1.2 equiv), DIEA (146.20 mg, 1.131 mmol, 3 equiv) and 6-(1-aminoethyl)pyridine-2-carbonitrile (66.59 mg, 0.452 mmol, 1.2 equiv) in DMF (3 mL) was stirred for 2 h at RT under argon. The crude residue was purified by reverse-phase chromatography with a C18 column eluting with MeCN/Water (0.1% FA to afford N-[1-(6-cyanopyridin-2-yl)ethyl]-1-(5,6-difluoro-2-oxo-1H-quinolin-3-yl)cyclopropane-1-carboxamide (100 mg, 67.25%). LC-MS: (ES1, m/z): $[M+H]^+=395$.

Rel-N-[(1S)-1-(6-cyanopyridin-2-yl)ethyl]-1-(5,6-difluoro-2-oxo-1H-quinolin-3-yl)cyclopropane-1-carboxamide (Compound 2570): The crude product (100 mg) was separated with a Prep-Chiral-HPLC eluting with Hex(0.1% DEA) and EtOH to afford rel-N-[(1S)-1-(6-cyanopyridin-2-yl)ethyl]-1-(5,6-difluoro-2-oxo-1H-quinolin-3-yl)cyclopropane-1-carboxamide (31.3 mg, 31.21%). LC-MS: (ESI, m/z): $[M+H]^+=395.05$.

$^1$H NMR (400 MHz, DMSO-$d_6$) δ 12.11 (s, 1H), 7.99-7.87 (m, 3H), 7.79 (t, J=8.0 Hz, 2H), 7.60 (d, J=10.0 Hz, 1H), 7.14-7.11 (m, 1H), 4.98 (t, J=7.6 Hz, 1H), 1.40-1.37 (m, 1H), 1.34-1.33 (m, 3H), 1.31-1.29 (m, 1H), 1.13 (s, 1H), 0.87 (d, J=2.8 Hz, 1H).

Rel-N-[(1R)-1-(6-cyanopyridin-2-yl)ethyl]-1-(5,6-difluoro-2-oxo-1H-quinolin-3-yl)cyclopropane-1-carboxamide (Compound 2569): The crude product (100 mg) was separated with a Prep-Chiral-HPLC eluting with Hex(0.1% DEA) and EtOH to afford rel-N-[(1R)-1-(6-cyanopyridin-2-yl)ethyl]-1-(5,6-difluoro-2-oxo-1H-quinolin-3-yl)cyclopropane-1-carboxamide (39.3 mg, 39.18%). LC-MS: (ESI, m/z): $[M+H]^+=395.05$.

$^1$H NMR (400 MHz, DMSO-$d_6$) δ 12.12 (s, 1H), 7.99-7.87 (m, 3H), 7.80-7.77 (m, 2H), 7.60 (d, J=10.0 Hz, 1H), 7.14-7.11 (m, 1H), 4.98 (t, J=7.2 Hz, 1H), 1.41-1.37 (m, 1H), 1.34 (d, J=7.2 Hz, 3H), 1.31-1.28 (m, 1H), 1.14-1.11 (m, 1H), 0.89 (s, 1H).

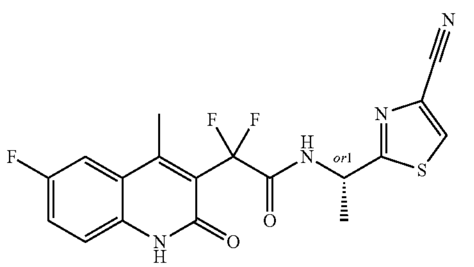

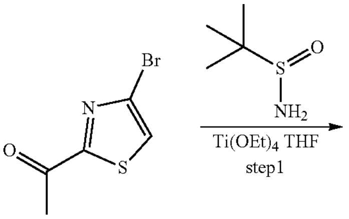

-continued

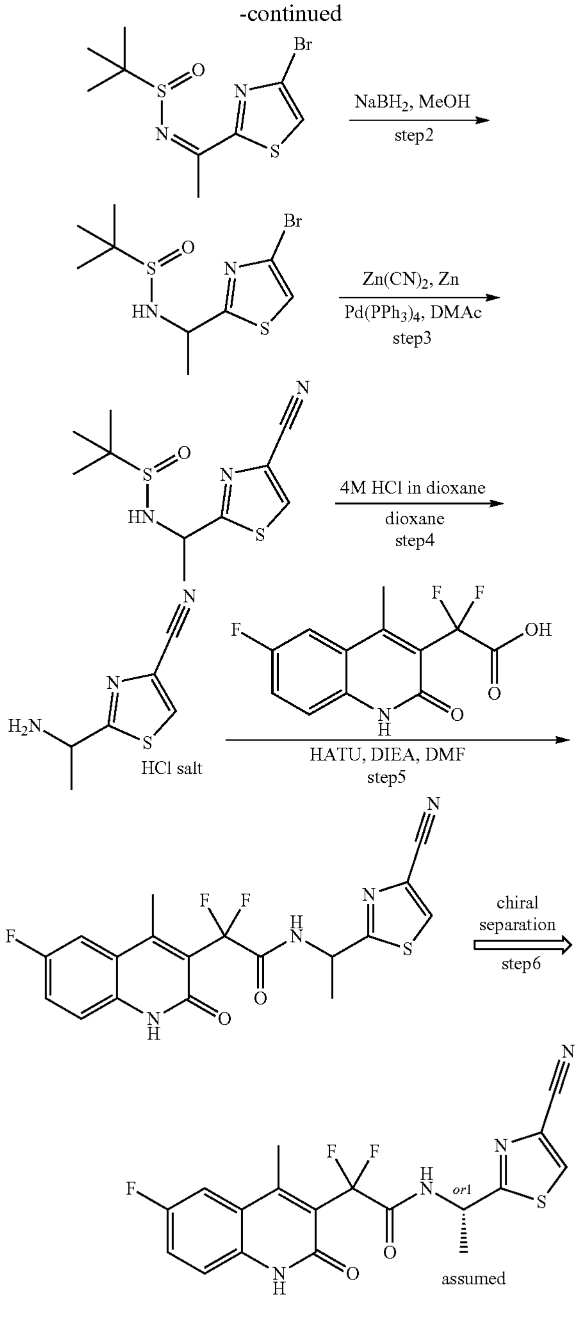

(Z)—N-(1-(4-bromothiazol-2-yl)ethylidene)-2-methylpropane-2-sulfinamide: To a stirred solution of 1-(4-bromothiazol-2-yl)ethan-1-one (3.80 g, 221 mmol, 1.00 equiv) and 2-methylpropane-2-sulfinamide (2.24 g, 9.22 mmol, 1.00 equiv) in THF (20 mL) was added $Ti(OEt)_4$ (8.42 g, 8.44 mmol, 2.00 equiv) at 0° C. The resulting mixture was stirred for 2 h at 50° C. The crude reaction was filtered and the solids were washed with DCM. The filtrate was concentrated under reduced pressure and purified by column chromatography, eluting with PE and EA to afford (Z)—N-(1-(4-bromothiazol-2-yl)ethylidene)-2-methylpropane-2-sulfinamide (5.60 g, 63.83%). LCMS (ES, m/z): 309/311 $[M+H]^+$ N-(1-(4-bromothiazol-2-yl)ethyl)-2-methylpropane-2-sulfinamide: To a stirred solution of 1-(4-bromo-1,3-thiazol-2-yl)ethanone (5.20 g, 25.2 mmol, 1.00 equiv) in MeOH (50 mL) was added $NaBH_4$ (1.43 g, 37.8 mmol, 1.50 equiv) at 0° C. The resulting mixture was stirred for 3 h at 25° C. under nitrogen. The reaction was quenched with ice water at 0° C. The crude material was extracted with EA, dried over anhydrous $Na_2SO_4$, filtered, and the filtrate was concentrated under reduced pressure. The crude residue was purified by column chromatography, eluting with PE and EA to afford N-(1-(4-bromothiazol-2-yl)ethyl)-2-methylpropane-2-sulfinamide (4.20 g, 48.27%). LCMS (ES, m/z): 311/313 $[M+H]^+$ N-(1-(4-cyanothiazol-2-yl)ethyl)-2-methylpropane-2-sulfinamide: In a 40 mL vial was added N-(1-(4-bromothiazol-2-yl)ethyl)-2-methylpropane-2-sulfinamide (1.40 g, 4.57 mmol, 1.00 equiv), $Zn(CN)_2$ (0.81 g, 6.86 mmol, 1.50 equiv), zinc powder (0.12 g, 1.83 mmol, 0.40 equiv), $Pd(dppf)Cl_2$ (0.67 g, 0.914 mmol, 0.20 equiv) in DMAc (10 mL) at 25° C. The resulting mixture was stirred for 3 h at 100° C. under argon. The reaction was quenched with water at 0° C. and extracted with EA. The organics were washed with water, dried over $Na_2SO_4$, and the filtrate was concentrated under reduced pressure. The crude residue was purified by column chromatography, eluting with PE and EA to afford N-(1-(4-cyanothiazol-2-yl)ethyl)-2-methylpropane-2-sulfinamide (1.00 g, 81.88%). LCMS (ES, m/z): 258 $[M+H]^+$ 2-(1-aminoethyl)thiazole-4-carbonitrile: To a stirred solution of N-(1-(4-cyanothiazol-2-yl)ethyl)-2-methylpropane-2-sulfinamide (600 mg, 2.33 mmol, 1.00 equiv) in dioxane (6 mL) was added 4 M HCl in 1,4-dioxane (3 mL) at 0° C. The resulting mixture was stirred for 0.5 h at 25° C. The reaction was concentrated under reduced pressure to afford 2-(1-aminoethyl)-1,3-thiazole-4-carbonitrile (440 mg crude, HCl salt). LCMS (ES, m/z): 154 $[M+H]^+$ N-(1-(4-cyanothiazol-2-yl)ethyl)-2,2-difluoro-2-(6-fluoro-4-methyl-2-oxo-1,2-dihydroquinolin-3-yl)acetamide: To a stirred solution of 2,2-difluoro-2-(6-fluoro-4-methyl-2-oxo-1,2-dihydroquinolin-3-yl)acetic acid (150 mg, 0.553 mmol, 1.00 equiv) and 2-(1-aminoethyl)-1,3-thiazole-4-carbonitrile (90.4 mg, 0.590 mmol, 1 equiv) in DMF (2 mL) was added and DIEA (228.7 mg, 1.77 mmol, 3.00 equiv) and HATU (224.3 mg, 0.590 mmol, 1.00 equiv) at 0° C. The resulting mixture was stirred for 2 h at 25° C. The reaction was quenched with water at 0° C. and was extracted with EA. The organics were washed with water, dried over anhydrous $Na_2SO_4$, filtered, and the filtrate was concentrated under reduced pressure. The crude residue was purified by column chromatography, eluting with PE and EA to afford N-(1-(4-cyanothiazol-2-yl)ethyl)-2,2-difluoro-2-(6-fluoro-4-methyl-2-oxo-1,2-dihydroquinolin-3-yl)acetamide (90 mg, 40.17%). LCMS (ES, m/z): 407.0 [M+H]+

(S)—N-(1-(4-cyanothiazol-2-yl)ethyl)-2,2-difluoro-2-(6-fluoro-4-methyl-2-oxo-1,2-dihydroquinolin-3-yl)acetamide (Compound 4010): N-(1-(4-Cyanothiazol-2-yl)ethyl)-2,2-difluoro-2-(6-fluoro-4-methyl-2-oxo-1,2-dihydroquinolin-3-yl)acetamide 154 mg) was purified by chiral-HPLC with a CHIRALPAK IG, 3*25 cm, 5 μm column eluting with MtBE(10 mM $NH_3$-MeOH) and MeOH to afford (S)—N-(1-(4-cyanothiazol-2-yl)ethyl)-2,2-difluoro-2-(6-fluoro-4-methyl-2-oxo-1,2-dihydroquinolin-3-yl)acetamide (assumed) (62.1 mg, 40.38%). LCMS (ES, m/z): 407.0 $[M+H]^+$ $^1$H NMR (400 MHz, DMSO-$d_6$) δ 12.14 (s, 1H), 9.35 (d, J=8.0 Hz, 1H), 8.80 (s, 1H), 7.82 (dd, J=10.6, 2.8 Hz, 1H), 7.54 (td, J=8.6, 2.4 Hz, 1H), 7.35 (dd, J=9.0, 5.2 Hz, 1H), 5.28 (p, J=7.2 Hz, 1H), 2.65 (t, J=3.2 Hz, 3H), 1.60 (d, J=7.0 Hz, 3H). $^{19}$F NMR (376 MHz, DMSO-$d_6$) δ −97.34, −119.54.

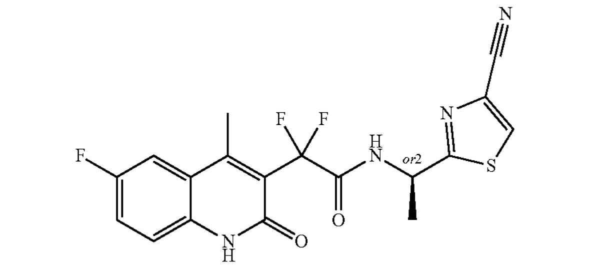

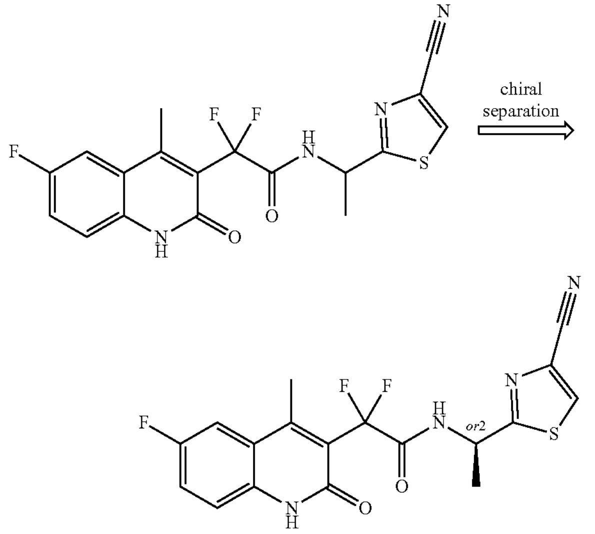

assumed

Rel-N-[(1R)-1-(4-cyano-1,3-thiazol-2-yl)ethyl]-2,2-difluoro-2-(6-fluoro-4-methyl-2-oxo-1H-quinolin-3-yl)acetamide: N-(1-(4-Cyanothiazol-2-yl)ethyl)-2,2-difluoro-2-(6-fluoro-4-methyl-2-oxo-1,2-dihydroquinolin-3-yl)acetamide (154 mg) was purified by chiral-HPLC with a CHIRALPAK IG, 3*25 cm, 5 μm column eluting with MtBE(10 mM $NH_3$-MeOH) and MeOH to afford rel-N-[(1R)-1-(4-cyano-1,3-thiazol-2-yl)ethyl]-2,2-difluoro-2-(6-fluoro-4-methyl-2-oxo-1H-quinolin-3-yl)acetamide (62.1 mg, 40.38%). LCMS (ES, m/z): 407.0 $[M+H]^+$ $^1$H NMR (400 MHz, DMSO-$d_6$) δ 12.15 (s, 1H), 9.35 (d, J=8.0 Hz, 1H), 8.80 (d, J=1.6 Hz, 1H), 7.82 (dd, J=10.6, 2.6 Hz, 1H), 7.59-7.49 (m, 1H), 7.35 (dd, J=9.0, 5.2 Hz, 1H), 5.28 (p, J=6.8 Hz, 1H), 2.65 (t, J=3.2 Hz, 3H), 1.60 (d, J=7.0 Hz, 3H).

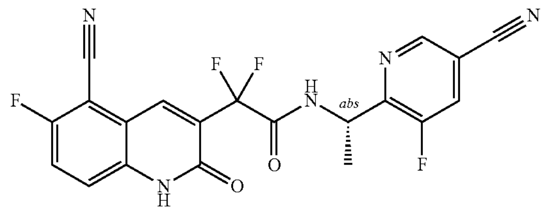

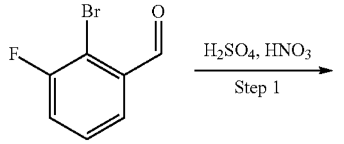

-continued

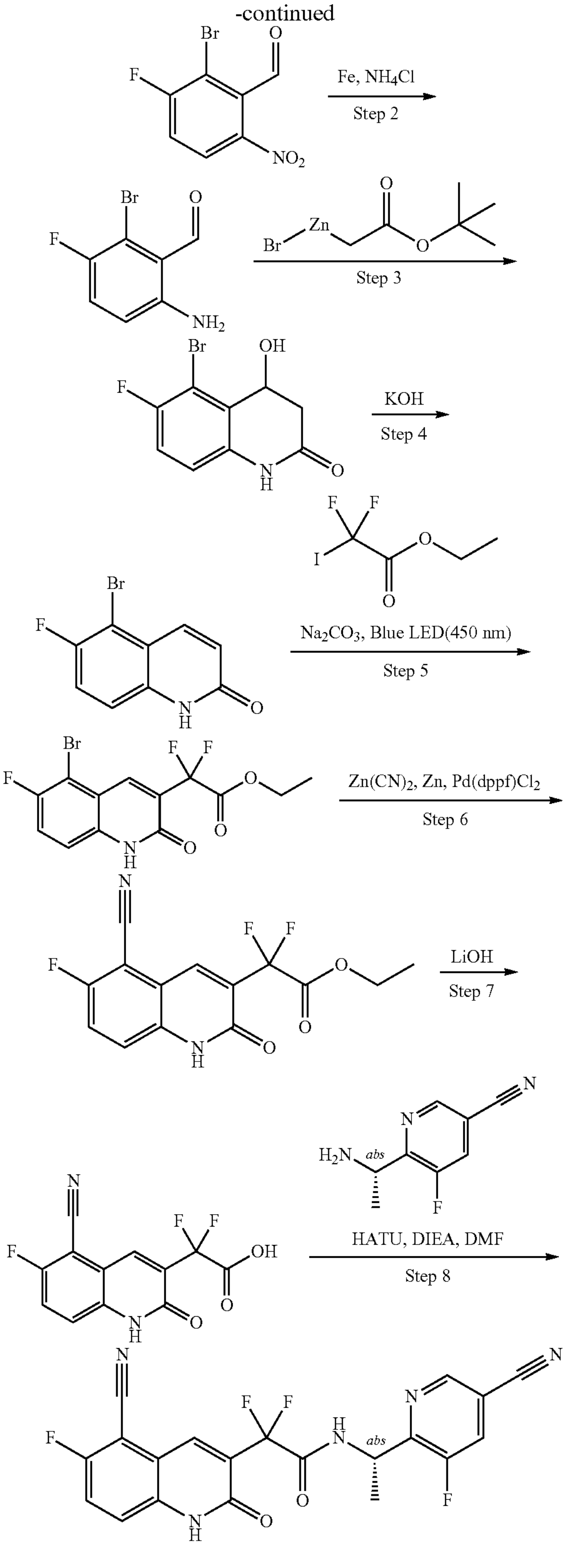

2-bromo-3-fluoro-6-nitrobenzaldehyde: To a stirred solution of 2-bromo-3-fluorobenzaldehyde (25 g, 123.147 mmol, 1 equiv) and $H_2SO_4$ (100 mL, 1876.211 mmol, 15.24 equiv) in DCM (200 mL) was added $HNO_3$ (100 mL, 2229.734 mmol, 18.11 equiv) portionwise at 0° C. The resulting mixture was stirred overnight at RT. The reaction was poured into water at 0° C. and extracted with $CH_2C12$. The organics were concentrated under reduced pressure. The crude residue was purified by column chromatography, eluting with PE and EA to afford 2-bromo-3-fluoro-6-nitrobenzaldehyde (18 g, 58.94%). LCMS (ES, m/z): 248 $[M+H]^+$.

6-amino-2-bromo-3-fluorobenzaldehyde: To a stirred solution of 2-bromo-3-fluoro-6-nitrobenzaldehyde (15 g, 60.482 mmol, 1 equiv) and Fe (16.89 g, 302.410 mmol, 5 equiv) in i-PrOH (450 mL) and $H_2O$ (90 mL) was added $NH_4Cl$ (32.35 g, 604.820 mmol, 10 equiv) portionwise at RT. The resulting mixture was stirred for 2 h at 80° C. The reaction was filtered and the solids was washed with ethanol. The filtrate was concentrated under reduced pressure and purified by column chromatography, eluting with PE and EA to afford 6-amino-2-bromo-3-fluorobenzaldehyde (3.5 g, 26.54%). LCMS (ES, m/z): 218 $[M+H]^+$ 5-bromo-6-fluoro-4-hydroxy-3,4-dihydro-1H-quinolin-2-one: To a stirred solution of 6-amino-2-bromo-3-fluorobenzaldehyde (2 g, 9.173 mmol, 1 equiv) and 6-amino-2-bromo-3-fluorobenzaldehyde (2 g, 9.173 mmol, 1 equiv) in THF (70 mL) at RT. The resulting mixture was stirred for 2 h at 80° C. The reaction was concentrated under reduced pressure and purified by column chromatography, eluting with $CH_2Cl_2$ and MeOH to afford 5-bromo-6-fluoro-4-hydroxy-3,4-dihydro-1H-quinolin-2-one (1.7 g, 71.26%). LCMS (ES, m/z): 261 $[M+H]^+$ 5-bromo-6-fluoro-1H-quinolin-2-one: To a stirred solution of 5-bromo-6-fluoro-4-hydroxy-3,4-dihydro-1H-quinolin-2-one (1.7 g, 6.537 mmol, 1 equiv) and KOH (1.83 g, 32.685 mmol, 5 equiv) in EtOH (50 mL) at RT. The resulting solution was stirred for 2 h at 80° C. The reaction was concentrated under reduced pressure and the residue was purified by column chromatography, eluting with $CH_2Cl_2$/MeOH to afford 5-bromo-6-fluoro-1H-quinolin-2-one (1 g, 63.20%). LCMS (ES, m/z): 242 $[M+H]^+$ Ethyl 2-(5-bromo-6-fluoro-2-oxo-1H-quinolin-3-yl)-2,2-difluoroacetate: To a stirred solution of 5-bromo-6-fluoro-1H-quinolin-2-one (1 g, 4.131 mmol, 1 equiv) and ethyl 2,2-difluoro-2-iodoacetate (3.10 g, 12.393 mmol, 3 equiv) in DMF (100 mL) and Acetone (100 mL) was added $Na_2CO_3$ (1751.53 mg, 16.526 mmol, 2 equiv) portionwise at RT. The resulting mixture was stirred overnight at RT under 460 nm blue LED conditions. The reaction was poured into water at RT and extracted with EA. The organics were washed with NaCl (sat.), dried over $Na_2SO_4$, filtered, and the filtrate was concentrated under reduced pressure. The crude residue was purified by column chromatography, eluting with PE/EA to afford ethyl 2-(5-bromo-6-fluoro-2-oxo-1H-quinolin-3-yl)-2,2-difluoroacetate (840 mg, 55.84%). LCMS (ES, m/z): 364 $[M+H]^+$ Ethyl 2-(5-cyano-6-fluoro-2-oxo-1H-quinolin-3-yl)-2,2-difluoroacetate: To a stirred solution of ethyl 2-(5-bromo-6-fluoro-2-oxo-1H-quinolin-3-yl)-2,2-difluoroacetate (500 mg, 1.373 mmol, 1 equiv) and zincdicarbonitrile (322.48 mg, 2.746 mmol, 2 equiv) in DMF (5 mL) was added Zn (35.91 mg, 0.549 mmol, 0.4 equiv) and $Pd(dppf)Cl_2$ (200.95 mg, 0.275 mmol, 0.2 equiv) portionwise at RT under argon. The resulting mixture was stirred for 2 h at 100° C. under argon. The reaction was poured into water at RT and extracted with EA. The combined organic layers were washed with NaCl (sat.), dried over $Na_2SO_4$, filtered and the filtrate was concentrated under reduced pressure. The residue was purified by column chromatography to afford ethyl 2-(5-cyano-6-fluoro-2-oxo-1H-quinolin-3-yl)-2,2-difluoroacetate (420 mg, 98.59%). LCMS (ES, m/z): 311 $[M+H]^+$ (5-cyano-6-fluoro-2-oxo-1H-quinolin-3-yl)difluoroacetic acid: To a stirred solution of ethyl 2-(5-cyano-6-fluoro-2-oxo-1H-quinolin-3-yl)-2,2-difluoroacetate (420 mg, 1.354 mmol, 1 equiv) and LiOH (64.85 mg, 2.708 mmol, 2 equiv) in THF (3 mL) and $H_2O$ (1 mL) at RT. The resulting mixture was stirred for 2 h at 50° C. The reaction was concentrated under reduced pressure and neutralized to pH 6 with HCl (4 M). The crude product (5-cyano-6-fluoro-2-oxo-1H-quinolin-3-yl)difluoroacetic acid (200 mg, 52.19%) was used in the next step after lyohilization without further purification. LCMS (ES, m/z): 283 $[M+H]^+$ N-[(1S)-1-(5-cyano-3-fluoropyridin-2-yl)ethyl]-2-(5-cyano-6-fluoro-2-oxo-1H-quinolin-3-yl)-2,2-difluoroacetamide (Compound 2530): To a stirred solution of (5-cyano-6-fluoro-2-oxo-1H-quinolin-3-yl)difluoroacetic acid (80 mg, 0.284 mmol, 1 equiv) and HATU (129.36 mg, 0.341 mmol, 1.2 equiv) in DMF (4 mL) were added DIEA (146.57 mg, 1.136 mmol, 4 equiv) and 6-[(1S)-1-aminoethyl]-5-fluoropyridine-3-carbonitrile (56.19 mg, 0.341 mmol, 1.2 equiv) portionwise at RT. The resulting mixture was stirred overnight at RT. The residue was purified by reverse-phase chromatography with a C18 column eluting with MeCN/Water (0.1% FA) to afford N-[(1S)-1-(5-cyano-3-fluoropyridin-2-yl)ethyl]-2-(5-cyano-6-fluoro-2-oxo-1H-quinolin-3-yl)-2,2-difluoroacetamide (16.2 mg, 12.98%). LCMS (ES, m/z): 430.05 $[M+H]^+$ $^1H$ NMR (400 MHz, DMSO-d6) δ 12.51 (s, 1H), 9.27 (d, J=6.8 Hz, 1H), 8.90 (s, 1H), 8.41 (d, J=9.2 Hz, 1H), 8.11 (s, 1H), 7.83 (t, J=9.2 Hz, 1H), 7.72-7.68 (m, 11H), 5.35-5.28 (m, 1H), 1.49 (d, J=6.8 Hz, 3H).

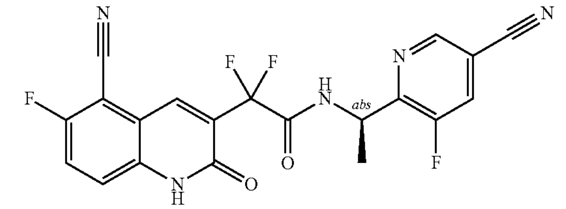

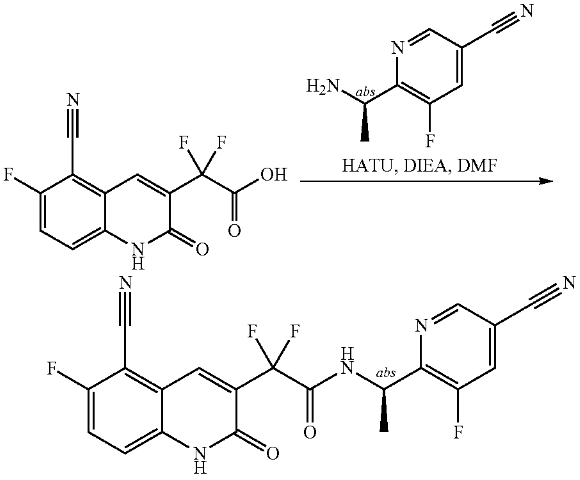

N-[(1R)-1-(5-cyano-3-fluoropyridin-2-yl)ethyl]-2-(5-cyano-6-fluoro-2-oxo-1H-quinolin-3-yl)-2,2-difluoroacetamide (Compound 2529): To a stirred solution of (5-cyano-6-fluoro-2-oxo-1H-quinolin-3-yl)difluoroacetic acid (80 mg, 0.284 mmol, 1 equiv) and HATU (129.36 mg, 0.341 mmol, 1.2 equiv) in DMF (4 mL) was added DIEA (146.57 mg, 1.136 mmol, 4 equiv) and 6-[(1R)-1-aminoethyl]-5-fluoropyridine-3-carbonitrile (56.19 mg, 0.341 mmol, 1.2 equiv) portionwise at RT. The resulting mixture was stirred overnight at RT. The residue was purified by reverse-phase chromatography with a C18 column eluting with MeCN/Water (0.1% FA) to afford N-[(1R)-1-(5-cyano-3-fluoropyridin-2-yl)ethyl]-2-(5-cyano-6-fluoro-2-oxo-1H-quinolin-3-yl)-2,2-difluoroacetamide (79.5 mg, 65.05%). LCMS (ES, m/z): 430.10 $[M+H]^+$ $^1$H NMR (400 MHz, DMSO-d6) δ 12.67 (s, 1H), 9.27 (d, J=7.2 Hz, 1H), 8.90 (s, 1H), 8.41 (d, J=1.6 Hz, 1H), 8.11 (s, 1H), 7.83 (t, J=9.2 Hz, 1H), 7.72-7.68 (m, 1H), 5.35-5.28 (m, 1H), 1.49 (d, J=6.8 Hz, 3H).

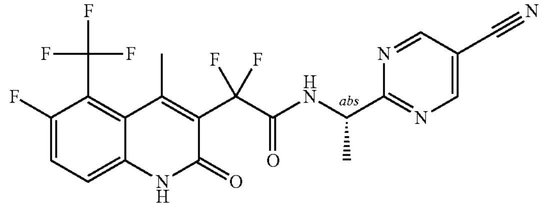

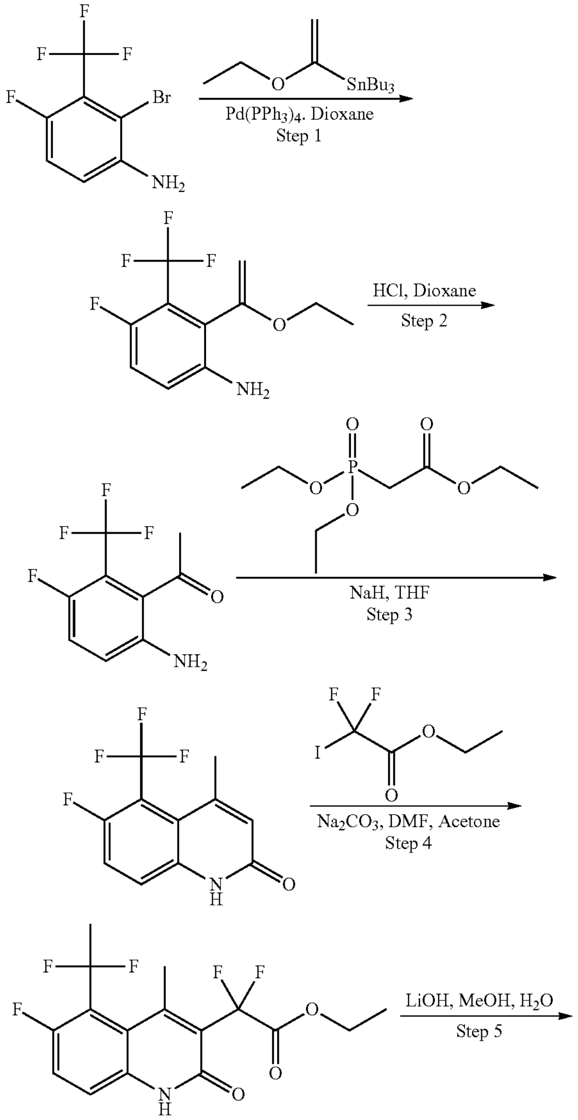

-continued

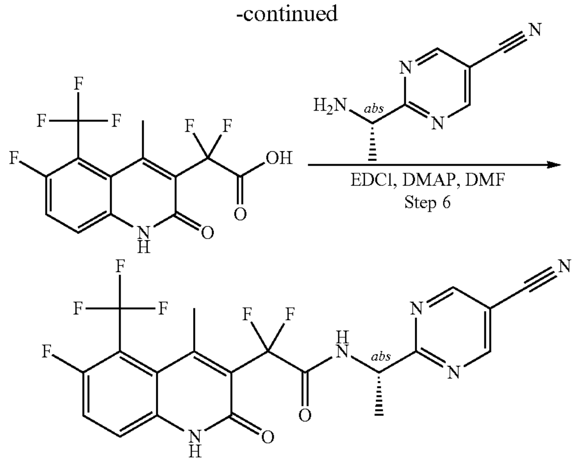

2-(1-ethoxyethenyl)-4-fluoro-3-(trifluoromethyl) aniline: To a stirred solution of 2-bromo-4-fluoro-3-(trifluoromethyl) aniline (2.5 g, 9.689 mmol, 1 equiv) and tributyl (1-ethoxyethenyl)stannane (7.00 g, 19.378 mmol, 2 equiv) in 1,4-dioxane-2-carbaldehyde (40 mL) was added $Pd(PPh_3)_4$ (2.24 g, 1.938 mmol, 0.2 equiv) at RT. The resulting mixture was stirred at 100° C. overnight under argon. The reaction was poured into water at RT and extracted with EA. The crude material was concentrated under reduced pressure and purified by column chromatography, eluting with PE/EA to afford 2-(1-ethoxyethenyl)-4-fluoro-3-(trifluoromethyl) aniline (2.5 g). LCMS (ES, m/z): 250 $[M+H]^+$.

1-[6-amino-3-fluoro-2-(trifluoromethyl)phenyl]ethanone: A solution of 2-(1-ethoxyethenyl)-4-fluoro-3-(trifluoromethyl) aniline (2.5 g, 10.032 mmol, 1 equiv) and HCl (6M) (10 mL) in dioxane (10 mL) was stirred at RT overnight. The reaction was poured into water and extracted with EA. The resulting solution was concentrated under reduced pressure and purified by column chromatography to afford 1-[6-amino-3-fluoro-2-(trifluoromethyl)phenyl]ethanone (1.5 g, 67.61%). LCMS (ES, m/z): 222 $[M+H]^+$.

6-fluoro-4-methyl-5-(trifluoromethyl)-1H-quinolin-2-one: A solution of triethyl phosphonoacetate (6.08 g, 27.132 mmol, 4 equiv) in THE (20 mL) was treated with sodium hydride (0.65 g, 27.132 mmol, 4 equiv) at RT for 30 min under nitrogen followed by the addition of 1-[6-amino-3-fluoro-2-(trifluoromethyl)phenyl]ethanone (1.5 g, 6.783 mmol, 1 equiv). The resulting solution was stirred at 80° C. overnight. The reaction was poured into water and extracted with EA. The crude was concentrated under reduced pressure and purified by column chromatography to afford 6-fluoro-4-methyl-5-(trifluoromethyl)-1H-quinolin-2-one (1.4 g). LCMS (ES, m/z): 246 $[M+H]^+$.

Ethyl 2,2-difluoro-2-[6-fluoro-4-methyl-2-oxo-5-(trifluoromethyl)-1H-quinolin-3-yl]acetate: To a stirred solution of 6-fluoro-4-methyl-5-(trifluoromethyl)-1H-quinolin-2-one (500 mg, 2.039 mmol, 1 equiv) and ethyl 2,2-difluoro-2-iodoacetate (1529.40 mg, 6.117 mmol, 3 equiv) in DMF/Acetone (v:v=1:1.20 mL) was added $Na_2CO_3$ (432.29 mg, 4.078 mmol, 2 equiv) at RT. The resulting mixture was stirred at RT overnight. The reaction was poured into water and extracted with EA. The crude was concentrated under reduced pressure and purified by column chromatography, eluting with PE/EA to afford ethyl 2,2-difluoro-2-[6-fluoro-4-methyl-2-oxo-5-(trifluoromethyl)-1H-quinolin-3-yl]acetate (310 mg). LCMS (ES, m/z): 368 $[M+H]^+$.

Difluoro[6-fluoro-4-methyl-2-oxo-5-(trifluoromethyl)-1H-quinolin-3-yl]acetic acid: A solution of ethyl 2,2-difluoro-2-[6-fluoro-4-methyl-2-oxo-5-(trifluoromethyl)-1H-quinolin-3-yl]acetate (300 mg, 0.817 mmol, 1 equiv) and LiOH (58.69 mg, 2.451 mmol, 3 equiv) in MeOH (2.5 mL) was stirred at RT for 2 h. The residue was adjusted to pH 4 with HCl (aq.) and concentrated under reduced pressure to afford difluoro[6-fluoro-4-methyl-2-oxo-5-(trifluoromethyl)-1H-quinolin-3-yl]acetic acid (400 mg, 86.62%). LCMS (ES, m/z): 340 $[M+H]^+$.

N-[(1S)-1-(5-cyanopyrimidin-2-yl)ethyl]-2,2-difluoro-2-[6-fluoro-4-methyl-2-oxo-5-(trifluoromethyl)-1H-quinolin-3-yl]acetamide (Compound 2514): To a stirred solution of difluoro[6-fluoro-4-methyl-2-oxo-5-(trifluoromethyl)-1H-quinolin-3-yl]acetic acid (100 mg, 0.295 mmol, 1 equiv) and 2-[(1S)-1-aminoethyl]pyrimidine-5-carbonitrile (52.42 mg, 0.354 mmol, 1.2 equiv) in DMF (3 mL) was added EDCI (54.92 mg, 0.354 mmol, 1.2 equiv) and DMAP (14.41 mg, 0.118 mmol, 0.4 equiv) at RT. The resulting solution was stirred overnight at RT. The residue was purified by reverse phase with a C18 column eluting with MeCN/Water (10 mmol/L $NH_4HCO_3$) to afford N-[(1S)-1-(5-cyanopyrimidin-2-yl)ethyl]-2,2-difluoro-2-[6-fluoro-4-methyl-2-oxo-5-(trifluoromethyl)-1H-quinolin-3-yl]acetamide (69.7 mg, 50.22%). L CMS (ES, m/z): 470.10 $[M-H]^+$.

$^1H$ NMR (300 MHz, DMSO-$d_6$) δ 12.35 (s, 1H), 9.32 (s, 2H), 9.00 (d, J=7.5 Hz, 1H), 7.77-7.70 (m, 1H), 7.66-7.61 (m, 1H), 5.17-5.07 (m, 1H), 2.55-2.50 (m, 3H), 1.54 (d, J=7.2 Hz, 3H).

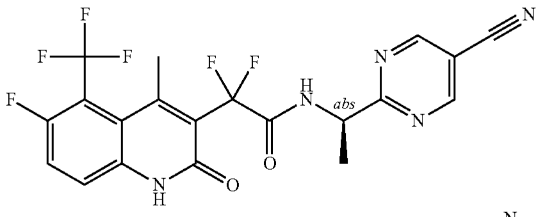

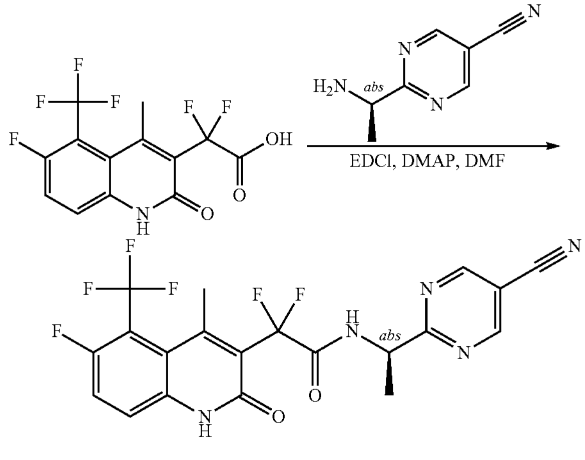

N-[(1R)-1-(5-cyanopyrimidin-2-yl)ethyl]-2,2-difluoro-2-[6-fluoro-4-methyl-2-oxo-5-(trifluoromethyl)-1H-quinolin-3-yl]acetamide (Compound 2513): To a stirred solution of difluoro[6-fluoro-4-methyl-2-oxo-5-(trifluoromethyl)-1H-quinolin-3-yl]acetic acid (100 mg, 0.295 mmol, 1 equiv) and 2-[(1R)-1-aminoethyl]pyrimidine-5-carbonitrile (52.42 mg, 0.354 mmol, 1.2 equiv) in DMF (3 mL) was added EDCI (54.92 mg, 0.354 mmol, 1.2 equiv) and DMAP (14.41 mg, 0.118 mmol, 0.4 equiv) at RT. The resulting mixture was stirred overnight at RT. The residue was purified by reverse phase with the following conditions (column, C18 column eluting with MeCN/Water (10 mmol/L $NH_4HCO_3$) to afford N-[(1R)-1-(5-cyanopyrimidin-2-yl)ethyl]-2,2-difluoro-2-[6-fluoro-4-methyl-2-oxo-5-(trifluoromethyl)-1H-quinolin-3-yl]acetamide (42.1 mg, 29.57%). LCMS (ES, m/z): 470.10 $[M-H]^+$.

$^1H$ NMR (300 MHz, DMSO-$d_6$) δ 12.34 (s, 1H), 9.31 (s, 2H), 8.99 (d, J=7.5 Hz, 1H), 7.76-7.70 (m, 1H), 7.66-7.61 (m, 1H), 5.14-5.09 (m, 1H), 2.54-2.50 (m, 3H), 1.54 (d, J=7.2 Hz, 3H).

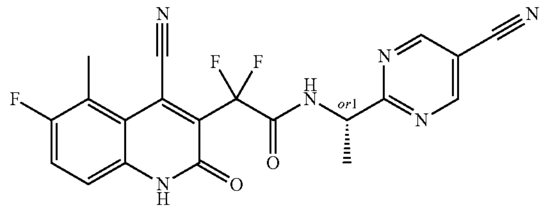

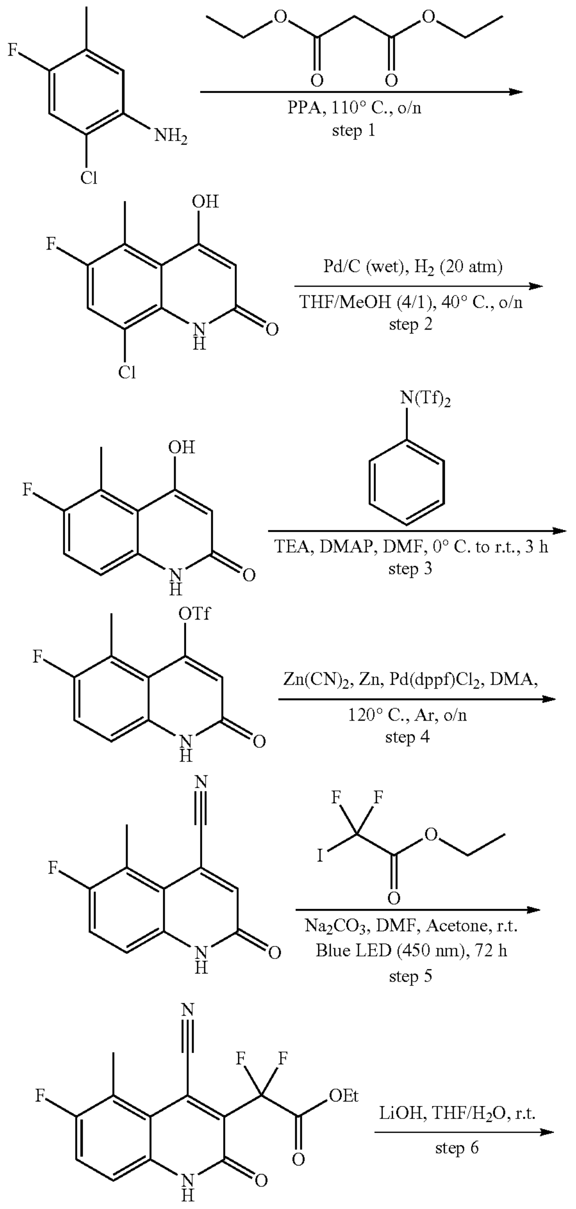

-continued

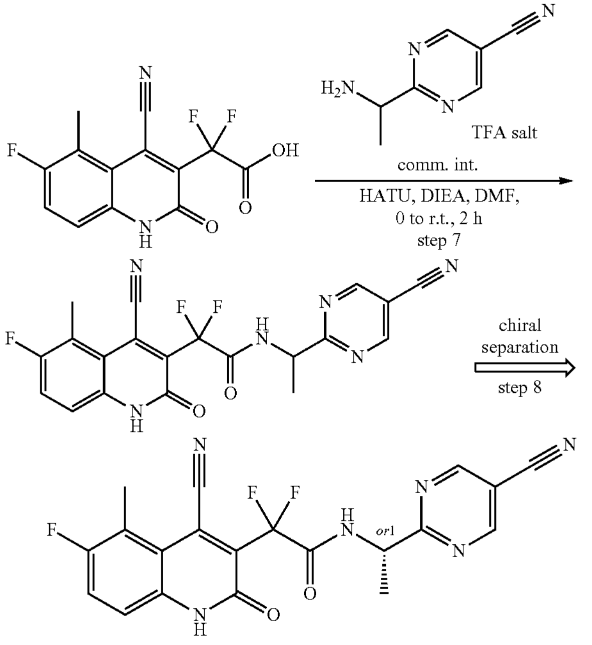

assumed 8-chloro-6-fluoro-4-hydroxy-5-methylquinolin-2(1H)-one: To a stirred solution of 2-chloro-4-fluoro-5-methylaniline (15.0 g, 94.0 mmol, 1.00 equiv) in PPA (30 mL) was added diethyl malonate (22.6 g, 141.0 mmol, 1.50 equiv) dropwise at RT under nitrogen. The resulting mixture was stirred overnight at 110° C. under nitrogen. The reaction was neutralized to about pH 7 with saturated $Na_2CO_3$(aq.) and extracted with EA. The combined organic layers were washed with brine, dried over anhydrous $Na_2SO_4$, filtered and the filtrate was concentrated under reduced pressure. The residue was purified by trituration with MeCN to afford 8-chloro-6-fluoro-4-hydroxy-5-methylquinolin-2(1H)-one (6.00 g, 28.04%). LCMS (ES, m/z): $228[M+H]^+$ 6-fluoro-4-hydroxy-5-methylquinolin-2(1H)-one: To a solution of 8-chloro-6-fluoro-4-hydroxy-5-methylquinolin-2(1H)-one (6.00 g, 26.4 mmol, 1.00 equiv) in 60 mL MeOH was added Pd/C (10%, 1.00 g) under nitrogen in a 250 mL round-bottom flask. The solution was hydrogenated at RT overnight under hydrogen using a hydrogen balloon, filtered through celite and concentrated under reduced pressure. The crude reaction was filtered, the filter cake was washed with MeOH. The filtrate was concentrated under reduced pressure and purified by column chromatography, eluting with PE/EA to afford 6-fluoro-4-hydroxy-5-methylquinolin-2(1H)-one (4.00 g, 78.55%). LCMS (ES, m/z): $194[M+H]^+$ 6-fluoro-5-methyl-2-oxo-1,2-dihydroquinolin-4-yl trifluoromethanesulfonate: To a stirred solution of 6-fluoro-4-hydroxy-5-methylquinolin-2(1H)-one (4.00 g, 20.7 mmol, 1.00 equiv) and TEA (4.19 g, 41.4 mmol, 2.00 equiv) and DMAP (0.25 g, 2.07 mmol, 0.10 equiv) in DCM (40 mL) was added 1,1,1-trifluoro-N-phenyl-N-((trifluoromethyl)sulfonyl)methanesulfonamide (11.10 g, 31.1 mmol, 1.50 equiv) dropwise at 0° C. under nitrogen. The resulting solution was stirred for 3 h at RT under nitrogen. The reaction was quenched by the addition of water at RT. The crude reaction was extracted with EA. The combined organic layers were washed with brine, dried over anhydrous $Na_2SO_4$, filtered and the filtrate was concentrated under reduced pressure. The residue was purified by trituration with MeCN to afford 6-fluoro-5-methyl-2-oxo-1,2-dihydroquinolin-4-yl trifluoromethanesulfonate (2.00 g, 29.70%). LCMS (ES, m/z): $326[M+H]^+$ 6-fluoro-5-methyl-2-oxo-1,2-dihydroquinoline-4-carbonitrile: To a stirred solution of 6-fluoro-5-methyl-2-oxo-1,2-dihydroquinolin-4-yl trifluoromethanesulfonate (2.00 g, 6.15 mmol, 1.00 equiv) and $Zn(CN)_2$ (1.44 g, 12.3 mmol, 2.00 equiv) and zinc powder (0.16 g, 2.46 mmol, 0.40 equiv) in DMAc (20 mL) was added $Pd(dppf)Cl_2$ (0.90 g, 1.23 mmol, 0.20 equiv) dropwise at RT under nitrogen. The resulting mixture was stirred for 2 h at 120° C. under nitrogen. The reaction was quenched by the addition of sat. sodium hyposulfite (aq.) (300 mL) at RT and extracted with EA. The combined organic layers were washed with brine, dried over anhydrous $Na_2SO_4$, filtered and the filtrate was concentrated under reduced pressure. The residue was purified by column chromatography, eluting with PE/EA to afford 6-fluoro-5-methyl-2-oxo-1,2-dihydroquinoline-4-carbonitrile (400 mg, 32.17%). LCMS (ES, m/z): $203[M+H]^+$ Ethyl 2-(4-cyano-6-fluoro-5-methyl-2-oxo-1,2-dihydroquinolin-3-yl)-2,2-difluoroacetate: To a stirred solution of 6-fluoro-5-methyl-2-oxo-1,2-dihydroquinoline-4-carbonitrile (400 mg, 1.98 mmol, 1.00 equiv) and ethyl 2,2-difluoro-2-iodoacetate (1.48 g, 5.93 mmol, 3.00 equiv) in acetone (2 mL) and DMF (2 mL) was added $Na_2CO_3$ (419.0 mg, 3.96 mmol, 2.00 equiv) dropwise at RT under nitrogen. The resulting mixture was stirred for 2 days at RT under nitrogen with blue LEDs. The reaction was quenched by the addition of water at RT. The resulting solution was extracted with EA. The combined organic layers were washed with brine, dried over anhydrous $Na_2SO_4$, filtered, and the filtrate was concentrated under reduced pressure. The residue was purified by column chromatography, eluting with PE/EA to afford ethyl 2-(4-cyano-6-fluoro-5-methyl-2-oxo-1,2-dihydroquinolin-3-yl)-2,2-difluoroacetate (200 mg, 31.18%). LCMS (ES, m/z): $325[M+H]^+$ 2-(4-cyano-6-fluoro-5-methyl-2-oxo-1,2-dihydroquinolin-3-yl)-2,2-difluoroacetic acid: To a stirred solution of ethyl 2-(4-cyano-6-fluoro-5-methyl-2-oxo-1,2-dihydroquinolin-3-yl)-2,2-difluoroacetate (100 mg, 0.31 mmol, 1.00 equiv) in THF (0.8 mL) and $H_2O$ (0.2 mL) was added $LiOH{\cdot}H_2O$ (51.8 mg, 1.23 mmol, 4.00 equiv) dropwise at RT under nitrogen. The resulting mixture was stirred for 4 h at RT under nitrogen. The solution was adjusted to pH 5 with 1M HCl (aq.) and extracted with EA. The combined organic layers were washed with brine, dried over anhydrous $Na_2SO_4$, filtered, and the filtrate was concentrated under reduced pressure. The crude product was purified by reverse chromatography with a 330 g C18 spherical 25-35 um column eluting with water (0.1% FA) and ACN to afford 2-(4-cyano-6-fluoro-5-methyl-2-oxo-1,2-dihydroquinolin-3-yl)-2,2-difluoroacetic acid (60 mg, 65.68%). LCMS (ES, m/z): $297[M+H]^+$ 2-(4-cyano-6-fluoro-5-methyl-2-oxo-1,2-dihydroquinolin-3-yl)-N-(1-(5-cyanopyrimidin-2-yl)ethyl)-2,2-difluoroacetamide: To a stirred solution of 2-(4-cyano-6-fluoro-5-methyl-2-oxo-1,2-dihydroquinolin-3-yl)-2,2-difluoroacetic acid (70 mg, 0.236 mmol, 1.00 equiv) and 2-(1-aminoethyl)pyrimidine-5-carbonitrile (35.02 mg, 0.236 mmol, 1.00 equiv) and HATU (107.8 mg, 0.283 mmol, 1.20 equiv) in DMF (1 mL) was added DIEA (91.6 mg, 0.71 mmol, 3.00 equiv) dropwise at RT under nitrogen. The resulting mixture was stirred for 4 h at RT under nitrogen. The reaction was quenched by the addition of water at RT and extracted with EA. The combined organic layers were washed with brine, dried over anhydrous $Na_2SO_4$, filtered and the filtrate was concentrated under reduced pressure. The residue was purified by Prep-TLC (PE/EA) to afford 2-(4-cyano-6-fluoro-5-methyl-2-oxo-1,2-dihydroquinolin-3-yl)-N-(1-(5-cyanopyrimidin-2-yl)ethyl)-2,2-difluoroacetamide (60 mg, 59.55%). LCMS (ES, m/z): 427[M+H]+

(S)-2-(4-cyano-6-fluoro-5-methyl-2-oxo-1,2-dihydroquinolin-3-yl)-N-(1-(5-cyanopyrimidin-2-yl)ethyl)-2,2-difluoroacetamide (assumed): The crude product (60 mg) was purified by Prep-HPLC with a CHIRAL ART Cellulose-SC, 3*25 cm, 5, μm column eluting with C02 and MeOH(20 mM NH3·M) to afford (S)-2-(4-cyano-6-fluoro-5-methyl-2-oxo-1,2-dihydroquinolin-3-yl)-N-(1-(5-cyanopyrimidin-2-yl)ethyl)-2,2-difluoroacetamide (assumed) (15 mg, 25.00%). LCMS (ES, m/z): 427.1[M+H]+

$^1$H NMR (400 MHz, DMSO-$d_6$) δ 12.82 (s, 1H), 9.31 (s, 2H), 9.26 (d, J=7.2 Hz, 1H), 7.65 (t, J=9.2 Hz, 1H), 7.35-7.32 (m, 1H), 5.14-5.09 (m, 1H), 2.76 (d, J=2.0 Hz, 3H), 1.52 (d, J=7.2 Hz, 3H). $^{19}$F NMR (377 MHz, DMSO-$d_6$) δ −101.07 (2F), −118.62 (1F).

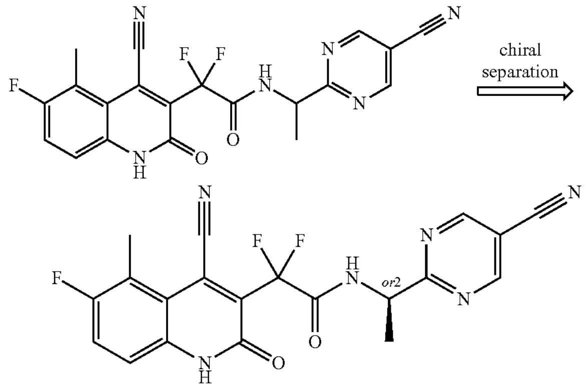

assumed

The racemic product (60 mg) was purified by Prep-HPLC with a CHIRAL ART Cellulose-SC, 3*25 cm, 5 m column eluting with C02 and MeOH(20 mM NH3·M) to afford (R)-2-(4-cyano-6-fluoro-5-methyl-2-oxo-1,2-dihydroquinolin-3-yl)-N-(1-(5-cyanopyrimidin-2-yl)ethyl)-2,2-difluoroacetamide (Compound 2511) (16.2 mg, 27.00%). LCMS (ES, m/z): 427.1[M+H]±$^1$H NMR (400 MHz, DMSO-$d_6$) δ 12.81 (s, 1H), 9.32 (s, 2H), 9.30 (t, J=5.6 Hz, 1H), 7.63 (t, J=9.2 Hz, 1H), 7.34-7.31 (m, 1H), 5.14-5.07 (m, 11H), 2.75 (d, J=2.0 Hz, 3H), 1.52 (d, J=7.2 Hz, 3H). $^{19}$F NMR (377 MHz, DMSO-$d_6$) δ −101.00 (2F), −118.83 (1F).

NUMBERED EMBODIMENTS

Some numbered examples of embodiments follow.

(1): A compound represented by Formula (I'):

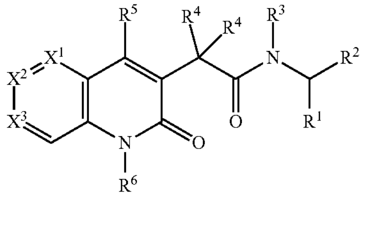

(I'); or a salt thereof, wherein: $X^1$, $X^2$, and $X^3$ are independently selected from C(R) and N wherein at least one of $X^1$, $X^2$, and $X^3$ is N and no more than two of $X^1$, $X^2$, and $X^3$ are N; each R is independently selected from: hydrogen, halogen, —$NO_2$, —CN, —$N_3$, —$OR^8$, —$SR^8$, —$N(R^8)_2$, —$C(O)R^8$, —$C(O)N(R^8)_2$, —$N(R^8)C(O)R^8$, —$N(R^8)C(O)N(R^8)_2$, —$OC(O)N(R^8)_2$, —$N(R^8)C(O)OR^8$, —$C(O)OR^8$, —$OC(O)R^8$, —$S(O)R^8$, and —$S(O)_2R^8$; $C_{1-6}$ alkyl, $C_{2-6}$ alkenyl, and $C_{2-6}$ alkynyl, each of which is optionally substituted with one or more substituents independently selected from halogen, —$OR^8$, —$SR^8$, —$N(R^8)_2$, —$C(O)R^8$, —$C(O)N(R^8)_2$, —$N(R^8)C(O)R^8$, —$C(O)OR^8$, —$OC(O)R^8$, —$N(R^8)C(O)N(R^8)_2$, —$OC(O)N(R^8)_2$, —$N(R^8)C(O)OR^8$, —$S(O)R^8$, —$S(O)_2R^8$, —$NO_2$, =O, =S, =$N(R^8)$, —CN, $C_{3-10}$ carbocycle and 3- to 10-membered heterocycle, wherein the $C_{3-10}$ carbocycle and 3- to 10-membered heterocycle are each optionally substituted with one or more $R^7$; and $C_{3-10}$ carbocycle and 3- to 10-membered heterocycle, each of which is optionally substituted with one or more substituents independently selected from halogen, —$OR^8$, —$SR^8$, —$N(R^8)_2$, —C(O)R, —$C(O)N(R^8)_2$, —$N(R^8)C(O)R^8$, —$N(R^8)C(O)N(R^8)_2$, —$OC(O)N(R^8)_2$, —$N(R^8)C(O)OR^8$, —$C(O)OR^8$, —$OC(O)R^8$, —$S(O)R^8$, —$S(O)_2R^8$, —$NO_2$, =O—, =S, =$N(R^8)$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^7$; $R^1$ is selected from: hydrogen; $C_{1-6}$ alkyl, $C_{2-6}$ alkenyl, and $C_{2-6}$ alkynyl, each of which is optionally substituted with one or more substituents independently selected from halogen, —$OR^{8a}$, —$SR^{8a}$, —$N(R^{8a})_2$, —$C(O)R^{8a}$, —$C(O)N(R^{8a})_2$, —$N(R^{8a})C(O)R^{8a}$, —$C(O)OR^{8a}$, —$OC(O)R^{8a}$, —$N(R^{8a})C(O)N(R^{8a})_2$, —$OC(O)N(R^{8a})_2$, —$N(R^{8a})C(O)OR^{8a}$, —$S(O)R^{8a}$, —$S(O)_2R^{8a}$, —$NO_2$, =O, =S, =$N(R^{8a})$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{7a}$; and $C_{3-10}$ carbocycle, and 3- to 10-membered heterocycle, each of which is optionally substituted with one or more substituents independently selected from halogen, —$OR^{8a}$, —$SR^{8a}$, —$N(R^{8a})_2$, —$C(O)R^{8a}$, —$C(O)N(R^{8a})_2$, —$N(R^{8a})C(O)R^{8a}$, —$N(R^{8a})C(O)N(R^{8a})_2$, —$OC(O)N(R^{8a})_2$, —$N(R^{8a})C(O)OR^{8a}$, —$C(O)OR^{8a}$, —$OC(O)R^{8a}$, —$S(O)R^{8a}$, —$S(O)_2R^{8a}$, —$NO_2$, =O—, =S, =$N(R^{8a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7a}$; or $R^1$ together with $R^2$ form a $C_{3-10}$ carbocycle, or 3- to 10-membered heterocycle, each of which is optionally substituted with one or more substituents independently selected from halogen, —$OR^{8a}$, —$SR^{8a}$, —$N(R^{8a})_2$, —$C(O)R^{8a}$, —$C(O)N(R^{8a})_2$, —$N(R^{8a})C(O)R^{8a}$, —$N(R^{8a})C(O)N(R^{8a})_2$, —$OC(O)N(R^{8a})_2$, —$N(R^{8a})C(O)OR^{8a}$, —$C(O)OR^{8a}$, —$OC(O)R^{8a}$, —$S(O)R^{8a}$, —$S(O)_2R^{8a}$, —$NO_2$, =O—, =S, =$N(R^{8a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$; $R^2$ is selected from: hydrogen; $C_{1-6}$ alkyl, $C_{2-6}$ alkenyl, and $C_{2-6}$ alkynyl, each of which is optionally substituted with one or more substituents independently selected from halogen, —$OR^{8b}$, —$SR^{8b}$, —$N(R^{8b})_2$, —$C(O)R^{8b}$, —$C(O)N(R^{8b})_2$, —$N(R^{8b})C(O)R^{8b}$, —$C(O)OR^{8b}$, —$OC(O)R^{8b}$, $N(R^{8b})C(O)N(R^{8b})_2$, —$OC(O)N(R^{8b})_2$, —$N(R^{8b})C(O)OR^{8b}$, —$S(O)R^{8b}$, —$S(O)_2R^{8b}$, —$NO_2$, =O, =S, =$N(R^{8b})$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{7b}$; and $C_{3-10}$ carbocycle, and 3- to 10-membered heterocycle, each of which is optionally substituted with one or more substituents independently selected from halogen, —$OR^{8b}$, —$SR^{8b}$, —$N(R^{8b})_2$, —C(O)

$R^{8b}$, —C(O)N($R^{8b}$)$_2$, —N($R^{8b}$)C(O)$R^{8b}$, —N($R^{8b}$)C(O)N($R^{8b}$)$_2$, —OC(O)N($R^{8b}$)$_2$, —N($R^{8b}$)C(O)O$R^{8b}$, —C(O)O$R^{8b}$, —OC(O)$R^{8b}$, —S(O)$R^{Bb}$, —S(O)$_2R^{8b}$, —NO$_2$, =O—, =S, =N($R^{8b}$), —CN, —N$_3$, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$; or $R^1$ together with $R^2$ form a $C_{3-10}$ carbocycle, or 3- to 10-membered heterocycle, each of which is optionally substituted with one or more substituents independently selected from halogen, —O$R^{8a}$, —S$R^{8a}$, —N($R^{8a}$)$_2$, —C(O)$R^{8a}$, —C(O)N($R^{8a}$)$_2$, —N($R^{8a}$)C(O)$R^{8a}$, —N($R^{8a}$)C(O)N($R^{8a}$)$_2$, —OC(O)N($R^{8a}$)$_2$, —N($R^{8a}$)C(O)O$R^{8a}$, —C(O)O$R^{8a}$, —OC(O)$R^{8a}$, —S(O)$R^{8a}$, —S(O)$_2R^{8a}$, —NO$_2$, =O—, =S, =N($R^{8a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$; $R^3$ is selected from: hydrogen, halogen, —O$R^{8c}$, —S$R^{8c}$, —N($R^{8c}$)$_2$, —NO$_2$, and —CN; and $C_{1-6}$ alkyl optionally substituted with one or more one or more $R^{7c}$; each $R^4$ is independently selected from: hydrogen, halogen, —O$R^{8d}$, —S$R^{8d}$, —N($R^{8d}$)$_2$, —NO$_2$, and —CN; and $C_{1-6}$ alkyl optionally substituted with one or more substituents independently selected from halogen, —O$R^{8d}$, —S$R^{8d}$, —N($R^{8d}$)$_2$, —NO$_2$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{7d}$; $R^5$ is selected from: hydrogen, halogen, —O$R^{8e}$, —S$R^{8e}$, —N($R^{8e}$)$_2$, —NO$_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more $R^{7e}$; $R^6$ is selected from: hydrogen, halogen, —O$R^{8f}$, —S$R^{8f}$, —N($R^{8f}$)$_2$, —NO$_2$, and —CN; and $C_{1-6}$ alkyl optionally substituted with one or more $R^{7f}$; each $R^7$ is independently selected from: halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; each $R^{7a}$ is independently selected from: halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; each $R^{7b}$ is independently selected from: halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; each $R^7$, is independently selected from: halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; each $R^{7d}$ is independently selected from: halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)OR's, —OC(O)$R^{8g}$, —S(O)$R^{8g}$, —S(O)$_2R^{8g}$, —NO$_2$, =O, =S, =N($R^{8g}$), and —CN; each $R^{7e}$ is independently selected from: halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; each $R^7$ is independently selected from: halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{8g}$, —S$R^{8g}$, —N($R^{8g}$)$_2$, —C(O)$R^{8g}$, —C(O)N($R^{8g}$)$_2$, —N($R^{8g}$)C(O)$R^{8g}$, —N($R^{8g}$)C(O)N($R^{8g}$)$_2$, —OC(O)N($R^{8g}$)$_2$, —N($R^{8g}$)C(O)O$R^{8g}$, —C(O)O$R^{8g}$, —OC(O)$R^{8g}$, —S(O)$R^{8g}$, —S(O)$_2R^{8g}$, —NO$_2$, =O, =S, =N($R^{8g}$), and —CN; each $R^8$ is independently selected from: hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —SO$_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{8a}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{8b}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{8c}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{8d}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{8e}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{8f}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; and each $R^{8g}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. (2): The compound or salt of embodiment 1, wherein $X^1$ is N. (3): The compound or salt of embodiment 1, wherein $X^1$ is C(R). (4): The compound or salt of any one of embodiments 1 to 3, wherein $X^2$ is N. (5): The compound or salt of any one of embodiments 1 to 3, wherein $X^2$ is C(R). (6): The compound or salt of any one of embodiments 1 to 5, wherein $X^3$ is N. (7): The compound or salt of any one of embodiments 1 to 5, wherein $X^3$ is C(R). (8): The compound or salt of any one of embodiments 1 to 1, wherein each R is independently selected from: hydrogen, halogen, —$NO_2$, —CN, —$N_3$, —$OR^8$, —$SR^8$, —N($R^8$)$_2$, —C(O)$R^8$, —C(O)N($R^8$)$_2$, —N($R^8$)C(O)$R^8$, and —N($R^8$)C(O)N($R^8$)$_2$; $C_{1-6}$ alkyl, $C_{2-6}$ alkenyl, and $C_{2-6}$ alkynyl, each of which is optionally substituted with one or more substituents independently selected from halogen, —$OR^8$, —$SR^8$, —N($R^8$)$_2$, —$NO_2$, =O, =S, =N($R^8$); and $C_{3-10}$ carbocycle and 3- to 10-membered heterocycle. (9): The compound or salt of embodiment 1, wherein each R is independently selected from: hydrogen, halogen, —CN, —$N_3$, —$OR^8$, —$SR^8$, —N($R^8$)$_2$; $C_{1-6}$ alkyl and $C_{2-6}$ alkynyl, each of which is optionally substituted with one or more substituents independently selected from halogen; and $C_{3-10}$ carbocycle and 3- to 10-membered heterocycle. (10): The compound or salt of embodiment 1, wherein each R is independently selected from: —H, —F, —Cl, —Br, —I, —CN, —$N_3$, —$OR^8$, —$SR^8$, —N($R^8$)$_2$, —$CF_3$, methyl, ethyl, cyclopropyl, —CCMe, —CCH, phenyl, N-morpholinyl, and N-pyrrolidinyl. (11): The compound or salt of embodiment 10, wherein each R is independently selected from: hydrogen, —F, —Cl, —Br, —I, —CN, —$N_3$, —$OR^8$, —N($R^8$)$_2$, —$CF_3$, methyl, ethyl, cyclopropyl, —CCMe, —CCH, phenyl, N-morpholinyl, and N-pyrrolidinyl. (12): The compound or salt of embodiment 11, wherein each R is independently selected from: hydrogen, —F, —Cl, —Br, —I, —CN, —$N_3$, —$OR^8$, —N($R^8$)$_2$, —$CF_3$, methyl, ethyl, cyclopropyl, —CCMe, —CCH, phenyl, N-morpholinyl, and N-pyrrolidinyl. (13): The compound or salt of embodiment 12, wherein each R is independently selected from: hydrogen, —F, —Cl, —Br, —I, —CN, —$N_3$, —OH, —OMe, —OEt, —O(n-Pr), —O(iPr), —O(i-Bu),

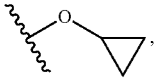, $OCF_3$,

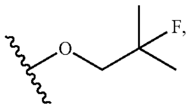, 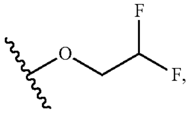,

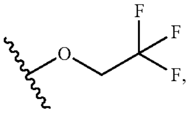,

—$NH_2$, —NH(Me), —NH(Et), —$N(Et)_2$, —NH(i-Bu), —NH(Ph), —NHBn,

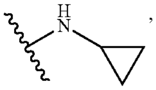, 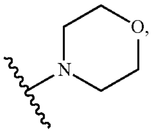, 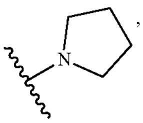,

—$CF_3$, -methyl, -ethyl, cyclopropyl, —CCMe, —CCH, phenyl, N-morpholinyl, and N-pyrrolidinyl. (14): The compound or salt of any one of embodiments 1 to 13, wherein each $R^8$ is independently selected from: hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —SH, —$NO_2$, —$NH_2$, $C_{3-10}$ carbocycle, 3- to 10-membered heterocycle; and $C_{3-10}$ carbocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —$N(C_{1-6}$ alkyl$)_2$, —$NH(C_{1-6}$ alkyl), $C_{1-6}$alkyl, $C_{2-6}$alkenyl, $C_{2-6}$ alkynyl, $C_{3-10}$ carbocycle, 3- to 10-membered heterocycle, and $C_{1-6}$ haloalkyl. (15): The compound or salt of embodiment 1, wherein each $R^8$ is independently selected from: hydrogen; and $C_{1-6}$ alkyl, and $C_{3-10}$ carbocycle, each of which is optionally substituted with one or more substituents independently selected from halogen, $C_{3-10}$ carbocycle; and $C_{3-10}$ carbocycle, each of which is optionally substituted with —OH. (16): The compound or salt of any one of embodiments 1 to 1 wherein each $R^8$ is independently selected from hydrogen, methyl, ethyl, propyl, isopropyl, cyclopropyl, isobutyl, —$CF_3$, —$CH_2CF_3$, —$CH_2CHF_2$, —$CH_2C(F)(Me)_2$, and —$CH_2$-phenyl. (17): The compound or salt of any one of embodiments 1 to 16, wherein two $R^8$ are taken together to form a $C_{3-10}$ carbocycle or 3- to 10-membered heterocycle. (18): The compound or salt of any one of embodiments 1 to 17, wherein two $R^8$ are taken together to form a $C_{3-10}$ carbocycle or 3- to 10-membered heterocycle selected from N-morpholino and N-pyrrolidinyl. (19): The compound or salt of any one of embodiments 1 to 18, wherein Rt is selected from: hydrogen; $C_{1-6}$ alkyl, $C_{2-6}$ alkenyl, and $C_{2-6}$ alkynyl, each of which is optionally substituted with one or more substituents independently selected from halogen, —$OR^{8a}$, —$SR^{8a}$, —$N(R^{8a})_2$, —$C(O)R^{8a}$, —$S(O)R^{8a}$, —$S(O)_2R^{8a}$, —$NO_2$, and —CN; and $C_{3-10}$ carbocycle, and 3- to 10-membered heterocycle, each of which is optionally substituted with one or more substituents independently selected from halogen, —$OR^{8a}$, —$SR^{8a}$, —$N(R^{8a})_2$, —$C(O)R^{8a}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7a}$, or $R^1$ together with $R^2$ form a $C_{3-10}$ carbocycle, or 3- to 10-membered heterocycle, each of which is optionally substituted with one or more substituents independently selected from halogen, —$OR^{8a}$, —$SR^{8a}$, —$N(R^{8a})_2$, —$C(O)R^{8a}$, —$S(O)R^{8a}$, —$S(O)_2R^{8a}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$. (20): The compound or salt of any one of embodiments 1 to 1, wherein $R^1$ is selected from: hydrogen; $C_{1-6}$ alkyl, $C_{2-6}$ alkenyl, and $C_{2-6}$ alkynyl, each of which is optionally substituted with one or more substituents independently selected from halogen, —$OR^{8a}$, —$SR^{8a}$, —$N(R^{8a})_2$, —$C(O)R^{8a}$, —$S(O)R^{8a}$, —$S(O)_2R^{8a}$, —$NO_2$, and —CN; and $C_{3-10}$ carbocycle, and 3- to 10-membered heterocycle, each of which is optionally substituted with one or more substituents independently selected from halogen, —$C(O)R^{8a}$, —CN, $C_{1-6}$ alkyl, or $R^1$ together with $R^2$ form a $C_{3-10}$ carbocycle, or 3- to 10-membered heterocycle, each of which is optionally substituted with one or more substituents independently selected from halogen, —$OR^{8a}$, —$SR^{8a}$, —$N(R^{8a})_2$, —$C(O)R^{8a}$, —$NO_2$, —CN, and $C_{1-6}$ alkyl, wherein $C_{1-6}$ alkyl is optionally substituted with one or more $R^{7b}$. (21): The compound or salt of any one of embodiments 1 to 1, wherein $R^1$ is hydrogen, methyl, —$CH_2OH$, —$CH_2CH_2OH$, $C(Me)_2OH$, —$CH_2OMe$, or $R^1$ together with $R^2$ form a $C_{3-10}$ carbocycle, or 3- to 10-membered heterocycle, each of which is optionally substituted with one or more substituents independently selected from —F, —COMe, —CN, and methyl. (22): The compound or salt of any one of embodiments 1 to 21, wherein $R^1$ is methyl, —$CH_2OH$, —$CH_2CH_2OH$, $C(Me)_2OH$, —$CH_2OMe$. (23): The compound or salt of any one of embodiments 1 to 22, wherein $R^1$ is methyl. (24): The compound or salt of any one of embodiments 1 to 23, wherein $R^2$ is selected from: hydrogen, $C_{1-6}$ alkyl, and $C_{2-6}$ alkenyl, each of which is optionally substituted with one or more substituents independently selected from halogen, —$OR^{8b}$, —$SR^{8b}$, —$N(R^{86})_2$, —$C(O)R^{8b}$, —$S(O)R^{8b}$, —$S(O)_2R^{8b}$, —$NO_2$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{7b}$; and $C_{3-10}$ carbocycle, and 3- to 10-membered heterocycle, each of which is optionally substituted with one or more substituents independently selected from halogen, —$OR^{8b}$, —$SR^{8b}$, —$N(R^{8b})_2$, —$C(O)R^{8b}$, —$S(O)R^{Bb}$, —$S(O)_2R^{8b}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$; or $R^1$ together with $R^2$ form a $C_{3-10}$ carbocycle, or 3- to 10-membered heterocycle, each of which is optionally substituted with one or more substituents independently selected from halogen, —$OR^{8a}$, —$SR^{8a}$, —$N(R^{8a})_2$, —$C(O)R^{8a}$, —$S(O)R^{8a}$, —$S(O)_2R^{8a}$, —$NO_2$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{7b}$. (25): The compound or salt of any one of embodiments 1 to 1, wherein $R^2$ is selected from: $C_{3-10}$ carbocycle and 3- to 10-membered heterocycle, each of which is optionally substituted with one or more substituents independently selected from halogen, —$OR^{8b}$, —$C(O)R^{8b}$, —$S(O)_2R^{8b}$, —CN, and $C_{1-6}$ alkyl, wherein $C_{1-6}$ alkyl is optionally substituted with one or more $R^{7b}$; or $R^1$ together with $R^2$ form a $C_{3-10}$ carbocycle, or 3- to 10-membered heterocycle, each of which is optionally substituted with one or more substituents independently selected from halogen, —$C(O)R^{8a}$, —CN, $N_3$, and $C_{1-6}$ alkyl, wherein $C_{1-6}$ alkyl is optionally substituted with one or more $R^{7b}$. (26): The compound or salt of any one of embodiments 1 to 25, wherein $R^2$ is selected from: $C_{3-10}$ carbocycle and 3- to 10-membered heterocycle, each of which is optionally substituted with one or more substituents independently selected from halogen, —$OR^{8b}$, —$S(O)_2R^{8b}$, —CN, and $C_{1-6}$ alkyl, wherein $C_{1-6}$ alkyl is optionally substituted with one or more $R^{7b}$; or $R^1$ together with $R^2$ form a $C_{3-10}$ carbocycle, or 3- to 10-membered heterocycle, each of which is optionally substituted with one or more substituents independently selected from halogen, —C(O) $R^{8a}$, —CN, $N_3$, and $C_{1-6}$ alkyl, wherein $C_{1-6}$ alkyl is optionally substituted with one or more $R^{7b}$. (27): The compound or salt of any one of embodiments 1 to 26, wherein $R^2$ is selected from phenyl, pyridinyl, pyrimadinyl, pyrazinyl, and pyridazinyl, each of which is optionally substituted with one or more substituents independently selected from —F, —OH, —OMe, —COMe, —$SO_2$Me, —CN, and methyl. (28): The compound or salt of any one of embodiments 1 to 27, wherein $R^2$ is selected from phenyl, pyridinyl, pyrimadinyl, pyrazinyl, and pyridazinyl, each of which is optionally substituted with one or more substituents independently selected from —F, —OH, —OMe, —$SO_2$Me, —CN, and methyl. (29): The compound or salt of any one of embodiments 1 to 28, wherein $R^2$ is selected from phenyl and pyridinyl, each of which is optionally substituted with one or more substituents independently selected from —F, —OH, —OMe, —$SO_2$Me, —CN, and methyl. (30): The compound or salt of any one of embodiments 1 to 29, wherein $R^2$ is selected from

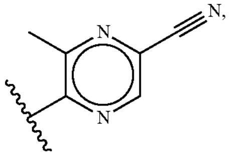
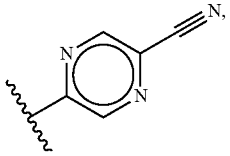

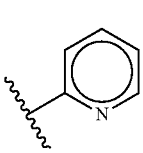,
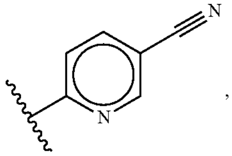,
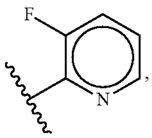,

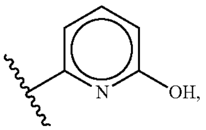
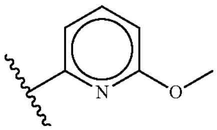,

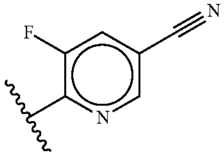,
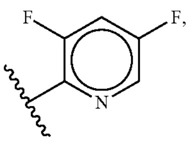

-continued

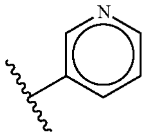,
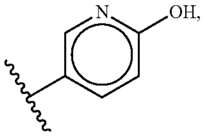
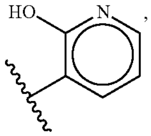,

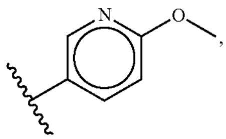,
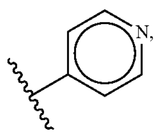
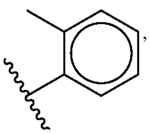

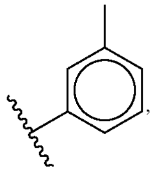,
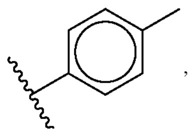,
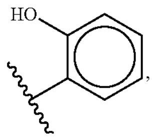,

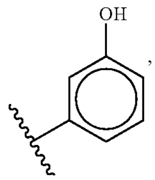,
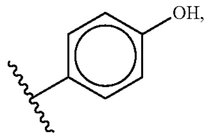
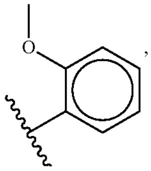,

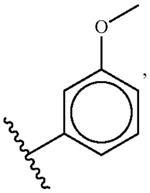,
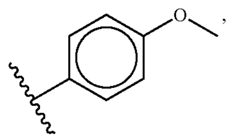,
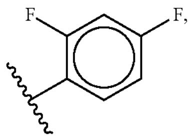

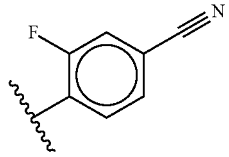,
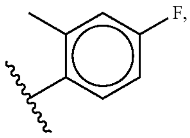

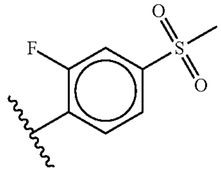,
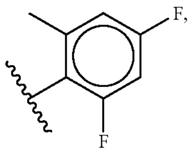

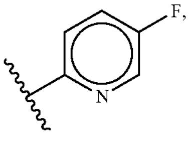
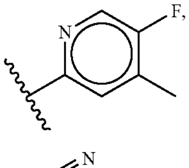
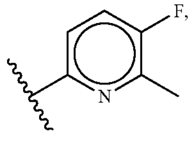

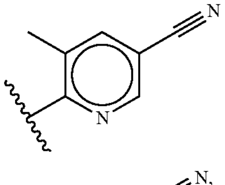,
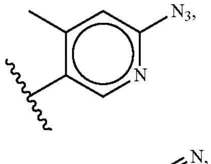

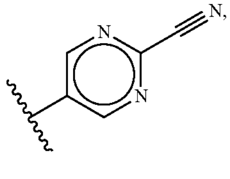
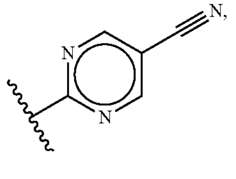

-continued

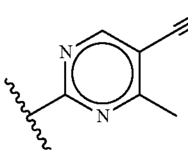

,

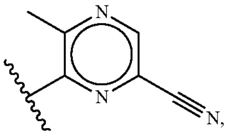

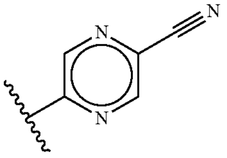

,

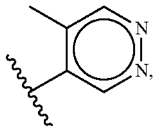

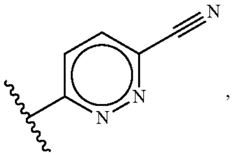

, and

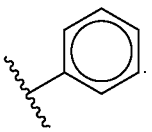

and (31): The compound or salt of any one of embodiments 1 to 23, wherein $R^1$ and $R^2$ are taken together to form a $C_{3-10}$ carbocycle or 3- to 10-membered heterocycle selected from

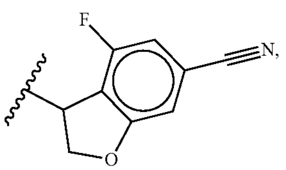

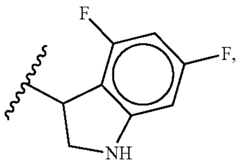

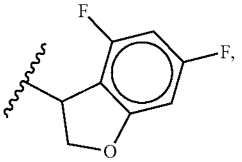

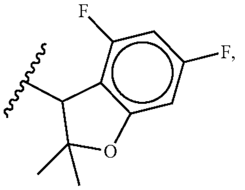

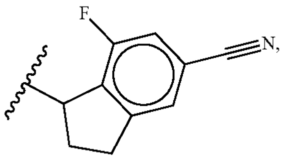

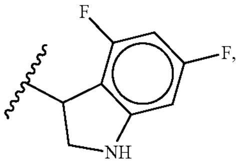

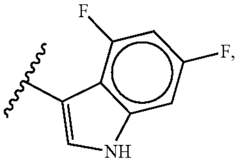

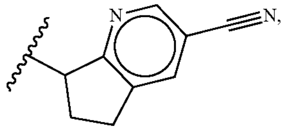

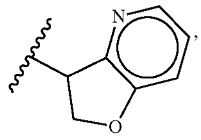

and

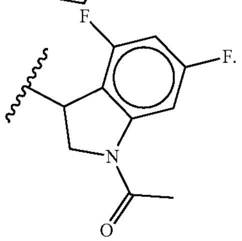

(32): The compound or salt of any one of embodiments 1 to 31, wherein $R^3$ is selected from hydrogen, halogen, —$OR^{8c}$, and $C_{1-6}$ alkyl optionally substituted with one or more one or more $R^{7c}$. (33): The compound or salt of embodiment 32, wherein $R^3$ is selected from hydrogen and $C_{1-6}$ alkyl. (34): The compound or salt of embodiment 1, wherein $R^3$ is hydrogen. (35): The compound or salt of any one of embodiments 1 to 16, wherein each $R^4$ is independently selected from: hydrogen, halogen, —$OR^{8d}$, and —CN; and $C_{1-6}$ alkyl optionally substituted with one or more substituents independently selected from halogen, —$OR^{8d}$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{7d}$. (36): The compound or salt of embodiment 17, wherein each $R^4$ is independently selected from hydrogen, halogen, —$OR^{8d}$, —$SR^{8d}$, —$N(R^{8d})_2$, —$NO_2$, and —CN; and $C_{1-6}$ alkyl optionally substituted with one or more substituents independently selected from $C_{3-10}$ carbocycle. (37): The compound or salt of embodiment 1, wherein each $R^4$ is independently selected from hydrogen, —F, and $C_1$ alkyl optionally substituted with phenyl. (38): The compound or salt of any one of embodiments 1 to 37, wherein each $R^4$ is independently selected from hydrogen. (39): The compound or salt of any one of embodiments 1 to 38, wherein $R^5$ is selected from: hydrogen, halogen, —$OR^{8c}$, —$N(R^{8c})_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more $R^{7e}$. (40): The compound or salt of any one of embodiments 1 to 23, wherein $R^5$ is selected from hydrogen, —Cl, —OH, —NHMe, —CN, $C_{1-2}$ alkyl, and cyclopropyl, wherein the $C_{1-2}$ alkyl and cyclopropyl are each optionally substituted with one or more —F. (41): The compound or salt of any one of embodiments 1 to 40, wherein $R^1$ is selected from hydrogen, $CH_3$, cyclopropyl, F Cl, CN, H, and $CF_3$. (42): The compound or salt of any one of embodiments 1 to 41, wherein $R^1$ is selected from hydrogen and $CH_3$. (43): The compound or salt of any one of embodiments 1 to 42, wherein $R^5$ is selected from $CH_3$. (44): The compound or salt of any one of embodiments 1 to 43, wherein $R^5$ is selected from H. (45): The compound or salt of any one of embodiments 1 to 44, wherein $R^6$ is selected from: hydrogen, halogen, —$OR^{8f}$; and $C_{1-6}$alkyl optionally substituted with one or more $R^{7f}$. (46): The compound or salt of any one of embodiments 1 to 1, wherein $R^6$ is selected from hydrogen and $C_{1-6}$ alkyl. (47): The compound or salt of any one of embodiments 1 to 1, wherein $R^6$ is hydrogen. (48): The compound or salt of any one of embodiments 1 to 26, selected from:

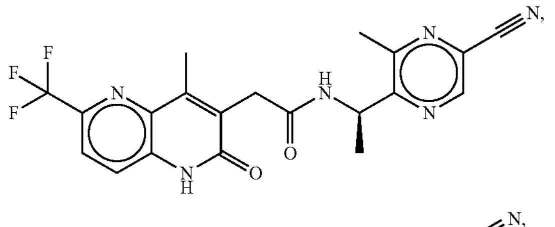

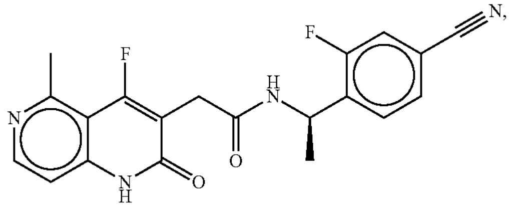

-continued
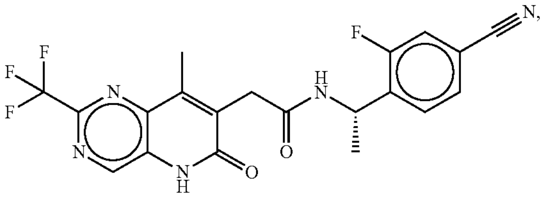
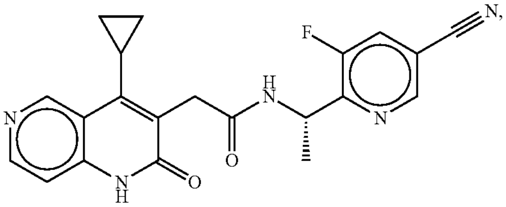
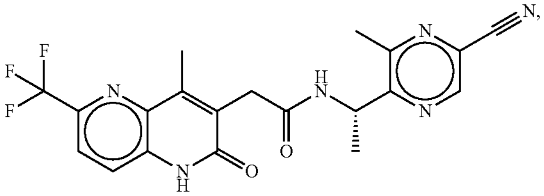
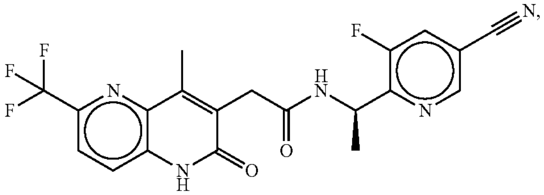
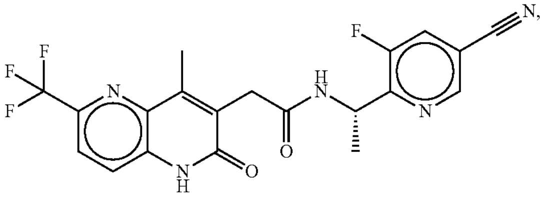
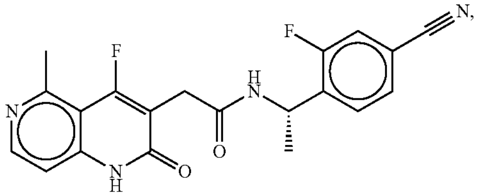
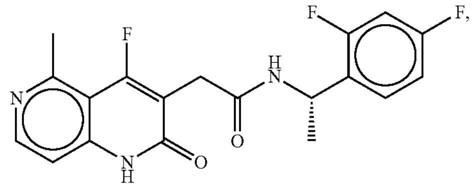
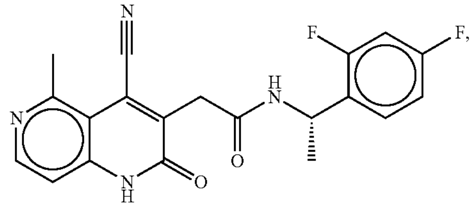
-continued
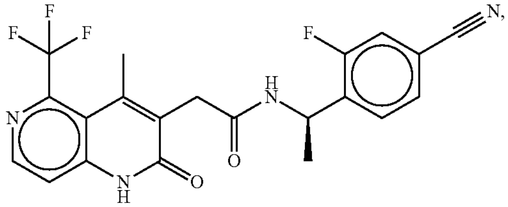
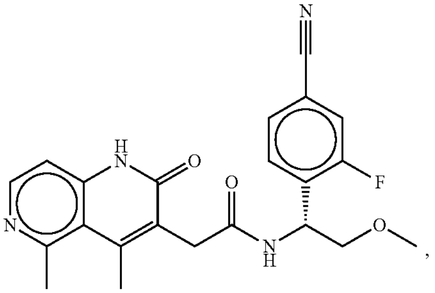
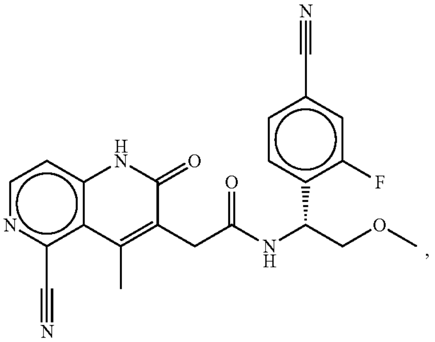
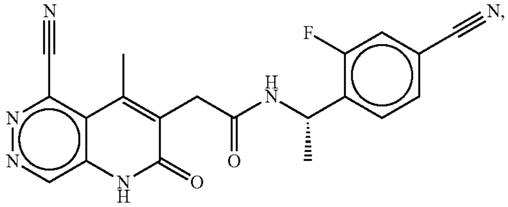
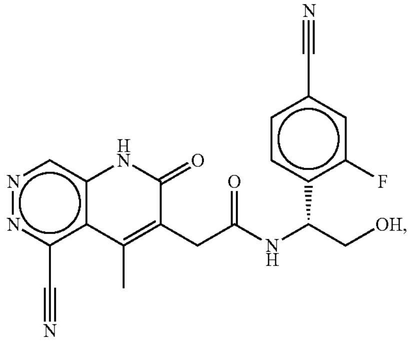

-continued
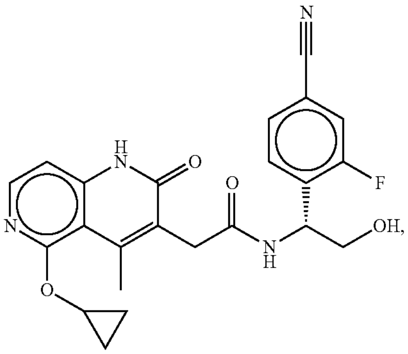
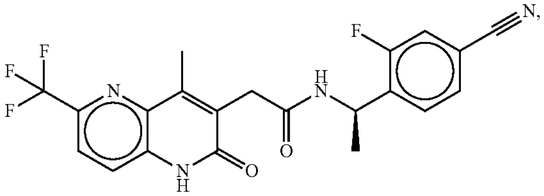
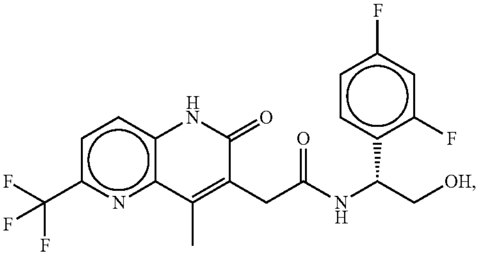
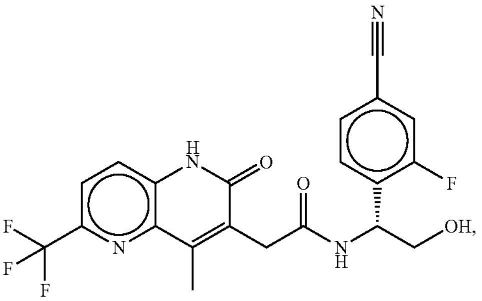
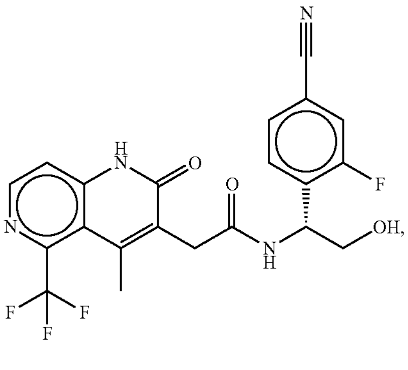
-continued
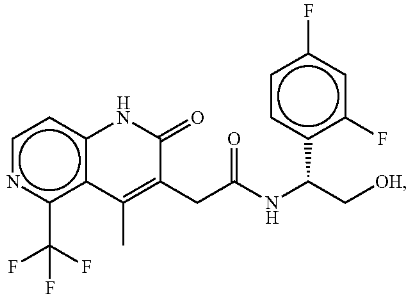
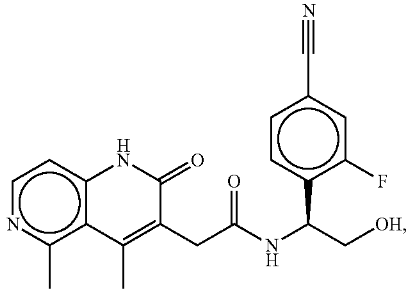
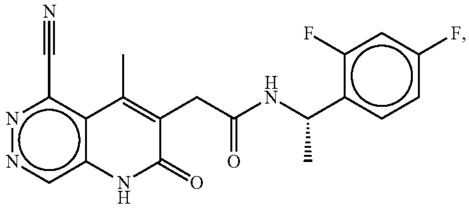
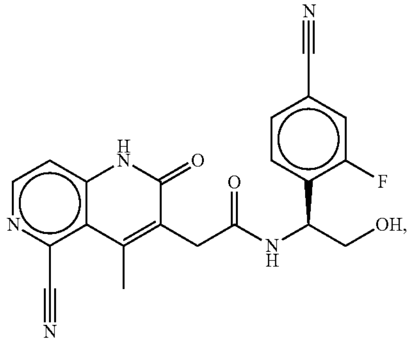
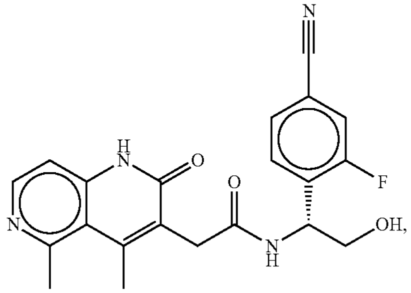
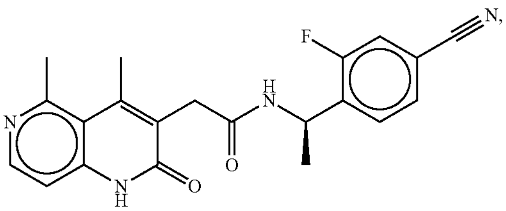

-continued
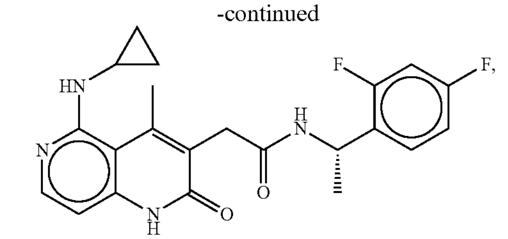
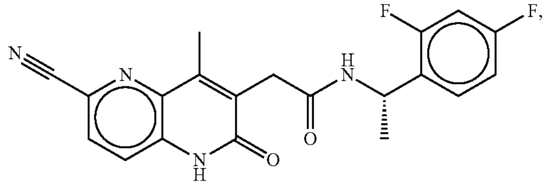
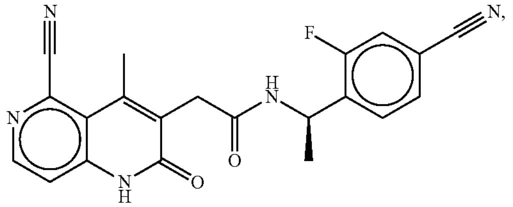
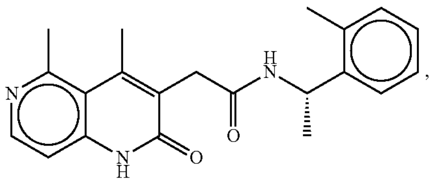
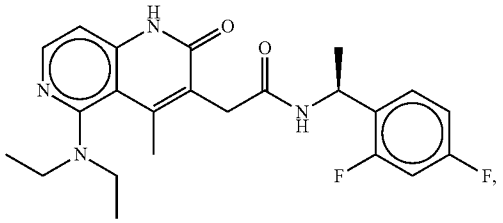
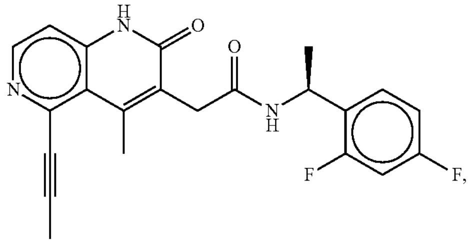
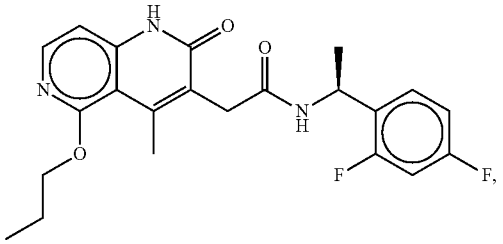
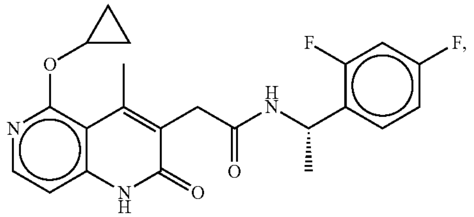
-continued
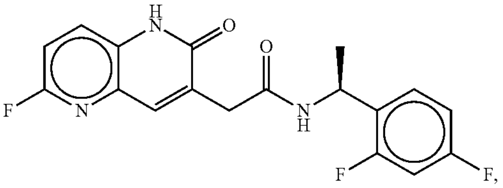
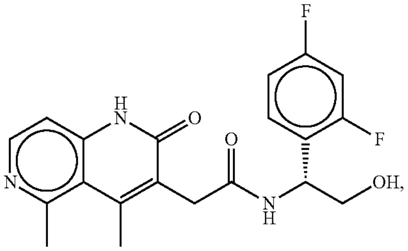
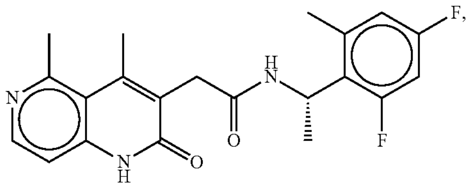
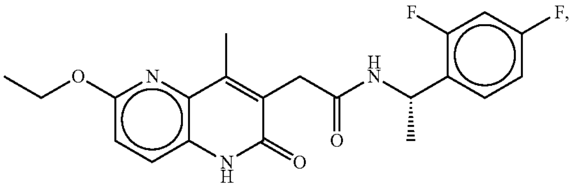
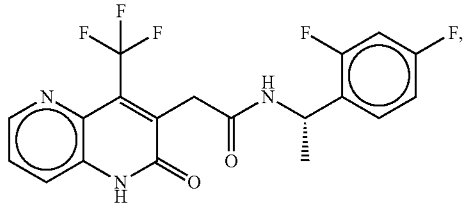
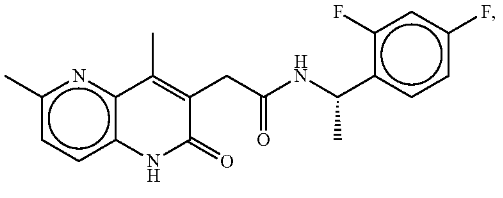
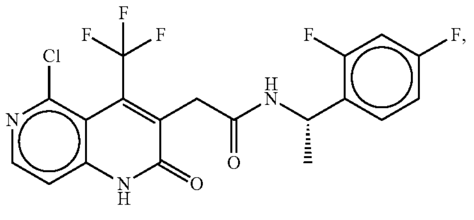
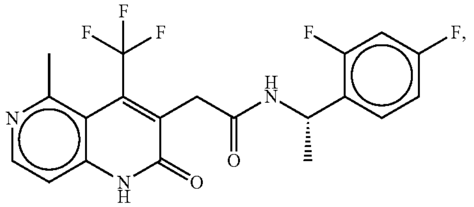

-continued
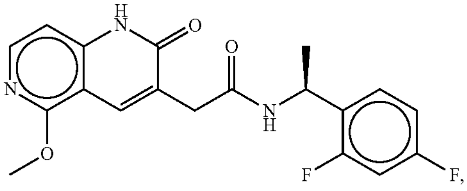
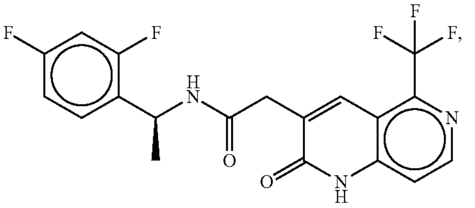
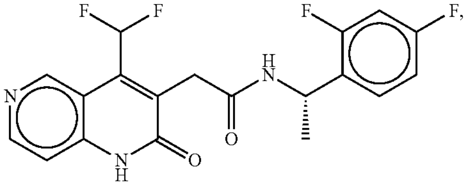
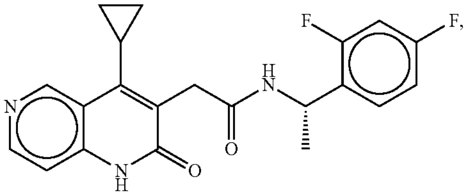
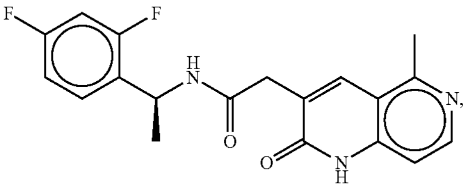
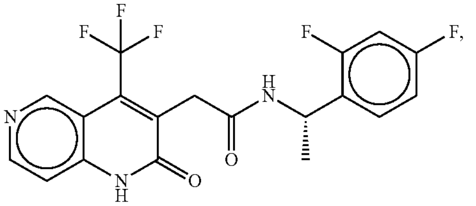
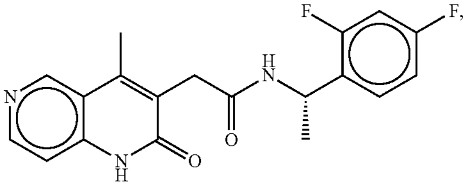
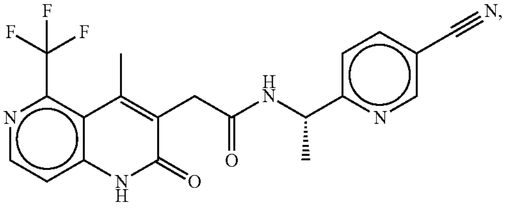
-continued
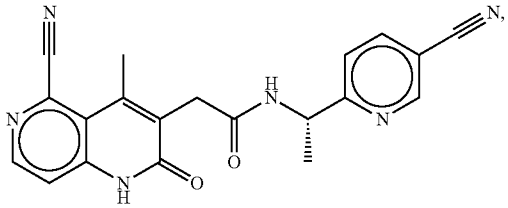
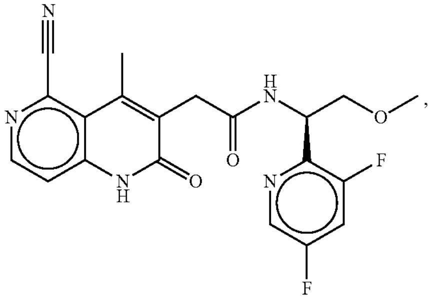
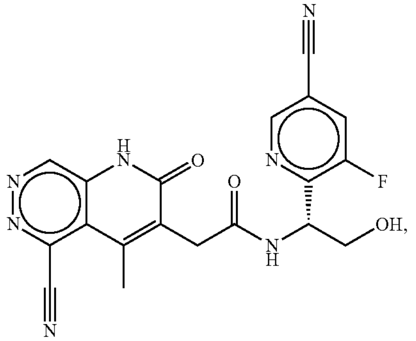
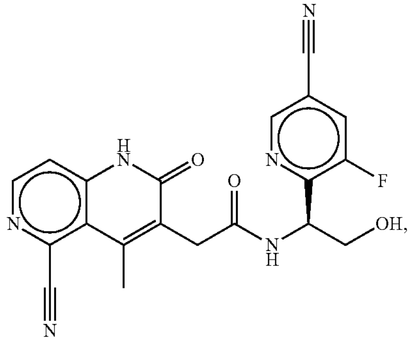
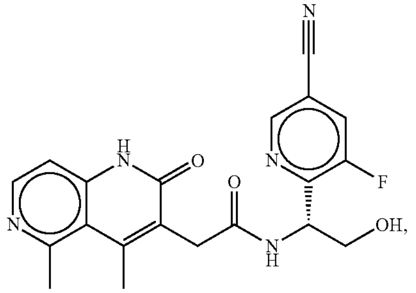

-continued
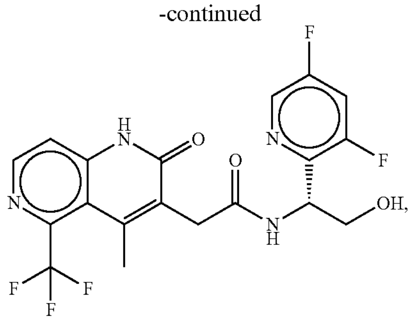
,
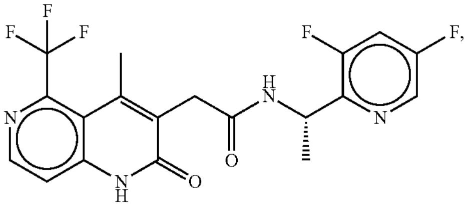
,
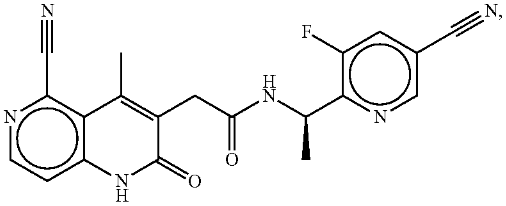
,
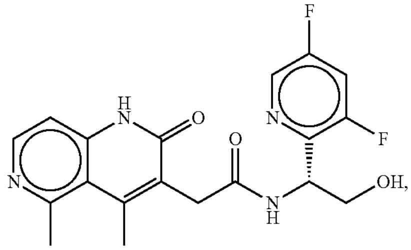
,
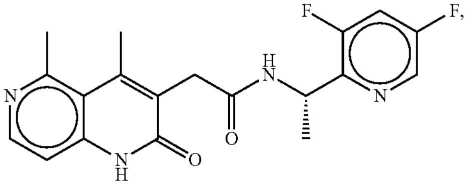
,
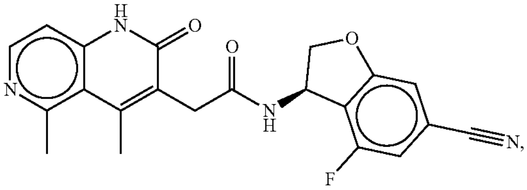
,
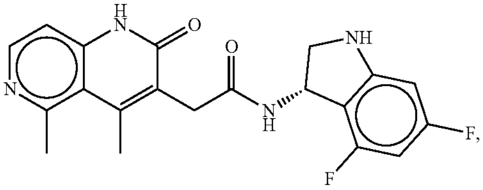
,
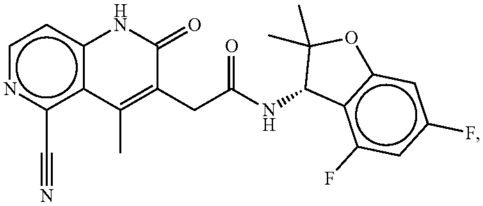
,
-continued
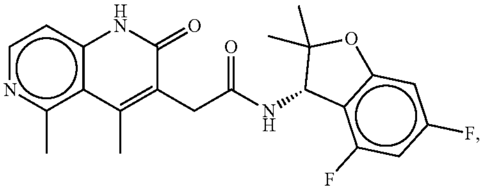
,
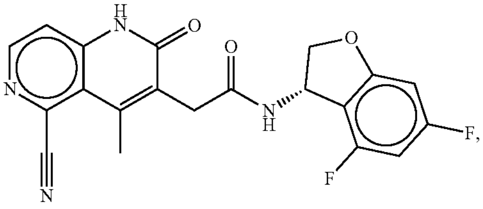
,
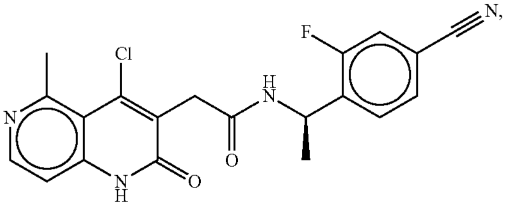
,
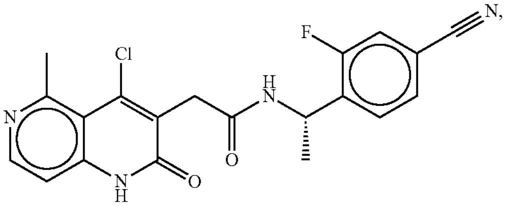
,
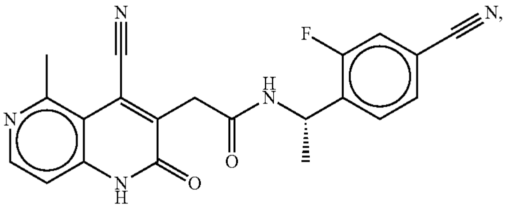
,
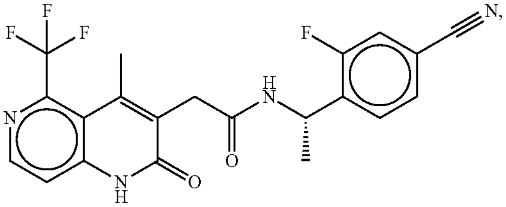
,
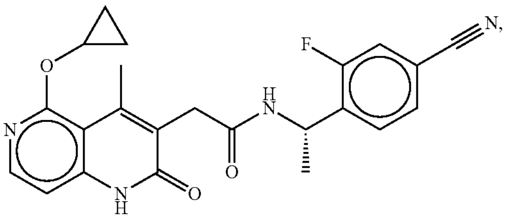
,
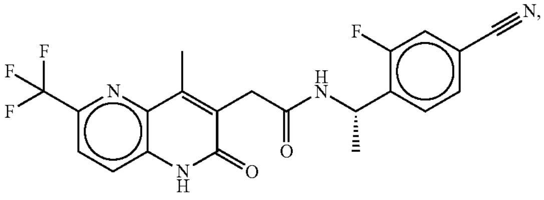
, -continued
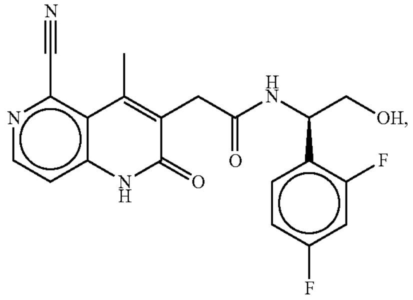
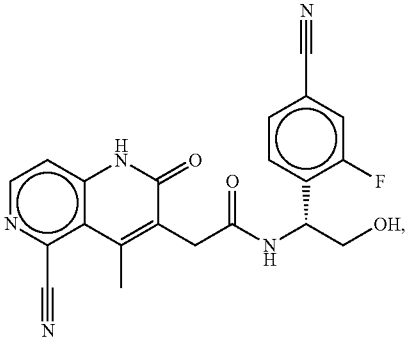
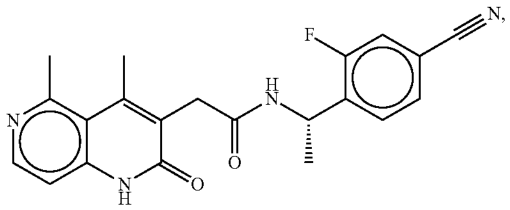
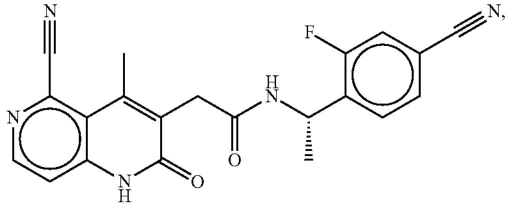
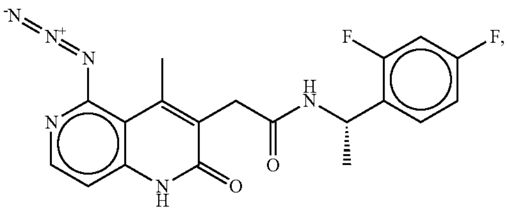
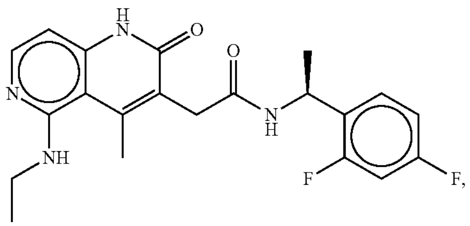
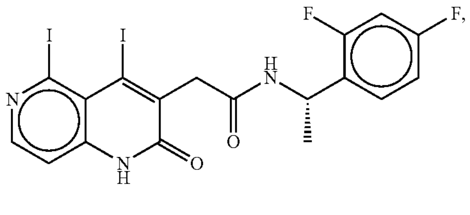
-continued
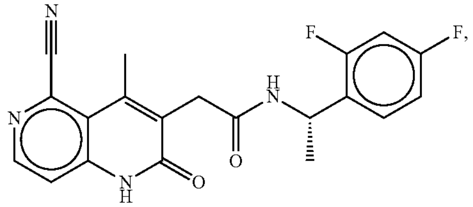
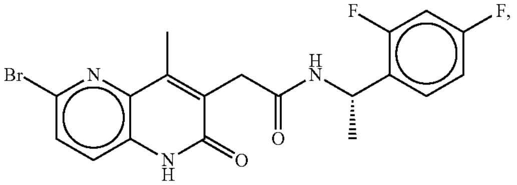
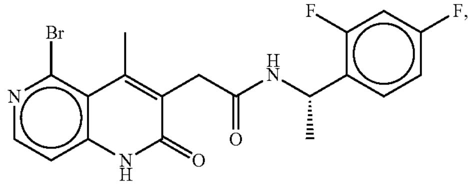
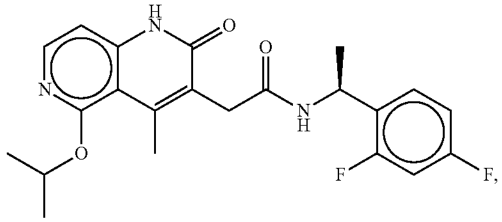
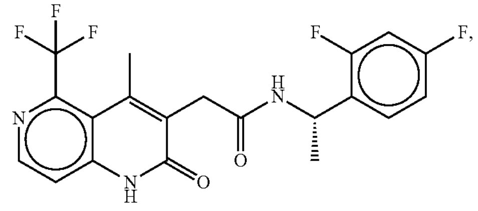
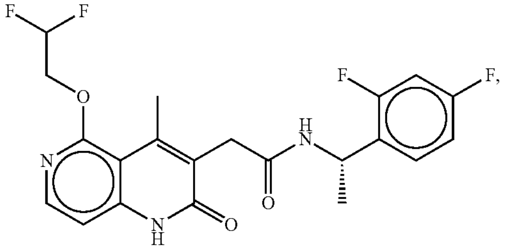
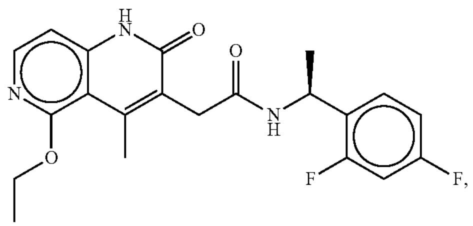
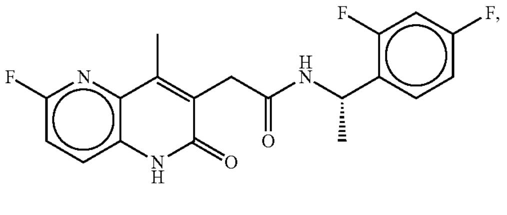

-continued
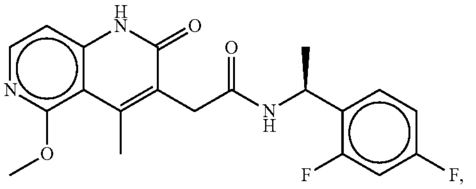
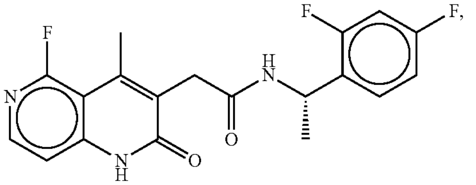
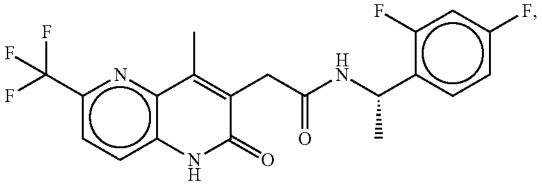
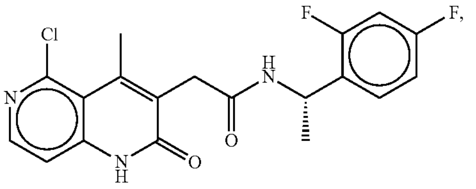
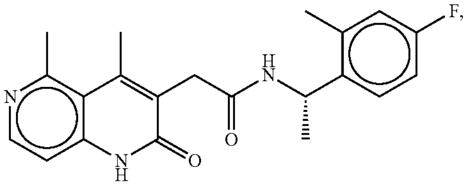
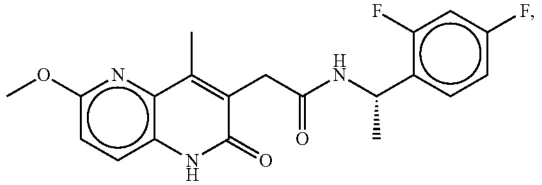
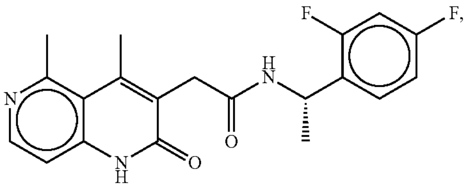
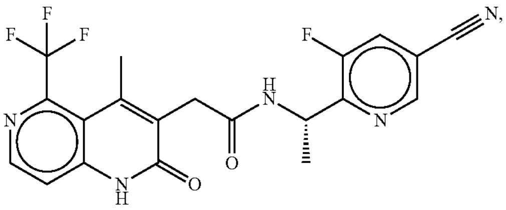
-continued
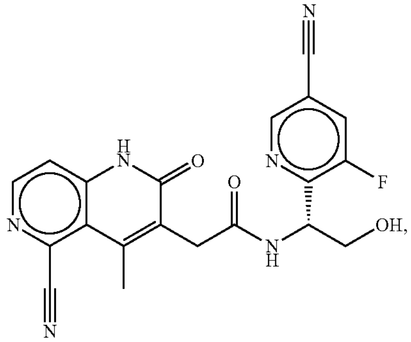
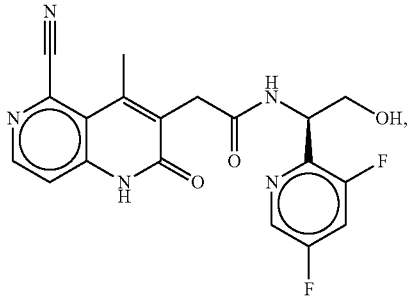
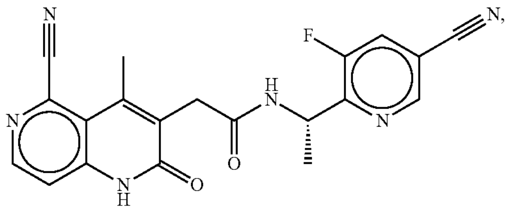
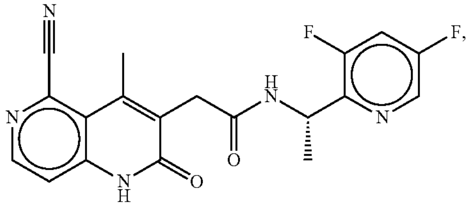
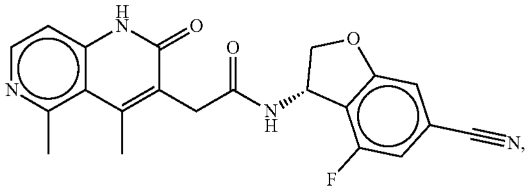
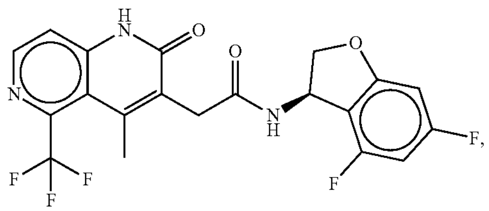
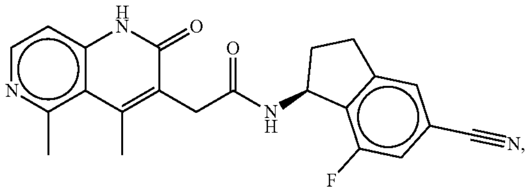

-continued
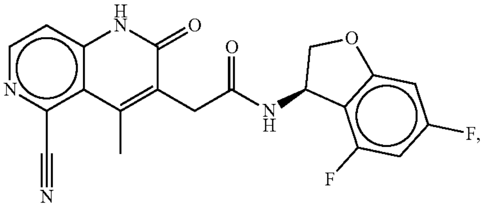
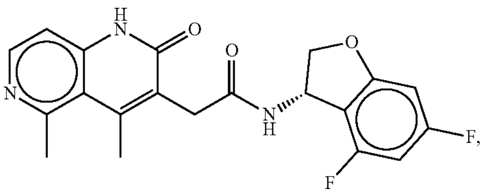
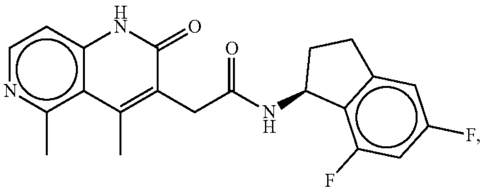
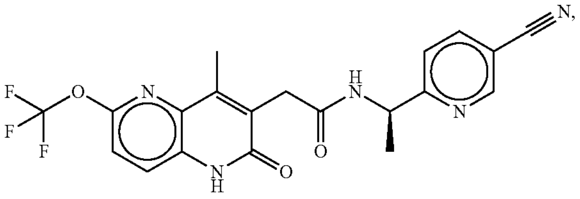
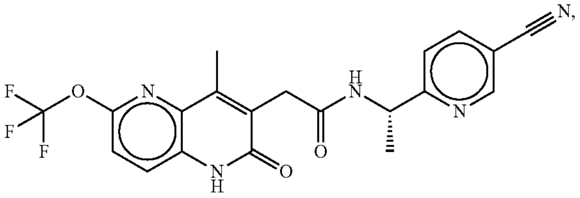
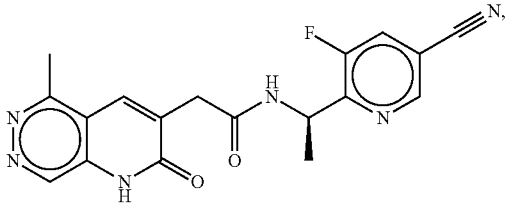
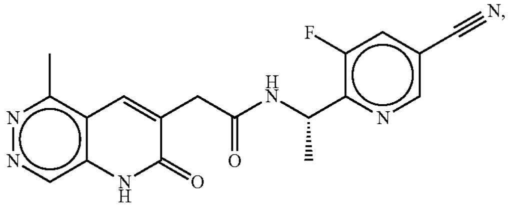
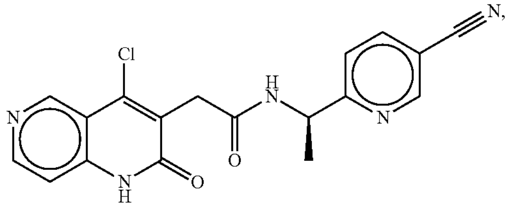
-continued
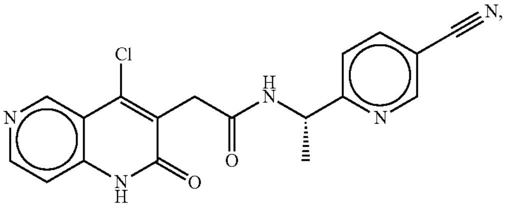
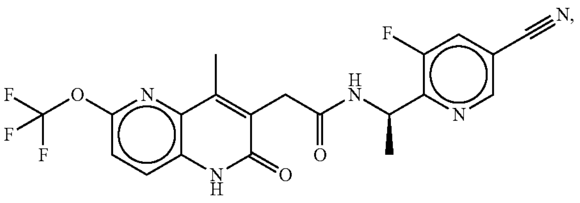
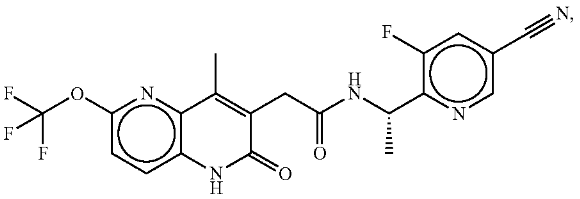
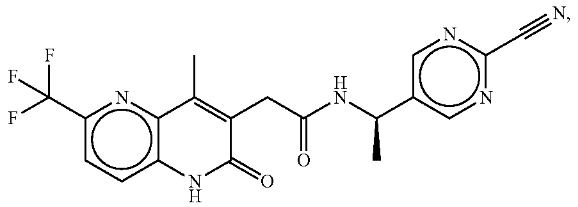
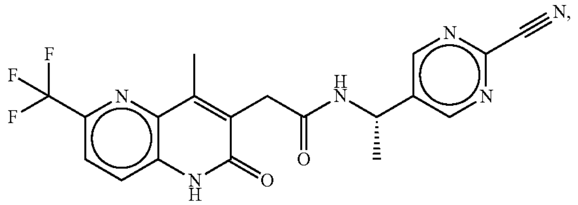
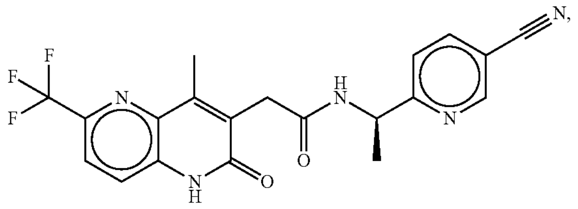
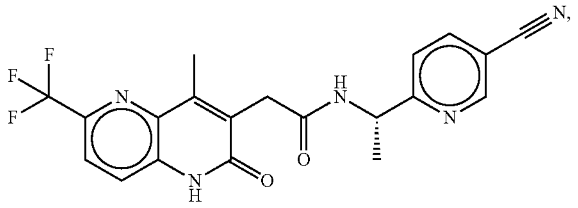
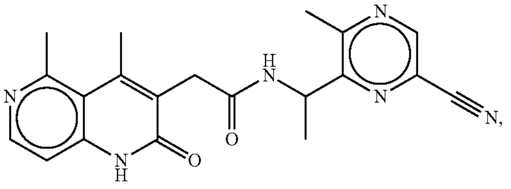

-continued
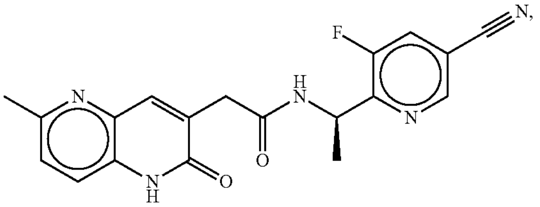
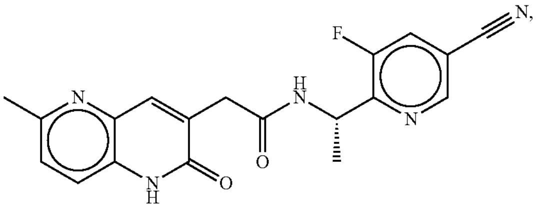
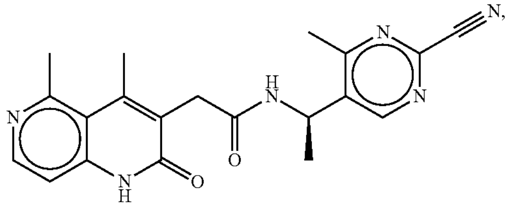
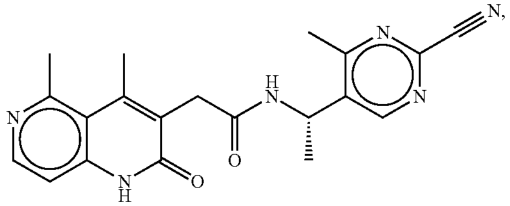
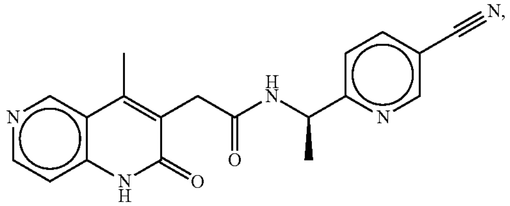
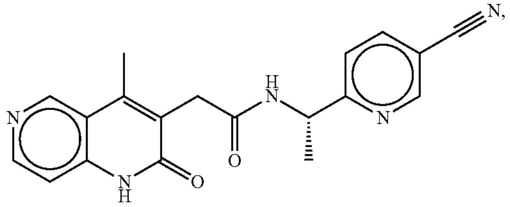
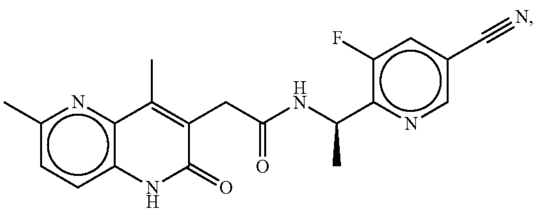
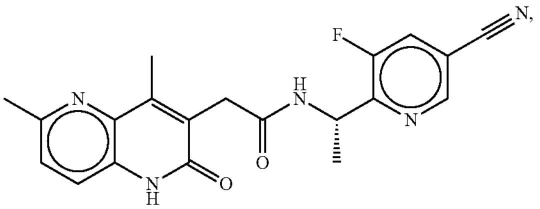
-continued
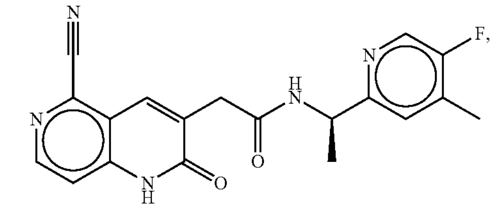
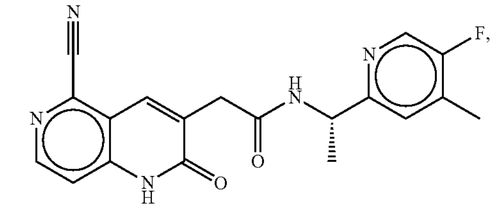
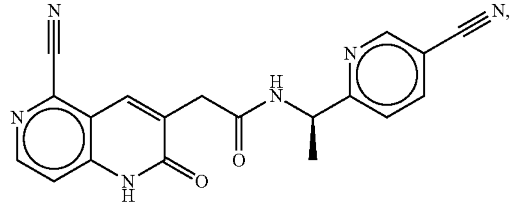
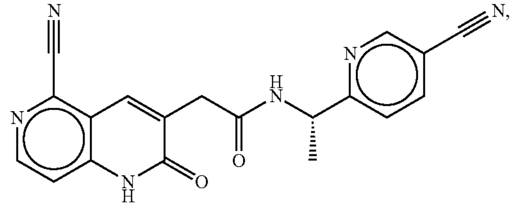
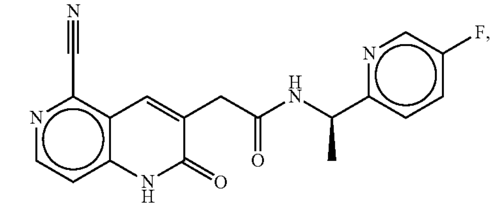
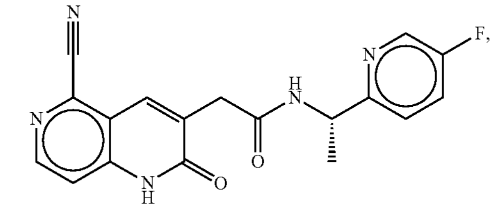
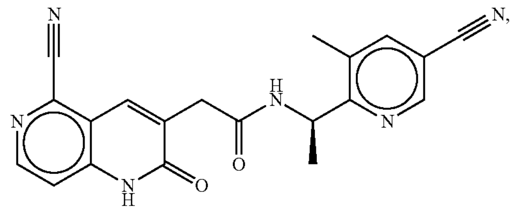
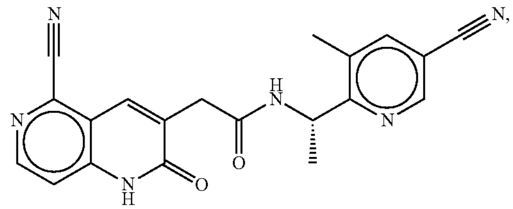

-continued
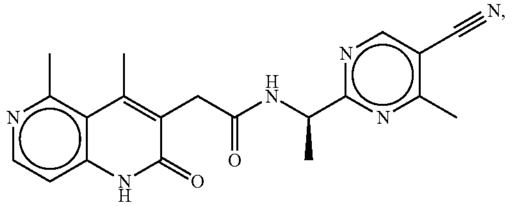
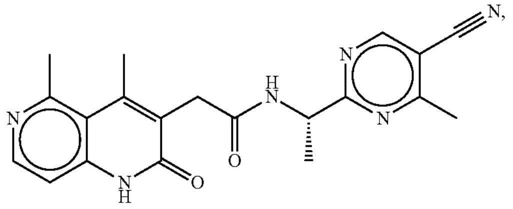
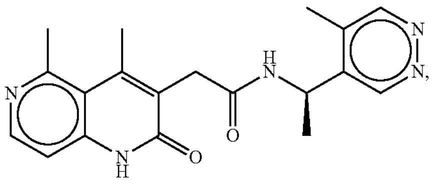
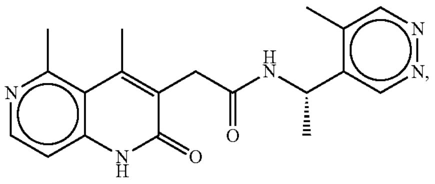
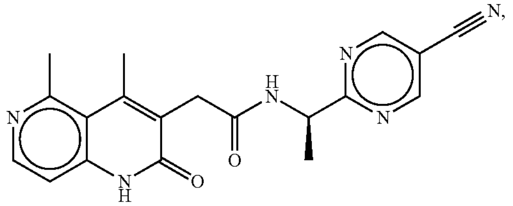
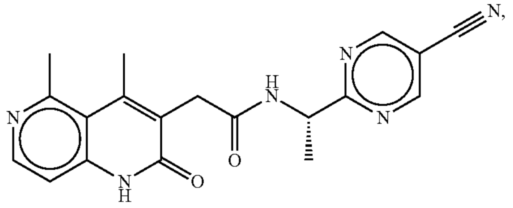
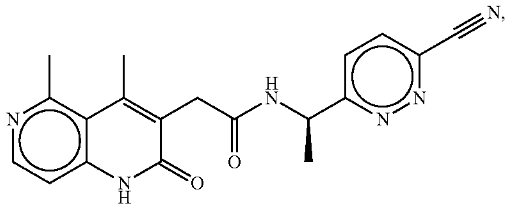
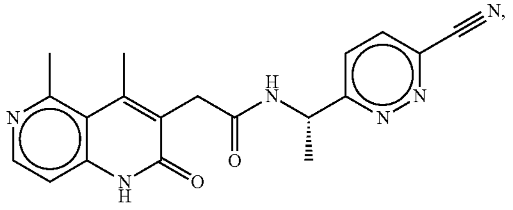
-continued
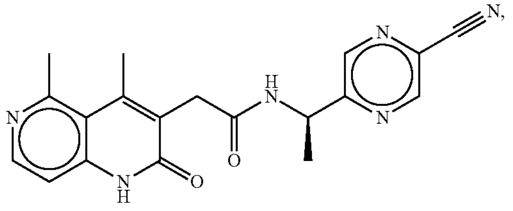
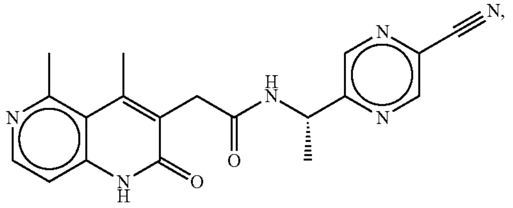
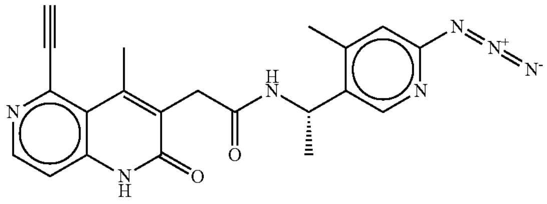
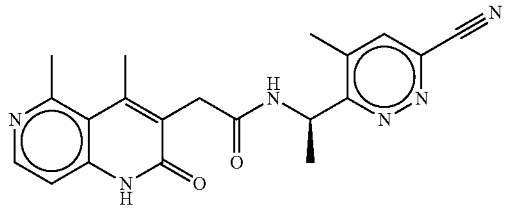
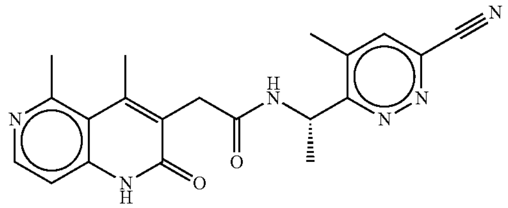
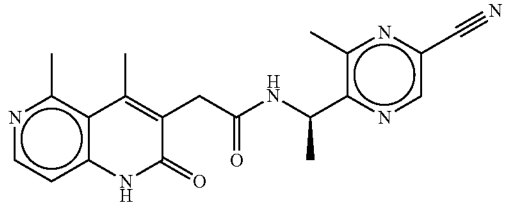
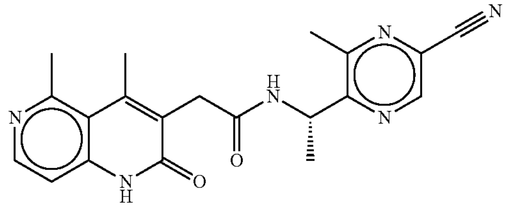
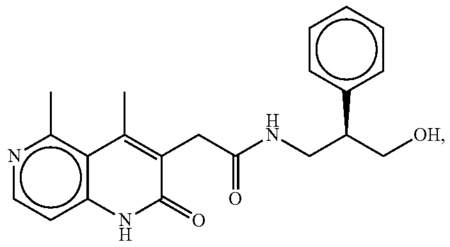

-continued
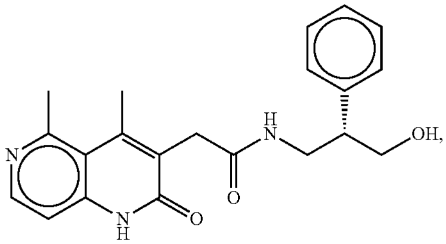,
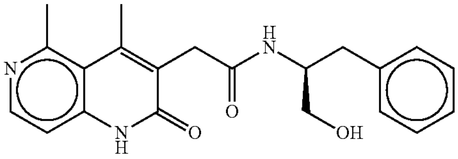,
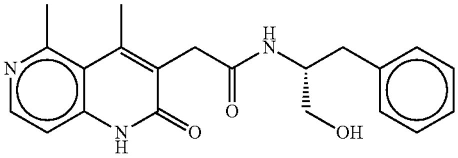,
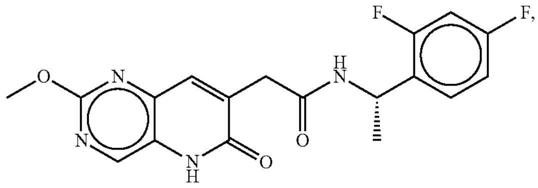,
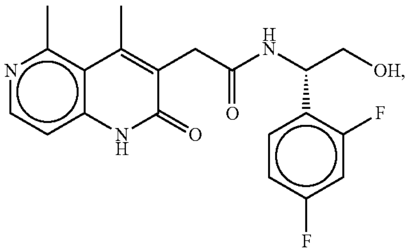,
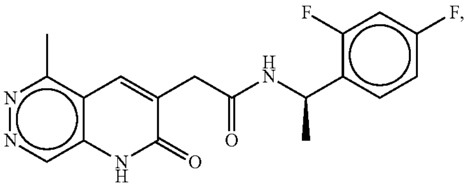,
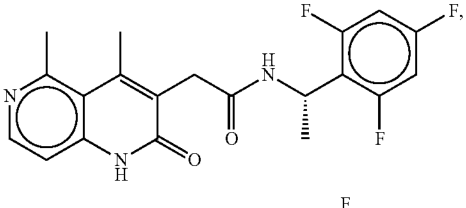, and
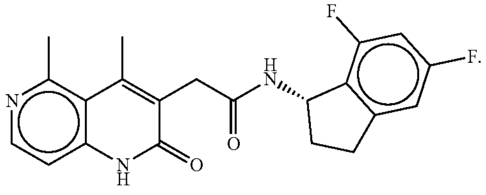.
(49): The compound or salt of any one of embodiments 1 to 27, selected from:
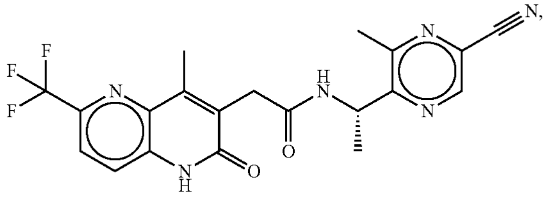,
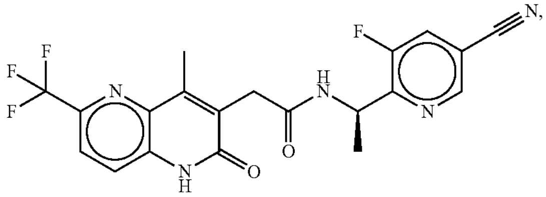,
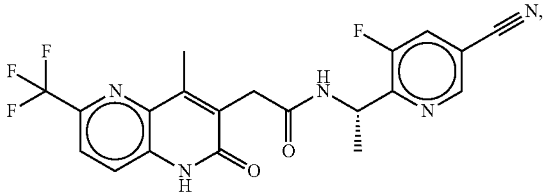,
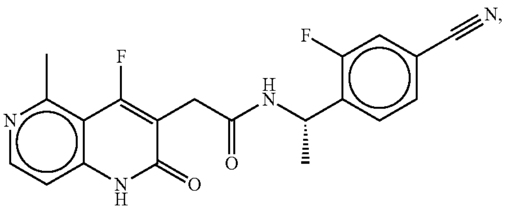,
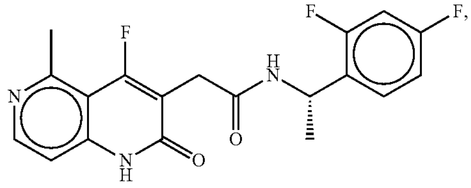,
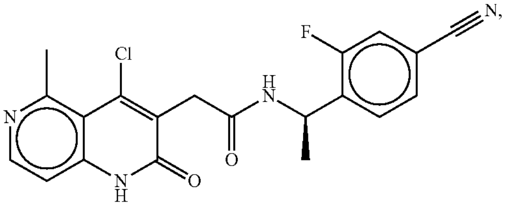,
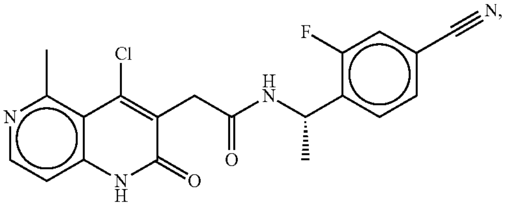,
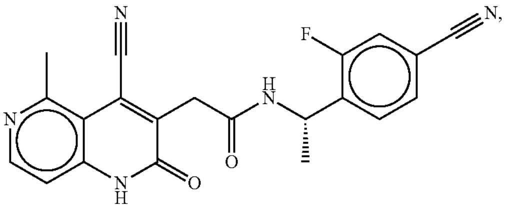, -continued
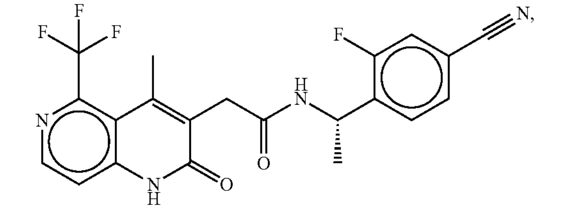
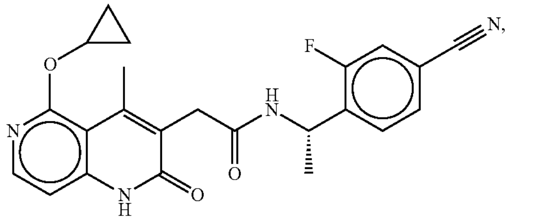
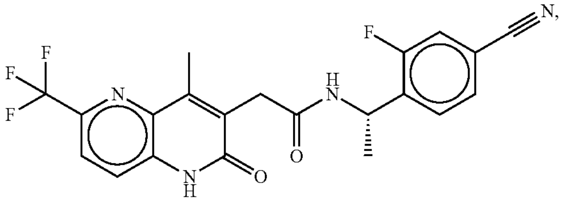
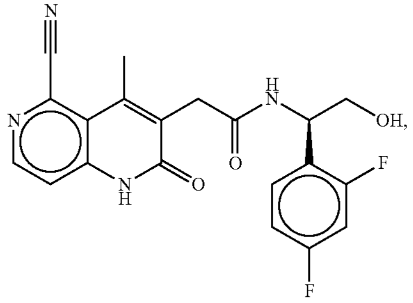
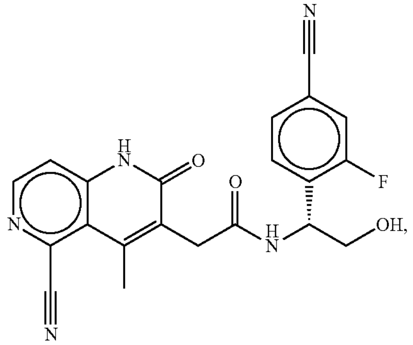
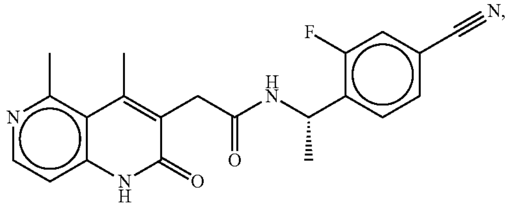
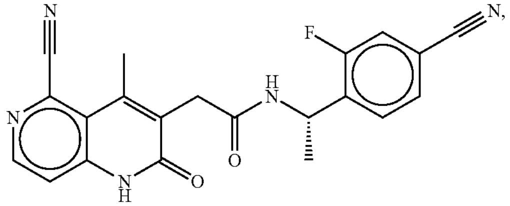
-continued
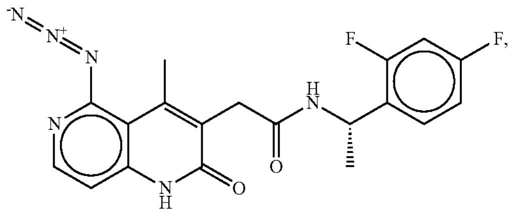
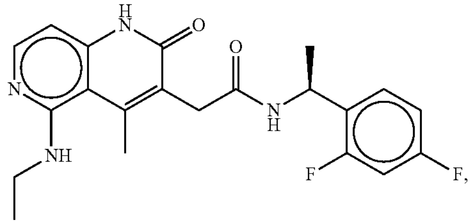
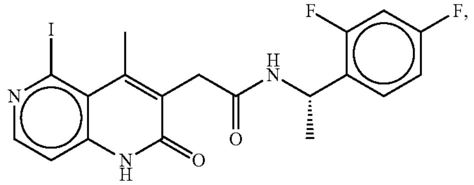
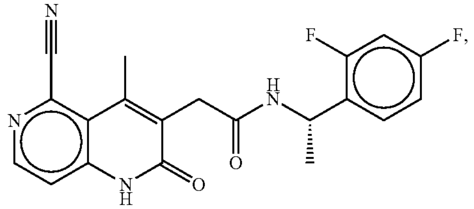
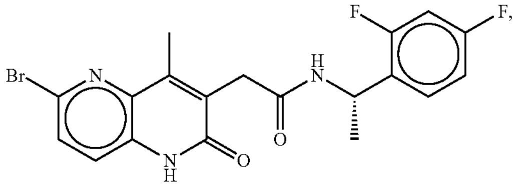
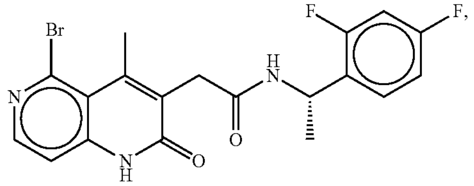
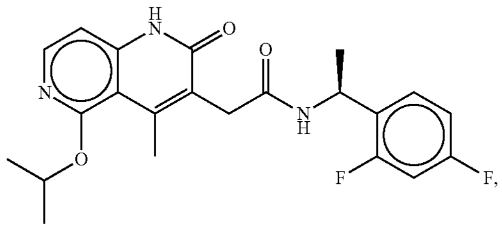
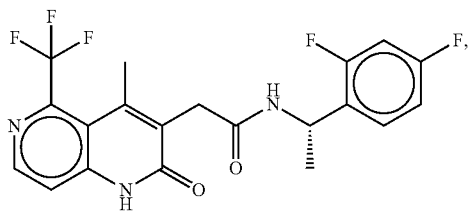

-continued
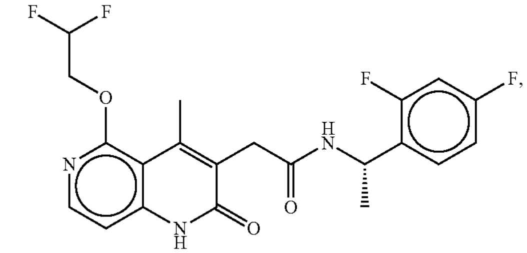
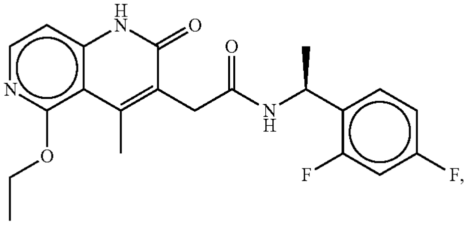
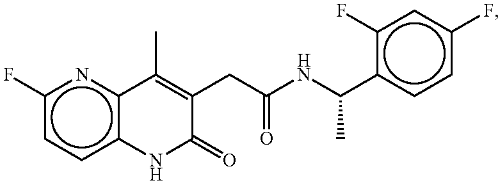
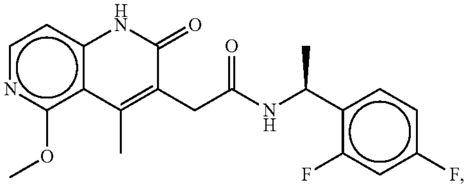
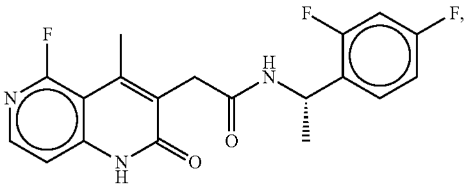
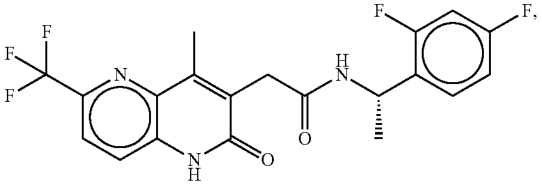
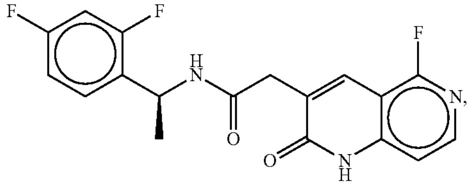
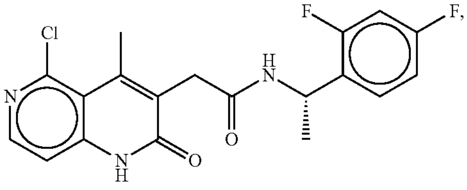
-continued
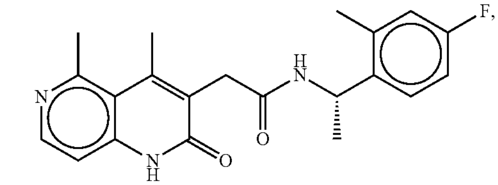
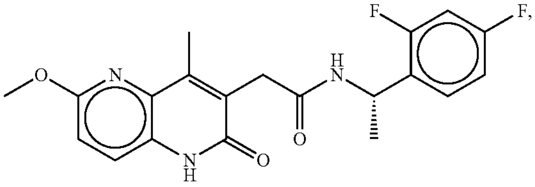
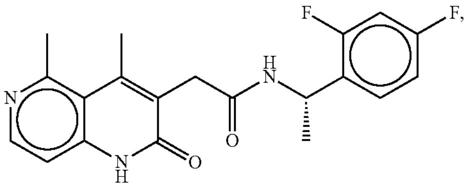
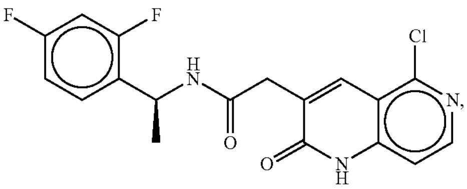
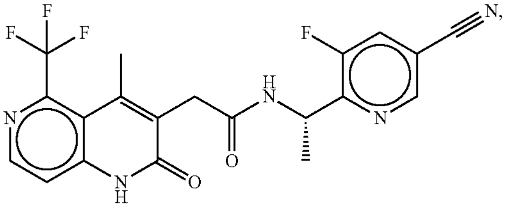
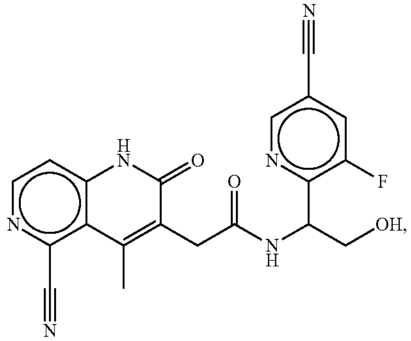
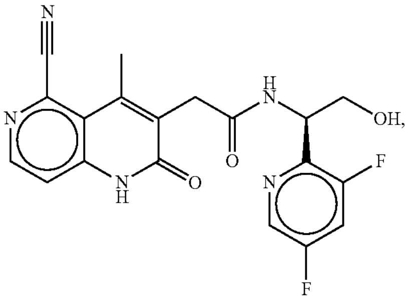

-continued
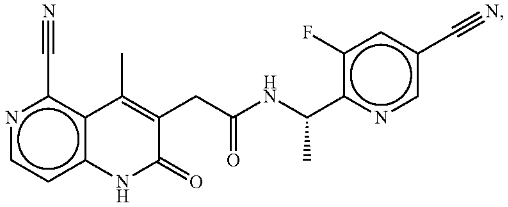
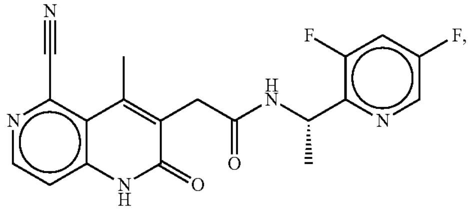
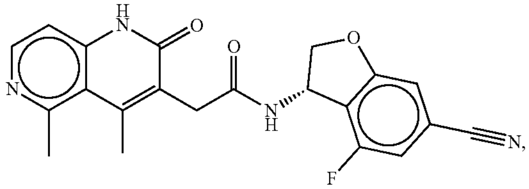
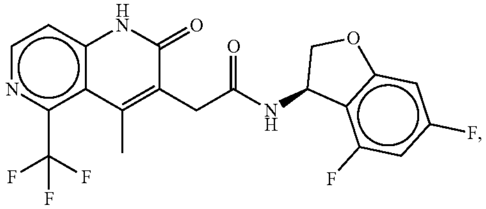
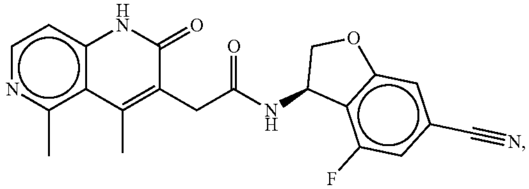
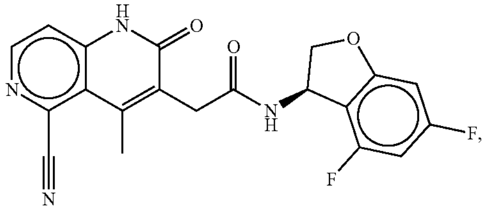
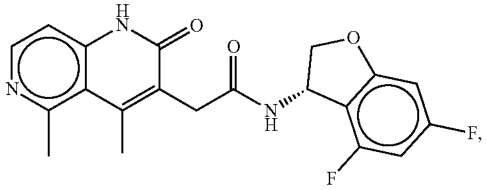
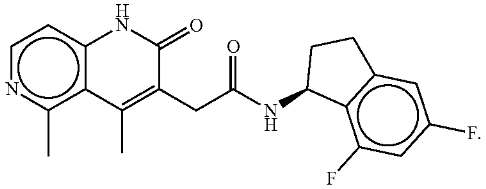
(50): The compound or salt of any one of embodiments 1 to 49, selected from:
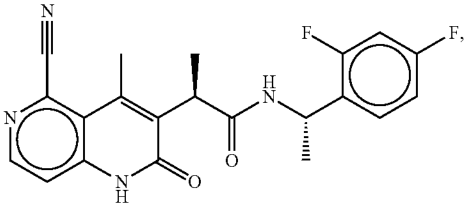
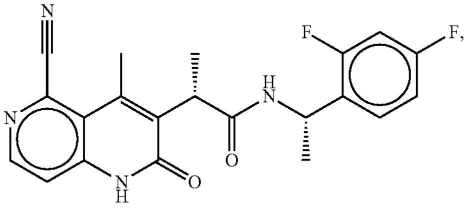
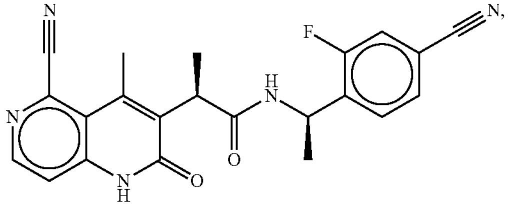
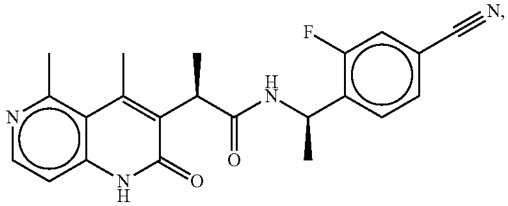
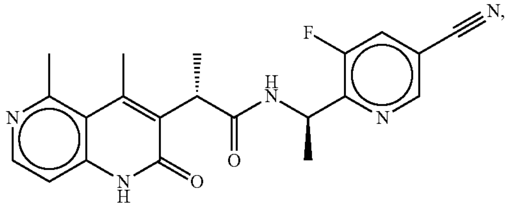
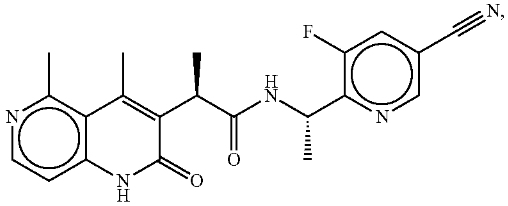
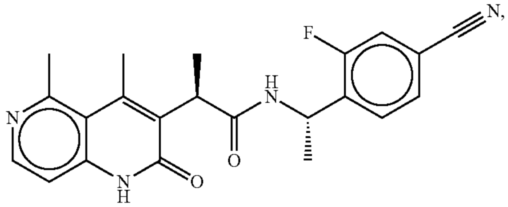
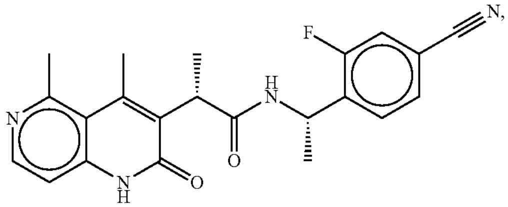

-continued
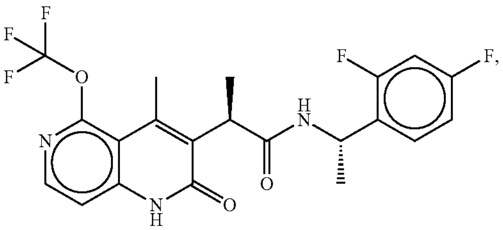
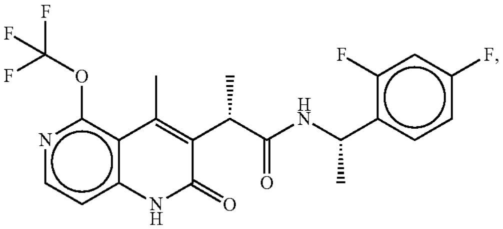
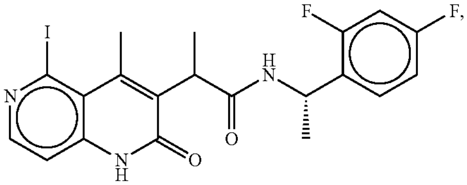
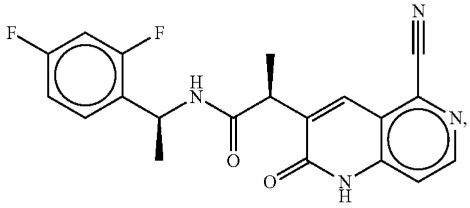
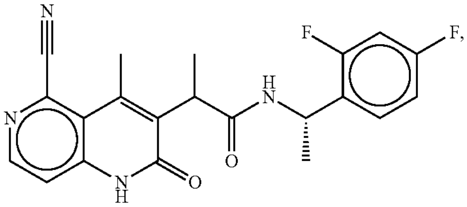
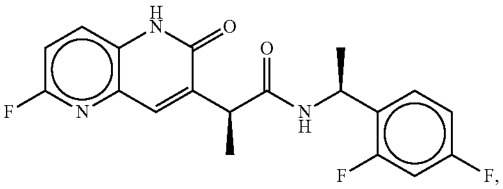
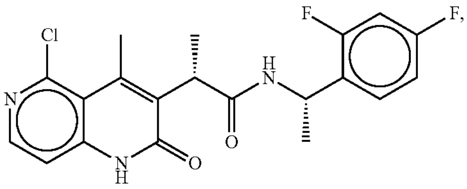
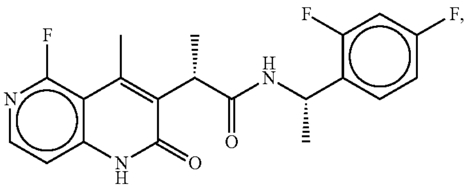
-continued
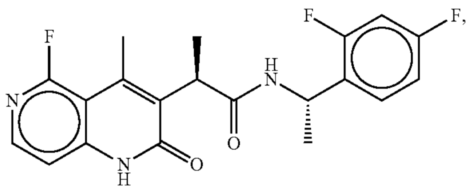
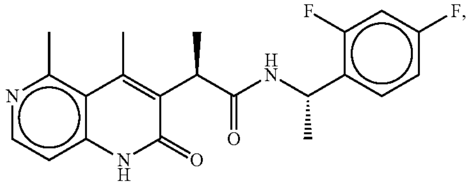
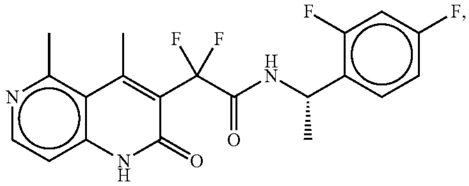
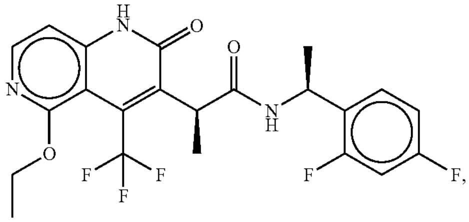
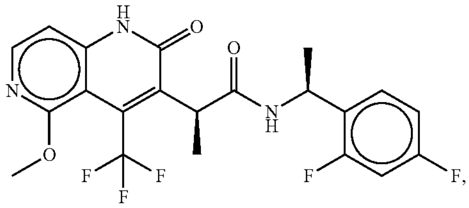
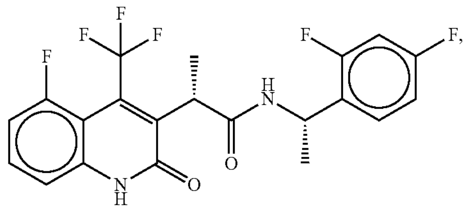
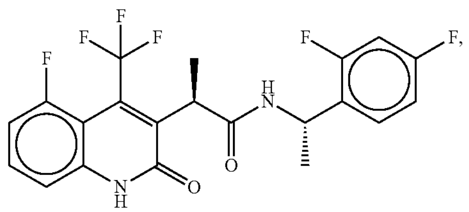
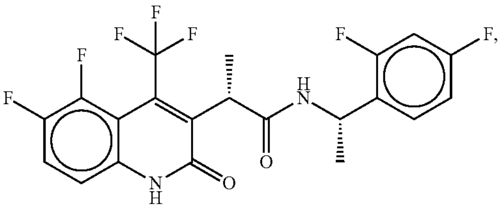

-continued

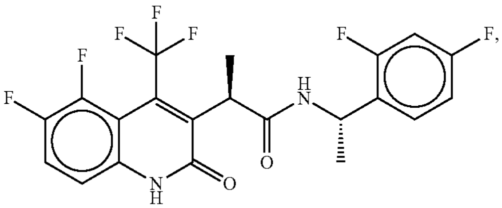

,

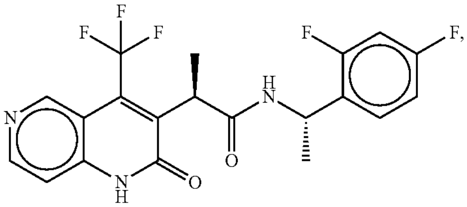

,

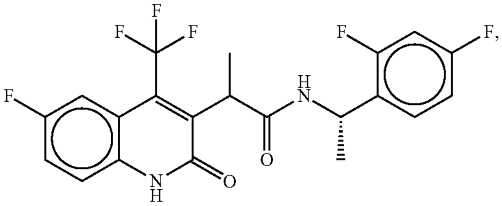

,

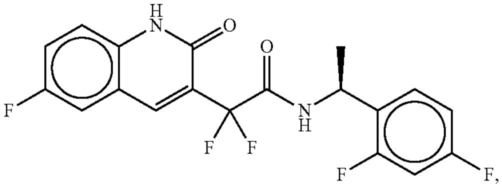

,

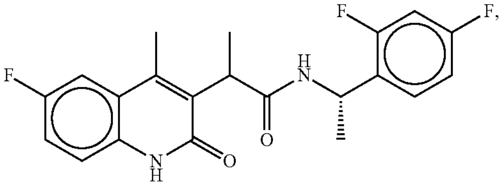

,

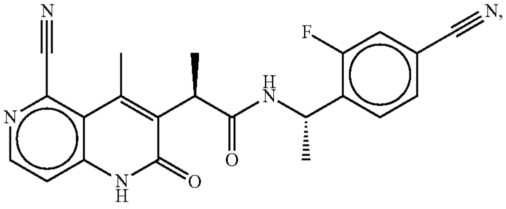

,

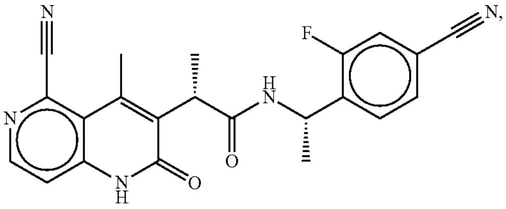

,

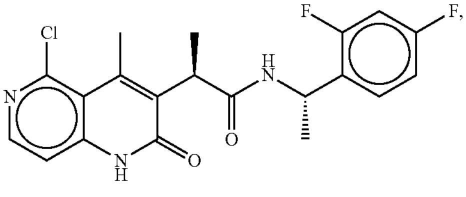

and

-continued

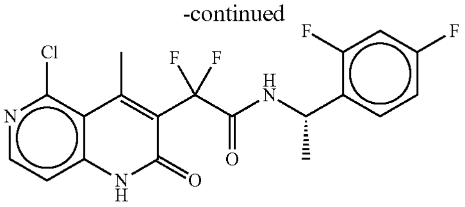

(51): The compound or salt of embodiment 0, selected from:

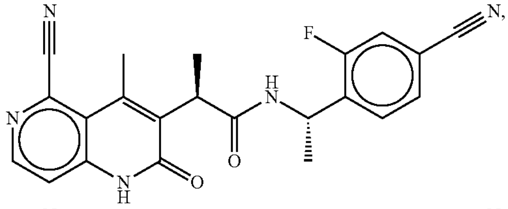

,

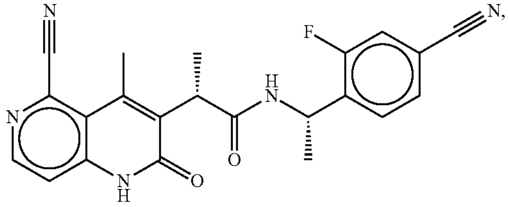

,

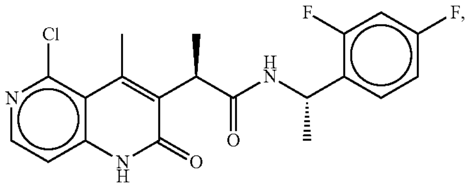

, and

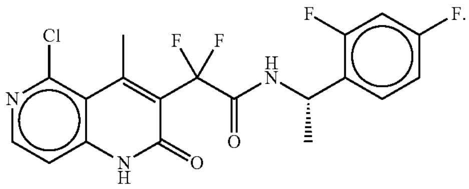

.

(52): A compound represented by Formula (II'):

(II')

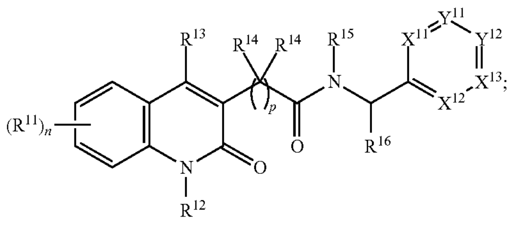

;

or a salt thereof, wherein: n is 1, 2, 3, or 4; p is 1; $X^{11}$ is selected from $C(R^{17a})$ and N; $X^{12}$ is selected from $C(R^{17b})$ and N; $X^{13}$ is selected from $C(R^{17c})$ and N; $Y^{11}$ is selected from $C(R^{17d})$ and further selected from N when $R^{16}$ is not hydrogen; $Y^{12}$ is selected from $C(R^{17e})$ and further selected from N when $R^{16}$ is not hydrogen; each $R^{11}$ is independently selected from: halogen, $-NO_2$, $-CN$, $-N_3$, $-OR^{19a}$, $-SR^{19a}$, $-N(R^{19a})_2$, $-C(O)R^{19a}$, $-C(O)N(R^{19a})_2$, $-N(R^{19a})C(O)R^{19a}$, $-N(R^{19a})C(O)N(R^{19a})_2$, $-OC(O)N(R^{19a})_2$, $-N(R^{19a})C(O)OR^{19a}$, $-C(O)OR^{19a}$, $-OC(O)$ $R^{19a}$, —S(O)$R^{19a}$, and —S(O)$_2R^{19a}$; $C_{1-6}$ alkyl, $C_{2-6}$ alkenyl, and $C_{2-6}$ alkynyl, each of which is optionally substituted with one or more substituents independently selected from halogen, —O$R^{19a}$, —S$R^{19a}$, —N($R^{19a}$)$_2$, —C(O)$R^{19a}$, —C(O)N($R^{19a}$)$_2$, —N($R^{19a}$)C(O)$R^{19a}$, —C(O)O$R^{19a}$, —OC(O)$R^{19a}$, —N($R^{19a}$)C(O)N($R^{19a}$)$_2$, —OC(O)N($R^{19a}$)$_2$, —N($R^{19a}$)C(O)O$R^{19a}$, —S(O)$R^{19a}$, —S(O)$_2R^{19a}$, —NO$_2$, ═O, ═S, ═N($R^{19a}$), —CN, $C_{3-10}$ carbocycle and 3- to 10-membered heterocycle, wherein the $C_{3-10}$ carbocycle and 3- to 10-membered heterocycle are each optionally substituted with one or more $R^{18a}$; and $C_{3-10}$ carbocycle and 3- to 10-membered heterocycle, each of which is optionally substituted with one or more substituents independently selected from halogen, —O$R^{19a}$, —S$R^{19a}$, —N($R^{19a}$)$_2$, —C(O)$R^{19a}$, —C(O)N($R^{19a}$)$_2$, —N($R^{19a}$)C(O)$R^{19a}$, —N($R^{19a}$)C(O)N($R^{19a}$)$_2$, —OC(O)N($R^{19a}$)$_2$, —N($R^{19a}$)C(O)O$R^{19a}$, —C(O)O$R^{19a}$, —OC(O)$R^{19a}$, —S(O)$R^{19a}$, —S(O)$_2R^{19a}$, —NO$_2$, ═O—, ═S, ═N($R^{19a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{18a}$; $R^{12}$ is selected from: hydrogen, halogen, —NO$_2$, —CN, —O$R^{19b}$, —S$R^{19b}$, —N($R^{19b}$)$_2$, —C(O)$R^{19b}$, —C(O)N($R^{19b}$)$_2$, —N($R^{19b}$)C(O)$R^{19b}$, N($R^{19b}$)C(O)N($R^{19b}$)$_2$, —OC(O)N($R^{19b}$)$_2$, —N($R^{19b}$)C(O)O$R^{19b}$, —C(O)O$R^{19b}$, —OC(O)$R^{19b}$, —S(O)$R^{19b}$, and —S(O)$_2R^{19b}$; $C_{1-6}$ alkyl, $C_{2-6}$ alkenyl, and $C_{2-6}$ alkynyl, each of which is optionally substituted with one or more substituents independently selected from halogen, —O$R^{19b}$, —S$R^{19b}$, —N($R^{19b}$)$_2$, —C(O)$R^{19b}$, —C(O)N($R^{19b}$)$_2$, —N($R^{19b}$)C(O)$R^{19b}$, —C(O)O$R^{19b}$, —OC(O)$R^{19b}$, —N($R^{19b}$)C(O)N($R^{19b}$)$_2$, —OC(O)N($R^{19b}$)$_2$, —N($R^{19b}$)C(O)O$R^{19b}$, —S(O)$R^{19b}$, —S(O)$_2R^{19b}$, —NO$_2$, ═O, ═S, ═N($R^{19b}$), —CN, $C_{3-10}$ carbocycle and 3- to 10-membered heterocycle, wherein the $C_{3-10}$ carbocycle and 3- to 10-membered heterocycle are each optionally substituted with one or more $R^{18b}$; and $C_{3-10}$ carbocycle and 3- to 10-membered heterocycle, each of which is optionally substituted with one or more substituents independently selected from halogen, —O$R^{19b}$, —S$R^{19b}$, —N($R^{19b}$)$_2$, —C(O)$R^{19b}$, —C(O)N($R^{19b}$)$_2$—N($R^{19b}$)C(O)$R^{19b}$, —N($R^{19b}$)C(O)N($R^{19b}$)$_2$, —OC(O)N($R^{19b}$)$_2$—N($R^{19b}$)C(O)O$R^{19b}$, —C(O)O$R^{19b}$, —OC(O)$R^{19b}$, —S(O)$R^{8g}$b, —S(O)$_2R^{19b}$, —NO$_2$, ═O—, ═S, ═N($R^{19b}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{18b}$; $R^{13}$ is selected from: hydrogen, halogen, —O$R^{19c}$, —S$R^{19c}$, —N($R^{19c}$)$_2$, —NO$_2$, and —CN; and $C_{1-6}$ alkyl optionally substituted with one or more substituents independently selected from halogen, —O$R^{19c}$, —S$R^{19c}$, —N($R^{19c}$)$_2$, —NO$_2$, and —CN; and $C_{3-10}$ carbocycle and 3- to 10-membered heterocycle, each of which is optionally substituted with one or more substituents independently selected from halogen, —O$R^{19c}$, —S$R^{19c}$, —N($R^{19c}$)$_2$, —C(O)$R^{19c}$, —C(O)N($R^{19c}$)$_2$, —N($R^{19c}$)C(O)$R^{19c}$, —N($R^{19c}$)C(O)N($R^{19c}$)$_2$, —OC(O)N($R^{19c}$)$_2$, —N($R^{19c}$)C(O)O$R^{19c}$, —C(O)O$R^{19c}$, —OC(O)$R^{19c}$, —S(O)$R^{19c}$, —S(O)$_2R^{19c}$, —NO$_2$, ═O—, ═S, ═N($R^{19c}$), and —CN; each $R^{14}$ is independently selected from: hydrogen, halogen, —O$R^{19d}$, —S$R^{19d}$, —N($R^{19d}$)$_2$, —NO$_2$, and —CN; and $C_{1-6}$ alkyl which is optionally substituted with one or more substituents independently selected from halogen, —O$R^{19d}$, —S$R^{19d}$, —N($R^{19d}$)$_2$, —NO$_2$, and —CN; and $C_{3-10}$ carbocycle and 3- to 10-membered heterocycle, each of which is optionally substituted with one or more substituents independently selected from halogen, —O$R^{19d}$, —S$R^{19d}$, —N($R^{19d}$)$_2$, —C(O)$R^{19d}$, —C(O)N($R^{19d}$)$_2$, —N($R^{19d}$)C(O)$R^{19d}$, —N($R^{19d}$)C(O)N($R^{19d}$)$_2$, —OC(O)N($R^{19d}$)$_2$, —N($R^{19d}$)C(O)O$R^{19d}$, —C(O)O$R^{19d}$, —OC(O)$R^{19d}$, —S(O)$R^{19d}$, —S(O)$_2R^{19d}$, —NO$_2$, ═O—, ═S, ═N($R^{19d}$), and —CN; or $R^{13}$ together with $R^{14}$ form a $C_{3-10}$ carbocycle, or 3- to 10-membered heterocycle, wherein the $C_{3-10}$ carbocycle, or 3- to 10-membered heterocycle, is optionally substituted with one or more $R^{18c}$; or two $R^{14}$ groups together form a $C_{3-10}$ carbocycle, or 3- to 10-membered heterocycle, wherein the $C_{3-10}$ carbocycle, or 3- to 10-membered heterocycle, is optionally substituted with one or more $R^{18c}$; $R^{15}$ is selected from: hydrogen, halogen, —O$R^{19e}$, —S$R^{19e}$, —N($R^{19e}$)$_2$, —NO$_2$, and —CN; and $C_{1-6}$ alkyl optionally substituted with one or more $R^{18d}$; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$; $R^{16}$ is selected from: hydrogen, halogen, —O$R^{19f}$, —S$R^{19f}$—N($R^{19f}$)$_2$, —NO$_2$, and —CN; and $C_{1-6}$ alkyl optionally substituted with one or more $R^{18e}$; or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$; each $R^{17a}$, $R^{17b}$, $R^{17c}$, $R^{17d}$, and $R^{17e}$ is independently selected from: hydrogen, halogen, —O$R^{19g}$, —S$R^{19g}$, —N($R^{19g}$)$_2$, —NO$_2$, —CN, —N$_3$; and $C_{1-6}$ alkyl, $C_{2-6}$ alkenyl, and $C_{2-6}$ alkynyl, each of which is optionally substituted with one or more $R^{18f}$; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{7a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$; each $R^{18a}$ is independently selected from: halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2R^{19h}$, —NO$_2$, ═O, ═S, ═N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2R^{19h}$, —NO$_2$, ═O, ═S, ═N($R^{19h}$), and —CN; each $R^{18b}$ is independently selected from: halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2R^{19h}$, —NO$_2$, ═O, ═S, ═N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2R^{19h}$, —NO$_2$, ═O, ═S, ═N($R^{19h}$), and —CN; each $R^{18e}$ is independently selected from: halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2$$R^{19h}$, —NO$_2$, =O, =S, =N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2$$R^{19h}$, —NO$_2$, =O, =S, =N($R^{19h}$), and —CN; each $R^{18d}$ is independently selected from: halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$—N($R^{19h}$)C(O)O$R^{19h}$, —C(O)O$R^{19h}$, —OC(O)$R^{19h}$, —S(O)$R^{19h}$, —S(O)$_2$$R^{19h}$, —NO$_2$, =O, =S, =N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2$$R^{19h}$, —NO$_2$, =O, =S, =N($R^{19h}$), and —CN; each $R^{18e}$ is independently selected from: halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2$$R^{19h}$, —NO$_2$, =O, =S, =N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2$$R^{19h}$, —NO$_2$, =O, =S, =N($R^{19h}$), and —CN; each $R^{18f}$ is independently selected from: halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2$$R^{19h}$, —NO$_2$, =O, =S, =N($R^{19h}$), and —CN; and $C_{1-3}$ alkyl, $C_{2-3}$ alkenyl, and $C_{2-3}$ alkynyl, each of which is optionally substituted with one or more substituents independently selected from halogen, —O$R^{19h}$, —S$R^{19h}$, —N($R^{19h}$)$_2$, —C(O)$R^{19h}$, —C(O)N($R^{19h}$)$_2$, —N($R^{19h}$)C(O)$R^{19h}$, —N($R^{19h}$)C(O)N($R^{19h}$)$_2$, —OC(O)N($R^{19h}$)$_2$, —N($R^{19h}$)C(O)O$R^{19h}$, —C(O)O$R^{19h}$, —OC(O)$R^{19h}$, —S(O)$R^{19h}$, —S(O)$_2$$R^{19h}$, —NO$_2$, =O, =S, =N($R^{19h}$), and —CN; each $R^{19a}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{19b}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{19c}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{19d}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_1$—. alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$alkyl, $C_{2-6}$alkenyl, $C_{2-6}$ alkynyl, $C_{3-10}$ carbocycle, 3- to 10-membered heterocycle, and $C_{1-6}$ haloalkyl; each $R^{19e}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{19f}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{19g}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; and each $R^{19h}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; wherein when at least one $R^{11}$ is OMe, then $R^{16}$ is not hydrogen. (53): The compound or salt of embodiment 30, wherein n is 1, 2, or 3. (54): The compound or salt of any one of embodiments 52 to 53, wherein n is 1 or 2. (55): The compound or salt of any one of embodiments 52 to 54, wherein n is 1. (56): The compound or salt of any one of embodiments 52 to 53, wherein n is 2. (57): The compound or salt of embodiment 30, wherein n is 3. (58): The compound or salt of any one of embodiments 52 to 57, wherein $R^6$ together with $R^7$ form a 3- to 10-membered heterocycle, wherein the 3- to 10-membered heterocycle is optionally substituted with one or more $R^{8f}$. (59): The compound or salt of any one of embodiments 30 to 58, wherein $X^1$ is C($R^{17a}$). (60): The compound or salt of any one of embodiments 30 to 58, wherein $X^{11}$ is N. (61): The compound or salt of any one of embodiments 30 to 32, wherein $X^{12}$ is C($R^{17b}$). (62): The compound or salt of any one of embodiments 30 to 32, wherein $X^{12}$ is N. (63): The compound or salt of any one of embodiments 30 to 34, wherein $X^{13}$ is C($R^{17c}$). (64): The compound or salt of any one of embodiments 30 to 34, wherein $X^{13}$ is N. (65): The compound or salt of any one of embodiments 30 to 58, wherein $X^{11}$ and $X^{13}$ are N. (66): The compound or salt of any one of embodiments 30 to 58, wherein $X^{11}$ and $X^{12}$ are N. (67): The compound or salt of any one of embodiments 30 to 66, wherein each $R^{11}$ is independently selected from: halogen, —$NO_2$, —CN, —$N_3$, —$OR^{19a}$, —$SR^{9a}$, —N($R^{19a}$)$_2$, —C(O)$R^{19a}$; $C_{1-6}$ alkyl, which is optionally substituted with one or more substituents independently selected from halogen, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —C(O)O$R^{19a}$, —OC(O)$R^{19a}$, —N($R^{19a}$)C(O)N($R^{19a}$)$_2$, —OC(O)N($R^{19a}$)$_2$, —N($R^{19a}$)C(O)O$R^{19a}$, —S(O)$R^{19a}$, —S(O)$_2R^{19a}$, —$NO_2$, ═O, ═S, ═N($R^{19a}$), —CN, $C_{3-10}$ carbocycle and 3- to 10-membered heterocycle; and $C_{3-10}$ carbocycle which is optionally substituted with one or more substituents independently selected from halogen, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, N($R^{19a}$)C(O)N($R^{19a}$)$_2$, —OC(O)N($R^{19a}$)$_2$, —N($R^{19a}$)C(O)O$R^{19a}$, —C(O)O$R^{19a}$, —OC(O)$R^{19a}$, —S(O)$R^{19a}$, —S(O)$_2R^{19a}$, —$NO_2$, ═O—, ═S, ═N($R^{19a}$), —CN, $C_{1-6}$ alkyl, $C_{2-6}$ alkenyl, and $C_{2-6}$ alkynyl. (68): The compound or salt of any one of embodiments 30 to 1, wherein each $R^{11}$ is independently selected from halogen, —CN, —$N_3$, —$OR^{19a}$, $C_{1-6}$ alkyl, and $C_{3-10}$ carbocycle. (69): The compound or salt of any one of embodiments 30 to 39, wherein each $R^{11}$ is independently selected from —Cl, —F, —Br, —CN, $N_3$, —OH, —OMe, methyl, cyclopropyl, and $CF_3$. (70): The compound or salt of any one of embodiments 30 to 69, wherein each $R^{11}$ is independently selected from —Cl, —F, —CN, methyl, and cyclopropyl. (71): The compound or salt of any one of embodiments 30 to 70, wherein each $R^{11}$ is independently selected from —F, —CN, and methyl. (72): The compound or salt of any one of embodiments 30 to 71, wherein each $R^{11}$ is independently selected from —F and —CN. (73): The compound or salt of any one of embodiments 30 to 72, wherein $R^{12}$ is selected from: hydrogen, halogen, —$NO_2$, —CN, —$OR^{19b}$, —$SR^{19b}$, —N($R^{19b}$)$_2$, —C(O)$R^{19b}$; and $C_{1-6}$ alkyl, which is optionally substituted with one or more substituents independently selected from halogen, —$OR^{19b}$, —$SR^{19b}$, —N($R^{19b}$)$_2$, —C(O)$R^{19b}$, —C(O)N($R^{19b}$)$_2$, —N($R^{19b}$)C(O)$R^{19b}$, —C(O)O$R^{19b}$, —OC(O)$R^{19b}$, —N($R^{19b}$)C(O)N($R^{19b}$)$_2$, —OC(O)N($R^{19b}$)$_2$, —N($R^{19b}$)C(O)O$R^{19b}$, —S(O)$R^{19b}$, S(O)$_2R^{19b}$, —$NO_2$, ═O, ═S, ═N($R^{19b}$), —CN, $C_{3-10}$ carbocycle and 3- to 10-membered heterocycle. (74): The compound or salt of any one of embodiments 30 to 73, wherein $R^{12}$ is hydrogen or $C_{1-6}$ alkyl. (75): The compound or salt of any one of embodiments 30 to 1, wherein $R^{12}$ is hydrogen. (76): The compound or salt of any one of embodiments 30 to 42, wherein $R^{13}$ is selected from: hydrogen, halogen, —$OR^{19c}$, —$SR^{19c}$, —N($R^{19c}$)$_2$; and $C_{1-6}$ alkyl which is optionally substituted with one or more substituents independently selected from halogen, —$OR^{19c}$, —$SR^{19c}$, —N($R^{19c}$)$_2$, —$NO_2$, and —CN; and $C_{3-10}$ carbocycle which is optionally substituted with one or more substituents independently selected from halogen, —$OR^{19c}$, —$SR^{19c}$, —N($R^{19c}$)$_2$, —C(O)$R^{19c}$, —C(O)N($R^{19c}$)$_2$, —N($R^{19c}$)C(O)$R^{19c}$, —N($R^{19c}$)C(O)N($R^{19c}$)$_2$, —OC(O)N($R^{19c}$)$_2$, —N($R^{19c}$)C(O)O$R^{19}$, —C(O)OR$^1$9c —OC(O)$R^{19c}$, —S(O)$R^{19c}$, —S(O)$_2R^{19c}$, —$NO_2$, ═O—, ═S, ═N($R^{19c}$), and —CN; or $R^{13}$ together with $R^{14}$ form a 3- to 10-membered heterocycle, wherein the 3- to 10-membered heterocycle is optionally substituted with one or more $R^{19c}$. (77): The compound or salt of any one of embodiments 30 to 43, wherein $R^{13}$ is selected from: hydrogen, $C_{1-6}$ alkyl and $C_{3-10}$ carbocycle; or $R^{13}$ together with $R^{14}$ form a 3- to 10-membered heterocycle. (78): The compound or salt of any one of embodiments 30 to 44, wherein $R^{13}$ is selected from hydrogen, methyl, ethyl, —OH, —OMe, —$CF_3$, —C(H)$F_2$, —N(H)Me, and cyclopropyl. (79): The compound or salt of any one of embodiments 30 to 78, wherein $R^{13}$ is selected from hydrogen, methyl, and cyclopropyl; or $R^{13}$ together with $R^{14}$ form a pyridinyl. (80): The compound or salt of any one of embodiments 30 to 79, wherein $R^{13}$ is selected from hydrogen, methyl, and cyclopropyl. (81): The compound or salt of any one of embodiments 30 to 80, wherein $R^{13}$ is selected from hydrogen and methyl. (82): The compound or salt of any one of embodiments 30 to 81, wherein each $R^{14}$ is independently selected from: hydrogen, halogen, —$OR^{19d}$, —$SR^{19d}$, —N($R^{19d}$)$_2$; and $C_{1-6}$ alkyl which is optionally substituted with one or more substituents independently selected from halogen, —$OR^{19d}$, —$SR^{19d}$, —N($R^{19d}$)$_2$, —$NO_2$, and —CN; or $R^{13}$ together with $R^{14}$ form a $C_{3-10}$ carbocycle, or 3- to 10-membered heterocycle, wherein the $C_{3-10}$ carbocycle, or 3- to 10-membered heterocycle, is optionally substituted with one or more $R^{18c}$. (83): The compound or salt of any one of embodiments 30 to 47, wherein each $R^{14}$ is independently selected from hydrogen, $C_{1-6}$ alkyl, and halogen; or $R^{13}$ together with $R^{14}$ form a $C_{3-10}$ carbocycle, or 3- to 10-membered heterocycle. (84): The compound or salt of any one of embodiments 30 to 48, wherein each $R^{14}$ is independently selected from hydrogen, methyl, and fluoro; or $R^{13}$ together with $R^{14}$ form a pyridinyl. (85): The compound or salt of any one of embodiments 30 to 84, wherein each $R^{14}$ is independently selected from hydrogen, methyl, and fluoro. (86): The compound or salt of any one of embodiments 30 to 85, wherein each $R^{14}$ is independently selected from hydrogen and methyl. (87): The compound or salt of any one of embodiments 30 to 86, wherein each $R^{14}$ is independently selected from hydrogen. (88): The compound or salt of any one of embodiments 30 to 87, wherein $R^{15}$ is selected from: hydrogen, —$OR^{19c}$, —$SR^{19c}$, —$N(R^{19c})_2$, and $C_{1-6}$ alkyl optionally substituted with one or more $R^{18d}$; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$. (89): The compound or salt of any one of embodiments 30 to 1, wherein $R^{15}$ is selected from hydrogen and $C_{1-6}$ alkyl; or $R^{15}$ together with $R^{17a}$ form a 3- to 10-membered heterocycle, wherein the 3- to 10-membered heterocycle is optionally substituted with one or more —$OR^{19h}$ or $C_{1-3}$ alkyl; or $R^{15}$ together with $R^{17b}$ form a 3- to 10-membered heterocycle, wherein the 3- to 10-membered heterocycle is optionally substituted with one or more —$OR^{19h}$ or $C_{1-3}$ alkyl. (90): The compound or salt of any one of embodiments 30 to 55, wherein $R^{15}$ is hydrogen; or $R^{15}$ together with $R^{17a}$ is tetrahydroisoquinoline optionally substituted with —OH or methyl; or $R^{15}$ together with $R^{17b}$ is tetrahydroisoquinoline optionally substituted with —OH or methyl. (91): The compound or salt of any one of embodiments 30 to 90, wherein $R^{15}$ is hydrogen. (92): The compound or salt of any one of embodiments 30 to 91, wherein $R^{16}$ is selected from: hydrogen, halogen, —$OR^{19f}$, —$SR^{19f}$. —$N(R^{19f})_2$; and $C_{1-6}$ alkyl optionally substituted with one or more $R^{18c}$; or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$. (93): The compound or salt of any one of embodiments 30 to 58, wherein $R^{16}$ is hydrogen, $C_{1-3}$ alkyl optionally substituted with —$OR^{19h}$; or $R^{16}$ together with $R^{17a}$ form a 3- to 10-membered heterocycle, wherein the 3- to 10-membered heterocycle is optionally substituted with one or more substituents independently selected from halogen, —$OR^{19h}$, —$SR^{19h}$, —$N(R^{19h})_2$, and —CN; or $R^{16}$ together with $R^{17b}$ form a 3- to 10-membered heterocycle, wherein the 3- to 10-membered heterocycle is optionally substituted with one or more substituents independently selected from halogen, —$OR^{19h}$, —$SR^{19h}$, —$N(R^{19h})_2$, and —CN. (94): The compound or salt of any one of embodiments 30 to 1, wherein $R^{16}$ is hydrogen, $C_1$ alkyl, optionally substituted with —OH; or $R^{16}$ together with $R^{17a}$ form a dihydrobenzofuranyl or dihydrofuropyridinyl, each of which is optionally substituted with one or more substituents independently selected from —F and —CN; or $R^{16}$ together with $R^{17b}$ form a dihydrobenzofuranyl or dihydrofuropyridinyl, each of which is optionally substituted with one or more substituents independently selected from —F and —CN. (95): The compound or salt of any one of embodiments 30 to 94, wherein $R^{16}$ is hydrogen, $C_1$ alkyl, optionally substituted with —OH. (96): The compound or salt of any one of embodiments 30 to 95, wherein $R^{16}$ is hydrogen, methyl, or $CH_2OH$. (97): The compound or salt of any one of embodiments 30 to 96, wherein $R^{16}$ is methyl, or $CH_2OH$. (98): The compound or salt of any one of embodiments 30 to 97, wherein $R^{16}$ is methyl. (99): The compound or salt of any one of embodiments 30 to 98, wherein each $R^{17a}$, $R^{17b}$, $R^{17c}$, $R^{17d}$, and $R^{17e}$ is independently selected from: hydrogen, halogen, —$OR^{19g}$, and —CN; and $C_{1-6}$ alkyl and $C_{2-6}$ alkynyl, each of which is optionally substituted with one or more $R^{18f}$; or $R^5$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$. (100): The compound or salt of any one of embodiments 30 to 62, wherein each $R^{17a}$, $R^{17b}$, $R^{17c}$, $R^{17d}$, and $R^{17e}$ is independently selected from: halogen and —CN; or $R^{15}$ together with $R^{17a}$ form a 3- to 10-membered heterocycle, wherein the 3- to 10-membered heterocycle is optionally substituted with one or more $R^{18f}$; or $R^{15}$ together with $R^{17b}$ form a 3- to 10-membered heterocycle, wherein the 3- to 10-membered heterocycle is optionally substituted with one or more $R^{18f}$; or $R^{16}$ together with $R^{17a}$ form a 3- to 10-membered heterocycle, wherein the 3- to 10-membered heterocycle is optionally substituted with one or more $R^{18f}$; or $R^{16}$ together with $R^{17b}$ form a 3- to 10-membered heterocycle, wherein the 3- to 10-membered heterocycle is optionally substituted with one or more $R^{18f}$. (101): The compound or salt of any one of embodiments 30 to 1, wherein each $R^{17a}$, $R^{17b}$, $R^{17c}$, $R^{17d}$, and $R^{17e}$ is independently selected from —F, and —CN; or $R^{15}$ together with $R^{17a}$ is tetrahydroisoquinoline optionally substituted with —OH; or methyl or $R^{16}$ together with $R^{17a}$ form a dihydrobenzofuranyl or dihydrofuropyridinyl optionally substituted with one or more —F or —CN. (102): The compound or salt of any one of embodiments 30 to 101, wherein each $R^{17a}$, $R^{17b}$, $R^{17c}$, $R^{17d}$, and $R^{17e}$ is independently selected from —F, and —CN; or $R^{15}$ together with $R^{17b}$ is tetrahydroisoquinoline optionally substituted with —OH; or methyl or $R^{16}$ together with $R^{17b}$ form a dihydrobenzofuranyl or dihydrofuropyridinyl optionally substituted with one or more —F or —CN. (103): The compound or salt of any one of embodiments 30 to 102, wherein each $R^{17a}$, $R^{17b}$, $R^{17c}$, $R^{17d}$, and $R^{17e}$ is independently selected from hydrogen, methyl, —CCH, —F, and —CN. (104): The compound or salt of any one of embodiments 30 to 103, wherein each $R^{17a}$, $R^{17b}$, $R^{17c}$, $R^{17d}$, and $R^{17e}$ is independently selected from hydrogen, methyl, —CCH, —F, and —CN. (105): The compound or salt of any one of embodiments 30 to 104, wherein each $R^{17a}$, $R^{17b}$, $R^{17c}$, $R^{17d}$, and $R^{17e}$ is independently selected from hydrogen, methyl, —F, and —CN. (106): The compound or salt of any one of embodiments 30 to 105, wherein each $R^{17a}$, $R^{17b}$, $R^{17c}$, $R^{17d}$, and $R^{17e}$ is independently selected from hydrogen, —F, and —CN. (107): The compound or salt of any one of embodiments 30 to 106, wherein each $R^{17a}$, $R^{17b}$, $R^{17c}$, $R^{17d}$, and $R^{17e}$ is independently selected from —F and hydrogen. (108): The compound or salt of any one of embodiments 30 to 107, wherein each $R^{17a}$, $R^{17b}$, $R^{7c}$, $R^{17d}$, and $R^{17e}$ is independently selected from —CN and hydrogen. (109): The compound or salt of any one of embodiments 30 to 108, wherein each $R^{17a}$, $R^{17b}$, $R^{17c}$, $R^{17d}$, and $R^{17e}$ is independently selected from hydrogen. (110): The compound or salt of any one of embodiments 30 to 109, wherein each $R^{17a}$ is independently selected from hydrogen, methyl, —CCH, —F, and —CN. (111): The compound or salt of any one of embodiments 30 to 110, wherein each $R^{17a}$ is independently selected from hydrogen, methyl, —CCH, —F, and —CN. (112): The compound or salt of any one of embodiments 30 to 111, wherein each $R^{17a}$ is independently selected from hydrogen, methyl, —F, and —CN. (113): The compound or salt of any one of embodiments 30 to 112, wherein each $R^{17a}$ is independently selected from hydrogen, —F, and —CN. (114): The compound or salt of any one of embodiments 30 to 113, wherein each $R^{17a}$ is independently selected from —F and hydrogen. (115): The compound or salt of any one of embodiments 30 to 114, wherein each $R^{17a}$ is independently selected from —CN and hydrogen. (116): The compound or salt of any one of embodiments 30 to 115, wherein each $R^{17a}$ is independently selected from hydrogen. (117): The compound or salt of any one of embodiments 30 to 116, wherein each $R^{17b}$ is independently selected from hydrogen, methyl, —CCH, —F, and —CN. (118): The compound or salt of any one of embodiments 30 to 117, wherein each $R^{17b}$ is independently selected from hydrogen, methyl, —CCH, —F, and —CN. (119): The compound or salt of any one of embodiments 30 to 118, wherein each $R^{17b}$ is independently selected from hydrogen, methyl, —F, and —CN. (120): The compound or salt of any one of embodiments 30 to 119, wherein each $R^{17b}$ is independently selected from hydrogen, —F, and —CN. (121): The compound or salt of any one of embodiments 30 to 120, wherein each $R^{17b}$ is independently selected from —F and hydrogen. (122): The compound or salt of any one of embodiments 30 to 121, wherein each $R^{17b}$ is independently selected from —CN and hydrogen. (123): The compound or salt of any one of embodiments 30 to 122, wherein each $R^{17b}$ is independently selected from hydrogen. (124): The compound or salt of any one of embodiments 30 to 123, wherein each $R^{17c}$ is independently selected from hydrogen, methyl, —CCH, —F, and —CN. (125): The compound or salt of any one of embodiments 30 to 124, wherein each $R^{17c}$ is independently selected from hydrogen, methyl, —CCH, —F, and —CN. (126): The compound or salt of any one of embodiments 30 to 125, wherein each $R^{17c}$ is independently selected from hydrogen, methyl, —F, and —CN. (127): The compound or salt of any one of embodiments 30 to 126, wherein each $R^{17'}$ is independently selected from hydrogen, —F, and —CN. (128): The compound or salt of any one of embodiments 30 to 127, wherein each $R^{17c}$, is independently selected from —F and hydrogen. (129): The compound or salt of any one of embodiments 30 to 128, wherein each $R^{17}$, is independently selected from —CN and hydrogen. (130): The compound or salt of any one of embodiments 30 to 129, wherein each $R^{17c}$ is independently selected from hydrogen. (131): The compound or salt of any one of embodiments 30 to 130, wherein each $R^{17d}$ is independently selected from hydrogen, methyl, —CCH, —F, and —CN. (132): The compound or salt of any one of embodiments 30 to 131, wherein each $R^{17d}$ is independently selected from hydrogen, methyl, —CCH, —F, and —CN. (133): The compound or salt of any one of embodiments 30 to 132, wherein each $R^{17d}$ is independently selected from hydrogen, methyl, —F, and —CN. (134): The compound or salt of any one of embodiments 30 to 133, wherein each $R^{17d}$ is independently selected from hydrogen, —F, and —CN. (135): The compound or salt of any one of embodiments 30 to 134, wherein each $R^{17d}$ is independently selected from —F and hydrogen. (136): The compound or salt of any one of embodiments 30 to 135, wherein each $R^{17d}$ is independently selected from —CN and hydrogen. (137): The compound or salt of any one of embodiments 30 to 136, wherein each $R^{17d}$ is independently selected from hydrogen. (138): The compound or salt of any one of embodiments 30 to 137, wherein each $R^{17e}$ is independently selected from hydrogen, methyl, —CCH, —F, and —CN. (139): The compound or salt of any one of embodiments 30 to 138, wherein each $R^{17e}$ is independently selected from hydrogen, methyl, —CCH, —F, and —CN. (140): The compound or salt of any one of embodiments 30 to 139, wherein each $R^{17e}$ is independently selected from hydrogen, methyl, —F, and —CN. (141): The compound or salt of any one of embodiments 30 to 140, wherein each $R^{17}$, is independently selected from hydrogen, —F, and —CN. (142): The compound or salt of any one of embodiments 30 to 141, wherein each $R^{17e}$ is independently selected from —F and hydrogen. (143): The compound or salt of any one of embodiments 30 to 142, wherein each $R^{17e}$ is independently selected from —CN and hydrogen. (144): The compound or salt of any one of embodiments 30 to 143, wherein each $R^{17e}$ is independently selected from hydrogen. (145): The compound or salt of any one of embodiments 30 to 144, wherein $R^{16}$ and $R^{17a}$ are taken together to form a $C_{3-10}$ carbocycle or 3- to 10-membered heterocycle, each of which is optionally substituted with one or more substituents selected from halogen and CN. (146): The compound or salt of any one of embodiments 30 to 145, wherein $R^{16}$ and $R^{17a}$ are taken together to form a $C_{3-10}$ carbocycle or 3- to 10-membered heterocycle, each of which is optionally substituted with one or more substituents selected from fluoro and CN. (147): The compound or salt of any one of embodiments 30 to 146, wherein $R^{16}$ and $R^{17a}$ are taken together to form a 3- to 10-membered heterocycle, each of which is optionally substituted with one or more substituents selected from —CN. (148): The compound or salt of any one of embodiments 30 to 147, wherein $R^{16}$ and $R^{17}$ are taken together to form a $C_{3-10}$ carbocycle or 3- to 10-membered heterocycle, each of which is optionally substituted with one or more substituents selected from halogen and —CN. (149): The compound or salt of any one of embodiments 30 to 149, wherein $R^{16}$ and $R^{17}$ are taken together to form a $C_{3-10}$ carbocycle or 3- to 10-membered heterocycle, each of which is optionally substituted with one or more substituents selected from fluoro and —CN. (150): The compound or salt of any one of embodiments 30 to 149, wherein $R^{16}$ and $R^{17b}$ are taken together to form a $C_{3-10}$ carbocycle or 3- to 10-membered heterocycle, each of which is optionally substituted with one or more substituents selected from —CN. (151): The compound or salt of any one of embodiments 30 to 150, wherein $R^{16}$ and $R^{17a}$ are taken together to form a 3- to 10-membered heterocycle selected from

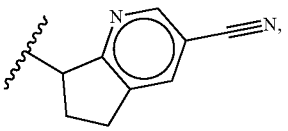
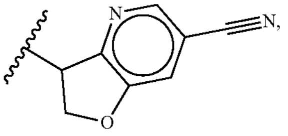
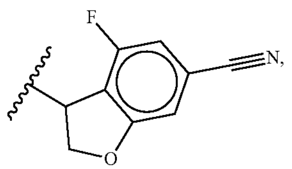
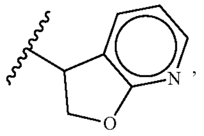

-continued
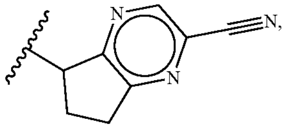
and
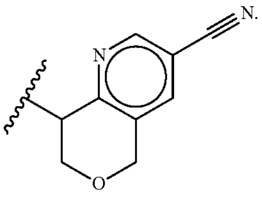
The compound or salt of any one of embodiments 30 to 151, wherein $R^{16}$ and $R^{17b}$ are taken together to form a 3- to 10-membered heterocycle selected from
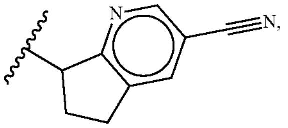
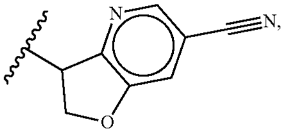
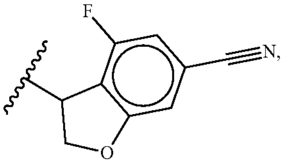
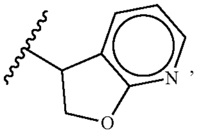
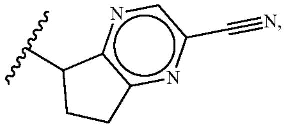
and
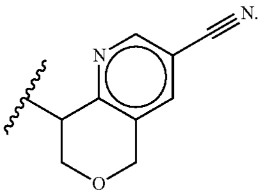
(153): The compound or salt of any one of embodiments 30 to 152, selected from:
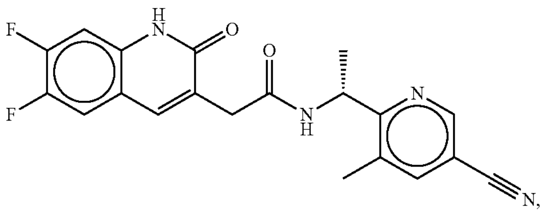
-continued
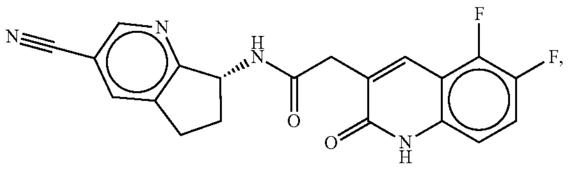
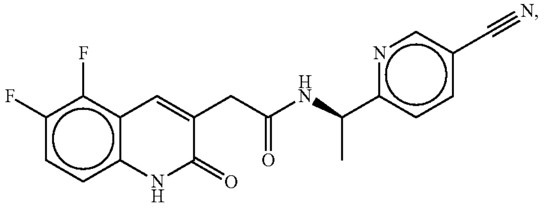
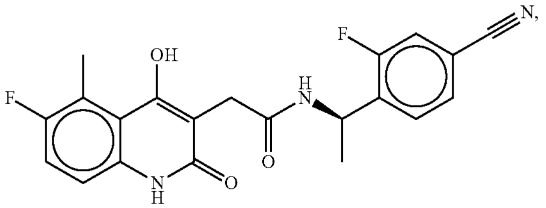
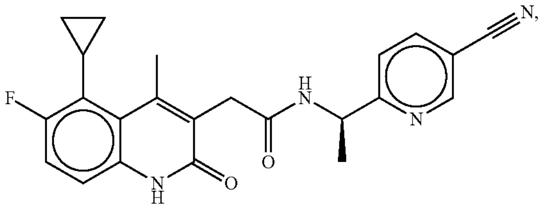
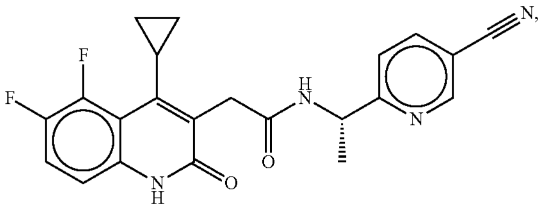
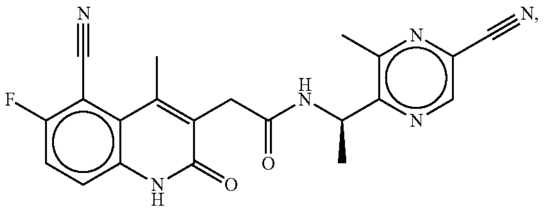
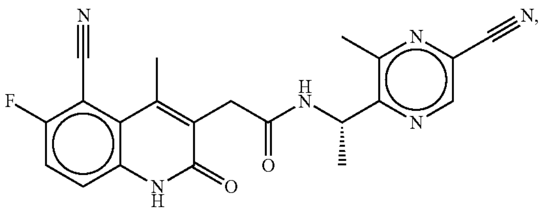
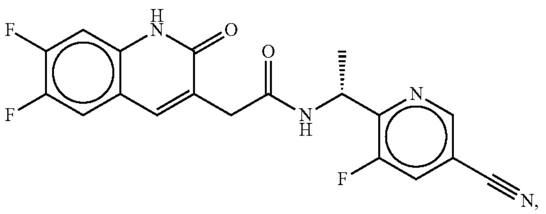

-continued
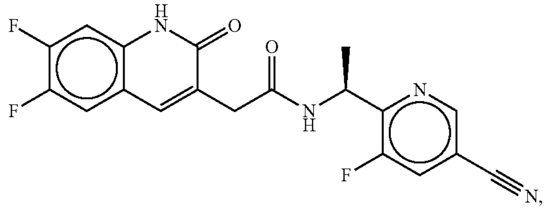
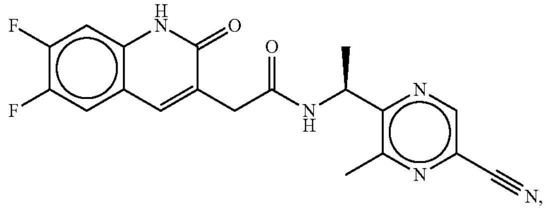
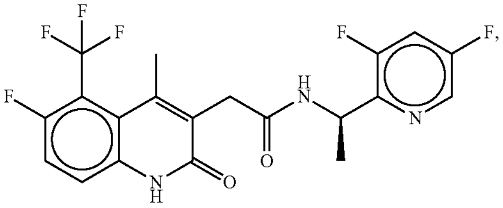
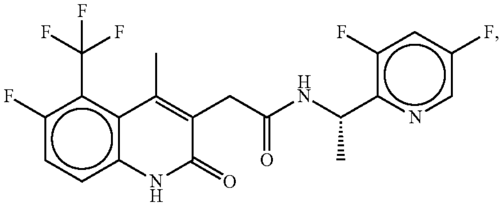
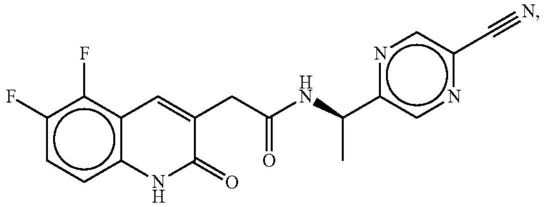
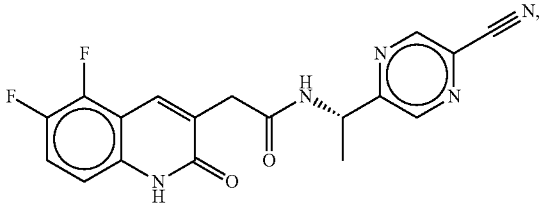
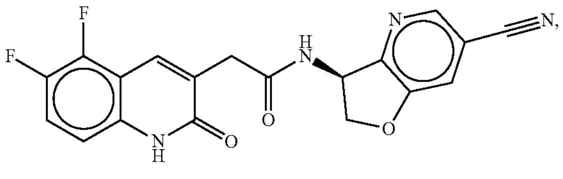
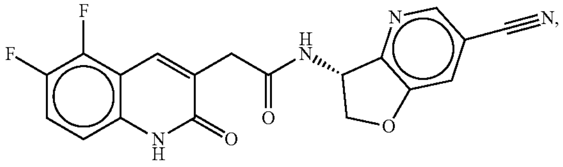
-continued
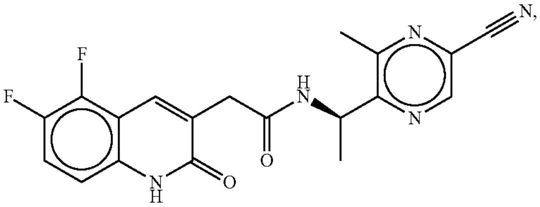
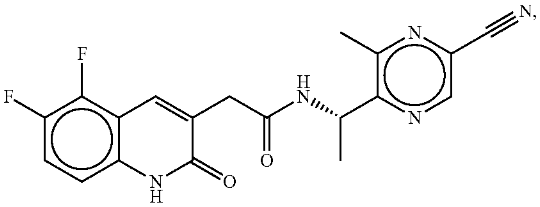
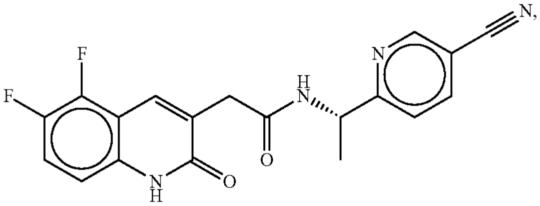
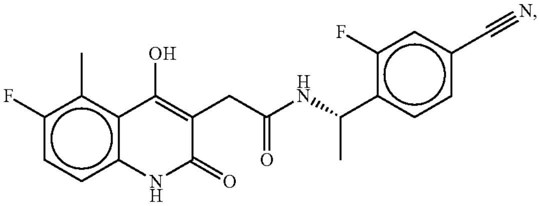
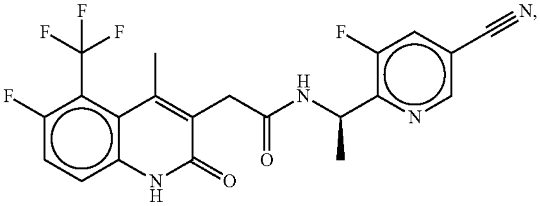
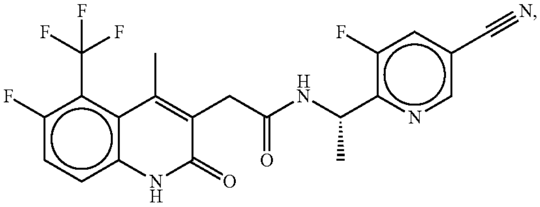
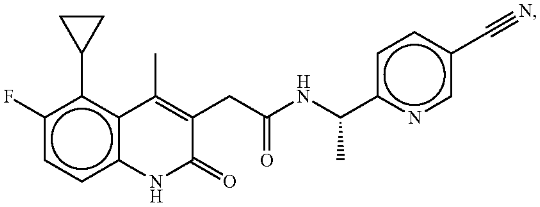
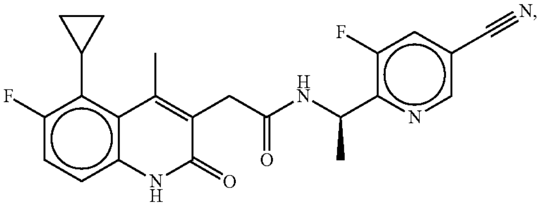

-continued
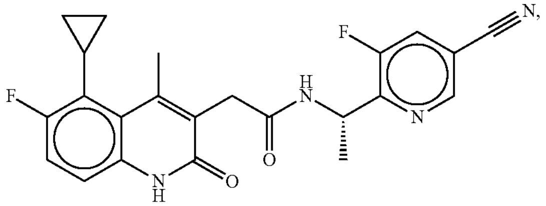
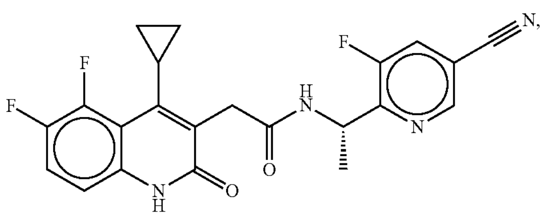
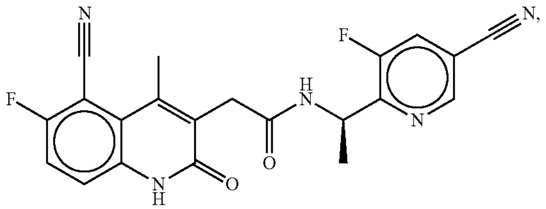
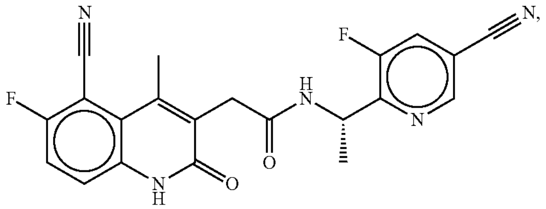
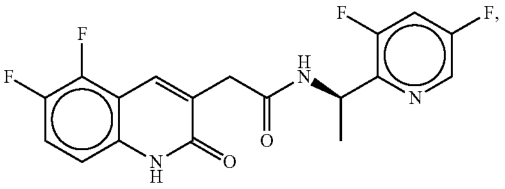
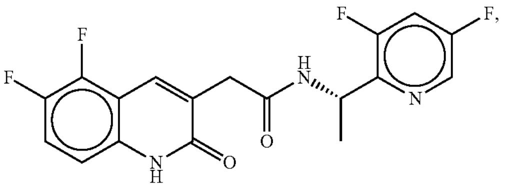
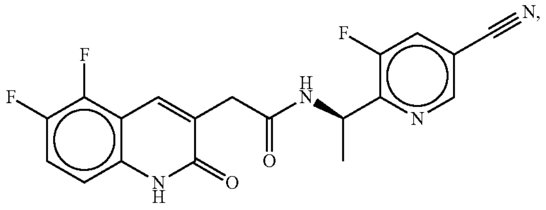
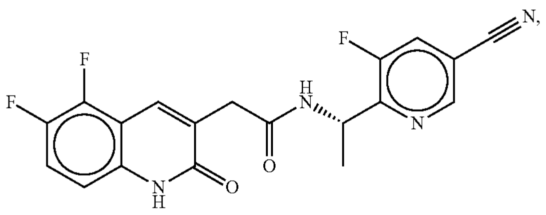
-continued
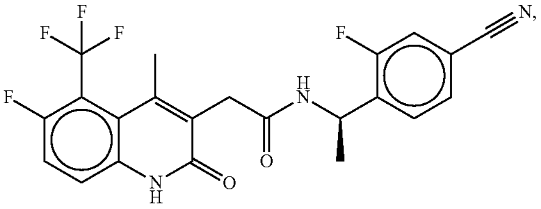
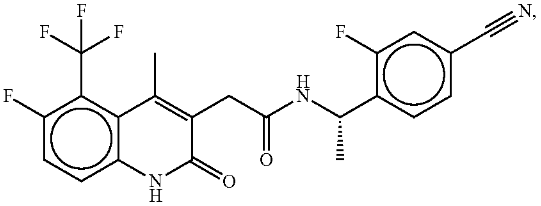
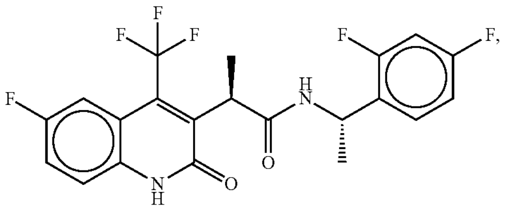
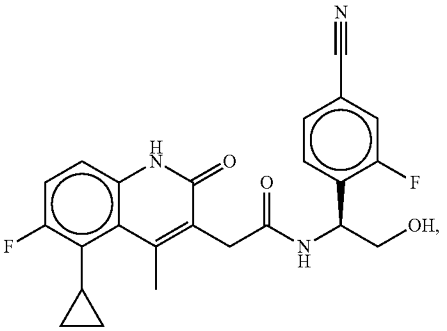
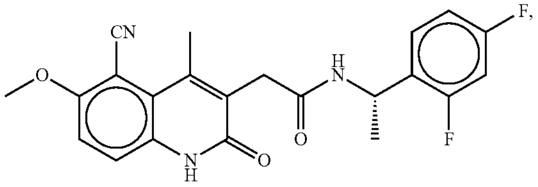
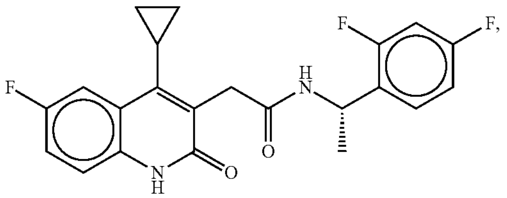
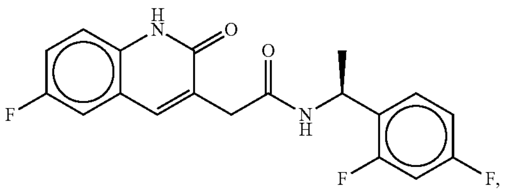
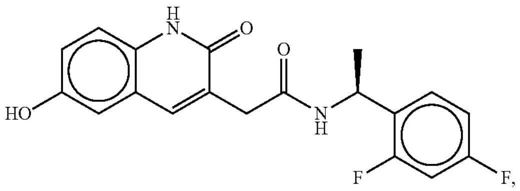

-continued
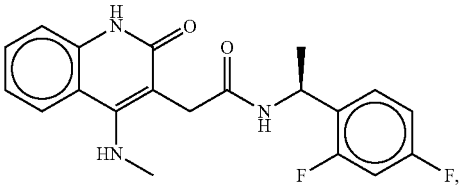
,
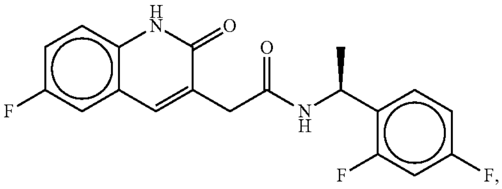
,
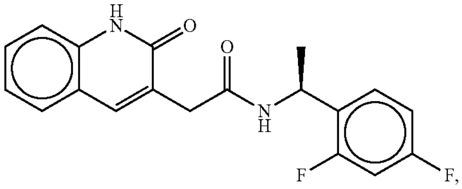
,
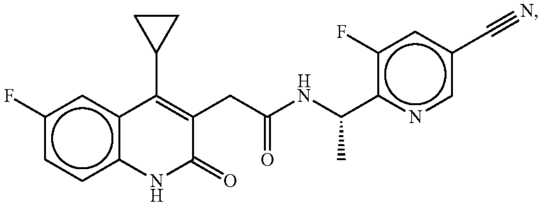
,
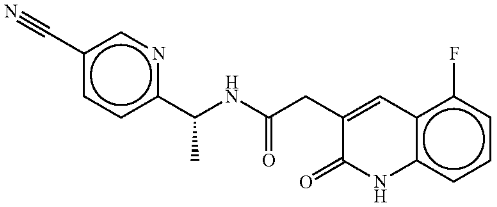
,
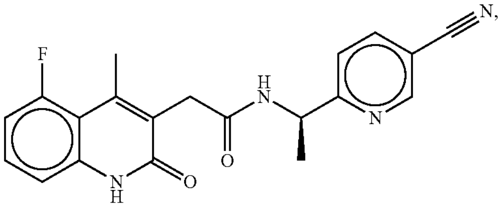
,
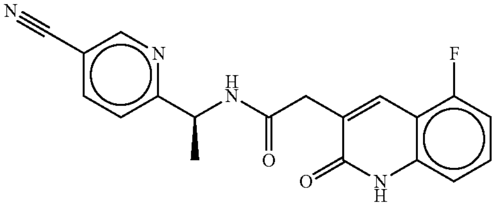
,
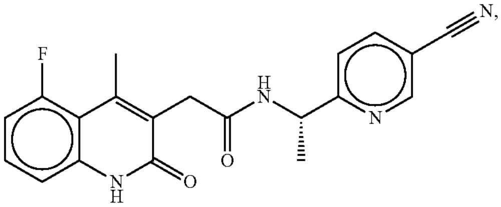
,
-continued
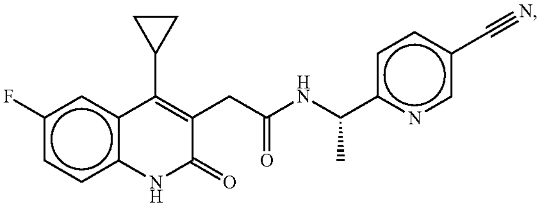
,
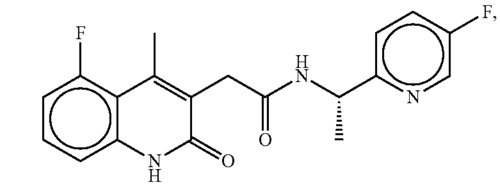
,
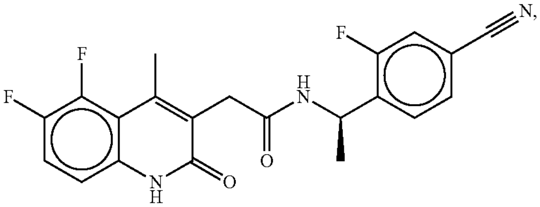
,
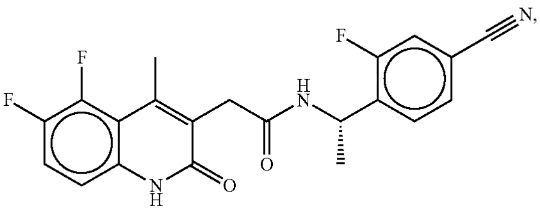
,
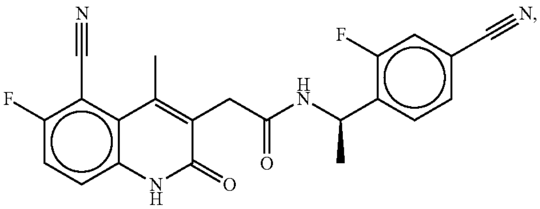
,
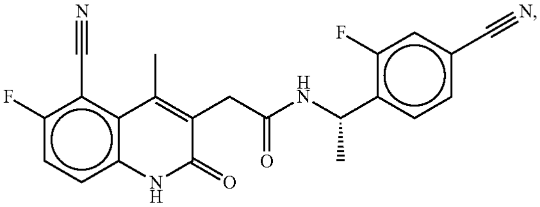
,
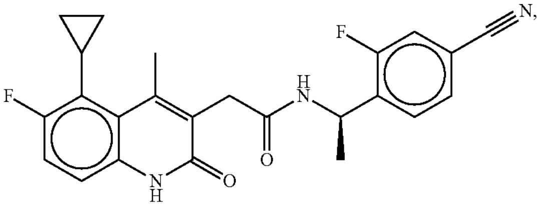
, -continued
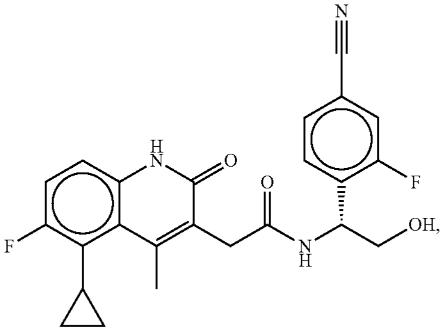
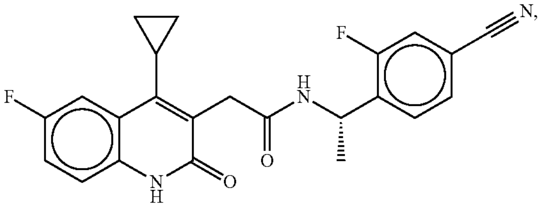
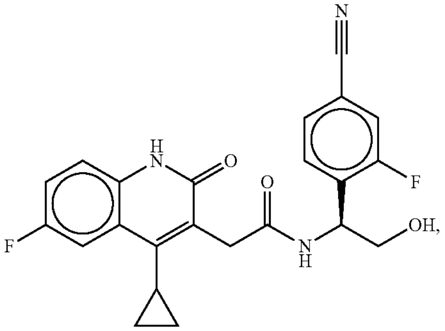
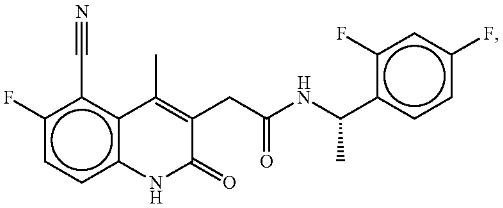
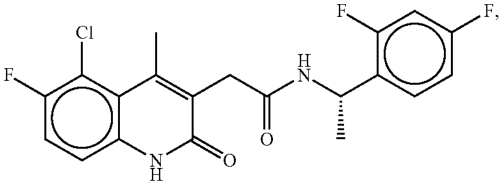
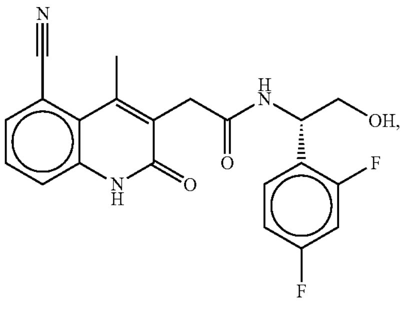
-continued
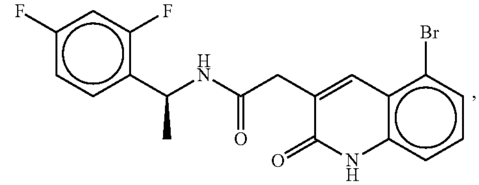
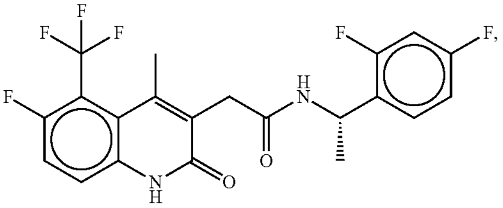
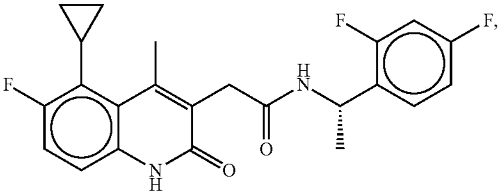
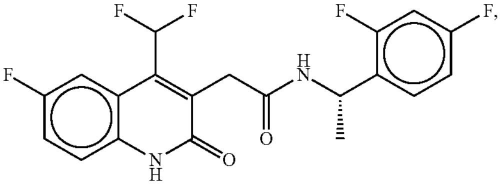
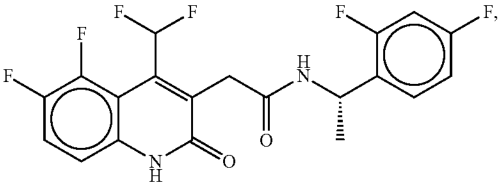
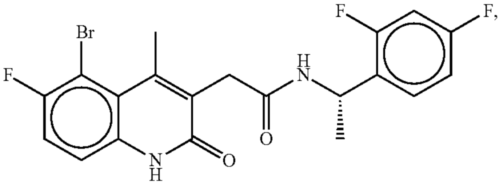
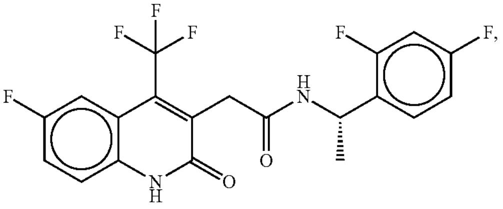
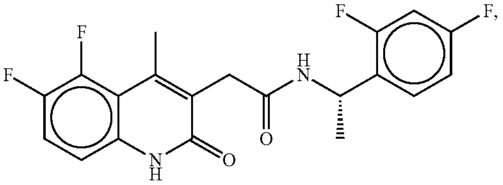
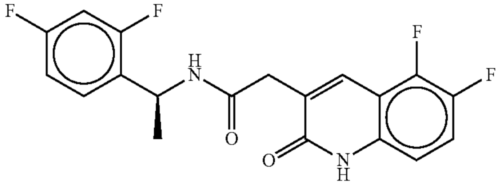

-continued
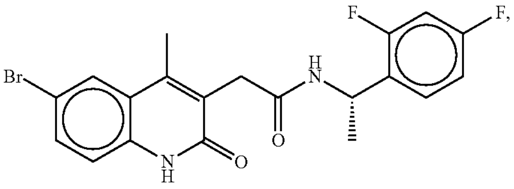
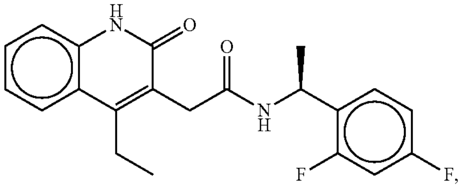
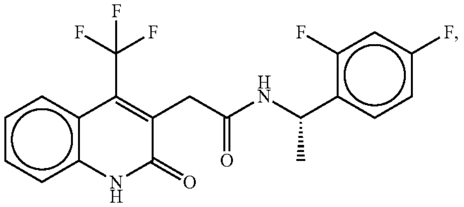
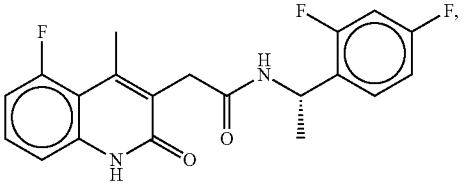
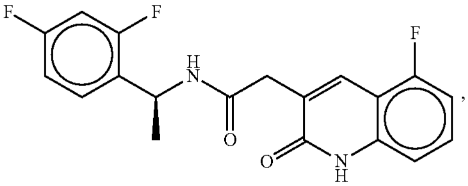
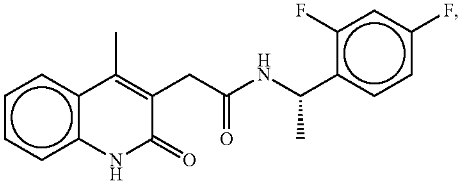
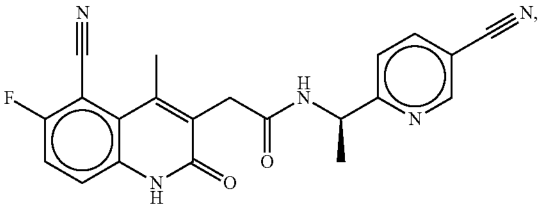
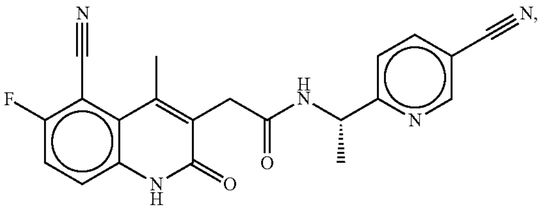
-continued
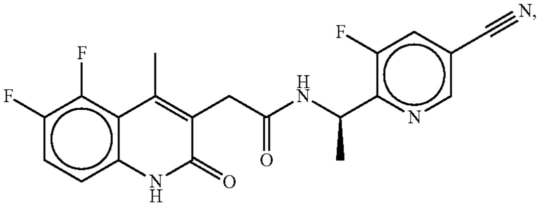
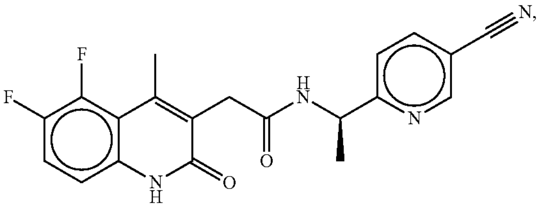
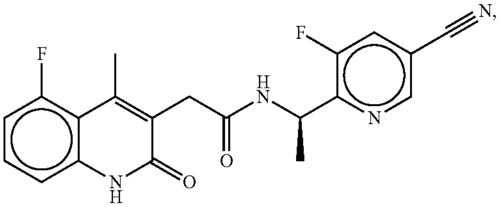
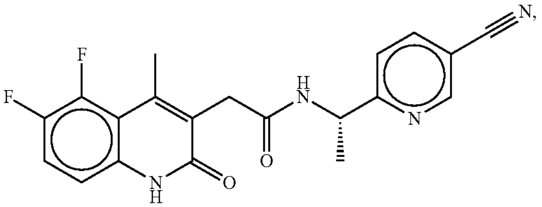
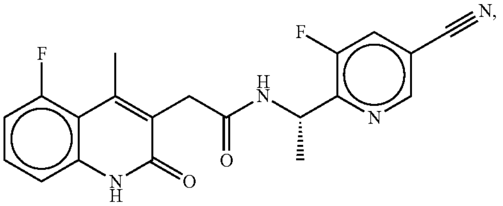
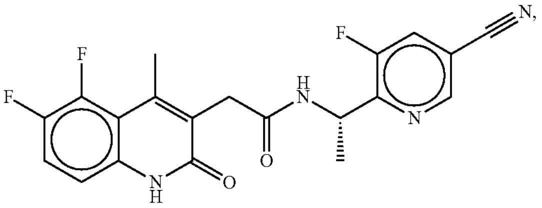
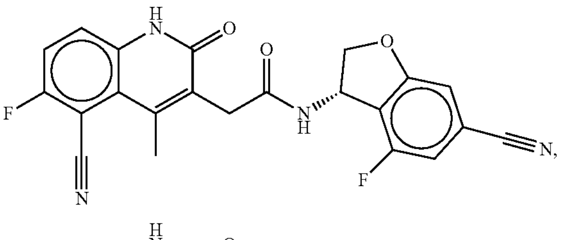
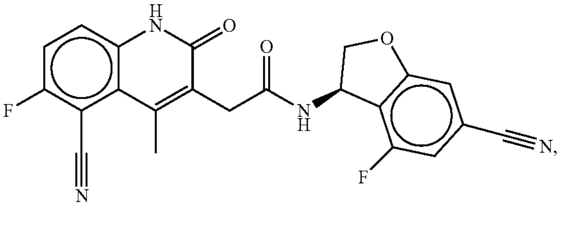

-continued
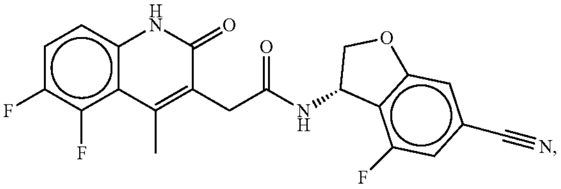
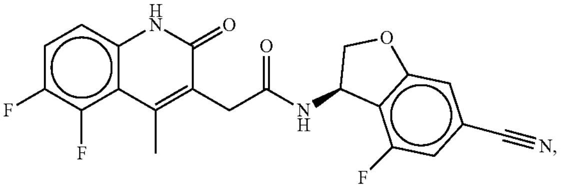
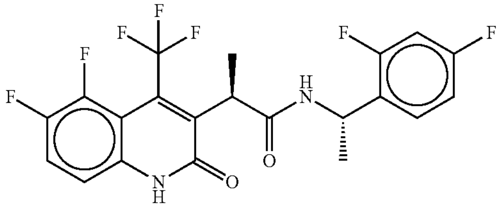
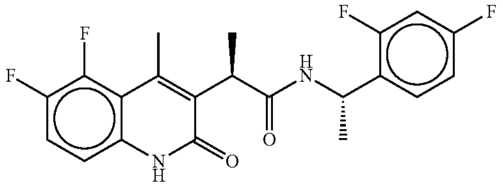
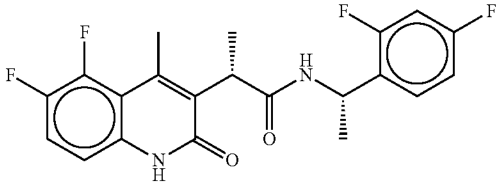
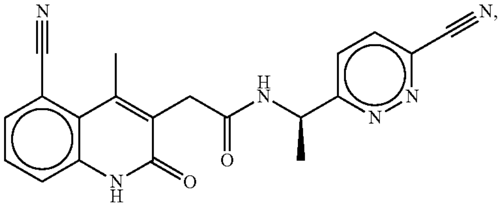
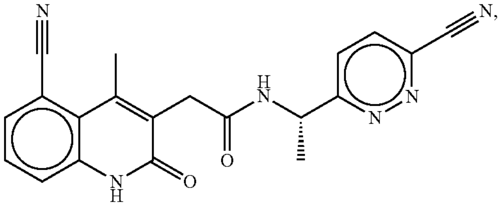
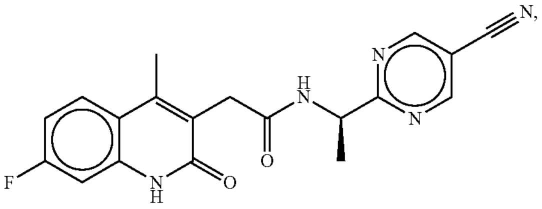
-continued
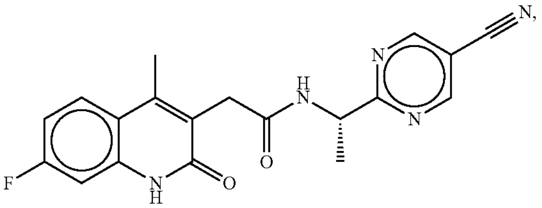
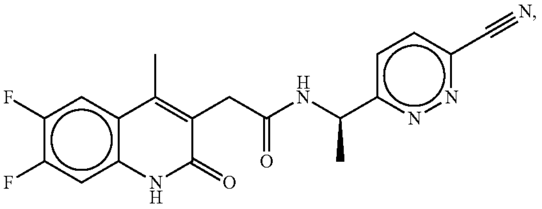
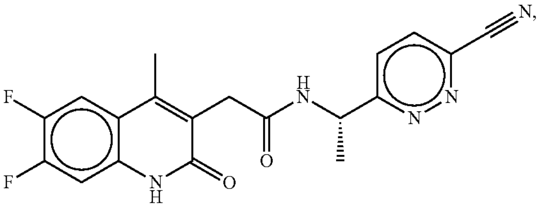
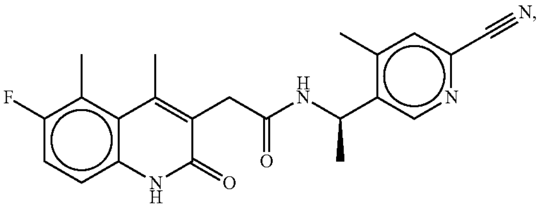
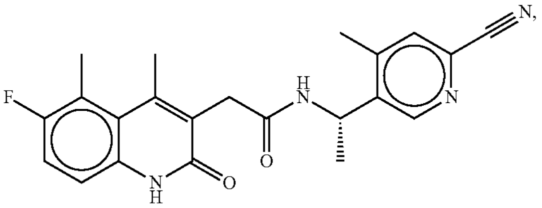
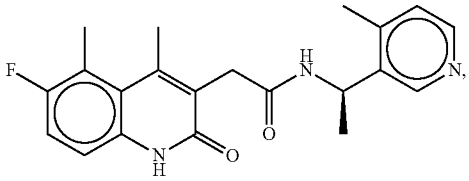
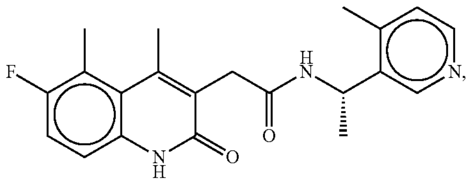
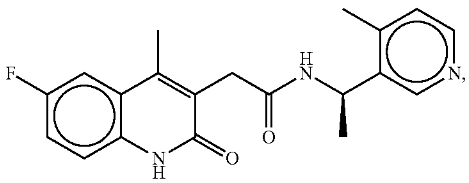

-continued
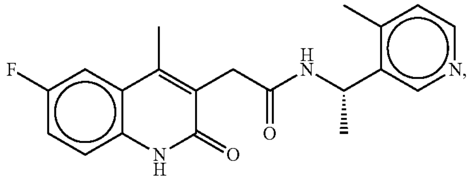
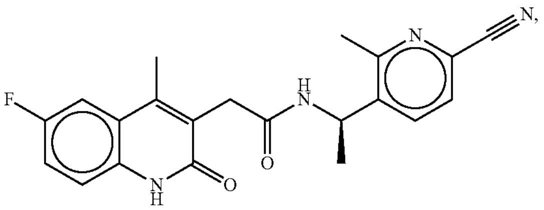
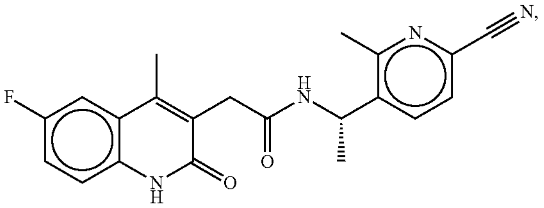
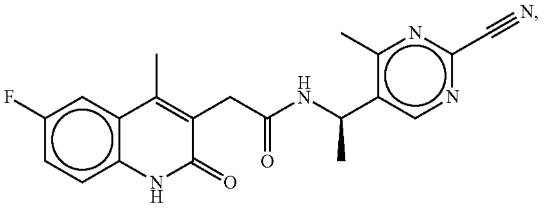
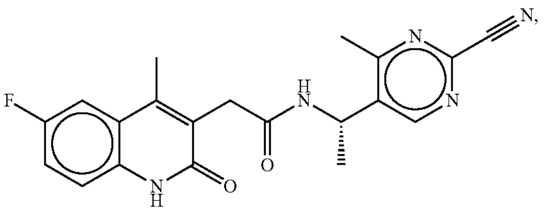
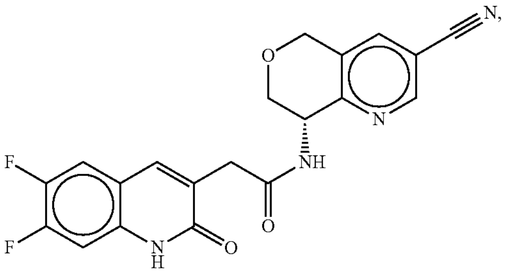
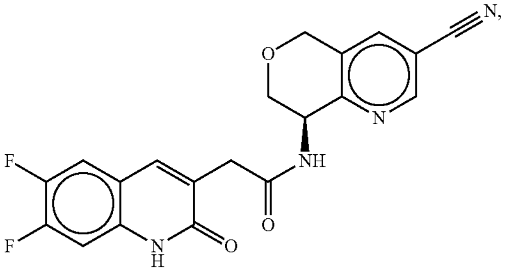
-continued
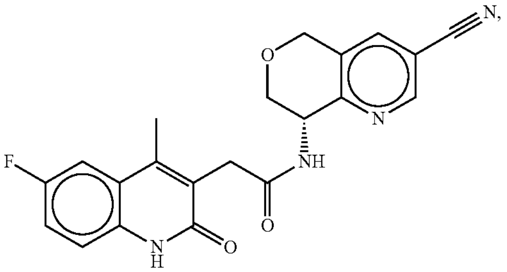
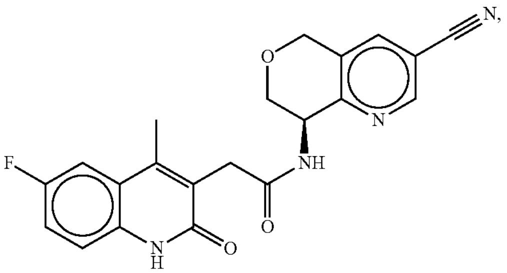
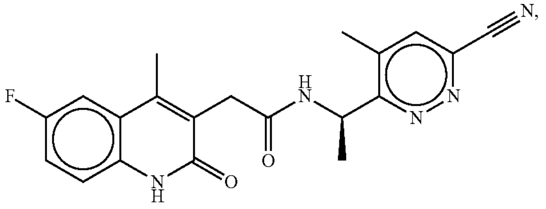
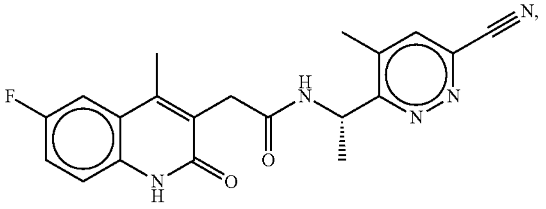
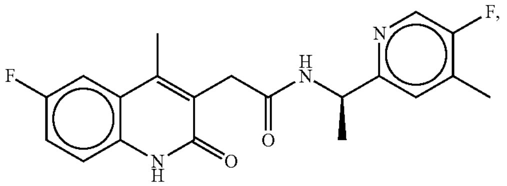
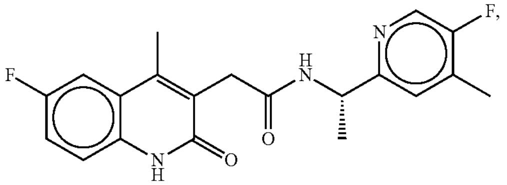
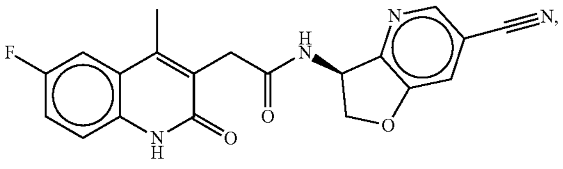
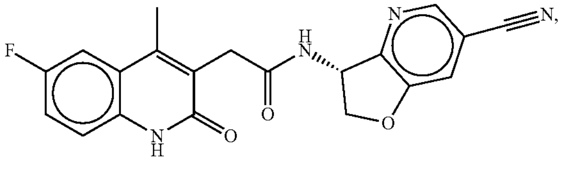

-continued
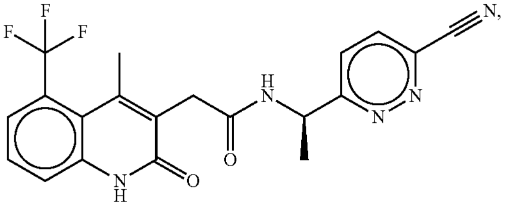,
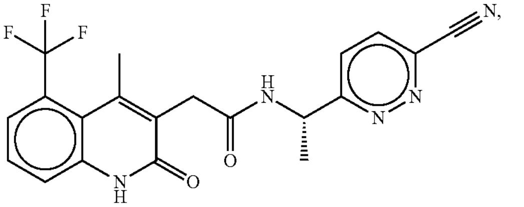,
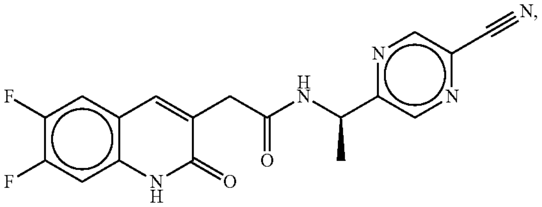,
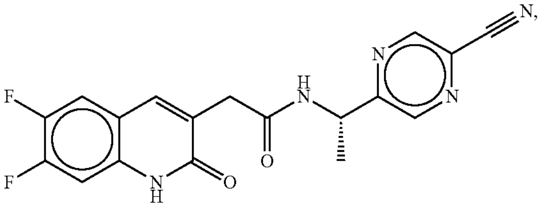,
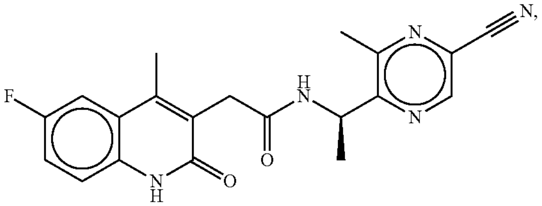,
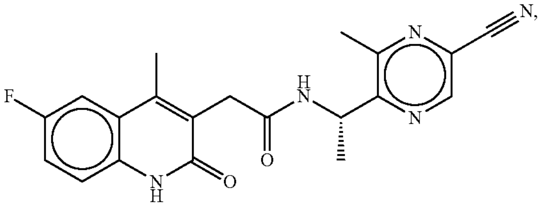,
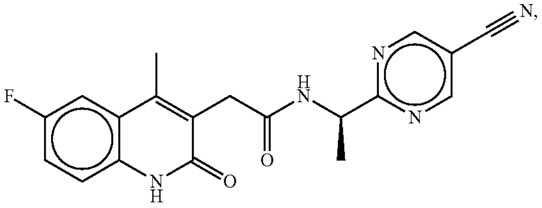,
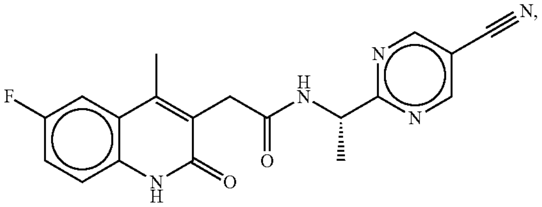,
-continued
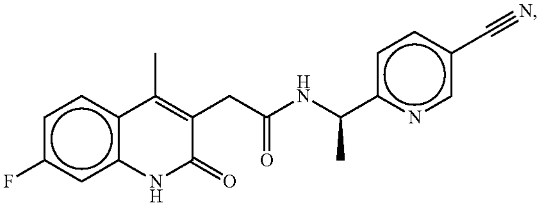,
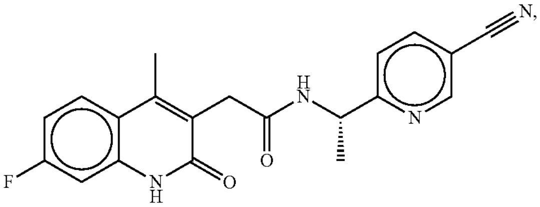,
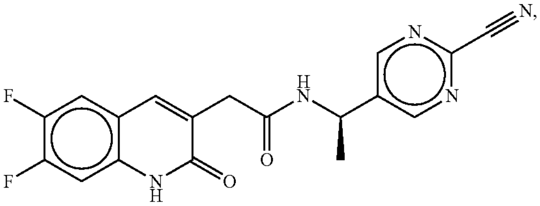,
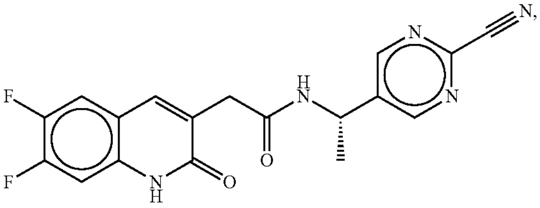,
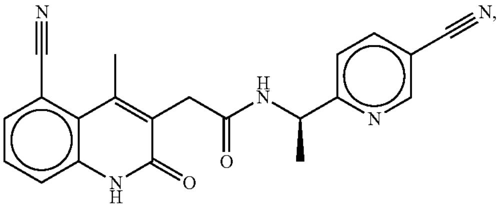,
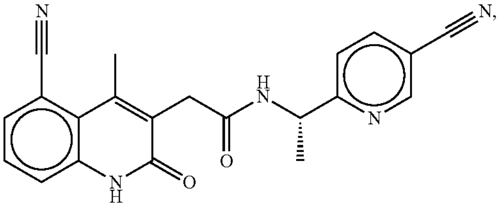,
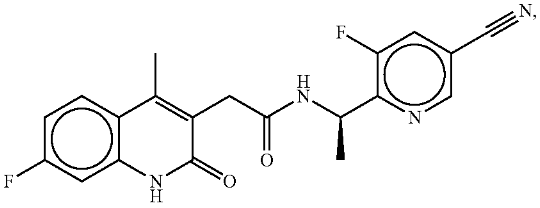,
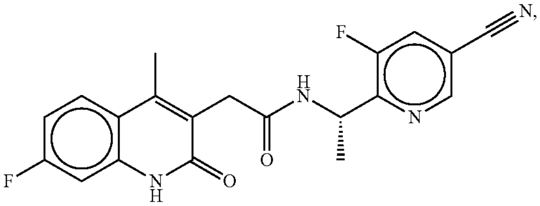, -continued
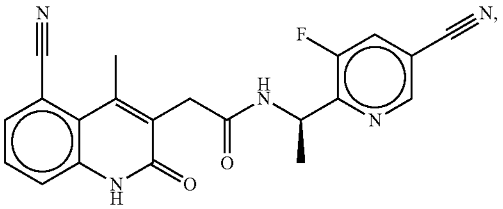
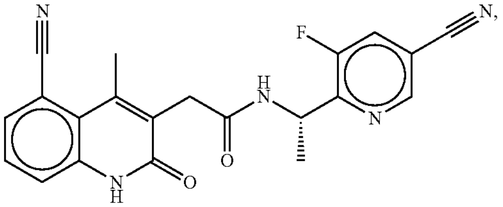
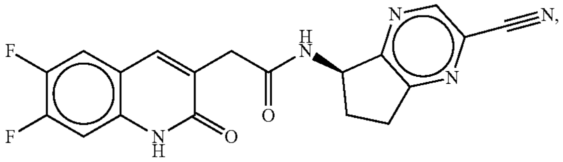
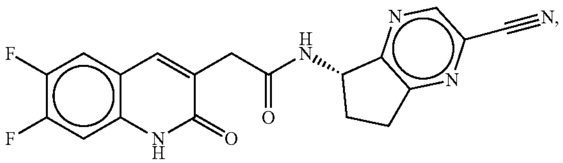
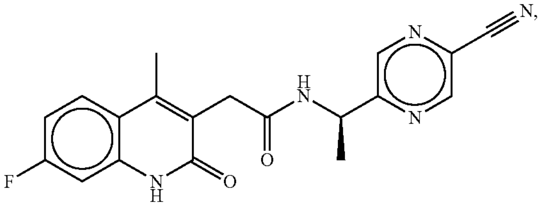
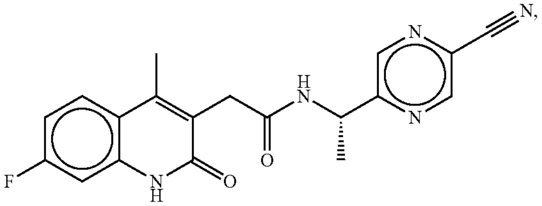
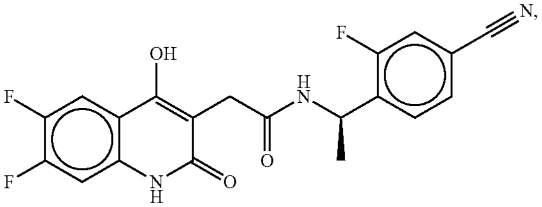
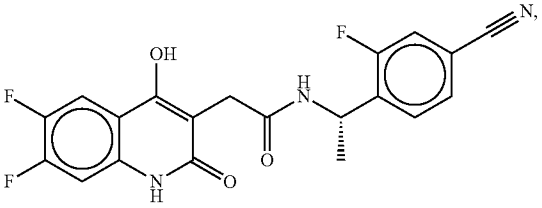
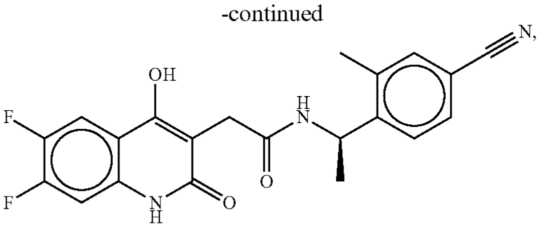
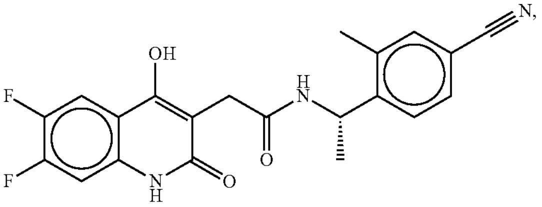
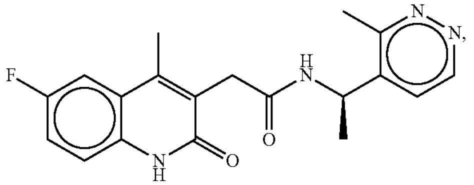
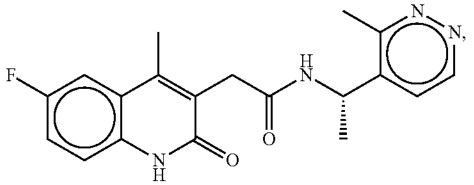
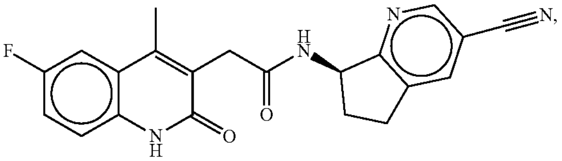
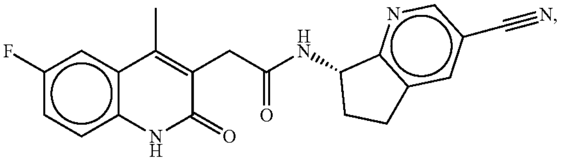
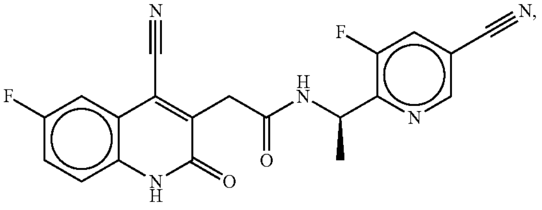
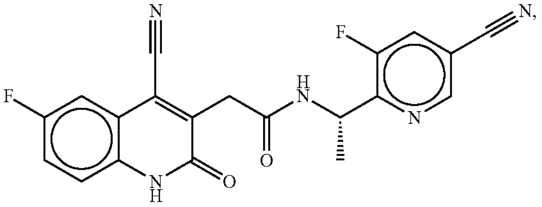
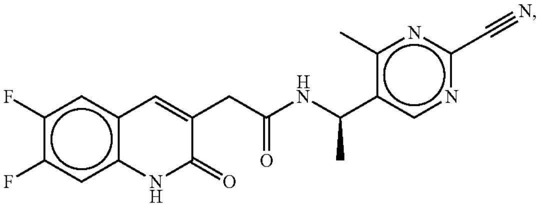

-continued
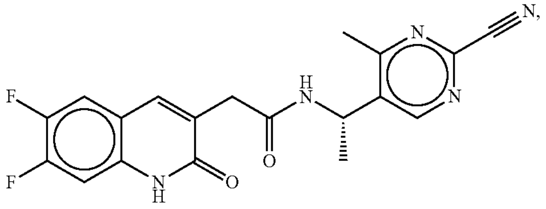
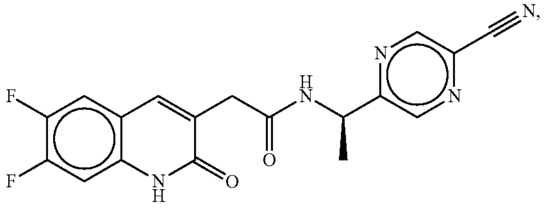
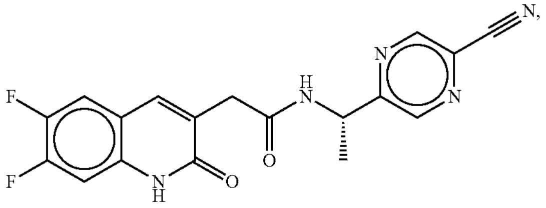
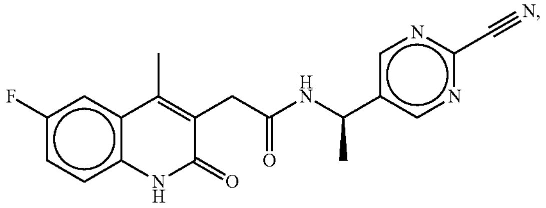
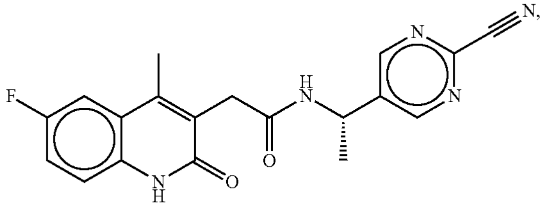
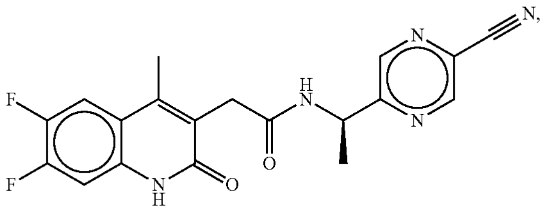
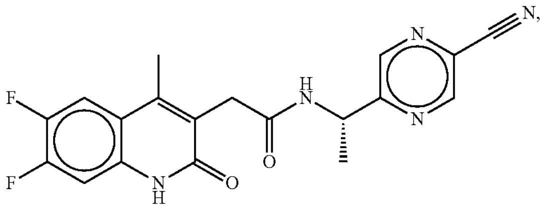
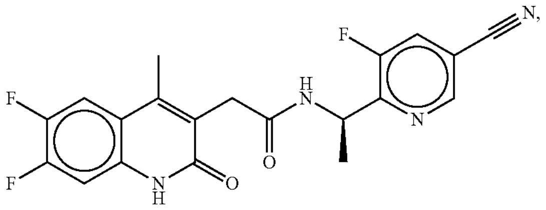
-continued
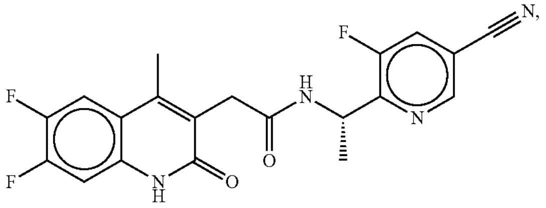
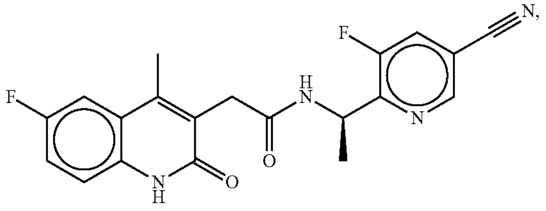
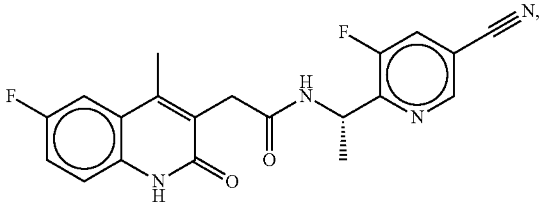
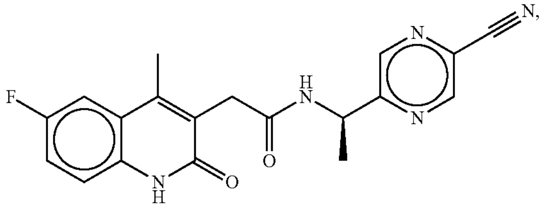
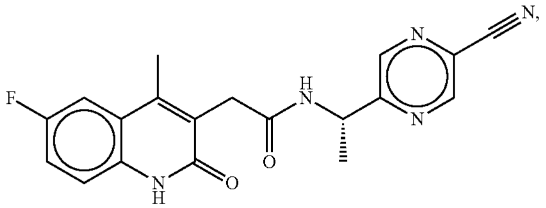
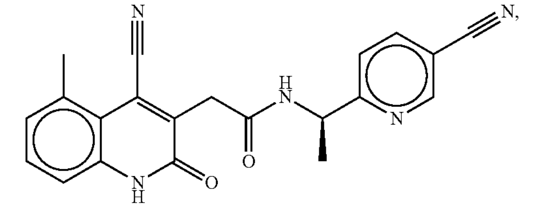
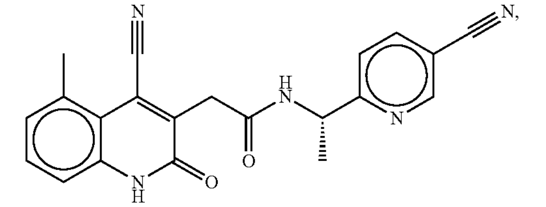
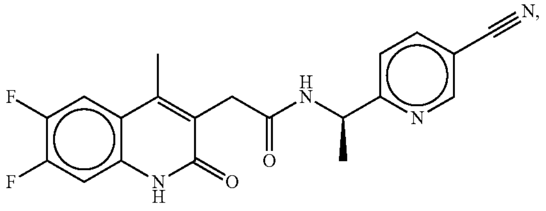

-continued
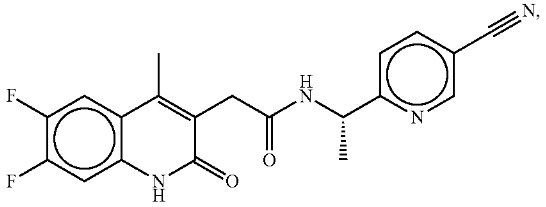
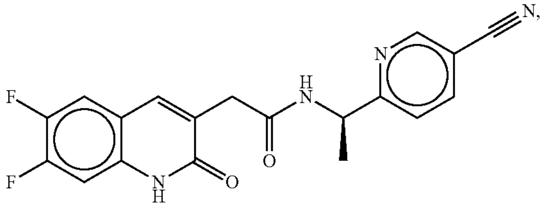
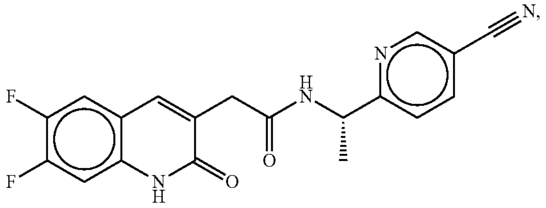
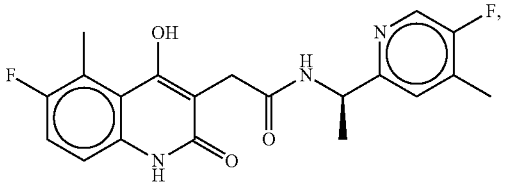
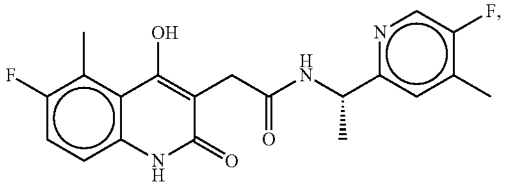
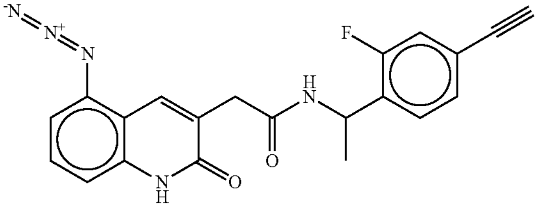
,
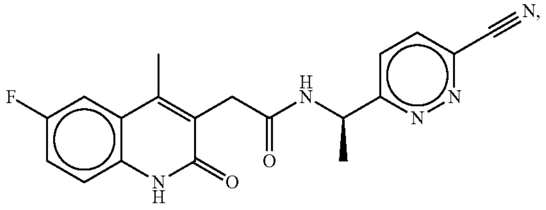
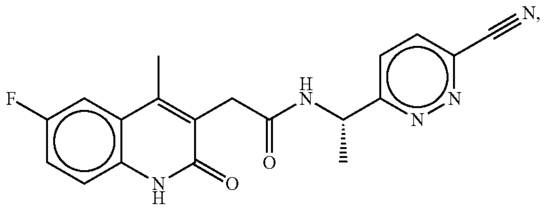
-continued
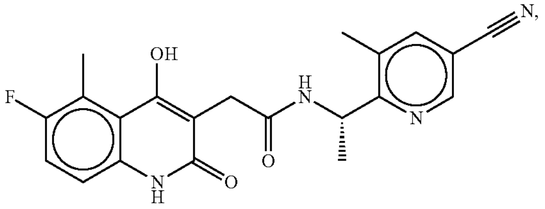
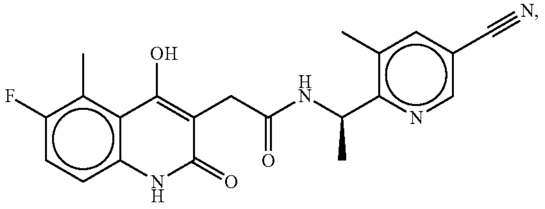
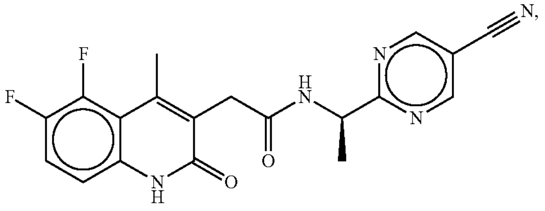
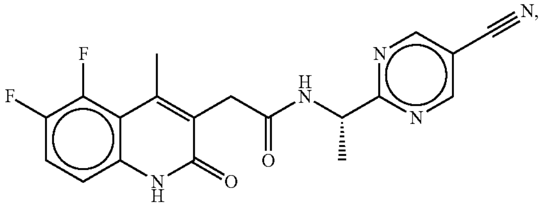
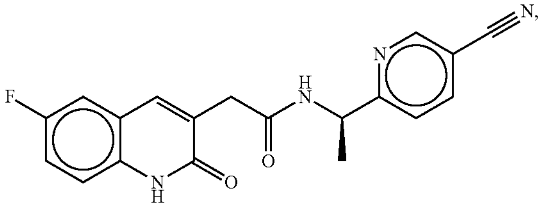
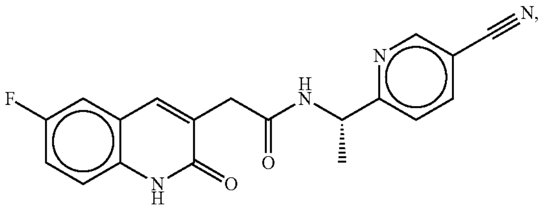
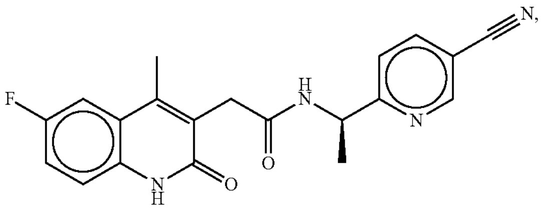
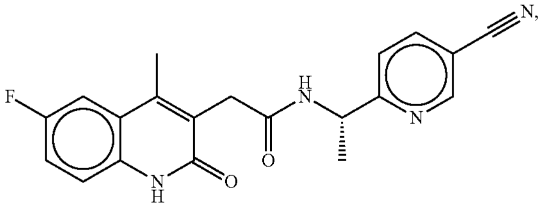

-continued
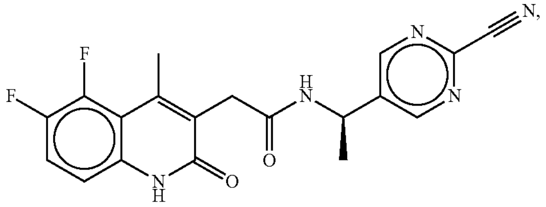
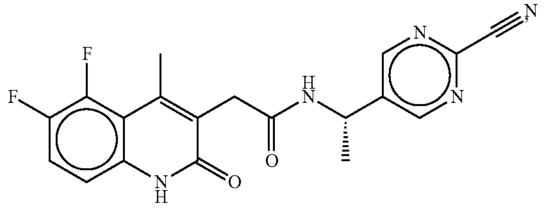
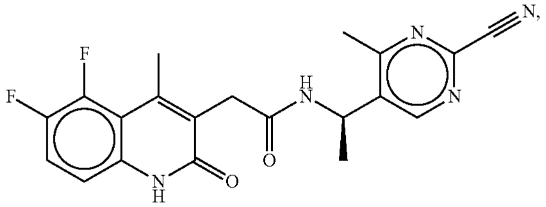
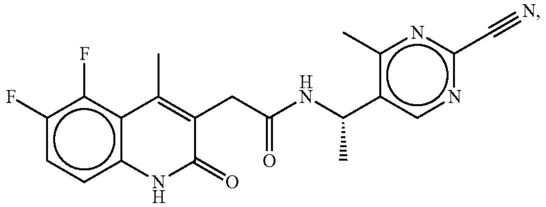
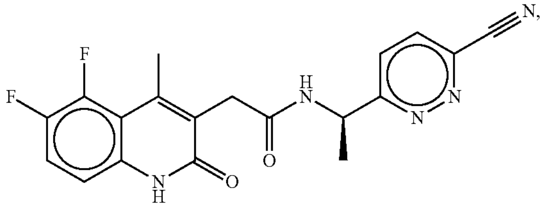
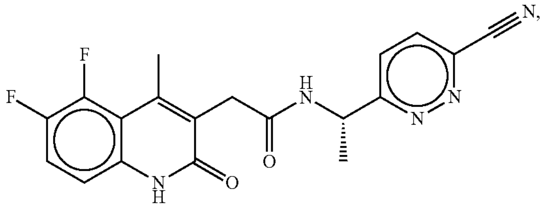
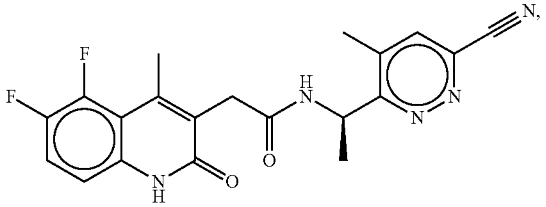
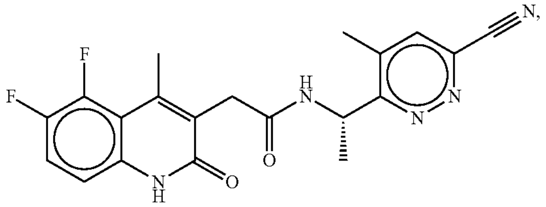
-continued
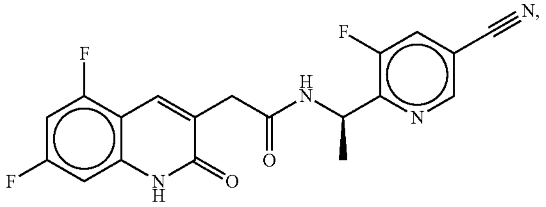
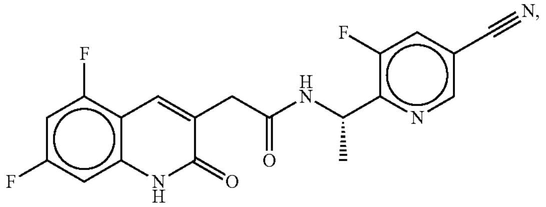
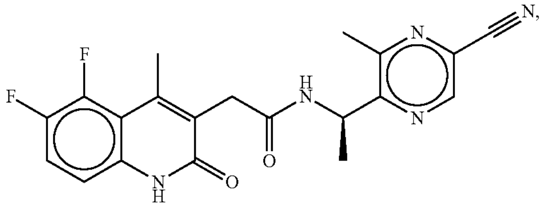
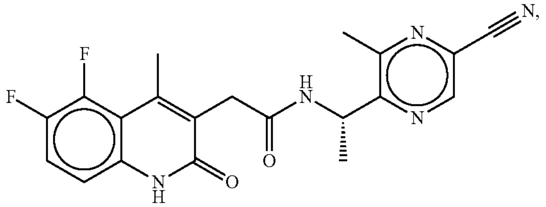
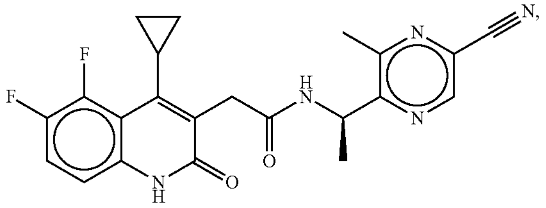
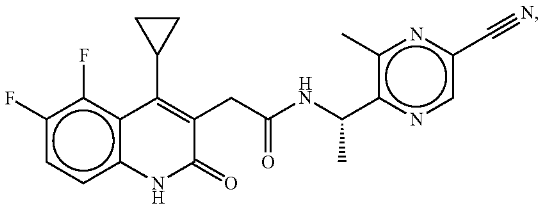
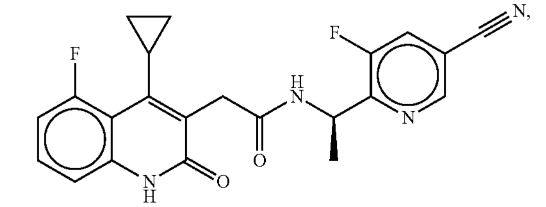
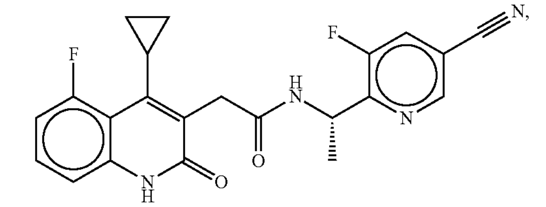

-continued
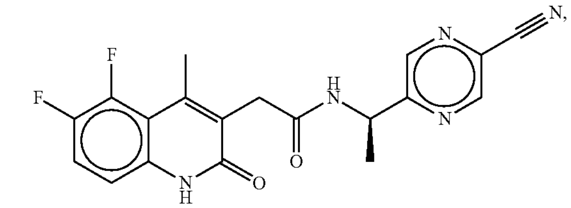
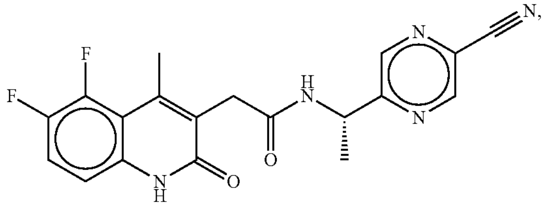
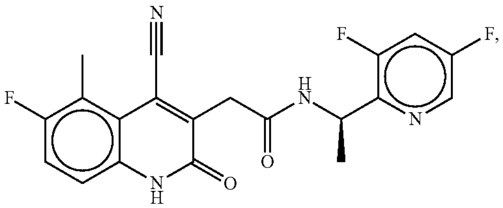
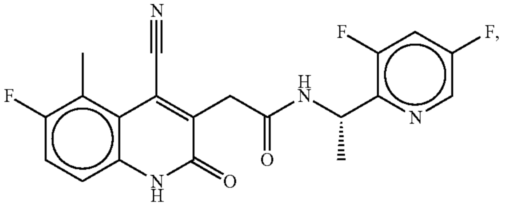
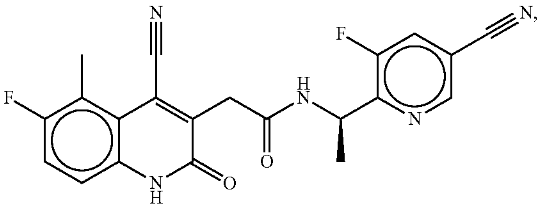
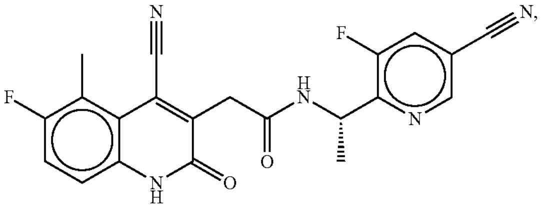
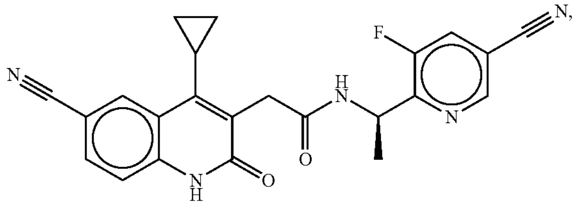
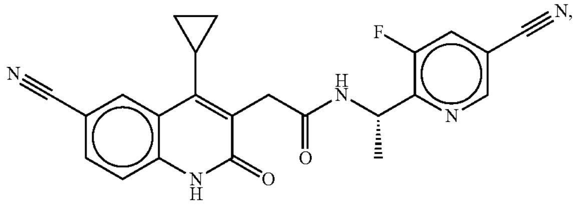
-continued
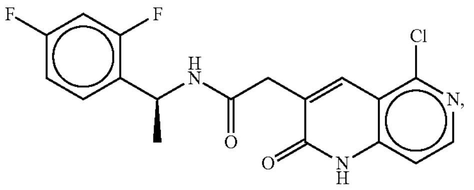
and
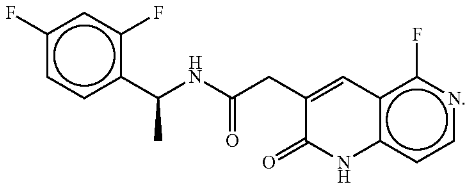
(154): The compound or salt of any one of embodiments 30 to 153, selected from:
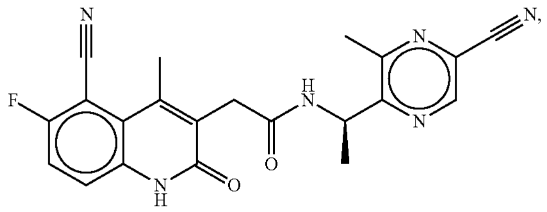
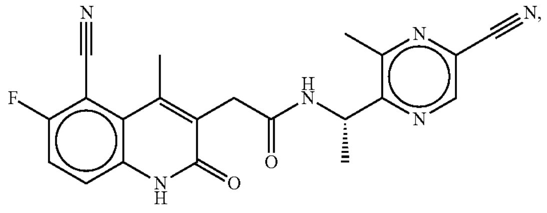
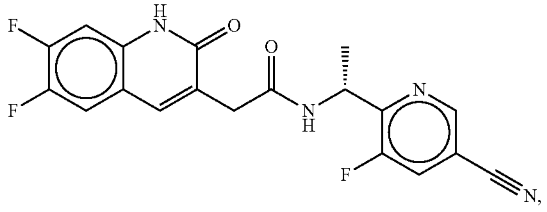
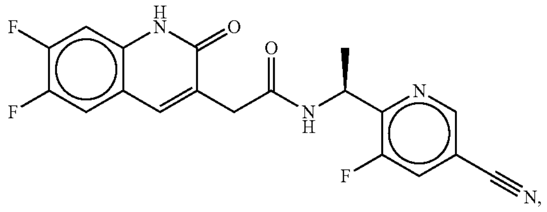
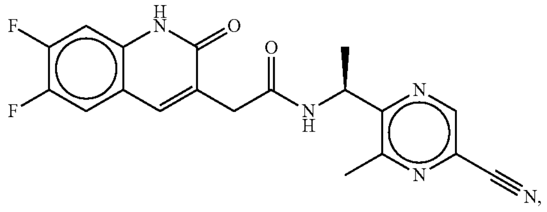

-continued
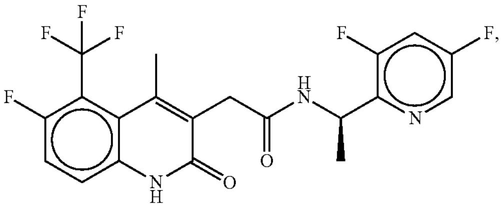
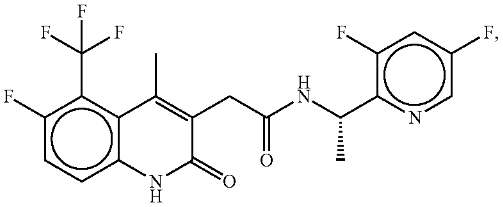
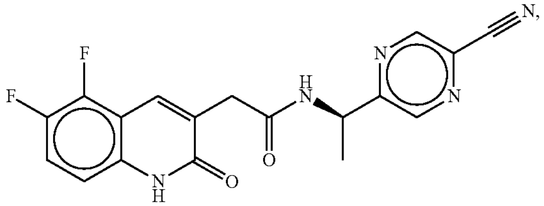
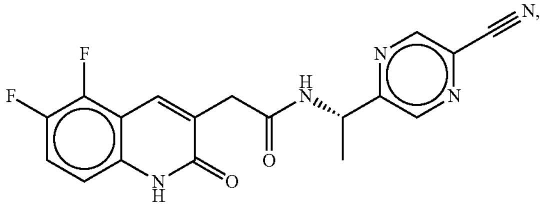
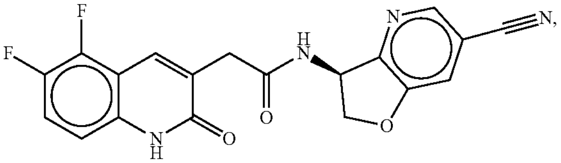
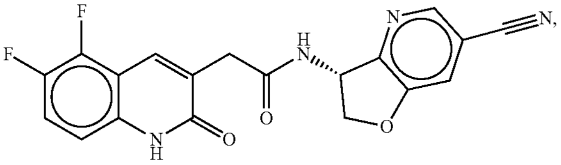
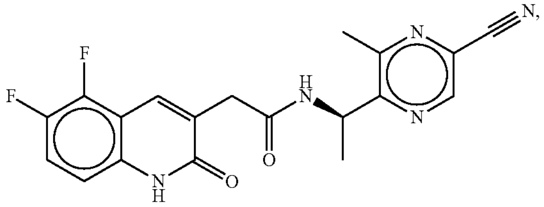
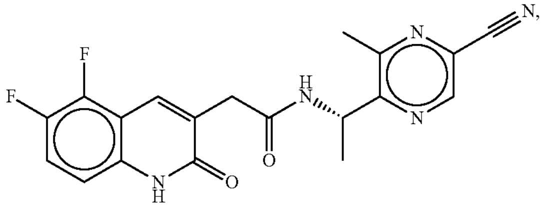
-continued
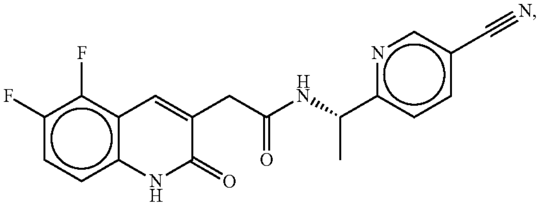
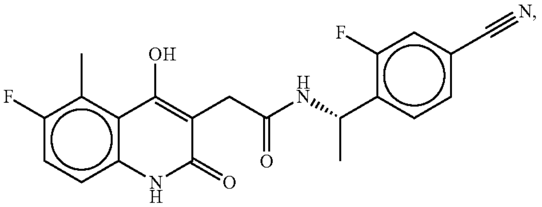
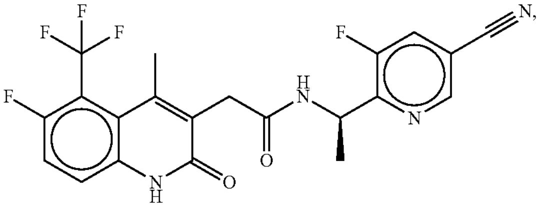
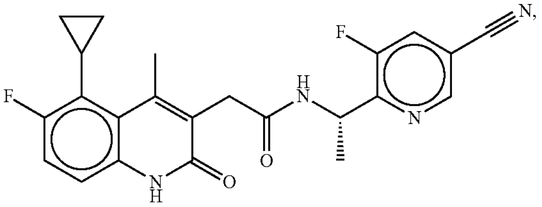
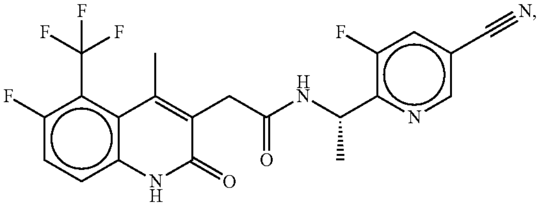
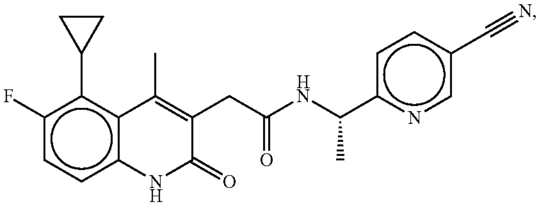
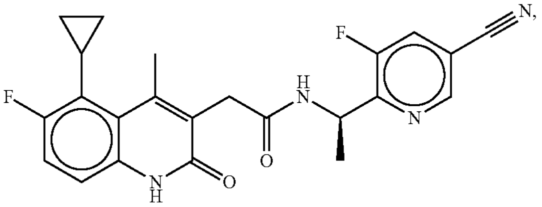
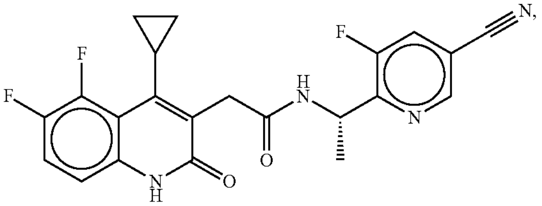

-continued
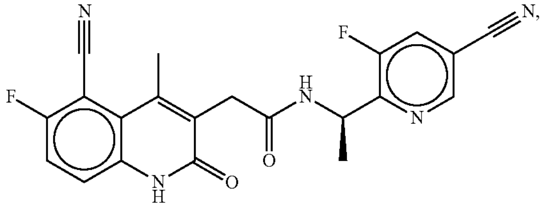
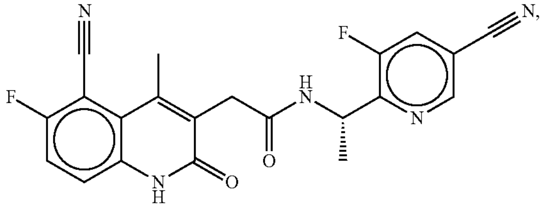
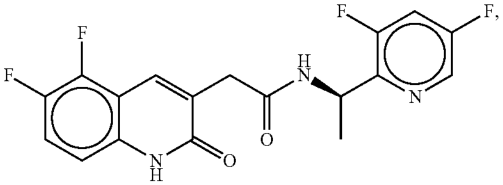
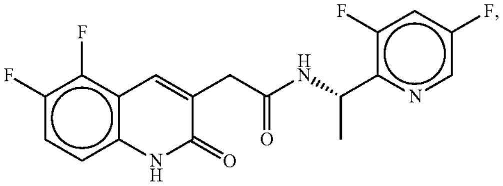
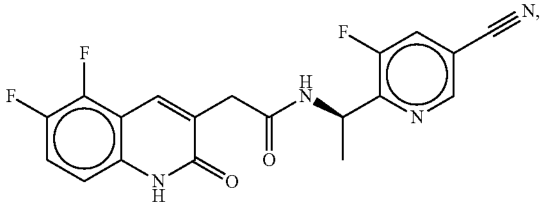
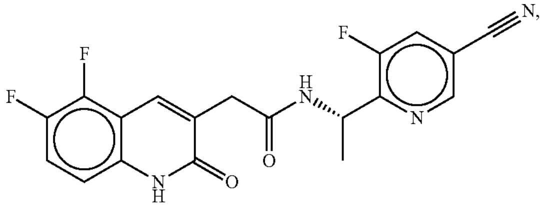
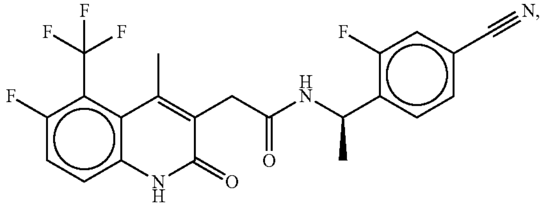
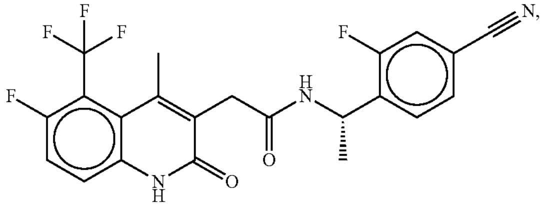
-continued
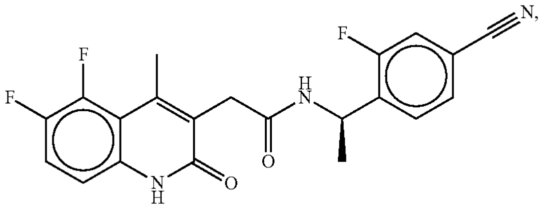
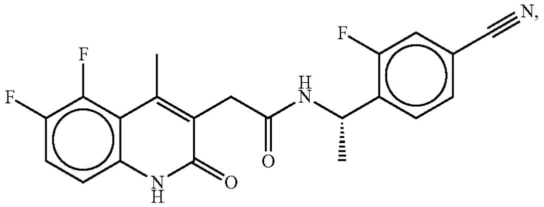
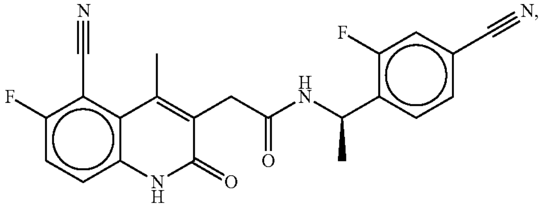
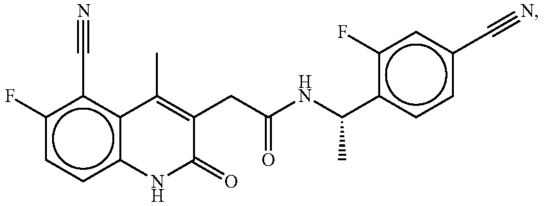
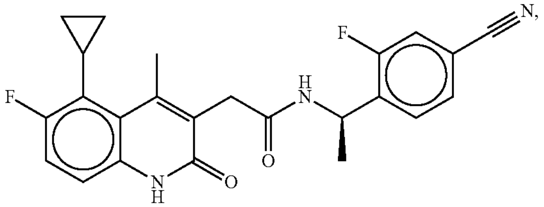
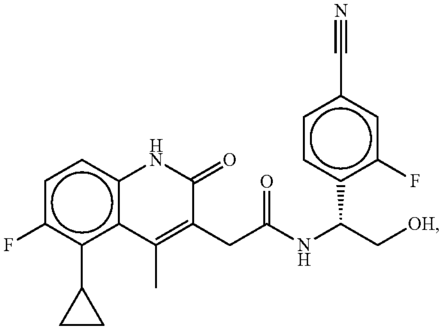
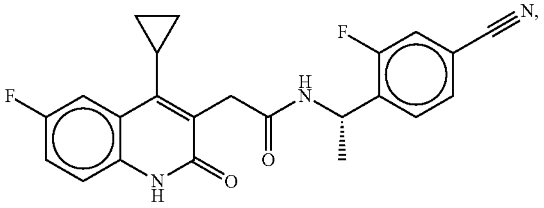

-continued
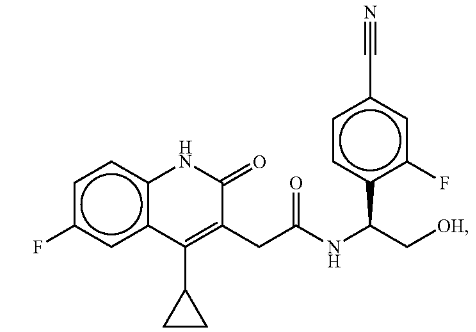
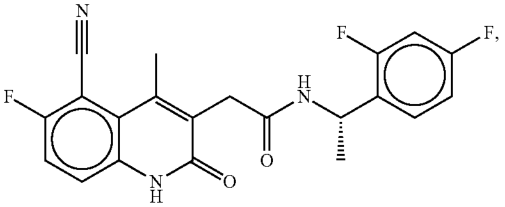
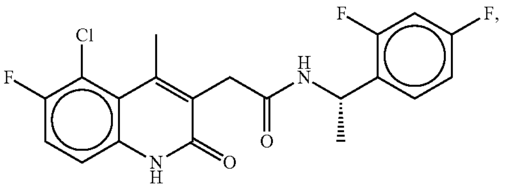
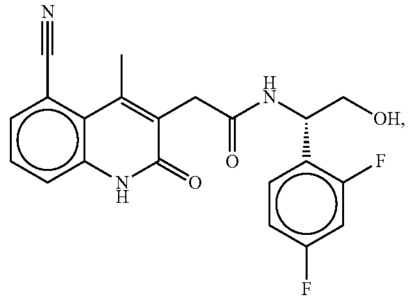
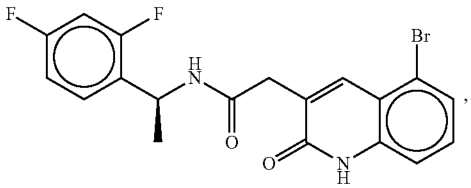
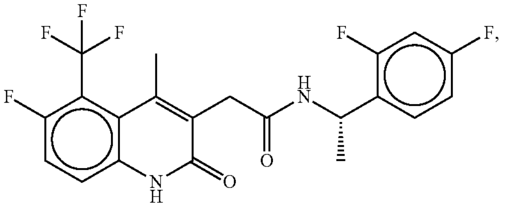
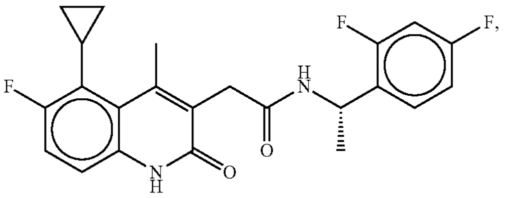
-continued
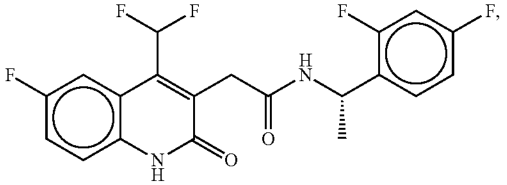
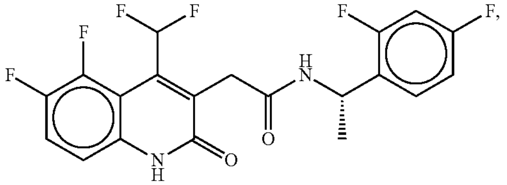
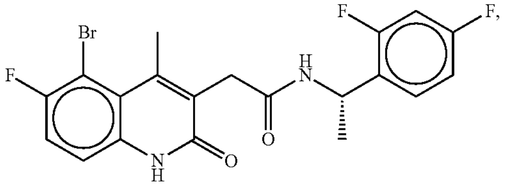
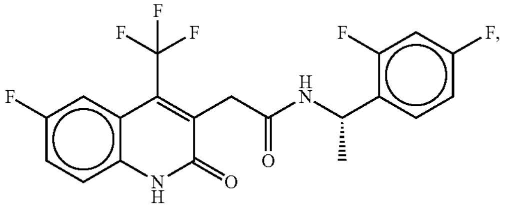
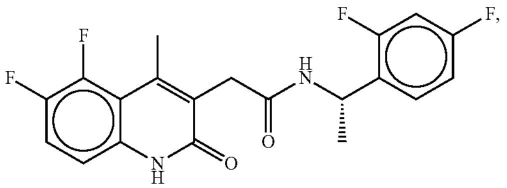
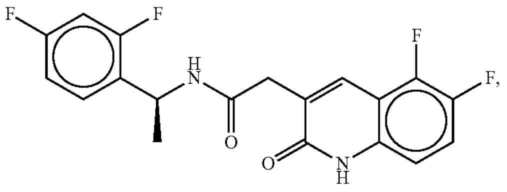
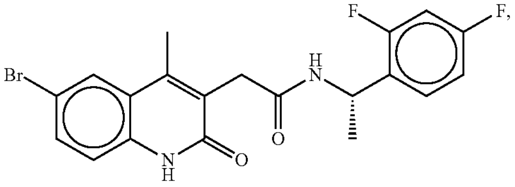
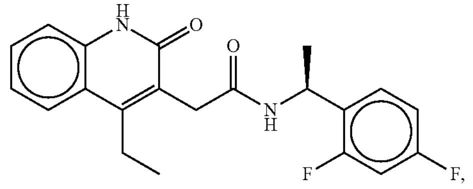
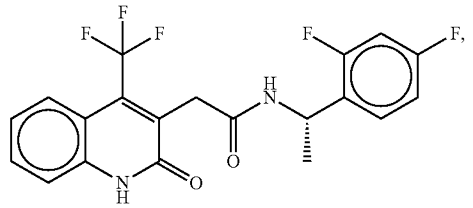

-continued
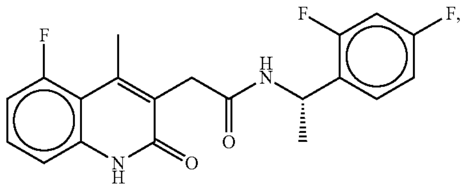
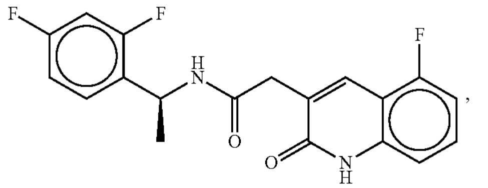
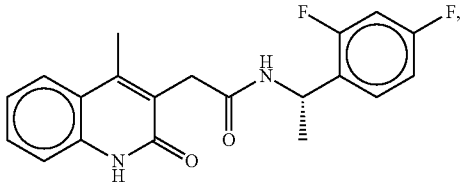
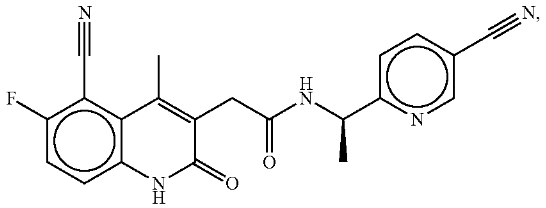
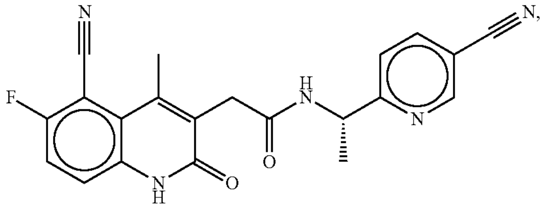
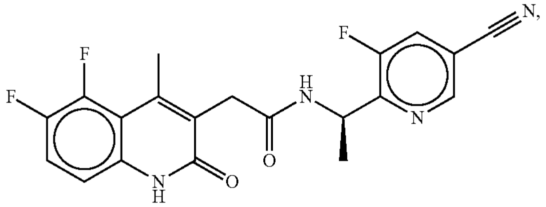
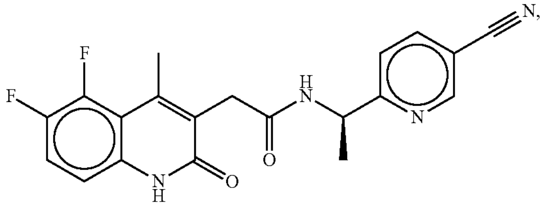
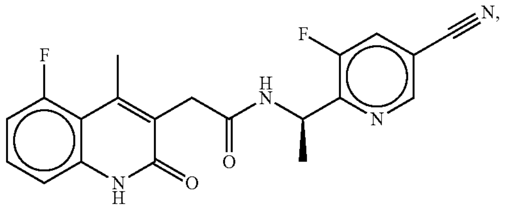
-continued
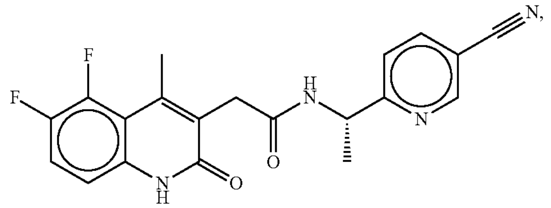
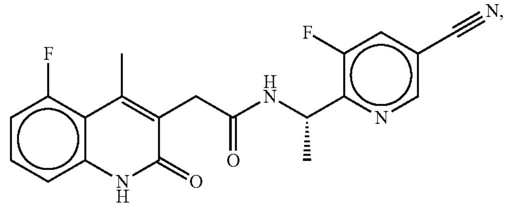
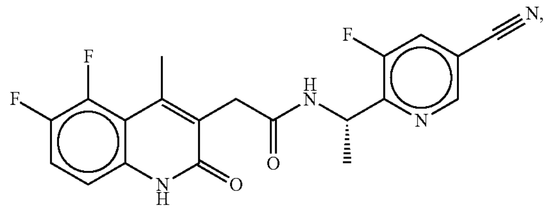
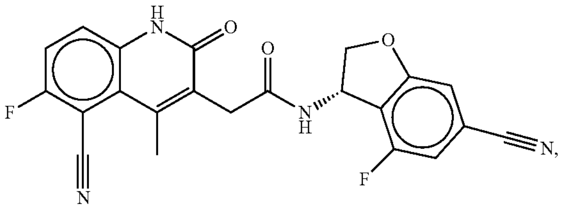
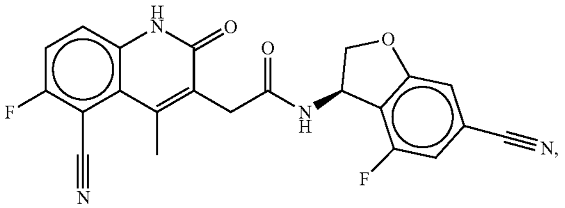
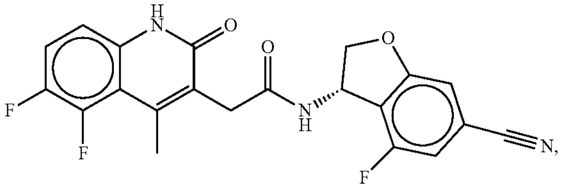
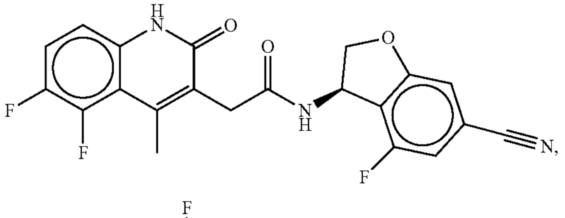
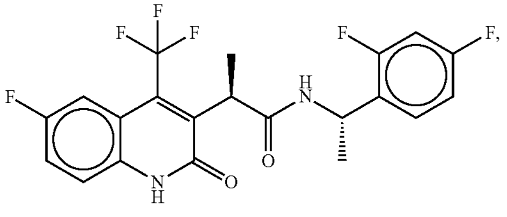

-continued

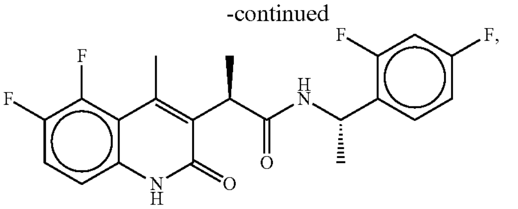

and

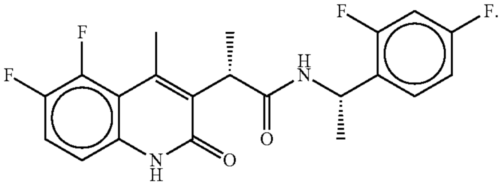

(155): A method of treating cardiovascular disease or a related condition comprising administering to a subject in need thereof a compound or salt of any one of embodiments 1 to 154. (156): A method of treating diastolic dysfunction or a related condition comprising administering to a subject in need thereof a compound or salt of any one of embodiments 1 to 154. (157): A method of treating a condition selected from hypertrophic cardiomyopathy (HCM); heart failure with preserved ejection fraction (HFpEF); heart failure with mid ranged ejection fraction disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; right ventricular (RV) hypertrophy; acute myocardial infarction; acute revascularization; ischemia; and angina; the method comprising administering to a subject in need thereof a compound or salt of any one of embodiments 1 to 154. (158): The method of embodiment 157, wherein said heart failure with preserved ejection fraction (HFpEF) comprises one or more disorders selected from disorders of relaxation and disorders of chamber stiffness (diabetic HFpEF). (159): The method of embodiment 157, wherein said left ventricular (LV) hypertrophy is malignant left ventricular (LV) hypertrophy. (160): The method of embodiment 157, wherein said restrictive cardiomyopathy comprises one or more subgroups selected from inflammatory subgroups, infiltrative subgroups, storage subgroups, idiopathic/inherited subgroups, congenital heart disease subgroups. (161): The method of embodiment 159, wherein said inflammatory subgroups comprise one or more subgroups selected from Loefilers and EMF. (162): The method of embodiment 159, wherein said inflammatory subgroups comprise one or more subgroups selected from amyloid, sarcoid, and XRT. (163): The method of embodiment 159, wherein said storage subgroups comprise one or more subgroups selected from hemochromatosis, Fabry, and glycogen storage disease. (164): The method of embodiment 159, wherein said idiopathic/inherited subgroups comprise one or more subgroups selected from Trop I (beta myosin HC), Trop T (alpha cardiac actin), and desmin related subgroups. (165): The method of embodiment 159, wherein said congenital heart disease subgroups comprise one or more subgroups selected from pressure-overloaded RV, Tetralogy of Fallot, and pulmonic stenosis. (166): A method of treating hypertrophic cardiomyopathy or a related condition comprising administering to a subject in need thereof a compound or salt of any one of embodiments 1 to 154. (167): A method of treating obstructive hypertrophic cardiomyopathy comprising administering to a subject in need thereof a compound or salt of any one of embodiments 1 to 154. (168): A method of treating non-obstructive hypertrophic cardiomyopathy comprising administering to a subject in need thereof a compound or salt of any one of embodiments 1 to 154. (169): A method of treating heart failure with preserved ejection fraction comprising administering to a subject in need thereof a compound or salt of any one of embodiments 1 to 210. (170): A method of treating left ventricle stiffness comprising administering to a subject in need thereof a compound or salt of any one of embodiments 1 to 210. (171): A pharmaceutical composition comprising a compound or salt of any one of embodiments 1 to 154 and a pharmaceutically acceptable excipient.

(172): A method of treating a cardiac disease in an individual in need thereof, the method comprising administering a therapeutically effective amount of a compound of Formula (III'):

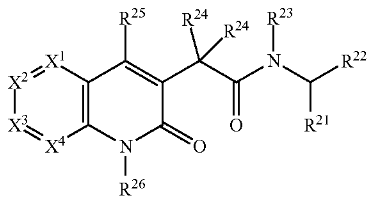

Formula (III') or a salt thereof, wherein: $X^1$, $X^2$, $X^3$, and $X^4$ are independently selected from C(R) and N wherein no more than two of $X^1$, $X^2$, $X^3$, and $X^4$ are N; each R is independently selected from: hydrogen, halogen, $—NO_2$, —CN, $—N_3$, $—OR^{28}$, $—SR^{28}$, $—N(R^{28})_2$, $—C(O)R^{28}$, $—C(O)N(R^{28})_2$, $—N(R^{28})C(O)R^{28}$, $—N(R^{28})C(O)N(R^{28})_2$, $—OC(O)N(R^{28})_2$, $—N(R^{28})C(O)OR^{28}$, $—C(O)OR^{28}$, $—OC(O)R^{28}$, $—S(O)R^{28}$, and $—S(O)_2R^{28}$; $C_{1-6}$ alkyl, $C_{2-6}$ alkenyl, and $C_{2-6}$ alkynyl, each of which is optionally substituted with one or more substituents independently selected from halogen, $—OR^{28}$, $—SR^{28}$, $—N(R^{28})_2$, $—C(O)R^{28}$, $—C(O)N(R^{28})_2$, $—N(R^{28})C(O)R^{28}$, $—C(O)OR^{28}$, $—OC(O)R^{28}$, $—N(R^{28})C(O)N(R^{28})_2$, $—OC(O)N(R^{28})_2$, $—N(R^{28})C(O)OR^{28}$, $—S(O)R^{28}$, $—S(O)_2R^{28}$, $—NO_2$, =O, =S, $=N(R^{28})$, —CN, $C_{3-10}$ carbocycle and 3- to 10-membered heterocycle, wherein the $C_{3-10}$ carbocycle and 3- to 10-membered heterocycle are each optionally substituted with one or more $R^{27}$; and $C_{3-10}$ carbocycle and 3- to 10-membered heterocycle, each of which is optionally substituted with one or more substituents independently selected from halogen, $—OR^{28}$, $—SR^{28}$, $—N(R^{28})_2$, $—C(O)R^{28}$, $—C(O)N(R^{28})_2$, $—N(R^{28})C(O)R^{28}$, $—N(R^{28})C(O)N(R^{28})_2$, $—OC(O)N(R^{28})_2$, $—N(R^{28})C(O)OR^{28}$, $—C(O)OR^{28}$, $—OC(O)R^{28}$, $—S(O)R^{28}$, $—S(O)_2R^{28}$, $—NO_2$, =O—, =S, $=N(R^{28})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27}$; $R^{21}$ is selected from: hydrogen, $C_{1-6}$ alkyl, $C_{2-6}$ alkenyl, and $C_{2-6}$ alkynyl, each of which is optionally substituted with one or more substituents independently selected from halogen, $—OR^{28a}$, $—SR^{28a}$, $—N(R^{28a})_2$, $—C(O)R^{28a}$, $—C(O)N(R^{28a})_2$, $—N(R^{28a})C(O)R^{28a}$, $—C(O)OR^{28a}$, $—OC(O)R^{28a}$, $—N(R^{28a})C(O)N(R^{28a})_2$, $—OC(O)N(R^{28a})_2$, $—N(R^{28a})C(O)OR^{28a}$, $—S(O)R^{28a}$, $—S(O)_2R^{28a}$, $—NO_2$, =O, =S, $=N(R^{28a})$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{27a}$; and $C_{3-10}$ carbocycle, and 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27a}$; $R^{22}$ is selected from: hydrogen, $C_{1-6}$ alkyl, $C_{2-6}$ alkenyl, and $C_{2-6}$ alkynyl, each of which is optionally substituted with one or more substituents independently selected from halogen, —$OR^{28b}$, —$SR^{28b}$, —$N(R^{28b})_2$, —$C(O)R^{28b}$, —$C(O)N(R^{28b})_2$, —$N(R^{28b})C(O)R^{28b}$, —$C(O)OR^{28b}$, —$OC(O)R^{28b}$, —$N(R^{28b})C(O)N(R^{28b})_2$, —$OC(O)N(R^{28b})_2$, —$N(R^{28b})C(O)OR^{28b}$, —$S(O)R^{28b}$, —$S(O)_2R^{28b}$, —$NO_2$, ═O, ═S, ═$N(R^{28b})$, —CN, $C_{3-10}$ carbocycle, and 3- to 10-membered heterocycle, wherein the $C_{3-10}$ carbocycle, and 3- to 10-membered heterocycle, are each optionally substituted with one or more $R^{27b}$; and $C_{3-10}$ carbocycle, and 3- to 10-membered heterocycle, each of which is optionally substituted with one or more substituents independently selected from halogen, —$OR^{28b}$, —$SR^{28b}$, —$N(R^{28b})_2$, —$C(O)R^{28b}$, —$C(O)N(R^{28b})_2$, —$N(R^{28b})C(O)R^{28b}$, —$N(R^{28b})C(O)N(R^{28b})_2$, —$OC(O)N(R^{28b})_2$, —$N(R^{28b})C(O)OR^{28b}$, —$C(O)OR^{28b}$, —$OC(O)R^{28b}$, —$S(O)R^{28b}$, —$S(O)_2R^{28b}$, —$NO_2$, ═O—, ═S, ═$N(R^{28b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27b}$; or $R^{21}$ together with $R^{22}$ form a $C_{3-10}$ carbocycle, or 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27b}$; $R^{23}$ is selected from: hydrogen, halogen, —$OR^{28c}$, —$SR^{28c}$, —$N(R^{28c})_2$, —$NO_2$, and —CN; and $C_{1-6}$ alkyl optionally substituted with one or more one or more $R^{27c}$; or $R^{21}$ together with $R^{23}$ form a 3- to 10-membered heterocycle, which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27c}$; $R^{22}$ together with $R^{23}$ form a $C_{3-10}$ carbocycle, or 3- to 10-membered heterocycle, each of which is optionally substituted with one or more substituents independently selected from halogen, —$OR^{28a}$, —$SR^{28a}$, —$N(R^{28a})_2$, —$C(O)R^{28a}$, —$C(O)N(R^{28a})_2$, —$N(R^{28a})C(O)R^{28a}$, —$N(R^{28a})C(O)N(R^{28a})_2$, —$OC(O)N(R^{28a})_2$, —$N(R^{28a})C(O)OR^{28a}$, —$C(O)OR^{28a}$, —$OC(O)R^{28a}$, —$S(O)R^{28a}$, —$S(O)_2R^{28a}$, —$NO_2$, ═O—, ═S, ═$N(R^{28a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{27c}$; each $R^{24}$ is independently selected from: hydrogen, halogen, —$OR^{28d}$, —$SR^{28d}$, —$N(R^{28d})_2$, —$NO_2$, and —CN; and $C_{1-6}$ alkyl optionally substituted with one or more substituents independently selected from halogen, —$OR^{28d}$, —$SR^{28d}$, —$N(R^{28d})_2$, —$NO_2$, and —CN, $C_{3-10}$ carbocycle, and 3- to 10-membered heterocycle, wherein the $C_{3-10}$ carbocycle, and 3- to 10-membered heterocycle, are each optionally substituted with one or more $R^{27d}$; $R^{25}$ is selected from: hydrogen, halogen, —$OR^{28c}$, —$SR^{28c}$, —$N(R^{28c})_2$, —$NO_2$, —CN, $C_{1-6}$ alkyl, $C_{3-10}$ carbocycle, and 3- to 10-membered heterocycle, wherein the $C_{1-6}$ alkyl, $C_{3-10}$ carbocycle, and 3- to 10-membered heterocycle are each optionally substituted with one or more $R^{27e}$; or $R^{24}$ together with $R^{25}$ form a 3- to 10-membered heterocycle, wherein the 3- to 10-membered heterocycle is optionally substituted with one or more $R^{27e}$; $R^{26}$ is selected from: hydrogen, halogen, —$OR^{28f}$, —$SR^{28f}$, —$N(R^{28f})_2$, —$NO_2$, and —CN; and $C_{1-6}$ alkyl optionally substituted with one or more $R^{27f}$; each $R^{27}$ is independently selected from: halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, ═O, ═S, ═$N(R^{28g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, ═O, ═S, ═$N(R^{28g})$, and —CN; or each $R^{27a}$ is independently selected from: halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, ═O, ═S, ═$N(R^{28g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, ═O, ═S, ═$N(R^{28g})$, and —CN; each $R^{27b}$ is independently selected from: halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, ═O, ═S, ═$N(R^{28g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, ═O, ═S, ═$N(R^{28g})$, and —CN; each $R^{27c}$ is independently selected from: halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, ═O, ═S, ═$N(R^{28g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —$OC(O)N(R^{28g})_2$, —$N(R^{28g})C(O)OR^{28g}$, —$C(O)OR^{28g}$, —$OC(O)R^{28g}$, —$S(O)R^{28g}$, —$S(O)_2R^{28g}$, —$NO_2$, ═O, ═S, ═$N(R^{28g})$, and —CN; each $R^{27d}$ is independently selected from: halogen, —$OR^{28g}$, —$SR^{28g}$, —$N(R^{28g})_2$, —$C(O)R^{28g}$, —$C(O)N(R^{28g})_2$, —$N(R^{28g})C(O)R^{28g}$, —$N(R^{28g})C(O)N(R^{28g})_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2$$R^{28g}$, —NO$_2$, =O, =S, =N($R^{28g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2$$R^{28g}$, —NO$_2$, =O, =S, =N($R^{28g}$), and —CN; each $R^{27e}$ is independently selected from: halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2$$R^{28g}$, —NO$_2$, =O, =S, =N($R^{28g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2$$R^{28g}$, —NO$_2$, =O, =S, =N($R^{28g}$), and —CN; each $R^{27f}$ is independently selected from: halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2$$R^{28g}$, —NO$_2$, =O, =S, =N($R^{28g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{28g}$, —S$R^{28g}$, —N($R^{28g}$)$_2$, —C(O)$R^{28g}$, —C(O)N($R^{28g}$)$_2$, —N($R^{28g}$)C(O)$R^{28g}$, —N($R^{28g}$)C(O)N($R^{28g}$)$_2$, —OC(O)N($R^{28g}$)$_2$, —N($R^{28g}$)C(O)O$R^{28g}$, —C(O)O$R^{28g}$, —OC(O)$R^{28g}$, —S(O)$R^{28g}$, —S(O)$_2$$R^{28g}$, —NO$_2$, =O, =S, =N($R^{28g}$), and —CN; each $R^{28}$ is independently selected from: hydrogen and halogen; and $C_{1-6}$ alkyl, $C_{2-6}$ alkenyl, $C_{2-6}$ alkynyl, and $C_{3-10}$ carbocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —SO$_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{28a}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —SO$_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{28b}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —SO$_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{28c}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —SO$_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{28d}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —SO$_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ Carbocycle, 3- to 10-membered heterocycle, and $C_{1-6}$ haloalkyl; each $R^{28e}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —SO$_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{28f}$ is independently selected from: hydrogen and halogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —SO$_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; and each $R^{28g}$ is independently selected from: hydrogen and halogen;

and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$SO_2$—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. (173): The method of embodiment 172, wherein cardiovascular disease or a related condition is selected from: hypertrophic cardiomyopathy (HCM); heart failure with preserved ejection fraction (HFpEF); heart failure with mid ranged ejection fraction disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; right ventricular (RV) hypertrophy; acute myocardial infarction; acute revascularization; ischemia; and angina. (174): The method of embodiment 173, wherein said heart failure with preserved ejection fraction (HFpEF) comprises one or more disorders selected from disorders of relaxation and disorders of chamber stiffness (diabetic HFpEF). (175): The method of embodiment 173, wherein said left ventricular (LV) hypertrophy is malignant left ventricular (LV) hypertrophy. (176): The method of embodiment 173, wherein said restrictive cardiomyopathy comprises one or more subgroups selected from inflammatory subgroups, infiltrative subgroups, storage subgroups, idiopathic/inherited subgroups, congenital heart disease subgroups. (177): The method of embodiment 176, wherein said inflammatory subgroups comprise one or more subgroups selected from Loefllers and EMF. (178): The method of embodiment 176, wherein said inflammatory subgroups comprise one or more subgroups selected from amyloid, sarcoid, and XRT. (179): The method of embodiment 176, wherein said storage subgroups comprise one or more subgroups selected from hemochromatosis, Fabry, and glycogen storage disease. (180): The method of embodiment 176, wherein said idiopathic/inherited subgroups comprise one or more subgroups selected from Trop I (beta myosin HC), Trop T (alpha cardiac actin), and desmin related subgroups. (181): The method of embodiment 176, wherein said congenital heart disease subgroups comprise one or more subgroups selected from pressure-overloaded RV, Tetralogy of Fallot, and pulmonic stenosis. (182): The method of any one of embodiments 173 to 181, wherein cardiovascular disease or a related condition is hypertrophic cardiomyopathy. (183): The method of any one of embodiments 173 to 181, wherein cardiovascular disease or a related condition is obstructive hypertrophic cardiomyopathy. (184): The method of any one of embodiments 173 to 181, wherein cardiovascular disease or a related condition is non-obstructive hypertrophic cardiomyopathy. (185): The method of any one of embodiments 173 to 181, wherein cardiovascular disease or a related condition is heart failure with preserved ejection fraction. (186): The method of any one of embodiments 173 to 181, wherein cardiovascular disease or a related condition is left ventricle stiffness. [0584](187) A pharmaceutical composition comprising the compound or salt of any one of embodiments 1 to 172.

What is claimed is:

1. A compound represented by Formula (II-A):

(II-A)

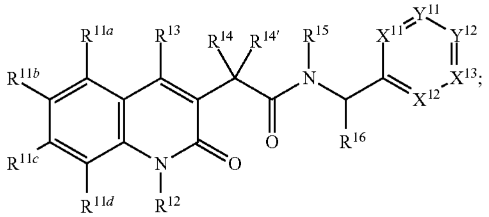

or a salt thereof, wherein:

$X^{11}$ is selected from C($R^{17a}$) and N;

$X^{12}$ is selected from C($R^{17b}$) and N;

$X^{13}$ is selected from C($R^{17c}$) and N;

$Y^{11}$ is selected from C($R^{17d}$) and N;

$Y^{12}$ is selected from C($R^{17e}$) and N;

$R^{11a}$, $R^{11b}$, $R^{11c}$ and $R^{11d}$ are each independently selected from:

hydrogen, halogen, —$NO_2$, —CN, —$N_3$, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —N($R^{19a}$)C(O)N($R^{19a}$)$_2$, —OC(O)N($R^{19a}$)$_2$, —N($R^{19a}$)C(O)O$R^{19a}$, —C(O)O$R^{19a}$, —OC(O)$R^{19a}$, —S(O)$R^{19a}$, and —S(O)$_2R^{19a}$;

$C_{1-6}$ alkyl, $C_{2-6}$ alkenyl, and $C_{2-6}$ alkynyl, each of which is optionally substituted with one or more substituents independently selected from halogen, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —C(O)O$R^{19a}$, —OC(O)$R^{19a}$, —N($R^{19a}$)C(O)N($R^{19a}$)$_2$, —OC(O)N($R^{19a}$)$_2$, —N($R^{19a}$)C(O)O$R^{19a}$, —S(O)$R^{19a}$, —S(O)$_2R^{19a}$, —$NO_2$, =O, =S, =N($R^{19a}$), —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{18a}$; and $C_{3-10}$ carbocycle and 3- to 10-membered heterocycle, each of which is optionally substituted with one or more substituents independently selected from halogen, —$OR^{19a}$, —$SR^{19a}$, —N($R^{19a}$)$_2$, —C(O)$R^{19a}$, —C(O)N($R^{19a}$)$_2$, —N($R^{19a}$)C(O)$R^{19a}$, —N($R^{19a}$)C(O)N($R^{19a}$)$_2$, —OC(O)N($R^{19a}$)$_2$, —N($R^{19a}$)C(O)O$R^{19a}$, —C(O)O$R^{19a}$, —OC(O)$R^{19a}$, —S(O)$R^{19a}$, —S(O)$_2R^{19a}$, —$NO_2$, =O, =S, =N($R^{19a}$), —CN, $C_{1-6}$ alkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with one or more substituents independently selected from $R^{18a}$;

wherein when $R^{11a}$, $R^{11b}$, and $R^{11c}$ are each hydrogen; then $R^{11d}$ is not hydrogen;

wherein when $R^{11b}$ is —$OCH_3$, then $R^{11c}$ is not —OMe;

$R^{12}$ is selected from:

hydrogen, halogen, —$NO_2$, —CN, —$OR^{19b}$, —$SR^{19b}$, —N($R^{19b}$)$_2$, —C(O)$R^{19b}$, —C(O)N($R^{19b}$)$_2$, —N($R^{19b}$)C(O)$R^{19b}$, —N($R^{19b}$)C(O)N($R^{19b}$)$_2$, —OC(O)N($R^{19b}$)$_2$, —N($R^{19b}$)C(O)O$R^{19b}$, —C(O)O$R^{19b}$, —OC(O)$R^{19b}$, —S(O)$R^{19b}$, and —S(O)$_2R^{19b}$;

$C_{1-6}$ alkyl, $C_{2-6}$ alkenyl, and $C_{2-6}$ alkynyl, each of which is optionally substituted with one or more substituents independently selected from halogen, —$OR^{19b}$, —$SR^{19b}$, —$N(R^{19b})_2$, —$C(O)R^{19b}$, —$C(O)N(R^{19b})_2$, —$N(R^{19b})C(O)R^{19b}$, —$C(O)OR^{19b}$, —$OC(O)R^{19b}$, —$N(R^{19b})C(O)N(R^{19b})_2$, —$OC(O)N(R^{19b})_2$, —$N(R^{19b})C(O)OR^{19b}$, —$S(O)R^{19b}$, —$S(O)_2R^{19b}$, —$NO_2$, =O, =S, =$N(R^{19b})$, —CN, $C_{3-10}$ carbocycle, and 3- to 10-membered heterocycle, wherein the $C_{3-10}$ carbocycle and 3- to 10-membered heterocycle are each optionally substituted with one or more substituents independently selected from $R^{18b}$; and $C_{3-10}$ carbocycle and 3- to 10-membered heterocycle, each of which is optionally substituted with one or more substituents independently selected from halogen, —$OR^{19b}$, —$SR^{19b}$, —$N(R^{19b})_2$, —$C(O)R^{19b}$, —$C(O)N(R^{19b})_2$, —$N(R^{19b})C(O)R^{19b}$, —$N(R^{19b})C(O)N(R^{19b})_2$, —$OC(O)N(R^{19b})_2$, —$N(R^{19b})C(O)OR^{19b}$, —$C(O)OR^{19b}$, —$OC(O)R^{19b}$, —$S(O)R^{19b}$, —$S(O)_2R^{19b}$, —$NO_2$, =O, =S, =$N(R^{19b})$, —CN, $C_{1-6}$ alkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with one or more substituents independently selected from $R^{18b}$;

$R^{13}$ is selected from:

hydrogen, halogen, —$OR^{19c}$, —$SR^{19c}$, —$N(R^{19c})_2$, —$NO_2$, and —CN;

$C_{1-6}$ alkyl optionally substituted with one or more substituents independently selected from halogen, —$OR^{19c}$, —$SR^{19c}$, —$N(R^{19c})_2$, —$NO_2$, and —CN; and $C_{3-10}$ carbocycle and 3- to 10-membered heterocycle, each of which is optionally substituted with one or more substituents independently selected from —$OR^{19c}$, —$SR^{19c}$, —$N(R^{19c})_2$, —$C(O)R^{19c}$, —$C(O)N(R^{19c})_2$, —$N(R^{19c})C(O)R^{19c}$, —$N(R^{19c})C(O)N(R^{19c})_2$, —$OC(O)N(R^{19c})_2$, —$N(R^{19c})C(O)OR^{19c}$, —$C(O)OR^{19c}$, —$OC(O)R^{19c}$, —$S(O)R^{19c}$, —$S(O)_2R^{19c}$, —$NO_2$, and —CN;

$R^{14}$ is selected from:

hydrogen, halogen, —$OR^{19d}$, —$SR^{19d}$, —$N(R^{19d})_2$, —$NO_2$, and —CN;

$C_{1-6}$ alkyl which is optionally substituted with one or more substituents independently selected from halogen, —$OR^{19d}$, —$SR^{19d}$, —$N(R^{19d})_2$, —$NO_2$, and —CN; and $C_{3-10}$ carbocycle and 3- to 10-membered heterocycle, each of which is optionally substituted with one or more substituents independently selected from halogen, —$OR^{19d}$, —$SR^{19d}$, —$N(R^{19d})_2$, —$C(O)R^{19d}$, —$C(O)N(R^{19d})_2$, —$N(R^{19d})C(O)R^{19d}$, —$N(R^{19d})C(O)N(R^{19d})_2$, —$OC(O)N(R^{19d})_2$, —$N(R^{19d})C(O)OR^{19d}$, —$C(O)OR^{19d}$, —$OC(O)R^{19d}$, —$S(O)R^{19d}$, —$S(O)_2R^{19d}$, —$NO_2$, =O, =S, =$N(R^{19d})$, and —CN;

$R^{14'}$ is selected from:

hydrogen, halogen, —$OR^{19d}$, —$SR^{19d}$, —$N(R^{19d})_2$, —$NO_2$, and —CN; and $C_{1-6}$ alkyl which is optionally substituted with one or more substituents independently selected from halogen, —$OR^{19d}$, —$SR^{19d}$, —$N(R^{19d})_2$, —$NO_2$, and —CN; and $C_{3-10}$ carbocycle and 3- to 10-membered heterocycle, each of which is optionally substituted with one or more substituents independently selected from halogen, —$OR^{19d}$, —$SR^{19d}$, —$N(R^{19d})_2$, —$C(O)R^{19d}$, —$C(O)N(R^{19d})_2$, —$N(R^{19d})C(O)R^{19d}$, —$N(R^{19d})C(O)N(R^{19d})_2$, —$OC(O)N(R^{19d})_2$, —$N(R^{19d})C(O)OR^{19d}$, —$C(O)OR^{19d}$, —$OC(O)R^{19d}$, —$S(O)R^{19d}$, —$S(O)_2R^{19d}$, —$NO_2$, =O, =S, =$N(R^{19d})$, and —CN; or $R^{14}$ together with $R^{14'}$ form a $C_{3-10}$ carbocycle, or 3- to 10-membered heterocycle, wherein the $C_{3-10}$ carbocycle or 3- to 10-membered heterocycle is optionally substituted with one or more substituents independently selected from $R^{18c}$;

$R^{15}$ is selected from:

hydrogen, halogen, —$OR^{19e}$, —$SR^{19e}$, —$N(R^{19e})_2$—$NO_2$, and —CN; and $C_{1-6}$ alkyl optionally substituted with one or more substituents independently selected from $R^{18d}$; or $R^{15}$ together with $R^{17a}$ form a 3- to 10-membered heterocycle, wherein the 3- to 10-membered heterocycle is optionally substituted with one or more substituents independently selected from $R^{18f}$; or $R^{15}$ together with $R^{17b}$ form a 3- to 10-membered heterocycle, wherein the 3- to 10-membered heterocycle is optionally substituted with one or more substituents independently selected from $R^{18f}$; or $R^{15}$, $R^{16}$, and $R^{17b}$ together form a bridged heterocycle, wherein the bridged heterocycle is optionally substituted with one or more substituents independently selected from $R^{18f}$;

$R^{16}$ is selected from:

hydrogen, halogen, —$OR^{19f}$, —$SR^{19f}$, —$N(R^{19f})_2$, —$NO_2$, and —CN; and $C_{1-6}$ alkyl optionally substituted with one or more substituents independently selected from $R^{18e}$; or $R^{16}$ together with $R^{17a}$ form a 3- to 10-membered heterocycle, wherein the 3- to 10-membered heterocycle is optionally substituted with one or more substituents independently selected from $R^{18f}$; or $R^{16}$ together with $R^{17b}$ form a 3- to 10-membered heterocycle, wherein the 3- to 10-membered heterocycle is optionally substituted with one or more substituents independently selected from $R^{18f}$; or $R^{15}$, $R^{16}$, and $R^{17b}$ together form a bridged heterocycle, wherein the bridged heterocycle is optionally substituted with one or more substituents independently selected from $R^{18f}$;

$R^{17a}$, $R^{17b}$, $R^{17c}$, $R^{17d}$, and $R^{17e}$ are each independently selected from:

hydrogen, halogen, —$OR^{19g}$, —$SR^{19g}$, —$N(R^{19g})_2$, —$NO_2$, —CN, and —$N_3$; and $C_{1-6}$ alkyl, $C_{2-6}$ alkenyl, and $C_{2-6}$ alkynyl, each of which is optionally substituted with one or more substituents independently selected from $R^{18f}$; or $R^{15}$ together with $R^{17a}$ form a 3- to 10-membered heterocycle, wherein the 3- to 10-membered heterocycle is optionally substituted with one or more substituents independently selected from $R^{18f}$; or $R^{15}$ together with $R^{17b}$ form a 3- to 10-membered heterocycle, wherein the 3- to 10-membered heterocycle is optionally substituted with one or more substituents independently selected from $R^{18f}$; or $R^{16}$ together with $R^{17a}$ form a 3- to 10-membered heterocycle, wherein the 3- to 10-membered heterocycle is optionally substituted with one or more substituents independently selected from $R^{18f}$; or $R^{16}$ together with $R^{17b}$ form a 3- to 10-membered heterocycle, wherein the 3- to 10-membered heterocycle is optionally substituted with one or more substituents independently selected from $R^{18f}$; or $R^{15}$, $R^{16}$, and $R^{17b}$ together form a bridged heterocycle, wherein the bridged heterocycle is optionally substituted with one or more substituents independently selected from $R^{18f}$;

each $R^{18a}$, $R^{18b}$, $R^{18c}$, $R^{18d}$, $R^{18e}$, and $R^{18f}$ is independently selected from:

halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, $OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, ═O, ═S, ═$N(R^{19h})$, and —CN; and $C_{1-3}$ alkyl, $C_{2-3}$ alkenyl, and $C_{2-3}$ alkynyl, each of which is optionally substituted with one or more substituents independently selected from halogen, —$OR^{19h}$, —$SR^{19h}$, —$N(R^{19h})_2$, —$C(O)R^{19h}$, —$C(O)N(R^{19h})_2$, —$N(R^{19h})C(O)R^{19h}$, —$N(R^{19h})C(O)N(R^{19h})_2$, —$OC(O)N(R^{19h})_2$, —$N(R^{19h})C(O)OR^{19h}$, —$C(O)OR^{19h}$, —$OC(O)R^{19h}$, —$S(O)R^{19h}$, —$S(O)_2R^{19h}$, —$NO_2$, ═O, ═S, ═$N(R^{19h})$, and —CN; and each $R^{19a}$, $R^{19b}$, $R^{19c}$, $R^{19d}$, $R^{19e}$, $R^{19f}$, $R^{19g}$, and $R^{19h}$ is independently selected from:

hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

2. The compound or salt of claim 1, wherein $R^{11a}$, $R^{11b}$, $R^{11c}$, and $R^{11d}$ are each independently selected from hydrogen, halogen, —CN, $C_{1-6}$ alkyl, and $C_{3-10}$ carbocycle;

wherein when $R^{11a}$, $R^{11b}$, and $R^{11c}$ are each hydrogen; then $R^{11d}$ is selected from: halogen, —CN, $C_{1-6}$ alkyl, and $C_{3-10}$ carbocycle.

3. The compound or salt of claim 1, wherein $R^{11b}$ is —F; and $R^{11a}R^{11c}$, and $R^{11d}$ are each independently selected from hydrogen, —F, —CN, and methyl.

4. The compound or salt of claim 1, wherein $R^{11a}$ is —F, $R^{11b}$ is —H, and $R^{11d}$ is —H.

5. The compound or salt of claim 1, wherein $R^{12}$ is hydrogen, and $R^{15}$ is hydrogen.

6. The compound or salt of claim 1, wherein $R^{12}$ is hydrogen, and $R^{15}$ is hydrogen, and $R^{16}$ is —$CH_3$.

7. The compound or salt of claim 1, wherein $R^{13}$ is selected from hydrogen, methyl, ethyl, —OH, —OMe, —$CF_3$, —$C(H)F_2$, —N(H)Me, and cyclopropyl.

8. The compound or salt of claim 1, wherein $R^{13}$ is selected from hydrogen.

9. The compound or salt of claim 1, wherein either: (i) $R^{14}$ is fluoro, and $R^{14'}$ is fluoro; or (ii) $R^{14}$ and $R^{14'}$ together form a cyclopropane ring that is optionally substituted; or (iii) $R^{14}$ is hydrogen, and $R^{14'}$ is hydrogen.

10. The compound or salt of claim 1, wherein each $R^{17a}$, $R^{17b}$, $R^{17c}$, $R^{17d}$, and $R^{17e}$ is independently selected from: hydrogen, halogen, —$OR^{19g}$, and —CN; and $C_{1-6}$ alkyl and $C_{2-6}$ alkynyl, each of which is optionally substituted with one or more substituents independently selected from $R^{18f}$.

11. The compound or salt of claim 1, wherein $R^{17a}$, $R^{17b}$, $R^{17c}$, $R^{17d}$, and $R^{17e}$ are each independently selected from hydrogen, methyl, —F, and —CN.

12. The compound or salt of claim 1, wherein $R^{17a}$, $R^{17b}$, $R^{17c}$, $R^{17d}$, and $R^{17}$ are each independently selected from hydrogen and —CN.

13. The compound or salt of claim 1, wherein one of $X^{11}$ and $X^{12}$ is N, or both $X^{11}$ and $X^{12}$ are N.

14. The compound or salt of claim 1, wherein $Y^{12}$ is C(CN).

15. The compound or salt of claim 1, wherein $Y^{11}$ is C(H), and $X^{13}$ is C(H).

16. The compound or salt of claim 1, wherein $R^{16}$ and $R^{17a}$ are taken together to form a 3- to 10-membered heterocycle which is optionally substituted with one or more substituents independently selected from halogen and—CN.

17. The compound of claim 1, wherein the compound is

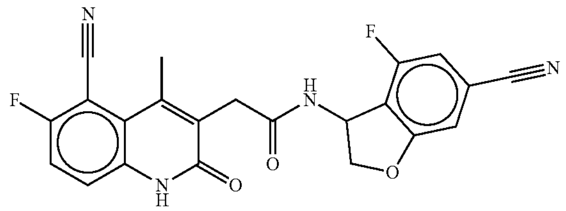

or a salt thereof.

18. The compound of claim 1, wherein the compound is

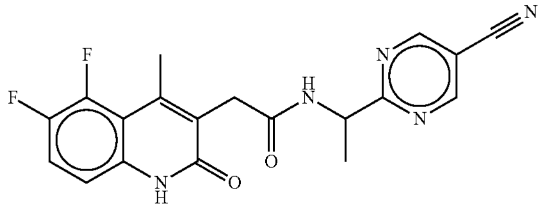

or a salt thereof.

19. The compound of claim 1, wherein the compound is

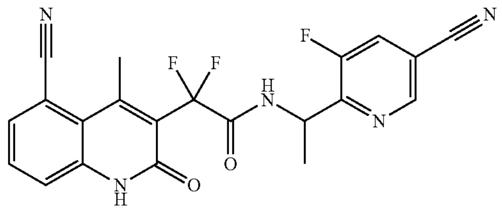 [SMILES: Cc1c(C(F)(F)C(=O)NC(C)c2ncc(C#N)cc2F)c(=O)[nH]c2cccc(C#N)c12]

or a salt thereof.

20. The compound of claim 1, wherein the compound is

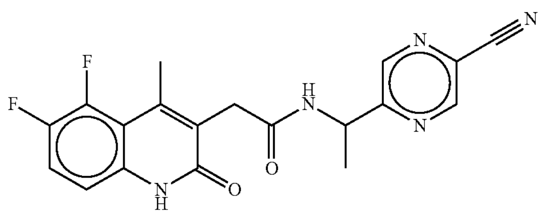

or a salt thereof.

21. The compound of claim 1, wherein the compound is

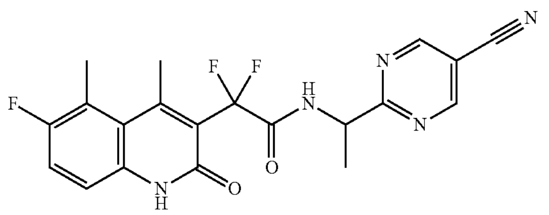

or a salt thereof.

22. The compound of claim 1, wherein the compound is

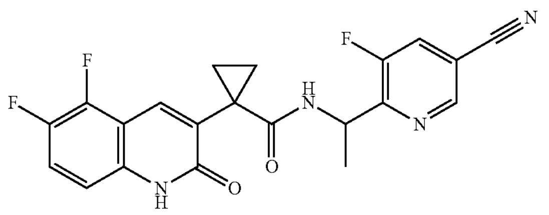 [SMILES: CC(NC(=O)C1(c2cc3c(F)c(F)ccc3[nH]c2=O)CC1)c1ncc(C#N)cc1F]

or a salt thereof.

23. The compound of claim 1, wherein the compound is

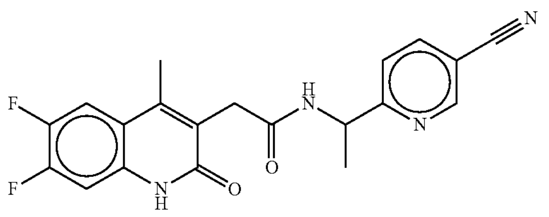

or a salt thereof.

24. The compound of claim 1, wherein the compound is

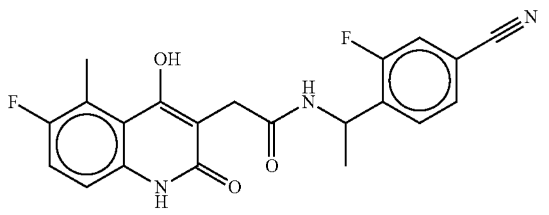

or a salt thereof.

25. The compound of claim 1, wherein the compound is

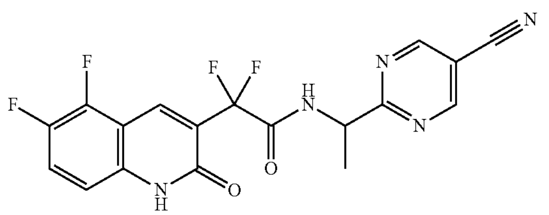 [SMILES: CC(NC(=O)C(F)(F)c1cc2c(F)c(F)ccc2[nH]c1=O)c1ncc(C#N)cn1]

or a salt thereof.

26. The compound of claim 1, wherein the compound is

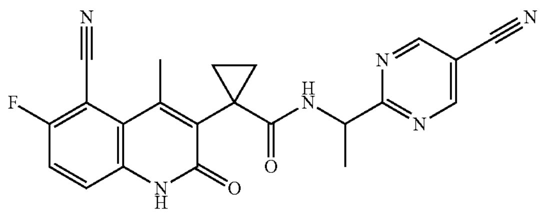 [SMILES: Cc1c(C2(C(=O)NC(C)c3ncc(C#N)cn3)CC2)c(=O)[nH]c2ccc(F)c(C#N)c12]

or a salt thereof.

27. A pharmaceutical composition comprising a compound or salt of claim 1 and a pharmaceutically acceptable excipient.

28. The compound of claim 1, wherein the compound is

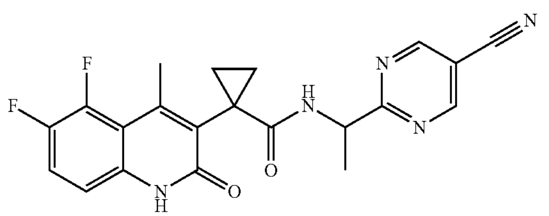 [SMILES: Cc1c(C2(C(=O)NC(C)c3ncc(C#N)cn3)CC2)c(=O)[nH]c2ccc(F)c(F)c12]

or a salt thereof.

29. The compound of claim 1, wherein the compound is

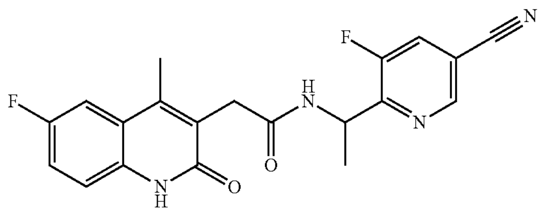 [SMILES: Cc1c(CC(=O)NC(C)c2ncc(C#N)cc2F)c(=O)[nH]c2ccc(F)cc12]

or a salt thereof.

30. The compound of claim 1, wherein the compound is

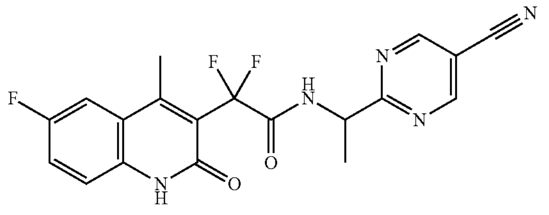 [SMILES: Cc1c(C(F)(F)C(=O)NC(C)c2ncc(C#N)cn2)c(=O)[nH]c2ccc(F)cc12]

or a salt thereof.

31. The compound of claim 1, wherein the compound is

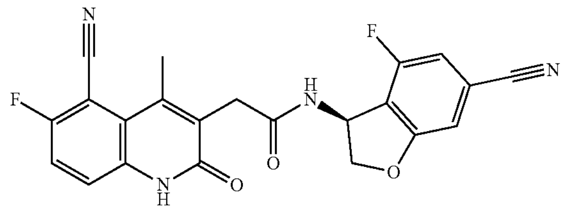 [SMILES: Cc1c(CC(=O)N[C@@H]2COc3cc(C#N)cc(F)c32)c(=O)[nH]c2ccc(F)c(C#N)c12]

or a salt thereof.

32. The compound of claim 1, wherein the compound is

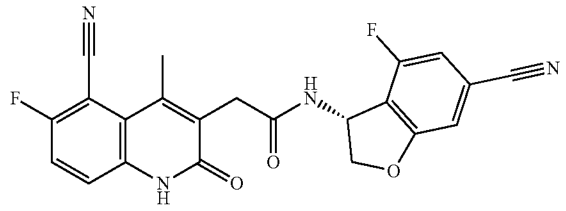 [SMILES: Cc1c(CC(=O)N[C@H]2COc3cc(C#N)cc(F)c32)c(=O)[nH]c2ccc(F)c(C#N)c12]

or a salt thereof.

33. The compound of claim 1, wherein the compound is

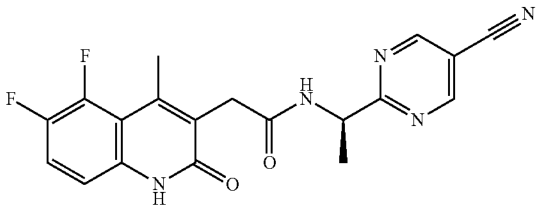 [SMILES: Cc1c(CC(=O)N[C@H](C)c2ncc(C#N)cn2)c(=O)[nH]c2ccc(F)c(F)c12]

or a salt thereof.

34. The compound of claim 1, wherein the compound is

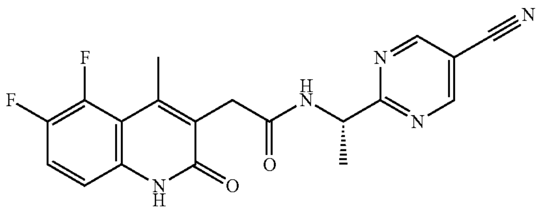 [SMILES: Cc1c(CC(=O)N[C@@H](C)c2ncc(C#N)cn2)c(=O)[nH]c2ccc(F)c(F)c12]

or a salt thereof.

35. The compound of claim 1, wherein the compound is

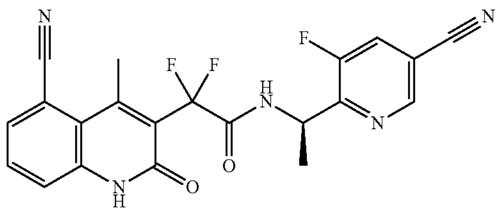 [SMILES: Cc1c(C(F)(F)C(=O)N[C@H](C)c2ncc(C#N)cc2F)c(=O)[nH]c2cccc(C#N)c12]

or a salt thereof.

36. The compound of claim 1, wherein the compound is

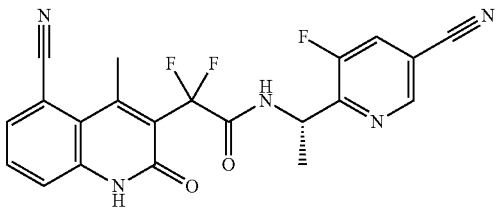 [SMILES: Cc1c(C(F)(F)C(=O)N[C@@H](C)c2ncc(C#N)cc2F)c(=O)[nH]c2cccc(C#N)c12]

or a salt thereof.

37. The compound of claim 1, wherein the compound is

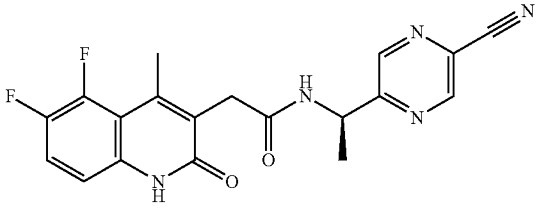 [SMILES: Cc1c(CC(=O)N[C@H](C)c2cnc(C#N)cn2)c(=O)[nH]c2ccc(F)c(F)c12]

or a salt thereof.

38. The compound of claim 1, wherein the compound is

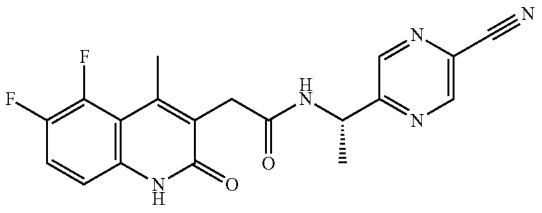 [SMILES: Cc1c(CC(=O)N[C@@H](C)c2cnc(C#N)cn2)c(=O)[nH]c2ccc(F)c(F)c12]

or a salt thereof.

39. The compound of claim 1, wherein the compound is

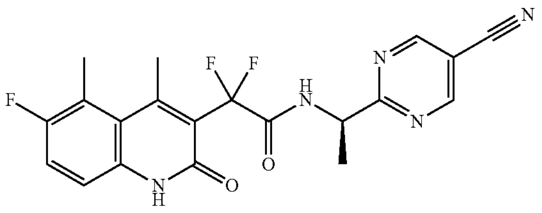 [SMILES: Cc1c(F)ccc2[nH]c(=O)c(C(F)(F)C(=O)N[C@H](C)c3ncc(C#N)cn3)c(C)c12]

or a salt thereof.

40. The compound of claim 1, wherein the compound is

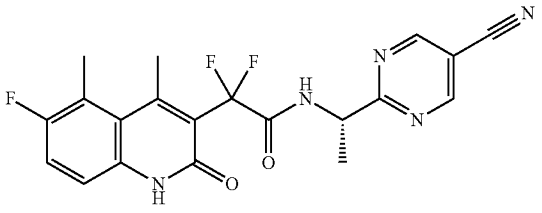 [SMILES: Cc1c(F)ccc2[nH]c(=O)c(C(F)(F)C(=O)N[C@@H](C)c3ncc(C#N)cn3)c(C)c12]

or a salt thereof.

41. The compound of claim 1, wherein the compound is

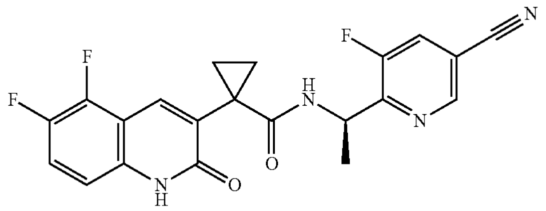 [SMILES: C[C@@H](NC(=O)C1(c2cc3c(F)c(F)ccc3[nH]c2=O)CC1)c1ncc(C#N)cc1F]

or a salt thereof.

42. The compound of claim 1, wherein the compound is

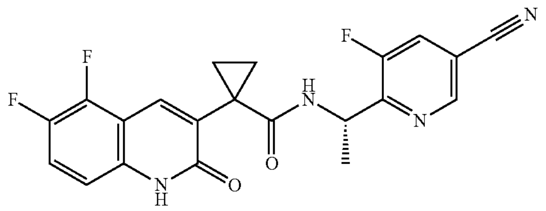 [SMILES: C[C@H](NC(=O)C1(c2cc3c(F)c(F)ccc3[nH]c2=O)CC1)c1ncc(C#N)cc1F]

or a salt thereof.

43. The compound of claim 1, wherein the compound is

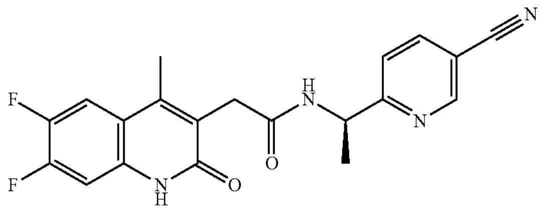 [SMILES: Cc1c(CC(=O)N[C@H](C)c2ccc(C#N)cn2)c(=O)[nH]c2cc(F)c(F)cc12]

or a salt thereof.

44. The compound of claim 1, wherein the compound is

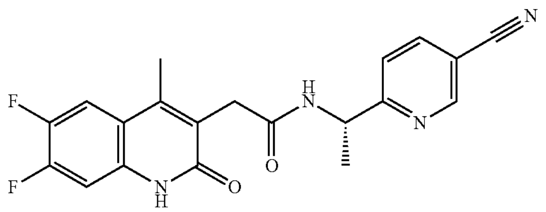 [SMILES: Cc1c(CC(=O)N[C@@H](C)c2ccc(C#N)cn2)c(=O)[nH]c2cc(F)c(F)cc12]

or a salt thereof.

45. The compound of claim 1, wherein the compound is

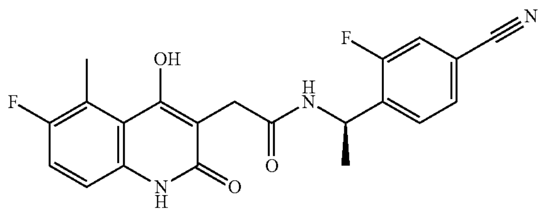 [SMILES: Cc1c(F)ccc2[nH]c(=O)c(CC(=O)N[C@H](C)c3ccc(C#N)cc3F)c(O)c12]

or a salt thereof.

46. The compound of claim 1, wherein the compound is

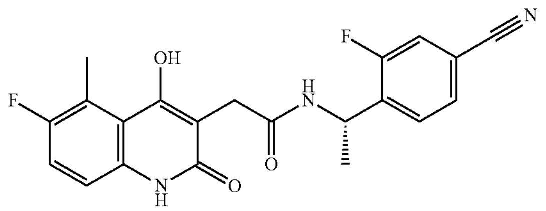 [SMILES: Cc1c(F)ccc2[nH]c(=O)c(CC(=O)N[C@@H](C)c3ccc(C#N)cc3F)c(O)c12]

or a salt thereof.

47. The compound of claim 1, wherein the compound is

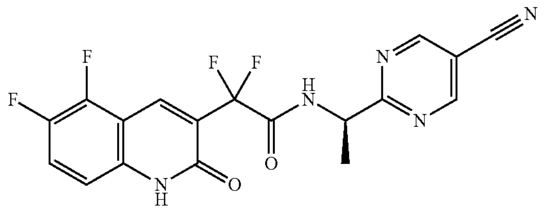 [SMILES: C[C@@H](NC(=O)C(F)(F)c1cc2c(F)c(F)ccc2[nH]c1=O)c1ncc(C#N)cn1]

or a salt thereof.

48. The compound of claim 1, wherein the compound is

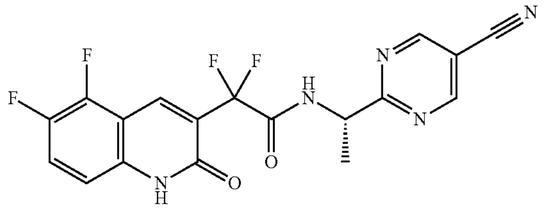 [SMILES: C[C@H](NC(=O)C(F)(F)c1cc2c(F)c(F)ccc2[nH]c1=O)c1ncc(C#N)cn1]

or a salt thereof.

49. The compound of claim 1, wherein the compound is

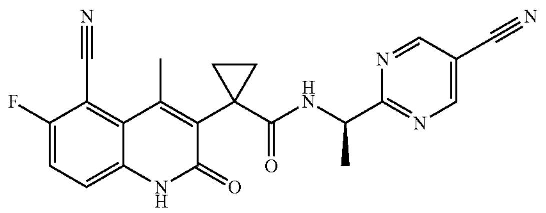 [SMILES: Cc1c(C2(C(=O)N[C@H](C)c3ncc(C#N)cn3)CC2)c(=O)[nH]c2ccc(F)c(C#N)c12]

or a salt thereof.

50. The compound of claim 1, wherein the compound is

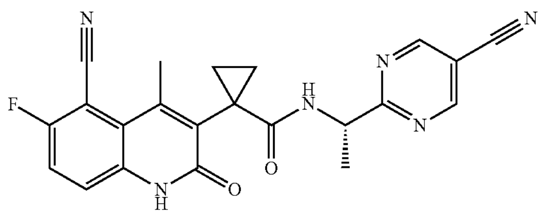 [SMILES: Cc1c(C2(C(=O)N[C@@H](C)c3ncc(C#N)cn3)CC2)c(=O)[nH]c2ccc(F)c(C#N)c12]

or a salt thereof.

51. The compound of claim 1, wherein the compound is

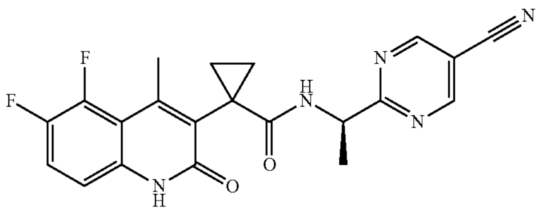 [SMILES: Cc1c(C2(C(=O)N[C@H](C)c3ncc(C#N)cn3)CC2)c(=O)[nH]c2ccc(F)c(F)c12]

or a salt thereof.

52. The compound of claim 1, wherein the compound is

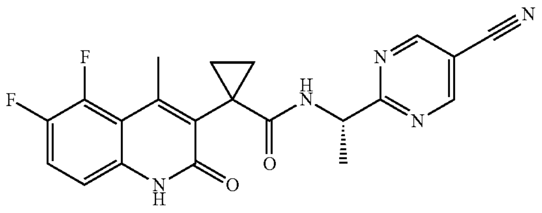 [SMILES: Cc1c(C2(C(=O)N[C@@H](C)c3ncc(C#N)cn3)CC2)c(=O)[nH]c2ccc(F)c(F)c12]

or a salt thereof.

53. The compound of claim 1, wherein the compound is

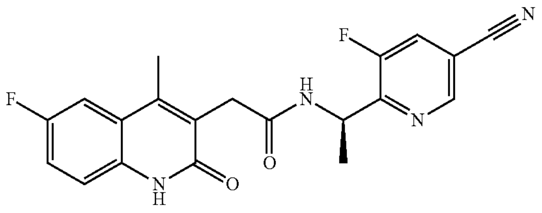 [SMILES: Cc1c(CC(=O)N[C@H](C)c2ncc(C#N)cc2F)c(=O)[nH]c2ccc(F)cc12]

or a salt thereof.

54. The compound of claim 1, wherein the compound is

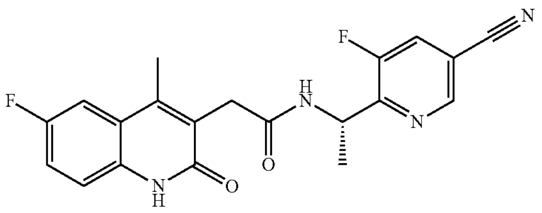 [SMILES: Cc1c(CC(=O)N[C@@H](C)c2ncc(C#N)cc2F)c(=O)[nH]c2ccc(F)cc12]

or a salt thereof.

55. The compound of claim 1, wherein the compound is

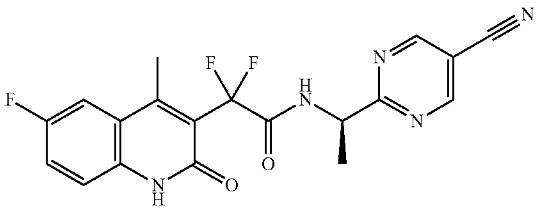 [SMILES: Cc1c(C(F)(F)C(=O)N[C@H](C)c2ncc(C#N)cn2)c(=O)[nH]c2ccc(F)cc12]

or a salt thereof.

56. The compound of claim 1, wherein the compound is

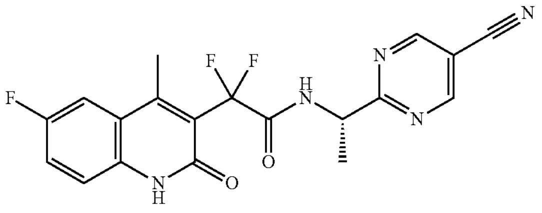 [SMILES: Cc1c(C(F)(F)C(=O)N[C@@H](C)c2ncc(C#N)cn2)c(=O)[nH]c2ccc(F)cc12]

or a salt thereof.

* * * * *